(12) United States Patent
Chakravarty et al.

(10) Patent No.: US 10,807,994 B2
(45) Date of Patent: Oct. 20, 2020

(54) HETEROCYCLIC COMPOUNDS AND USES THEREOF

(71) Applicant: NUVATION BIO INC., New York, NY (US)

(72) Inventors: Sarvajit Chakravarty, Edmond, OK (US); Son Minh Pham, San Francisco, CA (US); Jayakanth Kankanala, St. Paul, MN (US); Anil Kumar Agarwal, Noida (IN); Brahmam Pujala, Greater Noida (IN); Sanjeev Soni, Greater Noida (IN); Satish K. Arya, Noida (IN); Deepak Palve, Noida (IN); Varun Kumar, Noida (IN)

(73) Assignee: NUVATION BIO INC., New York, NY (US)

( * ) Notice: Subject to any disclaimer, the term of this patent is extended or adjusted under 35 U.S.C. 154(b) by 0 days.

(21) Appl. No.: 16/155,841

(22) Filed: Oct. 9, 2018

(65) Prior Publication Data

US 2019/0106436 A1 Apr. 11, 2019

Related U.S. Application Data

(60) Provisional application No. 62/570,054, filed on Oct. 9, 2017.

(51) Int. Cl.
| | | |
|---|---|---|
| *C07D 498/04* | (2006.01) | |
| *C07D 513/04* | (2006.01) | |
| *A61P 35/00* | (2006.01) | |
| *C07D 519/00* | (2006.01) | |
| *A61K 31/542* | (2006.01) | |
| *A61K 31/5365* | (2006.01) | |

(52) U.S. Cl.
CPC ........ *C07D 513/04* (2013.01); *A61K 31/5365* (2013.01); *A61K 31/542* (2013.01); *A61P 35/00* (2018.01); *C07D 498/04* (2013.01); *C07D 519/00* (2013.01)

(58) Field of Classification Search
CPC .............................. C07D 498/04; C07D 513/04
See application file for complete search history.

(56) References Cited

U.S. PATENT DOCUMENTS

| | | |
|---|---|---|
| 6,995,153 B2 | 2/2006 | Seto et al. |
| 7,834,019 B2 | 11/2010 | Sagara et al. |
| 8,329,711 B2 | 12/2012 | Furuyama et al. |
| 8,703,779 B2 | 4/2014 | Petrova et al. |
| 8,791,125 B2 | 7/2014 | Sagara et al. |
| 9,850,247 B2 | 12/2017 | Harrison et al. |
| 2006/0069093 A1 | 3/2006 | Scarborough et al. |
| 2006/0258651 A1 | 11/2006 | Linschoten |
| 2007/0254892 A1 | 11/2007 | Sagara et al. |
| 2010/0221211 A1 | 9/2010 | Furuyama |
| 2016/0008361 A1 | 1/2016 | Shumway |
| 2019/0084985 A1 | 3/2019 | Reigan et al. |
| 2019/0106427 A1 | 4/2019 | Chakravarty et al. |
| 2019/0248795 A1 | 8/2019 | Burkamp |

FOREIGN PATENT DOCUMENTS

| | | |
|---|---|---|
| WO | WO-2009/054332 A1 | 4/2009 |
| WO | WO-2010/067888 A1 | 6/2010 |
| WO | WO-2013/013031 A1 | 1/2013 |
| WO | WO-2013/059485 A1 | 4/2013 |
| WO | WO-2013/126656 A1 | 8/2013 |
| WO | WO-2014/167347 A1 | 10/2014 |
| WO | WO-2015/019037 A1 | 2/2015 |
| WO | WO-2015/092431 A1 | 6/2015 |
| WO | WO-2017/075629 A2 | 5/2017 |
| WO | WO-2018/011569 A1 | 1/2018 |
| WO | WO-2018/011570 A1 | 1/2018 |
| WO | WO-2018/0526621 A1 | 3/2018 |
| WO | WO-2018/090939 A1 | 5/2018 |
| WO | WO-2018/133829 A1 | 7/2018 |
| WO | WO-2018/162932 A1 | 9/2018 |
| WO | WO-2018/171633 A1 | 9/2018 |
| WO | WO-2018/183891 A1 | 10/2018 |
| WO | WO2019011228 A1 | 1/2019 |
| WO | WO-2019/028008 A1 | 2/2019 |
| WO | WO2019037678 A1 | 2/2019 |
| WO | WO2019096322 A1 | 5/2019 |
| WO | WO2019134539 A1 | 7/2019 |
| WO | WO2019165204 A1 | 8/2019 |

(Continued)

OTHER PUBLICATIONS

Bridges, K.A. et al. (Sep. 1, 2011; e-pub. Jul. 28, 2011). "MK-1775, a Novel Wee1 Kinase Inhibitor, Radiosensitizes p53-Defective Human Tumor Cells," Clinical Cancer Research 17(17):5638-5648.

(Continued)

*Primary Examiner* — Brian E McDowell
(74) *Attorney, Agent, or Firm* — Morrison & Foerster LLP

(57) ABSTRACT

Heterocyclic compounds of Formula (I):

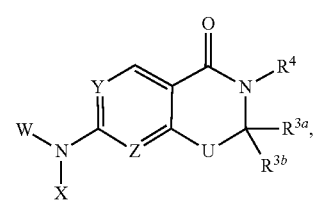

as Wee1 inhibitors are provided. The compounds may find use as therapeutic agents for the treatment of diseases and may find particular use in oncology.

59 Claims, No Drawings

(56) References Cited

FOREIGN PATENT DOCUMENTS

| WO | WO2019169065 A2 | 9/2019 |
|---|---|---|
| WO | WO2019173082 A1 | 9/2019 |

OTHER PUBLICATIONS

Brown, J.S. et al. (Feb. 6, 2018; e-pub. Nov. 9, 2017). "Combining DNA Damaging Therapeutics with Immunotherapy: More Haste, Less Speed," British Journal of Cancer 118(3):312-324.

Bukhari, A.B. et al. (Mar. 2019). "Inhibiting Wee1 and ATR Kinases Produces Tumor-Selective Synthetic Lethality and Suppresses Metastasis," The Journal of Clinical Investigation 129(3):1329-1344.

Chang, Q. et al. (2016; e-pub. Feb. 18, 2016). "Cytokinetic Effects of Wee1 Disruption in Pancreatic Cancer," Cell Cycle 15(4):593-604.

Chen, X. et al. (Dec. 2018; e-pub. Sep. 4, 2018). "Cyclin E Overexpression Sensitizes Triple-Negative Breast Cancer to Wee1 Kinase Inhibition," Clinical Cancer Research 24(24):6594-6610, (pre-published version is provided).

Chou, T.C. (Jan. 15, 2010; e-pub. Jan. 12, 2010). "Drug Combination Studies and Their Synergy Quantification Using the Chou-Talalay Method," Cancer Research 70(2):440-446.

Coyne, G.O.S. et al. (Jan. 2018). "Abstract B079: Single Agent AZD 1775, a Wee1 Inhibitor, Shows Activity in BRCA Deficient Patients," Molecular Cancer Therapeutics 17(1 Suppl):BO79, 4 pages.

De Gooijer, M.C. et al. (Jun. 2018; e-pub. Nov. 17, 2017). "ATP-binding Cassette Transporters Limit the Brain Penetration of Wee1 Inhibitors," Invest New Drugs 36(3):380-387.

Do, K. et al. (2013; e-pub. Aug. 26, 2013). "Wee1 Kinase as a Target for Cancer Therapy," Cell Cycle 12(19):3159-3164.

Do, K. et al. (Oct. 20, 2015; e-pub. May 11, 2015). "Phase I Study of Single-Agent AZD1775 (MK-1775), a Wee1 Kinase Inhibitor, in Patients With Refractory Solid Tumors," Journal of Clinical Oncology 33(30):3409-3415.

Francis, A.M. et al. (Sep. 2017; e-pub. Jun. 15, 2017). "CDK4/6 Inhibitors Sensitize Rb-Positive Sarcoma Cells to Wee1 Kinase Inhibition Through Reversible Cell Cycle Arrest," Molecular Cancer Therapeutics 16(9):1751-1764.

Friedman, J. et al. (2018). "Inhibition of WEE1 Kinase and Cell Cycle Checkpoint Activation Sensitizes Head and Neck Cancers to Natural Killer Cell Therapies," Journal for ImmunoTherapy of Cancer 6:59, 12 pages.

Fu, S. et al. (Sep. 2018; e-pub. Aug. 13, 2018). "Strategic Development of AZD1775, a Wee1 Kinase Inhibitor, for Cancer Therapy," Expert Opinion on Investigational Drugs 27(9):741-751.

Garcia, T.B. et al. (2018; e-pub. Nov. 11, 2017). "Increased Activity of Both CDK1 and CDK2 is Necessary for the Combinatorial Activity of WEE1 Inhibition and Cytarabine," Leukemia Research 64:30-33.

Garcia, T.B. et al. (Oct. 2017; e-pub. Jun. 27, 2017). "A Small Molecule Inhibitor of WEE1, AZD1775, Synergies with Olaparib by Impairing Homologous Recombination and Enhancing DNA Damaga and Apoptosis in Acute Leukemia," Molecular Cancer Therapeutics 16(10):2058-2068.

Garimella, S.V. et al. (Jan. 2012; e-pub. Nov. 23, 2011). "WEE1 Inhibition Sensitizes Basal Breast Cancer Cells to TRAIL-Induced Apoptosis," Molecular Cancer Research 10(1):75-85.

Gavory, G. et al. (Jul. 2016). "Novel, Potent & Selective Inhibitors of Wee1 with Robust Antitumor Activity in Various Cancer Xenograft Models," Poster presented at Proceedings: AACR 107th Annual Meeting 2016; Apr. 16-20, 2016; New Orleans, LA, 76(14):LB-159, 1 page.

Geenen, J.J.J. et al. (Aug. 15, 2017; e-pub. Apr. 25, 2017). "Molecular Pathways: Targeting the Protein Kinase Wee1 in Cancer," Clinical Cancer Research 23(16):OF1-OF5.

Guertin, A.D. et al. (2012). "Unique Functions of CHK1 and WEE1 Underlie Synergistic Anti-Tumor Activity Upon Pharmacologic Inhibition," Cancer Cell International 12:45, 12 pages.

Guertin, A.D. et al. (Aug. 2013; e-pub. May 22, 2013). "Preclinical Evaluation of the WEE1 Inhibitor MK-1775 as Single-Agent Anticancer Therapy," Molecular Cancer Therapeutics 12(8):1442-1452.

Hai, J. et al. (Nov. 15, 2017; e-pub. Aug. 18, 2017). "Synergy of WEE1 and mTOR Inhibition in Mutant KRAS-driven Lung Cancers," Clin Cancer Res 23(22):6993-7005.

Hamilton, D.H. et al. (May 1, 2014; e-pub. Mar. 13, 2014). "WEE1 Inhibition Alleviates Resistance to Immune Attack of Tumor Cells Undergoing Epithelial-Mesenchymal Transition," Cancer Research 74(9):2510-2519.

Hauge, S. et al. (Apr. 2019; e-pub. Apr. 3, 2019). "p21 Limits S Phase DNA Damage Caused by the Wee1 Inhibitor MK1775," Cell Cycle 18(8):834-847.

Hirai, H. et al. (Nov. 2009; e-pub. Nov. 3, 2009). "Small-Molecule Inhibition of Wee1 Kinase by MK-1775 Selectively Sensitizes P53-Deficient Tumor Cells to DNA-Damaging Agents," Molecular Cancer Therapeutics 8(11):2992-3000.

Hsieh, H.-J. et al. (2018). "Systems Biology Approach Reveals a Link Between mTORC1 and G2/M DNA Damage Checkpoint Recovery," Nature Communications 9:3982, 14 ppages.

International Search Report and Written Opinion dated Jan. 29, 2019 for PCT Application No. PCT/US2018/055093 filed on Oct. 9, 2018, 10 pages.

Invitation to Pay Additional Fees and, Where Applicable, Protest Fee dated Nov. 19, 2018 for PCT Application No. PCT/US2018/055093 filed on Oct. 9, 2018, 2 pages.

Iwai, A. et al. (Oct. 1, 2012; e-pub. Aug. 30, 2012). "Combined Inhibition of Wee1 and Hsp90 Activates Intrinsic Apoptosis in Cancer Cells," Cell Cycle 11(19):3649-3655.

Jin, J. et al. (May 2018). "Combined Inhibition of ATR and WEE1 as a Novel Therapeutic Strategy in Triple-Negative Breast Cancer," Neoplasia 20(5):478-488.

Karakashev, S. et al. (Dec. 19, 2017). "BET Bromodomain Inhibition Synergizes with PARP Inhibitor in Epithelial Ovarian Cancer," Cell Reports 21:3398-3405.

Karnak, D. et al. (Oct. 1, 2014; e-pub. Aug. 12, 2014). "Combined Inhibition of Wee1 and PARP1/2 for Radiosensitization in Pancreatic Cancer," Clinical Cancer Research 20(19):5085-5096.

Kausar, T. et al. (Oct. 2015). "Sensitization of Pancreatic Cancers to Gemcitabine Chemoradiation by WEE1 Kinase Inhibition Depends on Homologous Recombination Repair," Neoplasia 17(10):757-766.

Kaye, S.B. (2016). "DNA Repair Inhibitors in Ovarian Cancer: Current Status and Future Strategies," Presented at Progress and Controversies in Gynecologic Oncology Conference, 37 pages.

Kim, H.-Y et al. (Jun. 23, 2016). "Targeting the WEE1 Kinase as a Molecular Targeted Therapy for Gastric Cancer," Oncotarget 7(31):49902-49916.

Kreahling, J.M. et al. (Jan. 2012). "MK1775, A Selective Wee1 Inhibitor, Shows Single-Agent Antitumor Activity against Sarcoma Cells," Molecular Cancer Therapeutics 11(1):174-182, 15 pages.

Kreahling, J.M. et al. (Mar. 8, 2013). "Wee1 Inhibition by MK-1775 Leads to Tumor Inhibition and Enhances Efficacy of Gemcitabine in Human Sarcomas," PLOS One 8(3):e57523, 8 pages.

Kuzu, O.F. et al. (Sep. 28, 2017; e-pub. Jul. 13, 2017). "Improving Pharmacological Targeting of AKT in Melanoma," Cancer Letters 404:29-36.

Lallo, A. et al. (Oct. 15, 2018 e-pub. Jun. 25, 2018). "The Combination of the PARP Inhibitor Olaparib and the Wee1 Inhibitor AZD1775 as a New Therapeutic Option for Small Cell Lung Cancer," Clinical Cancer Research 24(20):5153-5164, 33 pages.

Lee, J.W. et al. (pre-published on Feb. 12, 2019). "Combined Aurora Kinase A (AURKA) and WEE1 Inhibition Demonstrates Synergistic Antitumor Effect in Squamous Cell Carcinoma of the Head and Neck," Clinical Cancer Research, 42 pages.

Leijen, S. et al. (Dec. 20, 2016; e-pub. Oct. 31, 2016). "Phase II Study of WEE1 Inhibitor AZD1775 Plus Carboplatin in Patients With TP53-Mutated Ovarian Cancer Refractory or Resistant to First-Line Therapy Within 3 Months," Journal of Clinical Oncology 34(36):4354-4361.

Leijen, S. et al. (Dec. 20, 2016; e-pub. Sep. 6, 2016). "Phase I Study Evaluating WEE1 Inhibitor AZD1775 as Monotherapy and in

(56) References Cited

OTHER PUBLICATIONS

Combination With Gemcitabine, Cisplatin, or Carboplatin in Patients With Advanced Solid Tumors," Journal of Clinical Oncology 34(36):4371-4380.

Lescarbeau, R.S. et al. (Jun. 2016; e-pub. Mar. 23, 2016). "Quantitative Phosphoproteomics Reveals Wee1 Kinase as a Therapeutic Target in a Model of Proneural Glioblastoma," Molecular Cancer Therapeutics 15(6):1332-1343.

Lewis, C.W. et al. (May 13, 2017). "Prolonged mitotic arrest induced by Wee1 inhibition sensitizes breast cancer cells to paclitaxel," Oncotarget 8(43):73705-73722.

Lübbehüsen, C. et al. (2019; e-pub. Apr. 23, 2019). "Characterization of Three Novel H3F3A-mutated Giant Cell Tumor Cell Lines and Targeting of Their Wee1 Pathway," Scientific Reports 9:6458, 10 pages.

Mastracchio, A. et al. (e-pub. Apr. 9, 2019). "Investigation of Biaryl Heterocycles as Inhibitors of Wee1 Kinase," Bioorganic & Medicinal Chemistry Letters 29(12):1481-1486.

Matheson, C.J. et al. (Apr. 15, 2016; e-pub. Jan. 8, 2016). "A WEE1 Inhibitor Analog of AZD1775 Maintains Synergy with Cisplatin and Demonstrates Reduced Single-Agent Cytotoxicity in Medulloblastoma Cells," ACS Chem. Biol. 11(4):921-930.

Matheson, C.J. et al. (Oct. 2016). "Targeting WEE1 Kinase in Cancer," Trends in Pharmacological Sciences 37(10):872-881.

Méndez, E. et al. (Jun. 15, 2018; e-pub. Mar. 13, 2018). "A Phase I Clinical Trial of AZD1775 in Combination with Neoadjuvant Weekly Docetaxel and Cisplatin Before Definitive Therapy in Head and Neck Squamous Cell Carcinoma," Clinical Cancer Research 24(12):2740-2748.

Mokyr, M.B. et al. (Dec. 1, 1998). "Realization of the Therapeutic Potential of CTLA-4 Blockade in Low-Dose Chemotherapy-treated Tumor-bearing Mice," Cancer Research 58:5301-5304.

Mueller, S. et al. (2014; e-pub. Dec. 4, 2013). "Targeting Wee1 for the Treatment of Pediatric High-Grade Gliomas," Neuro-Oncology 16(3):352-360.

Mueller, S. et al. (Oct. 20, 2015). "WEE1 Kinase as a Target for Cancer Therapy," Journal of Clinical Oncology 33(30):3485-3487.

Music, D. et al. (Apr. 2016; e-pub. Jan. 6, 2016). "Expression and Prognostic Value of the WEE1 Kinase in Gliomas," J Neurooncol 127(2):381-399, 9 pages.

O'Dowd, C. et al. (2019). "Antitumor Activity of the Novel Oral Highly Selective Wee1 Inhibitor Debio0123," Abstract #4423, Poster presented at AACR 2019, Atlanta, GA, US,1 page.

O'Neil, J. et al. (Jun. 2016; e-pub. Mar. 16, 2016). "An Unbiased Oncology Compound Screen to Identify Novel Combination Strategies," Molecular Cancer Therapeutics 15(6):1155-1162.

Palmer, B.D. et al. (2006; e-pub. Jul. 15, 2006). "4-Phenylpyrrolo[3,4-c]carbazole-1,3(2H,6H)-dione Inhibitors of the Checkpoint Kinase Wee1. Structure-Activity Relationships for Chromophore Modification and Phenyl Ring Substitution," J. Med. Chem. 49(16):4896-4911.

Pfister, S.X. et al. (Nov. 9, 2015). "Inhibiting WEE1 Selectively Kills Histone H3K36me3-Deficient Cancers by dNTP Starvation," Cancer Cell 28:557-568.

Pokorny, J.L. et al. (Apr. 15, 2015; e-pub. Jan. 21, 2015). "The Efficacy of the Wee1 Inhibitor MK-1775 Combined with Temozolomide is Limited by Heterogeneous Distribution across the Blood-Brain Barrier in Glioblastoma," Clinical Cancer Research 21(8):1916-1924.

Rajeshkumar, N.V. et al. (May 1, 2011; e-pub. Mar. 9, 2011). "MK-1775, a Potent Wee1 Inhibitor, Synergizes with Gemcitabine to Achieve Tumor Regressions, Selectively in p53-Deficient Pancreatic Cancer Xenografts," Clinical Cancer Research 17(9):2799-2806.

Restelli, V. et al. (pre-published May 7, 2019). "DNA Damage Response Inhibitor Combinations Exert Synergistic Antitumor Activity in Aggressive B Cell Lymphomas," Molecular Cancer Therapeutics, 25 pages, (Pre-published Copy provided).

Richer, A.L. et al. (Sep. 1, 2017; e-pub. Jun. 26, 2017). "WEE1 Kinase Inhibitor AZD1775 has Pre-Clinical Efficacy in LKB1-Deficient Non-small Cell Lung Cancer," The Journal of Cancer Research 77(17):4663-4672.

Sanai, N. et al. (Aug. 15, 2018; e-pub. May 24, 2018). "Phase 0 Trial of AZD1775 in First-Recurrence Glioblastoma Patients," Clinical Cancer Research 24(16):3820-3828.

Schmidt, M. et al. (Nov. 23, 2017). "Regulation of G2/M Transition by Inhibition of WEE1 and PKMYT1 Kinases," Molecules 22:2045, pp. 1-17.

Steino, A. et al. (Jul. 2018). "Dianhydrogalactitol (VAL-083) has the Potential to Overcome Major Challenges in the Treatment of Diffuse Intrinsic Pontine Glioma (DIPG)," Poster presented at AACR Annual Meeting 2018; Apr. 14-18, 2018; Chicago, IL, 78(13Supplement), 1 page.

Sun, A. et al. (Apr. 2010). "A Phase lb Study to Evaluate Induction of pCDC2 in Skin Biopsies from Patients with Solid Tumors Treated with DNA-damaging Chemotherapy," Poster presented at AACR 101st Annual Meeting 2010, Apr. 17-21, 2010, Washington D.C, Merck & Co., Inc., 70(8 Supplement), 1 page.

Sun, L. et al. (2018; e-pub. Jul. 23, 2018). "WEE1 Kinase Inhibition Reverses G2/M Cell Cycle Checkpoint Activation to Sensitize Cancer Cells to Immunotherapy," OncoImmunology 7(10):e1488359-1-e1488359-14.

Toledo, C.M. et al. (Dec. 22, 2015). "Genome-Wide CRISPR-Cas9 Screens Reveal Loss of Redundancy Between PKMYT1 and WEE1 in Glioblastoma Stem-like Cells," Cell Reports 13:2425-2439.

Tong, Y. et al. (2015). "Pyrimidine-Based Tricyclic Molecules as Potent and Orally Efficacious Inhibitors of Wee1 Kinase," ACS Med. Chem. Lett. 6:58-62.

Touat, M. et al. (2017; e-pub. Jun. 12, 2017). "Glioblastoma Targeted Therapy: Updated Approaches from Recent Biological Insights," Annals of Oncology 28:1457-1472.

Wang, Y. et al. (Mar. 2004). "Knockdown of Chk1, Wee1 and Myt1 by RNA Interference Abrogates G2 Checkpoint and Induces Apoptosis," Cancer Biology & Therapy 3(3):305-313.

Wichapong, K. et al. (2009; e-pub. Sep. 30, 2008). "Receptor-based 3D-QSAR Studies of Checkpoint Wee1 Kinase Inhibitors," European Journal of Medicinal Chemistry 44:1383-1395.

Wright, G. et al. (Jul. 21, 2017; e-pub. May 30, 2017). "Dual Targeting of WEE1 and PLK1 by AZD1775 Elicits Single Agent Cellular Anticancer Activity," ACS Chemical Biology 12(7):1883-1892., 18 pages.

Wu, M. et al. (2019). "miR-526b-3p Serves as a Prognostic Factor abd Regulates the Proliferation, Invasion, and Migration of Giloma through Targeting WEE1," Cancer Management and Research 11:3099-3110.

Wu, S. et al. (2018; e-pub. Jul. 7, 2017). "Activation of WEE1 Confers Resistance to PI3K Inhibition in Glioblastoma," Neuro-Oncology 20(1):78-91.

Zhang, M. et al. (2017). "WEE1 inhibition by MK1775 as a Single-Agent Therapy Inhibits Ovarian Cancer Viability," Oncology Letters 14:3580-3586.

Zhao, W. et al. (2015). "The Role and Mechanism of WEE1 on the Cisplatin Resistance Reversal of the HepG2/DDP Human Hepatic Cancer Cell Line," Oncology Letters 10:3081-3086.

Zhou, L. et al. (Apr. 2015). "A Regimen Combining the Wee1 Inhibitor AZD1775 With HDAC Inhibitors Targets Human Acute Myeloid Leukemia Cells Harboring Various Genetic Mutations," Leukemia 29(4):807-818, 24 pages.

Zhu, J.-Y. et al. (Aug. 9, 2017). "Structural Basis of Wee Kinases Functionality and Inactivation by Diverse Small Molecule Inhibitors," Journal of Medicinal Chemistry 60:7863-7875.

Zupkovitz, G. et al. (Mar. 2010; e-pub. Dec. 22, 2009). "The Cyclin-Dependent Kinase Inhibitor p21 is a Crucial Target for Histone Deacetylase 1 as a Regulator of Cellular Proliferation," Molecular and Cellular Biology 30(5):1171-1181.

Barbosa, R.S.S. et al. (2019). "Sequential Combination of Bortezomib and WEE1 Inhibitor, MK-1775, Induced Apoptosis in Multiple Myeloma Cell Lines," Biochemical and Biophysical Research Communication pp. 1-8.

Cuneo, K.C. et al. (Aug. 9, 2019). "Dose Escalation Trial of the Wee1 Inhibitor Adavosertib (AZD1775) in Combination With

(56) References Cited

OTHER PUBLICATIONS

Gemcitabine and Radiation for Patients With Locally Advanced Panceratic Cancer," Journal of Clinical Oncology 9 pages.

Hu, Y. et al. (2018, e-pub. Dec. 24, 2018). "Pharmacophore Modeling, Multiple Docking, and Molecular Dynamics Studies on Wee1 Kinase Inhibitors," Journal of Biomolecular Structure and Dynamics 1-14.

Jin, M.H. et al. (2019). "Therapeutic Co-Targeting of WEE1 and ATM Downregulates PD-L1 Expression in Pancreatic Cancer," Cancer Research and Treatment (CRT) pp. 1-40.

Li, J. et al. (Dec. 15, 2017; e-pub. Sep. 19, 2017). "Quantitative and Mechanistic Understanding of AZD1775 Penetration across Human Blood-Brain Barrier in Glioblastoma Patients Using an IVIVE-PBPK Modeling Approach," Clinical Cancer Research 23(24):7454-7466.

Liang, J. et al. (Sep. 24, 2019). "Genome-Wide CRIPSR-cas9 Screen Reveals Selective Vulnerability of ATRX-Mutant Cancers to WEE1 Inhibition," State Key Laboratory of Medical Molecular Biology, Institute of Basic Medical Sciences, Chinese Academy of Medical Sciences, Peking Union Medical School, Manuscript, 42 pages.

Liu, D. et al. (2019). "Enhancement of Chemosensitivity by WEE1 Inhibition in EGFR-TKIs Resistant Non-Small Cell Lung Cancer," Biomedicine & Pharmacotherapy 117(109185):1-8.

Liu, W. et al. (2019, e-pub. Jun. 13, 2019). "Targeting the WEE1 kinase strengthens the antitumor activity of imatinib via promoting KIT autophagic degradation in gastrointestinal stromal tumors," Gastric Cancer pp. 1-13.

Peer, C.J. et al. (Dec. 15, 2017; e-pub. Oct. 10, 2017). "Jumping the Barrier: Modeling Drug Penetration across the Blood-Brain Barrier," Clinical Cancer Research 23(24):7437-7439.

Serpico, A.F. et al. (2019, e-pub. Jun. 13, 2019). "Wee1 Rather Than PIk1 is Inhibited by AZD1775 at Therapeutically Relevant Concentrations," Cancers 11:1-10.

Takashima, Y. et al. (2019). "Bromodomain and Extraterminal Domain Inhibition Synergizes with WEE1-Inhibitor AZD1775 Effect by Impairing Non-Homologous End Joining and Enhancing DNA Damage in Non-Small Cell Lung Cancer," Department of Respiratory Medicine, Faculty of Medicine and Graduate School of Medicine, Hokkaido University pp. 1-33.

Zhang, P. et al. (2019, e-pub. Jul. 21, 2019). "BRD4 Inhibitor AZD5153 Suppresses the Proliferation of Colorectal Cancer Cells and Sensitizes the Anticancer Effect of PARP Inhibitor," Int. J. Biol. Sci. 15(9):1942-1954.

HETEROCYCLIC COMPOUNDS AND USES THEREOF

CROSS-REFERENCE TO RELATED APPLICATIONS

This application claims priority to U.S. Provisional Application No. 62/570,054, filed Oct. 9, 2017, the contents of which are hereby incorporated by reference in their entirety.

FIELD OF THE INVENTION

This disclosure relates generally to therapeutics engaged in inhibition of the DNA damage checkpoint kinase, Wee1, which potentiates genotoxic chemotherapies by abrogating cell-cycle arrest and proper DNA repair. The invention also provides pharmaceutically acceptable compositions comprising compounds of the present invention and methods of using said compositions in the treatment of diseases associated with this pathway.

BACKGROUND OF THE INVENTION

Wee1 is a tyrosine kinase that phosphorylates and inactivates Cdc2 and is involved in G checkpoint signaling. More particularly, Wee1 is involved in $G_2$-M checkpoint signaling. Because p53 is a key regulator in the G checkpoint, p53-deficient tumors rely only on the G checkpoint after DNA damage. More particularly, because p53 is a key regulator in the $G_1$-S checkpoint, p53-deficient tumors rely only on the $G_2$-M checkpoint after DNA damage. Hence, such tumors are selectively sensitized to DNA-damaging agents by Wee1 inhibition.

Wee1 belongs to a family of protein kinases involved in the terminal phosphorylation and inactivation of cyclin-dependent kinase 1-bound cyclin B, resulting in G cell cycle arrest in response to DNA damage. Wee1 was first identified in fission yeast, where Wee1 deficiency resulted in premature mitotic entry and replication of smaller-sized yeast. It is the major kinase responsible for the inhibitory phosphorylation of the tyrosine.

Before cells undergo mitosis, they progress through a tightly controlled cascade of $G_1$-S, intra-S, and $G_2$-M checkpoints. Wee1 kinase has emerged as a key $G_2$-M checkpoint regulator. This tyrosine kinase negatively regulates entry into mitosis by catalyzing an inhibitory phosphorylation of Cdc2 (the human homolog of cyclin-dependent kinase 1 (CDK1) on tyrosine-15 (Y15). This results in inactivation of the Cdc2/cyclin B complex, which arrests cells in $G_2$-M, allowing for DNA repair. Such inhibition also occurs through Chk1-mediated inhibition of Cdc25 phosphatases, which remove the inhibitory phosphorylation on Cdc2. Thus, entry into mitosis rests on a balance between the opposing activities of Wee1 and Chk1/Cdc25. Wee1 inhibition is thus expected to abrogate $G_2$-M arrest and propel cells into premature mitosis, a hypothesis confirmed by studies documenting that Wee1 inhibition by either small molecule inhibitors or small interference RNA leads to premature entry into mitosis and consequent cell death through mitotic catastrophe or apoptosis. (S. Muller, J. Clinical. Oncology, 2015).

Recently, a few classes of Wee1 inhibitors have been disclosed. Among them is a selective inhibitor, AZD-1775 (1,2-allyl-1-(6-(2-hydroxypropan-2-yl)pyridin-2-yl)-6-((4-(4methylpiperazin-1-yl)phenyl)amino)-1H-pyrazolo[3,4-d]pyrimidin-3 (2H)-one). AZD-1775 exhibited antitumor activity in various preclinical studies in potentiating chemo- and radiotherapy and is currently in phase I/II clinical trials.

Wee1 is highly expressed in several cancer types, including hepatocellular carcinoma, breast cancers, cervical cancers, lung cancers, squamous cell carcinoma, diffuse intrinsic pontine glioma (DIPG), glioblastoma, medulloblastoma, leukemia, melanoma, and ovarian cancers. (P. Reigan et al., Trends in Pharmacol. Sci., 2016).

There are few Wee1 inhibitors in clinical development. There is scope to improve Wee11 inhibitor selectivity and the properties of the inhibitors to permit targeting of specific cancer types.

BRIEF SUMMARY OF THE INVENTION

In one aspect, provided is a compound of Formula (I):

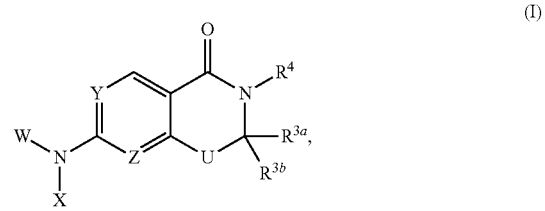

or a tautomer or isomer thereof, or a pharmaceutically acceptable salt of any of the foregoing, wherein U, W, X, Y, Z, $R^{3a}$, $R^{3b}$, and $R^4$ are as detailed herein.

In some embodiments, provided is a compound of Formula (Ia):

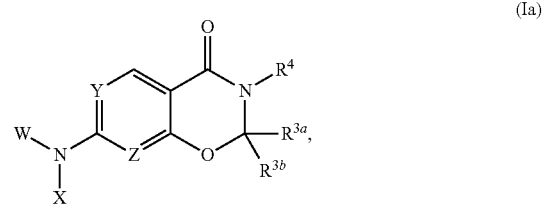

or a salt thereof, wherein W, X, Y, Z, $R^{3a}$, $R^{3b}$, and $R^4$ are as detailed herein.

In some embodiments, the compound of Formula (I), or a tautomer or isomer thereof, or a pharmaceutically acceptable salt of any of the foregoing, is of Formula (Ia), (Ib), (IIa), (IIb), (IIIa), (IIIb), (IVa) or (IVb), as detailed herein.

In another aspect, provided is a method of treating cancer in an individual in need thereof comprising administering to the individual a therapeutically effective amount of a compound detailed herein, such as a compound of Formula (I), or a pharmaceutically acceptable salt thereof. In some embodiments, provided is a method of treating cancer in an individual in need thereof comprising administering to the individual a therapeutically effective amount of a compound detailed herein, such as a compound of Formula (I), or a tautomer or isomer thereof, or a pharmaceutically acceptable salt of any of the foregoing. Also provided is a method of inhibiting Wee1 in a cell, comprising administering a compound detailed herein, or a salt thereof, to the cell. Also provided is a method of inhibiting Wee1 in a cell, comprising administering a compound detailed herein, or a tautomer or isomer thereof, or a pharmaceutically acceptable salt of any of the foregoing, to the cell.

In another aspect, provided are pharmaceutical compositions comprising a compound detailed herein and a pharmaceutically acceptable carrier or excipient. Pharmaceutical compositions comprising a compound detailed herein, or a tautomer or isomer thereof, or a pharmaceutically acceptable salt of any of the foregoing, and a pharmaceutically acceptable carrier or excipient. Kits comprising a compound detailed herein or a pharmaceutically acceptable salt thereof are also provided. Kits comprising a compound detailed herein, or a tautomer or isomer thereof, or a pharmaceutically acceptable salt of any of the foregoing, are also provided. Compounds as detailed herein or a pharmaceutically acceptable salt thereof are also provided for the manufacture of a medicament for the treatment of cancer. Compounds as detailed herein, or a tautomer or isomer thereof, or a pharmaceutically acceptable salt of any of the foregoing, are also provided for the manufacture of a medicament for the treatment of cancer.

DETAILED DESCRIPTION OF THE INVENTION

Definitions

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Carbonyl" refers to the group C=O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same or different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Compounds

In one aspect, provided is a compound of Formula (I):

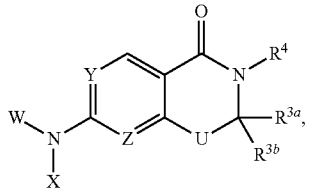

or a tautomer or isomer thereof, or a pharmaceutically acceptable salt of any of the foregoing,
wherein:
U is O or S;
W is A or AB, wherein A and B are fused together;
A is phenyl or 5- to 6-membered heteroaryl, each of which is optionally substituted with $R^{17a}$, wherein A and $R^{17a}$ together are

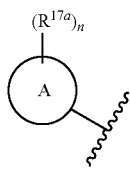

and n is 0, 1, 2, 3, or 4;
B is $C_3$-$C_6$ cycloalkyl, 3- to 7-membered heterocyclyl, 5- to 7-membered heteroaryl, or $C_6$ aryl, each of which is optionally substituted with $R^{17b}$, wherein A, B, $R^{17a}$, and $R^{17b}$ together are

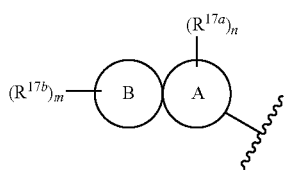

and m and n are independently 0, 1, 2, 3, or 4;
X is hydrogen or $C_1$-$C_6$ alkyl;
Y is N or $CR^1$;
Z is N or $CR^2$;
$R^1$ and $R^2$ are independently hydrogen or $R^{17a}$;
$R^{3a}$ and $R^{3b}$ are independently hydrogen or $R^{17a}$, or
$R^{3a}$ and $R^{3b}$ are taken together with the carbon to which they are attached to form a $C_3$-$C_6$ cycloalkyl;
each $R^{17b}$ is independently oxo or $R^{17a}$, or
any two $R^{17b}$ groups, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$;
each $R^{17a}$ is independently $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)OR^{10}$, —$Si(C_1$-$C_6$ alkyl$)_3$, —$C(O)NR^{11}R^{12}$, —$OC(O)NR^{11}R^{12}$, —$NR^{10}C(O)R^{11}$, —$NR^{10}C(O)NR^{11}R^{12}$, —$S(O)_2R^{10}$, —$NR^{10}S(O)_2R^{11}$, —$S(O)_2NR^{11}R^{12}$, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)CN, —($C_1$-$C_3$ alkylene)$OR^{10}$, —($C_1$-$C_3$ alkylene)$SR^{10}$, —($C_1$-$C_3$ alkylene)$NR^{11}R^{12}$, —($C_1$-$C_3$ alkylene)$CF_3$, —($C_1$-$C_3$ alkylene)$C(O)R^{10}$, —($C_1$-$C_3$ alkylene)$C(O)NR^{11}R^{12}$, —($C_1$-$C_3$ alkylene)$NR^{10}C(O)R^{11}$, —($C_1$-$C_3$ alkylene)$NR^{10}C(O)NR^{11}R^{12}$, —($C_1$-$C_3$ alkylene)$S(O)_2R^{10}$, —($C_1$-$C_3$ alkylene)$NR^{10}S(O)_2R^{11}$, —($C_1$-$C_3$ alkylene)$S(O)_2NR^{11}R^{12}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), wherein each $R^{17a}$ is independently optionally substituted by halogen, oxo, —$OR^{13}$, —$NR^{13}R^{14}$, —$C(O)R^{13}$, $C(O)NR^{13}R^{14}R$, —$NR^{13}C(O)R^{14}$, —$S(O)_2R^{13}$, —$NR^{13}S(O)_2R^{14}$, —$S(O)_2NR^{13}R^{14}$, —($C_1$-$C_3$ alkylene)$C(O)NR^{13}R^{14}$, —($C_1$-$C_3$ alkylene)$NR^{13}C(O)R^{14}$, —($C_1$-$C_3$ alkylene)$S(O)_2R^{13}$, —($C_1$-$C_3$ alkylene)$NR^{13}S(O)_2R^{14}$, —($C_1$-$C_3$ alkylene)$S(O)_2NR^{13}R^{14}$, —($C_1$-$C_3$ alkylene)($C_3$-$C_6$ cycloalkyl), —($C_1$-$C_3$ alkylene)(3- to 12-membered heterocyclyl), —$Si(C_1$-$C_6$ alkyl$)_3$, —CN, —($C_1$-$C_3$ alkylene)$OR^{13}$, —($C_1$-$C_3$ alkylene)$NR^{13}R^{14}$, —($C_1$-$C_3$ alkylene)$C(O)R^{13}$, $C_3$-$C_8$ cycloalkyl, or $C_1$-$C_6$ alkyl optionally substituted by oxo, —OH or halogen;
$R^4$ is hydrogen, $C_1$-$C_6$ alkyl, $C_2$-$C_6$ alkenyl, $C_2$-$C_6$ alkynyl, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), wherein $R^4$ is independently optionally substituted by halogen, oxo, —OR, —$NR^{13}R^{14}$, —$C(O)R^{13}$, —CN, $C_3$-$C_8$ cycloalkyl, or $C_1$-$C_6$ alkyl optionally substituted by oxo, —OH or halogen;
$R^{10}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —OR, —$NR^{15}R^{16}$, or $C_1$-$C_6$ alkyl optionally substituted by halogen, —OH or oxo;
$R^{11}$ and $R^{12}$ are each independently hydrogen, $C_1$-$C_6$ alkyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_3$-$C_6$ cycloalkyl, $C_6$-$C_{14}$ aryl, 5- to 6-membered heteroaryl and 3- to 6-membered heterocyclyl of $R^{11}$ and $R^{12}$ are independently optionally substituted by halogen, oxo, —CN, —$OR^{15}$, —$NR^{15}R^{16}$ or $C_1$-$C_6$ alkyl optionally substituted by halogen, —OH or oxo,
or $R^{11}$ and $R^{12}$ are taken together with the atom to which they attached to form a 3- to 6-membered heterocyclyl optionally substituted by halogen, oxo, or $C_1$-$C_6$ alkyl optionally substituted by halogen;
$R^{13}$ and $R^{14}$ are each independently hydrogen, $C_1$-$C_6$ alkyl, $C_3$-$C_6$ cycloalkyl, or 3- to 6-membered heterocyclyl, wherein the $C_1$-$C_6$ alkyl, $C_3$-$C_6$ cycloalkyl, or 3- to 6-membered heterocyclyl of $R^{13}$ and $R^{14}$ are optionally substituted by halogen, —CN, —OR, —$NR^{15}R^{16}$, or oxo,
or $R^{13}$ and $R^{14}$ are taken together with the atom to which they attached to form a 3- to 6-membered heterocyclyl optionally substituted by halogen, oxo or $C_1$-$C_6$ alkyl optionally substituted by halogen or oxo; and
$R^{15}$ and $R^{16}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo,
or $R^{15}$ and $R^{16}$ are taken together with the atom to which they attached to form a 3- to 6-membered heterocyclyl optionally substituted by halogen, oxo or $C_1$-$C_6$ alkyl optionally substituted by oxo or halogen.

In some embodiments of a compound of Formula (I), at least one of Y and Z is N.

In some embodiments, provided is a compound of Formula (Ia):

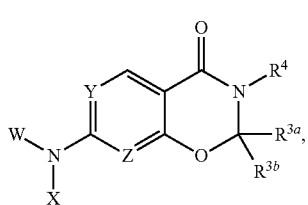

(Ia)

or a salt thereof, wherein:

W is A or AB, wherein A and B are fused together;

A is phenyl or 6-membered heteroaryl, each of which is optionally substituted with $R^{17a}$, wherein A and $R^{17a}$ together are

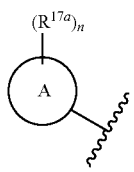

and n is 0, 1, 2, 3, or 4;

B is $C_3$-$C_6$ cycloalkyl, 3- to 7-membered heterocyclyl, 5- to 7-membered heteroaryl, or $C_6$ aryl, each of which is optionally substituted with $R^{17b}$, wherein A, B, $R^{17a}$, and $R^{17b}$ together are

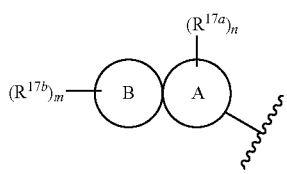

and m and n are independently 0, 1, 2, 3, or 4;

X is hydrogen or $C_1$-$C_6$ alkyl;

Y is N or $CR^1$;

Z is N or $CR^2$;

$R^1$ and $R^2$ are independently hydrogen or $R^{17a}$;

$R^{3a}$ and $R^{3b}$ are independently hydrogen or $R^{17a}$, or $R^{3a}$ and $R^{3b}$ are taken together with the carbon to which they are attached to form a $C_3$-$C_6$ cycloalkyl;

each $R^{17b}$ is independently oxo or $R^{17a}$, or any two $R^{17b}$ groups, when bound to the same carbon atom, are taken together with the carbon to which they are attached to form a $C_3$-$C_6$ cycloalkyl;

each $R^{17a}$ is independently $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$, —$OC(O)NR^{11}R^{12}$, —$NR^{10}C(O)R^{11}$, —$NR^{10}C(O)NR^{11}R^{12}$, —$S(O)_2R^1$, —$NR^{10}S(O)_2R^{11}$, —$S(O)_2NR^{11}R^{12}$, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)CN, —($C_1$-$C_3$ alkylene)$OR^{10}$, —($C_1$-$C_3$ alkylene)$SR^{10}$, —($C_1$-$C_3$ alkylene)$NR^{11}R^{12}$, —($C_1$-$C_3$ alkylene)$CF_3$, —($C_1$-$C_3$ alkylene)$C(O)R^{10}$, —($C_1$-$C_3$ alkylene)$C(O)NR^{11}R^{12}$, —($C_1$-$C_3$ alkylene)$NR^{10}C(O)R^{11}$, —($C_1$-$C_3$ alkylene)$NR^{10}C(O)NR^{11}R^{12}$, —($C_1$-$C_3$ alkylene)$S(O)_2R^{10}$, —($C_1$-$C_3$ alkylene)$NR^{10}S(O)_2R^{11}$, —($C_1$-$C_3$ alkylene)$S(O)_2NR^{11}R^{12}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), wherein each $R^{17a}$ is independently optionally substituted by halogen, oxo, —$OR^{13}$, —$NR^{13}R^{14}$, —$C(O)R^{13}$, —CN, —($C_1$-$C_3$ alkylene)$OR^{13}$, —($C_1$-$C_3$ alkylene)$NR^{13}R^{14}$, —($C_1$-$C_3$ alkylene)$C(O)R^{13}$, $C_3$-$C_8$ cycloalkyl, or $C_1$-$C_6$ alkyl optionally substituted by oxo, —OH or halogen;

$R^4$ is hydrogen, $C_1$-$C_6$ alkyl, $C_2$-$C_6$ alkenyl, $C_2$-$C_6$ alkynyl, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), wherein $R^4$ is independently optionally substituted by halogen, oxo, —$OR^{13}$, —$NR^{13}R^{14}$, —$C(O)R^{13}$, —CN, $C_3$-$C_8$ cycloalkyl, or $C_1$-$C_6$ alkyl optionally substituted by oxo, —OH or halogen;

$R^{10}$ is independently hydrogen, $C_1$-$C_6$ alkyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —$OR^{15}$, —$NR^{15}R^{16}$, or $C_1$-$C_6$ alkyl optionally substituted by halogen, —OH or oxo;

$R^{11}$ and $R^{12}$ are each independently hydrogen, $C_1$-$C_6$ alkyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_3$-$C_6$ cycloalkyl, $C_6$-$C_{14}$ aryl, 5- to 6-membered heteroaryl and 3- to 6-membered heterocyclyl of $R^{11}$ and $R^{12}$ are independently optionally substituted by halogen, oxo, —CN, —$OR^{15}$, —$NR^{15}R^{16}$ or $C_1$-$C_6$ alkyl optionally substituted by halogen, —OH or oxo, or $R^{11}$ and $R^{12}$ are taken together with the atom to which they attached to form a 3- to 6-membered heterocyclyl optionally substituted by halogen, oxo, or $C_1$-$C_6$ alkyl optionally substituted by halogen;

$R^{13}$ and $R^{14}$ are each independently hydrogen or $C_1$-$C_6$ alkyl, wherein the $C_1$-$C_6$ alkyl of $R^{13}$ and $R^{14}$ are optionally substituted by halogen, —OR, —$NR^{15}R^{16}$, or oxo, or $R^{13}$ and $R^{14}$ are taken together with the atom to which they attached to form a 3- to 6-membered heterocyclyl optionally substituted by halogen, oxo or $C_1$-$C_6$ alkyl optionally substituted by halogen or oxo; and $R^{15}$ and $R^{16}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo, or $R^{15}$ and $R^{16}$ are taken together with the atom to which they attached to form a 3- to 6-membered heterocyclyl optionally substituted by halogen, oxo or $C_1$-$C_6$ alkyl optionally substituted by oxo or halogen.

In some embodiments, provided is a compound of Formula (Ia), or a tautomer or isomer thereof, or a pharmaceutically acceptable salt of any of the foregoing.

In some embodiments, the compound of formula (I) is of Formula (Ib):

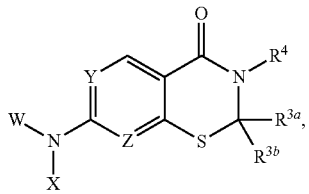

(Ib)

or a tautomer or isomer thereof, or a pharmaceutically acceptable salt of any of the foregoing, wherein W, X, Y, Z, $R^{3a}$, $R^{3b}$, and $R^4$ are as detailed herein.

In some embodiments, provided is a compound of Formula (IIa):

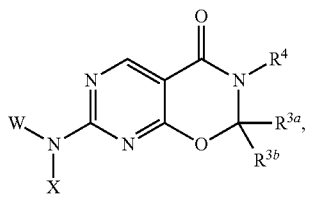

(IIa)

or a tautomer or isomer thereof, or a pharmaceutically acceptable salt of any of the foregoing, wherein W, X, $R^{3a}$, $R^{3b}$, and $R^4$ are as detailed herein.

In some embodiments, the compound of Formula (IIb):

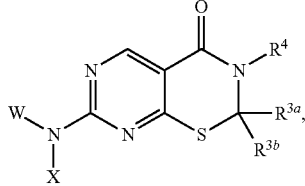

(IIb)

or a tautomer or isomer thereof, or a pharmaceutically acceptable salt of any of the foregoing, wherein W, X, $R^{3a}$, $R^{3b}$, and $R^4$ are as detailed herein.

In some embodiments, provided is a compound of Formula (IIIa):

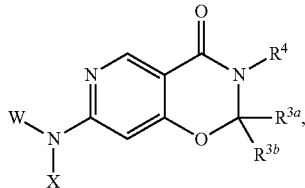

(IIIa)

or a tautomer or isomer thereof, or a pharmaceutically acceptable salt of any of the foregoing, wherein W, X, $R^{3a}$, $R^{3b}$, and $R^4$ are as detailed herein.

In some embodiments, the compound of Formula (IIIb):

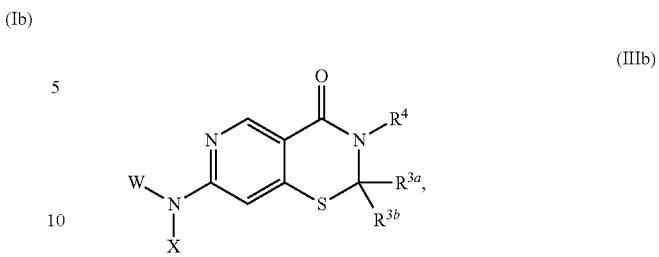

(IIIb)

or a tautomer or isomer thereof, or a pharmaceutically acceptable salt of any of the foregoing, wherein W, X, $R^{3a}$, $R^{3b}$, and $R^4$ are as detailed herein.

In some embodiments, provided is a compound of Formula (IVa):

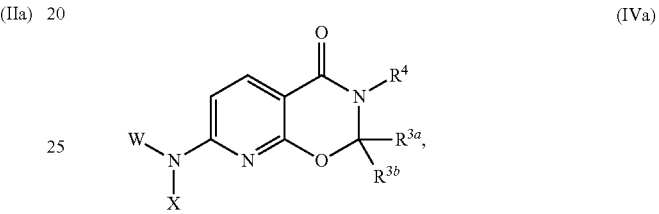

(IVa)

or a tautomer or isomer thereof, or a pharmaceutically acceptable salt of any of the foregoing, wherein W, X, $R^{3a}$, $R^{3b}$, and $R^4$ are as detailed herein.

In some embodiments, the compound of Formula (IVb):

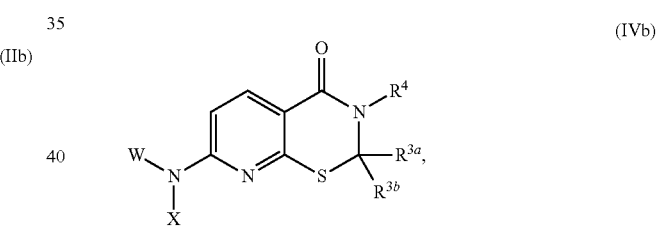

(IVb)

or a tautomer or isomer thereof, or a pharmaceutically acceptable salt of any of the foregoing, wherein W, X, $R^{3a}$, $R^{3b}$, and $R^4$ are as detailed herein.

In some embodiments of a compound of Formula (I), U is O. In some embodiments of a compound of Formula (I), U is S.

In some embodiments of a compound of Formula (I), (Ia), (Ib), (IIa), (IIb), (IIIa), (IIIb), (IVa) or (IVb), X is hydrogen. In some embodiments of a compound of Formula (I), (Ia), (Ib), (IIa), (IIb), (IIIa), (IIIb), (IVa) or (IVb), X is $C_1$-$C_6$ alkyl. In some embodiments of a compound of Formula (I), (Ia), (Ib), (IIa), (IIb), (IIIa), (IIIb), (IVa) or (IVb), X is methyl.

In some embodiments of a compound of Formula (I), Y is N. In some embodiments of a compound of Formula (I), Y is $CR^1$. In some embodiments of a compound of Formula (I), Y is CH.

In some embodiments of a compound of Formula (I), Z is N. In some embodiments of a compound of Formula (I), Z is $CR^1$. In some embodiments of a compound of Formula (I), Z is CH.

In some embodiments of a compound of Formula (I), Y is N and Z is N. In some embodiments of a compound of Formula (I), Y is N and Z is $CR^1$. In some embodiments of a compound of Formula (I), Y is $CR^1$ and Z is N. In some embodiments of a compound of Formula (I), Y is N and Z is CH. In some embodiments of a compound of Formula (I), Y is CH and Z is N.

In some embodiments of a compound of Formula (I), X is hydrogen; Y is N; and Z is N. In some embodiments of a compound of Formula (I), X is $C_1$-$C_6$ alkyl; Y is N; and Z is N. In some embodiments of a compound of Formula (I), X is hydrogen; Y is CH; and Z is N. In some embodiments of a compound of Formula (I), X is hydrogen; Y is N; and Z is CH.

In some embodiments of a compound of Formula (I), (Ia), (Ib), (IIa), (IIb), (IIIa), (IIIb), (IVa) or (IVb), $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl. In some embodiments of a compound of Formula (I), (Ia), (Ib), (IIa), (IIb), (IIIa), (IIIb), (IVa) or (IVb), $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl. In some embodiments of a compound of Formula (I), (Ia), (Ib), (IIa), (IIb), (IIIa), (IIIb), (IVa) or (IVb), $R^{3a}$ is hydrogen and $R^{3b}$ is $C_1$-$C_6$ alkyl. In some embodiments of a compound of Formula (I), (Ia), (Ib), (IIa), (IIb), (IIIa), (IIIb), (IVa) or (IVb), $R^{3a}$ is hydrogen and $R^{3b}$ is hydrogen. In some embodiments of a compound of Formula (I), (Ia), (Ib), (IIa), (IIb), (IIIa), (IIIb), (IVa) or (IVb), $R^{3a}$ is $C_1$-$C_6$ alkyl and $R^{3b}$ is $C_1$-$C_6$ alkyl. In some embodiments of a compound of Formula (I), (Ia), (Ib), (IIa), (IIb, (IIIa), (IIIb), (IVa) or (IVb), $R^{3a}$ is methyl and $R^{3b}$ is hydrogen. In some embodiments of a compound of Formula (I), (Ia), (Ib), (IIa), (IIb, (IIIa), (IIIb), (IVa) or (IVb), $R^{3a}$ is methyl and $R^{3b}$ is methyl. In some embodiments, $R^{3a}$ and $R^{3b}$ are taken together with the carbon to which they are attached to form a $C_3$-$C_6$ cycloalkyl.

In some embodiments of a compound of Formula (I), (Ia), or (Ib), X is hydrogen; Y is N; Z is N; $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^1$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl. In some embodiments of a compound of Formula (I), (Ia), or (Ib), X is $C_1$-$C_6$ alkyl; Y is N; Z is N; $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl. In some embodiments of a compound of Formula (I), (Ia), or (Ib), X is hydrogen; Y is CH; Z is N; $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl. In some embodiments of a compound of Formula (I), (Ia), or (Ib), X is hydrogen; Y is N; Z is CH; $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl.

In some embodiments of a compound of Formula (I), (Ia), or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl. In some embodiments of a compound of Formula (I), (Ia), or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl. In some embodiments of a compound of Formula (I), (Ia), or (Ib), X is hydrogen; Y is N; Z is N; $R^{3a}$ and $R^{3b}$ are independently hydrogen or $C_1$-$C_6$ alkyl. In some embodiments of a compound of Formula (I), (Ia), or (Ib), X is hydrogen; Y is N; Z is N; $R^{3a}$ and $R^{3b}$ are both hydrogen.

In some embodiments of a compound of Formula (I), (Ia), (Ib), (IIa), (IIb), (IIIa), (IIIb), (IVa) or (IVb), $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^1$, —$NR^{11}R^{12}$, —$C(O)R^{10}$, —$C(O)NR^{11}R^{12}$. In some embodiments of a compound of Formula (I), (Ia), (Ib), (IIa), (IIb), (IIIa), (IIIb), (IVa) or (IVb), $R^{3a}$ and $R^{3b}$ are taken together with the carbon to which they are attached to form a $C_3$-$C_6$ cycloalkyl. In some embodiments of a compound of Formula (I), (Ia), (Ib), (IIa), (IIb), (IIIa), (IIIb), (IVa) or (IVb), $R^{3a}$ and $R^{3b}$ are independently hydrogen or $C_1$-$C_6$ alkyl.

In some embodiments of a compound of Formula (I), (Ia), (Ib), (IIa), (IIb), (IIIa), (IIIb), (IVa) or (IVb), $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$ and $R^4$ is a 5- to 10-membered heteroaryl, $C_1$-$C_6$ alkyl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —($C_1$-$C_3$ alkylene)($C_6$-$C_{14}$ aryl), or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH. In one such embodiment, $R^{3a}$ and $R^{3b}$ are independently hydrogen or $C_1$-$C_6$ alkyl. In another such embodiment, $R^4$ is a 5- to 10-membered heteroaryl or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH. In some embodiments of a compound of Formula (I), (Ia), (Ib), (IIa), (IIb), (IIIa), (IIIb), (IVa) or (IVb), $R^{3a}$ and $R^{3b}$ are taken together with the carbon to which they are attached to form a $C_3$-$C_6$ cycloalkyl and $R^4$ is 5- to 10-membered heteroaryl, $C_1$-$C_6$ alkyl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —($C_1$-$C_3$ alkylene)($C_6$-$C_{14}$ aryl), or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH. In one such embodiment, $R^4$ is a 5- to 10-membered heteroaryl or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH.

In some embodiments of a compound of Formula (I), (Ia), (Ib), (IIa), (IIb), (IIIa), (IIIb), (IVa) or (IVb), $R^4$ is 5- to 10-membered heteroaryl, $C_1$-$C_6$ alkyl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —($C_1$-$C_3$ alkylene)($C_6$-$C_{14}$ aryl), or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH. In some embodiments of a compound of Formula (I), (Ia), (Ib), (IIa), (IIb), (IIIa), (IIIb), (IVa) or (IVb), $R^4$ is 5- to 10-membered heteroaryl or $C_6$-$C_{14}$ aryl, each of which is unsubstituted. In some embodiments of a compound of Formula (I), (Ia), (Ib), (IIa), (IIb), (IIIa), (IIIb), (IVa) or (IVb), $R^4$ is 5- to 10-membered heteroaryl or $C_6$-$C_{14}$ aryl, each of which is optionally substituted by halogen, oxo, —OR, —NR$^{13}$R$^{14}$, —C(O)R$^{13}$, —CN, C$_3$-C$_8$ cycloalkyl, or C$_1$-C$_6$ alkyl optionally substituted by oxo, —OH or halogen. In some embodiments of a compound of Formula (I), (Ia), (Ib), (IIa), (IIb), (IIIa), (IIIb), (IVa) or (IVb), R$^4$ is 5- to 10-membered heteroaryl or C$_6$-C$_{14}$ aryl, each of which is optionally substituted by halogen, —CN, —NR$^{13}$R$^{14}$, —C(O)R$^{13}$, —OR$^{13}$, or C$_1$-C$_6$ alkyl optionally substituted by —OH. In some embodiments of a compound of Formula (I), (Ia), (Ib), (IIa), (IIb), (IIIa), (IIIb), (IVa) or (IVb), R$^4$ is 5- to 10-membered heteroaryl optionally substituted by halogen, —CN, —NR$^{13}$R$^{14}$, —C(O)R$^{13}$, —OR$^{13}$, or C$_1$-C$_6$ alkyl optionally substituted by —OH. In some embodiments of a compound of Formula (I), (Ia), (Ib), (IIa), (IIb), (IIIa), (IIIb), (IVa) or (IVb), R$^4$ is C$_6$-C$_{14}$ aryl optionally substituted by halogen, —CN, —NR$^{13}$R$^{14}$, —C(O)R$^{13}$, —OR$^{13}$, or C$_1$-C$_6$ alkyl optionally substituted by —OH. In some embodiments of a compound of Formula (I), R$^4$ is phenyl optionally substituted by halogen, —CN, —NR$^{13}$R$^{14}$, —C(O)R$^{13}$, —OR$^{13}$, or C$_1$-C$_6$ alkyl optionally substituted by —OH. In some embodiments of a compound of Formula (I), (Ia), (Ib), (IIa), (IIb), (IIIa), (IIIb), (IVa) or (IVb), R$^4$ is phenyl optionally substituted by halogen or C$_1$-C$_6$ alkyl optionally substituted by —OH. In some embodiments of a compound of Formula (I), (Ia), (Ib), (IIa), (IIb), (IIIa), (IIIb), (IVa) or (IVb), R$^4$ is phenyl optionally substituted by halogen.

In some embodiments of a compound of Formula (I), (Ia), (Ib), (IIa), (IIb), (IIIa), (IIIb), (IVa) or (IVb), R$^4$ is selected from the group consisting of:
methyl, ethyl, isopropyl, cyclopropyl,

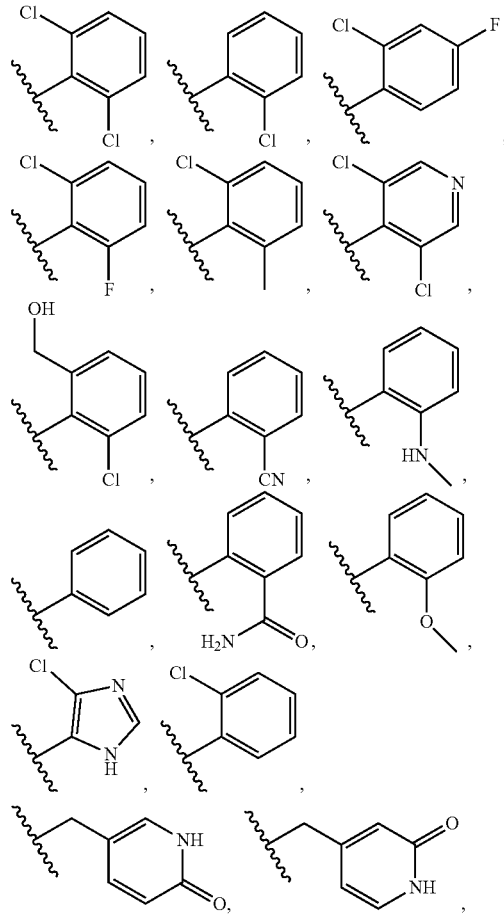

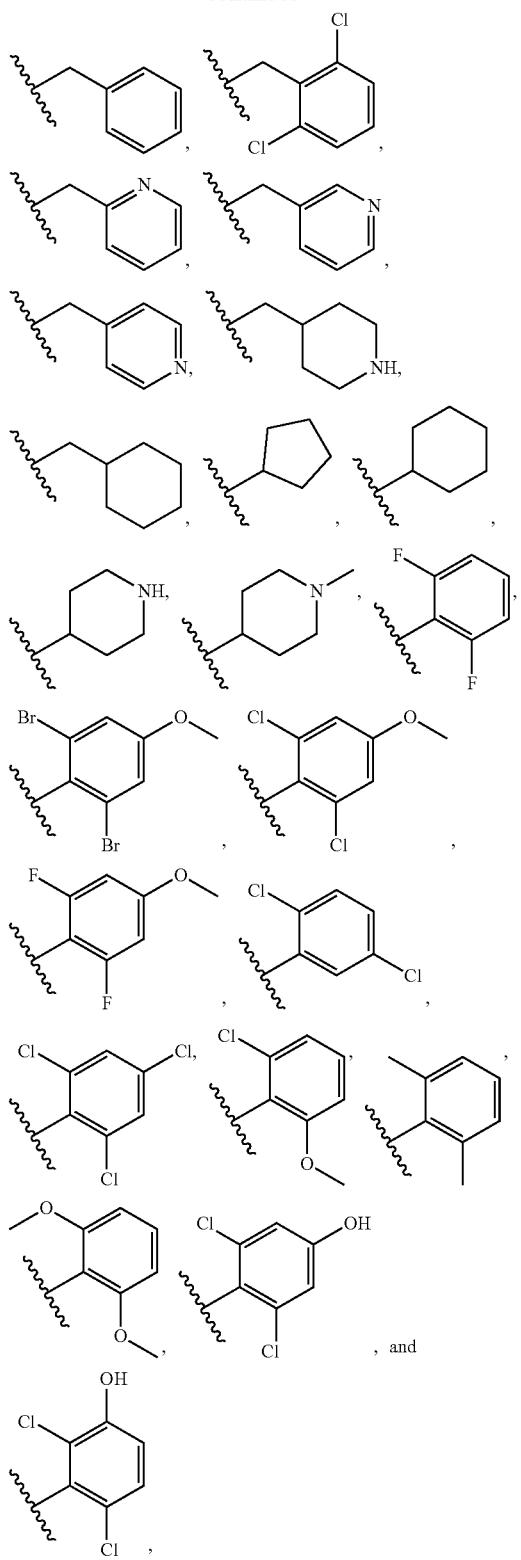

wherein the wavy lines denote attachment points to the parent molecule.

In some embodiments of a compound of Formula (I), (Ia), (Ib), (IIa), (IIb), (IIIa), (IIIb), (IVa) or (IVb), R$^4$ is selected from the group consisting of methyl, ethyl, isopropyl, cyclopropyl,

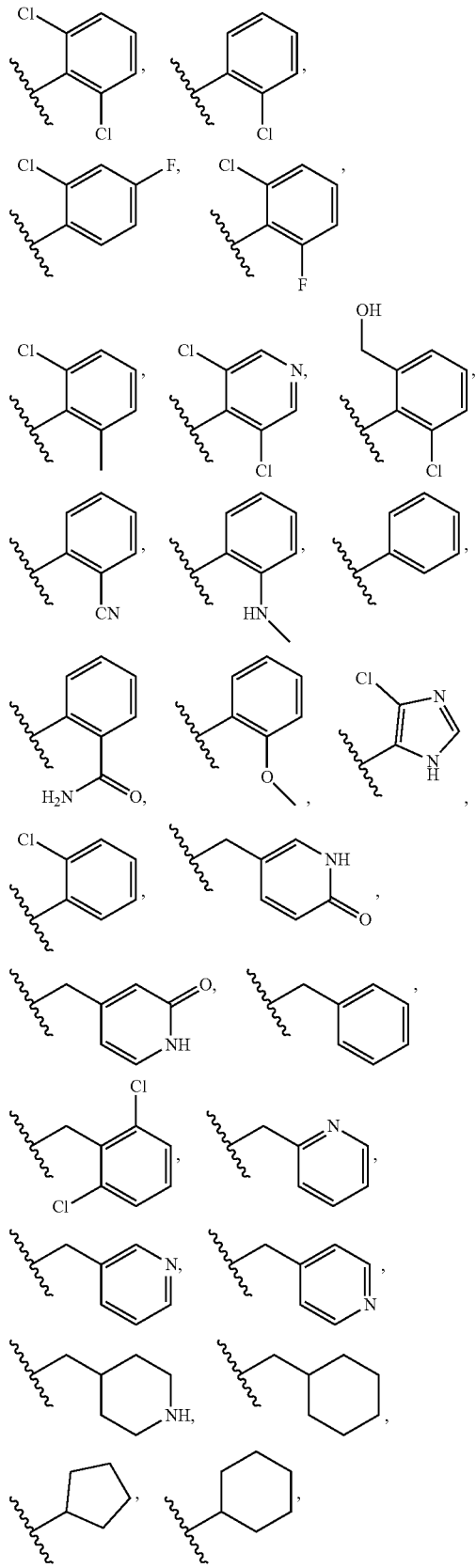

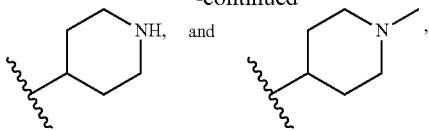

wherein the wavy lines denote attachment points to the parent molecule. In some embodiments, $R^4$ is

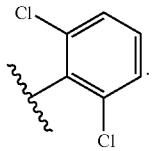

In some embodiments of a compound of Formula (I), (Ia), or (Ib), X is hydrogen; Y is N; Z is N; $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^1$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl; $R^4$ is 5- to 10-membered heteroaryl, $C_1$-$C_6$ alkyl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —($C_1$-$C_3$ alkylene)($C_6$-$C_{14}$ aryl), or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH. In some embodiments of a compound of Formula (I), (Ia), or (Ib), X is $C_1$-$C_6$ alkyl; Y is N; Z is N; $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^1$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH. In some embodiments of a compound of Formula (I), (Ia), or (Ib), X is hydrogen; Y is CH; Z is N; $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH. In some embodiments of a compound of Formula (I), (Ia), or (Ib), X is hydrogen; Y is N; Z is CH; $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH.

In some embodiments of a compound of Formula (I), (Ia), or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl, $C_1$-$C_6$ alkyl, —($C_1$-$C_3$ alkylene)($C_3$-$C_6$ cycloalkyl), —(C$_1$-C$_3$ alkylene)(3- to 12-membered heterocyclyl), —(C$_1$-C$_3$ alkylene)(5- to 10-membered heteroaryl), —(C$_1$-C$_3$ alkylene)(C$_6$-C$_{14}$ aryl), or C$_6$-C$_{14}$ aryl, each of which is optionally substituted by halogen, —CN, —NR$^{13}$R$^{14}$, —C(O)R$^{13}$, —OR$^{13}$, or C$_1$-C$_6$ alkyl optionally substituted by —OH. In some embodiments of a compound of Formula (I), (Ia), or (Ib), X is hydrogen; Y is N; Z is N; R$^{3a}$ and R$^{3b}$ are independently hydrogen or C$_1$-C$_6$ alkyl; or R$^{3a}$ and R$^{3b}$ are taken together with the carbon to which they are attached to form a C$_3$-C$_6$ cycloalkyl; R$^4$ is C$_6$-C$_{14}$ aryl optionally substituted by halogen, —CN, —NR$^{13}$R$^{14}$, —C(O)R$^{13}$, —OR$^{13}$, or C$_1$-C$_6$ alkyl optionally substituted by —OH. In some embodiments of a compound of Formula (I), (Ia), or (Ib), X is hydrogen; Y is N; Z is N; R$^{3a}$ and R$^{3b}$ are independently hydrogen or C$_1$-C$_6$ alkyl; R$^4$ is phenyl optionally substituted by halogen, —CN, —NR$^{13}$R$^{14}$, —C(O)R$^{13}$, —OR$^{13}$, or C$_1$-C$_6$ alkyl optionally substituted by —OH. In some embodiments of a compound of Formula (I), (Ia), or (Ib), X is hydrogen; Y is N; Z is N; R$^{3a}$ and R$^{3b}$ are both hydrogen; R$^4$ is selected from the group consisting of methyl, ethyl, isopropyl, cyclopropyl,

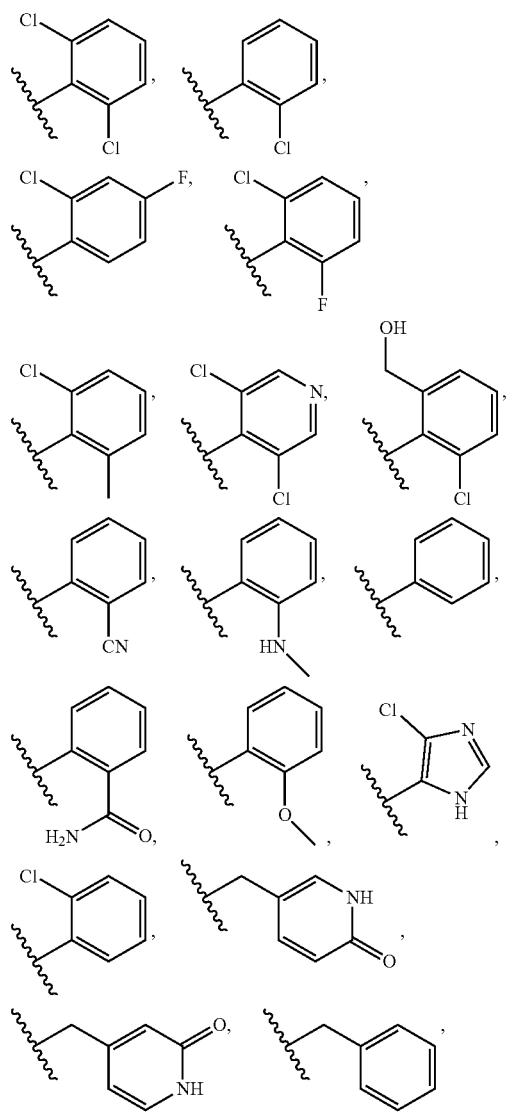

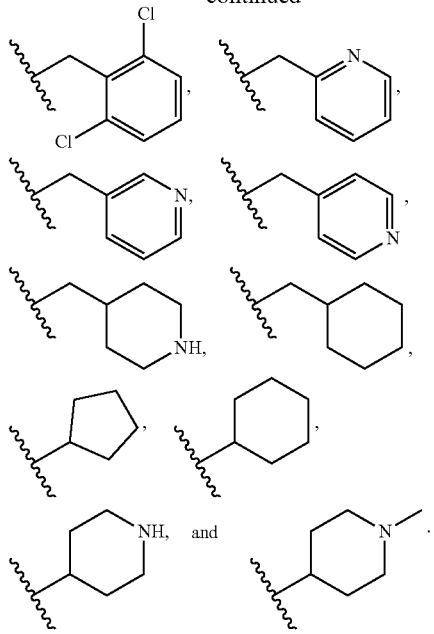

In some embodiments of a compound of Formula (IIa), (IIb), (IIIa), (IIIb), (IVa) or (IVb), X is hydrogen; R$^{3a}$ and R$^{3b}$ are both hydrogen; and R$^4$ is a member of the preceding group described for Formula (I), (Ia) or (Ib). In some embodiments of a compound of Formula (I), (Ia) or (Ib), X is hydrogen; Y is N; Z is N; R$^{3a}$ and R$^{3b}$ are both hydrogen; R$^4$ is phenyl optionally substituted by halogen. In some embodiments of a compound of Formula (IIa), (IIb), (IIIa), (IIIb), (IVa) or (IVb), X is hydrogen; R$^{3a}$ and R$^{3b}$ are both hydrogen; and R$^4$ is phenyl optionally substituted by halogen.

In some embodiments of a compound of Formula (I), (Ia), (Ib), (IIa), (IIb), (IIIa), (IIIb), (IVa) or (IVb), W is A, wherein A is phenyl or 5- to 6-membered heteroaryl, each of which is optionally substituted with R$^{17a}$. In some embodiments of a compound of Formula (I), (Ia), (Ib), (IIa), (IIb), (IIIa), (IIIb), (IVa) or (IVb), W is AB, wherein A and B are fused together; A is phenyl or 5- to 6-membered heteroaryl, each of which is optionally substituted with R$^{17a}$; and B is C$_3$-C$_6$ cycloalkyl, 3- to 7-membered heterocyclyl, 5- to 7-membered heteroaryl, or C$_6$ aryl, each of which is optionally substituted with R$^{17b}$. In some embodiments of a compound of Formula (I), (Ia), (Ib), (IIa), (IIb), (IIIa), (IIIb), (IVa) or (IVb), W is A, wherein A is phenyl or 5- to 6-membered heteroaryl, each of which is optionally substituted with R$^{17a}$, and wherein A and R$^{17a}$ together are

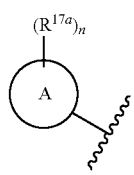

and n is 0, 1, 2, 3, or 4. In some embodiments of a compound of Formula (I), (Ia), (Ib), (IIa), (IIb), (IIIa), (IIIb), (IVa) or (IVb), W is AB, wherein A and B are fused together; A is phenyl or 5- to 6-membered heteroaryl, each of which is optionally substituted with R$^{17a}$; B is C$_3$-C$_6$ cycloalkyl, 3- to 7-membered heterocyclyl, 5- to 7-membered heteroaryl, or $C_6$ aryl, each of which is optionally substituted with $R^{17b}$; and wherein A, B, $R^{17a}$, and $R^{17b}$ together are

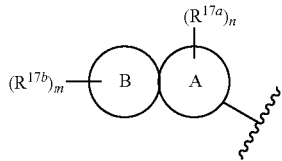

and m and n are independently 0, 1, 2, 3, or 4.

In some embodiments of a compound of Formula (I), (Ia), (Ib), (IIa), (IIb), (IIIa), (IIIb), (IVa) or (IVb), W is A, wherein A is phenyl or 6-membered heteroaryl, each of which is optionally substituted with $R^{17a}$. In some embodiments of a compound of Formula (I), (Ia), (Ib), (IIa), (IIb), (IIIa), (IIIb), (IVa) or (IVb), W is AB, wherein A and B are fused together; A is phenyl or 6-membered heteroaryl, each of which is optionally substituted with $R^{17a}$; and B is $C_3$-$C_6$ cycloalkyl, 3- to 7-membered heterocyclyl, 5- to 7-membered heteroaryl, or $C_6$ aryl, each of which is optionally substituted with $R^{17b}$. In some embodiments of a compound of Formula (I), (Ia), (Ib), (IIa), (IIb), (IIIa), (IIIb), (IVa) or (IVb), W is A, wherein A is phenyl or 6-membered heteroaryl, each of which is optionally substituted with $R^{17a}$, and wherein A and $R^{17a}$ together are

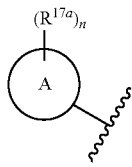

and n is 0, 1, 2, 3, or 4. In some embodiments of a compound of Formula (I), (Ia), (Ib), (IIa), (IIb), (IIIa), (IIIb), (IVa) or (IVb), W is AB, wherein A and B are fused together; A is phenyl or 6-membered heteroaryl, each of which is optionally substituted with $R^{17a}$; B is $C_3$-$C_6$ cycloalkyl, 3- to 7-membered heterocyclyl, 5- to 7-membered heteroaryl, or $C_6$ aryl, each of which is optionally substituted with $R^{17b}$; and wherein A, B, $R^{17a}$, and $R^{17b}$ together are

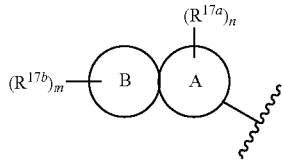

and m and n are independently 0, 1, 2, 3, or 4.

In some embodiments of a compound of Formula (I), (Ia), (Ib), (IIa), (IIb), (IIIa), (IIIb), (IVa) or (IVb), W is A, wherein A is phenyl or 5- to 6-membered heteroaryl, each of which is optionally substituted with $R^{17a}$. In some embodiments of a compound of Formula (I), (Ia), (Ib), (IIa), (IIb), (IIIa), (IIIb), (IVa) or (IVb), W is A, wherein A is phenyl or 5- to 6-membered heteroaryl, each of which is optionally substituted with $R^{17a}$, wherein A and $R^{17a}$ together are

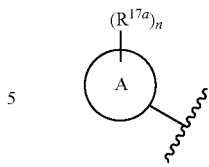

and n is 0, 1, 2, 3, or 4. In some embodiments of a compound of Formula (I), (Ia), (Ib), (IIa), (IIb), (IIIa), (IIIb), (IVa) or (IVb), n is 0. In some embodiments of a compound of Formula (I), (Ia), (Ib), (IIa), (IIb), (IIIa), (IIIb), (IVa) or (IVb), n is 1. In some embodiments of a compound of Formula (I), (Ia), (Ib), (IIa), (IIb), (IIIa), (IIIb), (IVa) or (IVb), n is 2. In some embodiments of a compound of Formula (I), (Ia), (Ib), (IIa), (IIb), (IIIa), (IIIb), (IVa) or (IVb), n is 3. In some embodiments of a compound of Formula (I), (Ia), (Ib), (IIa), (IIb), (IIIa), (IIIb), (IVa) or (IVb), $R^{17a}$ is independently 3- to 12-membered heterocyclyl, —($C_1$-$C_3$ alkylene)$OR^{10}$, $C_1$-$C_6$ alkyl optionally substituted by halogen or —OH, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$, wherein the 3- to 12-membered heterocyclyl of $R^{17a}$ is optionally substituted with $C_1$-$C_6$ alkyl optionally substituted by halogen or —OH, —C(O)$R^{13}$, —($C_1$-$C_3$ alkylene)$OR^{13}$, —S(O)$_2R^{13}$, $C_3$-$C_8$ cycloalkyl, oxo, halogen, or —$OR^{13}$, wherein the 3- to 12-membered heterocyclyl of $R^{17a}$ is optionally fused with 5- to 10-membered heteroaryl or $C_6$-$C_{14}$ aryl. In some embodiments of a compound of Formula (I), (Ia), (Ib), (IIa), (IIb), (IIIa), (IIIb), (IVa) or (IVb), $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH. In some embodiments of a compound of Formula (I), (Ia), (Ib), (IIa), (IIb), (IIIa), (IIIb), (IVa) or (IVb), W is A, wherein A is phenyl optionally substituted with $R^{17a}$, wherein $R^{17a}$ is independently 3- to 12-membered heterocyclyl, —($C_1$-$C_3$ alkylene)$OR^{10}$, $C_1$-$C_6$ alkyl optionally substituted by halogen or —OH, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$, wherein the 3- to 12-membered heterocyclyl of $R^{17a}$ is optionally substituted with $C_1$-$C_6$ alkyl optionally substituted by halogen or —OH, —C(O)$R^{13}$, —($C_1$-$C_3$ alkylene)$OR^{13}$, —S(O)$_2R^{13}$, $C_3$-$C_8$ cycloalkyl, oxo, halogen, or —$OR^{13}$, wherein the 3- to 12-membered heterocyclyl of $R^{17a}$ is optionally fused with 5- to 10-membered heteroaryl or $C_6$-$C_{14}$ aryl. In some embodiments of a compound of Formula (I), (Ia), (Ib), (IIa), (IIb), (IIIa), (IIIb), (IVa) or (IVb), W is A wherein A is phenyl optionally substituted with $R^{17a}$, wherein $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH.

In some embodiments of a compound of Formula (I), W is A, wherein A is phenyl or 6-membered heteroaryl, each of which is optionally substituted with $R^{17a}$. In some embodiments of a compound of Formula (I), W is A, wherein A is phenyl or 6-membered heteroaryl, each of which is optionally substituted with $R^{17a}$, wherein A and $R^{17a}$ together are

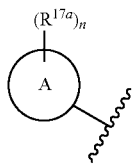

and n is 0, 1, 2, 3, or 4. In some embodiments of a compound of Formula (I), n is 0. In some embodiments of a compound of Formula (I), n is 1. In some embodiments of a compound of Formula (I), n is 2. In some embodiments of a compound of Formula (I), n is 3. In some embodiments of a compound of Formula (I), $R^{17a}$ is independently 3- to 12-membered heterocyclyl, —($C_1$-$C_3$ alkylene)$OR^{10}$, $C_1$-$C_6$ alkyl optionally substituted by halogen or —OH, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$, wherein the 3- to 12-membered heterocyclyl of $R^{17a}$ is optionally substituted with $C_1$-$C_6$ alkyl optionally substituted by halogen or —OH, —C(O)$R^{13}$, —($C_1$-$C_3$ alkylene)$OR^{13}$, —S(O)$_2R^{13}$, $C_3$-$C_8$ cycloalkyl, oxo, halogen, or —$OR^{13}$, wherein the 3- to 12-membered heterocyclyl of $R^{17a}$ is optionally fused with 5- to 10-membered heteroaryl or $C_6$-$C_{14}$ aryl. In some embodiments of a compound of Formula (I), $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH. In some embodiments of a compound of Formula (I), W is A, wherein A is phenyl optionally substituted with $R^{17a}$, wherein $R^{17a}$ is independently 3- to 12-membered heterocyclyl, —($C_1$-$C_3$ alkylene)$OR^{10}$, $C_1$-$C_6$ alkyl optionally substituted by halogen or —OH, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$, wherein the 3- to 12-membered heterocyclyl of $R^{17a}$ is optionally substituted with $C_1$-$C_6$ alkyl optionally substituted by halogen or —OH, —C(O)$R^{13}$, —($C_1$-$C_3$ alkylene)$OR^{13}$, —S(O)$_2R^{13}$, $C_3$-$C_8$ cycloalkyl, oxo, halogen, or —$OR^{13}$, wherein the 3- to 12-membered heterocyclyl of $R^{17a}$ is optionally fused with 5- to 10-membered heteroaryl or $C_6$-$C_{14}$ aryl. In some embodiments of a compound of Formula (I), W is A wherein A is phenyl optionally substituted with $R^{17a}$, wherein $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH.

In some embodiments of a compound of Formula (I), (Ia), (Ib), (IIa), (IIb), (IIIa), (IIIb), (IVa) or (IVb), W is A, wherein A is pyridinyl optionally substituted with $R^{17a}$. In some embodiments of a compound of Formula (I), (Ia), (Ib), (IIa), (IIb), (IIIa), (IIIb), (IVa) or (IVb), W is A, wherein A is pyridinyl optionally substituted with $R^{17a}$, wherein $R^{17a}$ is independently 3- to 12-membered heterocyclyl, —($C_1$-$C_3$ alkylene)$OR^{10}$, $C_1$-$C_6$ alkyl optionally substituted by halogen or —OH, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$, wherein the 3- to 12-membered heterocyclyl of $R^{17a}$ is optionally substituted with $C_1$-$C_6$ alkyl optionally substituted by halogen or —OH, —C(O)$R^{13}$, —($C_1$-$C_3$ alkylene)$OR^{13}$, —S(O)$_2R^{13}$, $C_3$-$C_8$ cycloalkyl, oxo, halogen, or —$OR^{13}$, wherein the 3- to 12-membered heterocyclyl of $R^{17a}$ is optionally fused with 5- to 10-membered heteroaryl or $C_6$-$C_{14}$ aryl. In some embodiments of a compound of Formula (I), (Ia), (Ib), (IIa), (IIb, (IIIa), (IIIb), (IVa) or (IVb), W is A, wherein A is pyridinyl optionally substituted with $R^{17a}$, wherein $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH.

In some embodiments of a compound of Formula (I), (Ia), (Ib), (IIa), (IIb), (IIIa), (IIIb), (IVa) or (IVb), W is selected from the group consisting of:

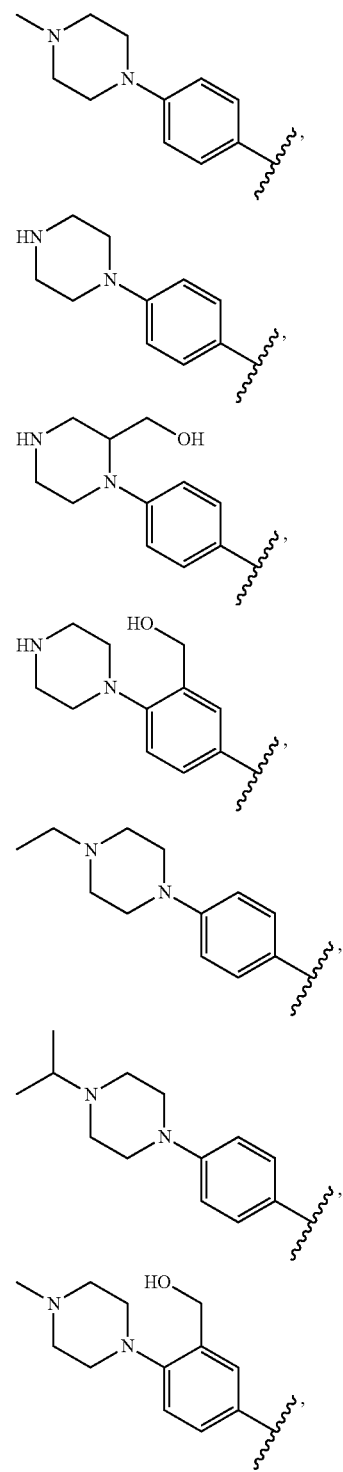

-continued
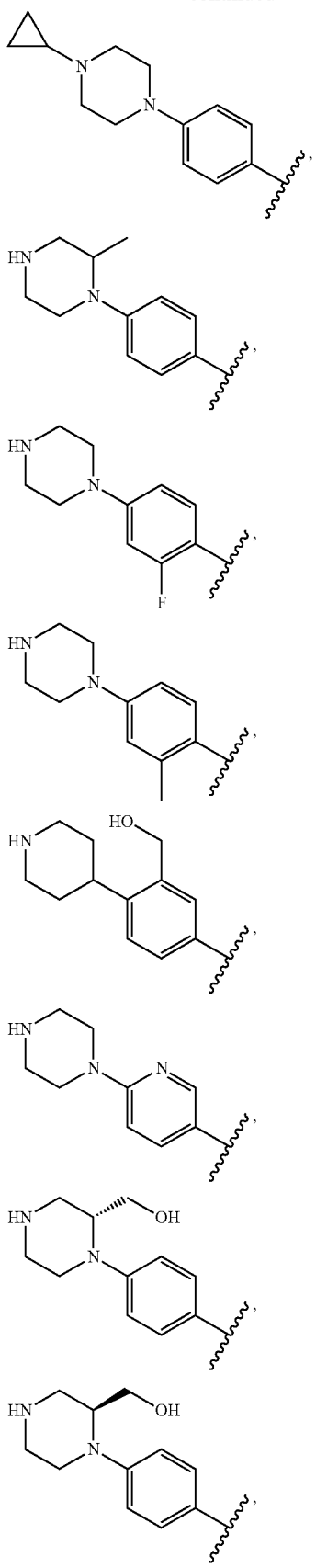
-continued
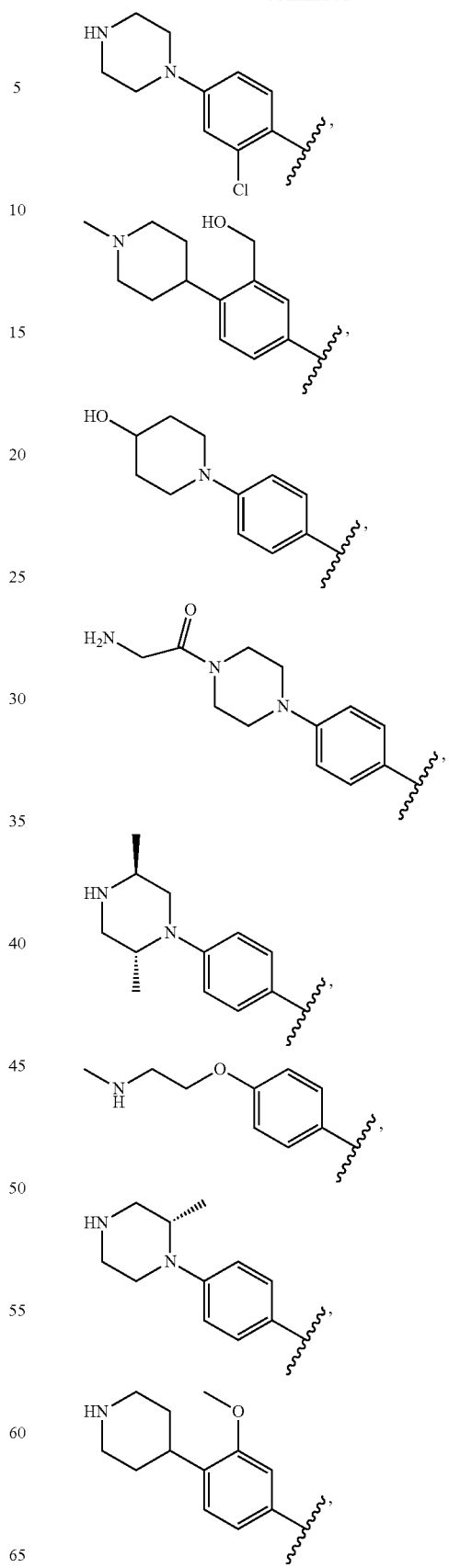

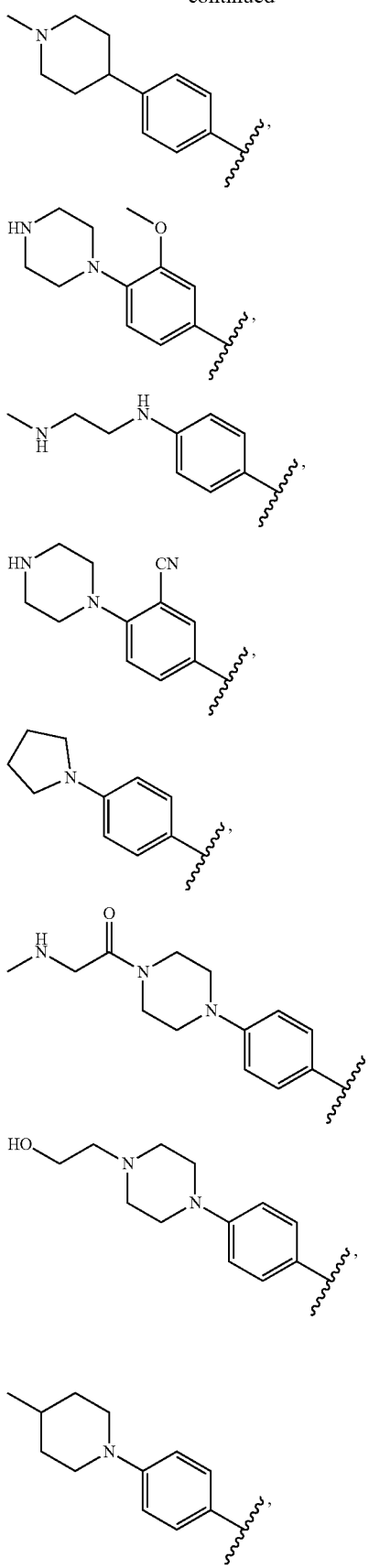
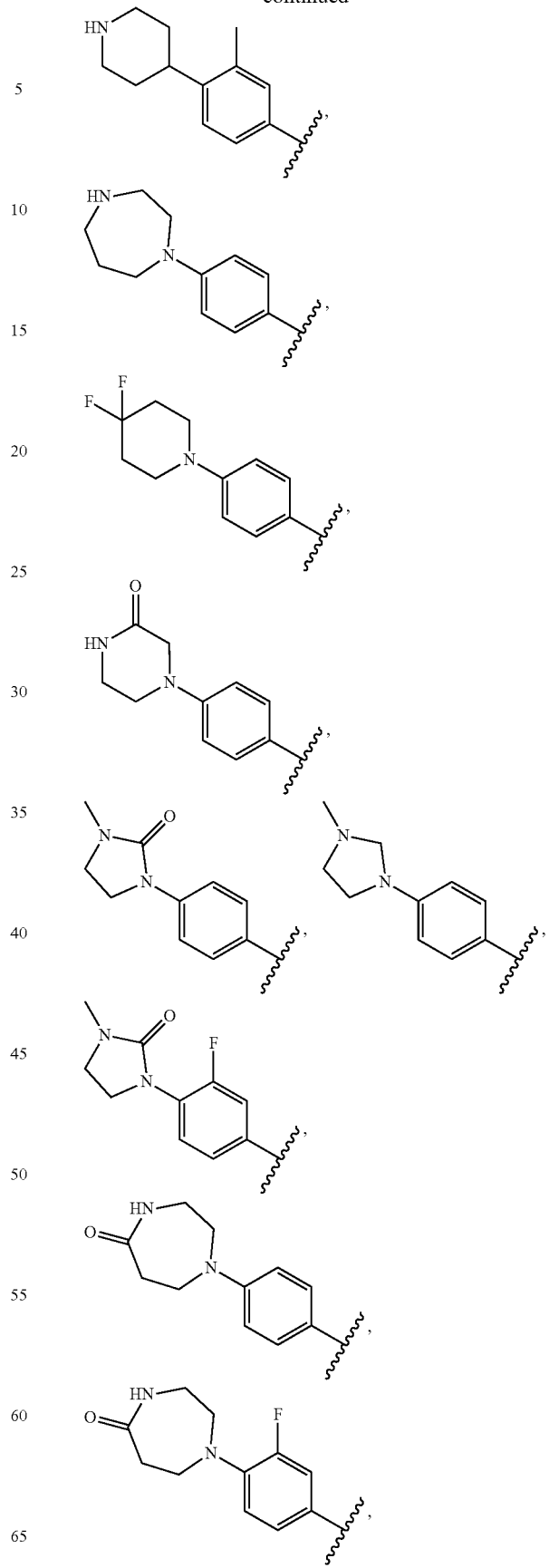

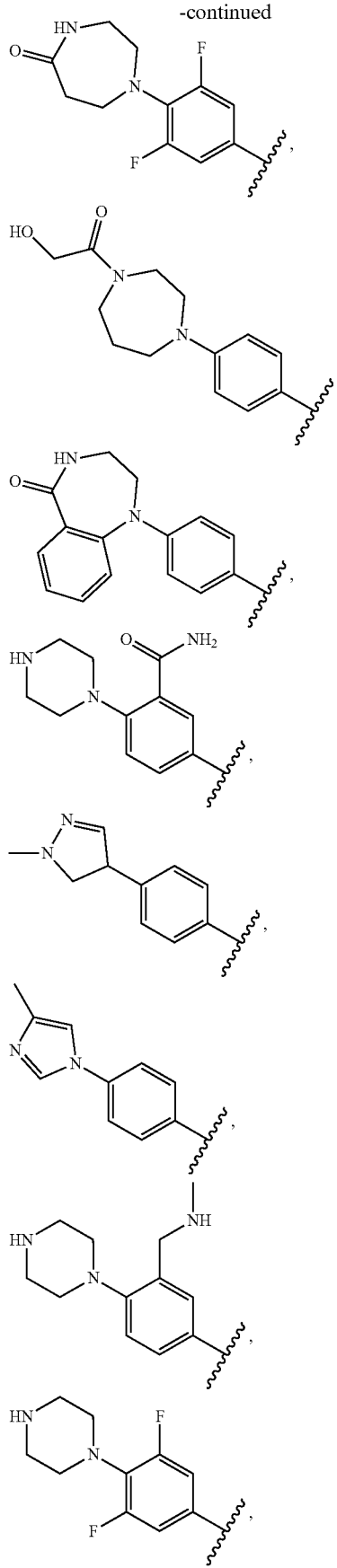
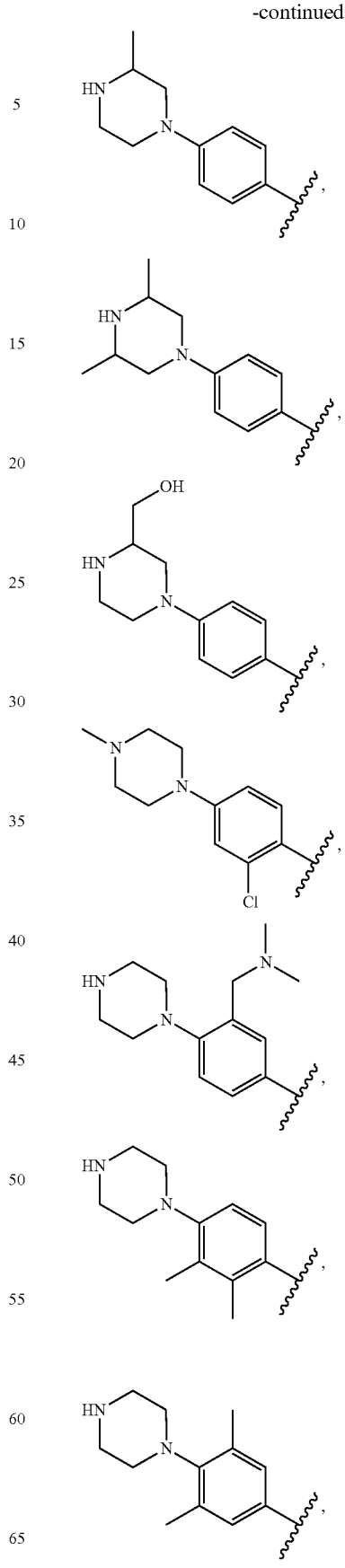

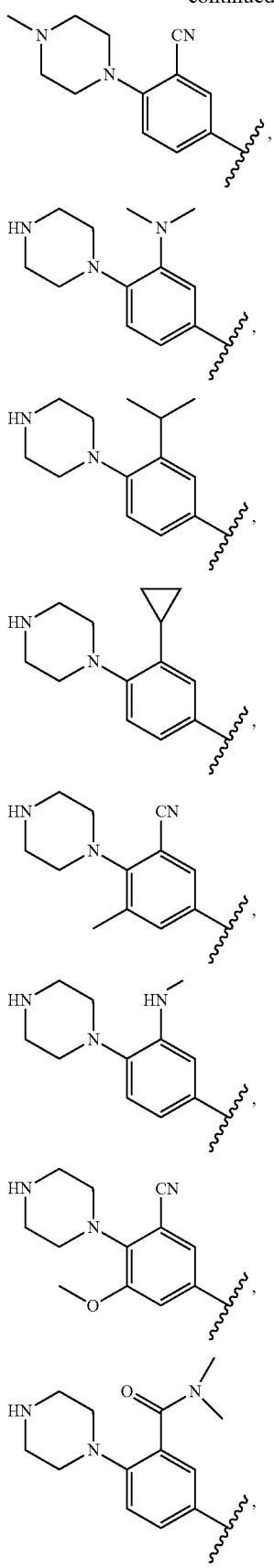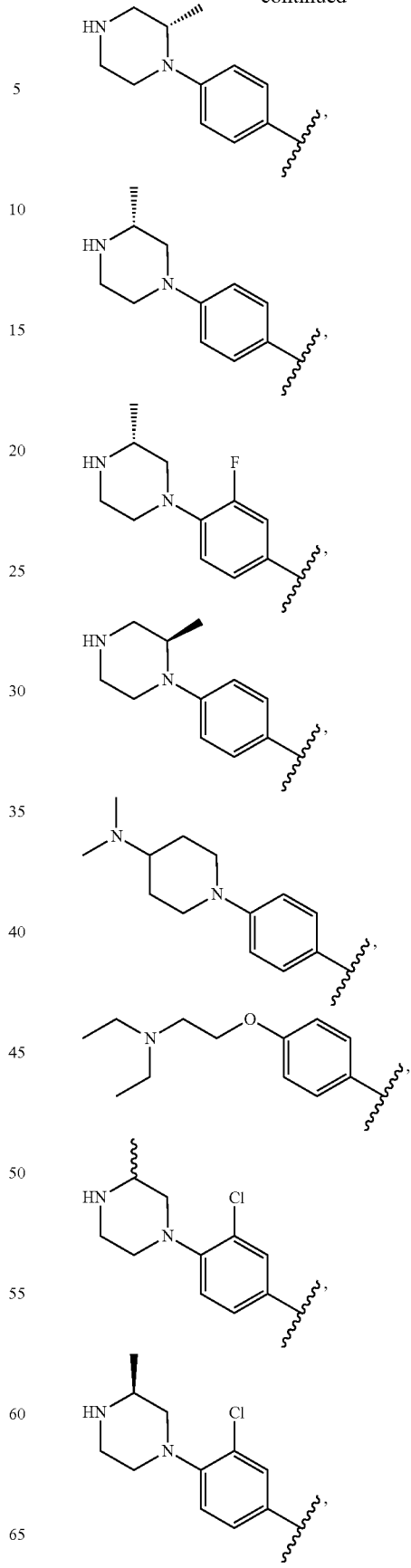

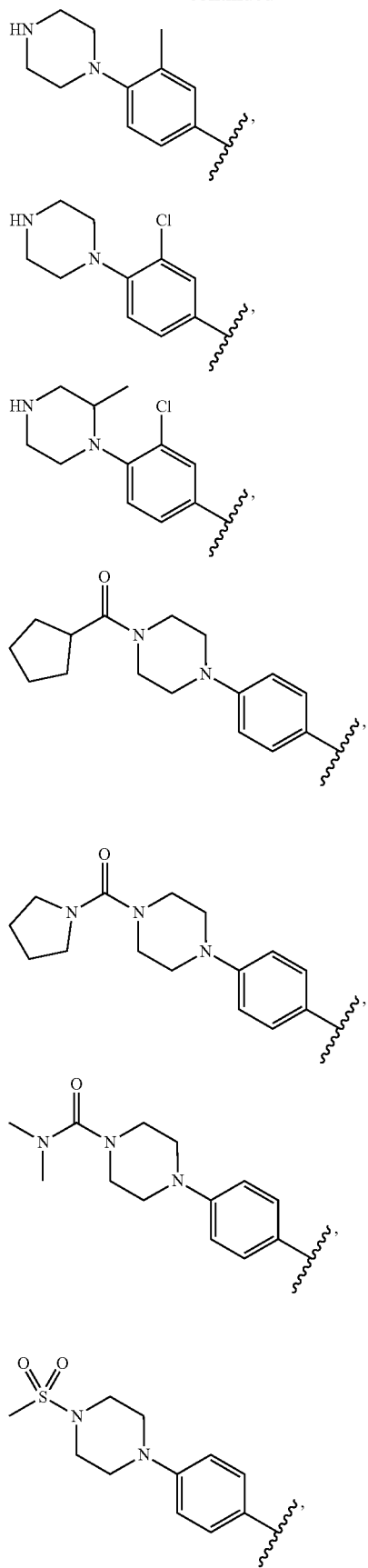
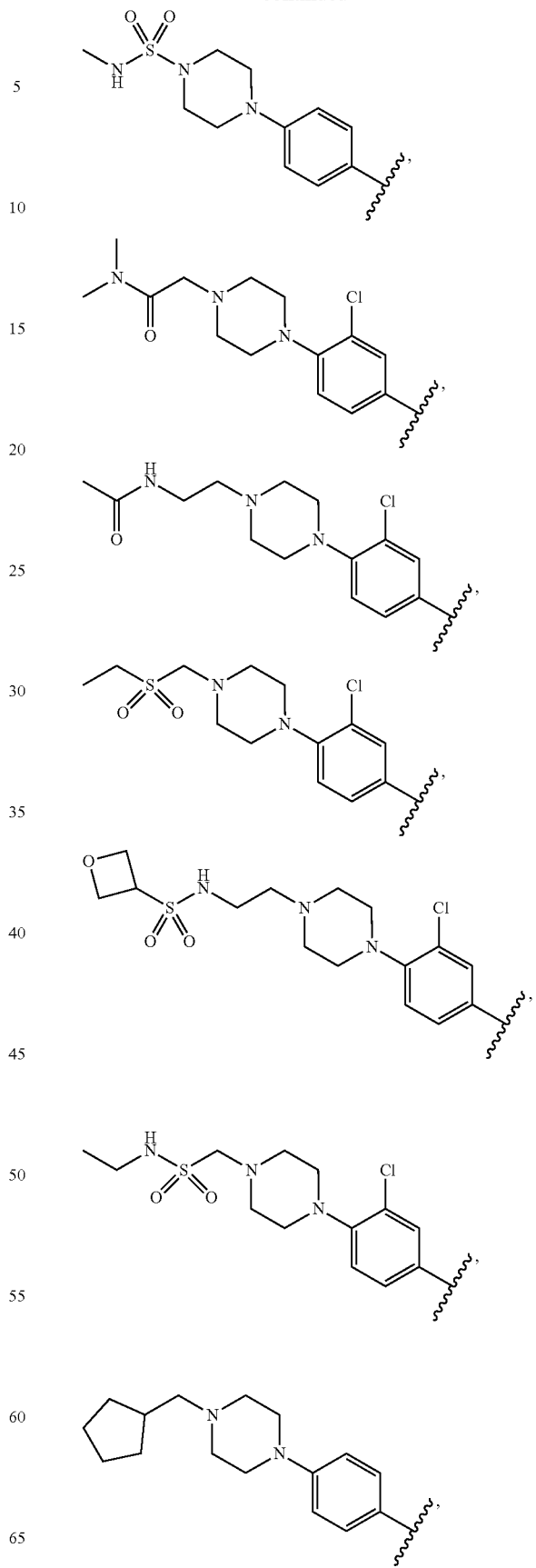

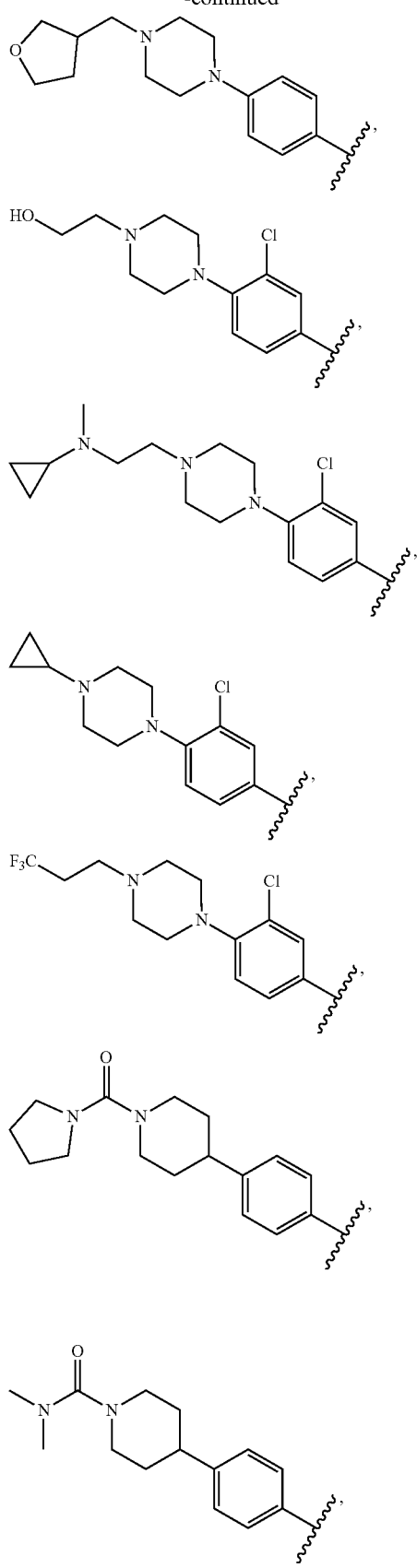
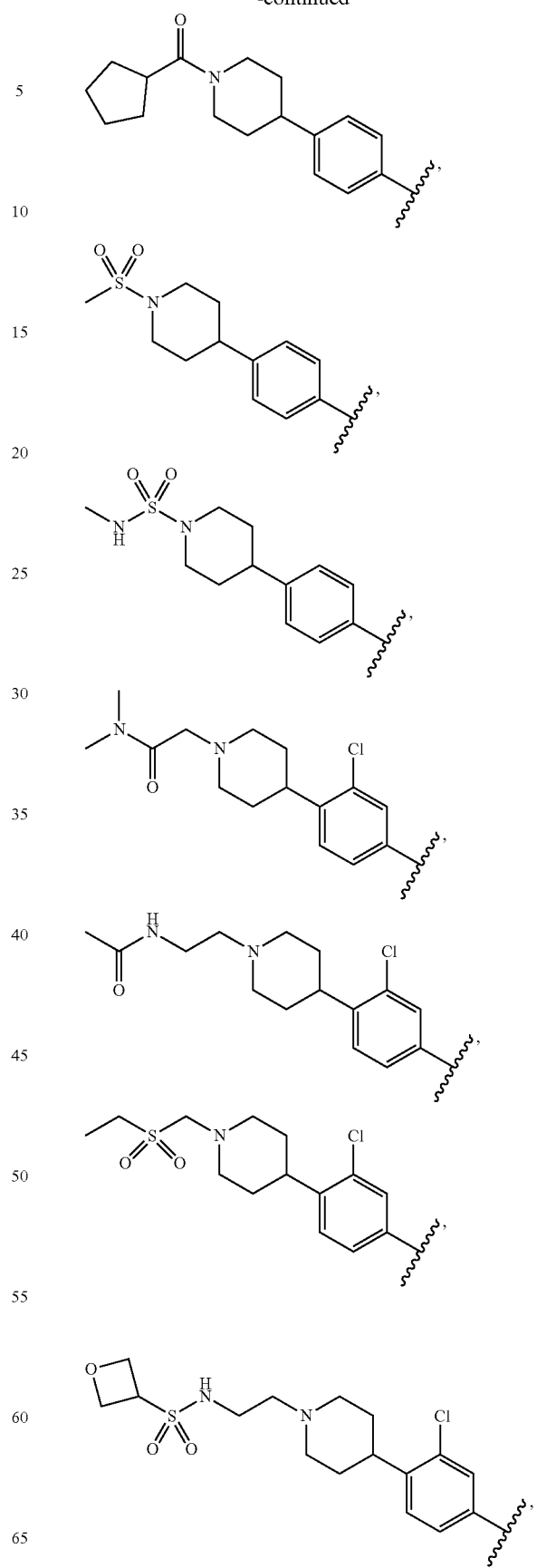

-continued
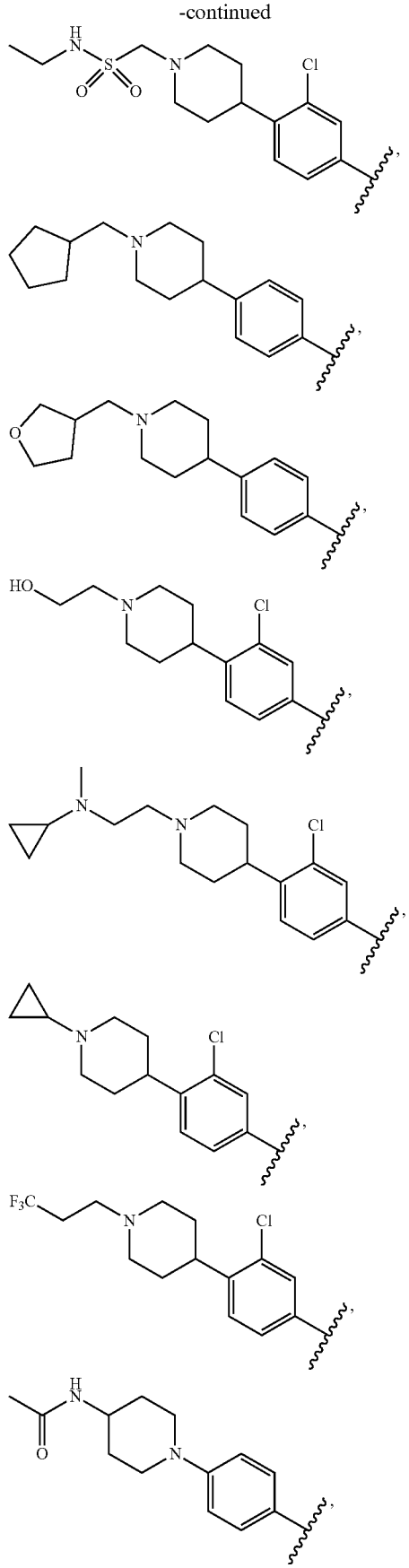
-continued
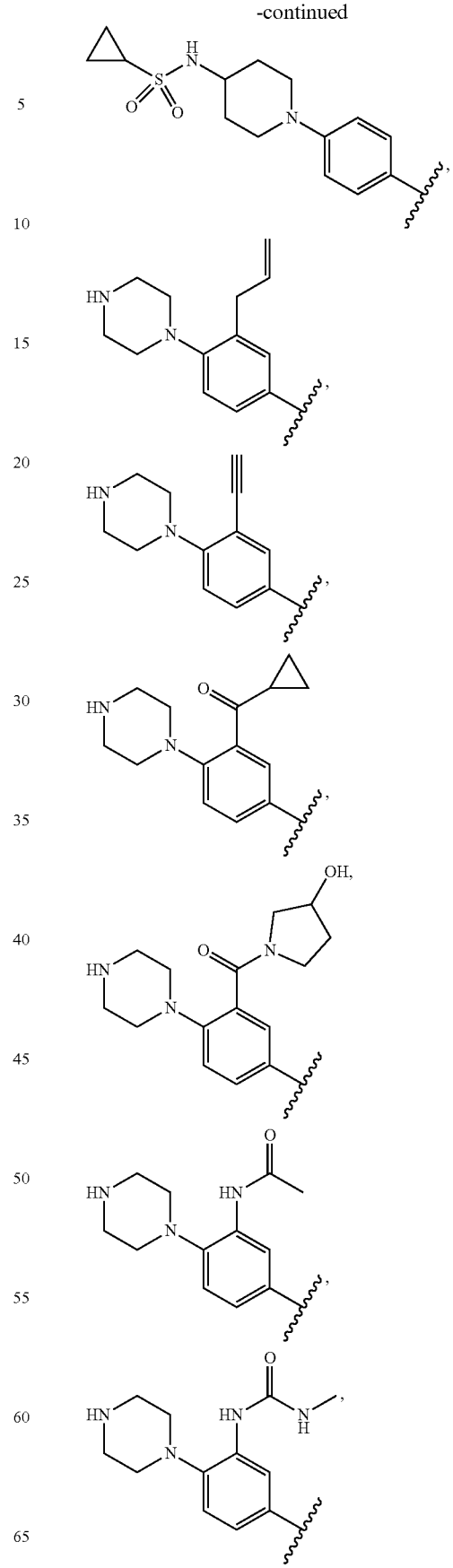

-continued
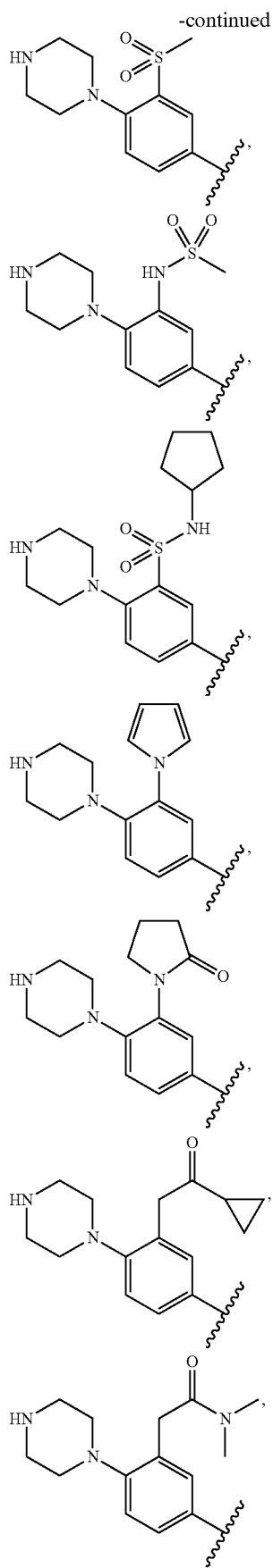
-continued
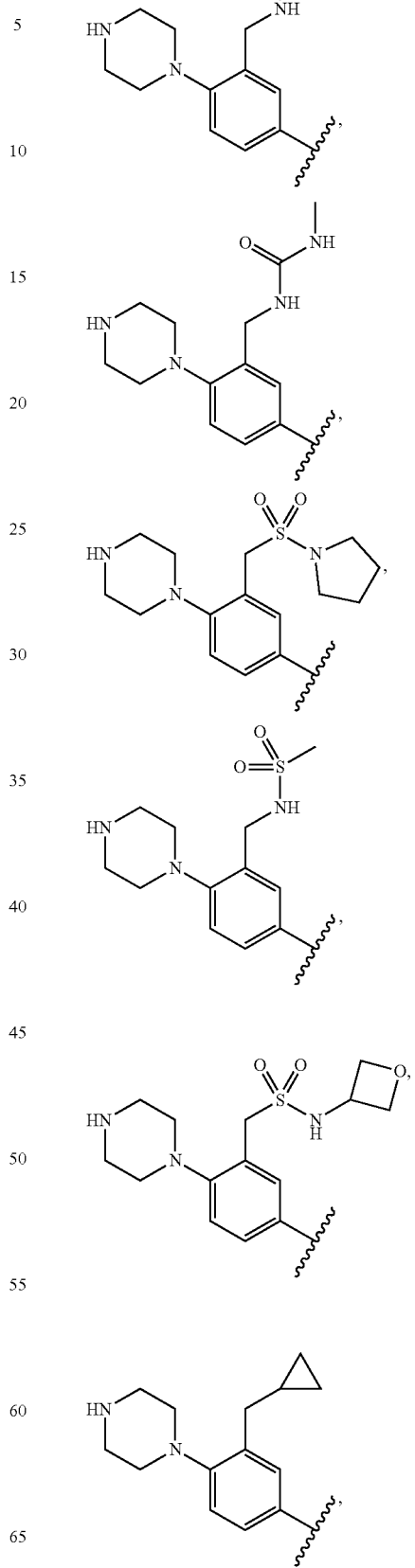

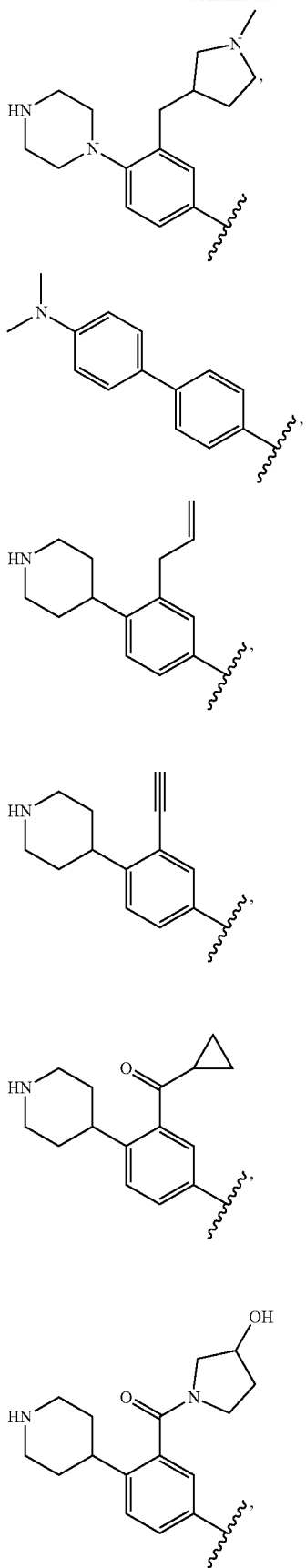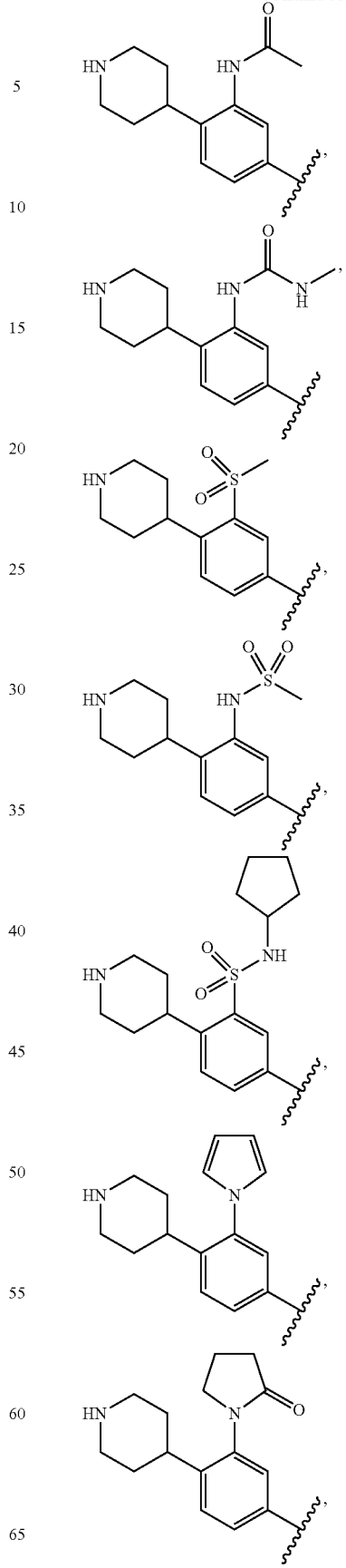

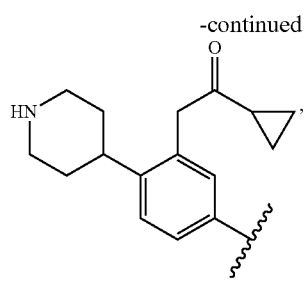
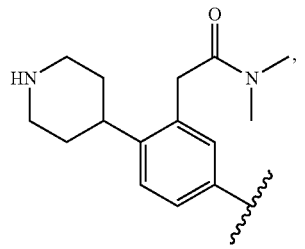
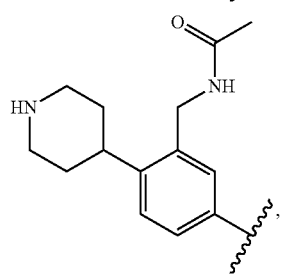
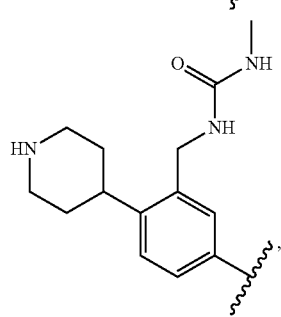
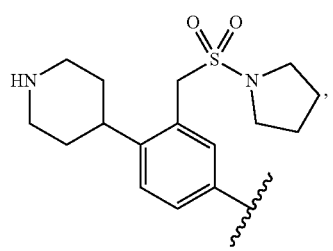
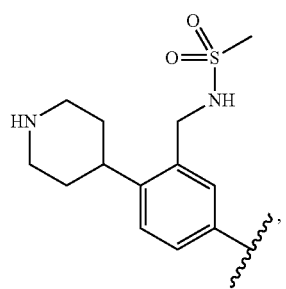
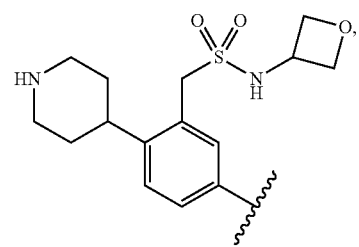
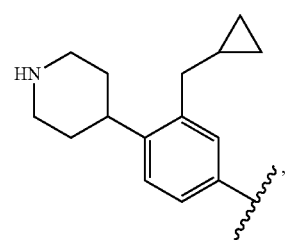
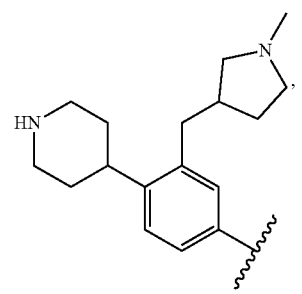
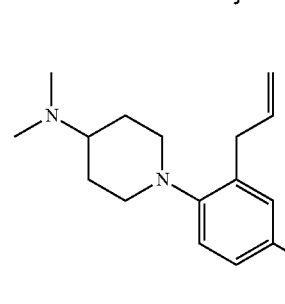
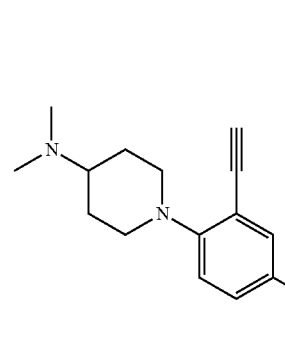
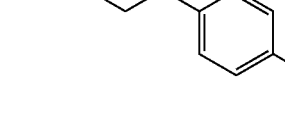

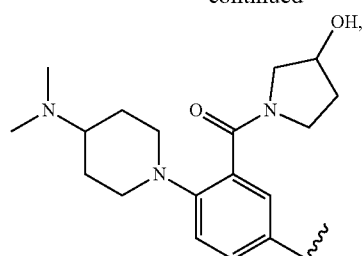
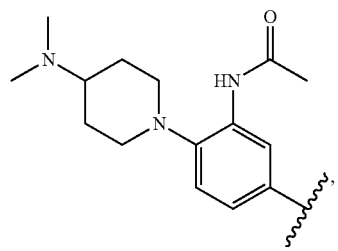
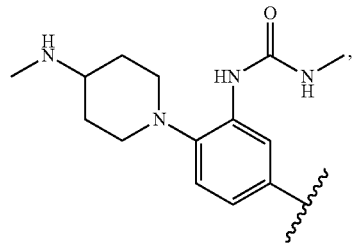
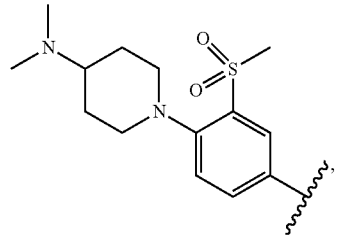
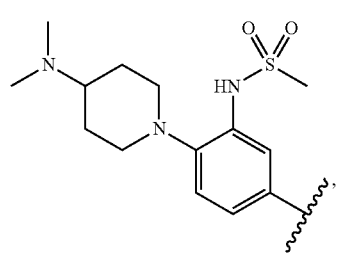
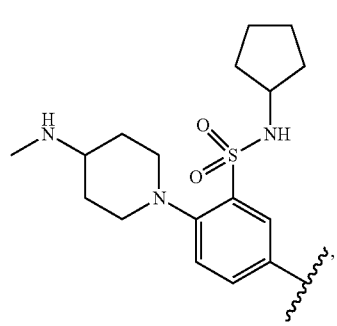
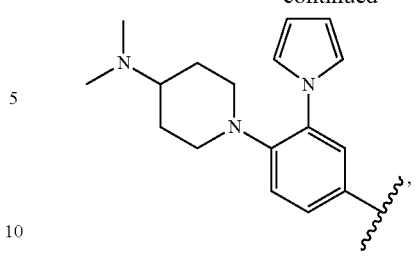
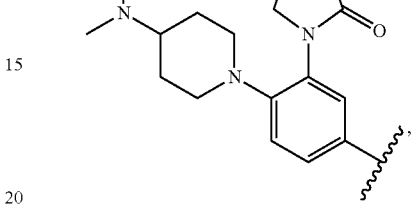
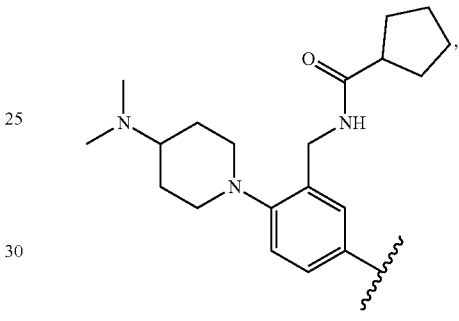
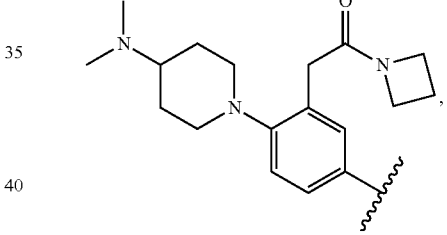
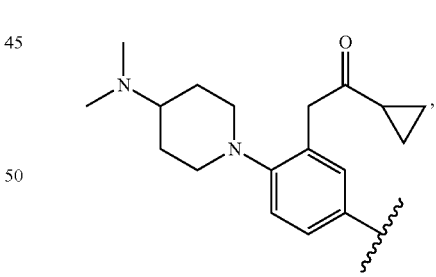
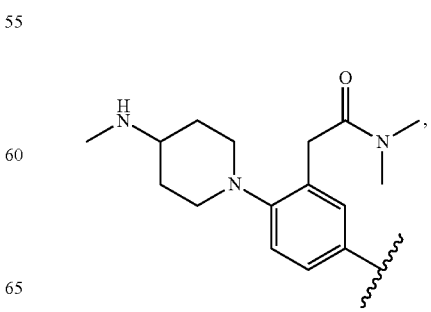

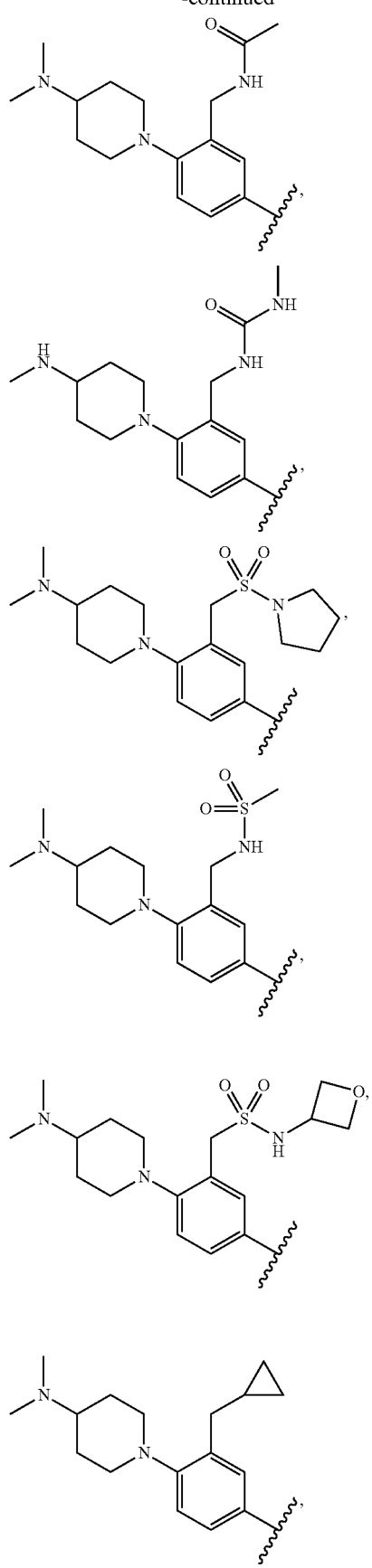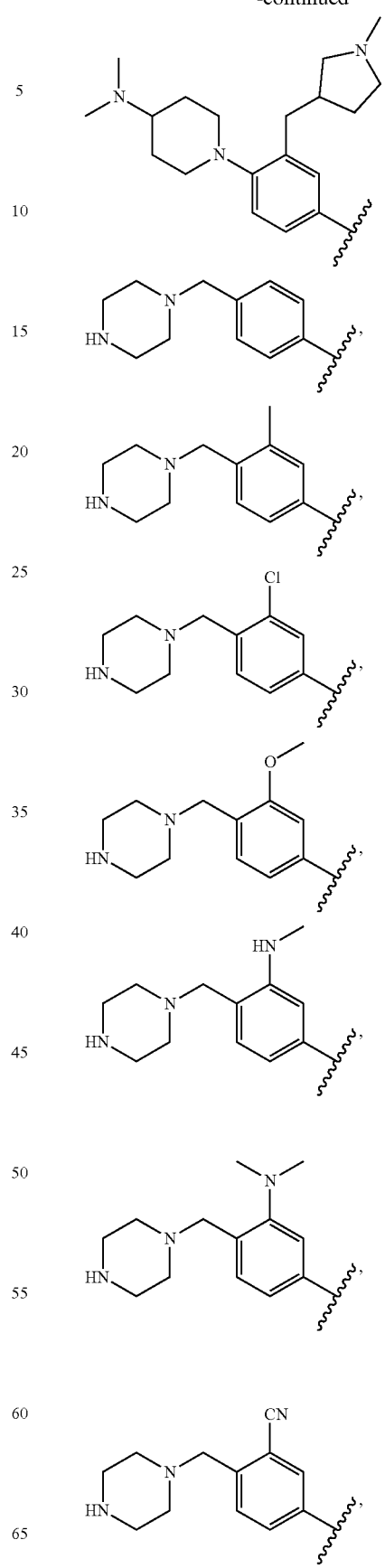

-continued
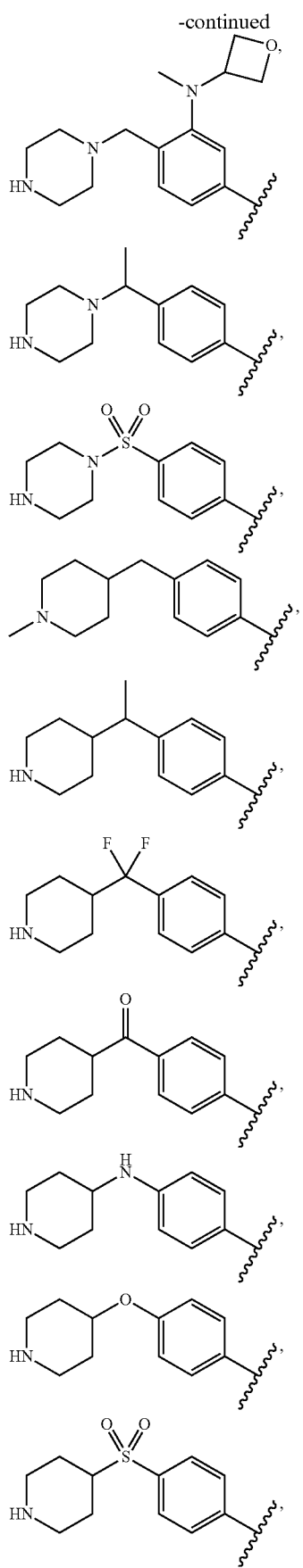
-continued
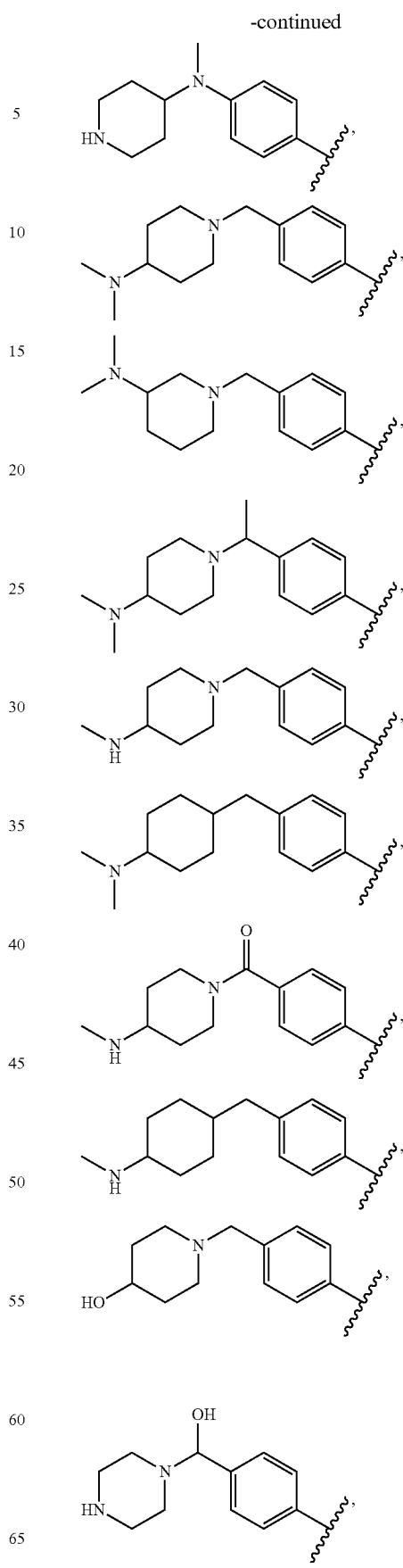

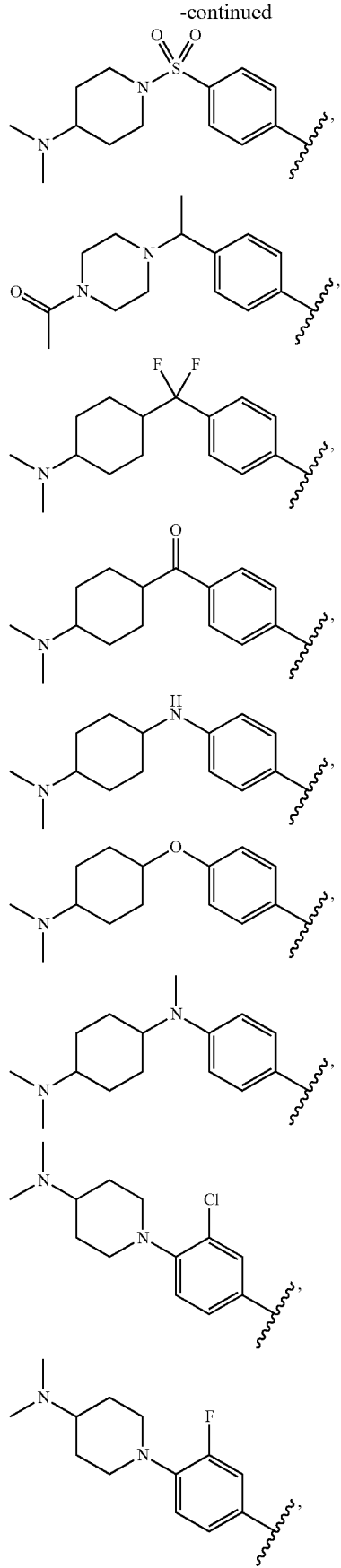
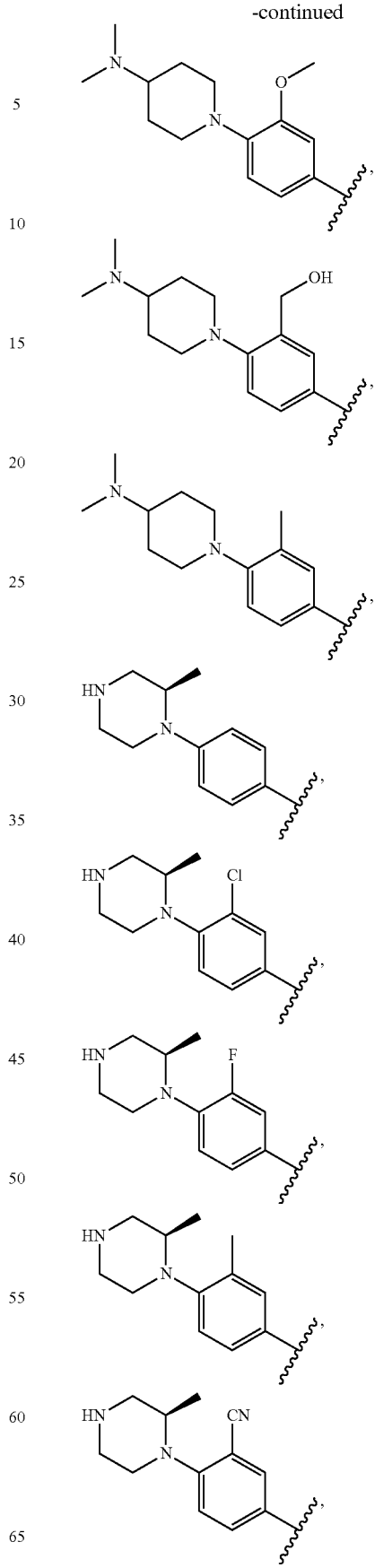

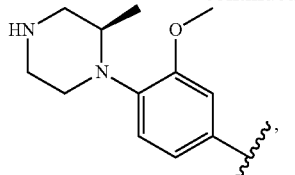

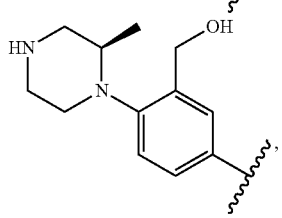

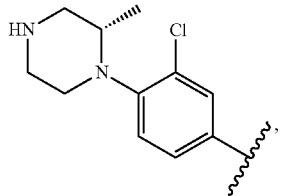

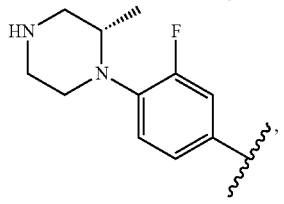

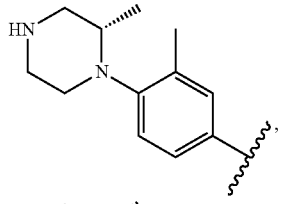

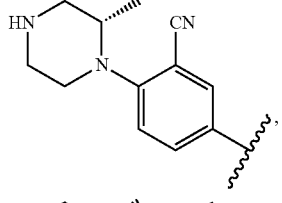

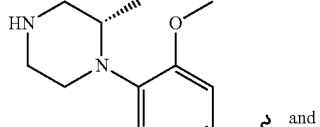

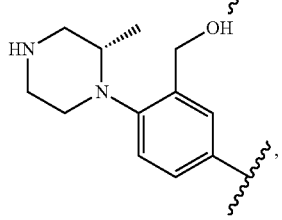

wherein the wavy lines denote attachment points to the parent molecule. In some embodiments of a compound of Formula (I), (Ia), (Ib), (IIa), (IIb), (IIIa), (IIIb), (IVa) or (IVb), W is

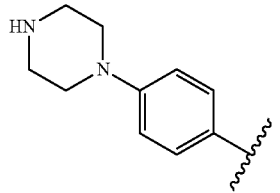

wherein the wavy line denotes attachment point to the parent molecule and W is optionally substituted by $R^{17a}$. In some embodiments of a compound of Formula (I), (Ia), (Ib), (IIa), (IIb), (IIIa) (IIIb), (IVa) or (IVb) W is

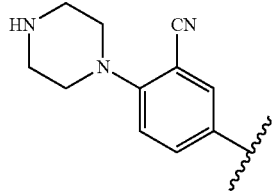

wherein the wavy line denotes attachment point to the parent molecule.

In some embodiments of a compound of Formula (I), (Ia), (Ib), (IIa), (IIb), (IIIa), (IIIb), (IVa) or (IVb), W is selected from the group consisting of:

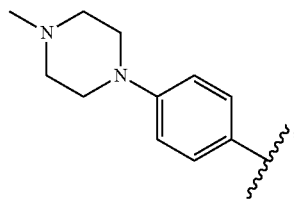

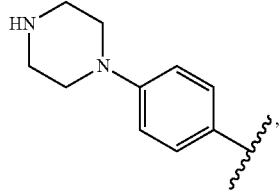

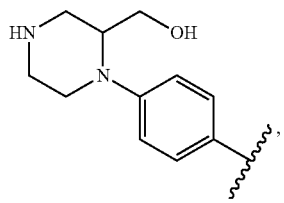

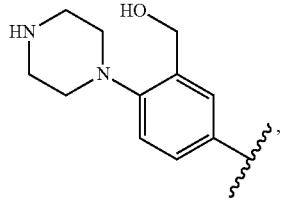

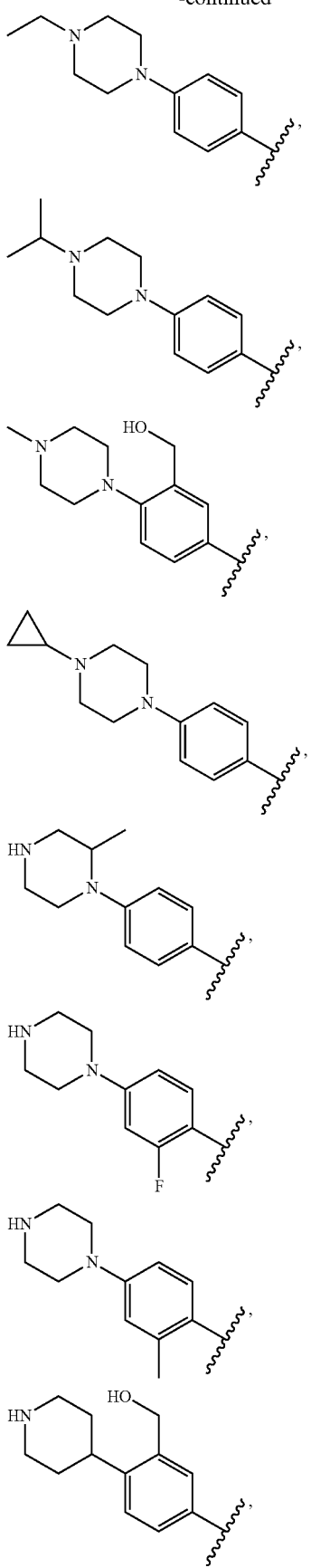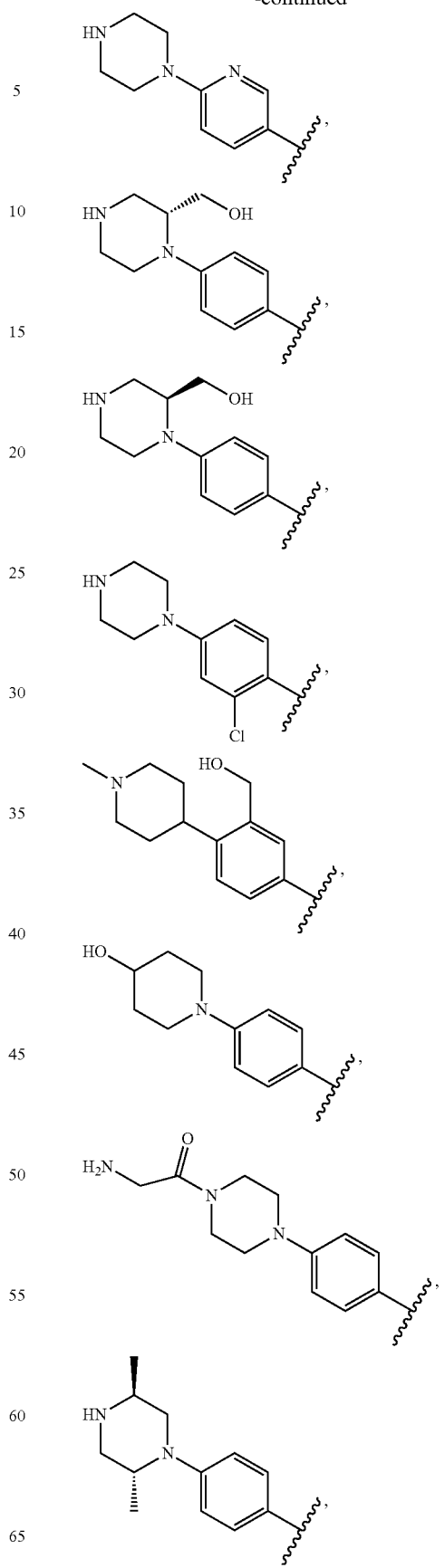

-continued
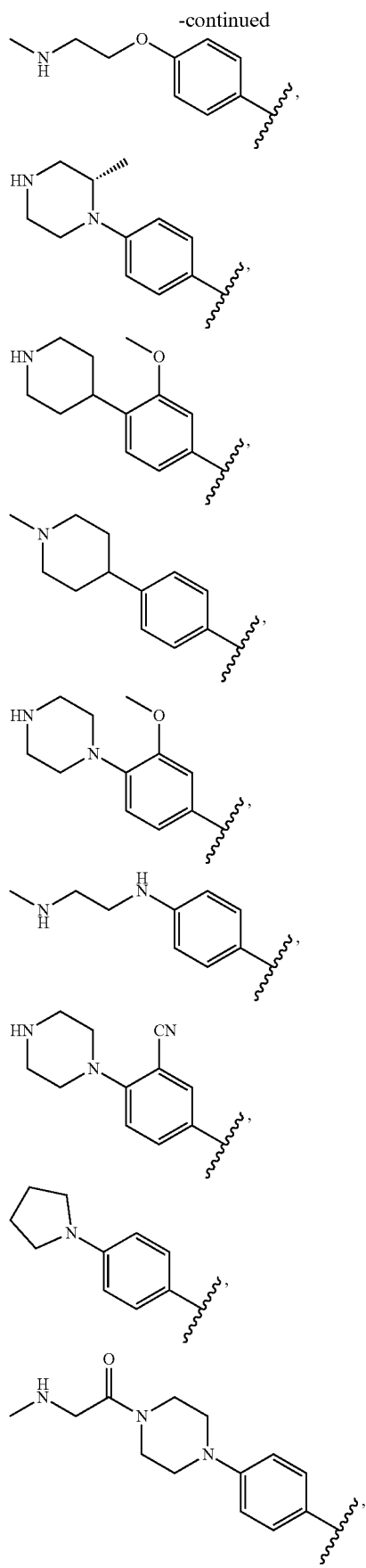
-continued
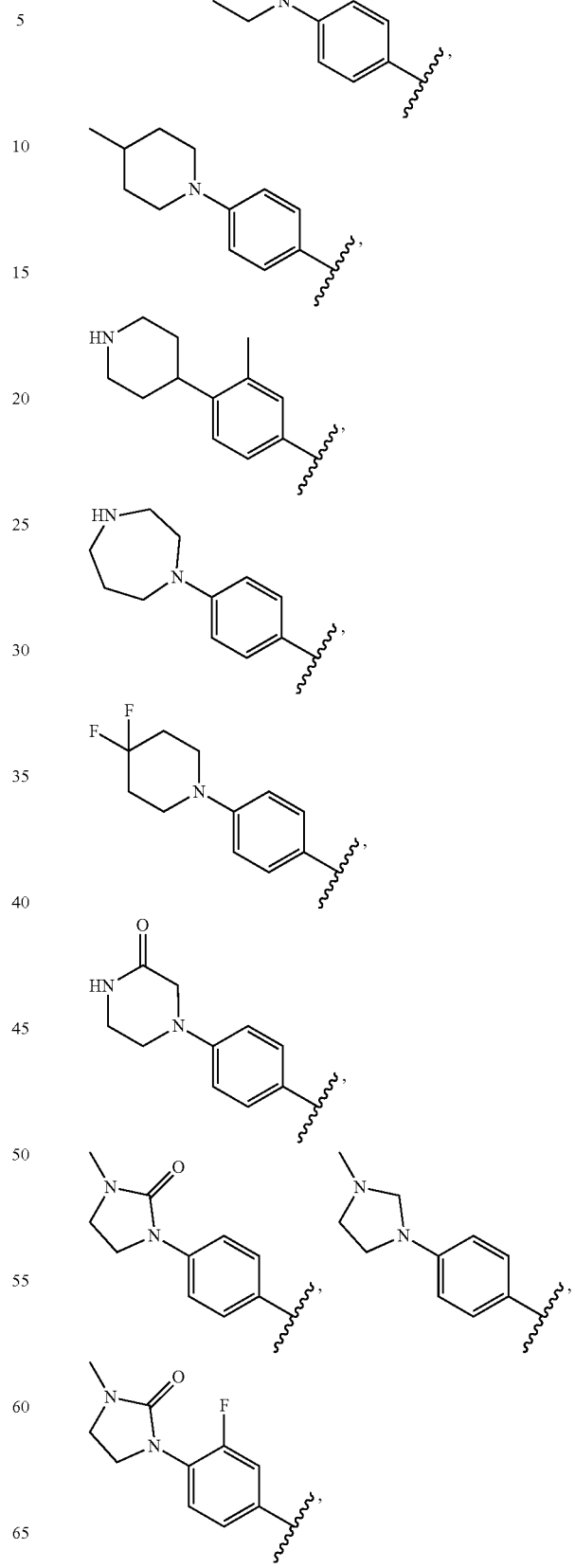

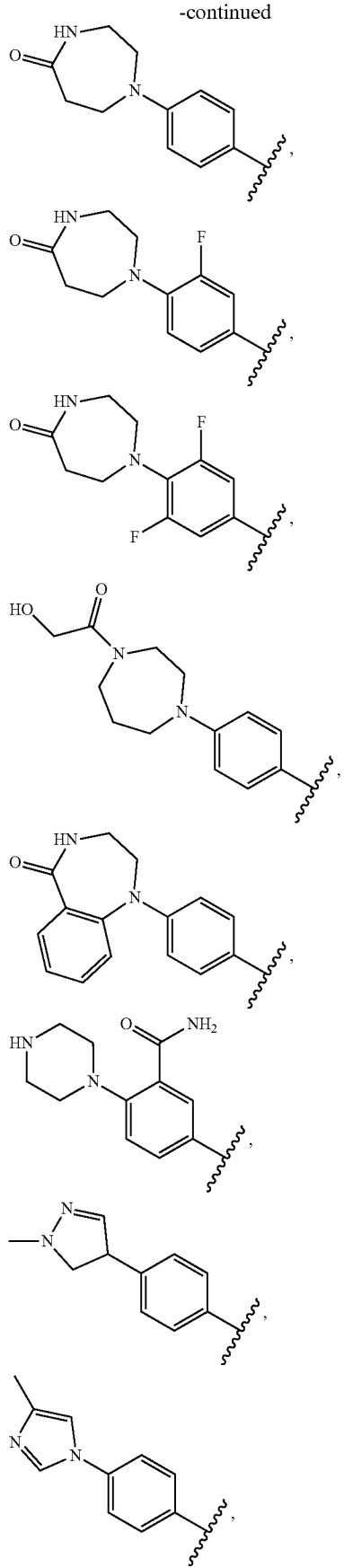
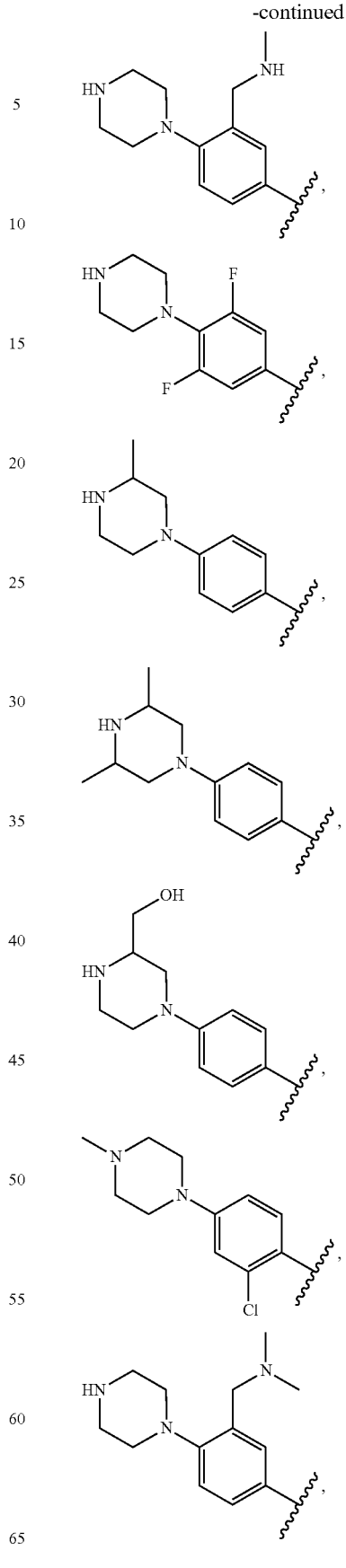

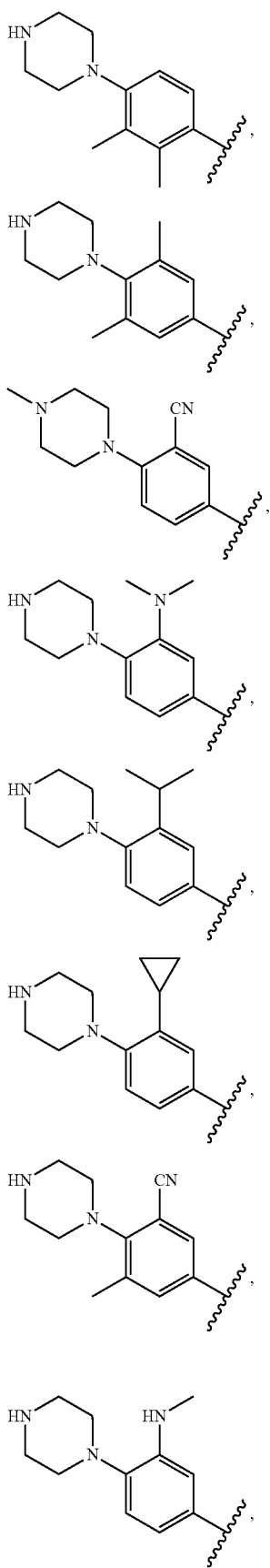
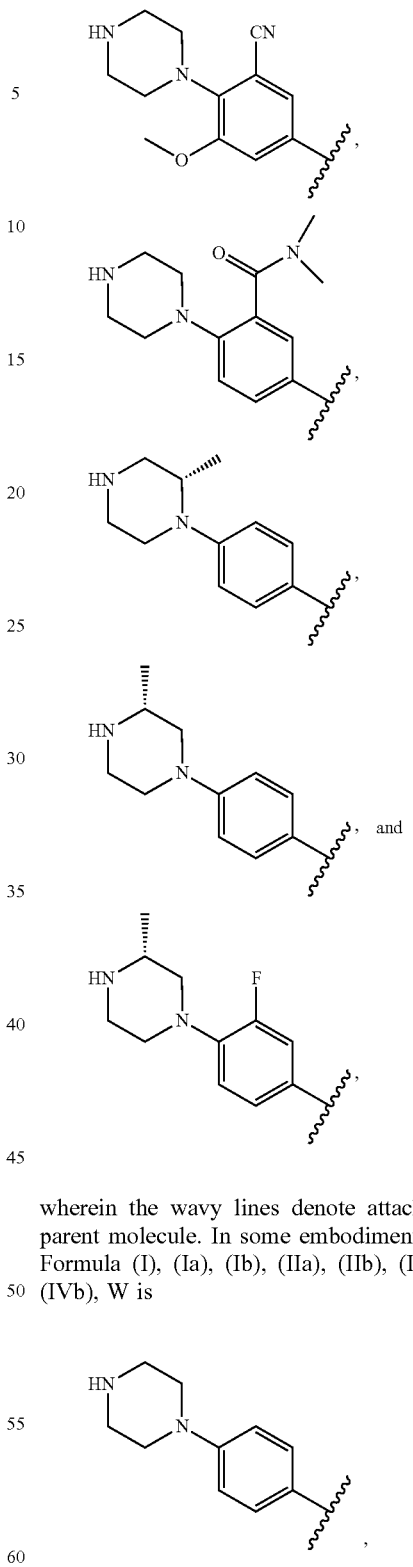
wherein the wavy lines denote attachment points to the parent molecule. In some embodiments of a compound of Formula (I), (Ia), (Ib), (IIa), (IIb), (IIIa), (IIIb), (IVa) or (IVb), W is
wherein the wavy line denotes attachment point to the parent molecule and W is optionally substituted by $R^{17a}$. In some embodiments of a compound of Formula (I), (Ia), (Ib), (IIa), (IIb), (IIIa), (IIIb), (IVa) or (IVb), W is

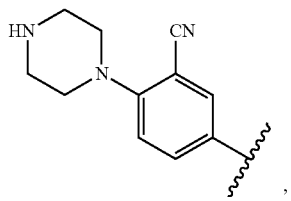 [SMILES: *c1ccc(N2CCNCC2)c(C#N)c1]

wherein the wavy line denotes attachment point to the parent molecule.

It is understood that each description of W may be combined with each description of X, Y, Z, $R^1$, $R^2$, $R^{3a}$, $R^{3b}$, and $R^4$. For example, in one aspect, it is understood that each description of W may be combined in one aspect with a variation in which X is hydrogen, Y is N, Z is N, $R^{3a}$ is hydrogen, $R^{3b}$ is hydrogen, and $R^4$ is 2,6-dichlorophenyl.

In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl, $C_1$-$C_6$ alkyl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —($C_1$-$C_3$ alkylene)($C_6$-$C_{14}$ aryl), or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH; W is A, wherein A is phenyl optionally substituted with $R^{17a}$, wherein $R^{17a}$ is independently 3- to 12-membered heterocyclyl, —($C_1$-$C_3$ alkylene)$OR^{10}$, $C_1$-$C_6$ alkyl optionally substituted by halogen or —OH, —$C(O)NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$, wherein the 3- to 12-membered heterocyclyl of $R^{17a}$ is optionally substituted with $C_1$-$C_6$ alkyl optionally substituted by halogen or —OH, —$C(O)R^{13}$, —($C_1$-$C_3$ alkylene)$OR^{13}$, —$S(O)_2R^{13}$, $C_3$-$C_5$ cycloalkyl, oxo, halogen, or —$OR^{13}$, wherein the 3- to 12-membered heterocyclyl of $R^{17a}$ is optionally fused with 5- to 10-membered heteroaryl or $C_6$-$C_{14}$ aryl. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is $C_6$-$C_{14}$ aryl optionally substituted by halogen, —CN, —$NR^{13}R^{14}$, —$C(O)R^{13}$, —$OR^{13}$, or $C_1$-$C_6$ alkyl optionally substituted by —OH; W is A, wherein A is phenyl optionally substituted with $R^{17a}$, wherein $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; $R^4$ is phenyl optionally substituted by halogen, —CN, —$NR^{13}R^{14}$, —$C(O)R^{13}$, —$OR^{13}$, or $C_1$-$C_6$ alkyl optionally substituted by —OH; W is A, wherein A is phenyl optionally substituted with $R^{17a}$, wherein $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH. In some embodiments of a compound of Formula (I), (Ia) or (Ib), X is hydrogen; Y is N; Z is N; $R^{3a}$ and $R^{3b}$ are both hydrogen; $R^4$ is selected from the group consisting of methyl, ethyl, isopropyl, cyclopropyl,

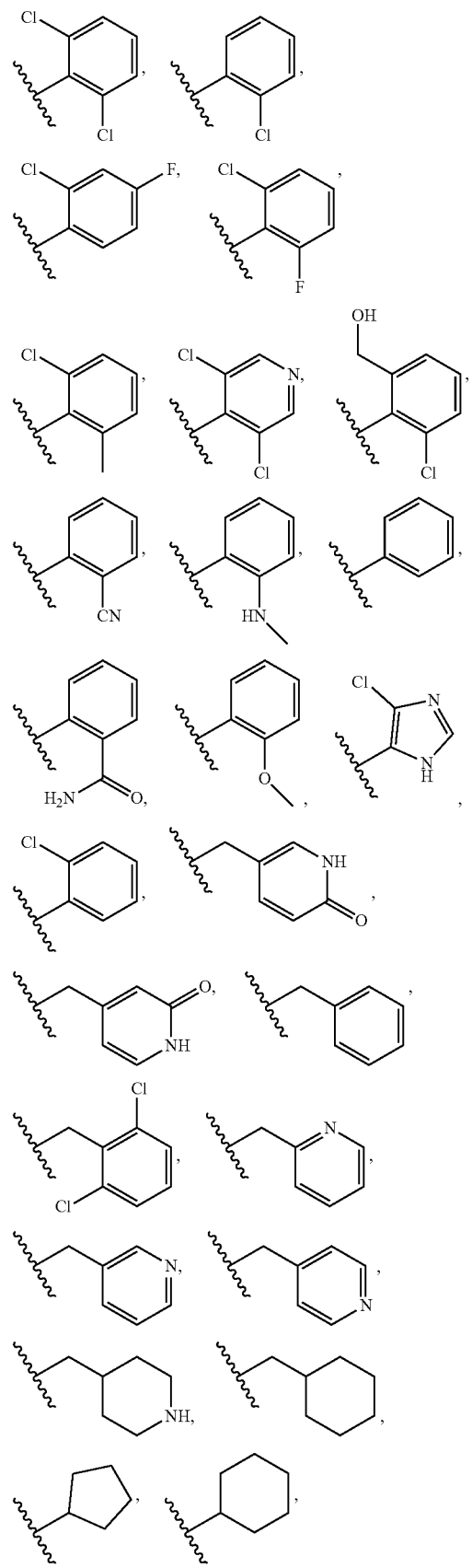

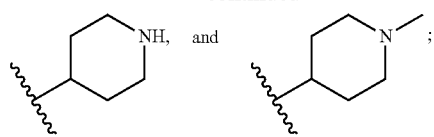
W is selected from the group consisting of:
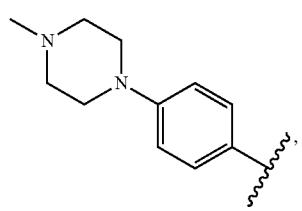
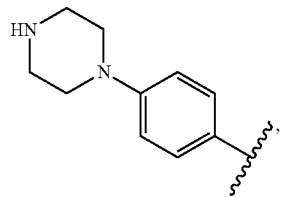
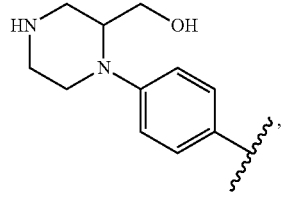
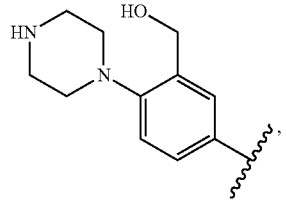
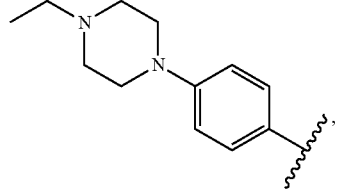
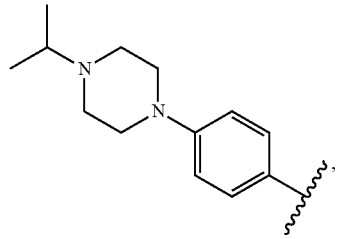
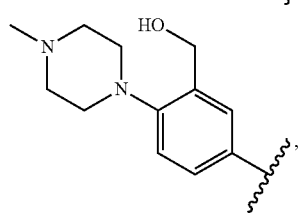
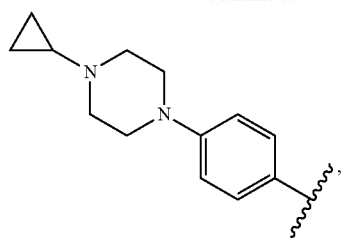
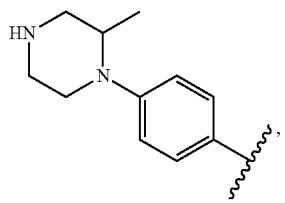
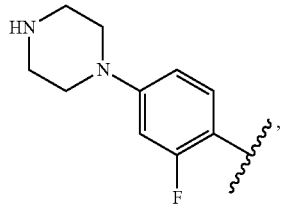
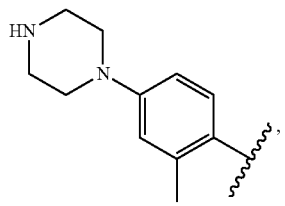
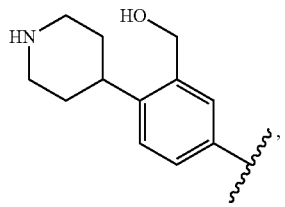
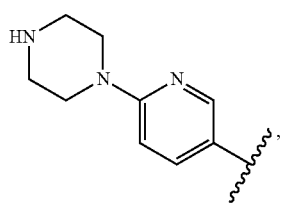
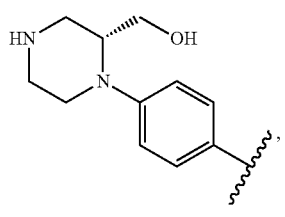
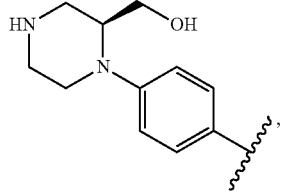

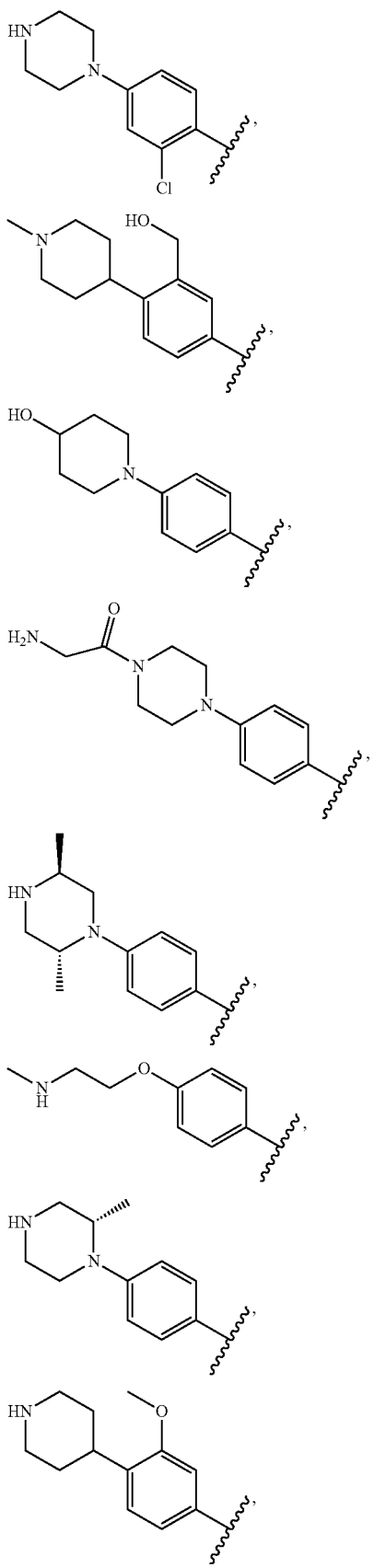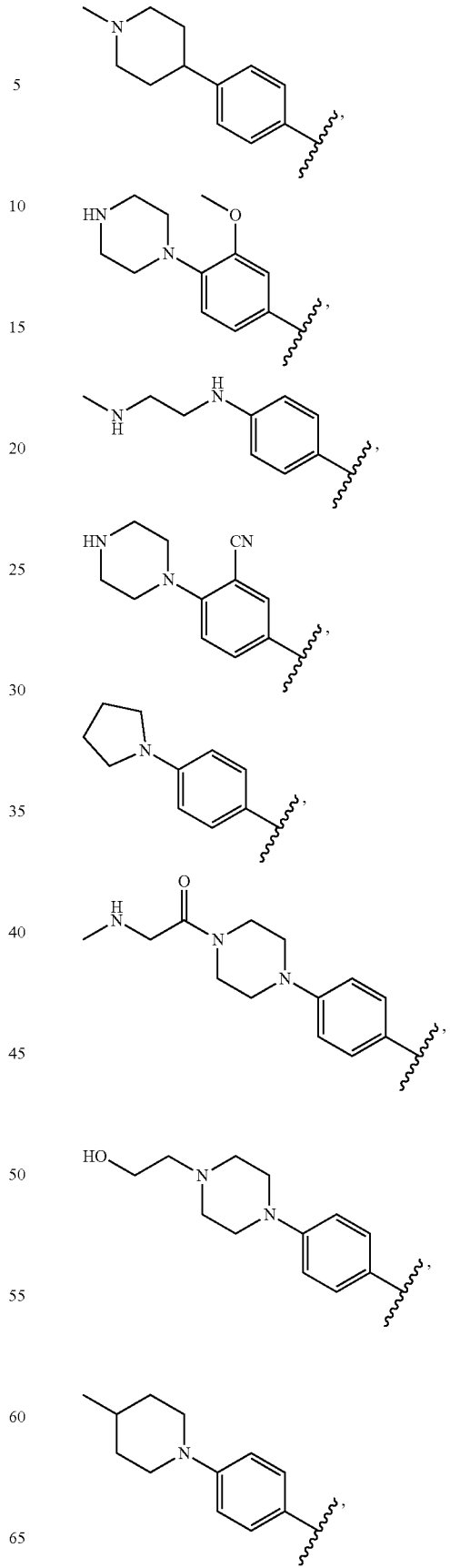

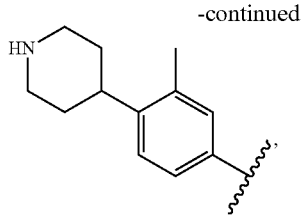,
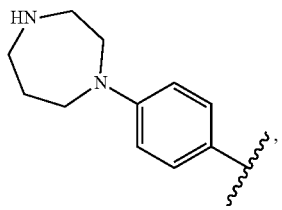,
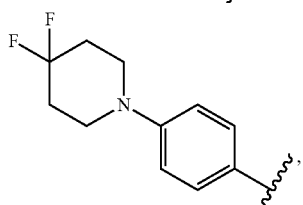,
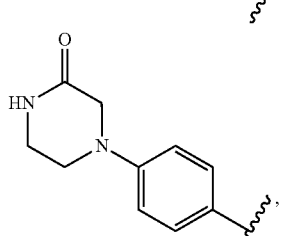,
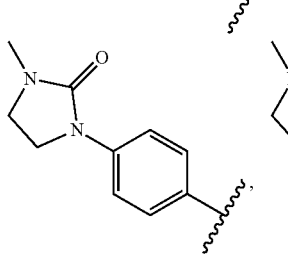,
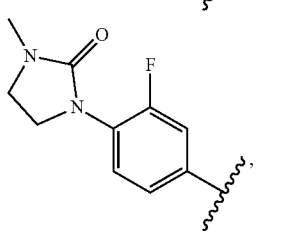,
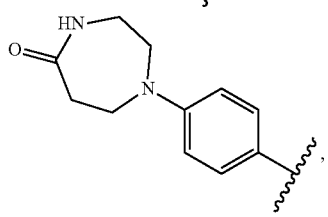,
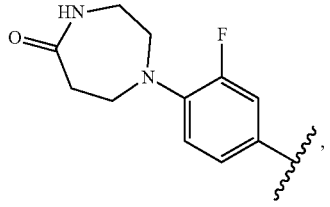,
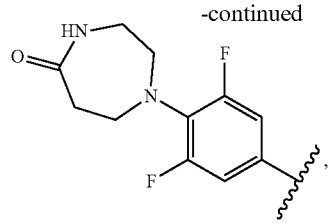,
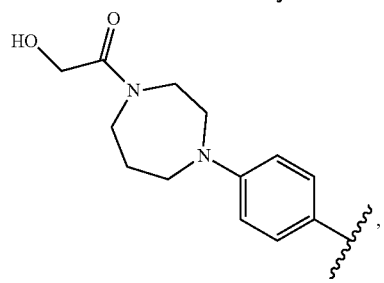,
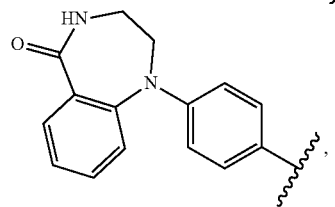,
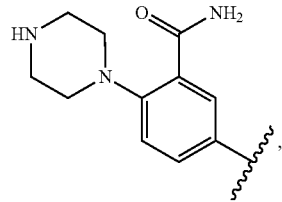,
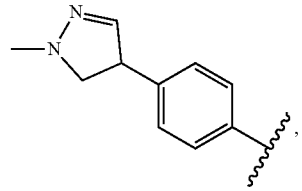,
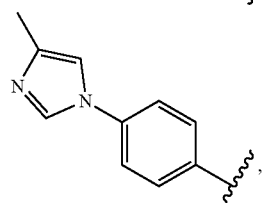,
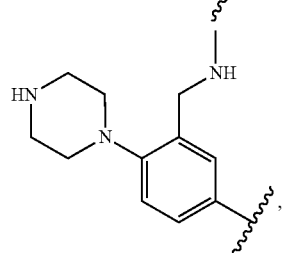,
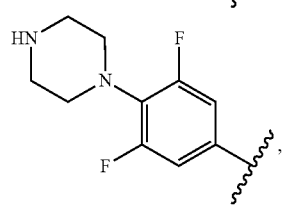,

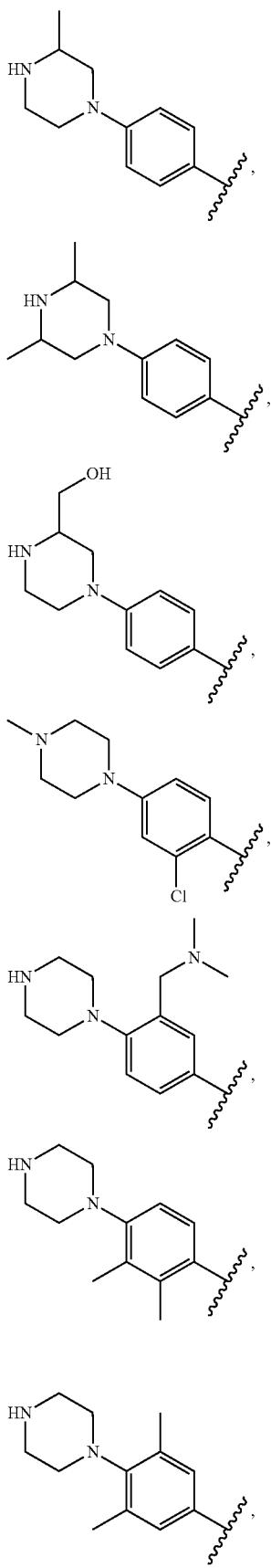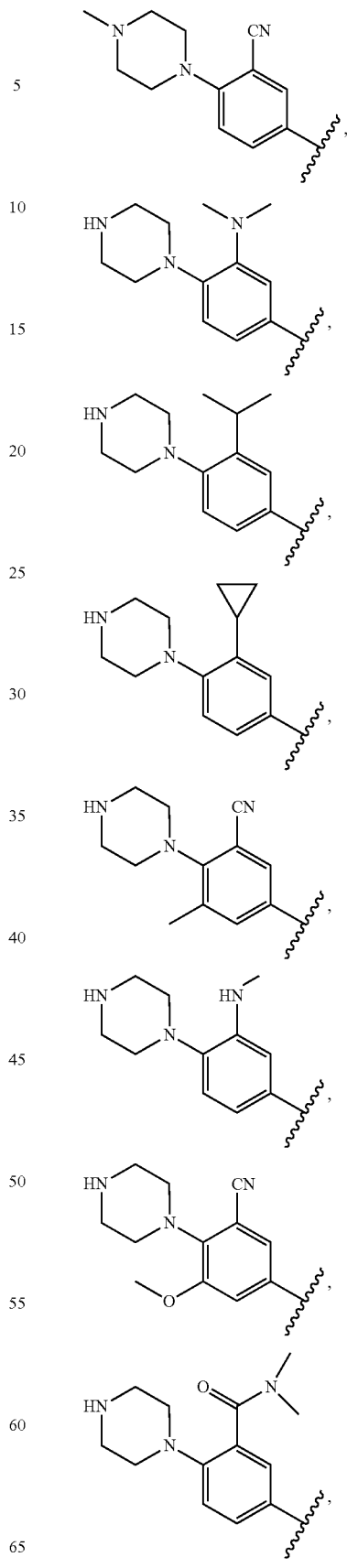

-continued
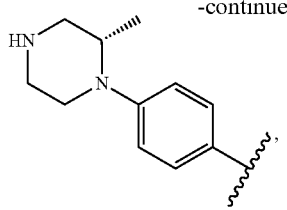
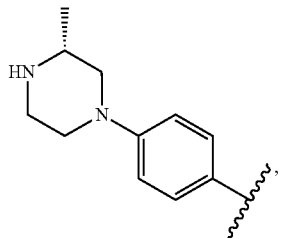
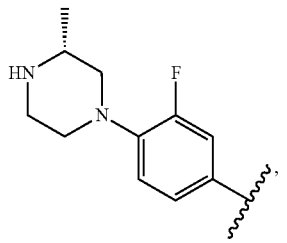
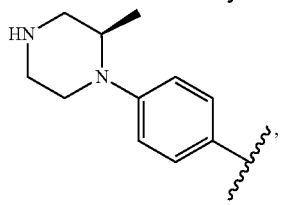
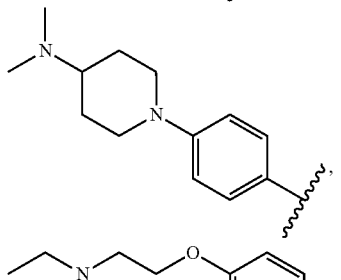
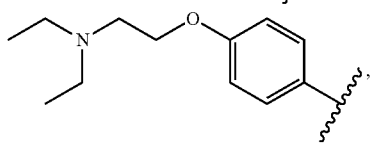
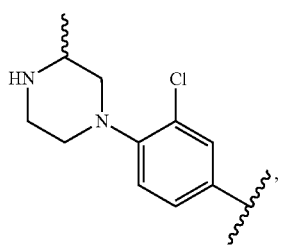
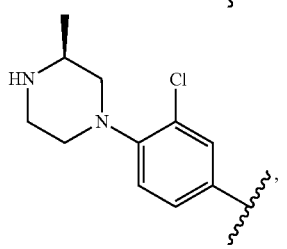
-continued
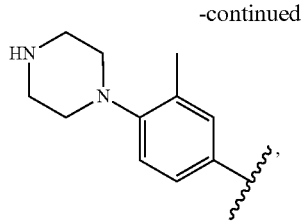
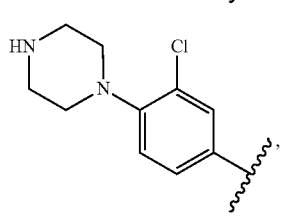
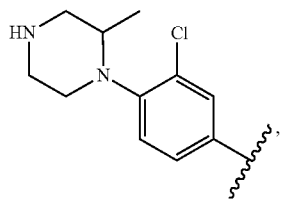
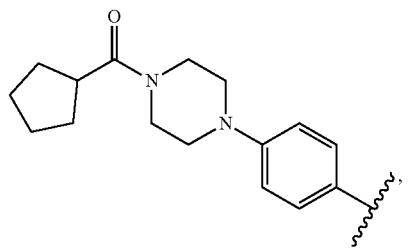
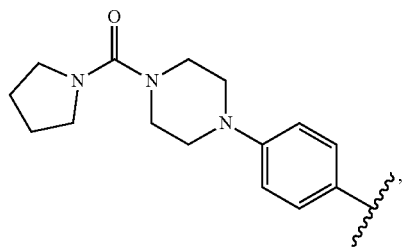
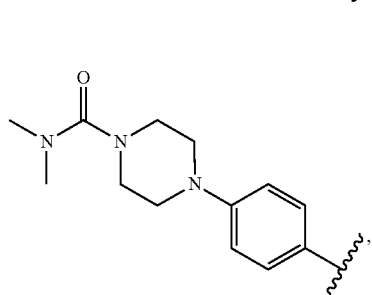
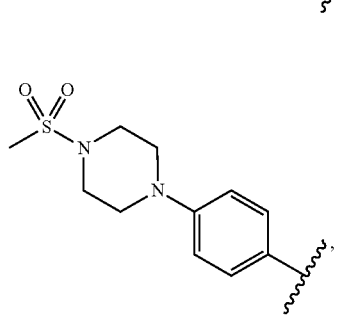

75
-continued
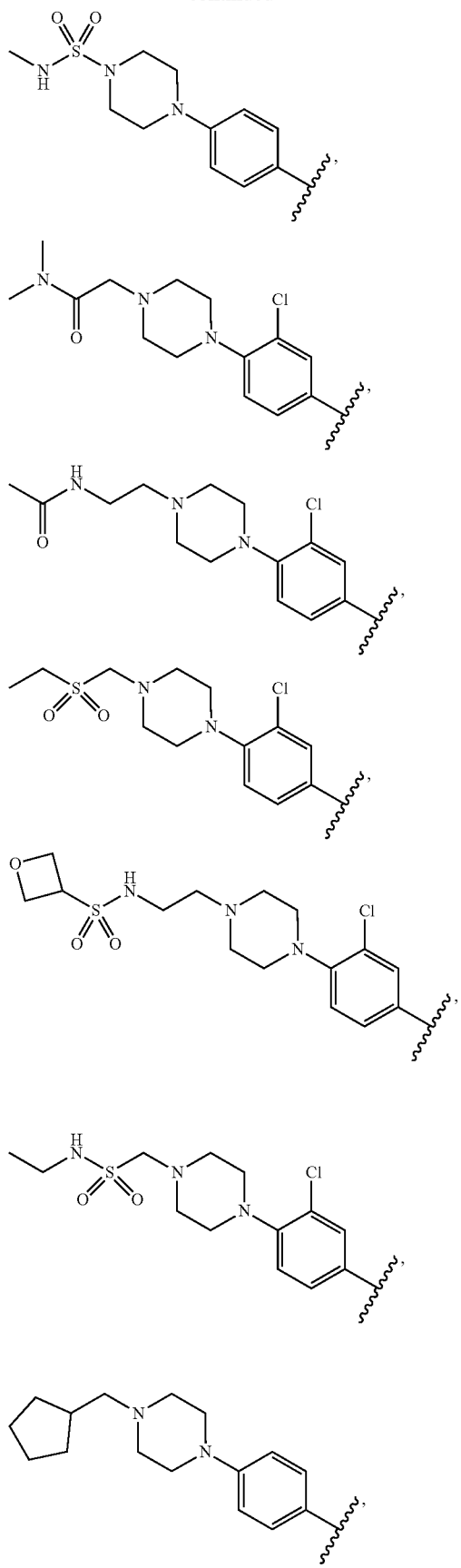
76
-continued
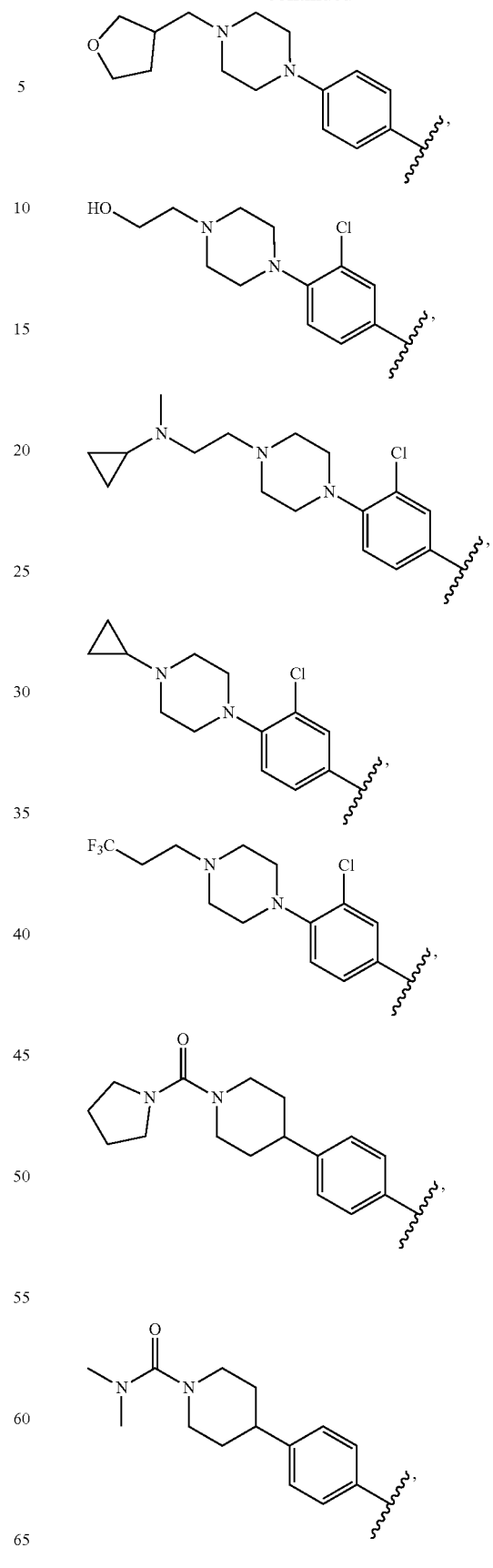

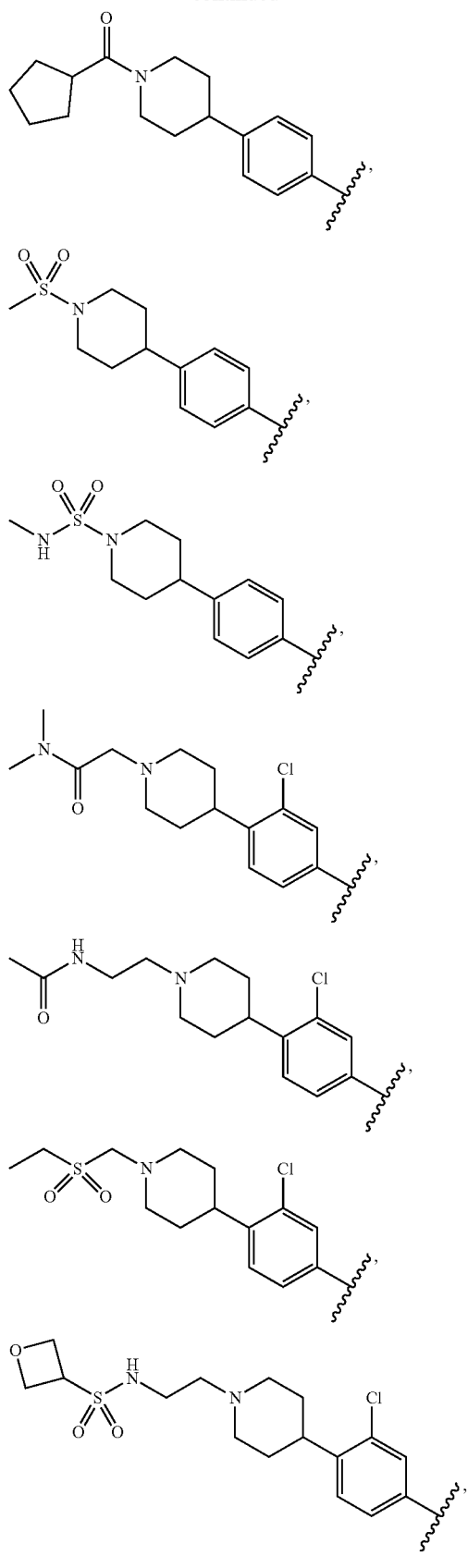
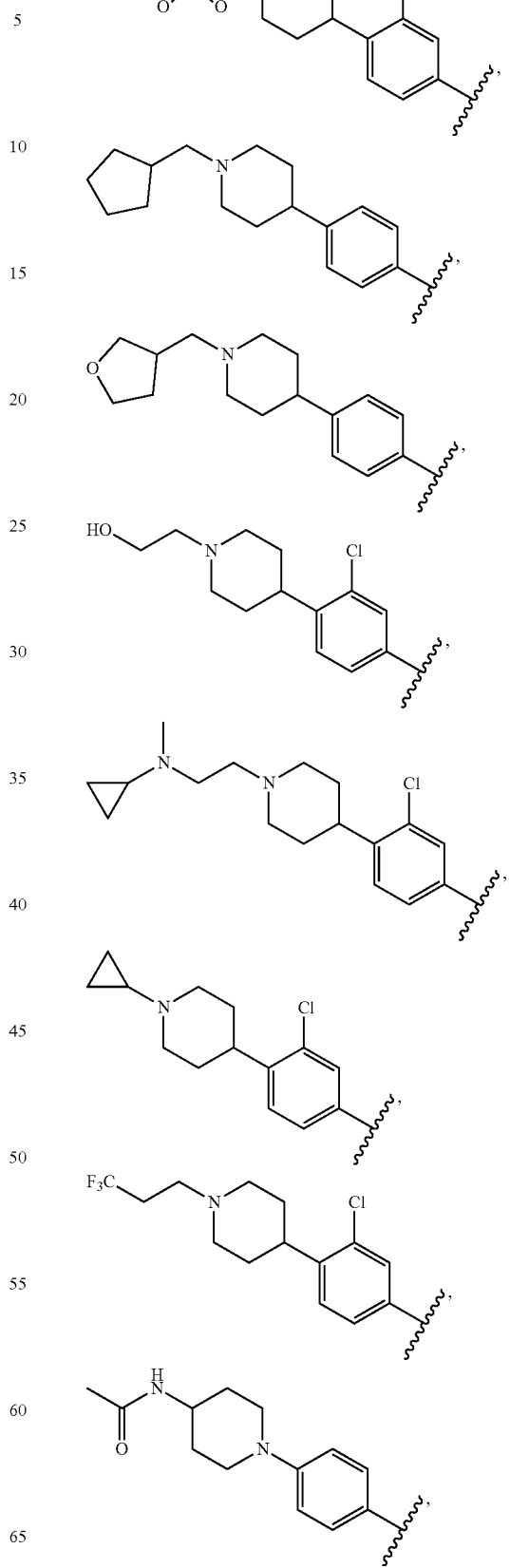

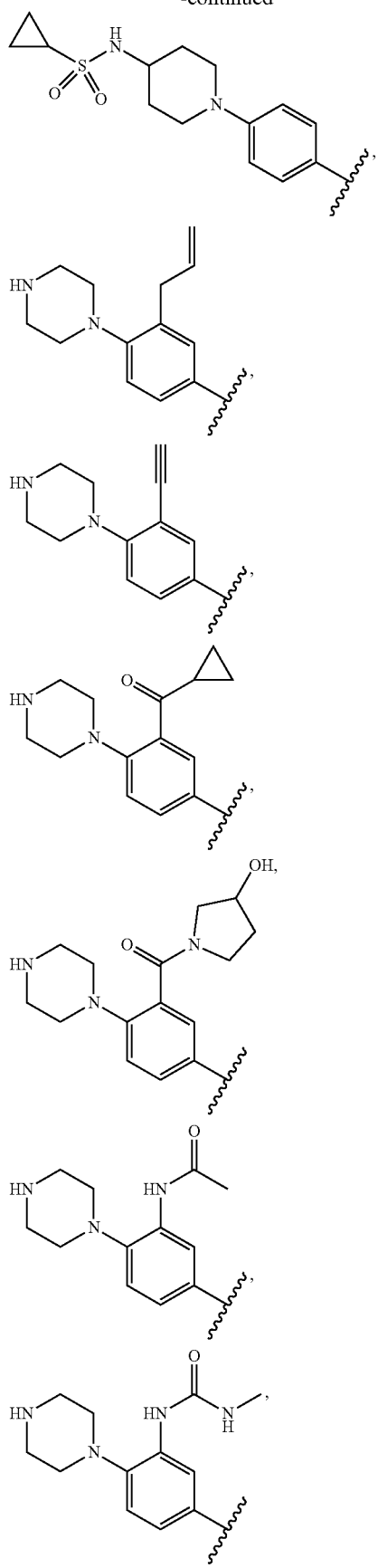
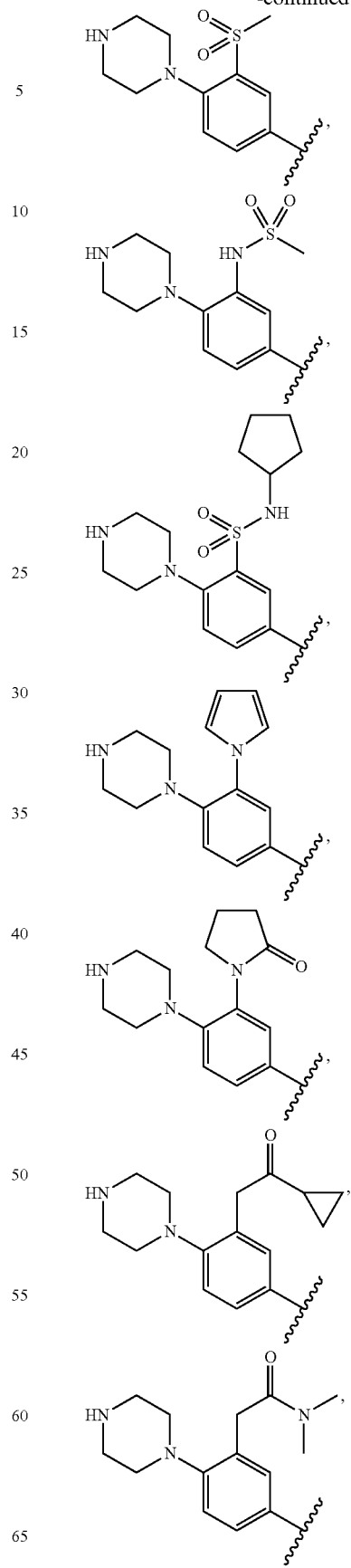

-continued
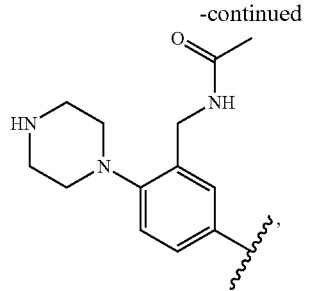
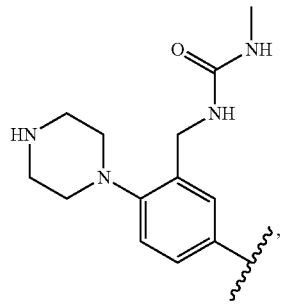
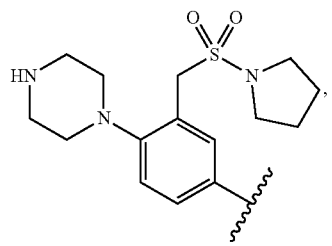
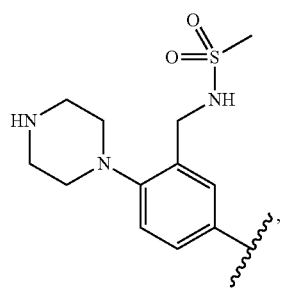
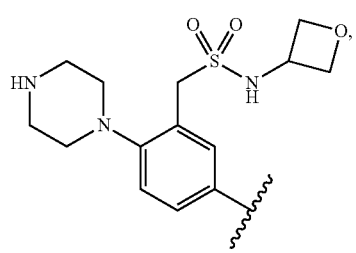
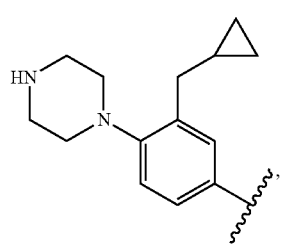
-continued
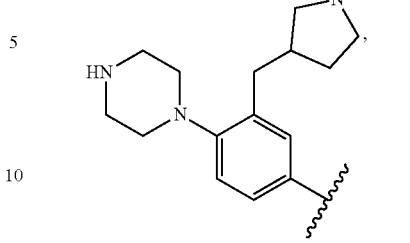
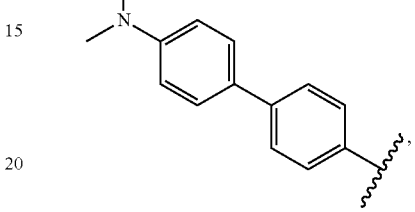
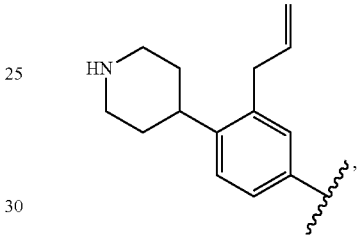
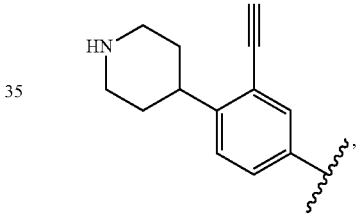
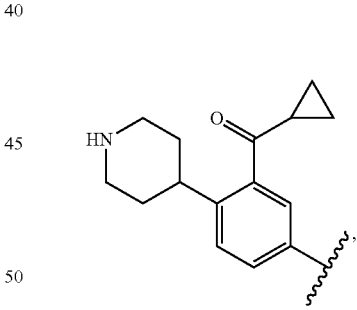
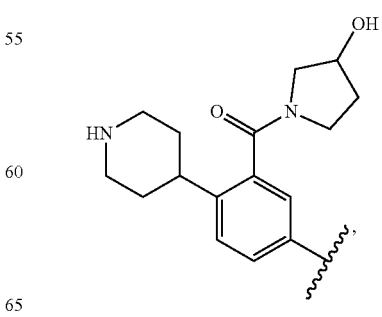

-continued
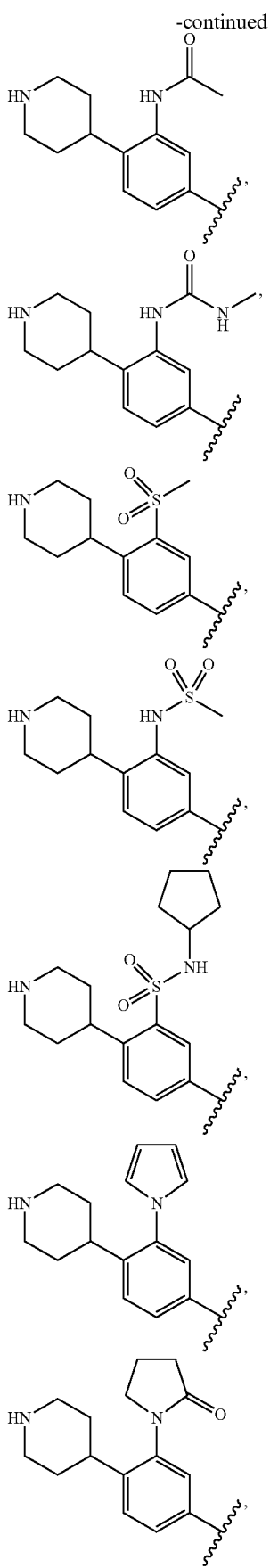
-continued
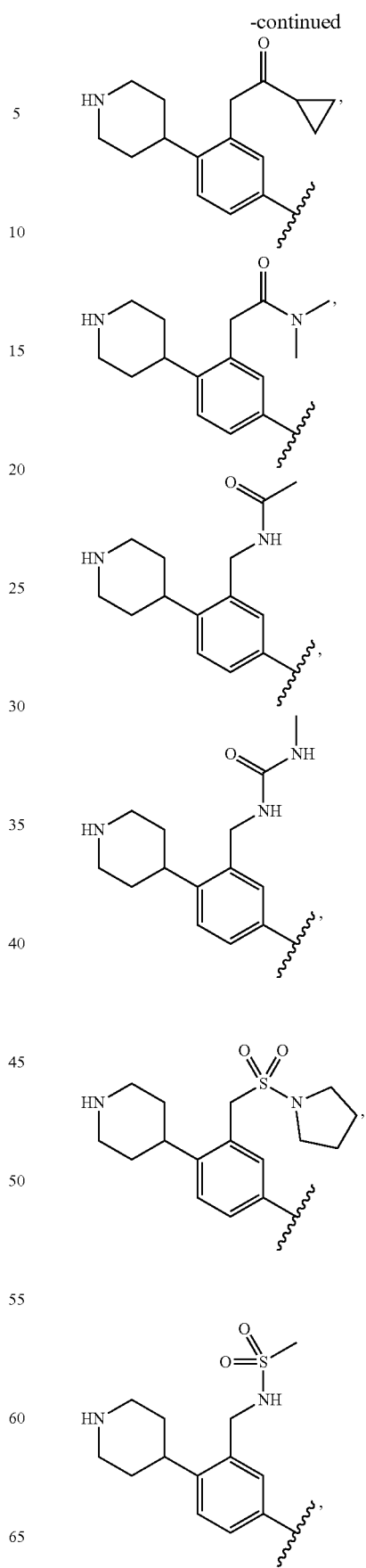

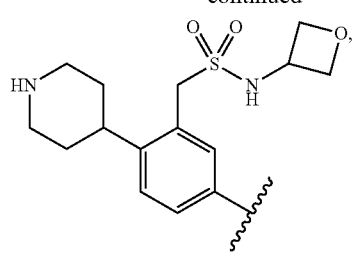
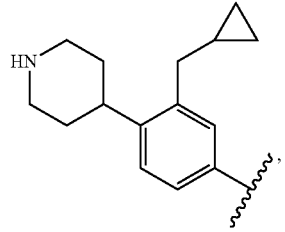
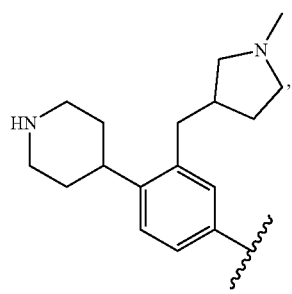
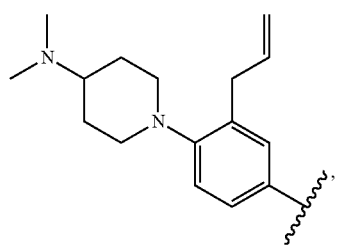
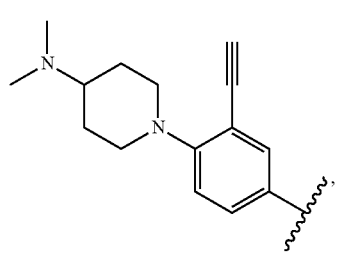
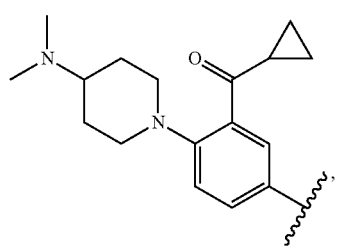
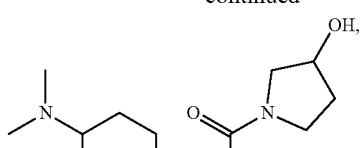
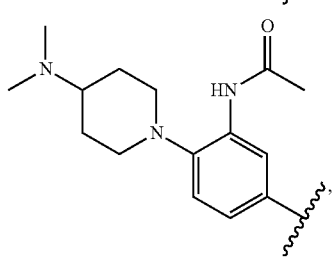
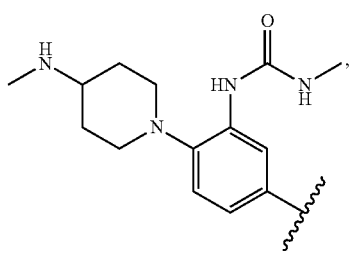
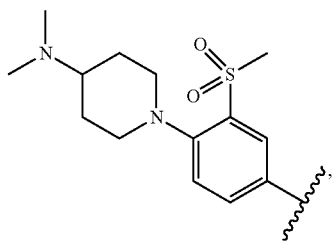
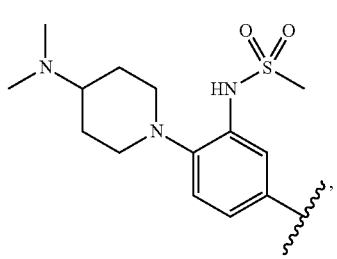
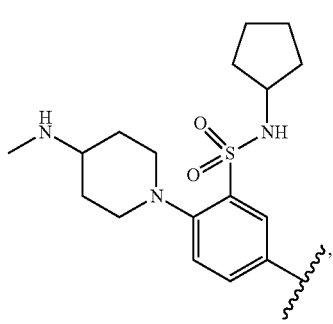

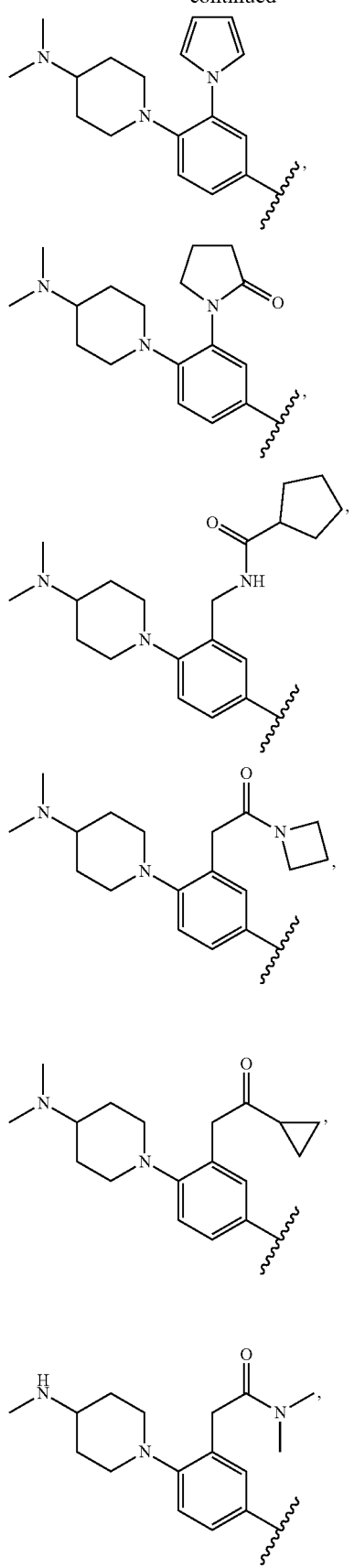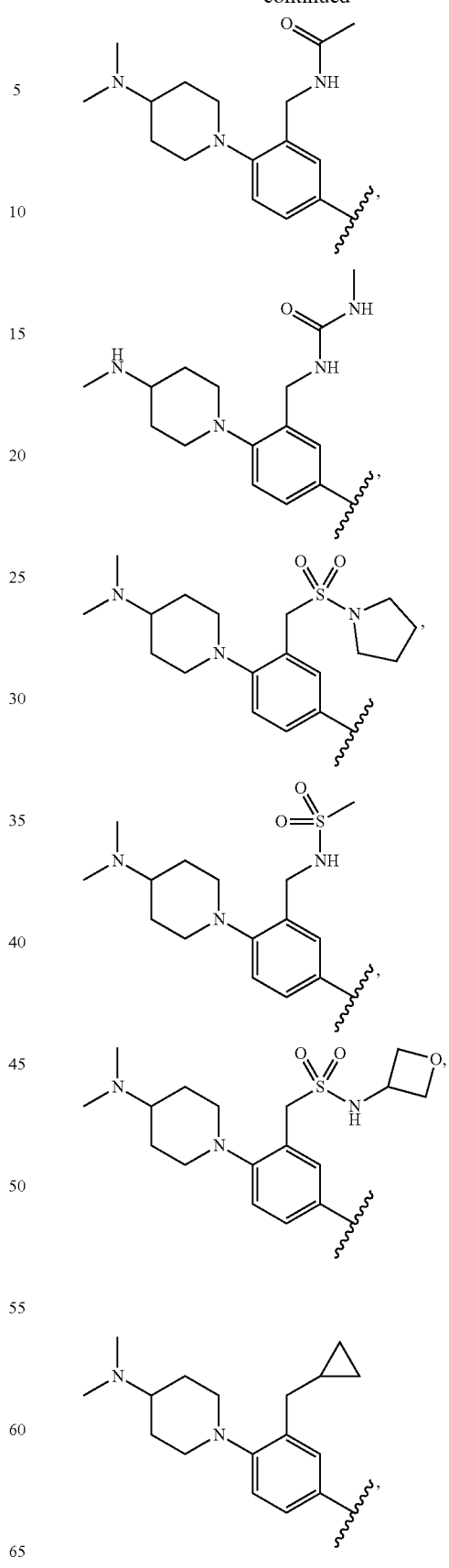

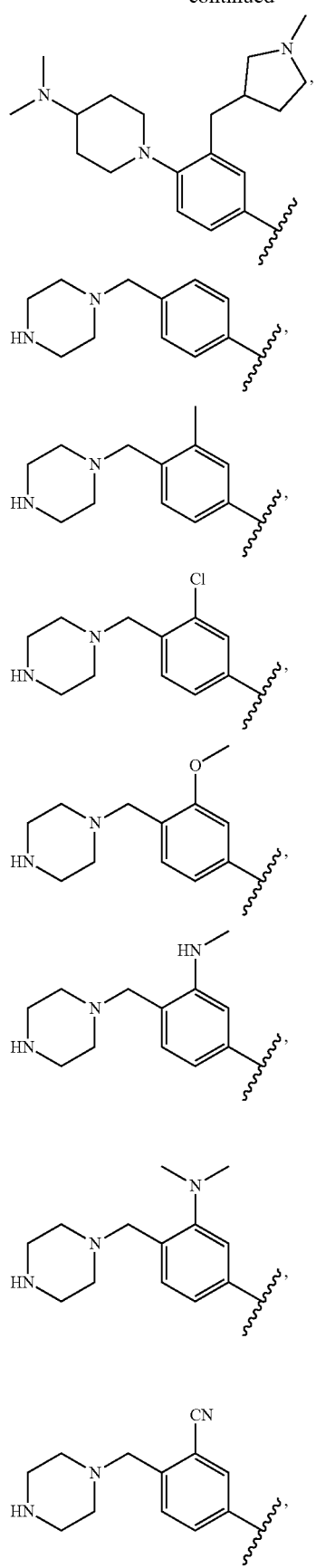
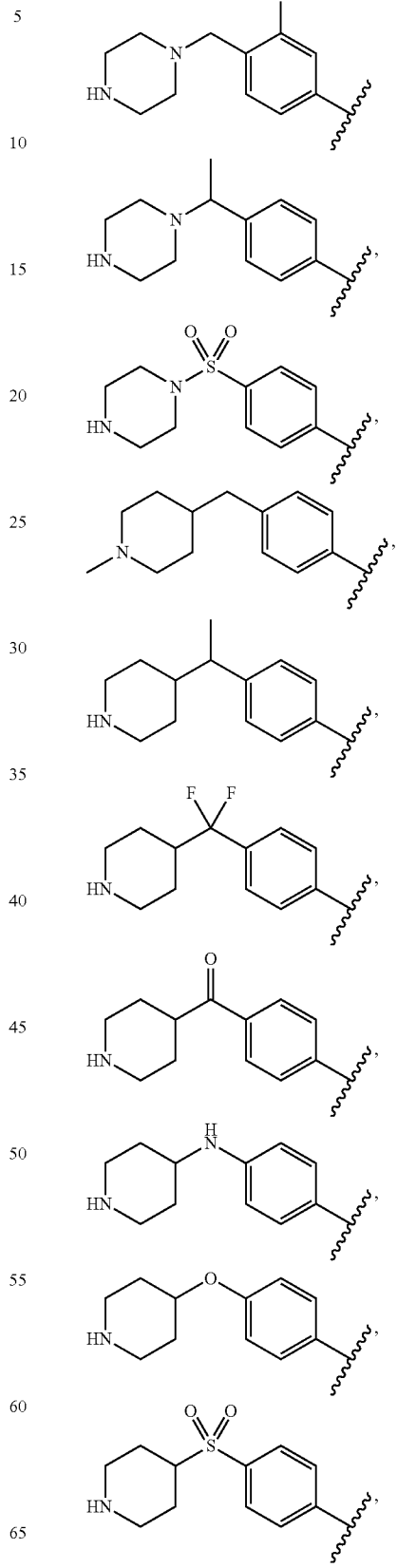

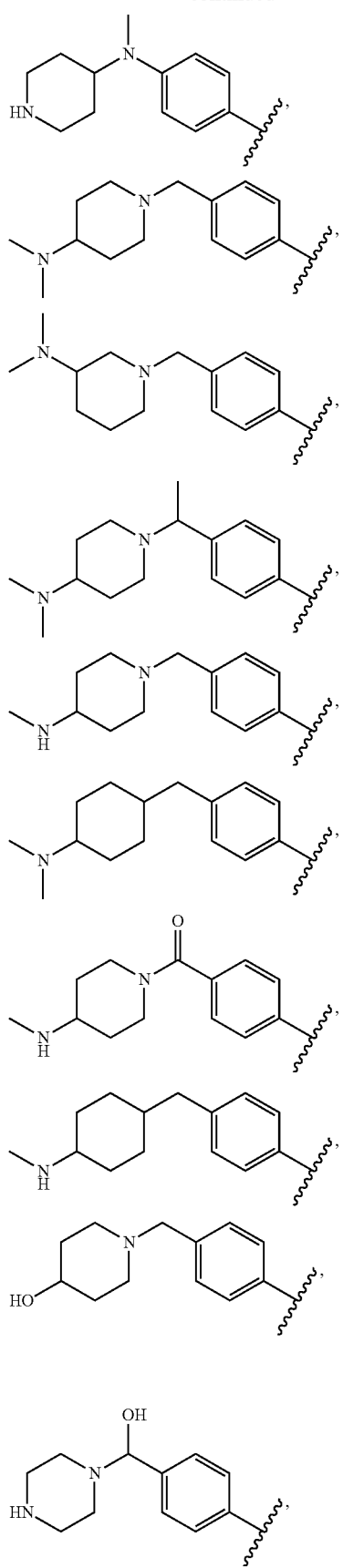
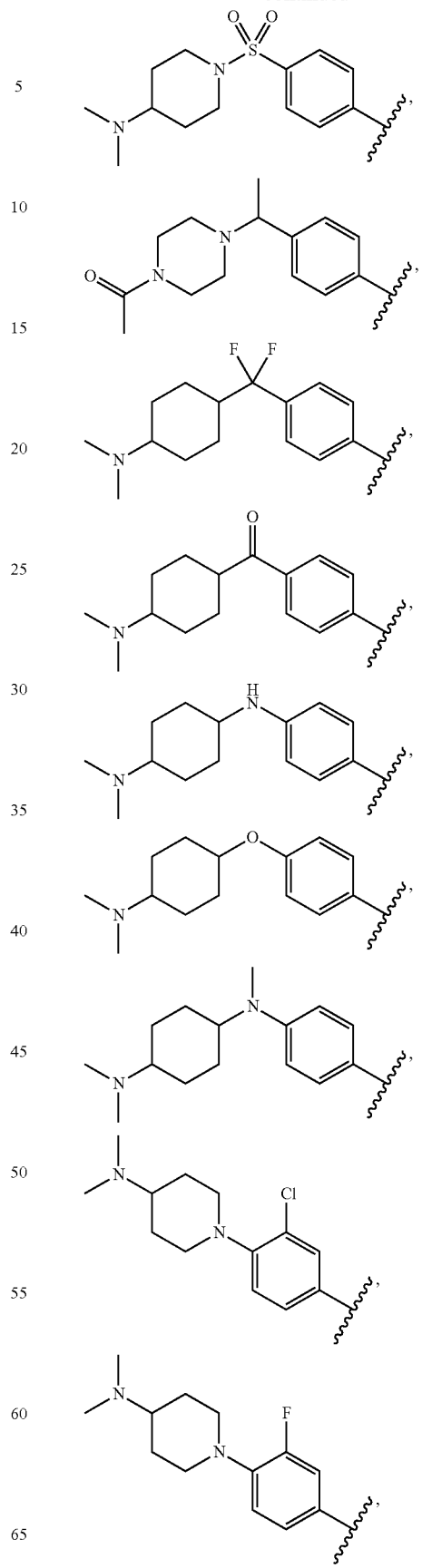

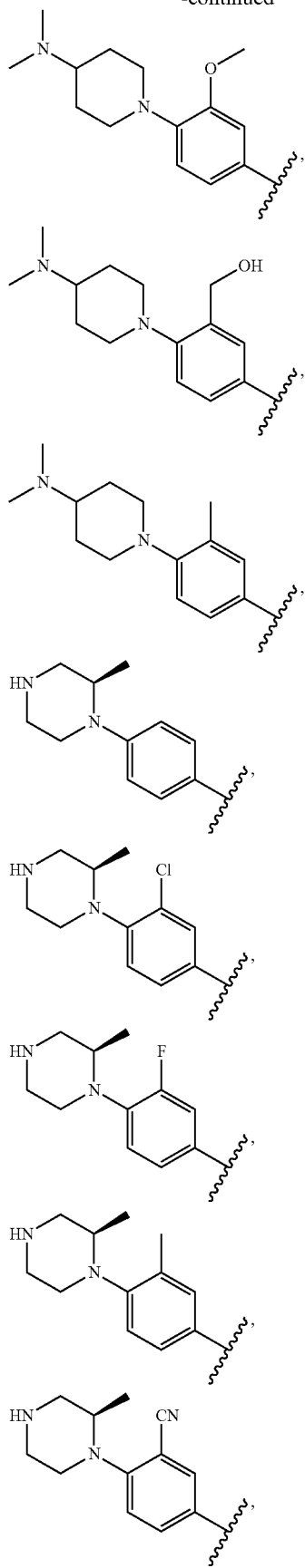
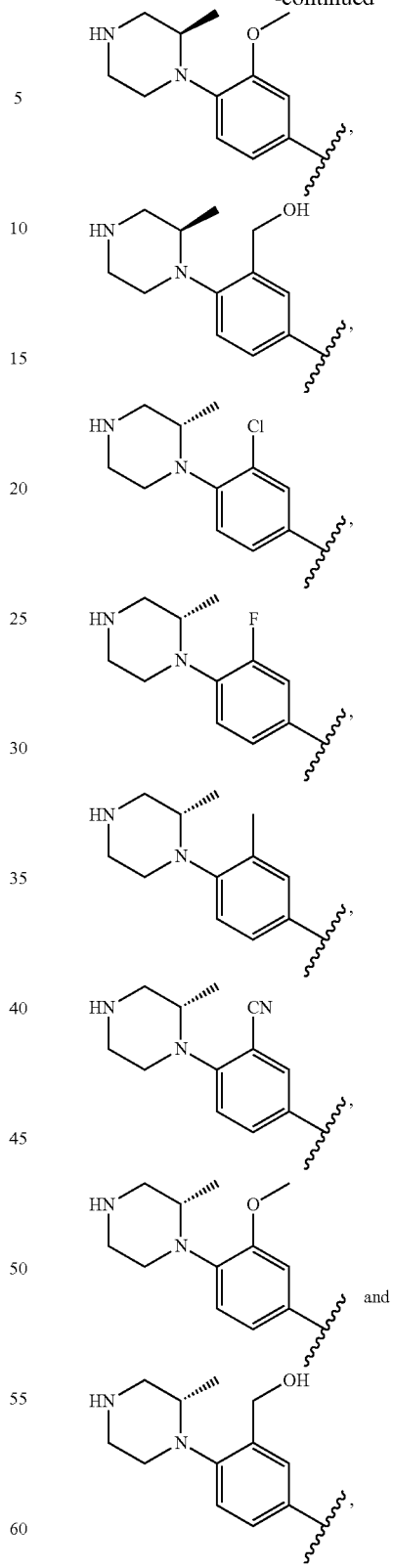
In some embodiments of a compound of Formula (I), (Ia) or (Ib), X is hydrogen; Y is N; Z is N; $R^{3a}$ and $R^{3b}$ are both hydrogen; $R^4$ is phenyl optionally substituted by halogen; W is

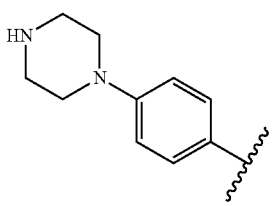 [SMILES: *c1ccc(N2CCNCC2)cc1]

optionally substituted by $R^{17a}$. In some embodiments of a compound of Formula (I), (Ia) or (Ib), X is hydrogen; Y is N; Z is N; $R^{3a}$ and $R^{3b}$ are both hydrogen; $R^4$ is phenyl optionally substituted by halogen; W is

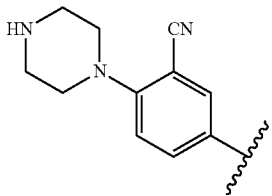

In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl, $C_1$-$C_6$ alkyl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —($C_1$-$C_3$ alkylene)($C_6$-$C_{14}$ aryl), or $C_6$-$C_{14}$ aryl, each of which is optionally substituted by halogen, —CN, —$NR^{13}R^{14}$, —C(O)$R^{13}$, —$OR^{13}$, or $C_1$-$C_6$ alkyl optionally substituted by —OH; W is A, wherein A is phenyl optionally substituted with $R^{17a}$, wherein $R^{17a}$ is independently 3- to 12-membered heterocyclyl, —($C_1$-$C_3$ alkylene)$OR^{10}$, $C_1$-$C_6$ alkyl optionally substituted by halogen or —OH, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$, wherein the 3- to 12-membered heterocyclyl of $R^{17a}$ is optionally substituted with $C_1$-$C_6$ alkyl optionally substituted by halogen or —OH, —C(O)$R^{13}$, —($C_1$-$C_3$ alkylene)$OR^{13}$, —S(O)$_2R^{13}$, $C_3$-$C_8$ cycloalkyl, oxo, halogen, or —$OR^{13}$, wherein the 3- to 12-membered heterocyclyl of $R^{17a}$ is optionally fused with 5- to 10-membered heteroaryl or $C_6$-$C_{14}$ aryl. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is $C_6$-$C_{14}$ aryl optionally substituted by halogen, —CN, —$NR^{13}R^{14}$, —C(O)$R^{13}$, —$OR^{13}$, or $C_1$-$C_6$ alkyl optionally substituted by —OH; W is A, wherein A is phenyl optionally substituted with $R^{17a}$, wherein $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; $R^4$ is phenyl optionally substituted by halogen, —CN, —$NR^{13}R^{14}$, —C(O)$R^{13}$, —$OR^{13}$, or $C_1$-$C_6$ alkyl optionally substituted by —OH; W is A, wherein A is phenyl optionally substituted with $R^{17a}$, wherein $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH. In some embodiments of a compound of Formula (I), (Ia) or (Ib), X is hydrogen; Y is N; Z is N; $R^{3a}$ and $R^{3b}$ are both hydrogen; $R^4$ is selected from the group consisting of methyl, ethyl, isopropyl, cyclopropyl,

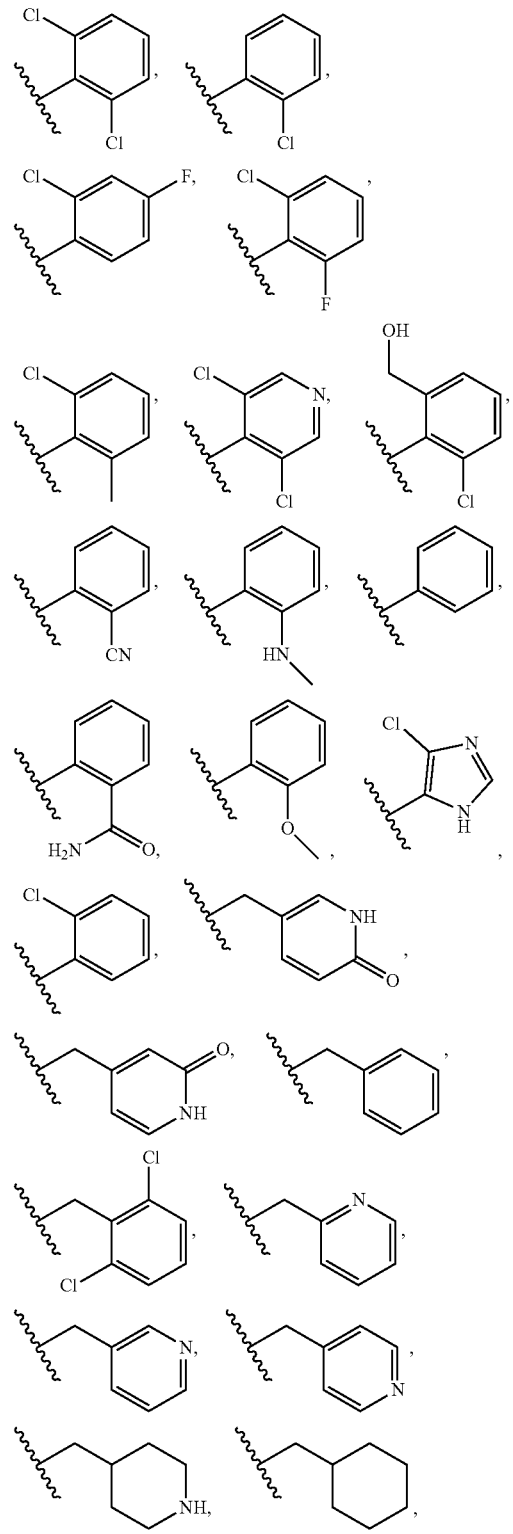

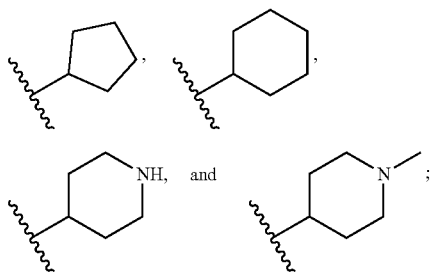
W is selected from the group consisting of:
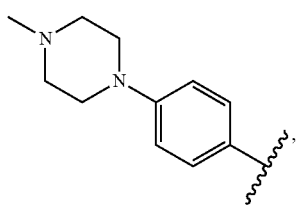
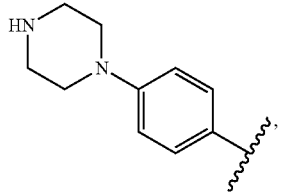
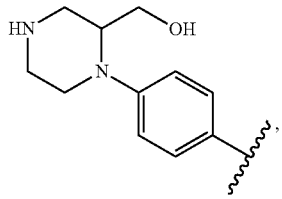
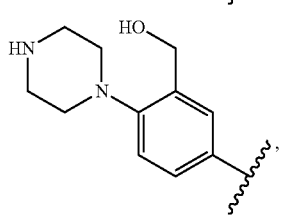
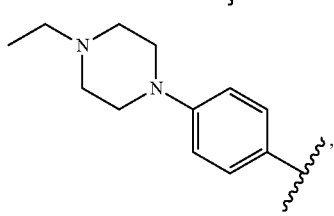
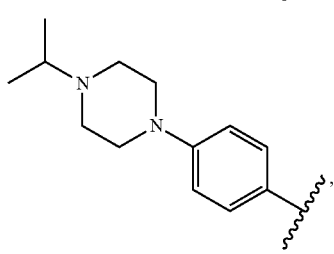
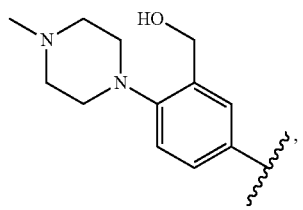
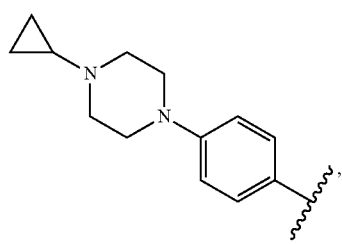
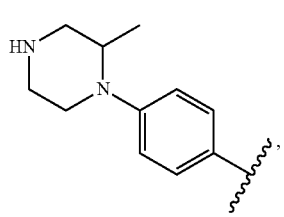
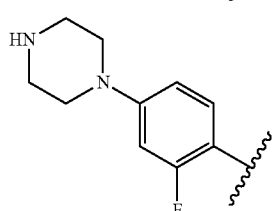
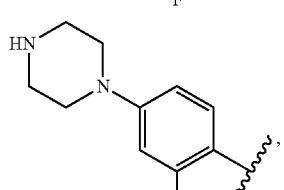
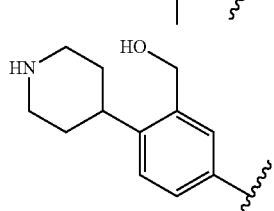
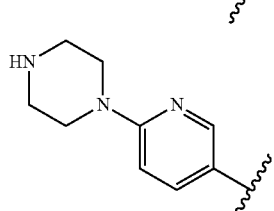
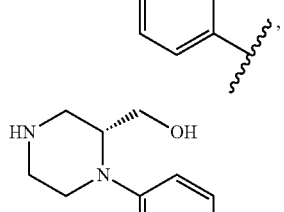
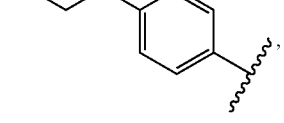

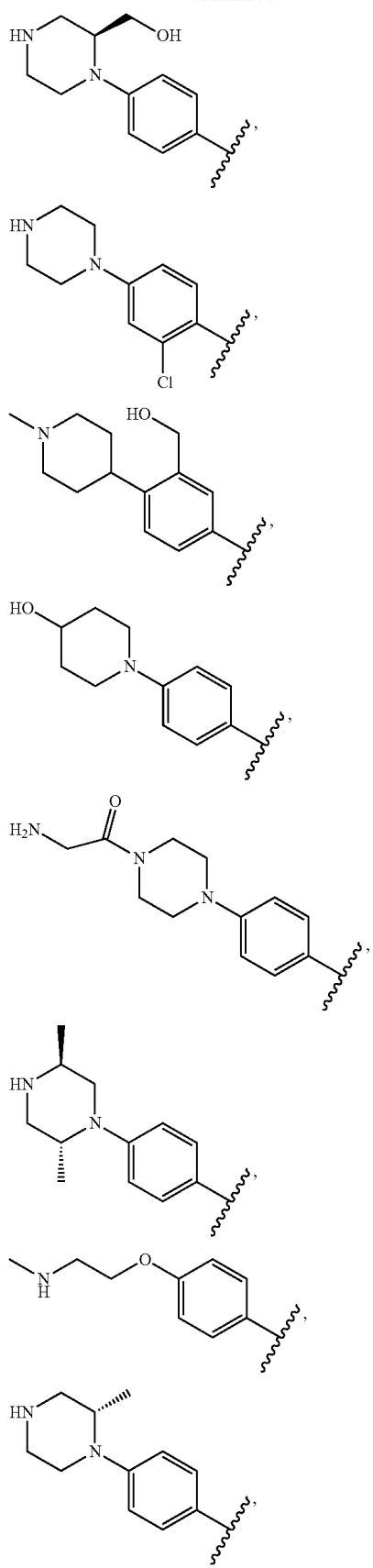
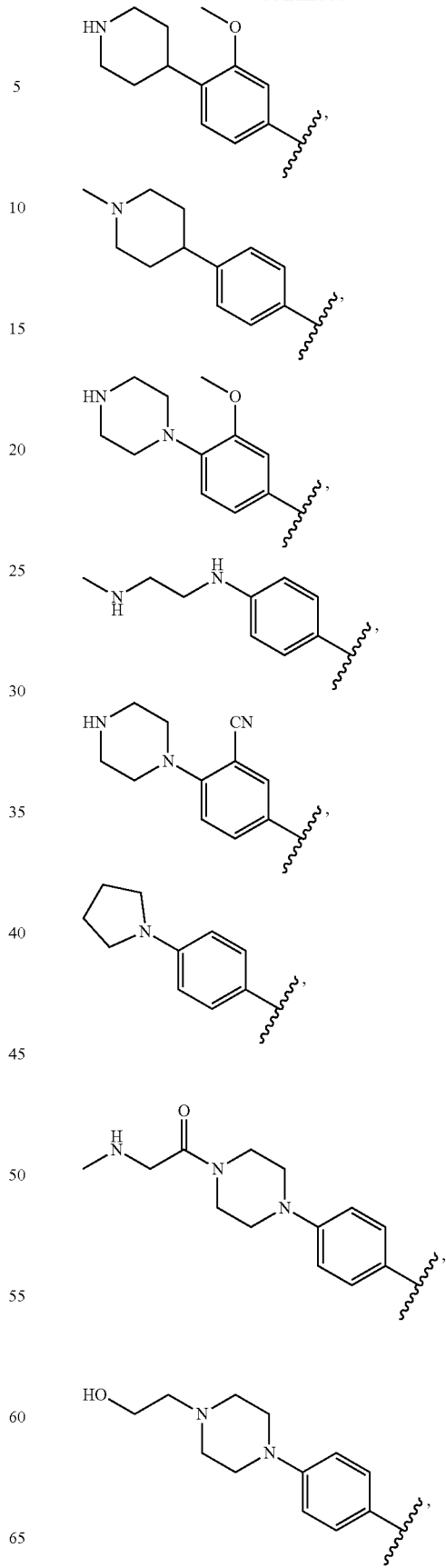

101
-continued
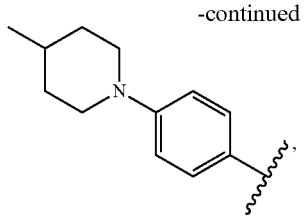
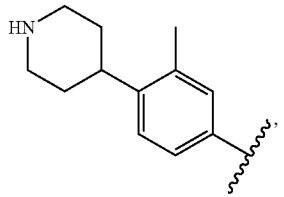
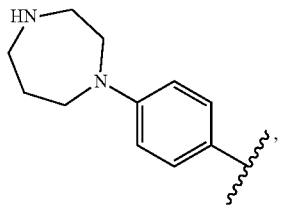
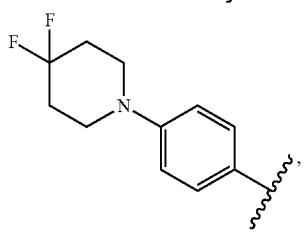
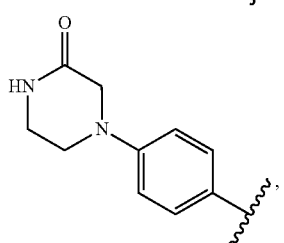
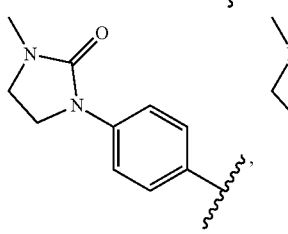
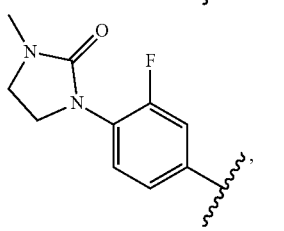
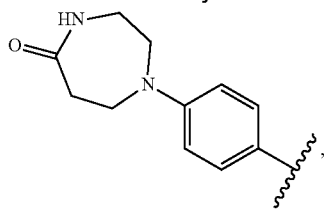
102
-continued
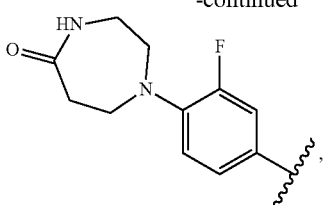
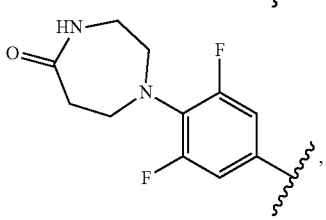
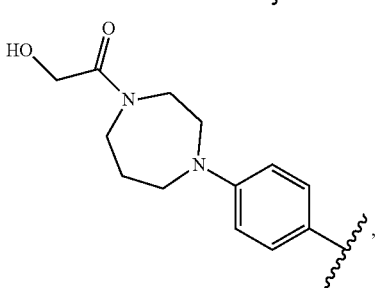
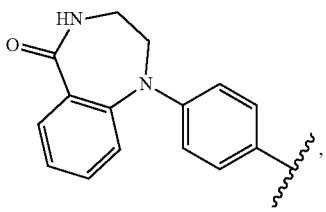
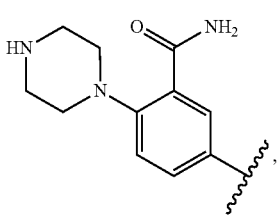
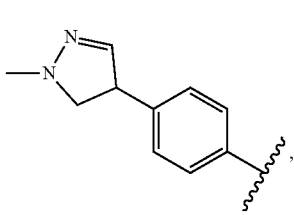
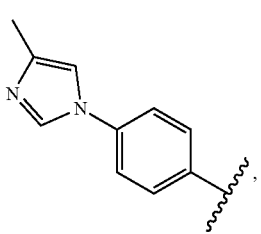

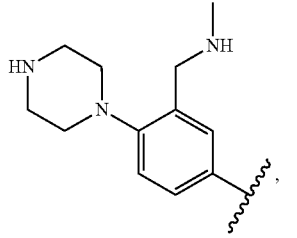,
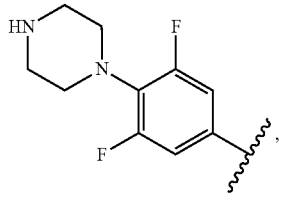,
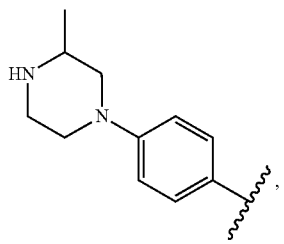,
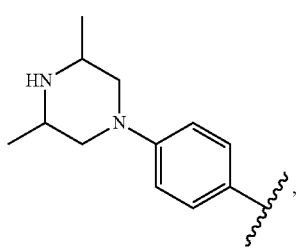,
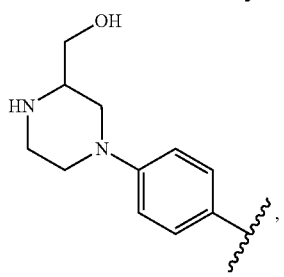,
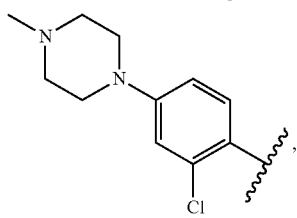,
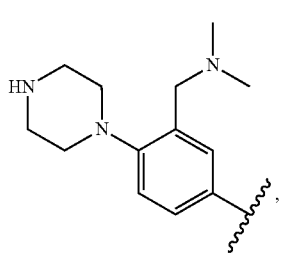,
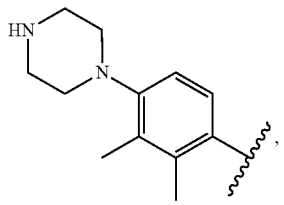,
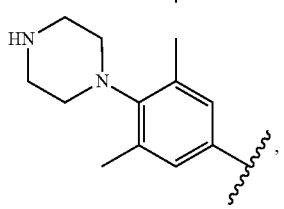,
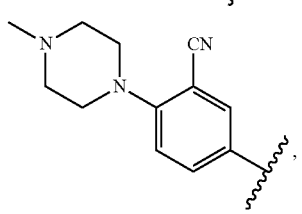,
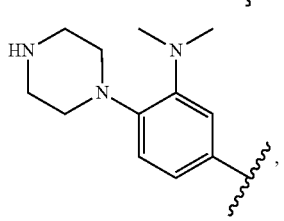,
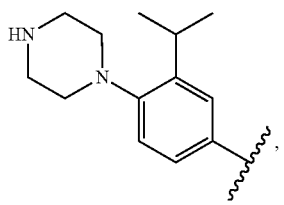,
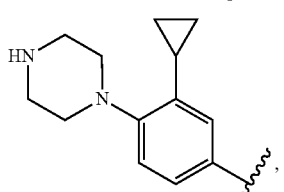,
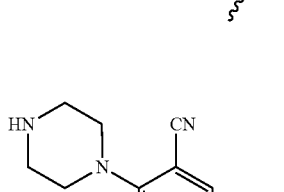,
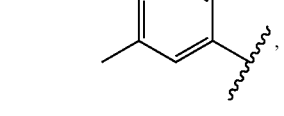
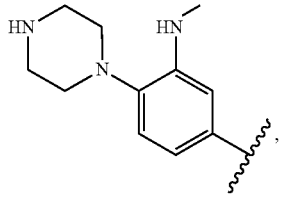, -continued

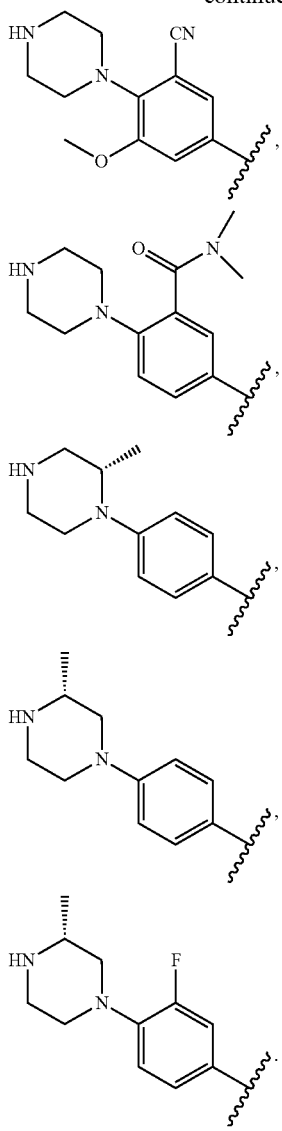

In some embodiments of a compound of Formula (I), X is hydrogen; Y is N; Z is N; $R^{3a}$ and $R^{3b}$ are both hydrogen; $R^4$ is phenyl optionally substituted by halogen; W is

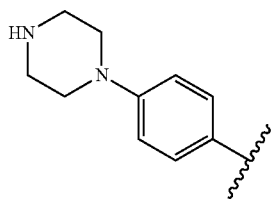 [SMILES: *c1ccc(N2CCNCC2)cc1]

optionally substituted by $R^{17a}$. In some embodiments of a compound of Formula (I), X is hydrogen; Y is N; Z is N; $R^{3a}$ and $R^{3b}$ are both hydrogen; $R^4$ is phenyl optionally substituted by halogen; W is

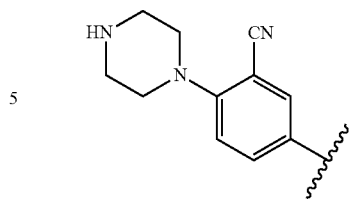

In some embodiments of a compound of Formula (I), (Ia), (Ib), (IIa), (IIb), (IIIa), (IIIb), (IVa) or (IVb), W is AB, wherein A and B are fused together; A is phenyl or 5- to 6-membered heteroaryl, each of which is optionally substituted with $R^{17a}$; B is $C_3$-$C_6$ cycloalkyl, 3- to 7-membered heterocyclyl, 5- to 7-membered heteroaryl, or $C_6$ aryl, each of which is optionally substituted with $R^{17b}$; and wherein A, B, $R^{17a}$, and $R^{17b}$ together are

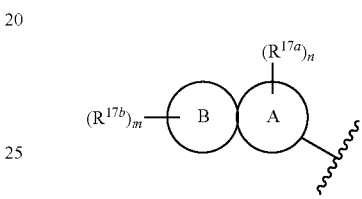

and m and n are independently 0, 1, 2, 3, or 4.

In some embodiments of a compound of Formula (I), (Ia), (Ib), (IIa), (IIb), (IIIa), (IIIb), (IVa) or (IVb), W is AB, wherein A and B are fused together; A is phenyl or 6-membered heteroaryl, each of which is optionally substituted with $R^{17a}$; B is $C_3$-$C_6$ cycloalkyl, 3- to 7-membered heterocyclyl, 5- to 7-membered heteroaryl, or $C_6$ aryl, each of which is optionally substituted with $R^{17b}$; and wherein A, B, $R^{17a}$, and $R^{17b}$ together are

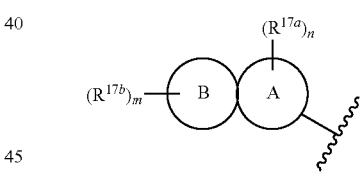

and m and n are independently 0, 1, 2, 3, or 4.

In some embodiments of a compound of Formula (I), (Ia), (Ib), (IIa), (IIb), (IIIa), (IIIb), (IVa) or (IVb), A, B, $R^{17a}$ and $R^{17b}$ together are

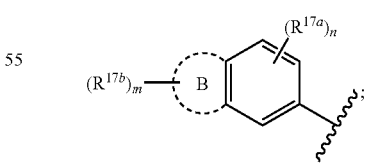

wherein B is $C_3$-$C_6$ cycloalkyl, 3- to 7-membered heterocyclyl, 5- to 7-membered heteroaryl, or $C_6$ aryl and m and n are independently 0, 1, 2, or 3. In some embodiments of a compound of Formula (I), (Ia), (Ib), (IIa), (IIb), (IIIa), (IIIb), (IVa) or (IVb), m is 0. In some embodiments of a compound of Formula (I), (Ia), (Ib), (IIa), (IIb), (IIIa), (IIIb), (IVa) or (IVb), m is 1. In some embodiments of a compound of Formula (I), m is 2. In some embodiments of a compound of Formula (I), (Ia), (Ib), (IIa), (IIb), (IIIa), (IIIb), (IVa) or (IVb), m is 3. In some embodiments of a compound of Formula (I), (Ia), (Ib), (IIa), (IIb), (IIIa), (IIIb), (IVa) or (IVb), m is 4. In some embodiments of a compound of Formula (I), n is 0. In some embodiments of a compound of Formula (I), (Ia), (Ib), (IIa), (IIb), (IIIa), (IIIb), (IVa) or (IVb), n is 1. In some embodiments of a compound of Formula (I), n is 2. In some embodiments of a compound of Formula (I), (Ia), (Ib), (IIa), (IIb), (IIIa), (IIIb), (IVa) or (IVb), n is 3. In some embodiments of a compound of Formula (I), (Ia), (Ib), (IIa), (IIb), (IIIa), (IIIb), (IVa) or (IVb), n is 4. In some embodiments, A, B, $R^{17a}$ and $R^{17b}$ together are

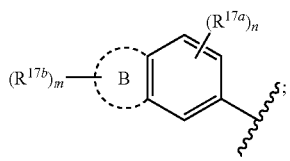

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments, A, B, $R^{17a}$ and $R^{17b}$ together are

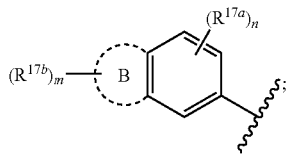

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments, A, B, $R^{17a}$ and $R^{17b}$ together are

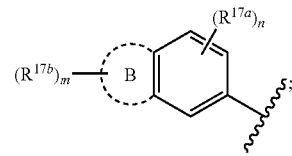

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —C(O)$R^{13}$, or oxo; and each m and n are independently 0, 1, 2, or 3. In some embodiments, A, B, $R^{17a}$ and $R^{17b}$ together are

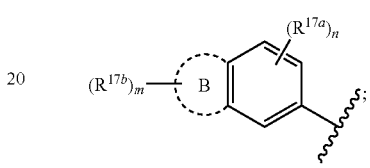

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia), (Ib), (IIa), (IIb), (IIIa), (IIIb), (IVa) or (IVb), A, B, $R^{17a}$ and $R^{17b}$ together are

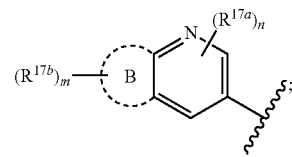

wherein B is $C_3$-$C_6$ cycloalkyl, 3- to 7-membered heterocyclyl, 5- to 7-membered heteroaryl, or $C_6$ aryl; and m and n are independently 0, 1, 2, or 3. In some embodiments of a compound of Formula (I), m is 0. In some embodiments of a compound of Formula (I), (Ia), (Ib), (IIa), (IIb), (IIIa), (IIIb), (IVa) or (IVb), m is 1. In some embodiments of a compound of Formula (I), (Ia), (Ib), (IIa), (IIb), (IIIa), (IIIb), (IVa) or (IVb), m is 2. In some embodiments of a compound of Formula (I), (Ia), (Ib), (IIa), (IIb), (IIIa), (IIIb), (IVa) or (IVb), m is 3. In some embodiments of a compound of Formula (I), m is 4. In some embodiments of a compound of Formula (I), (Ia), (Ib), (IIa), (IIb), (IIIa), (IIIb), (IVa) or (IVb), n is 0. In some embodiments of a compound of Formula (I), (Ia), (Ib), (IIa), (IIb), (IIIa), (IIIb), (IVa) or (IVb), n is 1. In some embodiments of a compound of Formula (I), (Ia), (Ib), (IIa), (IIb), (IIIa), (IIIb), (IVa) or (IVb), n is 2. In some embodiments of a compound of Formula (I), (Ia), (Ib), (IIa), (IIb), (IIIa), (IIIb), (IVa) or (IVb), n is 3. In some embodiments of a compound of Formula (I), (Ia), (Ib), (IIa), (IIb), (IIIa), (IIIb), (IVa) or (IVb), n is 4. In some embodiments, A, B, $R^{17a}$ and $R^{17b}$ together are

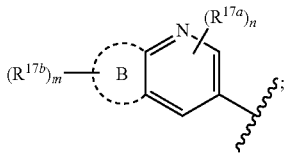

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments, A, B, $R^{17a}$ and $R^{17b}$ together are

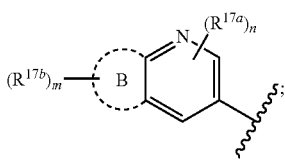

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments, A, B, $R^{17a}$ and $R^{17b}$ together are

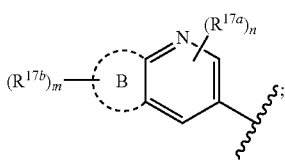

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —C(O)$R^{13}$, or oxo; and each m and n are independently 0, 1, 2, or 3. In some embodiments, A, B, $R^{17a}$ and $R^{17b}$ together are

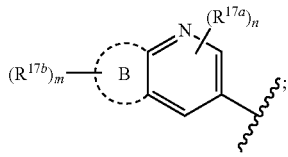

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia), (Ib), (IIa), (IIb), (IIIa), (IIIb), (IVa) or (IVb), A, B, $R^{17a}$ and $R^{17b}$ together are

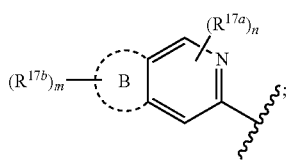

wherein B is $C_3$-$C_6$ cycloalkyl, 3- to 7-membered heterocyclyl, 5- to 7-membered heteroaryl, or $C_6$ aryl; and m and n are independently 0, 1, 2, or 3. In some embodiments of a compound of Formula (I), (Ia), (Ib), (IIa), (IIb), (IIIa), (IIIb), (IVa) or (IVb), m is 0. In some embodiments of a compound of Formula (I), m is 1. In some embodiments of a compound of Formula (I), (Ia), (Ib), (IIa), (IIb), (IIIa), (IIIb), (IVa) or (IVb), m is 2. In some embodiments of a compound of Formula (I), (Ia), (Ib), (IIa), (IIb), (IIIa), (IIIb), (IVa) or (IVb), m is 3. In some embodiments of a compound of Formula (I), m is 4. In some embodiments of a compound of Formula (I), (Ia), (Ib), (IIa), (IIb), (IIIa), (IIIb), (IVa) or (IVb), n is 0. In some embodiments of a compound of Formula (I), (Ia), (Ib), (IIa), (IIb), (IIIa), (IIIb), (IVa) or (IVb), n is 1. In some embodiments of a compound of Formula (I), (Ia), (Ib), (IIa), (IIb), (IIIa), (IIIb), (IVa) or (IVb), n is 2. In some embodiments of a compound of Formula (I), (Ia), (Ib), (IIa), (IIb), (IIIa), (IIIb), (IVa) or (IVb), n is 3. In some embodiments of a compound of Formula (I), (Ia), (Ib), (IIa), (IIb), (IIIa), (IIIb), (IVa) or (IVb), n is 4. In some embodiments, A, B, $R^{17a}$ and $R^{17b}$ together are

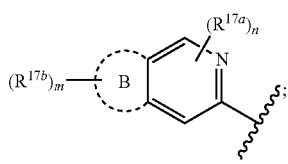

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$;

or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments, A, B, $R^{17a}$ and $R^{17b}$ together are

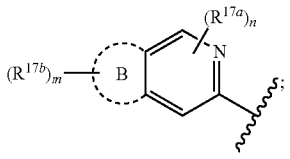

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments, A, B, $R^{17a}$ and $R^{17b}$ together are

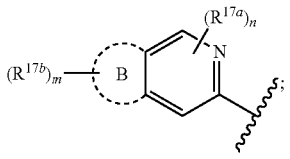

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —C(O)$R^{13}$, or oxo; and each m and n are independently 0, 1, 2, or 3. In some embodiments, A, B, $R^{17a}$ and $R^{17b}$ together are

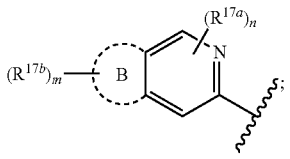

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia), (Ib), (IIa), (IIb), (IIIa), (IIIb), (IVa) or (IVb), A, B, $R^{17a}$ and $R^{17b}$ together are

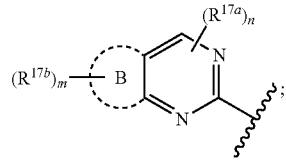

wherein B is $C_3$-$C_6$ cycloalkyl, 3- to 7-membered heterocyclyl, 5- to 7-membered heteroaryl, or $C_6$ aryl; and m and n are independently 0, 1, 2, or 3. In some embodiments of a compound of Formula (I), (Ia), (Ib), (IIa), (IIb), (IIIa), (IIIb), (IVa) or (IVb), m is 0. In some embodiments of a compound of Formula (I), (Ia), (Ib), (IIa), (IIb), (IIIa), (IIIb), (IVa) or (IVb), m is 1. In some embodiments of a compound of Formula (I), (Ia), (Ib), (IIa), (IIb), (IIIa), (IIIb), (IVa) or (IVb), m is 2. In some embodiments of a compound of Formula (I), (Ia), (Ib), (IIa), (IIb), (IIIa), (IIIb), (IVa) or (IVb), m is 3. In some embodiments of a compound of Formula (I), (Ia), (Ib), (IIa), (IIb), (IIIa), (IIIb), (IVa) or (IVb), m is 4. In some embodiments of a compound of Formula (I), (Ia), (Ib), (IIa), (IIb), (IIIa), (IIIb), (IVa) or (IVb), n is 0. In some embodiments of a compound of Formula (I), (Ia), (Ib), (IIa), (IIb), (IIIa), (IIIb), (IVa) or (IVb), n is 1. In some embodiments of a compound of Formula (I), (Ia), (Ib), (IIa), (IIb), (IIIa), (IIIb), (IVa) or (IVb), n is 2. In some embodiments of a compound of Formula (I), (Ia), (Ib), (IIa), (IIb), (IIIa), (IIIb), (IVa) or (IVb), n is 3. In some embodiments of a compound of Formula (I), (Ia), (Ib), (IIa), (IIb), (IIIa), (IIIb), (IVa) or (IVb), n is 4. In some embodiments, A, B, $R^{17a}$ and $R^{17b}$ together are

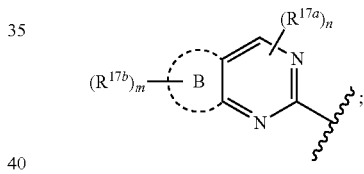

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments, A, B, $R^{17a}$ and $R^{17b}$ together are

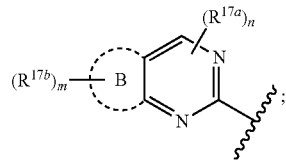

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments, A, B, $R^{17a}$ and $R^{17b}$ together are

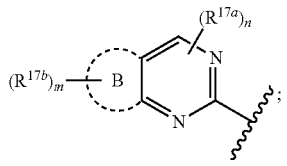

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —C(O)$R^{13}$, or oxo; and each m and n are independently 0, 1, 2, or 3. In some embodiments, A, B, $R^{17a}$ and $R^{17b}$ together are

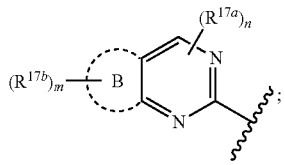

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia), (Ib), (IIa), (IIb), (IIIa), (IIIb), (IVa) or (IVb), A, B, $R^{17a}$ and $R^{17b}$ together are

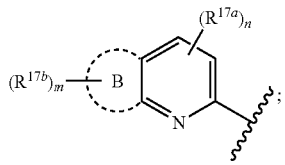

wherein B is $C_3$-$C_6$ cycloalkyl, 3- to 7-membered heterocyclyl, 5- to 7-membered heteroaryl, or $C_6$ aryl; and m and n are independently 0, 1, 2, or 3. In some embodiments of a compound of Formula (I), (Ia), (Ib), (IIa), (IIb), (IIIa), (IIIb), (IVa) or (IVb), m is 0. In some embodiments of a compound of Formula (I), (Ia), (Ib), (IIa), (IIb), (IIIa), (IIIb), (IVa) or (IVb), m is 1. In some embodiments of a compound of Formula (I), (Ia), (Ib), (IIa), (IIb), (IIIa), (IIIb), (IVa) or (IVb), m is 2. In some embodiments of a compound of Formula (I), (Ia), (Ib), (IIa), (IIb), (IIIa), (IIIb), (IVa) or (IVb), m is 3. In some embodiments of a compound of Formula (I), (Ia), (Ib), (IIa), (IIb), (IIIa), (IIIb), (IVa) or (IVb), m is 4. In some embodiments of a compound of Formula (I), (Ia), (Ib), (IIa), (IIb), (IIIa), (IIIb), (IVa) or (IVb), n is 0. In some embodiments of a compound of Formula (I), (Ia), (Ib), (IIa), (IIb), (IIIa), (IIIb), (IVa) or (IVb), n is 1. In some embodiments of a compound of Formula (I), n is 2. In some embodiments of a compound of Formula (I), (Ia), (Ib), (IIa), (IIb), (IIIa), (IIIb), (IVa) or (IVb), n is 3. In some embodiments of a compound of Formula (I), (Ia), (Ib), (IIa), (IIb), (IIIa), (IIIb), (IVa) or (IVb), n is 4. In some embodiments, A, B, $R^{17a}$ and $R^{17b}$ together are


wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments, A, B, $R^{17a}$ and $R^{17b}$ together are

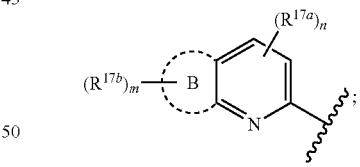

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments, A, B, $R^{17a}$ and $R^{17b}$ together are

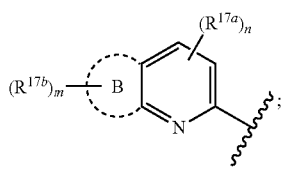

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —C(O)$R^{13}$, or oxo; and each m and n are independently 0, 1, 2, or 3. In some embodiments, A, B, $R^{17a}$ and $R^{17b}$ together are

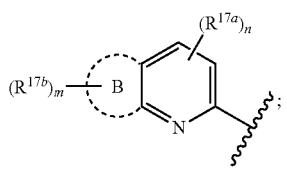

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia), (Ib), (IIa), (IIb), (IIIa), (IIIb), (IVa) or (IVb), W is AB, wherein A and B are fused together and AB is selected from the group consisting of:

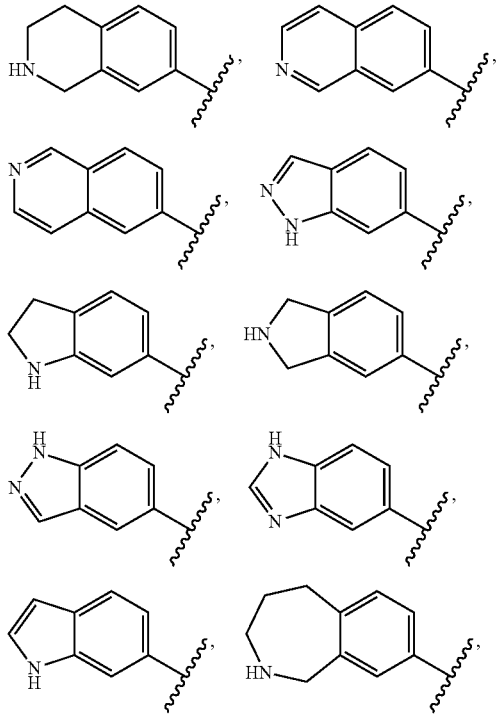

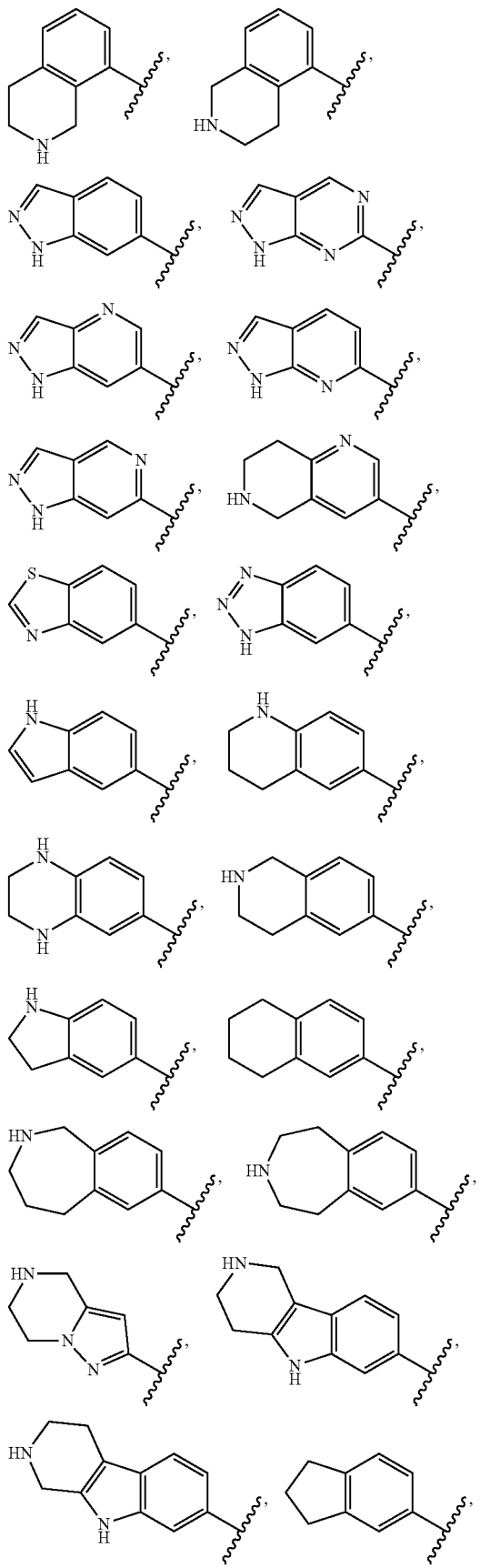

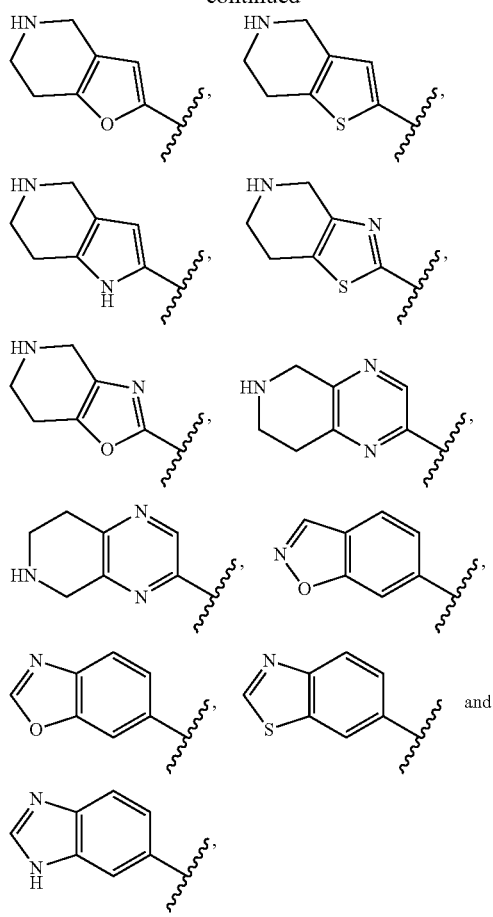

wherein the wavy lines denote attachment points to the parent molecule and each is optionally substituted by $R^{17a}$ and $R^{17b}$.

In some embodiments of a compound of Formula (I), W is AB, wherein A and B are fused together and AB is selected from the group consisting of:

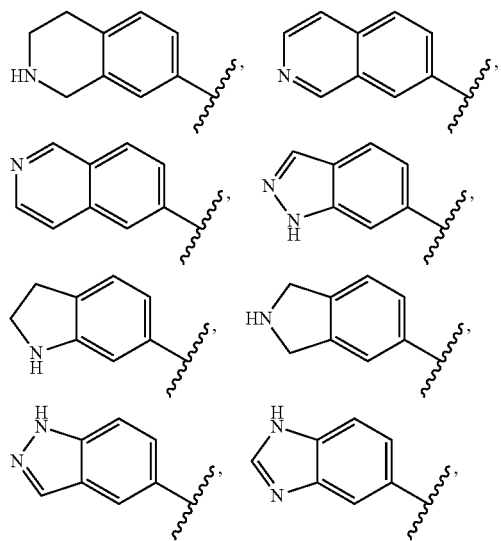

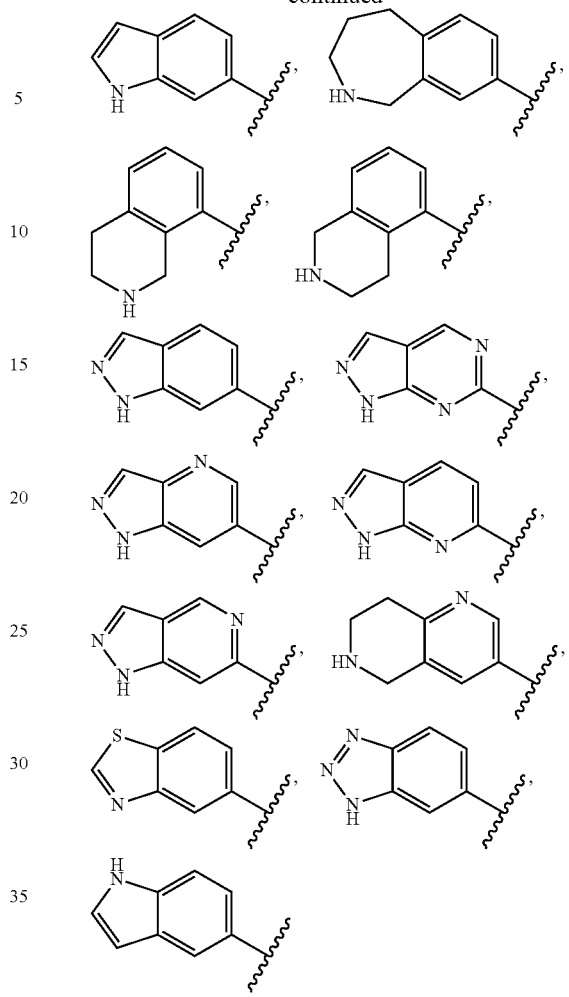

wherein the wavy lines denote attachment points to the parent molecule and each is optionally substituted by $R^{17a}$ and $R^{17b}$. In some embodiments, AB is

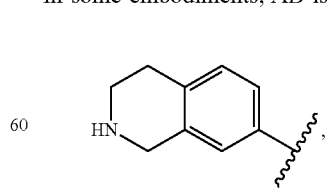

wherein the wavy line denotes attachment point to the parent molecule and AB is optionally substituted by $R^{17a}$ and $R^{17b}$. In some embodiments, AB is wherein the wavy line denotes attachment points to the parent molecule and AB is substituted by $C_1$-$C_6$ alkyl. In some embodiments, A, B, $R^{17a}$, and $R^{17b}$ together are

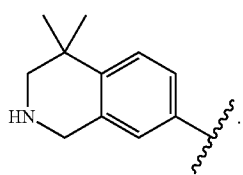 [SMILES: *c1ccc2c(c1)CNCC2(C)C]
In some embodiments of a compound of Formula (I), (Ia), (Ib), (IIa), (IIb), (IIIa), (IIIb), (IVa) or (IVb), W is selected from the group consisting of:
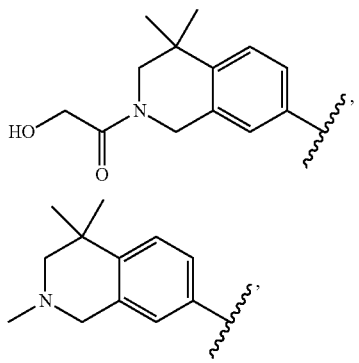
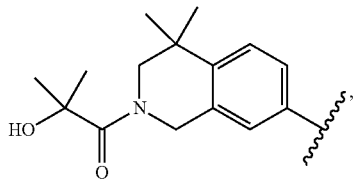
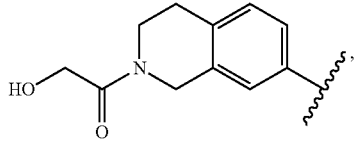
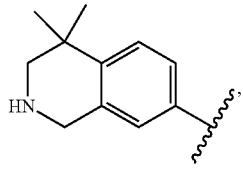
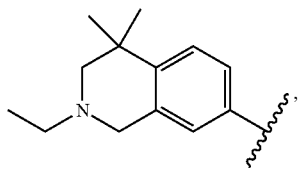
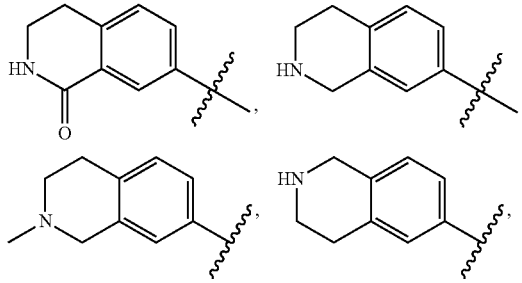
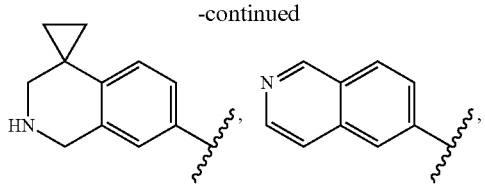
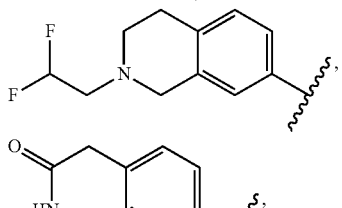
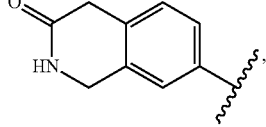
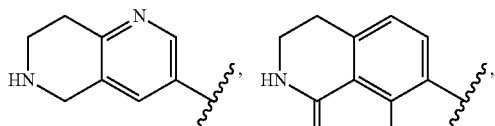
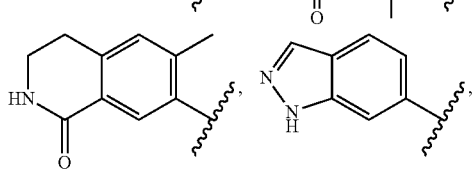
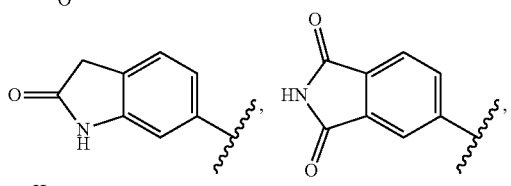
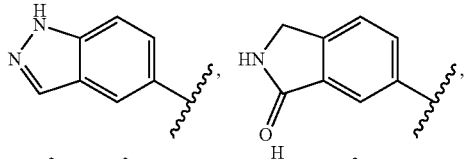
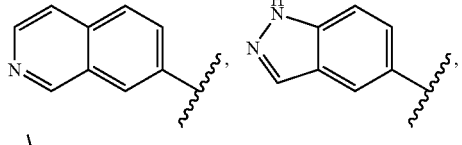
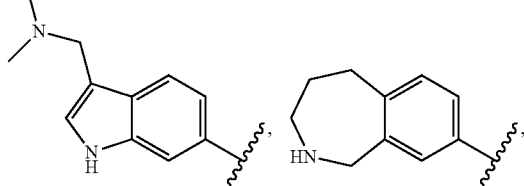
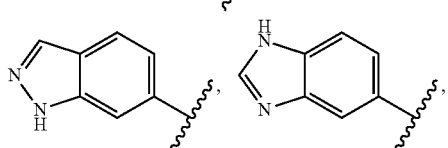
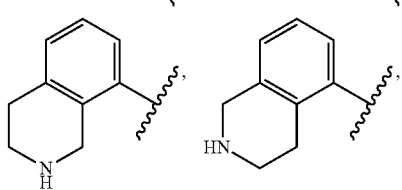

121
-continued
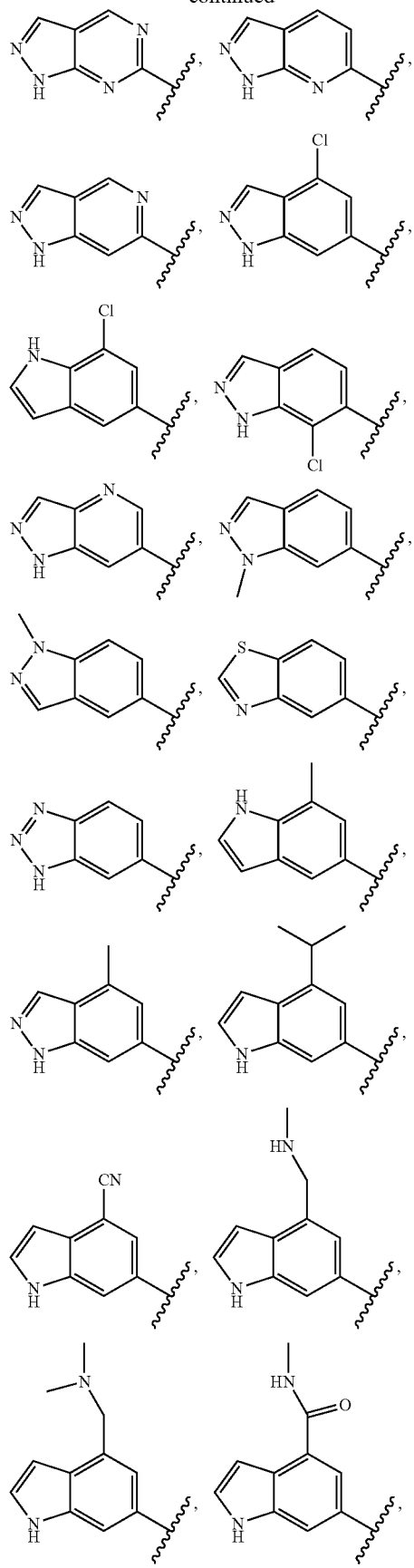
122
-continued
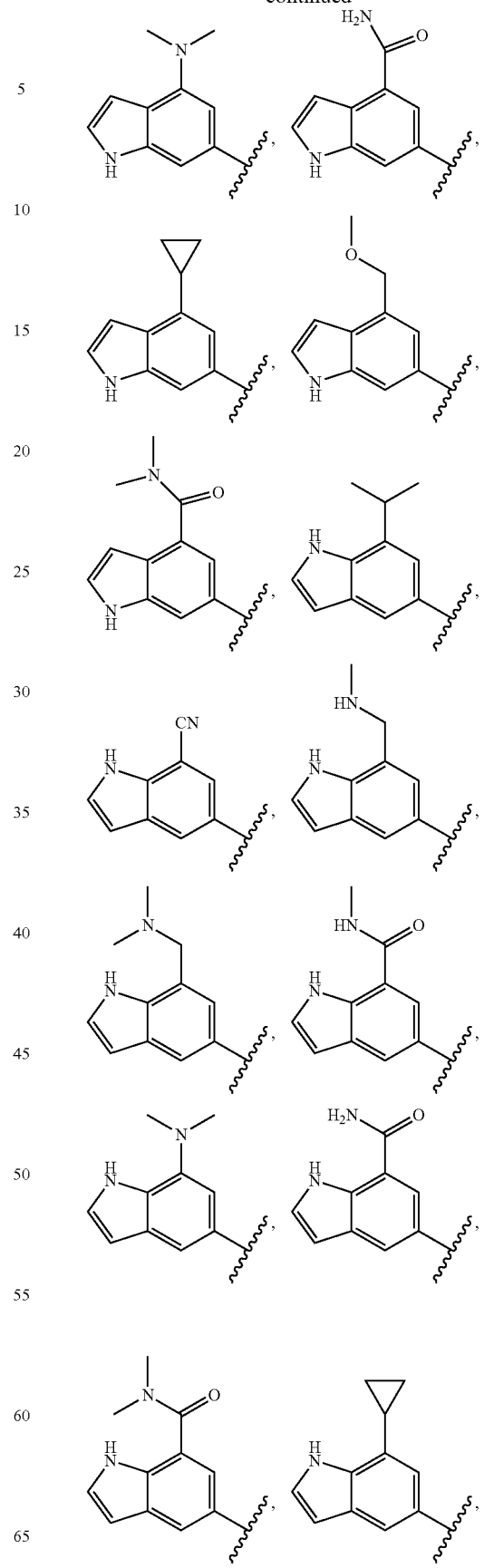

123
-continued
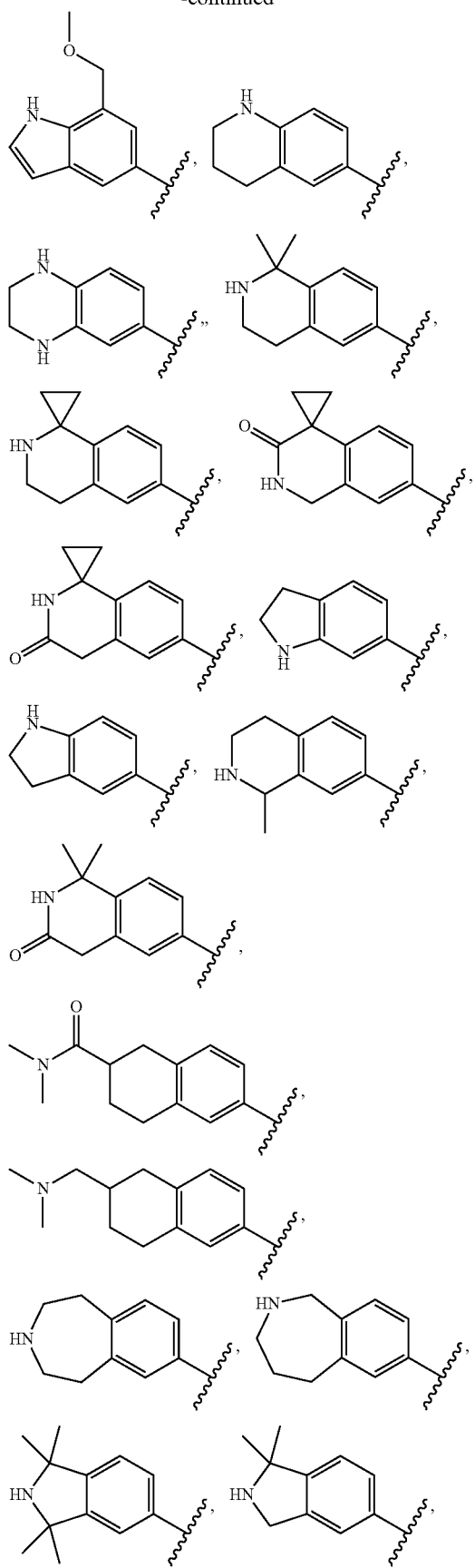
124
-continued
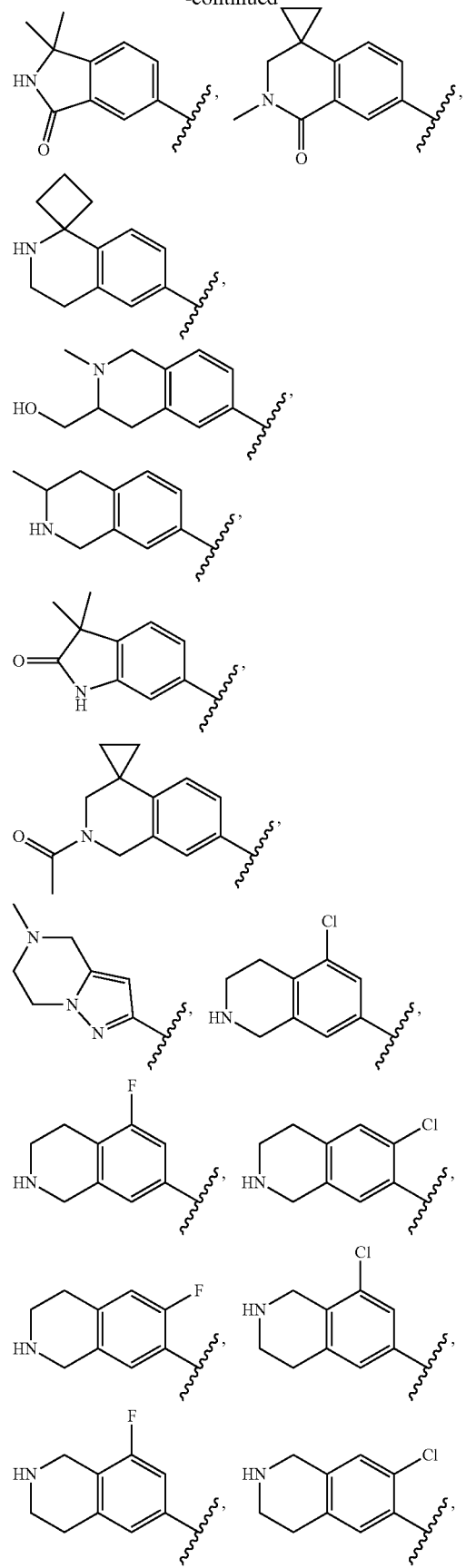

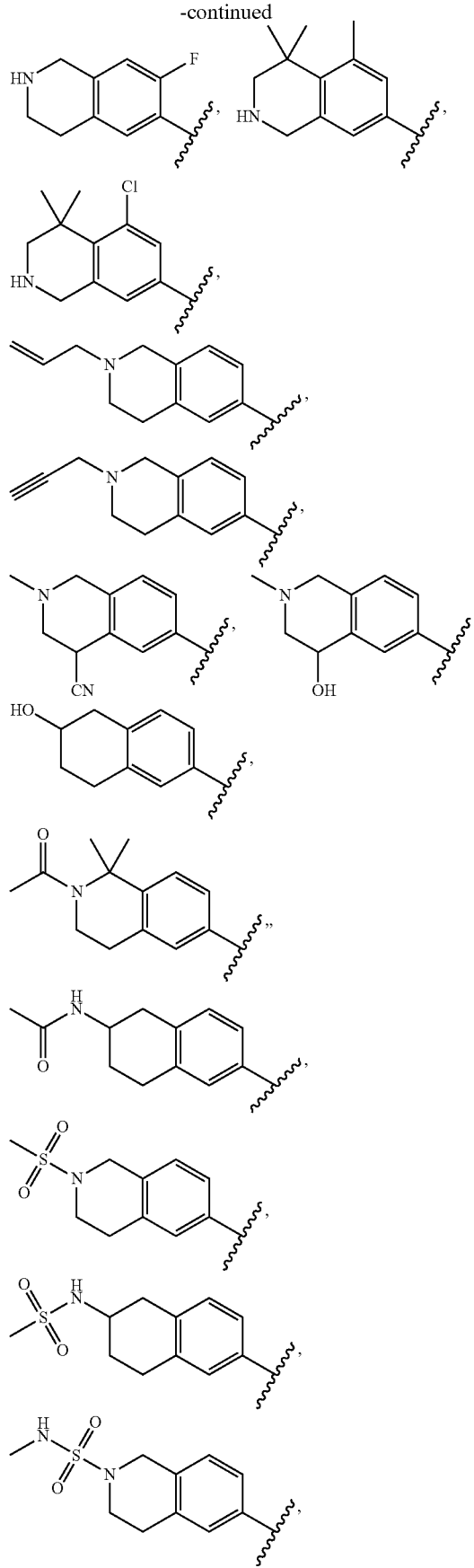
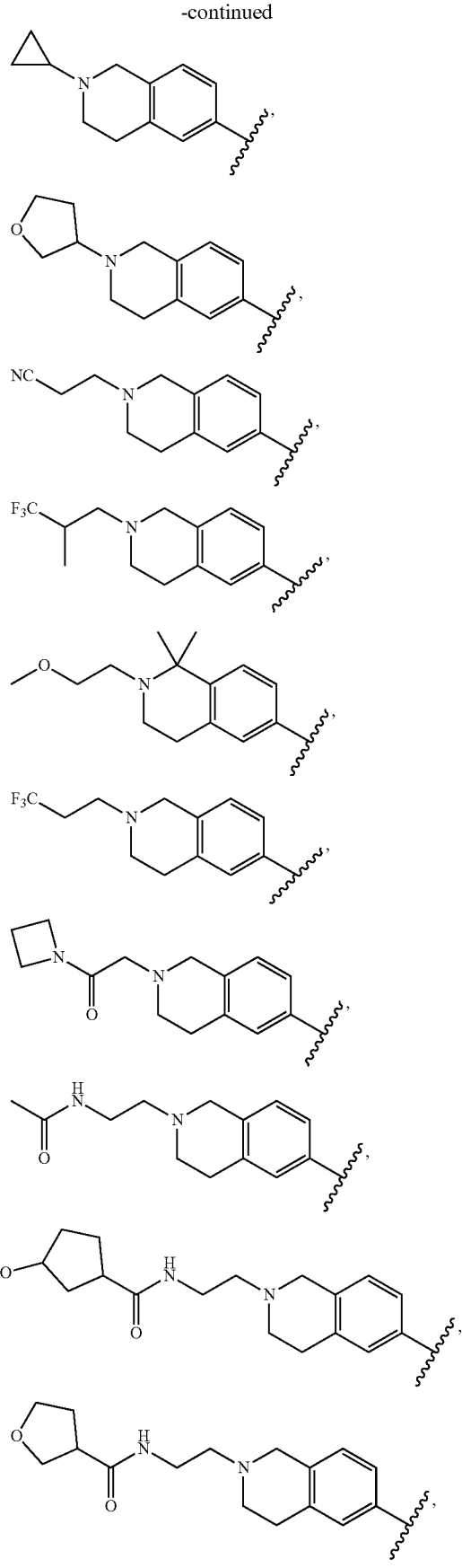

127
-continued
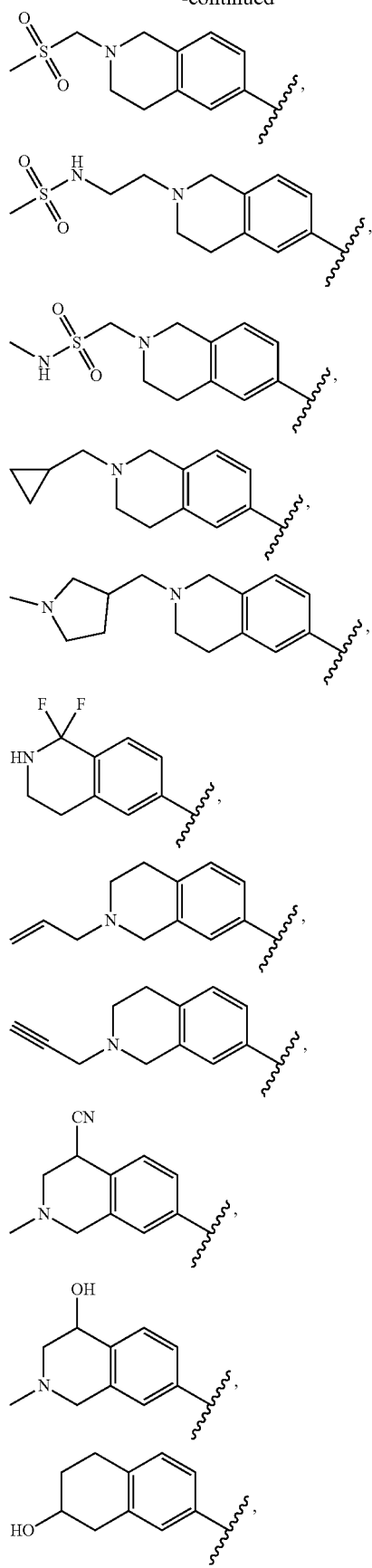
128
-continued
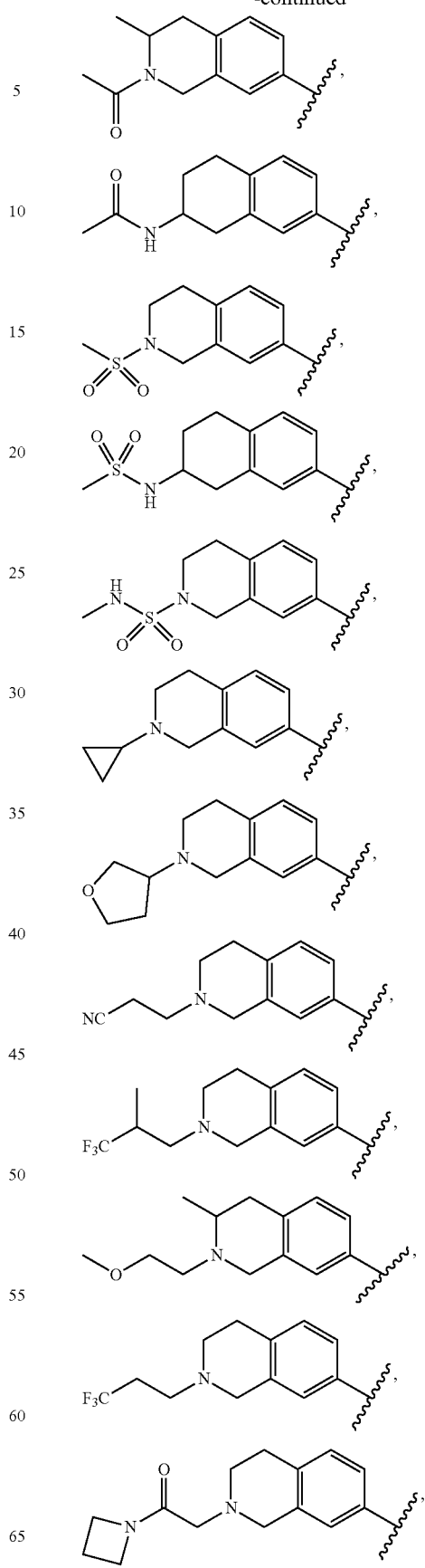

-continued
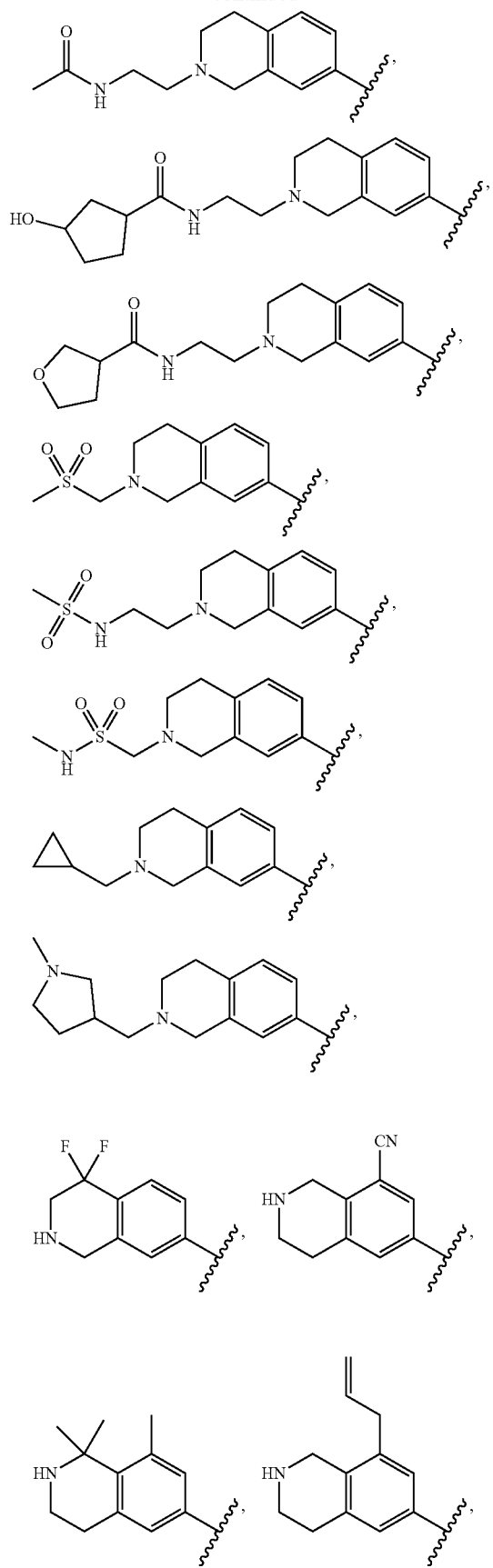
-continued
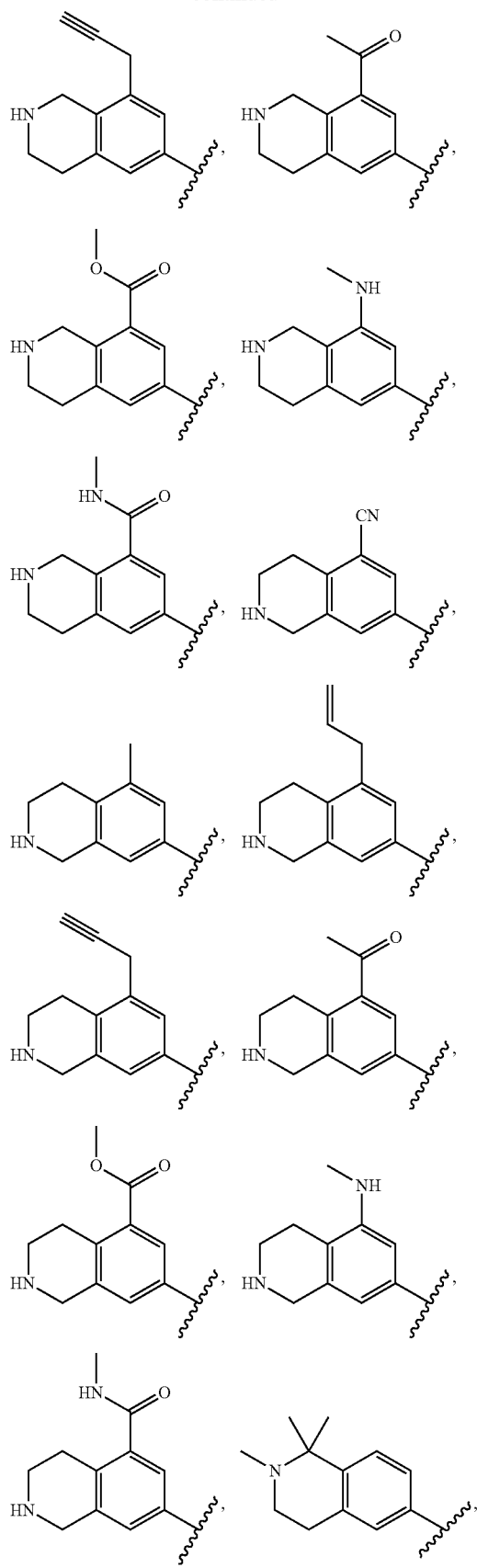

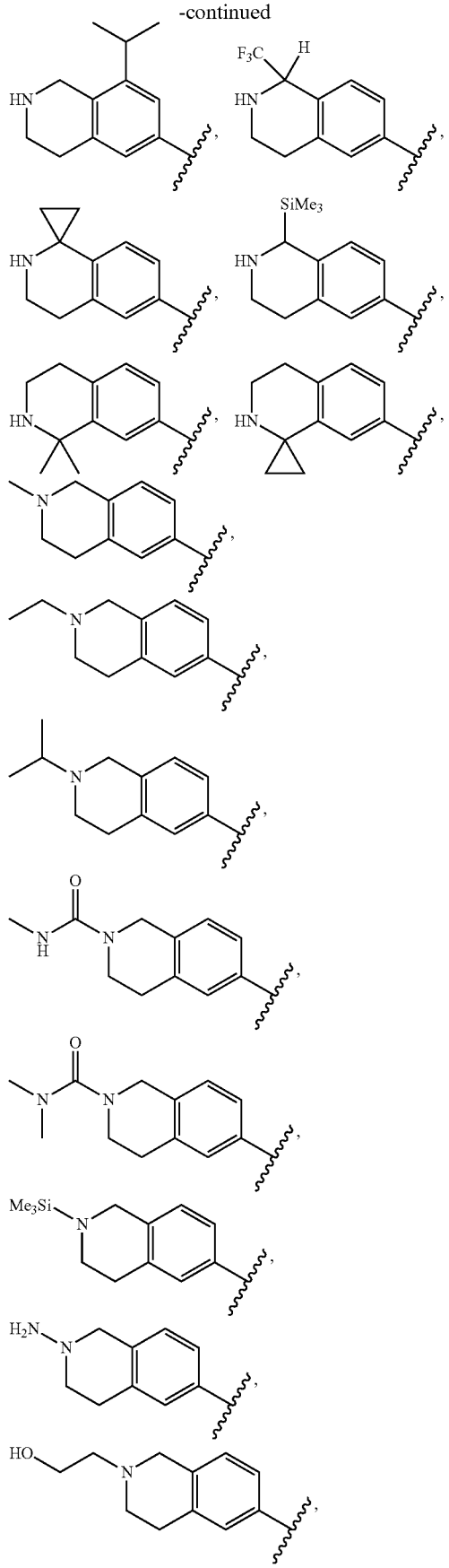
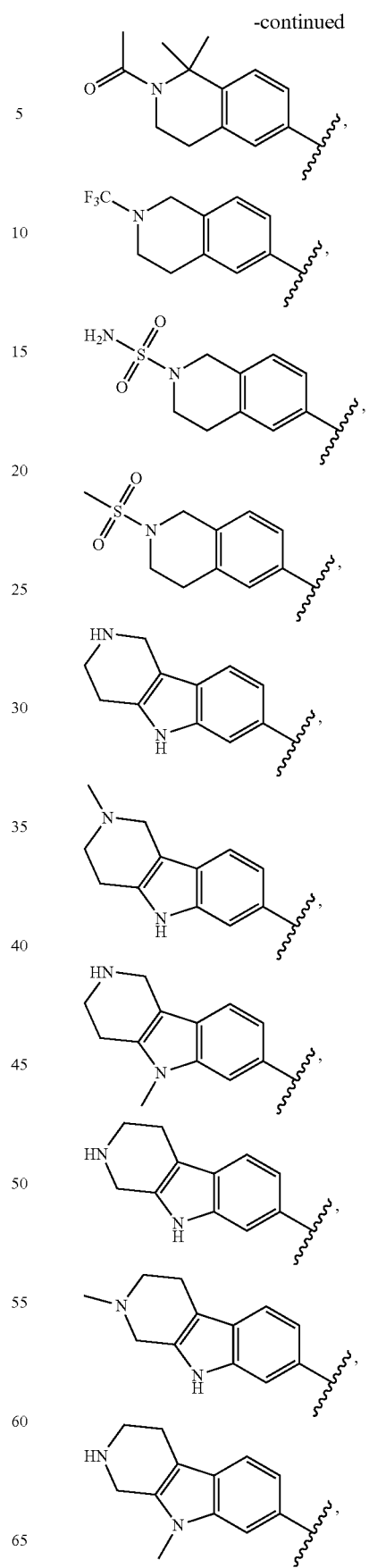

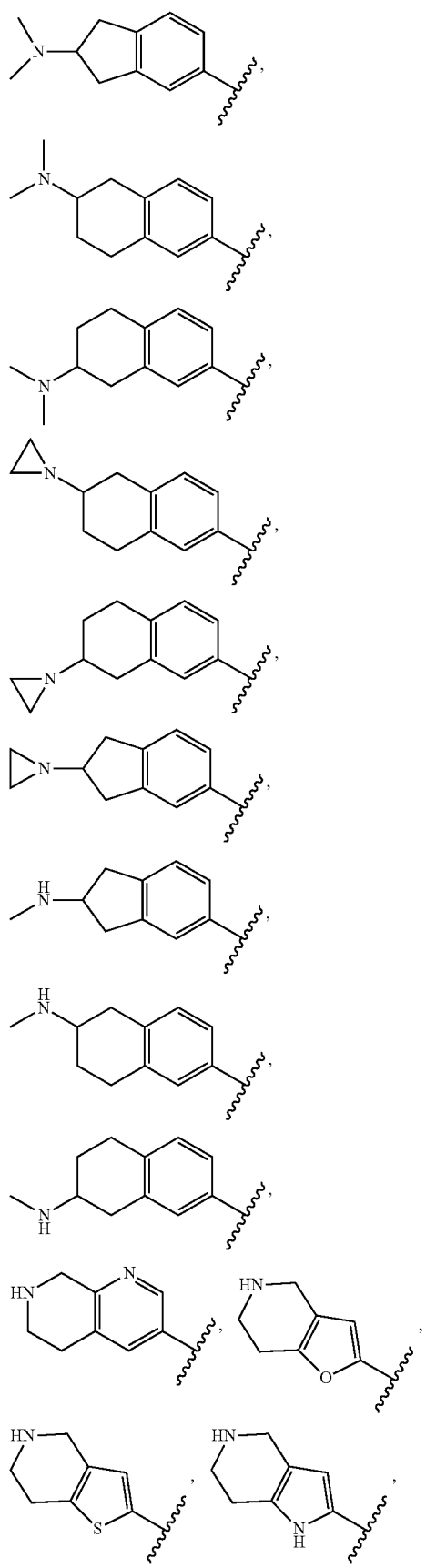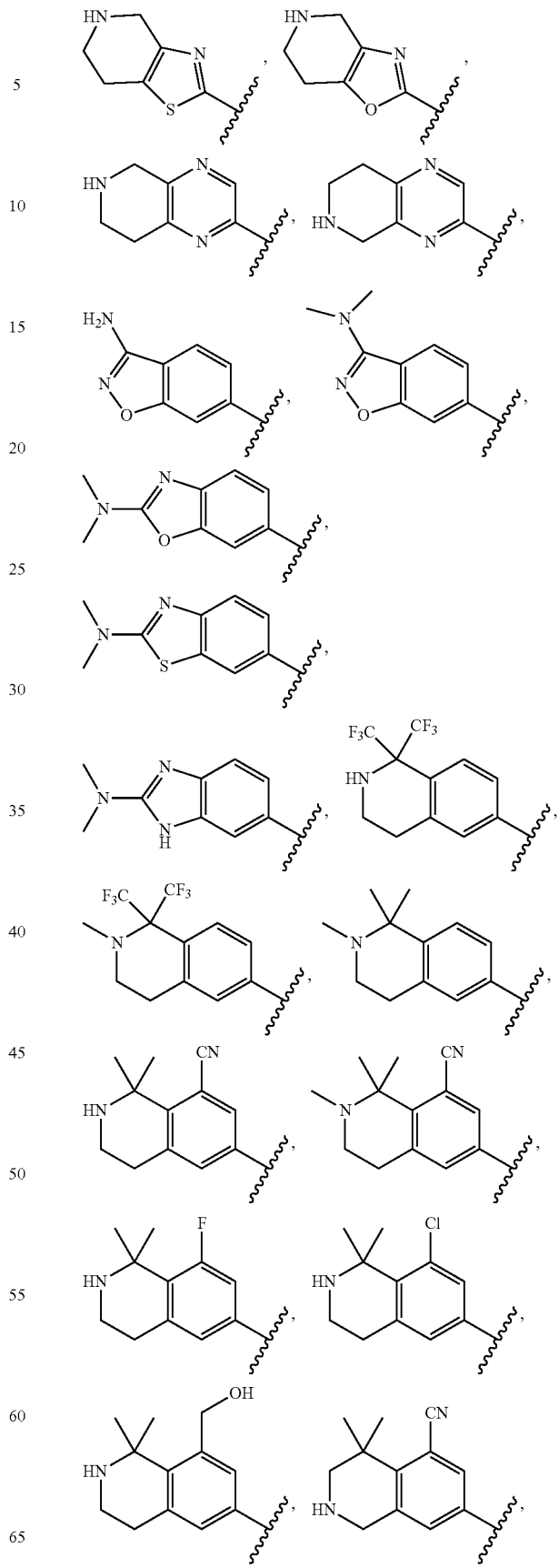

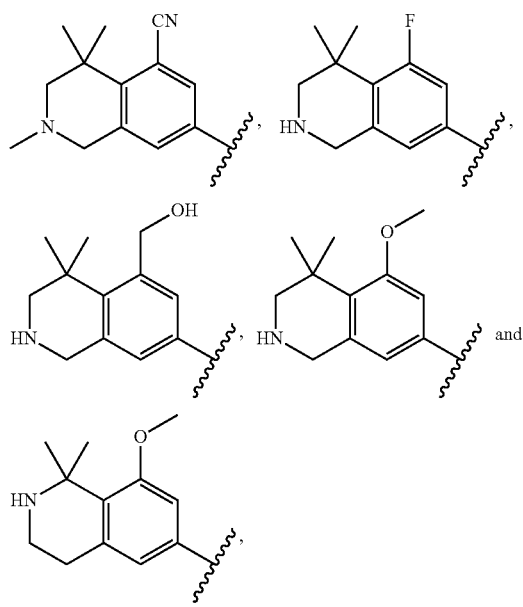
wherein the wavy lines denote attachment points to the parent molecule.
In some embodiments of a compound of Formula (I), (Ia), (Ib), (IIa), (IIb), (IIIa), (IIIb), (IVa) or (IVb), W is selected from the group consisting of:
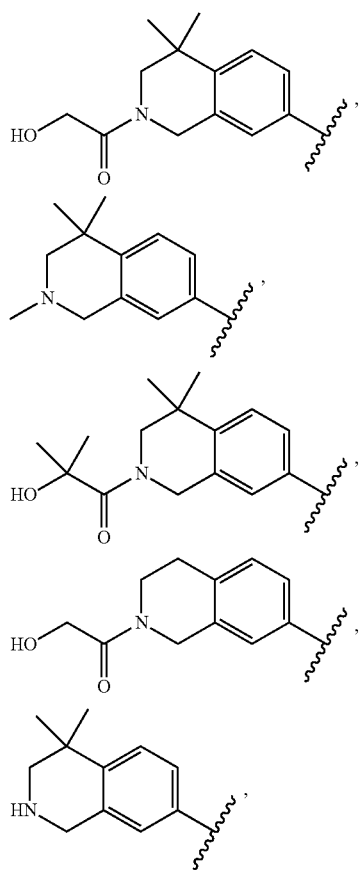
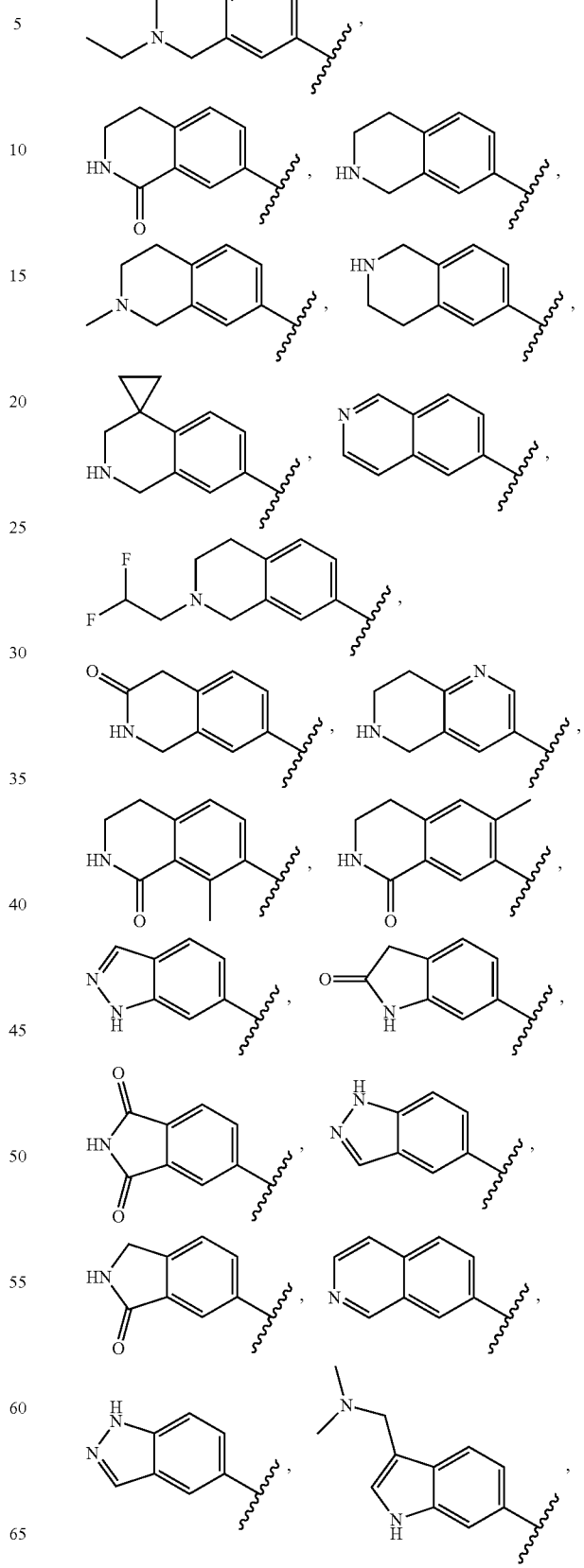

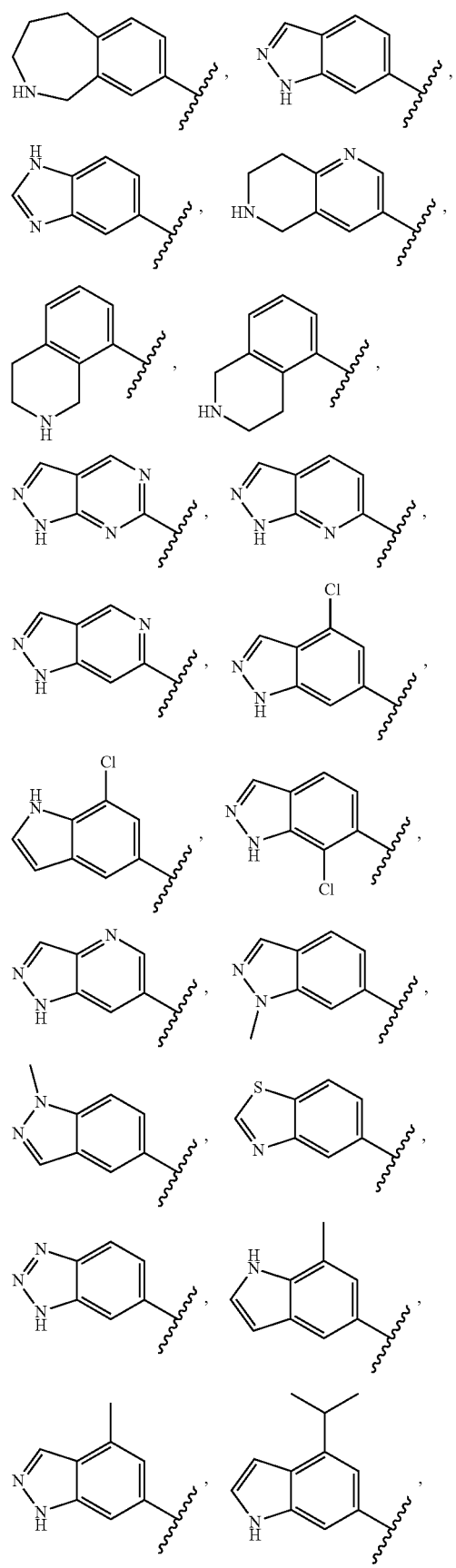
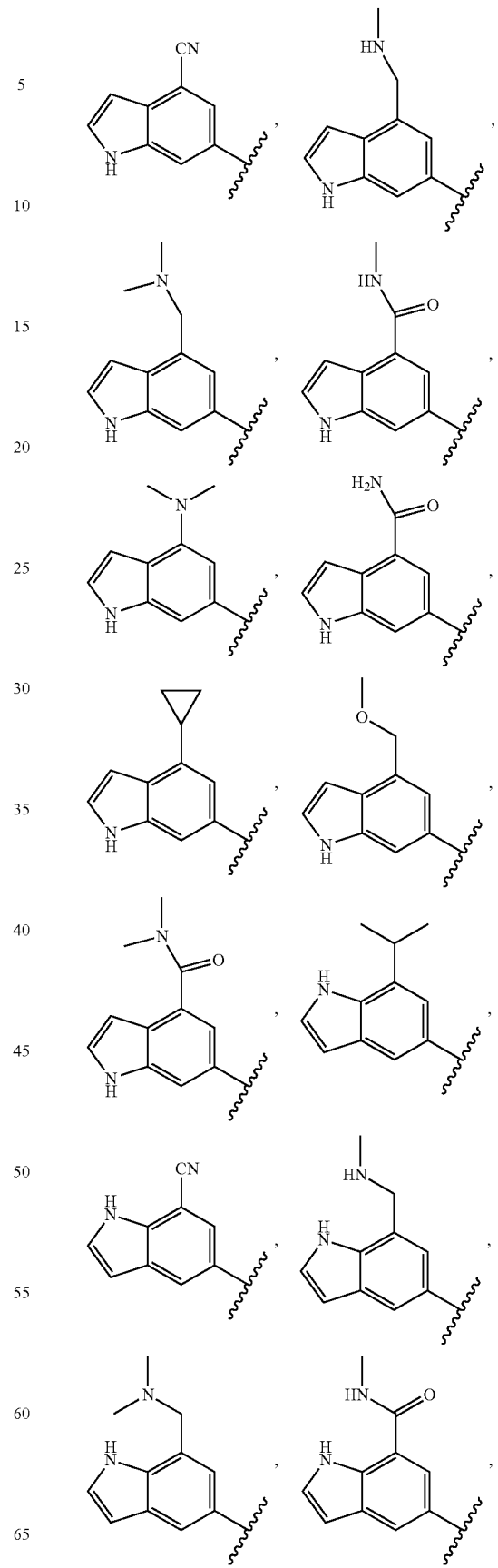

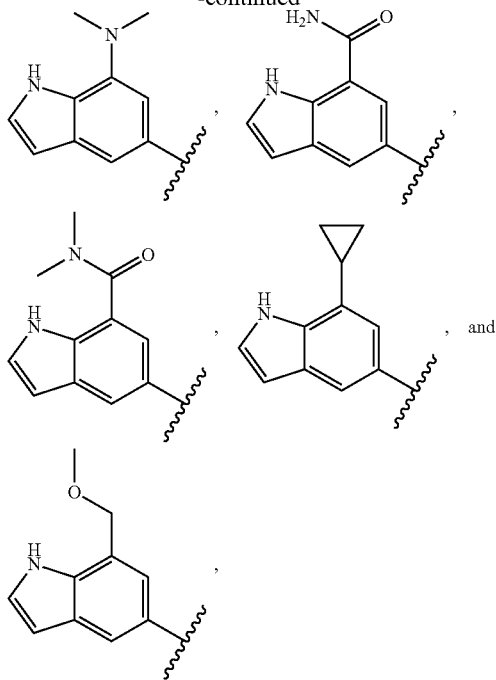

wherein the wavy lines denote attachment points to the parent molecule.

It is understood that each description of AB may be combined with each description of X, Y, Z, $R^1$, $R^2$, $R^{3a}$, $R^{3b}$, and $R^4$. For example, in one aspect, it is understood that each description of AB may be combined in one aspect with a variation in which X is hydrogen, Y is N, Z is N, $R^{3a}$ is hydrogen, $R^{3b}$ is hydrogen, and $R^4$ is 2,6-dichlorophenyl.

In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —C(O)$R^{13}$, —$OR^{13}$, or $C_1$-$C_6$ alkyl optionally substituted by —OH; W is

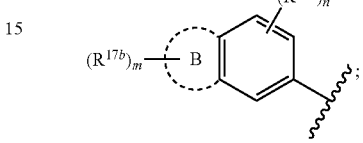

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —C(O)$R^{13}$, —$OR^{13}$, or $C_1$-$C_6$ alkyl optionally substituted by —OH; W is

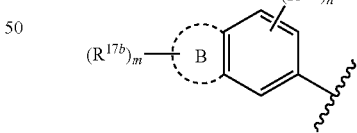

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is $C_6$-$C_{14}$ aryl optionally substituted by halogen, —CN, —$NR^{13}R^{14}$, —C(O)$R^{13}$, —$OR^{13}$, or $C_1$-$C_6$ alkyl optionally substituted by —OH; W is

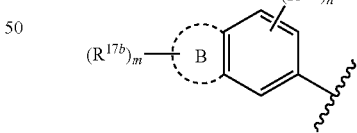

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —C(O)$R^{13}$, or oxo; and each m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; $R^4$ is phenyl optionally substituted by halogen, —CN, —$NR^{13}R^{14}$, —C(O)$R^{13}$, —$OR^{13}$, or $C_1$-$C_6$ alkyl optionally substituted by —OH; W is

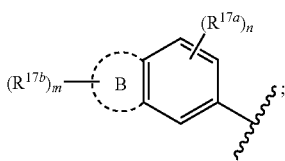

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —NR$^{13}$R$^{14}$, —C(O)R$^{13}$, —OR$^{13}$, or $C_1$-$C_6$ alkyl optionally substituted by —OH; W is

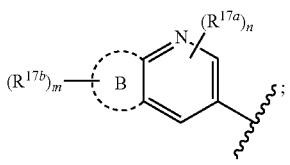

wherein B is $C_3$-$C_6$ cycloalkyl, 3- to 7-membered heterocyclyl, 5- to 7-membered heteroaryl, or $C_6$ aryl; each $R^{17a}$ is independently —(C$_1$-C$_3$ alkylene)OR$^{10}$, $C_1$-$C_6$ alkyl optionally substituted by halogen, —C(O)NR$^{11}$R$^{12}$, —(C$_1$-C$_3$ alkylene)NR$^{11}$R$^{12}$, —CN, halogen, —NR$^{11}$R$^{12}$, $C_3$-$C_6$ cycloalkyl, or —OR$^{10}$; each $R^{17b}$ is independently oxo, —(C$_1$-C$_3$ alkylene)OR$^{10}$, $C_1$-$C_6$ alkyl optionally substituted by halogen, —C(O)NR$^{11}$R$^{12}$, —(C$_1$-C$_3$ alkylene)NR$^{11}$R$^{12}$, —CN, halogen, —NR$^{11}$R$^{12}$, $C_3$-$C_6$ cycloalkyl, or —OR$^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by R$^{10}$; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —NR$^{13}$R$^{14}$, —C(O)R$^{13}$, —OR$^{13}$, or $C_1$-$C_6$ alkyl optionally substituted by —OH; W is

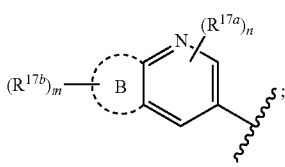

wherein B is $C_3$-$C_6$ cycloalkyl, 3- to 7-membered heterocyclyl, 5- to 7-membered heteroaryl, or $C_6$ aryl; each $R^{17a}$ is independently —(C$_1$-C$_3$ alkylene)OR$^{10}$, $C_1$-$C_6$ alkyl optionally substituted by halogen, —C(O)NR$^{11}$R$^{12}$, —(C$_1$-C$_3$ alkylene)NR$^{11}$R$^{12}$, —CN, halogen, —NR$^{11}$R$^{12}$, $C_3$-$C_6$ cycloalkyl, or —OR$^{10}$; each $R^{17b}$ is independently oxo, —(C$_1$-C$_3$ alkylene)OR$^{10}$, $C_1$-$C_6$ alkyl optionally substituted by halogen, —C(O)NR$^{11}$R$^{12}$, —(C$_1$-C$_3$ alkylene)NR$^{11}$R$^{12}$, —CN, halogen, —NR$^{11}$R$^{12}$, $C_3$-$C_6$ cycloalkyl, or —OR$^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is $C_6$-$C_{14}$ aryl optionally substituted by halogen, —CN, —NR$^{13}$R$^{14}$, —C(O)R$^{13}$, —OR$^{13}$, or $C_1$-$C_6$ alkyl optionally substituted by —OH; W is

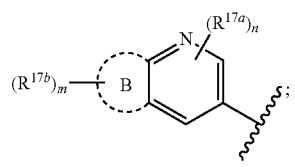

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —C(O)R$^{13}$ or oxo; and each m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; $R^4$ is phenyl optionally substituted by halogen, —CN, —NR$^{13}$R$^{14}$, —C(O)R$^{13}$, —OR$^{13}$ or $C_1$-$C_6$ alkyl optionally substituted by —OH; A, B, $R^{17a}$ and $R^{17b}$ are

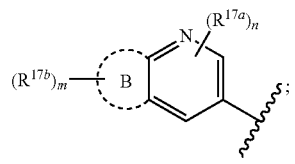

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —NR$^{13}$R$^{14}$, —C(O)R$^{13}$, —OR$^{13}$, or $C_1$-$C_6$ alkyl optionally substituted by —OH; W is

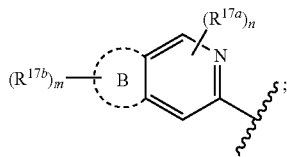

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —C(O)$R^{13}$, —$OR^{13}$, or $C_1$-$C_6$ alkyl optionally substituted by —OH; W is

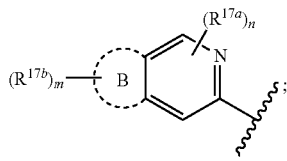

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is $C_6$-$C_{14}$ aryl optionally substituted by halogen, —CN, —$NR^{13}R^{14}$, —C(O)$R^{13}$, —$OR^{13}$, or $C_1$-$C_6$ alkyl optionally substituted by —OH; W is

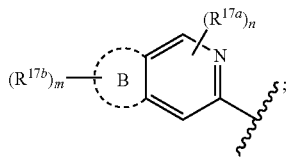

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —C(O)$R^{13}$, or oxo; and each m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; $R^4$ is phenyl optionally substituted by halogen, —CN, —$NR^{13}R^{14}$, —C(O)$R^{13}$, —$OR^{13}$, or $C_1$-$C_6$ alkyl optionally substituted by —OH; W is

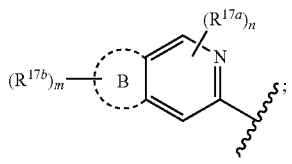

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —C(O)$R^{13}$, —$OR^{13}$, or $C_1$-$C_6$ alkyl optionally substituted by —OH; W is

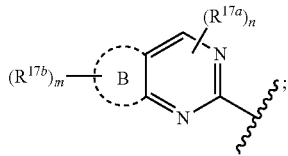

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH; W is

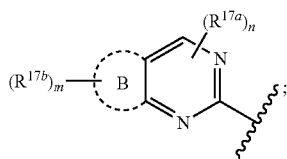

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —$C(O)NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —$C(O)NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is $C_6$-$C_{14}$ aryl optionally substituted by halogen, —CN, —$NR^{13}R^{14}$, —$C(O)R^{13}$, —$OR^{13}$, or $C_1$-$C_6$ alkyl optionally substituted by —OH; W is

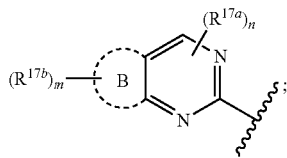

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —$C(O)R^{13}$, or oxo; and each m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; $R^4$ is phenyl optionally substituted by halogen, —CN, —$NR^{13}R^{14}$, —$C(O)R^{13}$, —$OR^{13}$, or $C_1$-$C_6$ alkyl optionally substituted by —OH; W is

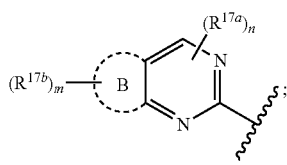

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH; W is

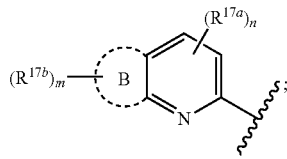

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —$C(O)NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —$C(O)NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom or two different carbon atoms, are taken together with the carbon or carbons to which they are attached to form a $C_3$-$C_6$ cycloalkyl or 3- to 7-membered heterocyclyl, each is optionally substituted by $R^{10}$; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is 5- to 10-membered heteroaryl or $C_6$-$C_{14}$ aryl, each of which is optionally substituted by halogen, —CN, —$NR^{13}R^{14}$, —$C(O)R^{13}$, —$OR^{13}$, or $C_1$-$C_6$ alkyl optionally substituted by —OH; W is

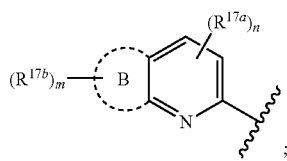

wherein B is $C_3$-$C_6$ cycloalkyl, 3- to 7-membered heterocyclyl, 5- to 7-membered heteroaryl, or $C_6$ aryl; each $R^{17a}$ is independently —($C_1$-$C_3$ alkylene)$OR^{10}$, $C_1$-$C_6$ alkyl optionally substituted by halogen, —$C(O)NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; each $R^{17b}$ is independently oxo, —($C_1$-$C_3$ alkylene)$OR^{10}$, $C_1$-$C_6$ alkyl optionally substituted by halogen, —$C(O)NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$; or any two groups $R^{17b}$, when bound to the same carbon atom, are taken together with the carbon to which they are attached to form a $C_3$-$C_6$ cycloalkyl; and m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl; $R^4$ is $C_6$-$C_{14}$ aryl optionally substituted by halogen, —CN, —$NR^{13}R^{14}$, —$C(O)R^{13}$, —$OR^{13}$, or $C_1$-$C_6$ alkyl optionally substituted by —OH; W is

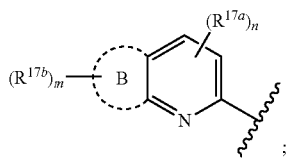

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; each $R^{17b}$ is independently $C_1$-$C_6$ alkyl optionally substituted by halogen, —$C(O)R^{13}$, or oxo; and each m and n are independently 0, 1, 2, or 3. In some embodiments of a compound of Formula (I), (Ia) or (Ib), X is hydrogen; Y is N; Z is N; $R^{3a}$ and $R^{3b}$ are independently hydrogen or $C_1$-$C_6$ alkyl; $R^4$ is phenyl optionally substituted by halogen, —CN, —$NR^{13}R^{14}$, —$C(O)R^{13}$, —$OR^{13}$, or $C_1$-$C_6$ alkyl optionally substituted by —OH; W is

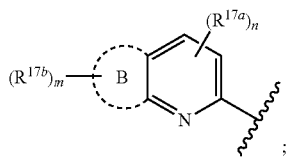

wherein B is $C_3$-$C_6$ cycloalkyl, 3- to 7-membered heterocyclyl, 5- to 7-membered heteroaryl, or $C_6$ aryl; each $R^{17a}$ is independently $C_1$-$C_6$ alkyl; two groups $R^{17b}$ are taken together with the carbon to which they are attached to form a $C_3$-$C_6$ cycloalkyl; and each m and n are independently 0, 1, 2, or 3.

In some embodiments of a compound of Formula (I), (Ia) or (Ib), X is hydrogen; Y is N; Z is N; $R^{3a}$ and $R^{3b}$ are both hydrogen; $R^4$ is selected from the group consisting of methyl, ethyl, isopropyl, cyclopropyl,

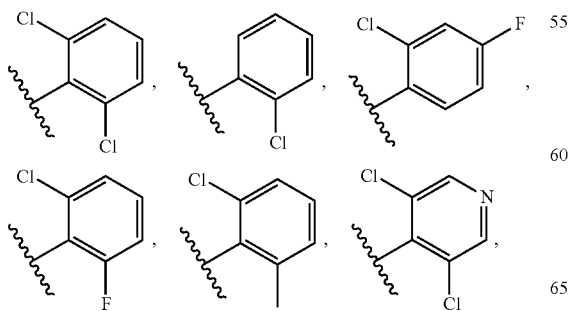

W is selected from the group consisting of:

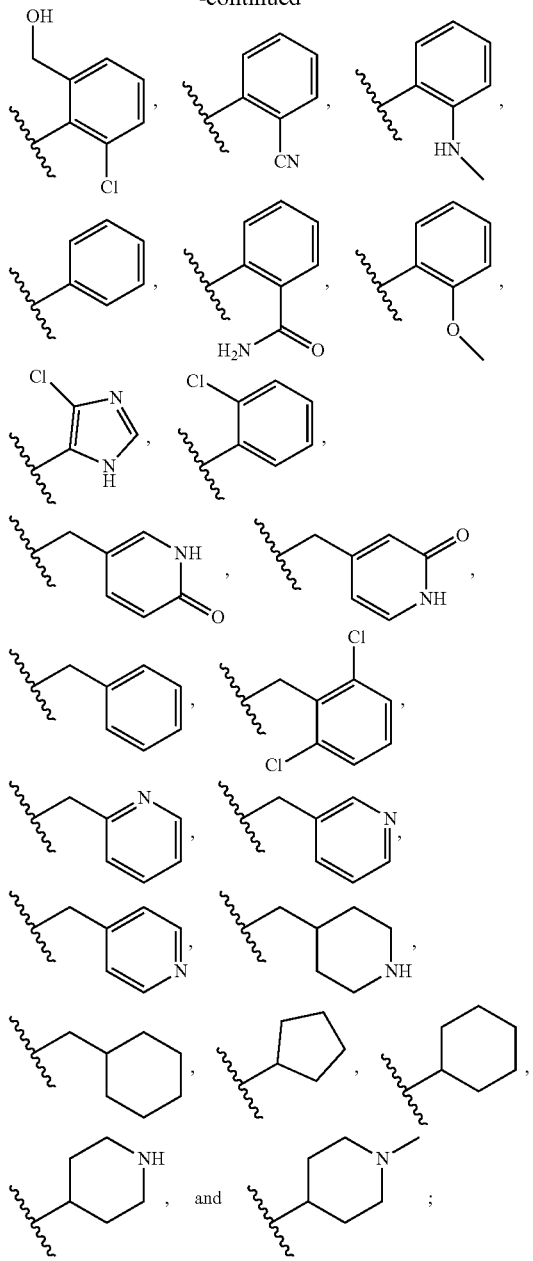

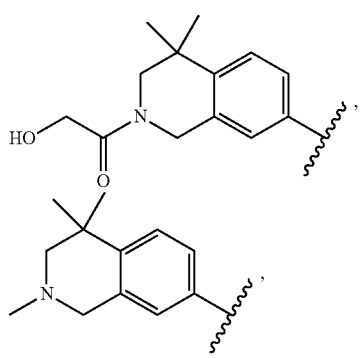

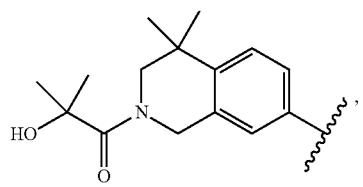,
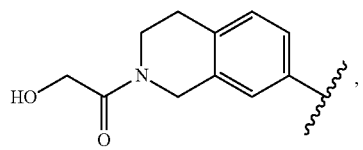,
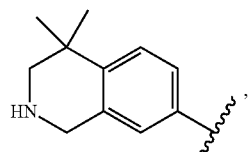,
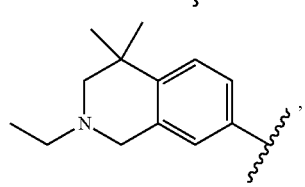,
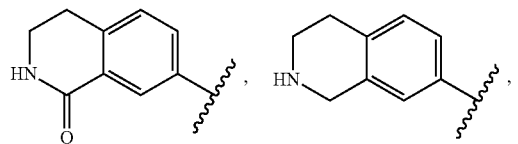,
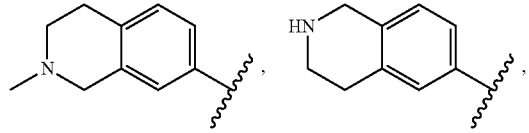,
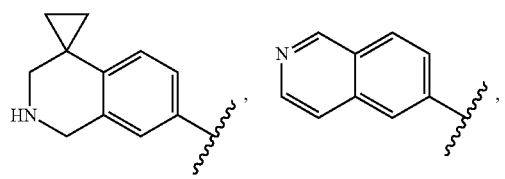,
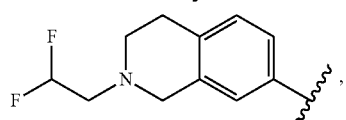,
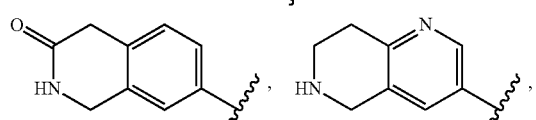,
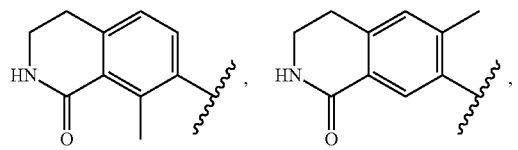,
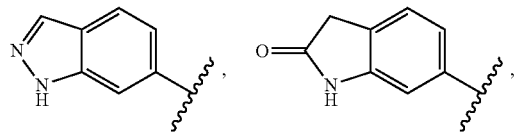,
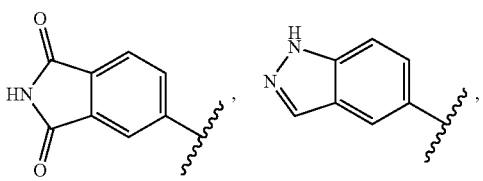,
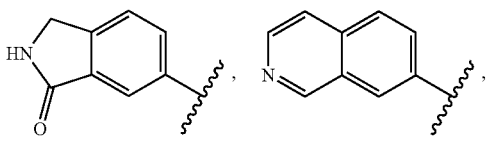,
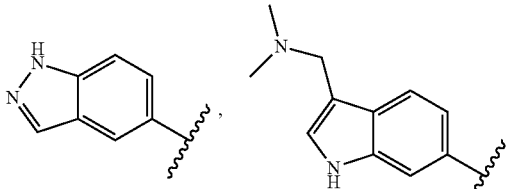,
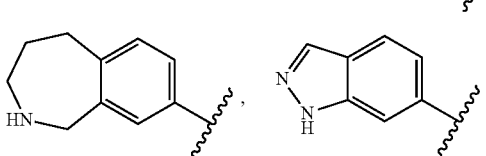,
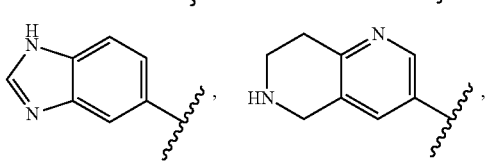,
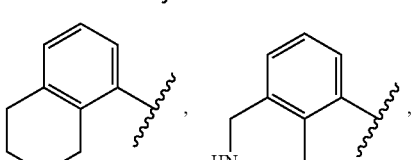,
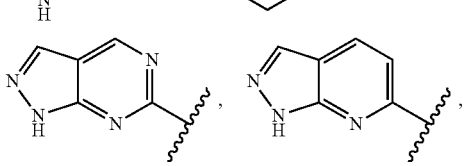,
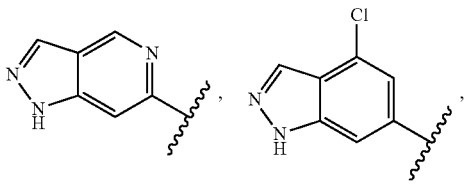,
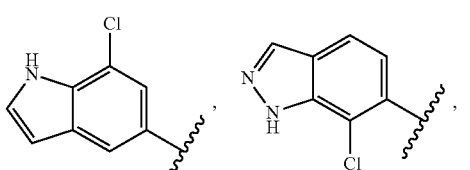,
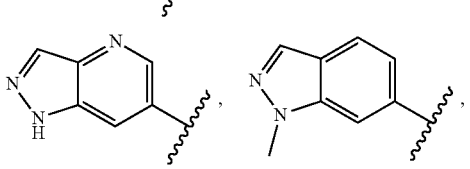, 151
-continued
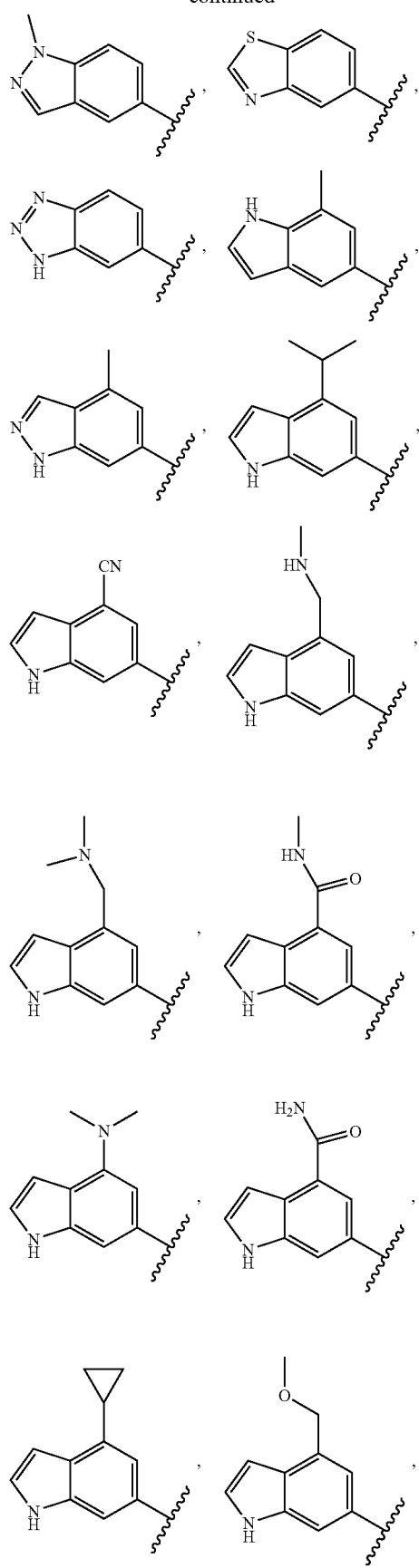
152
-continued
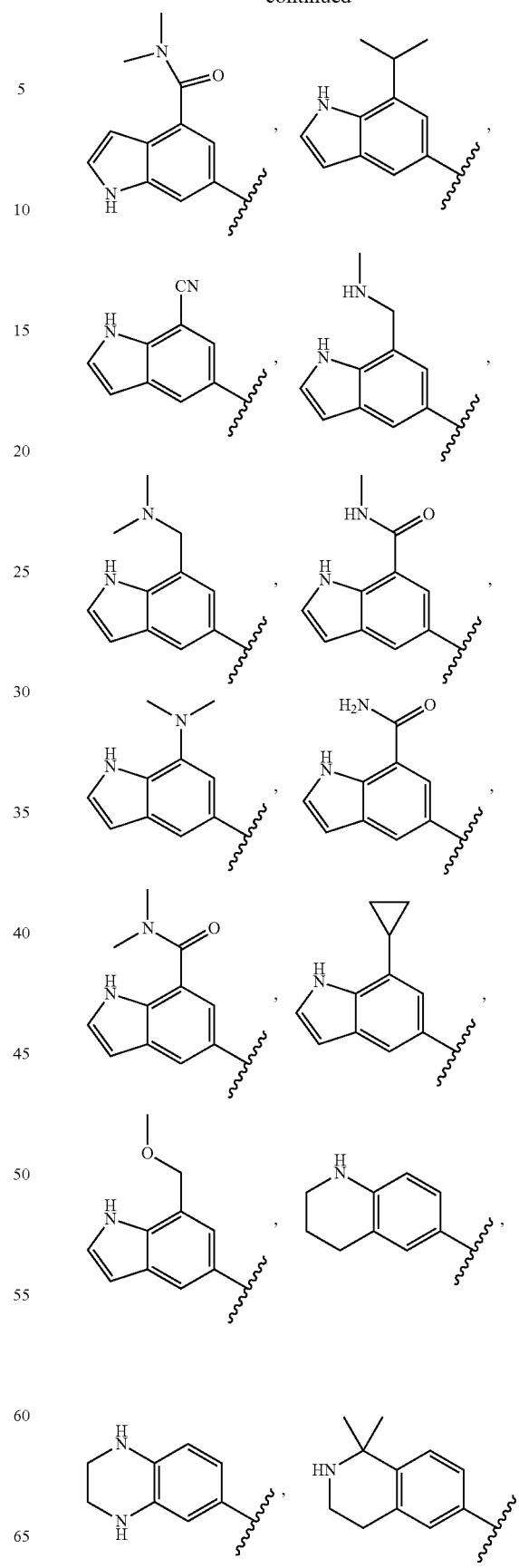

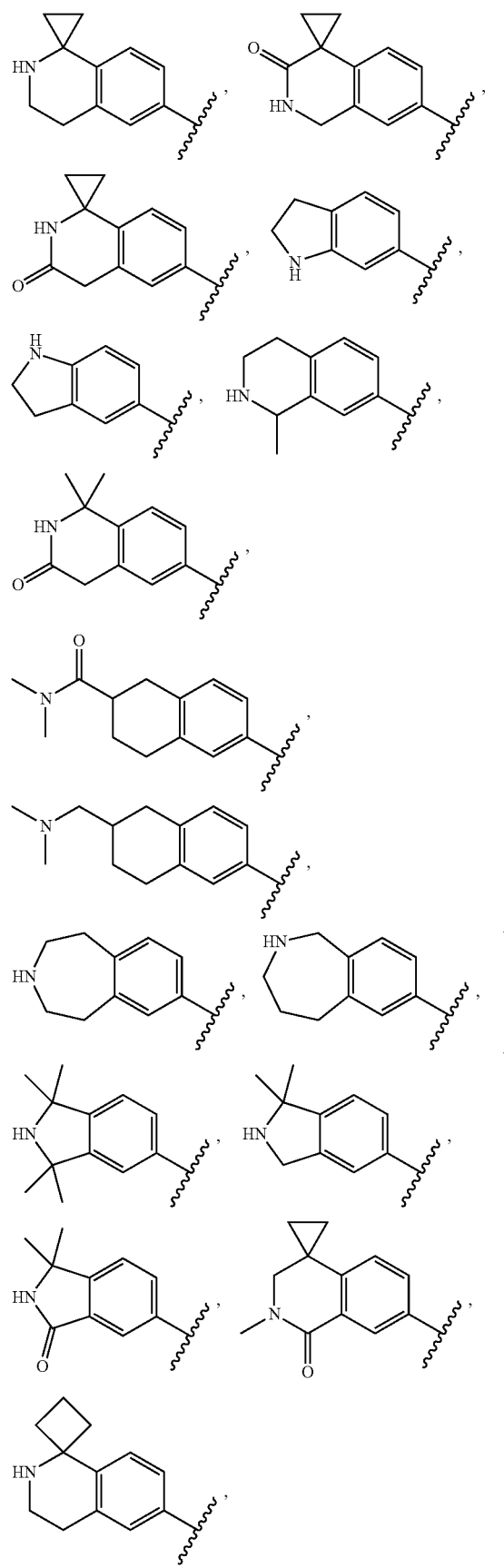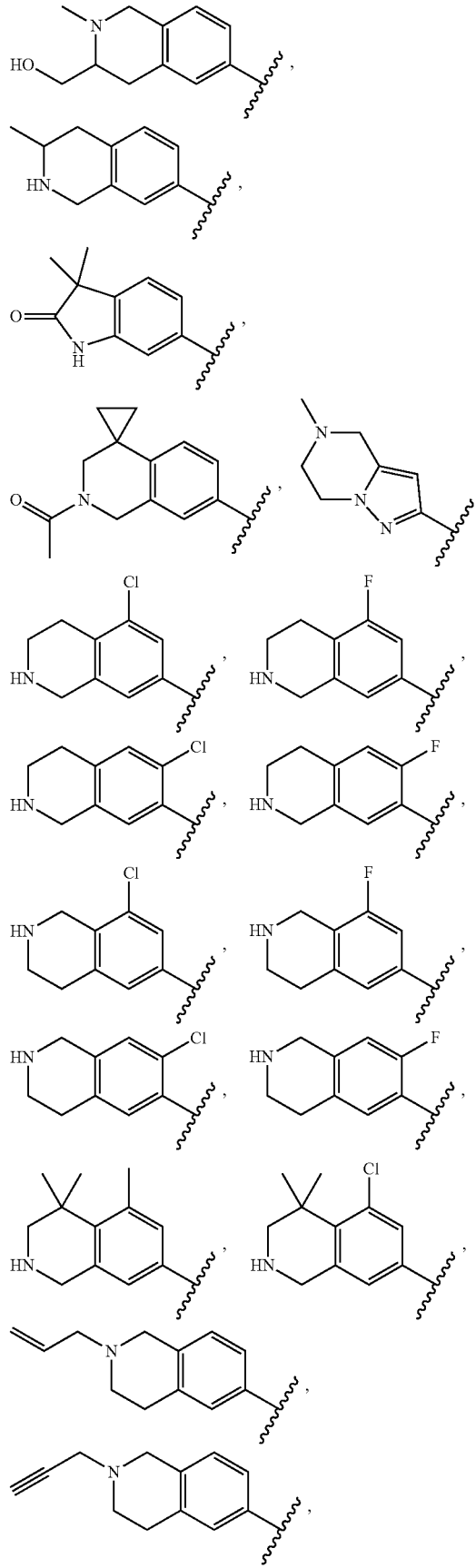

155
-continued
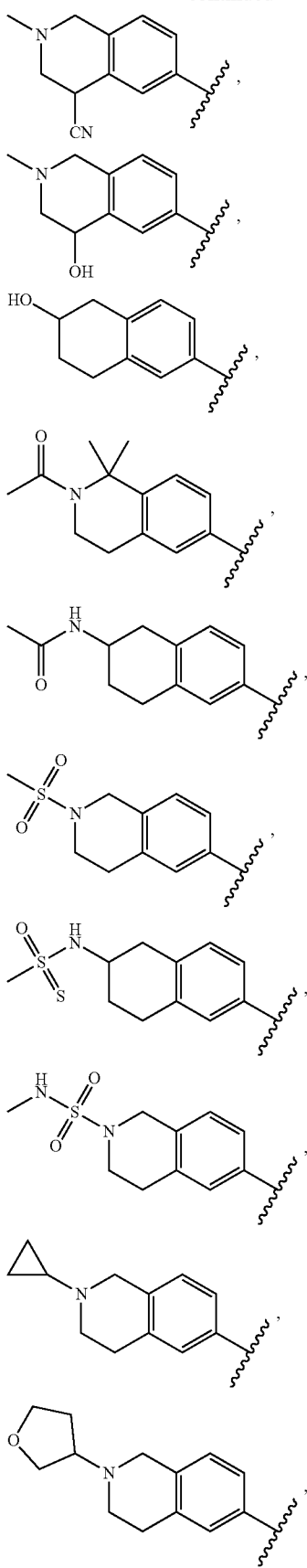
156
-continued
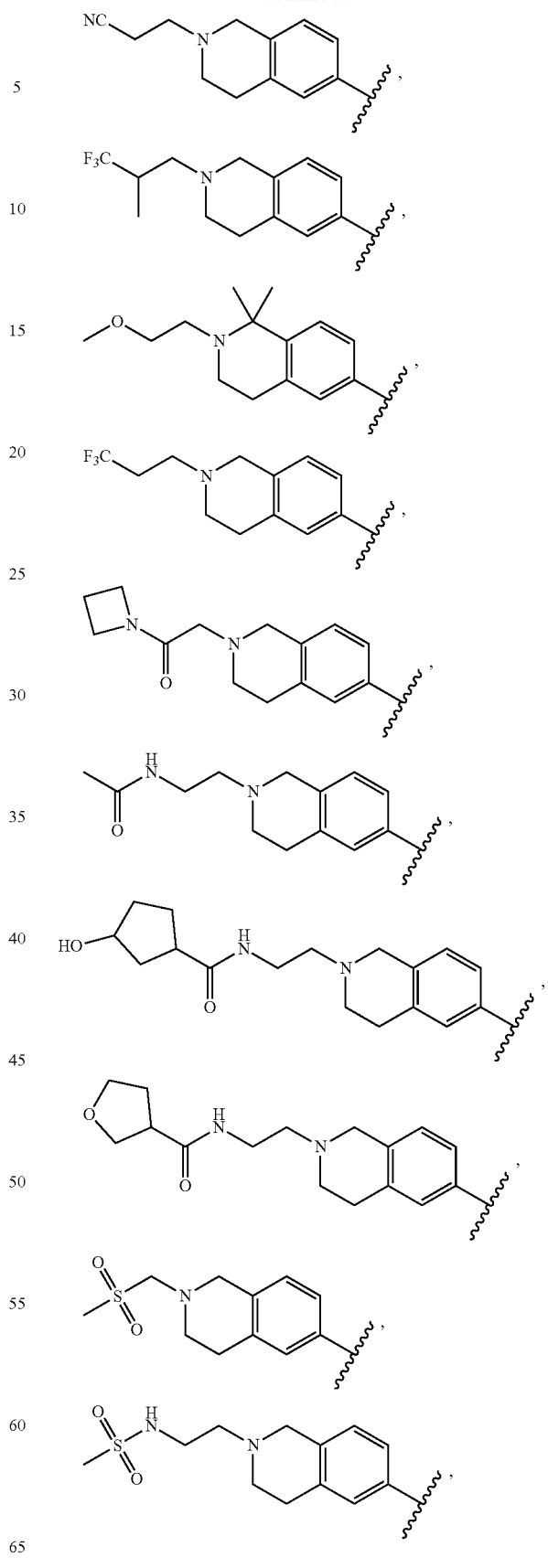

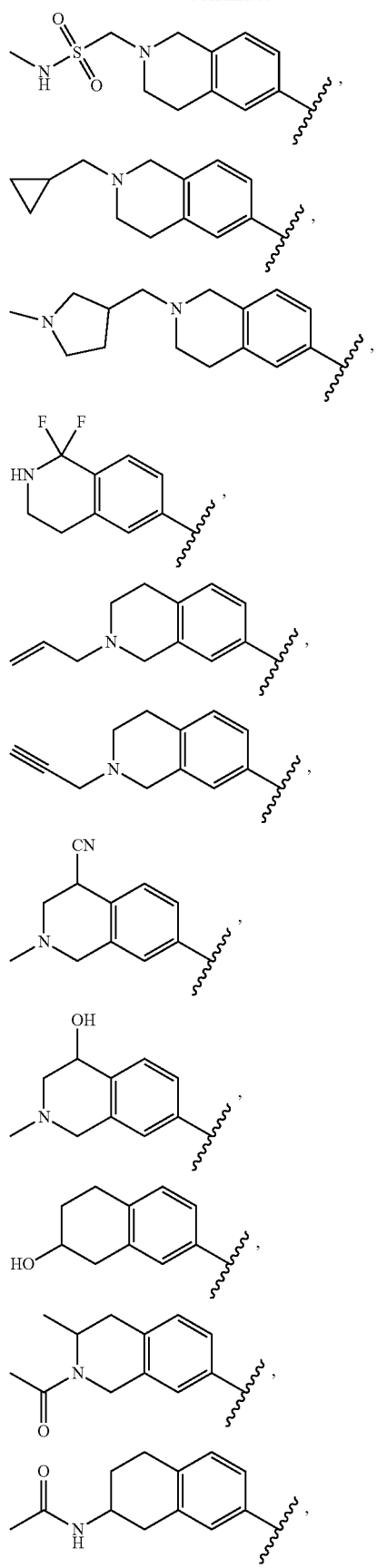
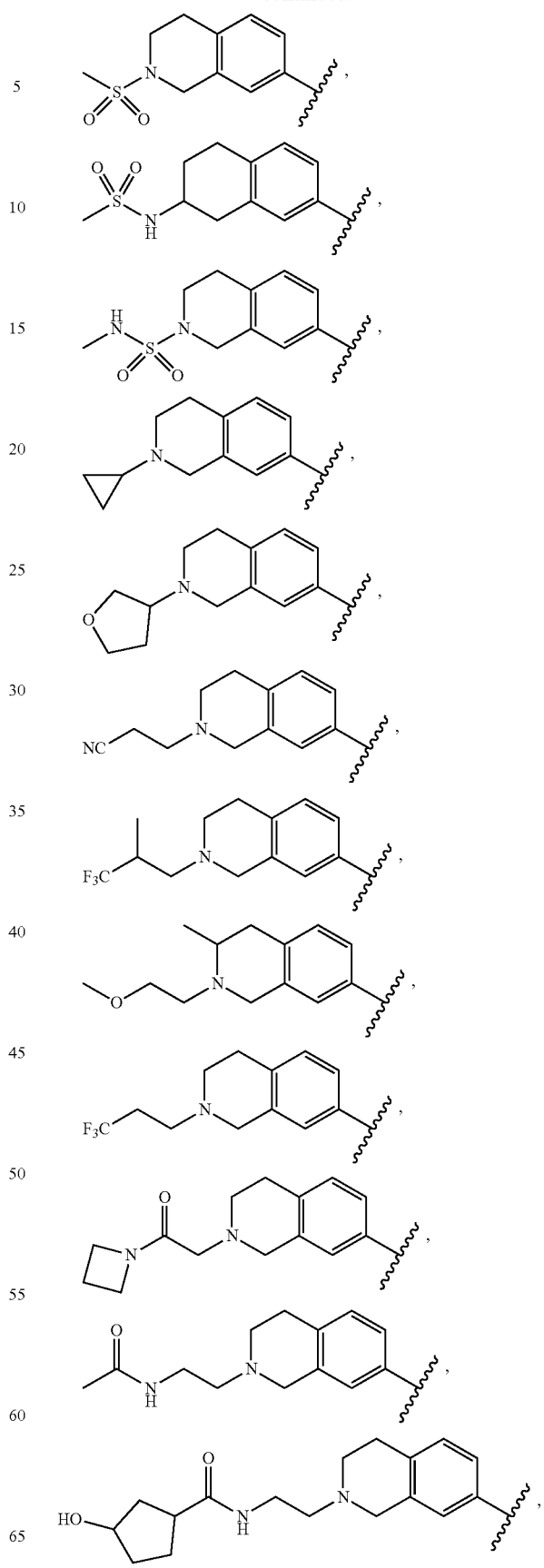

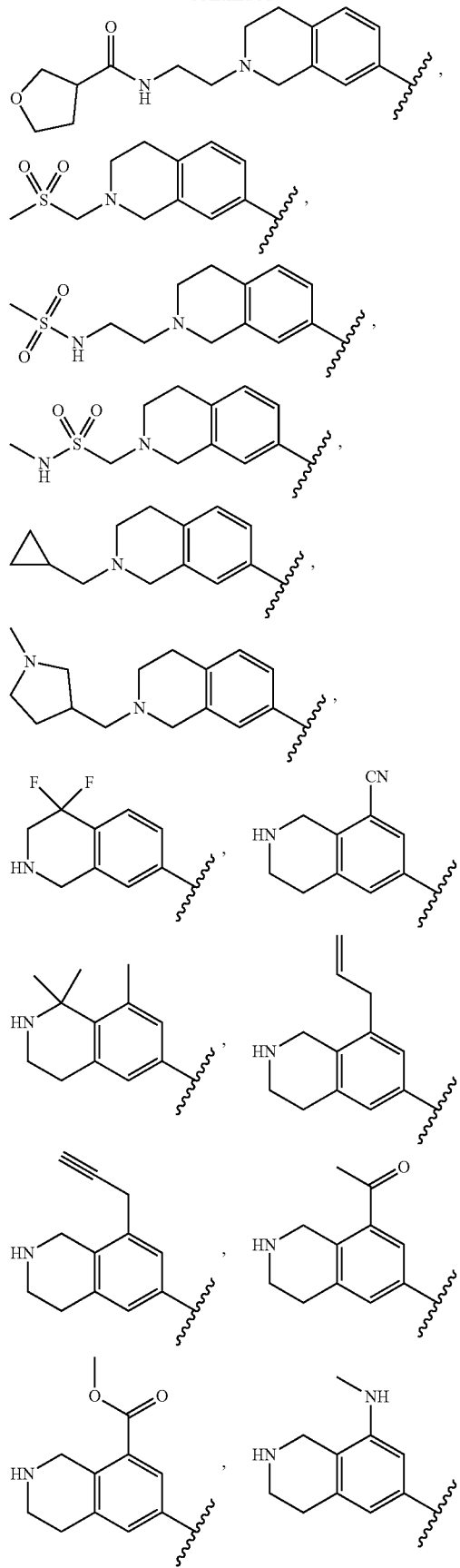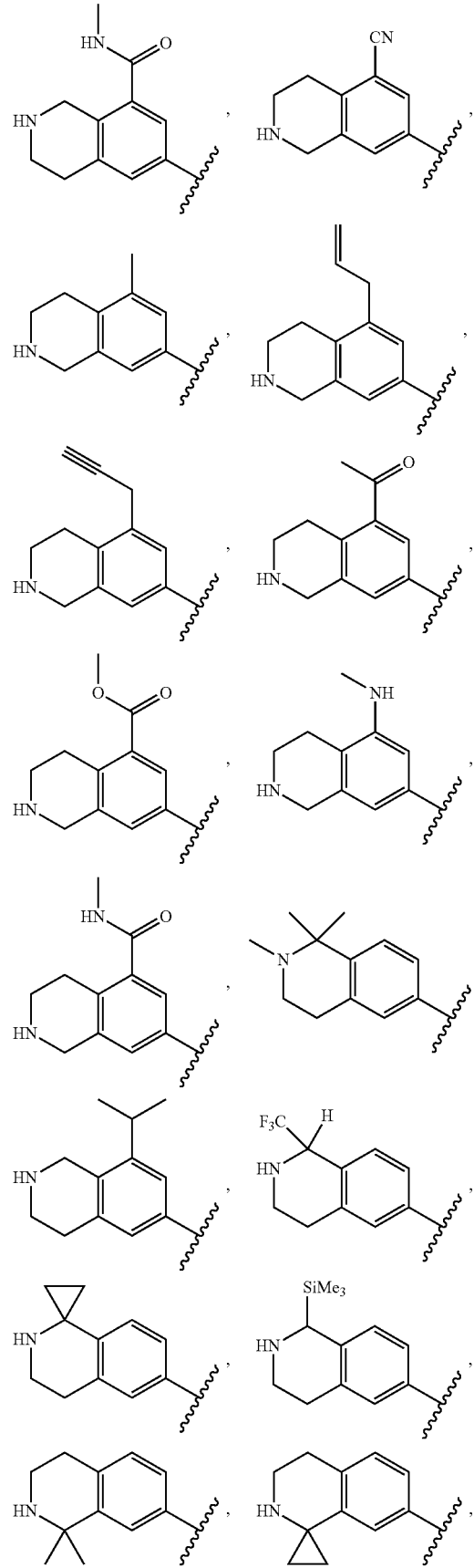

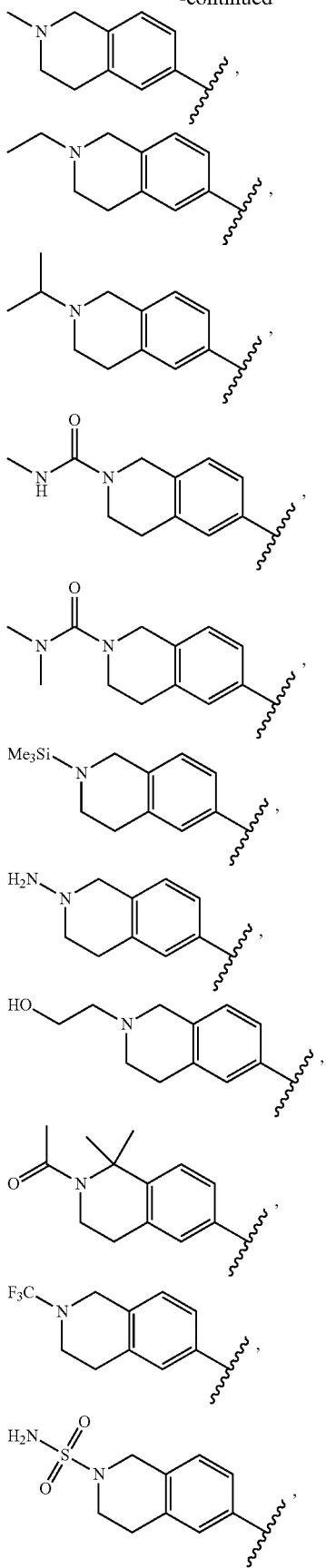
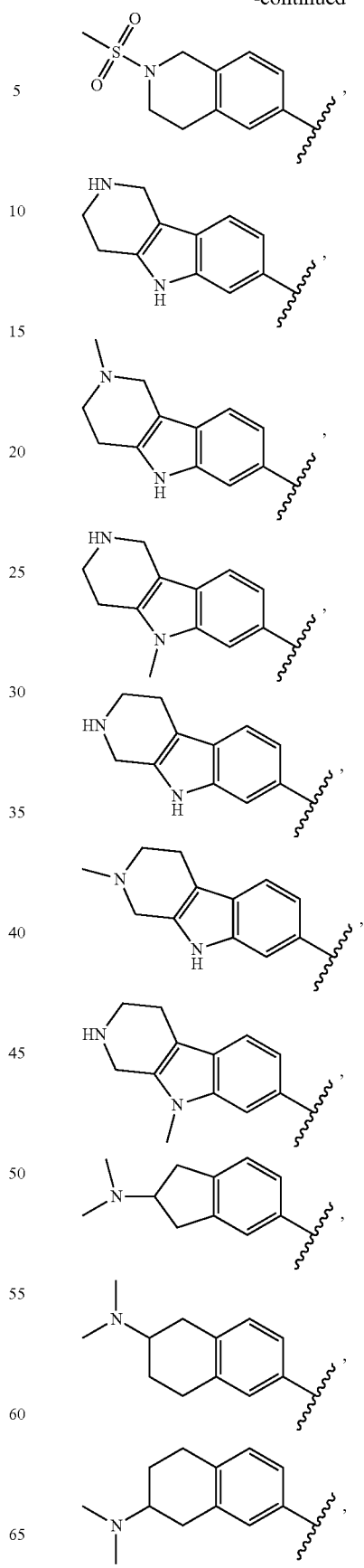

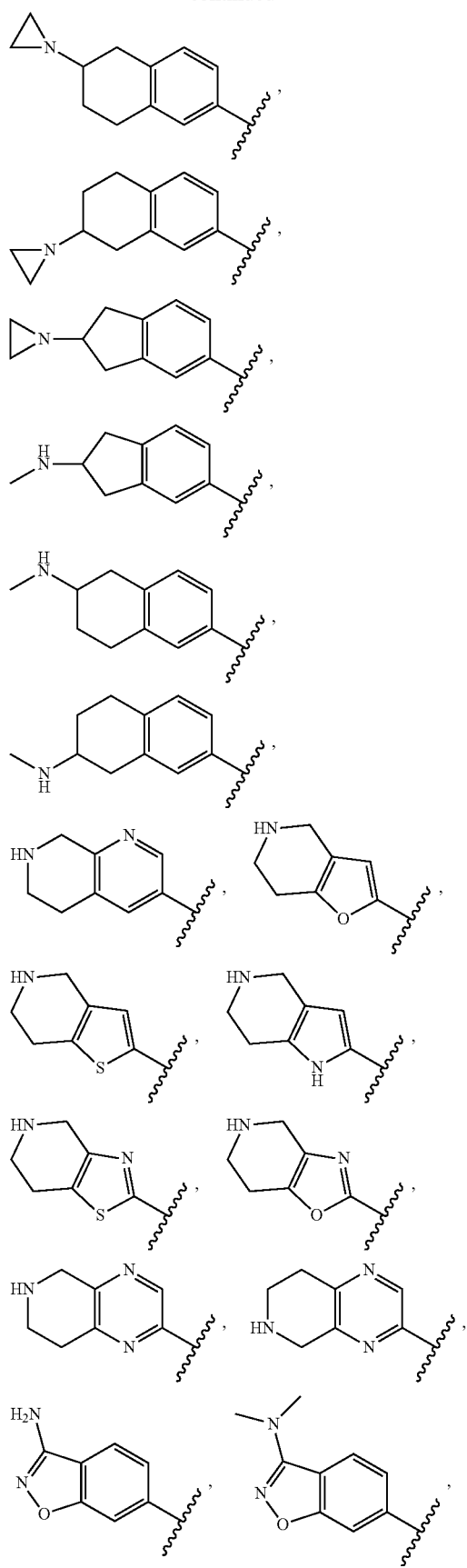
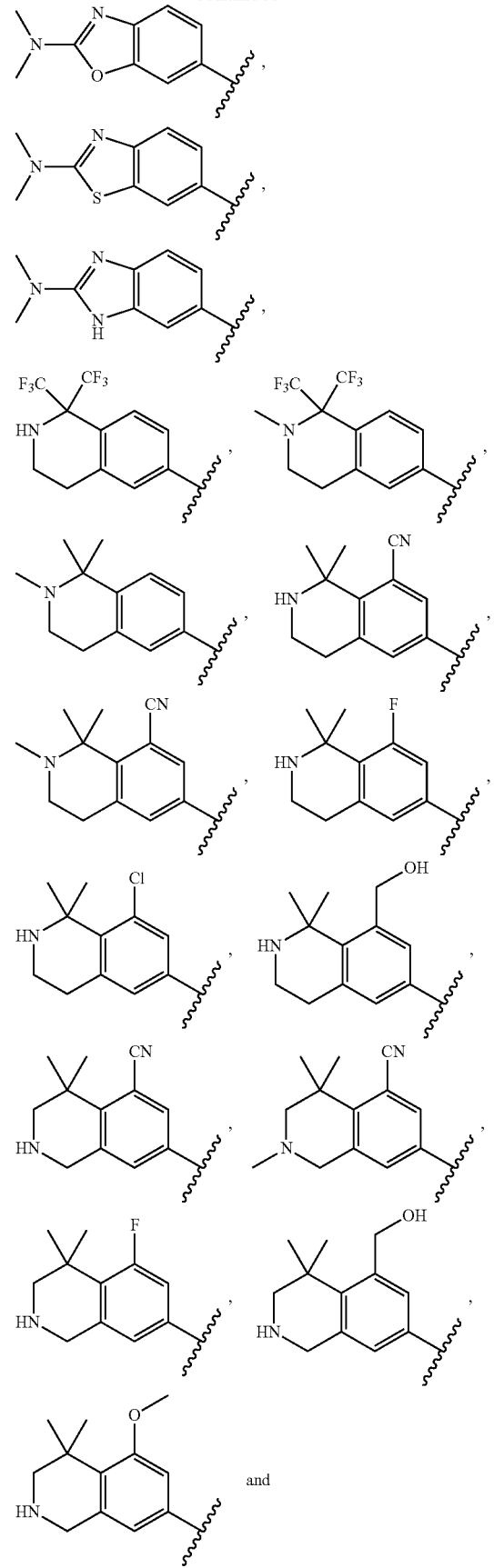

-continued
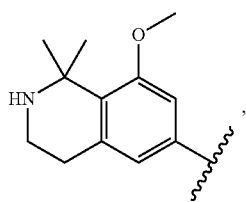
wherein the wavy lines denote attachment points to the parent molecule.
In some embodiments of a compound of Formula (I), (Ia) or (Ib), X is hydrogen; Y is N; Z is N; $R^{3a}$ and $R^{3b}$ are both hydrogen; $R^4$ is selected from the group consisting of methyl, ethyl, isopropyl, cyclopropyl,
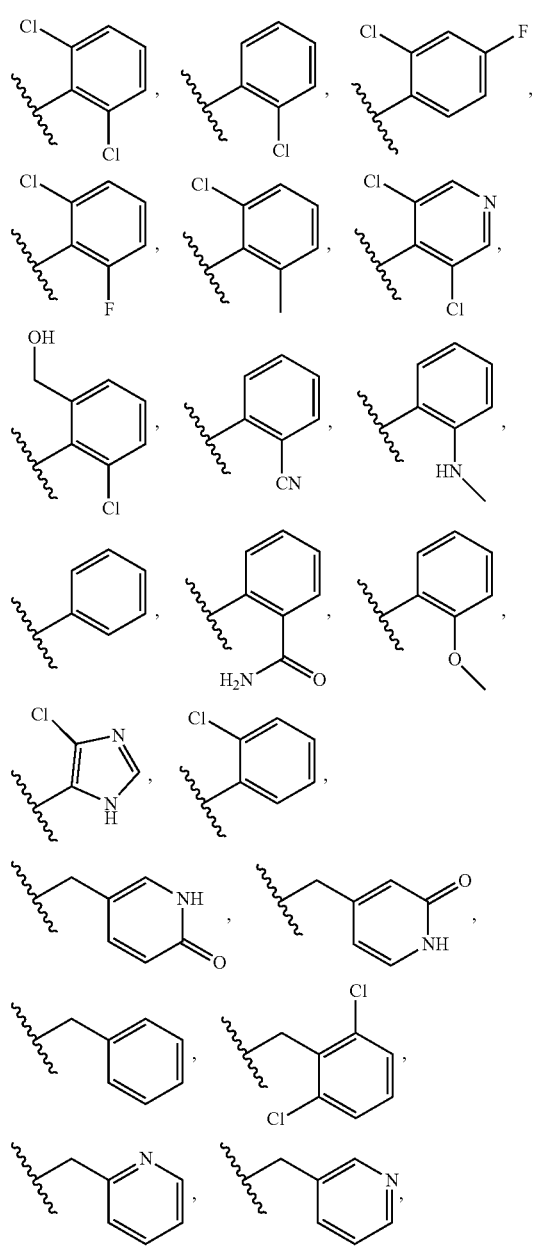
-continued
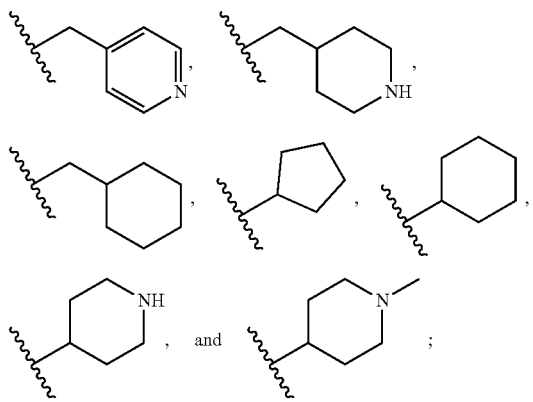
W is selected from the group consisting of:
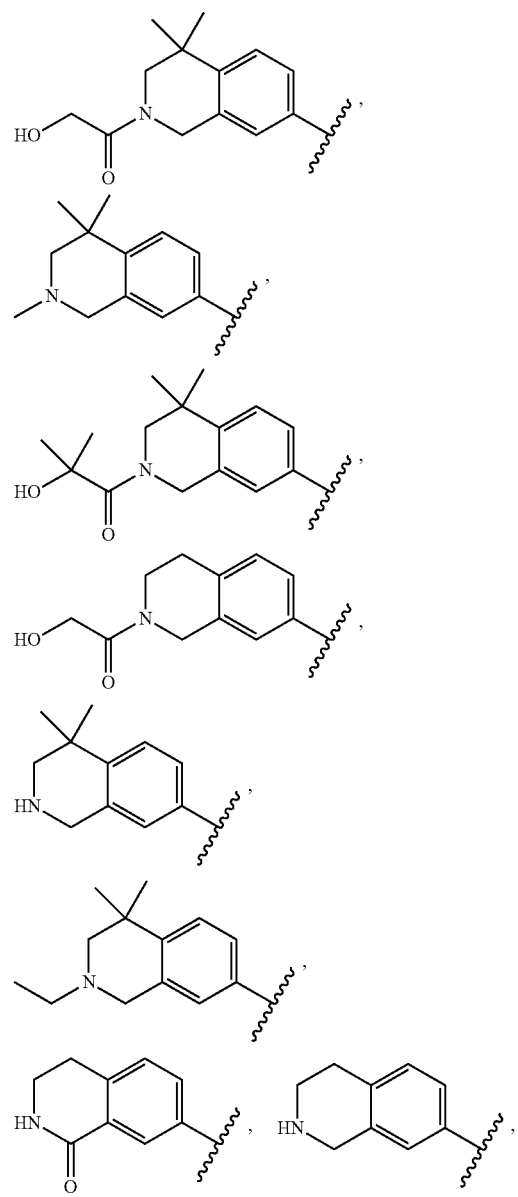

-continued

-continued

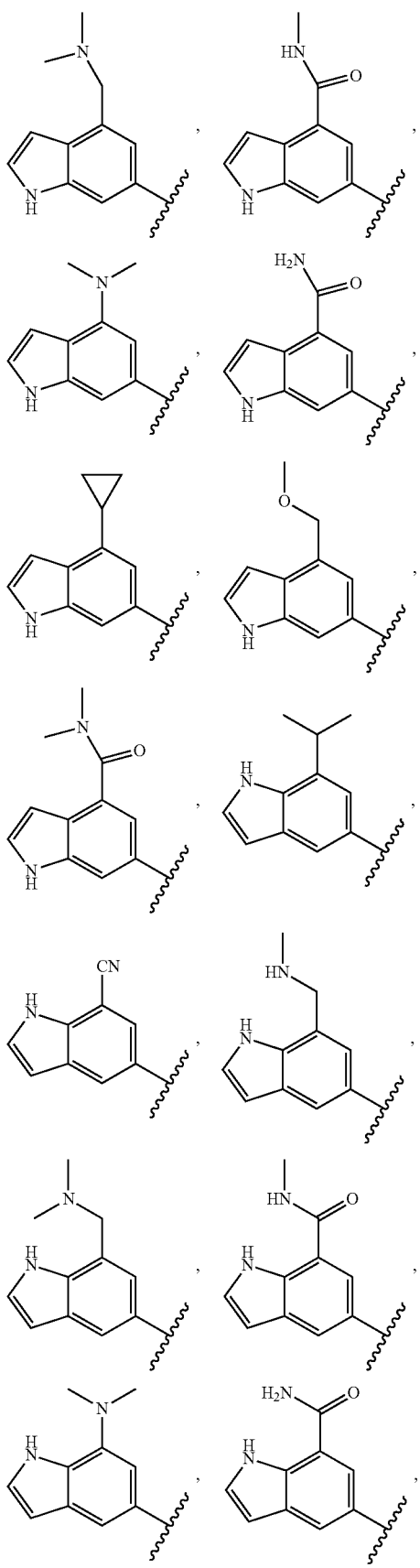

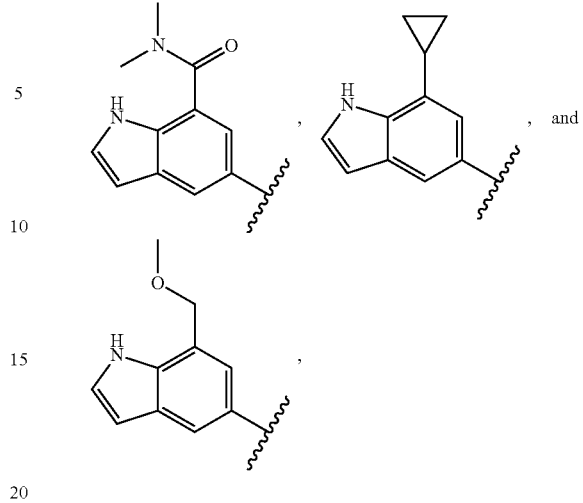

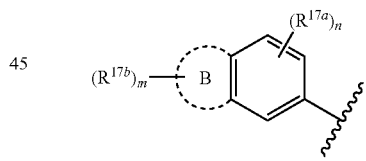

wherein the wavy lines denote attachment points to the parent molecule.

In some embodiments of a compound of Formula (I), (Ia) or (Ib), W is A, wherein A is phenyl optionally substituted with $R^{17a}$ and $R^{17a}$ is independently 3- to 12-membered heterocyclyl, —($C_1$-$C_3$ alkylene)$OR^{10}$, $C_1$-$C_6$ alkyl, —C(O)$NR^{11}R^{12}$, —($C_1$-$C_3$ alkylene)$NR^{11}R^{12}$, —CN, halogen, —$NR^{11}R^{12}$, or —$OR^{10}$, wherein the 3- to 12-membered heterocyclyl of $R^{17a}$ is optionally substituted with $C_1$-$C_6$ alkyl, —C(O)$R^{13}$, —($C_1$-$C_3$ alkylene)$OR^{13}$, —S(O)$_2R^{13}$, $C_3$-$C_8$ cycloalkyl, oxo, halogen, or —$OR^{13}$; X is hydrogen; Y is N; Z is N; $R^{3a}$ is hydrogen; $R^{3b}$ is hydrogen; and $R^4$ is 2,6-dichlorophenyl. In some embodiments of a compound of Formula (I), (Ia) or (Ib), W is A, wherein A is phenyl optionally substituted with $R^{17a}$ and $R^{17a}$ is independently 3- to 12-membered heterocyclyl or —CN; X is hydrogen; Y is N; Z is N; $R^{3a}$ is hydrogen; $R^{3b}$ is hydrogen; and $R^4$ is 2,6-dichlorophenyl.

In some embodiments of a compound of Formula (I), (Ia) or (Ib), W is

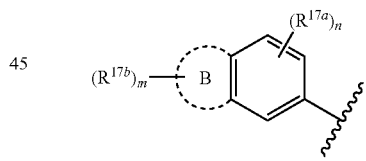

wherein B is 3- to 7-membered heterocyclyl; each $R^{17a}$ is independently $C_1$-$C_6$ alkyl; each $R^{17b}$ is independently $C_1$-$C_6$ alkyl optionally substituted by halogen, —C(O)$R^{13}$, or oxo; X is hydrogen; Y is N; Z is N; $R^{3a}$ is hydrogen; $R^{3b}$ is hydrogen; and $R^4$ is 2,6-dichlorophenyl. In some embodiments of a compound of Formula (I), (Ia) or (Ib), W is

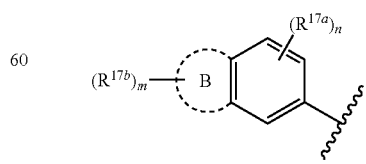

wherein B is 6-membered heterocyclyl; each $R^{17a}$ is independently $C_1$-$C_6$ alkyl; each $R^{17b}$ is independently $C_1$-$C_6$ alkyl optionally substituted by halogen, —C(O)R$^{13}$, or oxo; X is hydrogen; Y is N; Z is N; R$^{3a}$ is hydrogen; R$^{3b}$ is hydrogen; and R$^4$ is 2,6-dichlorophenyl. In some embodiments of a compound of Formula (I), (Ia) or (Ib), W is

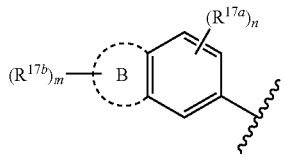

wherein B is 6-membered heterocyclyl; each R$^{17a}$ is independently C$_1$-C$_6$ alkyl; each R$^{17b}$ is independently C$_1$-C$_6$ alkyl; X is hydrogen; Y is N; Z is N; R$^{3a}$ is hydrogen; R$^{3b}$ is hydrogen; and R$^4$ is 2,6-dichlorophenyl.

In some embodiments of a compound of Formula (I), (Ia) or (Ib), W is selected from the group consisting of:

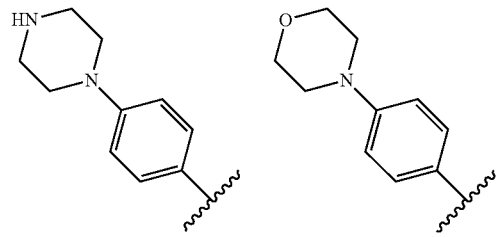

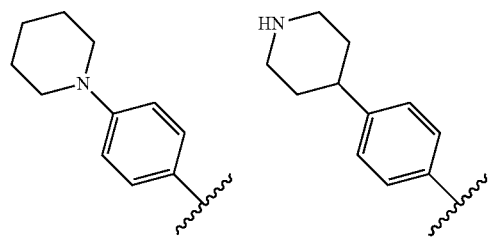

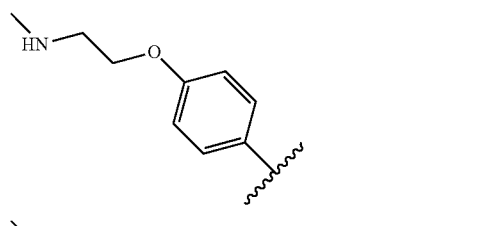

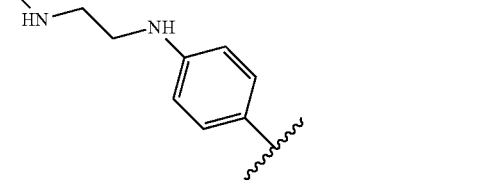

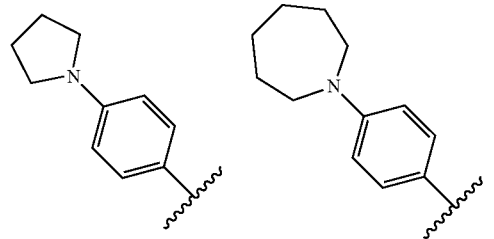

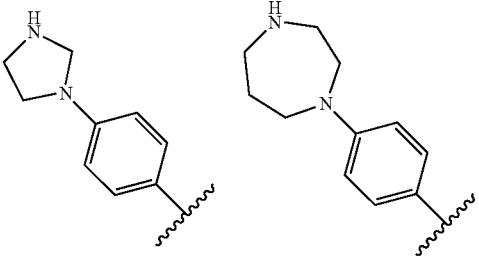

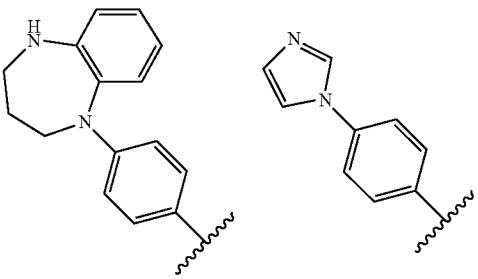

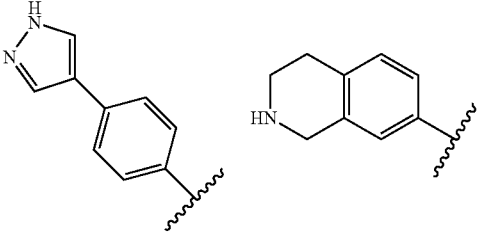

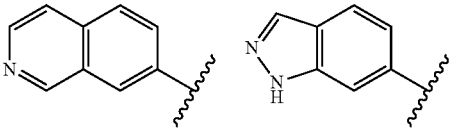

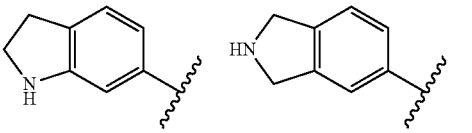

wherein the wavy lines denote attachment points to the parent molecule and each is optionally substituted with R$^{17a}$ and R$^{17b}$; X is hydrogen; Y is N; Z is N; R$^{3a}$ is hydrogen; R$^{3b}$ is hydrogen; and R$^4$ is 2,6-dichlorophenyl.

In some embodiments of a compound of Formula (I), (Ia) or (Ib), W is

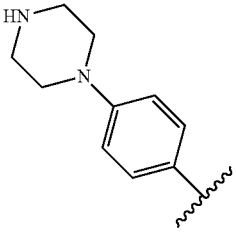 [SMILES: *c1ccc(N2CCNCC2)cc1]

substituted by —CN; X is hydrogen; Y is N; Z is N; $R^{3a}$ is hydrogen; $R^{3b}$ is hydrogen; and $R^4$ is 2,6-dichlorophenyl. In some embodiments of a compound of Formula (I), (Ia) or (Ib), W is

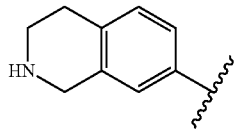

substituted by $C_1$-$C_6$ alkyl; X is hydrogen; Y is N; Z is N; $R^{3a}$ is hydrogen; $R^{3b}$ is hydrogen; and $R^4$ is 2,6-dichlorophenyl.

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. Compositions comprising a compound as detailed herein, or a tautomer or isomer thereof, or a pharmaceutically acceptable salt of any of the foregoing, are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 1.

TABLE 1

| Compound No. | Structure |
|---|---|
| 1.1 | 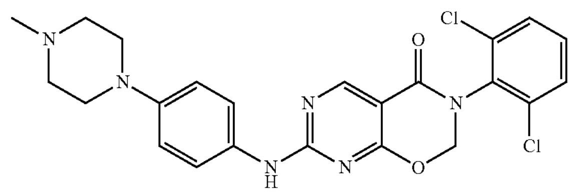 |
| 1.2 | 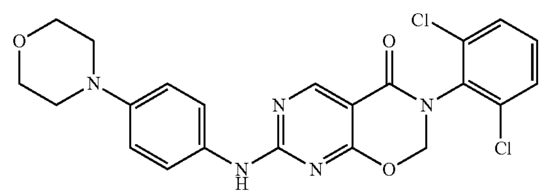 [SMILES: O=C1c2cnc(Nc3ccc(N4CCOCC4)cc3)nc2OCN1c1c(Cl)cccc1Cl] |
| 1.3 | 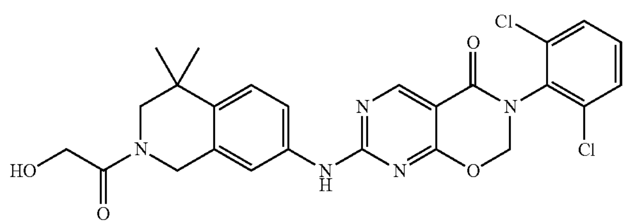 [SMILES: CC1(C)CN(C(=O)CO)Cc2cc(Nc3ncc4c(n3)OCN(c3c(Cl)cccc3Cl)C4=O)ccc21] |
| 1.4 | 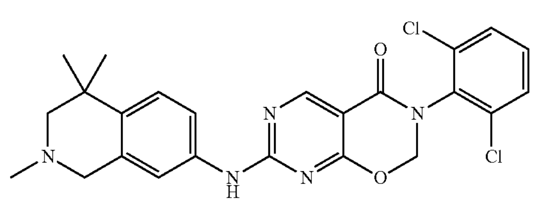 [SMILES: CN1Cc2cc(Nc3ncc4c(n3)OCN(c3c(Cl)cccc3Cl)C4=O)ccc2C(C)(C)C1] |
| 1.5 | 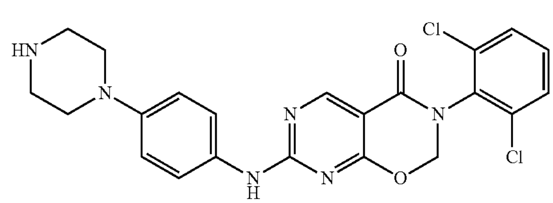 [SMILES: O=C1c2cnc(Nc3ccc(N4CCNCC4)cc3)nc2OCN1c1c(Cl)cccc1Cl] |

TABLE 1-continued

| Compound No. | Structure |
|---|---|
| 1.6 | 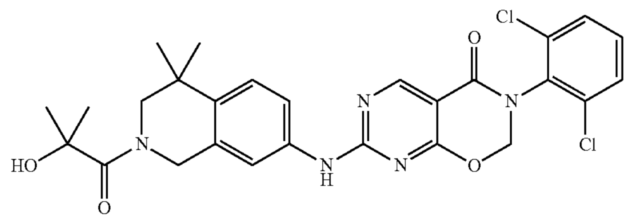 [SMILES: CC(C)(O)C(=O)N1Cc2cc(Nc3ncc4c(n3)OCN(c3c(Cl)cccc3Cl)C4=O)ccc2C(C)(C)C1] |
| 1.7 | 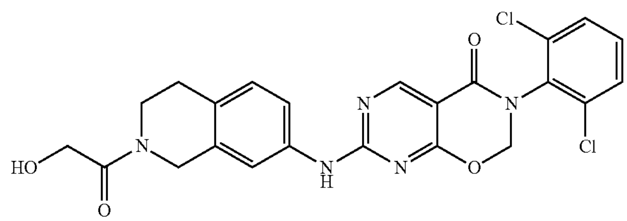 [SMILES: O=C(CO)N1CCc2ccc(Nc3ncc4c(n3)OCN(c3c(Cl)cccc3Cl)C4=O)cc2C1] |
| 1.8 | 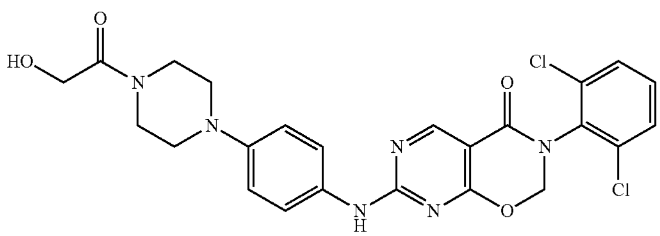 [SMILES: O=C(CO)N1CCN(c2ccc(Nc3ncc4c(n3)OCN(c3c(Cl)cccc3Cl)C4=O)cc2)CC1] |
| 1.9 | 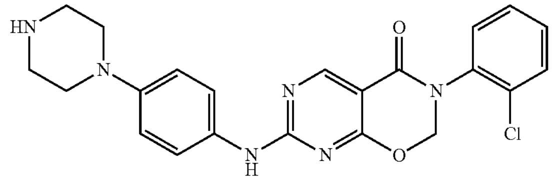 [SMILES: O=C1c2cnc(Nc3ccc(N4CCNCC4)cc3)nc2OCN1c1ccccc1Cl] |
| 1.10 | 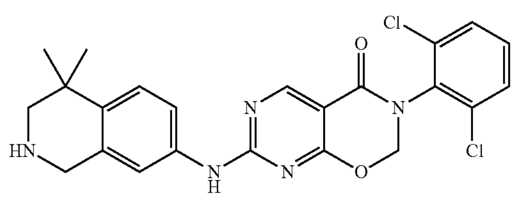 [SMILES: CC1(C)CNCc2cc(Nc3ncc4c(n3)OCN(c3c(Cl)cccc3Cl)C4=O)ccc21] |
| 1.11 | 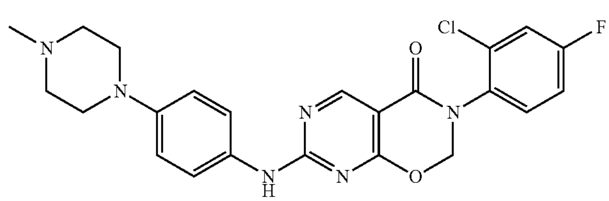 [SMILES: CN1CCN(c2ccc(Nc3ncc4c(n3)OCN(c3ccc(F)cc3Cl)C4=O)cc2)CC1] |
| 1.12 | 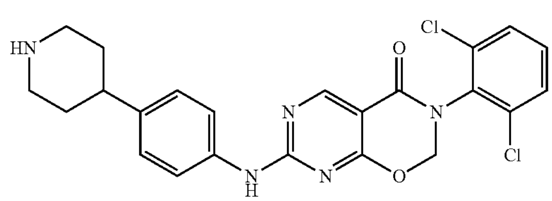 [SMILES: O=C1c2cnc(Nc3ccc(C4CCNCC4)cc3)nc2OCN1c1c(Cl)cccc1Cl] |

TABLE 1-continued

| Compound No. | Structure |
|---|---|
| 1.13 | 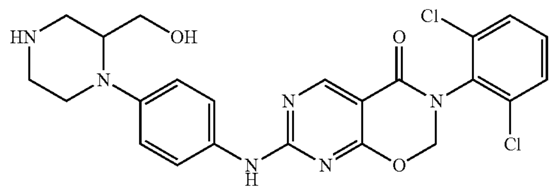 [SMILES: O=C1c2cnc(Nc3ccc(N4CCNCC4CO)cc3)nc2OCN1c1c(Cl)cccc1Cl] |
| 1.14 | 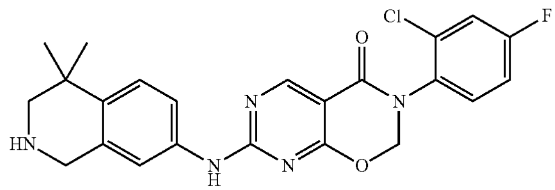 [SMILES: CC1(C)CNCc2cc(Nc3ncc4c(n3)OCN(c3ccc(F)cc3Cl)C4=O)ccc21] |
| 1.15 | 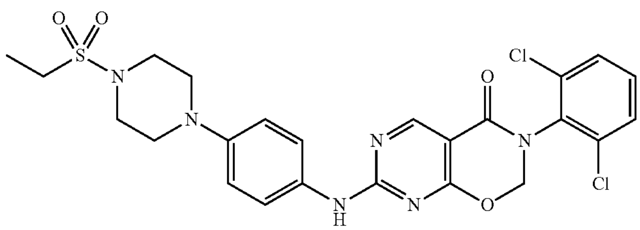 [SMILES: CCS(=O)(=O)N1CCN(c2ccc(Nc3ncc4c(n3)OCN(c3c(Cl)cccc3Cl)C4=O)cc2)CC1] |
| 1.16 | 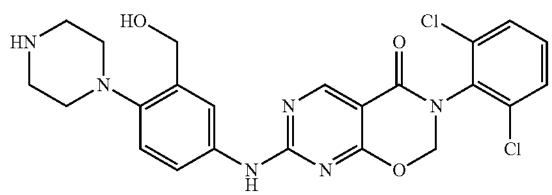 [SMILES: O=C1c2cnc(Nc3ccc(N4CCNCC4)c(CO)c3)nc2OCN1c1c(Cl)cccc1Cl] |
| 1.17 | 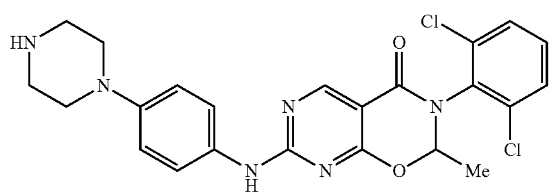 [SMILES: CC1Oc2nc(Nc3ccc(N4CCNCC4)cc3)ncc2C(=O)N1c1c(Cl)cccc1Cl] |
| 1.18 | 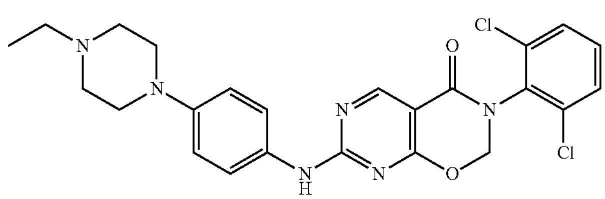 [SMILES: CCN1CCN(c2ccc(Nc3ncc4c(n3)OCN(c3c(Cl)cccc3Cl)C4=O)cc2)CC1] |
| 1.19 | 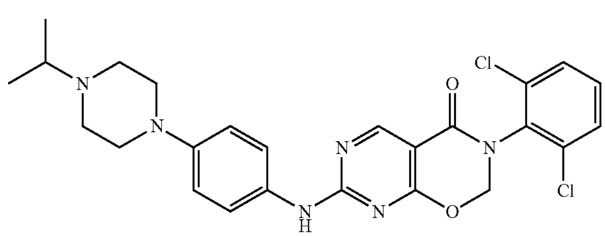 [SMILES: CC(C)N1CCN(c2ccc(Nc3ncc4c(n3)OCN(c3c(Cl)cccc3Cl)C4=O)cc2)CC1] |

TABLE 1-continued
| Compound No. | Structure |
|---|---|
| 1.20 | 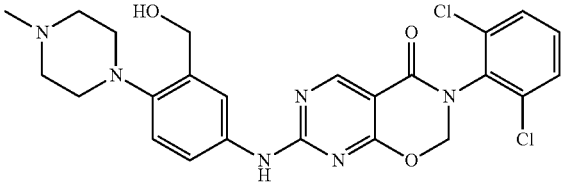 [SMILES: CN1CCN(c2ccc(Nc3ncc4c(n3)OCN(c3c(Cl)cccc3Cl)C4=O)cc2CO)CC1] |
| 1.21 | 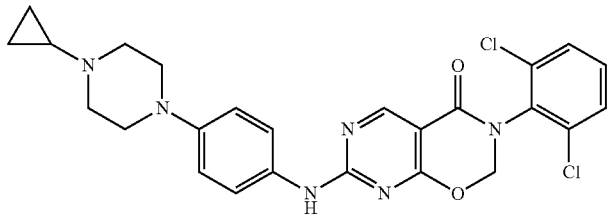 [SMILES: O=C1c2cnc(Nc3ccc(N4CCN(C5CC5)CC4)cc3)nc2OCN1c1c(Cl)cccc1Cl] |
| 1.22 | 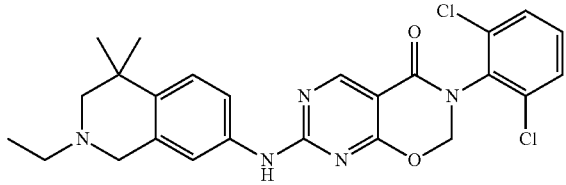 [SMILES: CCN1Cc2cc(Nc3ncc4c(n3)OCN(c3c(Cl)cccc3Cl)C4=O)ccc2C(C)(C)C1] |
| 1.23 | 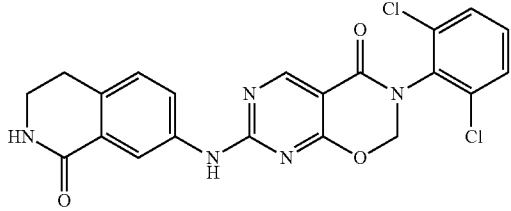 [SMILES: O=C1NCCc2ccc(Nc3ncc4c(n3)OCN(c3c(Cl)cccc3Cl)C4=O)cc21] |
| 1.24 | 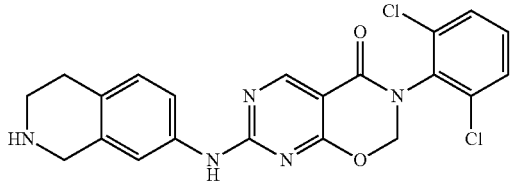 [SMILES: O=C1c2cnc(Nc3ccc4c(c3)CNCC4)nc2OCN1c1c(Cl)cccc1Cl] |
| 1.25 | 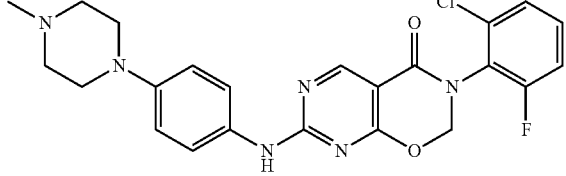 |
| 1.26 | 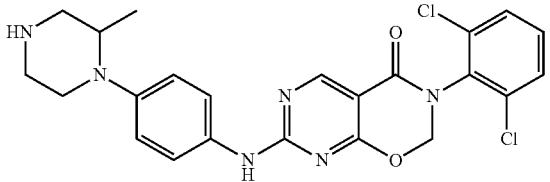 [SMILES: CC1CNCCN1c1ccc(Nc2ncc3c(n2)OCN(c2c(Cl)cccc2Cl)C3=O)cc1] |

TABLE 1-continued

| Compound No. | Structure |
|---|---|
| 1.27 | 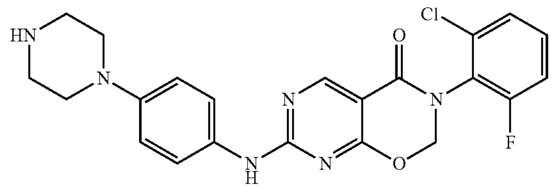 [SMILES: O=C1c2cnc(Nc3ccc(N4CCNCC4)cc3)nc2OCN1c1c(F)cccc1Cl] |
| 1.28 | 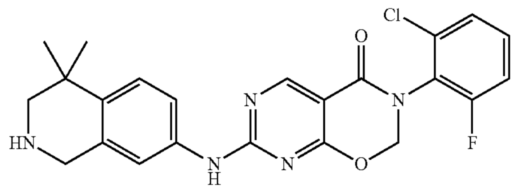 [SMILES: CC1(C)CNCc2cc(Nc3ncc4c(n3)OCN(c3c(F)cccc3Cl)C4=O)ccc21] |
| 1.29 | 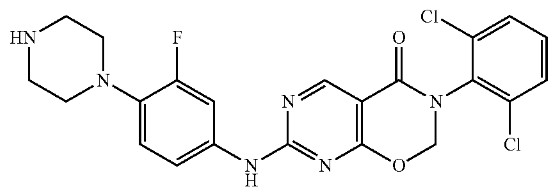 [SMILES: O=C1c2cnc(Nc3ccc(N4CCNCC4)c(F)c3)nc2OCN1c1c(Cl)cccc1Cl] |
| 1.30 | 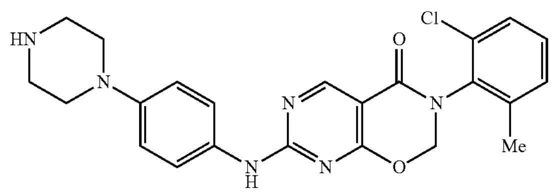 [SMILES: Cc1cccc(Cl)c1N1COc2nc(Nc3ccc(N4CCNCC4)cc3)ncc2C1=O] |
| 1.31 | 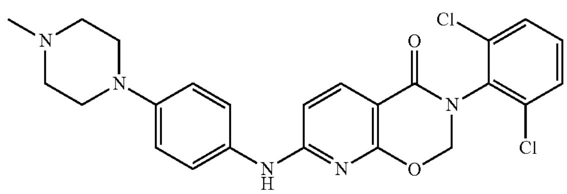 [SMILES: CN1CCN(c2ccc(Nc3ccc4c(n3)OCN(c3c(Cl)cccc3Cl)C4=O)cc2)CC1] |
| 1.32 | 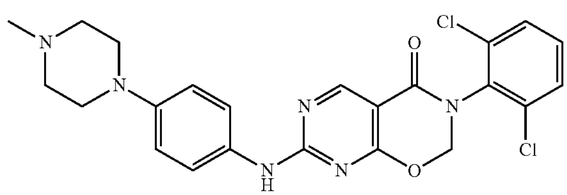 [SMILES: CN1CCN(c2ccc(Nc3ncc4c(n3)OCN(c3c(Cl)cccc3Cl)C4=O)cc2)CC1] |
| 1.33 | 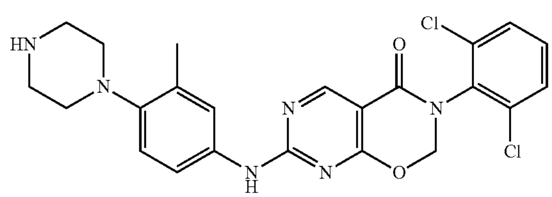 [SMILES: Cc1cc(Nc2ncc3c(n2)OCN(c2c(Cl)cccc2Cl)C3=O)ccc1N1CCNCC1] |
| 1.34 | 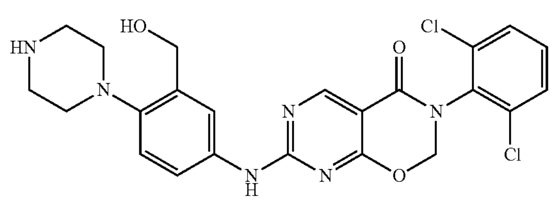 [SMILES: O=C1c2cnc(Nc3ccc(N4CCNCC4)c(CO)c3)nc2OCN1c1c(Cl)cccc1Cl] |

TABLE 1-continued
| Compound No. | Structure |
|---|---|
| 1.35 | 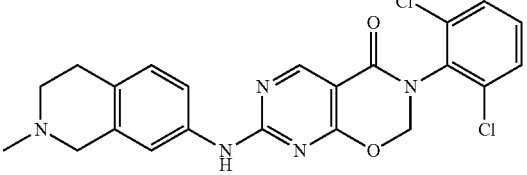 |
| 1.36 | 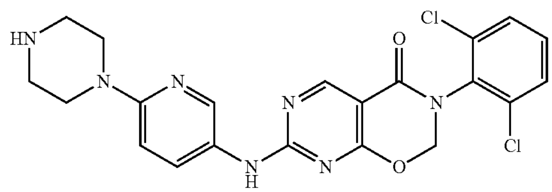 [SMILES: O=C1c2cnc(Nc3ccc(N4CCNCC4)nc3)nc2OCN1c1c(Cl)cccc1Cl] |
| 1.37 | 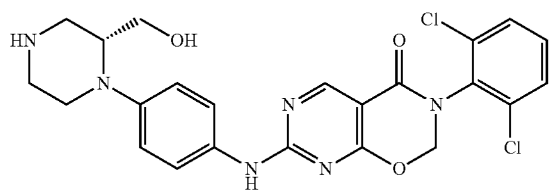 [SMILES: O=C1c2cnc(Nc3ccc(N4CCNC[C@@H]4CO)cc3)nc2OCN1c1c(Cl)cccc1Cl] |
| 1.38 | 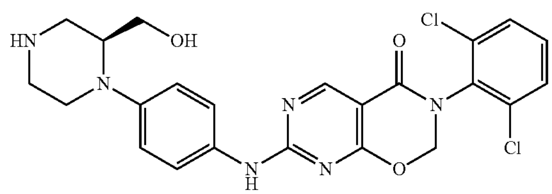 [SMILES: O=C1c2cnc(Nc3ccc(N4CCNC[C@H]4CO)cc3)nc2OCN1c1c(Cl)cccc1Cl] |
| 1.39 | 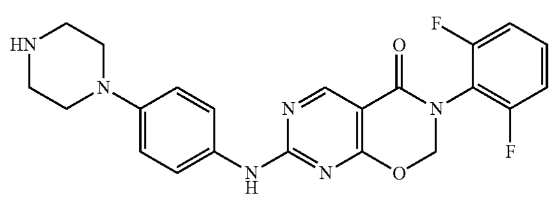 [SMILES: O=C1c2cnc(Nc3ccc(N4CCNCC4)cc3)nc2OCN1c1c(F)cccc1F] |
| 1.40 | 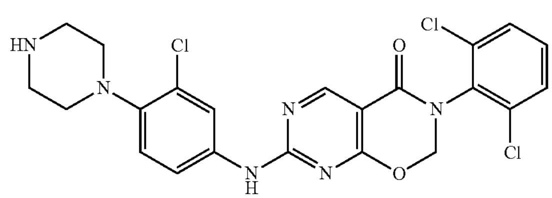 [SMILES: O=C1c2cnc(Nc3ccc(N4CCNCC4)c(Cl)c3)nc2OCN1c1c(Cl)cccc1Cl] |
| 1.41 | 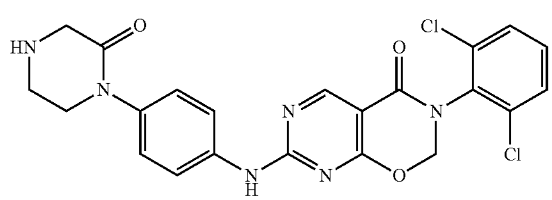 [SMILES: O=C1CNCCN1c1ccc(Nc2ncc3c(n2)OCN(c2c(Cl)cccc2Cl)C3=O)cc1] |
| 1.42 | 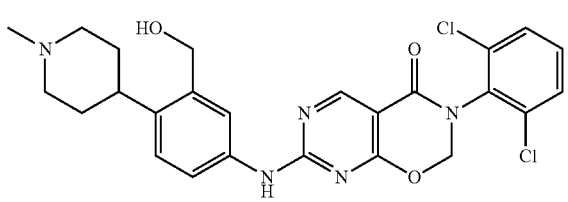 [SMILES: CN1CCC(c2ccc(Nc3ncc4c(n3)OCN(c3c(Cl)cccc3Cl)C4=O)cc2CO)CC1] |

TABLE 1-continued

| Compound No. | Structure |
|---|---|
| 1.43 | 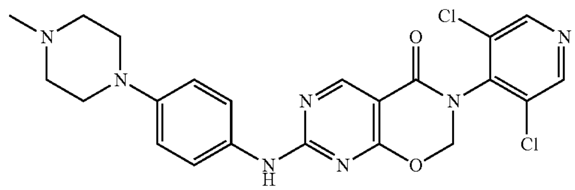 [SMILES: CN1CCN(c2ccc(Nc3ncc4c(n3)OCN(c3c(Cl)cncc3Cl)C4=O)cc2)CC1] |
| 1.44 | 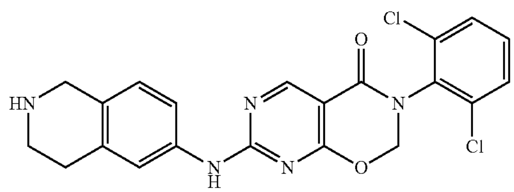 [SMILES: O=C1c2cnc(Nc3ccc4c(c3)CCNC4)nc2OCN1c1c(Cl)cccc1Cl] |
| 1.45 | 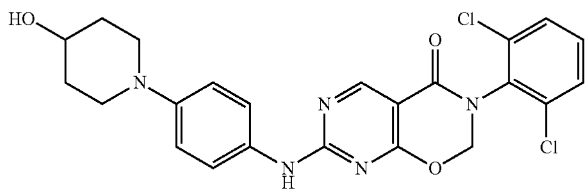 [SMILES: O=C1c2cnc(Nc3ccc(N4CCC(O)CC4)cc3)nc2OCN1c1c(Cl)cccc1Cl] |
| 1.46 | 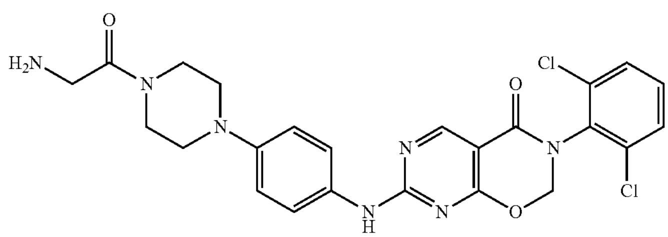 [SMILES: NCC(=O)N1CCN(c2ccc(Nc3ncc4c(n3)OCN(c3c(Cl)cccc3Cl)C4=O)cc2)CC1] |
| 1.47 | 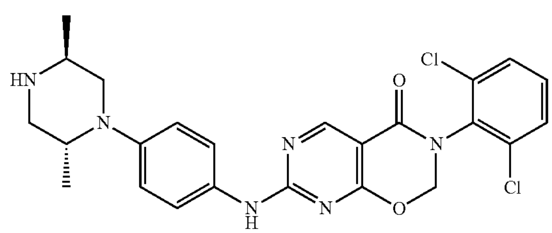 [SMILES: C[C@@H]1CN[C@@H](C)CN1c1ccc(Nc2ncc3c(n2)OCN(c2c(Cl)cccc2Cl)C3=O)cc1] |
| 1.48 | 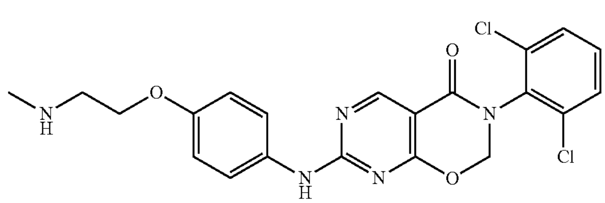 [SMILES: CNCCOc1ccc(Nc2ncc3c(n2)OCN(c2c(Cl)cccc2Cl)C3=O)cc1] |
| 1.49 | 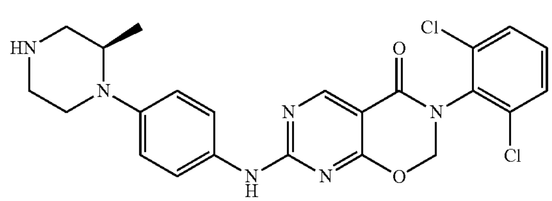 [SMILES: C[C@@H]1CNCCN1c1ccc(Nc2ncc3c(n2)OCN(c2c(Cl)cccc2Cl)C3=O)cc1] |

TABLE 1-continued

| Compound No. | Structure |
|---|---|
| 1.50 | 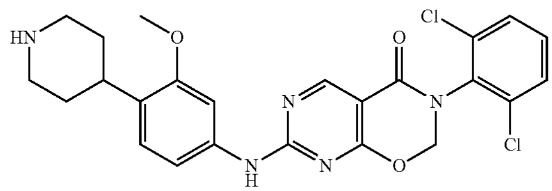 [SMILES: COc1cc(Nc2ncc3c(n2)OCN(c2c(Cl)cccc2Cl)C3=O)ccc1C1CCNCC1] |
| 1.51 | 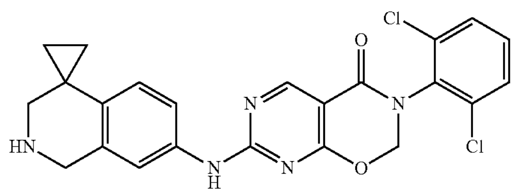 [SMILES: O=C1c2cnc(Nc3ccc4c(c3)CNCC43CC3)nc2OCN1c1c(Cl)cccc1Cl] |
| 1.52 | 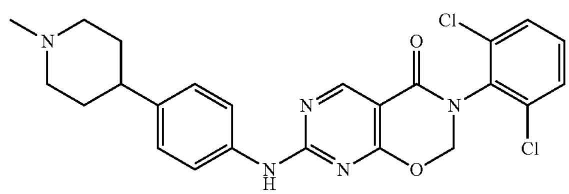 [SMILES: CN1CCC(c2ccc(Nc3ncc4c(n3)OCN(c3c(Cl)cccc3Cl)C4=O)cc2)CC1] |
| 1.53 | 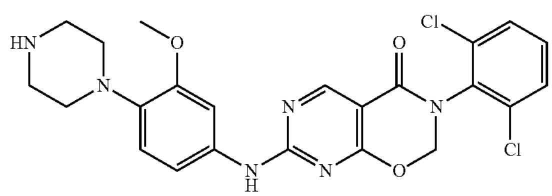 [SMILES: COc1cc(Nc2ncc3c(n2)OCN(c2c(Cl)cccc2Cl)C3=O)ccc1N1CCNCC1] |
| 1.54 | 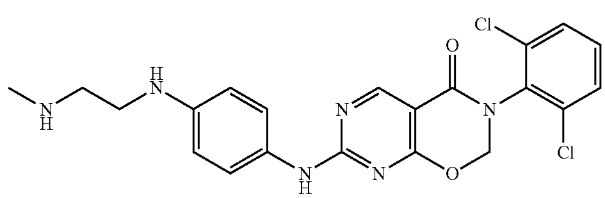 [SMILES: CNCCNc1ccc(Nc2ncc3c(n2)OCN(c2c(Cl)cccc2Cl)C3=O)cc1] |
| 1.55 | 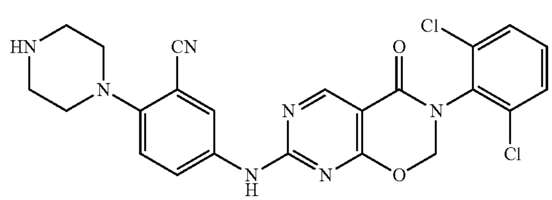 [SMILES: N#Cc1cc(Nc2ncc3c(n2)OCN(c2c(Cl)cccc2Cl)C3=O)ccc1N1CCNCC1] |
| 1.56 | 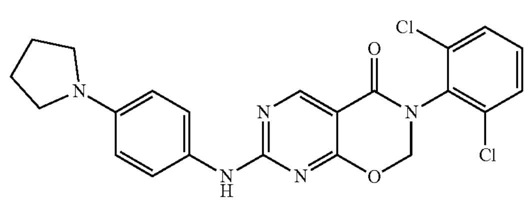 [SMILES: O=C1c2cnc(Nc3ccc(N4CCCC4)cc3)nc2OCN1c1c(Cl)cccc1Cl] |

TABLE 1-continued
| Compound No. | Structure |
|---|---|
| 1.57 | 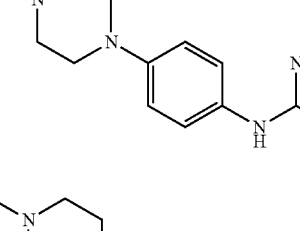 |
| 1.58 | 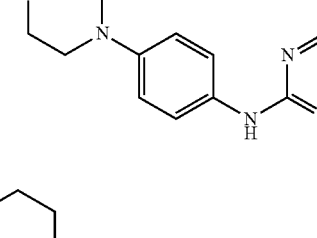 |
| 1.59 | 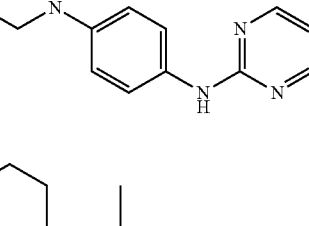 |
| 1.60 | 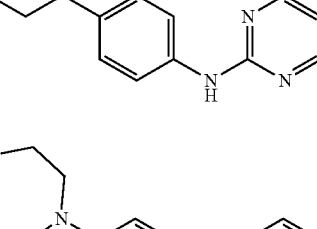 |
| 1.61 | 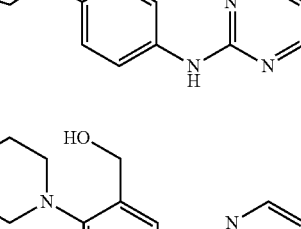 |
| 1.62 | 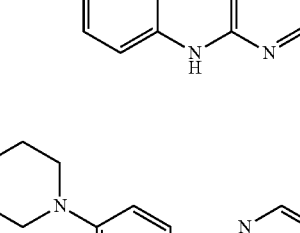 |
| 1.63 | 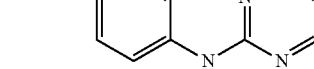 |

TABLE 1-continued

| Compound No. | Structure |
|---|---|
| 1.64 | 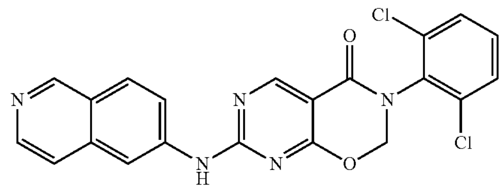 [SMILES: O=C1c2cnc(Nc3ccc4cnccc4c3)nc2OCN1c1c(Cl)cccc1Cl] |
| 1.65 | 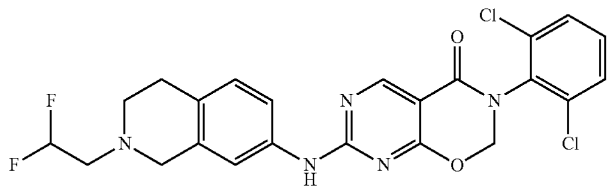 [SMILES: O=C1c2cnc(Nc3ccc4c(c3)CN(CC(F)F)CC4)nc2OCN1c1c(Cl)cccc1Cl] |
| 1.66 | 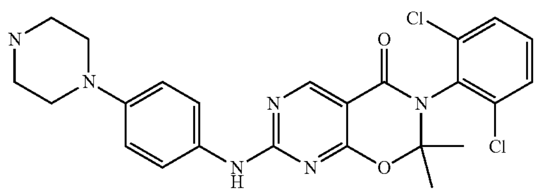 [SMILES: CC1(C)Oc2nc(Nc3ccc(N4CCNCC4)cc3)ncc2C(=O)N1c1c(Cl)cccc1Cl] |
| 1.67 | 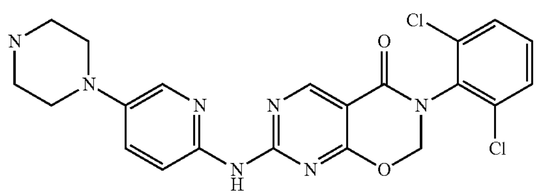 [SMILES: O=C1c2cnc(Nc3ccc(N4CCNCC4)cn3)nc2OCN1c1c(Cl)cccc1Cl] |
| 1.68 | 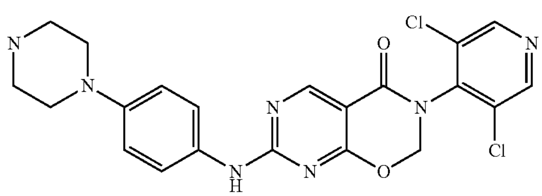 [SMILES: O=C1c2cnc(Nc3ccc(N4CCNCC4)cc3)nc2OCN1c1c(Cl)cncc1Cl] |
| 1.69 | 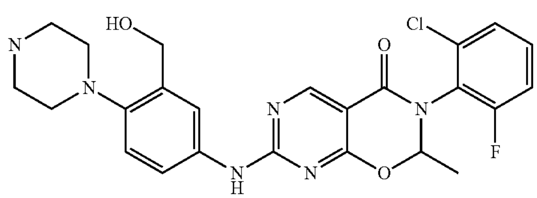 [SMILES: CC1Oc2nc(Nc3ccc(N4CCNCC4)c(CO)c3)ncc2C(=O)N1c1c(F)cccc1Cl] |
| 1.70 | 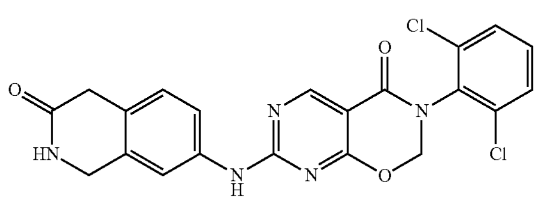 [SMILES: O=C1Cc2ccc(Nc3ncc4c(n3)OCN(c3c(Cl)cccc3Cl)C4=O)cc2CN1] |

TABLE 1-continued

| Compound No. | Structure |
|---|---|
| 1.71 | 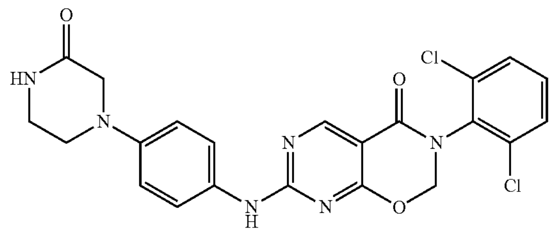 [SMILES: O=C1CN(c2ccc(Nc3ncc4c(n3)OCN(c3c(Cl)cccc3Cl)C4=O)cc2)CCN1] |
| 1.72 | 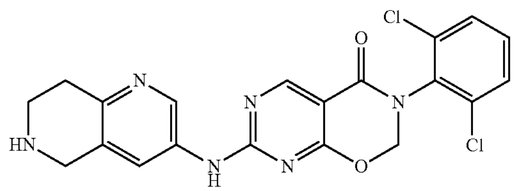 [SMILES: O=C1c2cnc(Nc3cnc4c(c3)CNCC4)nc2OCN1c1c(Cl)cccc1Cl] |
| 1.73 | 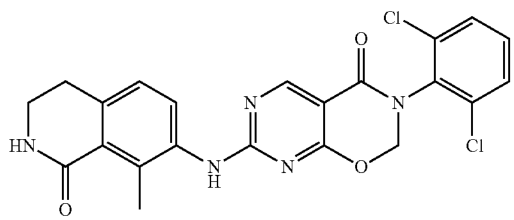 [SMILES: Cc1c(Nc2ncc3c(n2)OCN(c2c(Cl)cccc2Cl)C3=O)ccc2c1C(=O)NCC2] |
| 1.74 | 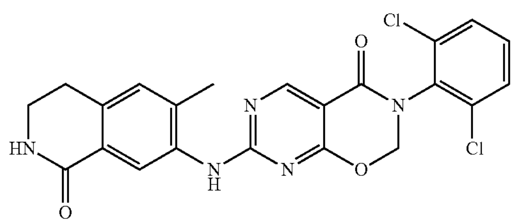 [SMILES: Cc1cc2c(cc1Nc1ncc3c(n1)OCN(c1c(Cl)cccc1Cl)C3=O)C(=O)NCC2] |
| 1.75 | 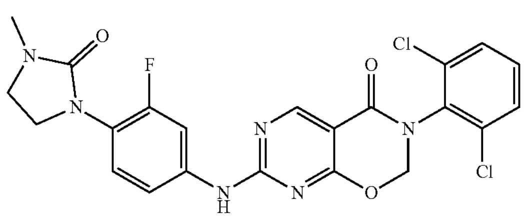 [SMILES: CN1CCN(c2ccc(Nc3ncc4c(n3)OCN(c3c(Cl)cccc3Cl)C4=O)cc2F)C1=O] |
| 1.76 | 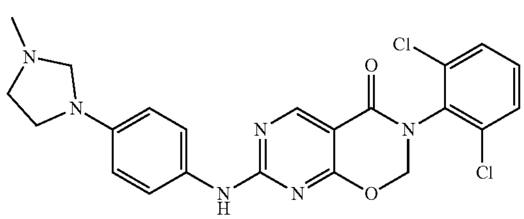 [SMILES: CN1CCN(c2ccc(Nc3ncc4c(n3)OCN(c3c(Cl)cccc3Cl)C4=O)cc2)C1] |
| 1.77 | 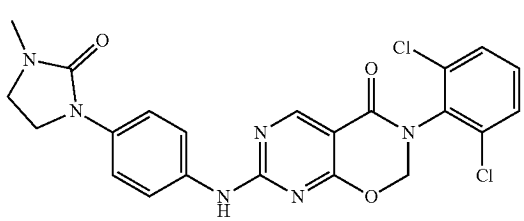 [SMILES: CN1CCN(c2ccc(Nc3ncc4c(n3)OCN(c3c(Cl)cccc3Cl)C4=O)cc2)C1=O] |

TABLE 1-continued
| Compound No. | Structure |
|---|---|
| 1.78 | 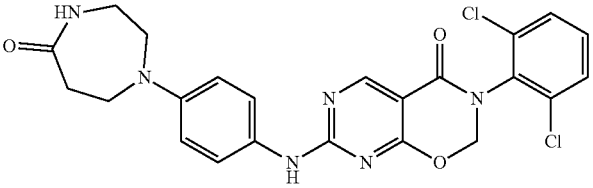 [SMILES: O=C1CCN(c2ccc(Nc3ncc4c(n3)OCN(c3c(Cl)cccc3Cl)C4=O)cc2)CCN1] |
| 1.79 | 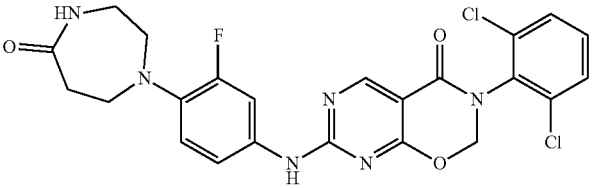 [SMILES: O=C1CCN(c2ccc(Nc3ncc4c(n3)OCN(c3c(Cl)cccc3Cl)C4=O)cc2F)CCN1] |
| 1.80 | 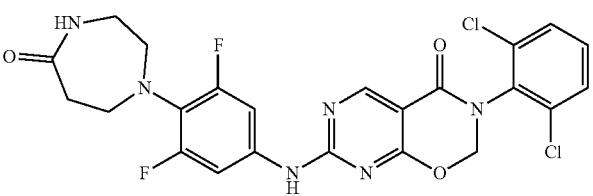 [SMILES: O=C1CCN(c2c(F)cc(Nc3ncc4c(n3)OCN(c3c(Cl)cccc3Cl)C4=O)cc2F)CCN1] |
| 1.81 | 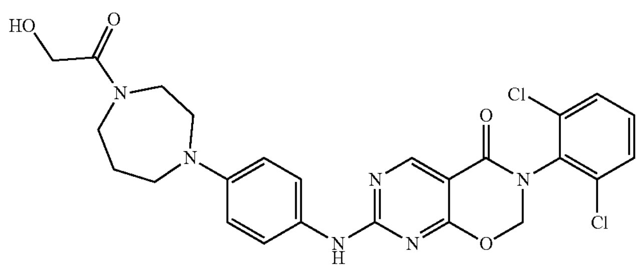 [SMILES: O=C(CO)N1CCCN(c2ccc(Nc3ncc4c(n3)OCN(c3c(Cl)cccc3Cl)C4=O)cc2)CC1] |
| 1.82 | 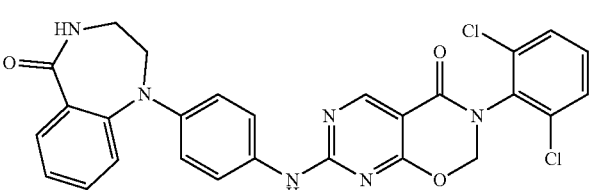 |
| 1.83 | 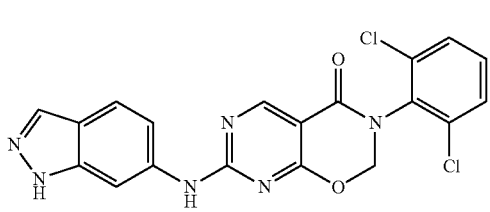 |
| 1.84 | 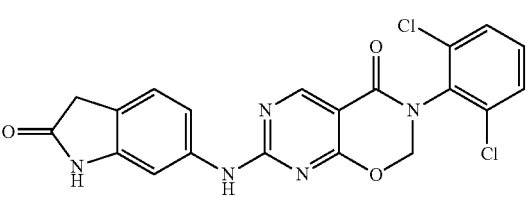 [SMILES: O=C1Cc2ccc(Nc3ncc4c(n3)OCN(c3c(Cl)cccc3Cl)C4=O)cc2N1] |

TABLE 1-continued

| Compound No. | Structure |
| --- | --- |
| 1.85 | 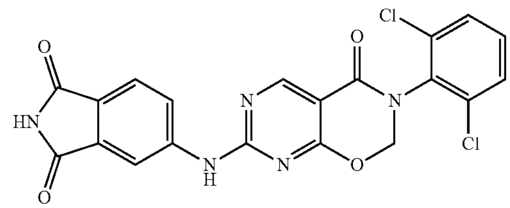 [SMILES: O=C1NC(=O)c2cc(Nc3ncc4c(n3)OCN(c3c(Cl)cccc3Cl)C4=O)ccc21] |
| 1.86 | 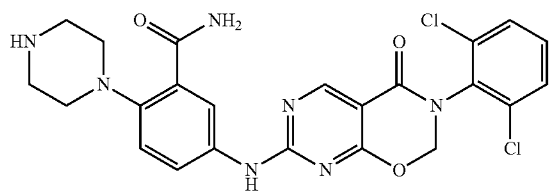 [SMILES: NC(=O)c1cc(Nc2ncc3c(n2)OCN(c2c(Cl)cccc2Cl)C3=O)ccc1N1CCNCC1] |
| 1.87 | 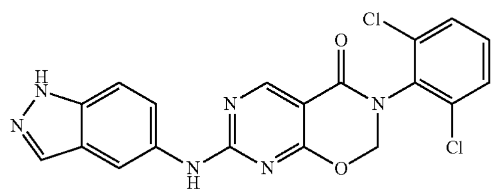 [SMILES: O=C1c2cnc(Nc3ccc4[nH]ncc4c3)nc2OCN1c1c(Cl)cccc1Cl] |
| 1.88 | 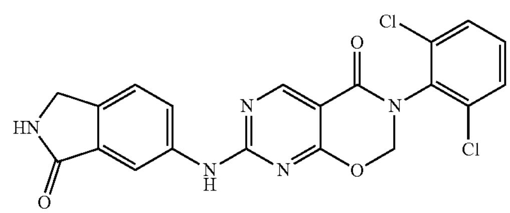 [SMILES: O=C1NCc2ccc(Nc3ncc4c(n3)OCN(c3c(Cl)cccc3Cl)C4=O)cc21] |
| 1.89 | 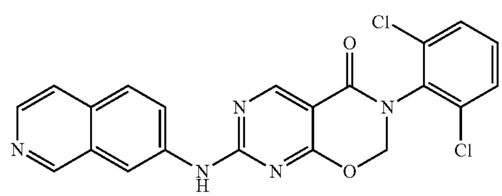 [SMILES: O=C1c2cnc(Nc3ccc4ccncc4c3)nc2OCN1c1c(Cl)cccc1Cl] |
| 1.90 | 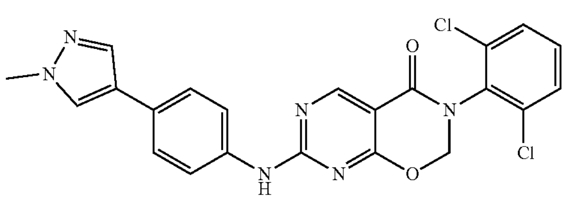 [SMILES: Cn1cc(-c2ccc(Nc3ncc4c(n3)OCN(c3c(Cl)cccc3Cl)C4=O)cc2)cn1] |
| 1.91 | 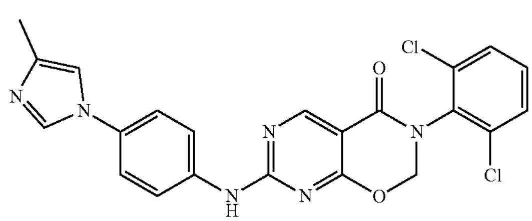 [SMILES: Cc1cn(-c2ccc(Nc3ncc4c(n3)OCN(c3c(Cl)cccc3Cl)C4=O)cc2)cn1] |

TABLE 1-continued
| Compound No. | Structure |
|---|---|
| 1.92 | 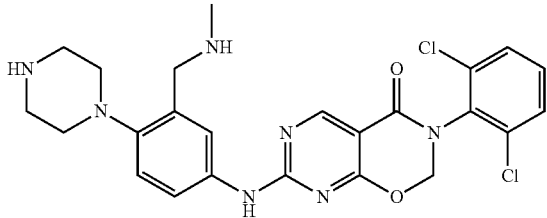 [SMILES: CNCc1cc(Nc2ncc3c(n2)OCN(c2c(Cl)cccc2Cl)C3=O)ccc1N1CCNCC1] |
| 1.93 | 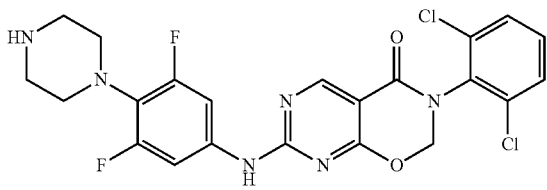 [SMILES: O=C1c2cnc(Nc3cc(F)c(N4CCNCC4)c(F)c3)nc2OCN1c1c(Cl)cccc1Cl] |
| 1.94 | 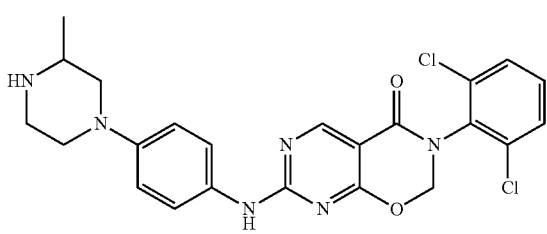 [SMILES: CC1CN(c2ccc(Nc3ncc4c(n3)OCN(c3c(Cl)cccc3Cl)C4=O)cc2)CCN1] |
| 1.95 | 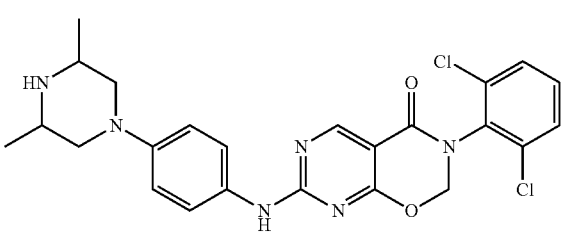 [SMILES: CC1CN(c2ccc(Nc3ncc4c(n3)OCN(c3c(Cl)cccc3Cl)C4=O)cc2)CC(C)N1] |
| 1.96 | 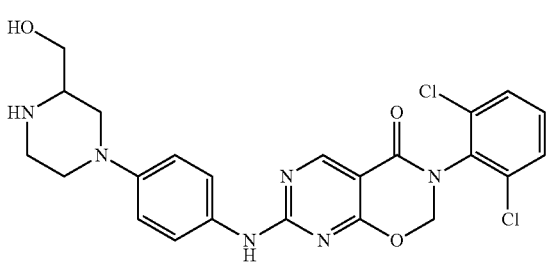 [SMILES: O=C1c2cnc(Nc3ccc(N4CCNC(CO)C4)cc3)nc2OCN1c1c(Cl)cccc1Cl] |
| 1.97 | 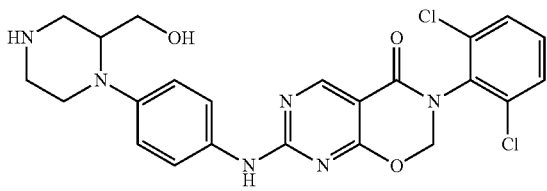 [SMILES: O=C1c2cnc(Nc3ccc(N4CCNCC4CO)cc3)nc2OCN1c1c(Cl)cccc1Cl] |
| 1.98 | 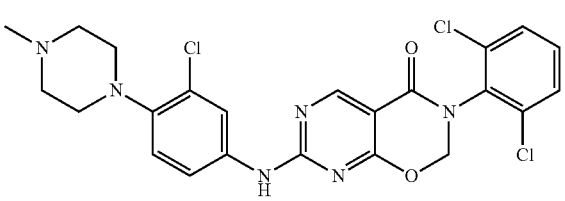 [SMILES: CN1CCN(c2ccc(Nc3ncc4c(n3)OCN(c3c(Cl)cccc3Cl)C4=O)cc2Cl)CC1] |

TABLE 1-continued
| Compound No. | Structure |
|---|---|
| 1.99 | 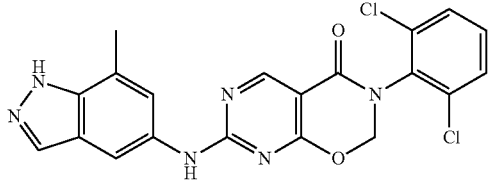 [SMILES: Cc1cc(Nc2ncc3c(n2)OCN(c2c(Cl)cccc2Cl)C3=O)cc2cn[nH]c12] |
| 1.100 | 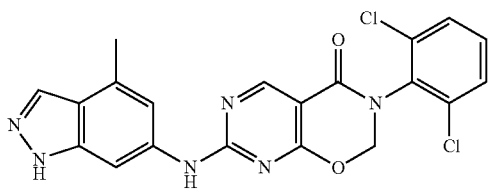 [SMILES: Cc1cc(Nc2ncc3c(n2)OCN(c2c(Cl)cccc2Cl)C3=O)cc2[nH]ncc12] |
| 1.101 | 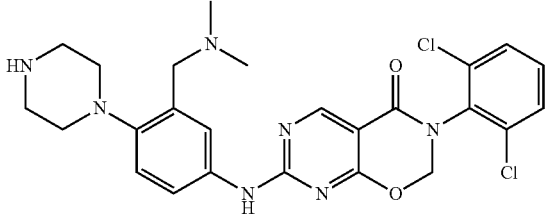 [SMILES: CN(C)Cc1cc(Nc2ncc3c(n2)OCN(c2c(Cl)cccc2Cl)C3=O)ccc1N1CCNCC1] |
| 1.102 | 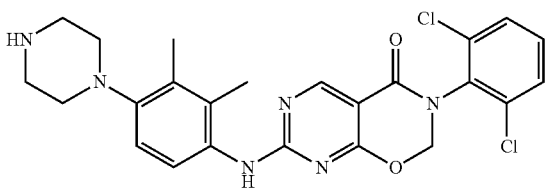 [SMILES: Cc1c(Nc2ncc3c(n2)OCN(c2c(Cl)cccc2Cl)C3=O)ccc(N2CCNCC2)c1C] |
| 1.103 | 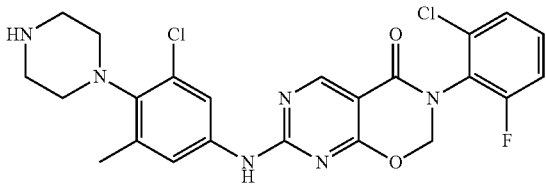 [SMILES: Cc1cc(Nc2ncc3c(n2)OCN(c2c(F)cccc2Cl)C3=O)cc(Cl)c1N1CCNCC1] |
| 1.104 | 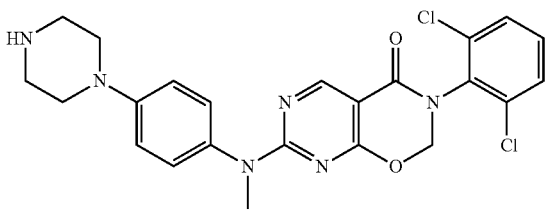 [SMILES: CN(c1ccc(N2CCNCC2)cc1)c1ncc2c(n1)OCN(c1c(Cl)cccc1Cl)C2=O] |
| 1.105 | 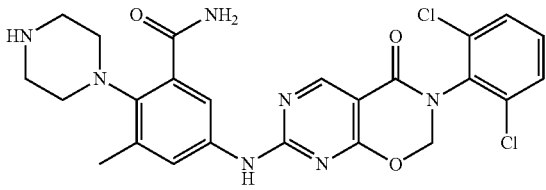 [SMILES: Cc1cc(Nc2ncc3c(n2)OCN(c2c(Cl)cccc2Cl)C3=O)cc(C(N)=O)c1N1CCNCC1] |

TABLE 1-continued

| Compound No. | Structure |
|---|---|
| 1.106 | *(chemical structure)* |
| 1.107 | *(chemical structure)* |
| 1.108 | *(chemical structure)* |
| 1.109 | *(chemical structure)* |
| 1.110 | *(chemical structure)* |
| 1.111 | *(chemical structure)* |
| 1.112 | *(chemical structure)* |

TABLE 1-continued

| Compound No. | Structure |
|---|---|
| 1.113 | 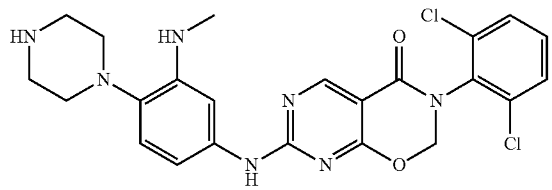 [SMILES: CNc1cc(Nc2ncc3c(n2)OCN(c2c(Cl)cccc2Cl)C3=O)ccc1N1CCNCC1] |
| 1.114 | 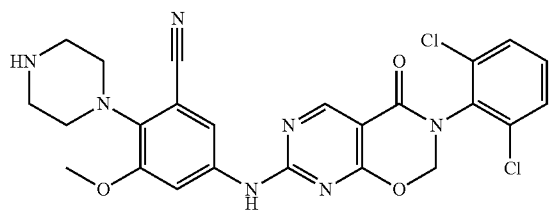 [SMILES: COc1cc(Nc2ncc3c(n2)OCN(c2c(Cl)cccc2Cl)C3=O)cc(C#N)c1N1CCNCC1] |
| 1.115 | 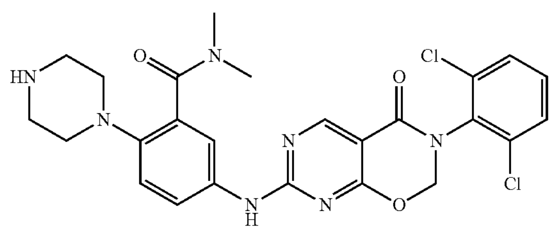 [SMILES: CN(C)C(=O)c1cc(Nc2ncc3c(n2)OCN(c2c(Cl)cccc2Cl)C3=O)ccc1N1CCNCC1] |
| 1.116 | 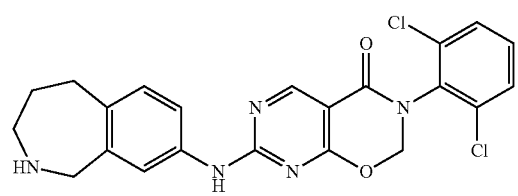 [SMILES: O=C1c2cnc(Nc3ccc4c(c3)CNCCC4)nc2OCN1c1c(Cl)cccc1Cl] |
| 1.117 | 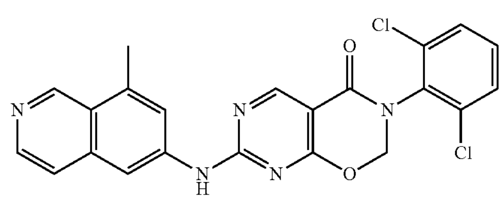 [SMILES: Cc1cc(Nc2ncc3c(n2)OCN(c2c(Cl)cccc2Cl)C3=O)cc2ccncc12] |
| 1.118 | 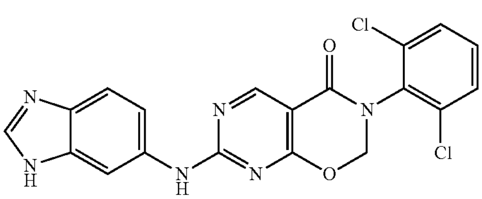 [SMILES: O=C1c2cnc(Nc3ccc4nc[nH]c4c3)nc2OCN1c1c(Cl)cccc1Cl] |
| 1.119 | 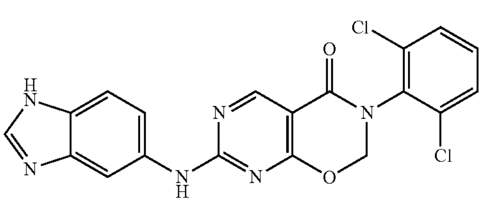 [SMILES: O=C1c2cnc(Nc3ccc4[nH]cnc4c3)nc2OCN1c1c(Cl)cccc1Cl] |

TABLE 1-continued
| Compound No. | Structure |
|---|---|
| 1.120 | 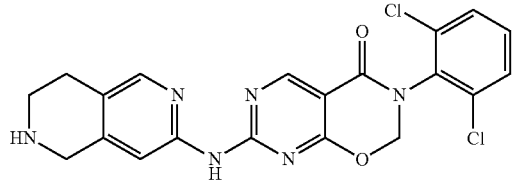 [SMILES: O=C1c2cnc(Nc3cc4c(cn3)CCNC4)nc2OCN1c1c(Cl)cccc1Cl] |
| 1.121 | 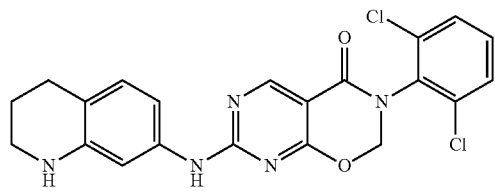 [SMILES: O=C1c2cnc(Nc3ccc4c(c3)NCCC4)nc2OCN1c1c(Cl)cccc1Cl] |
| 1.122 | 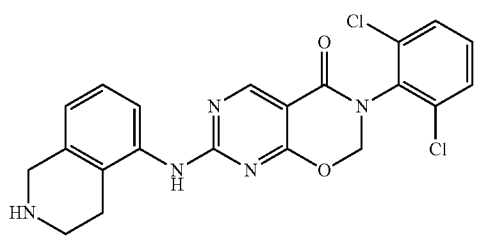 [SMILES: O=C1c2cnc(Nc3cccc4c3CCNC4)nc2OCN1c1c(Cl)cccc1Cl] |
| 1.123 | 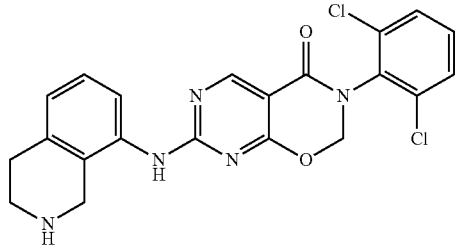 [SMILES: O=C1c2cnc(Nc3cccc4c3CNCC4)nc2OCN1c1c(Cl)cccc1Cl] |
| 1.124 | 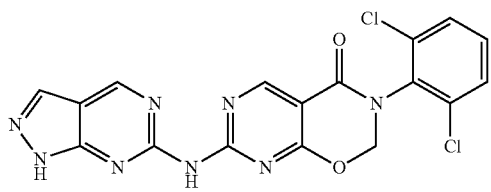 [SMILES: O=C1c2cnc(Nc3ncc4cn[nH]c4n3)nc2OCN1c1c(Cl)cccc1Cl] |
| 1.125 | 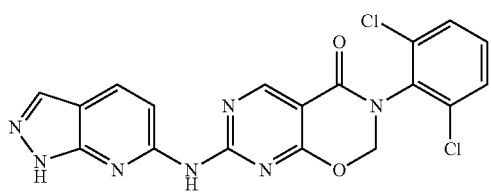 [SMILES: O=C1c2cnc(Nc3ccc4cn[nH]c4n3)nc2OCN1c1c(Cl)cccc1Cl] |
| 1.126 | 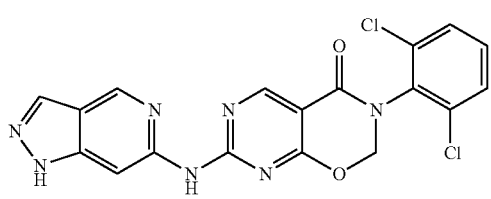 [SMILES: O=C1c2cnc(Nc3cc4[nH]ncc4cn3)nc2OCN1c1c(Cl)cccc1Cl] |

TABLE 1-continued

| Compound No. | Structure |
|---|---|
| 1.127 | 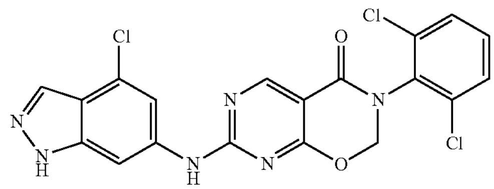 [SMILES: O=C1c2cnc(Nc3cc(Cl)c4cn[nH]c4c3)nc2OCN1c1c(Cl)cccc1Cl] |
| 1.128 | 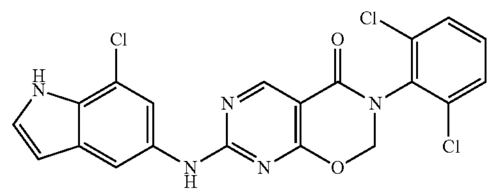 [SMILES: O=C1c2cnc(Nc3cc(Cl)c4[nH]ccc4c3)nc2OCN1c1c(Cl)cccc1Cl] |
| 1.129 | 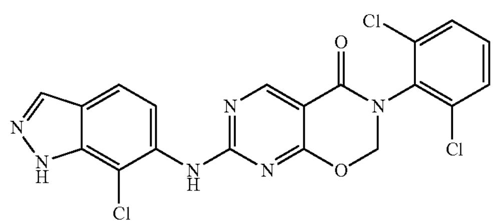 [SMILES: O=C1c2cnc(Nc3ccc4cn[nH]c4c3Cl)nc2OCN1c1c(Cl)cccc1Cl] |
| 1.130 | 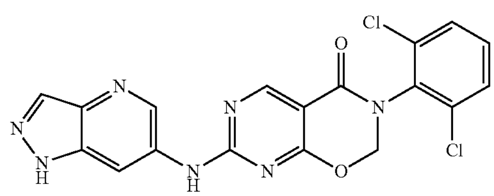 [SMILES: O=C1c2cnc(Nc3cnc4cn[nH]c4c3)nc2OCN1c1c(Cl)cccc1Cl] |
| 1.131 | 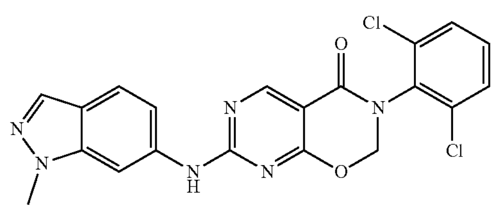 [SMILES: Cn1ncc2ccc(Nc3ncc4c(n3)OCN(c3c(Cl)cccc3Cl)C4=O)cc21] |
| 1.132 | 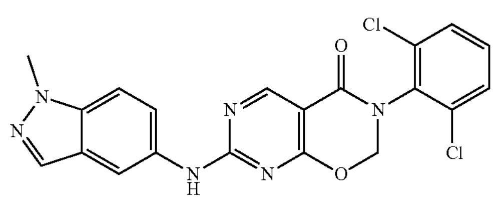 [SMILES: Cn1ncc2cc(Nc3ncc4c(n3)OCN(c3c(Cl)cccc3Cl)C4=O)ccc21] |
| 1.133 | 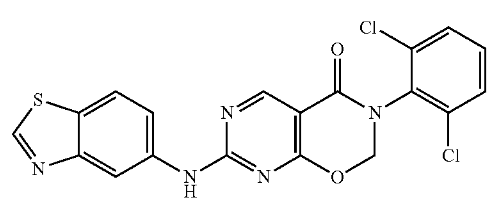 [SMILES: O=C1c2cnc(Nc3ccc4scnc4c3)nc2OCN1c1c(Cl)cccc1Cl] |

TABLE 1-continued

| Compound No. | Structure |
|---|---|
| 1.134 | 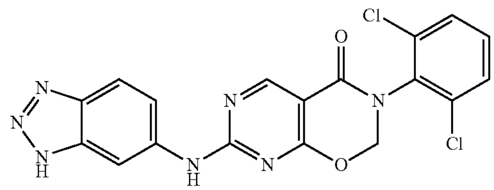 [SMILES: O=C1c2cnc(Nc3ccc4nn[nH]c4c3)nc2OCN1c1c(Cl)cccc1Cl] |
| 1.135 | 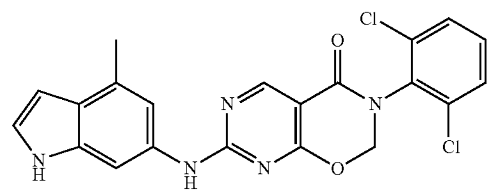 [SMILES: Cc1cc(Nc2ncc3c(n2)OCN(c2c(Cl)cccc2Cl)C3=O)cc2[nH]ccc12] |
| 1.136 | 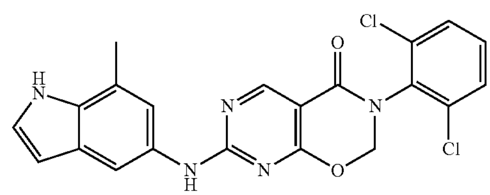 [SMILES: Cc1cc(Nc2ncc3c(n2)OCN(c2c(Cl)cccc2Cl)C3=O)cc2cc[nH]c12] |
| 1.137 | 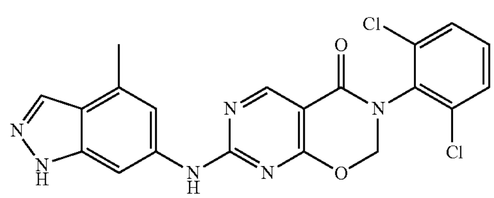 [SMILES: Cc1cc(Nc2ncc3c(n2)OCN(c2c(Cl)cccc2Cl)C3=O)cc2[nH]ncc12] |
| 1.138 | 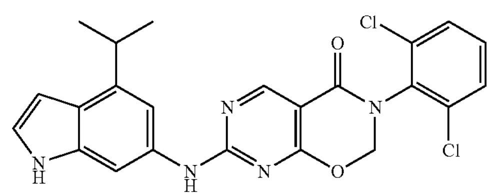 [SMILES: CC(C)c1cc(Nc2ncc3c(n2)OCN(c2c(Cl)cccc2Cl)C3=O)cc2[nH]ccc12] |
| 1.139 | 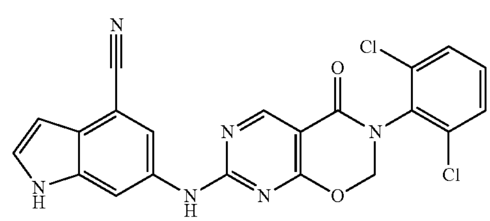 [SMILES: N#Cc1cc(Nc2ncc3c(n2)OCN(c2c(Cl)cccc2Cl)C3=O)cc2[nH]ccc12] |
| 1.140 | 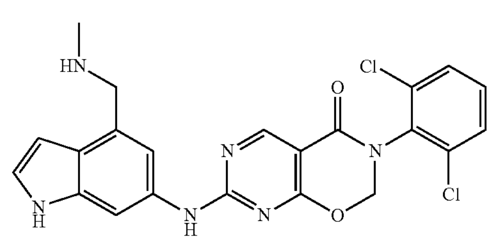 [SMILES: CNCc1cc(Nc2ncc3c(n2)OCN(c2c(Cl)cccc2Cl)C3=O)cc2[nH]ccc12] |

TABLE 1-continued

| Compound No. | Structure |
|---|---|
| 1.141 | 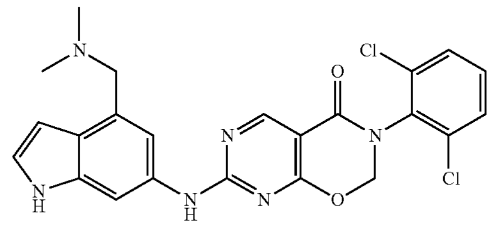 [SMILES: CN(C)Cc1cc(Nc2ncc3c(n2)OCN(c2c(Cl)cccc2Cl)C3=O)cc2[nH]ccc12] |
| 1.142 | 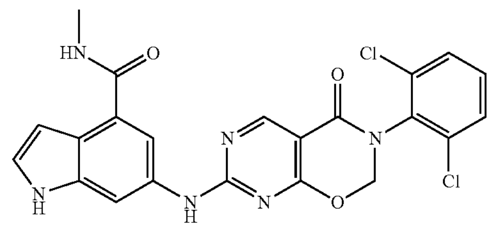 [SMILES: CNC(=O)c1cc(Nc2ncc3c(n2)OCN(c2c(Cl)cccc2Cl)C3=O)cc2[nH]ccc12] |
| 1.143 | 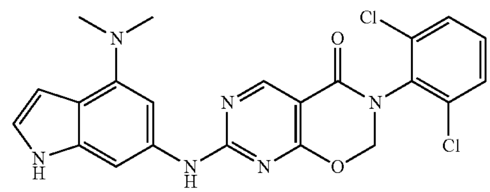 [SMILES: CN(C)c1cc(Nc2ncc3c(n2)OCN(c2c(Cl)cccc2Cl)C3=O)cc2[nH]ccc12] |
| 1.144 | 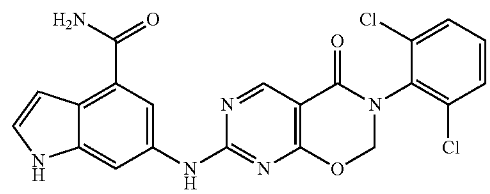 [SMILES: NC(=O)c1cc(Nc2ncc3c(n2)OCN(c2c(Cl)cccc2Cl)C3=O)cc2[nH]ccc12] |
| 1.145 | 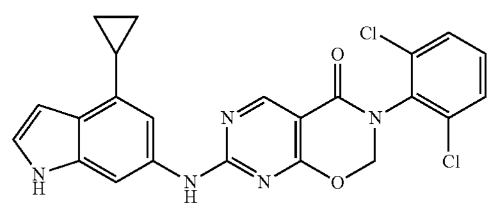 [SMILES: O=C1c2cnc(Nc3cc(C4CC4)c4cc[nH]c4c3)nc2OCN1c1c(Cl)cccc1Cl] |
| 1.146 | 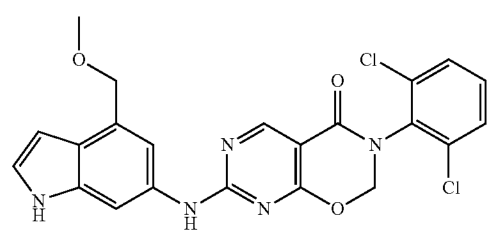 [SMILES: COCc1cc(Nc2ncc3c(n2)OCN(c2c(Cl)cccc2Cl)C3=O)cc2[nH]ccc12] |
| 1.147 | 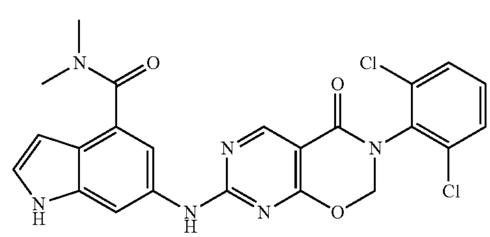 [SMILES: CN(C)C(=O)c1cc(Nc2ncc3c(n2)OCN(c2c(Cl)cccc2Cl)C3=O)cc2[nH]ccc12] |

TABLE 1-continued
| Compound No. | Structure |
|---|---|
| 1.148 | 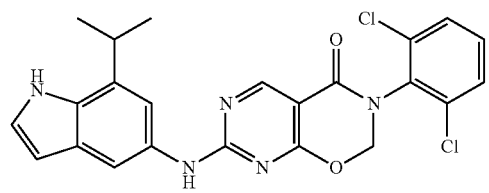 [SMILES: CC(C)c1cc(Nc2ncc3c(n2)OCN(c2c(Cl)cccc2Cl)C3=O)cc2cc[nH]c12] |
| 1.149 | 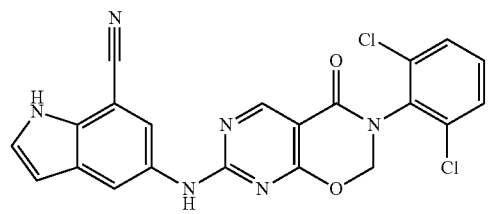 [SMILES: N#Cc1cc(Nc2ncc3c(n2)OCN(c2c(Cl)cccc2Cl)C3=O)cc2cc[nH]c12] |
| 1.150 | 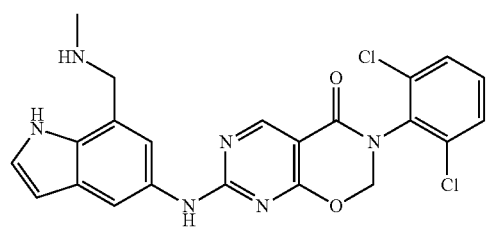 [SMILES: CNCc1cc(Nc2ncc3c(n2)OCN(c2c(Cl)cccc2Cl)C3=O)cc2cc[nH]c12] |
| 1.151 | 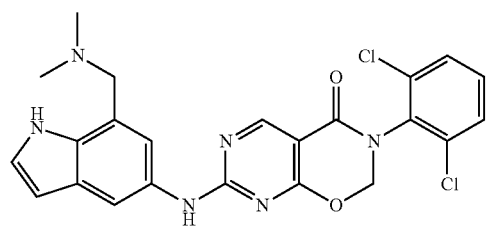 [SMILES: CN(C)Cc1cc(Nc2ncc3c(n2)OCN(c2c(Cl)cccc2Cl)C3=O)cc2cc[nH]c12] |
| 1.152 | 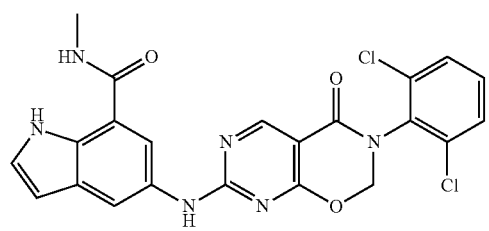 [SMILES: CNC(=O)c1cc(Nc2ncc3c(n2)OCN(c2c(Cl)cccc2Cl)C3=O)cc2cc[nH]c12] |
| 1.153 | 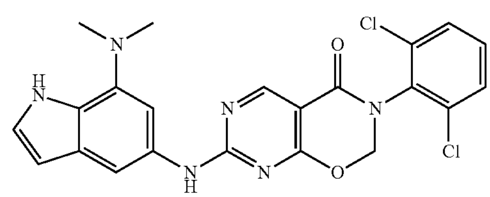 [SMILES: CN(C)c1cc(Nc2ncc3c(n2)OCN(c2c(Cl)cccc2Cl)C3=O)cc2cc[nH]c12] |
| 1.154 | 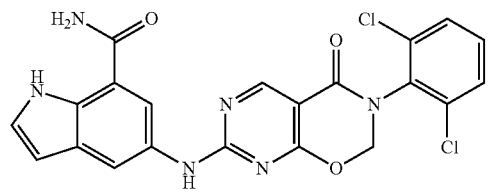 [SMILES: NC(=O)c1cc(Nc2ncc3c(n2)OCN(c2c(Cl)cccc2Cl)C3=O)cc2cc[nH]c12] |

217 218
TABLE 1-continued
| Compound No. | Structure |
|---|---|
| 1.155 | 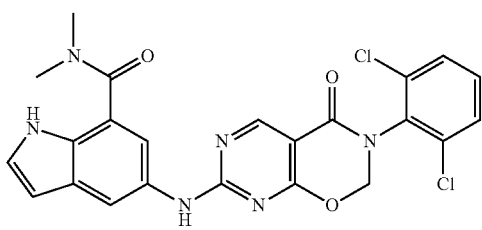 [SMILES: CN(C)C(=O)c1cc(Nc2ncc3c(n2)OCN(c2c(Cl)cccc2Cl)C3=O)cc2cc[nH]c12] |
| 1.156 | 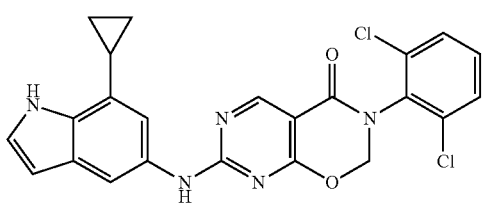 [SMILES: O=C1c2cnc(Nc3cc(C4CC4)c4[nH]ccc4c3)nc2OCN1c1c(Cl)cccc1Cl] |
| 1.157 | 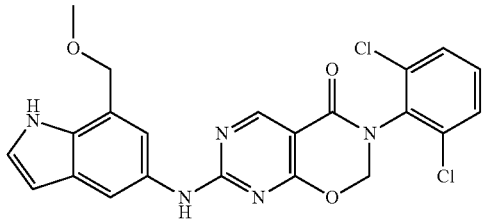 [SMILES: COCc1cc(Nc2ncc3c(n2)OCN(c2c(Cl)cccc2Cl)C3=O)cc2cc[nH]c12] |
| 1.158 | 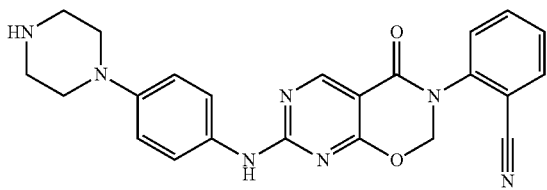 [SMILES: N#Cc1ccccc1N1COc2nc(Nc3ccc(N4CCNCC4)cc3)ncc2C1=O] |
| 1.159 | 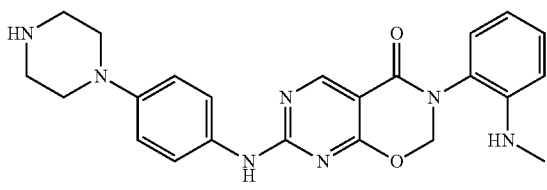 [SMILES: CNc1ccccc1N1COc2nc(Nc3ccc(N4CCNCC4)cc3)ncc2C1=O] |
| 1.160 | 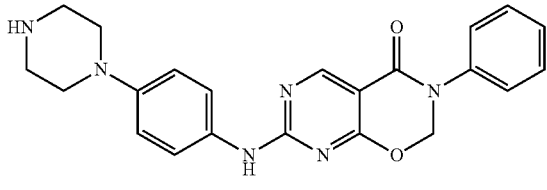 [SMILES: O=C1c2cnc(Nc3ccc(N4CCNCC4)cc3)nc2OCN1c1ccccc1] |
| 1.161 | 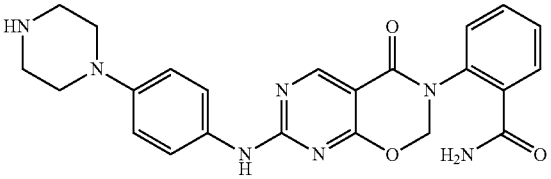 [SMILES: NC(=O)c1ccccc1N1COc2nc(Nc3ccc(N4CCNCC4)cc3)ncc2C1=O] |

US 10,807,994 B2
219                                                                                          220
TABLE 1-continued
| Compound No. | Structure |
|---|---|
| 1.162 | 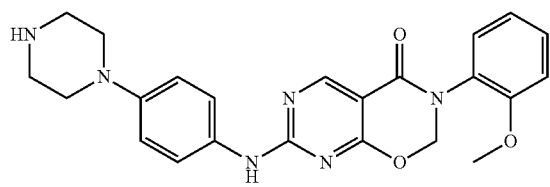 [SMILES: COc1ccccc1N1COc2nc(Nc3ccc(N4CCNCC4)cc3)ncc2C1=O] |
| 1.163 | 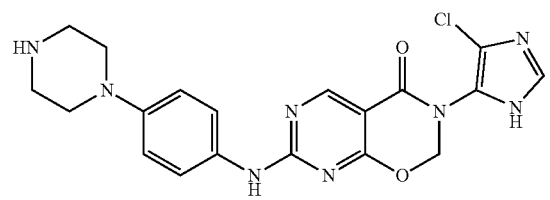 [SMILES: O=C1c2cnc(Nc3ccc(N4CCNCC4)cc3)nc2OCN1c1[nH]cnc1Cl] |
| 1.164 | 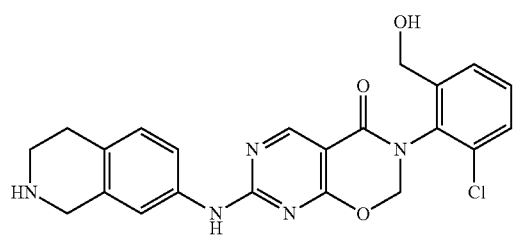 [SMILES: O=C1c2cnc(Nc3ccc4c(c3)CNCC4)nc2OCN1c1c(Cl)cccc1CO] |
| 1.165 | 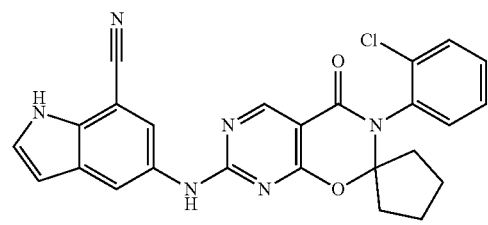 [SMILES: N#Cc1cc(Nc2ncc3c(n2)OC2(CCCC2)N(c2ccccc2Cl)C3=O)cc2cc[nH]c12] |
| 1.166 | 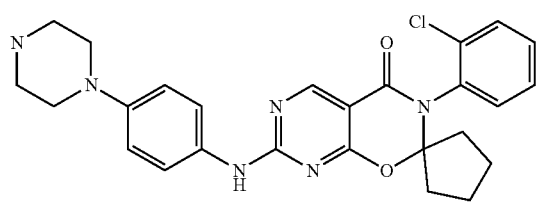 [SMILES: O=C1c2cnc(Nc3ccc(N4CCNCC4)cc3)nc2OC2(CCCC2)N1c1ccccc1Cl] |
| 1.167 | 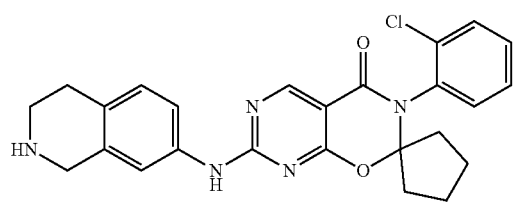 [SMILES: O=C1c2cnc(Nc3ccc4c(c3)CNCC4)nc2OC2(CCCC2)N1c1ccccc1Cl] |
| 1.168 | 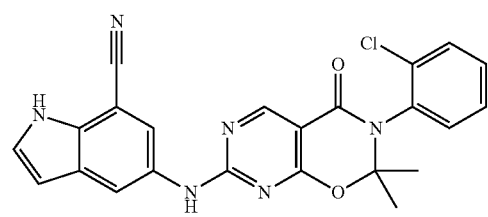 [SMILES: CC1(C)Oc2nc(Nc3cc(C#N)c4[nH]ccc4c3)ncc2C(=O)N1c1ccccc1Cl] |

US 10,807,994 B2
TABLE 1-continued
| Compound No. | Structure |
|---|---|
| 1.169 | 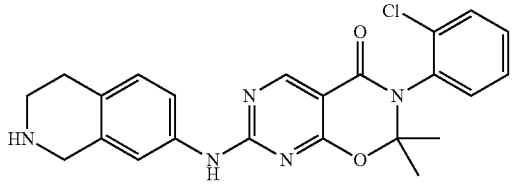 [SMILES: CC1(C)Oc2nc(Nc3ccc4c(c3)CNCC4)ncc2C(=O)N1c1ccccc1Cl] |
| 1.170 | 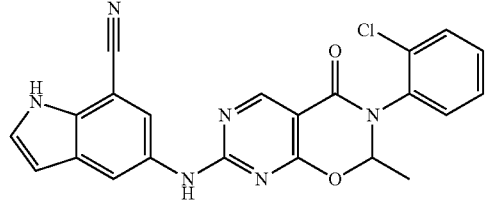 [SMILES: CC1Oc2nc(Nc3cc(C#N)c4[nH]ccc4c3)ncc2C(=O)N1c1ccccc1Cl] |
| 1.171 | 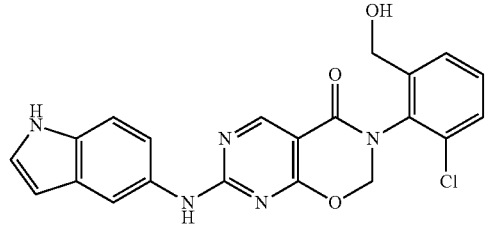 [SMILES: O=C1c2cnc(Nc3ccc4[nH]ccc4c3)nc2OCN1c1c(Cl)cccc1CO] |
| 1.172 | 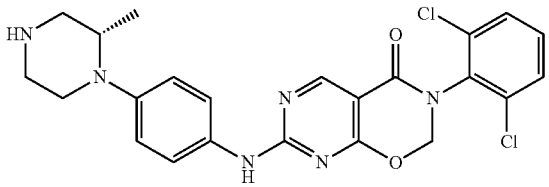 |
| 1.173 | 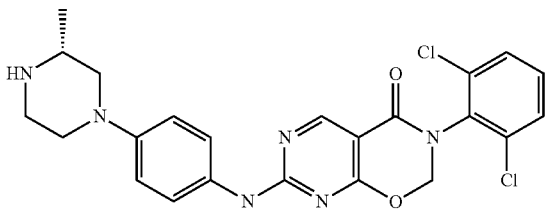 |
| 1.174 | 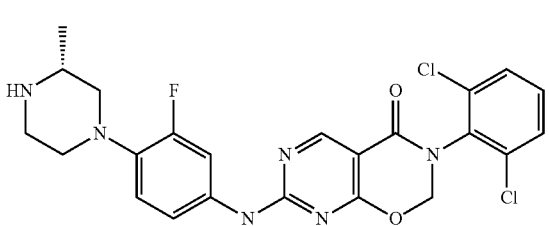 |
| 1.175 | 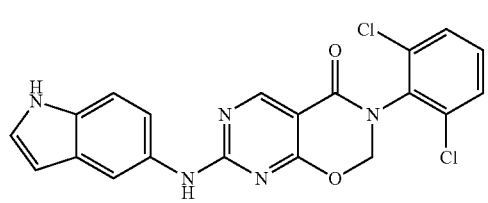 [SMILES: O=C1c2cnc(Nc3ccc4[nH]ccc4c3)nc2OCN1c1c(Cl)cccc1Cl] |

TABLE 1-continued

| Compound No. | Structure |
|---|---|
| 1.176 | 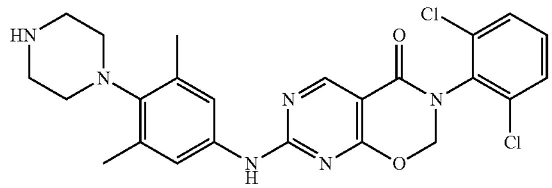 [SMILES: Cc1cc(Nc2ncc3c(n2)OCN(c2c(Cl)cccc2Cl)C3=O)cc(C)c1N1CCNCC1] |
| 1.177 | 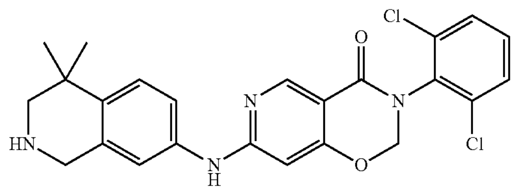 [SMILES: CC1(C)CNCc2cc(Nc3cc4c(cn3)C(=O)N(c3c(Cl)cccc3Cl)CO4)ccc21] |
| 1.178 | 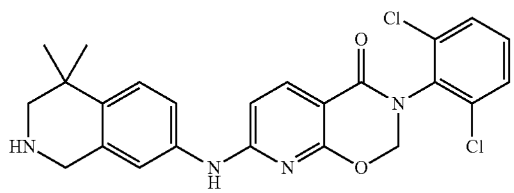 [SMILES: CC1(C)CNCc2cc(Nc3ccc4c(n3)OCN(c3c(Cl)cccc3Cl)C4=O)ccc21] |
| 1.179 | 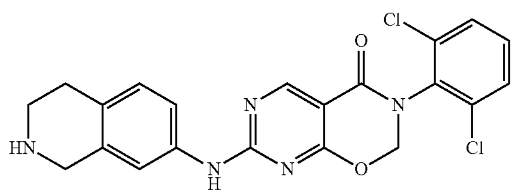 [SMILES: O=C1c2cnc(Nc3ccc4c(c3)CNCC4)nc2OCN1c1c(Cl)cccc1Cl] |
| 1.180 | 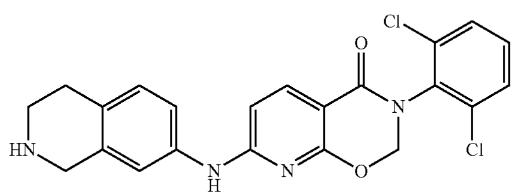 [SMILES: O=C1c2ccc(Nc3ccc4c(c3)CNCC4)nc2OCN1c1c(Cl)cccc1Cl] |
| 1.181 | 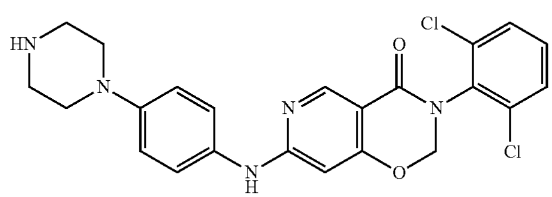 [SMILES: O=C1c2cnc(Nc3ccc(N4CCNCC4)cc3)cc2OCN1c1c(Cl)cccc1Cl] |
| 1.182 | 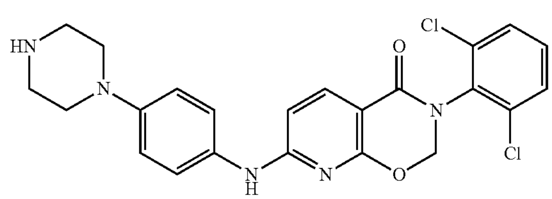 |
| 1.183 | 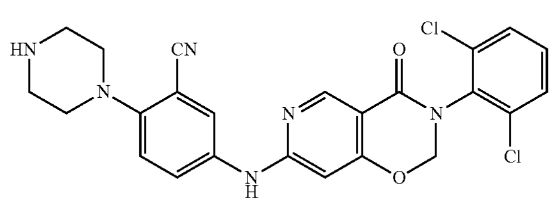 [SMILES: N#Cc1cc(Nc2cc3c(cn2)C(=O)N(c2c(Cl)cccc2Cl)CO3)ccc1N1CCNCC1] |

TABLE 1-continued
| Compound No. | Structure |
|---|---|
| 1.184 | 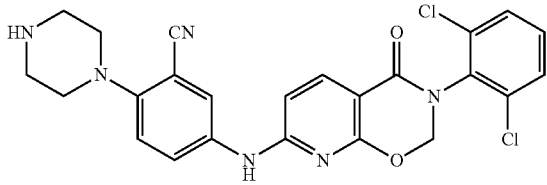 |
| 1.185 | 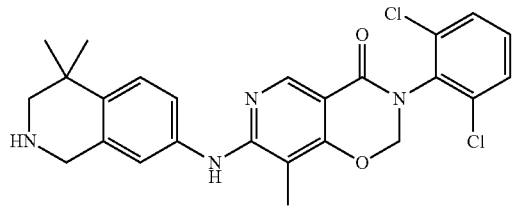 [SMILES: Cc1c(Nc2ccc3c(c2)CNCC3(C)C)ncc2c1OCN(c1c(Cl)cccc1Cl)C2=O] |
| 1.186 | 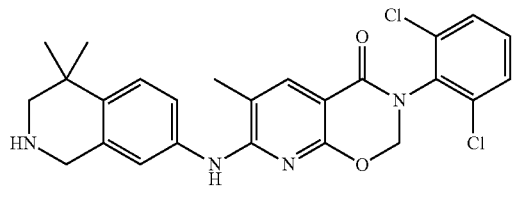 [SMILES: Cc1cc2c(nc1Nc1ccc3c(c1)CNCC3(C)C)OCN(c1c(Cl)cccc1Cl)C2=O] |
| 1.187 | 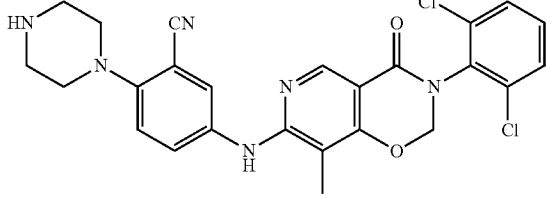 |
| 1.188 | 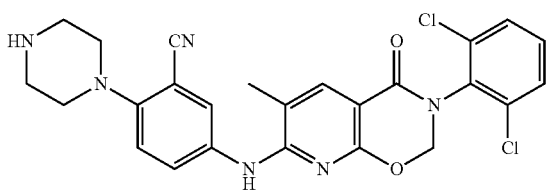 [SMILES: Cc1cc2c(nc1Nc1ccc(N3CCNCC3)c(C#N)c1)OCN(c1c(Cl)cccc1Cl)C2=O] |
| 1.189 | 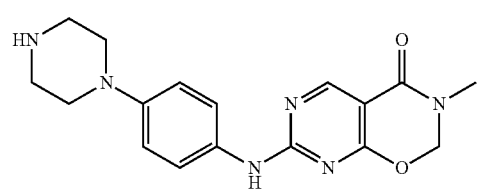 [SMILES: CN1COc2nc(Nc3ccc(N4CCNCC4)cc3)ncc2C1=O] |
| 1.190 | 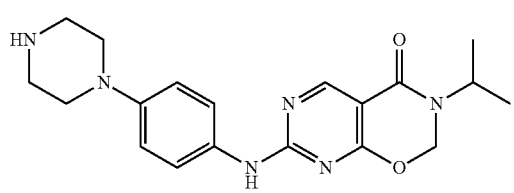 [SMILES: CC(C)N1COc2nc(Nc3ccc(N4CCNCC4)cc3)ncc2C1=O] |

TABLE 1-continued

| Compound No. | Structure |
|---|---|
| 1.191 | 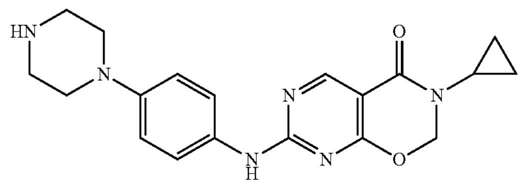 [SMILES: O=C1c2cnc(Nc3ccc(N4CCNCC4)cc3)nc2OCN1C1CC1] |
| 1.192 | 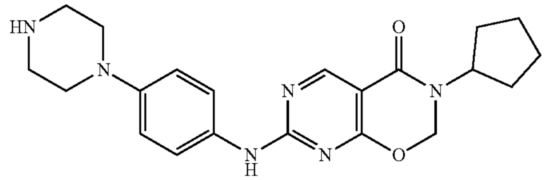 [SMILES: O=C1c2cnc(Nc3ccc(N4CCNCC4)cc3)nc2OCN1C1CCCC1] |
| 1.193 | 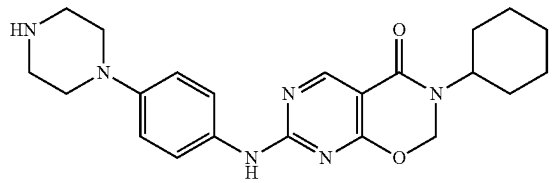 [SMILES: O=C1c2cnc(Nc3ccc(N4CCNCC4)cc3)nc2OCN1C1CCCCC1] |
| 1.194 | 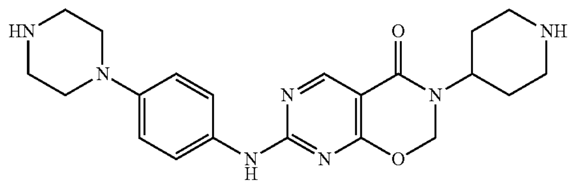 [SMILES: O=C1c2cnc(Nc3ccc(N4CCNCC4)cc3)nc2OCN1C1CCNCC1] |
| 1.195 | 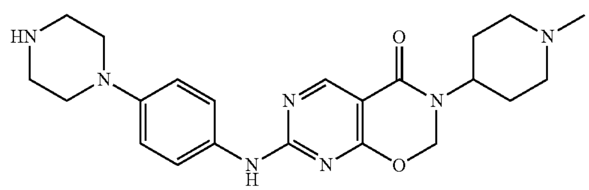 [SMILES: CN1CCC(N2COc3nc(Nc4ccc(N5CCNCC5)cc4)ncc3C2=O)CC1] |
| 1.196 | 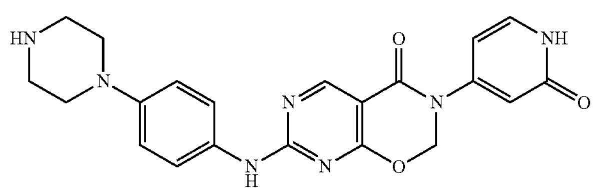 [SMILES: O=C1c2cnc(Nc3ccc(N4CCNCC4)cc3)nc2OCN1c1cc[nH]c(=O)c1] |
| 1.197 | 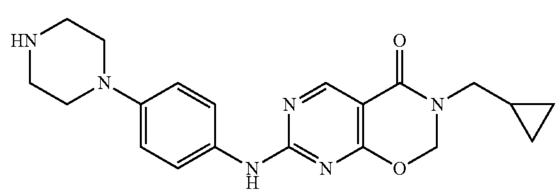 [SMILES: O=C1c2cnc(Nc3ccc(N4CCNCC4)cc3)nc2OCN1CC1CC1] |
| 1.198 | 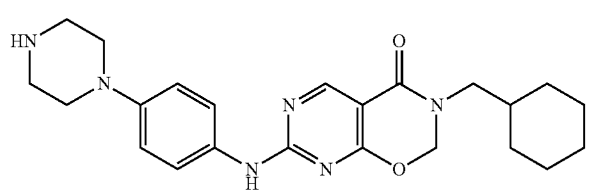 [SMILES: O=C1c2cnc(Nc3ccc(N4CCNCC4)cc3)nc2OCN1CC1CCCCC1] |

TABLE 1-continued

| Compound No. | Structure |
|---|---|
| 1.199 | 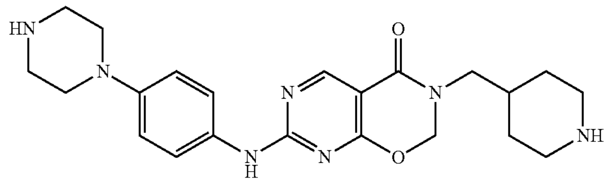 [SMILES: O=C1c2cnc(Nc3ccc(N4CCNCC4)cc3)nc2OCN1CC1CCNCC1] |
| 1.200 | 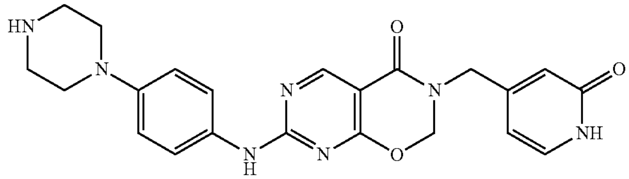 [SMILES: O=C1c2cnc(Nc3ccc(N4CCNCC4)cc3)nc2OCN1Cc1cc[nH]c(=O)c1] |
| 1.201 | 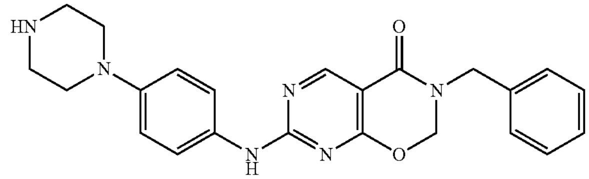 [SMILES: O=C1c2cnc(Nc3ccc(N4CCNCC4)cc3)nc2OCN1Cc1ccccc1] |
| 1.202 | 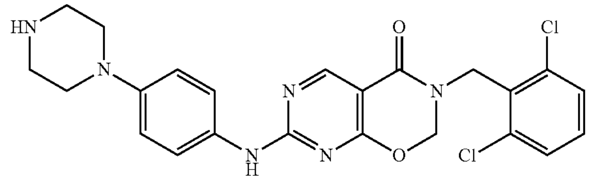 [SMILES: O=C1c2cnc(Nc3ccc(N4CCNCC4)cc3)nc2OCN1Cc1c(Cl)cccc1Cl] |
| 1.203 | 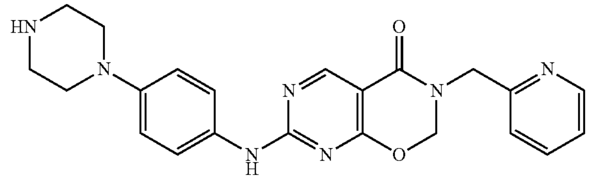 [SMILES: O=C1c2cnc(Nc3ccc(N4CCNCC4)cc3)nc2OCN1Cc1ccccn1] |
| 1.204 | 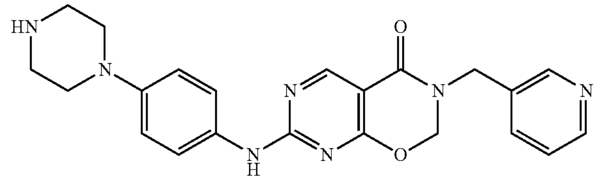 [SMILES: O=C1c2cnc(Nc3ccc(N4CCNCC4)cc3)nc2OCN1Cc1cccnc1] |
| 1.205 | 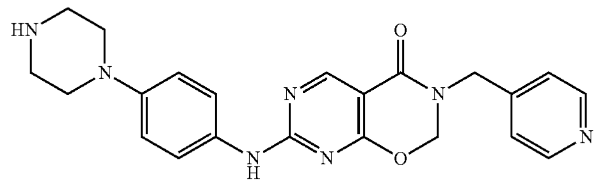 [SMILES: O=C1c2cnc(Nc3ccc(N4CCNCC4)cc3)nc2OCN1Cc1ccncc1] |
| 1.206 | 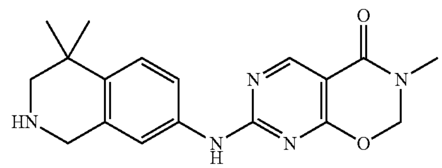 [SMILES: CN1COc2nc(Nc3ccc4c(c3)CNCC4(C)C)ncc2C1=O] |

TABLE 1-continued

| Compound No. | Structure |
|---|---|
| 1.207 | 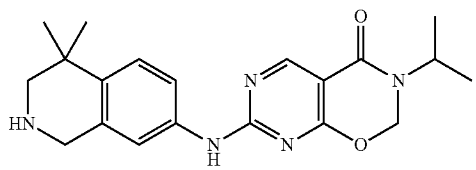 [SMILES: CC(C)N1COc2nc(Nc3ccc4c(c3)CNCC4(C)C)ncc2C1=O] |
| 1.208 | 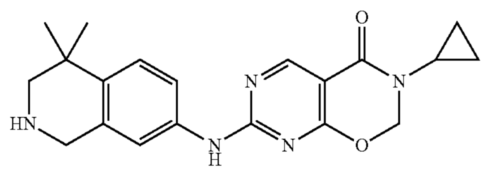 [SMILES: CC1(C)CNCc2cc(Nc3ncc4c(n3)OCN(C3CC3)C4=O)ccc21] |
| 1.209 | 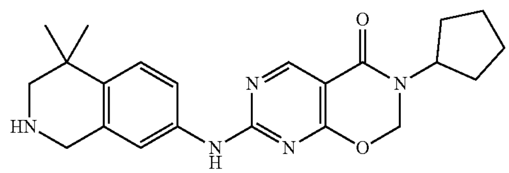 [SMILES: CC1(C)CNCc2cc(Nc3ncc4c(n3)OCN(C3CCCC3)C4=O)ccc21] |
| 1.210 | 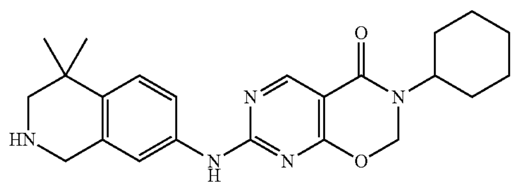 [SMILES: CC1(C)CNCc2cc(Nc3ncc4c(n3)OCN(C3CCCCC3)C4=O)ccc21] |
| 1.211 | 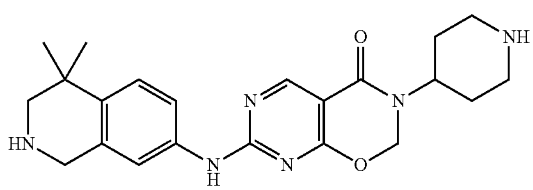 [SMILES: CC1(C)CNCc2cc(Nc3ncc4c(n3)OCN(C3CCNCC3)C4=O)ccc21] |
| 1.212 | 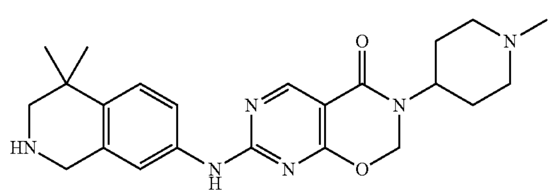 [SMILES: CN1CCC(N2COc3nc(Nc4ccc5c(c4)CNCC5(C)C)ncc3C2=O)CC1] |
| 1.213 | 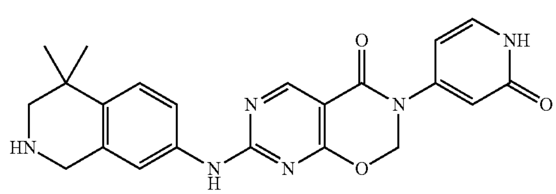 [SMILES: CC1(C)CNCc2cc(Nc3ncc4c(n3)OCN(c3cc[nH]c(=O)c3)C4=O)ccc21] |
| 1.214 | 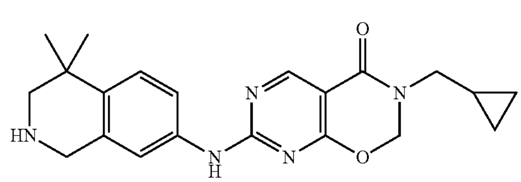 [SMILES: CC1(C)CNCc2cc(Nc3ncc4c(n3)OCN(CC3CC3)C4=O)ccc21] |

TABLE 1-continued

| Compound No. | Structure |
|---|---|
| 1.215 | 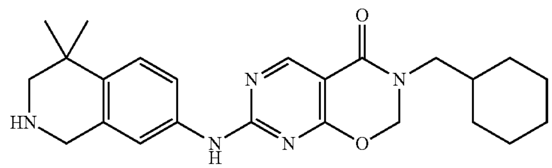 [SMILES: CC1(C)CNCc2cc(Nc3ncc4c(n3)OCN(CC3CCCCC3)C4=O)ccc21] |
| 1.216 | 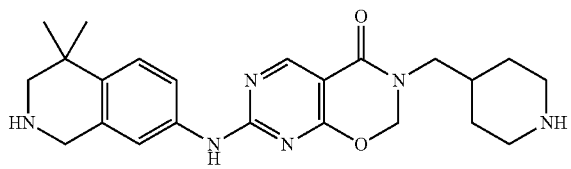 [SMILES: CC1(C)CNCc2cc(Nc3ncc4c(n3)OCN(CC3CCNCC3)C4=O)ccc21] |
| 1.217 | 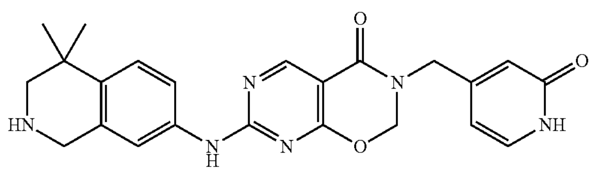 [SMILES: CC1(C)CNCc2cc(Nc3ncc4c(n3)OCN(Cc3cc[nH]c(=O)c3)C4=O)ccc21] |
| 1.218 | 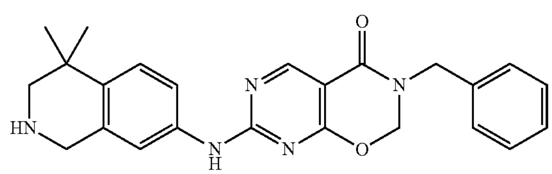 [SMILES: CC1(C)CNCc2cc(Nc3ncc4c(n3)OCN(Cc3ccccc3)C4=O)ccc21] |
| 1.219 | 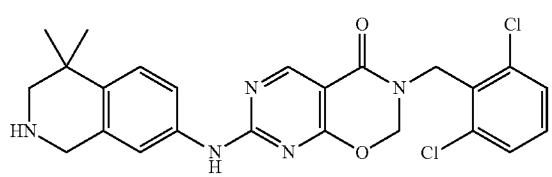 [SMILES: CC1(C)CNCc2cc(Nc3ncc4c(n3)OCN(Cc3c(Cl)cccc3Cl)C4=O)ccc21] |
| 1.220 | 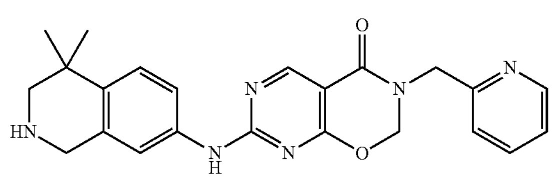 [SMILES: CC1(C)CNCc2cc(Nc3ncc4c(n3)OCN(Cc3ccccn3)C4=O)ccc21] |
| 1.221 | 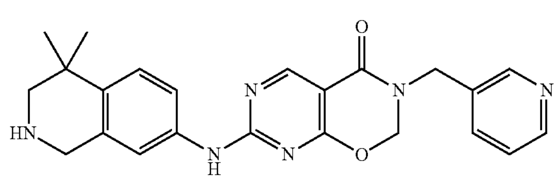 [SMILES: CC1(C)CNCc2cc(Nc3ncc4c(n3)OCN(Cc3cccnc3)C4=O)ccc21] |
| 1.222 | 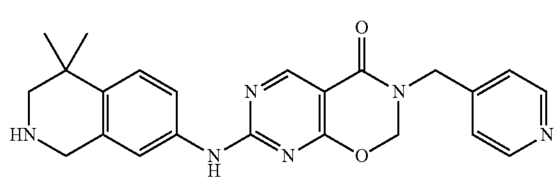 [SMILES: CC1(C)CNCc2cc(Nc3ncc4c(n3)OCN(Cc3ccncc3)C4=O)ccc21] |

TABLE 1-continued
| Compound No. | Structure |
|---|---|
| 1.223 | 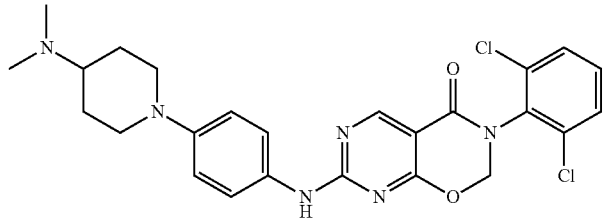 [SMILES: CN(C)C1CCN(c2ccc(Nc3ncc4c(n3)OCN(c3c(Cl)cccc3Cl)C4=O)cc2)CC1] |
| 1.224 | 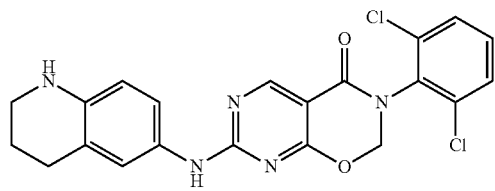 [SMILES: O=C1c2cnc(Nc3ccc4c(c3)CCCN4)nc2OCN1c1c(Cl)cccc1Cl] |
| 1.225 | 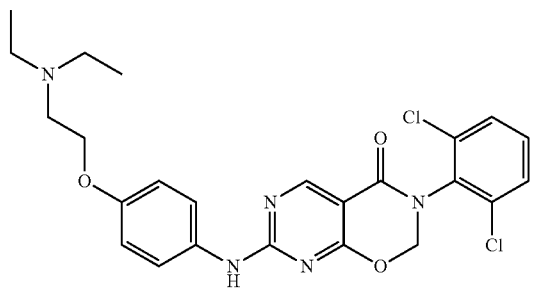 [SMILES: CCN(CC)CCOc1ccc(Nc2ncc3c(n2)OCN(c2c(Cl)cccc2Cl)C3=O)cc1] |
| 1.226 | 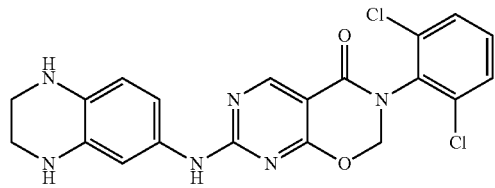 [SMILES: O=C1c2cnc(Nc3ccc4c(c3)NCCN4)nc2OCN1c1c(Cl)cccc1Cl] |
| 1.227 | 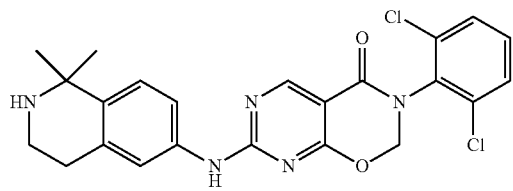 [SMILES: CC1(C)NCCc2cc(Nc3ncc4c(n3)OCN(c3c(Cl)cccc3Cl)C4=O)ccc21] |
| 1.228 | 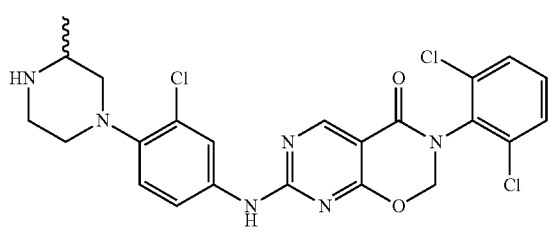 [SMILES: CC1CN(c2ccc(Nc3ncc4c(n3)OCN(c3c(Cl)cccc3Cl)C4=O)cc2Cl)CCN1] |
| 1.229 | 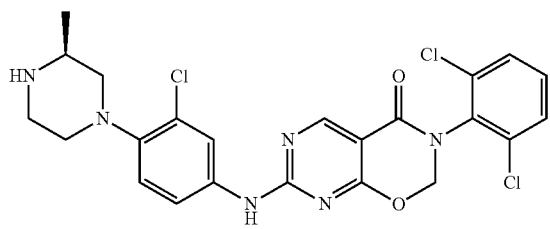 [SMILES: C[C@H]1CN(c2ccc(Nc3ncc4c(n3)OCN(c3c(Cl)cccc3Cl)C4=O)cc2Cl)CCN1] |

TABLE 1-continued
| Compound No. | Structure |
|---|---|
| 1.230 | 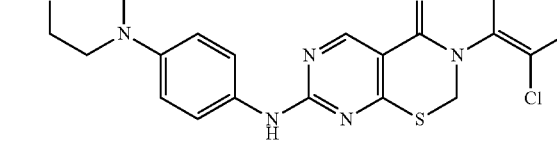 |
| 1.231 | 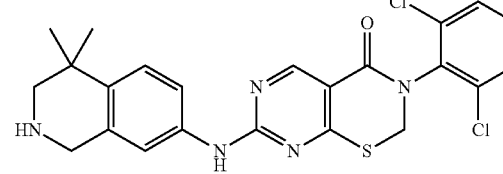 |
| 1.232 | 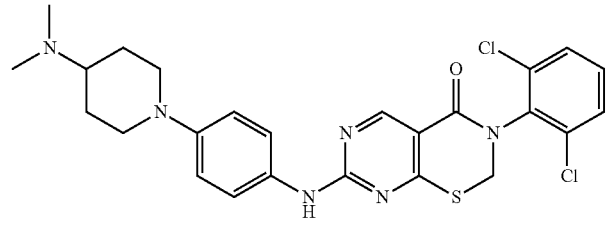 [SMILES: CN(C)C1CCN(c2ccc(Nc3ncc4c(n3)SCN(c3c(Cl)cccc3Cl)C4=O)cc2)CC1] |
| 1.233 | 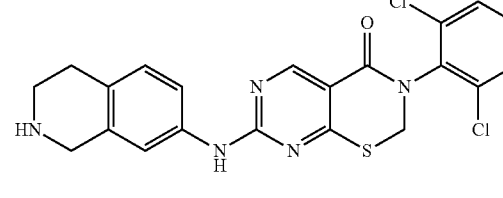 |
| 1.234 | 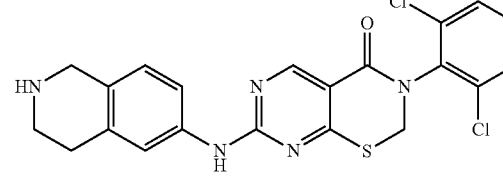 |
| 1.235 | 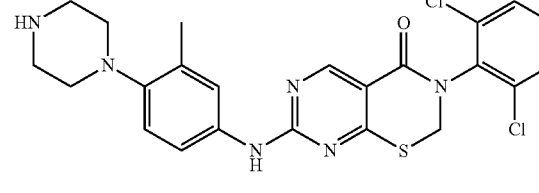 |
| 1.236 | 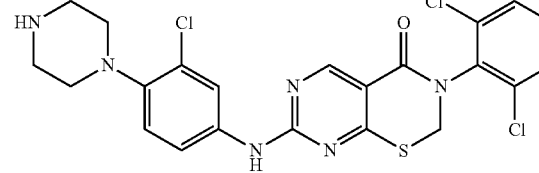 |

TABLE 1-continued
| Compound No. | Structure |
|---|---|
| 1.237 | 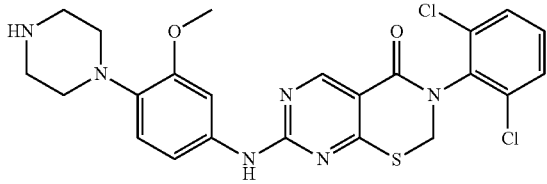 [SMILES: COc1cc(Nc2ncc3c(n2)SCN(c2c(Cl)cccc2Cl)C3=O)ccc1N1CCNCC1] |
| 1.238 | 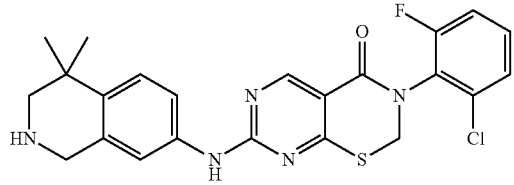 [SMILES: CC1(C)CNCc2cc(Nc3ncc4c(n3)SCN(c3c(F)cccc3Cl)C4=O)ccc21] |
| 1.239 | 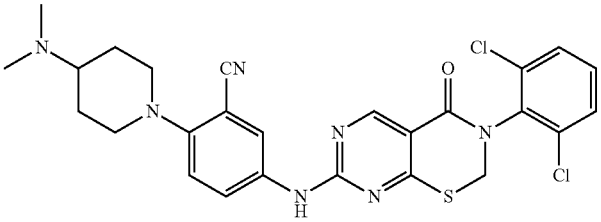 [SMILES: CN(C)C1CCN(c2ccc(Nc3ncc4c(n3)SCN(c3c(Cl)cccc3Cl)C4=O)cc2C#N)CC1] |
| 1.240 | 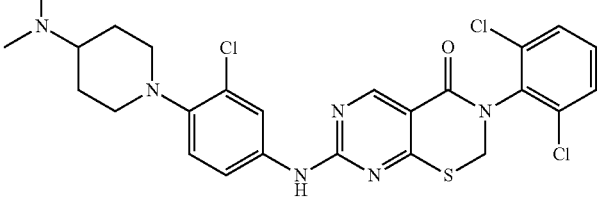 |
| 1.241 | 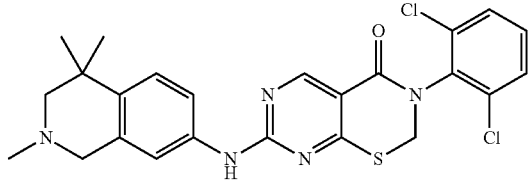 [SMILES: CN1Cc2cc(Nc3ncc4c(n3)SCN(c3c(Cl)cccc3Cl)C4=O)ccc2C(C)(C)C1] |
| 1.242 | 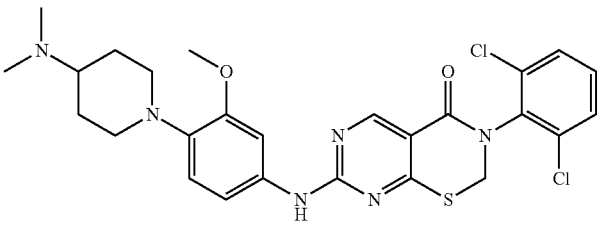 [SMILES: COc1cc(Nc2ncc3c(n2)SCN(c2c(Cl)cccc2Cl)C3=O)ccc1N1CCC(N(C)C)CC1] |
| 1.243 | 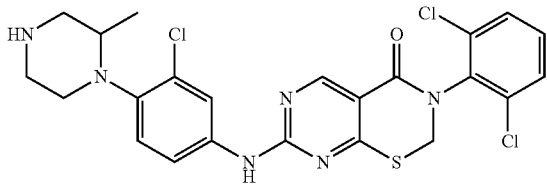 [SMILES: CC1CNCCN1c1ccc(Nc2ncc3c(n2)SCN(c2c(Cl)cccc2Cl)C3=O)cc1Cl] |

TABLE 1-continued

| Compound No. | Structure |
|---|---|
| 1.244 | 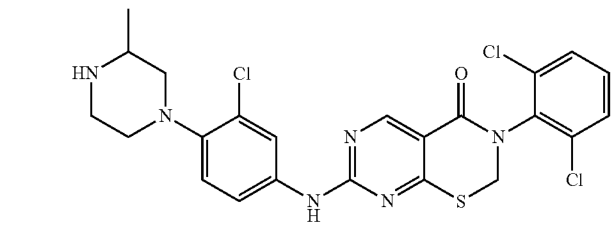 [SMILES: CC1CN(c2ccc(Nc3ncc4c(n3)SCN(c3c(Cl)cccc3Cl)C4=O)cc2Cl)CCN1] |
| 1.245 | 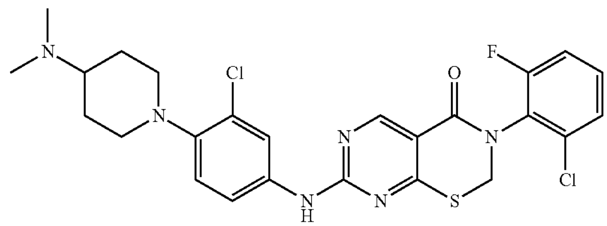 [SMILES: CN(C)C1CCN(c2ccc(Nc3ncc4c(n3)SCN(c3c(F)cccc3Cl)C4=O)cc2Cl)CC1] |
| 1.246 | 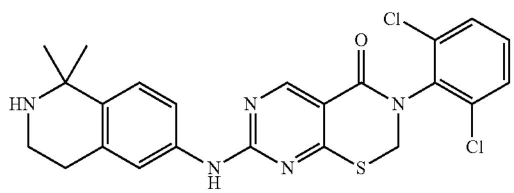 [SMILES: CC1(C)NCCc2cc(Nc3ncc4c(n3)SCN(c3c(Cl)cccc3Cl)C4=O)ccc21] |
| 1.247 | 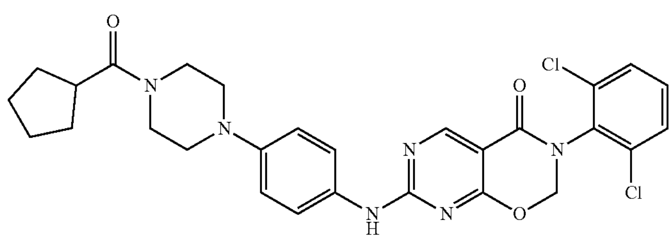 [SMILES: O=C(C1CCCC1)N1CCN(c2ccc(Nc3ncc4c(n3)OCN(c3c(Cl)cccc3Cl)C4=O)cc2)CC1] |
| 1.248 | 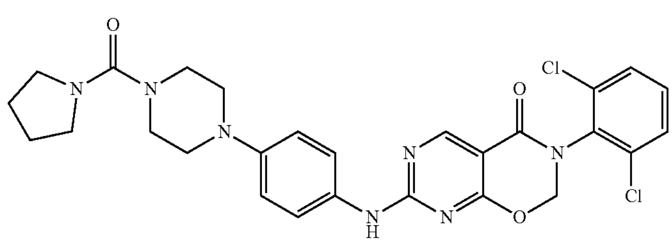 [SMILES: O=C(N1CCCC1)N1CCN(c2ccc(Nc3ncc4c(n3)OCN(c3c(Cl)cccc3Cl)C4=O)cc2)CC1] |
| 1.249 | 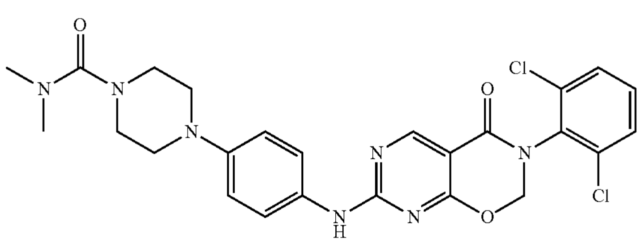 [SMILES: CN(C)C(=O)N1CCN(c2ccc(Nc3ncc4c(n3)OCN(c3c(Cl)cccc3Cl)C4=O)cc2)CC1] |

TABLE 1-continued

| Compound No. | Structure |
|---|---|
| 1.250 | 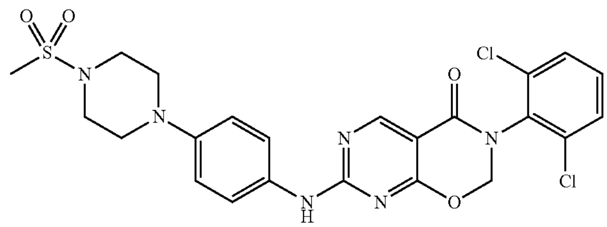 [SMILES: CS(=O)(=O)N1CCN(c2ccc(Nc3ncc4c(n3)OCN(c3c(Cl)cccc3Cl)C4=O)cc2)CC1] |
| 1.251 | 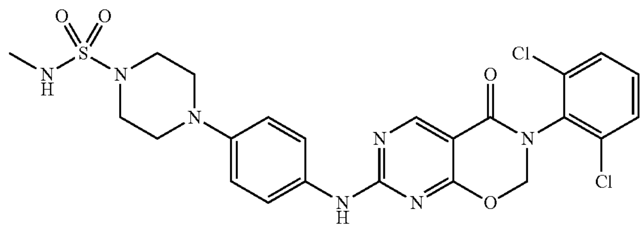 [SMILES: CNS(=O)(=O)N1CCN(c2ccc(Nc3ncc4c(n3)OCN(c3c(Cl)cccc3Cl)C4=O)cc2)CC1] |
| 1.252 | 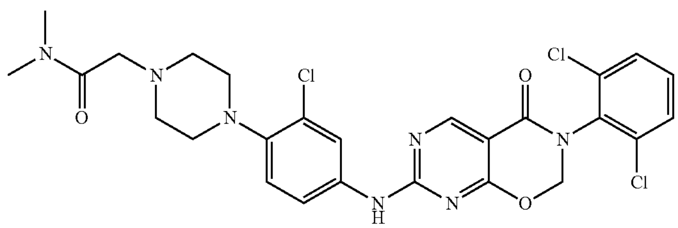 [SMILES: CN(C)C(=O)CN1CCN(c2ccc(Nc3ncc4c(n3)OCN(c3c(Cl)cccc3Cl)C4=O)cc2Cl)CC1] |
| 1.253 | 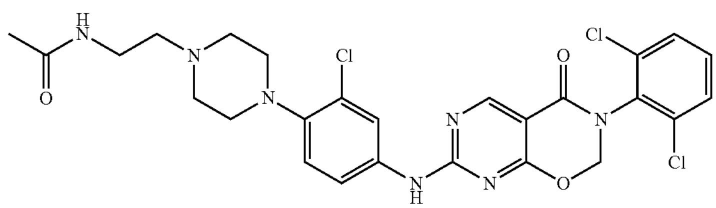 [SMILES: CC(=O)NCCN1CCN(c2ccc(Nc3ncc4c(n3)OCN(c3c(Cl)cccc3Cl)C4=O)cc2Cl)CC1] |
| 1.254 | 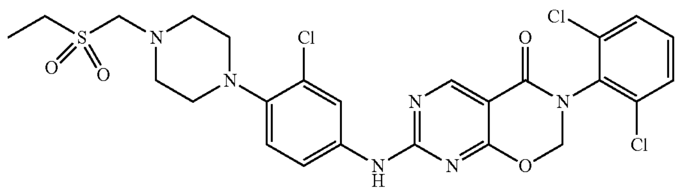 [SMILES: CCS(=O)(=O)CN1CCN(c2ccc(Nc3ncc4c(n3)OCN(c3c(Cl)cccc3Cl)C4=O)cc2Cl)CC1] |
| 1.255 | 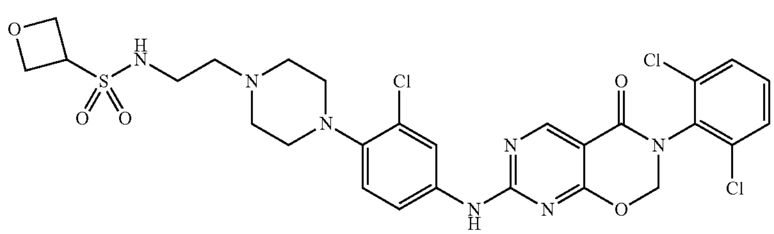 [SMILES: O=C1c2cnc(Nc3ccc(N4CCN(CCNS(=O)(=O)C5COC5)CC4)c(Cl)c3)nc2OCN1c1c(Cl)cccc1Cl] |
| 1.256 | 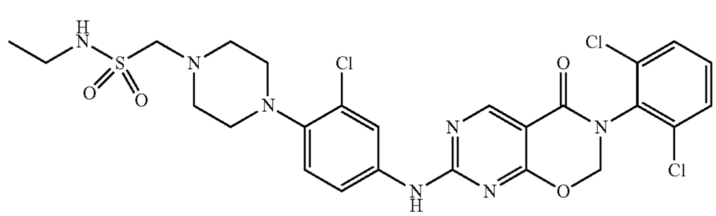 [SMILES: CCNS(=O)(=O)CN1CCN(c2ccc(Nc3ncc4c(n3)OCN(c3c(Cl)cccc3Cl)C4=O)cc2Cl)CC1] |

TABLE 1-continued
| Compound No. | Structure |
|---|---|
| 1.257 | 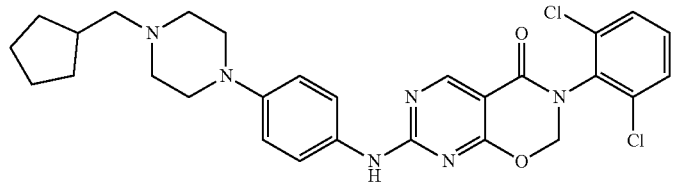 [SMILES: O=C1c2cnc(Nc3ccc(N4CCN(CC5CCCC5)CC4)cc3)nc2OCN1c1c(Cl)cccc1Cl] |
| 1.258 | 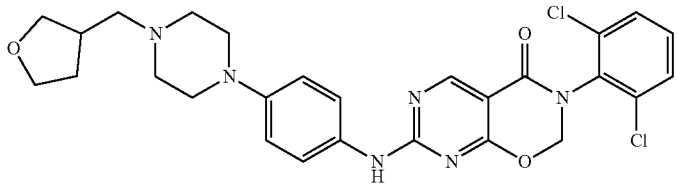 [SMILES: O=C1c2cnc(Nc3ccc(N4CCN(CC5CCOC5)CC4)cc3)nc2OCN1c1c(Cl)cccc1Cl] |
| 1.259 | 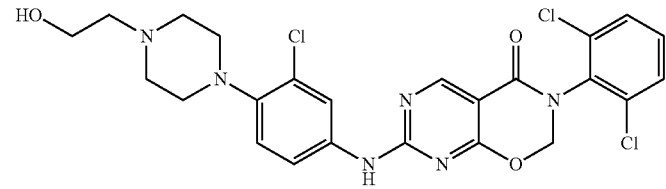 [SMILES: O=C1c2cnc(Nc3ccc(N4CCN(CCO)CC4)c(Cl)c3)nc2OCN1c1c(Cl)cccc1Cl] |
| 1.260 | 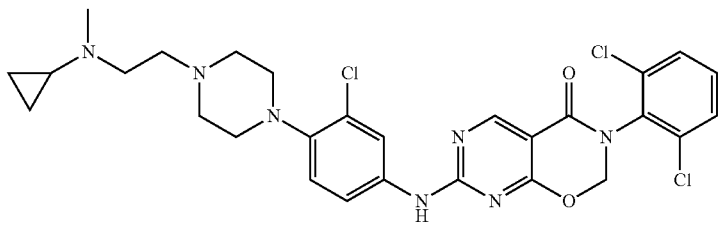 [SMILES: CN(CCN1CCN(c2ccc(Nc3ncc4c(n3)OCN(c3c(Cl)cccc3Cl)C4=O)cc2Cl)CC1)C1CC1] |
| 1.261 | 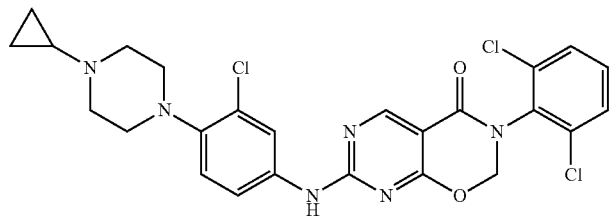 [SMILES: O=C1c2cnc(Nc3ccc(N4CCN(C5CC5)CC4)c(Cl)c3)nc2OCN1c1c(Cl)cccc1Cl] |
| 1.262 | 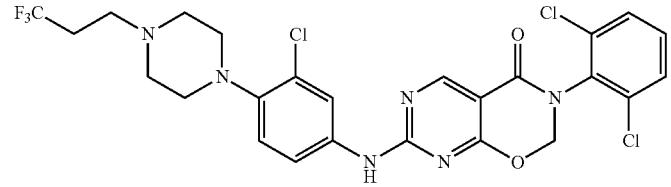 |
| 1.263 | 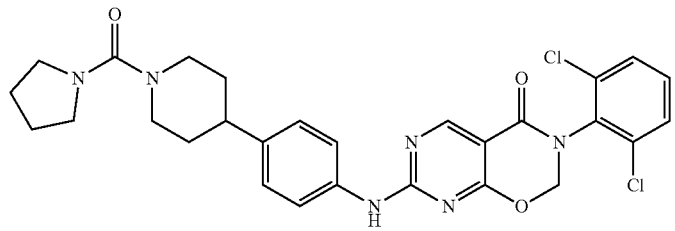 [SMILES: O=C(N1CCCC1)N1CCC(c2ccc(Nc3ncc4c(n3)OCN(c3c(Cl)cccc3Cl)C4=O)cc2)CC1] |

TABLE 1-continued
| Compound No. | Structure |
|---|---|
| 1.264 | 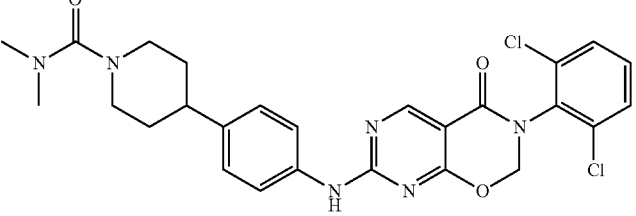 |
| 1.265 | 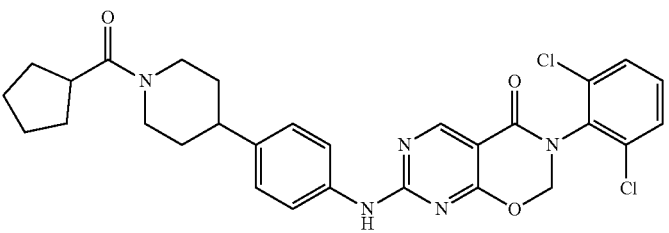 [SMILES: O=C(C1CCCC1)N1CCC(c2ccc(Nc3ncc4c(n3)OCN(c3c(Cl)cccc3Cl)C4=O)cc2)CC1] |
| 1.266 | 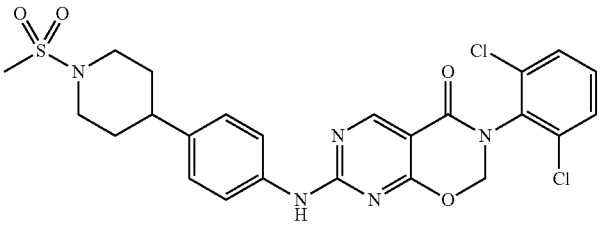 [SMILES: CS(=O)(=O)N1CCC(c2ccc(Nc3ncc4c(n3)OCN(c3c(Cl)cccc3Cl)C4=O)cc2)CC1] |
| 1.267 | 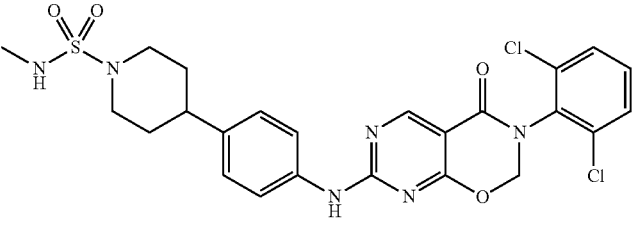 [SMILES: CNS(=O)(=O)N1CCC(c2ccc(Nc3ncc4c(n3)OCN(c3c(Cl)cccc3Cl)C4=O)cc2)CC1] |
| 1.268 | 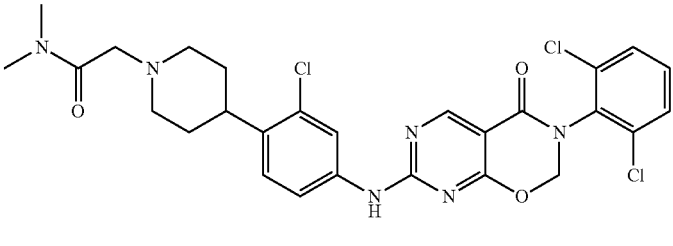 [SMILES: CN(C)C(=O)CN1CCC(c2ccc(Nc3ncc4c(n3)OCN(c3c(Cl)cccc3Cl)C4=O)cc2Cl)CC1] |
| 1.269 | 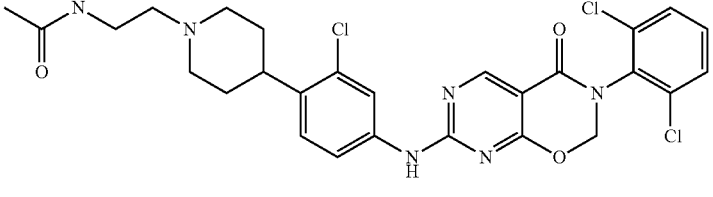 |
| 1.270 | 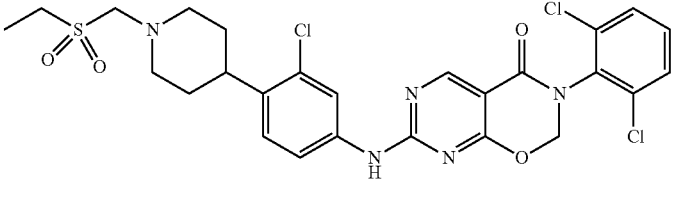 [SMILES: CCS(=O)(=O)CN1CCC(c2ccc(Nc3ncc4c(n3)OCN(c3c(Cl)cccc3Cl)C4=O)cc2Cl)CC1] |

TABLE 1-continued

| Compound No. | Structure |
| --- | --- |
| 1.271 | 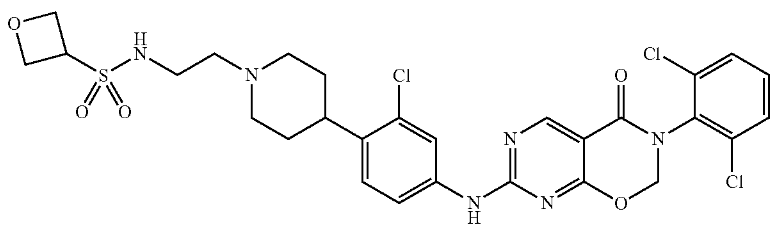 [SMILES: O=C1c2cnc(Nc3ccc(C4CCN(CCNS(=O)(=O)C5COC5)CC4)c(Cl)c3)nc2OCN1c1c(Cl)cccc1Cl] |
| 1.272 | 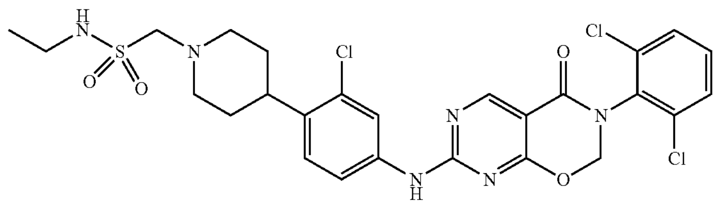 [SMILES: CCNS(=O)(=O)CN1CCC(c2ccc(Nc3ncc4c(n3)OCN(c3c(Cl)cccc3Cl)C4=O)cc2Cl)CC1] |
| 1.273 | 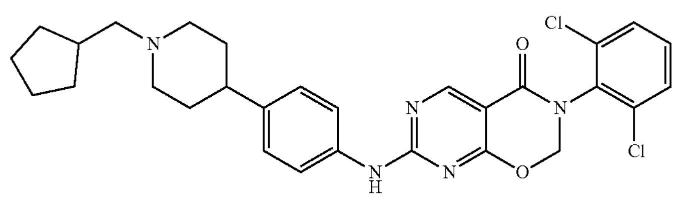 [SMILES: O=C1c2cnc(Nc3ccc(C4CCN(CC5CCCC5)CC4)cc3)nc2OCN1c1c(Cl)cccc1Cl] |
| 1.274 | 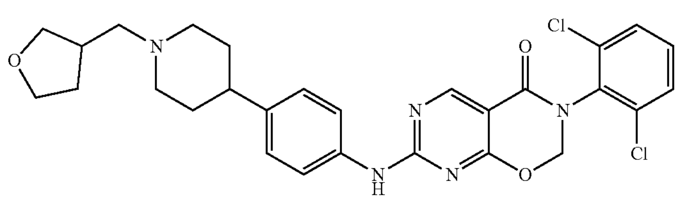 [SMILES: O=C1c2cnc(Nc3ccc(C4CCN(CC5CCOC5)CC4)cc3)nc2OCN1c1c(Cl)cccc1Cl] |
| 1.275 | 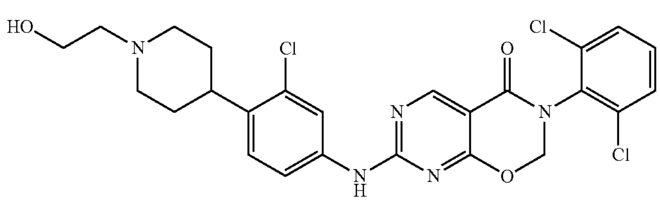 [SMILES: O=C1c2cnc(Nc3ccc(C4CCN(CCO)CC4)c(Cl)c3)nc2OCN1c1c(Cl)cccc1Cl] |
| 1.276 | 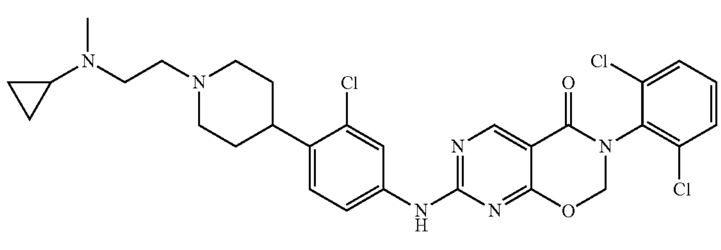 [SMILES: CN(CCN1CCC(c2ccc(Nc3ncc4c(n3)OCN(c3c(Cl)cccc3Cl)C4=O)cc2Cl)CC1)C1CC1] |
| 1.277 | 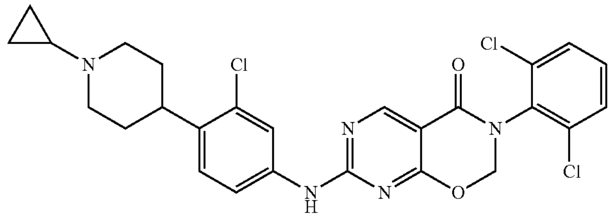 [SMILES: O=C1c2cnc(Nc3ccc(C4CCN(C5CC5)CC4)c(Cl)c3)nc2OCN1c1c(Cl)cccc1Cl] |

TABLE 1-continued

| Compound No. | Structure |
|---|---|
| 1.278 | 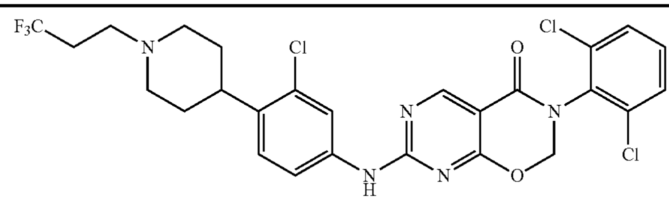 |
| 1.279 | 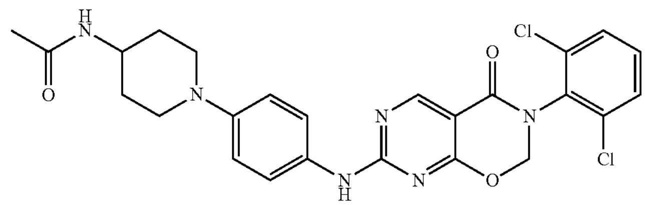 [SMILES: CC(=O)NC1CCN(c2ccc(Nc3ncc4c(n3)OCN(c3c(Cl)cccc3Cl)C4=O)cc2)CC1] |
| 1.280 | 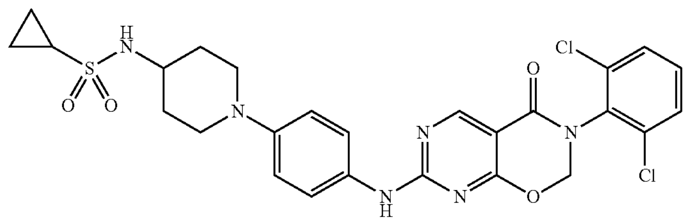 [SMILES: O=C1c2cnc(Nc3ccc(N4CCC(NS(=O)(=O)C5CC5)CC4)cc3)nc2OCN1c1c(Cl)cccc1Cl] |
| 1.281 | 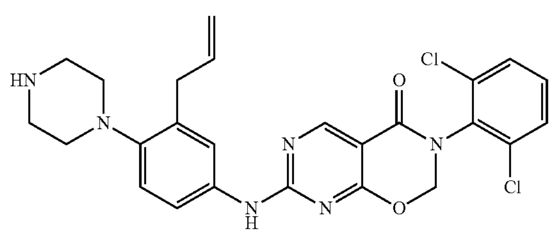 [SMILES: C=CCc1cc(Nc2ncc3c(n2)OCN(c2c(Cl)cccc2Cl)C3=O)ccc1N1CCNCC1] |
| 1.282 | 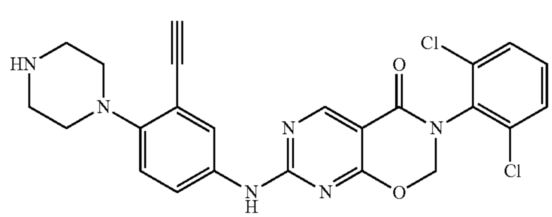 [SMILES: C#Cc1cc(Nc2ncc3c(n2)OCN(c2c(Cl)cccc2Cl)C3=O)ccc1N1CCNCC1] |
| 1.283 | 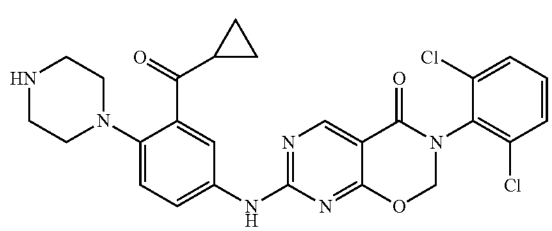 [SMILES: O=C(c1cc(Nc2ncc3c(n2)OCN(c2c(Cl)cccc2Cl)C3=O)ccc1N1CCNCC1)C1CC1] |
| 1.284 | 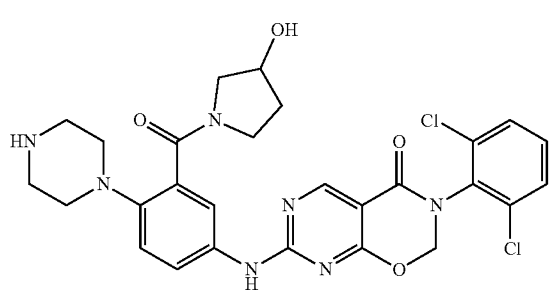 [SMILES: O=C(c1cc(Nc2ncc3c(n2)OCN(c2c(Cl)cccc2Cl)C3=O)ccc1N1CCNCC1)N1CCC(O)C1] |

TABLE 1-continued

| Compound No. | Structure |
|---|---|
| 1.285 | 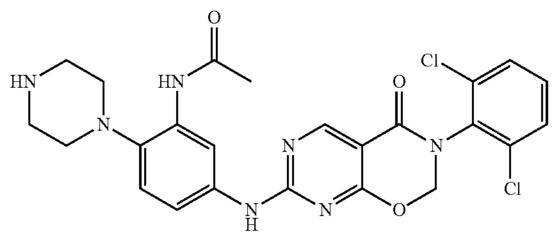 [SMILES: CC(=O)Nc1cc(Nc2ncc3c(n2)OCN(c2c(Cl)cccc2Cl)C3=O)ccc1N1CCNCC1] |
| 1.286 | 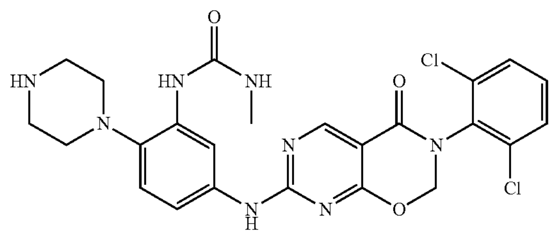 [SMILES: CNC(=O)Nc1cc(Nc2ncc3c(n2)OCN(c2c(Cl)cccc2Cl)C3=O)ccc1N1CCNCC1] |
| 1.287 | 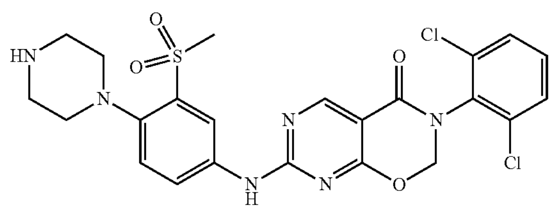 [SMILES: CS(=O)(=O)c1cc(Nc2ncc3c(n2)OCN(c2c(Cl)cccc2Cl)C3=O)ccc1N1CCNCC1] |
| 1.288 | 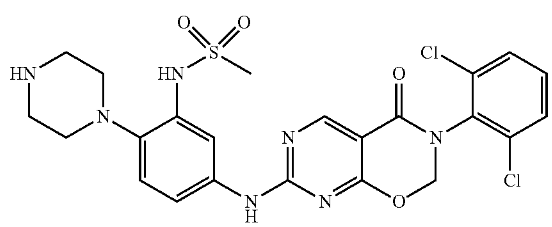 [SMILES: CS(=O)(=O)Nc1cc(Nc2ncc3c(n2)OCN(c2c(Cl)cccc2Cl)C3=O)ccc1N1CCNCC1] |
| 1.289 | 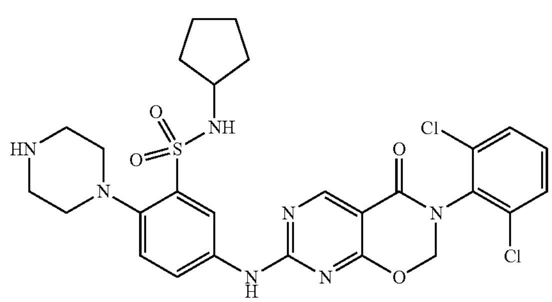 [SMILES: O=C1c2cnc(Nc3ccc(N4CCNCC4)c(S(=O)(=O)NC4CCCC4)c3)nc2OCN1c1c(Cl)cccc1Cl] |
| 1.290 | 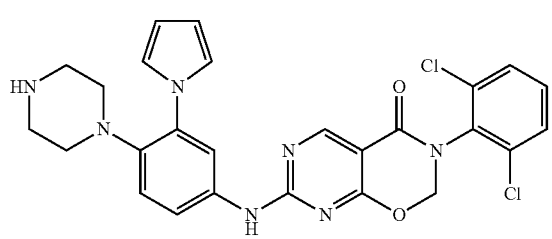 [SMILES: O=C1c2cnc(Nc3ccc(N4CCNCC4)c(-n4cccc4)c3)nc2OCN1c1c(Cl)cccc1Cl] |

TABLE 1-continued
| Compound No. | Structure |
|---|---|
| 1.291 | 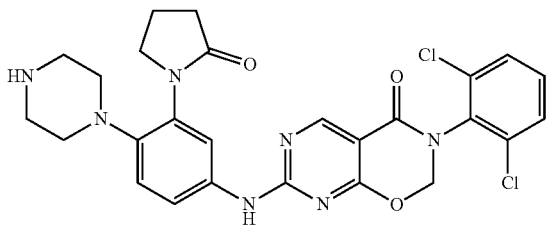 |
| 1.292 | 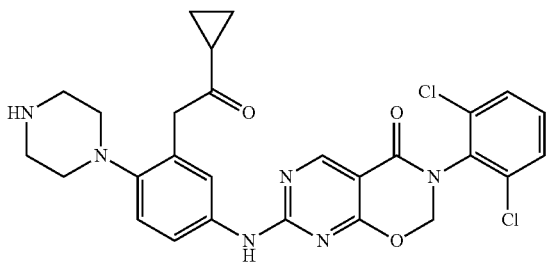 |
| 1.293 | 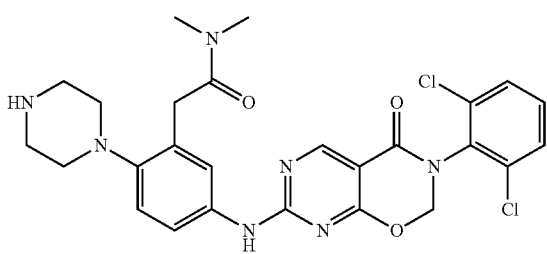 [SMILES: CN(C)C(=O)Cc1cc(Nc2ncc3c(n2)OCN(c2c(Cl)cccc2Cl)C3=O)ccc1N1CCNCC1] |
| 1.294 | 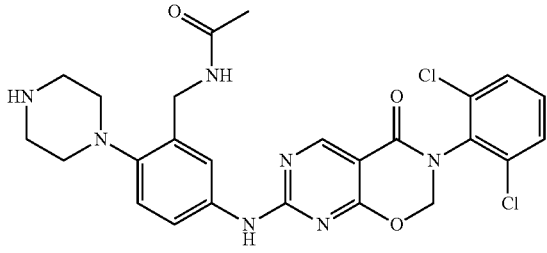 [SMILES: CC(=O)NCc1cc(Nc2ncc3c(n2)OCN(c2c(Cl)cccc2Cl)C3=O)ccc1N1CCNCC1] |
| 1.295 | 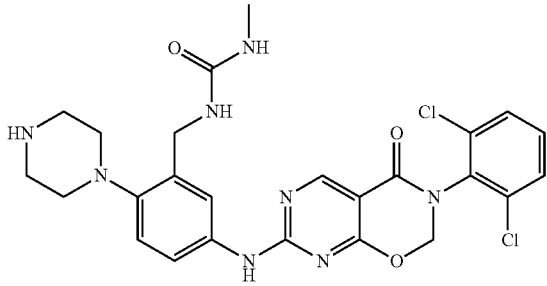 [SMILES: CNC(=O)NCc1cc(Nc2ncc3c(n2)OCN(c2c(Cl)cccc2Cl)C3=O)ccc1N1CCNCC1] |

TABLE 1-continued

| Compound No. | Structure |
|---|---|
| 1.296 | 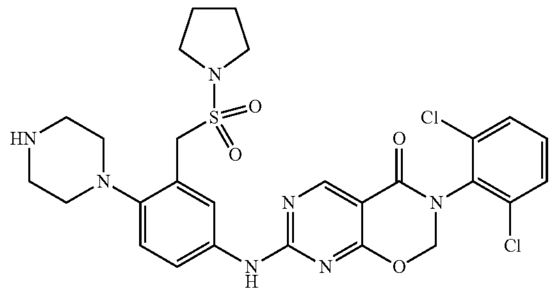 [SMILES: O=C1c2cnc(Nc3ccc(N4CCNCC4)c(CS(=O)(=O)N4CCCC4)c3)nc2OCN1c1c(Cl)cccc1Cl] |
| 1.297 | 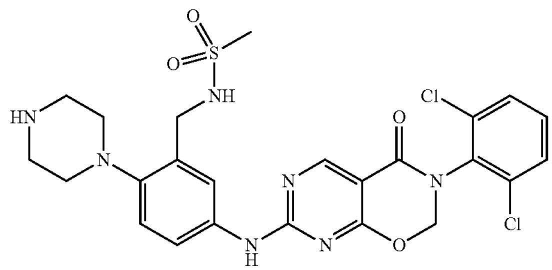 [SMILES: CS(=O)(=O)NCc1cc(Nc2ncc3c(n2)OCN(c2c(Cl)cccc2Cl)C3=O)ccc1N1CCNCC1] |
| 1.298 | 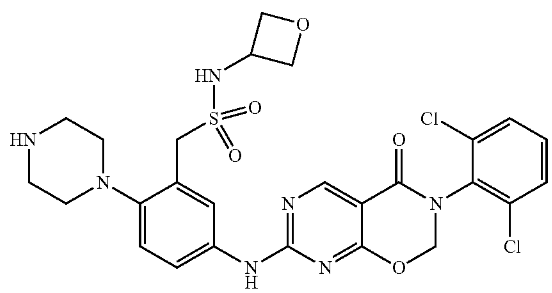 [SMILES: O=C1c2cnc(Nc3ccc(N4CCNCC4)c(CS(=O)(=O)NC4COC4)c3)nc2OCN1c1c(Cl)cccc1Cl] |
| 1.299 | 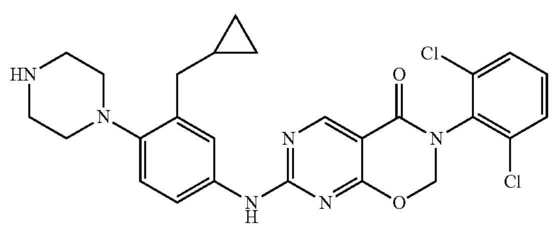 [SMILES: O=C1c2cnc(Nc3ccc(N4CCNCC4)c(CC4CC4)c3)nc2OCN1c1c(Cl)cccc1Cl] |
| 1.300 | 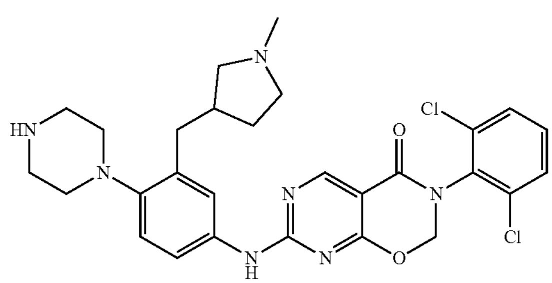 [SMILES: CN1CCC(Cc2cc(Nc3ncc4c(n3)OCN(c3c(Cl)cccc3Cl)C4=O)ccc2N2CCNCC2)C1] |
| 1.301 | 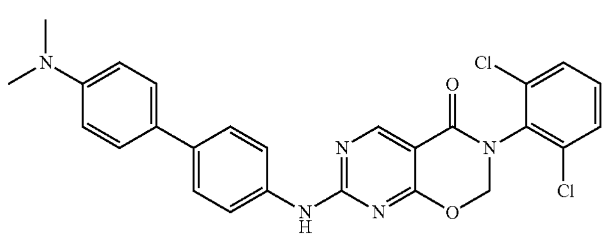 [SMILES: CN(C)c1ccc(-c2ccc(Nc3ncc4c(n3)OCN(c3c(Cl)cccc3Cl)C4=O)cc2)cc1] |

TABLE 1-continued
| Compound No. | Structure |
|---|---|
| 1.302 | 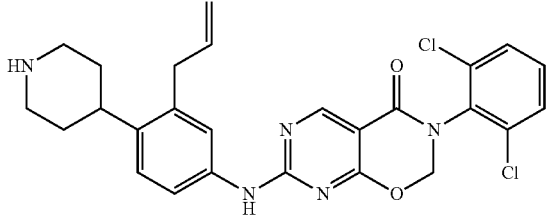 |
| 1.303 | 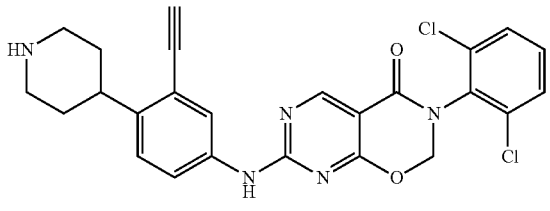 [SMILES: C#Cc1cc(Nc2ncc3c(n2)OCN(c2c(Cl)cccc2Cl)C3=O)ccc1C1CCNCC1] |
| 1.304 | 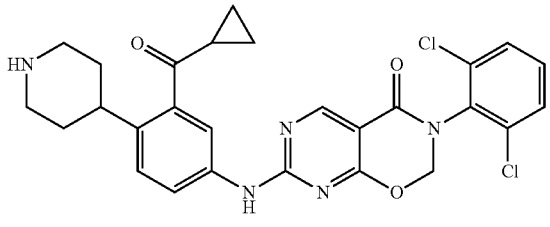 [SMILES: O=C(c1cc(Nc2ncc3c(n2)OCN(c2c(Cl)cccc2Cl)C3=O)ccc1C1CCNCC1)C1CC1] |
| 1.305 | 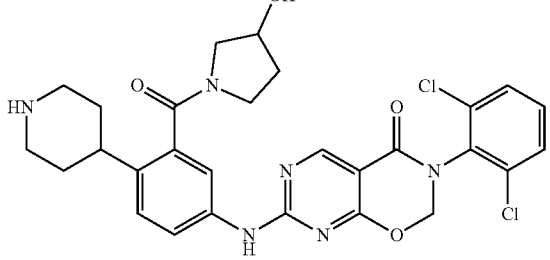 |
| 1.306 | 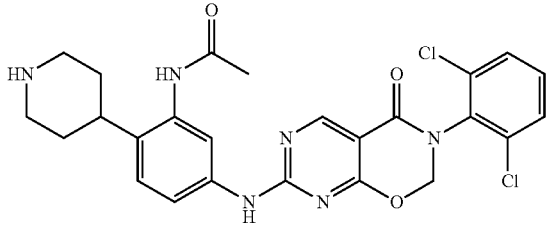 [SMILES: CC(=O)Nc1cc(Nc2ncc3c(n2)OCN(c2c(Cl)cccc2Cl)C3=O)ccc1C1CCNCC1] |
| 1.307 | 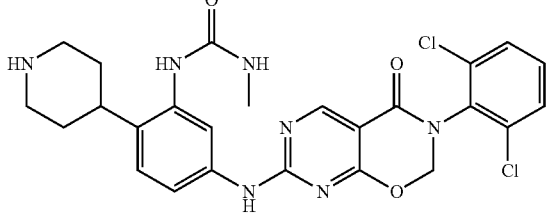 |

TABLE 1-continued
| Compound No. | Structure |
|---|---|
| 1.308 | 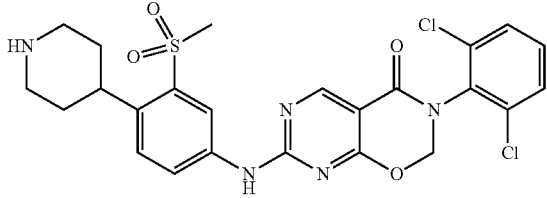 [SMILES: CS(=O)(=O)c1cc(Nc2ncc3c(n2)OCN(c2c(Cl)cccc2Cl)C3=O)ccc1C1CCNCC1] |
| 1.309 | 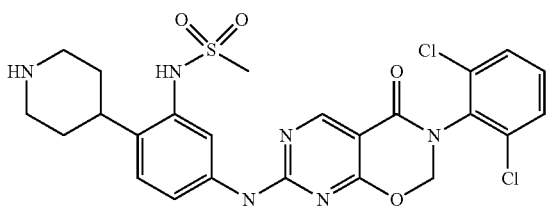 |
| 1.310 | 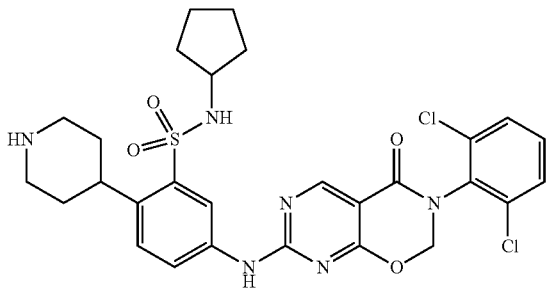 |
| 1.311 | 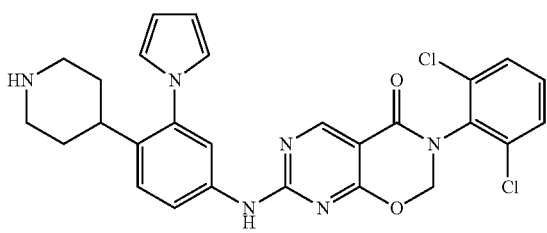 |
| 1.312 | 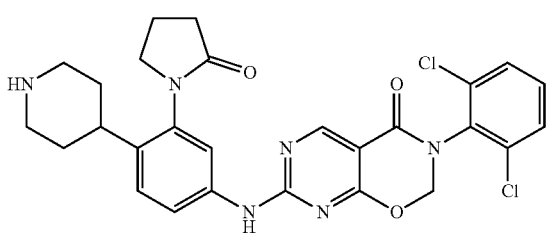 |
| 1.313 | 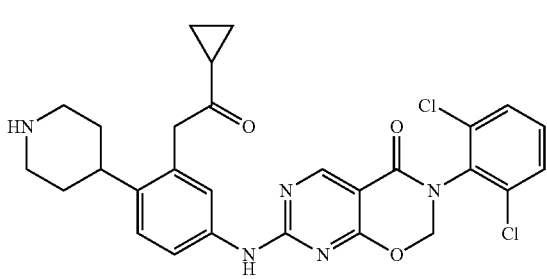 [SMILES: O=C(Cc1cc(Nc2ncc3c(n2)OCN(c2c(Cl)cccc2Cl)C3=O)ccc1C1CCNCC1)C1CC1] |

TABLE 1-continued
| Compound No. | Structure |
|---|---|
| 1.314 | 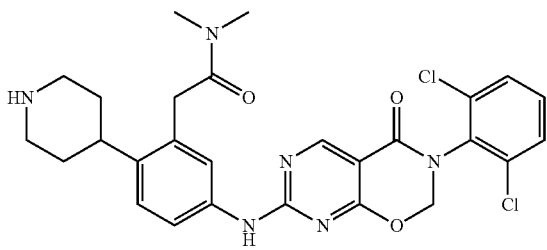 [SMILES: CN(C)C(=O)Cc1cc(Nc2ncc3c(n2)OCN(c2c(Cl)cccc2Cl)C3=O)ccc1C1CCNCC1] |
| 1.315 | 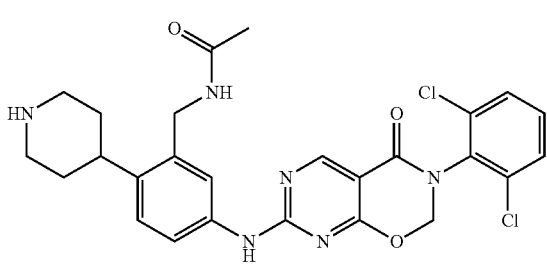 [SMILES: CC(=O)NCc1cc(Nc2ncc3c(n2)OCN(c2c(Cl)cccc2Cl)C3=O)ccc1C1CCNCC1] |
| 1.316 | 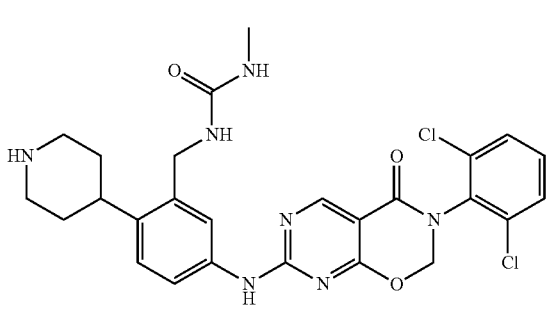 [SMILES: CNC(=O)NCc1cc(Nc2ncc3c(n2)OCN(c2c(Cl)cccc2Cl)C3=O)ccc1C1CCNCC1] |
| 1.317 | 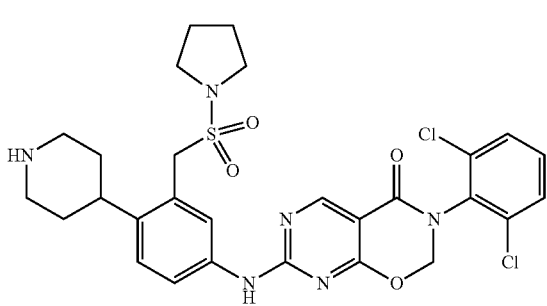 |
| 1.318 | 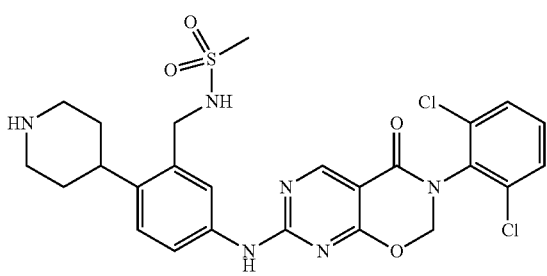 |

TABLE 1-continued
| Compound No. | Structure |
|---|---|
| 1.319 | 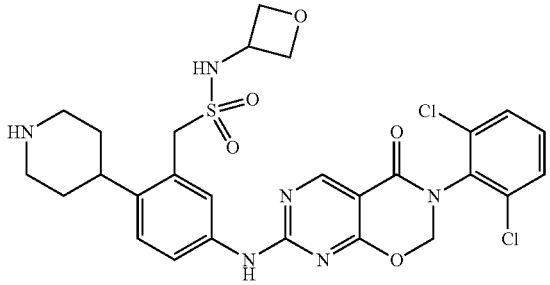 [SMILES: O=C1c2cnc(Nc3ccc(C4CCNCC4)c(CS(=O)(=O)NC4COC4)c3)nc2OCN1c1c(Cl)cccc1Cl] |
| 1.320 | 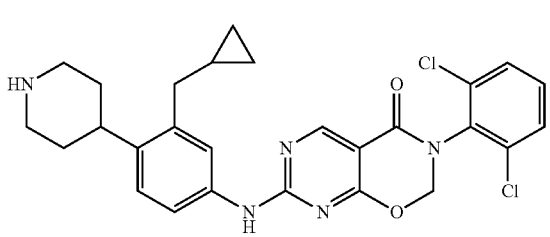 |
| 1.321 | 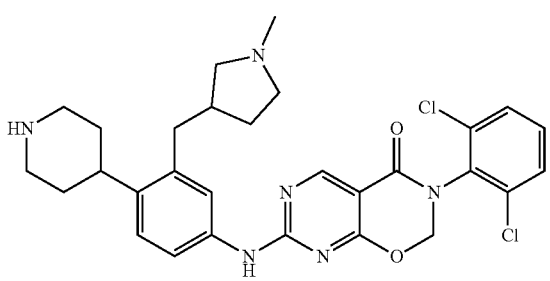 [SMILES: CN1CCC(Cc2cc(Nc3ncc4c(n3)OCN(c3c(Cl)cccc3Cl)C4=O)ccc2C2CCNCC2)C1] |
| 1.322 | 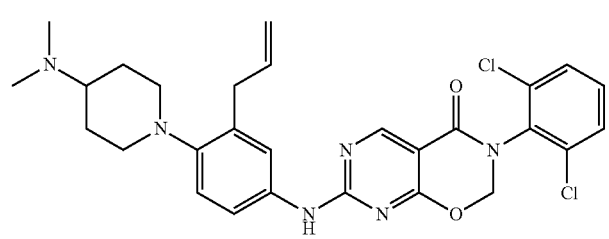 [SMILES: C=CCc1cc(Nc2ncc3c(n2)OCN(c2c(Cl)cccc2Cl)C3=O)ccc1N1CCC(N(C)C)CC1] |
| 1.323 | 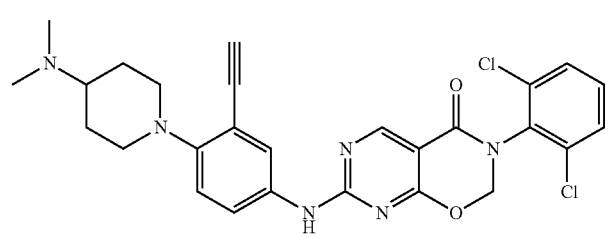 [SMILES: C#Cc1cc(Nc2ncc3c(n2)OCN(c2c(Cl)cccc2Cl)C3=O)ccc1N1CCC(N(C)C)CC1] |
| 1.324 | 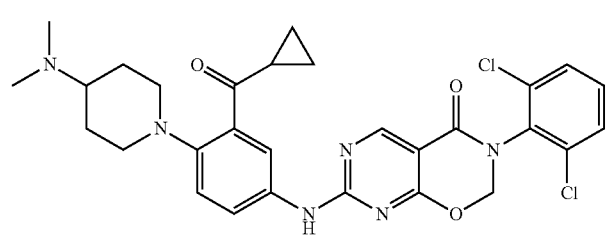 [SMILES: CN(C)C1CCN(c2ccc(Nc3ncc4c(n3)OCN(c3c(Cl)cccc3Cl)C4=O)cc2C(=O)C2CC2)CC1] |

TABLE 1-continued
| Compound No. | Structure |
|---|---|
| 1.325 | 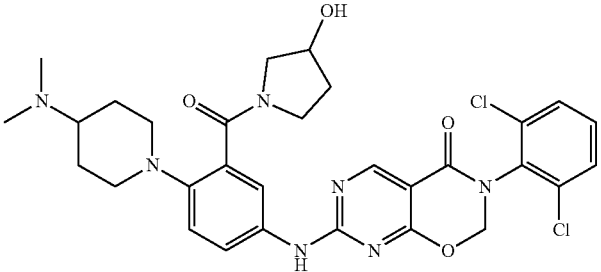 |
| 1.326 | 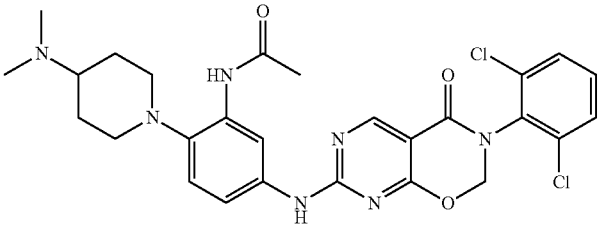 [SMILES: CC(=O)Nc1cc(Nc2ncc3c(n2)OCN(c2c(Cl)cccc2Cl)C3=O)ccc1N1CCC(N(C)C)CC1] |
| 1.327 | 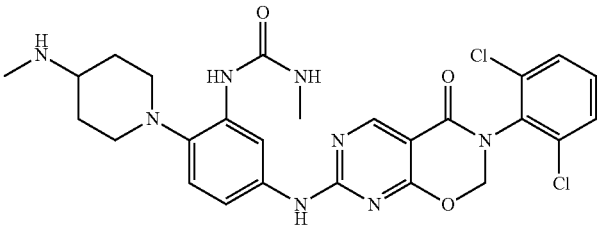 [SMILES: CNC(=O)Nc1cc(Nc2ncc3c(n2)OCN(c2c(Cl)cccc2Cl)C3=O)ccc1N1CCC(NC)CC1] |
| 1.328 | 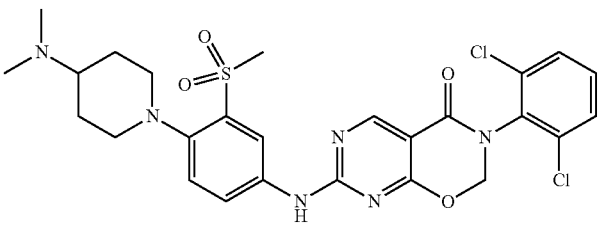 [SMILES: CN(C)C1CCN(c2ccc(Nc3ncc4c(n3)OCN(c3c(Cl)cccc3Cl)C4=O)cc2S(C)(=O)=O)CC1] |
| 1.329 | 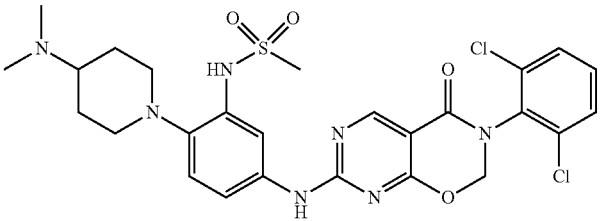 [SMILES: CN(C)C1CCN(c2ccc(Nc3ncc4c(n3)OCN(c3c(Cl)cccc3Cl)C4=O)cc2NS(C)(=O)=O)CC1] |
| 1.330 | 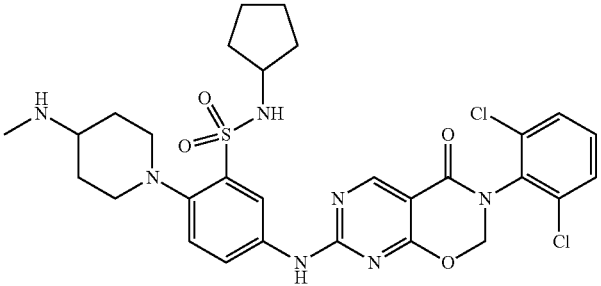 [SMILES: CNC1CCN(c2ccc(Nc3ncc4c(n3)OCN(c3c(Cl)cccc3Cl)C4=O)cc2S(=O)(=O)NC2CCCC2)CC1] |

TABLE 1-continued
| Compound No. | Structure |
|---|---|
| 1.331 | 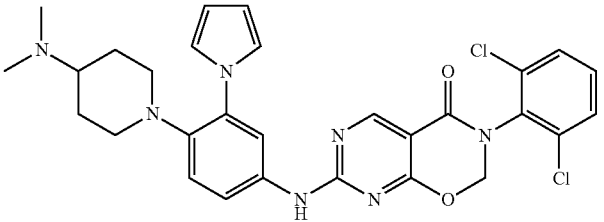 [SMILES: CN(C)C1CCN(c2ccc(Nc3ncc4c(n3)OCN(c3c(Cl)cccc3Cl)C4=O)cc2-n2cccc2)CC1] |
| 1.332 | 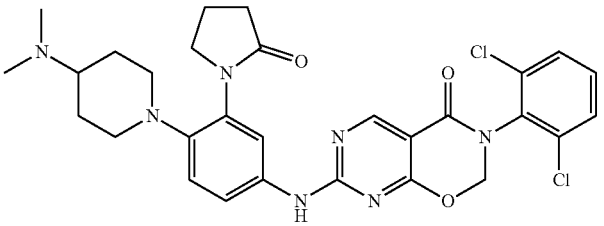 |
| 1.333 | 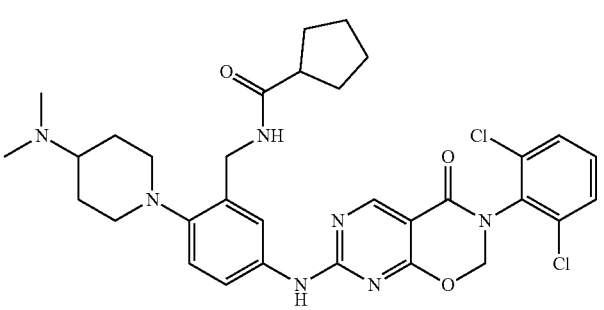 [SMILES: CN(C)C1CCN(c2ccc(Nc3ncc4c(n3)OCN(c3c(Cl)cccc3Cl)C4=O)cc2CNC(=O)C2CCCC2)CC1] |
| 1.334 | 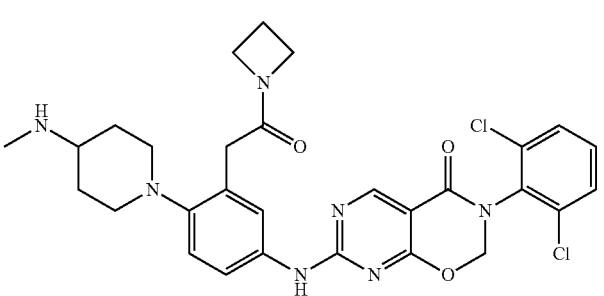 [SMILES: CNC1CCN(c2ccc(Nc3ncc4c(n3)OCN(c3c(Cl)cccc3Cl)C4=O)cc2CC(=O)N2CCC2)CC1] |
| 1.335 | 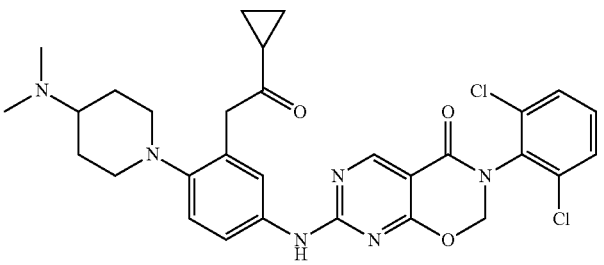 [SMILES: CN(C)C1CCN(c2ccc(Nc3ncc4c(n3)OCN(c3c(Cl)cccc3Cl)C4=O)cc2CC(=O)C2CC2)CC1] |
| 1.336 | 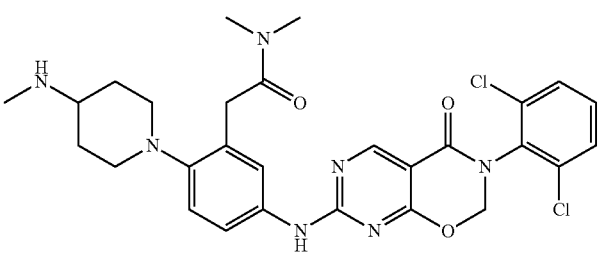 [SMILES: CNC1CCN(c2ccc(Nc3ncc4c(n3)OCN(c3c(Cl)cccc3Cl)C4=O)cc2CC(=O)N(C)C)CC1] |

TABLE 1-continued

| Compound No. | Structure |
|---|---|
| 1.337 | 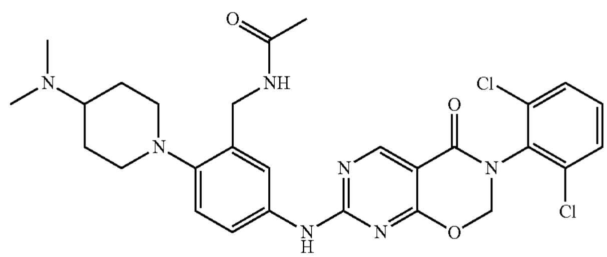 [SMILES: CC(=O)NCc1cc(Nc2ncc3c(n2)OCN(c2c(Cl)cccc2Cl)C3=O)ccc1N1CCC(N(C)C)CC1] |
| 1.338 | 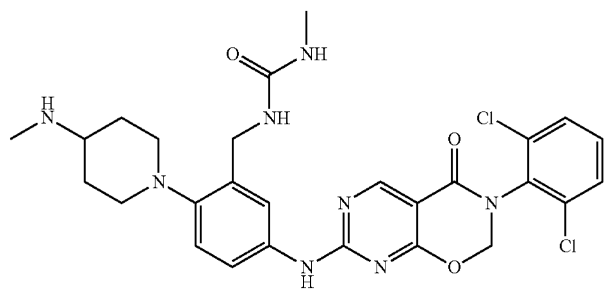 [SMILES: CNC(=O)NCc1cc(Nc2ncc3c(n2)OCN(c2c(Cl)cccc2Cl)C3=O)ccc1N1CCC(NC)CC1] |
| 1.339 | 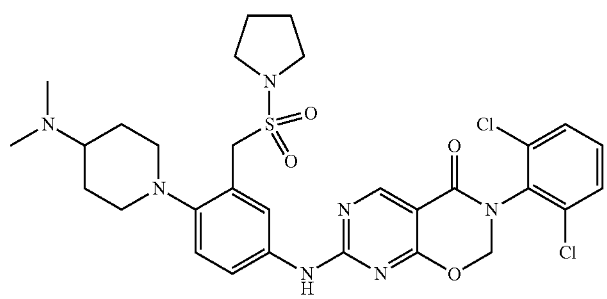 [SMILES: CN(C)C1CCN(c2ccc(Nc3ncc4c(n3)OCN(c3c(Cl)cccc3Cl)C4=O)cc2CS(=O)(=O)N2CCCC2)CC1] |
| 1.340 | 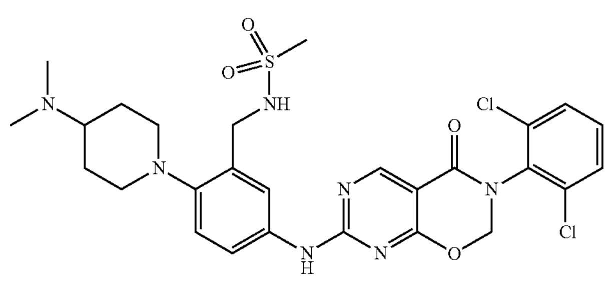 |
| 1.341 | 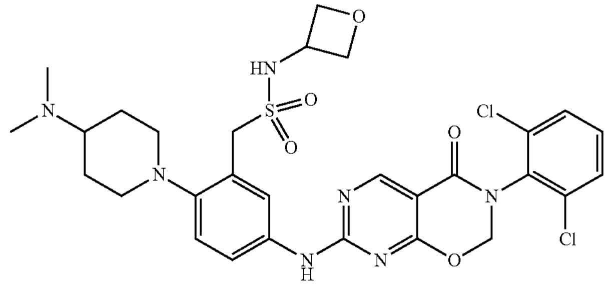 [SMILES: CN(C)C1CCN(c2ccc(Nc3ncc4c(n3)OCN(c3c(Cl)cccc3Cl)C4=O)cc2CS(=O)(=O)NC2COC2)CC1] |

TABLE 1-continued

| Compound No. | Structure |
|---|---|
| 1.342 | 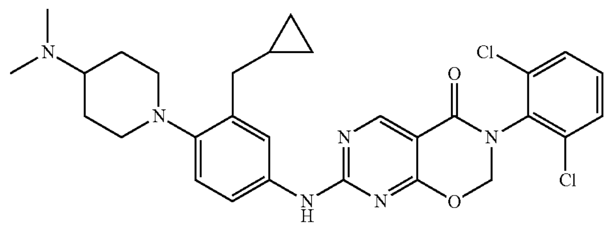 [SMILES: CN(C)C1CCN(c2ccc(Nc3ncc4c(n3)OCN(c3c(Cl)cccc3Cl)C4=O)cc2CC2CC2)CC1] |
| 1.343 | 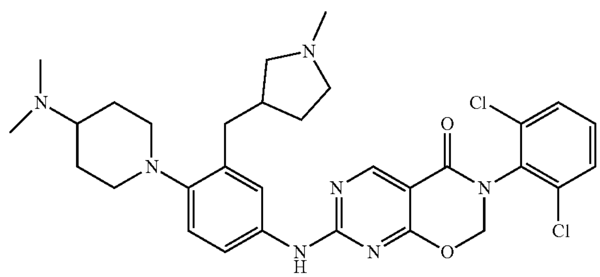 [SMILES: CN1CCC(Cc2cc(Nc3ncc4c(n3)OCN(c3c(Cl)cccc3Cl)C4=O)ccc2N2CCC(N(C)C)CC2)C1] |
| 1.344 | 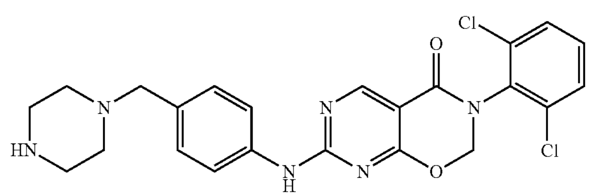 [SMILES: O=C1c2cnc(Nc3ccc(CN4CCNCC4)cc3)nc2OCN1c1c(Cl)cccc1Cl] |
| 1.345 | 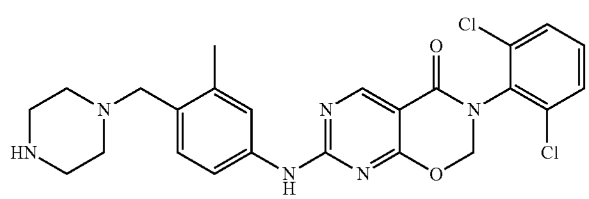 [SMILES: Cc1cc(Nc2ncc3c(n2)OCN(c2c(Cl)cccc2Cl)C3=O)ccc1CN1CCNCC1] |
| 1.346 | 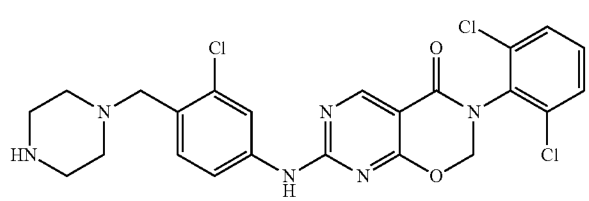 [SMILES: O=C1c2cnc(Nc3ccc(CN4CCNCC4)c(Cl)c3)nc2OCN1c1c(Cl)cccc1Cl] |
| 1.347 | 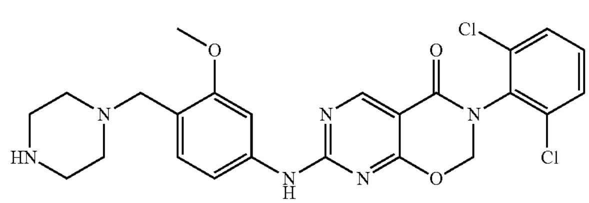 [SMILES: COc1cc(Nc2ncc3c(n2)OCN(c2c(Cl)cccc2Cl)C3=O)ccc1CN1CCNCC1] |
| 1.348 | 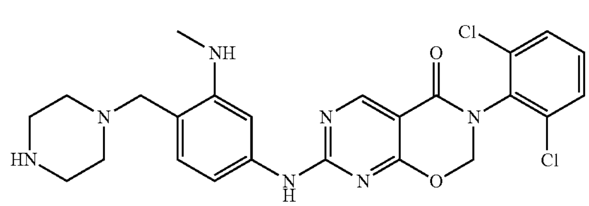 [SMILES: CNc1cc(Nc2ncc3c(n2)OCN(c2c(Cl)cccc2Cl)C3=O)ccc1CN1CCNCC1] |

TABLE 1-continued

| Compound No. | Structure |
|---|---|
| 1.349 | 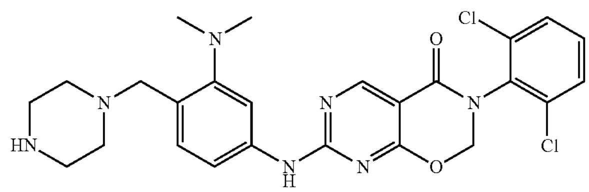 [SMILES: CN(C)c1cc(Nc2ncc3c(n2)OCN(c2c(Cl)cccc2Cl)C3=O)ccc1CN1CCNCC1] |
| 1.350 | 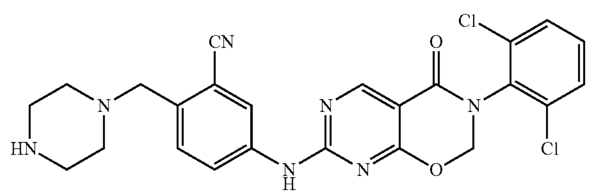 [SMILES: N#Cc1cc(Nc2ncc3c(n2)OCN(c2c(Cl)cccc2Cl)C3=O)ccc1CN1CCNCC1] |
| 1.351 | 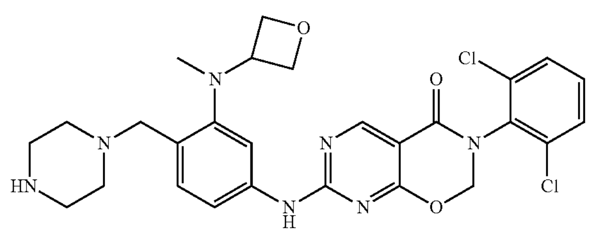 [SMILES: CN(c1cc(Nc2ncc3c(n2)OCN(c2c(Cl)cccc2Cl)C3=O)ccc1CN1CCNCC1)C1COC1] |
| 1.352 | 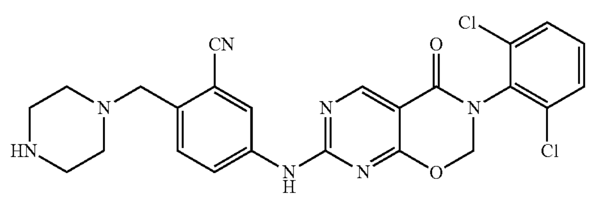 [SMILES: N#Cc1cc(Nc2ncc3c(n2)OCN(c2c(Cl)cccc2Cl)C3=O)ccc1CN1CCNCC1] |
| 1.353 | 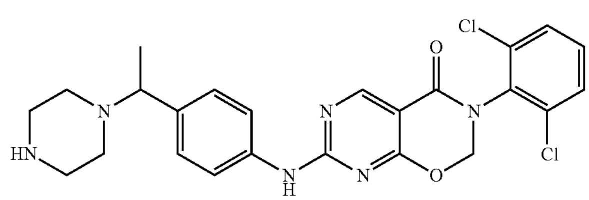 [SMILES: CC(c1ccc(Nc2ncc3c(n2)OCN(c2c(Cl)cccc2Cl)C3=O)cc1)N1CCNCC1] |
| 1.354 | 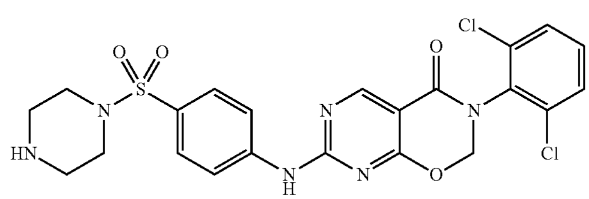 [SMILES: O=C1c2cnc(Nc3ccc(S(=O)(=O)N4CCNCC4)cc3)nc2OCN1c1c(Cl)cccc1Cl] |
| 1.355 | 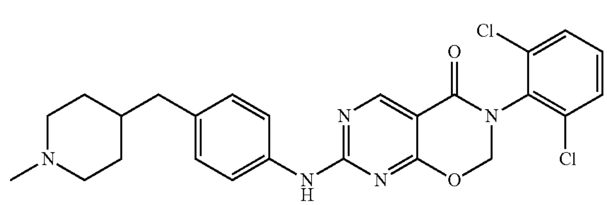 [SMILES: CN1CCC(Cc2ccc(Nc3ncc4c(n3)OCN(c3c(Cl)cccc3Cl)C4=O)cc2)CC1] |

TABLE 1-continued
| Compound No. | Structure |
|---|---|
| 1.356 | 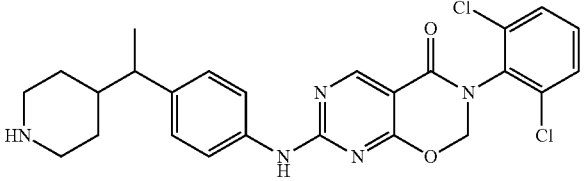 [SMILES: CC(c1ccc(Nc2ncc3c(n2)OCN(c2c(Cl)cccc2Cl)C3=O)cc1)C1CCNCC1] |
| 1.357 | 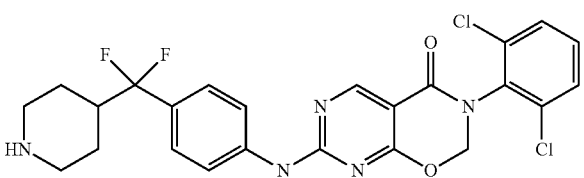 |
| 1.358 | 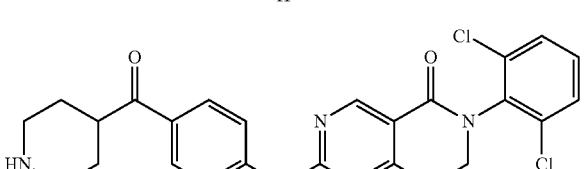 |
| 1.359 | 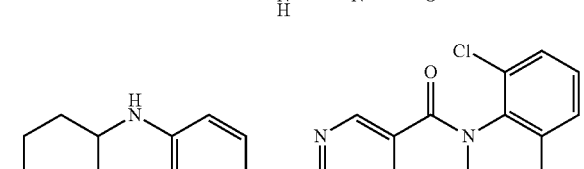 |
| 1.360 | 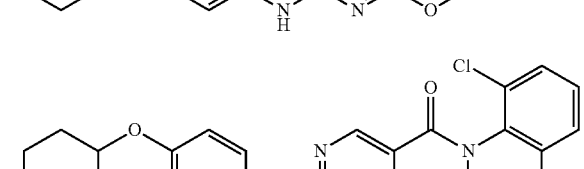 |
| 1.361 | 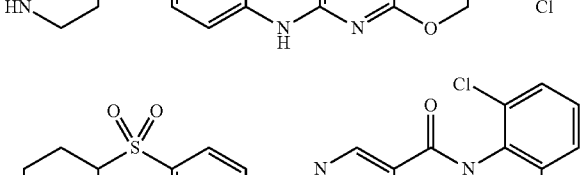 |
| 1.362 | 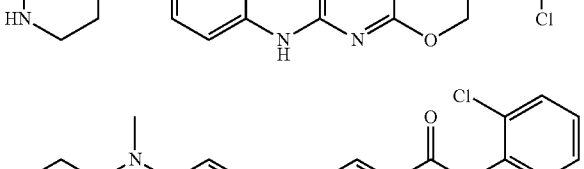 |
| 1.363 | 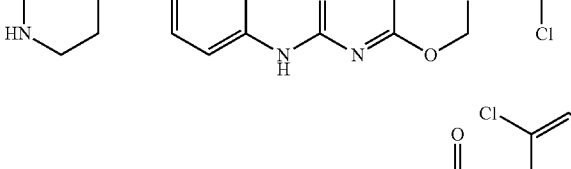 |

TABLE 1-continued
| Compound No. | Structure |
|---|---|
| 1.364 | 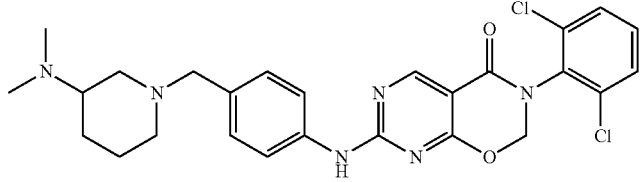 [SMILES: CN(C)C1CCCN(Cc2ccc(Nc3ncc4c(n3)OCN(c3c(Cl)cccc3Cl)C4=O)cc2)C1] |
| 1.365 | 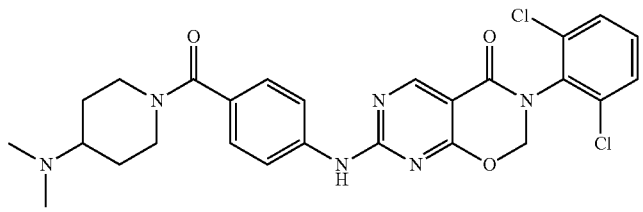 [SMILES: CN(C)C1CCN(C(=O)c2ccc(Nc3ncc4c(n3)OCN(c3c(Cl)cccc3Cl)C4=O)cc2)CC1] |
| 1.366 | 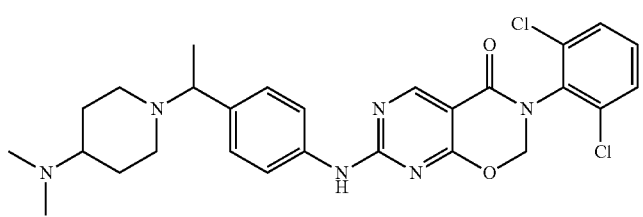 [SMILES: CC(c1ccc(Nc2ncc3c(n2)OCN(c2c(Cl)cccc2Cl)C3=O)cc1)N1CCC(N(C)C)CC1] |
| 1.367 | 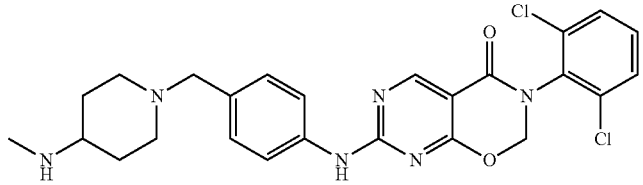 [SMILES: CNC1CCN(Cc2ccc(Nc3ncc4c(n3)OCN(c3c(Cl)cccc3Cl)C4=O)cc2)CC1] |
| 1.368 | 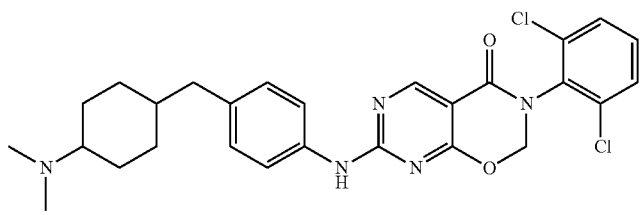 [SMILES: CN(C)C1CCC(Cc2ccc(Nc3ncc4c(n3)OCN(c3c(Cl)cccc3Cl)C4=O)cc2)CC1] |
| 1.369 | 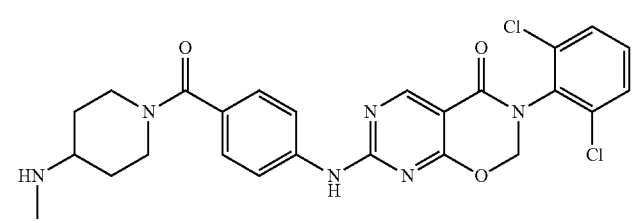 [SMILES: CNC1CCN(C(=O)c2ccc(Nc3ncc4c(n3)OCN(c3c(Cl)cccc3Cl)C4=O)cc2)CC1] |
| 1.370 | 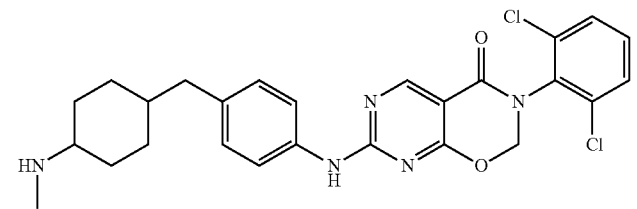 [SMILES: CNC1CCC(Cc2ccc(Nc3ncc4c(n3)OCN(c3c(Cl)cccc3Cl)C4=O)cc2)CC1] |

TABLE 1-continued

| Compound No. | Structure |
|---|---|
| 1.371 | 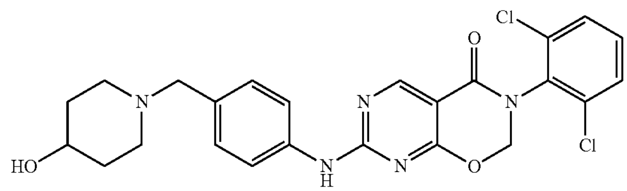 [SMILES: O=C1c2cnc(Nc3ccc(CN4CCC(O)CC4)cc3)nc2OCN1c1c(Cl)cccc1Cl] |
| 1.372 | 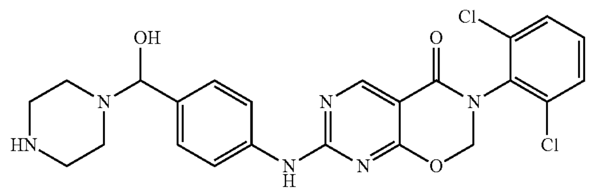 [SMILES: O=C1c2cnc(Nc3ccc(C(O)N4CCNCC4)cc3)nc2OCN1c1c(Cl)cccc1Cl] |
| 1.373 | 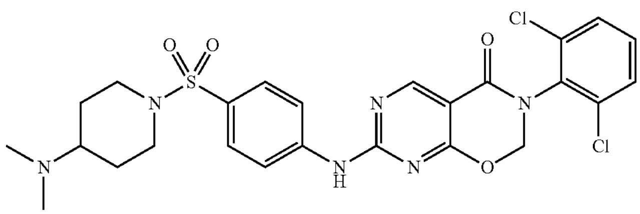 [SMILES: CN(C)C1CCN(S(=O)(=O)c2ccc(Nc3ncc4c(n3)OCN(c3c(Cl)cccc3Cl)C4=O)cc2)CC1] |
| 1.374 | 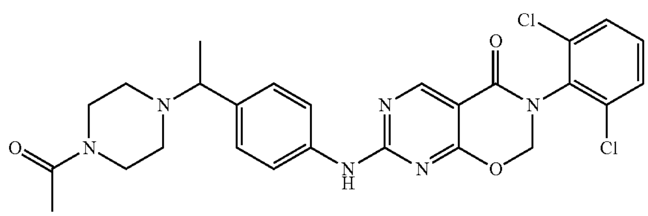 [SMILES: CC(=O)N1CCN(C(C)c2ccc(Nc3ncc4c(n3)OCN(c3c(Cl)cccc3Cl)C4=O)cc2)CC1] |
| 1.375 | 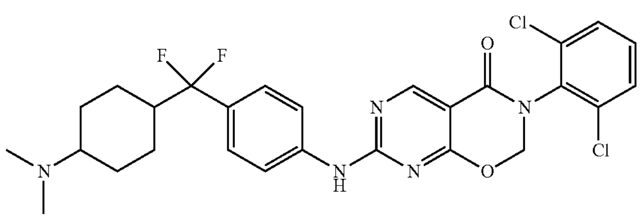 [SMILES: CN(C)C1CCC(C(F)(F)c2ccc(Nc3ncc4c(n3)OCN(c3c(Cl)cccc3Cl)C4=O)cc2)CC1] |
| 1.376 | 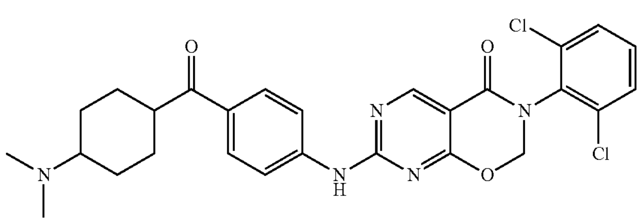 [SMILES: CN(C)C1CCC(C(=O)c2ccc(Nc3ncc4c(n3)OCN(c3c(Cl)cccc3Cl)C4=O)cc2)CC1] |
| 1.377 | 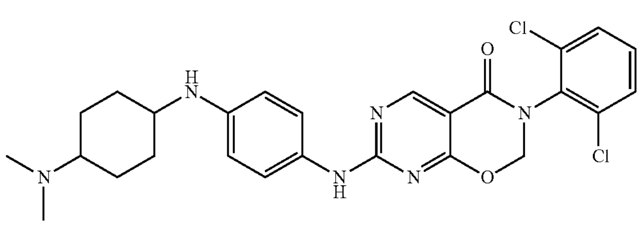 [SMILES: CN(C)C1CCC(Nc2ccc(Nc3ncc4c(n3)OCN(c3c(Cl)cccc3Cl)C4=O)cc2)CC1] |

TABLE 1-continued

| Compound No. | Structure |
|---|---|
| 1.378 | 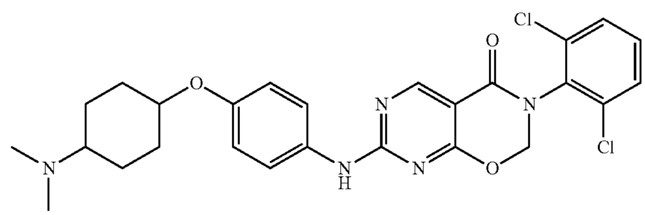 [SMILES: CN(C)C1CCC(Oc2ccc(Nc3ncc4c(n3)OCN(c3c(Cl)cccc3Cl)C4=O)cc2)CC1] |
| 1.379 | 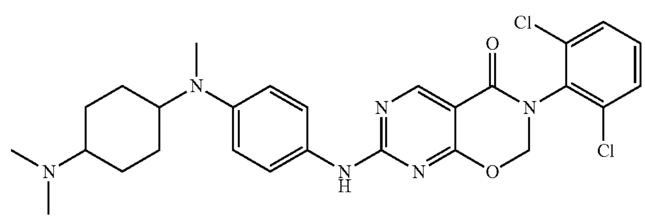 [SMILES: CN(C)C1CCC(N(C)c2ccc(Nc3ncc4c(n3)OCN(c3c(Cl)cccc3Cl)C4=O)cc2)CC1] |
| 1.380 | 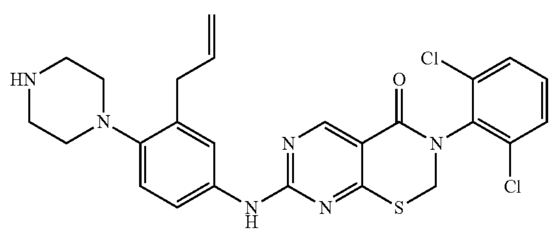 [SMILES: C=CCc1cc(Nc2ncc3c(n2)SCN(c2c(Cl)cccc2Cl)C3=O)ccc1N1CCNCC1] |
| 1.381 | 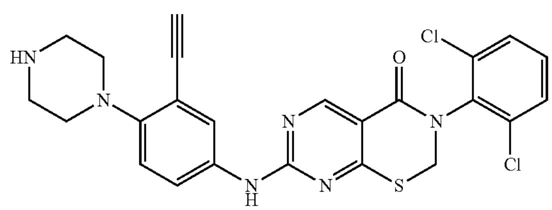 [SMILES: C#Cc1cc(Nc2ncc3c(n2)SCN(c2c(Cl)cccc2Cl)C3=O)ccc1N1CCNCC1] |
| 1.382 | 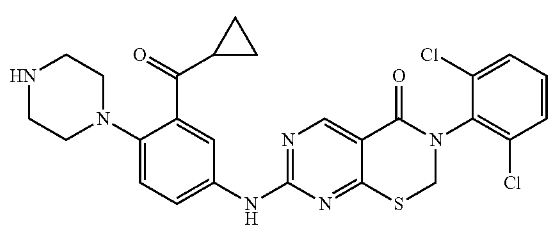 [SMILES: O=C(c1cc(Nc2ncc3c(n2)SCN(c2c(Cl)cccc2Cl)C3=O)ccc1N1CCNCC1)C1CC1] |
| 1.383 | 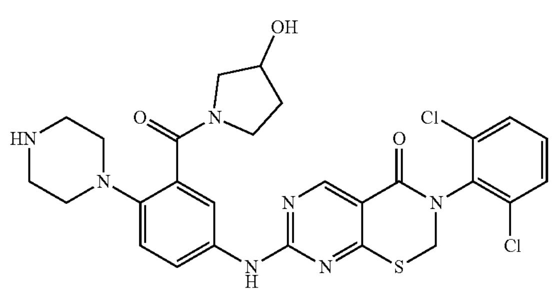 [SMILES: O=C(c1cc(Nc2ncc3c(n2)SCN(c2c(Cl)cccc2Cl)C3=O)ccc1N1CCNCC1)N1CCC(O)C1] |

US 10,807,994 B2
285                                                                                                                              286
TABLE 1-continued
| Compound No. | Structure |
|---|---|
| 1.384 | 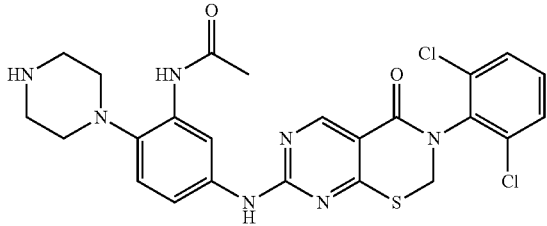 [SMILES: CC(=O)Nc1cc(Nc2ncc3c(n2)SCN(c2c(Cl)cccc2Cl)C3=O)ccc1N1CCNCC1] |
| 1.385 | 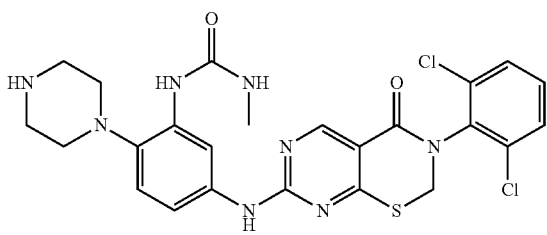 [SMILES: CNC(=O)Nc1cc(Nc2ncc3c(n2)SCN(c2c(Cl)cccc2Cl)C3=O)ccc1N1CCNCC1] |
| 1.386 | 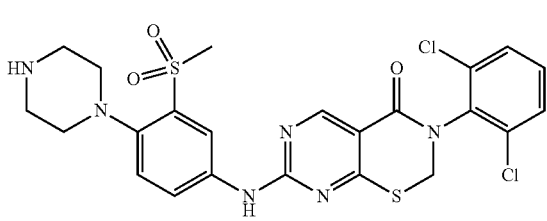 [SMILES: CS(=O)(=O)c1cc(Nc2ncc3c(n2)SCN(c2c(Cl)cccc2Cl)C3=O)ccc1N1CCNCC1] |
| 1.387 | 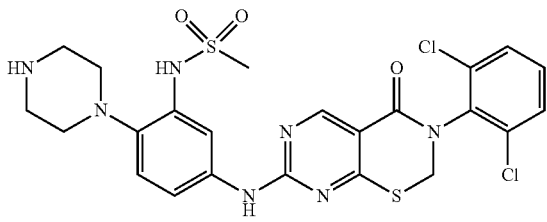 |
| 1.388 | 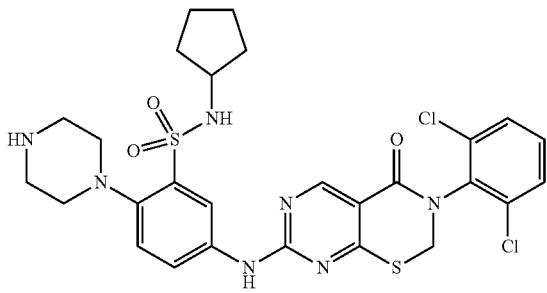 [SMILES: O=C1c2cnc(Nc3ccc(N4CCNCC4)c(S(=O)(=O)NC4CCCC4)c3)nc2SCN1c1c(Cl)cccc1Cl] |
| 1.389 | 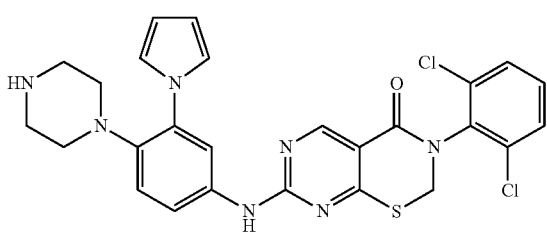 |

TABLE 1-continued

| Compound No. | Structure |
|---|---|
| 1.390 | 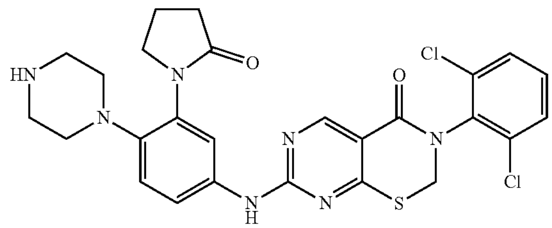 [SMILES: O=C1CCCN1c1cc(Nc2ncc3c(n2)SCN(c2c(Cl)cccc2Cl)C3=O)ccc1N1CCNCC1] |
| 1.391 | 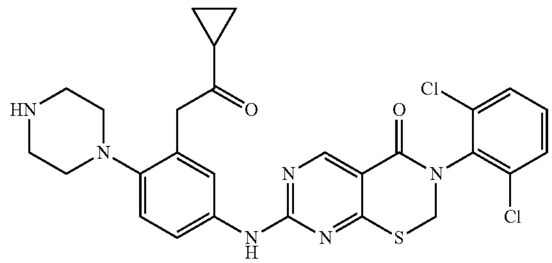 [SMILES: O=C(Cc1cc(Nc2ncc3c(n2)SCN(c2c(Cl)cccc2Cl)C3=O)ccc1N1CCNCC1)C1CC1] |
| 1.392 | 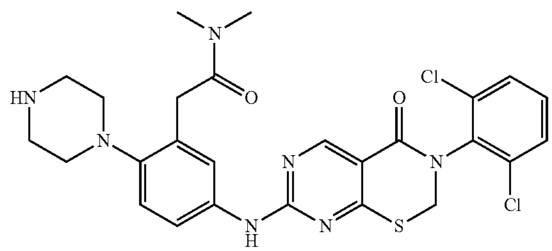 [SMILES: CN(C)C(=O)Cc1cc(Nc2ncc3c(n2)SCN(c2c(Cl)cccc2Cl)C3=O)ccc1N1CCNCC1] |
| 1.393 | 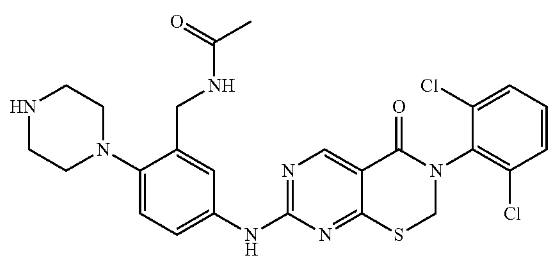 [SMILES: CC(=O)NCc1cc(Nc2ncc3c(n2)SCN(c2c(Cl)cccc2Cl)C3=O)ccc1N1CCNCC1] |
| 1.394 | 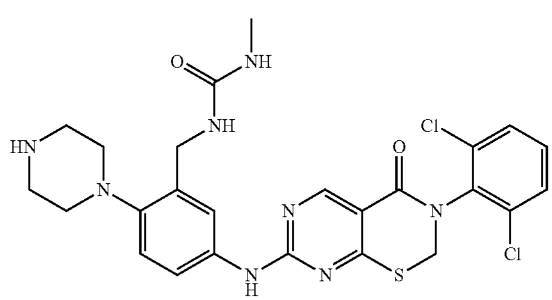 [SMILES: CNC(=O)NCc1cc(Nc2ncc3c(n2)SCN(c2c(Cl)cccc2Cl)C3=O)ccc1N1CCNCC1] |

TABLE 1-continued

| Compound No. | Structure |
|---|---|
| 1.395 | 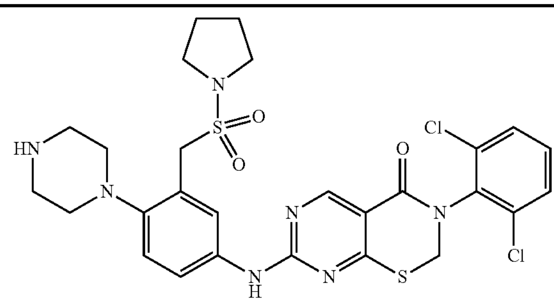 |
| 1.396 | 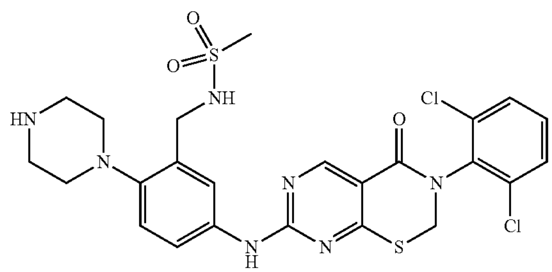 [SMILES: CS(=O)(=O)NCc1cc(Nc2ncc3c(n2)SCN(c2c(Cl)cccc2Cl)C3=O)ccc1N1CCNCC1] |
| 1.397 | 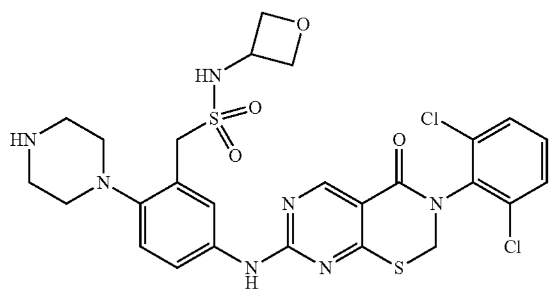 [SMILES: O=C1c2cnc(Nc3ccc(N4CCNCC4)c(CS(=O)(=O)NC4COC4)c3)nc2SCN1c1c(Cl)cccc1Cl] |
| 1.398 | 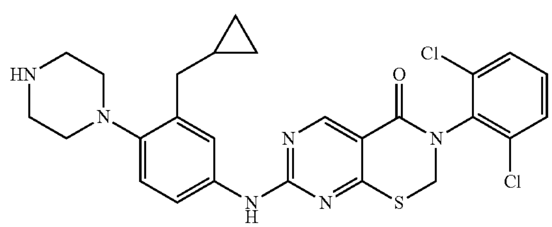 [SMILES: O=C1c2cnc(Nc3ccc(N4CCNCC4)c(CC4CC4)c3)nc2SCN1c1c(Cl)cccc1Cl] |
| 1.399 | 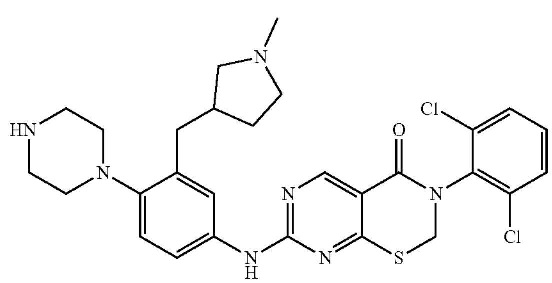 [SMILES: CN1CCC(Cc2cc(Nc3ncc4c(n3)SCN(c3c(Cl)cccc3Cl)C4=O)ccc2N2CCNCC2)C1] |
| 1.400 | 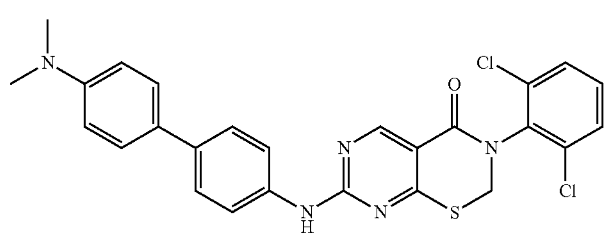 |

US 10,807,994 B2
291                                                                  292
TABLE 1-continued
| Compound No. | Structure |
|---|---|
| 1.401 | 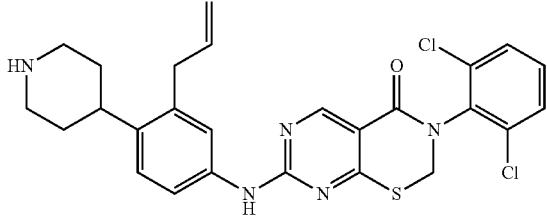 |
| 1.402 | 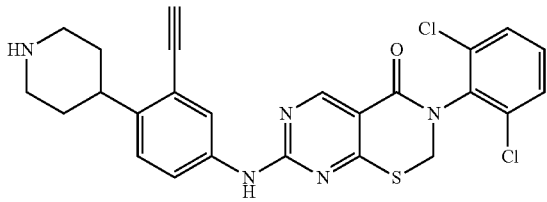 [SMILES: C#Cc1cc(Nc2ncc3c(n2)SCN(c2c(Cl)cccc2Cl)C3=O)ccc1C1CCNCC1] |
| 1.403 | 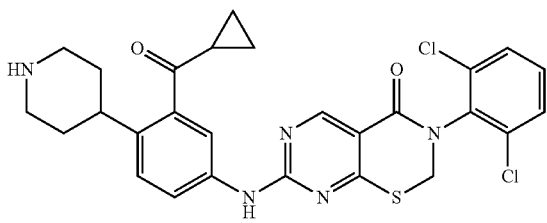 [SMILES: O=C(c1cc(Nc2ncc3c(n2)SCN(c2c(Cl)cccc2Cl)C3=O)ccc1C1CCNCC1)C1CC1] |
| 1.404 | 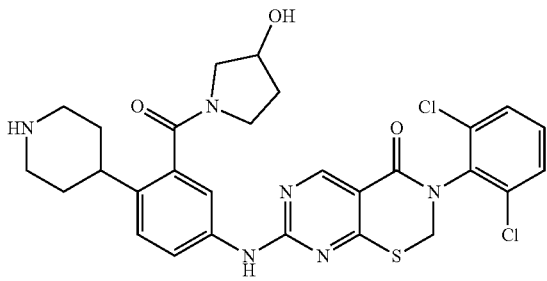 |
| 1.405 | 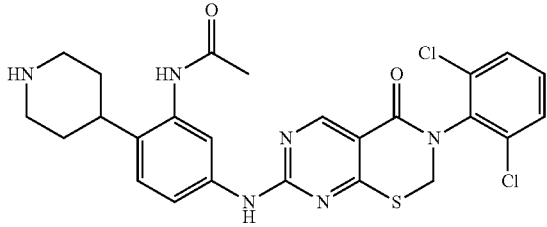 [SMILES: CC(=O)Nc1cc(Nc2ncc3c(n2)SCN(c2c(Cl)cccc2Cl)C3=O)ccc1C1CCNCC1] |
| 1.406 | 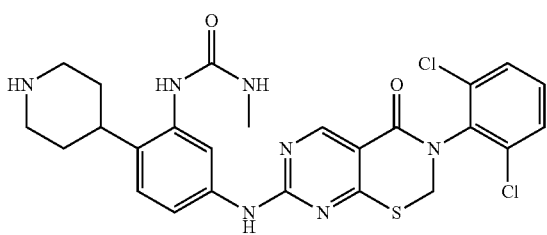 [SMILES: CNC(=O)Nc1cc(Nc2ncc3c(n2)SCN(c2c(Cl)cccc2Cl)C3=O)ccc1C1CCNCC1] |

TABLE 1-continued

| Compound No. | Structure |
|---|---|
| 1.407 | 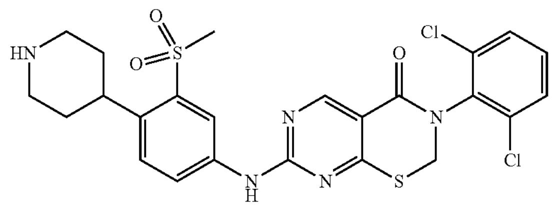 [SMILES: CS(=O)(=O)c1cc(Nc2ncc3c(n2)SCN(c2c(Cl)cccc2Cl)C3=O)ccc1C1CCNCC1] |
| 1.408 | 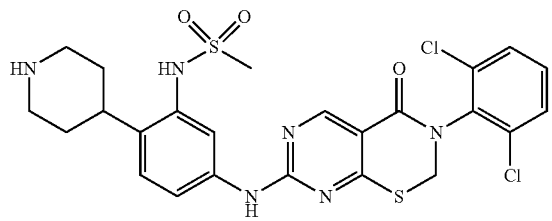 [SMILES: CS(=O)(=O)Nc1cc(Nc2ncc3c(n2)SCN(c2c(Cl)cccc2Cl)C3=O)ccc1C1CCNCC1] |
| 1.409 | 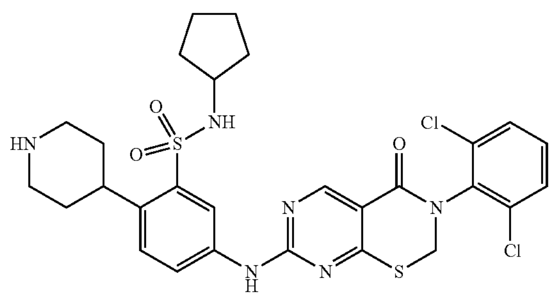 [SMILES: O=C1c2cnc(Nc3ccc(C4CCNCC4)c(S(=O)(=O)NC4CCCC4)c3)nc2SCN1c1c(Cl)cccc1Cl] |
| 1.410 | 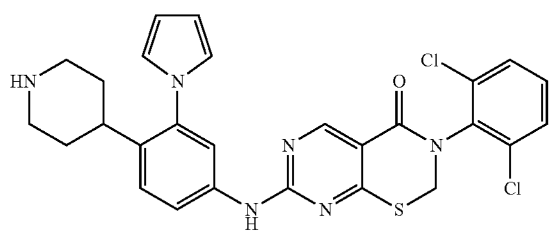 [SMILES: O=C1c2cnc(Nc3ccc(C4CCNCC4)c(-n4cccc4)c3)nc2SCN1c1c(Cl)cccc1Cl] |
| 1.411 | 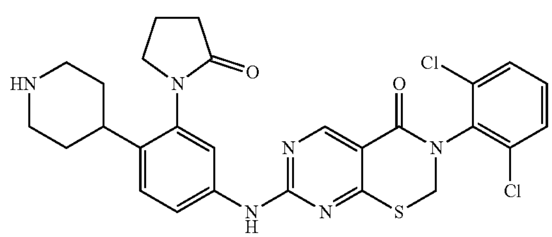 [SMILES: O=C1CCCN1c1cc(Nc2ncc3c(n2)SCN(c2c(Cl)cccc2Cl)C3=O)ccc1C1CCNCC1] |
| 1.412 | 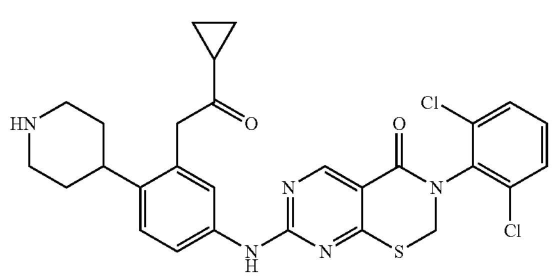 [SMILES: O=C(Cc1cc(Nc2ncc3c(n2)SCN(c2c(Cl)cccc2Cl)C3=O)ccc1C1CCNCC1)C1CC1] |

TABLE 1-continued
| Compound No. | Structure |
|---|---|
| 1.413 | 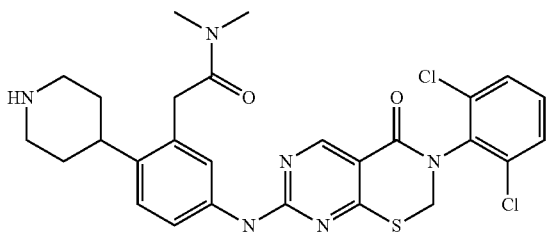 |
| 1.414 | 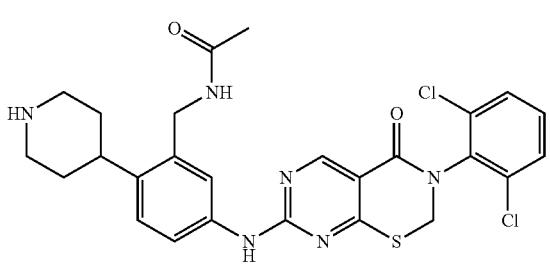 [SMILES: CC(=O)NCc1cc(Nc2ncc3c(n2)SCN(c2c(Cl)cccc2Cl)C3=O)ccc1C1CCNCC1] |
| 1.415 | 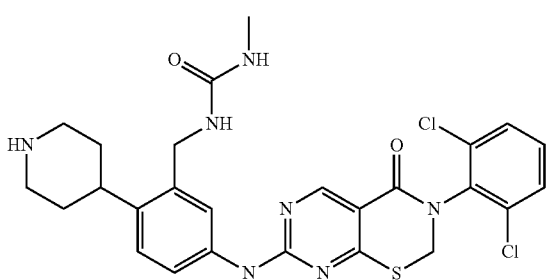 |
| 1.416 | 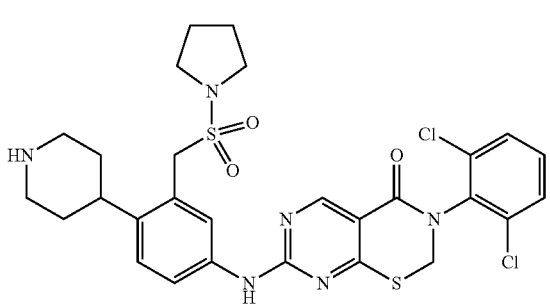 |
| 1.417 | 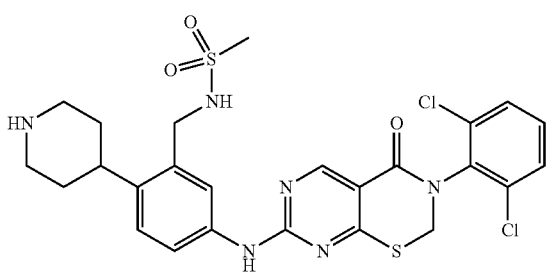 |

| Compound No. | Structure |
|---|---|
| 1.418 | 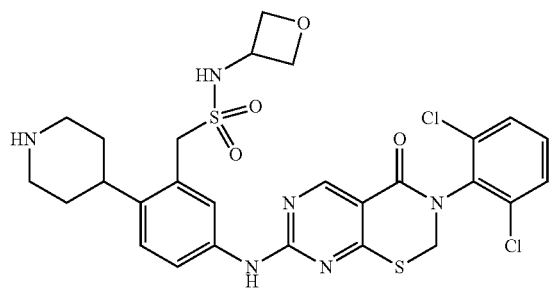 [SMILES: O=C1c2cnc(Nc3ccc(C4CCNCC4)c(CS(=O)(=O)NC4COC4)c3)nc2SCN1c1c(Cl)cccc1Cl] |
| 1.419 | 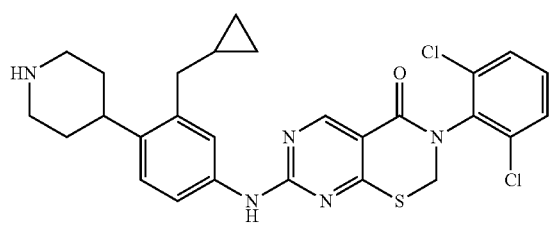 |
| 1.420 | 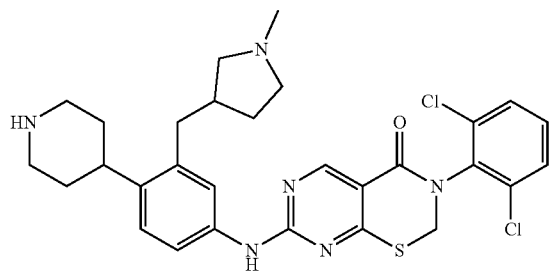 [SMILES: CN1CCC(Cc2cc(Nc3ncc4c(n3)SCN(c3c(Cl)cccc3Cl)C4=O)ccc2C2CCNCC2)C1] |
| 1.421 | 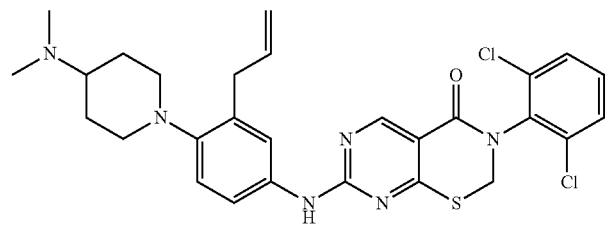 |
| 1.422 | 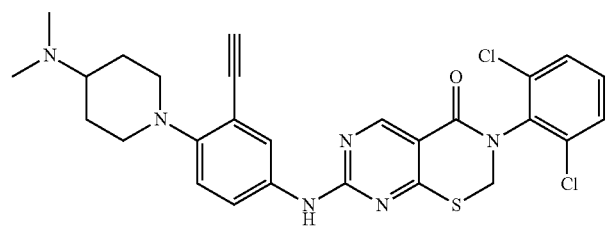 |
| 1.423 | 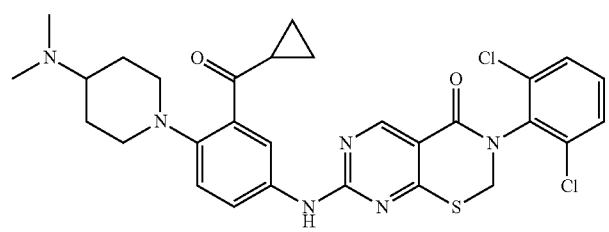 |

TABLE 1-continued

| Compound No. | Structure |
|---|---|
| 1.424 | 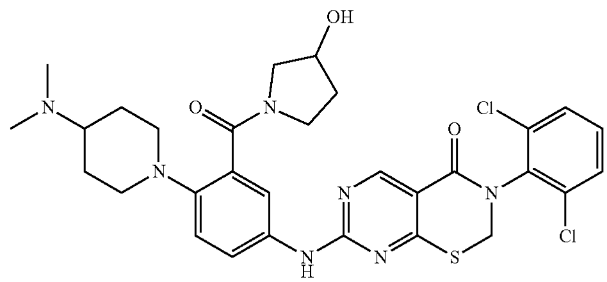 [SMILES: CN(C)C1CCN(c2ccc(Nc3ncc4c(n3)SCN(c3c(Cl)cccc3Cl)C4=O)cc2C(=O)N2CCC(O)C2)CC1] |
| 1.425 | 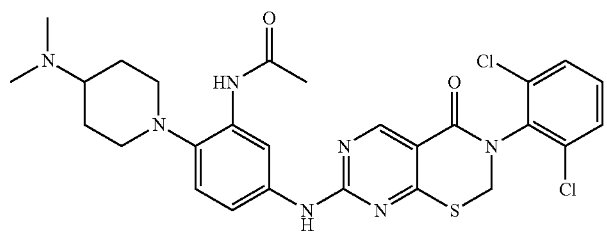 [SMILES: CC(=O)Nc1cc(Nc2ncc3c(n2)SCN(c2c(Cl)cccc2Cl)C3=O)ccc1N1CCC(N(C)C)CC1] |
| 1.426 | 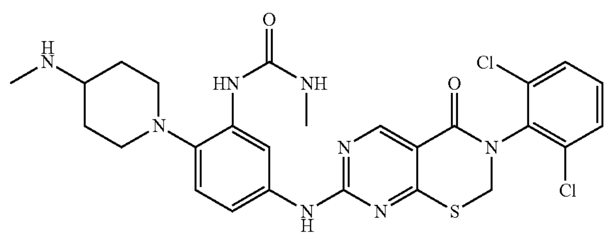 [SMILES: CNC(=O)Nc1cc(Nc2ncc3c(n2)SCN(c2c(Cl)cccc2Cl)C3=O)ccc1N1CCC(NC)CC1] |
| 1.427 | 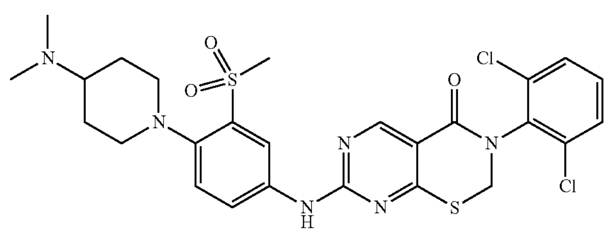 [SMILES: CN(C)C1CCN(c2ccc(Nc3ncc4c(n3)SCN(c3c(Cl)cccc3Cl)C4=O)cc2S(C)(=O)=O)CC1] |
| 1.428 | 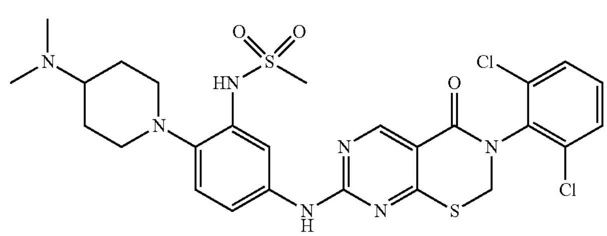 |
| 1.429 | 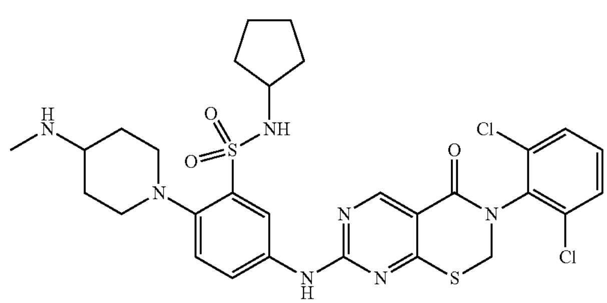 [SMILES: CNC1CCN(c2ccc(Nc3ncc4c(n3)SCN(c3c(Cl)cccc3Cl)C4=O)cc2S(=O)(=O)NC2CCCC2)CC1] |

TABLE 1-continued
| Compound No. | Structure |
|---|---|
| 1.430 | 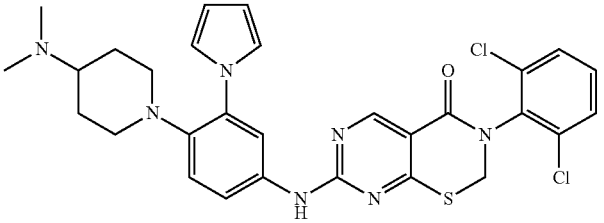 [SMILES: CN(C)C1CCN(c2ccc(Nc3ncc4c(n3)SCN(c3c(Cl)cccc3Cl)C4=O)cc2-n2cccc2)CC1] |
| 1.431 | 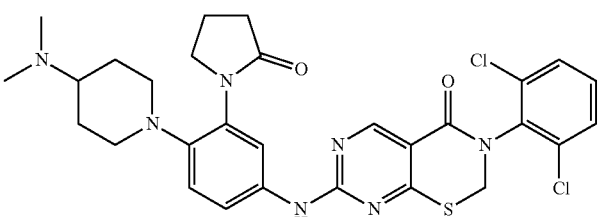 |
| 1.432 | 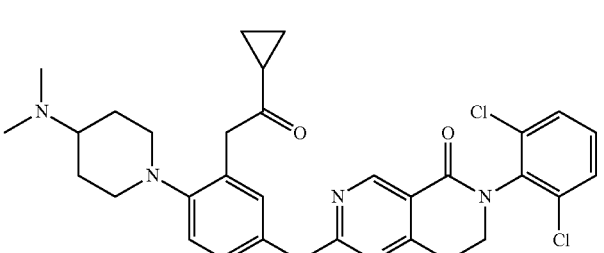 |
| 1.433 | 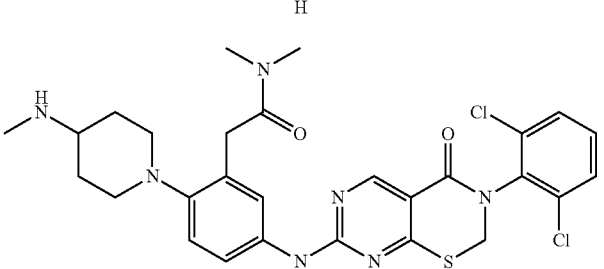 |
| 1.434 | 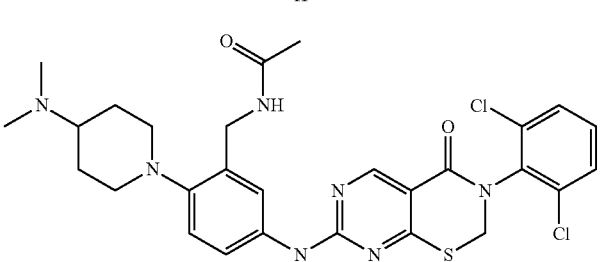 |
| 1.435 | 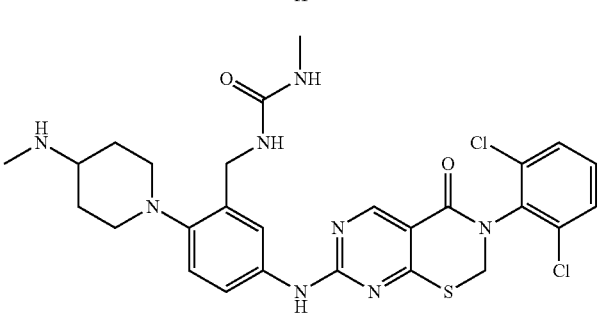 |

TABLE 1-continued
| Compound No. | Structure |
|---|---|
| 1.436 | 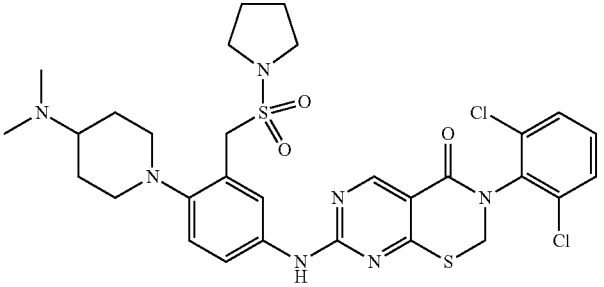 |
| 1.437 | 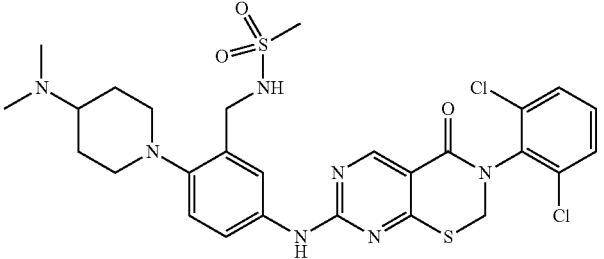 [SMILES: CN(C)C1CCN(c2ccc(Nc3ncc4c(n3)SCN(c3c(Cl)cccc3Cl)C4=O)cc2CNS(C)(=O)=O)CC1] |
| 1.438 | 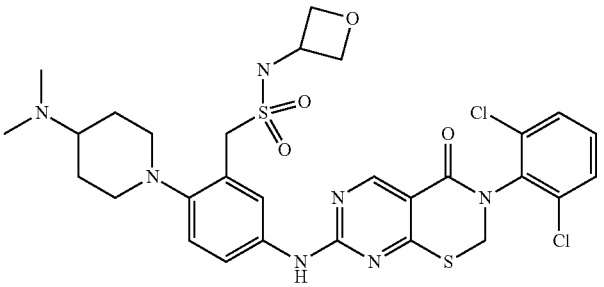 [SMILES: CN(C)C1CCN(c2ccc(Nc3ncc4c(n3)SCN(c3c(Cl)cccc3Cl)C4=O)cc2CS(=O)(=O)NC2COC2)CC1] |
| 1.439 | 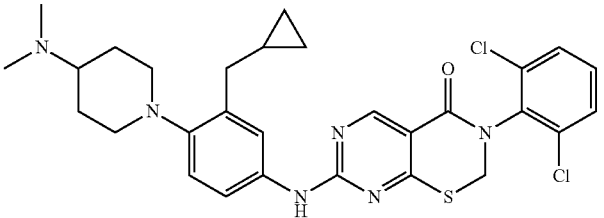 |
| 1.440 | 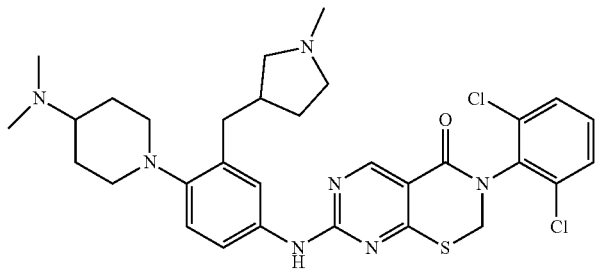 [SMILES: CN1CCC(Cc2cc(Nc3ncc4c(n3)SCN(c3c(Cl)cccc3Cl)C4=O)ccc2N2CCC(N(C)C)CC2)C1] |
| 1.441 | 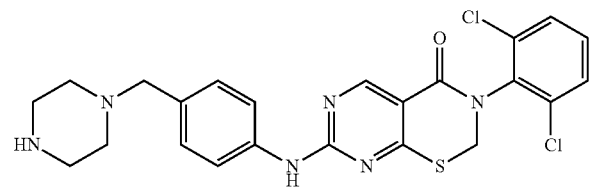 |

TABLE 1-continued
| Compound No. | Structure |
|---|---|
| 1.442 | 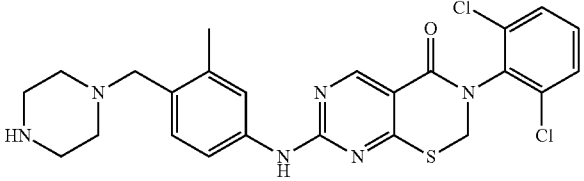 [SMILES: Cc1cc(Nc2ncc3c(n2)SCN(c2c(Cl)cccc2Cl)C3=O)ccc1CN1CCNCC1] |
| 1.443 | 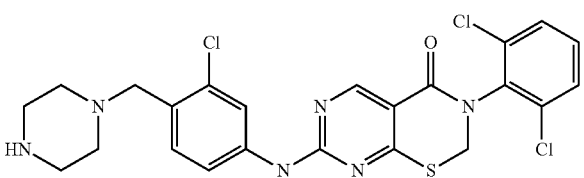 |
| 1.444 | 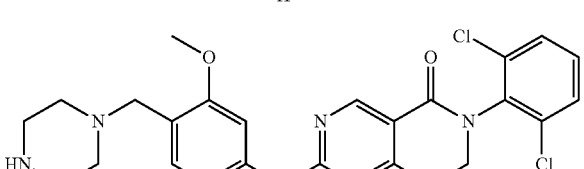 |
| 1.445 | 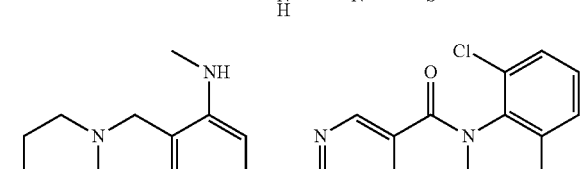 |
| 1.446 | 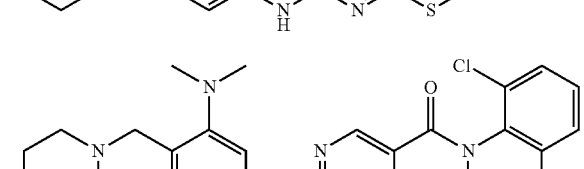 |
| 1.447 | 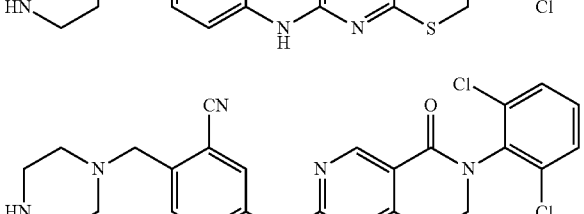 |
| 1.448 | 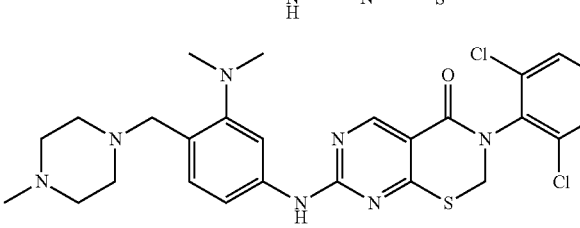 |
| 1.449 | 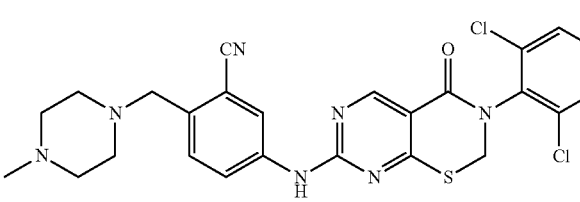 |

TABLE 1-continued

| Compound No. | Structure |
| --- | --- |
| 1.450 | (chemical structure) |
| 1.451 | (chemical structure) |
| 1.452 | (chemical structure) |
| 1.453 | (chemical structure) |
| 1.454 | (chemical structure) |
| 1.455 | (chemical structure) |
| 1.456 | (chemical structure) |
| 1.457 | (chemical structure) |

TABLE 1-continued
| Compound No. | Structure |
|---|---|
| 1.458 | 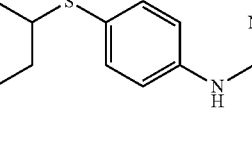 |
| 1.459 | 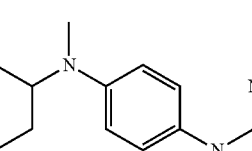 |
| 1.460 | 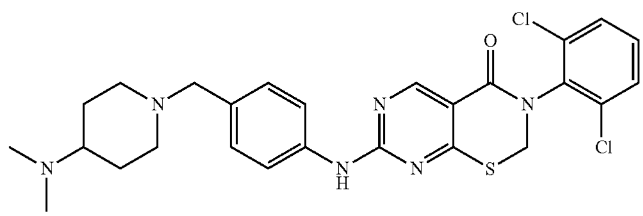 [SMILES: CN(C)C1CCN(Cc2ccc(Nc3ncc4c(n3)SCN(c3c(Cl)cccc3Cl)C4=O)cc2)CC1] |
| 1.461 | 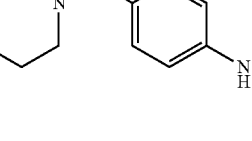 |
| 1.462 | 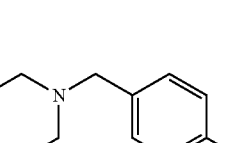 |
| 1.463 | 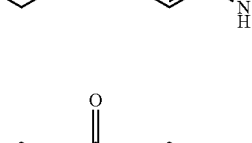 |
| 1.464 | 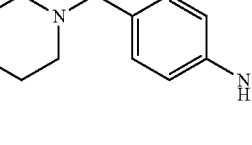 |

TABLE 1-continued

| Compound No. | Structure |
|---|---|
| 1.465 | 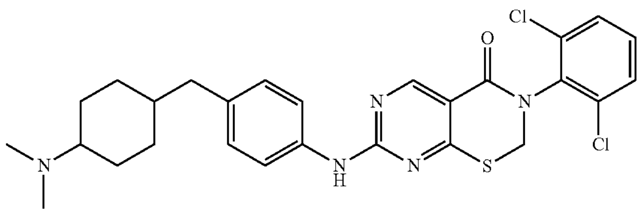 [SMILES: CN(C)C1CCC(Cc2ccc(Nc3ncc4c(n3)SCN(c3c(Cl)cccc3Cl)C4=O)cc2)CC1] |
| 1.466 | 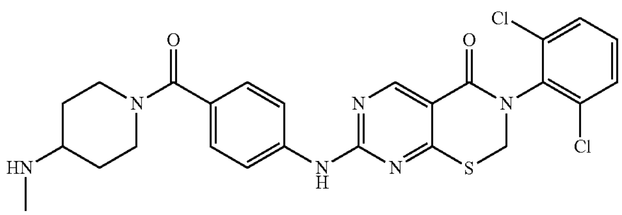 [SMILES: CNC1CCN(C(=O)c2ccc(Nc3ncc4c(n3)SCN(c3c(Cl)cccc3Cl)C4=O)cc2)CC1] |
| 1.467 | 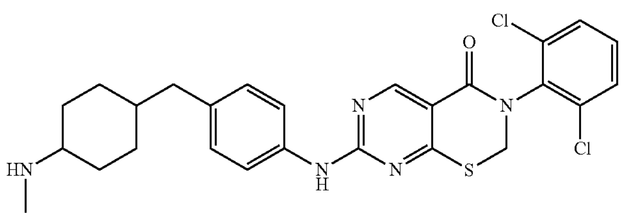 [SMILES: CNC1CCC(Cc2ccc(Nc3ncc4c(n3)SCN(c3c(Cl)cccc3Cl)C4=O)cc2)CC1] |
| 1.468 | 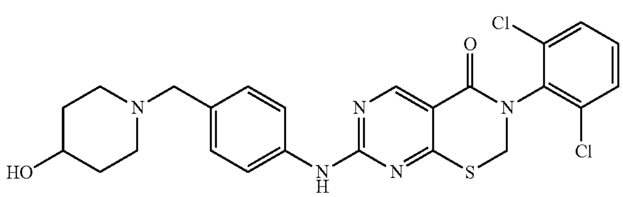 [SMILES: O=C1c2cnc(Nc3ccc(CN4CCC(O)CC4)cc3)nc2SCN1c1c(Cl)cccc1Cl] |
| 1.469 | 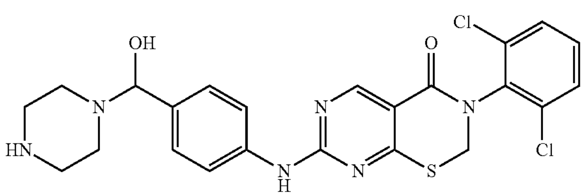 [SMILES: O=C1c2cnc(Nc3ccc(C(O)N4CCNCC4)cc3)nc2SCN1c1c(Cl)cccc1Cl] |
| 1.470 | 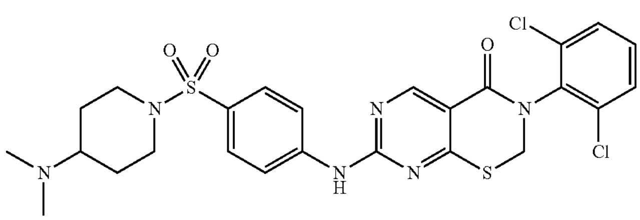 [SMILES: CN(C)C1CCN(S(=O)(=O)c2ccc(Nc3ncc4c(n3)SCN(c3c(Cl)cccc3Cl)C4=O)cc2)CC1] |
| 1.471 | 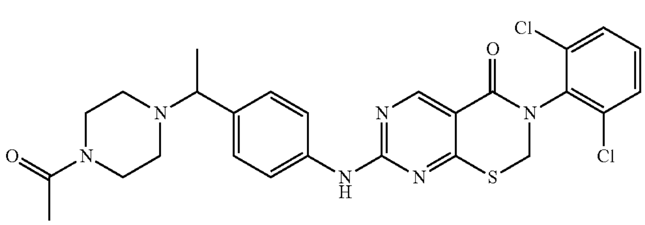 [SMILES: CC(=O)N1CCN(C(C)c2ccc(Nc3ncc4c(n3)SCN(c3c(Cl)cccc3Cl)C4=O)cc2)CC1] |

TABLE 1-continued

| Compound No. | Structure |
|---|---|
| 1.472 | 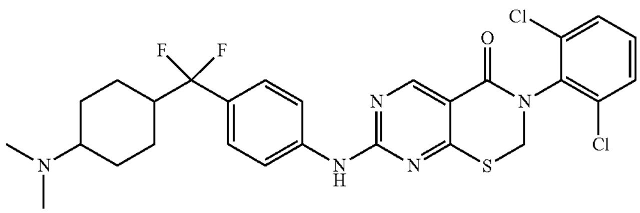 [SMILES: CN(C)C1CCC(C(F)(F)c2ccc(Nc3ncc4c(n3)SCN(c3c(Cl)cccc3Cl)C4=O)cc2)CC1] |
| 1.473 | 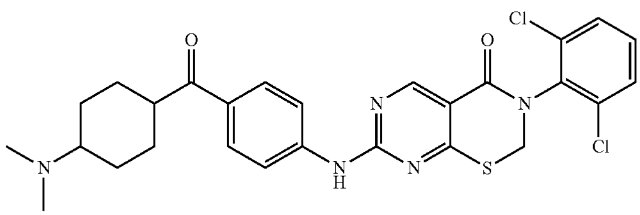 [SMILES: CN(C)C1CCC(C(=O)c2ccc(Nc3ncc4c(n3)SCN(c3c(Cl)cccc3Cl)C4=O)cc2)CC1] |
| 1.474 | 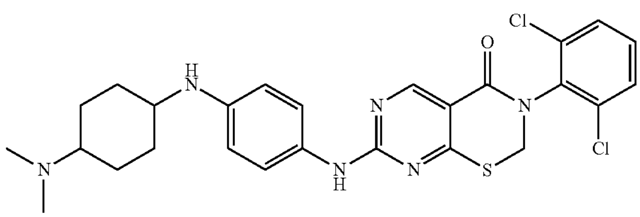 [SMILES: CN(C)C1CCC(Nc2ccc(Nc3ncc4c(n3)SCN(c3c(Cl)cccc3Cl)C4=O)cc2)CC1] |
| 1.475 | 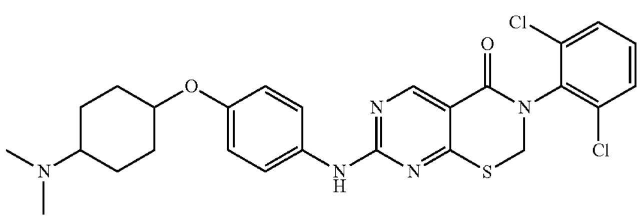 |
| 1.476 | 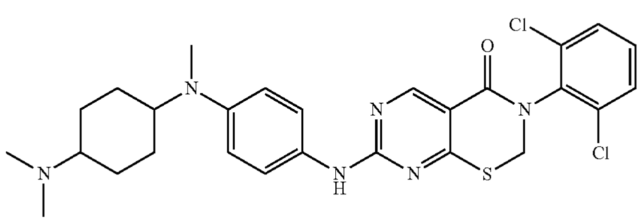 [SMILES: CN(C)C1CCC(N(C)c2ccc(Nc3ncc4c(n3)SCN(c3c(Cl)cccc3Cl)C4=O)cc2)CC1] |
| 1.477 | 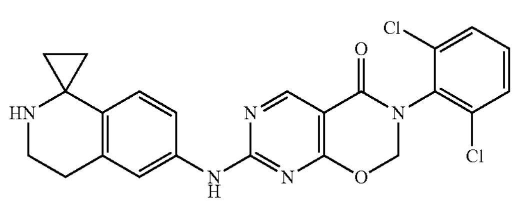 [SMILES: O=C1c2cnc(Nc3ccc4c(c3)CCNC43CC3)nc2OCN1c1c(Cl)cccc1Cl] |
| 1.478 | 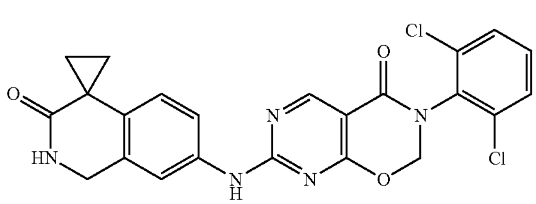 [SMILES: O=C1c2cnc(Nc3ccc4c(c3)CNC(=O)C43CC3)nc2OCN1c1c(Cl)cccc1Cl] |

TABLE 1-continued

| Compound No. | Structure |
|---|---|
| 1.479 | 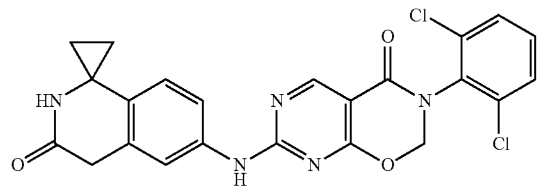 |
| 1.480 | 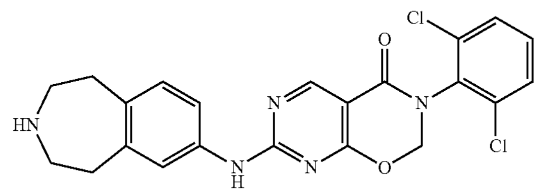 [SMILES: O=C1c2cnc(Nc3ccc4c(c3)CCNCC4)nc2OCN1c1c(Cl)cccc1Cl] |
| 1.481 | 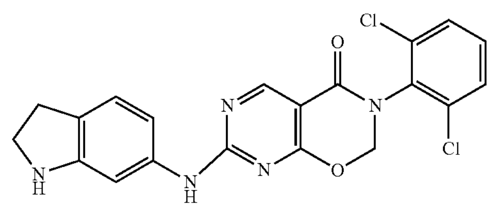 [SMILES: O=C1c2cnc(Nc3ccc4c(c3)NCC4)nc2OCN1c1c(Cl)cccc1Cl] |
| 1.482 | 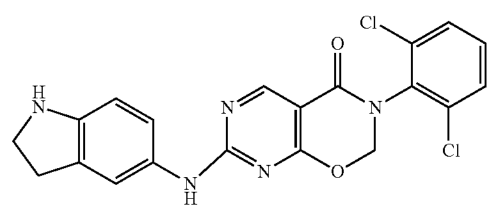 [SMILES: O=C1c2cnc(Nc3ccc4c(c3)CCN4)nc2OCN1c1c(Cl)cccc1Cl] |
| 1.483 | 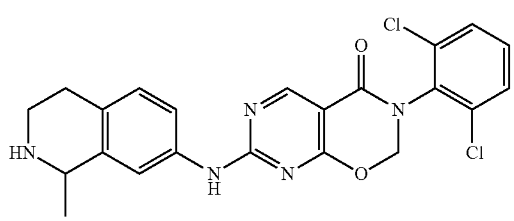 [SMILES: CC1NCCc2ccc(Nc3ncc4c(n3)OCN(c3c(Cl)cccc3Cl)C4=O)cc21] |
| 1.484 | 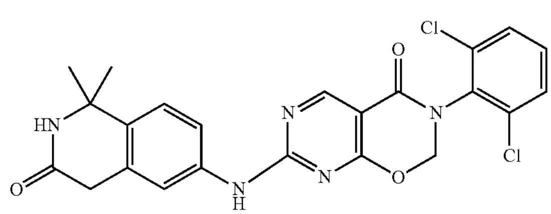 [SMILES: CC1(C)NC(=O)Cc2cc(Nc3ncc4c(n3)OCN(c3c(Cl)cccc3Cl)C4=O)ccc21] |
| 1.485 | 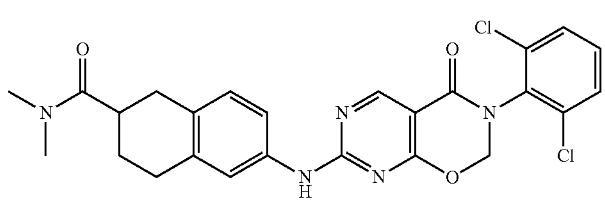 [SMILES: CN(C)C(=O)C1CCc2cc(Nc3ncc4c(n3)OCN(c3c(Cl)cccc3Cl)C4=O)ccc2C1] |

TABLE 1-continued
| Compound No. | Structure |
|---|---|
| 1.486 | 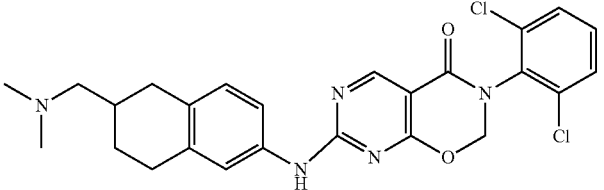 [SMILES: CN(C)CC1CCc2cc(Nc3ncc4c(n3)OCN(c3c(Cl)cccc3Cl)C4=O)ccc2C1] |
| 1.487 | 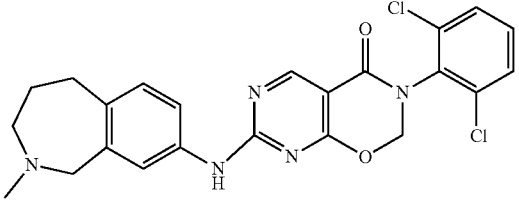 [SMILES: CN1CCCc2ccc(Nc3ncc4c(n3)OCN(c3c(Cl)cccc3Cl)C4=O)cc2C1] |
| 1.488 | 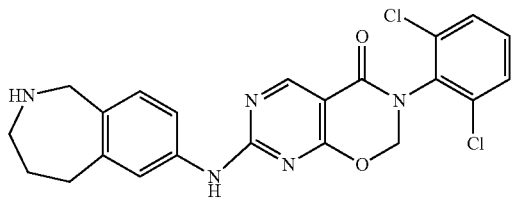 [SMILES: O=C1c2cnc(Nc3ccc4c(c3)CCCNC4)nc2OCN1c1c(Cl)cccc1Cl] |
| 1.489 | 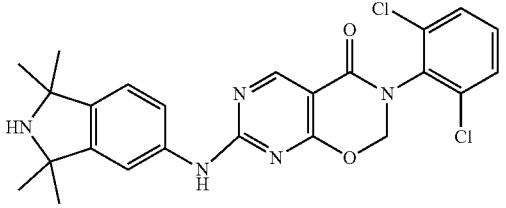 [SMILES: CC1(C)NC(C)(C)c2cc(Nc3ncc4c(n3)OCN(c3c(Cl)cccc3Cl)C4=O)ccc21] |
| 1.490 | 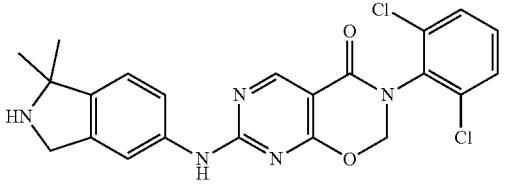 [SMILES: CC1(C)NCc2cc(Nc3ncc4c(n3)OCN(c3c(Cl)cccc3Cl)C4=O)ccc21] |
| 1.491 | 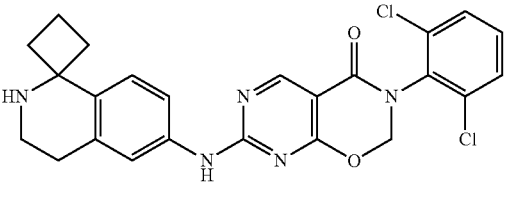 [SMILES: O=C1c2cnc(Nc3ccc4c(c3)CCNC43CCC3)nc2OCN1c1c(Cl)cccc1Cl] |
| 1.492 | 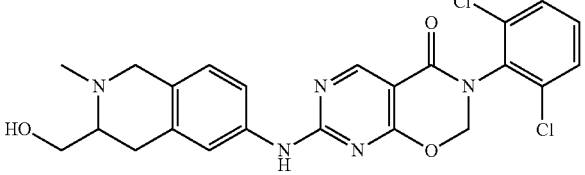 |

TABLE 1-continued

| Compound No. | Structure |
|---|---|
| 1.493 | 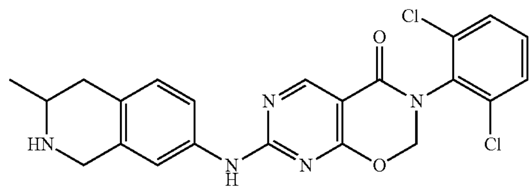 [SMILES: CC1Cc2ccc(Nc3ncc4c(n3)OCN(c3c(Cl)cccc3Cl)C4=O)cc2CN1] |
| 1.494 | 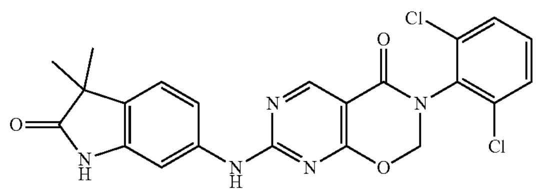 [SMILES: CC1(C)C(=O)Nc2cc(Nc3ncc4c(n3)OCN(c3c(Cl)cccc3Cl)C4=O)ccc21] |
| 1.495 | 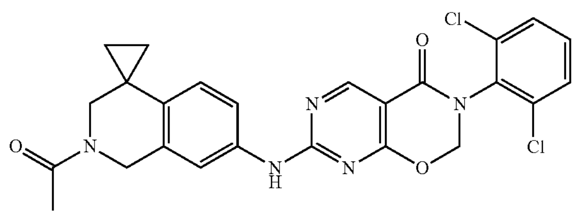 [SMILES: CC(=O)N1Cc2cc(Nc3ncc4c(n3)OCN(c3c(Cl)cccc3Cl)C4=O)ccc2C2(CC2)C1] |
| 1.496 | 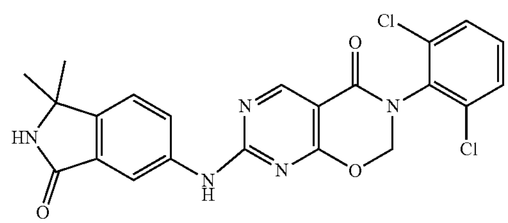 [SMILES: CC1(C)NC(=O)c2cc(Nc3ncc4c(n3)OCN(c3c(Cl)cccc3Cl)C4=O)ccc21] |
| 1.497 | 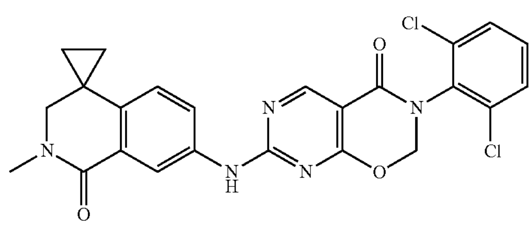 [SMILES: CN1CC2(CC2)c2ccc(Nc3ncc4c(n3)OCN(c3c(Cl)cccc3Cl)C4=O)cc2C1=O] |
| 1.498 | 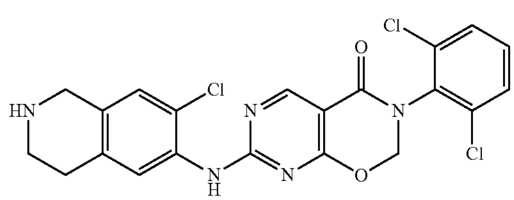 [SMILES: O=C1c2cnc(Nc3cc4c(cc3Cl)CNCC4)nc2OCN1c1c(Cl)cccc1Cl] |
| 1.499 | 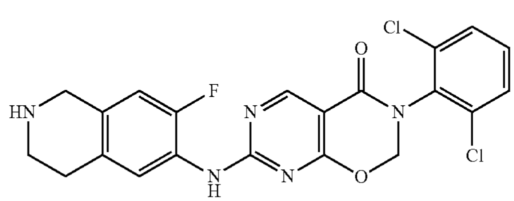 [SMILES: O=C1c2cnc(Nc3cc4c(cc3F)CNCC4)nc2OCN1c1c(Cl)cccc1Cl] |

TABLE 1-continued

| Compound No. | Structure |
|---|---|
| 1.500 | 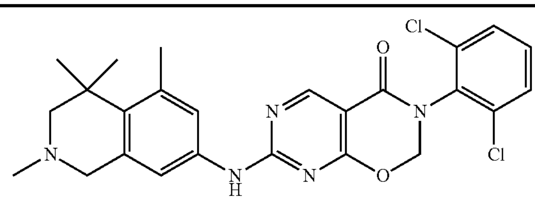 |
| 1.501 | 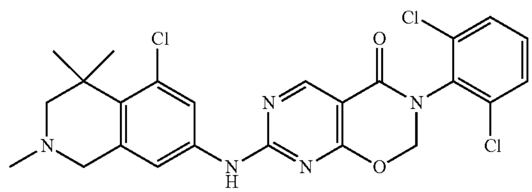 [SMILES: CN1Cc2cc(Nc3ncc4c(n3)OCN(c3c(Cl)cccc3Cl)C4=O)cc(Cl)c2C(C)(C)C1] |
| 1.502 | 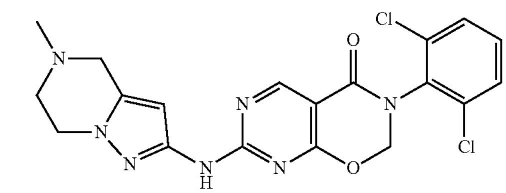 [SMILES: CN1CCn2nc(Nc3ncc4c(n3)OCN(c3c(Cl)cccc3Cl)C4=O)cc2C1] |
| 1.503 | 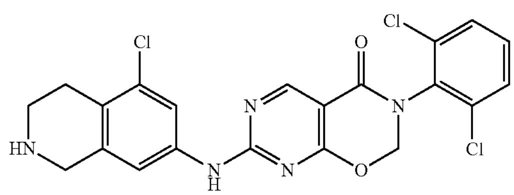 [SMILES: O=C1c2cnc(Nc3cc(Cl)c4c(c3)CNCC4)nc2OCN1c1c(Cl)cccc1Cl] |
| 1.504 | 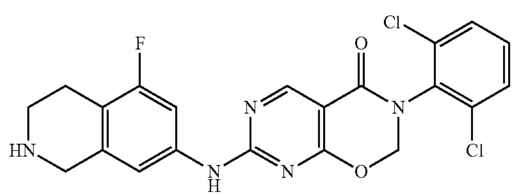 [SMILES: O=C1c2cnc(Nc3cc(F)c4c(c3)CNCC4)nc2OCN1c1c(Cl)cccc1Cl] |
| 1.505 | 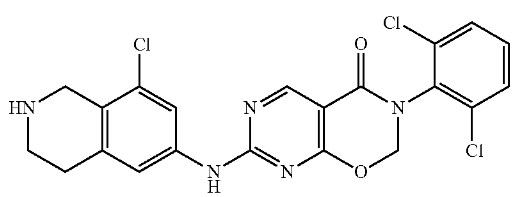 [SMILES: O=C1c2cnc(Nc3cc(Cl)c4c(c3)CCNC4)nc2OCN1c1c(Cl)cccc1Cl] |
| 1.506 | 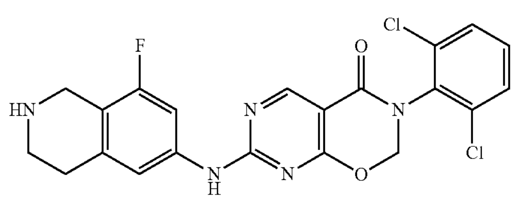 [SMILES: O=C1c2cnc(Nc3cc(F)c4c(c3)CCNC4)nc2OCN1c1c(Cl)cccc1Cl] |
| 1.507 | 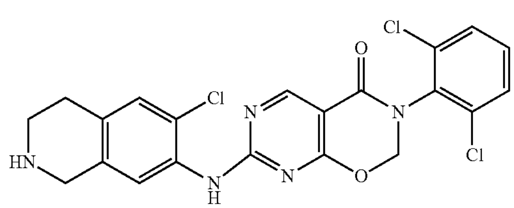 [SMILES: O=C1c2cnc(Nc3cc4c(cc3Cl)CCNC4)nc2OCN1c1c(Cl)cccc1Cl] |

TABLE 1-continued
| Compound No. | Structure |
|---|---|
| 1.508 | 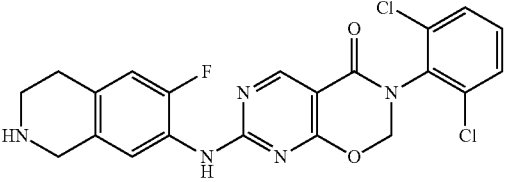 [SMILES: O=C1c2cnc(Nc3cc4c(cc3F)CCNC4)nc2OCN1c1c(Cl)cccc1Cl] |
| 1.509 | 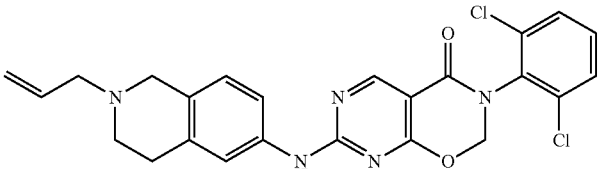 |
| 1.510 | 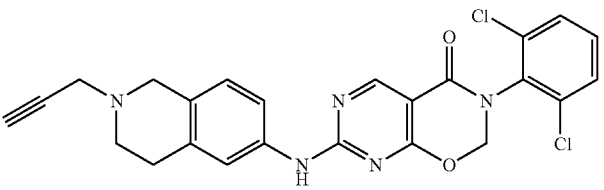 |
| 1.511 | 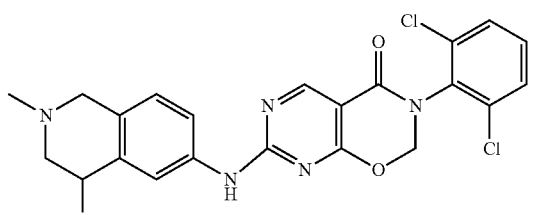 |
| 1.512 | 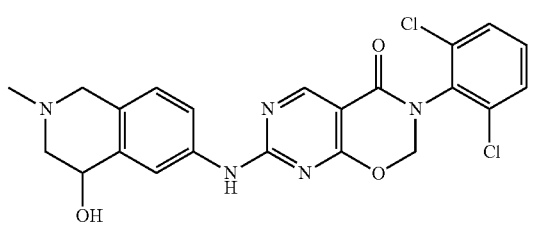 [SMILES: CN1Cc2ccc(Nc3ncc4c(n3)OCN(c3c(Cl)cccc3Cl)C4=O)cc2C(O)C1] |
| 1.513 | 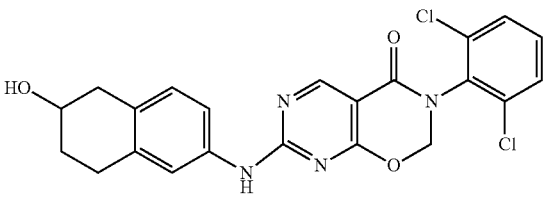 [SMILES: O=C1c2cnc(Nc3ccc4c(c3)CCC(O)C4)nc2OCN1c1c(Cl)cccc1Cl] |
| 1.514 | 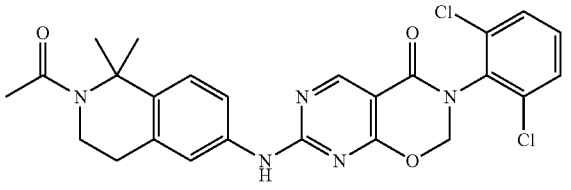 [SMILES: CC(=O)N1CCc2cc(Nc3ncc4c(n3)OCN(c3c(Cl)cccc3Cl)C4=O)ccc2C1(C)C] |

US 10,807,994 B2
TABLE 1-continued
| Compound No. | Structure |
|---|---|
| 1.515 | 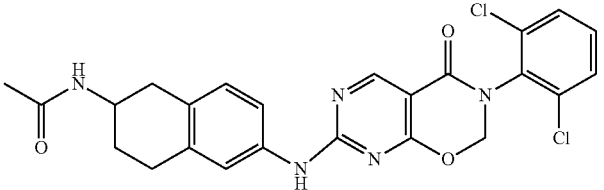 [SMILES: CC(=O)NC1CCc2cc(Nc3ncc4c(n3)OCN(c3c(Cl)cccc3Cl)C4=O)ccc2C1] |
| 1.516 | 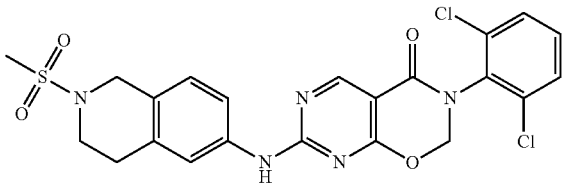 [SMILES: CS(=O)(=O)N1CCc2cc(Nc3ncc4c(n3)OCN(c3c(Cl)cccc3Cl)C4=O)ccc2C1] |
| 1.517 | 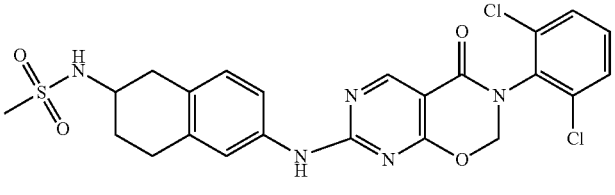 [SMILES: CS(=O)(=O)NC1CCc2cc(Nc3ncc4c(n3)OCN(c3c(Cl)cccc3Cl)C4=O)ccc2C1] |
| 1.518 | 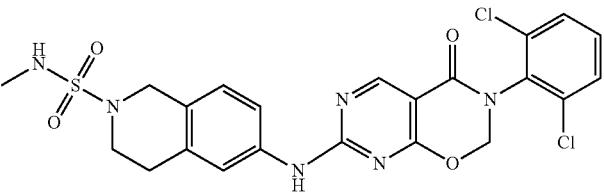 [SMILES: CNS(=O)(=O)N1CCc2cc(Nc3ncc4c(n3)OCN(c3c(Cl)cccc3Cl)C4=O)ccc2C1] |
| 1.519 | 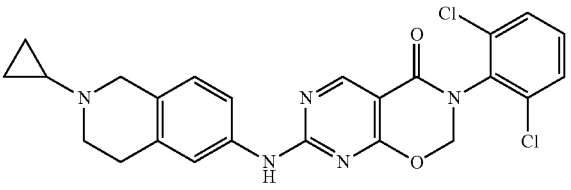 [SMILES: O=C1c2cnc(Nc3ccc4c(c3)CCN(C3CC3)C4)nc2OCN1c1c(Cl)cccc1Cl] |
| 1.520 | 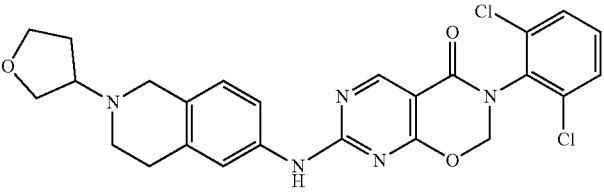 [SMILES: O=C1c2cnc(Nc3ccc4c(c3)CCN(C3CCOC3)C4)nc2OCN1c1c(Cl)cccc1Cl] |
| 1.521 | 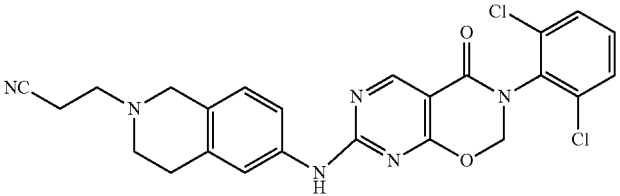 [SMILES: N#CCCN1CCc2cc(Nc3ncc4c(n3)OCN(c3c(Cl)cccc3Cl)C4=O)ccc2C1] |

US 10,807,994 B2
TABLE 1-continued
| Compound No. | Structure |
|---|---|
| 1.522 | 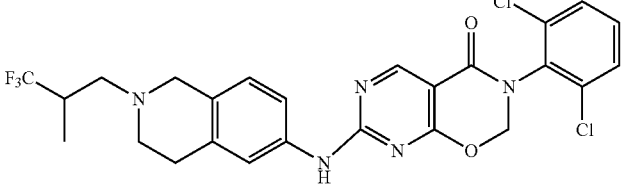 |
| 1.523 | 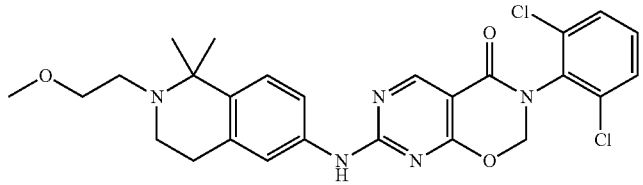 |
| 1.524 | 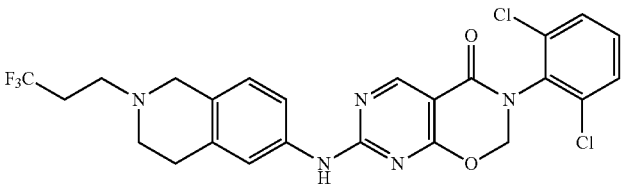 [SMILES: O=C1c2cnc(Nc3ccc4c(c3)CCN(CCC(F)(F)F)C4)nc2OCN1c1c(Cl)cccc1Cl] |
| 1.525 | 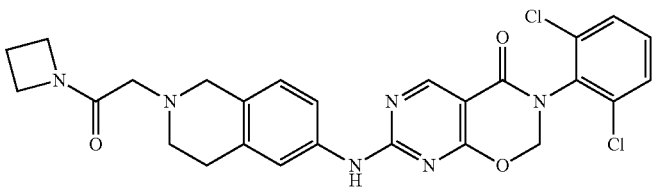 [SMILES: O=C(CN1CCc2cc(Nc3ncc4c(n3)OCN(c3c(Cl)cccc3Cl)C4=O)ccc2C1)N1CCC1] |
| 1.526 | 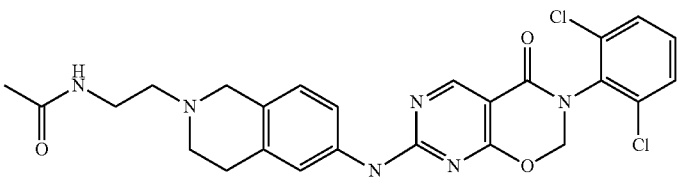 |
| 1.527 | 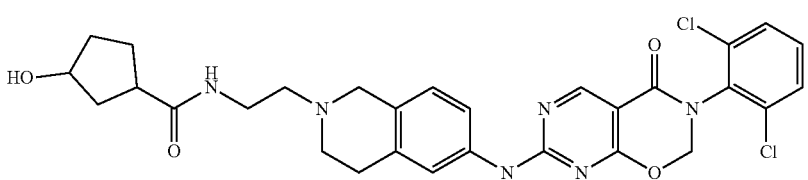 |
| 1.528 | 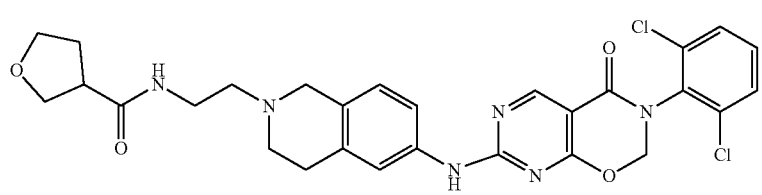 [SMILES: O=C(NCCN1CCc2cc(Nc3ncc4c(n3)OCN(c3c(Cl)cccc3Cl)C4=O)ccc2C1)C1CCOC1] |
| 1.529 | 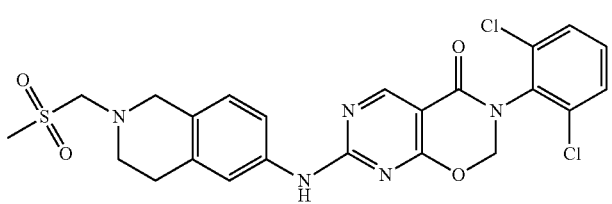 [SMILES: CS(=O)(=O)CN1CCc2cc(Nc3ncc4c(n3)OCN(c3c(Cl)cccc3Cl)C4=O)ccc2C1] |

TABLE 1-continued

| Compound No. | Structure |
|---|---|
| 1.530 | 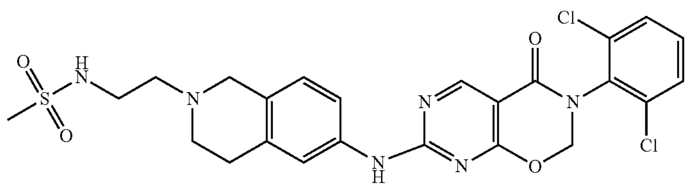 [SMILES: CS(=O)(=O)NCCN1CCc2cc(Nc3ncc4c(n3)OCN(c3c(Cl)cccc3Cl)C4=O)ccc2C1] |
| 1.531 | 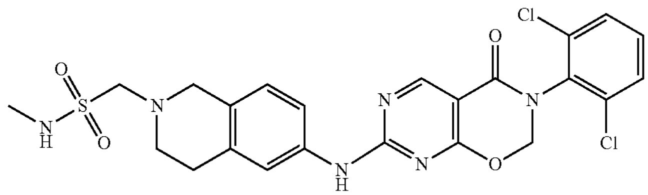 [SMILES: CNS(=O)(=O)CN1CCc2cc(Nc3ncc4c(n3)OCN(c3c(Cl)cccc3Cl)C4=O)ccc2C1] |
| 1.532 | 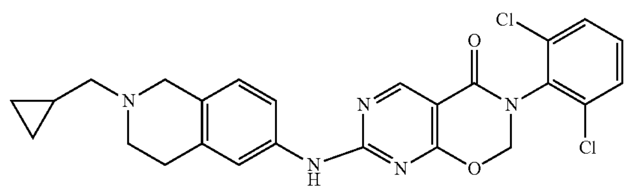 [SMILES: O=C1c2cnc(Nc3ccc4c(c3)CCN(CC3CC3)C4)nc2OCN1c1c(Cl)cccc1Cl] |
| 1.533 | 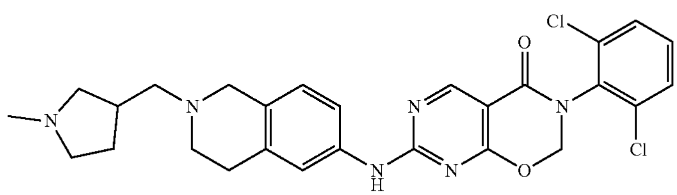 [SMILES: CN1CCC(CN2CCc3cc(Nc4ncc5c(n4)OCN(c4c(Cl)cccc4Cl)C5=O)ccc3C2)C1] |
| 1.534 | 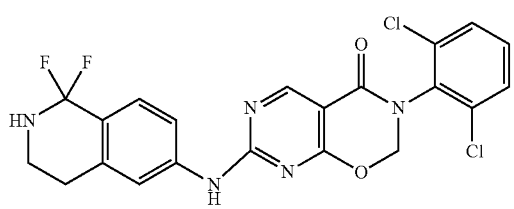 [SMILES: O=C1c2cnc(Nc3ccc4c(c3)CCNC4(F)F)nc2OCN1c1c(Cl)cccc1Cl] |
| 1.535 | 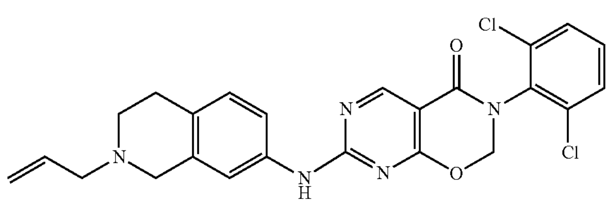 [SMILES: C=CCN1CCc2ccc(Nc3ncc4c(n3)OCN(c3c(Cl)cccc3Cl)C4=O)cc2C1] |
| 1.536 | 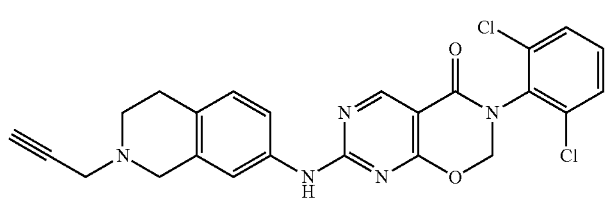 [SMILES: C#CCN1CCc2ccc(Nc3ncc4c(n3)OCN(c3c(Cl)cccc3Cl)C4=O)cc2C1] |

TABLE 1-continued

| Compound No. | Structure |
|---|---|
| 1.537 | 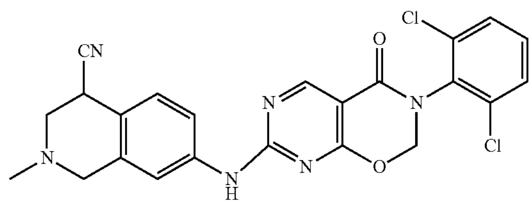 [SMILES: CN1Cc2cc(Nc3ncc4c(n3)OCN(c3c(Cl)cccc3Cl)C4=O)ccc2C(C#N)C1] |
| 1.538 | 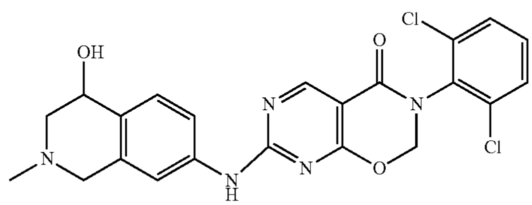 [SMILES: CN1Cc2cc(Nc3ncc4c(n3)OCN(c3c(Cl)cccc3Cl)C4=O)ccc2C(O)C1] |
| 1.539 | 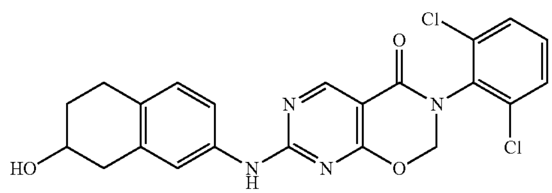 [SMILES: O=C1c2cnc(Nc3ccc4c(c3)CC(O)CC4)nc2OCN1c1c(Cl)cccc1Cl] |
| 1.540 | 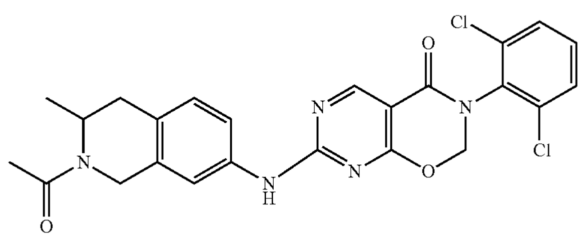 [SMILES: CC(=O)N1Cc2cc(Nc3ncc4c(n3)OCN(c3c(Cl)cccc3Cl)C4=O)ccc2CC1C] |
| 1.541 | 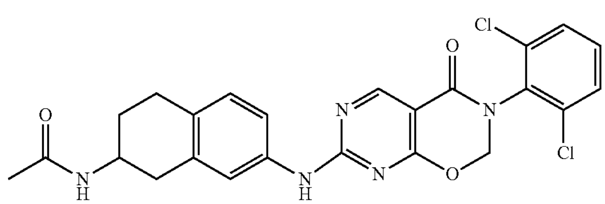 [SMILES: CC(=O)NC1CCc2ccc(Nc3ncc4c(n3)OCN(c3c(Cl)cccc3Cl)C4=O)cc2C1] |
| 1.542 | 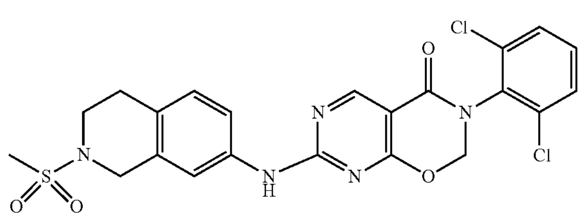 [SMILES: CS(=O)(=O)N1CCc2ccc(Nc3ncc4c(n3)OCN(c3c(Cl)cccc3Cl)C4=O)cc2C1] |
| 1.543 | 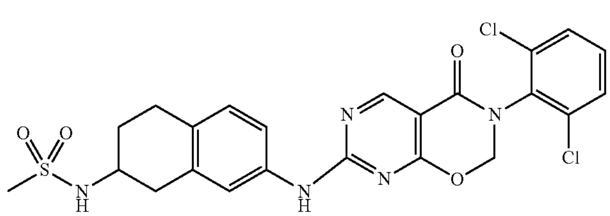 [SMILES: CS(=O)(=O)NC1CCc2ccc(Nc3ncc4c(n3)OCN(c3c(Cl)cccc3Cl)C4=O)cc2C1] |

TABLE 1-continued
| Compound No. | Structure |
|---|---|
| 1.544 | 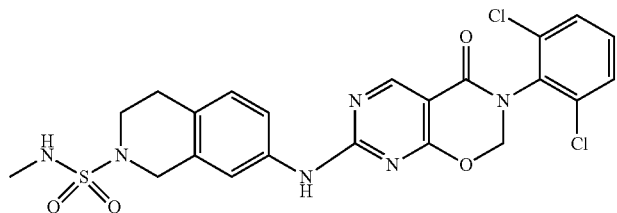 [SMILES: CNS(=O)(=O)N1CCc2ccc(Nc3ncc4c(n3)OCN(c3c(Cl)cccc3Cl)C4=O)cc2C1] |
| 1.545 | 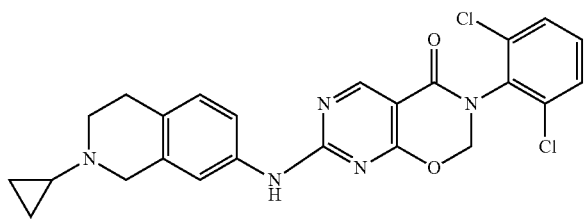 [SMILES: O=C1c2cnc(Nc3ccc4c(c3)CN(C3CC3)CC4)nc2OCN1c1c(Cl)cccc1Cl] |
| 1.546 | 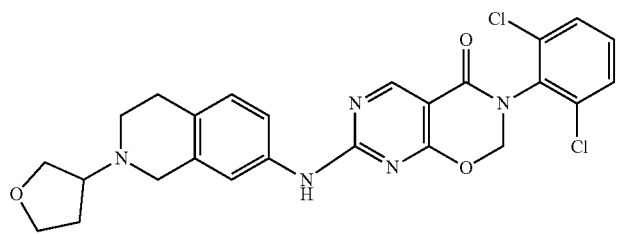 [SMILES: O=C1c2cnc(Nc3ccc4c(c3)CN(C3CCOC3)CC4)nc2OCN1c1c(Cl)cccc1Cl] |
| 1.547 | 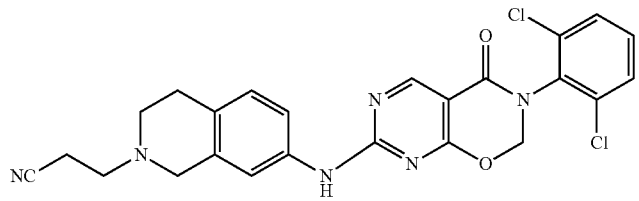 [SMILES: N#CCCN1CCc2ccc(Nc3ncc4c(n3)OCN(c3c(Cl)cccc3Cl)C4=O)cc2C1] |
| 1.548 | 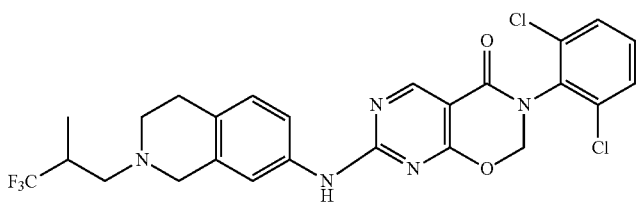 [SMILES: CC(CN1CCc2ccc(Nc3ncc4c(n3)OCN(c3c(Cl)cccc3Cl)C4=O)cc2C1)C(F)(F)F] |
| 1.549 | 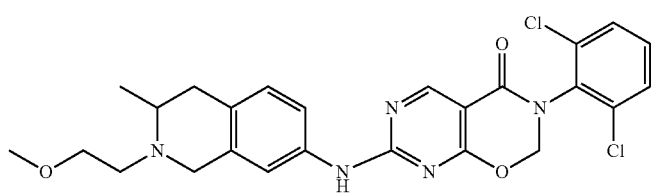 [SMILES: COCCN1Cc2cc(Nc3ncc4c(n3)OCN(c3c(Cl)cccc3Cl)C4=O)ccc2CC1C] |
| 1.550 | 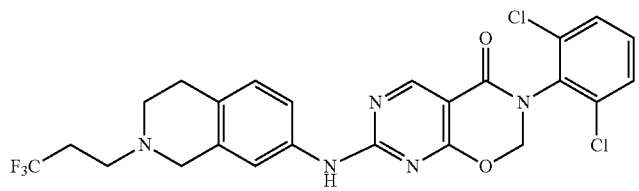 [SMILES: O=C1c2cnc(Nc3ccc4c(c3)CN(CCC(F)(F)F)CC4)nc2OCN1c1c(Cl)cccc1Cl] |

TABLE 1-continued

| Compound No. | Structure |
|---|---|
| 1.551 | 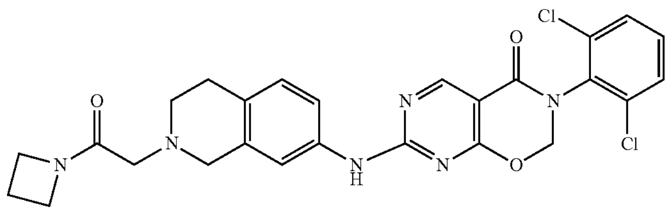 [SMILES: O=C(CN1CCc2ccc(Nc3ncc4c(n3)OCN(c3c(Cl)cccc3Cl)C4=O)cc2C1)N1CCC1] |
| 1.552 | 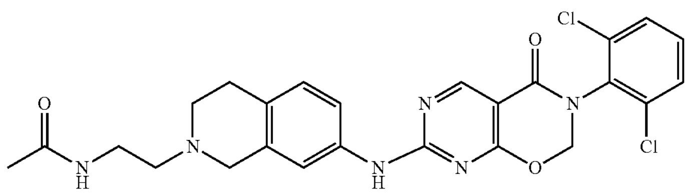 [SMILES: CC(=O)NCCN1CCc2ccc(Nc3ncc4c(n3)OCN(c3c(Cl)cccc3Cl)C4=O)cc2C1] |
| 1.553 | 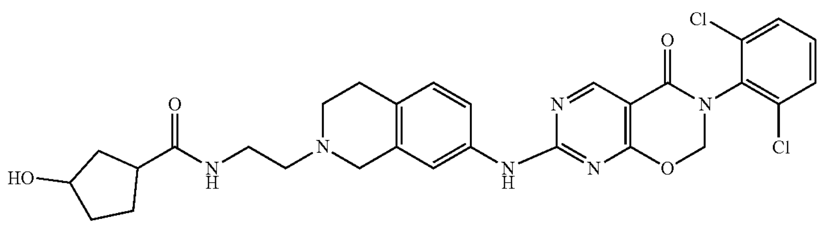 [SMILES: O=C(NCCN1CCc2ccc(Nc3ncc4c(n3)OCN(c3c(Cl)cccc3Cl)C4=O)cc2C1)C1CCC(O)C1] |
| 1.554 | 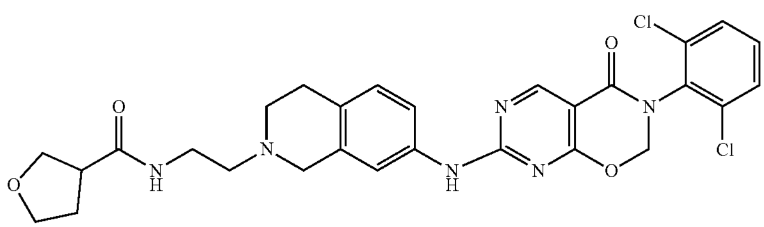 [SMILES: O=C(NCCN1CCc2ccc(Nc3ncc4c(n3)OCN(c3c(Cl)cccc3Cl)C4=O)cc2C1)C1CCOC1] |
| 1.555 | 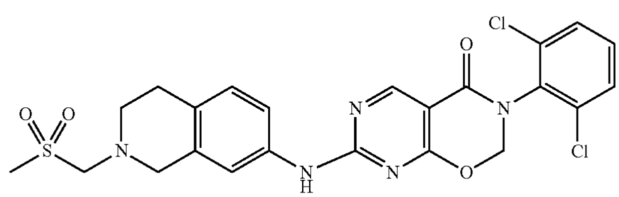 [SMILES: CS(=O)(=O)CN1CCc2ccc(Nc3ncc4c(n3)OCN(c3c(Cl)cccc3Cl)C4=O)cc2C1] |
| 1.556 | 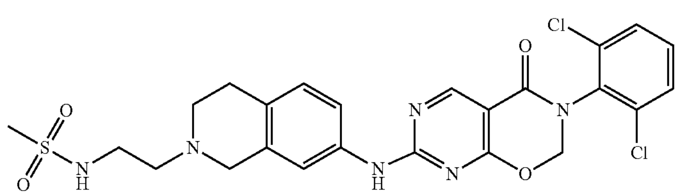 [SMILES: CS(=O)(=O)NCCN1CCc2ccc(Nc3ncc4c(n3)OCN(c3c(Cl)cccc3Cl)C4=O)cc2C1] |
| 1.557 | 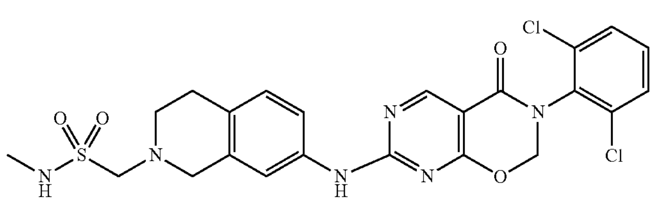 [SMILES: CNS(=O)(=O)CN1CCc2ccc(Nc3ncc4c(n3)OCN(c3c(Cl)cccc3Cl)C4=O)cc2C1] |

TABLE 1-continued

| Compound No. | Structure |
|---|---|
| 1.558 | 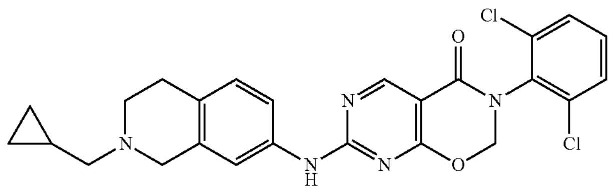 [SMILES: O=C1c2cnc(Nc3ccc4c(c3)CN(CC3CC3)CC4)nc2OCN1c1c(Cl)cccc1Cl] |
| 1.559 | 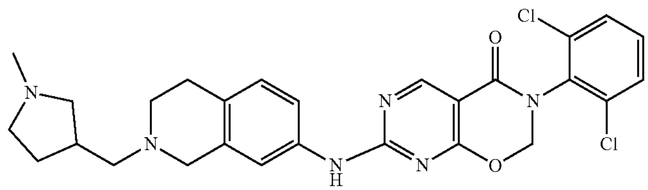 [SMILES: CN1CCC(CN2CCc3ccc(Nc4ncc5c(n4)OCN(c4c(Cl)cccc4Cl)C5=O)cc3C2)C1] |
| 1.560 | 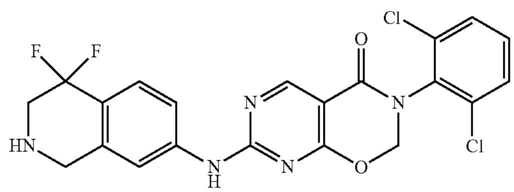 [SMILES: O=C1c2cnc(Nc3ccc4c(c3)CNCC4(F)F)nc2OCN1c1c(Cl)cccc1Cl] |
| 1.561 | 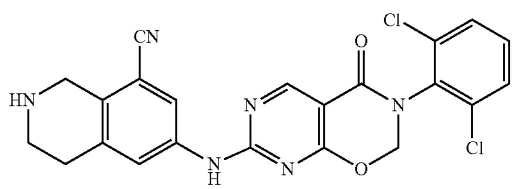 [SMILES: N#Cc1cc(Nc2ncc3c(n2)OCN(c2c(Cl)cccc2Cl)C3=O)cc2c1CNCC2] |
| 1.562 | 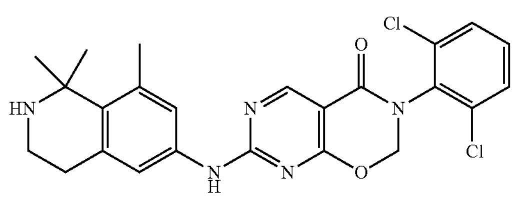 [SMILES: Cc1cc(Nc2ncc3c(n2)OCN(c2c(Cl)cccc2Cl)C3=O)cc2c1C(C)(C)NCC2] |
| 1.563 | 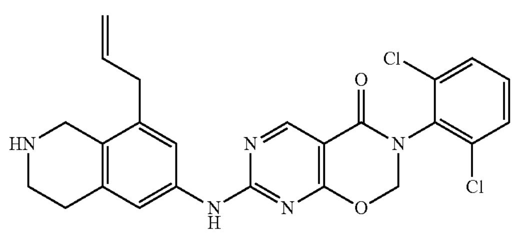 [SMILES: C=CCc1cc(Nc2ncc3c(n2)OCN(c2c(Cl)cccc2Cl)C3=O)cc2c1CNCC2] |
| 1.564 | 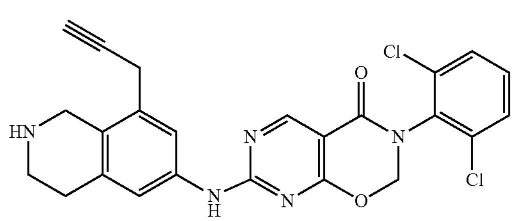 [SMILES: C#CCc1cc(Nc2ncc3c(n2)OCN(c2c(Cl)cccc2Cl)C3=O)cc2c1CNCC2] |

US 10,807,994 B2
TABLE 1-continued
| Compound No. | Structure |
|---|---|
| 1.565 | 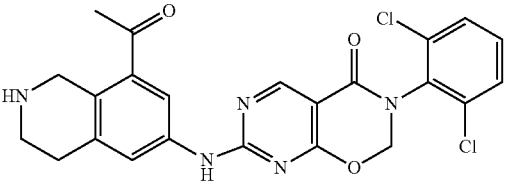 [SMILES: CC(=O)c1cc(Nc2ncc3c(n2)OCN(c2c(Cl)cccc2Cl)C3=O)cc2c1CNCC2] |
| 1.566 | 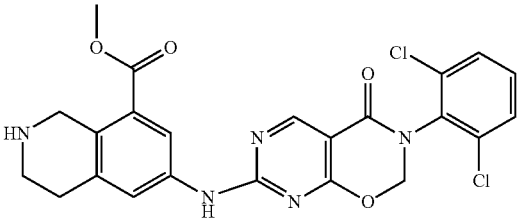 [SMILES: COC(=O)c1cc(Nc2ncc3c(n2)OCN(c2c(Cl)cccc2Cl)C3=O)cc2c1CNCC2] |
| 1.567 | 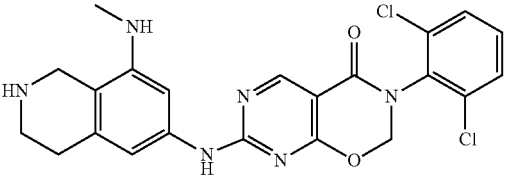 [SMILES: CNc1cc(Nc2ncc3c(n2)OCN(c2c(Cl)cccc2Cl)C3=O)cc2c1CNCC2] |
| 1.568 | 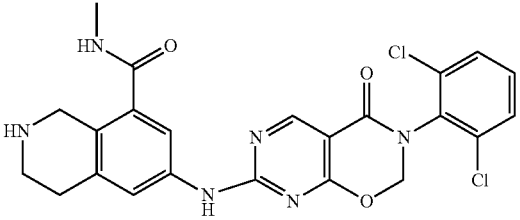 [SMILES: CNC(=O)c1cc(Nc2ncc3c(n2)OCN(c2c(Cl)cccc2Cl)C3=O)cc2c1CNCC2] |
| 1.569 | 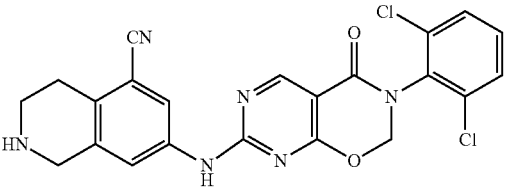 [SMILES: N#Cc1cc(Nc2ncc3c(n2)OCN(c2c(Cl)cccc2Cl)C3=O)cc2c1CCNC2] |
| 1.570 | 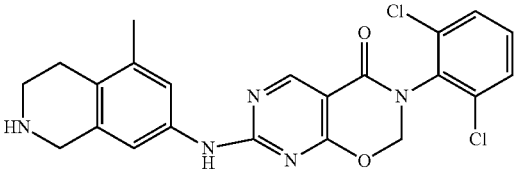 [SMILES: Cc1cc(Nc2ncc3c(n2)OCN(c2c(Cl)cccc2Cl)C3=O)cc2c1CCNC2] |
| 1.571 | 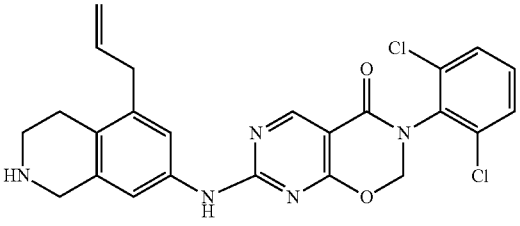 |

US 10,807,994 B2
341                                                                                              342
TABLE 1-continued
| Compound No. | Structure |
|---|---|
| 1.572 | 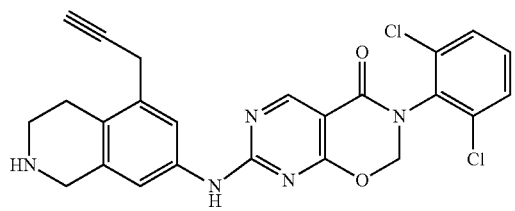 [SMILES: C#CCc1cc(Nc2ncc3c(n2)OCN(c2c(Cl)cccc2Cl)C3=O)cc2c1CCNC2] |
| 1.573 | 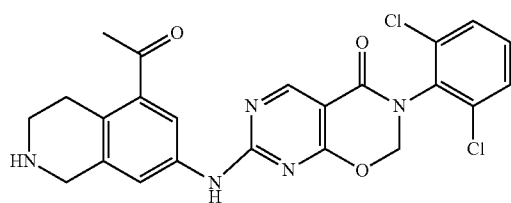 [SMILES: CC(=O)c1cc(Nc2ncc3c(n2)OCN(c2c(Cl)cccc2Cl)C3=O)cc2c1CCNC2] |
| 1.574 | 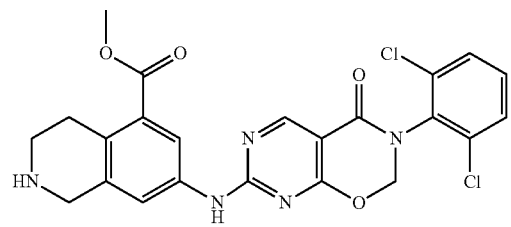 [SMILES: COC(=O)c1cc(Nc2ncc3c(n2)OCN(c2c(Cl)cccc2Cl)C3=O)cc2c1CCNC2] |
| 1.575 | 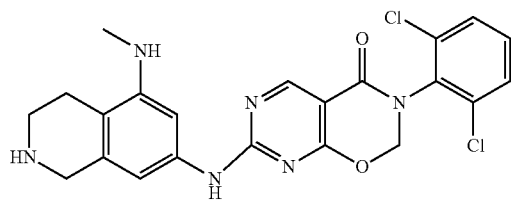 [SMILES: CNc1cc(Nc2ncc3c(n2)OCN(c2c(Cl)cccc2Cl)C3=O)cc2c1CCNC2] |
| 1.576 | 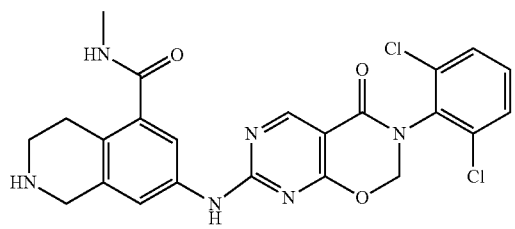 [SMILES: CNC(=O)c1cc(Nc2ncc3c(n2)OCN(c2c(Cl)cccc2Cl)C3=O)cc2c1CCNC2] |
| 1.577 | 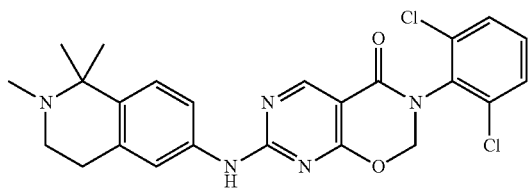 |
| 1.578 | 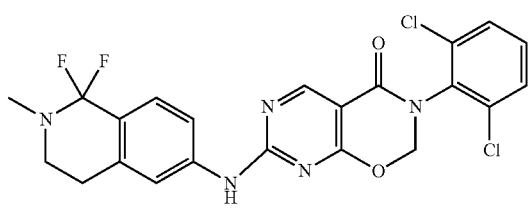 [SMILES: CN1CCc2cc(Nc3ncc4c(n3)OCN(c3c(Cl)cccc3Cl)C4=O)ccc2C1(F)F] |

TABLE 1-continued

| Compound No. | Structure |
|---|---|
| 1.579 | 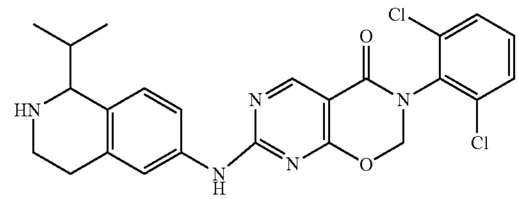 [SMILES: CC(C)C1NCCc2cc(Nc3ncc4c(n3)OCN(c3c(Cl)cccc3Cl)C4=O)ccc21] |
| 1.580 | 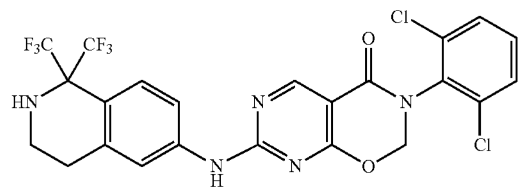 [SMILES: O=C1c2cnc(Nc3ccc4c(c3)CCNC4(C(F)(F)F)C(F)(F)F)nc2OCN1c1c(Cl)cccc1Cl] |
| 1.581 | 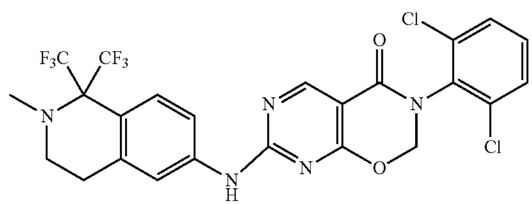 [SMILES: CN1CCc2cc(Nc3ncc4c(n3)OCN(c3c(Cl)cccc3Cl)C4=O)ccc2C1(C(F)(F)F)C(F)(F)F] |
| 1.582 | 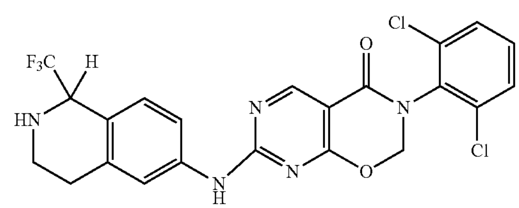 [SMILES: O=C1c2cnc(Nc3ccc4c(c3)CCNC4C(F)(F)F)nc2OCN1c1c(Cl)cccc1Cl] |
| 1.583 | 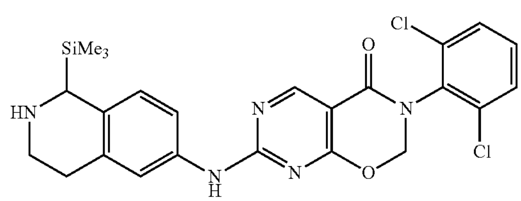 [SMILES: C[Si](C)(C)C1NCCc2cc(Nc3ncc4c(n3)OCN(c3c(Cl)cccc3Cl)C4=O)ccc21] |
| 1.584 | 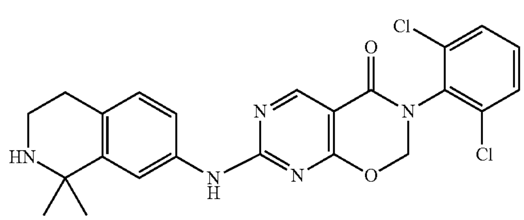 [SMILES: CC1(C)NCCc2ccc(Nc3ncc4c(n3)OCN(c3c(Cl)cccc3Cl)C4=O)cc21] |
| 1.585 | 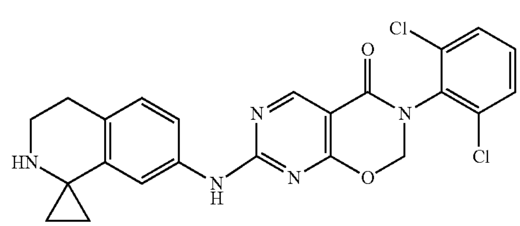 [SMILES: O=C1c2cnc(Nc3ccc4c(c3)C3(CC3)NCC4)nc2OCN1c1c(Cl)cccc1Cl] |

TABLE 1-continued

| Compound No. | Structure |
|---|---|
| 1.586 | 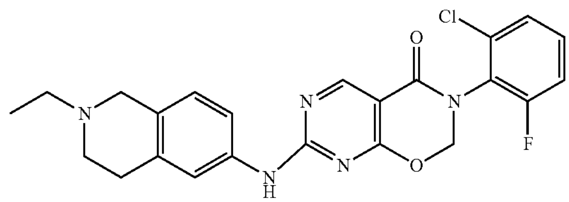 [SMILES: CCN1CCc2cc(Nc3ncc4c(n3)OCN(c3c(F)cccc3Cl)C4=O)ccc2C1] |
| 1.587 | 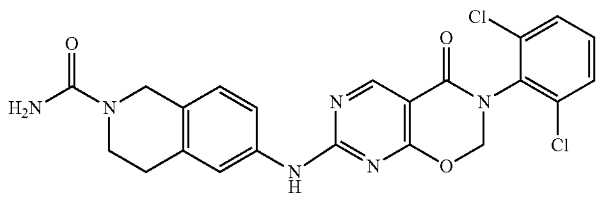 [SMILES: NC(=O)N1CCc2cc(Nc3ncc4c(n3)OCN(c3c(Cl)cccc3Cl)C4=O)ccc2C1] |
| 1.588 | 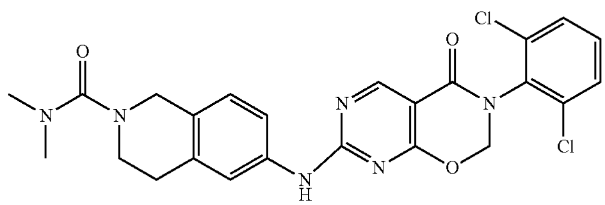 [SMILES: CN(C)C(=O)N1CCc2cc(Nc3ncc4c(n3)OCN(c3c(Cl)cccc3Cl)C4=O)ccc2C1] |
| 1.589 | 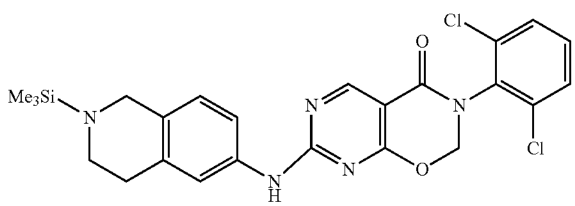 [SMILES: C[Si](C)(C)N1CCc2cc(Nc3ncc4c(n3)OCN(c3c(Cl)cccc3Cl)C4=O)ccc2C1] |
| 1.590 | 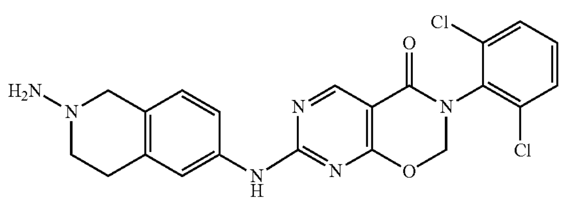 |
| 1.591 | 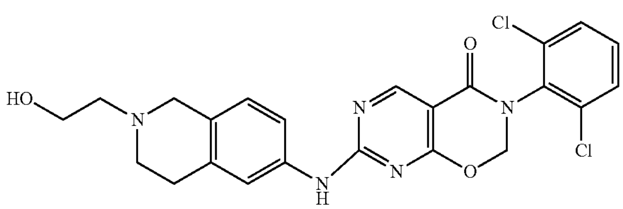 |
| 1.592 | 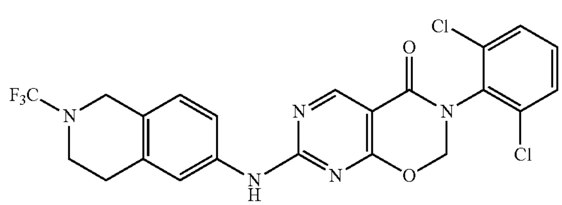 [SMILES: O=C1c2cnc(Nc3ccc4c(c3)CCN(C(F)(F)F)C4)nc2OCN1c1c(Cl)cccc1Cl] |

TABLE 1-continued

| Compound No. | Structure |
|---|---|
| 1.593 | 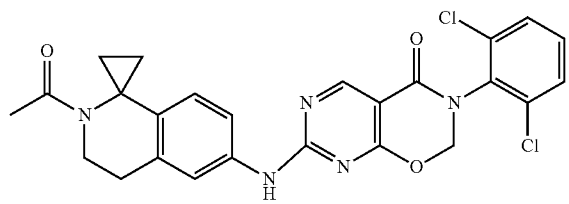 [SMILES: CC(=O)N1CCc2cc(Nc3ncc4c(n3)OCN(c3c(Cl)cccc3Cl)C4=O)ccc2C12CC2] |
| 1.594 | 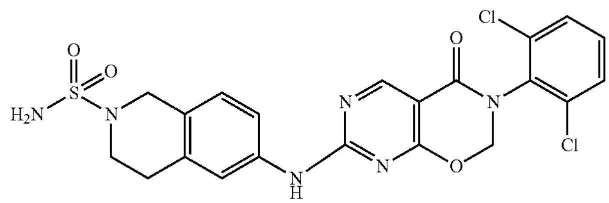 [SMILES: NS(=O)(=O)N1CCc2cc(Nc3ncc4c(n3)OCN(c3c(Cl)cccc3Cl)C4=O)ccc2C1] |
| 1.595 | 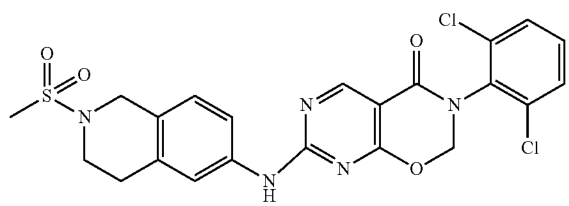 [SMILES: CS(=O)(=O)N1CCc2cc(Nc3ncc4c(n3)OCN(c3c(Cl)cccc3Cl)C4=O)ccc2C1] |
| 1.596 | 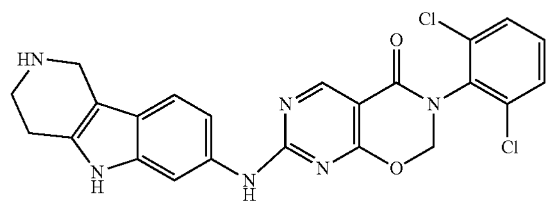 [SMILES: O=C1c2cnc(Nc3ccc4c5c([nH]c4c3)CCNC5)nc2OCN1c1c(Cl)cccc1Cl] |
| 1.597 | 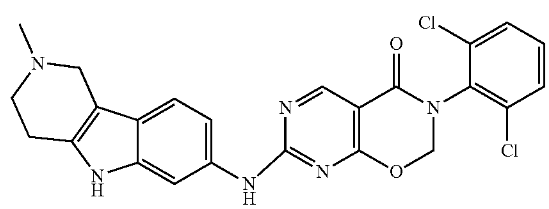 [SMILES: CN1CCc2[nH]c3cc(Nc4ncc5c(n4)OCN(c4c(Cl)cccc4Cl)C5=O)ccc3c2C1] |
| 1.598 | 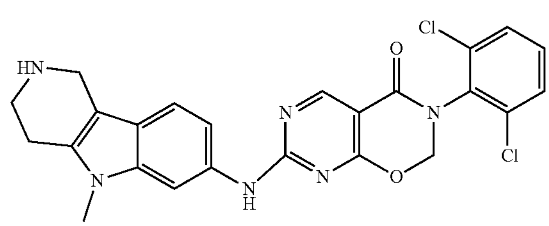 [SMILES: Cn1c2c(c3ccc(Nc4ncc5c(n4)OCN(c4c(Cl)cccc4Cl)C5=O)cc31)CNCC2] |
| 1.599 | 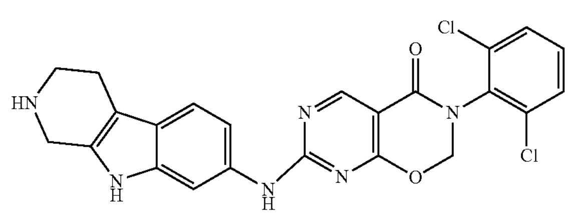 [SMILES: O=C1c2cnc(Nc3ccc4c5c([nH]c4c3)CNCC5)nc2OCN1c1c(Cl)cccc1Cl] |

TABLE 1-continued

| Compound No. | Structure |
| --- | --- |
| 1.600 | 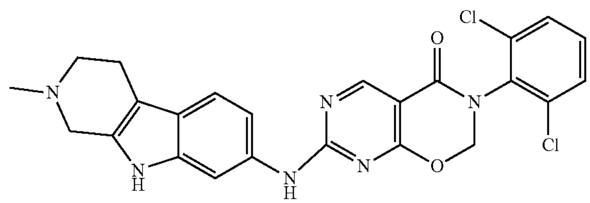 [SMILES: CN1CCc2c([nH]c3cc(Nc4ncc5c(n4)OCN(c4c(Cl)cccc4Cl)C5=O)ccc23)C1] |
| 1.601 | 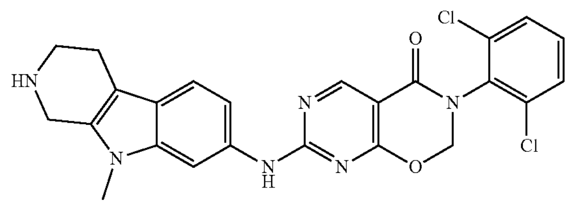 [SMILES: Cn1c2c(c3ccc(Nc4ncc5c(n4)OCN(c4c(Cl)cccc4Cl)C5=O)cc31)CCNC2] |
| 1.602 | 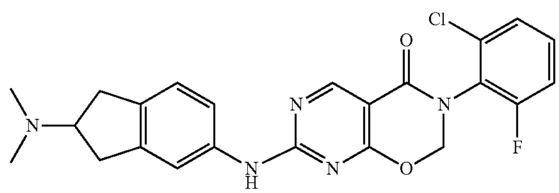 [SMILES: CN(C)C1Cc2ccc(Nc3ncc4c(n3)OCN(c3c(F)cccc3Cl)C4=O)cc2C1] |
| 1.603 | 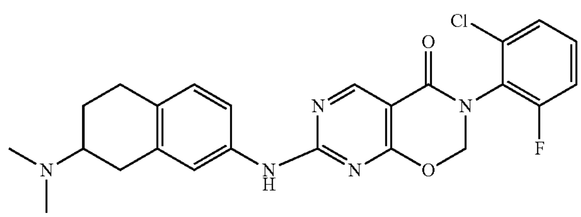 [SMILES: CN(C)C1CCc2ccc(Nc3ncc4c(n3)OCN(c3c(F)cccc3Cl)C4=O)cc2C1] |
| 1.604 | 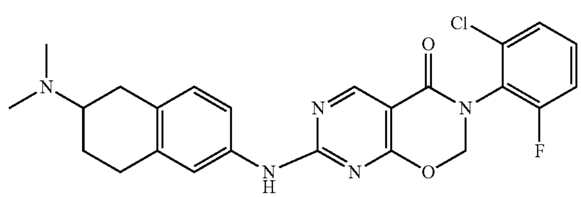 [SMILES: CN(C)C1CCc2cc(Nc3ncc4c(n3)OCN(c3c(F)cccc3Cl)C4=O)ccc2C1] |
| 1.605 | 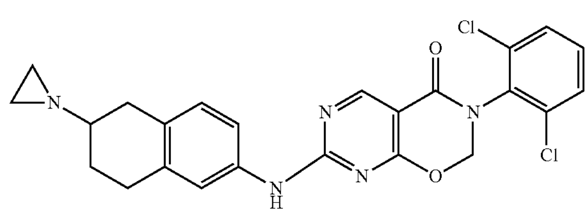 [SMILES: O=C1c2cnc(Nc3ccc4c(c3)CCC(N3CC3)C4)nc2OCN1c1c(Cl)cccc1Cl] |
| 1.606 | 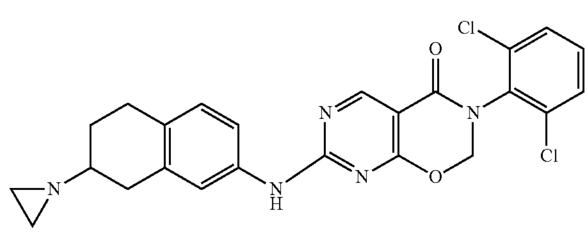 [SMILES: O=C1c2cnc(Nc3ccc4c(c3)CC(N3CC3)CC4)nc2OCN1c1c(Cl)cccc1Cl] |

US 10,807,994 B2
TABLE 1-continued
| Compound No. | Structure |
|---|---|
| 1.607 | 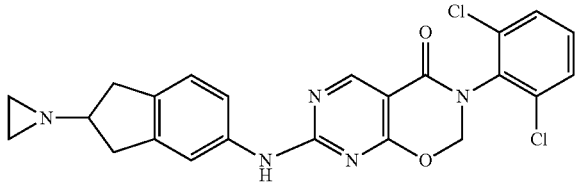 [SMILES: O=C1c2cnc(Nc3ccc4c(c3)CC(N3CC3)C4)nc2OCN1c1c(Cl)cccc1Cl] |
| 1.608 | 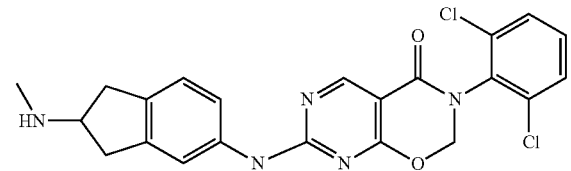 |
| 1.609 | 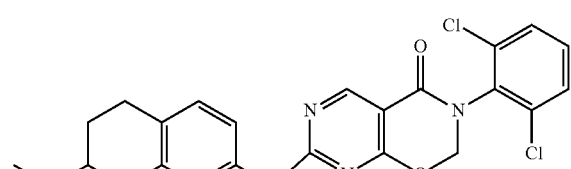 |
| 1.610 | 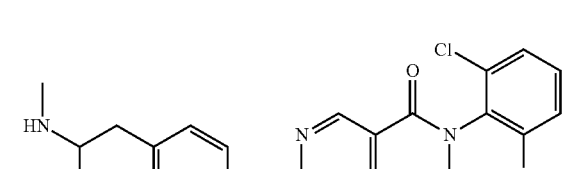 |
| 1.611 | 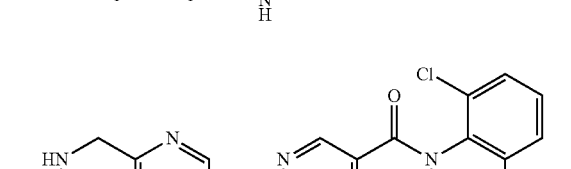 |
| 1.612 | 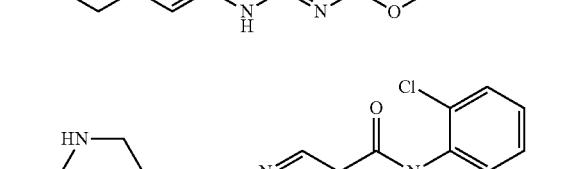 |
| 1.613 | 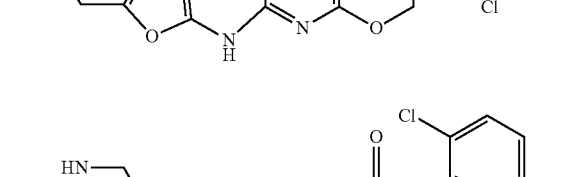 |

TABLE 1-continued

| Compound No. | Structure |
|---|---|
| 1.614 | 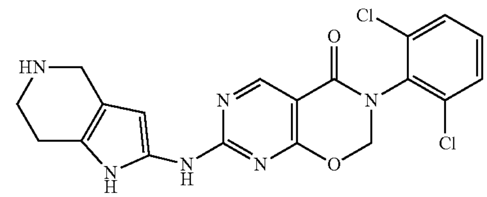 [SMILES: O=C1c2cnc(Nc3cc4c([nH]3)CCNC4)nc2OCN1c1c(Cl)cccc1Cl] |
| 1.615 | 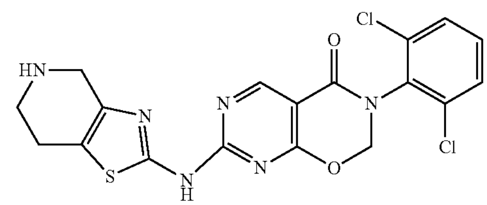 |
| 1.616 | 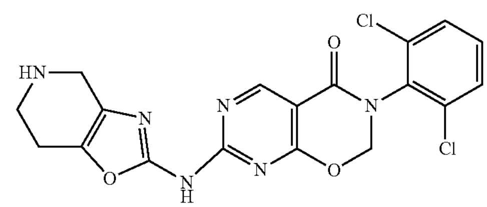 [SMILES: O=C1c2cnc(Nc3nc4c(o3)CCNC4)nc2OCN1c1c(Cl)cccc1Cl] |
| 1.617 | 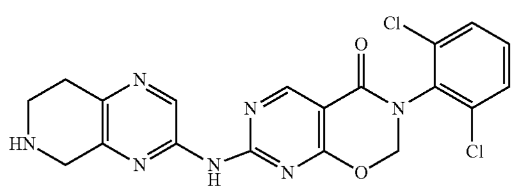 [SMILES: O=C1c2cnc(Nc3cnc4c(n3)CNCC4)nc2OCN1c1c(Cl)cccc1Cl] |
| 1.618 | 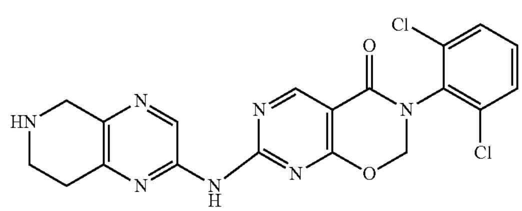 [SMILES: O=C1c2cnc(Nc3cnc4c(n3)CCNC4)nc2OCN1c1c(Cl)cccc1Cl] |
| 1.619 | 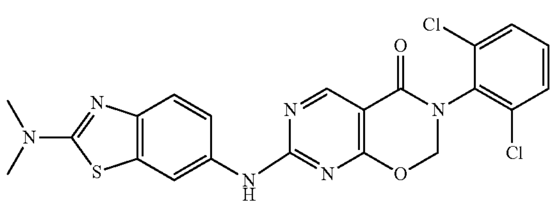 [SMILES: CN(C)c1nc2ccc(Nc3ncc4c(n3)OCN(c3c(Cl)cccc3Cl)C4=O)cc2s1] |
| 1.620 | 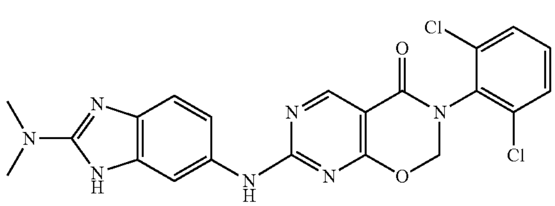 [SMILES: CN(C)c1nc2ccc(Nc3ncc4c(n3)OCN(c3c(Cl)cccc3Cl)C4=O)cc2[nH]1] |

TABLE 1-continued

| Compound No. | Structure |
|---|---|
| 1.621 | 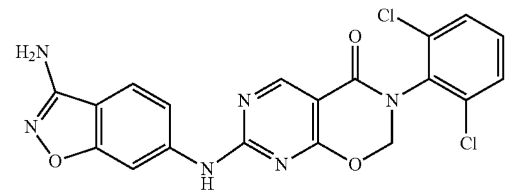 [SMILES: Nc1noc2cc(Nc3ncc4c(n3)OCN(c3c(Cl)cccc3Cl)C4=O)ccc12] |
| 1.622 | 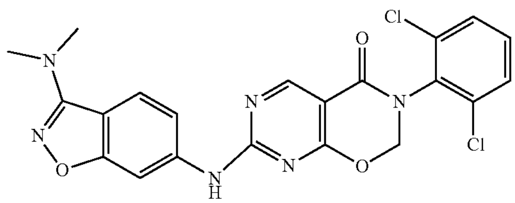 [SMILES: CN(C)c1noc2cc(Nc3ncc4c(n3)OCN(c3c(Cl)cccc3Cl)C4=O)ccc12] |
| 1.623 | 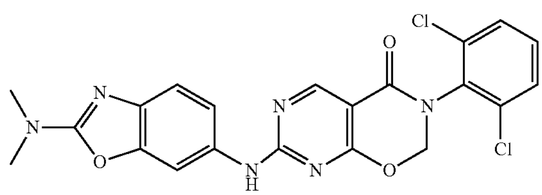 [SMILES: CN(C)c1nc2ccc(Nc3ncc4c(n3)OCN(c3c(Cl)cccc3Cl)C4=O)cc2o1] |
| 1.624 | 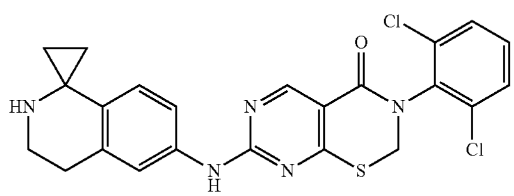 [SMILES: O=C1c2cnc(Nc3ccc4c(c3)CCNC43CC3)nc2SCN1c1c(Cl)cccc1Cl] |
| 1.625 | 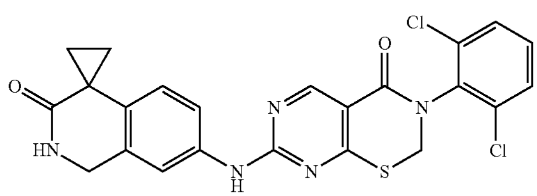 [SMILES: O=C1c2cnc(Nc3ccc4c(c3)CNC(=O)C43CC3)nc2SCN1c1c(Cl)cccc1Cl] |
| 1.626 | 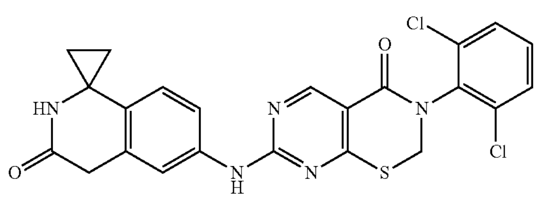 [SMILES: O=C1Cc2cc(Nc3ncc4c(n3)SCN(c3c(Cl)cccc3Cl)C4=O)ccc2C2(CC2)N1] |
| 1.627 | 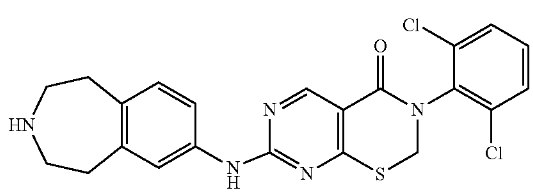 [SMILES: O=C1c2cnc(Nc3ccc4c(c3)CCNCC4)nc2SCN1c1c(Cl)cccc1Cl] |

TABLE 1-continued

| Compound No. | Structure |
|---|---|
| 1.628 | 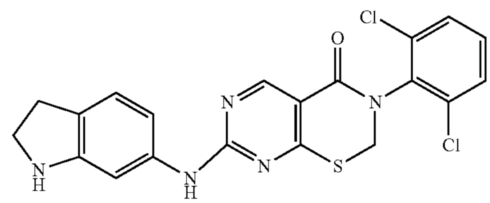 |
| 1.629 | 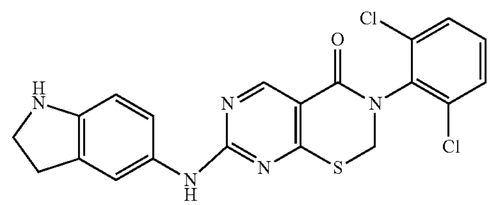 |
| 1.630 | 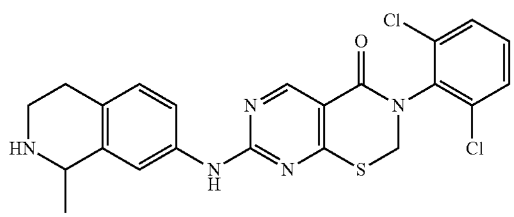 [SMILES: CC1NCCc2ccc(Nc3ncc4c(n3)SCN(c3c(Cl)cccc3Cl)C4=O)cc21] |
| 1.631 | 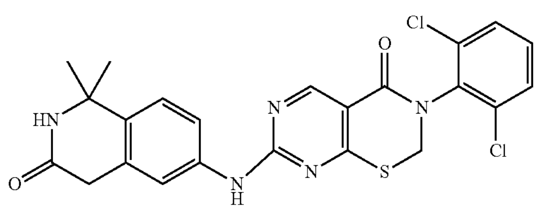 [SMILES: CC1(C)NC(=O)Cc2cc(Nc3ncc4c(n3)SCN(c3c(Cl)cccc3Cl)C4=O)ccc21] |
| 1.632 | 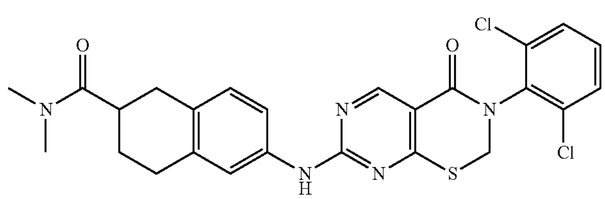 |
| 1.633 | 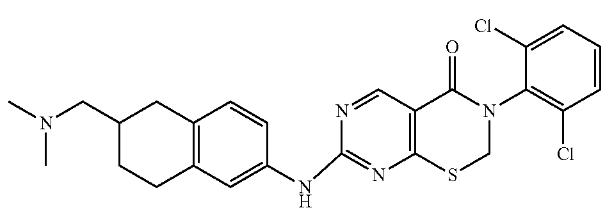 |
| 1.634 | 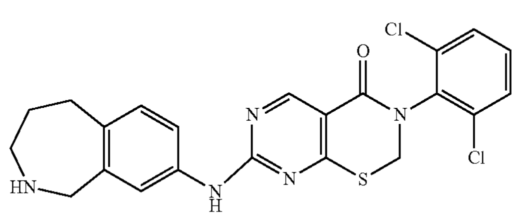 [SMILES: O=C1c2cnc(Nc3ccc4c(c3)CNCCC4)nc2SCN1c1c(Cl)cccc1Cl] |

TABLE 1-continued

| Compound No. | Structure |
|---|---|
| 1.635 | 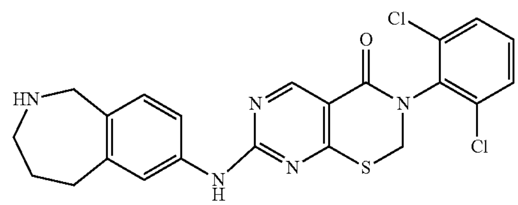 |
| 1.636 | 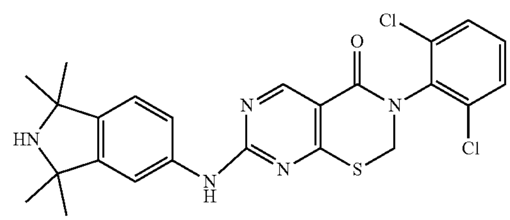 |
| 1.637 | 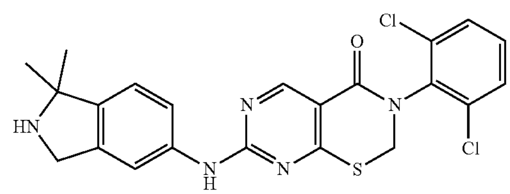 |
| 1.638 | 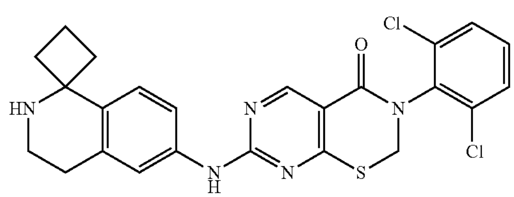 [SMILES: O=C1c2cnc(Nc3ccc4c(c3)CCNC43CCC3)nc2SCN1c1c(Cl)cccc1Cl] |
| 1.639 | 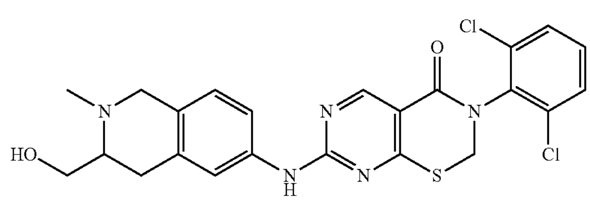 |
| 1.640 | 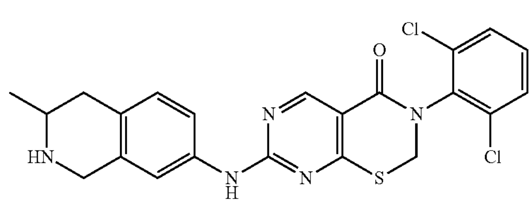 [SMILES: CC1Cc2ccc(Nc3ncc4c(n3)SCN(c3c(Cl)cccc3Cl)C4=O)cc2CN1] |
| 1.641 | 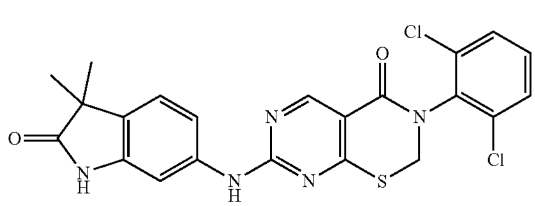 [SMILES: CC1(C)C(=O)Nc2cc(Nc3ncc4c(n3)SCN(c3c(Cl)cccc3Cl)C4=O)ccc21] |

TABLE 1-continued

| Compound No. | Structure |
|---|---|
| 1.642 | 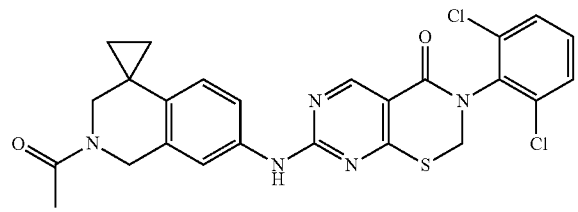 [SMILES: CC(=O)N1Cc2cc(Nc3ncc4c(n3)SCN(c3c(Cl)cccc3Cl)C4=O)ccc2C2(CC2)C1] |
| 1.643 | 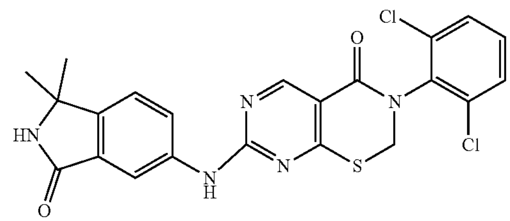 [SMILES: CC1(C)NC(=O)c2cc(Nc3ncc4c(n3)SCN(c3c(Cl)cccc3Cl)C4=O)ccc21] |
| 1.644 | 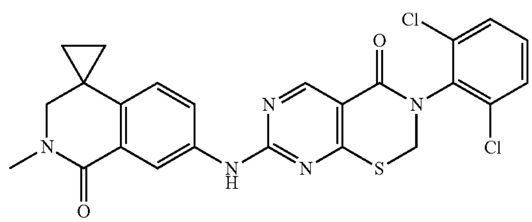 [SMILES: CN1CC2(CC2)c2ccc(Nc3ncc4c(n3)SCN(c3c(Cl)cccc3Cl)C4=O)cc2C1=O] |
| 1.645 | 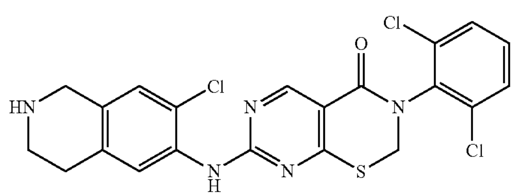 [SMILES: O=C1c2cnc(Nc3cc4c(cc3Cl)CNCC4)nc2SCN1c1c(Cl)cccc1Cl] |
| 1.646 | 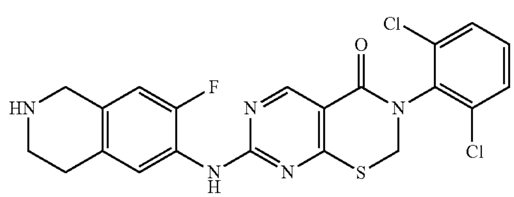 [SMILES: O=C1c2cnc(Nc3cc4c(cc3F)CNCC4)nc2SCN1c1c(Cl)cccc1Cl] |
| 1.647 | 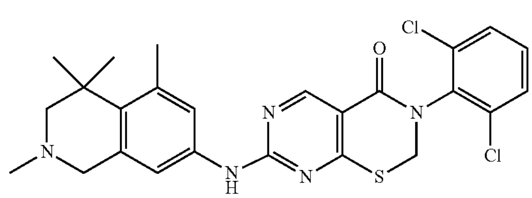 [SMILES: Cc1cc(Nc2ncc3c(n2)SCN(c2c(Cl)cccc2Cl)C3=O)cc2c1C(C)(C)CN(C)C2] |
| 1.648 | 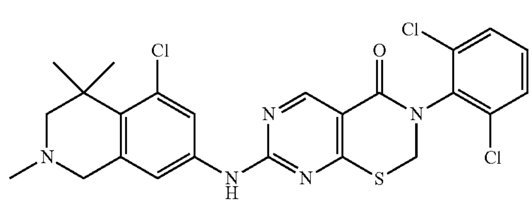 [SMILES: CN1Cc2cc(Nc3ncc4c(n3)SCN(c3c(Cl)cccc3Cl)C4=O)cc(Cl)c2C(C)(C)C1] |

TABLE 1-continued

| Compound No. | Structure |
|---|---|
| 1.649 | 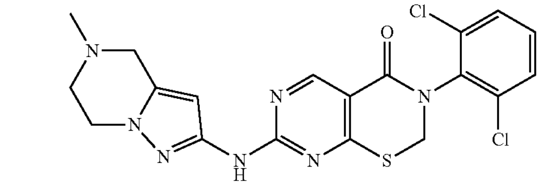 [SMILES: CN1CCn2nc(Nc3ncc4c(n3)SCN(c3c(Cl)cccc3Cl)C4=O)cc2C1] |
| 1.650 | 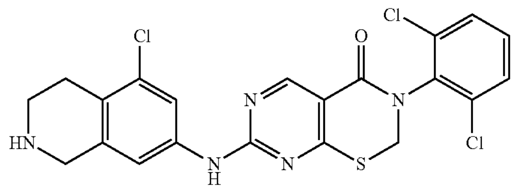 [SMILES: O=C1c2cnc(Nc3cc(Cl)c4c(c3)CNCC4)nc2SCN1c1c(Cl)cccc1Cl] |
| 1.651 | 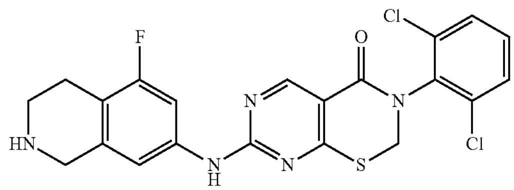 [SMILES: O=C1c2cnc(Nc3cc(F)c4c(c3)CNCC4)nc2SCN1c1c(Cl)cccc1Cl] |
| 1.652 | 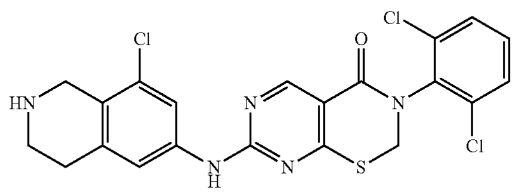 [SMILES: O=C1c2cnc(Nc3cc(Cl)c4c(c3)CCNC4)nc2SCN1c1c(Cl)cccc1Cl] |
| 1.653 | 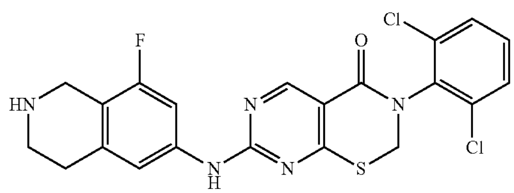 [SMILES: O=C1c2cnc(Nc3cc(F)c4c(c3)CCNC4)nc2SCN1c1c(Cl)cccc1Cl] |
| 1.654 | 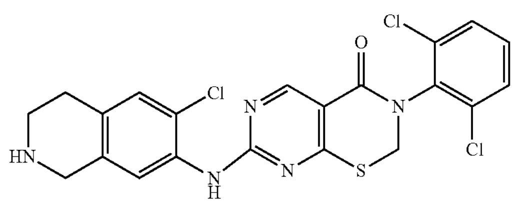 [SMILES: O=C1c2cnc(Nc3cc4c(cc3Cl)CCNC4)nc2SCN1c1c(Cl)cccc1Cl] |
| 1.655 | 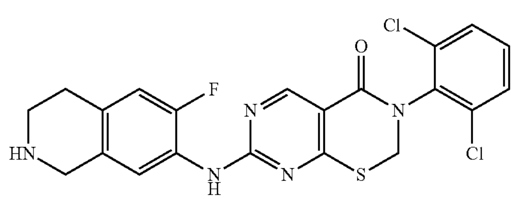 [SMILES: O=C1c2cnc(Nc3cc4c(cc3F)CCNC4)nc2SCN1c1c(Cl)cccc1Cl] |
| 1.656 | 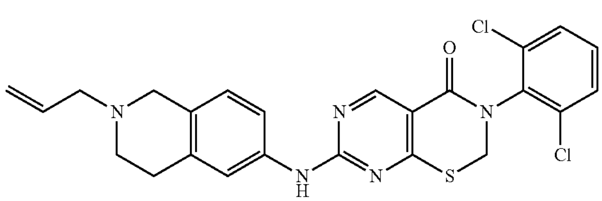 |

TABLE 1-continued

| Compound No. | Structure |
|---|---|
| 1.657 | 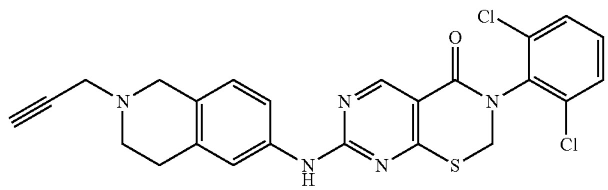 [SMILES: C#CCN1CCc2cc(Nc3ncc4c(n3)SCN(c3c(Cl)cccc3Cl)C4=O)ccc2C1] |
| 1.658 | 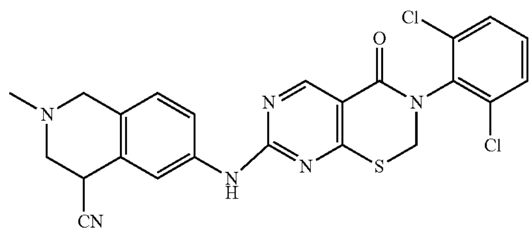 [SMILES: CN1Cc2ccc(Nc3ncc4c(n3)SCN(c3c(Cl)cccc3Cl)C4=O)cc2C(C#N)C1] |
| 1.659 | 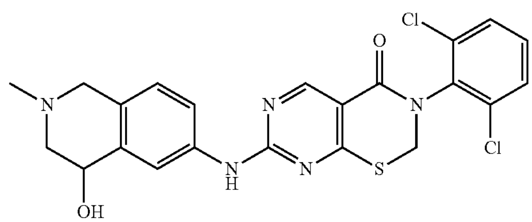 [SMILES: CN1Cc2ccc(Nc3ncc4c(n3)SCN(c3c(Cl)cccc3Cl)C4=O)cc2C(O)C1] |
| 1.660 | 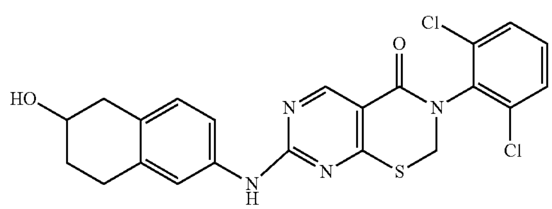 [SMILES: O=C1c2cnc(Nc3ccc4c(c3)CCC(O)C4)nc2SCN1c1c(Cl)cccc1Cl] |
| 1.661 | 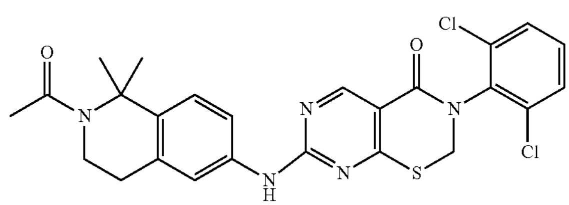 [SMILES: CC(=O)N1CCc2cc(Nc3ncc4c(n3)SCN(c3c(Cl)cccc3Cl)C4=O)ccc2C1(C)C] |
| 1.662 | 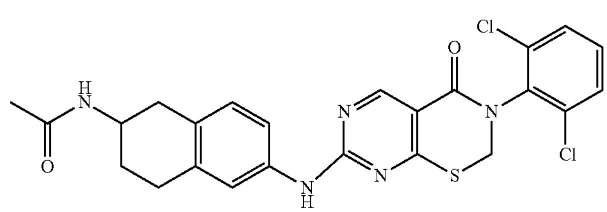 [SMILES: CC(=O)NC1CCc2cc(Nc3ncc4c(n3)SCN(c3c(Cl)cccc3Cl)C4=O)ccc2C1] |
| 1.663 | 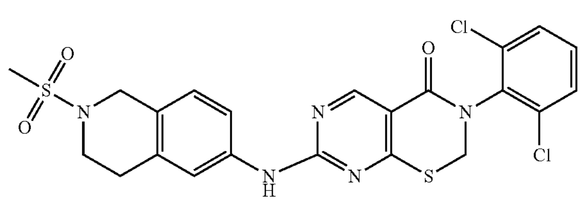 [SMILES: CS(=O)(=O)N1CCc2cc(Nc3ncc4c(n3)SCN(c3c(Cl)cccc3Cl)C4=O)ccc2C1] |

US 10,807,994 B2
TABLE 1-continued
| Compound No. | Structure |
|---|---|
| 1.664 | 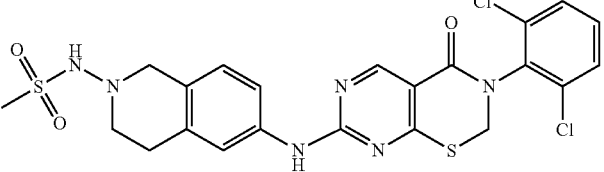 |
| 1.665 | 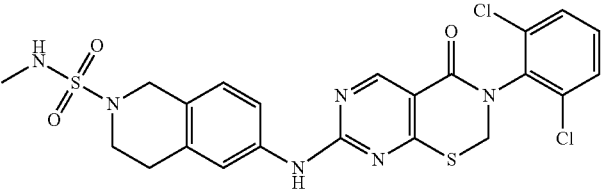 [SMILES: CNS(=O)(=O)N1CCc2cc(Nc3ncc4c(n3)SCN(c3c(Cl)cccc3Cl)C4=O)ccc2C1] |
| 1.666 | 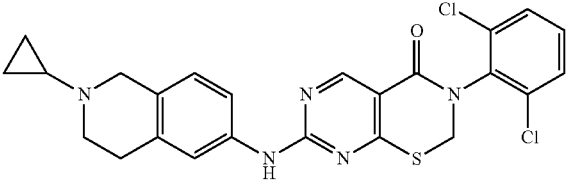 [SMILES: O=C1c2cnc(Nc3ccc4c(c3)CCN(C3CC3)C4)nc2SCN1c1c(Cl)cccc1Cl] |
| 1.667 | 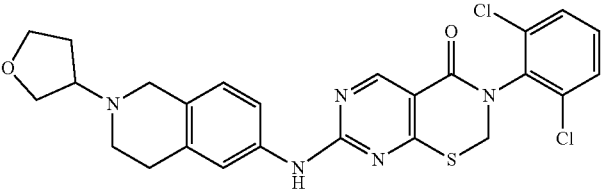 [SMILES: O=C1c2cnc(Nc3ccc4c(c3)CCN(C3CCOC3)C4)nc2SCN1c1c(Cl)cccc1Cl] |
| 1.668 | 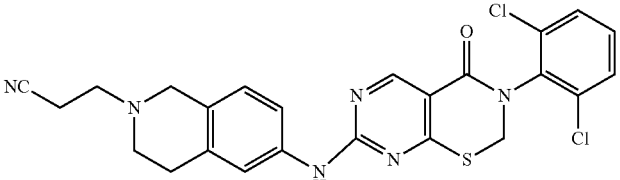 |
| 1.669 | 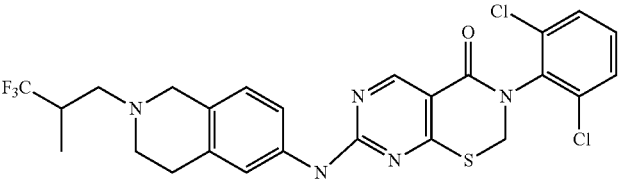 |
| 1.670 | 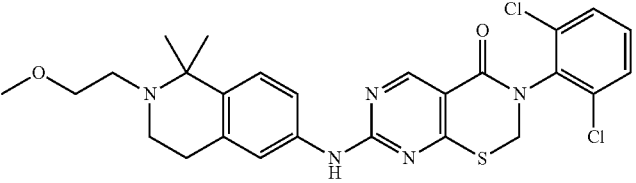 [SMILES: COCCN1CCc2cc(Nc3ncc4c(n3)SCN(c3c(Cl)cccc3Cl)C4=O)ccc2C1(C)C] |

TABLE 1-continued

| Compound No. | Structure |
|---|---|
| 1.671 | 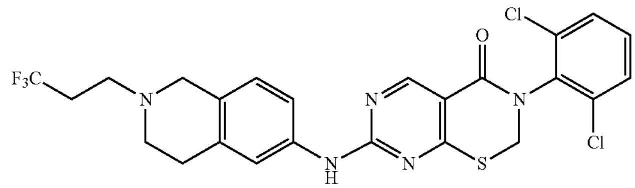 [SMILES: O=C1c2cnc(Nc3ccc4c(c3)CCN(CCC(F)(F)F)C4)nc2SCN1c1c(Cl)cccc1Cl] |
| 1.672 | 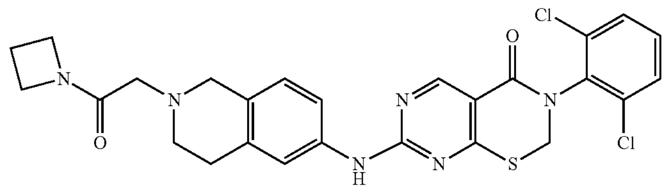 [SMILES: O=C(CN1CCc2cc(Nc3ncc4c(n3)SCN(c3c(Cl)cccc3Cl)C4=O)ccc2C1)N1CCC1] |
| 1.673 | 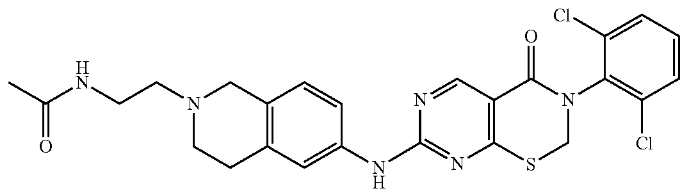 [SMILES: CC(=O)NCCN1CCc2cc(Nc3ncc4c(n3)SCN(c3c(Cl)cccc3Cl)C4=O)ccc2C1] |
| 1.674 | 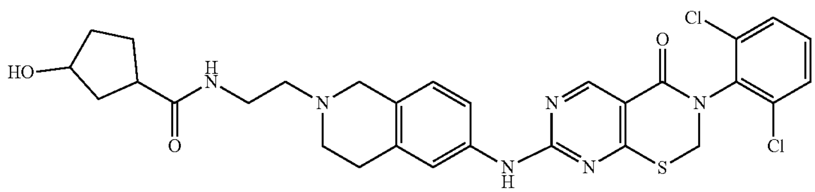 [SMILES: O=C(NCCN1CCc2cc(Nc3ncc4c(n3)SCN(c3c(Cl)cccc3Cl)C4=O)ccc2C1)C1CCC(O)C1] |
| 1.675 | 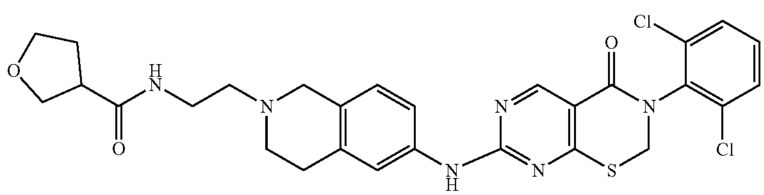 [SMILES: O=C(NCCN1CCc2cc(Nc3ncc4c(n3)SCN(c3c(Cl)cccc3Cl)C4=O)ccc2C1)C1CCOC1] |
| 1.676 | 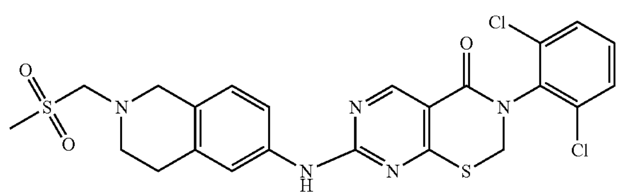 [SMILES: CS(=O)(=O)CN1CCc2cc(Nc3ncc4c(n3)SCN(c3c(Cl)cccc3Cl)C4=O)ccc2C1] |
| 1.677 | 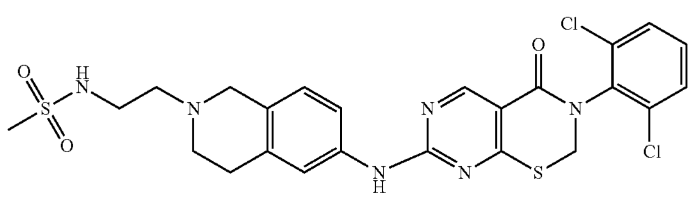 [SMILES: CS(=O)(=O)NCCN1CCc2cc(Nc3ncc4c(n3)SCN(c3c(Cl)cccc3Cl)C4=O)ccc2C1] |
| 1.678 | 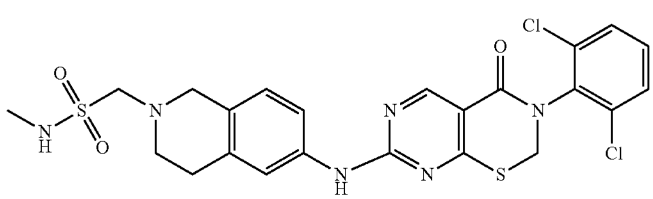 [SMILES: CNS(=O)(=O)CN1CCc2cc(Nc3ncc4c(n3)SCN(c3c(Cl)cccc3Cl)C4=O)ccc2C1] |

TABLE 1-continued
| Compound No. | Structure |
|---|---|
| 1.679 | 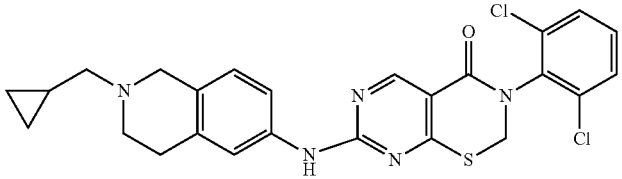 [SMILES: O=C1c2cnc(Nc3ccc4c(c3)CCN(CC3CC3)C4)nc2SCN1c1c(Cl)cccc1Cl] |
| 1.680 | 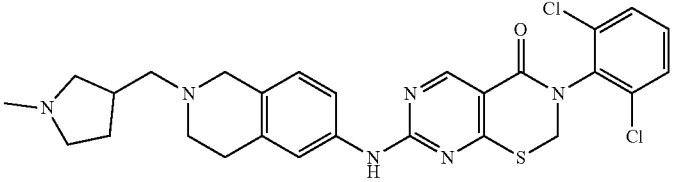 [SMILES: CN1CCC(CN2CCc3cc(Nc4ncc5c(n4)SCN(c4c(Cl)cccc4Cl)C5=O)ccc3C2)C1] |
| 1.681 | 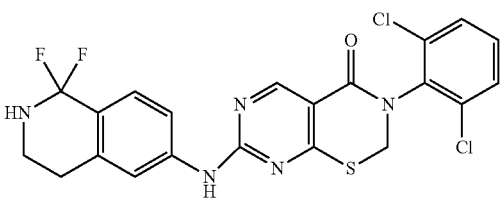 [SMILES: O=C1c2cnc(Nc3ccc4c(c3)CCNC4(F)F)nc2SCN1c1c(Cl)cccc1Cl] |
| 1.682 | 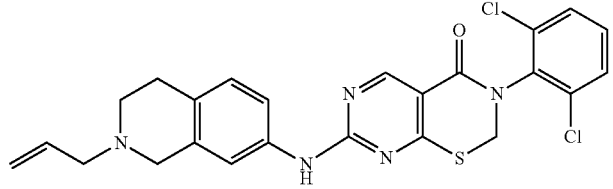 [SMILES: C=CCN1CCc2ccc(Nc3ncc4c(n3)SCN(c3c(Cl)cccc3Cl)C4=O)cc2C1] |
| 1.683 | 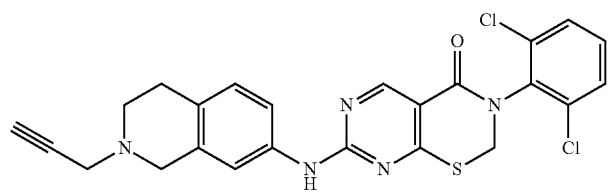 [SMILES: C#CCN1CCc2ccc(Nc3ncc4c(n3)SCN(c3c(Cl)cccc3Cl)C4=O)cc2C1] |
| 1.684 | 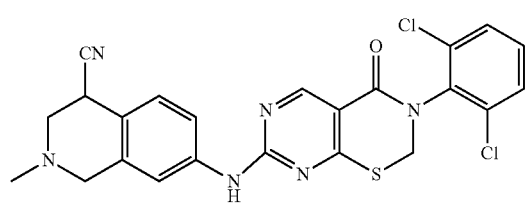 [SMILES: CN1Cc2cc(Nc3ncc4c(n3)SCN(c3c(Cl)cccc3Cl)C4=O)ccc2C(C#N)C1] |
| 1.685 | 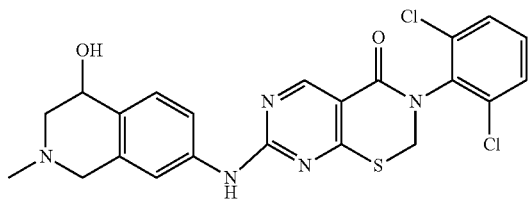 |

TABLE 1-continued
| Compound No. | Structure |
|---|---|
| 1.686 | 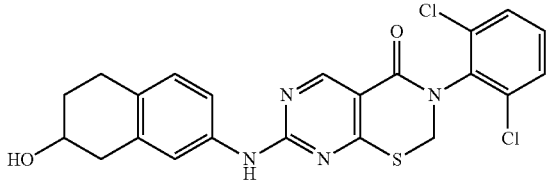 [SMILES: O=C1c2cnc(Nc3ccc4c(c3)CC(O)CC4)nc2SCN1c1c(Cl)cccc1Cl] |
| 1.687 | 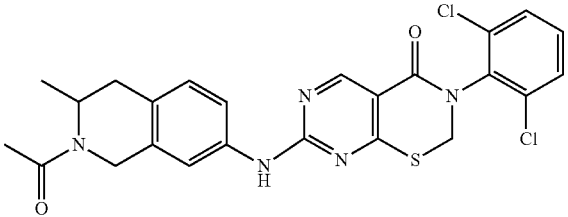 [SMILES: CC(=O)N1Cc2cc(Nc3ncc4c(n3)SCN(c3c(Cl)cccc3Cl)C4=O)ccc2CC1C] |
| 1.688 | 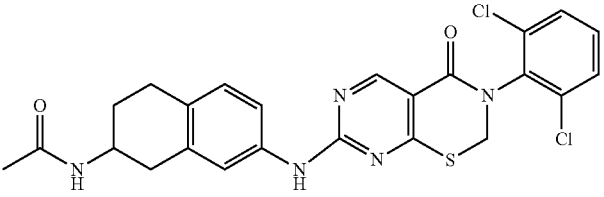 [SMILES: CC(=O)NC1CCc2ccc(Nc3ncc4c(n3)SCN(c3c(Cl)cccc3Cl)C4=O)cc2C1] |
| 1.689 | 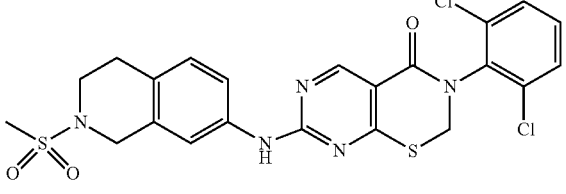 |
| 1.690 | 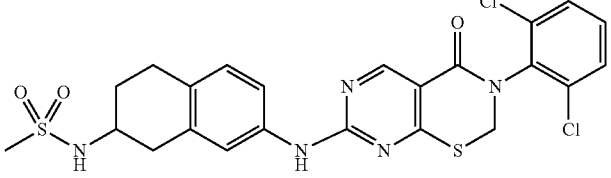 |
| 1.691 | 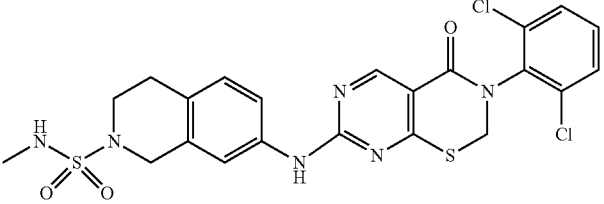 [SMILES: CNS(=O)(=O)N1CCc2ccc(Nc3ncc4c(n3)SCN(c3c(Cl)cccc3Cl)C4=O)cc2C1] |
| 1.692 | 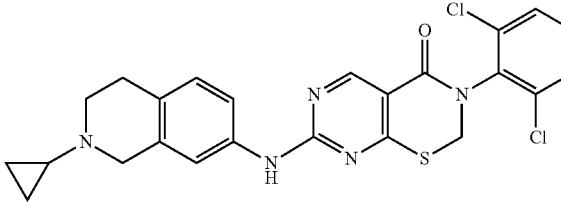 |

TABLE 1-continued

| Compound No. | Structure |
|---|---|
| 1.693 | 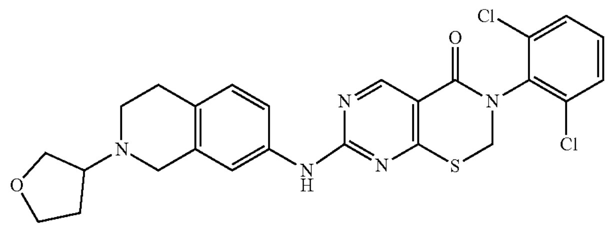 [SMILES: O=C1c2cnc(Nc3ccc4c(c3)CN(C3CCOC3)CC4)nc2SCN1c1c(Cl)cccc1Cl] |
| 1.694 | 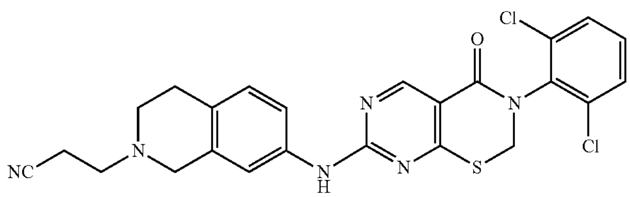 [SMILES: N#CCCN1CCc2ccc(Nc3ncc4c(n3)SCN(c3c(Cl)cccc3Cl)C4=O)cc2C1] |
| 1.695 | 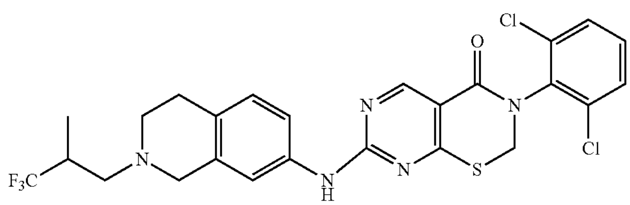 [SMILES: CC(CN1CCc2ccc(Nc3ncc4c(n3)SCN(c3c(Cl)cccc3Cl)C4=O)cc2C1)C(F)(F)F] |
| 1.696 | 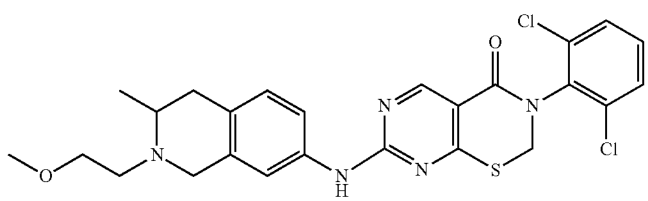 [SMILES: COCCN1Cc2cc(Nc3ncc4c(n3)SCN(c3c(Cl)cccc3Cl)C4=O)ccc2CC1C] |
| 1.697 | 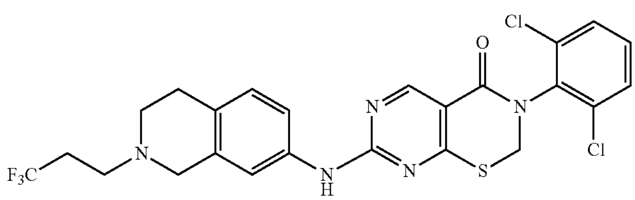 [SMILES: O=C1c2cnc(Nc3ccc4c(c3)CN(CCC(F)(F)F)CC4)nc2SCN1c1c(Cl)cccc1Cl] |
| 1.698 | 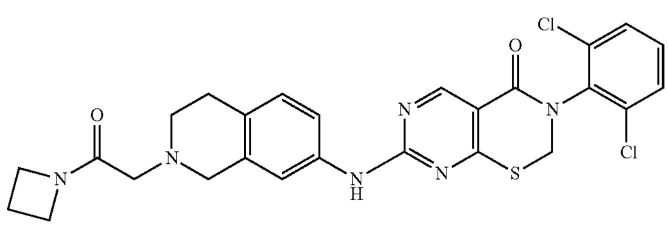 [SMILES: O=C(CN1CCc2ccc(Nc3ncc4c(n3)SCN(c3c(Cl)cccc3Cl)C4=O)cc2C1)N1CCC1] |
| 1.699 | 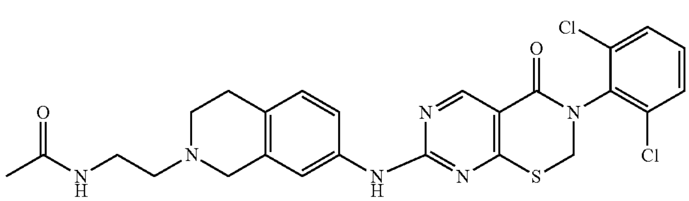 |

TABLE 1-continued

| Compound No. | Structure |
|---|---|
| 1.700 | 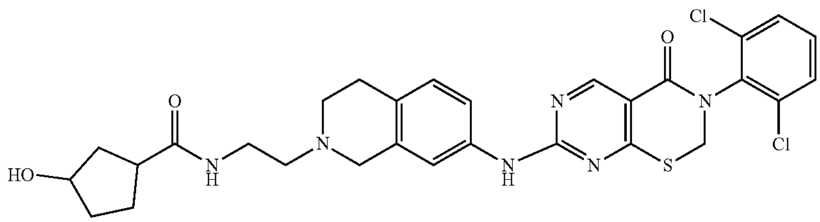 |
| 1.701 | 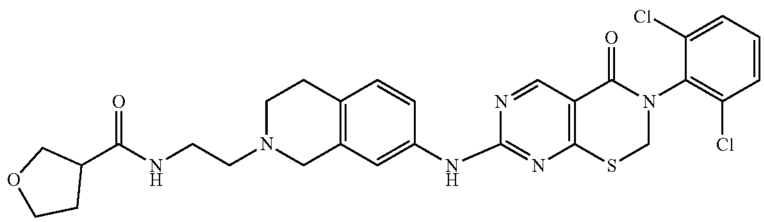 |
| 1.702 | 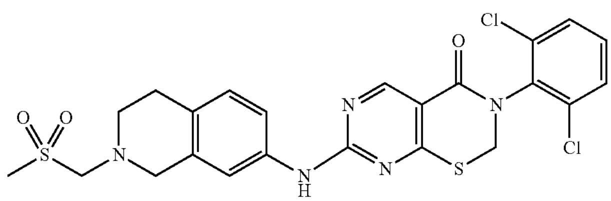 [SMILES: CS(=O)(=O)CN1CCc2ccc(Nc3ncc4c(n3)SCN(c3c(Cl)cccc3Cl)C4=O)cc2C1] |
| 1.703 | 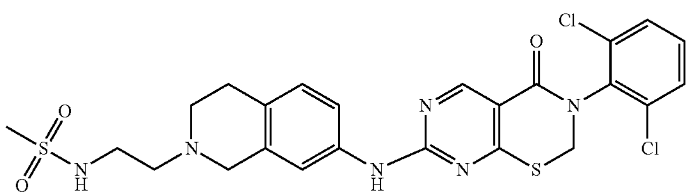 [SMILES: CS(=O)(=O)NCCN1CCc2ccc(Nc3ncc4c(n3)SCN(c3c(Cl)cccc3Cl)C4=O)cc2C1] |
| 1.704 | 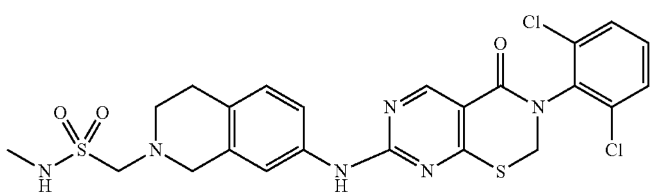 |
| 1.705 | 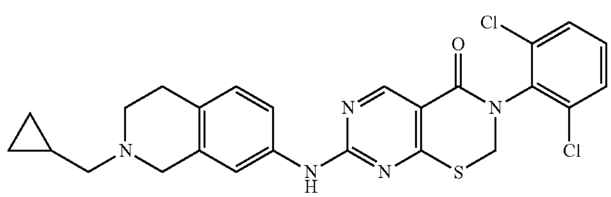 [SMILES: O=C1c2cnc(Nc3ccc4c(c3)CN(CC3CC3)CC4)nc2SCN1c1c(Cl)cccc1Cl] |
| 1.706 | 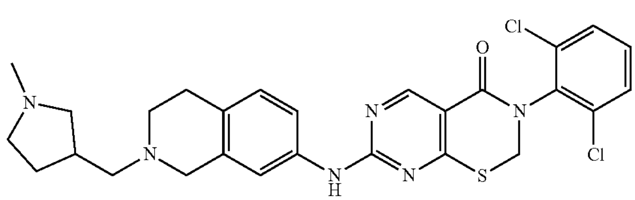 [SMILES: CN1CCC(CN2CCc3ccc(Nc4ncc5c(n4)SCN(c4c(Cl)cccc4Cl)C5=O)cc3C2)C1] |

TABLE 1-continued

| Compound No. | Structure |
|---|---|
| 1.707 | 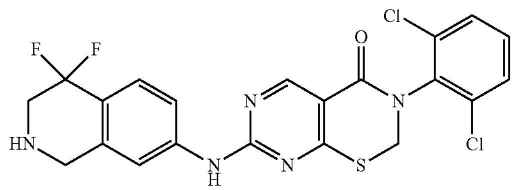 [SMILES: O=C1c2cnc(Nc3ccc4c(c3)CNCC4(F)F)nc2SCN1c1c(Cl)cccc1Cl] |
| 1.708 | 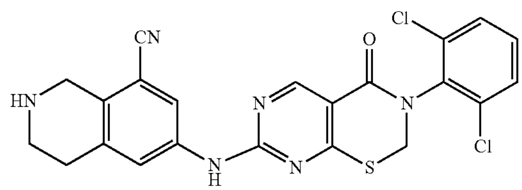 [SMILES: N#Cc1cc(Nc2ncc3c(n2)SCN(c2c(Cl)cccc2Cl)C3=O)cc2c1CNCC2] |
| 1.709 | 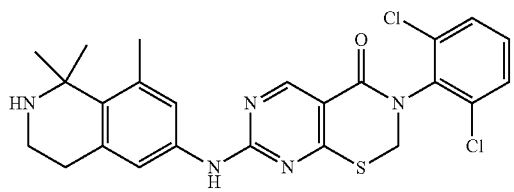 [SMILES: Cc1cc(Nc2ncc3c(n2)SCN(c2c(Cl)cccc2Cl)C3=O)cc2c1C(C)(C)NCC2] |
| 1.710 | 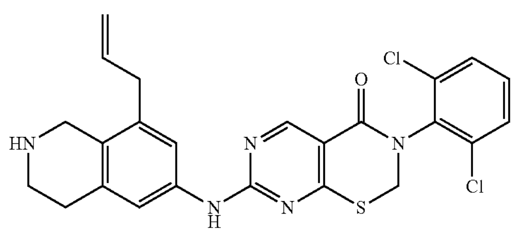 [SMILES: C=CCc1cc(Nc2ncc3c(n2)SCN(c2c(Cl)cccc2Cl)C3=O)cc2c1CNCC2] |
| 1.711 | 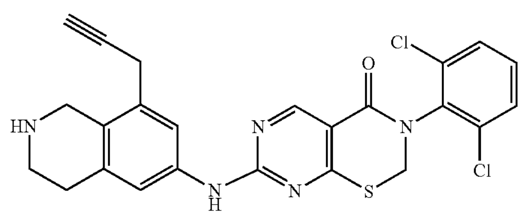 [SMILES: C#CCc1cc(Nc2ncc3c(n2)SCN(c2c(Cl)cccc2Cl)C3=O)cc2c1CNCC2] |
| 1.712 | 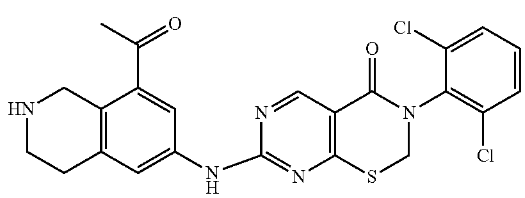 [SMILES: CC(=O)c1cc(Nc2ncc3c(n2)SCN(c2c(Cl)cccc2Cl)C3=O)cc2c1CNCC2] |
| 1.713 | 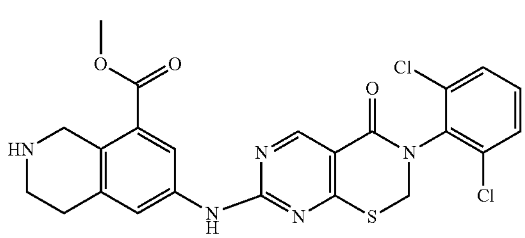 [SMILES: COC(=O)c1cc(Nc2ncc3c(n2)SCN(c2c(Cl)cccc2Cl)C3=O)cc2c1CNCC2] |

TABLE 1-continued

| Compound No. | Structure |
|---|---|
| 1.714 | 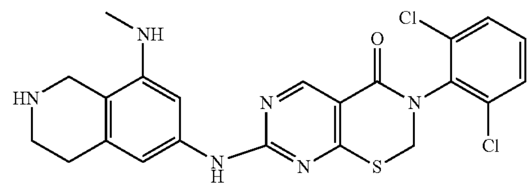 [SMILES: CNc1cc(Nc2ncc3c(n2)SCN(c2c(Cl)cccc2Cl)C3=O)cc2c1CNCC2] |
| 1.715 | 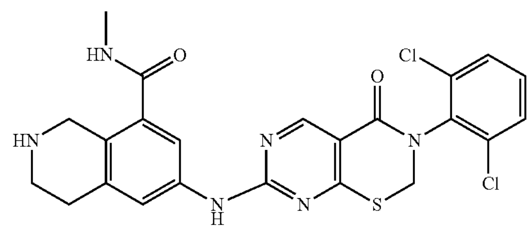 [SMILES: CNC(=O)c1cc(Nc2ncc3c(n2)SCN(c2c(Cl)cccc2Cl)C3=O)cc2c1CNCC2] |
| 1.716 | 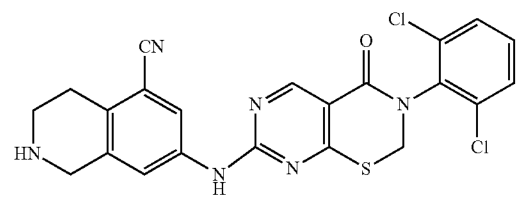 [SMILES: N#Cc1cc(Nc2ncc3c(n2)SCN(c2c(Cl)cccc2Cl)C3=O)cc2c1CCNC2] |
| 1.717 | 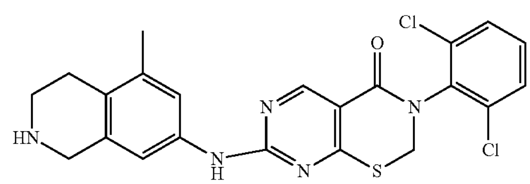 |
| 1.718 | 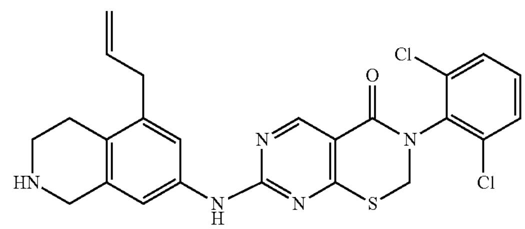 [SMILES: C=CCc1cc(Nc2ncc3c(n2)SCN(c2c(Cl)cccc2Cl)C3=O)cc2c1CCNC2] |
| 1.719 | 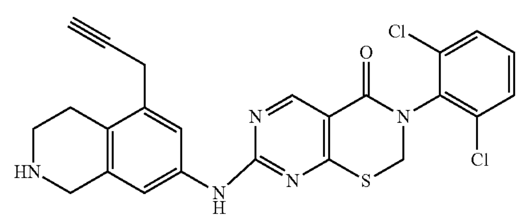 [SMILES: C#CCc1cc(Nc2ncc3c(n2)SCN(c2c(Cl)cccc2Cl)C3=O)cc2c1CCNC2] |
| 1.720 | 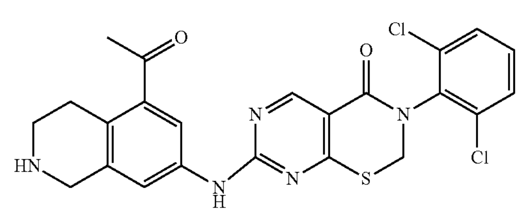 [SMILES: CC(=O)c1cc(Nc2ncc3c(n2)SCN(c2c(Cl)cccc2Cl)C3=O)cc2c1CCNC2] |

TABLE 1-continued
| Compound No. | Structure |
|---|---|
| 1.721 | 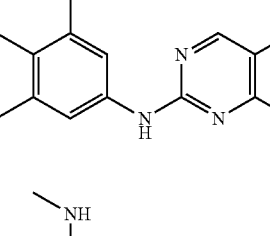 |
| 1.722 | 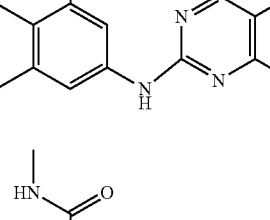 |
| 1.723 | 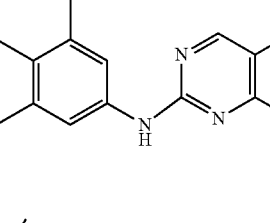 |
| 1.724 | 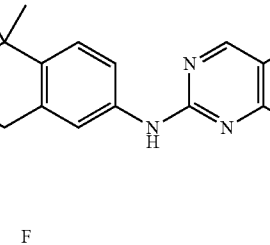 |
| 1.725 | 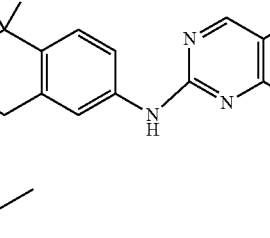 |
| 1.726 | 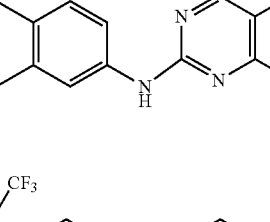 |
| 1.727 | 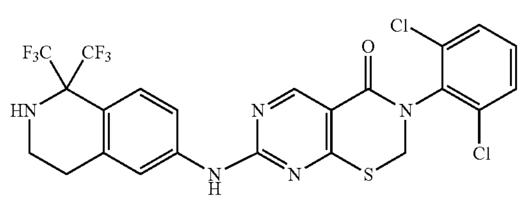 [SMILES: O=C1c2cnc(Nc3ccc4c(c3)CCNC4(C(F)(F)F)C(F)(F)F)nc2SCN1c1c(Cl)cccc1Cl] |

TABLE 1-continued

| Compound No. | Structure |
|---|---|
| 1.728 | 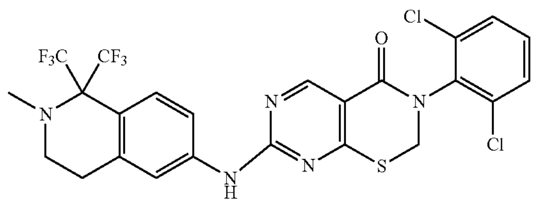 [SMILES: CN1CCc2cc(Nc3ncc4c(n3)SCN(c3c(Cl)cccc3Cl)C4=O)ccc2C1(C(F)(F)F)C(F)(F)F] |
| 1.729 | 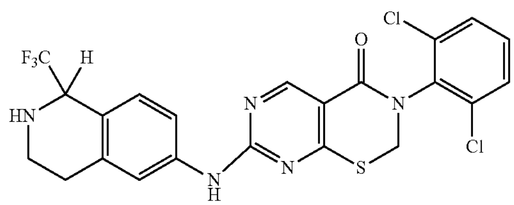 [SMILES: O=C1c2cnc(Nc3ccc4c(c3)CCNC4C(F)(F)F)nc2SCN1c1c(Cl)cccc1Cl] |
| 1.730 | 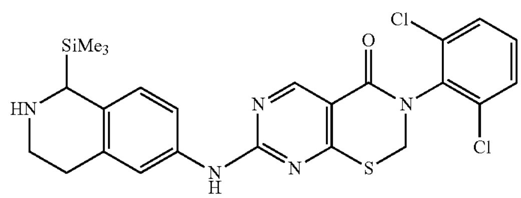 [SMILES: C[Si](C)(C)C1NCCc2cc(Nc3ncc4c(n3)SCN(c3c(Cl)cccc3Cl)C4=O)ccc21] |
| 1.731 | 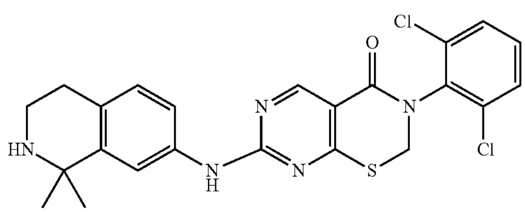 [SMILES: CC1(C)NCCc2ccc(Nc3ncc4c(n3)SCN(c3c(Cl)cccc3Cl)C4=O)cc21] |
| 1.732 | 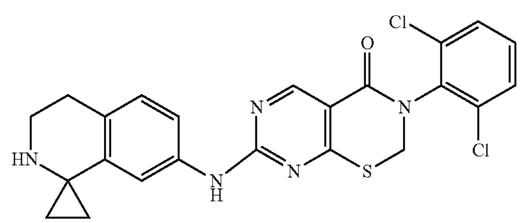 [SMILES: O=C1c2cnc(Nc3ccc4c(c3)C3(CC3)NCC4)nc2SCN1c1c(Cl)cccc1Cl] |
| 1.733 | 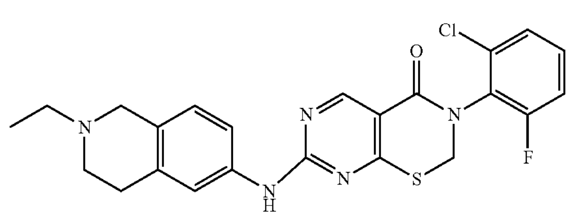 [SMILES: CCN1CCc2cc(Nc3ncc4c(n3)SCN(c3c(F)cccc3Cl)C4=O)ccc2C1] |
| 1.734 | 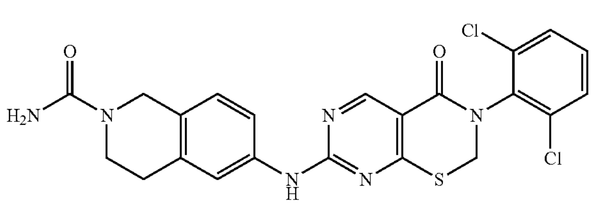 [SMILES: NC(=O)N1CCc2cc(Nc3ncc4c(n3)SCN(c3c(Cl)cccc3Cl)C4=O)ccc2C1] |

TABLE 1-continued

| Compound No. | Structure |
|---|---|
| 1.735 | 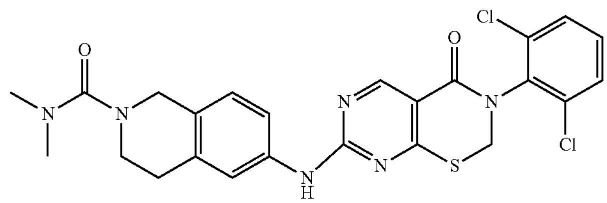 [SMILES: CN(C)C(=O)N1CCc2cc(Nc3ncc4c(n3)SCN(c3c(Cl)cccc3Cl)C4=O)ccc2C1] |
| 1.736 | 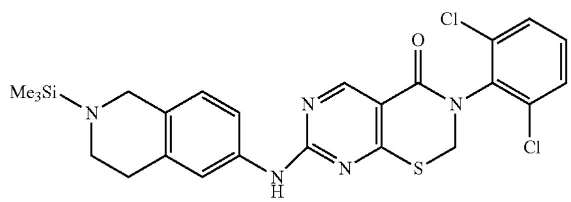 [SMILES: C[Si](C)(C)N1CCc2cc(Nc3ncc4c(n3)SCN(c3c(Cl)cccc3Cl)C4=O)ccc2C1] |
| 1.737 | 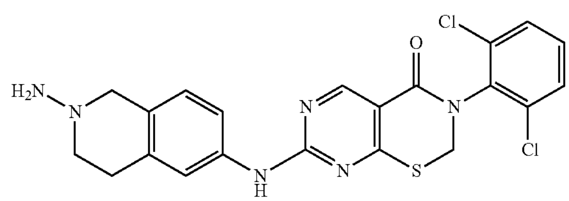 [SMILES: NN1CCc2cc(Nc3ncc4c(n3)SCN(c3c(Cl)cccc3Cl)C4=O)ccc2C1] |
| 1.738 | 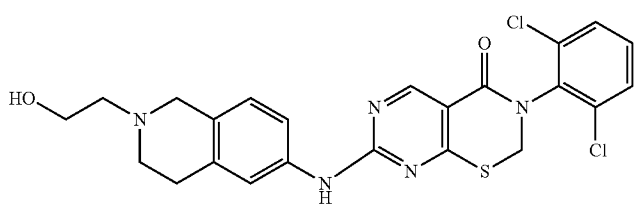 [SMILES: O=C1c2cnc(Nc3ccc4c(c3)CCN(CCO)C4)nc2SCN1c1c(Cl)cccc1Cl] |
| 1.739 | 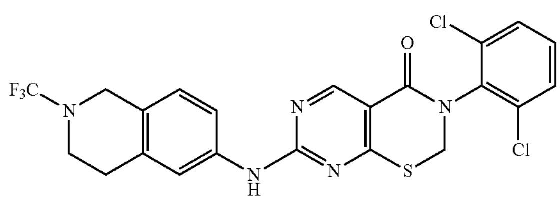 [SMILES: O=C1c2cnc(Nc3ccc4c(c3)CCN(C(F)(F)F)C4)nc2SCN1c1c(Cl)cccc1Cl] |
| 1.740 | 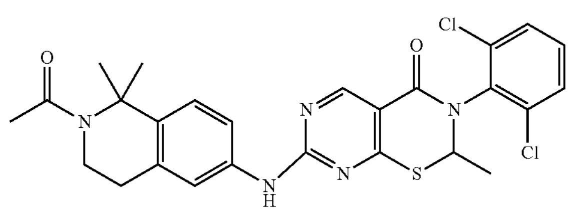 [SMILES: CC(=O)N1CCc2cc(Nc3ncc4c(n3)SC(C)N(c3c(Cl)cccc3Cl)C4=O)ccc2C1(C)C] |
| 1.741 | 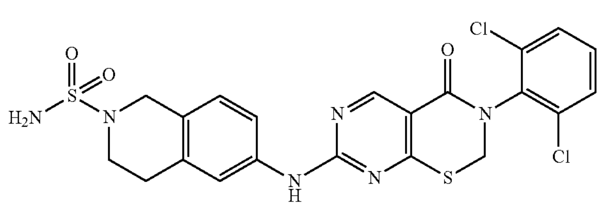 [SMILES: NS(=O)(=O)N1CCc2cc(Nc3ncc4c(n3)SCN(c3c(Cl)cccc3Cl)C4=O)ccc2C1] |

TABLE 1-continued

| Compound No. | Structure |
|---|---|
| 1.742 | 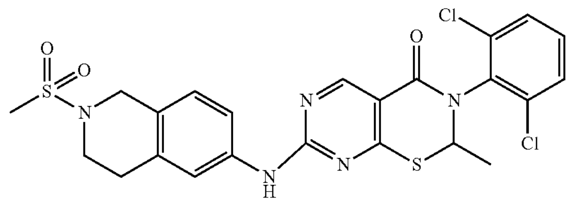 [SMILES: CC1Sc2nc(Nc3ccc4c(c3)CCN(S(C)(=O)=O)C4)ncc2C(=O)N1c1c(Cl)cccc1Cl] |
| 1.743 | 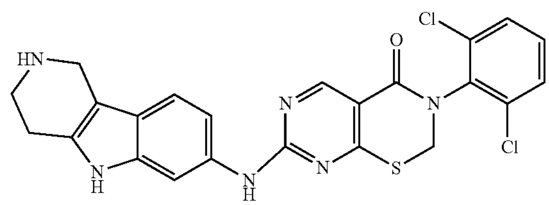 [SMILES: O=C1c2cnc(Nc3ccc4c5c([nH]c4c3)CCNC5)nc2SCN1c1c(Cl)cccc1Cl] |
| 1.744 | 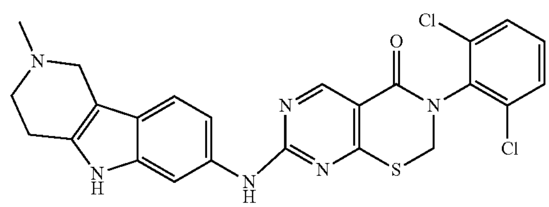 [SMILES: CN1CCc2[nH]c3cc(Nc4ncc5c(n4)SCN(c4c(Cl)cccc4Cl)C5=O)ccc3c2C1] |
| 1.745 | 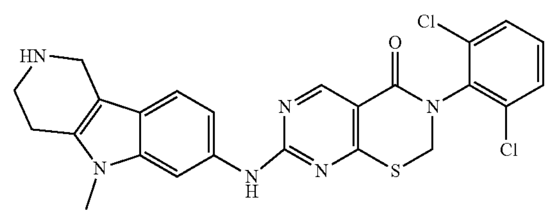 [SMILES: Cn1c2c(c3ccc(Nc4ncc5c(n4)SCN(c4c(Cl)cccc4Cl)C5=O)cc31)CNCC2] |
| 1.746 | 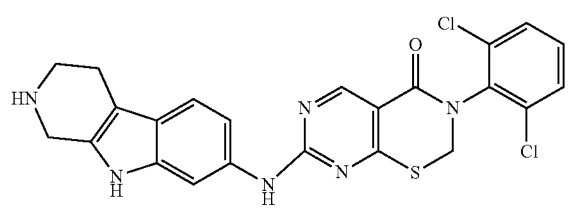 [SMILES: O=C1c2cnc(Nc3ccc4c5c([nH]c4c3)CNCC5)nc2SCN1c1c(Cl)cccc1Cl] |
| 1.747 | 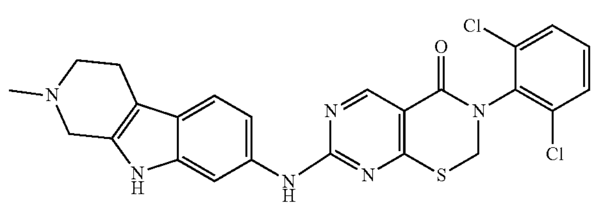 [SMILES: CN1CCc2c([nH]c3cc(Nc4ncc5c(n4)SCN(c4c(Cl)cccc4Cl)C5=O)ccc23)C1] |
| 1.748 | 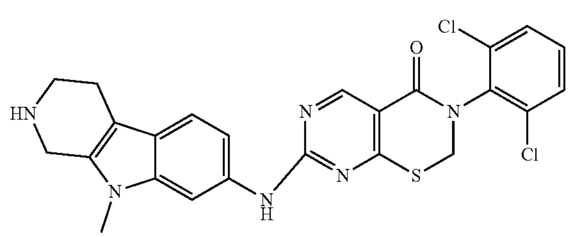 [SMILES: Cn1c2c(c3ccc(Nc4ncc5c(n4)SCN(c4c(Cl)cccc4Cl)C5=O)cc31)CCNC2] |

TABLE 1-continued

| Compound No. | Structure |
|---|---|
| 1.749 | 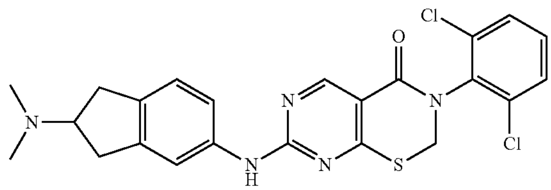 [SMILES: CN(C)C1Cc2ccc(Nc3ncc4c(n3)SCN(c3c(Cl)cccc3Cl)C4=O)cc2C1] |
| 1.750 | 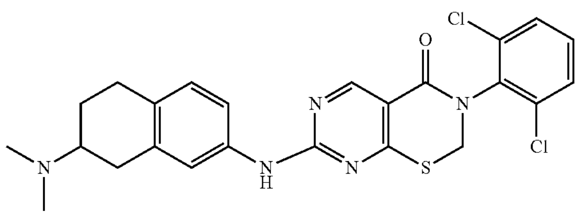 [SMILES: CN(C)C1CCc2ccc(Nc3ncc4c(n3)SCN(c3c(Cl)cccc3Cl)C4=O)cc2C1] |
| 1.751 | 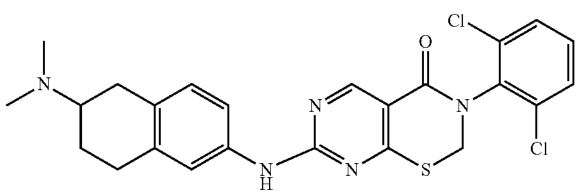 [SMILES: CN(C)C1CCc2cc(Nc3ncc4c(n3)SCN(c3c(Cl)cccc3Cl)C4=O)ccc2C1] |
| 1.752 | 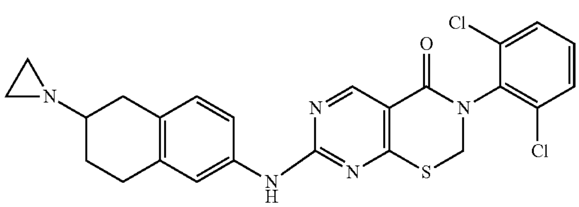 [SMILES: O=C1c2cnc(Nc3ccc4c(c3)CCC(N3CC3)C4)nc2SCN1c1c(Cl)cccc1Cl] |
| 1.753 | 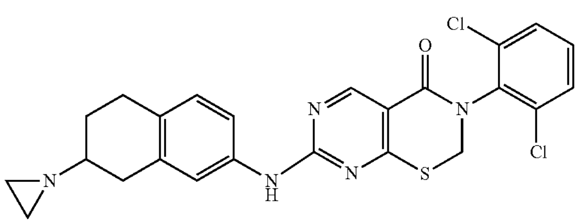 [SMILES: O=C1c2cnc(Nc3ccc4c(c3)CC(N3CC3)CC4)nc2SCN1c1c(Cl)cccc1Cl] |
| 1.754 | 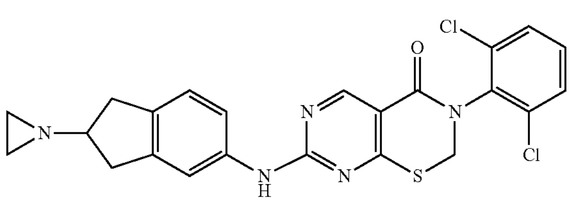 [SMILES: O=C1c2cnc(Nc3ccc4c(c3)CC(N3CC3)C4)nc2SCN1c1c(Cl)cccc1Cl] |
| 1.755 | 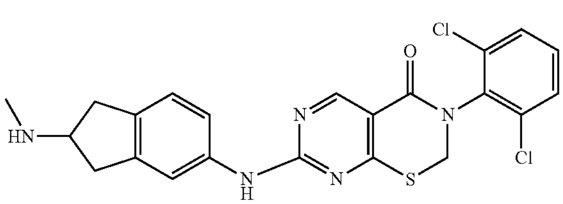 [SMILES: CNC1Cc2ccc(Nc3ncc4c(n3)SCN(c3c(Cl)cccc3Cl)C4=O)cc2C1] |

TABLE 1-continued

| Compound No. | Structure |
|---|---|
| 1.756 | 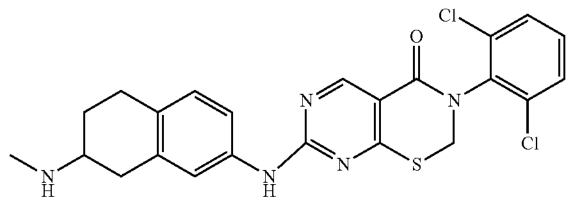 [SMILES: CNC1CCc2ccc(Nc3ncc4c(n3)SCN(c3c(Cl)cccc3Cl)C4=O)cc2C1] |
| 1.757 | 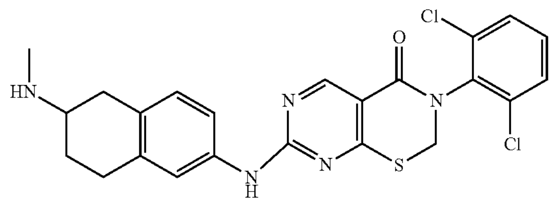 [SMILES: CNC1CCc2cc(Nc3ncc4c(n3)SCN(c3c(Cl)cccc3Cl)C4=O)ccc2C1] |
| 1.758 | 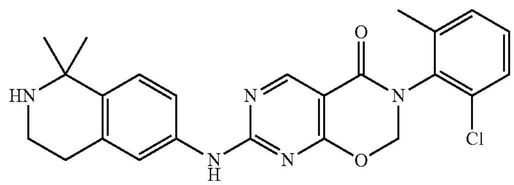 [SMILES: Cc1cccc(Cl)c1N1COc2nc(Nc3ccc4c(c3)CCNC4(C)C)ncc2C1=O] |
| 1.759 | 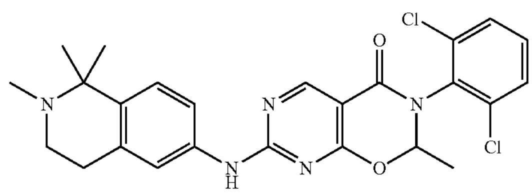 [SMILES: CC1Oc2nc(Nc3ccc4c(c3)CCN(C)C4(C)C)ncc2C(=O)N1c1c(Cl)cccc1Cl] |
| 1.760 | 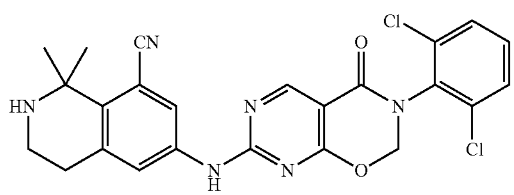 |
| 1.761 | 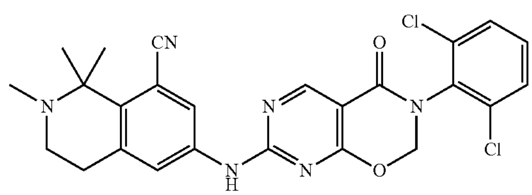 [SMILES: CN1CCc2cc(Nc3ncc4c(n3)OCN(c3c(Cl)cccc3Cl)C4=O)cc(C#N)c2C1(C)C] |
| 1.762 | 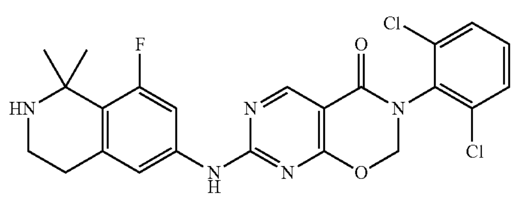 [SMILES: CC1(C)NCCc2cc(Nc3ncc4c(n3)OCN(c3c(Cl)cccc3Cl)C4=O)cc(F)c21] |
| 1.763 | 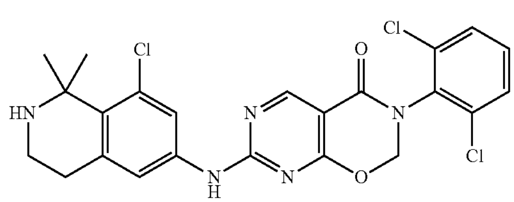 |

TABLE 1-continued

| Compound No. | Structure |
|---|---|
| 1.764 | 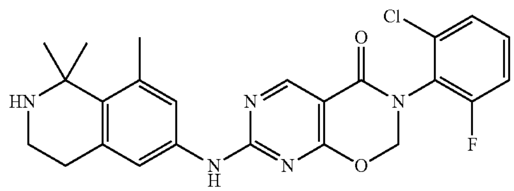 [SMILES: Cc1cc(Nc2ncc3c(n2)OCN(c2c(F)cccc2Cl)C3=O)cc2c1C(C)(C)NCC2] |
| 1.765 | 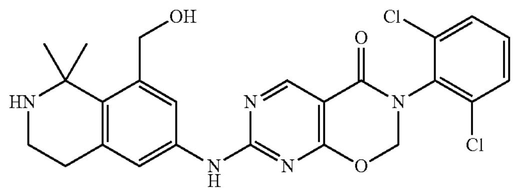 |
| 1.766 | 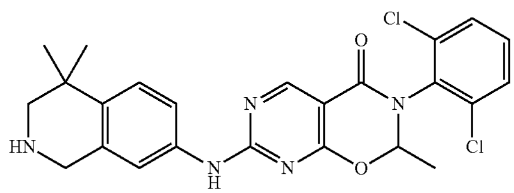 [SMILES: CC1Oc2nc(Nc3ccc4c(c3)CNCC4(C)C)ncc2C(=O)N1c1c(Cl)cccc1Cl] |
| 1.767 | 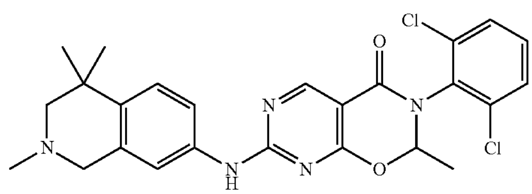 [SMILES: CC1Oc2nc(Nc3ccc4c(c3)CN(C)CC4(C)C)ncc2C(=O)N1c1c(Cl)cccc1Cl] |
| 1.768 | 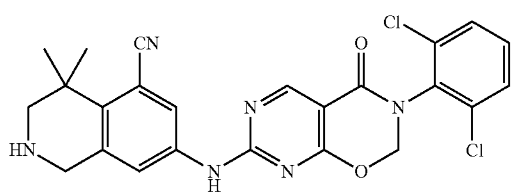 |
| 1.769 | 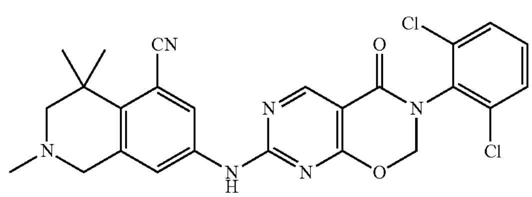 [SMILES: CN1Cc2cc(Nc3ncc4c(n3)OCN(c3c(Cl)cccc3Cl)C4=O)cc(C#N)c2C(C)(C)C1] |
| 1.770 | 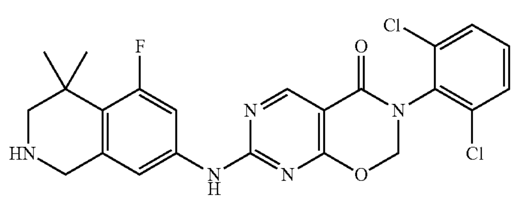 |
| 1.771 | 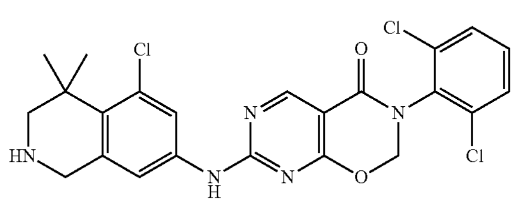 |

TABLE 1-continued

| Compound No. | Structure |
|---|---|
| 1.772 | 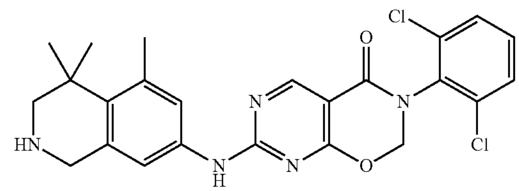 [SMILES: Cc1cc(Nc2ncc3c(n2)OCN(c2c(Cl)cccc2Cl)C3=O)cc2c1C(C)(C)CNC2] |
| 1.773 | 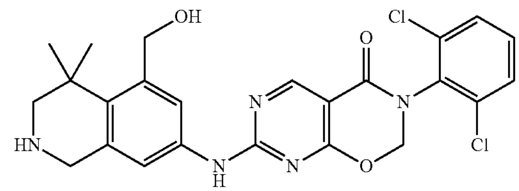 |
| 1.774 | 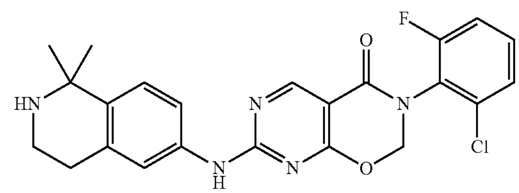 [SMILES: CC1(C)NCCc2cc(Nc3ncc4c(n3)OCN(c3c(F)cccc3Cl)C4=O)ccc21] |
| 1.775 | 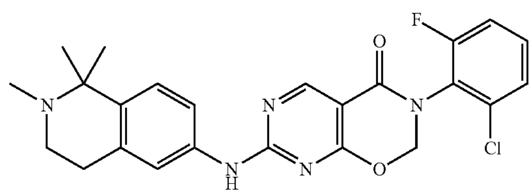 [SMILES: CN1CCc2cc(Nc3ncc4c(n3)OCN(c3c(F)cccc3Cl)C4=O)ccc2C1(C)C] |
| 1.776 | 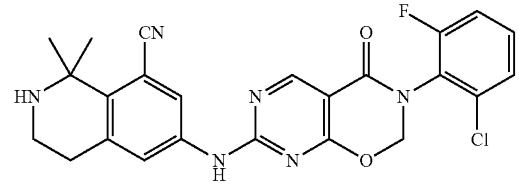 |
| 1.777 | 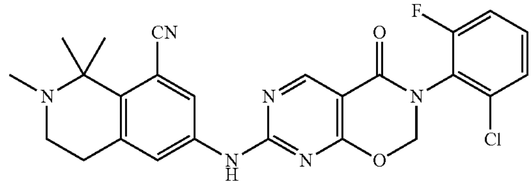 |
| 1.778 | 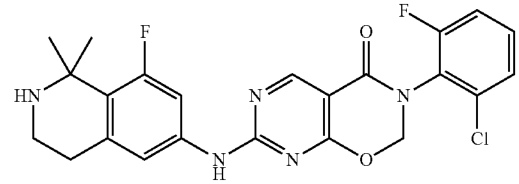 [SMILES: CC1(C)NCCc2cc(Nc3ncc4c(n3)OCN(c3c(F)cccc3Cl)C4=O)cc(F)c21] |
| 1.779 | 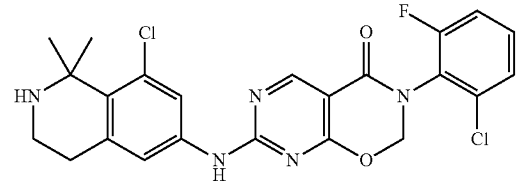 [SMILES: CC1(C)NCCc2cc(Nc3ncc4c(n3)OCN(c3c(F)cccc3Cl)C4=O)cc(Cl)c21] |

TABLE 1-continued

| Compound No. | Structure |
|---|---|
| 1.780 | 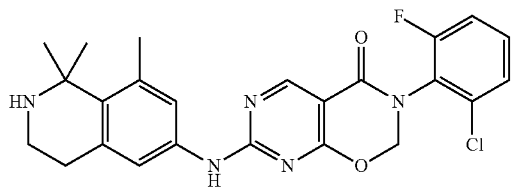 [SMILES: Cc1cc(Nc2ncc3c(n2)OCN(c2c(F)cccc2Cl)C3=O)cc2c1C(C)(C)NCC2] |
| 1.781 | 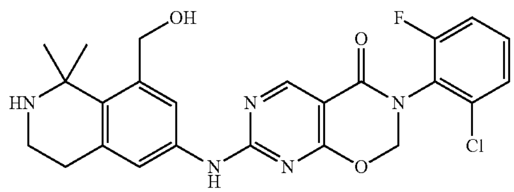 [SMILES: CC1(C)NCCc2cc(Nc3ncc4c(n3)OCN(c3c(F)cccc3Cl)C4=O)cc(CO)c21] |
| 1.782 | 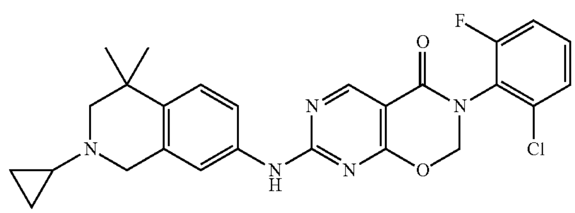 [SMILES: CC1(C)CN(C2CC2)Cc2cc(Nc3ncc4c(n3)OCN(c3c(F)cccc3Cl)C4=O)ccc21] |
| 1.783 | 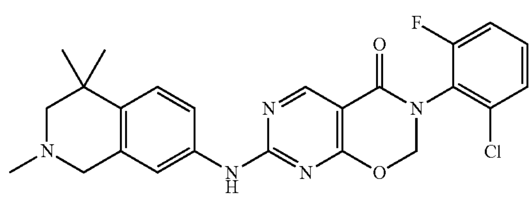 [SMILES: CN1Cc2cc(Nc3ncc4c(n3)OCN(c3c(F)cccc3Cl)C4=O)ccc2C(C)(C)C1] |
| 1.784 | 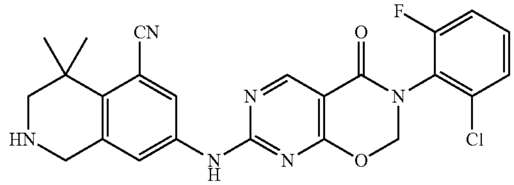 [SMILES: CC1(C)CNCc2cc(Nc3ncc4c(n3)OCN(c3c(F)cccc3Cl)C4=O)cc(C#N)c21] |
| 1.785 | 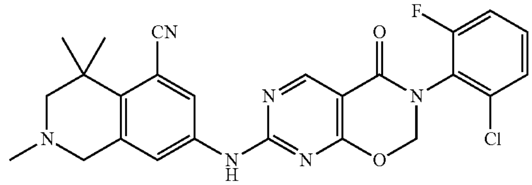 [SMILES: CN1Cc2cc(Nc3ncc4c(n3)OCN(c3c(F)cccc3Cl)C4=O)cc(C#N)c2C(C)(C)C1] |
| 1.786 | 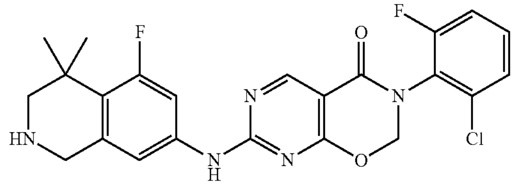 [SMILES: CC1(C)CNCc2cc(Nc3ncc4c(n3)OCN(c3c(F)cccc3Cl)C4=O)cc(F)c21] |

TABLE 1-continued

| Compound No. | Structure |
|---|---|
| 1.787 | 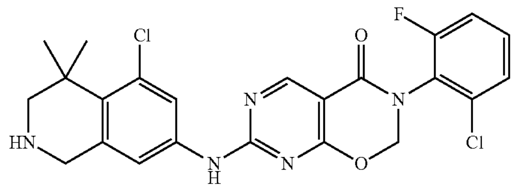 [SMILES: CC1(C)CNCc2cc(Nc3ncc4c(n3)OCN(c3c(F)cccc3Cl)C4=O)cc(Cl)c21] |
| 1.788 | 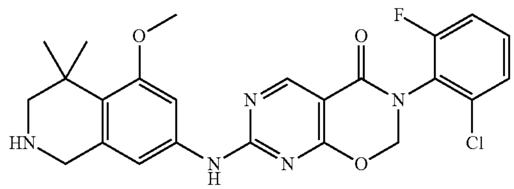 [SMILES: COc1cc(Nc2ncc3c(n2)OCN(c2c(F)cccc2Cl)C3=O)cc2c1C(C)(C)CNC2] |
| 1.789 | 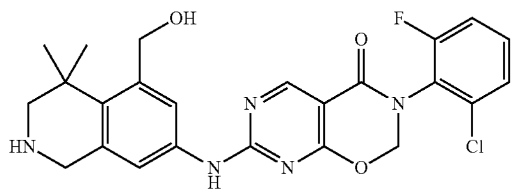 [SMILES: CC1(C)CNCc2cc(Nc3ncc4c(n3)OCN(c3c(F)cccc3Cl)C4=O)cc(CO)c21] |
| 1.790 | 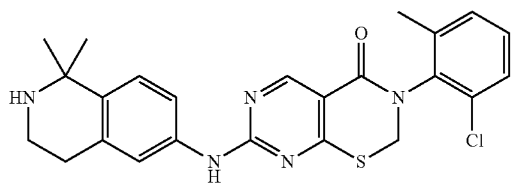 [SMILES: Cc1cccc(Cl)c1N1CSc2nc(Nc3ccc4c(c3)CCNC4(C)C)ncc2C1=O] |
| 1.791 | 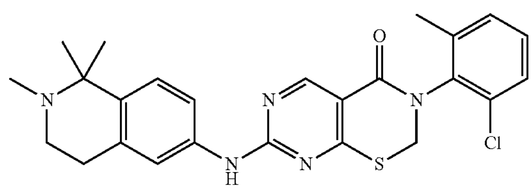 [SMILES: Cc1cccc(Cl)c1N1CSc2nc(Nc3ccc4c(c3)CCN(C)C4(C)C)ncc2C1=O] |
| 1.792 | 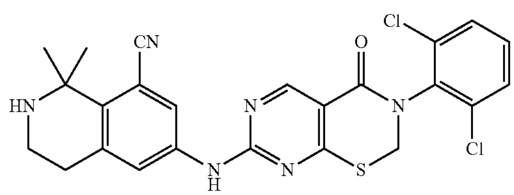 [SMILES: CC1(C)NCCc2cc(Nc3ncc4c(n3)SCN(c3c(Cl)cccc3Cl)C4=O)cc(C#N)c21] |
| 1.793 | 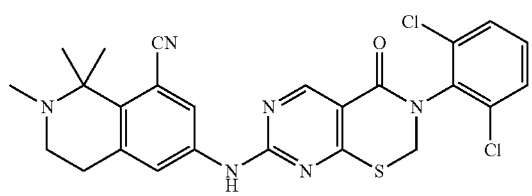 |
| 1.794 | 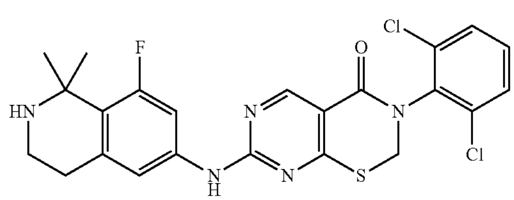 |

TABLE 1-continued

| Compound No. | Structure |
|---|---|
| 1.795 | 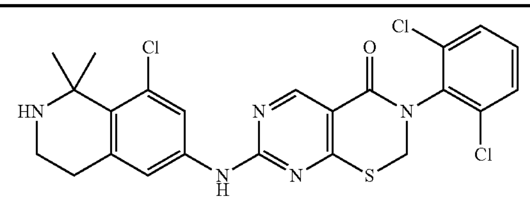 |
| 1.796 | 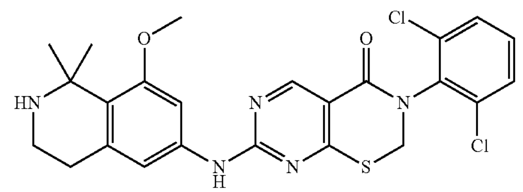 |
| 1.797 | 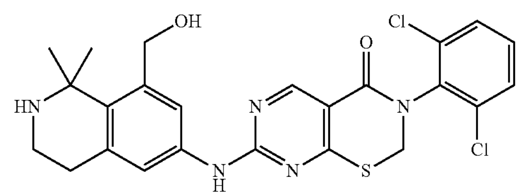 [SMILES: CC1(C)NCCc2cc(Nc3ncc4c(n3)SCN(c3c(Cl)cccc3Cl)C4=O)cc(CO)c21] |
| 1.798 | 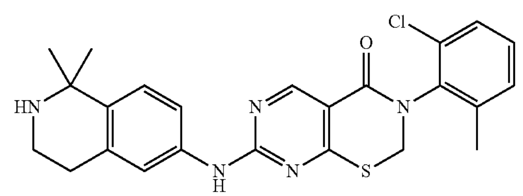 [SMILES: Cc1cccc(Cl)c1N1CSc2nc(Nc3ccc4c(c3)CCNC4(C)C)ncc2C1=O] |
| 1.799 | 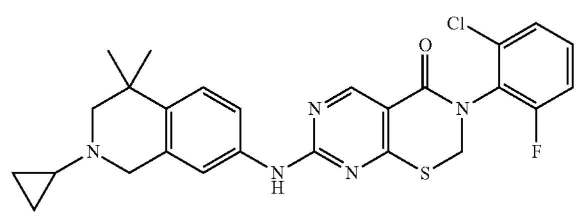 [SMILES: CC1(C)CN(C2CC2)Cc2cc(Nc3ncc4c(n3)SCN(c3c(F)cccc3Cl)C4=O)ccc21] |
| 1.800 | 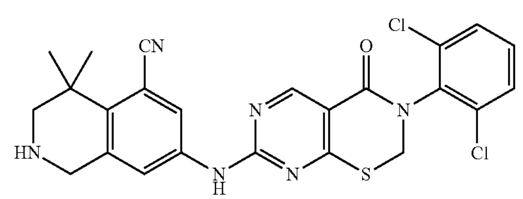 [SMILES: CC1(C)CNCc2cc(Nc3ncc4c(n3)SCN(c3c(Cl)cccc3Cl)C4=O)cc(C#N)c21] |
| 1.801 | 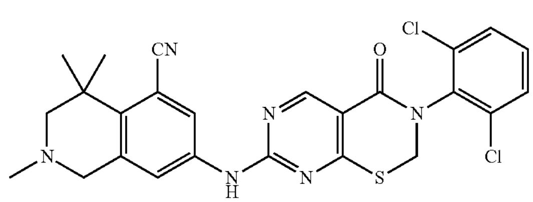 |
| 1.802 | 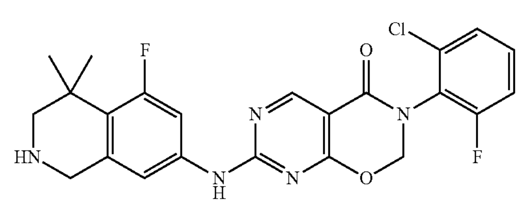 [SMILES: CC1(C)CNCc2cc(Nc3ncc4c(n3)OCN(c3c(F)cccc3Cl)C4=O)cc(F)c21] |

TABLE 1-continued

| Compound No. | Structure |
|---|---|
| 1.803 | 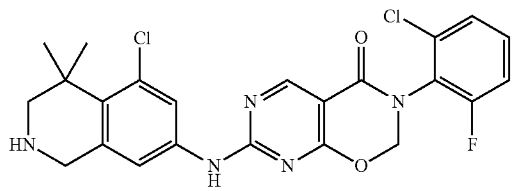 [SMILES: CC1(C)CNCc2cc(Nc3ncc4c(n3)OCN(c3c(F)cccc3Cl)C4=O)cc(Cl)c21] |
| 1.804 | 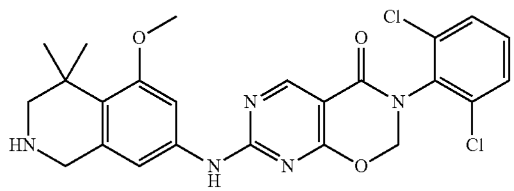 |
| 1.805 | 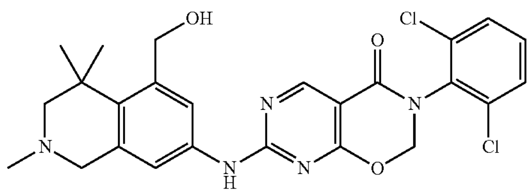 [SMILES: CN1Cc2cc(Nc3ncc4c(n3)OCN(c3c(Cl)cccc3Cl)C4=O)cc(CO)c2C(C)(C)C1] |
| 1.806 | 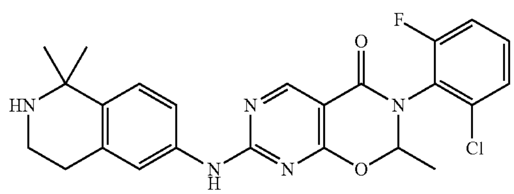 [SMILES: CC1Oc2nc(Nc3ccc4c(c3)CCNC4(C)C)ncc2C(=O)N1c1c(F)cccc1Cl] |
| 1.807 | 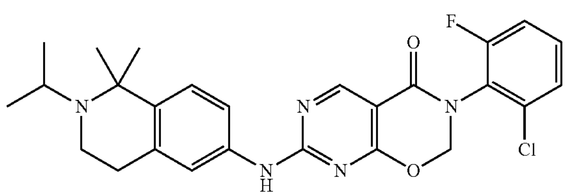 [SMILES: CC(C)N1CCc2cc(Nc3ncc4c(n3)OCN(c3c(F)cccc3Cl)C4=O)ccc2C1(C)C] |
| 1.808 | 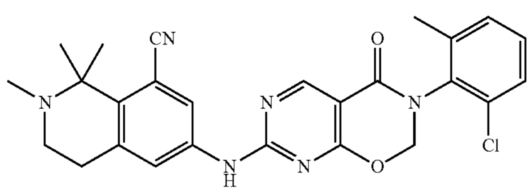 [SMILES: Cc1cccc(Cl)c1N1COc2nc(Nc3cc(C#N)c4c(c3)CCN(C)C4(C)C)ncc2C1=O] |
| 1.809 | 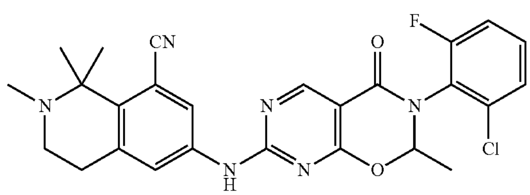 [SMILES: CC1Oc2nc(Nc3cc(C#N)c4c(c3)CCN(C)C4(C)C)ncc2C(=O)N1c1c(F)cccc1Cl] |
| 1.810 | 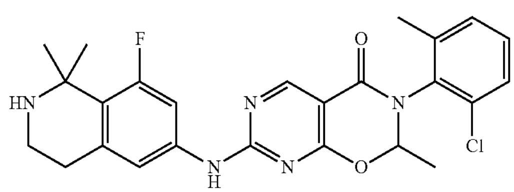 [SMILES: Cc1cccc(Cl)c1N1C(=O)c2cnc(Nc3cc(F)c4c(c3)CCNC4(C)C)nc2OC1C] |

TABLE 1-continued

| Compound No. | Structure |
|---|---|
| 1.811 | 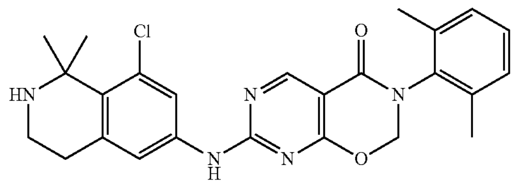 [SMILES: Cc1cccc(C)c1N1COc2nc(Nc3cc(Cl)c4c(c3)CCNC4(C)C)ncc2C1=O] |
| 1.812 | 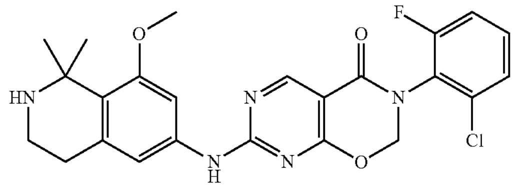 [SMILES: COc1cc(Nc2ncc3c(n2)OCN(c2c(F)cccc2Cl)C3=O)cc2c1C(C)(C)NCC2] |
| 1.813 | 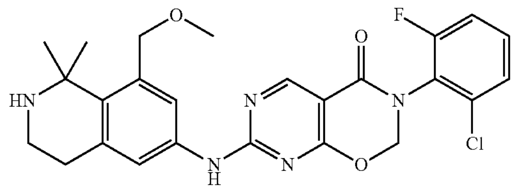 [SMILES: COCc1cc(Nc2ncc3c(n2)OCN(c2c(F)cccc2Cl)C3=O)cc2c1C(C)(C)NCC2] |
| 1.814 | 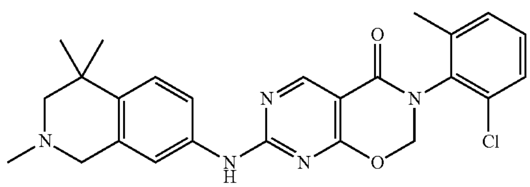 [SMILES: Cc1cccc(Cl)c1N1COc2nc(Nc3ccc4c(c3)CN(C)CC4(C)C)ncc2C1=O] |
| 1.815 | 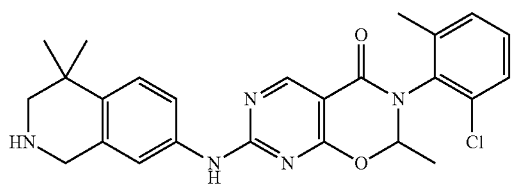 [SMILES: Cc1cccc(Cl)c1N1C(=O)c2cnc(Nc3ccc4c(c3)CNCC4(C)C)nc2OC1C] |
| 1.816 | 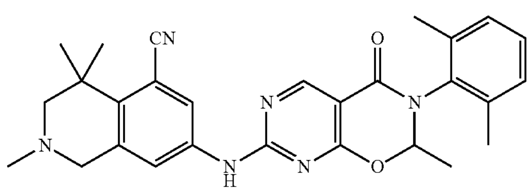 [SMILES: Cc1cccc(C)c1N1C(=O)c2cnc(Nc3cc(C#N)c4c(c3)CN(C)CC4(C)C)nc2OC1C] |
| 1.817 | 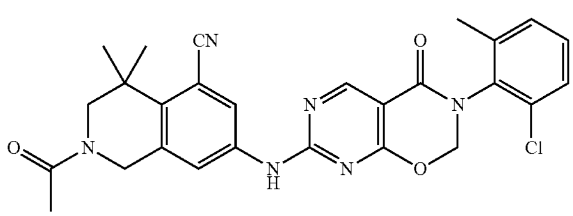 [SMILES: CC(=O)N1Cc2cc(Nc3ncc4c(n3)OCN(c3c(C)cccc3Cl)C4=O)cc(C#N)c2C(C)(C)C1] |

TABLE 1-continued
| Compound No. | Structure |
|---|---|
| 1.818 | 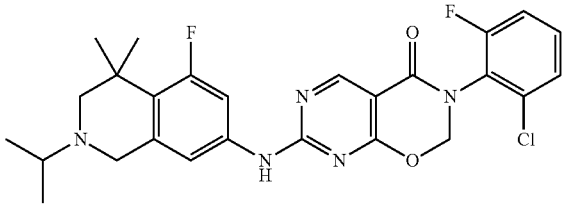 [SMILES: CC(C)N1Cc2cc(Nc3ncc4c(n3)OCN(c3c(F)cccc3Cl)C4=O)cc(F)c2C(C)(C)C1] |
| 1.819 | 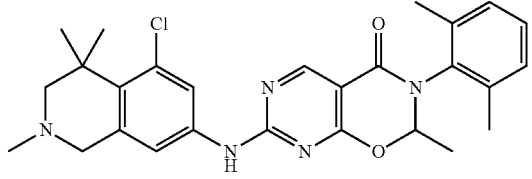 [SMILES: Cc1cccc(C)c1N1C(=O)c2cnc(Nc3cc(Cl)c4c(c3)CN(C)CC4(C)C)nc2OC1C] |
| 1.820 | 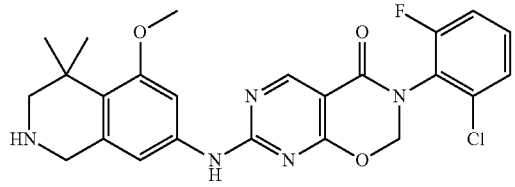 [SMILES: COc1cc(Nc2ncc3c(n2)OCN(c2c(F)cccc2Cl)C3=O)cc2c1C(C)(C)CNC2] |
| 1.821 | 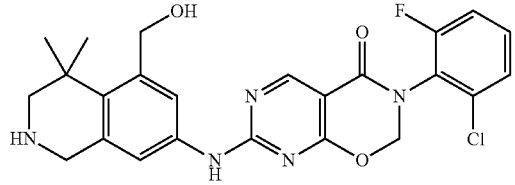 [SMILES: CC1(C)CNCc2cc(Nc3ncc4c(n3)OCN(c3c(F)cccc3Cl)C4=O)cc(CO)c21] |
| 1.822 | 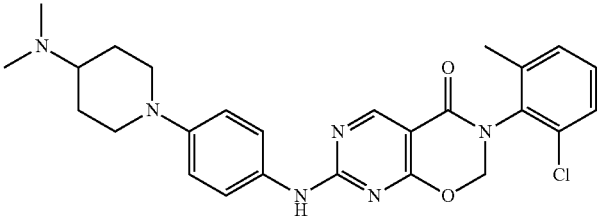 [SMILES: Cc1cccc(Cl)c1N1COc2nc(Nc3ccc(N4CCC(N(C)C)CC4)cc3)ncc2C1=O] |
| 1.823 | 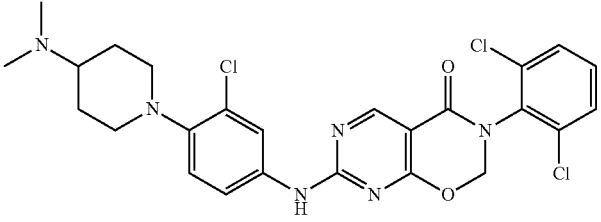 [SMILES: CN(C)C1CCN(c2ccc(Nc3ncc4c(n3)OCN(c3c(Cl)cccc3Cl)C4=O)cc2Cl)CC1] |
| 1.824 | 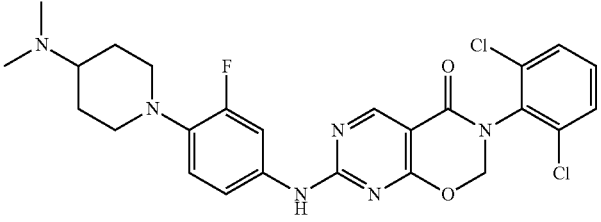 [SMILES: CN(C)C1CCN(c2ccc(Nc3ncc4c(n3)OCN(c3c(Cl)cccc3Cl)C4=O)cc2F)CC1] |

TABLE 1-continued

| Compound No. | Structure |
|---|---|
| 1.825 | 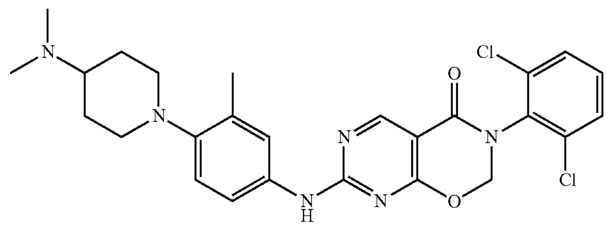 [SMILES: Cc1cc(Nc2ncc3c(n2)OCN(c2c(Cl)cccc2Cl)C3=O)ccc1N1CCC(N(C)C)CC1] |
| 1.826 | 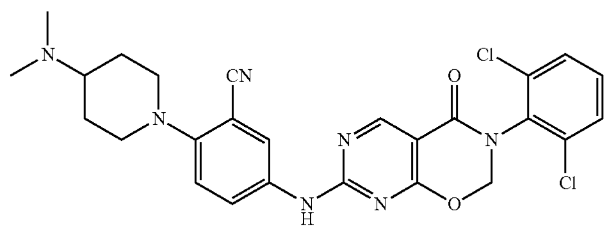 |
| 1.827 | 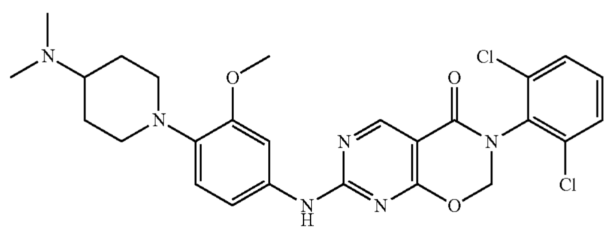 [SMILES: COc1cc(Nc2ncc3c(n2)OCN(c2c(Cl)cccc2Cl)C3=O)ccc1N1CCC(N(C)C)CC1] |
| 1.828 | 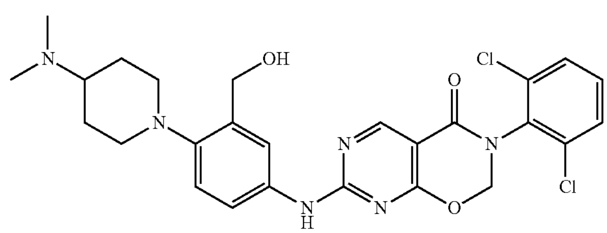 [SMILES: CN(C)C1CCN(c2ccc(Nc3ncc4c(n3)OCN(c3c(Cl)cccc3Cl)C4=O)cc2CO)CC1] |
| 1.829 | 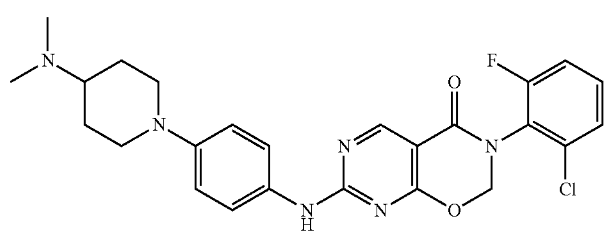 [SMILES: CN(C)C1CCN(c2ccc(Nc3ncc4c(n3)OCN(c3c(F)cccc3Cl)C4=O)cc2)CC1] |
| 1.830 | 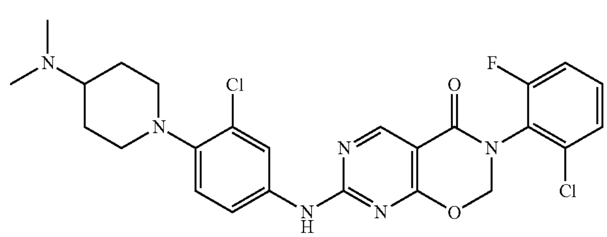 [SMILES: CN(C)C1CCN(c2ccc(Nc3ncc4c(n3)OCN(c3c(F)cccc3Cl)C4=O)cc2Cl)CC1] |

TABLE 1-continued

| Compound No. | Structure |
|---|---|
| 1.831 | 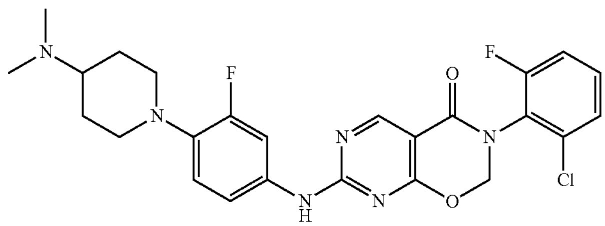 [SMILES: CN(C)C1CCN(c2ccc(Nc3ncc4c(n3)OCN(c3c(F)cccc3Cl)C4=O)cc2F)CC1] |
| 1.832 | 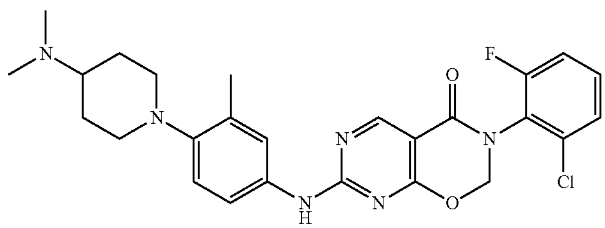 [SMILES: Cc1cc(Nc2ncc3c(n2)OCN(c2c(F)cccc2Cl)C3=O)ccc1N1CCC(N(C)C)CC1] |
| 1.833 | 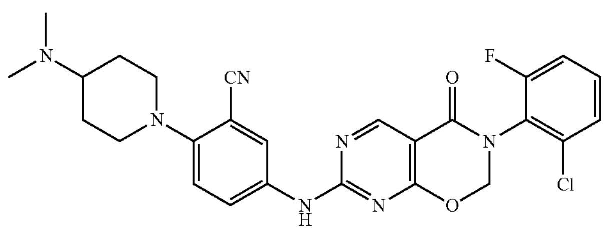 [SMILES: CN(C)C1CCN(c2ccc(Nc3ncc4c(n3)OCN(c3c(F)cccc3Cl)C4=O)cc2C#N)CC1] |
| 1.834 | 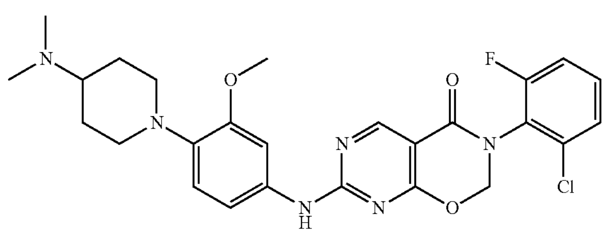 [SMILES: COc1cc(Nc2ncc3c(n2)OCN(c2c(F)cccc2Cl)C3=O)ccc1N1CCC(N(C)C)CC1] |
| 1.835 | 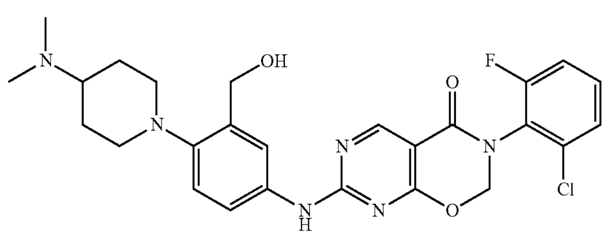 [SMILES: CN(C)C1CCN(c2ccc(Nc3ncc4c(n3)OCN(c3c(F)cccc3Cl)C4=O)cc2CO)CC1] |
| 1.836 | 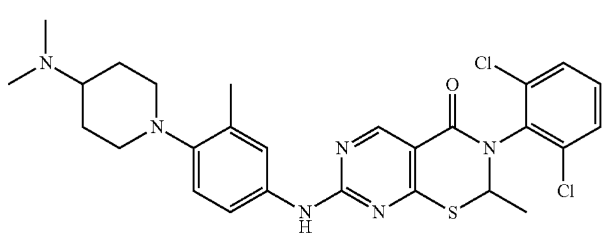 [SMILES: Cc1cc(Nc2ncc3c(n2)SC(C)N(c2c(Cl)cccc2Cl)C3=O)ccc1N1CCC(N(C)C)CC1] |

TABLE 1-continued

| Compound No. | Structure |
|---|---|
| 1.837 | 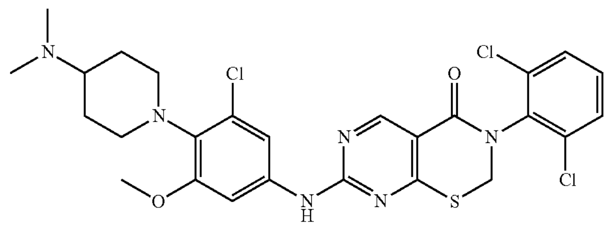 [SMILES: COc1cc(Nc2ncc3c(n2)SCN(c2c(Cl)cccc2Cl)C3=O)cc(Cl)c1N1CCC(N(C)C)CC1] |
| 1.838 | 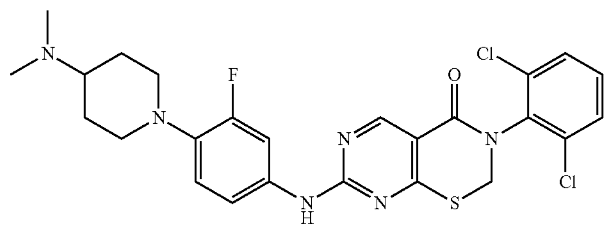 |
| 1.839 | 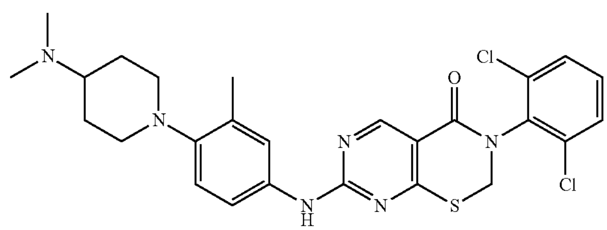 [SMILES: Cc1cc(Nc2ncc3c(n2)SCN(c2c(Cl)cccc2Cl)C3=O)ccc1N1CCC(N(C)C)CC1] |
| 1.840 | 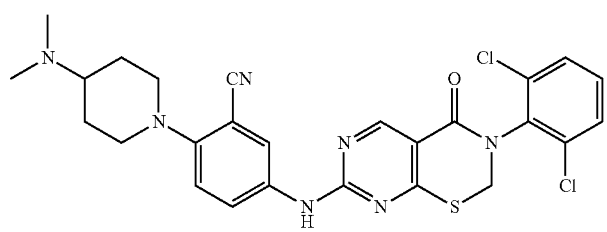 |
| 1.841 | 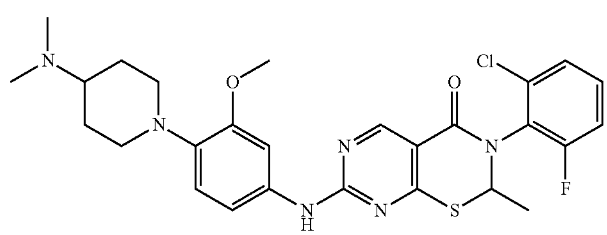 [SMILES: COc1cc(Nc2ncc3c(n2)SC(C)N(c2c(F)cccc2Cl)C3=O)ccc1N1CCC(N(C)C)CC1] |
| 1.842 | 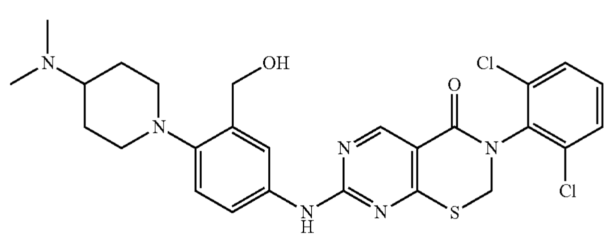 |

TABLE 1-continued

| Compound No. | Structure |
|---|---|
| 1.843 | 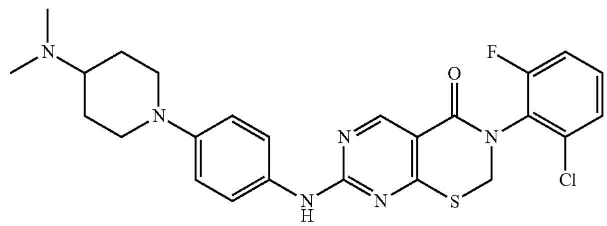 |
| 1.844 | 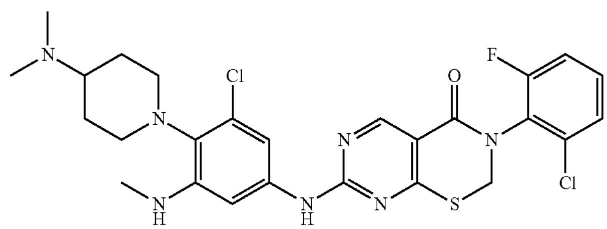 [SMILES: CNc1cc(Nc2ncc3c(n2)SCN(c2c(F)cccc2Cl)C3=O)cc(Cl)c1N1CCC(N(C)C)CC1] |
| 1.845 | 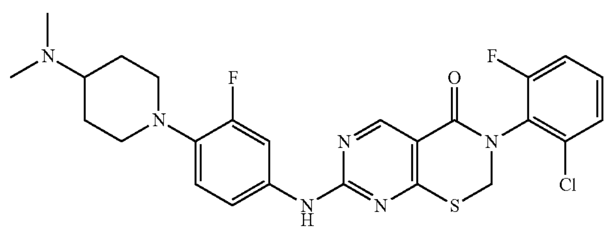 [SMILES: CN(C)C1CCN(c2ccc(Nc3ncc4c(n3)SCN(c3c(F)cccc3Cl)C4=O)cc2F)CC1] |
| 1.846 | 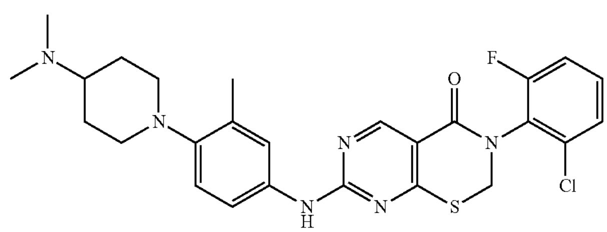 |
| 1.847 | 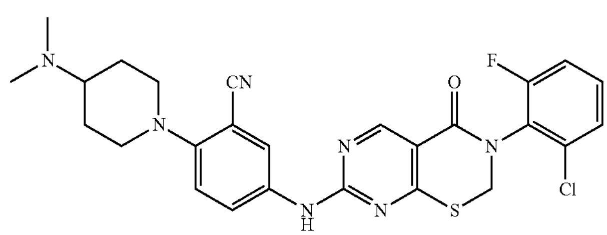 |
| 1.848 | 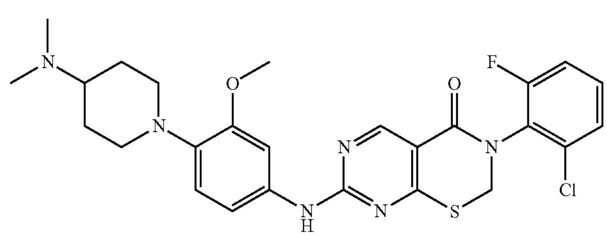 |

TABLE 1-continued
| Compound No. | Structure |
|---|---|
| 1.849 | 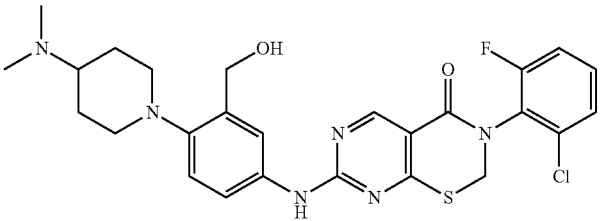 |
| 1.850 | 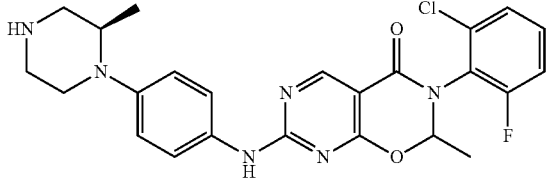 [SMILES: CC1Oc2nc(Nc3ccc(N4CCNC[C@H]4C)cc3)ncc2C(=O)N1c1c(F)cccc1Cl] |
| 1.851 | 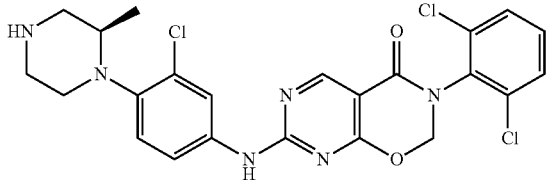 |
| 1.852 | 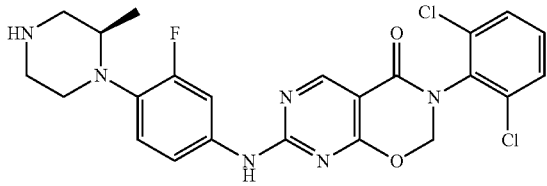 |
| 1.853 | 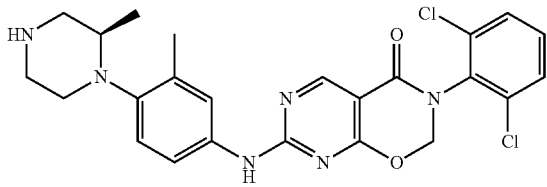 [SMILES: Cc1cc(Nc2ncc3c(n2)OCN(c2c(F)cccc2Cl)C3=O)ccc1N1CCNC[C@H]1C] |
| 1.854 | 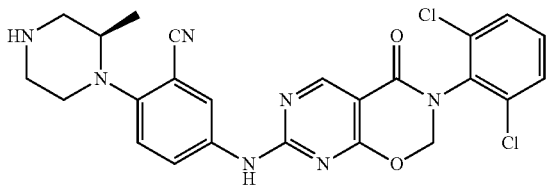 [SMILES: C[C@@H]1CNCCN1c1ccc(Nc2ncc3c(n2)OCN(c2c(F)cccc2Cl)C3=O)cc1C#N] |
| 1.855 | 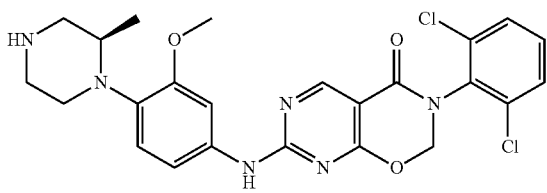 |

TABLE 1-continued

| Compound No. | Structure |
|---|---|
| 1.856 | 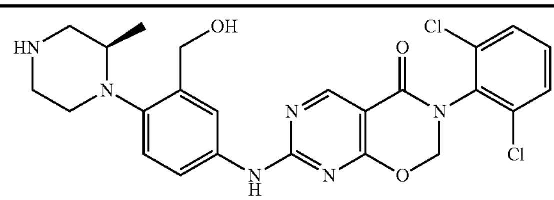 |
| 1.857 | 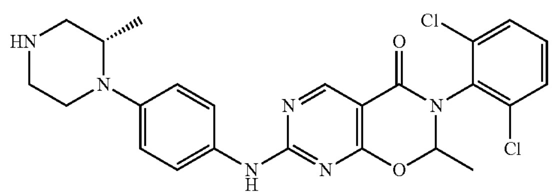 |
| 1.858 | 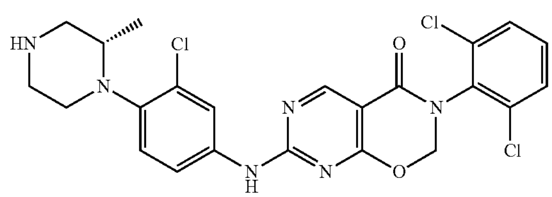 [SMILES: C[C@H]1CNCCN1c1ccc(Nc2ncc3c(n2)OCN(c2c(F)cccc2Cl)C3=O)cc1Cl] |
| 1.859 | 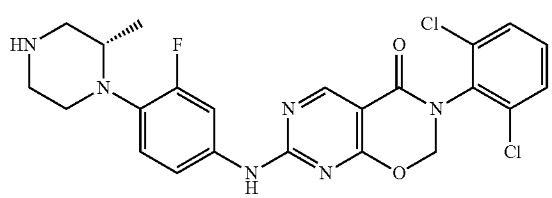 [SMILES: C[C@H]1CNCCN1c1ccc(Nc2ncc3c(n2)OCN(c2c(F)cccc2Cl)C3=O)cc1F] |
| 1.860 | 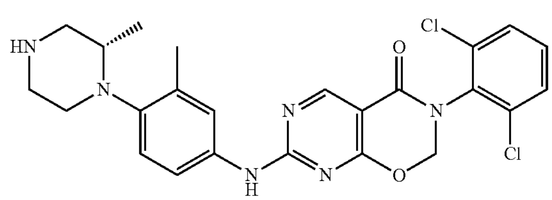 |
| 1.861 | 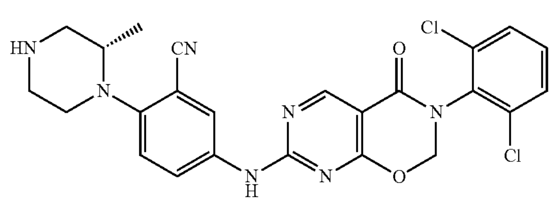 [SMILES: C[C@H]1CNCCN1c1ccc(Nc2ncc3c(n2)OCN(c2c(F)cccc2Cl)C3=O)cc1C#N] |
| 1.862 | 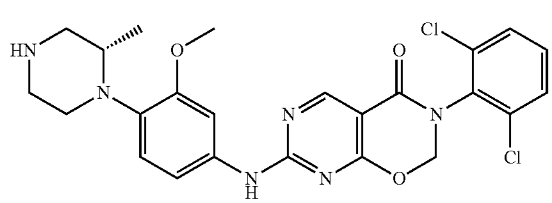 [SMILES: COc1cc(Nc2ncc3c(n2)OCN(c2c(F)cccc2Cl)C3=O)ccc1N1CCNC[C@@H]1C] |
| 1.863 | 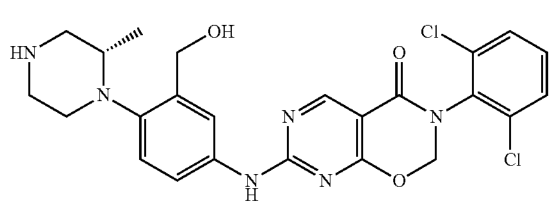 [SMILES: C[C@H]1CNCCN1c1ccc(Nc2ncc3c(n2)OCN(c2c(F)cccc2Cl)C3=O)cc1CO] |

TABLE 1-continued

| Compound No. | Structure |
|---|---|
| 1.864 | 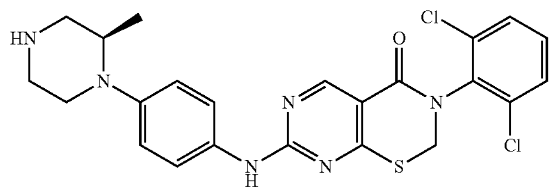 [SMILES: C[C@@H]1CNCCN1c1ccc(Nc2ncc3c(n2)SCN(c2c(F)cccc2Cl)C3=O)cc1] |
| 1.865 | 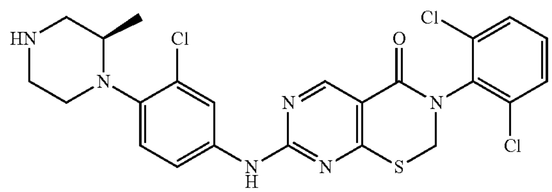 [SMILES: C[C@@H]1CNCCN1c1ccc(Nc2ncc3c(n2)SCN(c2c(F)cccc2Cl)C3=O)cc1Cl] |
| 1.866 | 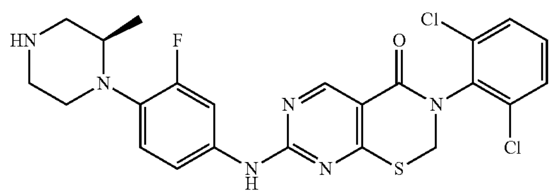 [SMILES: C[C@@H]1CNCCN1c1ccc(Nc2ncc3c(n2)SCN(c2c(F)cccc2Cl)C3=O)cc1F] |
| 1.867 | 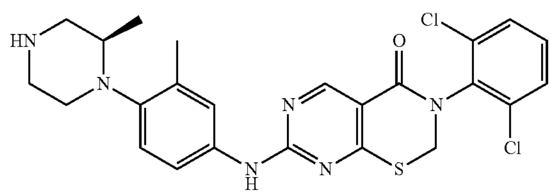 [SMILES: Cc1cc(Nc2ncc3c(n2)SCN(c2c(F)cccc2Cl)C3=O)ccc1N1CCNC[C@H]1C] |
| 1.868 | 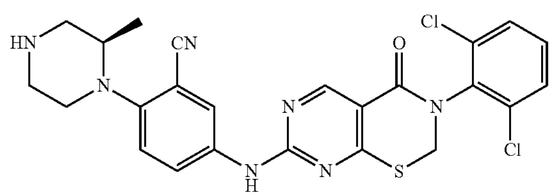 |
| 1.869 | 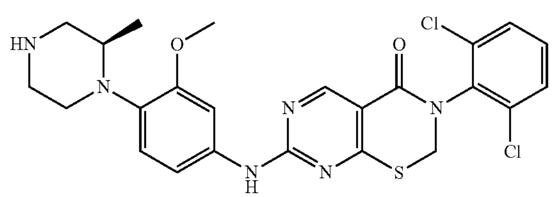 [SMILES: COc1cc(Nc2ncc3c(n2)SCN(c2c(F)cccc2Cl)C3=O)ccc1N1CCNC[C@H]1C] |
| 1.870 | 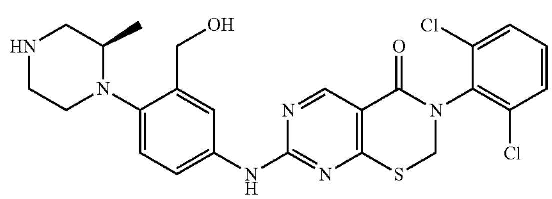 |
| 1.871 | 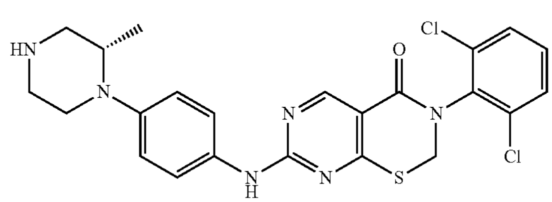 [SMILES: C[C@H]1CNCCN1c1ccc(Nc2ncc3c(n2)SCN(c2c(F)cccc2Cl)C3=O)cc1] |

TABLE 1-continued

| Compound No. | Structure |
|---|---|
| 1.872 | 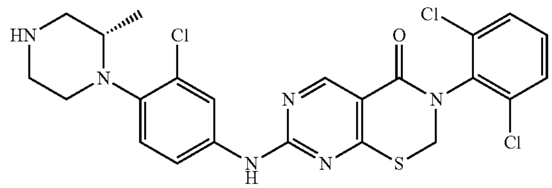 [SMILES: C[C@H]1CNCCN1c1ccc(Nc2ncc3c(n2)SCN(c2c(F)cccc2Cl)C3=O)cc1Cl] |
| 1.873 | 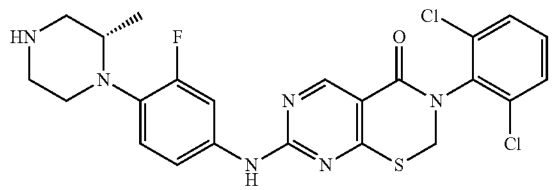 [SMILES: C[C@H]1CNCCN1c1ccc(Nc2ncc3c(n2)SCN(c2c(F)cccc2Cl)C3=O)cc1F] |
| 1.874 | 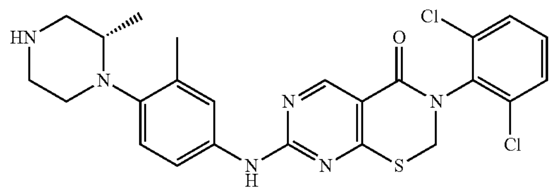 [SMILES: Cc1cc(Nc2ncc3c(n2)SCN(c2c(F)cccc2Cl)C3=O)ccc1N1CCNC[C@@H]1C] |
| 1.875 | 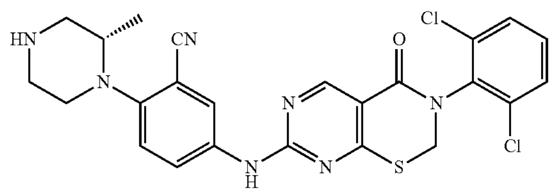 [SMILES: C[C@H]1CNCCN1c1ccc(Nc2ncc3c(n2)SCN(c2c(F)cccc2Cl)C3=O)cc1C#N] |
| 1.876 | 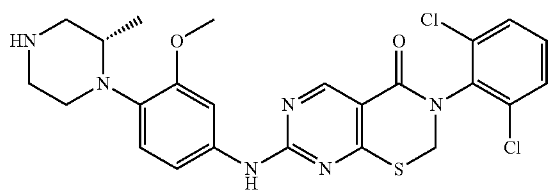 |
| 1.877 | 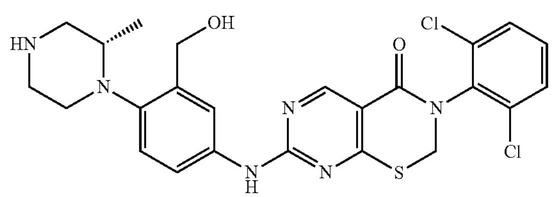 |
| 1.878 | 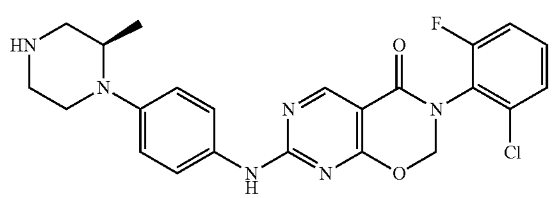 |
| 1.879 | 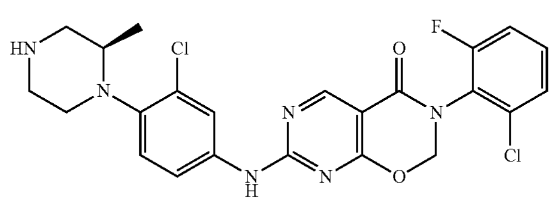 |

TABLE 1-continued
| Compound No. | Structure |
|---|---|
| 1.880 | 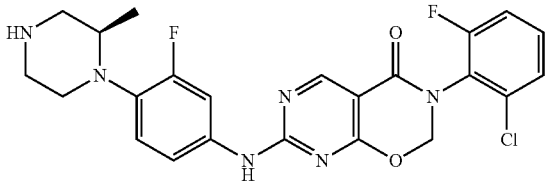 |
| 1.881 | 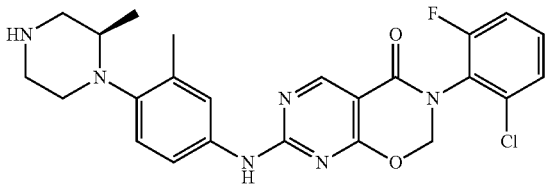 |
| 1.882 | 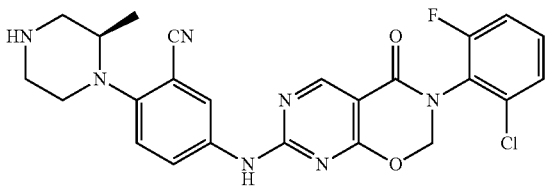 |
| 1.883 | 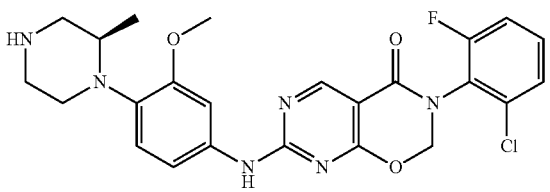 |
| 1.884 | 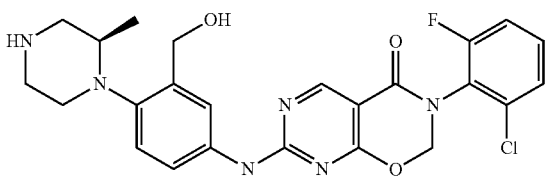 |
| 1.885 | 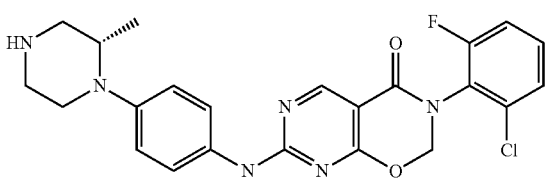 |
| 1.886 | 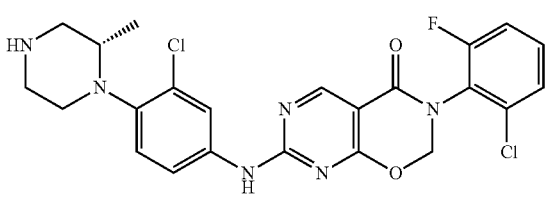 |
| 1.887 | 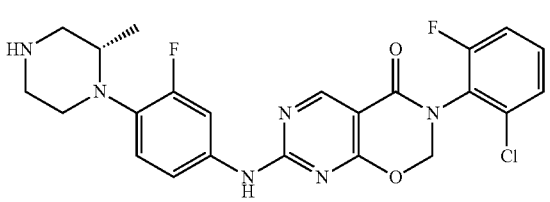 |

TABLE 1-continued
| Compound No. | Structure |
|---|---|
| 1.888 | 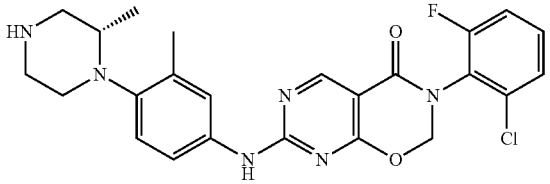 |
| 1.889 | 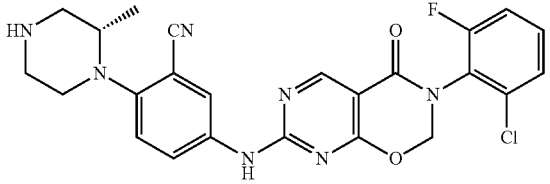 |
| 1.890 | 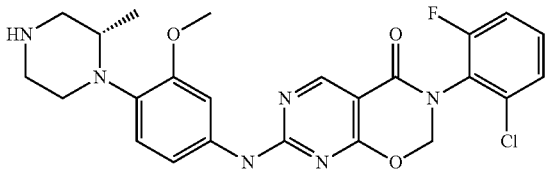 |
| 1.891 | 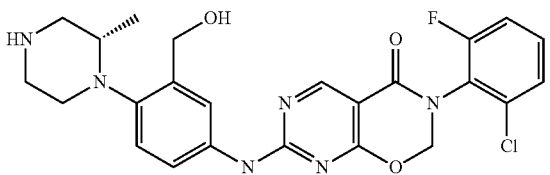 |
| 1.892 | 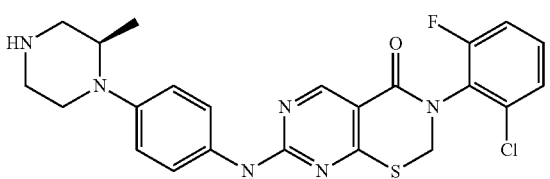 |
| 1.893 | 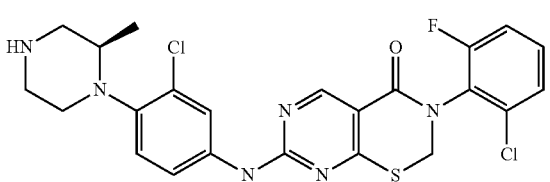 |
| 1.894 | 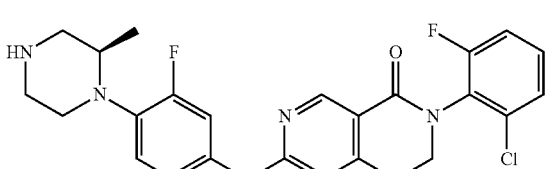 |
| 1.895 | 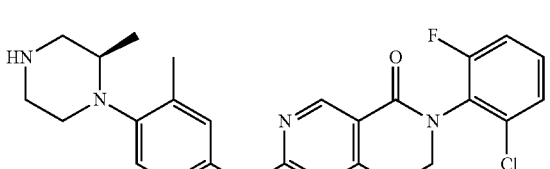 |

TABLE 1-continued
| Compound No. | Structure |
|---|---|
| 1.896 | 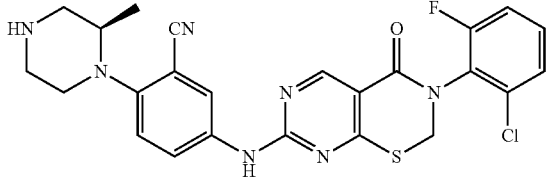 |
| 1.897 | 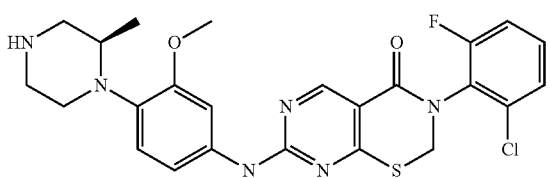 |
| 1.898 | 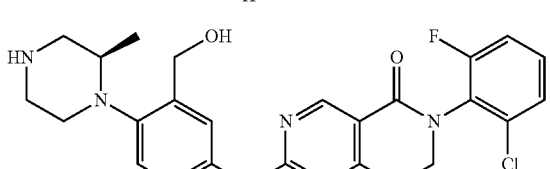 |
| 1.899 | 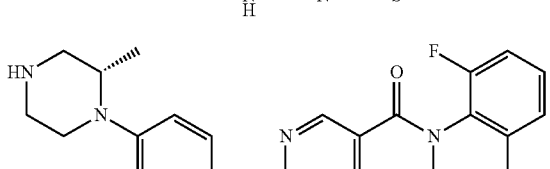 |
| 1.900 | 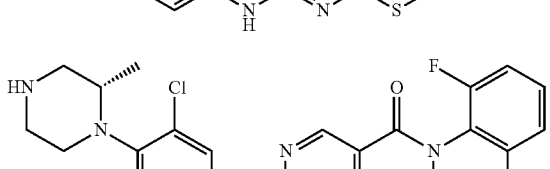 |
| 1.901 | 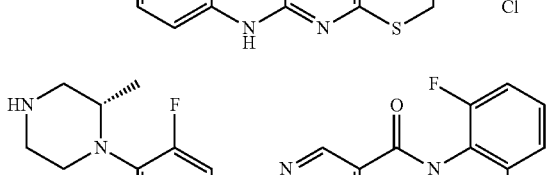 |
| 1.902 | 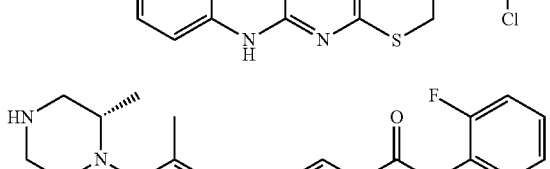 |
| 1.903 | 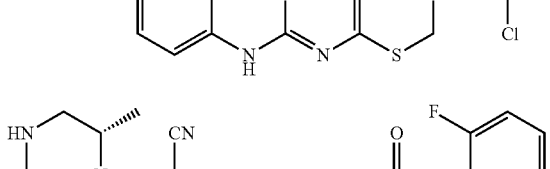 |

TABLE 1-continued
| Compound No. | Structure |
|---|---|
| 1.904 | 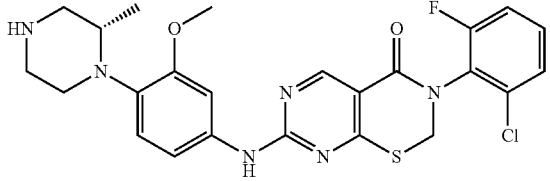 [SMILES: COc1cc(Nc2ncc3c(n2)SCN(c2c(F)cccc2Cl)C3=O)ccc1N1CCNC[C@@H]1C] |
| 1.905 | 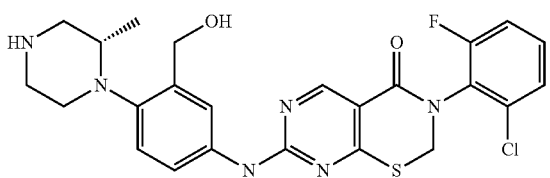 |
| 1.906 | 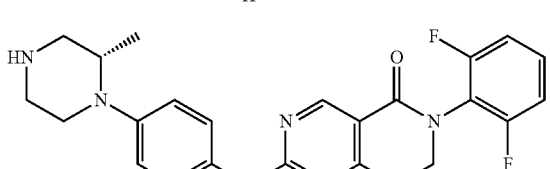 |
| 1.907 | 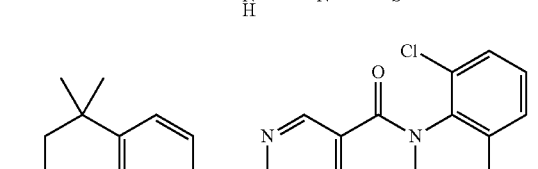 |
| 1.908 | 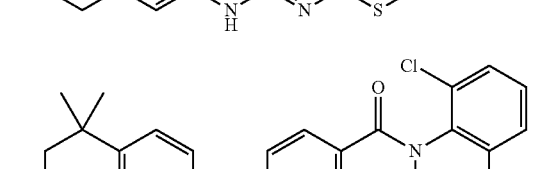 |
| 1.909 | 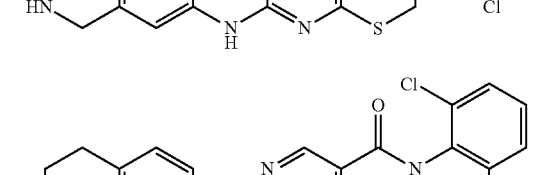 |
| 1.910 | 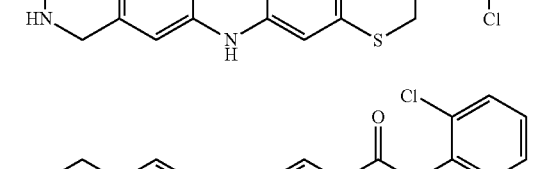 |
| 1.911 | 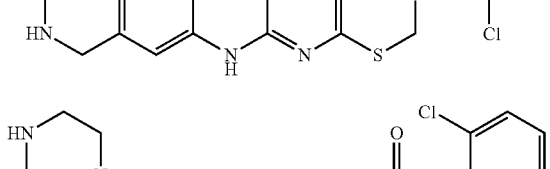 |

TABLE 1-continued

| Compound No. | Structure |
|---|---|
| 1.912 | 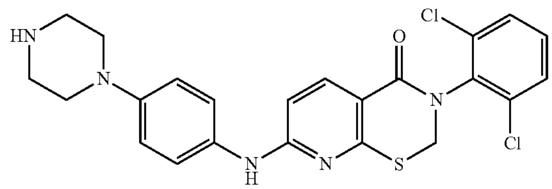 [SMILES: O=C1c2ccc(Nc3ccc(N4CCNCC4)cc3)nc2SCN1c1c(Cl)cccc1Cl] |
| 1.913 | 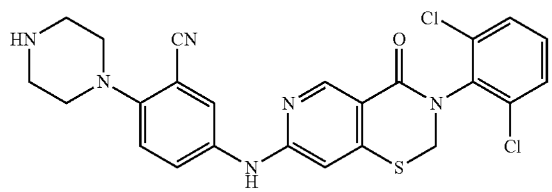 [SMILES: N#Cc1cc(Nc2cc3c(cn2)C(=O)N(c2c(Cl)cccc2Cl)CS3)ccc1N1CCNCC1] |
| 1.914 | 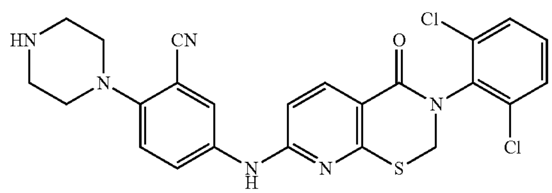 [SMILES: N#Cc1cc(Nc2ccc3c(n2)SCN(c2c(Cl)cccc2Cl)C3=O)ccc1N1CCNCC1] |
| 1.915 | 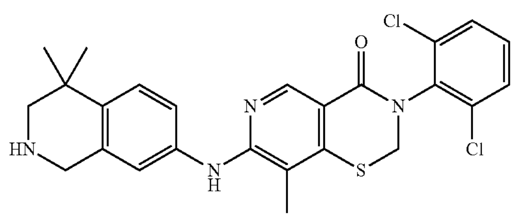 [SMILES: Cc1c(Nc2ccc3c(c2)CNCC3(C)C)ncc2c1SCN(c1c(Cl)cccc1Cl)C2=O] |
| 1.916 | 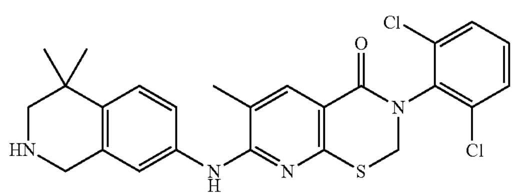 [SMILES: Cc1cc2c(nc1Nc1ccc3c(c1)CNCC3(C)C)SCN(c1c(Cl)cccc1Cl)C2=O] |
| 1.917 | 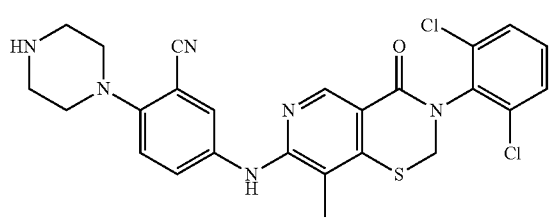 [SMILES: Cc1c(Nc2ccc(N3CCNCC3)c(C#N)c2)ncc2c1SCN(c1c(Cl)cccc1Cl)C2=O] |
| 1.918 | 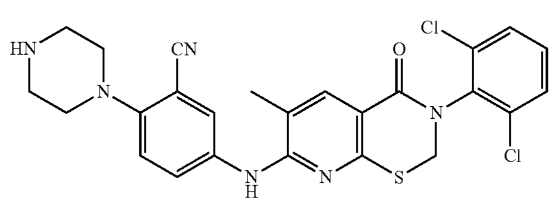 [SMILES: Cc1cc2c(nc1Nc1ccc(N3CCNCC3)c(C#N)c1)SCN(c1c(Cl)cccc1Cl)C2=O] |

TABLE 1-continued

| Compound No. | Structure |
|---|---|
| 1.919 | 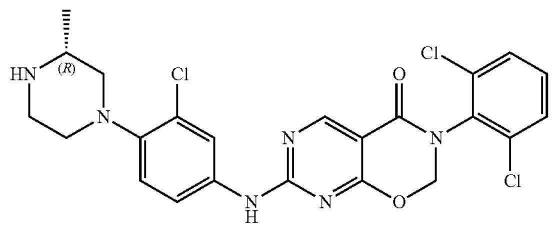 |
| 1.920 | 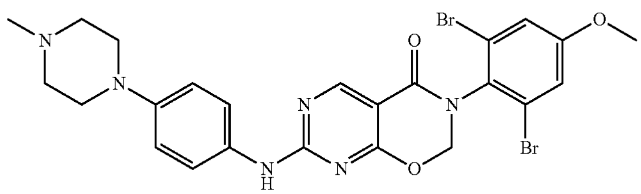 |
| 1.921 | 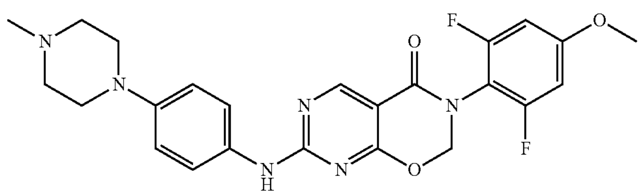 |
| 1.922 | 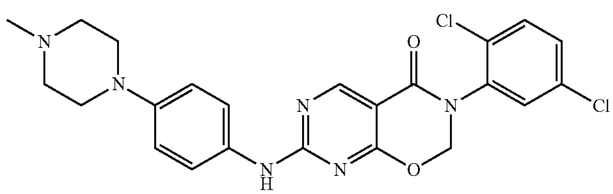 [SMILES: CN1CCN(c2ccc(Nc3ncc4c(n3)OCN(c3cc(Cl)ccc3Cl)C4=O)cc2)CC1] |
| 1.923 | 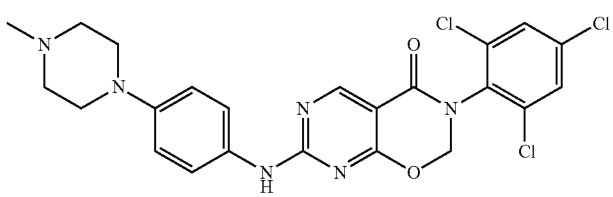 [SMILES: CN1CCN(c2ccc(Nc3ncc4c(n3)OCN(c3c(Cl)cc(Cl)cc3Cl)C4=O)cc2)CC1] |
| 1.924 | 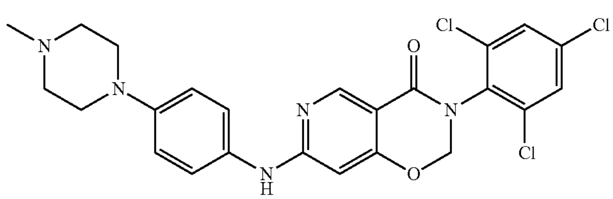 [SMILES: CN1CCN(c2ccc(Nc3cc4c(cn3)C(=O)N(c3c(Cl)cc(Cl)cc3Cl)CO4)cc2)CC1] |
| 1.925 | 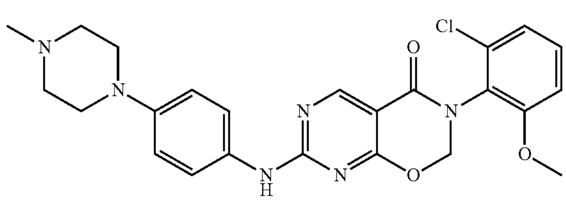 |

TABLE 1-continued
| Compound No. | Structure |
|---|---|
| 1.926 | 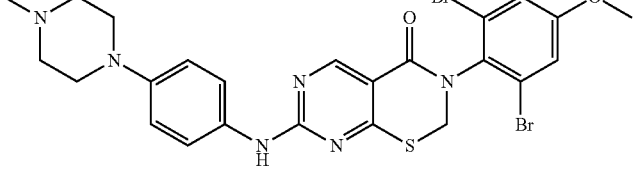 |
| 1.927 | 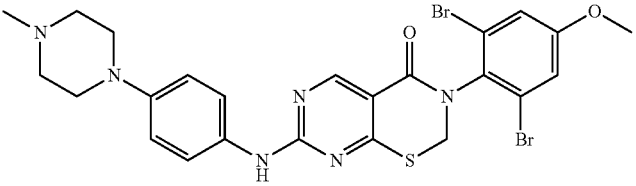 |
| 1.928 | 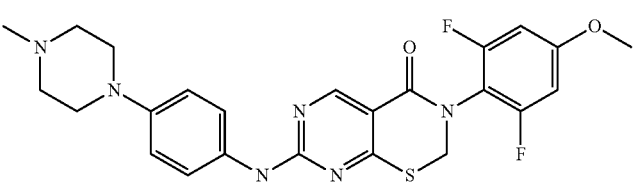 |
| 1.929 | 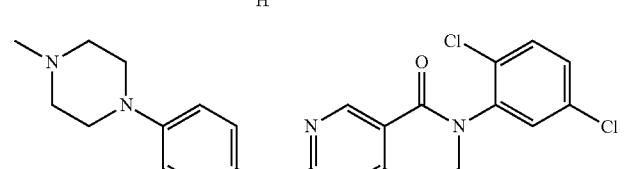 |
| 1.930 | 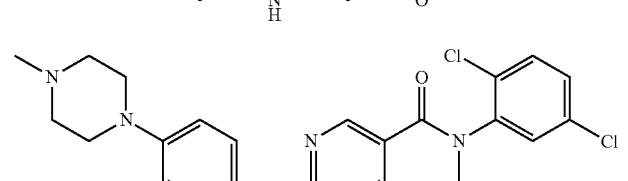 |
| 1.931 | 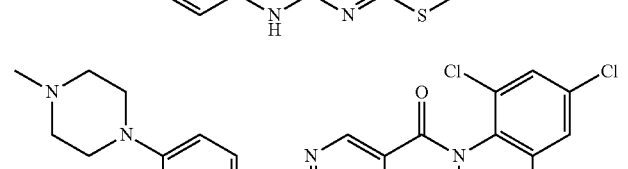 |
| 1.932 | 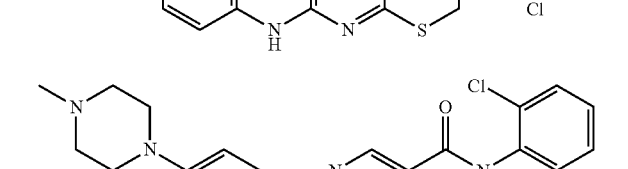 |
| 1.933 | 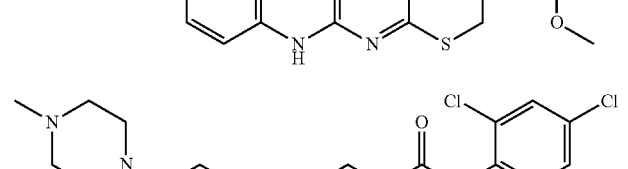 |

TABLE 1-continued
| Compound No. | Structure |
|---|---|
| 1.934 | 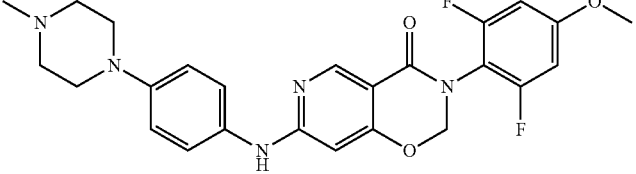 |
| 1.935 | 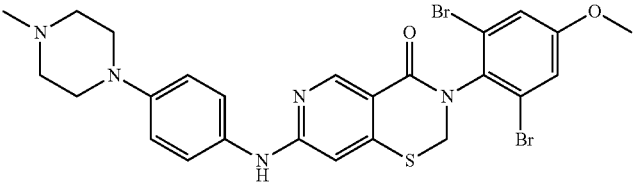 |
| 1.936 | 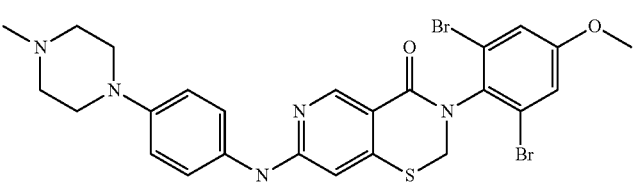 |
| 1.937 | 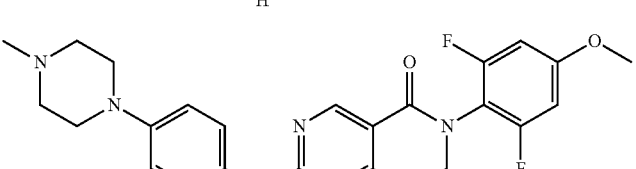 |
| 1.938 | 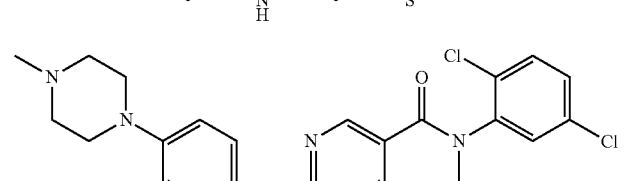 |
| 1.939 | 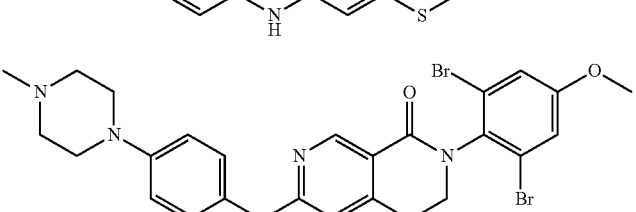 |
| 1.940 | 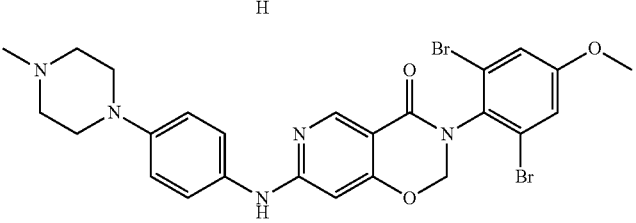 |
| 1.941 | 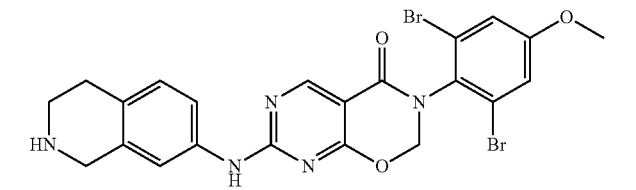 |

TABLE 1-continued

| Compound No. | Structure |
|---|---|
| 1.942 | 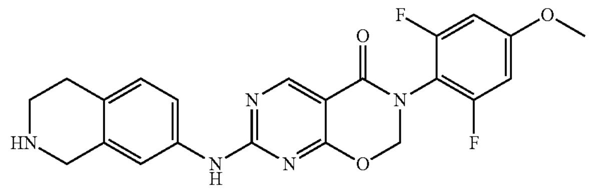 [SMILES: COc1cc(F)c(N2COc3nc(Nc4ccc5c(c4)CNCC5)ncc3C2=O)c(F)c1] |
| 1.943 | 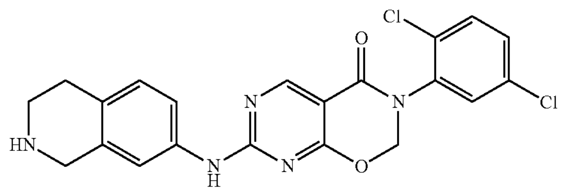 [SMILES: O=C1c2cnc(Nc3ccc4c(c3)CNCC4)nc2OCN1c1cc(Cl)ccc1Cl] |
| 1.944 | 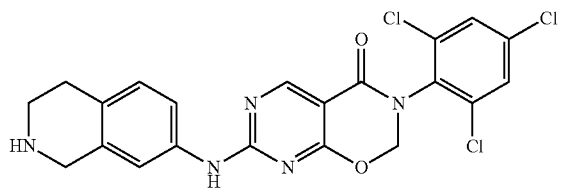 [SMILES: O=C1c2cnc(Nc3ccc4c(c3)CNCC4)nc2OCN1c1c(Cl)cc(Cl)cc1Cl] |
| 1.945 | 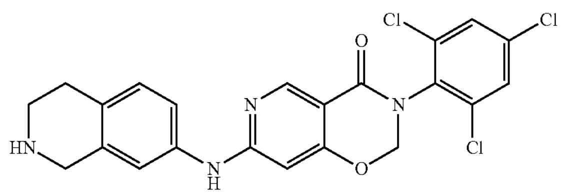 [SMILES: O=C1c2cnc(Nc3ccc4c(c3)CNCC4)cc2OCN1c1c(Cl)cc(Cl)cc1Cl] |
| 1.946 | 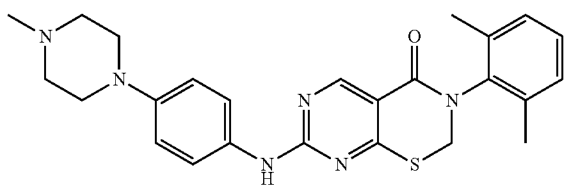 [SMILES: Cc1cccc(C)c1N1CSc2nc(Nc3ccc(N4CCN(C)CC4)cc3)ncc2C1=O] |
| 1.947 | 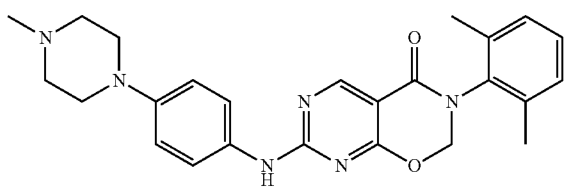 [SMILES: Cc1cccc(C)c1N1COc2nc(Nc3ccc(N4CCN(C)CC4)cc3)ncc2C1=O] |
| 1.948 | 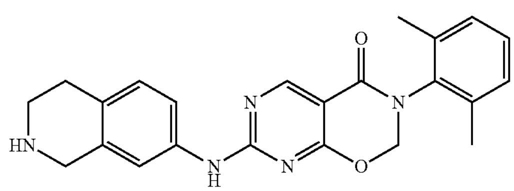 [SMILES: Cc1cccc(C)c1N1COc2nc(Nc3ccc4c(c3)CNCC4)ncc2C1=O] |
| 1.949 | 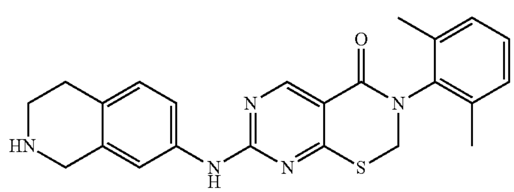 [SMILES: Cc1cccc(C)c1N1CSc2nc(Nc3ccc4c(c3)CNCC4)ncc2C1=O] |

TABLE 1-continued

| Compound No. | Structure |
|---|---|
| 1.950 | 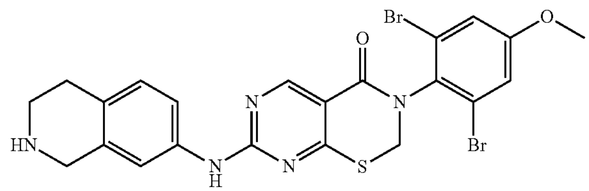 [SMILES: COc1cc(Br)c(N2CSc3nc(Nc4ccc5c(c4)CNCC5)ncc3C2=O)c(Br)c1] |
| 1.951 | 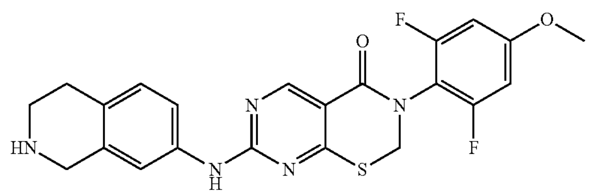 [SMILES: COc1cc(F)c(N2CSc3nc(Nc4ccc5c(c4)CNCC5)ncc3C2=O)c(F)c1] |
| 1.952 | 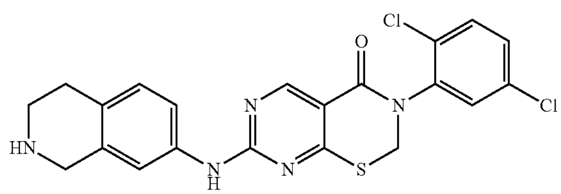 [SMILES: O=C1c2cnc(Nc3ccc4c(c3)CNCC4)nc2SCN1c1cc(Cl)ccc1Cl] |
| 1.953 | 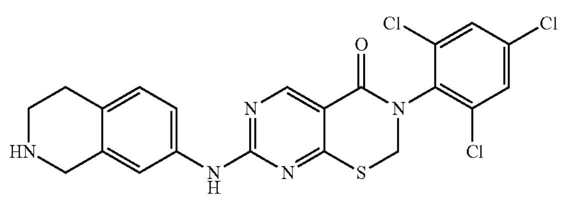 [SMILES: O=C1c2cnc(Nc3ccc4c(c3)CNCC4)nc2SCN1c1c(Cl)cc(Cl)cc1Cl] |
| 1.954 | 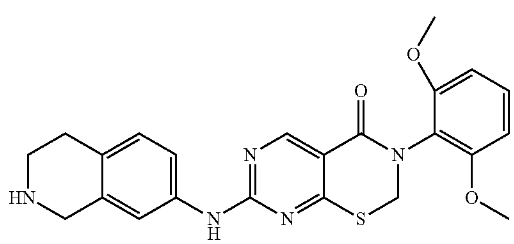 [SMILES: COc1cccc(OC)c1N1CSc2nc(Nc3ccc4c(c3)CNCC4)ncc2C1=O] |
| 1.955 | 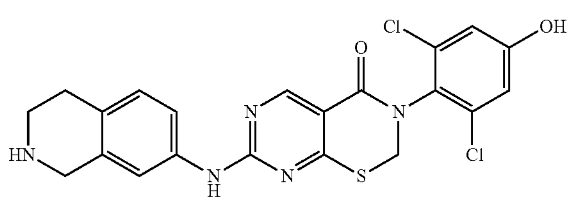 [SMILES: O=C1c2cnc(Nc3ccc4c(c3)CNCC4)nc2SCN1c1c(Cl)cc(O)cc1Cl] |
| 1.956 | 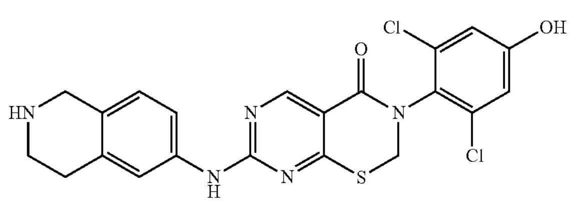 [SMILES: O=C1c2cnc(Nc3ccc4c(c3)CCNC4)nc2SCN1c1c(Cl)cc(O)cc1Cl] |

TABLE 1-continued
| Compound No. | Structure |
|---|---|
| 1.957 | 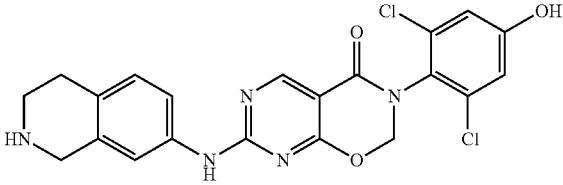 [SMILES: O=C1c2cnc(Nc3ccc4c(c3)CNCC4)nc2OCN1c1c(Cl)cc(O)cc1Cl] |
| 1.958 | 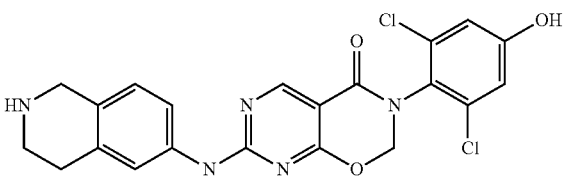 |
| 1.959 | 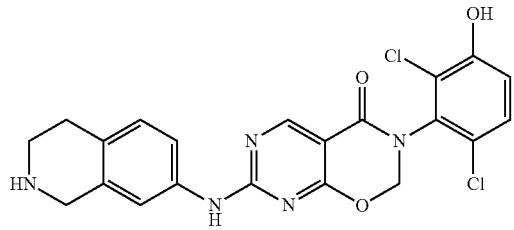 [SMILES: O=C1c2cnc(Nc3ccc4c(c3)CNCC4)nc2OCN1c1c(Cl)ccc(O)c1Cl] |
| 1.960 | 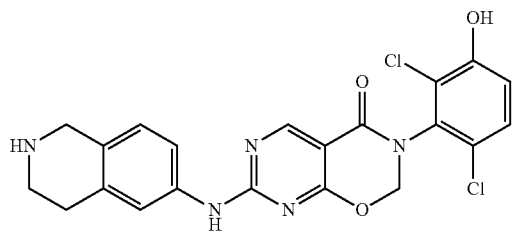 [SMILES: O=C1c2cnc(Nc3ccc4c(c3)CCNC4)nc2OCN1c1c(Cl)ccc(O)c1Cl] |
| 1.961 | 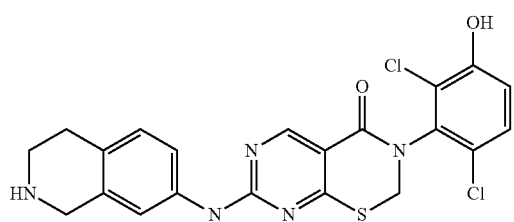 |
| 1.962 | 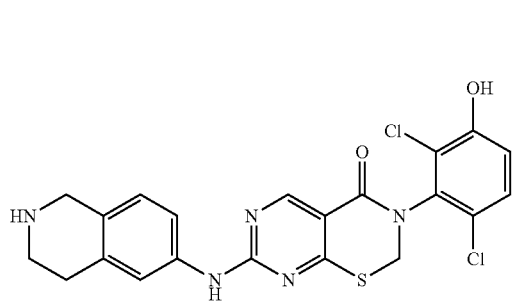 [SMILES: O=C1c2cnc(Nc3ccc4c(c3)CCNC4)nc2SCN1c1c(Cl)ccc(O)c1Cl] |

In some embodiments, provided herein is a compound described in Table 1, or a tautomer thereof, or a salt of any of the foregoing, and uses thereof. In some embodiments, provided herein is a compound described in Table 1, or a salt thereof. In some embodiments, provided herein is a compound described in Table 1, or a tautomer or isomer thereof, or a pharmaceutically acceptable salt of any of the foregoing.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein. It is understood that tautomeric forms of a compound of the formulae described herein may be present, for example, when tautomeric forms of a substituent are present, such as when a substituent embraces a keto-enol tautomer or the like.

The present disclosure also includes any or all of the stereochemical forms, including any enantiomeric or diastereomeric forms of the compounds described, such as compounds of Table 1. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of Formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2$H, $^3$H, $^{11}$C, $^{13}$C, $^{14}$C $^{13}$N, $^{15}$O, $^{17}$O, $^{32}$P, $^{35}$S, $^{18}$F, $^{36}$Cl. Certain isotope labeled compounds (e.g. $^3$H and $^{14}$C) are useful in compound or substrate tissue distribution studies. Incorporation of heavier isotopes such as deuterium ($^2$H) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate In some embodiments, compounds of Formula (I) may be synthesized according to Schemes 1-3.

Scheme 1

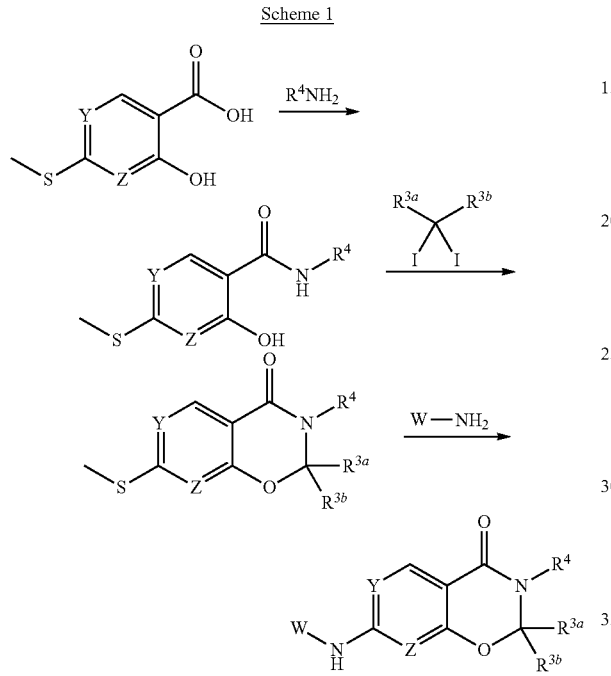

Scheme 2

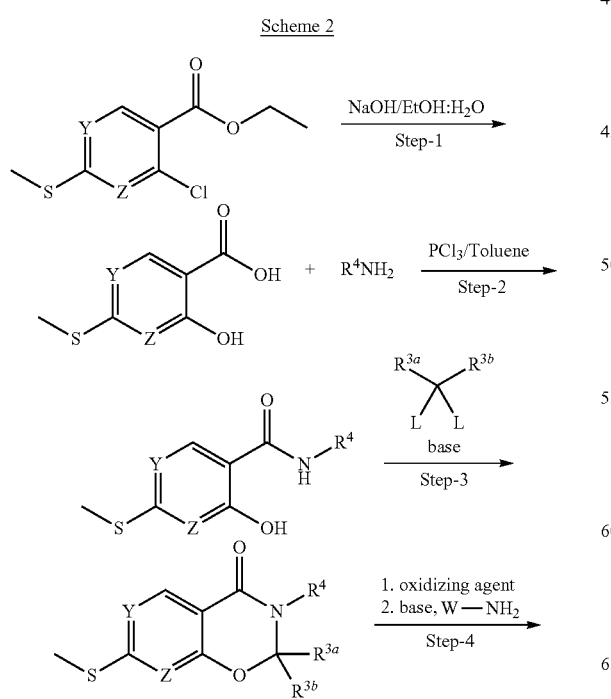

Scheme 3

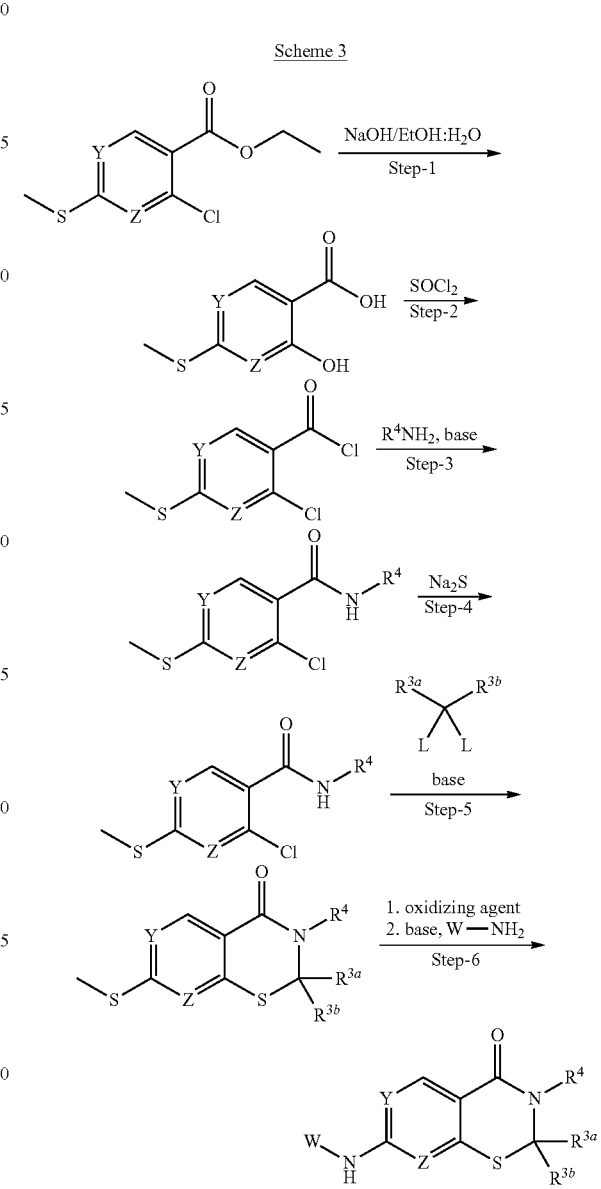

wherein W, Y, Z, $R^{3a}$, $R^{3b}$, and $R^4$ are as defined for Formula (I). Particular examples are provided in the Example Section below. Here L is a leaving group like Br, Cl or I etc.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. The present disclosure also includes pharmaceutical compositions comprising a compound as detailed herein or a tautomer or isomer thereof, or a pharmaceutically acceptable salt of any of the foregoing and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. Compounds and compositions detailed herein, such as a pharmaceutical composition containing a compound of any formula provided herein, or a tautomer or isomer thereof, or a pharmaceutically acceptable salt of any of the foregoing, and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease in an individual comprising administering an effective amount of a compound of Formula (I), (Ia), (Ib), (IIa), (IIb), (IIIa), (IIIb), (IVa) or (IVb), or any embodiment, variation or aspect thereof (collectively, a compound of Formula (I), (Ia), (Ib), (IIa), (IIb), (IIIa), (IIIb), (IVa) or (IVb), or the present compounds or the compounds detailed or described herein) or a pharmaceutically acceptable salt thereof, to the individual. Further provided herein is a method of treating a proliferative disease in an individual, comprising administering an effective amount of the compound of Formula (I), (Ia), (Ib), (IIa), (IIb), (IIIa), (IIIb), (IVa) or (IVb), or a pharmaceutically acceptable salt thereof, to the individual. Also provided herein is a method of treating cancer in an individual comprising administering an effective amount of the compound of Formula (I), (Ia), (Ib), (IIa), (IIb), (IIIa), (IIIb), (IVa) or (IVb), or a pharmaceutically acceptable salt thereof, to the individual. In some embodiments, the compound is administered to the individual according to a dosage and/or method of administration described herein.

In some embodiments, the cancer in the individual has one or more TP53 gene mutations or expresses mutant p53. TP53 is the human gene that encodes p53. In some embodiments, provided herein is a method of treating a cancer in an individual, comprising (a) selecting the individual for treatment based on (i) the presence of one or more mutations of the TP53 gene in the cancer, or (ii) expression of mutant p53 in the cancer, and administering an effective amount of the compound of Formula (I), (Ia), (Ib), (IIa), (IIb), (IIIa), (IIIb), (IVa) or (IVb), or a pharmaceutically acceptable salt thereof, to the individual. In some embodiments, the cancer is assayed for the expression of mutant p53. In some embodiments, the TP53 gene of the cancer is sequenced to detect the one or more mutations. In some embodiments, the TP53 gene is sequenced by biopsying the cancer and sequencing the TP53 gene from the biopsied cancer. In some embodiments, the TP53 gene is sequenced by sequencing circulating-tumor DNA (ctDNA) from the individual.

In some embodiments, provided herein is a method of using a compound of Formula (I), (Ia), (Ib), (IIa), (IIb), (IIIa), (IIIb), (IVa) or (IVb), or any embodiment in the manufacture of a medicament for treatment of a disease. In some embodiments, provided herein is a method of using a compound of Formula (I), (Ia), (Ib), (IIa), (IIb), (IIIa), (IIIb), (IVa) or (IVb), or any embodiment in the manufacture of a medicament for treatment of cancer.

In some embodiments, a compound of formula (I), (Ia), (Ib), (IIa), (IIb), (IIIa), (IIIb), (IVa) or (IVb), or a salt thereof is used to treat an individual having a proliferative disease, such as cancer as described herein. In some embodiments, the individual is at risk of developing a proliferative disease, such as cancer. In some of these embodiments, the individual is determined to be at risk of developing cancer based upon one or more risk factors. In some of these embodiments, the risk factor is a family history and/or gene associated with cancer.

The present compounds or salts thereof are believed to be effective for treating a variety of diseases and disorders. For example, in some embodiments, the present compositions may be used to treat a proliferative disease, such as cancer. In some embodiments the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma, cutaneous T cell lymphoma, Hodgkin's lymphoma, non-Hodgkin's lymphoma, cancer of the adrenal cortex, ACTH-producing tumors, lung cancer, including small cell carcinoma and nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the compounds and compositions described herein suppress $G_2$-M checkpoint in a cell (such as a cancer cell). In some embodiments, the cancer cell is a cancer cell from any of the cancer types described herein. Suppression of the $G_2$-M DNA damage checkpoint results in premature mitosis of the cell, and consequently apoptosis. In some embodiments, provided herein is a method of suppressing the $G_2$-M DNA damage checkpoint in a cell comprising administering an effective amount of the compound of Formula (I), (Ia), (Ib), (IIa), (IIb), (IIIa), (IIIb), (IVa) or (IVb), or a pharmaceutically acceptable salt thereof, to the cell. In some embodiments, the $G_2$-M DNA damage checkpoint is suppressed in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, the $G_2$-M DNA damage checkpoint is suppressed in up to about 99%, up to about 98%, up to about 97%, up to about 96%, up to about 95%, up to about 90%, up to about 85%, or up to about 80% of cells in the cell population.

In some embodiments, provided herein is a method of inducing premature mitosis in a cell comprising administering an effective amount of the compound of Formula (I), (Ia), (Ib), (IIa), (IIb), (IIIa), (IIIb), (IVa) or (IVb), or a pharmaceutically acceptable salt thereof, to the cell. In some embodiments, premature mitosis is induced in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, premature mitosis is induced in up to about 99%, up to about 98%, up to about 97%, up to about 96%, up to about 95%, up to about 90%, up to about 85%, or up to about 80% of cells in the cell population.

In some embodiments, provided herein is a method of inducing apoptosis in a cell comprising administering an effective amount of the compound of Formula (I), (Ia), (Ib), (IIa), (IIb), (IIIa), (IIIb), (IVa) or (IVb), or a pharmaceutically acceptable salt thereof, to the cell. In some embodiments, apoptosis is induced in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, apoptosis is induced in up to about 99%, up to about 98%, up to about 97%, up to about 96%, up to about 95%, up to about 90%, up to about 85%, or up to about 80% of cells in the cell population.

In some embodiments, provided herein is a method of inhibiting Wee1 in a cell comprising administering an effective amount of the compound of Formula (I), (Ia), (Ib), (IIa), (IIb), (IIIa), (IIIb), (IVa) or (IVb), or a pharmaceutically acceptable salt thereof, to the cell. In some embodiments, Wee1 is inhibited by about 10% or more, about 20% or more, about 30% or more, about 40% or more, about 50% or more, about 60% or more, about 70% or more, about 75% or more, about 80% or more, about 90% or more, about 95% or more, about 96% or more, about 97% or more, about 98% or more, or about 99% or more. In some embodiments, Wee1 is inhibited up to about 99%, up to about 98%, up to about 97%, up to about 96%, up to about 95%, up to about 90%, up to about 85%, up to about 80%, up to about 70%, or up to about 60%. In some embodiments, the activity of Wee1 is measured according to a kinase assay.

In some embodiments, provided herein is a method of inhibiting Wee1 comprising contacting Wee1 with an effective amount of the compound of Formula (I), (Ia), (Ib), (IIa), (IIb), (IIIa), (IIIb), (IVa) or (IVb), or a pharmaceutically acceptable salt thereof. In some embodiments, the compound of Formula (I), (Ia), (Ib), (IIa), (IIb), (IIIa), (IIIb), (IVa) or (IVb), or a pharmaceutically acceptable salt thereof binds to Wee1 with an $IC_{50}$ of less than 1 μM, less than 900 nM, less than 800 nM, less than 700 nM, less than 600 nM, less than 500 nM, less than 400 nM, less than 300 nM, less than 200 nM, less than 100 nM, less than 50 nM, or less than 10 nM. In some embodiments, the compound of Formula (I) or a pharmaceutically acceptable salt thereof binds to Wee1 with an $IC_{50}$ between 1 nM and 10 nM, between 10 nM and 50 nM, between 50 nM and 100 nM, between 100 nM and 200 nM, between 200 nM and 300 nM, between 300 nM and 400 nM, between 400 nM and 500 nM, between 500 nM and 600 nM, between 600 nM and 700 nM, between 700 nM and 800 nM, between 800 nM and 900 nM, or between 900 nM and 1 μM. In some embodiments, the $IC_{50}$ is measured according to a kinase assay. In some embodiments, the $IC_{50}$ is measured according to a cell cytotoxicity assay.

In some embodiments, provided herein is a method of inhibiting the proliferation of a cell, comprising contacting the cell with an effective amount of the compound of Formula (I), (Ia), (Ib), (IIa), (IIb), (IIIa), (IIIb), (IVa) or (IVb), or a pharmaceutically acceptable salt thereof. In some embodiments, the compound of Formula (I), (Ia), (Ib), (IIa), (IIb), (IIIa), (IIIb), (IVa) or (IVb), or a pharmaceutically acceptable salt thereof is effective in inhibiting the proliferation of the cell with an $IC_{50}$ of less than 10 μM, less than 5 μM, or less than 2 μM, or less than 1 μM. In some embodiments, the compound of Formula (I), (Ia), (Ib), (IIa), (IIb), (IIIa), (IIIb), (IVa) or (IVb), or a pharmaceutically acceptable salt is effective in inhibiting the proliferation of the cell with an $IC_{50}$ between 1 μM and 2 μM, between 2 μM and 2 μM, or between 2 μM and 10 μM. In some embodiments, the $IC_{50}$ is measured according to a cell proliferation assay.

Combination Therapy

As provided herein, the presently disclosed compounds or a salt thereof may activate the immune system, for example by inducing apoptosis or suppressing mitosis of cancer cells. Accordingly, the present compounds or a salt thereof may be used in combination with other anti-cancer agents to enhance tumor immunotherapy. In some embodiments, provided herein is a method of treating a disease in an individual comprising administering an effective amount of a compound of Formula (I), (Ia), (Ib), (IIa), (IIb), (IIIa), (IIIb), (IVa) or (IVb), or a pharmaceutically acceptable salt thereof, and an additional therapeutic agent to the individual. In some embodiments, the disease is a proliferative disease such as cancer.

In some embodiments, the additional therapeutic agent is a cancer immunotherapy agent. In some embodiments, the additional therapeutic agent is a chemotherapeutic agent. In some embodiments, the additional therapeutic agent is an immunostimulatory agent. In some embodiments, the additional therapeutic agent targets a checkpoint protein (for example an immune checkpoint inhibitor). In some embodiments, the additional therapeutic agent is effective to stimulate, enhance or improve an immune response against a tumor. In some embodiments, the additional chemotherapeutic agent is a DNA alkylating agent, a platinum-based chemotherapeutic agent, a kinase inhibitor or a DNA damage repair (DDR) pathway inhibitor. In some embodiments, the additional chemotherapeutic agent is a DNA alkylating agent. In some embodiments, the additional chemotherapeutic agent is a platinum-based chemotherapeutic agent. In some embodiments, the additional chemotherapeutic agent is a kinase inhibitor. In some embodiments, the additional chemotherapeutic agent is a DNA damage repair (DDR) pathway inhibitor.

In another aspect, provided herein is a combination therapy for the treatment of a disease, such as cancer. In some embodiments, provided herein is a method of treating a disease in an individual comprising administering an effective amount of a compound of Formula (I), (Ia), (Ib), (IIa), (IIb), (IIIa), (IIIb), (IVa) or (IVb), or a pharmaceutically acceptable salt thereof, in combination with a radiation therapy.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of an additional chemotherapeutic agent. In some embodiments, the chemotherapeutic agent is a kinase inhibitor or an agent that inhibits one or more DNA damage repair (DDR) pathways. In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the additional chemotherapeutic agent. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the additional chemotherapeutic agent.

Examples of chemotherapeutic agents that can be used in combination with a compound of Formula (I), (Ia), (Ib), (IIa), (IIb), (IIIa), (IIIb), (IVa) or (IVb), or a pharmaceutically acceptable salt thereof include DNA-targeted agents, a DNA alkylating agent (such as cyclophosphamide, mechlorethamine, chlorambucil, melphalan, dacarbazine, or nitrosoureas), a topoisomerase inhibitor (such as a Topoisomerase I inhibitor (e.g., irinotecan or topotecan) or a Topoisomerase II inhibitor (e.g., etoposide or teniposide)), an anthracycline (such as daunorubicin, doxorubicin, epirubicin, idarubicin, mitoxantrone, or valrubicin), a histone deacetylase inhibitor (such as vorinostat or romidepsin), a bromodomain inhibitor, other epigenetic inhibitors, a taxane (such as paclitaxel or docetaxel), a kinase inhibitor (such as bortezomib, erlotinib, gefitinib, imatinib, vemurafenib, or vismodegib), an anti-angiogenic inhibitor, a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine), or a platinum-based chemotherapeutic agent (such as cisplatin, carboplatin, or oxaliplatin), pemetrexed, or a combination thereof.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a kinase inhibitor (such as bortezomib, erlotinib, gefitinib, imatinib, vemurafenib, or vismodegib). In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the kinase inhibitor. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the kinase inhibitor.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a DNA damaging agent. In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the DNA damaging agent. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the DNA damaging agent.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a DNA alkylating agent (such as cyclophosphamide, mechlorethamine, chlorambucil, melphalan, dacarbazine, or nitrosoureas). In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the DNA alkylating agent. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the DNA alkylating agent.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a topoisomerase inhibitor (such as a Topoisomerase I inhibitor (e.g., irinotecan or topotecan) or a Topoisomerase II inhibitor (e.g., etoposide or teniposide)). In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the topoisomerase inhibitor. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the topoisomerase inhibitor.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of an anthracycline (such as daunorubicin, doxorubicin, epirubicin, idarubicin, mitoxantrone, or valrubicin). In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the anthracycline. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the anthracycline.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a histone deacetylase inhibitor (such as vorinostat or romidepsin). In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the histone deacetylase inhibitor. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the histone deacetylase inhibitor.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a taxane (such as paclitaxel or docetaxel). In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the taxane. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the taxane.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine). In some embodiments, a compound of Formula (I) or a pharmaceutically acceptable salt thereof is administered prior to, after, or simultaneously co-administered with the nucleotide analog or precursor analog. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the nucleotide analog or precursor analog.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a platinum-based chemotherapeutic agent (such as cisplatin, carboplatin, or oxaliplatin).

In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the platinum-based chemotherapeutic agent. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the platinum-based chemotherapeutic agent.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of pemetrexed. In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the pemetrexed. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the pemetrexed.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a DDR pathway inhibitor. In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the DDR pathway inhibitor. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the DDR pathway inhibitor. Examples of inhibitors of the DDR pathway include poly (ADP-ribose) polymerase (PARP) inhibitors (such as olaparib, rucaparib, niraparib, or talazoparib), ataxia telangiectasia mutated (ATM) protein inhibitors, ataxia telangiectasia and Rad3-related (ATR) protein inhibitors, checkpoint kinase 1 (Chk1) inhibitors, or combinations thereof.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of a PARP inhibitor (such as olaparib, rucaparib, niraparib, or talazoparib). In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the PARP inhibitor. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the PARP inhibitor.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of an ATM protein inhibitor. In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the ATM protein inhibitor. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the ATM protein inhibitor.

In some embodiments, provided herein is a method of treating a disease in an individual comprising (a) administering an effective amount of a compound of Formula (I), (Ia), (Ib), (IIa), (IIb), (IIIa), (IIIb), (IVa) or (IVb), or a pharmaceutically acceptable salt thereof, and (b) administering an effective amount of an ATR protein inhibitor. In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the ATR protein inhibitor. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the ATR protein inhibitor.

In some embodiments, provided herein is a method of treating a disease in an individual comprising (a) administering an effective amount of a compound of (I), (Ia), (Ib), (IIa), (IIb), (IIIa), (IIIb), (IVa) or (IVb), or a pharmaceutically acceptable salt thereof, and (b) administering an effective amount of an Chk1 inhibitor. In some embodiments, a compound of Formula (I), (Ia), (Ib), (IIa), (IIb), (IIIa), (IIIb), (IVa) or (IVb), or a pharmaceutically acceptable salt thereof is administered prior to, after, or simultaneously co-administered with the Chk1 inhibitor. In some embodiments, a compound of Formula (I), (Ia), (Ib), (IIa), (IIb), (IIIa), (IIIb), (IVa) or (IVb), or a pharmaceutically acceptable salt thereof is administered 1 or more hours (such as 2 or more hours, 4 or more hours, 8 or more hours, 12 or more hours, 24 or more hours, or 48 or more hours) prior to or after the Chk1 inhibitor.

In another aspect, provided herein is a combination therapy in which a compound of Formula (I), (Ia), (Ib), (IIa), (IIb), (IIIa), (IIIb), (IVa) or (IVb), is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of Formula (I), (Ia), (Ib), (IIa), (IIb), (IIIa), (IIIb), (IVa) or (IVb), or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of Formula (I), (Ia), (Ib), (IIa), (IIb), (IIIa), (IIIb), (IVa) or (IVb), or a salt thereof and an anti-PD-1 antibody. In another embodiment, the subject is administered a compound of Formula (I), (Ia), (Ib), (IIa), (IIb), (IIIa), (IIIb), (IVa) or (IVb), or a salt thereof and an anti-PD-L1 antibody. In yet another embodiment, the subject is administered a compound of Formula (I), (Ia), (Ib), (IIa), (IIb), (IIIa), (IIIb), (IVa) or (IVb), or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody).

In one embodiment, the present disclosure provides a method for treating a proliferative disease (e.g., cancer), comprising administering a compound of Formula (I), (Ia), (Ib), (IIa), (IIb), (IIIa), (IIIb), (IVa) or (IVb), or a salt thereof and an anti-PD-1 antibody to a subject. In further embodiments, a compound of Formula (I), (Ia), (Ib), (IIa), (IIb), (IIIa), (IIIb), (IVa) or (IVb), or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of Formula (I), (Ia), (Ib), (IIa), (IIb), (IIIa), (IIIb), (IVa) or (IVb), or a salt thereof and a subtherapeutic dose of anti-PD-1 antibody to a subject. In certain embodiments, the subject is human. In certain embodiments, the anti-PD-1 antibody is a human sequence monoclonal antibody.

In one embodiment, the present invention provides a method for treating a hyperproliferative disease (e.g., cancer), comprising administering a compound of Formula (I), (Ia), (Ib), (IIa), (IIb), (IIIa), (IIIb), (IVa) or (IVb), or a salt thereof and an anti-PD-L1 antibody to a subject. In further embodiments, a compound of Formula (I), (Ia), (Ib), (IIa), (IIb), (IIIa), (IIIb), (IVa) or (IVb), or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of Formula (I), (Ia), (Ib), (IIa), (IIb), (IIIa), (IIIb), (IVa) or (IVb), or a salt thereof and a subtherapeutic dose of anti-PD-L1 antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of Formula (I), (Ia), (Ib), (IIa), (IIb), (IIIa), (IIIb), (IVa) or (IVb), or a salt thereof can be administered sequentially, such as anti-CTLA-4 antibody being administered first and a compound of Formula (I), (Ia), (Ib), (IIa), (IIb), (IIIa), (IIIb), (IVa) or (IVb), or a salt thereof second, or a compound of Formula (I), (Ia), (Ib), (IIa), (IIb), (IIIa), (IIIb), (IVa) or (IVb), or a salt thereof being administered first and anti-CTLA-4 antibody second. Additionally or alternatively, an anti-PD-1 antibody and a compound of Formula (I), (Ia), (Ib), (IIa), (IIb), (IIIa), (IIIb), (IVa) or (IVb), or a salt thereof can be administered sequentially, such as anti-PD-1 antibody being administered first and a compound of Formula (I), (Ia), (Ib), (IIa), (IIb), (IIIa), (IIIb), (IVa) or (IVb), or a salt thereof second, or a compound of Formula (I), (Ia), (Ib), (IIa), (IIb), (IIIa), (IIIb), (IVa) or (IVb), or a salt thereof being administered first and anti-PD-1 antibody second. Additionally or alternatively, an anti-PD-L1 antibody and a compound of Formula (I), (Ia), (Ib), (IIa), (IIb), (IIIa), (IIIb), (IVa) or (IVb), or a salt thereof can be administered sequentially, such as anti-PD-L1 antibody being administered first and a compound of Formula (I), (Ia), (Ib), (IIa), (IIb), (IIIa), (IIIb), (IVa) or (IVb), or a salt thereof second, or a compound of Formula (I), (Ia), (Ib), (IIa), (IIb), (IIIa), (IIIb), (IVa) or (IVb), or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of Formula (I), (Ia), (Ib), (IIa), (IIb), (IIIa), (IIIb), (IVa) or (IVb), or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of Formula (I), (Ia), (Ib), (IIa), (IIb), (IIIa), (IIIb), (IVa) or (IVb), or a salt thereof can also be further combined with standard cancer treatments. For example, a compound of Formula (I), (Ia), (Ib), (IIa), (IIb), (IIIa), (IIIb), (IVa) or (IVb), or a salt thereof can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). Other combination therapies with a compound of Formula (I), (Ia), (Ib), (IIa), (IIb), (IIIa), (IIIb), (IVa) or (IVb), or a salt thereof include radiation, surgery, or hormone deprivation. Angiogenesis inhibitors can also be combined with a compound of Formula (I), (Ia), (Ib), (IIa), (IIb), (IIIa), (IIIb), (IVa) or (IVb), or a salt thereof. Inhibition of angiogenesis leads to tumor cell death, which can be a source of tumor antigen fed into host antigen presentation pathways.

In another example, a compound of Formula (I), (Ia), (Ib), (IIa), (IIb), (IIIa), (IIIb), (IVa) or (IVb), or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of Formula (I), (Ia), (Ib), (IIa), (IIb), (IIIa), (IIIb), (IVa) or (IVb), or a salt thereof. In an exemplary embodiment, a treatment of a hyperproliferative disease (e.g., a cancer tumor) can include an anti-cancer antibody in combination with a compound of Formula (I), (Ia), (Ib), (IIa), (IIb), (IIIa), (IIIb), (IVa) or (IVb), or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of Formula (I), (Ia), (Ib), (IIa), (IIb), (IIIa), (IIIb), (IVa) or (IVb), or a salt thereof.

In some embodiments, a compound of Formula (I), (Ia), (Ib), (IIa), (IIb), (IIIa), (IIIb), (IVa) or (IVb), or a salt thereof can be combined with an anti-CD73 therapy, such as an anti-CD73 antibody.

In yet further embodiments, the compound of Formula (I), (Ia), (Ib), (IIa), (IIb), (IIIa), (IIIb), (IVa) or (IVb), or a salt thereof is administered in combination with another Wee1 inhibitor.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The present disclosure further provides kits for carrying out the methods of the invention, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

Example S1. Synthesis of 3-(2,6-dichlorophenyl)-7-((4-(4-methylpiperazin-1-yl)phenyl)amino)-2,3-dihydro-4H-pyrimido[5,4-e][1,3]oxazin-4-one (Compound No. 1.1)

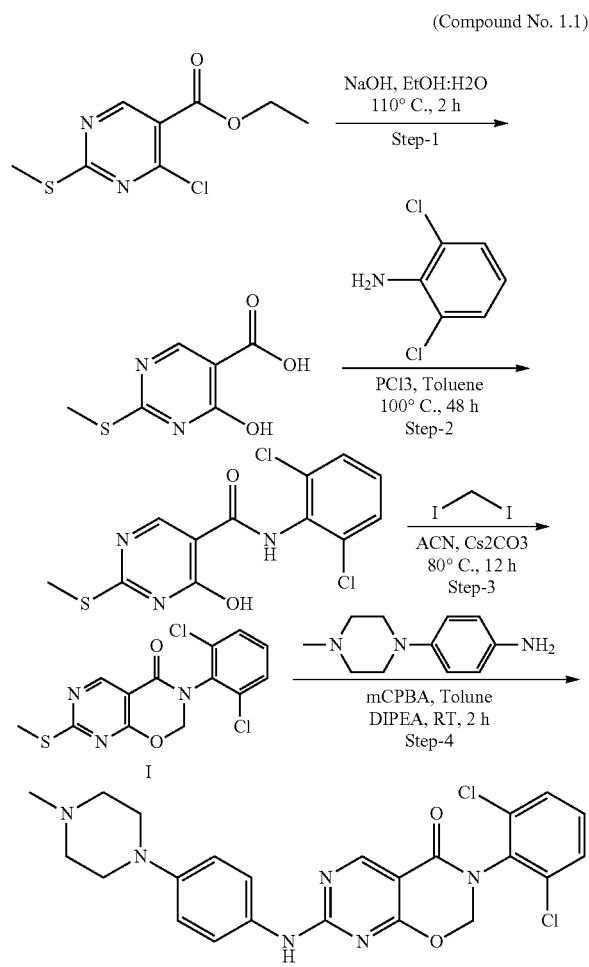

Step-1: Synthesis of 4-hydroxy-2-methylsulfanyl-pyrimidine-5-carboxylic Acid To a stirred solution of ethyl 4-chloro-2-methylsulfanyl-pyrimidine-5-carboxylate (10 g, 43.1 mmol, 1.0 eq) in 150 mL of ethanol:water (2:1) was added NaOH (17.2 g, 431 mmol, 10 eq). Reaction was heated at 110° C. for 2 h. Progress of reaction was monitored by LCMS. Upon the consumption of starting material, solvent was removed under reduced pressure. Residue was diluted with 100 mL of water and pH of mixture was adjusted up to 5 with 3N HCl solution. Precipitated compound was filtered off, washed with water (50 mL) and dried under vacuum to obtain the desired product, 4-hydroxy-2-methyl sulfanyl-pyrimidine-5-carboxylic acid (6.0 g, 75%).

LCMS: 187 [M+1]$^+$

Step-2: Synthesis of N-(2,6-dichlorophenyl)-4-hydroxy-2-methylsulfanyl-pyrimidine-5-carboxamide A stirred solution of N-(2,6-dichlorophenyl)-4-hydroxy-2-methylsulfanyl-pyrimidine-5-carboxamide (6.0 g, 32.2 mmol, 1.0 eq) and 2,6-dichloroaniline (5.20 g, 32.2 mmol, 1.0 eq) in 200 mL of toluene was purged with nitrogen gas for 15 min. To the above solution PCl$_3$ (30 mL) was added. Reaction mixture was heated at 100° C. for 48 h. Progress of reaction was monitored by LCMS. After completion of reaction, solvent was removed under reduced pressure, residue was diluted with 100 mL of mixture of diethyl ether:MeOH (10:1), stirred for 15 min then filtered off. Solid was suspended in MeOH (20 mL), stirred for 5 min, filtered off and washed with MeOH (10 mL), and then dried under vacuum to obtain N-(2,6-dichlorophenyl)-4-hydroxy-2-methylsulfanyl-pyrimidine-5-carboxamide (6.0 g, 57%).

LCMS: 330 [M+1]$^+$

Step-3: Synthesis of 3-(2,6-dichlorophenyl)-7-methylsulfanyl-2H-pyrimido[5,4-e][1,3]oxazin-4-one To a solution of N-(2,6-dichlorophenyl)-4-hydroxy-2-methylsulfanyl-pyrimidine-5-carboxamide (4.0 g, 12.1 mmol, 1.0 eq) in CH$_3$CN (200 mL) was added CH$_2$I$_2$ (4.90 g, 18.5 mmol, 1.5 eq) and Cs$_2$CO$_3$ (12.0 g, 36.4 mmol, 3.0 eq). Reaction mixture was heated at 80° C. for 12 h. Progress of reaction was monitored by LCMS. After completion of the reaction, solvent was removed under reduced pressure, residue was diluted with 50 mL of water and extracted with ethyl acetate (100 mL×3). The combined organic layer was washed with water (50 mL×3), dried over anhydrous Na$_2$SO$_4$ and concentrated under reduced pressure. Crude product obtained was purified by flash chromatography using ethyl acetate: hexane (3-5%) as eluents to obtain 3-(2,6-dichlorophenyl)-7-methylsulfanyl-2H-pyrimido[5,4-e][1,3]oxazin-4-one (400 mg, 10%).

LCMS: 342 [M+1]$^+$

Step-4: Synthesis of 3-(2,6-dichlorophenyl)-7-[4-(4-methylpiperazin-1-yl)anilino]-2H-pyrimido[5,4-e][1,3]oxazin-4-one To a stirred solution of 3-(2,6-dichlorophenyl)-7-methylsulfanyl-2H-pyrimido[5,4-e][1,3]oxazin-4-one (200 mg, 0.587 mmol, 1.0 eq) in toluene (5 mL) was added m-CPBA (202 mg, 1.17 mmol, 2.0 eq) and allowed to stir at rt for 30 min. 4-(4-methylpiperazin-1-yl)aniline (123 mg, 0.646 mmol, 1.10 eq) and DIPEA (378 mg, 2.94 mmol, 5.0 eq) were added and allowed to stir at rt for 2 h. Progress of reaction was monitored by LCMS. After completion of reaction, precipitated compound was filtered off and washed with toluene (5 mL) and dried under vacuum. Solid was triturated with MeOH (3 mL) then filtered off and dried under vacuum to afford 3-(2,6-dichlorophenyl)-7-[4-(4-methylpiperazin-1-yl)anilino]-2H-pyrimido[5,4-e][1,3]oxazin-4-one (45 mg, 16%). This 45 mg compound was dissolved in 2 mL of MeOH and 0.5 mL of 2M HCl in MeOH was then added to it. Solvent was removed under reduced pressure and thereafter compound was freeze dried to afford 3-(2,6-dichlorophenyl)-7-[4-(4-methylpiperazin-1-yl)anilino]-2H-pyrimido[5,4-e][1,3]oxazin-4-one (50 mg) as HCl salt.

LCMS: 485 [M+1]$^+$ $^1$H NMR (400 MHz, DMSO-d$_6$): δ 10.41 (br s, 1H), 10.30 (br s, 1H), 8.80 (s, 1H), 7.65 (d, J=8.33 Hz, 2H), 7.60 (d, J=8.77 Hz, 2H), 7.50 (dd, J=7.67, 8.55 Hz, 1H), 7.01 (d,

J=9.21 Hz, 2H), 5.72 (s, 2H), 3.77 (d, J=13.59 Hz, 2H), 3.08-3.26 (m, 2H), 2.92-3.08 (m, 2H), 2.83 (d, J=4.82 Hz, 3H).

Example S2. Synthesis of 3-(2,6-dichlorophenyl)-7-(4-morpholinoanilino)-2H-pyrimido[5,4-e][1,3]oxazin-4-one (Compound No. 1.2)

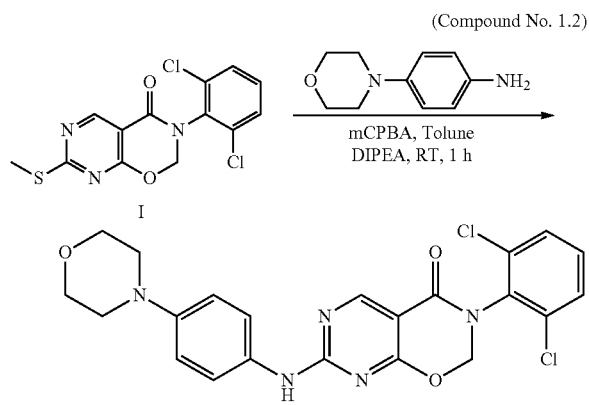

Synthesis of 3-(2,6-dichlorophenyl)-7-(4-morpholinoanilino)-2H-pyrimido[5,4-e][1,3]oxazin-4-one To a stirred solution of 3-(2,6-dichlorophenyl)-7-methylsulfanyl-2H-pyrimido[5,4-e][1,3]oxazin-4-one (130 mg, 0.381 mmol, 1.0 eq) in toluene (2 mL) was added m-CPBA (164 mg, 0.953 mmol, 2.5 eq) and allowed to stir at rt for 30 min. 4-Morpholinoaniline (75 mg, 0.420 mmol, 1.1 eq) and DIPEA (196 mg, 1.52 mmol, 5.0 eq) were added and stirred at rt for 1 h. Progress of reaction was monitored by LCMS. After completion of reaction, precipitated compound was filtered off and washed with toluene (5 mL) and dried under vacuum to afford 3-(2,6-dichlorophenyl)-7-(4-morpholinoanilino)-2H-pyrimido[5,4-e][1,3]oxazin-4-one (50 mg, 28%).

LCMS: 472 [M+1]$^+$ $^1$H NMR (400 MHz, DMSO-d$_6$): δ 10.28 (br s, 1H), 8.79 (s, 1H), 7.65 (d, J=8.11 Hz, 2H), 7.56 (d, J=7.45 Hz, 2H), 7.47-7.52 (m, 1H), 6.94 (d, J=8.99 Hz, 2H), 5.71 (s, 2H), 3.71-3.77 (m, 4H), 3.04-3.10 (m, 4H).

Example S3. Synthesis of 3-(2,6-dichlorophenyl)-7-((2-(2-hydroxyacetyl)-4,4-dimethyl-1,2,3,4-tetrahydroisoquinolin-7-yl)amino)-2,3-dihydro-4H-pyrimido[5,4-e][1,3]oxazin-4-one (Compound No. 1.3)

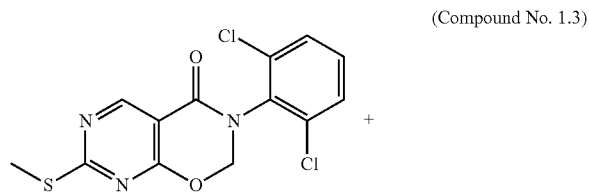

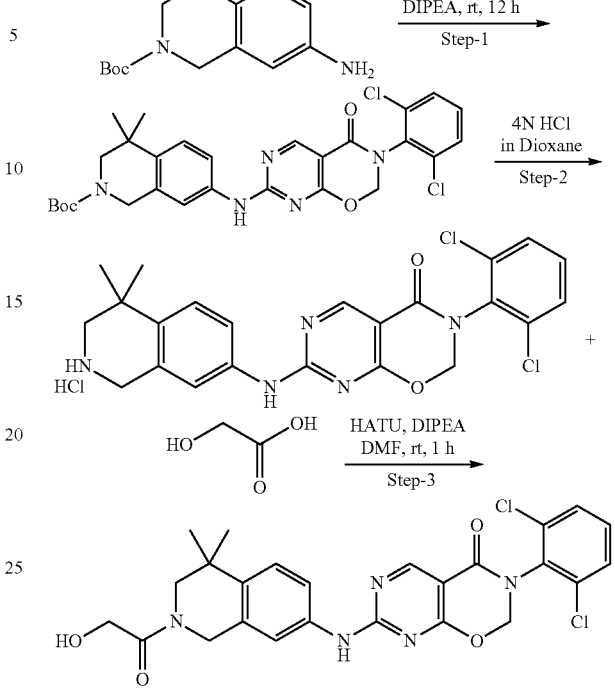

Step-1: Synthesis of tert-butyl 7-[[3-(2,6-dichlorophenyl)-4-oxo-2H-pyrimido[5,4-e][1,3]oxazin-7-yl]amino]-4,4-dimethyl-1,3-dihydroisoquinoline-2-carboxylate To a stirred solution of 3-(2,6-dichlorophenyl)-7-methylsulfanyl-2H-pyrimido[5,4-e][1,3]oxazin-4-one (400 mg, 1.17 mmol, 1.0 eq) in toluene (10 mL) was added m-CPBA (504 mg, 2.94 mmol, 2.5 eq) and allowed to stir at rt for 30 min. Tert-butyl-7-amino-4,4-dimethyl-1,3-dihydroisoquinoline-2-carboxylate (323 mg, 1.17 mmol, 1.0 eq) and DIPEA (606 mg, 4.70 mmol, 4.0 eq) were added and stirred at rt for 1 h. After completion of reaction, mixture was diluted with water (50 mL) and extracted with ethyl acetate (50 mL×2). The combined organic extracts were washed with water (50 mL) and brine (50 mL), dried over Na$_2$SO$_4$ and concentrated under reduced pressure. Crude product obtained was purified by flash chromatography to afford tert-butyl-7-[[3-(2,6-dichlorophenyl)-4-oxo-2H-pyrimido[5,4-e][1,3]oxazin-7-yl]amino]-4,4-dimethyl-1,3-dihydroisoquinoline-2-carboxylate (300 mg, 45.1%).

LCMS: 570 [M+1]$^+$

Step-2: Synthesis of 3-(2,6-dichlorophenyl)-7-[(4,4-dimethyl-2,3-dihydro-1H-isoquinolin-7-yl)amino]-2H-pyrimido[5,4-e][1,3]oxazin-4-one tert-Butyl 7-[[3-(2,6-dichlorophenyl)-4-oxo-2H-pyrimido [5,4-e][1,3]oxazin-7-yl]amino]-4,4-dimethyl-1,3-dihydroisoquinoline-2-carboxylate (300 mg, 0.528 mmol) was dissolved in 4M HCl in dioxane (6 mL) at 0° C. Reaction was stirred at rt for 2 h. Progress of reaction was monitored by LCMS. After completion of reaction, precipitated compound was filtered off, washed with dioxane (3 mL) and dried under reduced pressure to obtain 3-(2,6-dichlorophenyl)-7-[(4,4-dimethyl-2,3-dihydro-1H-isoquinolin-7-yl)amino]-2H-pyrimido[5,4-e][1,3]oxazin-4-one (200 mg, 80.6%) as HCl salt.

LCMS: 470 [M+1]+

Step-3 Synthesis of 3-(2,6-dichlorophenyl)-7-((2-(2-hydroxyacetyl)-4,4-dimethyl-1,2,3,4-tetrahydroisoquinolin-7-yl)amino)-2,3-dihydro-4H-pyrimido[5,4-e][1,3]oxazin-4-one To a stirred solution of glycolic acid (36 mg, 0.473 mmol, 1.2 eq) in DMF (5 mL) was added HATU (225 mg, 0.592 mmol, 1.5 eq) at rt. The resulting mixture was stirred at rt for 5 min. 3-(2,6-dichlorophenyl)-7-((4,4-dimethyl-1,2,3,4-tetrahydroisoquinolin-7-yl)amino)-2,3-dihydro-4H-pyrimido[5,4-e][1,3]oxazin-4-one hydrochloride (200 mg, 0.395 mmol, 1.0 eq) and DIPEA (0.135 mL, 0.790 mmol, 2.0 eq) were added and stirred at rt for 1 h. Progress of reaction was monitored by LCMS. After completion of reaction, mixture was diluted with water (50 mL) and extracted with ethyl acetate (50 mL×2). The combined organic extracts were washed with water (50 mL) and brine (50 mL), dried over $Na_2SO_4$ and concentrated under reduced pressure. Crude residue was purified by flash chromatography to afford 3-(2,6-dichlorophenyl)-7-((2-(2-hydroxyacetyl)-4,4-dimethyl-1,2,3,4-tetrahydroisoquinolin-7-yl)amino)-2,3-dihydro-4H-pyrimido[5,4-e][1,3]oxazin-4-one (50 mg, 24%).

LCMS: 528 [M+1]+

$^1$H NMR (400 MHz, DMSO-$d_6$): δ 10.41 (d, J=10.96 Hz, 1H), 8.84 (s, 1H), 7.66 (d, J=8.11 Hz, 2H), 7.47-7.58 (m, 3H), 7.36 (dd, J=5.04, 8.99 Hz, 1H), 5.74 (s, 2H), 4.62 (d, J=14.03 Hz, 3H), 4.21 (dd, J=5.48, 19.51 Hz, 2H), 3.50 (s, 1H), 3.36 (s, 1H), 1.20 (s, 3H), 1.23 (s, 3H).

Example S4. Synthesis of 3-(2,6-dichlorophenyl)-7-((2,4,4-trimethyl-1,2,3,4-tetrahydroisoquinolin-7-yl)amino)-2,3-dihydro-4H-pyrimido[5,4-e][1,3]oxazin-4-one

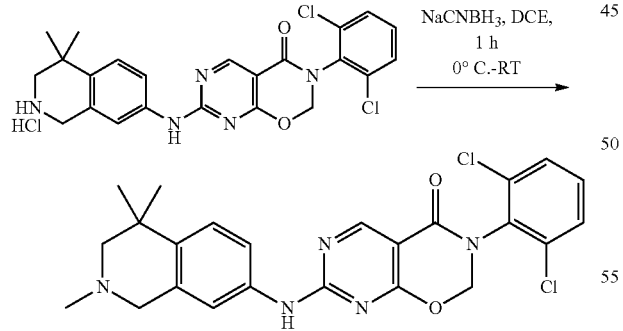

(Compound No. 1.4)

Synthesis of 3-(2,6-dichlorophenyl)-7-((2,4,4-trimethyl-1,2,3,4-tetrahydro isoquinolin-7-yl)amino)-2,3-dihydro-4H-pyrimido[5,4-e][1,3]oxazin-4-one To a stirred solution of 3-(2,6-dichlorophenyl)-7-((4,4-dimethyl-1,2,3,4-tetrahydroisoquinolin-7-yl)amino)-2,3-dihydro-4H-pyrimido[5,4-e][1,3]oxazin-4-one hydrochloride (200 mg, 0.394 mmol, 1.0 eq) and HCHO (0.096 mL, 1.184 mmol, 3.0 eq) in dichloroethane (10 mL) acetic acid (0.120 mL, 1.970 mmol, 5.0 eq) was added drop-wise at 0° C. The resulting mixture was stirred at rt for 1 h followed by addition of $NaCNBH_3$ (74 mg, 1.182 mmol, 3.0 eq) at 0° C. The resulting mixture was stirred at rt for 1 h. The progress of reaction was monitored by LCMS. After completion of reaction, solvent was removed under reduced pressure, residue was basified with saturated solution of $NaHCO_3$ (50 mL) and extracted with ethyl acetate (100 mL×2). The combined organic layer was washed with water (50 mL) and brine (50 mL), dried over anhydrous $Na_2SO_4$ and concentrated under reduced. Crude residue was purified by flash chromatography to afford 3-(2,6-dichlorophenyl)-7-((2,4,4-trimethyl-1,2,3,4-tetrahydroisoquinolin-7-yl)amino)-2,3-dihydro-4H-pyrimido[5,4-e][1,3]oxazin-4-one (15 mg, 8%).

LCMS: 484 [M+1]+

$^1$H NMR (400 MHz, DMSO-$d_6$): δ 10.31 (br s, 1H), 8.82 (s, 1H), 7.66 (d, J 8.33 Hz, 2H), 7.44-7.56 (m, 2H), 7.26-7.40 (m, 2H), 5.73 (s, 2H), 3.43 (s, 2H), 2.32 (s, 5H), 1.15-1.32 (m, 6H).

Example S5. Synthesis of 3-(2,6-dichlorophenyl)-7-(4-piperazin-1-ylanilino)-2H-pyrimido[5,4-e][1,3]oxazin-4-one

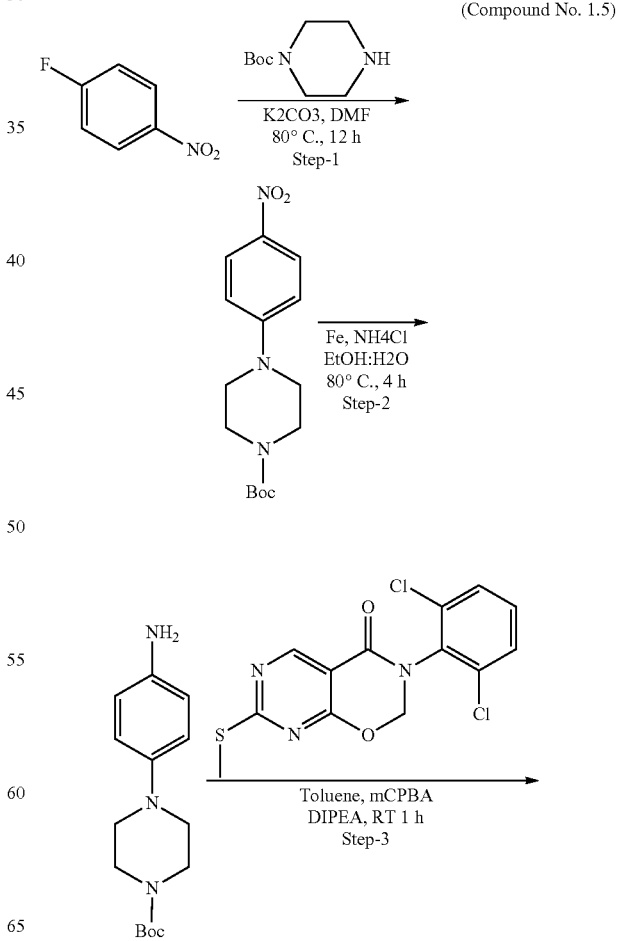

(Compound No. 1.5)

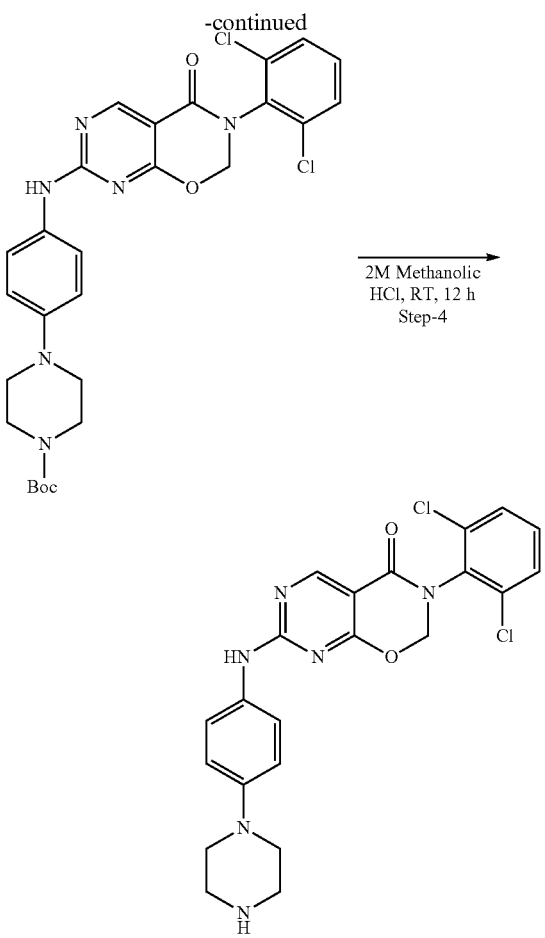

Step-1: Synthesis of tert-butyl 4-(4-nitrophenyl)piperazine-1-carboxylate

To a stirred solution of 5-bromo-2-nitro-pyridine (4.0 g, 21.5 mmol) and tert-butyl piperazine-1-carboxylate (3.30 g, 23.7 mmol, 1.0 eq) in 30 mL of DMF was added $K_2CO_3$ (3.30 g, 23.7 mmol, 1.0 eq). Reaction mixture was heated at 80° C. for 12 h. Progress of the reaction was monitored by LCMS. Upon the consumption of starting material, the reaction mixture was acidified up to pH 5 with 1N HCl solution and extracted with ethyl acetate (200 mL×2). Combined organic layer was washed with water (50 mL×3), dried over anhydrous $Na_2SO_4$ and concentrated under reduced pressure to obtain 6.5 g (89%) of tert-butyl 4-(4-nitrophenyl)piperazine-1-carboxylate. LCMS: 308 [M+1]$^+$ Step-2: Synthesis of tert-butyl 4-(4-aminophenyl)piperazine-1-carboxylate To a stirred solution of tert-butyl 4-(4-nitrophenyl)piperazine-1-carboxylate (6.50 g, 21.17 mmol, 1.0 eq) in 100 mL of ethanol: water (1:1) mixture were added $NH_4Cl$ (11.40 g, 211 mmol, 10 eq) and Fe(0) (4.70 g, 84.68 mmol, 4.0 eq). Reaction mixture was heated at 80° C. for 4 h. Progress of reaction was monitored by LCMS. Upon the consumption of starting material, solvent was removed under reduced pressure. Aqueous layer was basified with saturated solution of sodium carbonate and extracted with ethyl acetate (200 mL×2). Combined organic layer was washed with 50 mL of brine solution, dried over anhydrous $Na_2SO_4$ and concentrated under reduced pressure to obtain 4.0 g (68%) of tert-butyl 4-(4-aminophenyl)piperazine-1-carboxylate. LCMS: 278 [M+1]$^+$ Step-3: Synthesis of tert-butyl 4-[4-[[3-(2,6-dichlorophenyl)-4-oxo-2H-pyrimido[5,4-e][1,3]oxazin-7-yl]amino]phenyl]piperazine-1-carboxylate To a stirred solution of 3-(2,6-dichlorophenyl)-7-methylsulfanyl-2H-pyrimido[5,4-e][1,3]oxazin-4-one (200 mg, 0.587 mmol, 1.0 eq) in 3 mL of toluene was added m-CPBA (252 mg, 1.47 mmol, 2.5 eq) and allowed to stir at rt for 30 min. Tert-butyl 4-(4-aminophenyl)piperazine-1-carboxylate (179 mg, 0.65 mmol, 1.1 eq) and DIPEA (303 mg, 2.35 mmol, 4.0 eq) were added and stirred at rt for 1 h. Progress of reaction was monitored by LCMS. After consumption of starting material, precipitated compound was filtered off and washed with toluene (5 mL) and dried under vacuum to afford tert-butyl 4-[4-[[3-(2,6-dichlorophenyl)-4-oxo-2H-pyrimido[5,4-e][1,3]oxazin-7-yl]amino]phenyl]piperazine-1-carboxylate (140 mg, 41.8%).
LCMS: 571 [M+1]$^+$ Step-4: Synthesis of 3-(2,6-dichlorophenyl)-7-(4-piperazin-1-ylanilino)-2H-pyrimido[5,4-e][1,3]oxazin-4-one 2M MeOHic HCl solution (5 mL) was added in to a RB flask containing tert-butyl 4-[4-[[3-(2,6-dichlorophenyl)-4-oxo-2H-pyrimido[5,4-e][1,3]oxazin-7yl]amino]phenyl]piperazine-1-carboxylate (140 mg, 0.246 mmol, 1.0 eq) at 0° C. Mixture was stirred at rt for 12 h. Progress of reaction was monitored by LCMS. After consumption of starting material, precipitated compound was filtered off and washed with MeOH (3 mL) and dried under vacuum to afford 3-(2,6-dichlorophenyl)-7-(4-piperazin-1-ylanilino)-2H-pyrimido[5,4-e][1,3]oxazin-4-one (40 mg, 32%) as HCl salt.
LCMS: 471 [M+1]$^+$ $^1$H NMR (400 MHz, DMSO-d$_6$): δ 10.31 (br s, 1H), 9.08 (br s, 2H), 8.80 (s, 1H), 7.66 (d, J=7.89 Hz, 2H), 7.55-7.64 (m, J=8.77 Hz, 2H), 7.42-7.55 (m, 1H), 6.91-7.08 (m, J=9.21 Hz, 2H), 5.72 (s, 2H), 3.27-3.37 (m, 4H), 3.23 (br s, 4H).

Example S6. Synthesis of 3-(2,6-dichlorophenyl)-7-((2-(2-hydroxy-2-methylpropanoyl)-4,4-dimethyl-1,2,3,4-tetrahydroisoquinolin-7-yl)amino)-2,3-dihydro-4H-pyrimido[5,4-e][1,3]oxazin-4-one (Compound No. 1.6)

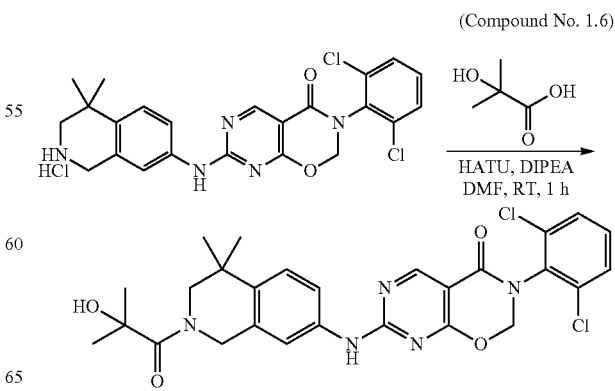

Synthesis of 3-(2,6-dichlorophenyl)-7-((2-(2-hydroxy-2-methylpropanoyl)-4,4-dimethyl-1,2,3,4-tetrahydroisoquinolin-7-yl)amino)-2,3-dihydro-4H-pyrimido[5,4-e][1,3]oxazin-4-one To a stirred solution of 2-hydroxy-2-methylpropanoic acid (49 mg, 0.473 mmol, 1.2 eq) in DMF (5 mL) was added HATU (225 mg, 0.591 mmol, 1.5 eq) at rt. The resulting mixture was stirred at rt for 5 min, followed by addition of 3-(2,6-dichlorophenyl)-7-((4,4-dimethyl-1,2,3,4-tetrahydroisoquinolin-7-yl)amino)-2,3-dihydro-4H-pyrimido[5,4-e][1,3]oxazin-4-one hydrochloride (200 mg, 0.395 mmol, 1.0 eq) and DIPEA (0.135 mL, 0.788 mmol, 2.0 eq), and stirred at rt for 1 h. Progress of reaction was monitored by LCMS. After consumption of starting material mixture was diluted with water (50 mL) and extracted with ethyl acetate (50 mL×2). The combined organic layer was washed with water (50 mL) and brine (50 mL), dried over anhydrous Na$_2$SO$_4$ and concentrated under reduced. Crude residue was purified by SFC to afford 3-(2,6-dichlorophenyl)-7-((2-(2-hydroxy-2-methylpropanoyl)-4,4-dimethyl-1,2,3,4-tetrahydroisoquinolin-7-yl)amino)-2,3-dihydro-4H-pyrimido[5,4-e][1,3]oxazin-4-one (35 mg, 16%).

LCMS: 556 [M+1]$^+$ $^1$H NMR (400 MHz, DMSO-d$_6$): δ 10.38 (br s, 1H), 8.85 (s, 1H), 7.66 (d, J=8.31 Hz, 2H), 7.46-7.58 (m, 3H), 7.36 (d, J=8.80 Hz, 1H), 5.74 (s, 2H), 5.51 (br s, 1H), 5.15 (br s, 2H), 3.54 (br s, 2H), 1.34 (s, 6H), 1.20 (br s, 6H).

Example S7. Synthesis of 3-(2,6-dichlorophenyl)-7-[[2-(2-hydroxyacetyl)-3,4-dihydro-1H-isoquinolin-7 yl]amino]-2H-pyrimido[5,4-e][1,3]oxazin-4-one (Compound No. 1.7)

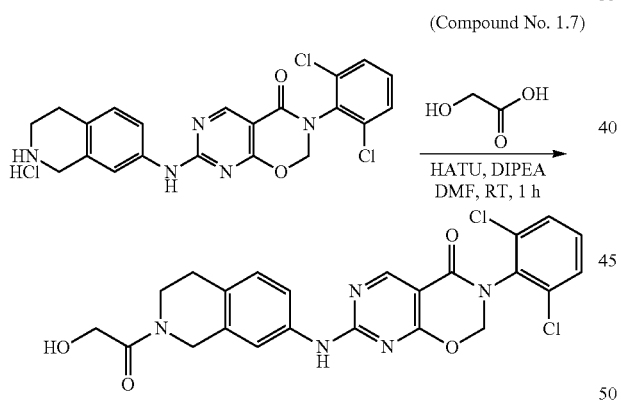

Synthesis of 3-(2,6-dichlorophenyl)-7-[[2-(2-hydroxyacetyl)-3,4-dihydro-1H-isoquinolin-7 yl]amino]-2H-pyrimido[5,4-e][1,3]oxazin-4-one To a stirred solution of glycolic acid (19 mg, 0.253 mmol, 1.1 eq) in 3 mL of DMF was added HATU (131 mg, 0.345 mmol, 1.5 eq) at rt. The resulting mixture was stirred at rt for 5 min, followed by addition of 3-(2,6-dichlorophenyl)-7-(1,2,3,4-tetrahydroisoquinolin-7-ylamino)-2H-pyrimido[5,4-e][1,3]oxazin-4-one hydrochloride (100 mg, 0.230 mmol, 1.0 eq) and DIPEA (59 mg, 0.460 mmol, 2.0 eq) and stirred at rt for 1 h. Reaction was monitored by LCMS. After completion of reaction, mixture was poured on ice cold water (20 mL). Precipitated compound was filtered off, washed with water (30 mL) and dried under reduced pressure. Crude residue was purified by flash chromatography using MeOH:CH$_2$Cl$_2$ as eluents to afford 3-(2,6-dichlorophenyl)-7-[[2-(2-hydroxyacetyl)-3,4-dihydro-1H-isoquinolin-7-yl]amino]-2H-pyrimido[5,4-e][1,3]oxazin-4-one (20 mg, 17.4%).

LCMS: 500 [M+1]$^+$ $^1$H NMR (400 MHz, DMSO-d$_6$): δ 10.42 (br s, 1H), 8.85 (s, 1H), 7.63-7.71 (m, J=8.33 Hz, 2H), 7.59 (br s, 1H), 7.48-7.55 (m, 2H), 7.15 (d, J=8.33 Hz, 1H), 5.74 (s, 2H), 4.52-4.70 (m, 3H), 4.18 (d, J=4.82 Hz, 2H), 3.65 (br s, 2H), 2.75 (br s, 2H).

Example S8. Synthesis of 3-(2,6-dichlorophenyl)-7-[4-[4-(2-hydroxyacetyl)piperazin-1-yl]anilino]-2H-pyrimido[5,4-e][1,3]oxazin-4-one (Compound No. 1.8)

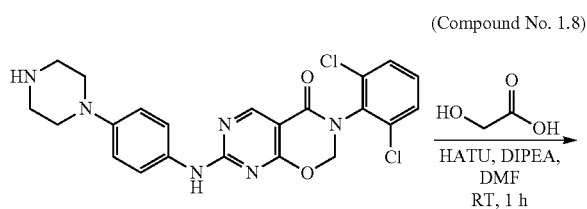

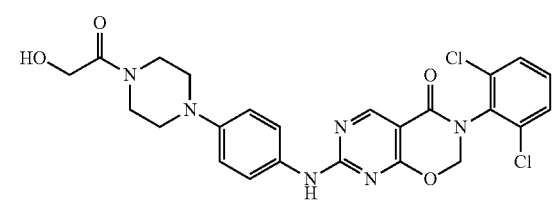

Synthesis of 3-(2,6-dichlorophenyl)-7-[4-[4-(2-hydroxyacetyl)piperazin-1-yl]anilino]-2H-pyrimido[5,4-e][1,3]oxazin-4-one To a stirred solution of glycolic acid (23 mg, 0.304 mmol, 1.1 eq) in 2 mL of DMF was added HATU (160 mg, 0.420 mmol, 2.0 eq) at rt. The resulting mixture was stirred at rt for 5 min, followed by addition of 3-(2,6-dichlorophenyl)-7-(4-piperazin-1-ylanilino)-2H-pyrimido[5,4-e][1,3]oxazin-4-one hydrochloride (130 mg, 0.280 mmol, 1.0 eq) and DIPEA (108 mg, 0.840 mmol, 3.0 eq), then stirred at rt for 1 hr. Reaction was monitored by LCMS. After completion of reaction, mixture was poured on ice cold water (20 mL). Precipitated compound was filtered off, washed with water (30 mL) and dried under reduced pressure to afford 3-(2,6-dichlorophenyl)-7-[4-[4-(2-hydroxyacetyl)piperazin-1-yl]anilino]-2H-pyrimido[5,4-e][1,3]oxazin-4-one (70 mg, 47.3%).

LCMS: 529 [M+1]$^+$ $^1$H NMR (400 MHz, DMSO-d$_6$): δ 10.29 (br s, 1H), 8.79 (s, 1H), 7.62-7.72 (m, J=8.33 Hz, 2H), 7.52-7.62 (m, 2H), 7.47-7.52 (m, 1H), 6.85-7.00 (m, J=8.77 Hz, 2H), 5.71 (s, 2H), 4.63 (t, J=5.48 Hz, 1H), 4.13 (d, J=5.70 Hz, 2H), 3.62 (br s, 2H), 3.49 (br s, 2H), 3.10 (br s, 4H).

Example S9. Synthesis of 3-(2-chlorophenyl)-7-(4-piperazin-1-ylanilino)-2H-pyrimido[5,4-e][1,3]oxazin-4-one (Compound No. 1.9)

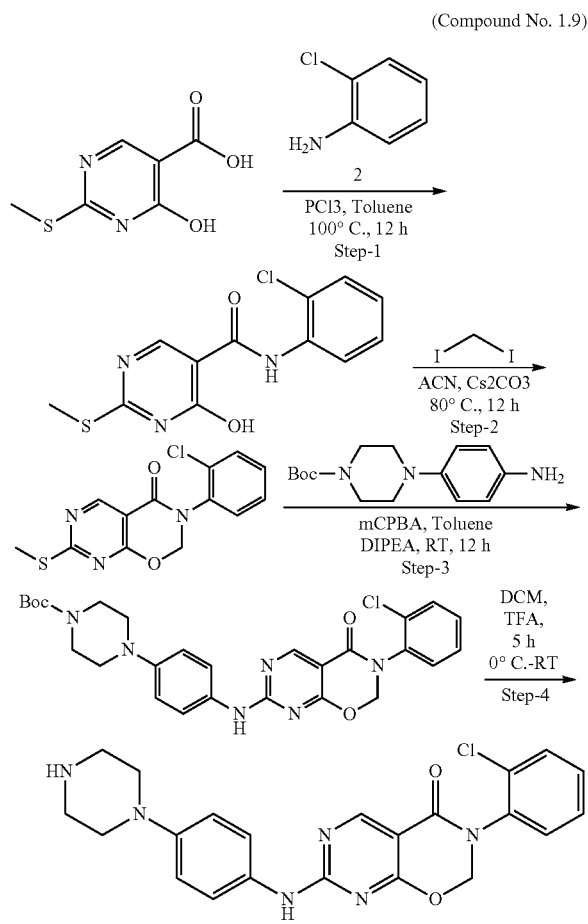

Step-1: Synthesis of N-(2-chlorophenyl)-4-hydroxy-2-methylsulfanyl-pyrimidine-5-carboxamide To a stirred suspension of 4-hydroxy-2-methyl sulfanyl-pyrimidine-5-carboxylic acid (5.0 g, 26.88 mmol, 1.0 eq) and 2-chloroaniline (3.75 g, 29.56 mmol, 1.1 eq) in toluene (200 mL) was added $PCl_3$ (30 mL) and heated at 100° C. for 12 h. Reaction was monitored by LCMS. After completion of reaction, solvent was removed under reduced pressure; residue was cooled to 0° C. and basified by saturated $NaHCO_3$ solution. Ethyl acetate (50 mL) was added into it and extracted. Product was insoluble in this biphasic system which was filtered and dried to afford N-(2-chlorophenyl)-4-hydroxy-2-methylsulfanyl-pyrimidine-5-carboxamide (2.6 g, 29.7%) as solid product.

LCMS: 296 $[M+1]^+$

Step-2: Synthesis of 3-(2-chlorophenyl)-7-methylsulfanyl-2H-pyrimido[5,4-e][1,3]oxazin-4-one To a stirred suspension of N-(2-chlorophenyl)-4-hydroxy-2-methylsulfanyl-pyrimidine-5-carboxamide (1.0 g, 3.38 mmol, 1.0 eq) in $CH_3CN$ (30 mL) and DMSO (5 mL) was added cesium carbonate (3.29 g, 10.14 mmol, 3.0 eq) and stirred at rt for 5 min. $CH_2I_2$ (1.36 g, 5.08 mmol, 1.5 eq) was added and heated at 80° C. for 12 h. Reaction was monitored by LCMS. After completion of reaction, solvent was removed under reduced pressure; residue was diluted with ice-cold water and extracted with ethyl acetate (100 mL×2). Combined organic layer was washed with brine solution (50 mL), dried over anhydrous $Na_2SO_4$ and concentrated under reduced pressure to give crude product which was purified by flash chromatography to afford 3-(2-chlorophenyl)-7-methylsulfanyl-2H-pyrimido[5,4-e][1,3]oxazin-4-one (150 mg, 14.4%) of as white solid.

LCMS: 308 $[M+1]^+$

Step-3: Synthesis of tert-butyl 4-[4-[[3-(2-chlorophenyl)-4-oxo-2H-pyrimido[5,4-e][1,3]oxazin-7-yl]amino]phenyl]piperazine-1-carboxylate To a stirred solution of 3-(2-chlorophenyl)-7-methylsulfanyl-2H-pyrimido[5,4-e][1,3]oxazin-4-one (130 mg, 0.423 mmol, 1.0 eq) in 5 mL of toluene was added m-CPBA (224 mg, 0.84 mmol, 2.0 eq) and stirred at rt for 30 min. Tert-butyl 4-(4-aminophenyl)piperazine-1-carboxylate (117 mg, 0.423 mmol, 1.0 eq) and DIPEA (163 mg, 1.27 mmol, 3.0 eq) were added and allowed to stir at rt for 12 h. Reaction was monitored by LCMS. After completion of reaction, solvent was removed under reduced pressure. Residue was diluted with saturated $NaHCO_3$ solution and extracted with $CH_2Cl_2$ (100 mL×2). Combined organic layer was washed with brine solution (50 mL), dried over anhydrous $Na_2SO_4$ and concentrated under reduced pressure to give crude product which was purified by flash chromatography to afford tert-butyl 4-[4-[[3-(2-chlorophenyl)-4-oxo-2H-pyrimido[5,4-e][1,3]oxazin-7-yl]amino]phenyl]piperazine-1-carboxylate (120 mg, 52.8%).

LCMS: 537 $[M+1]^+$

Step-4: Synthesis of 3-(2-chlorophenyl)-7-(4-piperazin-1-ylanilino)-2H-pyrimido[5,4-e][1,3]oxazin-4-one To a stirred solution of tert-butyl 4-[4-[[3-(2-chlorophenyl)-4-oxo-2H-pyrimido[5,4-e][1,3]oxazin-7-yl]amino]phenyl]piperazine-1-carboxylate (120 mg, 0.22 mmol, 1.0 eq) in $CH_2Cl_2$ (5 mL) was added TFA (0.5 mL) at 0° C. and allowed to stir at rt for 5 h. After completion of reaction, solvent was removed under reduced pressure to dryness. Residue was recrystallized with ethanol. Precipitated product was filtered and dried to afford 3-(2-chlorophenyl)-7-(4-piperazin-1-ylanilino)-2H-pyrimido[5,4-e][1,3]oxazin-4-one (52 mg, TFA salt, 43%) as an off-white solid.

LCMS: 437 $[M+1]^+$ $^1$H NMR (400 MHz, $CD_3OD$): δ 8.82 (br s, 1H), 7.62 (d, J=8.33 Hz, 3H), 7.45 (br s, 3H), 7.04 (d, J=8.33 Hz, 2H), 5.65 (br s, 2H), 3.38 (br s, 8H).

Example S10. Synthesis of 3-(2,6-dichlorophenyl)-7-[(4,4-dimethyl-2,3-dihydro-1H-isoquinolin-7-yl)amino]-2H-pyrimido[5,4-e][1,3]oxazin-4-one (Compound No. 1.10)

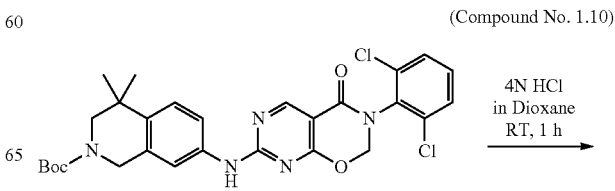

4N HCl in Dioxane RT, 1 h

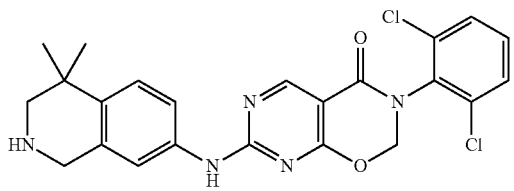

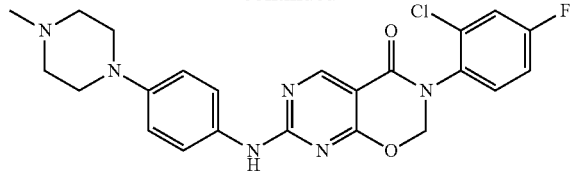

Step-1: Synthesis of N-(2-chloro-4-fluoro-phenyl)-4-hydroxy-2-methylsulfanyl-pyrimidine-5-carboxamide A stirred solution of 4-hydroxy-2-methylsulfanyl-pyrimidine-5-carboxylic acid (5.0 g, 26.9 mmol) and 2-chloro-4-fluoro-aniline (4.30 g, 29.57 mmol) in 200 mL of Toluene was purged with nitrogen gas for 15 min. To the above solution $PCl_3$ (50 mL) was added. Reaction was heated at 100° C. for 48 h. Progress of reaction was monitored by LCMS. After completion of reaction, solvent was removed under reduced pressure, residue was basified with saturated solution of sodium bicarbonate. In basified layer, ethyl acetate (200 mL) was added, and then stirred for 10 m in. Precipitated compound was filtered off and washed with 50 mL of water and dried under vacuum to obtain N-(2-chloro-4-fluoro-phenyl)-4-hydroxy-2-methylsulfanyl-pyrimidine-5-carboxamide (2.60 g).

LCMS: 314 $[M+1]^+$

Step-2: Synthesis of 3-(2-chloro-4-fluoro-phenyl)-7-methylsulfanyl-2H-pyrimido[5,4-e][1,3]oxazin-4-one To a solution of N-(2-chloro-4-fluoro-phenyl)-4-hydroxy-2-methylsulfanyl-pyrimidine-5-carboxamide (2.40 g, 7.52 mmol) in mixture of $CH_3CN$ (200 mL) and DMSO (10 mL) was added diiodomethane (3.02 g, 11.28 mmol) and cesium carbonate (7.30 g, 22.53 mmol). Reaction was heated at 80° C. for 12 h. Progress of reaction was monitored by LCMS. After the completion of the reaction, solvent was removed under reduced pressure, residue was diluted with 50 mL of water and extracted with ethyl acetate (100 mL×3). Combined organic layer was washed with water (50 mL×3), dried over anhydrous $Na_2SO_4$ and concentrated under reduced pressure. Crude was purified by flash chromatography using ethyl acetate: hexane (3-5%) as eluents to obtain 3-(2-chloro-4-fluoro-phenyl)-7-methylsulfanyl-2H-pyrimido[5,4-e][1,3]oxazin-4-one (300 mg).

LCMS: 326 $[M+1]^+$

Step-3: Synthesis of 3-(2-chloro-4-fluoro-phenyl)-7-[4-(4-methylpiperazin-1-yl)anilino]-2H-pyrimido[5,4-e][1,3]oxazin-4-one To a stirred solution of 3-(2-chloro-4-fluoro-phenyl)-7-methylsulfanyl-2H-pyrimido[5,4-e][1,3]oxazin-4-one (80 mg, 0.256 mmol) in 3 mL of toluene was added m-CPBA (110 mg, 0.64 mmol) and allowed to stir at rt for 30 min. 4-(4-Methylpiperazin-1-yl) aniline (49 mg, 0.256 mmol) and DIPEA (132 mg, 1.024 mmol) were then added and allowed to stir at rt for 2 h. Progress of reaction was monitored by LCMS. After completion of reaction solvent was removed under reduced pressure, residue was diluted with water (20 mL) and extracted with ethyl acetate (50 mL×3). Combined organic layer was washed with water (20 mL×3), dried over anhydrous $Na_2SO_4$ and concentrated Synthesis of 3-(2,6-dichlorophenyl)-7-[(4,4-dimethyl-2,3-dihydro-1H-isoquinolin-7-yl)amino]-2H-pyrimido[5,4-e][1,3]oxazin-4-one tert-Butyl 7-[[3-(2,6-dichlorophenyl)-4-oxo-2H-pyrimido[5,4-e][1,3]oxazin-7-yl]amino]-4,4-dimethyl-1,3-dihydroisoquinoline-2-carboxylate (100 m g, 0.176 mmol) was dissolved in 4M HCl (2 mL) in dioxane solution at 0° C. Reaction was stirred at rt for 2 h. Progress of reaction was monitored by LCMS. After completion of reaction, precipitated compound was filtered off, washed with dioxane (3 mL) and dried under reduced pressure to obtain 3-(2,6-dichlorophenyl)-7-[(4,4-dimethyl-2,3-dihydro-1H-isoquinolin-7-yl)amino]-2H-pyrimido[5,4-e][1,3]oxazin-4-one (40 mg, HCl salt).

$^1H$ NMR (400 MHz, DMSO-$d_6$): δ 10.48 (br s, 1H), 9.24 (br s, 2H), 8.85 (s, 1H), 7.66 (d, J=7.83 Hz, 2H), 7.60 (d, J=8.31 Hz, 1H), 7.56 (s, 1H), 7.52 (d, J=7.83 Hz, 1H), 7.46 (d, J=8.31 Hz, 1H), 5.75 (s, 2H), 4.26 (br s, 2H), 3.22 (br s, 2H), 1.35 (s, 6H).

Example S11. Synthesis of 3-(2-chloro-4-fluoro-phenyl)-7-[4-(4-methylpiperazin-1-yl)anilino]-2H-pyrimido[5,4-e][1,3]oxazin-4-one (Compound No. 1.11)

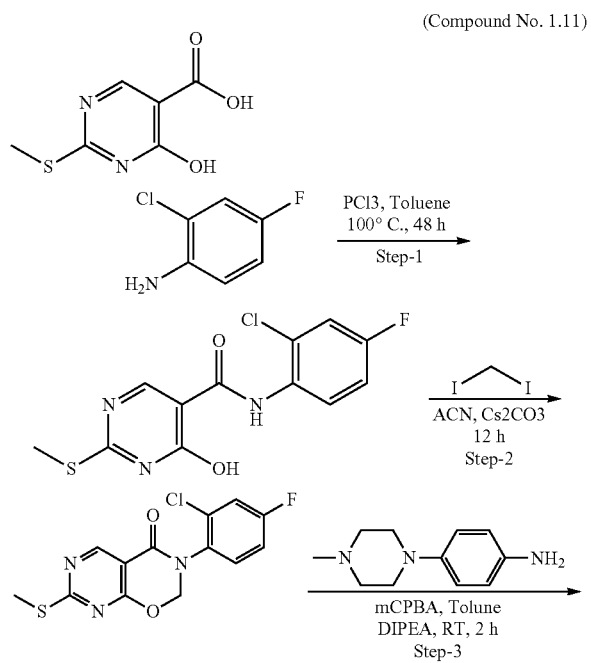

under reduced pressure. Crude residue was purified by reversed phase chromatography to obtain 3-(2-chloro-4-fluoro-phenyl)-7-[4-(4-methylpiperazin-1-yl)anilino]-2H-pyrimido[5,4-e][1,3]oxazin-4-one (25 mg).

LCMS: 469 [M+1]$^+$ $^1$H NMR (400 MHz, DMSO-d$_6$): δ 10.20 (br s, 1H), 8.76 (s, 1H), 7.66 (dd, J=2.85, 8.55 Hz, 1H), 7.47-7.63 (m, 3H), 7.35 (dt, J=3.07, 8.55 Hz, 1H), 6.92 (d, J=9.21 Hz, 2H), 5.73 (br s, 1H), 5.61 (br s, 1H), 3.02-3.15 (m, 4H), 2.35-2.47 (m, 4H), 2.22 (s, 3H).

Example S12. Synthesis of 3-(2,6-dichlorophenyl)-7-[4-(4-piperidyl)anilino]-2H-pyrimido[5,4-e][1,3]oxazin-4-one (Compound No. 1.12)

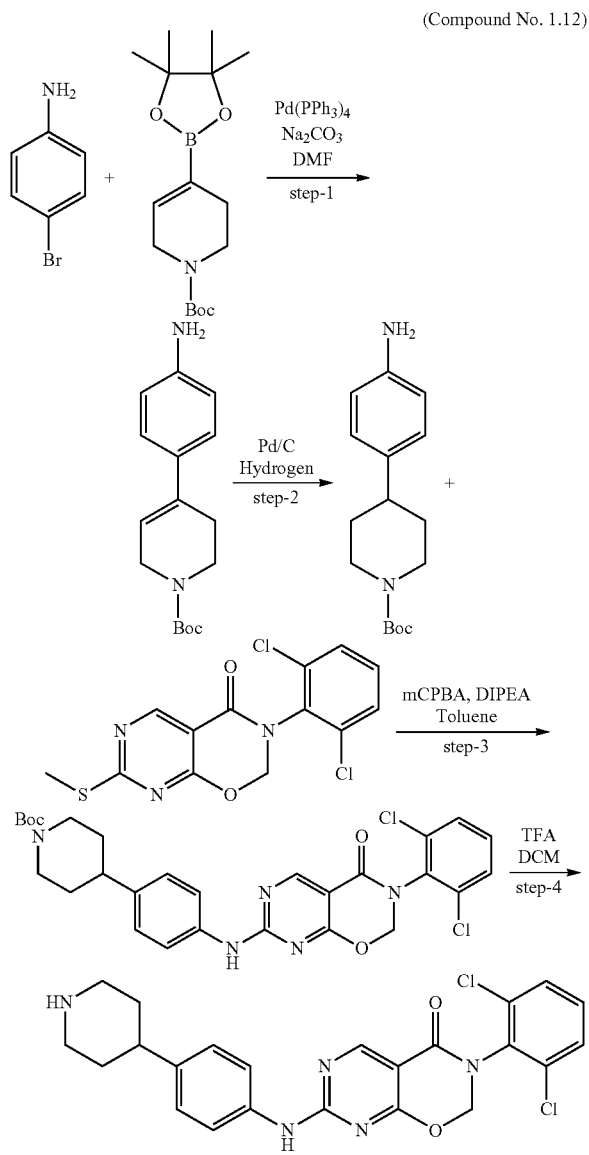

Step-1: Synthesis of tert-butyl 4-(4-aminophenyl)-3,6-dihydro-2H-pyridine-1-carboxylate To a stirred solution of 4-bromoaniline (1.0 g, 5.81 mmol) and tert-butyl 4-(4,4,5,5-tetramethyl-1,3,2-dioxaborolan-2-yl)-3,6-dihydro-2H-pyridine-1-carboxylate (2.15 g, 6.97 mmol) in DMF (15 mL) was added sodium carbonate (1.23 g, 11.62 mmol, 2M aqueous solution). Nitrogen purging was done for 10 min and then added Pd(PPh$_3$)$_4$ (335 mg, 0.29 mmol) into it. Reaction mixture was stirred at 90° C. for 3 h. After completion of reaction, reaction mixture was cooled to rt, diluted with ice-cold water (10 mL) and extracted with ethyl acetate (50 mL×3). Combined organic layer was washed with brine solution (10 mL×5), dried over anhydrous Na$_2$SO$_4$ and concentrated under reduced pressure to afford crude product, which was purified by combi-flash chromatography (eluent-0-30% ethyl acetate in hexane) to afford the desired product (1.0 g).

LCMS: 275 [M+1]$^+$

Step-2: Synthesis of tert-butyl 4-(4-aminophenyl)piperidine-1-carboxylate

To a stirred solution of tert-butyl 4-(4-aminophenyl)-3,6-dihydro-2H-pyridine-1-carboxylate (274 mg, 1.0 mmol) in MeOH (10 mL) was added Pd/C (50 mg) and stirred under hydrogen atmosphere. After completion of reaction, mixture was filtered through celite and filtrate was concentrated under reduced pressure to afford the desired product (250 mg) as viscous oil. LCMS: 221 [M+1]$^+$ Step-3: synthesis of tert-butyl 4-[4-[[3-(2,6-dichlorophenyl)-4-oxo-2H-pyrimido[5,4-e][1,3]oxazin-7-yl]amino]phenyl]piperidine-1-carboxylate To a stirred solution of 3-(2,6-dichlorophenyl)-7-methylsulfanyl-2H-pyrimido[5,4-e][1,3]oxazin-4-one (100 mg, 0.292 mmol) in toluene (4 mL) was added m-CPBA (155 mg, 0.584 mmol. 65% purity) and stirred at rt for 30 min. Tert-butyl 4-(4-aminophenyl)piperidine-1-carboxylate (81 mg, 0.292 mmol) and DIPEA (113 mg, 0.876 mmol) were added and allowed to stir at rt for 3 h. After completion of reaction, solvent was removed under reduced pressure, diluted with saturated NaHCO$_3$ solution (20 mL) and extracted with CH$_2$Cl$_2$ (20 mL×3). Combined organic layer was washed with brine solution, dried over anhydrous Na$_2$SO$_4$ and concentrated under reduced pressure to give crude product which was purified by combi-flash chromatography to afford tert-butyl 4-[4-[[3-(2,6-dichlorophenyl)-4-oxo-2H-pyrimido[5,4-e][1,3]oxazin-7-yl]amino]phenyl]piperidine-1-carboxylate (70 mg).

LCMS: 570 [M+1]$^+$

Step-4: Synthesis of 3-(2,6-dichlorophenyl)-7-[4-(4-piperidyl)anilino]-2H-pyrimido[5,4-e][1,3]oxazin-4-one To a stirred solution of tert-butyl 4-[4-[[3-(2,6-dichlorophenyl)-4-oxo-2H-pyrimido[5,4-e][1,3]oxazin-7-yl]amino]phenyl]piperidine-1-carboxylate (70 mg, 0.22 mmol) in CH$_2$Cl$_2$ (3 mL) was added TFA (0.5 mL) at 0° C. and allowed to stir at rt for 3 h. After completion of reaction, solvent was removed under reduced pressure to dryness, basified by using saturated NaHCO$_3$ solution (20 mL) and extracted with CH$_2$Cl$_2$ (20 mL×3). Combined organic layer was washed with brine solution, dried over anhydrous Na$_2$SO$_4$ and concentrated under reduced pressure to afford crude product which was recrystallized by CH$_2$Cl$_2$ and n-pentane to afford 3-(2,6-dichlorophenyl)-7-[4-(4-piperidyl)anilino]-2H-pyrimido[5,4-e][1,3]oxazin-4-one (11 mg).

LCMS: 470 [M+1]$^+$ $^1$H NMR (400 MHz, DMSO-d$_6$): δ 10.39 (br s, 1H), 8.83 (s, 1H), 7.56-7.83 (m, 4H), 7.41-7.54 (m, 1H), 7.20 (d, J=8.31 Hz, 2H), 5.57-5.86 (m, 2H), 3.05 (d, J=12.23 Hz, 2H), 2.55-2.74 (m, 2H), 1.69 (d, J=12.23 Hz, 2H), 1.39-1.61 (m, 2H), 1.21 (s, 1H).

Example S13. Synthesis of 3-(2,6-dichlorophenyl)-7-[4-[2-(hydroxymethyl)piperazin-1-yl]anilino]-2H-pyrimido[5,4-e][1,3]oxazin-4-one (Compound No. 1.13)

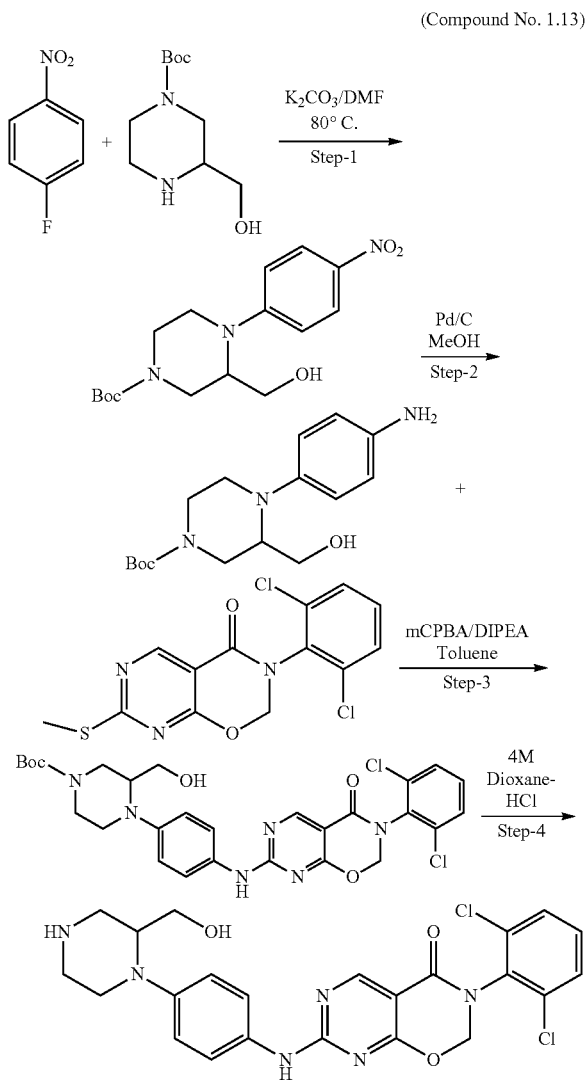

Step-1: Synthesis of tert-butyl 3-(hydroxymethyl)-4-(4-nitrophenyl)piperazine-1-carboxylate To a stirred solution of 1-fluoro-4-nitro-benzene (500 mg, 3.54 mmol, 1.0 eq) and tert-butyl 3-(hydroxymethyl)piperazine-1-carboxylate (560 mg, 3.54 mmol, 1.0 eq) in DMF (10 mL) was added K$_2$CO$_3$ (732 mg, 5.31 mmol, 1.5 eq). Reaction mixture was heated at 50° C. for 12 h. Progress of the reaction was monitored by LCMS. Upon the consumption of starting material, the reaction mixture was diluted with water (100 mL) and extracted with ethyl acetate (200 mL×2). Combined organic layer was washed with water (50 mL×3), dried over anhydrous Na$_2$SO$_4$ and concentrated under reduced pressure to obtain the crude. The crude was purified by combi-flash (0-50% EtOAc-hexane) to obtain tert-butyl 3-(hydroxymethyl)-4-(4-nitrophenyl) piperazine-1-carboxylate (400 mg, 33%).

LCMS: 338.3 [M+1]$^+$

Step-2: Synthesis of tert-butyl 4-(4-aminophenyl)-3-(hydroxymethyl)piperazine-1-carboxylate To a stirred solution of tert-butyl 3-(hydroxymethyl)-4-(4-nitrophenyl)piperazine-1-carboxylate (0.3 g, 0.890 mmol, 1.0 eq) in MeOH (10 mL) was added Pd/C (100 mg, 10 mol %). Reaction mixture was stirred at rt under hydrogen atmosphere for 1 h. Progress of reaction was monitored by LCMS. Upon the consumption of starting material, the reaction mixture was filtered through celite bed and washed with MeOH (20 mL), solvent was removed under reduced pressure. The solid obtained was triturated with ether to obtain tert-butyl 4-(4-aminophenyl)-3-(hydroxymethyl) piperazine-1-carboxylate (200 mg, 73.26%).

LCMS: 308 [M+1]$^+$

Step-3: Synthesis tert-butyl 4-[4-[[3-(2,6-dichlorophenyl)-4-oxo-2H-pyrimido[5,4-e][1,3]oxazin-7-yl] amino]phenyl]-3-(hydroxymethyl)piperazine-1-carboxylate To a stirred solution of 3-(2,6-dichlorophenyl)-7-methylsulfanyl-2H-pyrimido[5,4-e][1,3]oxazin-4-one (200 mg, 0.587 mmol, 1.0 eq) in toluene (10 mL) was added m-CPBA (252 mg, 1.47 mmol, 2.5 eq) and allowed to stir at rt for 30 min. Tert-butyl 4-(4-aminophenyl)-3-(hydroxymethyl) piperazine-1-carboxylate (197 mg, 0.65 mmol, 1.1 eq) and DIPEA (0.4 mL, 2.35 mmol, 4.0 eq) were added and stirred at rt for 1 h. Progress of reaction was monitored by LCMS. After consumption of starting material, the reaction mixture was diluted with water (10 mL) and was extracted with EtOAc (10 mL×2). The organic layer was dried and purified by combi-flash using 0-10% MeOH—CH$_2$Cl$_2$ as eluent to afford tert-butyl 4-[4-[[3-(2,6-dichlorophenyl)-4-oxo-2H-pyrimido[5,4-e][1,3]oxazin-7-yl]amino]phenyl]-3-(hydroxymethyl) piperazine-1-carboxylate (200 mg, 51.28%).

LCMS: 601 [M+1]$^+$

Step-4: Synthesis of 3-(2,6-dichlorophenyl)-7-[4-[2-(hydroxymethyl)piperazin-1-yl]anilino]-2H-pyrimido[5,4-e][1,3]oxazin-4-one To the stirred solution of tert-butyl 4-[4-[[3-(2,6-dichlorophenyl)-4-oxo-2H-pyrimido[5,4-e][1,3]oxazin-7-yl] amino]phenyl]-3-(hydroxymethyl) piperazine-1-carboxylate (200 mg, 0.33 mmol, 1.0 eq) in Dioxane (2 mL) was added 4M Dioxane-HCl at rt. Mixture was stirred at rt for 1 h. Progress of reaction was monitored by LCMS. After consumption of starting material solvent was removed under vacuum and the HCl salt obtained was purified by Reverse phase column chromatography to afford 3-(2,6-dichlorophenyl)-7-[4-[2-(hydroxymethyl)piperazin-1-yl]anilino]-2H-pyrimido[5,4-e][1,3]oxazin-4-one (40 mg, 24%).

LCMS: 501 [M+1]$^+$ $^1$H NMR (400 MHz, DMSO-d$_6$): δ 10.33 (br s, 1H), 8.81 (s, 1H), 8.38 (br s, 1H), 7.65 (d, J=8.31 Hz, 2H), 7.54-7.63 (m, J=8.31 Hz, 2H), 7.42-7.54 (m, 1H), 6.86-7.02 (m, J=8.80 Hz, 2H), 5.72 (s, 2H), 3.74-3.94 (m, 3H), 2.97 (br s, 3H), 2.84 (br s, 3H).

485

Example S14. Synthesis of 3-(2-chloro-4-fluoro-phenyl)-7-[(4,4-dimethyl-2,3-dihydro-1H-isoquinolin-7-yl)amino]-2H-pyrimido[5,4-e][1,3]oxazin-4-one (Compound No. 1.14)

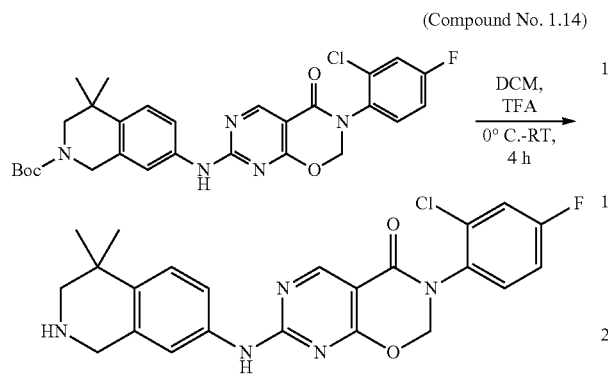

Synthesis of 3-(2-chloro-4-fluoro-phenyl)-7-[(4,4-dimethyl-2,3-dihydro-111H-isoquinolin-7-yl)amino]-2H-pyrimido[5,4-e][1,3]oxazin-4-one Tert-butyl 7-[[3-(2-chloro-4-fluoro-phenyl)-4-oxo-2H-pyrimido[5,4-e][1,3]oxazin-7-yl]amino]-4,4-dimethyl-1,33-dihydroisoquinoline-2-carboxylate (80 mg, 0.144 mmol, 1.0 eq) was dissolved in CH$_2$Cl$_2$ (15 mL) was added trifluoro acetic acid (0.4 mL) at 0° C. Reaction was stirred at rt for 4 h. Progress of reaction was monitored by LCMS. After completion of reaction, solvent was removed under reduced pressure. Residue was triturated with diethyl ether; solid was filtered off, dried under vacuum and basified with NaHCO$_3$ solution. Precipitated compound was filtered off and purified by reversed phase chromatography to obtain 3-(2-chloro-4-fluoro-phenyl)-7-[(4,4-dimethyl-2,3-dihydro-1H-isoquinolin-7-yl)amino]-2H-pyrimido[5,4-e][1,3]oxazin-4-one (4 mg, 5%).

$^1$H NMR (400 MHz, DMSO-d$_6$): δ 10.27 (br s, 1H), 8.80 (s, 1H), 7.66 (dd, J 2.45, 8.31 Hz, 1H), 7.58 (dd, J 5.62, 8.56 Hz, 1H), 7.47 (d, J 8.80 Hz, 1H), 7.21-7.39 (m, 2H), 5.75 (br s, 1H), 5.62 (br s, 1H), 3.85 (s, 2H), 2.66-2.77 (m, 2H), 1.91 (s, 1H), 1.21 (s, 6H).

Example S15. Synthesis of 3-(2,6-dichlorophenyl)-7-[4-(4-ethylsulfonylpiperazin-1-yl)anilino]-2H-pyrimido[5,4-e][1,3]oxazin-4-one (Compound No. 1.15)

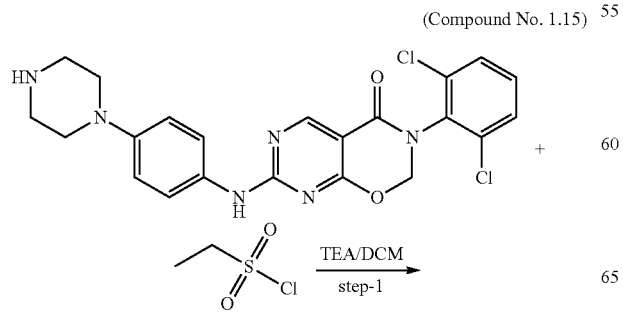

486

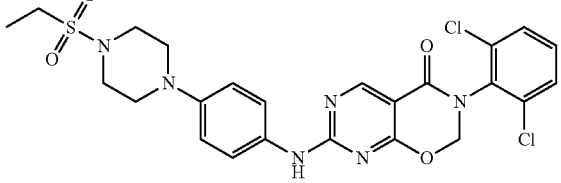

Synthesis of 3-(2,6-dichlorophenyl)-7-[4-(4-ethylsulfonylpiperazin-1-yl)anilino]-2H-pyrimido[5,4-e][1,3]oxazin-4-one To a stirred solution of 3-(2,6-dichlorophenyl)-7-(4-piperazin-1-ylanilino)-2H-pyrimido[5,4-e][1,3]oxazin-4-one (50 mg, 0.106 mmol) in CH$_2$Cl$_2$ (4 mL) were added TEA (21 mg, 0.212 mmol) and ethanesulfonyl chloride (13.5 mg, 0.106 mmol) and stirred at rt for 3 h. After completion of reaction, reaction mixture was diluted with water (10 mL) and extracted with CH$_2$Cl$_2$ (10 mL×3). Combined organic layer was washed with brine solution, dried over anhydrous Na$_2$SO$_4$ and concentrated under reduced pressure to afford crude product which was washed with diethyl ether and dried to afford the desired product (29 mg).

LCMS: 563 [M+1]$^+$ $^1$H NMR (400 MHz, CDCl$_3$): δ 8.96 (s, 1H), 7.51 (d, J=8.77 Hz, 2H), 7.45 (d, J=7.89 Hz, 1H), 7.24-7.35 (m, 2H), 6.95 (d, J=9.21 Hz, 2H), 5.54 (s, 2H), 3.35-3.54 (m, 5H), 3.09-3.34 (m, 4H), 3.01 (q, J=7.45 Hz, 2H), 1.41 (t, J=7.45 Hz, 3H).

Example S16. Synthesis of 3-(2,6-dichlorophenyl)-7-[3-(hydroxymethyl)-4-piperazin-1-yl-anilion]-2H-pyrimido[5,4-e][1,3]oxazin-4-one (Compound No. 1.16)

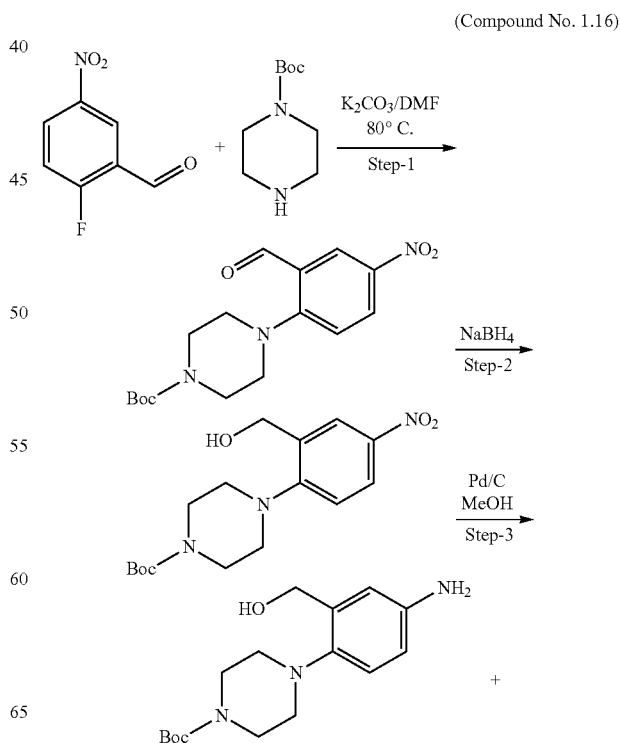

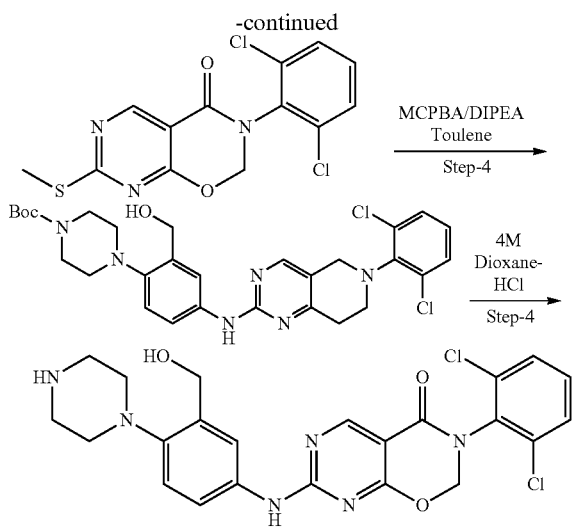

Step-1: Synthesis of tert-butyl 4-(3-formyl-4-nitrophenyl)piperazine-1-carboxylate To a stirred solution of 5-fluoro-2-nitro-benzaldehyde (500 mg, 2.95 mmol, 1.0 eq) and tert-butyl piperazine-1-carboxylate (550 mg, 2.95 mmol, 1.0 eq) in DMF (10 mL) was added $K_2CO_3$ (611 mg, 4.42 mmol, 1.5 eq). Reaction mixture was heated at 50° C. for 12 h. Progress of the reaction was monitored by LCMS. Upon the consumption of starting material, the reaction mixture was diluted with water (100 mL) and extracted with ethyl acetate (200 mL×2). Combined organic layer was washed with water (50 mL×3), dried over anhydrous $Na_2SO_4$ and concentrated under reduced pressure to obtain the crude. The crude was purified by combi-flash (0-50% EtOAc-hexane) to obtain tert-butyl 4-(3-formyl-4-nitro-phenyl)piperazine-1-carboxylate (500 mg, 55%).

LCMS: 336 [M+1]$^+$

Step-2: Synthesis of tert-butyl 4-[2-(hydroxymethyl)-4-nitro-phenyl]piperazine-1-carboxylate To a stirred solution of tert-butyl 4-(2-formyl-4-nitro-phenyl)piperazine-1-carboxylate (0.7 g, 2.57 mmol, 1.0 eq) in THF (10 mL) was added $NaBH_4$ (97 mg, 2.57 mmol, 1.0 eq) at 0° C. Reaction mixture was stirred at 0° C. for 2 h. Progress of the reaction was monitored by LCMS. Upon the consumption of starting material, the reaction mixture was diluted with water (20 mL) and extracted with $CH_2Cl_2$ (100 mL×2). Combined organic layer was dried over anhydrous $Na_2SO_4$ and concentrated under reduced pressure to obtain tert-butyl 4-[2-(hydroxymethyl)-4-nitro-phenyl]piperazine-1-carboxylate (0.5 g, 71%).

LCMS: 338 [M+1]$^+$

Step-3: Synthesis of tert-butyl 4-[4-amino-2-(hydroxymethyl)phenyl]piperazine-1-carboxylate To a stirred solution of tert-butyl 4-[2-(hydroxymethyl)-4-nitro-phenyl]piperazine-1-carboxylate (0.5 g, 1.483 mmol, 1.0 eq) in MeOH (10 mL) was added Pd/C (200 mg, 10 mol %). Reaction mixture was stirred at rt under hydrogen atmosphere for 1 h. Progress of reaction was monitored by LCMS. Upon the consumption of starting material, the reaction mixture was filtered through the celite bed and washed with MeOH (50 mL), solvent was removed under reduced pressure. The solid obtained was triturated with ether to obtain tert-butyl 4-[4-amino-2-(hydroxymethyl)phenyl]piperazine-1-carboxylate (400 mg, 87.91%).

LCMS: 308 [M+1]$^+$

Step-4: Synthesis tert-butyl 4-[4-[[3-(2,6-dichlorophenyl)-4-oxo-2H-pyrimido[5,4-e][1,3]oxazin-7-yl]amino]-2-(hydroxymethyl)phenyl]piperazine-1-carboxylate To a stirred solution of 3-(2,6-dichlorophenyl)-7-methylsulfanyl-2H-pyrimido[5,4-e][1,3]oxazin-4-one (300 mg, 0.877 mmol, 1.0 eq) in toluene (10 mL) was added m-CPBA (377 mg, 2.192 mmol, 2.5 eq) and allowed to stir at rt for 30 min. Tert-butyl 4-[4-[[3-(2,6-dichlorophenyl)-4-oxo-2H-pyrimido[5,4-e][1,3]oxazin-7-yl]amino]-2-(hydroxymethyl)phenyl]piperazine-1-carboxylate (296 mg, 0.96 mmol, 1.1 eq) and DIPEA (0.6 mL, 3.508 mmol, 4.0 eq) were added and stirred at rt for 1 h. Progress of reaction was monitored by LCMS. After consumption of starting material, the reaction mixture was diluted with water (10 mL) and was extracted with EtOAc (10 mL×2). The organic layer was dried and purified by combi-flash using 0-10% MeOH—$CH_2Cl_2$ as eluent to afford tert-butyl 4-[4-[[3-(2,6-dichlorophenyl)-4-oxo-2H-pyrimido[5,4-e][1,3]oxazin-7-yl]amino]-2-(hydroxymethyl)phenyl]piperazine-1-carboxylate (300 mg, 34.20%).

LCMS: 601 [M+1]$^+$

Step-5: Synthesis 3-(2,6-dichlorophenyl)-7-[3-(hydroxymethyl)-4-piperazin-1-yl-anilino]-2H-pyrimido[5,4-e][1,3]oxazin-4-one To a stirred solution of tert-butyl 4-[4-[[3-(2,6-dichlorophenyl)-4-oxo-2H-pyrimido[5,4-e][1,3]oxazin-7-yl]amino]-2(hydroxymethyl)phenyl]piperazine-1-carboxylate (300 mg, 0.50 mmol, 1.0 eq) in dioxane (2 mL) was added 4M dioxane-HCl (10 mL) and reaction mixture was stirred at rt for 1 hr. Progress of reaction was monitored by LCMS. After consumption of starting material, solvent was removed under vacuum and the HCl salt obtained was purified by reversed phase column chromatography to afford 3-(2,6-dichlorophenyl)-7-[3-(hydroxymethyl)-4-piperazin-1-yl-anilino]-2H-pyrimido[5,4-e][1,3]oxazin-4-one (200 mg, 80%).

LCMS: 501 [M+1]$^+$ $^1$H NMR (400 MHz, DMSO-d$_6$): δ 11.63 (br s, 1H), 10.10 (s, 1H), 9.56 (s, 1H), 9.03 (br s, 1H), 8.95 (d, J=7.89 Hz, 2H), 8.88 (d, J=8.33 Hz, 1H), 8.72-8.82 (m, 1H), 8.33 (d, J=8.77 Hz, 1H), 7.02 (s, 2H), 6.42 (br s, 1H), 5.84 (s, 2H), 4.21 (br s, 4H), 4.09 (br s, 4H).

Example S17. Synthesis of 3-(2,6-dichlorophenyl)-2-methyl-7-(4-piperazin-1-ylanilino)-2H-pyrimido[5,4-e][1,3]oxazin-4-one (Compound No. 1.17)

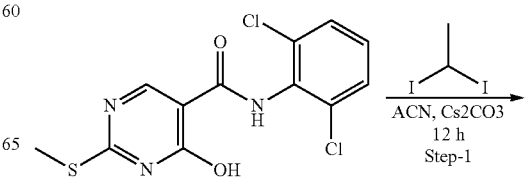

Step-1: Synthesis of 3-(2,6-dichlorophenyl)-2-methyl-7-methylsulfanyl-2H-pyrimido[5,4-e][1,3]oxazin-4-one

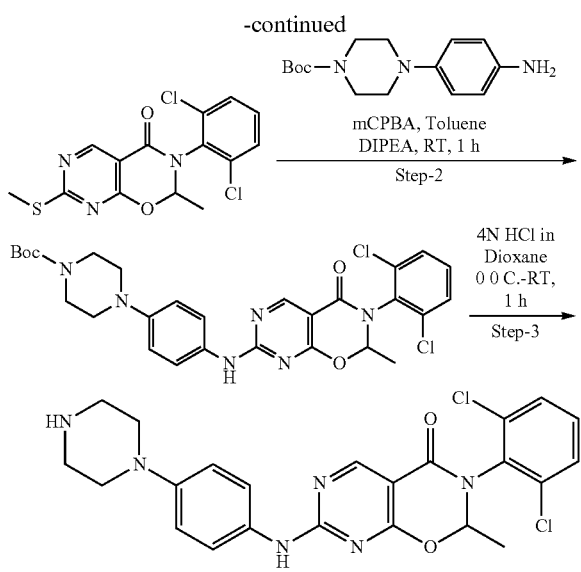

To a stirred solution of N-(2,6-dichlorophenyl)-4-hydroxy-2-methylsulfanyl-pyrimidine-5-carboxamide (2 g, 6.060 mmol, 1 eq) in CH₃CN (20 mL) was added cesium carbonate (5.9 g, 18.00 mmol, 3.0 eq). The reaction mixture was degassed with nitrogen for 10 min and CH₂I₂ (2 g, 9.09 mmol 1.5 eq) was added dropwise. The reaction mixture was heated at 80° C. for 12 h. Progress of the reaction was monitored by LCMS. Upon the consumption of starting material, the reaction mixture was diluted with water (200 mL) and extracted with ethyl acetate (200 mL×2). Combined organic layer was washed with water (50 mL×3), dried over anhydrous Na₂SO₄ and concentrated under reduced pressure. The crude residue obtained was purified by combi-flash 0-100% EtOAc-hexane to obtain (2,6-dichlorophenyl)-2-methyl-7-methylsulfanyl-2H-pyrimido[5,4-e][1,3]oxazin-4-one (150 mg, 7.5%).

LCMS: 356 [M+1]⁺

Step-2: Synthesis of tert-butyl 4-[4-[[3-(2,6-dichlorophenyl)-2-methyl-4-oxo-2H-pyrimido[5,4-e][1,3]oxazin-7-yl]amino]phenyl]piperazine-1-carboxylate To a stirred solution of 3-(2,6-dichlorophenyl)-2-methyl-7-methylsulfanyl-2H-pyrimido[5,4-e][1,3]oxazin-4-one (100 mg, 0.290 mmol, 1.0 eq) in toluene (10 mL) was added m-CPBA (100 mg, 0.58 mmol, 2.0 eq) and allowed to stir at rt for 30 min. Tert-butyl 4-(4-aminophenyl) piperazine-1-carboxylate (107 mg, 0.35 mmol, 1.10 eq) and DIPEA (149 mg, 1.16 mmol, and 4.0 eq) were added and allowed to stir at rt for 1 h. Progress of reaction was monitored by LCMS. After completion of reaction, solvent was removed under reduced pressure. Crude residue was suspended in 20 mL of water, extracted with ethyl acetate (50 mL×2). Combined organic layer was washed with water (20 mL), dried over anhydrous Na₂SO₄ and concentrated under reduced pressure. Crude residue was purified by flash chromatography using ethyl acetate: hexane to obtain tert-butyl 4-[4-[[3-(2,6-dichlorophenyl)-2-methyl-4-oxo-2H-pyrimido[5,4-e][1,3]oxazin-7-yl]amino]phenyl]piperazine-1-carboxylate (100 mg, 59.1%).

LCMS: 585 [M+1]⁺

Step-2: Synthesis of 3-(2,6-dichlorophenyl)-2-methyl-7-(4-piperazin-1-ylanilino)-2H-pyrimido[5,4-e][1,3]oxazin-4-one To a stirred solution of tert-butyl 4-[4-[[3-(2-chloro-6-fluoro-phenyl)-4-oxo-2H-pyrimido[5,4-e][1,3]oxazin-7-yl]amino]phenyl]piperazine-1-carboxylate (100 mg, 0.171 mmol, 1.0 eq) in 4M HCl in dioxane (3 mL). The reaction mixture was stirred at rt for 1 hr. Progress of reaction was monitored by LCMS. After consumption of starting material, precipitated compound was filtered off and washed with dioxane and dried under vacuum. Crude residue was purified by reversed phase chromatography to obtain 3-(2,6-dichlorophenyl)-2-methyl-7-(4-piperazin-1-ylanilino)-2H-pyrimido[5,4-e][1,3]oxazin-4-one (7 mg, 8.53%) as TFA salt.

LCMS: 485 [M+1]⁺

¹H NMR (400 MHz, DMSO-d₆): δ 10.30 (s, 1H), 8.78 (s, 1H), 8.67 (br s, 2H), 7.67 (dd, J=2.63, 8.33 Hz, 2H), 7.53-7.63 (m, 2H), 7.44-7.53 (m, 1H), 7.00 (d, J=9.21 Hz, 2H), 6.14 (d, J=5.70 Hz, 1H), 3.26 (br s, 5H), 3.16 (br s, 1H), 1.38 (d, J=5.70 Hz, 3H).

Example S18. Synthesis of 3-(2,6-dichlorophenyl)-7-[4-(4-ethylpiperazin-1-yl)anilino]-2H-pyrimido[5,4-e][1,3]oxazin-4-one (Compound No. 1.18)

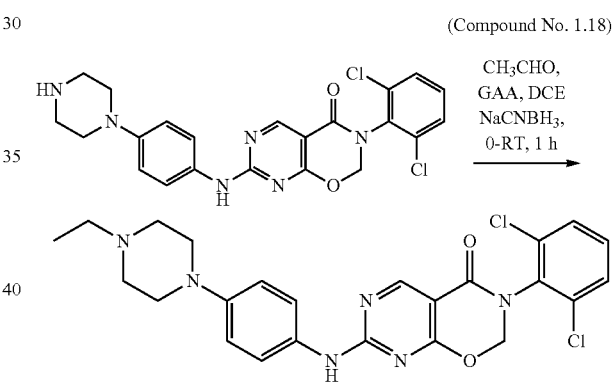

Synthesis of 3-(2,6-dichlorophenyl)-7-[4-(4-ethylpiperazin-1-yl)anilino]-2H-pyrimido[5,4-e][1,3]oxazin-4-one To a stirred solution of 3-(2,6-dichlorophenyl)-7-(4-piperazin-1-ylanilino)-2H-pyrimido[5,4-e][1,3]oxazin-4-one hydrochloride (80 mg, 0.169 mmol, 1.0 eq) and acetaldehyde (35%) (0.65 mL, 0.507 mmol, 3.0 eq) in CH₂Cl₂ (5 mL) acetic acid (51 mg, 0.845 mmol, 5.0 eq) was added drop-wise at 0° C. The resulting mixture was stirred at rt for 1 h, followed by addition of NaCNBH₃ (32 mg, 0.507 mmol, 3.0 eq) at 0° C. The resulting mixture was stirred at rt for 1 hr. The progress of reaction was monitored by LCMS. After completion of reaction, solvent was removed under reduced pressure, residue was basified with saturated solution of NaHCO₃ (50 mL). Precipitated compound was filtered off, dried under vacuum and purified by flash chromatography using MeOH: CH₂Cl₂ as eluents to afford 3-(2,6-dichlorophenyl)-7-[4-(4-ethylpiperazin-1-yl)anilino]-2H-pyrimido[5,4-e][1,3]oxazin-4-one (25 mg, 29.76%).

LCMS: 499 [M+1]⁺

¹H NMR (400 MHz, CD₃OD): δ 8.82 (s, 1H), 7.57 (d, J=7.89 Hz, 3H), 7.39-7.48 (m, 1H), 7.00 (d, J=9.21 Hz, 2H), 5.66 (s, 2H), 3.26 (br s, 4H), 2.83 (br s, 4H), 2.66 (s, 2H), 1.21 (t, J=7.24 Hz, 3H).

Example S19. Synthesis of 3-(2,6-dichlorophenyl)-7-[4-(4-isopropylpiperazin-1-yl)anilino]-2H-pyrimido[5,4-e][1,3]oxazin-4-one (Compound No. 1.19)

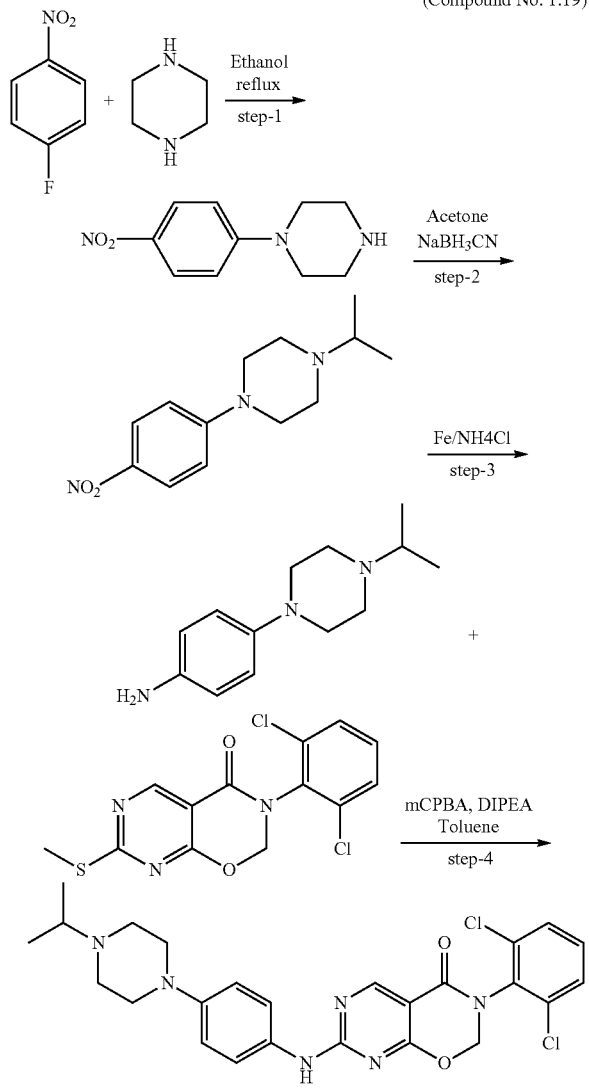

Step-1: Synthesis of 1-(4-nitrophenyl)piperazine

To a stirred solution of 1-fluoro-4-nitro-benzene (5.0 g, 35.46 mmol) in ethanol (30 mL) was added piperazine (7.62 g, 88.65 mmol) and stirred at reflux for 3 h. After completion of reaction, solvent was removed under reduced pressure. Residue obtained was basified by saturated NaHCO₃ solution (20 mL) and extracted with CH₂Cl₂ (20 mL×3). Combined organic layer was washed with brine solution, dried over anhydrous Na₂SO₄ and concentrated under reduced pressure to afford 1-(4-nitrophenyl)piperazine (6.60 g) as a yellow solid.

LCMS: 208 [M+1]⁺

Step-2: Synthesis of 1-isopropyl-4-(4-nitrophenyl)piperazine

To a stirred solution of 1-(4-nitrophenyl)piperazine (500 mg, 2.41 mmol) and acetone (420 mg, 7.24 mmol) in MeOH (10 mL) was added glacial acetic acid (0.2 mL) and allowed to stir at rt 12 h. NaCNBH₃ (302 mg, 4.82 mmol) was then added portion-wise and allowed to stir at rt for 3 h. After completion of reaction, solvent was removed under reduced pressure, residue obtained was diluted with saturated NaHCO₃ solution (20 mL) and extracted with CH₂Cl₂ (20 mL×3). Combined organic layer was washed with brine solution, dried over anhydrous Na₂SO₄ and concentrated under reduced pressure to afford 1-isopropyl-4-(4-nitrophenyl)piperazine (450 mg). LCMS: 250 [M+1]⁺

Step-3: Synthesis of 4-(4-isopropylpiperazin-1-yl)aniline

To a stirred solution of 1-isopropyl-4-(4-nitrophenyl)piperazine (450 mg, 1.80 mmol) in ethanol (15 mL) and water (3 mL) were added iron powder (695 mg, 12.65 mmol) and NH₄Cl (670 mg, 12.65 mmol). The reaction mixture was stirred at 80° C. for 4 h. After completion of reaction, solvent was removed under reduced pressure, diluted with water (20 mL) and extracted with CH₂Cl₂ (20 mL×3). Combined organic layer was washed with brine solution, dried over anhydrous Na₂SO₄ and concentrated under reduced pressure to afford the desired product (300 mg).

LCMS: 220 [M+1]⁺

Step-4: Synthesis of 3-(2,6-dichlorophenyl)-7-[4-(4-isopropylpiperazin-1-yl)anilino]-2H-pyrimido[5,4-e][1,3]oxazin-4-one To a stirred solution of 3-(2,6-dichlorophenyl)-7-methylsulfanyl-2H-pyrimido[5,4-e][1,3]oxazin-4-one (70 mg, 0.204 mmol) in toluene (3 mL) was added m-CPBA (71 mg, 0.408 mmol) and stirred at rt for 30 min. 4-(4-Isopropylpiperazin-1-yl)aniline (44 mg, 0.204 mmol) and DIPEA (78 mg, 0.614 mmol) were then added and allowed to stir at rt for 12 h. After completion of reaction, solvent was removed under reduced pressure, diluted with saturated NaHCO₃ solution (20 mL) and extracted with CH₂Cl₂ (20 mL×3). Combined organic layer was washed with brine solution, dried over anhydrous Na₂SO₄ and concentrated under reduced pressure to afford crude product which was purified by combi-flash chromatography to afford 3-(2,6-dichlorophenyl)-7-[4-(4-isopropylpiperazin-1-yl)anilino]-2H-pyrimido[5,4-e][1,3]oxazin-4-one (18 mg).

LCMS: 513 [M+1]⁺

¹H NMR (400 MHz, DMSO-d₆): δ 10.24 (br s, 1H), 8.78 (s, 1H), 7.59-7.72 (m, J=8.33 Hz, 2H), 7.39-7.59 (m, 3H), 6.79-7.01 (m, J=8.77 Hz, 2H), 5.70 (s, 2H), 3.08 (br s, 4H), 2.67 (br s, 1H), 2.58 (br s, 4H), 1.01 (d, J=6.14 Hz, 6H).

Example S20. Synthesis of 3-(2,6-dichlorophenyl)-7-[3-(hydroxymethyl)-4-(4-methylpiperazin-1-yl)anilino]-2H-pyrimido[5,4-e][1,3]oxazin-4-one (Compound No. 1.20)

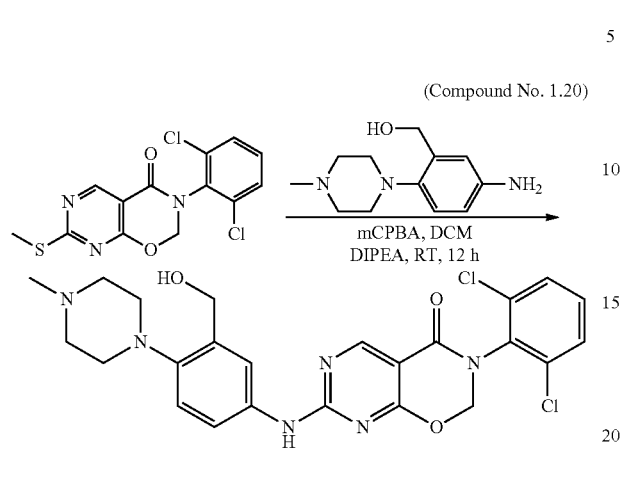

Synthesis of 3-(2,6-dichlorophenyl)-7-[3-(hydroxymethyl)-4-(4-methylpiperazin-1-yl)anilino]-2H-pyrimido[5,4-e][1,3]oxazin-4-one To a stirred solution of 3-(2,6-dichlorophenyl)-7-methylsulfanyl-2H-pyrimido[5,4-e][1,3]oxazin-4-one (300 mg, 0.879 mmol, 1.0 eq) in CH$_2$Cl$_2$ (15 mL) was added m-CPBA (454 mg, 2.64 mmol, 2.5 eq) and allowed to stir at rt for 30 min. [5-amino-2-(4-methylpiperazin-1-yl)phenyl]MeOH (194 mg, 0.879 mmol, 1.0 eq) and DIPEA (567 mg, 12.9 mmol, 4.0 eq) were added and allowed to stir at rt for 12 h. Progress of reaction was monitored by LCMS. After completion of reaction solvent was removed under reduced pressure, residue was diluted with water (20 mL) and extracted with ethyl acetate (50 mL×3). Combined organic layer was washed with water (20 mL×3), dried over anhydrous Na$_2$SO$_4$ and concentrated under reduced pressure. Crude was purified by reversed phase chromatography to obtain 3-(2,6-dichlorophenyl)-7-[3-(hydroxymethyl)-4-(4-methylpiperazin-1-yl)anilino]-2H-pyrimido[5,4-e][1,3]oxazin-4-one (20 mg, 4.4%).

$^1$H NMR (400 MHz, DMSO-d$_6$): δ 10.31 (br s, 1H), 8.80 (s, 1H), 8.28 (br s, 1H), 7.74 (br s, 1H), 7.65 (d, J=8.33 Hz, 2H), 7.57 (dd, J=2.63, 8.33 Hz, 1H), 7.50 (dd, J=7.67, 8.55 Hz, 1H), 7.04 (d, J=8.77 Hz, 1H), 5.72 (s, 2H), 5.09 (br s, 1H), 4.54 (s, 2H), 3.51 (s, 1H), 2.82 (t, J=4.38 Hz, 4H), 2.23 (s, 3H), 1.24 (br s, 3H).

Example S21. Synthesis of 7-[4-(4-cyclopropylpiperazin-1-yl)anilino]-3-(2,6-dichlorophenyl)-2H-pyrimido[5,4-e][1,3]oxazin-4-one (Compound No. 1.21)

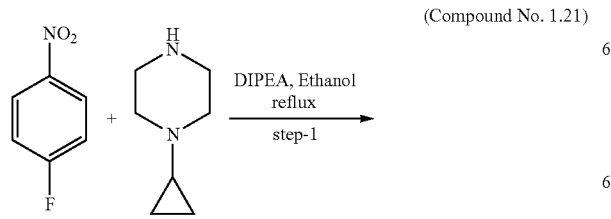

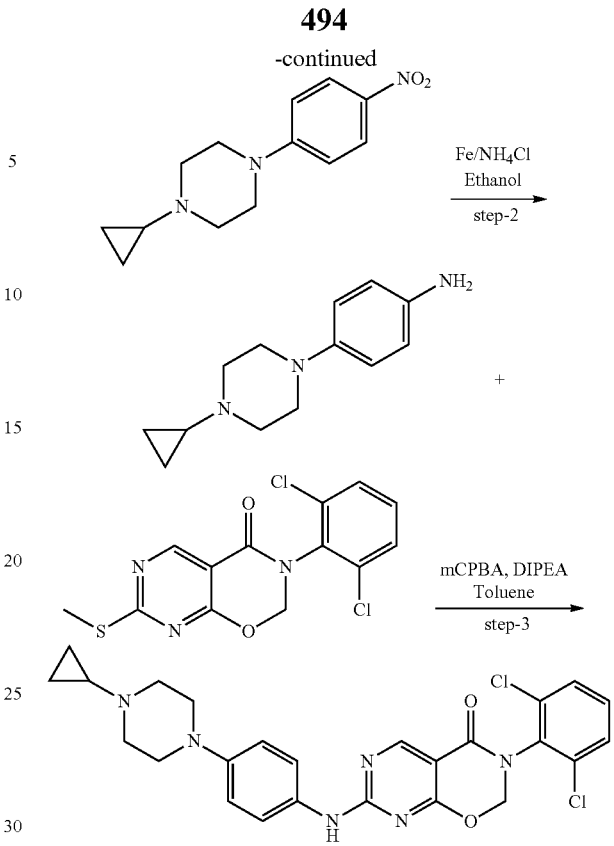

Step-1: Synthesis of 1-cyclopropyl-4-(4-nitrophenyl)piperazine

To a stirred solution of 1-fluoro-4-nitro-benzene (500 mg, 3.54 mmol) and 1-cyclopropylpiperazine (536 mg, 4.25 mmol) in 10 mL of ethanol was added DIPEA (913 mg, 7.08 mmol) and stirred at reflux for 12 h. After completion of reaction, solvent was removed under reduced pressure, diluted with water (20 mL) and extracted with CH$_2$Cl$_2$ (20 mL×3). Combined organic layer was washed with brine solution, dried over anhydrous Na$_2$SO$_4$ and concentrated under reduced pressure to afford crude product which was washed with diethyl ether and dried to afford 1-cyclopropyl-4-(4-nitrophenyl)piperazine (450 mg).

LCMS: 248 [M+1]$^+$

Step-2: Synthesis of 4-(4-cyclopropylpiperazin-1-yl)aniline

To a stirred solution of 1-cyclopropyl-4-(4-nitrophenyl)piperazine (450 mg, 1.82 mmol) in ethanol (15 mL) and water (3 mL) were added iron powder (675 mg, 12.75 mmol) and ammonium chloride (701 mg, 12.75 mmol). The reaction mixture was stirred at 80° C. for 4 h. After completion of reaction, solvent was removed under reduced pressure, diluted with water (20 mL) and extracted with CH$_2$Cl$_2$ (20 mL×3). Combined organic layer was washed with brine solution, dried over anhydrous Na$_2$SO$_4$ and concentrated under reduced pressure to afford the desired product (300 mg).

LCMS: 218 [M+1]$^+$

Step-3: Synthesis of 7-[4-(4-cyclopropylpiperazin-1-yl)anilino]-3-(2,6-dichlorophenyl)-2H-pyrimido[5,4-e][1,3]oxazin-4-one To a stirred solution of 3-(2,6-dichlorophenyl)-7-methylsulfanyl-2H-pyrimido[5,4-e][1,3]oxazin-4-one (100 mg, 0.292 mmol) in toluene (4 mL) was added m-CPBA (155 mg, 0.58 mmol) and stirred at rt for 30 min. 4-(4-Cyclopropylpiperazin-1-yl)aniline (63 mg, 0.292 mmol) and DIPEA (113 mg, 0.876 mmol) were then added and allowed to stir at rt for 12 h. After completion of reaction, solvent was removed under reduced pressure, diluted with saturated NaHCO₃ solution (20 mL) and extracted with CH₂Cl₂ (20 mL×3). Combined organic layer was washed with brine solution, dried over anhydrous Na₂SO₄ and concentrated under reduced pressure to afford crude product which was purified by flash chromatography to afford 7-[4-(4-cyclopropylpiperazin-1-yl)anilino]-3-(2,6-dichlorophenyl)-2H-pyrimido[5,4-e][1,3]oxazin-4-one (30 mg).

LCMS: 511 [M+1]⁺

¹H NMR (400 MHz, DMSO-d₆): δ 10.24 (br s, 1H), 8.78 (s, 1H), 7.65 (d, J=7.89 Hz, 2H), 7.41-7.60 (m, 3H), 6.92 (d, J=8.77 Hz, 2H), 5.71 (s, 2H), 3.05 (br s, 4H), 2.67 (br s, 4H), 1.65 (br s, 1H), 0.44 (d, J=3.95 Hz, 2H), 0.34 (br s, 2H).

Example S22. Synthesis of 3-(2,6-dichlorophenyl)-7-[(2-ethyl-4,4-dimethyl-1,3-dihydroisoquinolin-7-yl)amino]-2H-pyrimido[5,4-e][1,3]oxazin-4-one (Compound No. 1.22)

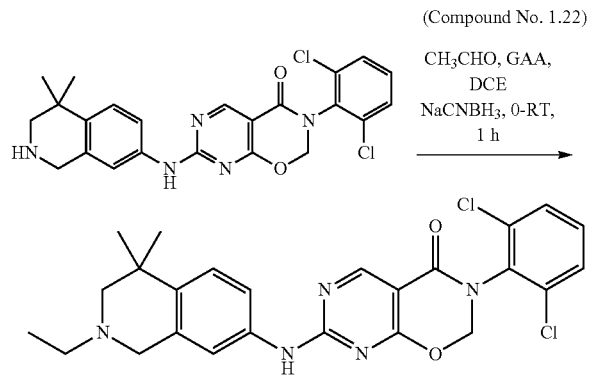

Synthesis of 3-(2,6-dichlorophenyl)-7-[(2-ethyl-4,4-dimethyl-1,3-dihydroisoquinolin-7-yl)amino]-2H-pyrimido[5,4-e][1,3]oxazin-4-one To a stirred solution of 3-(2,6-dichlorophenyl)-7-[(4,4-dimethyl-2,3-dihydro-1H-isoquinolin-7-yl)amino]-2H-pyrimido[5,4-e][1,3]oxazin-4-one hydrochloride (100 mg, 0.213 mmol, 1.0 eq) and acetaldehyde (35%) (0.8 mL, 0.638 mmol, 3.0 eq) in CH₂Cl₂ (5 mL) acetic acid (64 mg, 1.10 mmol, 5.0 eq) was added dropwise at 0° C. The resulting mixture was stirred at rt for 1 h, followed by addition of NaCNBH₃ (40 mg, 0.638 mmol, 3.0 eq) at 0° C. The resulting mixture was stirred at rt for 1 hr. The progress of reaction was monitored by LCMS. After completion of reaction, solvent was removed under reduced pressure, residue was basified with saturated solution of NaHCO₃ (50 mL). Precipitated compound was filtered off, dried under vacuum and purified by reversed phase chromatography using to afford 3-(2,6-dichlorophenyl)-7-[(2-ethyl-4,4-dimethyl-1,3-dihydroisoquinolin-7-yl)amino]-2H-pyrimido[5,4-e][1,3]oxazin-4-one (25 mg, 23.6%).

LCMS: 498 [M+1]⁺

¹H NMR (400 MHz, DMSO-d₆): δ 10.31 (br s, 1H), 8.82 (s, 1H), 7.66 (d, J=8.31 Hz, 2H), 7.47 (d, J=8.80 Hz, 1H), 7.51 (d, J=7.83 Hz, 1H), 7.37 (br s, 1H), 7.30 (d, J=8.31 Hz, 2H), 5.73 (s, 2H), 3.49 (s, 2H), 2.39-2.47 (m, 2H), 2.28-2.39 (m, 2H), 1.83 (s, 2H), 1.23 (s, 6H), 1.09 (t, J=7.09 Hz, 3H).

Example S23. Synthesis of 3-(2,6-dichlorophenyl)-7-((1-oxo-1,2,3,4-tetrahydroisoquinolin-7-yl)amino)-2,3-dihydro-4H-pyrimido[5,4-e][1,3]oxazin-4-one (Compound No. 1.23)

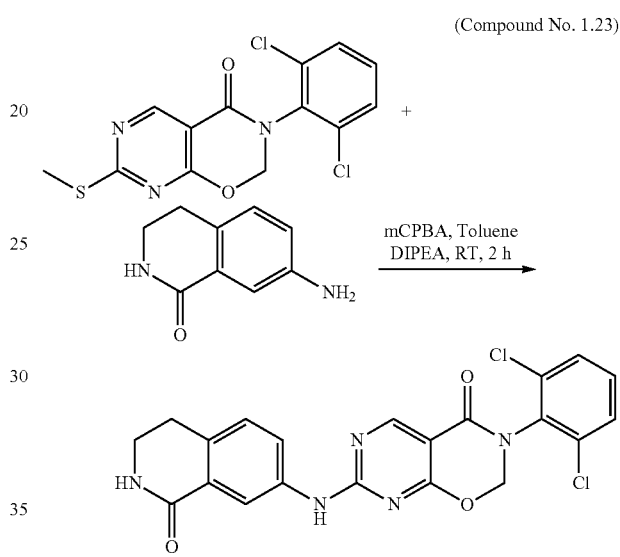

Synthesis of 3-(2,6-dichlorophenyl)-7-((1-oxo-1,2,3,4-tetrahydroisoquinolin-7-yl)amino)-2,3-dihydro-4H-pyrimido[5,4-e][1,3]oxazin-4-one To a stirred solution of 3-(2,6-dichlorophenyl)-7-methylsulfanyl-2H-pyrimido[5,4-e][1,3]oxazin-4-one (200 mg, 0.59 mmol, 1.0 eq) in toluene (15 mL) was added m-CPBA (203 mg, 1.18 mmol, 2.0 eq) and allowed to stir at rt for 30 min. 7-Amino-3,4-dihydro-2H-isoquinolin-1-one (100 mg, 0.590 mmol, 1.0 eq) and DIPEA (300 mg, 2.36 mmol, 4.0 eq) were added and allowed to stir at rt for 2 h. Progress of reaction was monitored by LCMS. After completion of reaction solvent was removed under reduced pressure, residue was diluted with water (20 mL) and extracted with CH₂Cl₂ (50 mL×3). Combined organic layer was washed with water (20 mL×3), dried over anhydrous Na₂SO₄ and concentrated under reduced pressure. Crude residue was purified by reversed phase chromatography to obtain 3-(2,6-dichlorophenyl)-7-((1-oxo-1,2,3,4-tetrahydroisoquinolin-7-yl)amino)-2,3-dihydro-4H-pyrimido[5,4-e][1,3]oxazin-4-one (13 mg, 4.8%).

LCMS: 456 [M+1]⁺

¹H NMR (400 MHz, DMSO-d₆): δ 10.51 (br s, 1H), 8.86 (s, 1H), 8.22 (br s, 1H), 7.95 (br s, 1H), 7.83 (dd, J=1.97, 8.11 Hz, 1H), 7.59-7.71 (m, 2H), 7.48-7.56 (m, 1H), 7.28 (d, J=8.33 Hz, 1H), 5.75 (s, 2H), 3.35 (d, J=3.95 Hz, 2H), 2.86 (t, J=6.58 Hz, 2H).

Example S24. Synthesis of 3-(2,6-dichlorophenyl)-7-((1,2,3,4-tetrahydroisoquinolin-7-yl)amino)-2,3-dihydro-4H-pyrimido[5,4-e][1,3]oxazin-4-one Hydrochloride

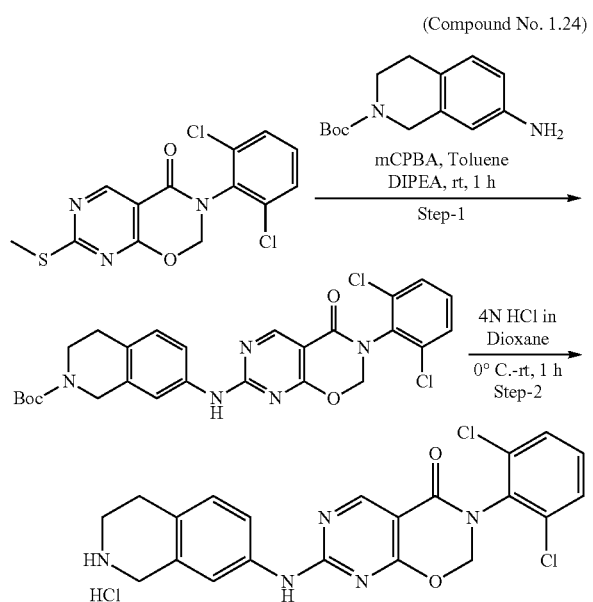

(Compound No. 1.24)

Step-1: Synthesis of tert-butyl 7-[[3-(2,6-dichlorophenyl)-4-oxo-2H-pyrimido[5,4-e][1,3]oxazin-7-yl]amino]-3,4-dihydro-1H-isoquinoline-2-carboxylate To a stirred solution of 3-(2,6-dichlorophenyl)-7-methylsulfanyl-2H-pyrimido[5,4-e][1,3]oxazin-4-one (200 mg, 0.59 mmol, 1.0 eq) in toluene (3 mL) was added m-CPBA (250 mg, 0.147 mmol, 2.5 eq) and allowed to stir at rt for 30 min. Tert-butyl 7-amino-3,4-dihydro-1H-isoquinoline-2-carboxylate (150 mg, 0.590 mmol, 1.0 eq) and DIPEA (300 mg, 2.36 mmol, 4.0 eq) were added and allowed to stir at rt for 1 h. Progress of reaction was monitored by LCMS. After completion of reaction solvent was removed under reduced pressure, residue was diluted with water (20 mL) and extracted with ethyl acetate (50 mL×3). Combined organic layer was washed with water (20 mL×3), dried over anhydrous $Na_2SO_4$ and concentrated under reduced pressure. Crude residue was purified by reversed phase chromatography to obtain tert-butyl 7-[[3-(2,6-dichlorophenyl)-4-oxo-2H-pyrimido[5,4-e][1,3]oxazin-7-yl]amino]-3,4-dihydro-1H-isoquinoline-2-carboxylate (150 mg, 45.6%).

LCMS: 542 [M+1]$^+$

Step-2: Synthesis of 3-(2,6-dichlorophenyl)-7-(1,2,3,4-tetrahydroisoquinolin-7-ylamino)-2H-pyrimido[5,4-e][1,3]oxazin-4-one Hydrochloride tert-Butyl 7-[[3-(2,6-dichlorophenyl)-4-oxo-2H-pyrimido[5,4-e][1,3]oxazin-7-yl]amino]-3,4-dihydro-1H-isoquinoline-2-carboxylate (150 mg, 0.277 mmol, 1.0 eq) was dissolved in 4M HCl in dioxane (2 mL) at 0° C. The reaction mixture was stirred at rt for 1 h. Progress of reaction was monitored by LCMS. After completion of reaction, precipitated compound was filtered off, washed with dioxane (3 mL) and dried under reduced pressure to obtain 3-(2,6-dichlorophenyl)-7-(1,2,3,4-tetrahydroisoquinolin-7-ylamino)-2H-pyrimido[5,4-e][1,3]oxazin-4-one hydrochloride (30 mg, 24.5%) as HCl salt.

LCMS: 442 [M+1]$^+$ $^1$H NMR (400 MHz, DMSO-d$_6$): δ 10.48 (br s, 1H), 9.21 (br s, 2H), 8.85 (s, 1H), 7.66 (d, J=8.31 Hz, 2H), 7.55-7.63 (m, 2H), 7.46-7.54 (m, 1H), 7.21 (d, J=8.31 Hz, 1H), 5.75 (s, 2H), 4.27 (br s, 2H), 3.57 (s, 2H), 3.36 (br s, 2H), 2.97 (t, J=5.87 Hz, 2H).

Example S25. Synthesis of 3-(2-chloro-6-fluorophenyl)-7-[4-(4-methylpiperazin-1-yl)anilino]-2H-pyrimido[5,4-e][1,3]oxazin-4-one

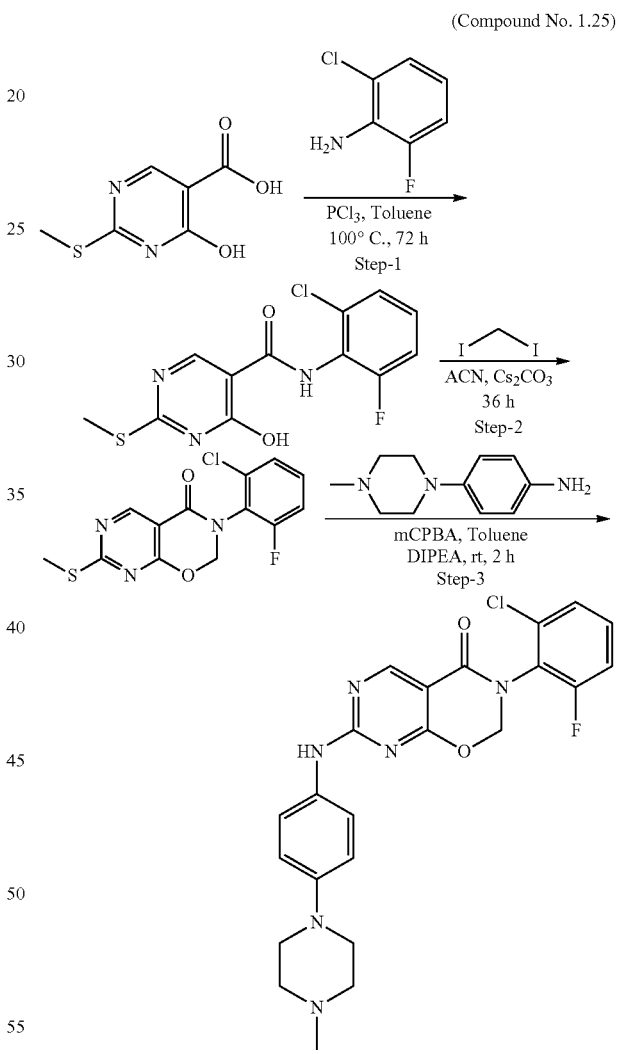

(Compound No. 1.25)

Step-1: Synthesis of N-(2-chloro-6-fluoro-phenyl)-4-hydroxy-2-methylsulfanyl-pyrimidine-5-carboxamide A stirred solution of 4-hydroxy-2-methylsulfanyl-pyrimidine-5-carboxylic acid (5.70 g, 30.65 mmol, 1.0 eq) and 2-chloro-6-fluoro-aniline (4.50 g, 30.65 mmol, 1.0 eq) in toluene (200 mL) was purged with nitrogen gas for 15 min. To the above solution PCl$_3$ (30 mL) was added. The reaction was heated at 100° C. for 72 h. Progress of reaction was monitored by LCMS. After completion of reaction, solvent was removed under reduced pressure, residue was diluted with a mixture of diethyl ether: MeOH (10:1) (100 mL) stirred for 15 min then filtered off. Solid was suspended in MeOH (20 mL), stirred for 5 min, filtered off and washed with MeOH (10 mL), and then dried under vacuum to obtain of N-(2-chloro-6-fluoro-phenyl)-4-hydroxy-2-methylsulfanyl-pyrimidine-5-carboxamide (5.0 g, 52.8%).

LCMS: 314 [M+1]+

Step-2: Synthesis 3-(2-chloro-6-fluoro-phenyl)-7-methylsulfanyl-2H-pyrimido[5,4-e][1,3]oxazin-4-one To a stirred solution of N-(2-chloro-6-fluoro-phenyl)-4-hydroxy-2-methylsulfanyl-pyrimidine-5-carboxamide (5.0 g, 15.97 mmol, 1.0 eq) in $CH_3CN:DMSO$ (200 mL:10 mL) was added $CH_2I_2$ (6.40 g, 23.96 mmol, 1.5 eq) and $Cs_2CO_3$ (15.60 g, 47.91 mmol, 3.0 eq). The reaction mixture was heated at 80° C. for 36 h. Progress of reaction was monitored by LCMS. After the completion of the reaction, solvent was removed under reduced pressure, residue was diluted with water (50 mL) and extracted with ethyl acetate (100 mL×3). Combined organic layer was washed with water (50 mL×3), dried over anhydrous $Na_2SO_4$ and concentrated under reduced pressure. Crude was purified by flash chromatography using ethyl acetate: hexane as eluents to obtain 3-(2-chloro-6-fluoro-phenyl)-7-methylsulfanyl-2H-pyrimido[5,4-e][1,3]oxazin-4-one (300 mg, 5.76%).

LCMS: 326 [M+1]+

Step-3: Synthesis of 3-(2-chloro-6-fluoro-phenyl)-7-[4-(4-methylpiperazin-1-yl)anilino]-2H-pyrimido[5,4-e][1,3]oxazin-4-one To a stirred solution of 3-(2-chloro-6-fluoro-phenyl)-7-methylsulfanyl-2H-pyrimido[5,4-e][1,3]oxazin-4-one (60 mg, 0.185 mmol, 1.0 eq) in toluene (2 mL) was added m-CPBA (79 mg, 0.452 mmol, 2.5 eq) and allowed to stir at rt for 30 min. 4-(4-Methylpiperazin-1-yl) aniline (35 mg, 0.185 mmol, 1.0 eq) and DIPEA (96 mg, 0.744 mmol, 4.0 eq) were added and allowed to stir at rt for 1 h. Progress of reaction was monitored by LCMS. After completion of reaction, precipitated compound was filtered off and washed with toluene (2 mL) and dried under vacuum. Solid was triturated with MeOH (2 mL) then filtered off and dried under vacuum to afford 3-(2-chloro-6-fluoro-phenyl)-7-[4-(4-methylpiperazin-1-yl)anilino]-2H-pyrimido[5,4-e][1,3]oxazin-4-one (15 mg, 17.6%).

LCMS: 469 [M+1]+

$^1H$ NMR (400 MHz, DMSO-$d_6$): δ 10.25 (br s, 1H), 8.78 (s, 1H), 7.45-7.60 (m, 4H), 7.38-7.45 (m, 1H), 6.92 (d, J=8.80 Hz, 2H), 5.65-5.77 (m, 2H), 3.01-3.16 (m, 4H), 2.42-2.48 (m, 4H), 2.22 (s, 3H).

Example S26. Synthesis of 3-(2,6-dichlorophenyl)-7-((4-(2-methylpiperazin-1-yl)phenyl)amino)-2,3-dihydro-4H-pyrimido[5,4-e][1,3]oxazin-4-one (Compound No. 1.26)

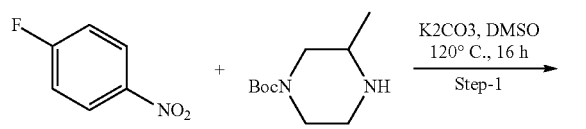

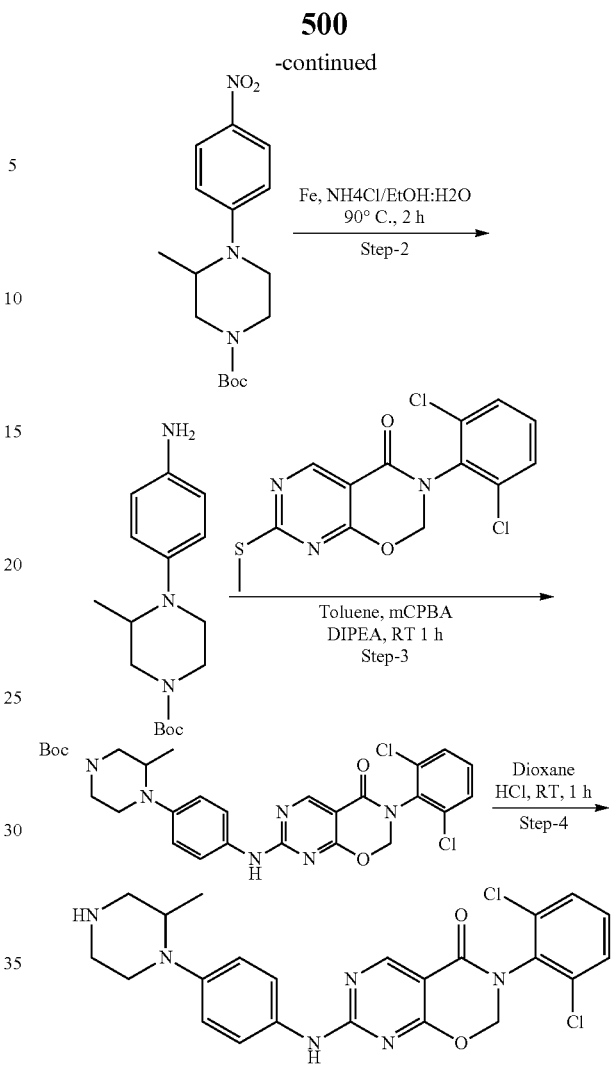

Step-1: Synthesis of tert-butyl 3-methyl-4-(4-nitrophenyl)piperazine-1-carboxylate To a stirred solution of 1-fluoro-4-nitrobenzene (5.0 g, 35.46 mmol, 1.0 eq) and tert-butyl 3-methylpiperazine-1-carboxylate (7.09 g, 35.46 mmol, 1.0 eq) in DMSO (40 mL) was added $K_2CO_3$ (9.78 g, 70.92 mmol, 2.0 eq). The reaction mixture was heated at 120° C. for 16 h. Progress of the reaction was monitored by LCMS. Upon the consumption of starting material, mixture was diluted with water (100 mL) and extracted with ethyl acetate (200 mL×2). Combined organic layer was washed with water (50 mL×3), dried over anhydrous $Na_2SO_4$ and concentrated under reduced pressure. Crude residue was purified by flash chromatography using ethyl acetate: hexane as eluents to obtain tert-butyl 3-methyl-4-(4-nitrophenyl)piperazine-1-carboxylate (5.5 g, 48.67%).

LCMS: 322 [M+1]+

Step-2: Synthesis of tert-butyl 4-(4-aminophenyl)-3-methylpiperazine-1-carboxylate To a stirred solution of tert-butyl 3-methyl-4-(4-nitrophenyl)piperazine-1-carboxylate (5 g, 15.57 mmol, 1.0 eq) in 100 mL of ethanol: water (1:1) mixture were added $NH_4Cl$ (1.65 g, 31.15 mmol, 2 eq) and Iron (2.75 g, 46.73 mmol, 3.0 eq). The reaction mixture was heated at 90° C. for 2 h. Progress of reaction was monitored by LCMS. Upon the consumption of starting material, solvent was removed under reduced pressure. Aqueous layer was basified with saturated solution of sodium carbonate solution and extracted with ethyl acetate (200 mL×2). Combined organic layer was washed with 50 mL of brine solution, dried over anhydrous Na$_2$SO$_4$ and concentrated under reduced pressure. Crude residue was purified by flash chromatography using MeOH: CH$_2$Cl$_2$ as eluents to obtain tert-butyl 4-(4-aminophenyl)-3-methylpiperazine-1-carboxylate (1.5 g, 33%).

LCMS: 291 [M+1]$^+$

Step-3: Synthesis of tert-butyl 4-(4-((3-(2,6-dichlorophenyl)-4-oxo-3,4-dihydro-2H-pyrimido[5,4-e][1,3]oxazin-7-yl)amino)phenyl)-3-methylpiperazine-1-carboxylate To a stirred solution of 3-(2,6-dichlorophenyl)-7-(methylthio)-2,3-dihydro-4H-pyrimido[5,4-e][1,3]oxazin-4-one (250 mg, 0.733 mmol, 1.0 eq) in toluene (15 mL) was added m-CPBA (315 mg, 1.83 mmol, 2.5 eq) and allowed to stir at rt for 30 min. Tert-butyl 4-(4-aminophenyl)-3-methylpiperazine-1-carboxylate (256 mg, 0.87 mmol, 1.2 eq) and DIPEA (37/8 mg, 2.93 mmol, 4.0 eq) were added and stirred at rt for 1 h. Progress of reaction was monitored by LCMS. After consumption of starting material, the reaction mixture was extracted with ethyl acetate (200 mL×2). Combined organic layer was washed with water (50 mL×3), dried over anhydrous Na$_2$SO$_4$ and concentrated under reduced pressure. Crude residue was purified by flash chromatography using MeOH: CH$_2$Cl$_2$ as eluents to obtain tert-butyl 4-(4-((3-(2,6-dichlorophenyl)-4-oxo-3,4-dihydro-2H-pyrimido[5,4-e][1,3]oxazin-7-yl)amino)phenyl)-3-methylpiperazine-1-carboxylate (120 mg, 28%).

LCMS: 585 [M+1]$^+$

Step-4: Synthesis of 3-(2,6-dichlorophenyl)-7-((4-(2-methylpiperazin-1-yl)-114-pyridin-1-yl)amino)-2,3-dihydro-4H-pyrimido[5,4-e][1,3]oxazin-4-one A solution of tert-butyl 4-(4-((3-(2,6-dichlorophenyl)-4-oxo-3,4-dihydro-2H-pyrimido[5,4-e][1,3]oxazin-7-yl)amino)phenyl)-3-methylpiperazine-1-carboxylate (100 mg, 0.170 mmol, 1 eq) in 4M dioxane HCl (2 mL) was stirred at rt for 1 h. Progress of reaction was monitored by LCMS. After consumption of starting material, precipitated compound was filtered off and washed with diethyl ether and dried under vacuum. Crude residue was purified by reversed phase chromatography to obtain 3-(2,6-dichlorophenyl)-7-((4-(2-methylpiperazin-1-yl)-114-pyridin-1-yl)amino)-2,3-dihydro-4H-pyrimido[5,4-e][1,3]oxazin-4-one (15 mg, 18%).

LCMS: 485 [M+1]$^+$ $^1$H NMR (400 MHz, DMSO-d$_6$): δ 8.78 (s, 1H), 7.65 (d, J=8.31 Hz, 2H), 7.42-7.56 (m, 3H), 6.88 (d, J=8.80 Hz, 2H), 5.70 (s, 2H), 3.76 (br s, 1H), 3.07 (d, J=11.25 Hz, 2H), 2.94 (d, J=8.31 Hz, 2H), 2.84 (d, J=8.80 Hz, 1H), 2.74 (d, J=9.78 Hz, 2H), 1.90 (s, 2H), 0.95 (d, J=6.36 Hz, 3H).

Example S27. Synthesis of 3-(2-chloro-6-fluorophenyl)-7-(4-piperazin-1-ylanilino)-2H-pyrimido[5,4-e][1,3]oxazin-4-one (Compound No. 1.27)

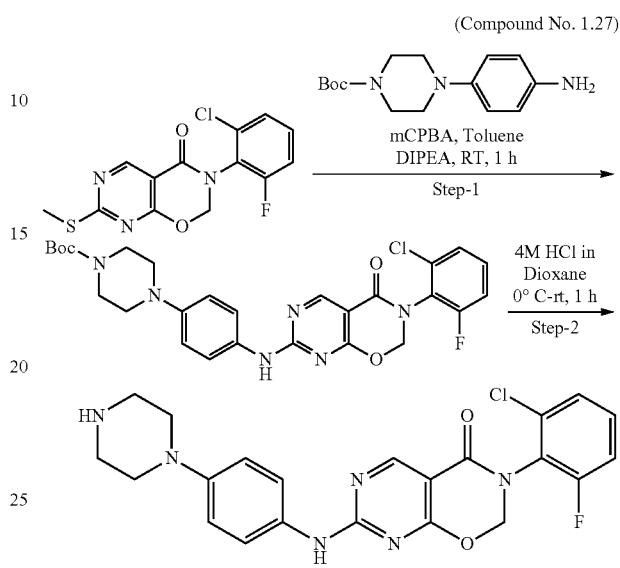

Step-1: tert-butyl 4-[4-[[3-(2-chloro-6-fluoro-phenyl)-4-oxo-2H-pyrimido[5,4-e][1,3]oxazin-7-yl]amino]phenyl]piperazine-1-carboxylate To a stirred solution of 3-(2-chloro-6-fluoro-phenyl)-7-methylsulfanyl-2H-pyrimido[5,4-e][1,3]oxazin-4-one (150 mg, 0.462 mmol, 1.0 eq) in toluene (3 mL) was added m-CPBA (199 mg, 1.16 mmol, 2.5 eq) and allowed to stir at rt for 30 min. Tert-butyl 4-(4-aminophenyl) piperazine-1-carboxylate (128 mg, 0.462 mmol, 1.0 eq) and DIPEA (238 mg, 1.85 mmol, and 4.0 eq) were added and allowed to stir at rt for 1 h. Progress of reaction was monitored by LCMS. After completion of reaction, precipitated compound was filtered off and washed with toluene (2 mL) and dried under vacuum to afford tert-butyl 4-[4-[[3-(2-chloro-6-fluoro-phenyl)-4-oxo-2H-pyrimido[5,4-e][1,3]oxazin-7-yl]amino]phenyl]piperazine-1-carboxylate (90 mg, 35.1%). LCMS: 555 [M+1]$^+$ Step-2: Synthesis of 3-(2-chloro-6-fluoro-phenyl)-7-(4-piperazin-1-ylanilino)-2H-pyrimido[5,4-e][1,3]oxazin-4-one To a stirred solution of tert-butyl 4-[4-[[3-(2-chloro-6-fluoro-phenyl)-4-oxo-2H-pyrimido[5,4-e][1,3]oxazin-7-yl]amino]phenyl]piperazine-1-carboxylate (80 mg, 0.144 mmol, 1.0 eq) in 4M HCl in dioxane (2 mL). The reaction mixture was stirred at rt for 1 h. Progress of reaction was monitored by LCMS. After consumption of starting material, precipitated compound was filtered off and washed with dioxane and dried under vacuum. Crude residue was purified by reversed phase chromatography to obtain 3-(2-chloro-6-fluoro-phenyl)-7-(4-piperazin-1-ylanilino)-2H-pyrimido[5,4-e][1,3]oxazin-4-one (30 mg, 46.8%).

LCMS: 444 [M+1]$^+$

¹H NMR (400 MHz, DMSO-d₆): δ 10.27 (br s, 1H), 8.78 (s, 1H), 7.48-7.73 (m, 4H), 7.40-7.45 (m, 1H), 6.91 (d, J 8.80 Hz, 2H), 5.67-5.75 (m, 2H), 2.97-3.03 (m, 4H), 2.83 (d, J 4.89 Hz, 4H), 1.83 (s, 1H).

Example S28. Synthesis of 3-(2-chloro-6-fluorophenyl)-7-(4,4-dimethyl-1,2,3,4-tetrahydroisoquinolin-7-ylamino)-2H-pyrimido[5,4-e][1,3]oxazin-4(3H)-one (Compound No. 1.28)

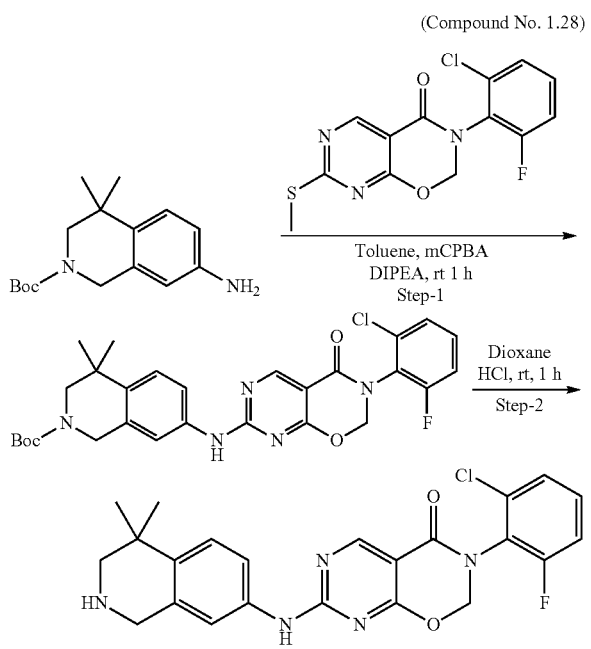

Step-1: Synthesis of tert-butyl 7-((3-(2-chloro-6-fluorophenyl)-4-oxo-3,4-dihydro-2H-pyrimido[5,4-e][1,3]oxazin-7-yl)amino)-4,4-dimethyl-3,4-dihydroisoquinoline-2(1H)-carboxylate To a stirred solution of 3-(2-chloro-6-fluorophenyl)-7-(methylthio)-2,3-dihydro-4H-pyrimido[5,4-e][1,3]oxazin-4-one (250 mg, 0.769 mmol, 1.0 eq) in toluene (5 mL) was added m-CPBA (330 mg, 1.923 mmol, 2.5 eq) and allowed to stir at rt for 30 min. Tert-butyl 7-amino-4,4-dimethyl-3,4-dihydroisoquinoline-2(1H)-carboxylate (254 mg, 0.92 mmol, 1.2 eq) and DIPEA (396 mg, 3.07 mmol, 4.0 eq) were added and stirred at rt for 1 h. Progress of reaction was monitored by LCMS. After consumption of starting material, the reaction mixture was extracted with ethyl acetate (200 mL×2). The combined organic layer was washed with water (50 mL×3), dried over anhydrous Na₂SO₄ and concentrated under reduced pressure. Crude was purified by flash chromatography using MeOH: CH₂Cl₂ as eluents to obtain tert-butyl 7-((3-(2-chloro-6-fluorophenyl)-4-oxo-3,4-dihydro-2H-pyrimido[5,4-e][1,3]oxazin-7-yl)amino)-4,4-dimethyl-3,4-dihydroisoquinoline-2(1H)carboxylate (280 mg, 65%).

LCMS: 554 [M+1]⁺

Step-2: Synthesis of 3-(2-chloro-6-fluorophenyl)-7-((4,4-dimethyl-1,2,3,4-tetrahydroisoquinolin-7-yl)amino)-2,3-dihydro-4H-pyrimido[5,4-e][1,3]oxazin-4-one To a stirred solution of tert-butyl 7-((3-(2-chloro-6-fluorophenyl)-4-oxo-3,4-dihydro-2H-pyrimido[5,4-e][1,3]oxazin-7-yl)amino)-4,4-dimethyl-3,4-dihydroisoquinoline-2(1H)-carboxylate (250 mg, 0.450 mmol, 1 eq) in 4M HCl in dioxane (2 mL). Mixture was stirred at rt for 1 hr. Progress of reaction was monitored by LCMS. After consumption of starting material, precipitated compound was filtered off and washed with dioxane and dried under vacuum to obtain 3-(2,6-dichlorophenyl)-7-((4-(2-methylpiperazin-1-yl)-114-pyridin-1-yl)amino)-2,3-dihydro-4H-pyrimido[5,4-e][1,3]oxazin-4-one (200 mg, 90%).

LCMS: 453 [M+1]⁺

¹H NMR (400 MHz, DMSO-d₆): δ 8.78 (s, 1H), 7.48-7.61 (m, 4H), 7.39-7.46 (m, 1H), 6.91 (d, J=8.80 Hz, 2H), 5.66-5.79 (m, 2H), 2.91-3.06 (m, 4H), 2.83 (d, J=4.89 Hz, 4H), 1.83 (s, 1H).

Example S29. Synthesis of 3-(2,6-dichlorophenyl)-7-(3-fluoro-4-piperazin-1-yl-anilino)-2H-pyrimido[5,4-e][1,3]oxazin-4-one (Compound No. 1.29)

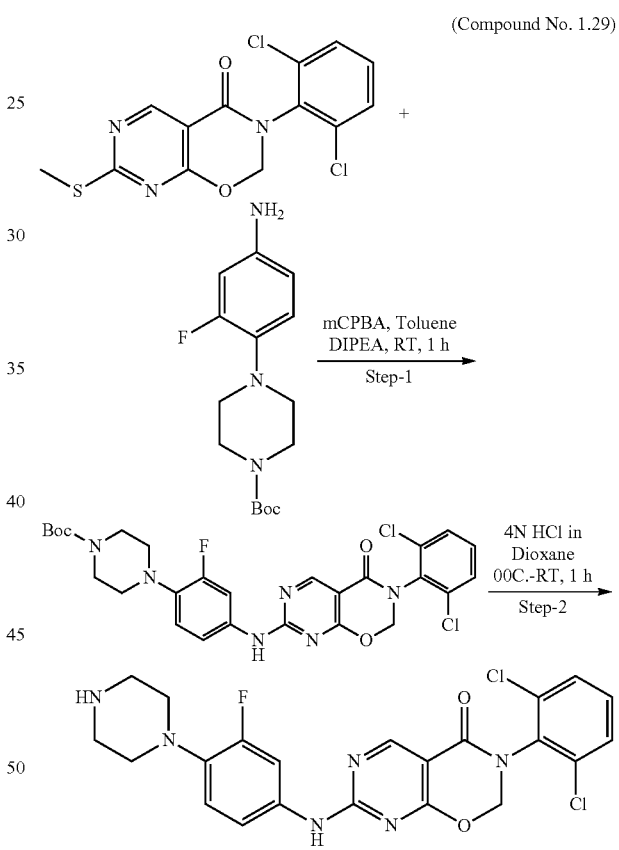

Step-1: Synthesis of tert-butyl 4-[4-[[3-(2,6-dichlorophenyl)-4-oxo-2H-pyrimido[5,4-e][1,3]oxazin-7-yl]amino]-2-fluoro-phenyl]piperazine-1-carboxylate To a stirred solution of 3-(2,6-dichlorophenyl)-7-methylsulfanyl-2H-pyrimido[5,4-e][1,3]oxazin-4-one (250 mg, 0.733 mmol, 1.0 eq) in toluene (3 mL) was added m-CPBA (315 mg, 1.83 mmol, 2.5 eq) and allowed to stir at rt for 30 min. Tert-butyl 4-(4-amino-2-fluoro-phenyl)piperazine-1-carboxylate (216 mg, 0.733 mmol, 1.0 eq) and DIPEA (378 mg, 2.93 mmol, 4.0 eq) were added and allowed to stir at rt for 1 hr. Progress of reaction was monitored by LCMS. After completion of reaction solvent was removed under reduced pressure, residue was diluted with water (20 mL) and extracted with ethyl acetate (50 mL×3). The combined organic layer was washed with water (20 mL×3), dried over anhydrous Na$_2$SO$_4$ and concentrated under reduced pressure. Crude residue was purified by reversed phase chromatography to obtain tert-butyl 4-[4-[[3-(2,6-dichlorophenyl)-4-oxo-2H-pyrimido[5,4-e][1,3]oxazin-7-yl]amino]-2-fluoro-phenyl]piperazine-1-carboxylate (250 mg, 70%).

LCMS: 589 [M+1]$^+$

Step-2: Synthesis of 3-(2,6-dichlorophenyl)-7-(3-fluoro-4-piperazin-1-yl-anilino)-2H-pyrimido[5,4-e][1,3]oxazin-4-one tert-Butyl 4-[4-[[3-(2,6-dichlorophenyl)-4-oxo-2H-pyrimido[5,4-e][1,3]oxazin-7-yl]amino]-2-fluoro-phenyl]piperazine-1-carboxylate (250 mg, 0.425 mmol, 1.0 eq) was dissolved in 4M HCl in dioxane (4 mL) at 0° C. The reaction mixture was stirred at rt for 1 h. Progress of reaction was monitored by LCMS. After completion of reaction, precipitated compound was filtered off, washed with dioxane (3 mL) and dried under reduced pressure. Crude residue was purified by reversed phase chromatography to obtain 3-(2,6-dichlorophenyl)-7-(3-fluoro-4-piperazin-1-yl-anilino)-2H-pyrimido[5,4-e][1,3]oxazin-4-one (50 mg, 24.15%).

LCMS: 489 [M+1]$^+$ $^1$H NMR (400 MHz, DMSO-d$_6$): δ 10.48 (br s, 1H), 8.85 (s, 1H), 8.26 (br s, 1H), 7.60-7.74 (m, 3H), 7.46-7.56 (m, 1H), 7.40 (br s, 1H), 7.03 (br s, 1H), 5.74 (s, 2H), 3.17 (br. s., 1H), 2.98 (br s, 7H).

Example S30. Synthesis of 3-(2-chloro-6-methylphenyl)-7-((4-(piperazin-1-yl)phenyl)amino)-2,3-dihydro-4H-pyrimido[5,4-e][1,3]oxazin-4-one (Compound No. 1.30)

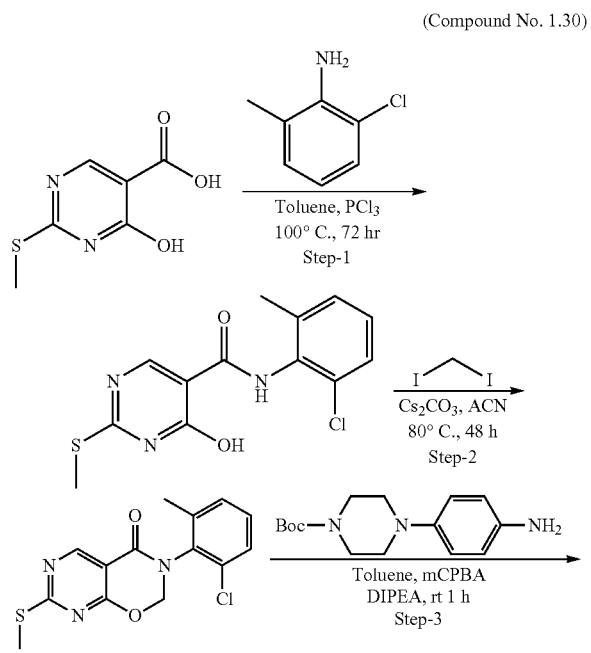

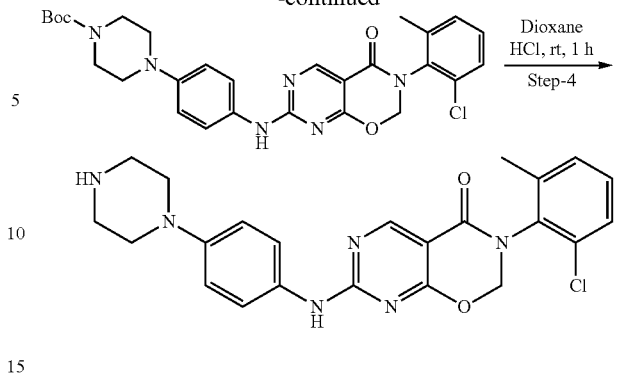

Step-1: Synthesis of N-(2-chloro-6-methylphenyl)-4-hydroxy-2-(methylthio)pyrimidine-5-carboxamide To a stirred solution of 4-hydroxy-2-(methylthio)pyrimidine-5-carboxylic acid (5 g, 26.88 mmol, 1.0 eq) in toluene (100 mL) were added 2-chloro-6-methylaniline (3.8 g, 26.88 mmol, 1 eq) and PCl$_3$ (25 mL). The reaction mixture was allowed to stir at 100° C. for 72 h. Progress of reaction was monitored by LCMS. After consumption of starting material, solvent was removed under reduced pressure, residue was diluted with diethyl ether (100 mL) and MeOH (10 mL) stirred at rt for 10 min then filtered off and dried under vacuum to obtain N-(2-chloro-6-methylphenyl)-4-hydroxy-2-(methylthio)pyrimidine-5-carboxamide (4 g, 48%).

LCMS: 310 [M+1]$^+$

Step-2: Synthesis of 3-(2-chloro-6-methylphenyl)-7-(methylthio)-2,3-dihydro-4H-pyrimido[5,4-e][1,3]oxazin-4-one To a stirred solution of N-(2-chloro-6-methylphenyl)-4-hydroxy-2-(methylthio)pyrimidine-5-carboxamide (5 g, 16.18 mmol, 1.0 eq) in CH$_3$CN (150 mL) were added Cs$_2$CO$_3$ (15.75 g, 48.53 mmol, 3 eq) and DMSO (10 mL). The reaction mixture was purged with nitrogen for 10 min. CH$_2$I$_2$(6.5 g, 24.27 mmol, 1.5 eq) was added and allowed to stir at 80° C. for 48 h. Progress of reaction was monitored by LCMS. After consumption of starting material, solvent was removed under reduced pressure; residue was diluted with water (200 mL) and extracted with ethyl acetate (400 mL×2). The combined organic layer was washed with water (50 mL×3), dried over anhydrous Na$_2$SO$_4$ and concentrated under reduced pressure. Crude residue was purified by flash chromatography was using ethyl acetate: hexane as eluents to obtain 3-(2-chloro-6-methylphenyl)-7-(methylthio)-2,3-dihydro-4H-pyrimido[5,4-e][1,3]oxazin-4-one (800 mg, 15%).

LCMS: 322 [M+1]$^+$

Step-3: Synthesis of tert-butyl 4-(4-((3-(2-chloro-6-methylphenyl)-4-oxo-3,4-dihydro-2H-pyrimido[5,4-e][1,3]oxazin-7-yl)amino)phenyl)piperazine-1-carboxylate To a stirred solution of 3-(2-chloro-6-methylphenyl)-7-(methylthio)-2,3-dihydro-4H-pyrimido[5,4-e][1,3]oxazin-4-one (200 mg, 0.643 mmol, 1.0 eq) in toluene (5 mL) was added m-CPBA (267 mg, 1.557 mmol, 2.5 eq) and allowed to stir at rt for 30 min. Tert-butyl 4-(4-aminophenyl)piperazine-1-carboxylate (207 mg, 0.747 mmol, 1.2 eq) and DIPEA (321 mg, 2.40 mmol, 4.0 eq) were added and stirred at rt for 1 h. Progress of reaction was monitored by LCMS. After consumption of starting material, precipitated compound was filtered off to obtain tert-butyl 4-(4-((3-(2-chloro-6-methylphenyl)-4-oxo-3,4-dihydro-2H-pyrimido[5,4-e][1,3]oxazin-7-yl)amino)phenyl) piperazine-1-carboxylate (85 mg, 24.85%).

LCMS: 551 [M+1]$^+$

Step-4: Synthesis of 3-(2-chloro-6-methylphenyl)-7-((4-(piperazin-1-yl)phenyl)amino)-2,3-dihydro-4H-pyrimido[5,4-e][1,3]oxazin-4-one To a stirred solution of tert-butyl 4-(4-((3-(2-chloro-6-methylphenyl)-4-oxo-3,4-dihydro-2H-pyrimido[5,4-e][1,3]oxazin-7-yl)amino)phenyl) piperazine-1-carboxylate (80 mg, 0.145 mmol, 1 eq) in 4M HCl in dioxane (3 mL). The reaction mixture was stirred at rt for 1 h. Progress of reaction was monitored by LCMS. After consumption of starting material, precipitated compound was filtered off and dried under reduced pressure. Crude residue was purified by reversed phase chromatography to obtain 3-(2-chloro-6-methylphenyl)-7-((4-(piperazin-1-yl)phenyl)amino)-2,3-dihydro-4H-pyrimido[5,4-e][1,3]oxazin-4-one (30 mg, 46.15%).

LCMS: 451 [M+1]$^+$ $^1$H NMR (400 MHz, DMSO-d$_6$): δ 8.77 (s, 1H), 7.53 (d, J=8.33 Hz, 2H), 7.45 (d, J=5.26 Hz, 1H), 7.35 (d, J=5.26 Hz, 2H), 6.90 (d, J=9.21 Hz, 2H), 5.58-5.70 (m, 2H), 3.00 (br s, 4H), 2.84 (br s, 4H), 2.18-2.28 (m, 3H), 1.90 (s, 1H).

Example S31. Synthesis of 3-(2,6-dichlorophenyl)-7-(4-(4-methylpiperazin-1-yl)phenylamino)-2H-pyrido[3,2-e][1,3]oxazin-4(3H)-one (Compound No. 1.31)

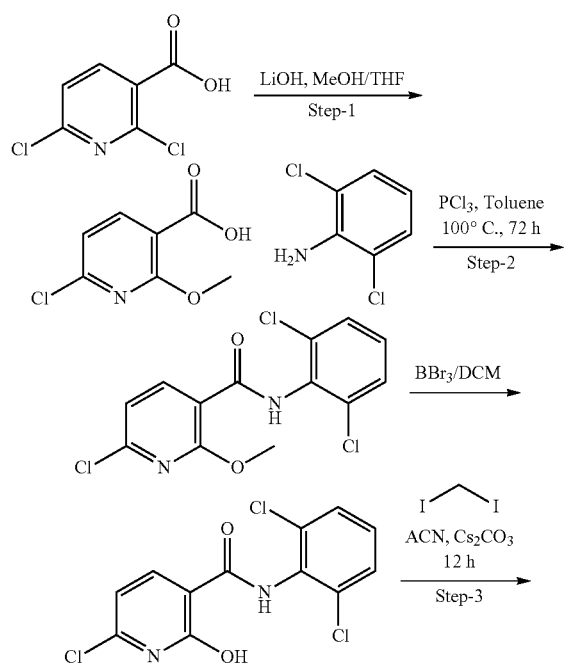

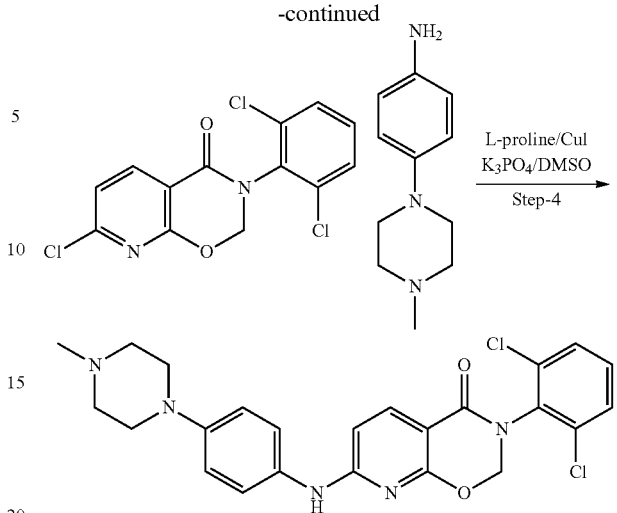

Step-1: Synthesis of 6-chloro-2-methoxynicotinic Acid

To a stirred solution of 2,6-dichloronicotinic acid (20.0 g, 104.16 mmol, 1.0 eq) in THF (80 mL) and MeOH (40 mL) was added LiOH.H$_2$O (13.11 g, 312.49 mmol, 3.0 eq) at rt. The resulting mixture was stirred at same temperature for 12 h. Progress of reaction was monitored by LCMS. After completion of reaction, mixture was concentrated and diluted with water (100 mL), followed by dropwise addition of 1N HCl (50 mL), the formation of white precipitate was observed which was filtered and dried under vacuum to afford 6-chloro-2-methoxynicotinic acid as white solid (19.0 g, 97.23%).

LCMS: 188 [M+1]$^+$

Step-2: Synthesis of 6-chloro-N-(2,6-dichlorophenyl)-2-methoxynicotinamide

A solution of 6-chloro-2-methoxynicotinic acid (10.0 g, 53.310 mmol, 1.0 eq) and 2,6-dichloroaniline (9.5 g, 58.641 mmol, 1.1 eq) in toluene (100 mL) was purged with nitrogen for 10 min at rt, followed by addition of PCl$_3$ (50 mL). The resulting solution was stirred at 100° C. for 48 h. The progress of reaction was monitored by LCMS. The reaction mixture was concentrated, basified with saturated solution of NaHCO$_3$ (500 mL), extracted with EtOAc (100 mL×2). The combined organic layers were washed with water (50 mL), with brine (50 mL), dried over Na$_2$SO$_4$, concentrated and purified by flash chromatography using ethyl acetate:hexane to afford 6-chloro-N-(2,6-dichlorophenyl)-2-methoxynicotinamide (6.5 g, 36.77%) as off white solid.

LCMS: 331[M+1]$^+$

Step-3: Synthesis of 6-chloro-N-(2,6-dichlorophenyl)-2-hydroxynicotinamide

To a stirred solution of 6-chloro-N-(2,6-dichlorophenyl)-2-methoxynicotinamide (4.0 g, 12.06 mmol, 1.0 eq), in CH$_2$Cl$_2$ (50 mL) was drop-wise added 1M solution of BBr$_3$ (36.19 mL, 36.19 mmol, 3.0 eq) at 0° C. The resulting mixture was stirred at the same temperature for 10 min. Progress of reaction was monitored by LCMS. After completion the reaction mixture was basified with saturated solution of NaHCO$_3$ (100 mL), extracted with CH$_2$Cl$_2$ (100 mL×2). The combined organic layers were washed with water (50 mL), with brine (50 mL), dried over Na$_2$SO$_4$, concentrated and purified by flash chromatography using ethylacetate:hexane to afford 6-chloro-N-(2,6-dichlorophenyl)-2-hydroxynicotinamide as white solid (3.81 g, 99.47%). LCMS: 317[M+1]$^+$ Step-4: Synthesis of 7-chloro-3-(2,6-dichlorophenyl)-2,3-dihydro-4H-pyrido[3,2-e][1,3]oxazin-4-one To a stirred solution of 6-chloro-N-(2,6-dichlorophenyl)-2-hydroxynicotinamide (3.8 g, 11.96 mmol, 1.0 eq), in CH$_3$CN (50 mL) was added Cs$_2$CO$_3$ (11.70 g, 35.898 mmol, 3.0 eq) at rt. The resulting mixture was stirred and purged with nitrogen for 10 min followed by addition of diiodomethane (6.41 g, 23.933 mmol, 2.0 eq) at rt. The reaction mixture was heated at 90° C. for 48 h. The progress of reaction was monitored by LCMS. The reaction mixture was diluted with water (100 mL), extracted with ethyl acetate (100 mL×2). The combined organic layers were washed with water (50 mL), with brine (50 mL), dried over Na$_2$SO$_4$, concentrated and purified by flash chromatography using ethyl acetate: hexane to afford 7-chloro-3-(2,6-dichlorophenyl)-2,3-dihydro-4H-pyrido[3,2-e][1,3]oxazin-4-one as off white solid (0.235 g, 5.95%,).
LCMS: 329[M+1]$^+$ Step-5: Synthesis of 3-(2,6-dichlorophenyl)-7-((4-(4-methylpiperazin-1-yl)phenyl)amino)-2,3-dihydro-4H-pyrido[3,2-e][1,3]oxazin-4-one To a stirred solution of 7-chloro-3-(2,6-dichlorophenyl)-2,3-dihydro-4H-pyrido[3,2-e][1,3]oxazin-4-one (0.230 g, 0.697 mmol, 1.0 eq), and 4-(4-methylpiperazin-1-yl)aniline (0.134 g, 0.697 mmol, 1.0 eq) in DMSO (5.0 mL) was added K$_3$PO$_4$ (0.296 g, 1.394 mmol, 2.0 eq) at rt. The resulting mixture was stirred and purged with nitrogen for 10 min. followed by addition of CuI (0.014 g, 0.0697 mmol, 0.1 eq) and L-proline (0.016 g, 0.1394 mmol, 0.2 eq) and again purged with nitrogen. The reaction mixture was heated at 90° C. for 24 h. The progress of reaction was monitored by LCMS. The reaction mixture was diluted with water (100 mL), extracted with EtOAc (100 mL×2). The combined organic layer was washed with water (50 mL), with brine (50 mL), dried over Na$_2$SO$_4$, concentrated and purified by reversed phase chromatography to afford 3-(2,6-dichlorophenyl)-7-((4-(4-methylpiperazin-1-yl)phenyl)amino)-2,3-dihydro-4H-pyrido[3,2-e][1,3]oxazin-4-one (7 mg, 2.08%) as an off white solid.
LCMS: 484 [M+1]$^+$
$^1$H NMR (400 MHz, DMSO-d$_6$): δ 9.61 (s, 1H), 7.91 (d, J=8.33 Hz, 1H), 7.64 (d, J=8.33 Hz, 2H), 7.44-7.52 (m, 3H), 6.93 (d, J=9.21 Hz, 2H), 6.54 (s, 1H), 5.57 (s, 2H), 3.09 (t, 4H), 2.45 (t, 4H), 2.22 (s, 3H).

Example S32. Synthesis of 3-(2,6-dichlorophenyl)-7-(4-(4-methylpiperazin-1-yl)phenylamino)-2H-pyrido[3,4-e][1,3]oxazin-4(3H)-one (Compound No. 1.32)

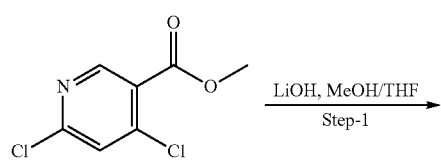

Step-1: Synthesis of 6-chloro-4-methoxynicotinic Acid

To a stirred solution of methyl 4,6-dichloronicotinate (20.0 g, 97.09 mmol, 1.0 eq), in THF (80 mL) and MeOH (40 mL) was added LiOH.H$_2$O (12.22 g, 291.29 mmol, 3.0 eq) at rt. The resulting mixture was stirred at the same temperature for 12 h. The reaction mixture was concentrated and diluted with water (100 mL), followed by dropwise addition of 1N HCl (50 mL), white precipitate formed was collected by filtered and dried under vacuum to afford the desired compound, 6-chloro-4-methoxynicotinic acid (10.0 g, 49.45%) as white solid.
LCMS: 188[M+1]$^+$

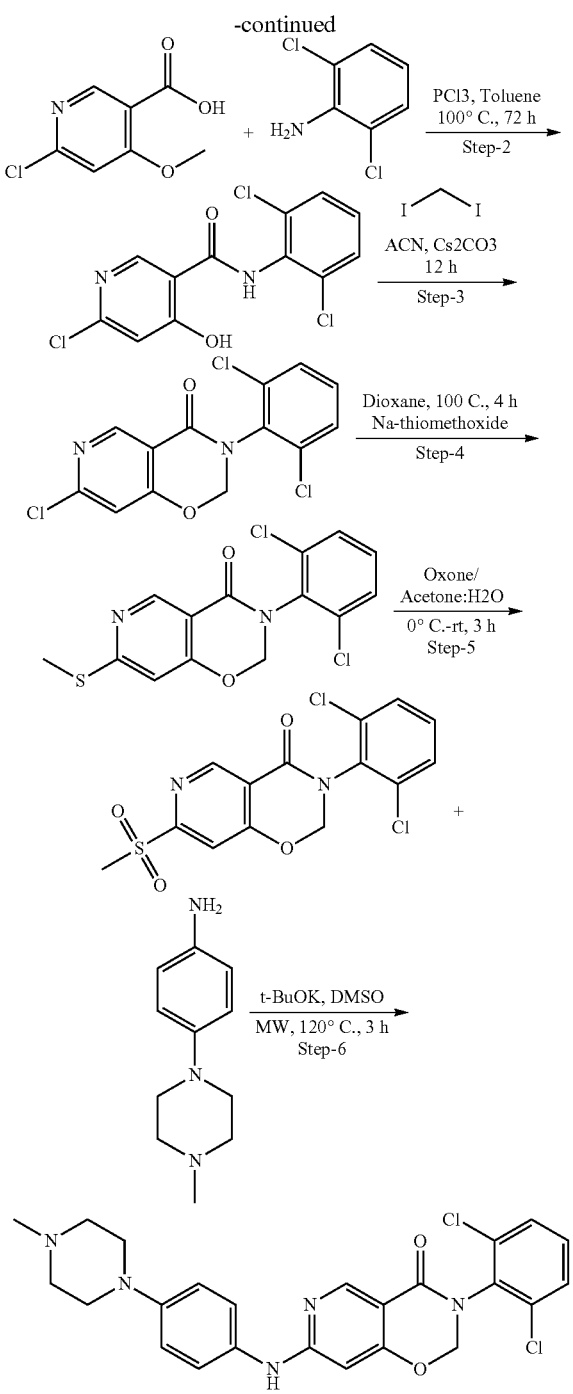

Step-2: Synthesis of 6-chloro-N-(2,6-dichlorophenyl)-4-hydroxynicotinamide

A solution of 6-chloro-4-methoxynicotinic acid (9.0 g, 47.97 mmol, 1.0 eq) and 2,6-dichloroaniline (7.77 g, 47.97 mmol, 1.0 eq) in toluene (270 mL) was purged with nitrogen for 10 min at rt, followed by addition of PCl$_3$ (45 mL). The resulting solution was stirred at 100° C. for 48 h. The progress of reaction was monitored by LCMS. The reaction mixture was concentrated, basified with saturated solution of NaHCO$_3$ (500 mL), extracted with EtOAc (2×100 mL). The combined organic layers were washed with water (50 mL), with brine (50 mL), dried over Na$_2$SO$_4$, concentrated and purified by combi-flash [Silica gel 100-200 mesh; elution 0-30 EtOAc in hexane] to afford the desired compound, 6-chloro-N-(2,6-dichlorophenyl)-4-hydroxynicotinamide (3.5 g, 22.98%) as an off white solid.
LCMS: 317[M+1]$^+$ Step-3: Synthesis of 7-chloro-3-(2,6-dichlorophenyl)-2,3-dihydro-4H-pyrido[3,4-e][1,3]oxazin-4-one To a stirred solution of 6-chloro-N-(2,6-dichlorophenyl)-4-hydroxynicotinamide (3.05 g, 9.60 mmol, 1.0 eq), in CH$_3$CN (120 mL) was added Cs$_2$CO$_3$ (9.38 g, 28.80 mmol, 3.0 eq) at rt. The resulting mixture was stirred and purged with nitrogen for 10 min followed by addition of diiodomethane (5.14 g, 19.20 mmol, 2.0 eq) at rt. The reaction mixture was heated at 90° C. for 48 h. The progress of reaction was monitored by LCMS. The reaction mixture was diluted with water (100 mL), extracted with EtOAc (2×100 mL). The combined organic layers were washed with water (50 mL), with brine (50 mL), dried over Na$_2$SO$_4$, concentrated and purified with combi-flash [Silica gel 100-200 mesh; elution 0-20 EtOAc in hexane] to afford the desired compound, 7-chloro-3-(2,6-dichlorophenyl)-2,3-dihydro-4H-pyrido[3,4-e][1,3]oxazin-4-one (1.71 g, 54.11%) as light yellow solid.
LCMS: 329.1[M+1]$^+$ Step-4: Synthesis of 3-(2,6-dichlorophenyl)-7-(methylthio)-2,3-dihydro-4H-pyrido[3,4-e][1,3]oxazin-4-one A stirred solution of 7-chloro-3-(2,6-dichlorophenyl)-2,3-dihydro-4H-pyrido[3,4-e][1,3]oxazin-4-one (0.500 g, 1.517 mmol, 1.0 eq) and sodium-thiomethoxide (0.531 g, 7.585 mmol, 5.0 eq) in dioxane (10.0 mL) was stirred at rt for 4 h. The progress of reaction was monitored by LCMS. The reaction mixture was diluted with water (100 mL), extracted with EtOAc (2×100 mL). The combined organic layers were washed with water (50 mL), with brine (50 mL), dried over Na$_2$SO$_4$, concentrated and purified by flash chromatography (elution 0-50 EtOAc in hexane) to afford the desired compound, 3-(2,6-dichlorophenyl)-7-(methylthio)-2,3-dihydro-4H-pyrido[3,4-e][1,3]oxazin-4-one (0.292 g, 53.39%) as an off white solid.
LCMS: 341.2[M+1]$^+$ Step-5:—Synthesis of 3-(2,6-dichlorophenyl)-7-(methylsulfonyl)-2,3-dihydro-4H-pyrido[3,4-e][1,3]oxazin-4-one To a stirred solution of 3-(2,6-dichlorophenyl)-7-(methylthio)-2,3-dihydro-4H-pyrido[3,4-e][1,3]oxazin-4-one (0.290 g, 0.852 mmol, 1.0 eq) in Acetone (6 mL) at 0° C. was added Oxone (1.94 g, 12.79 mmol in 1 mL of water). The resulting mixture was stirred at rt for 3 h. The progress of reaction was monitored by LCMS. The reaction mixture was concentrated, diluted with water (100 mL), extracted with EtOAc (2×100 mL). The combined organic layers were washed with water (50 mL), with brine (50 mL), dried over Na$_2$SO$_4$, concentrated and purified by flash chromatography (Elution: 0-60% EtOAc in hexane) to afford the desired compound, 3-(2,6-dichlorophenyl)-7-(methylsulfonyl)-2,3-dihydro-4H-pyrido[3,4-e][1,3]oxazin-4-one (0.202 g, 63.68%) as an off white solid.
LCMS: 373.2 [M+1]$^+$ Step-6:—Synthesis of 3-(2,6-dichlorophenyl)-7-((4-(4-methylpiperazin-1-yl)phenyl)amino)-2,3-dihydro-4H-pyrido[3,4-e][1,3]oxazin-4-one To a stirred solution of 3-(2,6-dichlorophenyl)-7-(methylsulfonyl)-2,3-dihydro-4H-pyrido[3,4-e][1,3]oxazin-4-one (0.150 g, 0.403 mmol, 1.0 eq), and 4-(4-methylpiperazin-1-yl)aniline (0.084 g, 0.443 mmol, 1.1 eq) in DMSO (5.0 mL) was added tBuOK (0.090 g, 0.806 mmol, 2.0 eq) at rt. The resulting mixture was heated at 120° C. in microwave for 30 min. The progress of reaction was monitored by LCMS. The reaction mixture was diluted with water (100 mL), extracted with EtOAc (2×100 mL). The combined organic layers were washed with water (50 mL), with brine (50 mL), dried over Na$_2$SO$_4$, concentrated and purified by reversed phase purification to afford the desired compound, 3-(2,6-dichlorophenyl)-7-((4-(4-methylpiperazin-1-yl)phenyl)amino)-2,3-dihydro-4H-pyrido[3,4-e][1,3]oxazin-4-one (0.004 g, 2.05%) as an off white solid.
LCMS: 484.2 [M+1]$^+$ $^1$H NMR (400 MHz, DMSO-d$_6$): δ 9.37 (s, 1H), 8.54 (s, 3H), 7.64 (d, J=7.89 Hz, 4H), 7.49 (d, J 8.33 Hz, 3H), 7.39 (d, J=8.33 Hz, 4H), 6.92 (d, J=8.77 Hz, 3H), 6.24 (s, 2H), 5.55 (s, 4H), 4.10 (d, J=4.82 Hz, 4H), 3.16 (d, J=5.26 Hz, 3H), 3.08 (br s, 4H), 2.22 (s, 3H).

Example S33. Synthesis of 3-(2,6-dichlorophenyl)-7-(3-methyl-4-(piperazin-1-yl)phenylamino)-2H-pyrimido[5,4-e][1,3]oxazin-4(3H)-one (Compound No. 1.33)

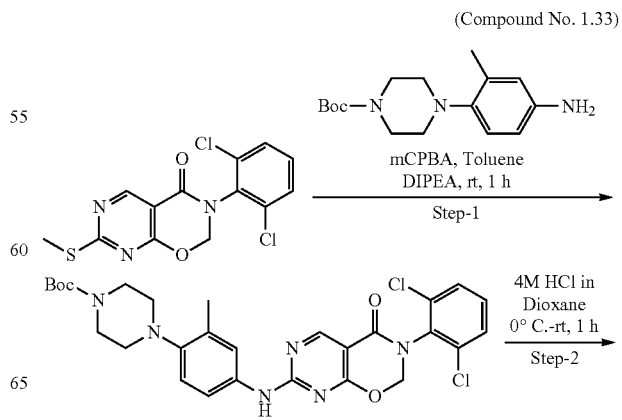

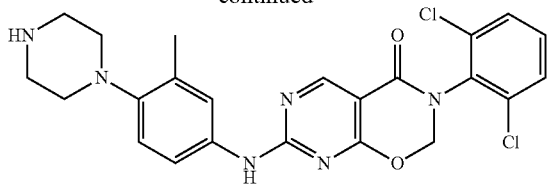

Step-1: Synthesis of tert-butyl 4-[4-[[3-(2,6-dichlorophenyl)-4-oxo-2H-pyrimido[5,4-e][1,3]oxazin-7-yl]amino]-2-methyl-phenyl]piperazine-1-carboxylate To a stirred solution of 3-(2,6-dichlorophenyl)-7-methylsulfanyl-2H-pyrimido[5,4-e][1,3]oxazin-4-one (250 mg, 0.733 mmol, 1.0 eq) in 3 mL of toluene was added m-CPBA (315 mg, 1.83 mmol, 2.5 eq) and allowed to stir at rt for 30 min. Tert-butyl 4-(4-amino-2-methyl-phenyl)piperazine-1-carboxylate (213 mg, 0.733 mmol, 1.0 eq) and DIPEA (378 mg, 2.93 mmol, 4.0 eq) were added and allowed to stir at rt for 1 hr. Progress of reaction was monitored by LCMS. After completion of reaction solvent was removed under reduced pressure, residue was diluted with 20 mL of water and extracted with ethyl acetate (50 mL×3). Combined organic layer was washed with water (20 mL×3), dried over anhydrous Na2SO4 and concentrated under reduced pressure. Crude was purified by flash chromatography using MeOH:CH$_2$Cl$_2$ as eluents to obtain 180 mg of tert-butyl 4-[4-[[3-(2,6-dichlorophenyl)-4-oxo-2H-pyrimido[5,4-e][1,3]oxazin-7-yl]amino]-2-methyl-phenyl]piperazine-1-carboxylate as a freebase.

LCMS: 585 [M+1]$^+$

Step-2: Synthesis of 3-(2,6-dichlorophenyl)-7-(3-methyl-4-piperazin-1-yl-anilino)-2H-pyrimido[5,4-e][1,3]oxazin-4-one Hydrochloride Salt Tert-butyl 4-[4-[[3-(2,6-dichlorophenyl)-4-oxo-2H-pyrimido[5,4-e][1,3]oxazin-7-yl]amino]-2-methyl-phenyl]piperazine-1-carboxylate (150 mg, 0.256 mmol, 1.0 eq) was dissolved in 4 mL of 4M HCl in dioxane solution at 0° C. Reaction was stirred at rt for 1 hr. Progress of reaction was monitored by LCMS. After completion of reaction, precipitated compound was filtered off, washed with 3 mL of dioxane and dried under reduced pressure to obtain 3-(2,6-dichlorophenyl)-7-(3-methyl-4-piperazin-1-yl-anilino)-2H-pyrimido[5,4-e][1,3]oxazin-4-one (90 mg, 67.7%) as an HCl salt.

LCMS: 485 [M+1]$^+$ $^1$H NMR (400 MHz, DMSO-d$_6$): δ 10.31 (br s, 1H), 8.97 (br. s., 2H), 8.82 (s, 1H), 7.66 (d, J=7.89 Hz, 2H), 7.42-7.59 (m, 3H), 7.04 (d, J=8.33 Hz, 2H), 5.72 (s, 2H), 3.23 (br s, 3H), 3.16 (br s, 1H), 3.02 (br. s., 4H), 2.26 (s, 3H).

Example S34. Synthesis of 3-(2,6-dichlorophenyl)-7-(3-(hydroxymethyl)-4-(piperidin-4-yl)phenylamino)-2H-pyrimido[5,4-e][1,3]oxazin-4(3H)-one (Compound No. 1.34)

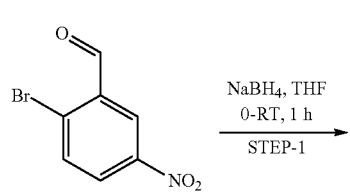

Step-1: Synthesis of (2-bromo-5-nitrophenyl)MeOH

To a stirred solution of 2-bromo-5-nitrobenzaldehyde (5 g, 21.73 mmol, 1.0 eq) in 100 mL of THF: MeOH (1:1) was added NaBH$_4$ (1.67 g, 43.47 mmol, 2.eq) at 0° C. and allowed to stir at rt for 1 hr. Progress of reaction was monitored by TLC. After consumption of starting material, solvent was removed under reduced pressure; the residue was diluted with 100 mL of water and extracted with ethyl acetate (200 mL×2). Combined organic layer was washed with water (50 mL×3), dried over anhydrous Na$_2$SO$_4$ and concentrated under reduced pressure to obtain 4.5 g (89.28%) of (2-bromo-5-nitrophenyl) MeOH.

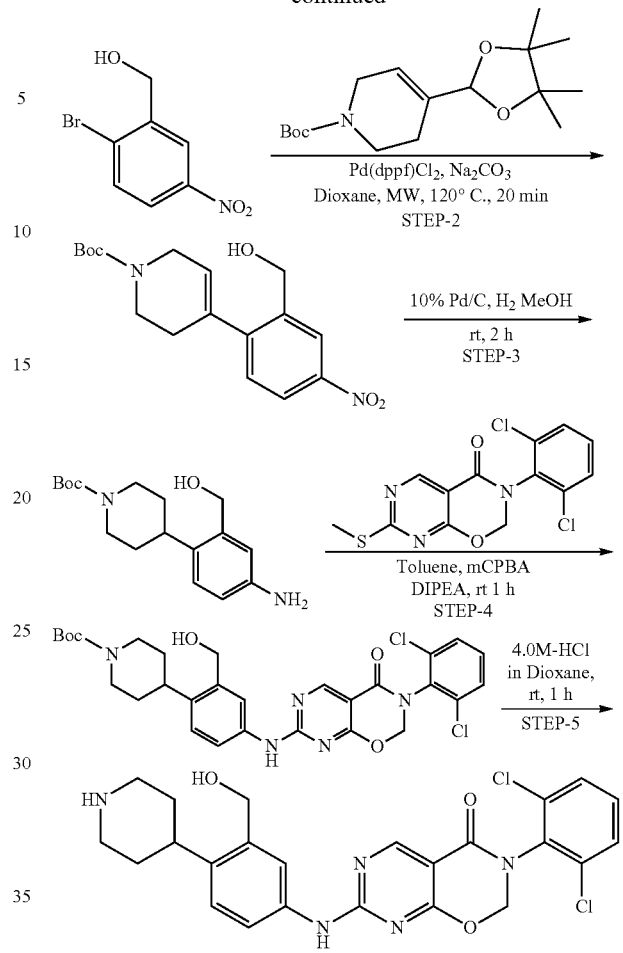

Step-2: Synthesis of tert-butyl 4-(2-(hydroxymethyl)-4-nitrophenyl)-3,6-dihydropyridine-1(2H)-carboxylate To a stirred solution of (2-bromo-5-nitrophenyl)MeOH (1 g, 4.31 mmol, 1.0 eq) in 5 mL of dioxane were added tert-butyl 4-(4,4,5,5-tetramethyl-1,3-dioxolan-2-yl)-3,6-dihydropyridine-1(2H)-carboxylate (1.59 g, 5.17 mmol, 1.2 eq) and solution of Na$_2$CO$_3$ (1.35 g, 12.93 mmol, 3 eq) in 2 mL of water. The reaction mixture was purged with nitrogen for 15 min. PdCl$_2$(dppf) (0.351 g, 0.431 mmol, 0.1 eq) was added. The reaction mixture was stirred at 120° C. for 20 min in microwave. Progress of reaction was monitored by LCMS. After consumption of starting material, solvent was removed under reduced pressure; residue was diluted with 50 mL of water and extracted with ethyl acetate (200 mL×2). The combined organic layer was washed with water (50 mL×3), dried over anhydrous Na$_2$SO$_4$ and concentrated under reduced pressure. Crude was purified by flash chromatography using ethyl acetate: hexane as eluents to obtain 460 mg (46%) of tert-butyl 4-(2-(hydroxymethyl)-4-nitrophenyl)-3,6-dihydropyridine-1(2H)-carboxylate.
LCMS: 334 [M+1]$^+$ Step-3: Synthesis of tert-butyl 4-(4-amino-2-(hydroxymethyl)phenyl)piperidine-1-carboxylate To a stirred solution of tert-butyl 4-(2-(hydroxymethyl)-4-nitrophenyl)-3,6-dihydropyridine-1(2H)-carboxylate (1.2 g, 3.58 mmol, 1.0 eq) in 50 mL of MeOH was added Pd/C (200 mg). The reaction mixture was stirred at rt under hydrogen environment for 2 h. Progress of reaction is monitored by LCMS. After consumption of starting material, reaction mixture was filtered off using celite bed. The filtrate was collected and concentrated under reduce pressure to obtain 0.891 g (97%) of tert-butyl 4-(4-amino-2-(hydroxymethyl)phenyl)piperidine-1-carboxylate.
LCMS: 306 [M+1]$^+$ Step-4: Synthesis of tert-butyl 4-(4-((3-(2,6-dichlorophenyl)-4-oxo-3,4-dihydro-2H-pyrimido[5,4-e][1,3]oxazin-7-yl)amino)-2-(hydroxymethyl)phenyl)piperidine-1-carboxylate To a stirred solution of 3-(2,6-dichlorophenyl)-7-(methylthio)-2,3-dihydro-4H-pyrimido[5,4-e][1,3]oxazin-4-one (300 mg, 0.879 mmol, 1.0 eq) in 5 mL of toluene was added m-CPBA (378 mg, 2.199 mmol, 2.5 eq) and allowed to stir at rt for 30 min. Tert-butyl 4-(4-amino-2-(hydroxymethyl)phenyl)piperidine-1-carboxylate (323 mg, 1.05 mmol, 1.2 eq) and DIPEA (453 mg, 3.51 mmol, 4.0 eq) were added and stirred at rt for 1 hr. Progress of reaction was monitored by LCMS. After consumption of starting material, solvent was removed under reduced pressure; residue was diluted with 50 mL of water and extracted with ethyl acetate (200 mL×2). The combined organic layer was washed with water (50 mL×3), dried over anhydrous Na2SO4 and concentrated under reduced pressure. Crude was purified by flash chromatography using MeOH:CH2Cl2 as eluents to obtain 180 mg (34%) tert-butyl 4-(4-((3-(2,6-dichlorophenyl)-4-oxo-3,4-dihydro-2H-pyrimido[5,4-e][1,3]oxazin-7-yl)amino)-2-(hydroxymethyl)phenyl) piperidine-1-carboxylate.
LCMS: 599 [M+1]$^+$ Step-5: Synthesis of 3-(2,6-dichlorophenyl)-7-((3-(hydroxymethyl)-4-(piperidin-4-yl)phenyl)amino)-2,3-dihydro-4H-pyrimido[5,4-e][1,3]oxazin-4-one To a stirred solution of tert-butyl 4-(4-((3-(2,6-dichlorophenyl)-4-oxo-3,4-dihydro-2H-pyrimido[5,4-e][1,3]oxazin-7-yl)amino)-2-(hydroxymethyl)phenyl) piperidine-1-carboxylate (180 mg, 0.300 mmol, 1 eq) in 4M HCl in dioxane (3 mL). Mixture was stirred at rt for 1 hr. Progress of reaction was monitored by LCMS. After consumption of starting material, precipitated compound was filtered off and washed with dioxane and dried under vacuum. Crude was purified by reversed phase chromatography to obtain 30 mg (20%) of 3-(2,6-dichlorophenyl)-7-((3-(hydroxymethyl)-4-(piperidin-4-yl)phenyl)amino)-2,3-dihydro-4H-pyrimido[5,4-e][1,3]oxazin-4-one.

LCMS: 500 [M+1]$^+$
$^1$H NMR (400 MHz, DMSO-d$_6$): δ 10.39 (br s, 1H), 8.82 (s, 1H), 8.43 (br s, 2H), 7.55-7.74 (m, 4H), 7.47-7.54 (m, 1H), 7.19 (d, J=8.77 Hz, 1H), 5.73 (s, 2H), 4.55 (s, 2H), 3.19 (br s, 4H), 2.93 (br s, 2H), 2.80 (br s, 2H), 1.70 (br s, 4H).

Example S35. Synthesis of 3-(2,6-dichlorophenyl)-7-(2-methyl-1,2,3,4-tetrahydroisoquinolin-7-ylamino)-2H-pyrimido[5,4-e][1,3]oxazin-4(3H)-one (Compound No. 1.35)

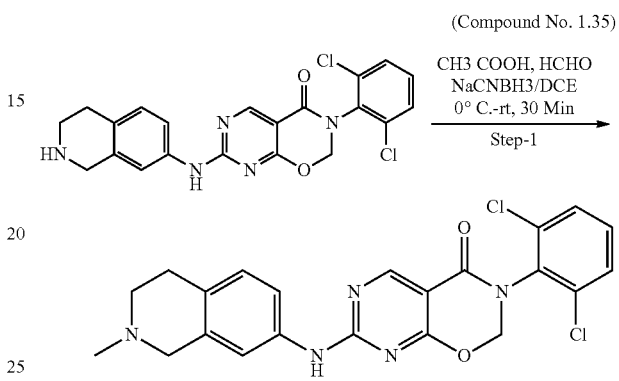

Synthesis of 3-(2,6-dichlorophenyl)-7-[(2-methyl-3,4-dihydro-1H-isoquinolin-7-yl)amino]-2H-pyrimido[5,4-e][1,3]oxazin-4-one To a stirred solution of 3-(2,6-dichlorophenyl)-7-(1,2,3,4-tetrahydroisoquinolin-7-ylamino)-2H-pyrimido[5,4-e][1,3]oxazin-4-one hydrochloride (150 mg, 0.340 mmol, 1.0 eq) and HCHO (0.096 mL, 1.02 mmol, 3.0 eq) in dichloroethane (5 mL) was added acetic acid (102 mg, 1.70 mmol, 5.0 eq) dropwise at 0° C. The resulting mixture was stirred at rt for 1 hr followed by addition of NaCNBH$_3$ (64 mg, 1.02 mmol, 3.0 eq) at 0° C. The resulting mixture was stirred at rt for 30 min. The progress of reaction was monitored by LCMS. After completion of reaction, mixture was basified with saturated solution of NaHCO$_3$ (20 mL) and extracted with CH$_2$Cl$_2$ (50 mL×2). The combined organic layer was washed with water (50 mL) and brine (50 mL), dried over anhydrous Na$_2$SO$_4$ and concentrated under reduced. Crude was purified by reversed phase chromatography to afford 3 mg (1.58%) formate salt of 3-(2,6-dichlorophenyl)-7-[(2-methyl-3,4-dihydro-1H-isoquinolin-7-yl)amino]-2H-pyrimido[5,4-e][1,3]oxazin-4-one.
LCMS: 456 [M+1]$^+$
$^1$H NMR (400 MHz, DMSO-d$_6$): δ 8.78 (s, 1H), 7.62-7.69 (m, J=8.33 Hz, 2H), 7.50 (d, J=7.45 Hz, 2H), 7.54 (d, J=7.89 Hz, 1H), 6.87-6.96 (m, J=8.77 Hz, 2H), 5.70 (s, 2H), 3.04 (d, J=5.26 Hz, 4H), 2.89 (d, J=4.82 Hz, 4H), 1.90 (s, 1H).

Example S36. Synthesis of 3-(2,6-dichlorophenyl)-7-(6-(piperazin-1-yl)pyridin-3-ylamino)-2H-pyrimido[5,4-e][, 3]oxazin-4(3H)-one (Compound No. 1.36)

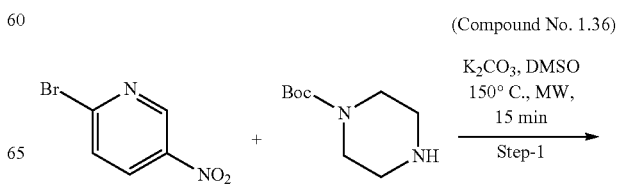

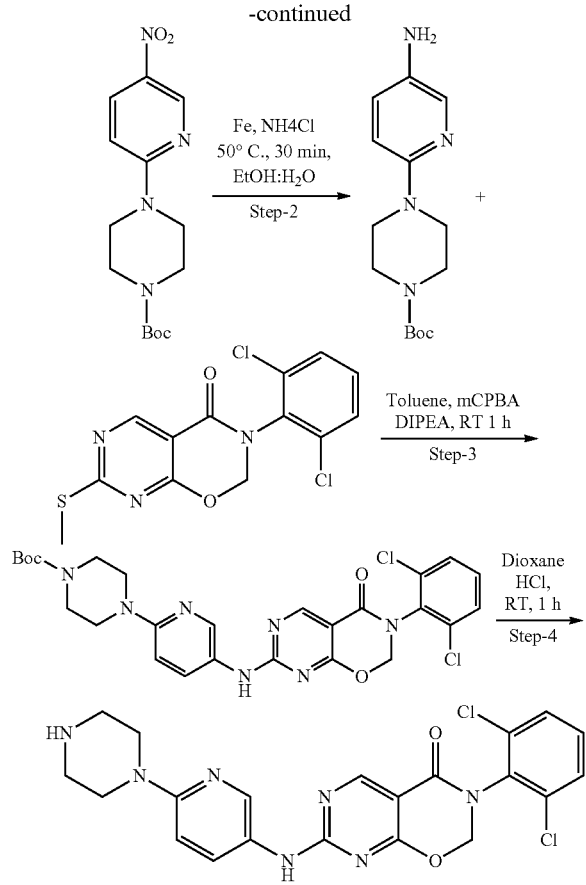

Step-1: Synthesis of tert-butyl 4-(5-nitropyridin-2-yl)piperazine-1-carboxylate To a stirred solution of 2-bromo-5-nitropyridine (1.0 g, 4.926 mmol, 1 eq) and tert-butyl piperazine-1-carboxylate (0.917 g, 4.926 mmol, 1.0 eq) in 4 mL of $H_2O$ was added $K_2CO_3$ (1.02 g, 7.389 mmol, 1.5 eq). The reaction mixture was heated at 150° C. for 15 min in microwave. The progress of reaction was monitored by LCMS. Upon the consumption of starting material, the precipitated compound was filtered off and dried to obtain the desired product, tert-butyl 4-(5-nitropyridin-2-yl)piperazine-1-carboxylate (1.283 g, 84.18%) as a yellow solid.

LCMS: 309 [M+1]$^+$

Step-2: Synthesis of tert-butyl 4-(5-aminopyridin-2-yl)piperazine-1-carboxylate To a stirred solution of tert-butyl 4-(5-nitropyridin-2-yl)piperazine-1-carboxylate (2.9 g, 9.405 mmol, 1.0 eq) in 6 mL of ethanol: water (1:1) mixture were added ammonium chloride (4.04 g, 75.24 mmol, 4 eq) and Fe(0) (2.10 g, 37.62 mmol, 4.0 eq). Reaction mixture was heated at 50° C. for 30 min. Progress of reaction was monitored by LCMS. Upon the consumption of starting material, the reaction mixture was filtered over celite and filtrate was concentrated under reduced pressure. The crude obtained was diluted with 50 mL of water and extracted with ethyl acetate (200 mL×2). Combined organic layer was washed with water and brine, dried over $Na_2SO_4$ and concentrated under reduced pressure. The crude was purified by flash chromatography using 0-2% MeOH in $CH_2Cl_2$ as eluents to obtain the desired product, tert-butyl 4-(5-aminopyridin-2-yl)piperazine-1-carboxylate (1.072 g, 40%).

LCMS: 279 [M+1]$^+$

Step-3: Synthesis of tert-butyl 4-(5-(((3-(2,6-dichlorophenyl)-4-oxo-3,4-dihydro-2H-pyrimido[5,4-e][1,3]oxazin-7-yl)amino)pyridin-2-yl)piperazine-1-carboxylate To a stirred solution of 3-(2,6-dichlorophenyl)-7-(methylthio)-2,3-dihydro-4H-pyrimido[5,4-e][1,3]oxazin-4-one (300 mg, 0.876 mmol, 1.0 eq) in 3 mL of toluene was added mCPBA (376.9 mg, 2.19 mmol, 2.5 eq) and allowed to stir at rt for 30 min. Tert-butyl 4-(5-aminopyridin-2-yl)piperazine-1-carboxylate (244.03 mg, 0.876 mmol, 1 eq) and DIPEA (453 mg, 3.50 mmol, 4.0 eq) were added and allowed to stirred at rt for 1 hr. Progress of reaction was monitored by LCMS. After consumption of starting material, the reaction mixture was extracted with ethyl acetate (50 mL×2). Combined organic layer was washed with water (20 mL×3), dried over anhydrous $Na_2SO_4$ and concentrated under reduced pressure. The crude was purified by flash chromatography using MeOH: $CH_2Cl_2$ as eluents to obtain 105 mg (20%) of tert-butyl 4-(5-(((3-(2,6-dichlorophenyl)-4-oxo-3,4-dihydro-2H-pyrimido[5,4-e][1,3]oxazin-7-yl)amino)pyridin-2-yl)piperazine-1-carboxylate.

LCMS: 571 [M+1]$^+$

Step-4: Synthesis of 3-(2,6-dichlorophenyl)-7-((6-(piperazin-1-yl)pyridin-3-yl)amino)-2,3-dihydro-4H-pyrimido[5,4-e][1,3]oxazin-4-one tert-Butyl 4-(5-(((3-(2,6-dichlorophenyl)-4-oxo-3,4-dihydro-2H-pyrimido[5,4-e][1,3]oxazin-7-yl)amino)pyridin-2-yl)piperazine-1-carboxylate (100 mg, 0.175 mmol, 1 eq) was dissolved in 4N HCl in dioxane (3 mL). Reaction mixture was stirred at rt for 1 hr. Progress of reaction was monitored by LCMS. After consumption of starting material, precipitated compound was filtered off and washed with diethyl ether and dried under vacuum. The crude was purified by reversed phase to obtain 70 mg (84.86%) 3-(2,6-dichlorophenyl)-7-((6-(piperazin-1-yl)pyridin-3-yl)amino)-2,3-dihydro-4H-pyrimido[5,4-e][1,3]oxazin-4-one.

LCMS: 471 [M+1]$^+$ $^1$H NMR (400 MHz, DMSO-$d_6$): δ 9.24 (br s, 2H), 8.83 (s, 1H), 8.47 (br. s., 1H), 8.02 (d, J=7.89 Hz, 1H), 7.66 (d, J=7.89 Hz, 2H), 7.42-7.54 (m, 1H), 7.14 (d, J=9.21 Hz, 1H), 5.73 (s, 2H), 3.73-3.84 (m, 3H), 3.70 (br s, 1H), 3.03-3.25 (m, 4H).

Example S37. Synthesis of (R)-3-(2,6-dichlorophenyl)-7-(4-(2-(hydroxymethyl)piperazin-1-yl)phenylamino)-2H-pyrimido[5,4-e][1,3]oxazin-4(3H)-one (Compound No. 1.37)

Synthesis of (R)-3-(2,6-dichlorophenyl)-7-(4-(2-(hydroxymethyl)piperazin-1-yl)phenylamino)-2H-pyrimido[5,4-e][1,3]oxazin-4(3H)-one (R)-3-(2,6-dichlorophenyl)-7-(4-(2-(hydroxymethyl)piperazin-1-yl)phenylamino)-2H-pyrimido[5,4-e][1,3]oxazin-4(3H)-one is separated from the product synthesized in the scheme described in Example S13.

Example S38. Synthesis of (S)-3-(2,6-dichlorophenyl)-7-(4-(2-(hydroxymethyl)piperazin-1-yl)phenylamino)-2H-pyrimido[5,4-e][1,3]oxazin-4(3H)-one (Compound No. 1.38)

Synthesis of (S)-3-(2,6-dichlorophenyl)-7-(4-(2-(hydroxymethyl)piperazin-1-yl)phenylamino)-2H-pyrimido[5,4-e][1,3]oxazin-4(3H)-one (S)-3-(2,6-dichlorophenyl)-7-(4-(2-(hydroxymethyl)piperazin-1-yl)phenylamino)-2H-pyrimido[5,4-e][1,3]oxazin-4(3H)-one is separated from the product synthesized in the scheme described in Example S13.

Example S39. Synthesis of 3-(2,6-difluorophenyl)-7-(4-(piperazin-1-yl)phenylamino)-2H-pyrimido[5,4-e][1,3]oxazin-4(3H)-one (Compound No. 1.39)

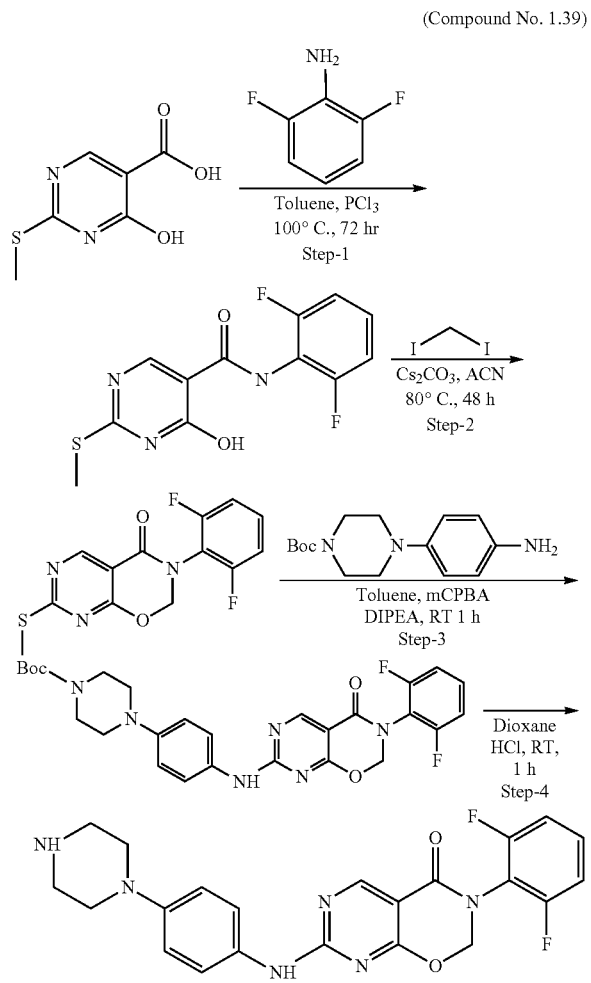

Step-1: Synthesis of N-(2,6-difluorophenyl)-4-hydroxy-2-(methylthio)pyrimidine-5-carboxamide To a stirred solution of 4-hydroxy-2-(methylthio)pyrimidine-5-carboxylic acid (5 g, 26.88 mmol, 1.0 eq) in 100 mL of Toluene was added 2,6-difluoroaniline (3.81 g, 29.55 mmol, 1.1 eq) and PCl$_3$ (25 mL). Reaction was allowed to stir at 100° C. for 72 hr. Progress of reaction was monitored by LCMS. After consumption of starting material, solvent was removed under reduced pressure, residue was diluted with diethyl ether (100 mL) and 10 mL of MeOH. Solid was filtered out and dried under vacuum to obtain 7 g (88%) of N-(2,6-difluorophenyl)-4-hydroxy-2-(methylthio)pyrimidine-5-carboxamide.

LCMS: 298 [M+1]$^+$

Step-2: Synthesis of 3-(2,6-difluorophenyl)-7-(methylthio)-2,3-dihydro-4H-pyrimido[5,4-e][1,3]oxazin-4-one To a stirred solution of N-(2,6-difluorophenyl)-4-hydroxy-2-(methylthio)pyrimidine-5-carboxamide (7 g, 23.56 mmol, 1.0 eq) in 200 mL of CH$_3$CN were added Cs$_2$CO$_3$ (22.97 g, 70.70 mmol, 3 eq) and DMSO (15 mL). Reaction mixture was purged with nitrogen for 10 min. Diiodomethane (9.47 g, 35.35 mmol, 1.5 eq) was added and reaction was allowed to stir at 80° C. for 48 h. Progress of reaction was monitored by LCMS. After consumption of starting material, solvent was removed under reduced pressure; residue was diluted with 100 mL of water and extracted with ethyl acetate (400 mL×2). Combined organic layer was washed with water (100 mL×3), dried over anhydrous Na$_2$SO$_4$ and concentrated under reduced pressure. Crude was purified with flash chromatography using EtoAc: Hexane as eluents to obtain 400 mg (5%) of 3-(2,6-difluorophenyl)-7-(methylthio)-2,3-dihydro-4H-pyrimido[5,4-e][1,3]oxazin-4-one.

LCMS: 310 [M+1]$^+$

Step-3: Synthesis of tert-butyl 4-(4-((3-(2,6-difluorophenyl)-4-oxo-3,4-dihydro-2H-pyrimido[5,4-e][1,3]oxazin-7-yl)amino)phenyl)piperazine-1-carboxylate To a stirred solution of 3-(2,6-difluorophenyl)-7-(methylthio)-2,3-dihydro-4H-pyrimido[5,4-e][1,3]oxazin-4-one (220 mg, 0.711 mmol, 1.0 eq) in 5 mL of toluene was added mCPBA (306 mg, 1.779 mmol, 2.5 eq) and allowed to stir at rt for 30 min. Tert-butyl 4-(4-aminophenyl)piperazine-1-carboxylate (238 mg, 0.854 mmol, 1.2 eq) and DIPEA (367 mg, 2.84 mmol, 4.0 eq) were added and stirred at rt for 1 hr. Progress of reaction was monitored by LCMS. After consumption of starting material, solvent was removed under reduced pressure; residue was diluted with water (20 mL) and extracted with ethyl acetate (100 mL×2). Combined organic layer was washed with water (50 mL×3), dried over anhydrous Na$_2$SO$_4$ and concentrated under reduced pressure. To obtain 100 mg (26.10%) of tert-butyl 4-(4-((3-(2,6-difluorophenyl)-4-oxo-3,4-dihydro-2H-pyrimido[5,4-e][1,3]oxazin-7-yl)amino)phenyl)piperazine-1-carboxylate flash chromatography was used using MeOH: CH2Cl2.

LCMS: 539 [M+1]$^+$

Step-4: Synthesis of 3-(2,6-difluorophenyl)-7-((4-(piperazin-1-yl)phenyl)amino)-2,3-dihydro-4H-pyrimido[5,4-e][1,3]oxazin-4-one To a stirred solution of tert-butyl 4-(4-((3-(2,6-difluorophenyl)-4-oxo-3,4-dihydro-2H-pyrimido[5,4-e][1,3]oxazin-7-yl)amino)phenyl) piperazine-1-carboxylate (100 mg, 0.185 mmol, 1 eq) in dioxane HCl (4 mL). Reaction mixture was stirred at rt for 1 hr. Progress of reaction was monitored by LCMS. After consumption of starting material, precipitated compound was filtered off. Crude was purified by reversed phase to obtain 6 mg (7%) of 3-(2,6-difluorophenyl)-7-((4-(piperazin-1-yl)phenyl)amino)-2,3-dihydro-4H-pyrimido[5,4-e][1,3]oxazin-4-one.

LCMS: 439 [M+1]+

$^1$H NMR (400 MHz, DMSO-d$_6$) δ 8.83 (s, 1H), 7.58 (d, J=8.77 Hz, 3H), 7.34 (br s, 2H), 6.97 (d, J=9.65 Hz, 2H), 5.81 (br s, 2H), 3.23 (d, J=4.82 Hz, 2H), 3.06 (br s, 2H), 2.89 (br s, 2H).

Example S40. Synthesis of 7-(3-chloro-4-(piperazin-1-yl)phenylamino)-3-(2,6-dichlorophenyl)-2H-pyrimido[5,4-e][1,3]oxazin-4(3H)-one

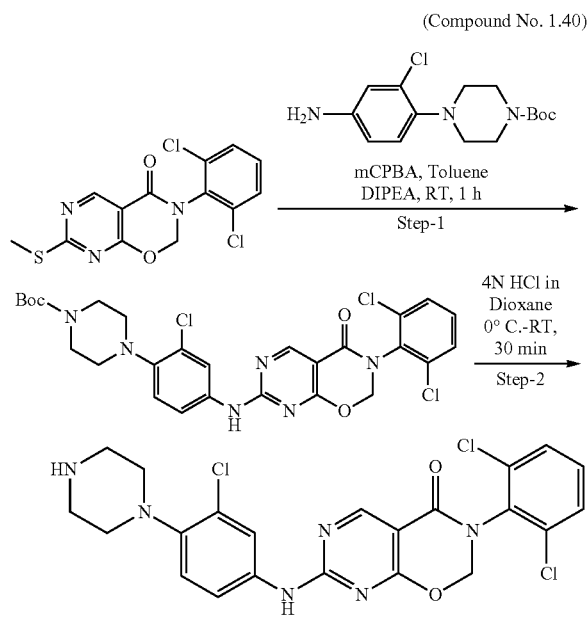

Step-1: Synthesis of tert-butyl 4-(2-chloro-4-(3-(2,6-dichlorophenyl)-4-oxo-3,4-dihydro-2H-pyrimido[5,4-e][1,3]oxazin-7-ylamino)phenyl)piperazine-1-carboxylate To a stirred solution of 3-(2,6-dichlorophenyl)-7-methylsulfanyl-2H-pyrimido[5,4-e][1,3]oxazin-4-one (250 mg, 0.733 mmol, 1.0 eq) in 3 mL of toluene was added mCPBA (315 mg, 1.83 mmol, 2.5 eq) and allowed to stir at rt for 30 min. Tert-butyl 4-(4-amino-2-chlorophenyl)piperazine-1-carboxylate (227 mg, 0.733 mmol, 1.0 eq) and DIPEA (378 mg, 2.93 mmol, 4.0 eq) were added and allowed to stir at rt for 1 h. Progress of reaction was monitored by LCMS. After completion of reaction solvent was removed under reduced pressure, residue was diluted with 20 mL of water and extracted with ethyl acetate (50 mL×3). Combined organic layer was washed with water (20 mL×3), dried over anhydrous Na$_2$SO$_4$ and concentrated under reduced pressure. Crude was purified by reversed phase chromatography to obtain 140 mg (45.5%) of tert-butyl 4-(2-chloro-4-(3-(2,6-dichlorophenyl)-4-oxo-3,4-dihydro-2H-pyrimido[5,4-e][1,3]oxazin-7-ylamino)phenyl)piperazine-1-carboxylate.

LCMS: 605 [M+1]+

Step-2: Synthesis of 7-(3-chloro-4-(piperazin-1-yl)phenylamino)-3-(2,6-dichlorophenyl)-2H-pyrimido[5,4-e][1,3]oxazin-4(3H)-one Tert-butyl 4-(2-chloro-4-(3-(2,6-dichlorophenyl)-4-oxo-3,4-dihydro-2H-pyrimido[5,4-e][1,3]oxazin-7-ylamino)phenyl)piperazine-1-carboxylate (200 mg, 0.33 mmol, 1.0 eq) was dissolved in 5 mL of 4N HCl in dioxane solution at 0° C. Reaction was stirred at rt for 30 min. Progress of reaction was monitored by LCMS. After completion of reaction, precipitated compound was filtered off, washed with 2 mL of dioxane and dried under reduced pressure. Crude was purified by reversed phase chromatography to obtain 20 mg (11.05%) formate salt of 7-(3-chloro-4-(piperazin-1-yl)phenylamino)-3-(2,6-dichlorophenyl)-2H-pyrimido[5,4-e][1,3]oxazin-4(3H)-one.

LCMS: 505 [M+1]+

$^1$H NMR (400 MHz, DMSO-d$_6$) δ 8.86 (s, 1H), 8.25 (s, 1H), 7.55-7.70 (m, 3H), 7.51 (d, J=7.89 Hz, 1H), 7.15 (d, J=8.77 Hz, 1H), 5.75 (s, 2H), 2.91 (s, 8H).

Example S41. Synthesis of 3-(2,6-dichlorophenyl)-7-(4-(2-oxopiperazin-1-yl)phenylamino)-2H-pyrimido[5,4-e][,3]oxazin-4(3H)-one

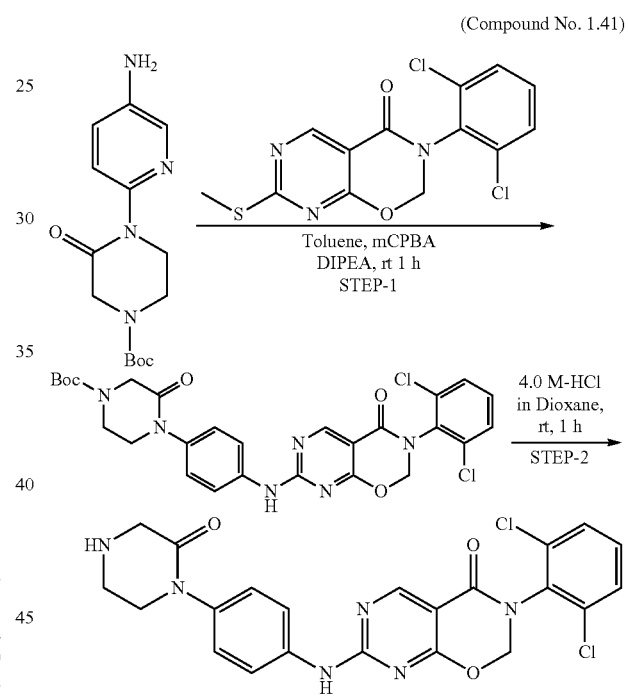

Step-1: Synthesis of tert-butyl 4-(4-((3-(2,6-dichlorophenyl)-4-oxo-3,4-dihydro-2H-pyrimido[5,4-e][1,3]oxazin-7-yl)amino)phenyl)-3-oxopiperazine-1-carboxylate To a stirred solution of 3-(2,6-dichlorophenyl)-7-(methylthio)-2,3-dihydro-4H-pyrimido[5,4-e][1,3]oxazin-4-one (300 mg, 0.934 mmol, 1.0 eq) in 4 mL of toluene was added mCPBA (401.86 mg, 2.336 mmol, 2.5 eq) and allowed to stir at rt for 30 min. Tert-butyl 4-(4-aminophenyl)-3-oxopiperazine-1-carboxylate (326.3 mg, 1.121 mmol, 1.2 eq) and DIPEA (482.24 mg, 3.78 mmol, 4.0 eq) were added and stirred at rt for 1 hr. Progress of reaction was monitored by LCMS. After consumption of starting material, solvent was evaporated under reduced pressure. Residue was diluted with 30 mL of water and extracted with ethyl acetate (200 mL×2). Combined organic layer was washed with water (50 mL×3), dried over anhydrous Na₂SO₄ and concentrated under reduced pressure. Crude was purified by flash chromatography using MeOH: CH₂Cl₂ as eluents to obtain 200 mg (38%) 4-(4-((3-(2,6-dichlorophenyl)-4-oxo-3,4-dihydro-2H-pyrimido[5,4-e][1,3]oxazin-7-yl)amino)phenyl)-3-oxopiperazine-1-carboxylate. LCMS: 585 [M+1]⁺

Step-5: Synthesis of 3-(2,6-dichlorophenyl)-7-((4-(2-oxopiperazin-1-yl)phenyl)amino)-2,3-dihydro-4H-pyrimido[5,4-e][1,3]oxazin-4-one To the tert-butyl 4-(4-((3-(2,6-dichlorophenyl)-4-oxo-3,4-dihydro-2H-pyrimido[5,4-e][1,3]oxazin-7-yl)amino)phenyl)-3-oxopiperazine-1-carboxylate (200 mg, 0.340 mmol, 1 eq) was added 4N HCl in dioxane (4 mL). Mixture was stirred at rt for 1 hr. Progress of reaction was monitored by LCMS. After consumption of starting material, precipitated compound was filtered off and washed with diethyl ether and dried under vacuum. Crude was purified by reversed phase chromatography to obtain 20 mg (12%) of 3-(2,6-dichlorophenyl)-7-((4-(2-oxopiperazin-1-yl)phenyl)amino)-2,3-dihydro-4H-pyrimido[5,4-e][1,3]oxazin-4-one.

LCMS: 485 [M+1]⁺

¹H NMR (400 MHz, DMSO-d₆): δ 10.50 (br s, 1H), 8.86 (s, 1H), 8.34 (br s, 1H), 7.70-7.78 (m, J 8.77 Hz, 2H), 7.66 (d, J=8.33 Hz, 2H), 7.49 (d, J=7.89 Hz, 1H), 7.24-7.32 (m, J=9.21 Hz, 2H), 5.75 (s, 2H), 3.58 (t, J=5.04 Hz, 2H), 3.37 (s, 2H), 3.01 (d, J=5.26 Hz, 2H).

Example S42. Synthesis of 3-(2,6-dichlorophenyl)-7-(3-(hydroxymethyl)-4-(1-methylpiperidin-4-yl)phenylamino)-2H-pyrimido[5,4-e][1,3]oxazin-4(3H)-one (Compound No. 1.42)

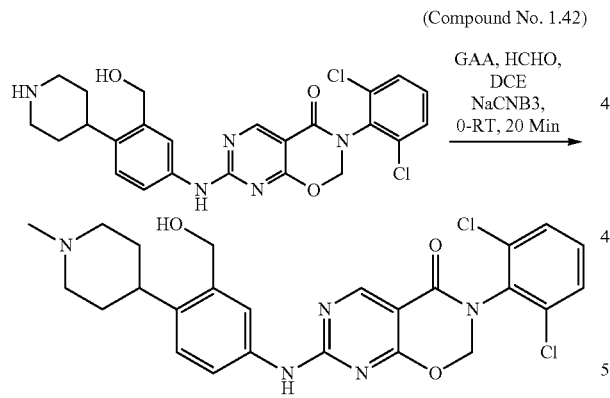

Synthesis of 3-(2,6-dichlorophenyl)-7-(3-(hydroxymethyl)-4-(1-methylpiperidin-4-yl)phenylamino)-2H-pyrimido[5,4-e][1,3]oxazin-4(3H)-one To a stirred solution of 3-(2,6-dichlorophenyl)-7-(3-(hydroxymethyl)-4-(piperidin-4-yl)phenylamino)-2H-pyrimido [5,4-e][1,3]oxazin-4(3H)-one (50 mg, 0.1 mmol, 1.0 eq) in 3 mL of dichloroethane were added HCHO (0.025 mL, 0.3 mmol, 3 eq) and CH₃COOH (30 mg, 0.5 mmol, 5 eq) at 0° C. and allowed to stir at rt for 45 min. NaCNBH₃ (18.9 mg, 0.3 mmol 3.0 eq) was added to the reaction mixture at 0° C. and stirred at rt for 20 min. Progress of reaction was monitored by LCMS. After consumption of starting material, the reaction mixture was diluted with NaHCO₃, extracted with CH₂Cl₂ (20 mL×2). The combined organic layer was washed with water (10 mL×3), dried over anhydrous Na₂SO₄ and concentrated under reduced pressure. Crude residue was purified by reversed phase column chromatography to obtain 20 mg (39.2%) of 3-(2,6-dichlorophenyl)-7-(3-(hydroxymethyl)-4-(1-methylpiperidin-4-yl)phenylamino)-2H-pyrimido[5,4-e][1,3]oxazin-4(3H)-one as an off white solid.

LCMS: 515 [M+1]⁺

¹H NMR (400 MHz, DMSO-d₆): δ 10.33 (s, 1H), 8.81 (s, 1H), 7.55-7.82 (m, 3H), 7.44-7.53 (m, 1H), 7.22 (d, J=8.33 Hz, 1H), 6.56 (s, 2H), 5.65-5.82 (m, 2H), 5.13 (s, 1H), 4.52 (d, J=4.38 Hz, 3H), 4.13 (s, 1H), 3.16 (d, J=4.38 Hz, 2H), 2.86 (d, J=11.40 Hz, 2H), 2.67 (s, 2H), 2.19 (br s, 3H).

Example S43. Synthesis of 3-(3,5-dichloropyridin-4-yl)-7-(4-(4-methylpiperazin-1-yl)phenylamino)-2H-pyrimido[5,4-e][1,3]oxazin-4(3H)-one (Compound No. 1.43)

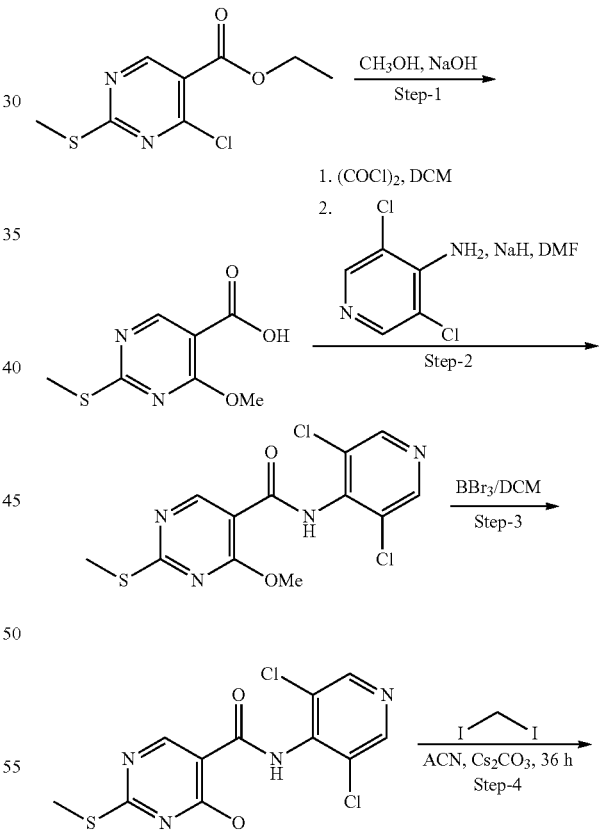

-continued

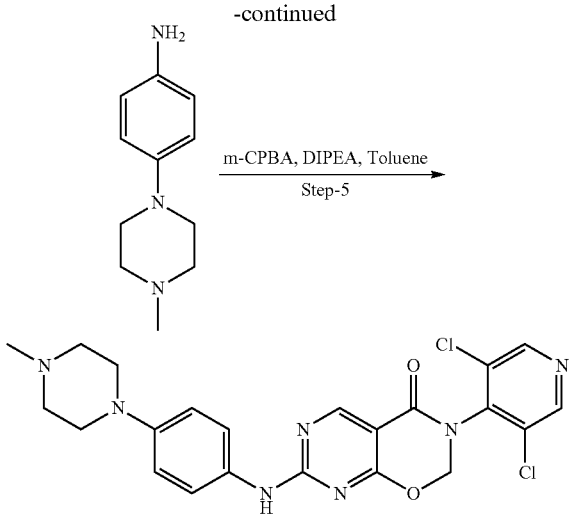

Step-1: Synthesis of 4-methoxy-2-(methylthio)pyrimidine-5-carboxylic acid

To a stirred solution of ethyl 4-chloro-2-(methylthio) pyrimidine-5-carboxylate (3.0 g, 12.893 mmol, 1.0 eq), in MeOH (15 mL) was added 1M solution of NaOH (20 mL) at rt. The resulting mixture was stirred at the same temperature for 3 h. The reaction mixture was concentrated and acidified with 1N HCl solution (10 mL) to adjusted the pH 4-5, the formation of white precipitate was observed which was filtered and dried under vacuum to afford the desired compound 4-methoxy-2-(methylthio)pyrimidine-5-carboxylic acid (1.71 g, 66.25%) as white solid.

LCMS: 201.1[M+1]$^+$

Step-2: Synthesis of N-(3,5-dichloropyridin-4-yl)-4-methoxy-2-(methylthio)pyrimidine-5-carboxamide To a stirred solution of 4-methoxy-2-(methylthio)pyrimidine-5-carboxylic acid (1.7 g, 8.491 mmol, 1.0 eq), in CH$_2$Cl$_2$ (50 mL) was added (COCl)$_2$ (1.45 mL, 16.982 mmol, 2.0 eq) and DMF (0.01 mL) at 0° C. The resulting mixture was stirred at rt for 5 h. The reaction mixture was concentrated, dissolved in CH$_2$Cl$_2$ (5.0 mL) and added to a stirred solution of 3,5-dichloropyridin-4-amine (1.385 g, 8.491 mmol, 1.0 eq) and NaH (680 mg, 16.982 mmol, 2.0 eq) in DMF (30 mL) at 0° C. The resulting mixture was stirred at rt for 2 h. The progress of reaction was monitored by LCMS. The reaction mixture was poured in ice cold water (50 mL), extracted with EtOAc (2×100 mL), the combined organic layers were washed with water (50 mL), with brine (50 mL), dried over Na$_2$SO$_4$ concentrated and purified by flash chromatography [silica gel 100-200 mesh elution 0-30% EtOAc in hexane] to afford the desired compound N-(3,5-dichloropyridin-4-yl)-4-methoxy-2-(methylthio)pyrimidine-5-carboxamide (2.2 g, 75.06%) as off white solid.

LCMS: 344.9[M+1]$^+$

Step-3: Synthesis of N-(3,5-dichloropyridin-4-yl)-4-hydroxy-2-(methylthio)pyrimidine-5-carboxamide To a stirred solution of N-(3,5-dichloropyridin-4-yl)-4-methoxy-2-(methylthio)pyrimidine-5-carboxamide (2.2 g, 6.373 mmol, 1.0 eq), in CH$_2$Cl$_2$ (50 mL) was added 1M BBr$_3$ (19.119 mL, 19.119 mmol, 3.0 eq) at 0° C. The resulting mixture was stirred at rt for 12 h. The reaction mixture was basified with saturated solution of NaHCO$_3$ (100 mL), extracted with CH$_2$Cl$_2$ (2×50 mL), the combined organic layers were washed with water (50 mL), with brine (50 mL), dried over Na$_2$SO$_4$, concentrated and purified by flash chromatography [Silica gel 100-200 mesh; elution 0-20% EtOAc in Hexane] to afford the desired compound N-(3,5-dichloropyridin-4-yl)-4-hydroxy-2-(methylthio)pyrimidine-5-carboxamide (2.0 g, 94.78%) off white solid.

Step-4: Synthesis of 3-(3,5-dichloropyridin-4-yl)-7-(methylthio)-2,3-dihydro-4H-pyrimido[5,4-e][1,3]oxazin-4-one To a stirred solution of N-(3,5-dichloropyridin-4-yl)-4-hydroxy-2-(methylthio)pyrimidine-5-carboxamide (2.0 g, 6.039 mmol, 1.0 eq), in C$_{H3}$CN (50 mL) was added Cs$_2$CO$_3$ (5.9 g, 18.117 mmol, 3.0 eq) at rt. The resulting mixture was stirred and purged with nitrogen for 10 min. followed by addition of diiodomethane (0.97 mL, 12.078 mmol, 2.0 eq) at rt. The reaction mixture was heated at 90° C. for 48 h. The progress of reaction was monitored by LCMS. The reaction mixture was diluted with water (100 mL), extracted with EtOAc (2×100 mL). The combined organic layers were washed with water (50 mL), with brine (50 mL), dried over Na$_2$SO$_4$, concentrated and purified with flash chromatography [Silica gel 100-200 mesh; elution 0-20% EtOAc in hexane] to afford the desired compound 3-(3,5-dichloropyridin-4-yl)-7-(methylthio)-2,3-dihydro-4H-pyrimido[5,4-e][1,3]oxazin-4-one (0.300 g, 14.47%) as off white solid.

LCMS: 343.1[M+1]$^+$

Step-5: Synthesis of 3-(3,5-dichloropyridin-4-yl)-7-((4-(4-methylpiperazin-1-yl)phenyl)amino)-2,3-dihydro-4H-pyrimido[5,4-e][1,3]oxazin-4-one To a stirred solution of 3-(3,5-dichloropyridin-4-yl)-(methylthio)-2,3-dihydro-4H-pyrimido[5,4-e][1,3]oxazin-4-one (0.100 g, 0.291 mmol, 1.0 eq), in toluene (5.0 mL) was added mCPBA (0.100 g, 0.582 mmol, 2.0 eq) at rt. The resulting mixture was stirred at rt for 10 min. followed by addition of and 4-(4-methylpiperazin-1-yl)aniline (0.061 g, 0.320 mmol, 1.1 eq) and DIPEA (0.200 mL, 1.164 mmol, 4.0 eq). The reaction mixture was stirred at rt for 30 min. The progress of reaction was monitored by LCMS. The reaction mixture was diluted with water (100 mL), extracted with EtOAc (2×100 mL). The combined organic layers were washed with water (50 mL), with brine (50 mL), dried over Na$_2$SO$_4$, concentrated and purified by reversed phase chromatography to afford the desired compound 3-(3,5-dichloropyridin-4-yl)-7-((4-(4-methylpiperazin-1-yl)phenyl)amino)-2,3-dihydro-4H-pyrimido[5,4-e][1,3]oxazin-4-one (0.0026 g, 18.44%) as a yellow solid.

LCMS: 486.2[M+1]$^+$ $^1$H NMR (400 MHz, DMSO-d$_6$): δ 10.35 (br s, 1H), 8.78-8.87 (m, 3H), 7.55 (d, J=6.58 Hz, 2H), 6.95 (d, J=8.77 Hz, 2H), 5.79 (s, 2H), 3.22-3.10 (m, 4H), 2.75-2.65 (m, 4H), 2.39 (br s, 3H).

Example S44. Synthesis of 3-(2,6-dichlorophenyl)-7-(1,2,3,4-tetrahydroisoquinolin-6-ylamino)-2H-pyrimido[5,4-e][1,3]oxazin-4(3H)-one (Compound No. 1.44)

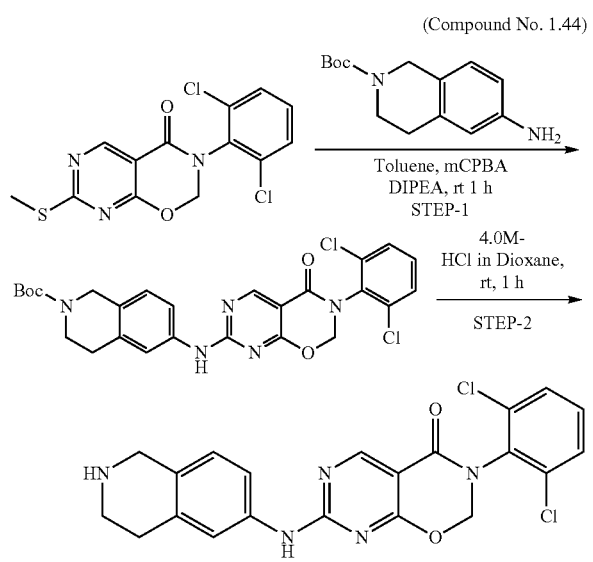

Step-1: Synthesis of tert-butyl 6-((3-(2,6-dichlorophenyl)-4-oxo-3,4-dihydro-2H-pyrimido[5,4-e][1,3]oxazin-7-yl)amino)-3,4-dihydroisoquinoline-2(1H)-carboxylate To a stirred solution of 3-(2,6-dichlorophenyl)-7-(methylthio)-2,3-dihydro-4H-pyrimido[5,4-e][1,3]oxazin-4-one (250 mg, 0.730 mmol, 1.0 eq) in 4 mL of toluene was added mCPBA (314 mg, 1.827 mmol, 2.5 eq) and allowed to stir at rt for 30 min. Tert-butyl 6-amino-3,4-dihydroisoquinoline-2(1H)-carboxylate (217 mg, 0.877 mmol, 1.2 eq) and DIPEA (377 mg, 2.923 mmol, 4.0 eq) were added and stirred at rt for 1 hr. Progress of reaction was monitored by LCMS. After consumption of starting material, solvent was removed under reduced pressure. Residue was diluted with 20 mL of water and extracted with ethyl acetate (200 mL×2). Combined organic layer was washed with water (50 mL×3), dried over anhydrous $Na_2SO_4$ and concentrated under reduced pressure. Crude was purified by flash chromatography using $MeOH:CH_2Cl_2$ as eluents to obtain 180 mg (37.87%) tert-butyl 6-((3-(2,6-dichlorophenyl)-4-oxo-3,4-dihydro-2H-pyrimido[5,4-e][1,3]oxazin-7-yl)amino)-3,4-dihydroisoquinoline-2(1H)-carboxylate.

LCMS: 543 [M+1]$^+$

Step-2: Synthesis of 3-(2,6-dichlorophenyl)-7-((1,2,3,4-tetrahydroisoquinolin-6-yl)amino)-2,3-dihydro-4H-pyrimido[5,4-e][1,3]oxazin-4-one To the tert-butyl 6-((3-(2,6-dichlorophenyl)-4-oxo-3,4-dihydro-2H-pyrimido[5,4-e][1,3]oxazin-7-yl)amino)-3,4-dihydroisoquinoline-2(1H)-carboxylate (150 mg, 0.276 mmol, 1 eq) was added 4 N HCl in dioxane (3 mL). Reaction mixture was stirred at rt for 1 hr. Progress of reaction was monitored by LCMS. After consumption of starting material, precipitated compound was filtered off and washed with diethyl ether and dried under vacuum to obtain 35 mg (28%) of 3-(2,6-dichlorophenyl)-7-((1,2,3,4-tetrahydroisoquinolin-6-yl)amino)-2,3-dihydro-4H-pyrimido[5,4-e][1,3]oxazin-4-one.

LCMS: 443 [M+1]$^+$ $^1$H NMR (400 MHz, DMSO-$d_6$): δ 10.49 (br s, 1H), 9.10 (br s, 2H), 8.87 (s, 1H), 7.54-7.81 (m, 4H), 7.46-7.54 (m, 1H), 7.20 (d, J=8.33 Hz, 1H), 5.75 (s, 2H), 4.23 (br s, 2H), 3.33 (br s, 2H), 3.00 (br s, 2H).

Example S45. Synthesis of 3-(2,6-dichlorophenyl)-7-(4-(4-hydroxypiperidin-1-yl)phenylamino)-2H-pyrimido[5,4-e][1,3]oxazin-4(3H)-one (Compound No. 1.45)

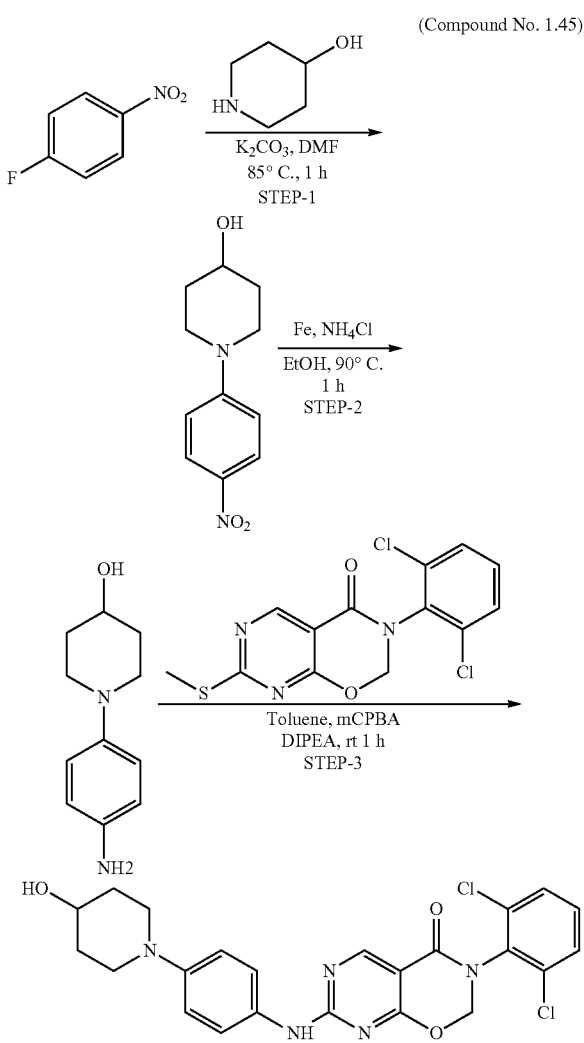

Step-1: Synthesis of 1-(4-nitrophenyl)piperidin-4-ol

To a stirred solution of 1-fluoro-4-nitrobenzene (3 g, 21.27 mmol, 1 eq) and piperidin-4-ol (3.2 g, 31.91 mmol, 1.5 eq) in DMF (20 mL) was added $K_2CO_3$ (3.8 g, 27.65 mmol, 1.3 eq). Reaction mixture was stirred at 85° C. for 1 hr. Progress of reaction was monitored by LCMS. After consumption of starting material, reaction mixture was poured on ice cold water and precipitated compound was filtered off and dried under vacuum. Solid was washed with diethyl ether and pentane to obtain 4 g (84.74%) of 1-(4-nitrophenyl)piperidin-4-ol.

LCMS: 223 [M+1]$^+$

Step-2: Synthesis of 1-(4-aminophenyl)piperidin-4-ol

To a stirred solution of 1-(4-nitrophenyl)piperidin-4-ol (3 g, 13.51 mmol, 1 eq) in EtOH (50 mL) was added Fe(0) (4.45 g, 81.08 mmole, 6 eq) and NH$_4$Cl (5.72 g, 108.10 m mole, 8 eq) solution in water (50 mL). Reaction mixture was stirred at 90° C. for 1 hr. Progress of reaction was monitored by LCMS. After consumption of starting material, the reaction mixture was filtered through celite bed. Filtrate was concentrated under reduced pressure. Residue was diluted with 50 mL of water and extracted with ethyl acetate (200 mL×2). Combined organic layer was washed with water (50 mL×3), dried over anhydrous Na$_2$SO$_4$ and concentrated under reduced pressure to obtain 2 g (80%) of 1-(4-aminophenyl)piperidin-4-ol.

LCMS: 193 [M+1]$^+$

Step-3: Synthesis of 3-(2,6-dichlorophenyl)-7-((4-(4-hydroxypiperidin-1-yl)phenyl)amino)-2,3-dihydro-4H-pyrimido[5,4-e][1,3]oxazin-4-one To a stirred solution of 3-(2,6-dichlorophenyl)-7-(methylthio)-2,3-dihydro-4H-pyrimido[5,4-e][1,3]oxazin-4-one (250 mg, 0.730 mmol, 1.0 eq) in 5 mL of toluene was added mCPBA (314.3 mg, 1.827 mmol, 2.5 eq) and allowed to stir at rt for 30 min. 1-(4-aminophenyl)piperidin-4-ol (168 mg, 0.877 mmol, 1.2 eq) and DIPEA (377 mg, 2.92 mmol, 4.0 eq) were added and stirred at rt for 1 h. Progress of reaction was monitored by LCMS. After consumption of starting material, solvent was removed under reduced pressure, 20 mL of water was added and extracted with ethyl acetate (200 mL×2). Combined organic layer was washed with water (50 mL×3), dried over anhydrous Na$_2$SO$_4$ and concentrated under reduced pressure. Crude was purified by reversed phase chromatography to obtain 50 mg (14.08%) of 3-(2,6-dichlorophenyl)-7-((4-(4-hydroxypiperidin-1-yl)phenyl)amino)-2,3-dihydro-4H-pyrimido[5,4-e][1,3]oxazin-4-one.

LCMS: 486 [M+1]$^+$ $^1$H NMR (400 MHz, DMSO-d$_6$): δ 10.24 (br s, 1H), 8.78 (s, 1H), 7.65 (d, J=7.89 Hz, 2H), 7.51 (d, J=7.89 Hz, 3H), 6.92 (d, J=8.77 Hz, 2H), 5.71 (s, 2H), 4.67 (d, J=4.38 Hz, 1H), 3.61 (dt, J=4.38, 8.55 Hz, 1H), 3.48 (d, J=12.72 Hz, 2H), 2.79 (t, J=10.09 Hz, 2H), 1.81 (d, J=9.21 Hz, 2H), 1.37-1.55 (m, 2H).

Example S46. Synthesis of 7-(4-(4-(2-aminoacetyl)piperazin-1-yl)phenylamino)-3-(2,6-dichlorophenyl)-2H-pyrimido[5,4-e][1,3]oxazin-4(3H)-one (Compound No. 1.46)

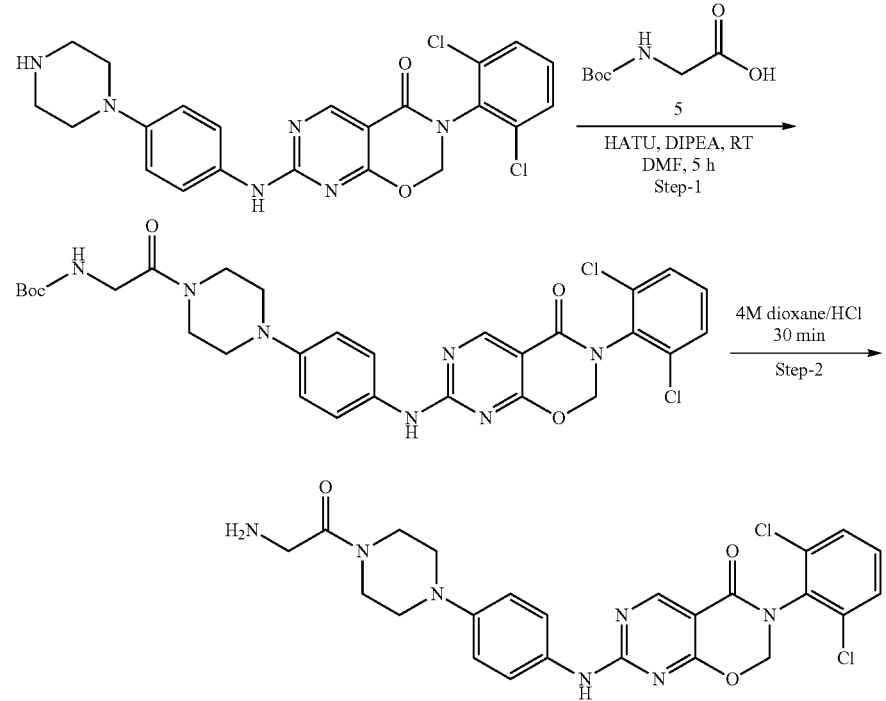

Step-1: Synthesis of tert-butyl 2-(4-(4-(3-(2,6-dichlorophenyl)-4-oxo-3,4-dihydro-2H-pyrimido[5,4-e][1,3]oxazin-7-ylamino)phenyl)piperazin-1-yl)-2-oxoethylcarbamate To a stirred solution of 2-(tert-butoxycarbonylamino) acetic acid (104 mg, 0.5940 mmol, 1.0 eq) in 4 mL of DMF was added HATU (338.7 mg, 0.8910 mmol, 1.5 eq) and allowed to stir at rt for 30 min. N,N-Diisopropylethylamine (0.25 mL, 1.485 mmol, 2.5 eq) and 3-(2,6-dichlorophenyl)-7-(4-(piperazin-1-yl)phenylamino)-2H-pyrimido[5,4-e][1,3]oxazin-4(3H)-one (280 mg, 0.5940 mmol 1.0 eq) were added to the reaction mixture and stirred at rt for 5 h. Progress of reaction was monitored by LCMS. After consumption of starting material, the reaction mixture was poured into ice cold water. The precipitate obtained was filtered and dried to afford tert-butyl 2-(4-(4-(3-(2,6-dichlorophenyl)-4-oxo-3,4-dihydro-2H-pyrimido[5,4-e][1,3]oxazin-7-ylamino)phenyl)piperazin-1-yl)-2-oxoethylcarbamate (273 mg, 73.19%) as a greenish solid.

LCMS: 628 [M+1]$^+$

Step-2: Synthesis of 7-(4-(4-(2-aminoacetyl)piperazin-1-yl)phenylamino)-3-(2,6-dichlorophenyl)-2H-pyrimido[5,4-e][1,3]oxazin-4(3H)-one To a stirred solution of tert-butyl 2-(4-(4-(3-(2,6-dichlorophenyl)-4-oxo-3,4-dihydro-2H-pyrimido[5,4-e][1,3]oxazin-7-ylamino)phenyl)piperazin-1-yl)-2-oxoethylcarbamate (100 mg) in 1 mL of 1,4-dioxane was added the solution of 4N HCl in 1,4-dioxane (2 mL) drop-wise and allowed to stir at rt for 30 min. Progress of reaction was monitored by LCMS. After consumption of starting material, the precipitate obtained was filtered and washed with diethyl ether to obtain the crude. Crude was purified by reversed phase column chromatography to obtain the desired compound, 7-(4-(4-(2-aminoacetyl)piperazin-1-yl)phenylamino)-3-(2,6-dichlorophenyl)-2H-pyrimido[5,4-e][1,3]oxazin-4(3H)-one (25 mg, 29.7%) as an off white solid.

LCMS: 528 [M+1]$^+$ $^1$H NMR (400 MHz, DMSO-d$_6$): δ 10.25 (br s, 1H), 8.79 (s, 1H), 7.65 (d, J=8.33 Hz, 2H), 7.53-7.61 (m, J=8.33 Hz, 2H), 7.45-7.53 (m, 1H), 6.91-7.06 (m, J=8.77 Hz, 2H), 5.71 (s, 2H), 3.62 (br s, 2H), 3.51 (br s, 2H), 3.41 (s, 2H), 3.09 (br s, 4H), 1.90 (s, 2H).

Example S47. Synthesis of 3-(2,6-dichlorophenyl)-7-(4-((2R,5S)-2,5-dimethylpiperazin-1-yl)phenylamino)-2H-pyrimido[5,4-e][1,3]oxazin-4(3H)-one hydrochloride (Compound No. 1.47)

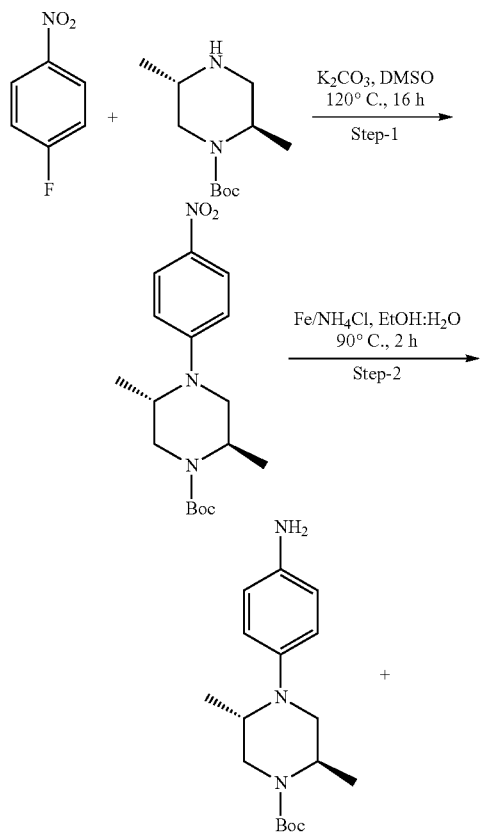

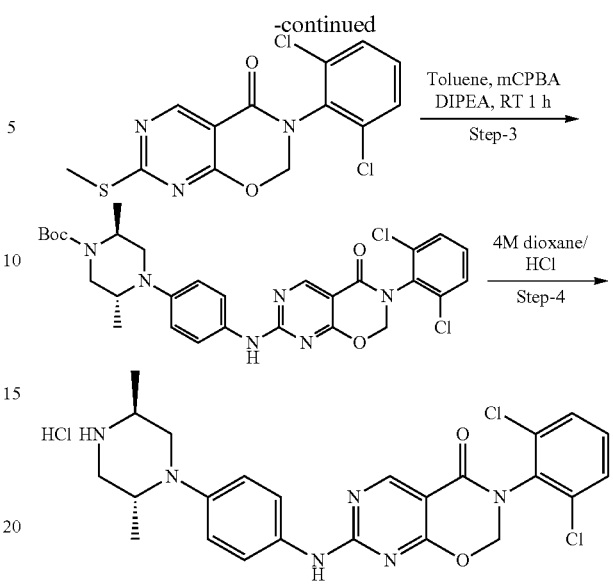

Step-1: Synthesis of tert-butyl (2R,5S)-2,5-dimethyl-4-(4-nitrophenyl)piperazine-1-carboxylate To a stirred solution of 1-fluoro-4-nitrobenzene (1 g, 7.08 mmol, 1 eq) and piperidin-4-ol (1.56 mL, 7.08 mmol, 1.0 eq) in DMSO (12 mL) was added K$_2$CO$_3$ (1.95 g, 14.16 mmol, 2.0 eq). Reaction mixture was stirred at 85° C. for 6 h. Progress of reaction was monitored by LCMS. After consumption of starting material, ice cold water was poured to the reaction mixture. The formation of precipitate was observed which was filtered to afford the desired compound, tert-butyl (2R,5 S)-2,5-dimethyl-4-(4-nitrophenyl)piperazine-1-carboxylate (840 mg, 35.44%) as a yellow solid.

LCMS: 336.2[M+1]$^+$

Step-2: Synthesis of tert-butyl (2R,5S)-4-(4-aminophenyl)-2,5-dimethylpiperazine-1-carboxylate To a stirred solution of tert-butyl (2R,5S)-2,5-dimethyl-4-(4-nitrophenyl)piperazine-1-carboxylate (840 mg, 2.50 mmol, 1 eq) in EtOH and water (1:1, 20 mL) was added Fe(0) (420 mg, 7.51 mmol, 3 eq) and NH$_4$Cl (267 mg, 5.00 mmol, 2 eq). The reaction mixture was stirred at 90° C. for 2 h. Progress of reaction was monitored by LCMS. After consumption of starting material, the reaction mixture was filtered through celite bed. The reaction mixture was concentrated, diluted with water, basified with NaHCO$_3$ solution and was extracted with EtOAc. The organic layers were dried over Na$_2$SO$_4$, concentrated and purified by flash chromatography (elution: 0-2% MeOH in CH$_2$Cl$_2$) to afford the desired product, tert-butyl (2R,5 S)-4-(4-aminophenyl)-2,5-dimethylpiperazine-1-carboxylate (472 mg, 61.70%) as an off white solid.

LCMS: 306.4 [M+1]$^+$

Step-3: Synthesis of tert-butyl (2S,5R)-4-(4-((3-(2,6-dichlorophenyl)-4-oxo-3,4-dihydro-2H-pyrimido[5,4-e][1,3]oxazin-7-yl)amino)phenyl)-2,5-dimethylpiperazine-1-carboxylate To a stirred solution of 3-(2,6-dichlorophenyl)-7-(methylthio)-2,3-dihydro-4H-pyrimido[5,4-e][1,3]oxazin-4-one (481 mg, 1.404 mmol, 1.0 eq) in 5 mL of toluene was added m-CPBA (485 mg, 2.808 mmol, 2.0 eq) and allowed to stir at rt for 30 min. Tert-butyl (2R,5S)-4-(4-aminophenyl)-2,5-dimethylpiperazine-1-carboxylate (472 mg, 1.545 mmol, 1.1 eq) and DIPEA (0.97 mL, 5.616 mmol, 4.0 eq) were added and stirred at rt for 10 h. The formation of precipitates was observed which was filtered to afford the desired compound, tert-butyl (2S,5R)-4-(4-((3-(2,6-dichlorophenyl)-4-oxo-3,4-dihydro-2H-pyrimido[5,4-e][1,3]oxazin-7-yl)amino)phenyl)-2,5-dimethylpiperazine-1-carboxylate (215 mg, 25.51%) as an off white solid.

LCMS: 598.2[M+1]$^+$

Step-4: Synthesis of 3-(2,6-dichlorophenyl)-7-((4-((2R,5S)-2,5-dimethylpiperazin-1-yl)phenyl)amino)-2,3-dihydro-4H-pyrimido[5,4-e][1,3]oxazin-4-one hydrochloride Tert-butyl (2S,5R)-4-(4-((3-(2,6-dichlorophenyl)-4-oxo-3,4-dihydro-2H-pyrimido[5,4-e][1,3]oxazin-7-yl)amino)phenyl)-2,5-dimethylpiperazine-1-carboxylate (50 mg, 0.136 mmol, 1.0 eq) was dissolved in (1 mL) of dioxane and added 4M dioxane-HCl (2 mL) and allowed to stir at rt for 1 hr. After completion of reaction, the reaction mixture was filtered and dried under reduced pressure to afford the desired compound, 3-(2,6-dichlorophenyl)-7-((4-((2R,5S)-2,5-dimethylpiperazin-1-yl)phenyl)amino)-2,3-dihydro-4H-pyrimido[5,4-e][1,3]oxazin-4-one hydrochloride (33 mg, 73.69%) as an off white solid.

LCMS: 499.2[M+1]$^+$ $^1$H NMR (400 MHz, DMSO-d$_6$): δ 10.43 (br s, 1H), 9.12 (br s, 1H), 8.84 (s, 2H), 7.66 (d, J=8.33 Hz, 2H), 7.69 (d, J=8.77 Hz, 1H), 7.50 (t, J=7.89 Hz, 1H), 7.13 (d, J=8.33 Hz, 2H), 5.74 (s, 2H), 3.20 (d, J=11.84 Hz, 2H), 2.85 (br s, 2H), 1.23 (d, J=6.58 Hz, 3H), 0.91 (d, J=6.14 Hz, 3H).

Example S48. Synthesis of 3-(2,6-dichlorophenyl)-7-(4-(2-(methylamino)ethoxy)phenylamino)-2H-pyrimido[5,4-e][1,3]oxazin-4(3H)-one (Compound No. 1.48)

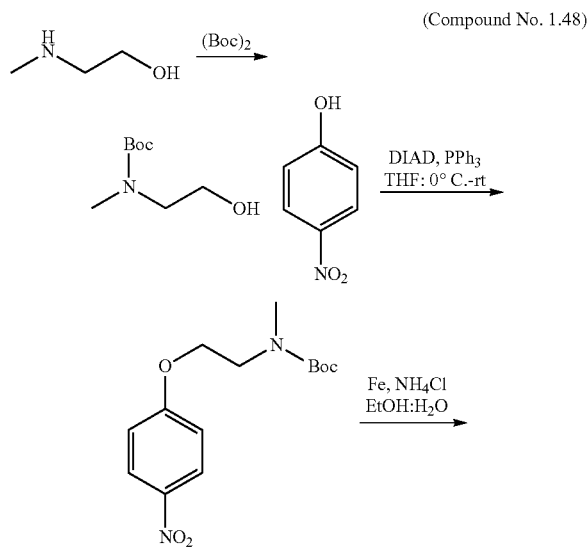

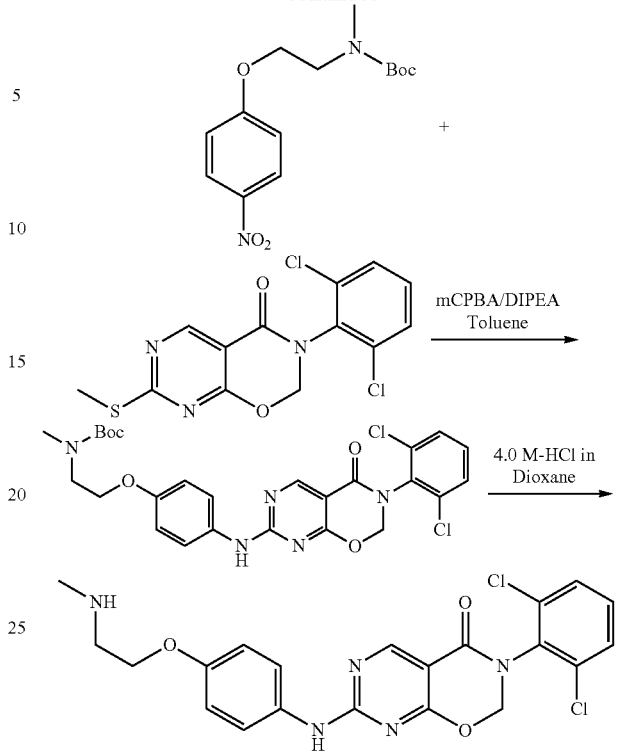

Step-1: Synthesis of tert-butyl (2-hydroxyethyl)(methyl)carbamate

To a stirred solution of 2-(methylamino)ethan-1-ol (1.0 g, 13.313 mmol, 1.0 eq), in CH$_2$Cl$_2$ (50 mL) was added di-tert-butyl dicarbonate (3.36 mL, 14.645 mmol, 1.1 eq) at 0° C. The resulting mixture was stirred at rt for 1 hr. The progress of reaction was monitored by $^1$HNMR. The reaction mixture was diluted with CH$_2$Cl$_2$ (50 mL) and washed with water (50 mL) and brine (50 mL) dried over Na$_2$SO$_4$, filtered and concentrated to afford the desired compound, tert-butyl (2-hydroxyethyl)(methyl)carbamate (2.30 g, 98.71%) as colorless liquid.

$^1$H NMR (400 MHz, CDCl$_3$): δ 3.75 (d, J=4.82 Hz, 2H), 3.40 (br s, 2H), 2.92 (s, 3H), 2.82 (br s, 1H), 1.46 (s, 9H).

Step-2: Synthesis of tert-butyl methyl(2-(4-nitrophenoxy)ethyl)carbamate

To a stirred solution of 4-nitrophenol (1.0 g, 7.188 mmol, 1.0 eq), tert-butyl (2-hydroxyethyl)(methyl)carbamate (1.51 g, 8.626 mmol, 1.2 eq) and triphenyl phosphine (2.26 g, 8.626 mmol, 1.2 eq) in THF (100 mL) was dropwise added a solution of DIAD (1.69 mL, 8.626 mmol, 1.2 eq) in THF (1.0 mL) at 0° C. The resulting mixture was stirred at rt for 12 h. The progress of reaction was monitored by LCMS. The reaction mixture was concentrated and purified by combi-flash [silic gel 100-200 mesh; elution 0-10% EtOAc in hexane] to afford the desired compound tert-butyl methyl (2-(4-nitrophenoxy)ethyl) carbamate (0.510 g, 23.94%) as yellow viscous.

LCMS: 297.2 [M+1]$^+$

Step-3: Synthesis of tert-butyl (2-(4-aminophenoxy)ethyl)(methyl) carbamate

To a stirred solution of tert-butyl methyl(2-(4-nitrophenoxy)ethyl)carbamate (0.500 g, 1.687 mmol, 1.0 eq) in EtOH (25 mL) was added Fe(0) (0.753, 13.498 mmol, 8.0 eq) and a solution of NH₄Cl (0.90 g, 16.87 mmol, 10.0 eq) at rt. The resulting mixture was heated at 90° C. for 60 min. The progress of reaction was monitored by LCMS. The reaction mixture was filtered through celite the residue was washed with EtOH (50 mL) the filtrate was concentrated and the residue was dissolved in EtOAc (50 mL), washed with water (2×50 mL), dried over Na₂SO₄, and concentrated to afford the desired compound tert-butyl (2-(4-aminophenoxy)ethyl) (methyl) carbamate (0.270 g, 60.13%) as yellow viscous oil.

LCMS: 267.2 [M+1]⁺

Step-4: Synthesis of tert-butyl (2-(4-((3-(2,6-dichlorophenyl)-4-oxo-3,4-dihydro-2H-pyrimido[5,4-e][1,3]oxazin-7-yl)amino)phenoxy)ethyl)(methyl)carbamate To a stirred solution of 3-(2,6-dichlorophenyl)-7-(methylthio)-2,3-dihydro-4H-pyrimido[5,4-e][1,3]oxazin-4-one (280 mg, 0.818 mmol, 1.0 eq) in (10 mL) of toluene was added m-CPBA (400 mg, 1.636 mmol, 2.0 eq) and allowed to stir at rt for 30 min. Tert-butyl (2-(4-aminophenoxy)ethyl) (methyl) carbamate (261 mg, 0.981 mmol, 1.2 eq) and DIPEA (0.570 mL, 3.272 mmol, 4.0 eq) were added and allowed to stir at rt 12 h. The reaction mixture was diluted with water (50 mL) and extracted with EtOAc (2×50 mL). The combined organic layers were washed with water (50 mL) and brine (50 mL), dried over Na₂SO₄, filtered, concentrated and purified by flash chromatography[silica gel 100-200 mesh; elution 0-30% EtOAc in hexane] to afford the desired compound tert-butyl (2-(4-((3-(2,6-dichlorophenyl)-4-oxo-3,4-dihydro-2H-pyrimido[5,4-e][1,3]oxazin-7-yl)amino)phenoxy)ethyl)(methyl)carbamate (250 mg, 54.58%) as brown solid.

LCMS: 560.2 [M+1]⁺

Step-5: Synthesis of 3-(2,6-dichlorophenyl)-7-((4-(2-(methylamino)ethoxy)phenyl)amino)-2,3-dihydro-4H-pyrimido[5,4-e][1,3]oxazin-4-one Tert-butyl (2-(4-((3-(2,6-dichlorophenyl)-4-oxo-3,4-dihydro-2H-pyrimido[5,4-e][1,3]oxazin-7-yl)amino)phenoxy)ethyl) (methyl) carbamate (250 mg, 0.444 mmol, 1.0 eq) was dissolved in 4M HCl in dioxane (4.0 mL) and allowed to stir at rt for 1 h. After completion of reaction, the reaction mixture was concentrated under reduced pressure and purified by reversed phase purification to afford the desired compound 3-(2,6-dichlorophenyl)-7-((4-(2-(methylamino)ethoxy)phenyl)amino)-2,3-dihydro-4H-pyrimido[5,4-e][1,3]oxazin-4-one (100 mg, 48.78%) as white solid.

LCMS: 460.1 [M+1]⁺

¹H NMR (400 MHz, DMSO-d₆): δ 10.31 (br s, 1H), 8.81 (s, 1H), 8.31 (br s, 1H), 7.57-7.69 (m, 4H), 7.45-7.55 (m, 1H), 6.96 (d, J=8.77 Hz, 2H), 5.72 (s, 2H), 4.08 (br s, 3H), 3.00 (br s, 2H), 2.44 (br s, 3H).

Example S49. Synthesis of (R)-3-(2,6-dichlorophenyl)-7-(4-(2-methylpiperazin-1-yl)phenylamino)-2H-pyrimido[5,4-e][1,3]oxazin-4(3H)-one (Compound No. 1.49)

Synthesis of (R)-3-(2,6-dichlorophenyl)-7-(4-(2-methylpiperazin-1-yl)phenylamino)-2H-pyrimido[5,4-e][1,3]oxazin-4(3H)-one (R)-3-(2,6-dichlorophenyl)-7-(4-(2-methylpiperazin-1-yl)phenylamino)-2H-pyrimido[5,4-e][1,3]oxazin-4(3H)-one was separated from the product synthesized in the scheme described in Example S26.

Example S50. Synthesis of 3-(2,6-dichlorophenyl)-7-(3-methoxy-4-(piperidin-4-yl)phenylamino)-2H-pyrimido[5,4-e][1,3]oxazin-4(3H)-one (Compound No. 1.50)

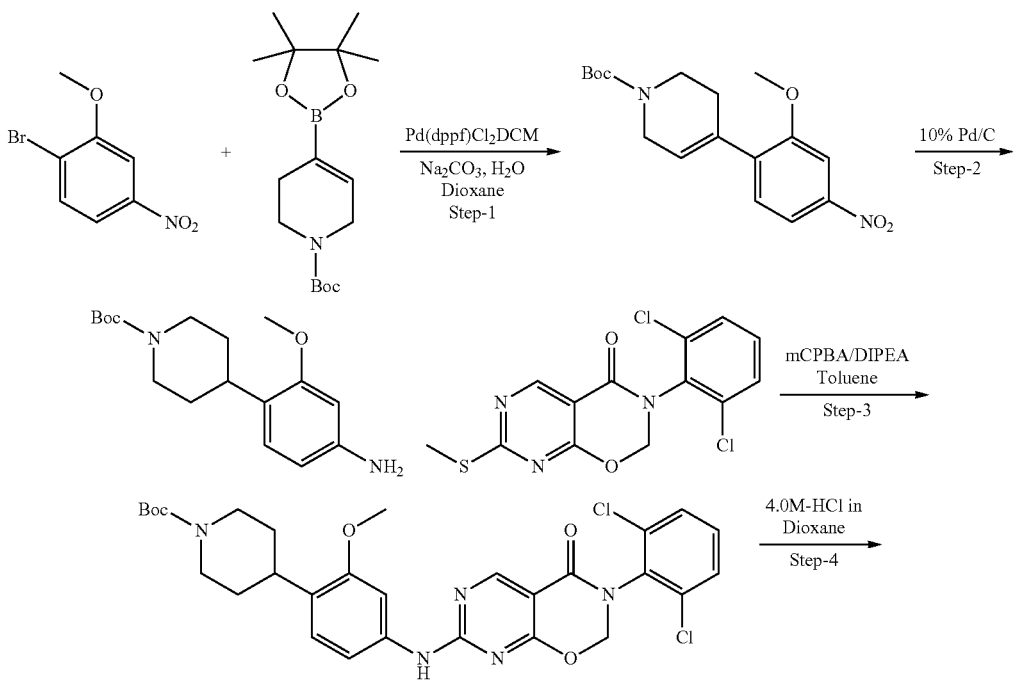

-continued

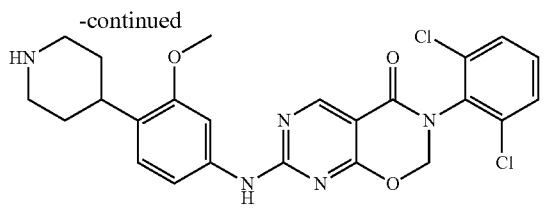

Step-1: Synthesis of tert-butyl 4-(2-methoxy-4-nitrophenyl)-3,6-dihydropyridine-1(2H)-carboxylate To a stirred solution of 1-bromo-2-methoxy-4-nitrobenzene (1.0 g, 4.310 mmol, 1.0 eq) and tert-butyl 4-(4,4,5,5-tetramethyl-1,3,2-dioxaborolan-2-yl)-3,6-dihydropyridine-1(2H)-carboxylate (1.46 g, 4.740 mmol, 1.1 eq) in dioxane (30 mL) was added a 2M solution of $Na_2CO_3$ (913 mg, 8.620 mmol, 2.0 eq) at rt. The resulting mixture was purged with nitrogen for 10 min, followed by addition of $Pd(dppf)Cl_2 \cdot CH_2Cl_2$ (352 mg, 0.431 mmol, 0.1 eq). The resulting mixture was heated at 90° C. for 12 h. The progress of reaction was monitored by $^1H$ NMR. The reaction mixture was filtered through celite the residue was washed with EtOAc (50 mL) the filtrate wash concentrated and purified by flash chromatography [silica gel 100-200 mesh; elution 0-10% EtOAc in hexane] to afford the desired compound tert-butyl 4-(2-methoxy-4-nitrophenyl)-3,6-dihydropyridine-1(2H)-carboxylate (1.12 g, 77.77%) as brown viscous.

$^1H$ NMR (400 MHz, $CDCl_3$): δ 7.82 (dd, J=2.19, 8.33 Hz, 1H), 7.72 (d, J=2.19 Hz, 1H), 7.28 (d, J=8.33 Hz, 1H), 5.88 (br s, 1H), 4.07 (br s, 2H), 3.61 (t, J=5.26 Hz, 2H), 2.49 (br s, 2H), 1.45-1.53 (m, 9H).

Step-2: Synthesis of tert-butyl 4-(4-amino-2-methoxyphenyl)piperidine-1-carboxylate To a stirred solution of tert-butyl 4-(2-methoxy-4-nitrophenyl)-3,6-dihydropyridine-1(2H)-carboxylate (1.1 g, 3.289 mmol, 1.0 eq) in MeOH (30 mL) was added 10% Pd/C (100 mg) at rt. The resulting mixture was purged with hydrogen for 60 min. The progress of reaction was monitored by LCMS. The reaction mixture was filtered through celite the residue was washed with MeOH (50 mL) the filtrate was concentrated and purified by pentane to afford the desired compound tert-butyl 4-(4-amino-2-methoxyphenyl)piperidine-1-carboxylate (0.760 g, 82.96%) as brown solid.

LCMS: 307.3 [M+1]$^+$

Step-3: Synthesis of tert-butyl 4-(4-((3-(2,6-dichlorophenyl)-4-oxo-3,4-dihydro-2H-pyrimido[5,4-e][1,3]oxazin-7-yl)amino)-2-methoxyphenyl)piperidine-1-carboxylate To a stirred solution of 3-(2,6-dichlorophenyl)-7-(methylthio)-2,3-dihydro-4H-pyrimido[5,4-e][1,3]oxazin-4-one (200 mg, 0.584 mmol, 1.0 eq) in (10 mL) of toluene was added mCPBA (201 mg, 1.168 mmol, 2.0 eq) and allowed to stir at rt for 30 min. Tert-butyl 4-(4-amino-2-methoxyphenyl)piperidine-1-carboxylate (197 mg, 0.642 mmol, 1.1 eq) and DIPEA (0.406 mL, 2.336 mmol, 4.0 eq) were added and allowed to stir at rt for 12 h. The reaction mixture was diluted with water (50 mL) and extracted with EtOAc (2×50 mL), the combined organic layers were washed with water (50 mL) with brine (50 mL) dried over $Na_2SO_4$, filtered and concentrated and purified by flash chromatography [silica gel 100-200 mesh; elution 0-30% EtOAc in hexane to afford the desired compound tert-butyl 4-(4-((3-(2,6-dichlorophenyl)-4-oxo-3,4-dihydro-2H-pyrimido[5,4-e][1,3]oxazin-7-yl)amino)-2-methoxy phenyl) piperidine-1-carboxylate (152 mg, 43.42%) as off white solid.

LCMS: 600.2[M+1]$^+$

Step-4: Synthesis of 3-(2,6-dichlorophenyl)-7-((3-methoxy-4-(piperidin-4-yl)phenyl)amino)-2,3-dihydro-4H-pyrimido[5,4-e][1,3]oxazin-4-one tert-butyl 4-(4-((3-(2,6-dichlorophenyl)-4-oxo-3,4-dihydro-2H-pyrimido[5,4-e][1,3]oxazin-7-yl)amino)-2-methoxy phenyl) piperidine-1-carboxylate (152 mg, 0.249 mmol, 1.0 eq) was dissolved in 4.0 M-HCl in dioxane (20.0 mL) and allowed to stir at rt for 1 hr. After completion of reaction, the reaction mixture was concentrated under reduced pressure and purified by reversed phase chromatography to afford the desired compound 3-(2,6-dichlorophenyl)-7-((3-methoxy-4-(piperidin-4-yl)phenyl)amino)-2,3-dihydro-4H-pyrimido[5,4-e][1,3]oxazin-4-one (32 mg, 25.39%) as white solid.

LCMS: 500.2 [M+1]$^+$ $^1H$ NMR (400 MHz, DMSO-$d_6$): δ 10.40 (br s, 1H), 8.85 (s, 1H), 7.66 (d, J=7.89 Hz, 2H), 7.51 (t, J=8.33 Hz, 1H), 7.45 (br s, 1H), 7.35 (d, J=8.33 Hz, 1H), 7.09 (d, J=7.89 Hz, 1H), 5.75 (s, 2H), 3.79 (s, 2H), 3.08 (br s, 2H), 2.96 (t, J=11.18 Hz, 2H), 1.79-1.88 (m, 2H), 1.65-1.79 (m, 2H).

Example S51. Synthesis of 3-(2,6-dichlorophenyl)-7-(2',3'-dihydro-1 $^1H$-spiro[cyclopropane-1,4'-isoquinoline]-7'-ylamino)-2H-pyrimido[5,4-e][1,3]oxazin-4(3H)-one (Compound No. 1.51)

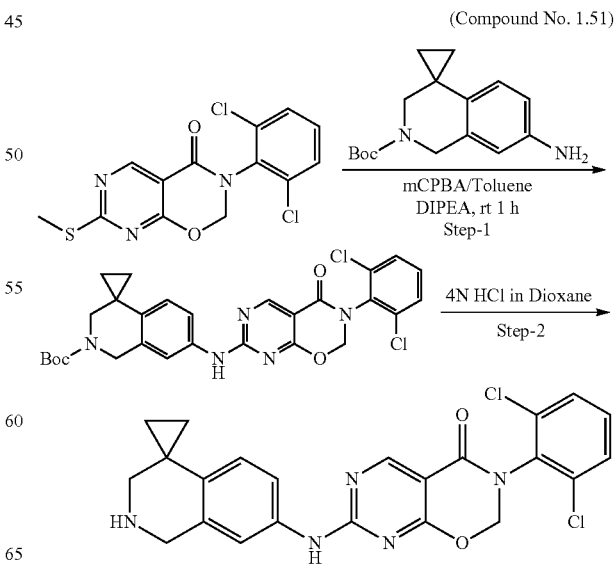

Step-1: Synthesis of tert-butyl 7'-(3-(2,6-dichlorophenyl)-4-oxo-3,4-dihydro-2H-pyrimido[5,4-e][1,3]oxazin-7-ylamino)-1'H-spiro[cyclopropane-1,4'-isoquinoline]-2'(3'H)-carboxylate To a stirred solution of 3-(2,6-dichlorophenyl)-7-(methylthio)-2H-pyrimido[5,4-e][1,3]oxazin-4(3H)-one (300 mg, 0.879 mmol, 1.0 eq) in 5 mL of toluene was added mCPBA (378 mg, 2.20 mmol, 2.5 eq) and allowed to stir at rt for 30 min. Tert-butyl 7'-amino-1'H-spiro[cyclopropane-1,4'-isoquinoline]-2'(3'H)-carboxylate (241 mg, 0.879 mmol, 1.0 eq) and DIPEA (453 mg, 3.52 mmol, 4.0 eq) were added and allowed to stir at rt for 1 h. Progress of reaction was monitored by LCMS. After completion of reaction solvent was removed under reduced pressure, residue was diluted with 20 mL of water and extracted with ethyl acetate (50 mL×3). Combined organic layer was washed with water (20 mL×3), dried over anhydrous Na$_2$SO$_4$ and concentrated under reduced pressure. Crude was purified by flash chromatography to obtain 200 mg (40.1%) of tert-butyl 7'-(3-(2,6-dichlorophenyl)-4-oxo-3,4-dihydro-2H-pyrimido[5,4-e][1,3]oxazin-7-ylamino)-1'H-spiro[cyclopropane-1,4'-isoquinoline]-2'(3'H)-carboxylate.

LCMS: 568 [M+1]$^+$

Step-2: Synthesis of 3-(2,6-dichlorophenyl)-7-(2',3'-dihydro-1'H-spiro[cyclopropane-1,4'-isoquinoline]-7'-ylamino)-2H-pyrimido[5,4-e][1,3]oxazin-4(3H)-one Tert-butyl 7'-(3-(2,6-dichlorophenyl)-4-oxo-3,4-dihydro-2H-pyrimido[5,4-e][1,3]oxazin-7-ylamino)-1'H-spiro[cyclopropane-1,4'-isoquinoline]-2'(3'H)-carboxylate (200 mg, 0.353 mmol, 1.0 eq) was dissolved in 5 mL of 4N HCl in dioxane solution at 0° C. Reaction was stirred at rt for 30 min. Progress of reaction was monitored by LCMS. After completion of reaction, precipitated compound was filtered off, washed with 2 mL of dioxane and dried under reduced pressure. Crude was purified by reversed phase chromatography to obtain 50 mg (36.40%) of 3-(2,6-dichlorophenyl)-7-(2',3'-dihydro-1'H-spiro[cyclopropane-1,4'-isoquinoline]-7'-ylamino)-2H-pyrimido[5,4-e][1,3]oxazin-4(3H)-one.

LCMS: 468 [M+1]$^+$ $^1$H NMR (400 MHz, DMSO-d$_6$): δ 10.30 (br s, 1H), 8.81 (s, 1H), 7.65 (d, J=8.33 Hz, 2H), 7.46-7.60 (m, 2H), 7.43 (d, J=8.33 Hz, 1H), 7.36 (br s, 1H), 6.70 (d, J=8.33 Hz, 1H), 5.72 (s, 2H), 3.91 (s, 2H), 2.74 (s, 2H), 1.88 (s, 2H), 0.89 (br s, 2H), 0.79 (br s, 2H).

Example S52. Synthesis of 3-(2,6-dichlorophenyl)-7-(4-(1-methylpiperidin-4-yl)phenylamino)-2H-pyrimido[5,4-e][1,3]oxazin-4(3H)-one (Compound No. 1.52)

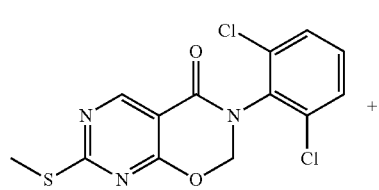

+

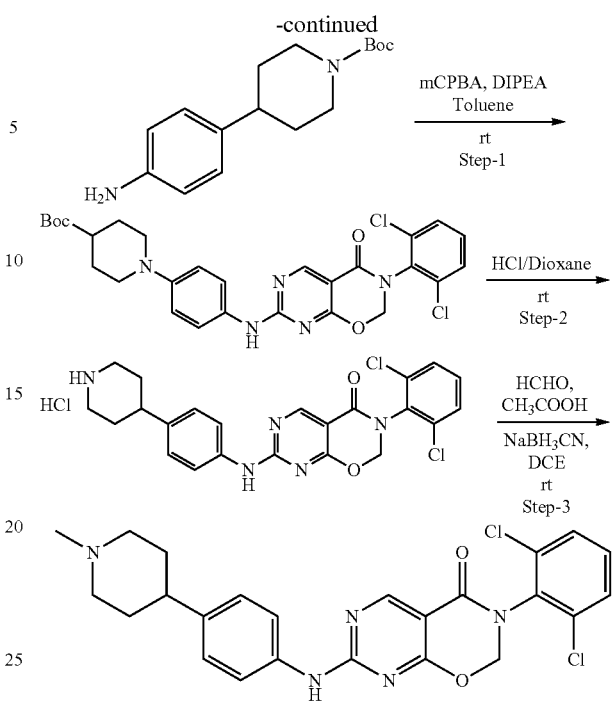

Step-1: Synthesis of tert-butyl 4-(4-((3-(2,6-dichlorophenyl)-4-oxo-3,4-dihydro-2H-pyrimido[5,4-e][1,3]oxazin-7-yl)amino)phenyl)piperidine-1-carboxylate To a stirred solution of 3-(2,6-dichlorophenyl)-7-(methylthio)-2,3-dihydro-4H-benzo[e][1,3]oxazin-4-one (700 mg, 2.04 mmol, 1.0 eq) in 6 mL toluene, m-CPBA (879 mg, 5.11 mmol, 2.5 eq) was added under stirring and resulting mixture was allowed to stir at rt for 30 min. Further, tert-butyl 4-(4-aminophenyl)piperidine-1-carboxylate (565 mg, 2.04 mmol, 1 eq) and DIPEA (1.075 g, 8.16 mmol, 4 eq) were added and the reaction was allowed to stir at rt for 12 h. The reaction was monitored by LCMS. After completion reaction was quenched with water and extracted with ethyl acetate (10 mL×3). The combined organic layer was washed with brine solution (20 mL), dried over anhydrous Na$_2$SO$_4$ and concentrated under reduced pressure to afford crude product which was purified by flash chromatography (elution: 0-10% MeOH in CH$_2$Cl$_2$) to afford the desired compound, tert-butyl 4-(4-((3-(2,6-dichlorophenyl)-4-oxo-3,4-dihydro-2H-pyrimido[5,4-e][1,3]oxazin-7-yl)amino) phenyl)piperidine-1-carboxylate (300 mg, 26%) as a yellow solid.

LCMS: 570.1 [M+1]$^+$

Step-2: Synthesis of 3-(2,6-dichlorophenyl)-7-((4-(piperidin-4-yl)phenyl)amino)-2,3-dihydro-4H-pyrimido[5,4-e][1,3]oxazin-4-one hydrochloride 20% HCl in dioxane (2 mL) was added to a stirred solution of tert-butyl 4-(4-((3-(2,6-dichlorophenyl)-4-oxo-3,4-dihydro-2H-pyrimido[5,4-e][1,3]oxazin-7-yl)amino)phenyl)piperidine-1-carboxylate (300 mg, 0.52 mmol, 1.0 eq) at 0° C. and the resulting solution was allowed to stir at rt for 3 h. After completion of reaction, solvent was removed under reduced pressure, and the resulting solid was filtered and washed with diethylether and dried in vacuo to yield, 3-(2,6-dichlorophenyl)-7-((4-(piperidin-4-yl)phenyl)amino)-2,3-dihydro-4H-pyrimido[5,4-e][1,3]oxazin-4-one hydrochloride (150 mg, 56%) as a white solid.

LCMS: 470.1 [M+1]$^+$

Step-3: Synthesis of 3-(2,6-dichlorophenyl)-7-((4-(1-methylpiperidin-4-yl)phenyl)amino)-2,3-dihydro-4H-pyrimido[5,4-e][1,3]oxazin-4-one To a solution of 3-(2,6-dichlorophenyl)-7-((4-(piperidin-4-yl)phenyl)amino)-2,3-dihydro-4H-pyrimido[5,4-e][1,3]oxazin-4-one hydrochloride (90 mg, 0.17 mmol, 1.0 eq) in 5 mL DCE at 0° C. HCHO (37%) (16.06 mg, 0.53 mmol, 3 eq) and acetic acid (53.5 mg, 0.85 mmol, 5 eq) were added under stirring under inert atmosphere. The resulting solution was stirred at rt for 1 hr. The mass was again cooled to 0° C., followed by the addition of NaCNBH$_3$ (33.6 mg, 0.51 mmol, 3 eq) under stirring. The reaction was stirred at rt for 15-20 min and monitored by LCMS. After completion, the reaction was quenched with ice cold water followed by extraction using ethyl acetate. The combined organic layer was washed with brine (50 mL) and concentrated under reduced pressure. The residue was purified by flash chromatography (elution 0-10% MeOH in CH$_2$Cl$_2$) to afford 3-(2,6-dichlorophenyl)-7-((4-(1-methylpiperidin-4-yl)phenyl)amino)-2,3-dihydro-4H-pyrimido[5,4-e][1,3]oxazin-4-one (15 mg, 17%) as white solid.

LCMS: 484.2 [M+1]$^+$ $^1$H NMR (400 MHz, DMSO-d$_6$): δ 10.39 (br s, 1H), 8.83 (s, 1H), 7.67-7.62 (m, 4H), 7.58-7.52 (m, 1H), 7.24-7.20 (m, 2H), 5.73 (s, 2H) 2.87-2.85 (m, 2H), 2.18 (s, 3H), 1.98-1.91 (m, 2H), 1.75-1.62 (m, 5H).

Example S53. Synthesis of 3-(2,6-dichlorophenyl)-7-(3-methoxy-4-(piperazin-1-yl)phenylamino)-2H-pyrimido[5,4-e][1,3]oxazin-4(3H)-one dihydrochloride

Step-1: Synthesis of tert-butyl 4-(2-methoxy-4-nitrophenyl)piperazine-1-carboxylate To a stirred solution of 1-fluoro-2-methoxy-4-nitrobenzene (1.0 g, 5.843 mmol, 1.0 eq) and tert-butyl 4-bromo-3,6-dihydropyridine-1(2H)-carboxylate (1.2 g, 6.427 mmol, 1.1 eq) in DMSO (20 mL) was added K$_2$CO$_3$ (2.43 g, 17.53 mmol, 3.0 eq) at rt. The resulting mixture was stirred at 90° C. for 12 h. The progress of reaction was monitored by LCMS. The reaction mixture was poured into ice cold water (100 mL), stirred for 5 min, formation of precipitates was observed, which was filtered and dried under vacuum to afford the desired compound tert-butyl 4-(2-methoxy-4-nitrophenyl)piperazine-1-carboxylate (1.75 g, 88.83%) as a yellow solid.

LCMS: 338.2 [M+1]$^+$

Step-2: Synthesis of tert-butyl 4-(4-amino-2-methoxyphenyl)piperazine-1-carboxylate To a stirred solution of tert-butyl 4-(2-methoxy-4-nitrophenyl)piperazine-1-carboxylate (1.0 g, 2.964 mmol, 1.0 eq) in EtOH (25 mL) was added Fe(0) (1.32 g, 23.712 mmol, 8.0 eq) and a solution of NH$_4$Cl (1.58 g, 29.64 mmol, 10.0 eq) at rt. The resulting mixture was heated at 90° C. for 1 h. The progress of reaction was monitored by LCMS. The reaction mixture was filtered through celite the residue was washed with EtOH (50 mL) the filtrate was concentrated and the residue was dissolved in EtOAc (100 mL), washed with water (2×100 mL), dried over Na$_2$SO$_4$, and concentrated to afford the desired compound tert-butyl 4-(4-amino-2-methoxyphenyl)piperazine-1-carboxylate (0.750 g, 82.22%) as brown viscous.

LCMS: 308.4 [M+1]$^+$ (Compound No. 1.53)

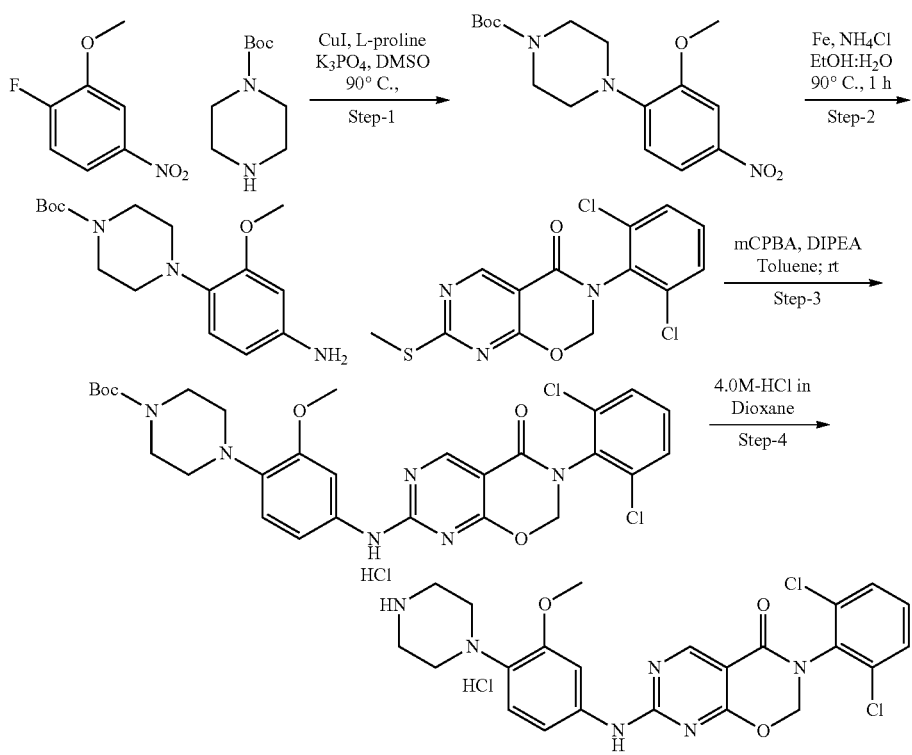

Step-3: Synthesis of tert-butyl 4-(4-((3-(2,6-dichlorophenyl)-4-oxo-3,4-dihydro-2H-pyrimido[5,4-e][1,3]oxazin-7-yl)amino)-2-methoxyphenyl)piperazine-1-carboxylate To a stirred solution of 3-(2,6-dichlorophenyl)-7-(methylthio)-2,3-dihydro-4H-pyrimido[5,4-e][1,3]oxazin-4-one (300 mg, 0.868 mmol, 1.0 eq) in (5.0 mL) of toluene was added m-CPBA (428 mg, 1.736 mmol, 2.0 eq) and allowed to stir at rt for 30 min. Tert-butyl 4-(4-amino-2-methoxyphenyl)piperazine-1-carboxylate (293 mg, 0.955 mmol, 1.1 eq) and DIPEA (0.606 mL, 3.472 mmol, 4.0 eq) were added and allowed to stir at rt for 12 h. The reaction mixture was diluted with water (50 mL) and extracted with EtOAc (2×50 mL), the combined organic layers were washed with water (50 mL) with brine (50 mL), dried over Na$_2$SO$_4$, filtered and concentrated and purified by flash chromatography (elution 0-35% EtOAc in Hexane) to afford the desired compound, tert-butyl 4-(4-((3-(2,6-dichlorophenyl)-4-oxo-3,4-dihydro-2H-pyrimido[5,4-e][1,3]oxazin-7-yl)amino)-2-methoxy phenyl) piperazine-1-carboxylate (150 mg, 28.79%) as an off white solid.

LCMS: 601.1 [M+1]$^+$

Step-4: Synthesis of 3-(2,6-dichlorophenyl)-7-((3-methoxy-4-(piperazin-1-yl)phenyl)amino)-2,3-dihydro-4H-pyrimido[5,4-e][1,3]oxazin-4-one dihydrochloride Tert-butyl 4-(4-((3-(2,6-dichlorophenyl)-4-oxo-3,4-dihydro-2H-pyrimido[5,4-e][1,3]oxazin-7-yl)amino)-2-methoxy phenyl) piperazine-1-carboxylate (150 mg, 0.249 mmol, 1.0 eq) was dissolved in 4.0M HCl in dioxane (3 mL) and allowed to stir at rt for 1 hr. After completion of reaction, the reaction mixture was filtered and dried under reduced pressure and purified by diethyl ether to afford the desired compound, 3-(2,6-dichlorophenyl)-7-((3-methoxy-4-(piperazin-1-yl)phenyl)amino)-2,3-dihydro-4H-pyrimido[5,4-e][1,3]oxazin-4-one dihydrochloride (110 mg, 76.92%) as a yellow solid.

LCMS: 501.2 [M+1]$^+$ $^1$H NMR (400 MHz, DMSO-d$_6$): δ 10.34 (br s, 1H), 9.00 (br s, 2H), 8.83 (s, 1H), 7.66 (d, J=8.33 Hz, 2H), 7.47-7.55 (m, 1H), 7.45 (br s, 1H), 7.31 (d, J=7.89 Hz, 1H), 6.93 (d, J=8.77 Hz, 1H), 5.73 (s, 2H), 3.79 (s, 3H), 3.22 (br s, 4H), 3.15 (br s, 4H).

Example S54. Synthesis of 3-(2,6-dichlorophenyl)-7-(4-(2-(methylamino)ethylamino)phenylamino)-2H-pyrimido[5,4-e][1,3]oxazin-4(3H)-one Hydrochloride (Compound No. 1.54)

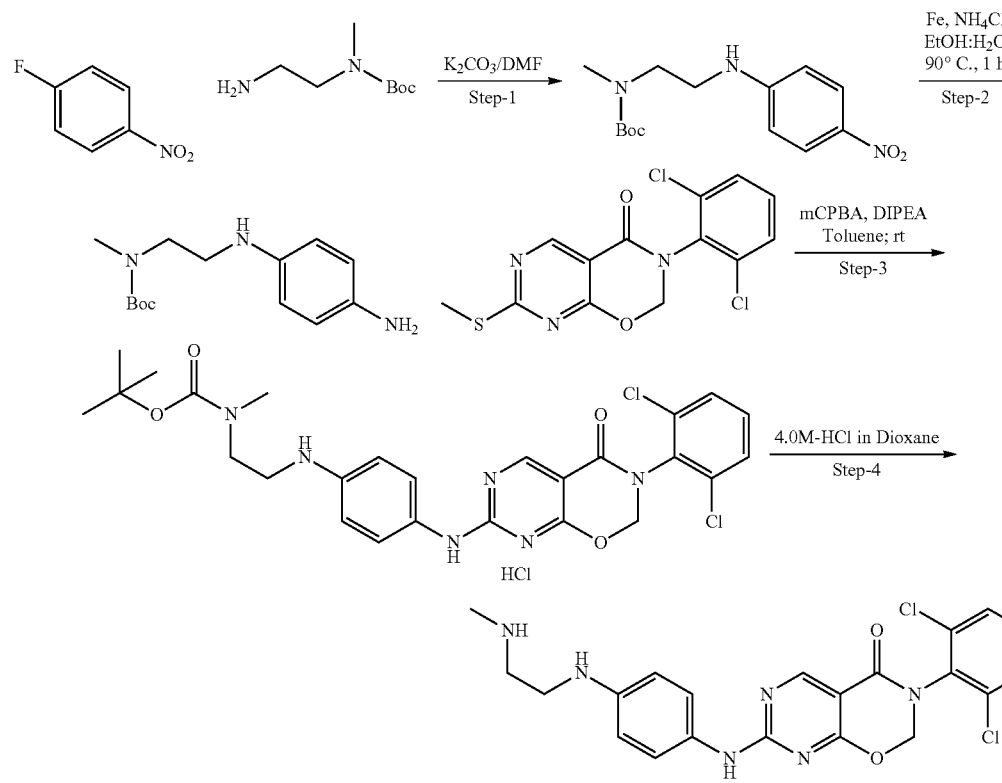

Step-1: Synthesis of tert-butyl methyl(2-((4-nitrophenyl)amino)ethyl)carbamate To a stirred solution of 1-fluoro-4-nitrobenzene (1.0 g, 7.09 mmol, 1.0 eq) and tert-butyl (2-aminoethyl)(methyl) carbamate (1.36 g, 7.79 mmol, 1.1 eq) in DMF (20 mL) was added K$_2$CO$_3$ (1.96 g, 14.18 mmol, 2.0 eq) at rt. The resulting mixture was stirred at 90° C. for 12 h. The progress of reaction was monitored by LCMS. The reaction mixture was poured into ice cold water (100 mL), stirred for 5 min, formation of precipitates was observed, which was filtered and dried under vacuum to afford the desired compound, tert-butyl methyl(2-((4-nitrophenyl)amino)ethyl)carbamate (1.72 g, 82.29%) as a yellow solid.

LCMS: 296.1 [M+1]$^+$

Step-2: Synthesis of tert-butyl (2-((4-aminophenyl)amino)ethyl)(methyl)carbamate To a stirred solution of tert-butyl methyl(2-((4-nitrophenyl)amino)ethyl)carbamate (0.50 g, 1.692 mmol, 1.0 eq) in EtOH (25 mL) was added Fe(0) (756 g, 13.543 mmol, 8.0 eq) and a solution of NH$_4$Cl (0.905 g, 16.920 mmol, 10.0 eq) at rt. The resulting mixture was heated at 90° C. for 1 hr. The progress of reaction was monitored by LCMS. The reaction mixture was filtered through celite the residue was washed with EtOH (50 mL), the filtrate was concentrated and the residue was dissolved in EtOAc (50 mL), washed with water (2×50 mL), dried over Na$_2$SO$_4$, and concentrated to afford the desired compound, tert-butyl (2-((4-aminophenyl)amino)ethyl)(methyl)carbamate (0.30 g, 66.81%) as brown viscous.

LCMS: 266.4 [M+1]$^+$

Step-3: Synthesis of tert-butyl (2-((4-((3-(2,6-dichlorophenyl)-4-oxo-3,4-dihydro-2H-pyrimido[5,4-e][1,3]oxazin-7-yl)amino)phenyl)amino)ethyl)(methyl)carbamate To a stirred solution of 3-(2,6-dichlorophenyl)-7-(methylthio)-2,3-dihydro-4H-pyrimido[5,4-e][1,3]oxazin-4-one (300 mg, 0.868 mmol, 1.0 eq) in (10.0 mL) of toluene was added m-CPBA (432 mg, 1.753 mmol, 2.0 eq) and allowed to stir at rt for 30 min. Tert-butyl (2-((4-aminophenyl)amino)ethyl)(methyl)carbamate (256 mg, 0.964 mmol, 1.1 eq) and DIPEA (0.611 mL, 3.504 mmol, 4.0 eq) were added and allowed to stir at rt for 12 h. The reaction mixture was diluted with water (50 mL) and extracted with EtOAc (2×50 mL). The combined organic layers were washed with water (50 mL) with brine (50 mL) dried over Na$_2$SO$_4$, filtered and concentrated and purified by flash chromatography (elution 0-35% EtOAc in Hexane) to afford the desired compound tert-butyl (2-((4-((3-(2,6-dichlorophenyl)-4-oxo-3,4-dihydro-2H-pyrimido[5,4-e][1,3]oxazin-7-yl)amino)phenyl)amino)ethyl)(methyl)carbamate (250 mg, 51.12%) as dark brown solid.

LCMS: 559.3 [M+1]$^+$

Step-4: Synthesis of 3-(2,6-dichlorophenyl)-7-((4-((2-(methylamino)ethyl)amino)phenyl)amino)-2,3-dihydro-4H-pyrimido[5,4-e][1,3]oxazin-4-one hydrochloride Tert-butyl (2-((4-((3-(2,6-dichlorophenyl)-4-oxo-3,4-dihydro-2H-pyrimido[5,4-e][1,3]oxazin-7-yl)amino)phenyl)amino)ethyl)(methyl)carbamate (220 mg, 0.393 mmol, 1.0 eq) was dissolved in 4M HCl in dioxane (2 mL) and allowed to stir at rt for 1 hr. After completion of reaction, the reaction mixture was filtered and dried under reduced pressure and purified by diethyl ether to afford the desired compound, 3-(2,6-dichlorophenyl)-7-((4-((2-(methylamino)ethyl)amino)phenyl)amino)-2,3-dihydro-4H-pyrimido[5,4-e][1,3]oxazin-4-one hydrochloride (161 mg, 89.44%) as brown solid.

LCMS: 459.2 [M+1]$^+$ $^1$H NMR (400 MHz, DMSO-d$_6$): δ 10.17 (br s, 1H), 8.67-8.97 (m, 3H), 7.61-7.70 (m, 3H), 7.50 (d, J=8.33 Hz, 1H), 7.41-7.48 (m, 2H), 6.62-6.74 (m, J=8.77 Hz, 2H), 5.70 (s, 2H), 3.35 (t, J=6.14 Hz, 2H), 3.07 (br s, 2H), 2.58 (br s, 3H).

Example S55. Synthesis of 5-(3-(2,6-dichlorophenyl)-4-oxo-3,4-dihydro-2H-pyrimido[5,4-e][1,3]oxazin-7-ylamino)-2-(piperazin-1-yl)benzonitrile (Compound No. 1.55)

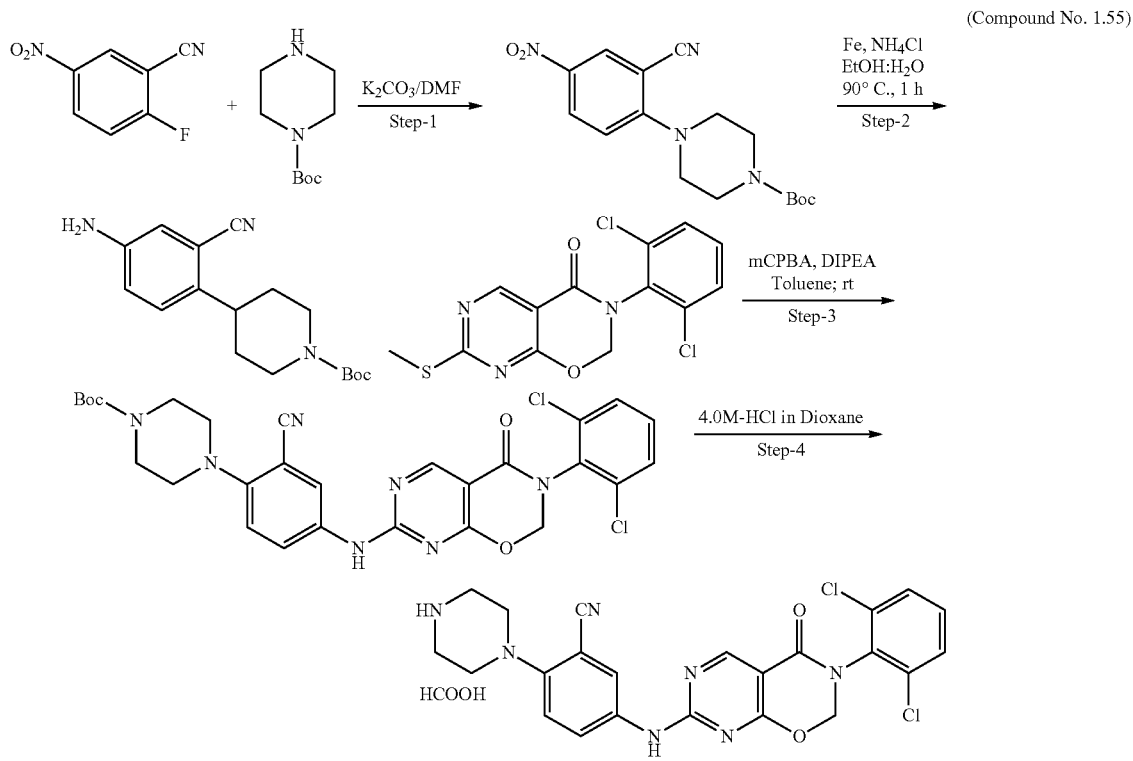

Step-1: tert-butyl 4-(2-cyano-4-nitrophenyl)piperazine-1-carboxylate

To a stirred solution of 2-fluoro-5-nitrobenzonitrile (4.0 g, 21.47 mmol, 1.0 eq) and tert-butyl piperidine-4 carboxylate (3.92 g, 23.62 mmol, 1.1 eq) in DMF (70 mL) was added $K_2CO_3$ (5.935 g, 42.95 mmol, 2.0 eq) at rt. The resulting mixture was stirred at 90° C. for 12 h. The progress of reaction was monitored by LCMS. The reaction mixture was poured into ice cold water (200 mL), stirred for 5 min, formation of precipitates was observed, which was filtered and dried under vacuum to afford the desired compound, tert-butyl 4-(2-cyano-4-nitrophenyl)piperazine-1-carboxylate (6.0 g, 84.26%) as a yellow solid.

LCMS: 333.1 [M+1]$^+$

Step-2: Synthesis of tert-butyl 4-(4-amino-2-cyanophenyl)piperazine-1-carboxylate To a stirred solution of tert-butyl 4-(2-cyano-4-nitrophenyl)piperazine-1-carboxylate (2.0 g, 6.021 mmol, 1.0 eq) in EtOH (30 mL) was added Fe(0) (1.0 g, 18.064 mmol, 3 eq) and a solution of $NH_4Cl$ (644 mg, 12.042 mmol, 2 eq) in water (30 mL) at rt. The resulting mixture was heated at 90° C. for 1 hr. The progress of reaction was monitored by LCMS. The reaction mixture was filtered through celite the residue was washed with EtOH (50 mL). The filtrate was concentrated and the residue was dissolved in EtOAc (100 mL), washed with water (2×100 mL), dried over $Na_2SO_4$, and concentrated to afford the desired compound, tert-butyl 4-(4-amino-2-cyanophenyl)piperazine-1-carboxylate (1.77 g, 88.5%).

LCMS: 303.2 [M+1]$^+$

Step-3: Synthesis of tert-butyl 4-(2-cyano-4-((3-(2,6-dichlorophenyl)-4-oxo-3,4-dihydro-2H-pyrimido[5,4-e][1,3]oxazin-7-yl)amino)phenyl)piperazine-1-carboxylate To a stirred solution of 3-(2,6-dichlorophenyl)-7-(methylthio)-2,3-dihydro-4H-pyrimido[5,4-e][1,3]oxazin-4-one (300 mg, 0.8767 mmol, 1.0 eq) in (10.0 mL) of toluene was added m-CPBA (376 mg, 2.1917 mmol, 2.5 eq) and allowed to stir at rt for 30 min followed by addition of tert-butyl 4-(4-amino-2-cyanophenyl)piperazine-1-carboxylate (265 mg, 0.8767 mmol, 1 eq) and DIPEA (452 mg, 3.506 mmol, 4.0 eq) and allowed to stir at rt for 12 h. The reaction mixture was diluted with water (50 mL) and extracted with EtOAc (2×50 mL). The combined organic layers were washed with water (50 mL), brine (50 mL), dried over $Na_2SO_4$, concentrated and purified by flash chromatography (elution 0-35% EtOAc in Hexane) to afford the desired compound, tert-butyl 4-(2-cyano-4-((3-(2,6-dichlorophenyl)-4-oxo-3,4-dihydro-2H-pyrimido[5,4-e][1,3]oxazin-7-yl)amino)phenyl)piperazine-1-carboxylate (150 mg, 28.68%) as an off white solid.

LCMS: 596.2 [M+1]$^+$

Step-4: Synthesis of 5-((3-(2,6-dichlorophenyl)-4-oxo-3,4-dihydro-2H-pyrimido[5,4-e][1,3]oxazin-7-yl)amino)-2-(piperazin-1-yl)benzonitrile tert-butyl 4-(2-cyano-4-((3-(2,6-dichlorophenyl)-4-oxo-3,4-dihydro-2H-pyrimido[5,4-e][1,3]oxazin-7-yl)amino) phenyl) piperazine-1-carboxylate (150 mg, 0.252 mmol, 1.0 eq) was dissolved in 4M HCl in dioxane (2 mL) and allowed to stir at rt for 1 h. After completion of reaction, the reaction mixture was filtered and dried under reduced pressure. Solid was triturated with diethyl ether, filtered off and dried under vacuum to afford the desired compound, 5-((3-(2,6-dichlorophenyl)-4-oxo-3,4-dihydro-2H-pyrimido[5,4-e][1,3]oxazin-7-yl)amino)-2-(piperazin-1-yl)benzonitrile (36 mg, 26.39%) as white solid.

LCMS: 496.2[M+1]$^+$ $^1$H NMR (400 MHz, DMSO-d$_6$): δ 10.54 (br s, 1H), 8.87 (s, 1H), 8.32 (s, 2H), 8.09 (br s, 1H), 7.85 (d, J=8.33 Hz, 2H), 7.66 (d, J=8.33 Hz, 1H), 7.51 (d, J=8.33 Hz, 1H), 7.18 (d, J=9.65 Hz, 1H), 5.75 (s, 2H), 3.02 (br s, 4H), 2.87 (br s, 4H).

Example S56. Synthesis of 3-(2,6-dichlorophenyl)-7-(4-(pyrrolidin-1-yl)phenylamino)-2H-pyrimido[5,4-e][1,3]oxazin-4(3H)-one (Compound No. 1.56)

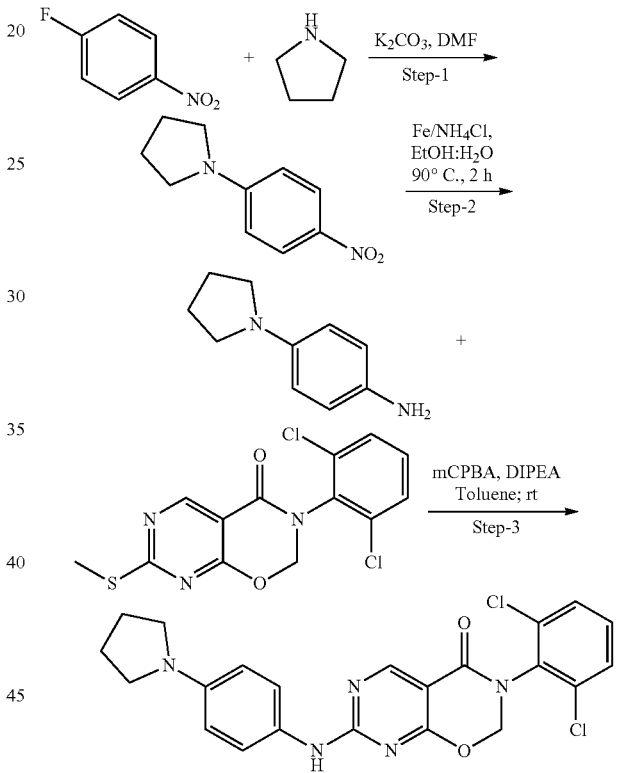

Step-1: Synthesis of 1-(4-nitrophenyl)pyrrolidine

To a stirred solution of 1-fluoro-4-nitrobenzene (0.50 g, 3.543 mmol, 1.0 eq) and pyrrolidine (0.277 g, 3.897 mmol, 1.1 eq) in DMF (10 mL) was added $K_2CO_3$ (0.980 g, 7.086 mmol, 2.0 eq) at rt. The resulting mixture was stirred at 90° C. for 12 h. The progress of reaction was monitored by LCMS. The reaction mixture was poured into ice cold water (100 mL), stirred for 5 min, formation of precipitates was observed, which was filtered and dried under vacuum to afford the desired compound, 1-(4-nitrophenyl)pyrrolidine (0.605 g, 88.83%) as a yellow solid.

LCMS: 193.2 [M+1]$^+$

Step-2: Synthesis of 4-(pyrrolidin-1-yl)anilin

To a stirred solution of 1-(4-nitrophenyl)pyrrolidine (0.60 g, 3.121 mmol, 1.0 eq) in EtOH (20 mL) was added Fe(0)

(1.395 g, 24.971 mmol, 8.0 eq) and a solution of NH₄Cl (1.67 g, 31.210 mmol, 10.0 eq) at rt. The resulting mixture was heated at 90° C. for 60 min. The progress of reaction was monitored by LCMS. The reaction mixture was filtered through celite the residue was washed with EtOH (50 mL) the filtrate was concentrated and the residue was dissolved in EtOAc (50 mL), washed with water (2×50 mL), dried over Na₂SO₄, and concentrated to afford 4-(pyrrolidin-1-yl) aniline (0.30 g, 59.28%) as brown viscous.

LCMS: 163.3 [M+1]⁺

Step-3: Synthesis of 3-(2,6-dichlorophenyl)-7-((4-(pyrrolidin-1-yl)phenyl)amino)-2,3-dihydro-4H-pyrimido[5,4-e][1,3]oxazin-4-one To a stirred solution of 3-(2,6-dichlorophenyl)-7-(methylthio)-2,3-dihydro-4H-pyrimido[5,4-e][1,3]oxazin-4-one (200 mg, 0.584 mmol, 1.0 eq) in (5.0 mL) of toluene was added mCPBA (288 mg, 1.168 mmol, 2.0 eq) and allowed to stir at rt for 30 min. 4-(Pyrrolidin-1-yl)aniline (105 mg, 0.642 mmol, 1.1 eq) and DIPEA (0.408 mL, 2.336 mmol, 4.0 eq) were added and allowed to stir at rt for 12 h. The reaction mixture was diluted with water (50 mL) and extracted with EtOAc (2×50 mL), the combined organic layers were washed with water (50 mL) with brine (50 mL) dried over Na₂SO₄, filtered and concentrated and purified by reversed phase chromatography to afford the desired compound 3-(2,6-dichlorophenyl)-7-((4-(pyrrolidin-1-yl)phenyl)amino)-2,3-dihydro-4H-pyrimido[5,4-e][1,3]oxazin-4-one (39 mg, 14.66%) as a yellow solid.

LCMS: 456.2 [M+1]⁺

¹H NMR (400 MHz, DMSO-d₆): δ 10.13 (br s, 1H), 8.75 (s, 1H), 7.65 (d, J=7.89 Hz, 2H), 7.50 (d, J=7.89 Hz, 2H), 7.46 (d, J=7.45 Hz, 1H), 6.53 (d, J=8.77 Hz, 2H), 5.69 (s, 2H), 3.01-3.28 (m, 4H), 1.95 (t, J=6.36 Hz, 4H).

Example S57. Synthesis of 3-(2,6-dichlorophenyl)-7-(4-(4-(2-(methylamino)acetyl)piperazin-1-yl)phenylamino)-2H-pyrimido[5,4-e][1,3]oxazin-4(3H)-one hydrochloride (Compound No. 1.57)

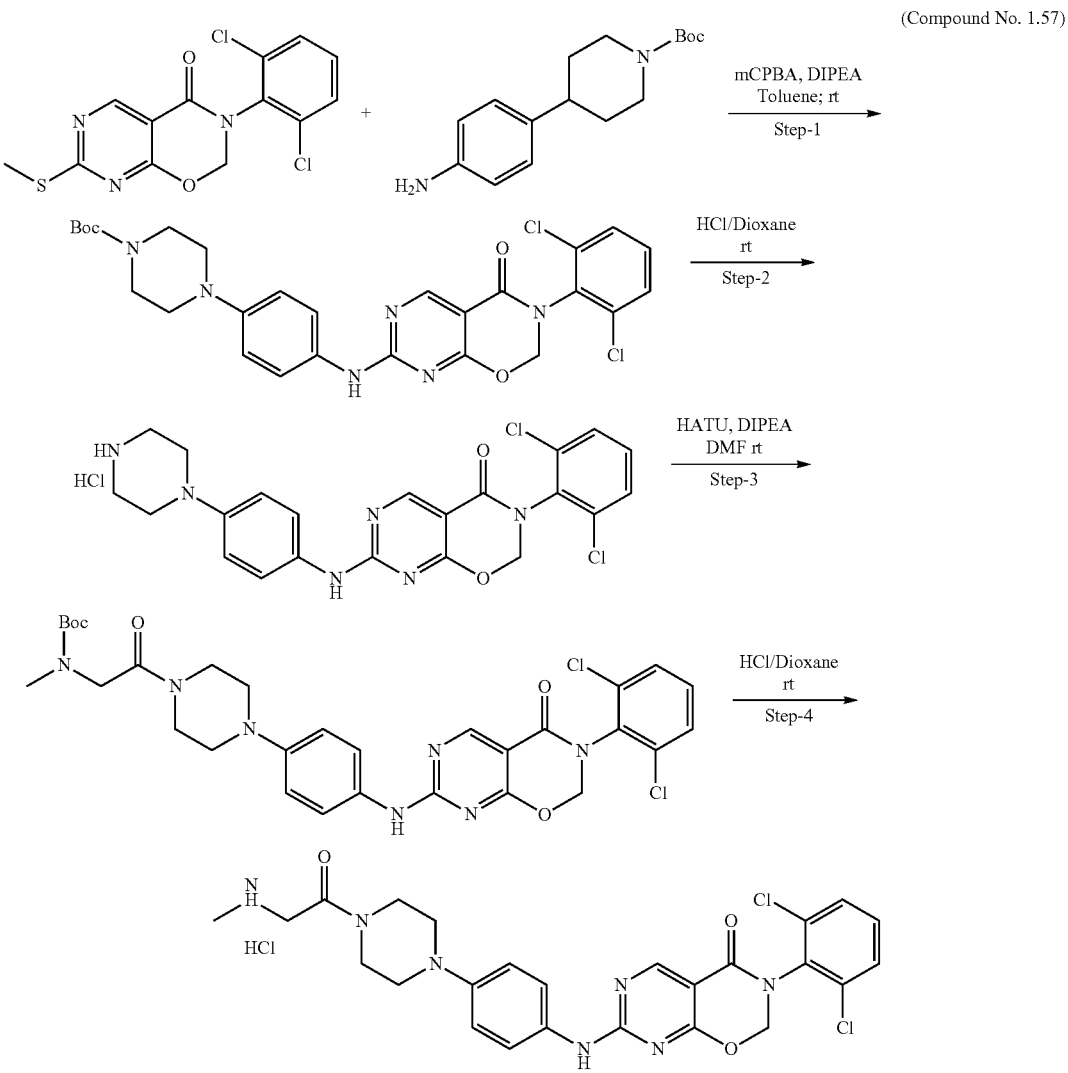

Step-1: Synthesis of tert-butyl 4-(4-((3-(2,6-dichlorophenyl)-4-oxo-3,4-dihydro-2H-pyrimido[5,4-e][1,3]oxazin-7-yl)amino)phenyl)piperazine-1-carboxylate To a stirred solution of 3-(2,6-dichlorophenyl)-7-(methylthio)-2,3-dihydro-4H-benzo[e][1,3]oxazin-4-one (0.5 g, 1.46 mmol, 1.0 eq) in 5 mL toluene mCPBA (0.628 g, 3.65 mmol, 2.5 eq) was added under stirring and resulting mixture was allowed to stir at rt for 30 min. Further, tert-butyl 4-(4-aminophenyl)piperazine-1-carboxylate (0.405 g, 1.46 mmol, 1 eq) and DIPEA (0.75 g, 5.85 mmol, 4 eq) were added and the reaction was allowed to stir at rt for 12 h. The reaction was monitored by LCMS. After completion reaction was quenched with water and extracted with ethyl acetate (10 mL×3). The combined organic layer was washed with brine solution (20 mL), dried over anhydrous $Na_2SO_4$ and concentrated under reduced pressure to afford crude product which was purified by flash chromatography (MeOH: $CH_2Cl_2$ 1-10%) to afford tert-butyl 4-(4-((3-(2,6-dichlorophenyl)-4-oxo-3,4-dihydro-2H-pyrimido[5,4-e][1,3]oxazin-7-yl)amino)phenyl) piperazine-1-carboxylate (0.270 g, 33%) as white solid.
LCMS: 570 [M+1]$^+$

Step-2: Synthesis of 3-(2,6-dichlorophenyl)-7-((4-(piperazin-1-yl)phenyl)amino)-2,3-dihydro-4H-pyrimido[5,4-e][1,3]oxazin-4-one Hydrochloride 20% HCl in dioxane (2 mL) was added to a stirred solution of tert-butyl 4-(4-((3-(2,6-dichlorophenyl)-4-oxo-3,4-dihydro-2H-pyrimido[5,4-e][1,3]oxazin-7-yl)amino)phenyl)piperazine-1-carboxylate (0.270 g, 0.47 mmol, 1.0 eq) at 0° C. and the resulting solution was allowed to stir at rt for 3 h. After completion of reaction, solvent was removed under reduced pressure, and the resulting solid was filtered, washed with diethylether, and dried to afford 3-(2,6-dichlorophenyl)-7-((4-(piperazin-1-yl)phenyl)amino)-2,3-dihydro-4H-pyrimido[5,4-e][1,3]oxazin-4-one hydrochloride (0.155 g, 65%) as a white solid.
LCMS: 506 [M+1]$^+$

Step-3: Synthesis of tert-butyl (2-(4-(4-((3-(2,6-dichlorophenyl)-4-oxo-3,4-dihydro-2H-pyrimido[5,4-e][1,3]oxazin-7-yl)amino)phenyl)piperazin-1-yl)-2-oxoethyl)(methyl)carbamate To a solution of 3-(2,6-dichlorophenyl)-7-((4-(piperazin-1-yl)phenyl)amino)-2,3-dihydro-4H-pyrimido[5,4-e][1,3]oxazin-4-one hydrochloride (0.150 g, 0.29 mmol, 1.0 eq) in 5 mL DMF, HATU (0.165 g, 0.43 mmol) was added under stirring at rt under inert atmosphere. The resulting solution was stirred for 5 min. Further N-(tert-butoxycarbonyl)-N-methylglycine (0.061 mg, 0.33 mmol) and DIPEA (0.131 g, 1.01 mmol) was added. The resulting mixture was stirred at rt for 1-2 h and monitored by LCMS. After completion, the reaction was quenched with water and the resulting solid was filtered and dried to afford tert-butyl (2-(4-(4-((3-(2,6-dichlorophenyl)-4-oxo-3,4-dihydro-2H-pyrimido[5,4-e][1,3]oxazin-7-yl)amino)phenyl)piperazin-1-yl)-2-oxoethyl)(methyl)carbamate (0.145 g, 76%) as white solid.
LCMS: 641 [M+1]$^+$

Step-4: Synthesis of 3-(2,6-dichlorophenyl)-7-((4-(4-(methylglycyl)piperazin-1-yl)phenyl)amino)-2,3-dihydro-4H-pyrimido[5,4-e][1,3]oxazin-4-one Hydrochloride 20% HCl in dioxane (2 mL) was added to a stirred solution of tert-butyl (2-(4-(4-((3-(2,6-dichlorophenyl)-4-oxo-3,4-dihydro-2H-pyrimido[5,4-e][1,3]oxazin-7-yl)amino)phenyl) piperazin-1-yl)-2-oxoethyl)(methyl)carbamate (0.14 g, 0.21 mmol, 1.0 eq) at 0° C. and the resulting solution was allowed to stir at rt for 3 h. After completion of reaction, solvent was removed under reduced pressure, and the resulting solid was filtered and washed with diethylether, and dried to afford 3-(2,6-dichlorophenyl)-7-((4-(piperazin-1-yl)phenyl)amino)-2,3-dihydro-4H-pyrimido[5,4-e][1,3]oxazin-4-one hydrochloride (0.155 g, 31%) as a white solid.
LCMS: 541 [M+1]$^+$
$^1$H NMR (400 MHz, DMSO-$d_6$): δ 10.2 (br s, 1H), 8.79 (s, 1H), 7.65 (d, J=7.89 Hz, 2H), 7.59-7.54 (m, 2H), 7.52-7.46 (m, 1H), 6.96 (d, J=8.77 Hz, 2H), 5.71 (s, 2H) 3.64-3.59 (m, 2H), 3.57-3.53 (m, 2H), 3.38-3.46 (m, 2H), 3.14-3.1 (m, 2H), 3.04-3.09 (m, 2H).

Example S58. Synthesis of 3-(2,6-dichlorophenyl)-7-(4-(4-(2-hydroxyethyl)piperazin-1-yl)phenylamino)-2H-pyrimido[5,4-e][1,3]oxazin-4(3H)-one (Compound No. 1.58)

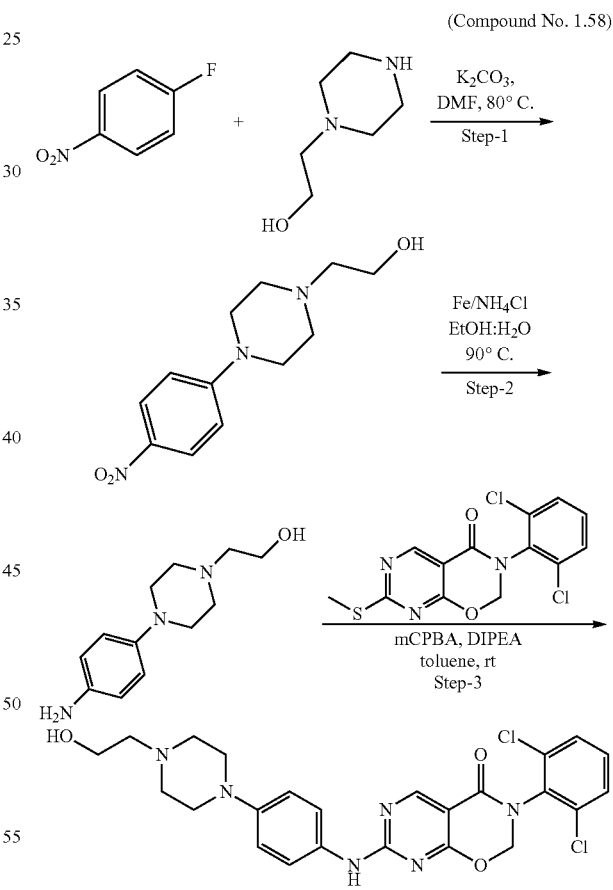

Step-1: Synthesis of 2-(4-(4-nitrophenyl)piperazin-1-yl)ethan-1-ol

To a stirred solution of 2-(piperazin-1-yl)ethan-1-ol (1.014 g, 7.79 mmol, 1.1 eq) in 5 mL DMF, $K_2CO_3$ (1.95 g, 14.16 mmol, 2 eq) was added under stirring and resulting mixture was allowed to stir at rt for 5-10 min. Further, 1-fluoro-4-nitrobenzene (1 g, 7.79 mmol, 1 eq) was added and the reaction was heated at 80° C. 12 h. The reaction was monitored by LCMS. After completion, reaction was cooled to rt and quenched with cold water. The resulting yellow precipitate was filtered and dried, washed with water to afford 2-(4-(4-nitrophenyl)piperazin-1-yl)ethan-1-ol (0.905 g, 51%) as a yellow solid.
LCMS: 252 [M+1]⁺

Step-2: Synthesis of 2-(4-(4-aminophenyl)piperazin-1-yl)ethan-1-ol 2-(4-(4-nitrophenyl)piperazin-1-yl)ethan-1-ol (0.9 g, 3.58 mmol) was dissolved in 10 mL EtOH, further 10 mL water was added under stirring. Iron powder (0.6 g, 10.75 mmol) and NH₄Cl (0.383 g, 7.16 mmol) were then added. The resulting mixture was heated at 90° C. for 1-2 h. The reaction was monitored by LCMS. After completion of reaction, mixture was filtered through celite bed, solvent form the filtrate was removed under reduced pressure. Water was added to the residue and extracted using MeOH: $CH_2Cl_2$ (10%), dried over $Na_2SO_4$. The solvent was removed under reduced pressure to afford 2-(4-(4-aminophenyl) piperazin-1-yl) ethan-1-ol (0.550 g, 70%) as a brown solid.
LCMS: 221 [M+1]⁺

Step-3: Synthesis of 3-(2,6-dichlorophenyl)-7-((4-(4-(2-hydroxyethyl)piperazin-1-yl)phenyl)amino)-2,3-dihydro-4H-pyrimido[5,4-e][1,3]oxazin-4-one To a stirred solution of 3-(2,6-dichlorophenyl)-7-(methylthio)-2,3-dihydro-4H-pyrimido[5,4-e][1,3]oxazin-4-one (0.2 g, 0.58 mmol, 1.0 eq) in 5 mL toluene m-CPBA (0.251 g, 1.46 mmol, 2.5 eq) was added under stirring and resulting mixture was allowed to stir at rt for 30 min. Further, 2-(4-(4-aminophenyl)piperazin-1-yl)ethan-1-ol (0.129 g, 0.58 mmol, 1.0 eq) and DIPEA (0.302 g, 2.33 mmol, 4 eq) were added and the reaction was allowed to stir at rt for 12 h. The reaction was monitored by LCMS. After completion reaction was quenched with water and extracted with ethyl acetate (5 mL×3). The combined organic layer was washed with brine solution (10 mL), dried over anhydrous $Na_2SO_4$ and concentrated under reduced pressure to afford crude product which was purified by flash chromatography (MeOH: $CH_2Cl_2$ 1-10%) to afford 3-(2,6-dichlorophenyl)-7-((4-(4-(2-hydroxyethyl)piperazin-1-yl)phenyl)amino)-2,3-dihydro-4H-pyrimido[5,4-e][1,3]oxazin-4-one (0.008 g, 10%) as white solid.
LCMS: 515 [M+1]⁺
¹H NMR (400 MHz, DMSO-d₆): δ 10.18 (s, 1H), 8.78 (s, 1H), 8.20 (s, 1H), 7.65 (d, J=8.33 Hz, 2H), 7.51 (d, J=7.45 Hz, 2H), 6.92 (d, J=8.33 Hz, 2H), 5.71 (br s, 2H), 4.43 (br s, 2H), 3.53 (d, J=6.14 Hz, 2H), 3.17 (d, J=5.26 Hz, 1H), 3.09 (br s, 1H), 1.23 (br s, 1H), 1.16 (d, J=10.09 Hz, 1H).

Example S59. Synthesis of 3-(2,6-dichlorophenyl)-7-(4-(4-methylpiperidin-1-yl)phenylamino)-2H-pyrimido[5,4-e][1,3]oxazin-4(3H)-one (Compound No. 1.59)

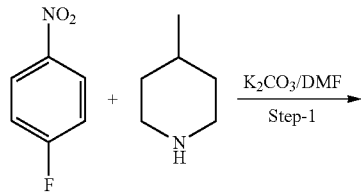

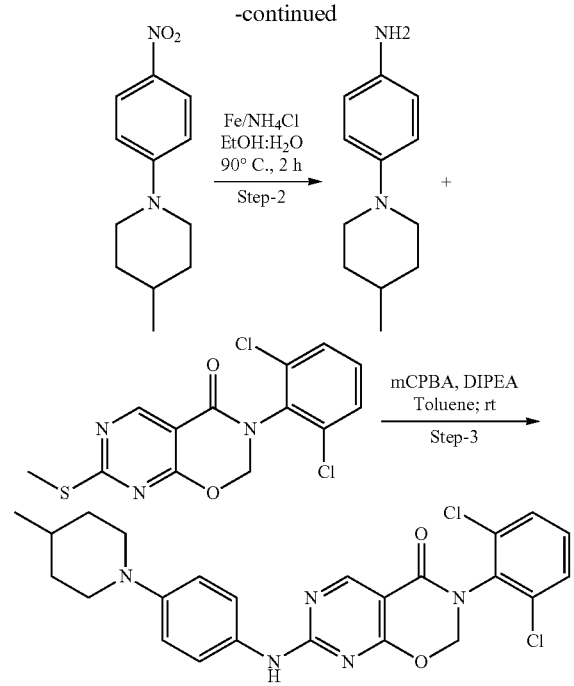

Step-1: Synthesis of 4-methyl-1-(4-nitrophenyl)piperidine

To a stirred solution of 1-fluoro-4-nitrobenzene (1.0 g, 7.087 mmol, 1.0 eq) and 4-methylpiperidine (0.773 g, 7.795 mmol, 1.1 eq) in DMF (20 mL) was added $K_2CO_3$ (1.95 g, 14.17 mmol, 2.0 eq) at rt. The resulting mixture was stirred at 90° C. for 12 h. The progress of reaction was monitored by LCMS. The reaction mixture was poured into ice cold water (150 mL), stirred for 5 min, formation of precipitates was observed, which was filtered and dried under vacuum to afford the desired compound, 4-methyl-1-(4-nitrophenyl) piperidine (1.5 g 96.09%) as a yellow solid.
LCMS: 221 [M+1]⁺

Step-2: Synthesis of 4-(4-methylpiperidin-1-yl)aniline

To a stirred solution of 4-methyl-1-(4-nitrophenyl)piperidine (1.5 g, 6.809 mmol, 1.0 eq) in EtOH (12 mL) was added Fe(0) (1.14 g, 20.42 mmol, 3 eq) and a solution of NH₄Cl (0.728 g, 13.619 mmol, 2 eq) in water (12 mL) at rt. The resulting mixture was heated at 90° C. for 1 hr. The progress of reaction was monitored by LCMS. The reaction mixture was filtered through celite the residue was washed with EtOH (50 mL). The filtrate was concentrated and the residue was dissolved in EtOAc (100 mL), washed with water (2×100 mL), dried over $Na_2SO_4$, and concentrated to afford the desired compound, 4-(4-methylpiperidin-1-yl)aniline (0.900 g, 69.52%).
LCMS: 191 [M+1]⁺

Step-3: Synthesis of 3-(2,6-dichlorophenyl)-7-((4-(4-methylpiperidin-1-yl)phenyl)amino)-2,3-dihydro-4H-pyrimido[5,4-e][1,3]oxazin-4-one To a stirred solution of 3-(2,6-dichlorophenyl)-7-(methylthio)-2,3-dihydro-4H-pyrimido[5,4-e][1,3]oxazin-4-one (0.200 g, 0.5844 mmol, 1.0 eq) in (5.0 mL) of toluene was added m-CPBA (0.201 g, 1.168 mmol, 2 eq) and allowed to stir at rt for 30 min followed by addition of 4-(4-methylpiperidin-1-yl)aniline (0.122 g, 0.6428 mmol, 1.1 eq) and DIPEA (0.301 g, 2.337 mmol, 4.0 eq) and allowed to stir at rt for 12 h. The reaction mixture was diluted with water (50 mL) and extracted with EtOAc (2×50 mL). The combined organic layers were washed with water (50 mL), brine (50 mL), dried over Na₂SO₄, concentrated and purified by combi-flash [silica gel-100-200 mesh; elution 0-35% EtOAc in hexane] to afford the desired compound, 3-(2,6-dichlorophenyl)-7-((4-(4-methylpiperidin-1-yl)phenyl)amino)-2,3-dihydro-4H-pyrimido[5,4-e][1,3]oxazin-4-one (0.110 g, 39.00%) as an off white solid.

LCMS: 484 [M+1]⁺

¹H NMR (400 MHz, DMSO-d₆): δ 10.21 (br s, 1H), 8.78 (s, 1H), 7.65 (d, J=8.33 Hz, 2H), 7.35-7.57 (m, 3H), 6.91 (d, J=9.21 Hz, 2H), 5.70 (s, 2H), 3.61 (d, J=13.15 Hz, 2H), 2.52-2.78 (m, 2H), 1.69 (d, J=12.72 Hz, 2H), 1.48 (br s, 1H), 1.18-1.31 (m, 2H), 0.94 (d, J=6.14 Hz, 3H).

Example S60. Synthesis of 3-(2,6-dichlorophenyl)-7-(3-methyl-4-(piperidin-4-yl)phenylamino)-2H-pyrimido[5,4-e][1,3]oxazin-4(3H)-one (Compound No. 1.60)

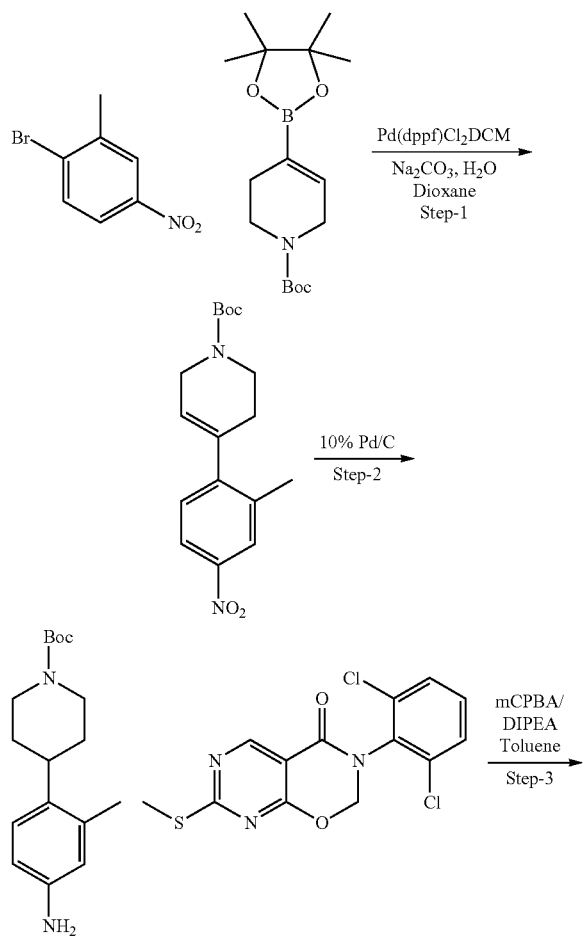

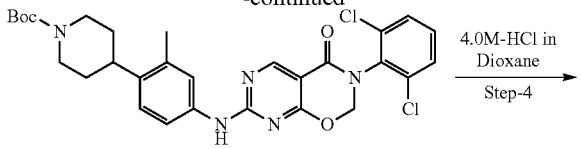

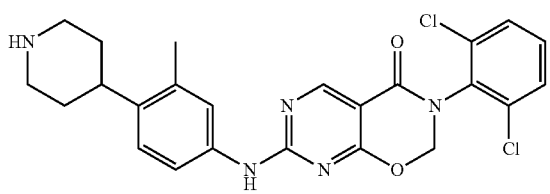

Step-1: Synthesis of tert-butyl 4-(2-methyl-4-nitrophenyl)-3,6-dihydropyridine-1(2H)-carboxylate To a stirred solution of 1-bromo-2-methyl-4-nitrobenzene (1.5 g, 6.94 mmol, 1.0 eq) and tert-butyl 4-(4,4,5,5-tetramethyl-1,3,2-dioxaborolan-2-yl)-3,6-dihydropyridine-1(2H)-carboxylate (3.0 g, 9.72 mmol, 1.4 eq) in dioxane (15 mL) was added a 2M solution of Na₂CO₃ (2.20 g, 20.82 mmol, 3.0 eq) at rt. The resulting mixture was purged with nitrogen for 10 min, followed by addition of Pd(dppf)Cl₂·CH₂Cl₂ (283 mg, 0.347 mmol, 0.05 eq). The resulting mixture was heated at 90° C. for 12 h. The progress of reaction was monitored by ¹H NMR. The reaction mixture was filtered through celite the residue was washed with EtOAc (50 mL) the filtrate wash concentrated and purified by flash chromatography (elution 0-10% EtOAc in hexane) to afford the desired compound, tert-butyl 4-(2-methyl-4-nitrophenyl)-3,6-dihydropyridine-1(2H)-carboxylate (2.0 g, 90.49%) as white solid.

LCMS: 319.2 [M+1]⁺

Step-2: Synthesis of tert-butyl 4-(4-amino-2-methylphenyl)piperidine-1-carboxylate To a stirred solution of tert-butyl 4-(2-methyl-4-nitrophenyl)-3,6-dihydropyridine-1(2H)-carboxylate (2.0 g, 6.28 mmol, 1.0 eq) in MeOH (24 mL) was added 10% Pd/C (200 mg) at rt. The resulting mixture was purged with hydrogen for 60 min. The progress of reaction was monitored by LCMS. The reaction mixture was filtered through celite the residue was washed with MeOH (50 mL) the filtrate was concentrated and purified by n-pentane to afford the desired compound, tert-butyl 4-(4-amino-2-methylphenyl)piperidine-1-carboxylate (0.900 g, 49.45%) as gray solid.

LCMS: 291.2 [M+1]⁺

Step-3: Synthesis of tert-butyl 4-(4-((3-(2,6-dichlorophenyl)-4-oxo-3,4-dihydro-2H-pyrimido[5,4-e][1,3]oxazin-7-yl)amino)-2-methylphenyl)piperidine-1-carboxylate To a stirred solution of 3-(2,6-dichlorophenyl)-7-(methylthio)-2,3-dihydro-4H-pyrimido[5,4-e][1,3]oxazin-4-one (500 mg, 1.46 mmol, 1.0 eq) in toluene (6 mL) was added m-CPBA (504 mg, 2.92 mmol, 2.0 eq) and allowed to stir at rt for 30 min. Tert-butyl 4-(4-amino-2-methylphenyl)piperidine-1-carboxylate (509 mg, 1.75 mmol, 1.2 eq) and DIPEA (1.01 mL, 5.84 mmol, 4.0 eq) were added and allowed to stir at rt for 12 h. The reaction mixture was diluted with water (50 mL) and extracted with EtOAc (2×50 mL), the combined organic layers were washed with water (50 mL) with brine (50 mL) dried over $Na_2SO_4$, filtered and concentrated and purified by flash chromatography (elution 0-30% EtOAc in hexane) to afford the desired compound, tert-butyl 4-(4-((3-(2,6-dichlorophenyl)-4-oxo-3,4-dihydro-2H-pyrimido [5,4-e][1,3]oxazin-7-yl)amino)-2-methylphenyl)piperidine-1-carboxylate (400 mg, 46.83%) as off white solid.

LCMS: 584.2 [M+1]$^+$

Step-4: Synthesis of 3-(2,6-dichlorophenyl)-7-((3-methyl-4-(piperidin-4-yl)phenyl)amino)-2,3-dihydro-4H-pyrimido[5,4-e][1,3]oxazin-4-one tert-butyl 4-(4-((3-(2,6-dichlorophenyl)-4-oxo-3,4-dihydro-2H-pyrimido[5,4-e][1,3]oxazin-7-yl)amino)-2-methoxy phenyl) piperidine-1-carboxylate (100 mg, 0.171 mmol, 1.0 eq) was dissolved in 4M HCl in dioxane (2.0 mL) and allowed to stir at rt for 1 h. After completion of reaction, the reaction mixture was concentrated under reduced pressure and purified by reversed phase purification to afford the desired compound, 3-(2,6-dichlorophenyl)-7-((3-methyl-4-(piperidin-4-yl)phenyl)amino)-2,3-dihydro-4H-pyrimido[5, 4-e][1,3]oxazin-4-one (24 mg, 28.96%) as white solid.

LCMS: 484.2 [M+1]$^+$ $^1$H NMR (400 MHz, DMSO-d$_6$): δ 10.33 (br. s., 1H), 8.83 (s, 1H), 7.66 (d, J=7.89 Hz, 2H), 7.57 (d, J=8.33 Hz, 1H), 7.52-7.47 (m, 2H), 7.13 (d, J=8.77 Hz, 1H), 5.73 (s, 2H), 3.32-3.29 (m 2H), 3.14 (br. s., 1H), 2.99-2.94 (m, 2H), 2.28 (m, 3H), 1.82-1.71 (m, 4H).

Example S61. Synthesis of 7-(4-(1,4-diazepan-1-yl) phenylamino)-3-(2,6-dichlorophenyl)-2H-pyrimido [5,4-e][, 3]oxazin-4(3H)-one (Compound No. 1.61)

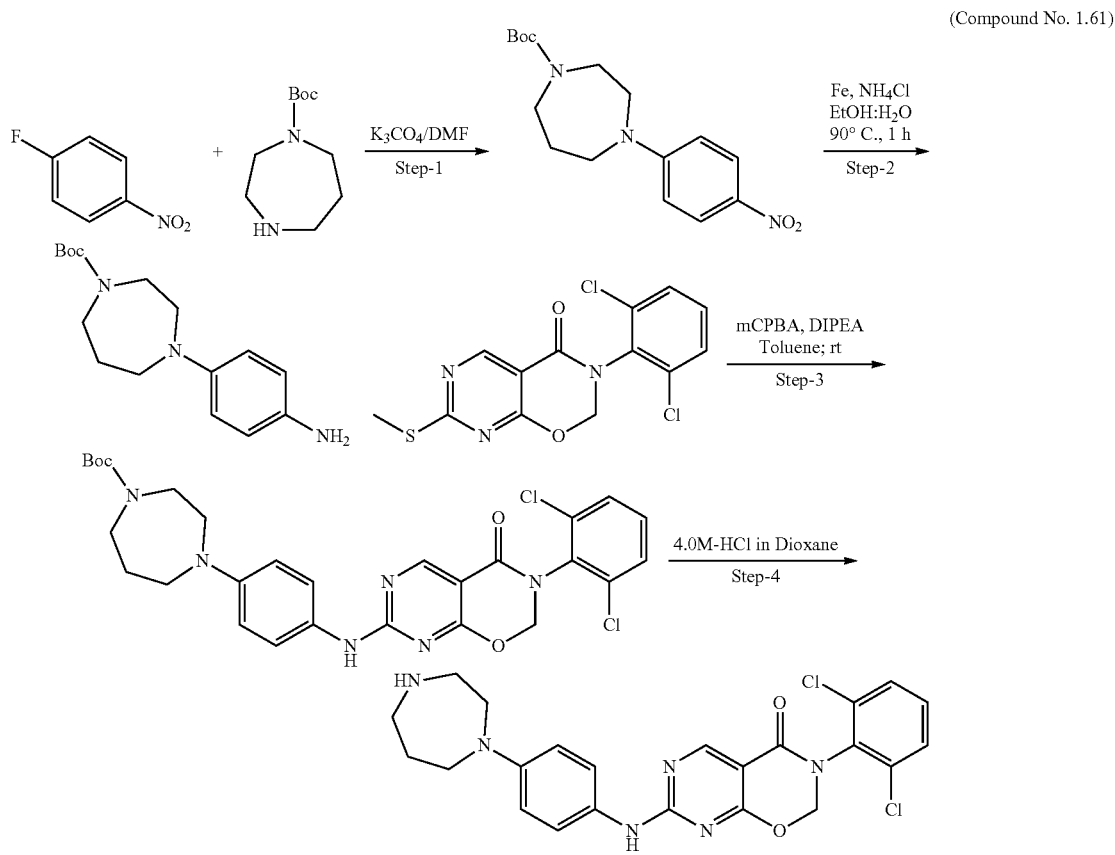

Step-1: Synthesis of tert-butyl 4-(4-nitrophenyl)-1,4-diazepane-1-carboxylate To a stirred solution of 1-fluoro-4-nitrobenzene (1.0 g, 7.087 mmol, 1.0 eq) and tert-butyl 1,4-diazepane-1-carboxylate (1.561 g, 7.795 mmol, 1.1 eq) in DMF (20 mL) was added $K_2CO_3$ (1.96 g, 14.174 mmol, 2.0 eq) at rt. The resulting mixture was stirred at 90° C. for 12 h. The progress of reaction was monitored by LCMS. The reaction mixture was poured into ice cold water (100 mL), stirred for 5 min, formation of precipitate was observed, which was filtered and dried under vacuum to afford the desired compound, tert-butyl 4-(4-nitrophenyl)-1,4-diazepane-1-carboxylate (1.9 g, 83.44%) as a yellow solid.

LCMS: 322.1 [M+1]$^+$

Step-2: Synthesis of tert-butyl 4-(4-aminophenyl)-1,4-diazepane-1-carboxylate To a stirred solution of tert-butyl 4-(4-nitrophenyl)-1,4-diazepane-1-carboxylate (1.0 g, 3.111 mmol, 1.0 eq) in EtOH (25 mL) was added Fe(0) (1.39 g, 24.892 mmol, 8.0 eq) and a solution of NH₄C₁ (1.66 g, 31.11 mmol, 10.0 eq) in water (25 mL) at rt. The resulting mixture was heated at 90° C. for 60 min. The progress of reaction was monitored by LCMS. The reaction mixture was filtered through celite the residue was washed with EtOH (50 mL). The filtrate was concentrated and the residue was dissolved in EtOAc (50 mL), washed with water (2×50 mL), dried over Na₂SO₄, and concentrated to yield tert-butyl 4-(4-aminophenyl)-1,4-diazepane-1-carboxylate (0.95 g, 95.28%) as brown viscous.

LCMS: 292.3 [M+1]⁺

Step-3: Synthesis of tert-butyl 4-(4-((3-(2,6-dichlorophenyl)-4-oxo-3,4-dihydro-2H-pyrimido[5,4-e][1,3]oxazin-7-yl)amino)phenyl)-1,4-diazepane-1

To a stirred solution of 3-(2,6-dichlorophenyl)-7-(methylthio)-2,3-dihydro-4H-pyrimido[5,4-e][1,3]oxazin-4-one stir at rt for 1 h. After completion of reaction, the reaction mixture was filtered and dried under reduced pressure and purified by diethyl ether to afford the desired compound, 7-((4-(1,4-diazepan-1-yl)phenyl)amino)-3-(2,6-dichlorophenyl)-2,3-dihydro-4H-pyrimido[5,4-e][1,3]oxazin-4-one formate (155 mg, 91.17%) as a yellow solid.

LCMS: 485.2 [M+1]⁺

¹H NMR (400 MHz, DMSO-d₆): δ 10.15 (br s, 1H), 8.75 (s, 1H), 8.42 (s, 1H), 7.65 (d, J=7.89 Hz, 2H), 7.31-7.57 (m, 3H), 6.69 (d, J=8.33 Hz, 2H), 5.69 (br s, 2H), 3.39-3.53 (m, 6H), 2.89 (br s, 2H), 2.68 (d, J=5.26 Hz, 2H), 1.83 (br s, 2H).

Example S62. Synthesis of 3-(2,6-dichlorophenyl)-7-(3-(hydroxymethyl)-4-(piperazin-1-yl)phenylamino)-2-methyl-2H-pyrimido[5,4-e][1,3]oxazin-4(3H)-one (Compound No. 1.62)

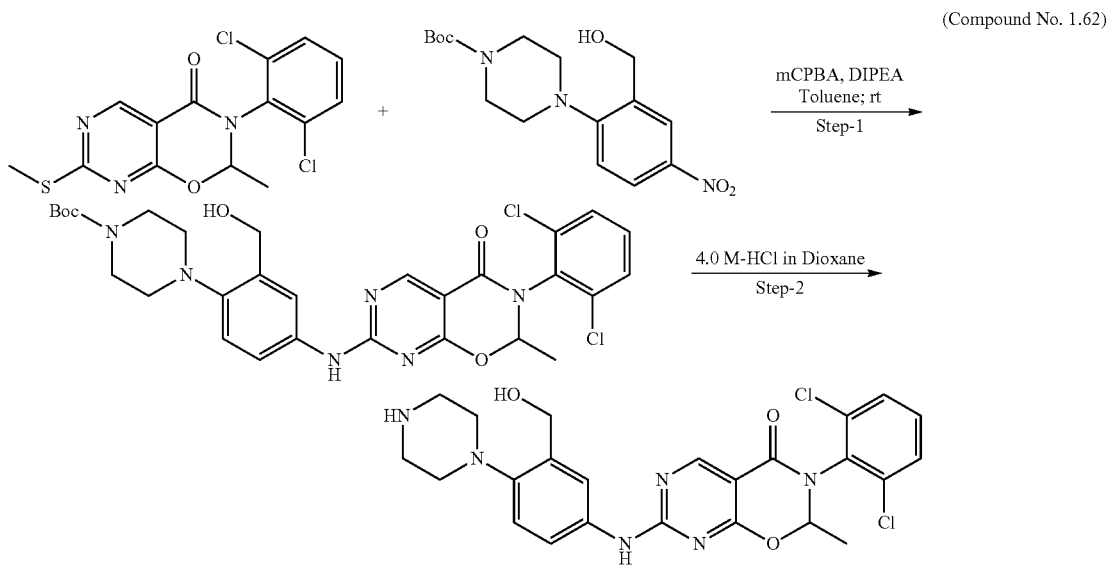

(300 mg, 0.879 mmol, 1.0 eq) in (10.0 mL) of toluene was added m-CPBA (432 mg, 1.753 mmol, 2.0 eq) and allowed to stir at rt for 30 min. Tert-butyl 4-(4-aminophenyl)-1,4-diazepane-1-carboxylate (281 mg, 0.964 mmol, 1.1 eq) and DIPEA (0.611 mL, 3.506 mmol, 4.0 eq) were added and allowed to stir at rt for 12 h. The reaction mixture was diluted with water (50 mL) and extracted with EtOAc (2×50 mL), the combined organic layers were washed with water (50 mL) with brine (50 mL) dried over Na₂SO₄, filtered and concentrated and purified by combi flash (elution 0-35% EtOAc in hexane) to afford the desired compound, tert-butyl 4-(4-((3-(2,6-dichlorophenyl)-4-oxo-3,4-dihydro-2H-pyrimido[5,4-e][1,3]oxazin-7-yl)amino)phenyl)-1,4-diazepane-1-carboxylate (195 mg, 38.16%) as brown solid.

LCMS: 585.3 [M+1]⁺

Step-4: Synthesis of 7-((4-(1,4-diazepan-1-yl)phenyl)amino)-3-(2,6-dichlorophenyl)-2,3-dihydro-4H-pyrimido[5,4-e][1,3]oxazin-4-one Tert-butyl 4-(4-((3-(2,6-dichlorophenyl)-4-oxo-3,4-dihydro-2H-pyrimido[5,4-e][1,3]oxazin-7-yl)amino)phenyl)-1,4-diazepane-1-carboxylate (190 mg, 0.325 mmol, 1.0 eq) was dissolved in 4M HCl in dioxane (2 mL) and allowed to Step-1: Synthesis of tert-butyl 4-(4-((3-(2,6-dichlorophenyl)-2-methyl-4-oxo-3,4-dihydro-2H-pyrimido[5,4-e][1,3]oxazin-7-yl)amino)-2-(hydroxymethyl)phenyl) piperazine-1-carboxylate To a stirred solution of 3-(2,6-dichlorophenyl)-7-(methylthio)-2,3-dihydro-4H-pyrimido[5,4-e][1,3]oxazin-4-one (140 mg, 0.393 mmol, 1.0 eq) in (3.0 mL) of toluene was added m-CPBA (200 mg, 0.786 mmol, 2.0 eq) and allowed to stir at rt for 30 min. Tert-butyl 4-(2-(hydroxymethyl)-4-nitrophenyl)piperazine-1-carboxylate (133 mg, 0.432 mmol, 1.1 eq) and DIPEA (0.275 mL, 1.572 mmol, 4.0 eq) were added and allowed to stir at rt for 12 h. The reaction mixture was diluted with water (50 mL) and extracted with EtOAc (2×50 mL), the combined organic layers were washed with water (50 mL) with brine (50 mL) dried over Na₂SO₄, filtered and concentrated and purified by flash chromatography (elution 0-35% EtOAc in hexane) to afford the desired compound, tert-butyl 4-(4-((3-(2,6-dichlorophenyl)-2-methyl-4-oxo-3,4-dihydro-2H-pyrimido[5,4-e][1,3]oxazin-7-yl)amino)-2-(hydroxymethyl)phenyl) piperazine-1-carboxylate (115 mg, 47.71%) as off white solid.

LCMS: 615.3 [M+1]⁺

Step-2: Synthesis of 3-(2,6-dichlorophenyl)-7-((3-(hydroxymethyl)-4-(piperazin-1-yl)phenyl)amino)-2-methyl-2,3-dihydro-4H-pyrimido[5,4-e][1,3]oxazin-4-one tert-butyl 4-(4-((3-(2,6-dichlorophenyl)-2-methyl-4-oxo-3,4-dihydro-2H-pyrimido[5,4-e][1,3]oxazin-7-yl)amino)-2-(hydroxymethyl)phenyl)piperazine-1-carboxylate (110 mg, 0.178 mmol, 1.0 eq) was dissolved in 4M HCl in dioxane (2 mL) and allowed to stir at rt for 1 h. After completion of reaction, the reaction mixture was filtered and dried under reduced pressure and purified by reversed phase purification to afford the desired compound, 3-(2,6-dichlorophenyl)-7-((3-(hydroxymethyl)-4-(piperazin-1-yl)phenyl)amino)-2-methyl-2,3-dihydro-4H-pyrimido[5,4-e][1,3]oxazin-4-one (formate salt) (39 mg, 42.39%) as brown solid.

LCMS: 515.2 [M+1]$^+$ $^1$H NMR (400 MHz, DMSO-d$_6$): δ 10.29 (br s., 1H), 8.78 (s, 1H), 8.28 (br s, 1H), 7.63-7.75 (m, 2H), 7.58 (d, 1H), 7.52 (t, J=8.11 Hz, 1H), 7.04 (d, J=9.21 Hz, 1H), 6.14 (d, J=5.70 Hz, 1H), 5.03 (br s, 2H), 4.55 (s, 2H), 2.91 (br s, 4H), 2.79 (br s, 4H), 1.38 (d, J=5.70 Hz, 3H).

Example S63. Synthesis of 3-(2,6-dichlorophenyl)-7-(4-(4,4-difluoropiperidin-1-yl)phenylamino)-2H-pyrimido[5,4-e][1,3]oxazin-4(3H)-one (Compound No. 1.63)

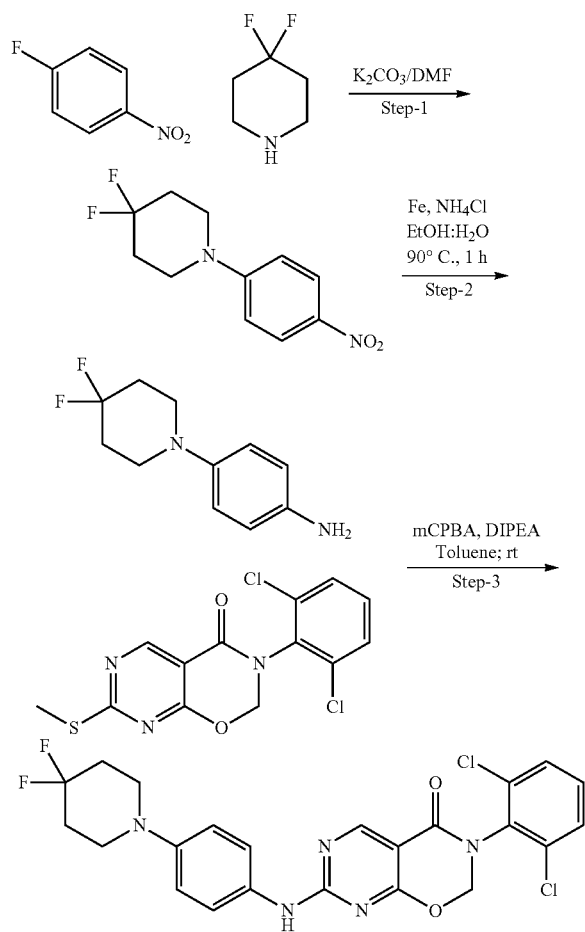

Step-1: Synthesis of 4,4-difluoro-1-(4-nitrophenyl)piperidine

To a stirred solution of 1-fluoro-4-nitrobenzene (0.5 g, 3.54 mmol, 1.0 eq) and 4,4-difluoropiperidine (0.615 g, 3.897 mmol, 1.1 eq) in DMF (10 mL) was added K$_2$CO$_3$ (0.978 g, 7.08 mmol, 2.0 eq) at rt. The resulting mixture was stirred at 90° C. for 12 h. The progress of reaction was monitored by LCMS. The reaction mixture was poured into ice cold water (100 mL), stirred for 5 min, formation of precipitate was observed, which was filtered and dried under vacuum to afford the desired compound, 4,4-difluoro-1-(4-nitrophenyl)piperidine (0.635 g, 74.0%) as a yellow solid.

LCMS: 243.1 [M+1]$^+$

Step-2: Synthesis of 4-(4,4-difluoropiperidin-1-yl)aniline

To a stirred solution of 4,4-difluoro-1-(4-nitrophenyl)piperidine (0.6 g, 2.476 mmol, 1.0 eq) in EtOH (20 mL) was added Fe(0) (1.1 g, 19.815 mmol, 8.0 eq) and a solution of NH$_4$Cl (1.33 g, 24.76 mmol, 10.0 eq) in water (20 mL) at rt. The resulting mixture was heated at 90° C. for 60 min. The progress of reaction was monitored by LCMS. The reaction mixture was filtered through celite the residue was washed with EtOH (50 mL) the filtrate was concentrated and the residue was dissolved in EtOAc (50 mL), washed with water (2×50 mL), dried over Na$_2$SO$_4$, and concentrated to yield 4-(4,4-difluoropiperidin-1-yl)aniline (0.95 g, 95.28%) as brown viscous.

LCMS: 213.2 [M+1]$^+$

Step-3: Synthesis of 3-(2,6-dichlorophenyl)-7-((4-(4,4-difluoropiperidin-1-yl)phenyl)amino)-2,3-dihydro-4H-pyrimido[5,4-e][1,3]oxazin-4-one To a stirred solution of 3-(2,6-dichlorophenyl)-7-(methylthio)-2,3-dihydro-4H-pyrimido[5,4-e][1,3]oxazin-4-one (300 mg, 0.876 mmol, 1.0 eq) in (5.0 mL) of toluene was added mCPBA (432 mg, 1.753 mmol, 2.0 eq) and allowed to stir at rt for 30 min. 4-(4,4-Difluoropiperidin-1-yl)aniline (205 mg, 0.963 mmol, 1.1 eq) and DIPEA (0.611 mL, 3.506 mmol, 4.0 eq) were added and allowed to stir at rt for 12 h. The reaction mixture was diluted with water (50 mL) and extracted with EtOAc (2×50 mL), the combined organic layers were washed with water (50 mL) with brine (50 mL) dried over Na$_2$SO$_4$, filtered and concentrated and purified by flash chromatography (elution 0-35% EtOAc in hexane) to afford the desired compound, 3-(2,6-dichlorophenyl)-7-((4-(4,4-difluoropiperidin-1-yl)phenyl)amino)-2,3-dihydro-4H-pyrimido[5,4-e][1,3]oxazin-4-one (139 mg, 31.30%) as an off white solid.

LCMS: 506.2 [M+1]$^+$ $^1$H NMR (400 MHz, DMSO-d$_6$): δ 10.27 (br s, 1H), 8.79 (s, 1H), 7.65 (d, J=7.89 Hz, 2H), 7.56 (d, J=8.33 Hz, 2H), 7.45-7.54 (m, 1H), 7.00 (d, J=9.21 Hz, 2H), 5.71 (s, 2H), 3.26-3.30 (m, 4H), 1.96-2.14 (m, 4H).

Example S64. Synthesis of 3-(2,6-dichlorophenyl)-7-(isoquinolin-6-ylamino)-2H-pyrimido[5,4-e][1,3]oxazin-4(3H)-one (Compound No. 1.64)

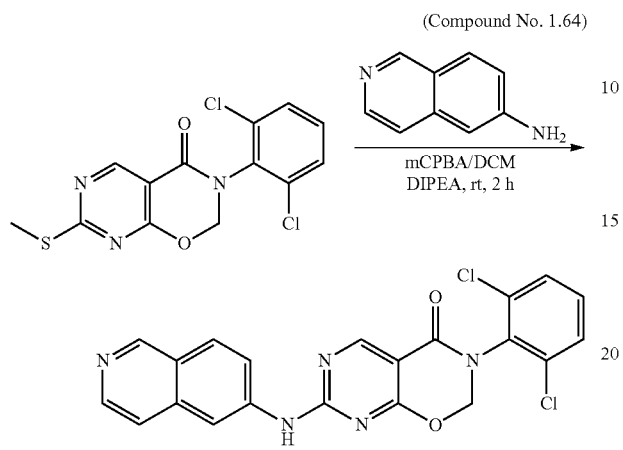

DIPEA (378 mg, 2.93 mmol, 4.0 eq) were added and stirred at rt for 2 h. Progress of reaction was monitored by LCMS. After consumption of starting material, precipitated compound was filtered off, dried and purified by reversed phase chromatography to afford 3-(2,6-dichlorophenyl)-7-(isoquinolin-6-ylamino)-2H-pyrimido[5,4-e][1,3]oxazin-4(3H)-one (6 mg, 1.86%).

LCMS: 438.2 [M+1]$^+$ $^1$H NMR (400 MHz, CD$_3$OD): δ 10.16 (s, 1H), 9.40 (s, 1H), 9.20 (d, J=6.14 Hz, 1H), 8.25 (d, J 9.21 Hz, 1H), 7.75 (d, J=7.45 Hz, 1H), 7.62 (d, J=8.33 Hz, 2H), 7.44-7.55 (m, 1H), 7.34 (d, J=9.21 Hz, 1H), 7.02 (s, 1H), 5.96 (s, 2H).

Example S65. Synthesis of 3-(2,6-dichlorophenyl)-7-(2-(2,2-difluoroethyl)-1,2,3,4-tetrahydroisoquinolin-7-ylamino)-2H-pyrimido[5,4-e][1,3]oxazin-4(3H)-one (Compound No. 1.65)

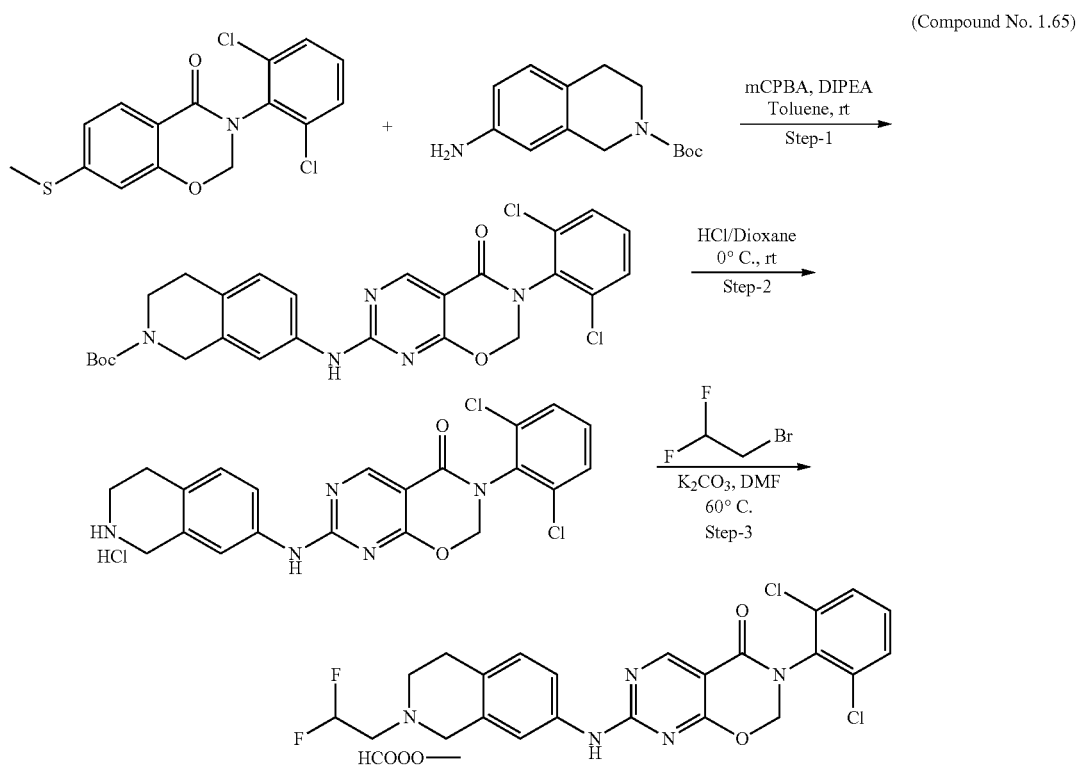

Synthesis of 3-(2,6-dichlorophenyl)-7-(isoquinolin-6-ylamino)-2H-pyrimido[5,4-e][1,3]oxazin-4(3H)-one To a stirred solution of 3-(2,6-dichlorophenyl)-7-(methylthio)-2H-pyrimido[5,4-e][1,3]oxazin-4(3H)-one (250 mg, 0.733 mmol, 1.0 eq) in toluene (10 mL) was added m-CPBA (315 mg, 1.83 mmol, 2.5 eq) and allowed to stir at rt for 30 min. isoquinolin-6-amine (105 mg, 0.733 mmol, 1.0 eq) and

Step-1: Synthesis of tert-butyl 7-((3-(2,6-dichlorophenyl)-4-oxo-3,4-dihydro-2H-pyrimido[5,4-e][1,3]oxazin-7-yl)amino)-3,4-dihydroisoquinoline-2(1H)-carboxylate To a stirred solution of 3-(2,6-dichlorophenyl)-7-(methylthio)-2,3-dihydro-4H-benzo[e][1,3]oxazin-4-one (200 mg, 0.58 mmol, 1.0 eq) in 5 mL toluene m-CPBA (251 mg, 1.48 mmol, 2.5 eq) was added under stirring and resulting mixture was allowed to stir at rt for 30 min. Further, tert-butyl 7-amino-3,4-dihydroisoquinoline-2(1H)-carboxylate (145 mg, 0.58 mmol, 1 eq) and DIPEA (0.4 mL, 2.33 mmol, 4 eq) were added and the reaction was allowed to stir at rt for 12 h. The progress of the reaction was monitored by LCMS. After completion reaction was quenched with water and extracted with ethyl acetate (10 mL×3). The combined organic layers were washed with brine solution (20 mL), dried over anhydrous $Na_2SO_4$ and concentrated under reduced pressure to afford crude product which was purified by flash chromatography (1-10% MeOH:$CH_2Cl_2$) to afford, tert-butyl 7-((3-(2,6-dichlorophenyl)-4-oxo-3,4-dihydro-2H-pyrimido[5,4-e][1,3]oxazin-7-yl)amino)-3,4-dihydroisoquinoline-2(1H)-carboxylate (225 mg, 71%) as white solid.

LCMS: 542 [M+1]$^+$

Step-2: Synthesis of 3-(2,6-dichlorophenyl)-7-((1,2,3,4-tetrahydroisoquinolin-7-yl)amino)-2,3-dihydro-4H-pyrimido[5,4-e][1,3]oxazin-4-one hydrochloride 20% HCl in dioxane (2 mL) was added to a stirred solution of tert-butyl 7-((3-(2,6-dichlorophenyl)-4-oxo-3,4-dihydro-2H-pyrimido[5,4-e][1,3]oxazin-7-yl)amino)-3,4-dihydroisoquinoline-2(1H)-carboxylate (220 mg, 0.40 mmol, 1.0 eq) in 1 mL dioxane maintained at 0° C. and the resulting solution was allowed to stir at rt for 3 h. The progress of reaction was monitored by LCMS. After completion of reaction, solvent was removed under reduced pressure, and the resulting solid was filtered and washed with ether, dried to afford 3-(2,6-dichlorophenyl)-7-((4-(piperidin-4-yl)phenyl)amino)-2,3-dihydro-4H-pyrimido[5,4-e][1,3]oxazin-4-one hydrochloride (160 mg, 82%) as a pale yellow solid.

LCMS: 441 [M+1]$^+$

Step-3: Synthesis of 3-(2,6-dichlorophenyl)-7-((2-(2,2-difluoroethyl)-1,2,3,4-tetrahydroisoquinolin-7-yl)amino)-2,3-dihydro-4H-pyrimido[5,4-e][1,3]oxazin-4-one To a solution of 3-(2,6-dichlorophenyl)-7-((4-(piperidin-4-yl)phenyl)amino)-2,3-dihydro-4H-pyrimido[5,4-e][1,3]oxazin-4-one hydrochloride (100 mg, 0.21 mmol, 1.0 eq) in 2 mL dry DMF at $K_2CO_3$ (86.6 mg, 0.63 mmol, 3 eq) was added under stirring under inert atmosphere. Further, 2-bromo-1,1-difluoroethane (61 mg, 0.42 mmol, 1.0 eq) was added and the resulting solution was heated at 80° C. 12 h. The progress of the reaction was monitored by LCMS. After completion, the reaction was cooled to rt and quenched with ice cold water followed by extraction using ethyl acetate (5 mL×3). The combined organic layer was washed with brine, dried over anhydrous $Na_2SO_4$ and concentrated under reduced pressure. The residue was purified by flash chromatography to afford 3-(2,6-dichlorophenyl)-7-((2-(2,2-difluoroethyl)-1,2,3,4-tetrahydroisoquinolin-7-yl)amino)-2,3-dihydro-4H-pyrimido[5,4-e][1,3]oxazin-4-one (14 mg, 13%) as white solid formate salt.

LCMS: 505 [M+1]$^+$ $^1$H NMR (400 MHz, DMSO-d$_6$): δ 10.36 (br s, 1H), 8.83 (s, 1H), 8.41 (br., 1H), 7.66 (d, J=7.89 Hz, 2H), 7.35-7.55 (m, 3H), 7.08 (d, J=8.33 Hz, 2H), 6.18-6.30 (m, 1H), 5.73 (s, 2H), 3.71 (s, 2H), 2.87-2.97 (m, 2H), 2.79 (dd, J=4.82, 13.59 Hz, 4H).

Example S66. Synthesis of 3-(2,6-dichlorophenyl)-7-((4-(3-(hydroxymethyl)piperazin-1-yl)phenyl)amino)-2,3-dihydro-4H-pyrimido[5,4-e][1,3]oxazin-4-one (Compound No. 1.96)

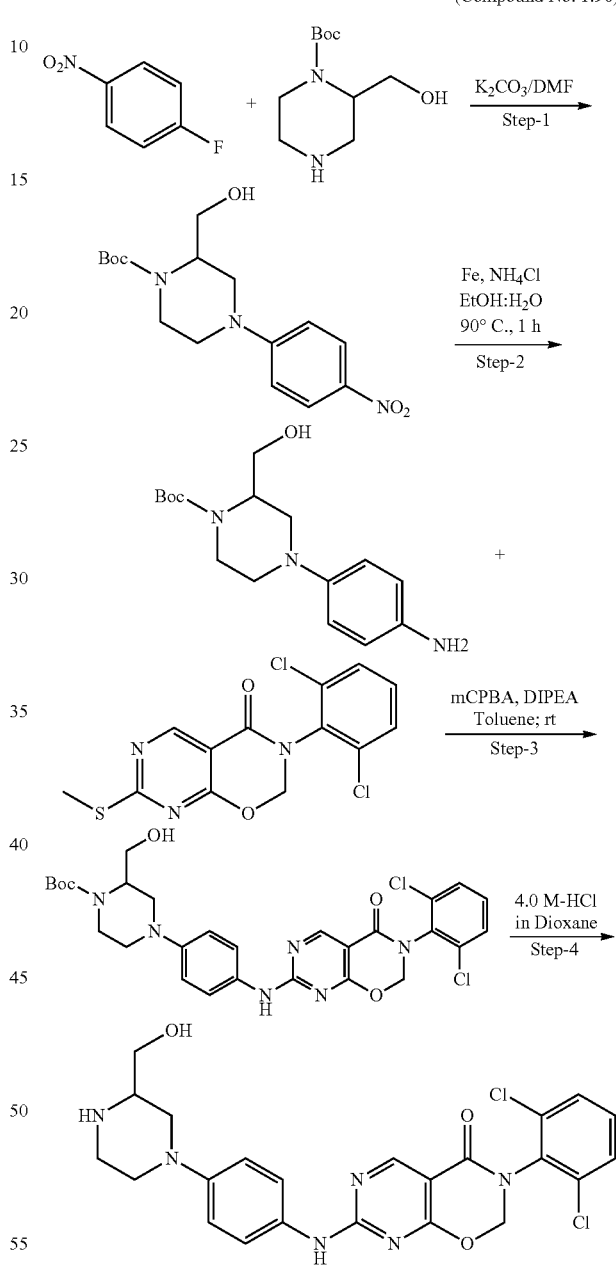

Step-1: tert-butyl 2-(hydroxymethyl)-4-(4-nitrophenyl)piperazine-1-carboxylate

To a stirred solution of 1-fluoro-4-nitrobenzene (1.0 g, 4.623 mmol, 1.0 eq) and tert-butyl 2-(hydroxymethyl)piperazine-1-carboxylate (0.717 g, 5.085 mmol, 1.1 eq) in DMF (20 mL) was added $K_2CO_3$ (1.27 g, 9.247 mmol, 2.0 eq) at rt. The resulting mixture was stirred at 90° C. for overnight. The progress of reaction was monitored by LCMS. The reaction mixture was poured into ice cold water (100 mL), stirred for 5 min, formation of precipitates was observed, which was filtered and dried under vacuum to afford the desired compound, tert-butyl 2-(hydroxymethyl)-4-(4-nitrophenyl)piperazine-1-carboxylate (600 mg, 32%) as yellow solid.
LCMS: 338 [M+1]+

Step-2: Synthesis of tert-butyl 4-(4-aminophenyl)-2-(hydroxymethyl)piperazine-1-carboxylate To a stirred solution of tert-butyl 4-(4-aminophenyl)-2-(hydroxymethyl)piperazine-1-carboxylate (0.5 g, 1.482 mmol, 1.0 eq) in EtOH (6 mL) was added Fe powder (0.248 g, 4.446 mmol, 3 eq) and a solution of NH$_4$Cl (0.158 g, 2.964 mmol, 2 eq) in water (6 ml) at rt. The resulting mixture was heated at 90° C. for 1 h. The progress of reaction was monitored by LCMS. The reaction mixture was filtered through celite the residue was washed with EtOH (30 mL). The filtrate was concentrated and the residue was dissolved in EtOAc (30 mL), washed with water (2×30 mL), dried over Na$_2$SO$_4$, and concentrated to afford the desired compound, tert-butyl 4-(4-aminophenyl)-2-(hydroxymethyl)piperazine-1-carboxylate (0.5 g, 96%).
LCMS: 308 [M+1]+

Step-3: Synthesis of tert-butyl 4-(4-((3-(2,6-dichlorophenyl)-4-oxo-3,4-dihydro-2H-pyrimido[5,4-e][1,3]oxazin-7-yl)amino)phenyl)-2-(hydroxymethyl)piperazine-1-carboxylate To a stirred solution of 3-(2,6-dichlorophenyl)-7-(methylthio)-2,3-dihydro-4H-pyrimido[5,4-e][1,3]oxazin-4-one (0.5 g 1.461 mmol, 1.0 eq) in (10.0 mL) of toluene was added m-CPBA (0.502 g, 2.922 mmol, 2 eq) and allowed to stir at rt for 30 min, followed by addition of tert-butyl 4-(4-aminophenyl)-2-(hydroxymethyl)piperazine-1-carboxylate (0.494 g, 1.607 mmol, 1.1 eq) and DIPEA (0.753 g 5.844 mmol, 4.0 eq) and allowed to stir at rt for overnight.

The reaction mixture was diluted with water (50 mL) and extracted with EtOAc (2×50 mL). The combined organic layers were washed with water (50 mL), brine (50 mL), dried over Na$_2$SO$_4$, concentrated and purified by combi flash [silica gel-100-200 mesh; elution 0-35% EtOAc in hexane] to afford the desired compound, tert-butyl 4-(4-((3-(2,6-dichlorophenyl)-4-oxo-3,4-dihydro-2H-pyrimido[5,4-e][1,3]oxazin-7-yl)amino)phenyl)-2-(hydroxymethyl)piperazine-1-carboxylate (0.230 g, 26%) as solid.
LCMS: 601 [M+1]+

Step-4: Synthesis of 3-(2,6-dichlorophenyl)-7-((4-(3-(hydroxymethyl)piperazin-1-yl)phenyl)amino)-2,3-dihydro-4H-pyrimido[5,4-e][1,3]oxazin-4-one tert-butyl 4-(4-((3-(2,6-dichlorophenyl)-4-oxo-3,4-dihydro-2H-pyrimido[5,4-e][1,3]oxazin-7-yl)amino)phenyl)-2-(hydroxymethyl)piperazine-1-carboxylate (0.230 mg, 0.3823 mmol, 1.0 eq) was dissolved in 4.0M-HCl in dioxane (2 mL) and allowed to stir at rt for 1 h. After completion of reaction, the reaction mixture was filtered and dried under reduced pressure and purified by diethyl ether to afford the desired compound, 3-(2,6-dichlorophenyl)-7-((4-(3-(hydroxymethyl)piperazin-1-yl)phenyl)amino)-2,3-dihydro-4H-pyrimido[5,4-e][1,3]oxazin-4-one (36 mg, 79%) as white solid.
LCMS [M+1]+: −501
UPLC @ 254 nm=95.36% and @ 220 nm=97.11%.
$^1$H NMR (400 MHz, DMSO-d$_6$): δ 10.26 (br s, 1H), 8.79 (s, 1H), 7.65 (d, J=8.33 Hz, 2H), 7.43-7.58 (m, 3H), 6.92 (d, J=8.77 Hz, 2H), 5.71 (s, 2H), 4.76 (brs, 1H), 3.55 (d, J=10.96 Hz, 1H), 3.48 (d, J=10.96 Hz, 1H), 3.40 (br s, 2H), 3.03 (d, J=12.28 Hz, 1H), 2.83 (br s, 2H), 2.56-2.72 (m, 2H), 2.23-2.36 (m, 2H).

Example S67. Synthesis of (R)-3-(2,6-dichlorophenyl)-7-((4-(3-methylpiperazin-1-yl)phenyl)amino)-2,3-dihydro-4H-pyrimido[5,4-e][1,3]oxazin-4-one (Compound No. 1.173)

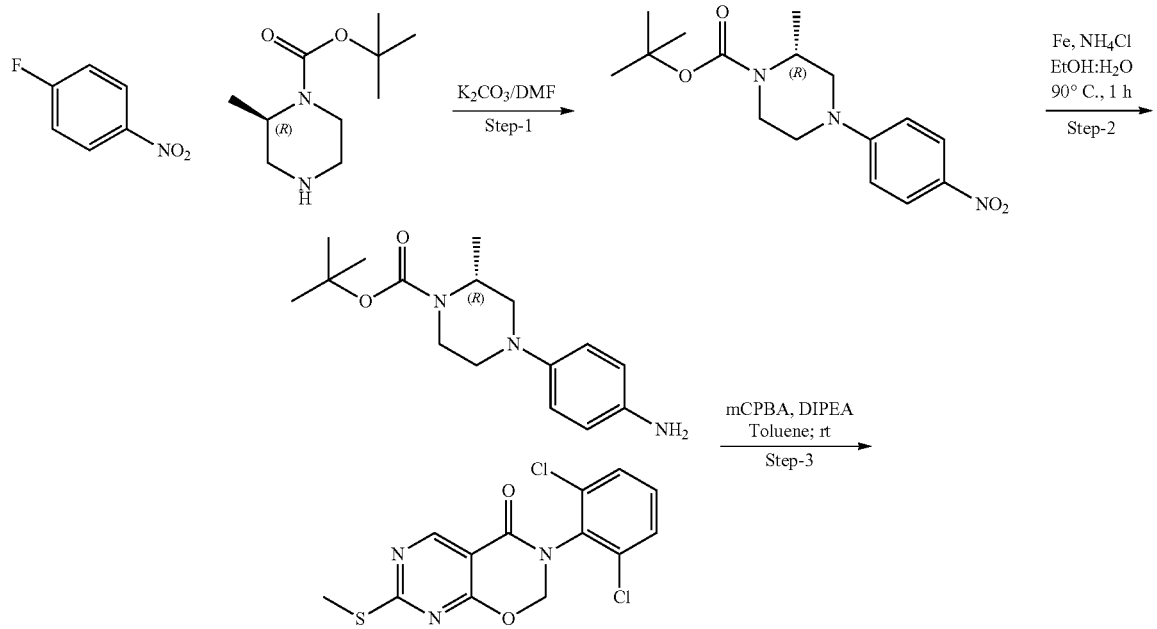

-continued

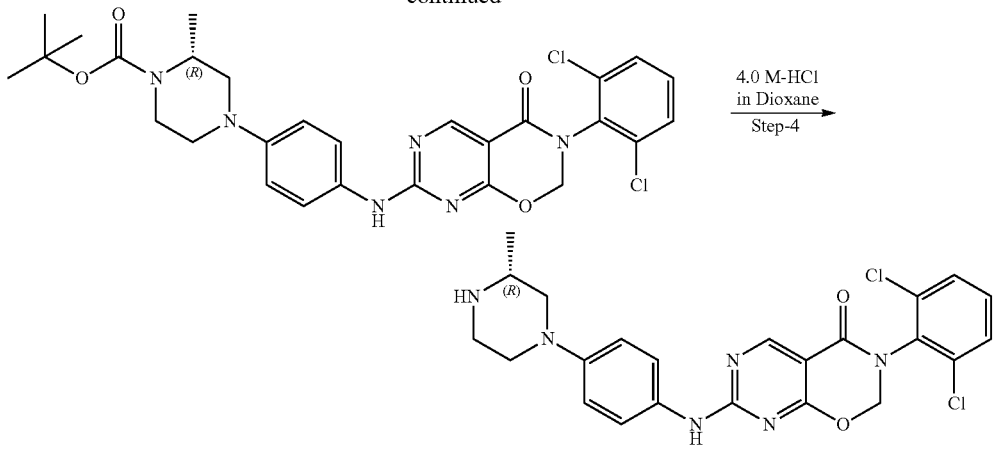

Step-1: Synthesis of tert-butyl 2-methyl-4-(4-nitrophenyl)piperazine-1-carboxylate To a stirred solution of 1-fluoro-4-nitrobenzene (1.0 g, 7.087 mmol, 1.0 eq) and tert-butyl 2-methylpiperazine-1-carboxylate (1.56 g, 7.795 mmol, 1.1 eq) in DMF (20 mL) was added $K_2CO_3$ (1.96 g, 14.174 mmol, 2.0 eq) at rt. The resulting mixture was stirred at 90° C. for overnight. The progress of reaction was monitored by LCMS. The reaction mixture was poured into ice cold water (50 mL), extracted with EtOAc (2×50 mL) the combined organic layers were washed with water (50 mL) with brine (50 mL) dried over $Na_2SO_4$, filtered and concentrated and purified by combi flash [silica gel 100-200 mesh; elution 0-5% EtOAc in hexane] to afford the desired compound, tert-butyl 2-methyl-4-(4-nitrophenyl)piperazine-1-carboxylate (1.4 g, 62%) as yellow solid.

LCMS: 322.3 [M+1]$^+$

Step-2: Synthesis of tert-butyl 4-(4-aminophenyl)-2-methylpiperazine-1-carboxylate To a stirred solution of tert-butyl 2-methyl-4-(4-nitrophenyl)piperazine-1-carboxylate (1.10 g, 3.422 mmol, 1.0 eq) in EtOH (25 mL) was added Fe (1.53 g, 27.381 mmol, 8.0 eq) and a solution of $NH_4Cl$ (1.83 g, 34.22 mmol, 10.0 eq) in water (25 mL) at rt. The resulting mixture was heated at 90° C. for 60 min. The progress of reaction was monitored by LCMS. The reaction mixture was filtered through celite the residue was washed with EtOH (50 mL) the filtrate was concentrated and the residue was dissolved in EtOAc (50 mL), washed with water (2×50 mL), dried over $Na_2SO_4$, and concentrated to afford the desired compound, tert-butyl 4-(4-aminophenyl)-2-methylpiperazine-1-carboxylate (0.95 g, 95%) as brown viscous oil.

LCMS: 291.3 [M+1]$^+$

Step-3: Synthesis of tert-butyl 4-(4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate To a stirred solution of 3-(2,6-dichlorophenyl)-7-(methylthio)-2,3-dihydro-4H-pyrimido[5,4-e][1,3]oxazin-4-one (500 mg, 1.461 mmol, 1.0 eq) in (20.0 mL) of toluene was added m-CPBA (720 mg, 2.922 mmol, 2.0 eq) and allowed to stir at rt for 30 min. tert-Butyl 4-(4-aminophenyl)-2-methylpiperazine-1-carboxylate (468 mg, 1.607 mmol, 1.1 eq) and DIPEA (1.02 mL, 5.844 mmol, 4.0 eq) were added and allowed to stir at rt for overnight. The reaction mixture was diluted with water (50 mL) and extracted with EtOAc (2×50 mL), the combined organic layers were washed with water (50 mL) with brine (50 mL) dried over $Na_2SO_4$, filtered and concentrated and purified by combi flash [silica gel 100-200 mesh; elution 0-35% EtOAc in hexane] to afford the desired compound, tert-butyl 4-(4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate (0.413 g, 48%) as grey solid.

LCMS: 585.3 [M+1]$^+$

Step-4: Synthesis of 3-(2,6-dichlorophenyl)-7-((4-(3-methylpiperazin-1-yl)phenyl)amino)-2,3-dihydro-4H-pyrimido[5,4-e][1,3]oxazin-4-one tert-butyl 4-(4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate (400 mg, 0.683 mmol, 1.0 eq) was dissolved in 4.0 M-HCl in dioxane (5 mL) and allowed to stir at rt for 1 h. After completion of reaction, the reaction mixture was filtered and dried under reduced pressure and purified by diethyl ether to afford the desired compound, 3-(2,6-dichlorophenyl)-7-((4-(3-methylpiperazin-1-yl)phenyl)amino)-2,3-dihydro-4H-pyrimido[5,4-e][1,3]oxazin-4-one hydrochloride (160 mg, 48%) as yellow solid.

LCMS [M+1]$^+$: 485.2

UPLC @ 254 nm=97.98% and @ 220 nm=98.24%.

$^1$H NMR (400 MHz, DMSO-d$_6$): δ 10.24 (brs, 1H), 8.78 (s, 1H), 7.59-7.71 (m, J=8.33 Hz, 2H), 7.42-7.58 (m, 3H), 6.80-6.98 (m, J=8.77 Hz, 2H), 5.71 (s, 2H), 3.47 (t, J=9.87 Hz, 2H), 2.96 (d, J=11.84 Hz, 1H), 2.73-2.86 (m, 2H), 2.26 (brs, 1H), 2.17 (t, J=10.74 Hz, 1H), 1.03 (d, J=6.58 Hz, 3H).

Example S68. Synthesis of (R)-3-(2,6-dichlorophenyl)-7-((3-fluoro-4-(3-methylpiperazin-1-yl)phenyl)amino)-2,3-dihydro-4H-pyrimido[5,4-e][1,3]oxazin-4-one (Compound No. 1.174)

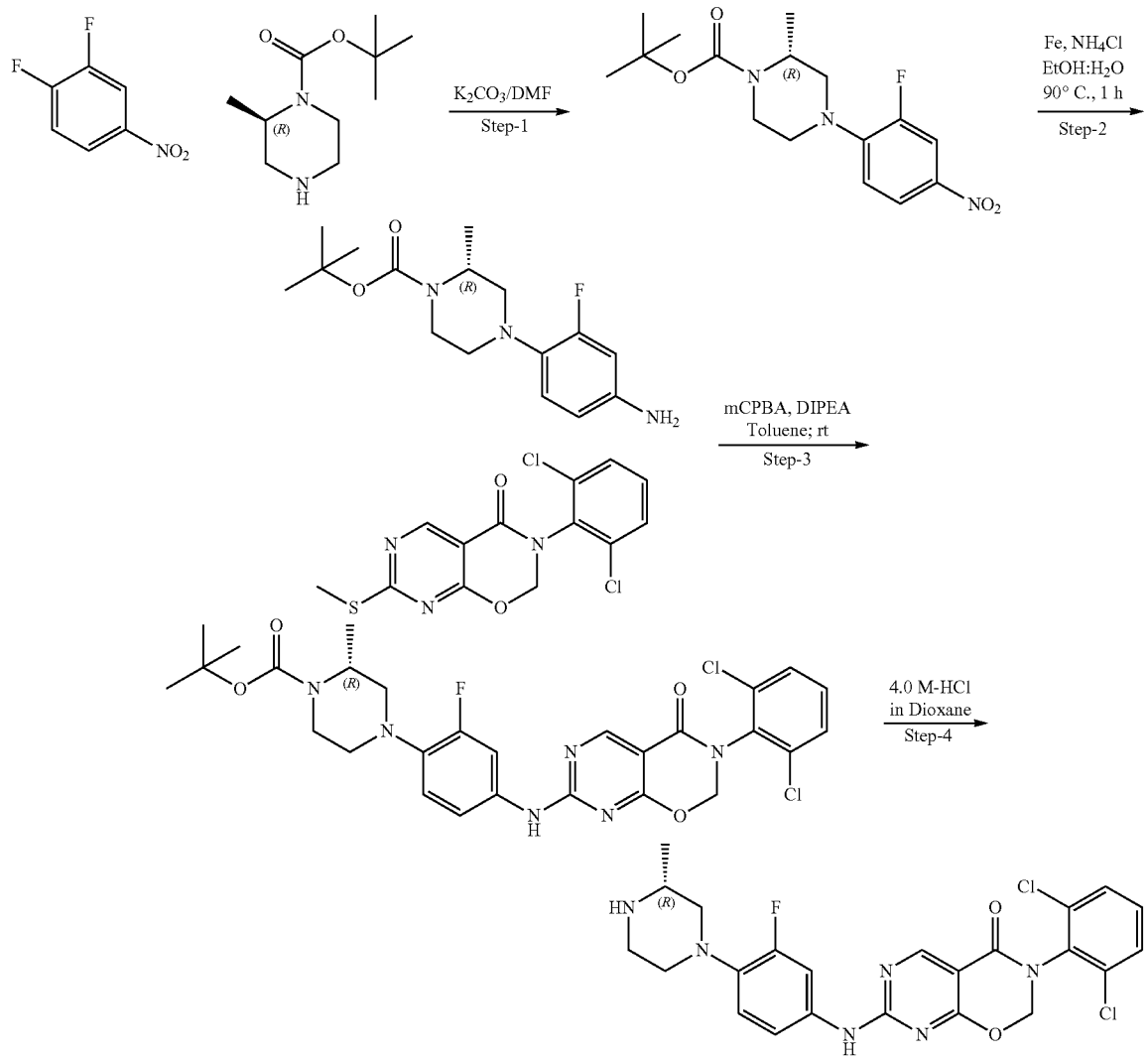

Step-1: Synthesis of tert-butyl 4-(2-fluoro-4-nitrophenyl)-2-methylpiperazine-1-carboxylate To a stirred solution of 1,2-difluoro-4-nitrobenzene (1.0 g, 6.285 mmol, 1.0 eq) and tert-butyl 2-methylpiperazine-1-carboxylate (1.38 g, 6.914 mmol, 1.1 eq) in DMF (20 mL) was added $K_2CO_3$ (3.47 g, 25.14 mmol, 4.0 eq) at rt. The resulting mixture was stirred at 90° C. for overnight. The progress of reaction was monitored by LCMS. The reaction mixture was poured into ice cold water (100 mL), stirred for 5 min, formation of precipitates was observed, which was filtered and dried under vacuum to afford the desired compound, tert-butyl 4-(2-fluoro-4-nitrophenyl)-2-methylpiperazine-1-carboxylate (1.92 g, 89%) as yellow solid.

LCMS: 340.1 [M+1]$^+$

Step-2: Synthesis of tert-butyl 4-(4-amino-2-fluorophenyl)-2-methylpiperazine-1-carboxylate To a stirred solution of tert-butyl 4-(2-fluoro-4-nitrophenyl)-2-methylpiperazine-1-carboxylate (1.0 g, 2.946 mmol, 1.0 eq) in EtOH (20 mL) was added Fe (1.32 g, 23.573 mmol, 8.0 eq) and a solution of $NH_4Cl$ (1.56 g, 29.46 mmol, 10.0 eq) in water (20 mL) at rt. The resulting mixture was heated at 90° C. for 60 min. The progress of reaction was monitored by LCMS. The reaction mixture was filtered through celite the residue was washed with EtOH (50 mL) the filtrate was concentrated and the residue was dissolved in EtOAc (50 mL), washed with water (2×50 mL), dried over $Na_2SO_4$, and concentrated to afford the desired compound, tert-butyl 4-(4-amino-2-fluorophenyl)-2-methylpiperazine-1-carboxylate (0.81 g, 89%) as brown viscous.

LCMS: 310.4 [M+1]$^+$

Step-3: Synthesis of tert-butyl 4-(4-((3-(2,6-dichlorophenyl)-4-oxo-3,4-dihydro-2H-pyrimido[5,4-e][1,3]oxazin-7-yl)amino)-2-fluorophenyl)-2-methylpiperazine-1-carboxylate To a stirred solution of 3-(2,6-dichlorophenyl)-7-(methylthio)-2,3-dihydro-4H-pyrimido[5,4-e][1,3]oxazin-4-one (350 mg, 1.461 mmol, 1.0 eq) in (10.0 mL) of toluene was added m-CPBA (720 mg, 2.922 mmol, 2.0 eq) and allowed to stir at rt for 30 min. tert-Butyl 4-(4-amino-2-fluorophenyl)-2-methylpiperazine-1-carboxylate (497 mg, 1.607 mmol, 1.1 eq) and DIPEA (1.02 mL, 5.844 mmol, 4.0 eq) were added and allowed to stir at rt for overnight. The reaction mixture was diluted with water (50 mL) and extracted with EtOAc (2×50 mL), the combined organic layers were washed with water (50 mL) with brine (50 mL) dried over Na$_2$SO$_4$, filtered and concentrated and purified by combi flash [silica gel 100-200 mesh; elution 0-35% EtOAc in hexane] to afford the desired compound, tert-butyl 4-(4-((3-(2,6-dichlorophenyl)-4-oxo-3,4-dihydro-2H-pyrimido[5,4-e][1,3]oxazin-7-yl)amino)-2-fluorophenyl)-2-methylpiperazine-1-carboxylate (360 mg, 41%) as dark brown solid.

LCMS: 603.3 [M+1]$^+$

Step-4: Synthesis of 3-(2,6-dichlorophenyl)-7-((3-fluoro-4-(3-methylpiperazin-1-yl)phenyl)amino)-2,3-dihydro-4H-pyrimido[5,4-e][1,3]oxazin-4-one tert-butyl 4-(4-((3-(2,6-dichlorophenyl)-4-oxo-3,4-dihydro-2H-pyrimido[5,4-e][1,3]oxazin-7-yl)amino)-2-fluorophenyl)-2-methylpiperazine-1-carboxylate (350 mg, 0.579 mmol, 1.0 eq) was dissolved in 4.0 M-HCl in dioxane (3 mL) and allowed to stir at rt for 1 h. After completion of reaction, the reaction mixture was filtered and dried under reduced pressure and purified by diethyl ether to afford the desired compound, 3-(2,6-dichlorophenyl)-7-((3-fluoro-4-(3-methylpiperazin-1-yl)phenyl)amino)-2,3-dihydro-4H-pyrimido[5,4-e][1,3]oxazin-4-one hydrochloride (45 mg, 15%) as light yellow solid.

LCMS [M+1]$^+$: –504.2
UPLC @ 254 nm=97.62% and @ 220 nm=98.34%
$^1$H NMR (400 MHz, DMSO-d$_6$): δ 10.46 (brs, 1H), 8.85 (s, 1H), 7.61-7.75 (m, 2H), 7.46-7.56 (m, 1H), 7.40 (d, J=7.02 Hz, 1H), 7.03 (t, J=9.21 Hz, 1H), 5.74 (s, 2H), 3.20 (d, J=11.40 Hz, 2H), 2.99-3.08 (m, 1H), 2.95 (d, J=9.21 Hz, 2H), 2.59-2.73 (m, 2H), 2.23-2.40 (m, 2H), 1.06 (d, J=6.58 Hz, 3H).

Example S69. Synthesis of 7-(1H-indol-5-ylamino)-3-(2,6-dichlorophenyl)-2H-pyrimido[5,4-e][1,3]oxazin-4(3H)-one (Compound No. 1.175)

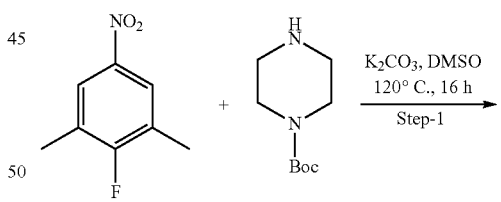

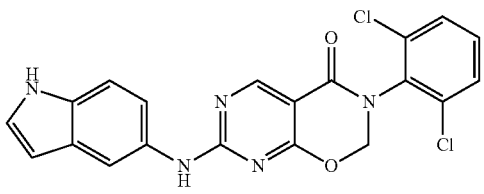

Synthesis of 7-(1H-indol-5-ylamino)-3-(2,6-dichlorophenyl)-2H-pyrimido[5,4-e][1,3]oxazin-4(3H)-one To a stirred solution of 3-(2,6-dichlorophenyl)-7-(methylthio)-2H-pyrimido[5,4-e][1,3]oxazin-4(3H)-one (250 mg, 0.733 mmol, 1.0 eq) in 10 mL of toluene was added m-CPBA (315 mg, 1.83 mmol, 2.5 eq) and allowed to stir at rt for 30 min. 1H-indol-5-amine (95 mg, 0.733 mmol, 1.0 eq) and DIPEA (378 mg, 2.93 mmol, 4.0 eq) were added and stirred at rt for 2 h. Progress of reaction was monitored by LCMS. After consumption of starting material, precipitated compound was filtered off, dried and purified by reverse phase chromatography to afford (40 mg, 13%) of 7-(1H-indol-5-ylamino)-3-(2,6-dichlorophenyl)-2H-pyrimido[5,4-e][1,3]oxazin-4(3H)-one.

LCMS: 426 [M+1]$^+$
$^1$H NMR (400 MHz, DMSO-d$_6$): δ 11.07 (br s, 1H), 8.80 (s, 1H), 7.93 (br s, 1H), 7.65 (d, J=7.89 Hz, 2H), 7.50 (t, J=8.11 Hz, 1H), 7.27-7.39 (m, 3H), 6.42 (brs, 1H), 5.71 (s, 2H).

Example S70. Synthesis of 3-(2,6-dichlorophenyl)-7-((3,5-dimethyl-4-(piperazin-1-yl)phenyl)amino)-2,3-dihydro-4H-pyrimido[5,4-e][1,3]oxazin-4-one hydrochloride (Compound No. 1.176)

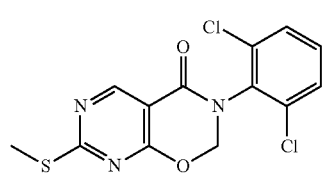 + 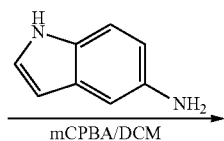 $\xrightarrow[\text{Step-1}]{\text{K}_2\text{CO}_3, \text{DMSO} \\ 120° \text{C., 16 h}}$

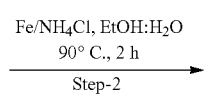 $\xrightarrow[\text{Step-2}]{\text{Fe/NH}_4\text{Cl, EtOH:H}_2\text{O} \\ 90° \text{C., 2 h}}$

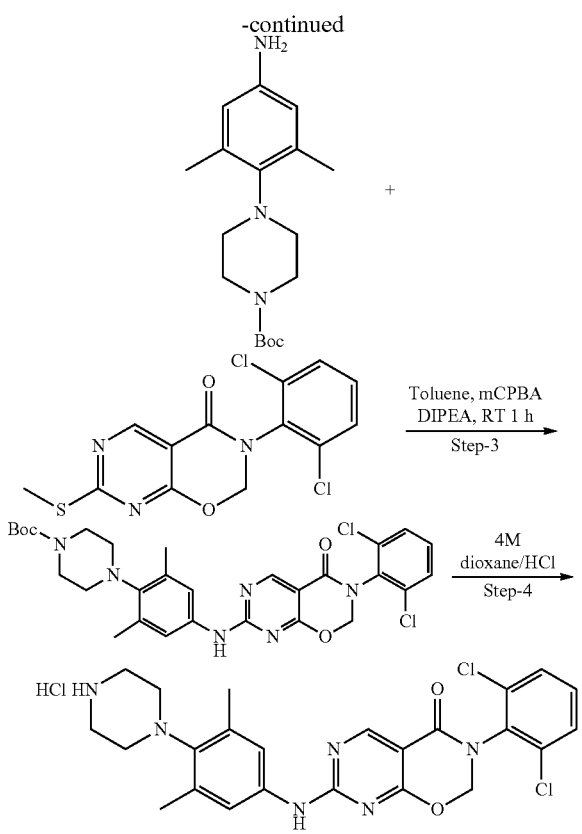

Step-1: Synthesis of tert-butyl 4-(2,6-dimethyl-4-nitrophenyl)piperazine-1-carboxylate To a stirred solution of 2-fluoro-1,3-dimethyl-5-nitrobenzene (1.43 g, 8.45 mmol, 1 eq) and tert-butyl piperazine-1-carboxylate (1.73 mL, 9.29 mmol, 1.1 eq) in DMSO (20 mL) was added $K_2CO_3$ (3.5 g, 25.36 mmol, 3.0 eq). Reaction mixture was stirred at 150° C. for 16 h. Progress of reaction was monitored by LCMS. After consumption of starting material, ice cold water poured to the reaction mixture. The formation of precipitates was observed which was filtered to afford the desired compound, tert-butyl 4-(2,6-dimethyl-4-nitrophenyl)piperazine-1-carboxylate (370 mg, 13%) as yellow solid.

LCMS: 336.2 [M+1]$^+$

Step-2: Synthesis of (5-amino-2-(4-(tert-butoxycarbonyl)piperazin-1-yl)-3-methylphenyl)methylium To a stirred solution of tert-butyl 4-(2,6-dimethyl-4-nitrophenyl)piperazine-1-carboxylate (365 mg, 1.08 mmol, 1 eq) in EtOH and water (1:1, 10 mL) was added Fe (182.3 mg, 3.26 mmol, 2 eq) and $NH_4Cl$ (116.4 mg, 2.17 mmol, 2 eq). The reaction mixture was stirred at 90° C. for 2 h. Progress of reaction was monitored by LCMS. After consumption of starting material, the reaction mixture was filtered through celite bed. The reaction mixture was concentrated, diluted with water, basified with $NaHCO_3$ solution and was extracted with EtOAc. The organic layers were dried over $Na_2SO_4$, concentrated and purified by column chromatography (Combiflash, elution: 0-2% MeOH in $CH_2Cl_2$) to afford the desired product, (5-amino-2-(4-(tert-butoxycarbonyl)piperazin-1-yl)-3-methylphenyl)methylium (180 mg, 54%) as an off white solid.

LCMS: 305.4 [M+1]$^+$

Step-3: Synthesis of tert-butyl 4-(4-((3-(2,6-dichlorophenyl)-4-oxo-3,4-dihydro-2H-pyrimido[5,4-e][1,3]oxazin-7-yl)amino)-2,6-dimethylphenyl)piperazine-1-carboxylate To a stirred solution of (5-amino-2-(4-(tert-butoxycarbonyl)piperazin-1-yl)-3-methylphenyl)methylium (168 mg, 0.491 mmol, 1.0 eq) in toluene (5 mL) was added m-CPBA (212 mg, 1.22 mmol, 2.5 eq) and allowed to stir at rt for 30 min. tert-Butyl (2R,5S)-4-(4-aminophenyl)-2,5-dimethylpiperazine-1-carboxylate (180 mg, 0.589 mmol, 1.2 eq) and DIPEA (0.33 mL, 1.96 mmol, 4.0 eq) were added and stirred at rt for 10 h. The formation of precipitates was observed which was filtered to afford the desired compound, tert-butyl 4-(4-((3-(2,6-dichlorophenyl)-4-oxo-3,4-dihydro-2H-pyrimido[5,4-e][1,3]oxazin-7-yl)amino)-2,6-dimethylphenyl)piperazine-1-carboxylate (100 mg, 30%) as an off white solid.

LCMS: 599.2 [M+1]$^+$

Step-4: Synthesis of 3-(2,6-dichlorophenyl)-7-((3,5-dimethyl-4-(piperazin-1-yl)phenyl)amino)-2,3-dihydro-4H-pyrimido[5,4-e][1,3]oxazin-4-one hydrochloride tert-Butyl 4-(4-((3-(2,6-dichlorophenyl)-4-oxo-3,4-dihydro-2H-pyrimido[5,4-e][1,3]oxazin-7-yl)amino)-2,6-dimethylphenyl)piperazine-1-carboxylate (100 mg, 0.136 mmol, 1.0 eq) was dissolved in dioxane (1 mL) and added 4M dioxane-HCl (2 mL) and allowed to stir at rt for 1 h. After completion of reaction, the reaction mixture was filtered and dried under reduced pressure to afford the desired compound, 3-(2,6-dichlorophenyl)-7-((3,5-dimethyl-4-(piperazin-1-yl)phenyl)amino)-2,3-dihydro-4H-pyrimido[5,4-e][1,3]oxazin-4-one hydrochloride (40 mg, 74%) as an off white solid.

LCMS: 499.3 [M+1]$^+$
UPLC: @ 254 nm=86.75% and @ 220 nm=89.17%
$^1$H NMR (400 MHz, DMSO-$d_6$, HCl salt): δ 10.32 (br s, 1H), 8.88-8.82 (m, 2H), 7.70 (d, J=8.33 Hz, 2H), 7.56-7.52 (m, 1H), 7.40 (br s, 2H), 5.77 (br s, 2H), 3.23-3.20 (m, 8H), 2.32 (s, 6H).

Example S71. Synthesis of 7-(1H-indazol-5-ylamino)-3-(2,6-dichlorophenyl)-2H-pyrimido[5,4-e][1,3]oxazin-4(3H)-one (Compound No.1.87)

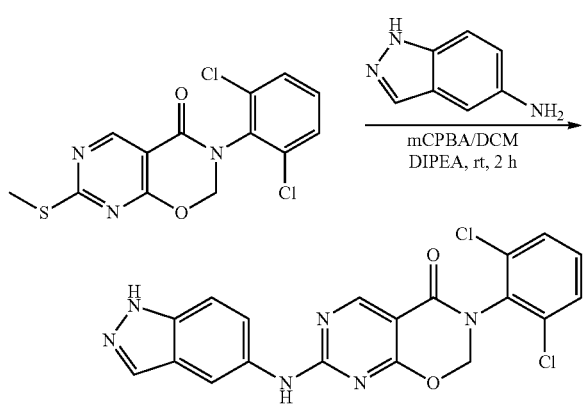

To a stirred solution of 3-(2,6-dichlorophenyl)-7-(methylthio)-2H-pyrimido[5,4-e][1,3]oxazin-4(3H)-one (250 mg, 0.733 mmol, 1.0 eq) in 10 mL of toluene was added m-CPBA (315 mg, 1.83 mmol, 2.5 eq) and allowed to stir at rt for 30 min. 1H-indazol-5-amine (98 mg, 0.733 mmol, 1.0 eq) and DIPEA (378 mg, 2.93 mmol, 4.0 eq) were added and stirred at rt for 2 h. Progress of reaction was monitored by LCMS. After consumption of starting material, precipitated compound was filtered off, dried and purified by reverse phase chromatography to afford (2 mg, 0.64%) of 7-(1H-indol-5-ylamino)-3-(2,6-dichlorophenyl)-2H-pyrimido[5,4-e][1,3]oxazin-4(3H)-one.

LCMS: 427 [M+1]$^+$ $^1$H NMR (400 MHz, DMSO-d$_6$): δ 13.02 (brs, 1H), 8.84 (s, 1H), 8.07 (s, 1H), 7.66 (d, J=8.33 Hz, 3H), 7.48-7.59 (m, 4H), 5.73 (s, 2H).

Example S72. Synthesis of 3-(2,6-dichlorophenyl)-7-(methyl(4-(piperazin-1-yl)phenyl)amino)-2,3-dihydro-4H-pyrimido[5,4-e][1,3]oxazin-4-one Hydrochloride

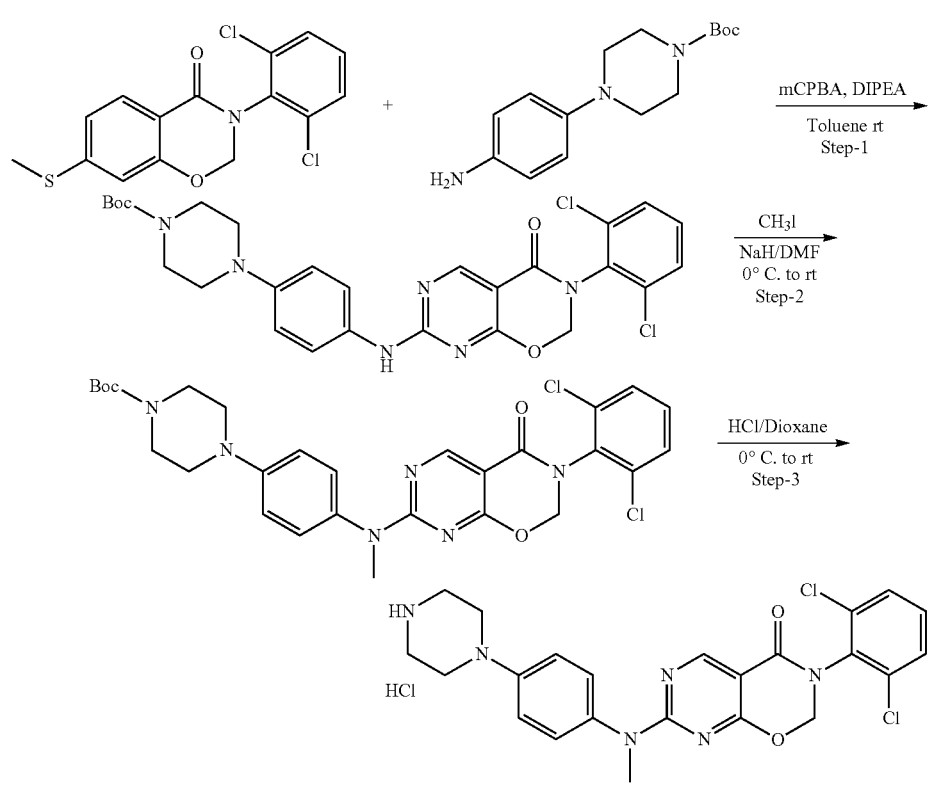

(Compound No.1.104)

Step-1: Synthesis of tert-butyl 4-(4-((3-(2,6-dichlorophenyl)-4-oxo-3,4-dihydro-2H-pyrimido[5,4-e][1,3]oxazin-7-yl)amino)phenyl)piperazine-1-carboxylate To a stirred solution of 3-(2,6-dichlorophenyl)-7-(methylthio)-2,3-dihydro-4H-benzo[e][1,3]oxazin-4-one (300 mg, 0.87 mmol, 1.0 eq) in toluene (4 mL); m-CPBA (376.9 mg, 2.19 mmol, 2.5 eq) was added under stirring and resulting mixture was allowed to stir at rt for 30 minutes. Tert-butyl 4-(4-aminophenyl)piperazine-1-carboxylate (243.1 mg, 0.87 mmol, 1 eq) and DIPEA (0.61 mL, 3.5 mmol, 4 eq) were then added and the reaction was allowed to stir at rt for 16 h. The progress of the reaction was monitored by LCMS. After completion reaction was quenched with water and extracted with ethyl acetate (10 mL×3). The combined organic layer was washed with brine solution (20 mL), dried over anhydrous Na$_2$SO$_4$ and concentrated under reduced pressure to afford crude product which was purified by flash chromatography (10-70% EtOAc/pet ether) to afford tert-butyl 4-(4-((3-(2,6-dichlorophenyl)-4-oxo-3,4-dihydro-2H-pyrimido[5,4-e][1,3]oxazin-7-yl)amino)phenyl)piperazine-1-carboxylate (205 mg, 41%) as yellow solid.

LCMS: 571 [M+1]$^+$

Step-2: Synthesis of tert-butyl 4-(4-((3-(2,6-dichlorophenyl)-4-oxo-3,4-dihydro-2H-pyrimido[5,4-e][1,3]oxazin-7-yl)(methyl)amino)phenyl)piperazine-1-carboxylate To a suspension of NaH (21 mg, 0.52 mmol, 1.5 eq) in dry DMF (2 mL), a solution of tert-butyl 4-(4-((3-(2,6-dichlorophenyl)-4-oxo-3,4-dihydro-2H-pyrimido[5,4-e][1,3]oxazin-7-yl)amino)phenyl)piperazine-1-carboxylate (200 mg, 0.34 mmol, 1 eq) in dry DMF (2 mL) was added dropwise at 0° C. under inert atmosphere. The resulting mixture was stirred for 1-2 h at rt; followed by addition of CH$_3$I (0.05 mL, 0.69 mmol, 2 eq). The resulting solution was stirred at same temperature for 16 h. The progress of the reaction was monitored by LCMS. After completion of water (10 mL), was added followed by extraction using MeOH/DCM (10 mL×3). The combined organic layer was washed with brine solution (10 mL×2), dried over anhydrous Na$_2$SO$_4$ and concentrated under reduced pressure to afford crude product which was purified by flash chromatography (MeOH/DCM 1-10%) to afford tert-butyl 4-(4-((3-(2,6-dichlorophenyl)-4-oxo-3,4-dihydro-2H-pyrimido[5,4-e][1,3]oxazin-7-yl)(methyl)amino)phenyl)piperazine-1-carboxylate (70 mg, 34%) as white solid.

LCMS: 585 [M+1]+

Step-3: Synthesis of 3-(2,6-dichlorophenyl)-7-(methyl(4-(piperazin-1-yl)phenyl)amino)-2,3-dihydro-4H-pyrimido[5,4-e][1,3]oxazin-4-one hydrochloride 20% HCl in dioxane (2 mL) was added to a stirred solution of tert-butyl 4-(4-((3-(2,6-dichlorophenyl)-4-oxo-3,4-dihydro-2H-pyrimido[5,4-e][1,3]oxazin-7-yl)(methyl)amino)phenyl)piperazine-1-carboxylate (65 mg, 0.11 mmol, 1.0 eq) in dioxane (1 mL) at 0° C. under inert atmosphere and the resulting solution was allowed to stir at rt for 3 h. After completion, solvent was removed under reduced pressure and the resulting solid was filtered and washed with ether, dried to afford 3-(2,6-dichlorophenyl)-7-((4-(piperidin-4-yl)phenyl)amino)-2,3-dihydro-4H-pyrimido[5,4-e][1,3]oxazin-4-one hydrochloride (7 mg, 12%) as a yellow solid.

LCMS: 485 [M+1]+

$^1$H NMR (400 MHz, DMSO-d$_6$, FB): δ 8.71 (br s, 1H), 7.64 (d, J=8.3 Hz, 2H) 7.51-7.46 (m, 1H) 7.21-7.18 (m, 2H), 7-6.98 (m, 2H), 5.65 (br s, 2H), 3.46 (br s, 3H), 3.19-3.17 (m, 4H), 2.99-2.97 (m, 4H).

Example S73. Synthesis of 3-(2,6-dichlorophenyl)-7-((3-((dimethyl)-H-indol-6-yl)amino)-2,3-dihydro-4H-pyrimido[5,4-e][1,3]oxazin-4-one

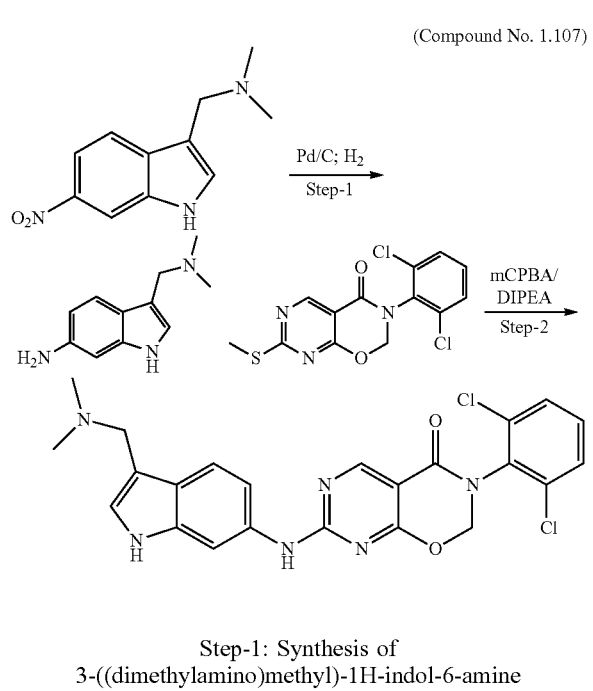

Step-1: Synthesis of 3-((dimethylamino)methyl)-1H-indol-6-amine

To a stirred solution of N,N-dimethyl-1-(6-nitro-1H-indol-3-yl)methanamine (500 mg, 2.28 mmol, 1.0 eq) in (20.0 mL) of methanol was added 10% pd/C (50 mg) and purged with H$_2$ at RT foe 1 h. The reaction mixture was filtered through celite and residue was washed with methanol. The filtrate was concentrated to afford the desired compound 3-((dimethylamino)methyl)-1H-indol-6-amine (400 mg, 92.80%) as brown viscous.

LCMS: 190.2 [M+1]+

Step-2: Synthesis of 3-(2,6-dichlorophenyl)-7-((3-((dimethylamino)methyl)-1H-indol-6-yl)amino)-2,3-dihydro-4H-pyrimido[5,4-e][1,3]oxazin-4-one 3-(2,6-dichlorophenyl)-7-(methylthio)-2,3-dihydro-4H-pyrimido[5,4-e][1,3]oxazin-4-one (180 mg, 0.526 mmol, 1.0 eq) in (3.0 mL) of toluene was added m-CPBA (260 mg, 1.052 mmol, 2.0 eq) and allowed to stir at rt for 30 minutes. 3-((dimethylamino)methyl)-1H-indol-6-amine (110 mg, 0.578 mmol, 1.1 eq) and DIPEA (0.37 mL, 2.104 mmol, 4.0 eq) were added and allowed to stir at rt for overnight. The reaction mixture was concentrated, diluted with EtOAc (50 mL), washed with water (50 mL), with brine (50 mL), dried over Na$_2$SO$_4$ and concentrated, purified by reverse phase purification 3-(2,6-dichlorophenyl)-7-((3-((dimethylamino)methyl)-1H-indol-6-yl)amino)-2,3-dihydro-4H-pyrimido[5,4-e][1,3]oxazin-4-one (4.0 mg, 1.57%%) as off white solid.

LCMS: 483.2 [M+1]+; UPLC @ 254 nm=95.79% and @ 220 nm=97.02%.

$^1$H NMR (400 MHz, DMSO-d$_6$) δ 11.03 (brs, 1H), 10.42 (s, 1H), 8.82 (s, 1H), 8.20 (brs, 1H), 8.02 (s, 1H), 7.66 (d, J=7.89 Hz, 2H), 7.33-7.61 (m, 2H), 7.10-7.33 (m, 2H), 5.74 (s, 2H), 3.68 (brs, 2H), 2.26 (s, 6H).), 1.95 (t, J=6.36 Hz, 4H).

Example S74. Synthesis of 3-(2,6-dichlorophenyl)-7-((4-(4-(dimethylamino)piperidin-1-yl)phenyl)amino)-2,3-dihydro-4H-pyrimido[5,4-e][1,3]oxazin-4-one

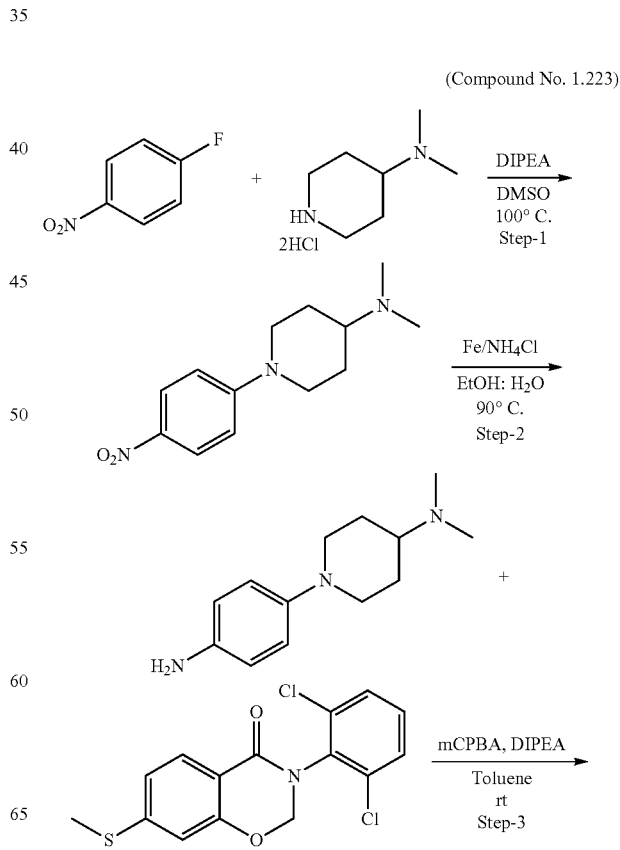

-continued

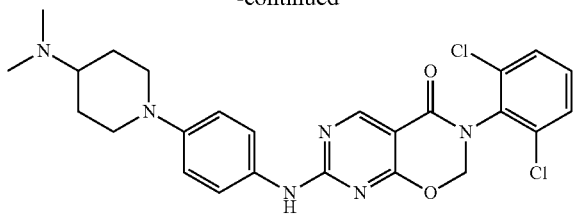

Step-1: Synthesis of N,N-dimethyl-1-(4-nitrophenyl)piperidin-4-amine

To a stirred solution of 1-fluoro-4-nitrobenzene (1 g, 7.08 mmol, 1.0 eq) in DMSO (10 mL); N,N-dimethylpiperidin-4-amine (1.56 g, 7.7 mmol, 2.5 eq) and DIPEA (4.93 mL, 28.3 mmol) were added under stirring and resulting mixture was heated at 100° C. The progress of the reaction was monitored by LCMS. After completion reaction was cooled and quenched with ice cold water. The resulting solid precipitate was filtered, dried to afford N,N-dimethyl-1-(4-nitrophenyl)piperidin-4-amine (1.6 g, 90%) as yellow solid.
LCMS: 250 [M+1]$^+$

Step-2: Synthesis of 1-(4-aminophenyl)-N,N-dimethylpiperidin-4-amine

To a solution of N,N-dimethyl-1-(4-nitrophenyl)piperidin-4-amine (1.5 g, 6.01 mmol, 1 eq) in EtOH (15 mL), Fe powder (1.008 g, 18.04 mmol, 3 eq) followed by NH$_4$Cl (0.643 g, 12.03 mmol, 2 eq) in water (15 mL) were added at rt under stirring. The resulting mixture was heated at 90° C. for 3-4 h. The progress of the reaction was monitored by LCMS. After completion reaction was cooled and the mixture was filtered through celite. The filtrate was concentrated, washed with water (5 mL×2), followed by extraction using MeOH/DCM (10 mL×3). The combined organic layer was dried over anhydrous Na$_2$SO$_4$ and concentrated under reduced pressure to afford 1-(4-aminophenyl)-N,N-dimethylpiperidin-4-amine (0.8 g, 37%) as brown solid.
LCMS: 220 [M+1]$^+$

Step-3: Synthesis of 3-(2,6-dichlorophenyl)-7-((4-(4-(dimethylamino)piperidin-1-yl)phenyl)amino)-2,3-dihydro-4H-pyrimido[5,4-e][1,3]oxazin-4-one To a stirred solution of 3-(2,6-dichlorophenyl)-7-(methylthio)-2,3-dihydro-4H-benzo[e][1,3]oxazin-4-one (200 mg, 0.58 mmol, 1.0 eq) in toluene (5 mL), m-CPBA (251 mg, 1.46 mmol, 2.5 eq) was added under stirring and resulting mixture was allowed to stir at rt for 30 minutes. Further, 1-(4-aminophenyl)-N,N-dimethylpiperidin-4-amine (128.1 mg, 0.58 mmol, 1 eq) and DIPEA (0.4 mL, 2.33 mmol, 4 eq) were added and the reaction was heated at 80° C. for 16 h. The progress of the reaction was monitored by LCMS. After completion reaction was quenched with water and extracted with MeOH/DCM (10 mL×3). The combined organic layer was washed with brine solution (20 mL), dried over anhydrous Na$_2$SO$_4$ and concentrated under reduced pressure to afford crude product which was purified by flash chromatography (1-10% MeOH/DCM) to afford 3-(2,6-dichlorophenyl)-7-((4-(4-(dimethylamino)piperidin-1-yl)phenyl)amino)-2,3-dihydro-4H-pyrimido[5,4-e][1,3]oxazin-4-one (100 mg, 33%) as white solid.
LCMS: 513 [M+1]$^+$ $^1$H NMR (400 MHz, DMSO-d$_6$): D 10.23 (s, 1H), 8.78 (s, 1H), 8.27 (brs, 1H), 7.65 (d, J=8.33 Hz, 2H), 7.40-7.58 (m, 3H), 6.92 (d, J=8.77 Hz, 2H), 5.70 (s, 2H), 3.80 (s, 2H), 2.55-2.70 (m, 2H), 2.20 (s, 6H), 1.83 (d, J=11.84 Hz, 2H), 1.29-1.57 (m, 2H)

Example S75. Synthesis of 3-(2,6-dichlorophenyl)-7-(1,2,3,4-tetrahydroquinolin-7-ylamino)-2H-pyrimido[5,4-e][, 3]oxazin-4(3H)-one (Compound No. 1.121)

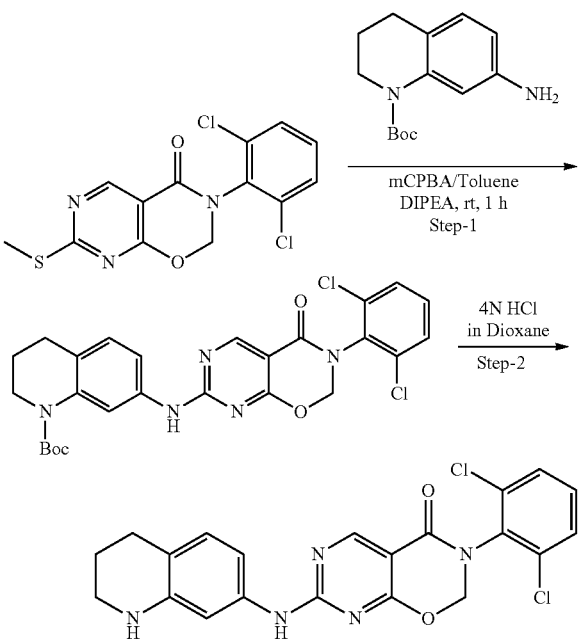

Step-1: Synthesis of tert-butyl 7-(3-(2,6-dichlorophenyl)-4-oxo-3,4-dihydro-2H-pyrimido[5,4-e][1,3]oxazin-7-ylamino)-3,4-dihydroquinoline-1(2H)-carboxylate To a stirred solution of 3-(2,6-dichlorophenyl)-7-(methylthio)-2H-pyrimido[5,4-e][1,3]oxazin-4(3H)-one (200 mg, 0.586 mmol, 1.0 eq.) in 3 mL of Toluene was added m-CPBA (352 mg, 1.46 mmol, 2.5 eq.) and allowed to stir at RT for 30 minutes. tert-butyl 7-amino-3,4-dihydroquinoline-1(2H)-carboxylate (144 mg, 0.586 mmol, 1.0 eq.) and DIPEA (302 mg, 2.30 mmol, 4.0 eq.) were added and allowed to stir at RT for 1 h. Progress of reaction was monitored by LCMS. After completion of reaction solvent was removed under reduced pressure, residue was diluted with 20 ml of water and extracted with ethyl acetate (50 mL×3). Combined organic layer was washed with water (20 ml×3), dried over anhydrous sodium sulfate and concentrated under reduced pressure. Crude was purified by flash chromatography to obtain 100 mg (31.5%) of tert-butyl 7-(3-(2,6-dichlorophenyl)-4-oxo-3,4-dihydro-2H-pyrimido[5,4-e][1,3]oxazin-7-ylamino)-3,4-dihydroquinoline-1(2H)-carboxylate.
LCMS: 542 [M+1]$^+$

Step-2: Synthesis of 3-(2,6-dichlorophenyl)-7-(1,2,3,4-tetrahydroquinolin-7-ylamino)-2H-pyrimido[5,4-e][1,3]oxazin-4(3H)-one tert-butyl tert-butyl 7-(3-(2,6-dichlorophenyl)-4-oxo-3,4-dihydro-2H-pyrimido[5,4-e][1,3]oxazin-7-ylamino)-3,4-dihydroquinoline-1(2H)-carboxylate (100 mg, 0.184 mmol, 1.0 eq.) was dissolved in 3 mL of 4N HCl in dioxane solution at 0° C. Reaction was stirred at RT for 1 h. Progress of reaction was monitored by LCMS. After completion of reaction, precipitated compound was filtered off, washed with 2 mL of dioxane and dried under reduced pressure. Crude was purified by reverse phase chromatography to obtain 12 mg (14.8%) free base of 3-(2,6-dichlorophenyl)-7-(1,2,3,4-tetrahydroquinolin-7-ylamino)-2H-pyrimido[5,4-e][1,3]oxazin-4(3H)-one.

LCMS: 442 [M+1]+

$^1$H NMR (400 MHz, DMSO-d6) δ 10.09 (br. s., 1H), 8.78 (s, 1H), 7.65 (d, J=8.33 Hz, 2H), 7.43-7.58 (m, 1H), 6.85 (br. s., 1H), 6.76 (br. s., 2H), 5.71 (s, 2H), 3.15 (br. s., 3H), 2.67 (br. s., 1H), 2.61 (d, J=6.58 Hz, 2H), 1.77 (br. s., 2H).

Example S76. Synthesis of 3-(2,6-dichlorophenyl)-7-(1,2,3,4-tetrahydroquinolin-6-ylamino)-2H-pyrimido[5,4-e][1,3]oxazin-4(3H)-one (Compound No. 1.224)

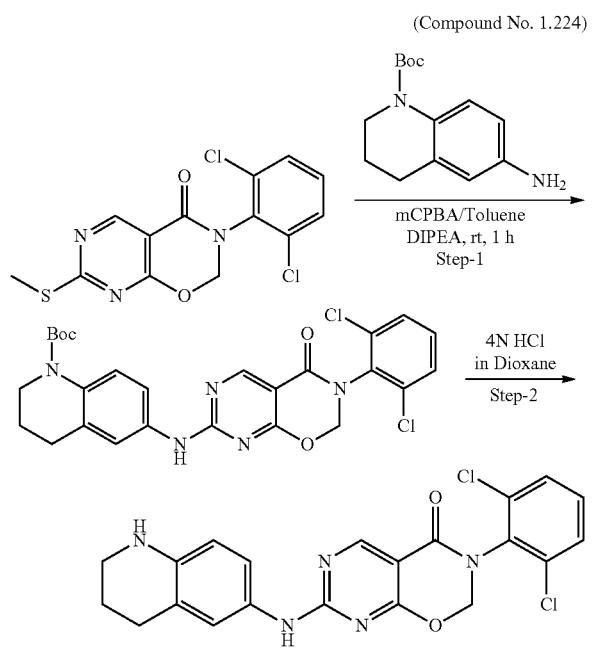

Step-1: Synthesis of tert-butyl 6-(3-(2,6-dichlorophenyl)-4-oxo-3,4-dihydro-2H-pyrimido[5,4-e][1,3]oxazin-7-ylamino)-3,4-dihydroquinoline-1(2H)-carboxylate To a stirred solution of 3-(2,6-dichlorophenyl)-7-(methylthio)-2H-pyrimido[5,4-e][1,3]oxazin-4(3H)-one (200 mg, 0.586 mmol, 1.0 eq.) in 3 mL of Toluene was added m-CPBA (352 mg, 1.46 mmol, 2.5 eq.) and allowed to stir at RT for 30 minutes. tert-butyl 6-amino-3,4-dihydroquinoline-1(2H)-carboxylate (144 mg, 0.586 mmol, 1.0 eq.) and DIPEA (302 mg, 2.30 mmol, 4.0 eq.) were added and allowed to stir at RT for 1 h. Progress of reaction was monitored by LCMS. After completion of reaction solvent was removed under reduced pressure, residue was diluted with 20 ml of water and extracted with ethyl acetate (50 mL×3). Combined organic layer was washed with water (20 ml×3), dried over anhydrous sodium sulfate and concentrated under reduced pressure. Crude was purified by flash chromatography to obtain 110 mg (34.7%) of tert-butyl 6-(3-(2,6-dichlorophenyl)-4-oxo-3,4-dihydro-2H-pyrimido[5,4-e][1,3]oxazin-7-ylamino)-3,4-dihydroquinoline-1(2H)-carboxylate.

LCMS: 542 [M+1]+

Step-2: Synthesis of 3-(2,6-dichlorophenyl)-7-(1,2,3,4-tetrahydroquinolin-6-ylamino)-2H-pyrimido[5,4-e][1,3]oxazin-4(3H)-one tert-butyl 6-(3-(2,6-dichlorophenyl)-4-oxo-3,4-dihydro-2H-pyrimido[5,4-e][1,3]oxazin-7-ylamino)-3,4-dihydroquinoline-1(2H)-carboxylate (90 mg, 0.166 mmol, 1.0 eq.) was dissolved in 3 mL of 4N HCl in dioxane solution at 0° C. Reaction was stirred at RT for 1 h. Progress of reaction was monitored by LCMS. After completion of reaction, precipitated compound was filtered off, washed with 2 mL of dioxane and dried under reduced pressure. Crude was purified by reverse phase chromatography to obtain 50 mg (68.5%) HCl of 3-(2,6-dichlorophenyl)-7-(1,2,3,4-tetrahydroquinolin-6-ylamino)-2H-pyrimido[5,4-e][1,3]oxazin-4(3H)-one.

LCMS: 442 [M+1]+

$^1$H NMR (400 MHz, DMSO-d$_6$): δ 10.84 (br. s., 1H), 10.54 (br. s., 1H), 8.87 (s, 1H), 7.66 (d, J=7.89 Hz, 3H), 7.41-7.53 (m, 1H), 7.22 (d, J=8.77 Hz, 1H), 5.76 (s, 2H), 3.57 (s, 4H), 3.35 (br. s., 2H), 2.83 (t, J=6.36 Hz, 2H), 2.00 (br. s., 2H).

Example S77. Synthesis of 3-(2,6-dichlorophenyl)-7-((4-(2-(diethylamino)ethoxy)phenyl)amino)-2,3-dihydro-4H-pyrimido[5,4-e][1,3]oxazin-4-one (Compound No. 1.225)

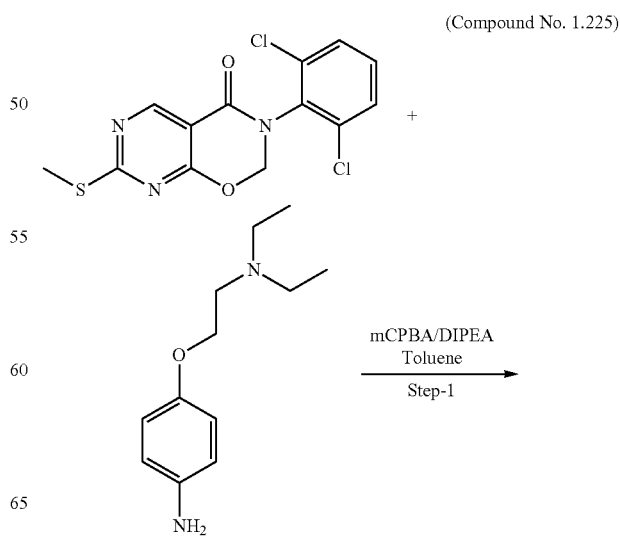

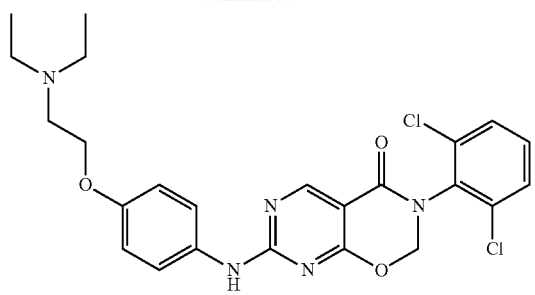

To a stirred solution of 3-(2,6-dichlorophenyl)-7-(methylthio)-2,3-dihydro-4H-pyrimido[5,4-e][1,3]oxazin-4-one (150 mg, 0.438 mmol, 1.0 eq) in (2.0 mL) of toluene was added m-CPBA (189 mg, 1.095 mmol, 2.0 eq) and allowed to stir at rt for 30 minutes. 4-(2-(diethylamino)ethoxy) aniline (110 mg, 0.526 mmol, 1.2 eq) and DIPEA (0.30 mL, 1.752 mmol, 4.0 eq) were added and allowed to stir at rt for overnight. The formation of precipitates was observed which was filtered to afford the desired compound 3-(2,6-dichlorophenyl)-7-((4-(2-(diethyl amino)ethoxy)phenyl) amino)-2,3-dihydro-4H-pyrimido[5,4-e][1,3]oxazin-4-one (18 mg, 8.17%) as white solid.

LCMS: 502.2 [M+1]$^+$; UPLC @ 220 nm=90.72%.

$^1$H NMR (400 MHz, DMSO-d$_6$) δ 10.31 (br. s., 1H), 8.81 (s, 1H), 7.67 (s, 1H), 7.58-7.62 (m, J=7.89 Hz, 2H), 7.48 (s, 1H), 6.89-6.95 (m, J=8.33 Hz, 2H), 5.72 (s, 2H), 2.75 (br. s., 2H), 1.23 (br. s., 2H), 1.00 (br. s., 9H).

Example S78. Synthesis of 3-(2,6-dichlorophenyl)-7-((1,2,3,4-tetrahydroquinoxalin-6-yl)amino)-2,3-dihydro-4H-pyrimido[5,4-e][1,3]oxazin-4-one Dihydrochloride (Compound No. 1.226)

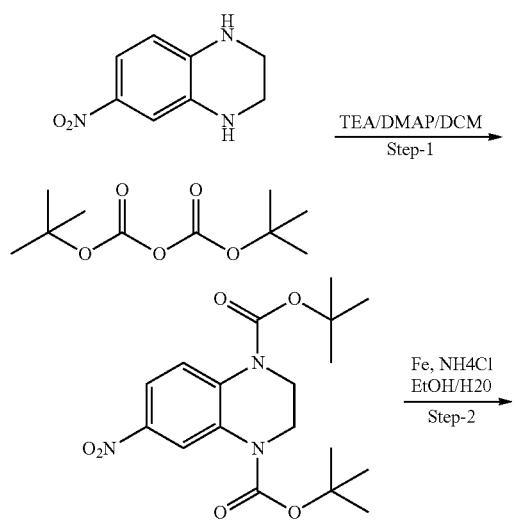

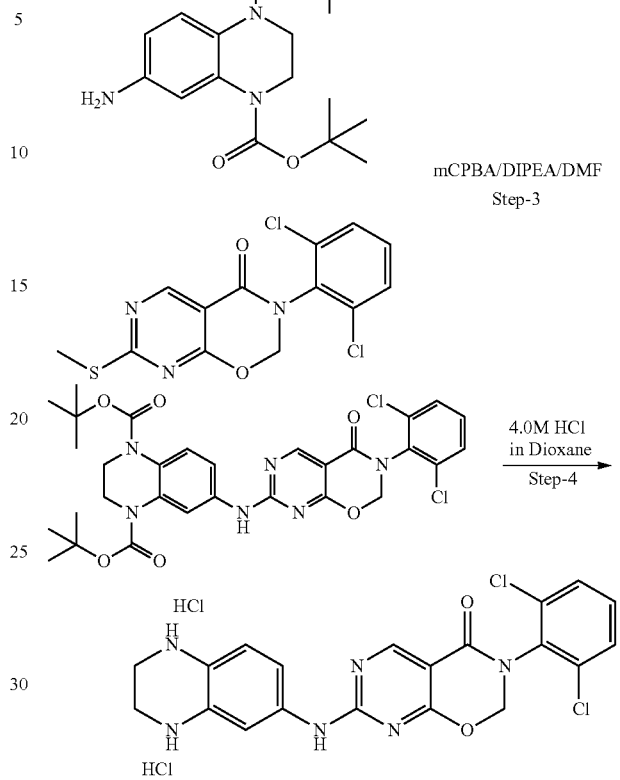

Step-1: Synthesis of di-tert-butyl 6-nitro-2,3-dihydroquinoxaline-1,4-dicarboxylate To a stirred solution of 6-nitro-1,2,3,4-tetrahydroquinoxaline (0.5 g, 2.79 mmol, 1.0 eq) in DCM (20 mL) was added triethylamine (1.17 mL, 8.37 mmol, 3.0 eq) and DMAP (68 mg, 0.558 mmol, 0.2 eq) at rt. The resulting mixture was allowed to cool to 0° C. followed by addition of di-tert-butyl dicarbonate (1.41 mL, 6.139 mmol, 2.2 eq), the reaction mixture was stirred at RT for overnight. The progress of reaction was monitored by LCMS. The reaction mixture was diluted with DCM (50 mL), and washed with water (2×50 mL) dried over Na$_2$SO$_4$, filtered and concentrated and purified by combi flash [silica gel 100-200 mesh; elution 0-35% EtOAc in Hexane] to afford the desired compound di-tert-butyl 6-nitro-2,3-dihydroquinoxaline-1,4-dicarboxylate (0.65 g, 61.43%) as yellow viscous.

LCMS: (M+1)$^+$380.4.

Step-2: Synthesis of di-tert-butyl 6-amino-2,3-dihydroquinoxaline-1,4-dicarboxylate To a stirred solution of di-tert-butyl 6-nitro-2,3-dihydroquinoxaline-1,4-dicarboxylate (0.65 g, 1.713 mmol, 1.0 eq) in EtOH (25 mL) was added Fe (765 g, 13.705 mmol, 8.0 eq) and a solution of NH$_4$Cl (0.916 g, 17.13 mmol, 10.0 eq) in water (25 mL) at rt. The resulting mixture was heated at 90° C. for 60 min. The progress of reaction was monitored by LCMS. The reaction mixture was filtered through celite the residue was washed with EtOH (50 mL) the filtrate was concentrated and the residue was dissolved in EtOAc (50 mL), washed with water (2×50 mL), dried over Na₂SO₄, and concentrated to afford the desired di-tert-butyl 6-amino-2,3-dihydroquinoxaline-1,4-dicarboxylate (0.45 g, 76.79%) as brown viscous.

LCMS: 350.3 [M+1]⁺

Step-3: Synthesis di-tert-butyl 6-((3-(2,6-dichloro-phenyl)-4-oxo-3,4-dihydro-2H-pyrimido[5,4-e][1,3]oxazin-7-yl)amino)-2,3-dihydroquinoxaline-1,4-dicarboxylate To a stirred solution of 3-(2,6-dichlorophenyl)-7-(methylthio)-2,3-dihydro-4H-pyrimido[5,4-e][1,3]oxazin-4-one (200 mg, 0.584 mmol, 1.0 eq) in (3.0 mL) of toluene was added m-CPBA (270 mg, 1.096 mmol, 2.0 eq) and allowed to stir at rt for 30 minutes. di-tert-butyl 6-amino-2,3-dihydroquinoxaline-1,4-dicarboxylate (245 mg, 0.701 mmol, 1.2 eq) and DIPEA (0.40 mL, 2.336 mmol, 4.0 eq) were added and allowed to stir at rt for overnight. The reaction mixture was diluted with water (50 mL) and extracted with EtOAc (2×50 mL), the combined organic layers were washed with water (50 mL) with brine (50 mL) dried over Na₂SO₄, filtered and concentrated and purified by combi flash [silica gel 100-200 mesh; elution 0-50% EtOAc in Hexane] to afford the desired compound di-tert-butyl 6-((3-(2,6-dichlorophenyl)-4-oxo-3,4-dihydro-2H-pyrimido[5,4-e][1,3]oxazin-7-yl)amino)-2,3-dihydroquinoxaline-1,4-dicarboxylate (100 mg, 26.59%) as off white solid.

LCMS: 643.3 [M+1]⁺

Step-4: Synthesis of 3-(2,6-dichlorophenyl)-7-((1,2,3,4-tetrahydroquinoxalin-6-yl)amino)-2,3-dihydro-4H-pyrimido[5,4-e][1,3]oxazin-4-one dihydrochloride di-tert-butyl 6-((3-(2,6-dichlorophenyl)-4-oxo-3,4-dihydro-2H-pyrimido[5,4-e][1,3]oxazin-7-yl)amino)-2,3-dihydroquinoxaline-1,4-dicarboxylate (100 mg, 0.155 mmol, 1.0 eq) was dissolved in 4.0 M-HCl in dioxane (2 mL) and allowed to stir at rt for 1 h. After completion of reaction, the reaction mixture was filtered and dried under reduced pressure to afford the desired compound 3-(2,6-dichlorophenyl)-7-((1,2,3,4-tetrahydroquinoxalin-6-yl)amino)-2,3-dihydro-4H-pyrimido[5,4-e][1,3]oxazin-4-one dihydrochloride (60 mg, 71.42%) as solid.

LCMS: 443.2 [M+1]⁺; UPLC @ 254 nm=88.06% and @ 220 nm=94.15%.

¹H NMR (400 MHz, DMSO-d₆) δ 10.38 (brs, 1H), 8.83 (s, 1H), 7.66 (d, J=8.33 Hz, 2H), 7.46-7.58 (m, 1H), 7.24-7.38 (m, 1H), 7.03 (brs, 2H), 5.95 (brs, 2H), 5.75 (s, 2H), 3.37 (d, J=8.33 Hz, 4H).

Example S79. Synthesis of 3-(2,6-dichlorophenyl)-7-((1,1-dimethyl-1,2,3,4-tetrahydroisoquinolin-6-yl)amino)-2,3-dihydro-4H-pyrimido[5,4-e][1,3]oxazin-4-one (Compound No. 1.227)

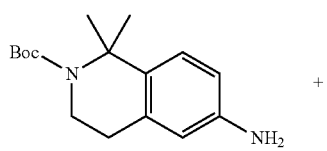

+

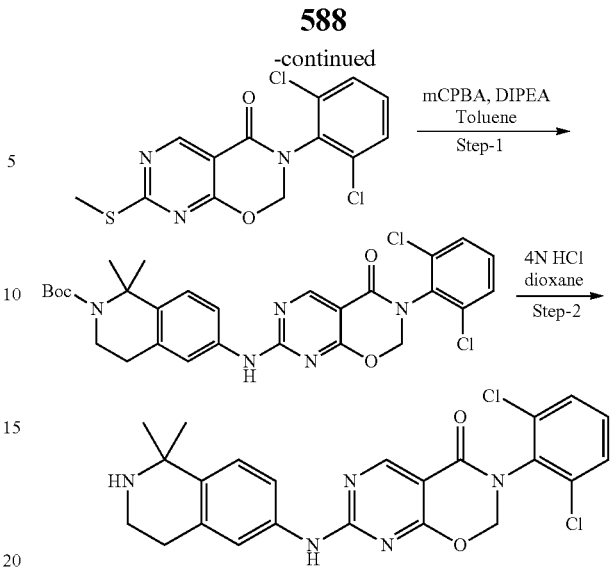

Step-1: Synthesis tert-butyl 6-((3-(2,6-dichlorophenyl)-4-oxo-3,4-dihydro-2H-pyrimido[5,4-e][1,3]oxazin-7-yl)amino)-1,1-dimethyl-3,4-dihydroisoquinoline-2(1H)-carboxylate To a stirred solution of 3-(2,6-dichlorophenyl)-7-(methylthio)-2,3-dihydro-4H-pyrimido[5,4-e][1,3]oxazin-4-one (137 mg, 0.4 mmol, 1.0 eq) in (2.0 mL) of toluene was added m-CPBA (121 mg, 0.44 mmol, 1.1 eq) and allowed to stir at rt for 30 minutes. tert-butyl 6-amino-1,1-dimethyl-3,4-dihydroisoquinoline-2(1H)-carboxylate (121 mg, 0.44 mmol, 1.1 eq) and DIPEA (0.28 mL, 0.28 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((3-(2,6-dichlorophenyl)-4-oxo-3,4-dihydro-2H-pyrimido[5,4-e][1,3]oxazin-7-yl)amino)-1,1-dimethyl-3,4-dihydroisoquinoline-2(1H)-carboxylate (50 mg, 21.9%) as sticky solid.

LCMS: 570.3 [M+1]⁺

Step-2: Synthesis of 3-(2,6-dichlorophenyl)-7-((1,1-dimethyl-1,2,3,4-tetrahydroisoquinolin-6-yl)amino)-2,3-dihydro-4H-pyrimido[5,4-e][1,3]oxazin-4-one tert-butyl 6-((3-(2,6-dichlorophenyl)-4-oxo-3,4-dihydro-2H-pyrimido[5,4-e][1,3]oxazin-7-yl)amino)-1,1-dimethyl-3,4-dihydroisoquinoline-2(1H)-carboxylate (40 mg, 0.07 mmol) was dissolved in dioxane (0.4 mL), followed by dropwise addition of 4.0 M-HCl (0.4 mL) and allowed to stir at rt for 2 h. After completion of reaction, the reaction mixture was filtered and dried to give 3-(2,6-dichlorophenyl)-7-((1,1-dimethyl-1,2,3,4-tetrahydroisoquinolin-6-yl)amino)-2,3-dihydro-4H-pyrimido[5,4-e][1,3]oxazin-4-one (10 mg, 30.3%) as off white solid.

LCMS: 470.2 [M+1]⁺; UPLC @ 254 nm=90.49% and @ 220 nm=91.73%.

¹H NMR (400 MHz, DMSO-d₆): δ 10.47 (brs., 1H), 9.12 (brs, 2H), 8.86 (s, 1H), 7.66 (d, J=7.89 Hz, 2H), 7.53-7.61 (m, 2H), 7.50 (d, J=7.45 Hz, 1H), 7.40 (d, J=8.33 Hz, 1H), 5.75 (s, 2H), 3.44 (brs, 2H), 3.01 (brs, 2H), 1.64 (s, 6H).

Example S80. Synthesis of 7-((3-chloro-4-(3-methylpiperazin-1-yl)phenyl)amino)-3-(2,6-dichlorophenyl)-2,3-dihydro-4H-pyrimido[5,4-e][1,3]oxazin-4-one (Compound No. 1.228)

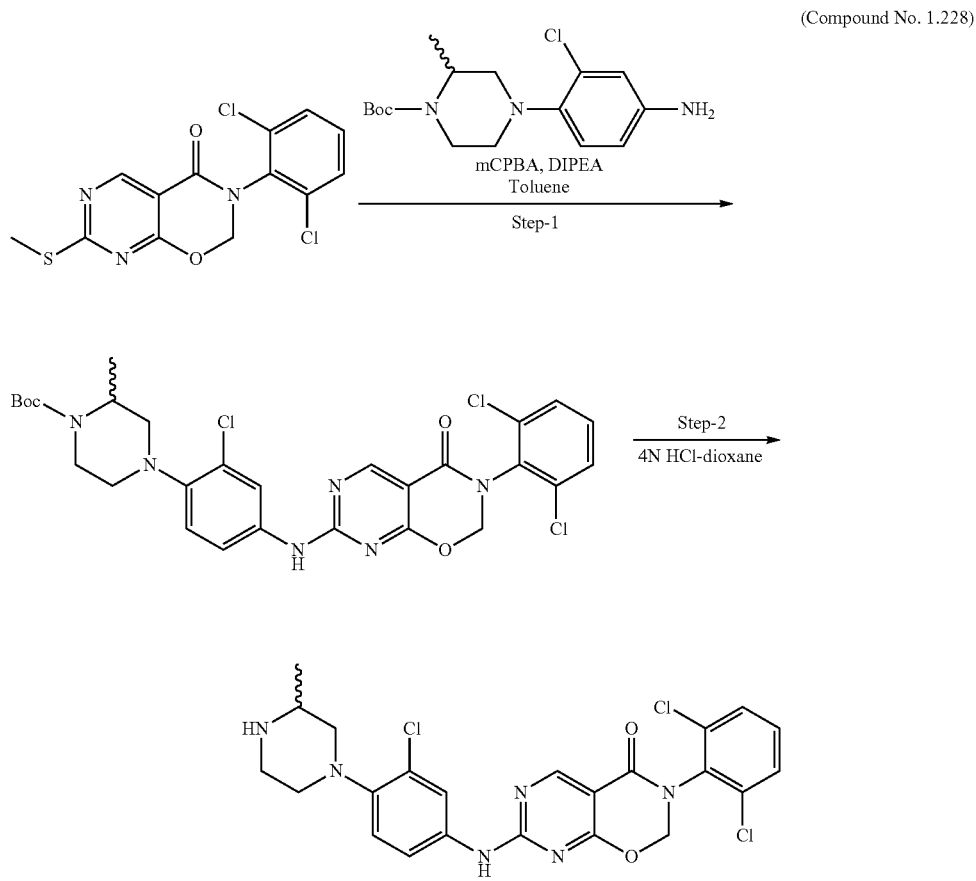

Step-1: tert-butyl 4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate To a stirred solution of 3-(2,6-dichlorophenyl)-7-(methylthio)-2,3-dihydro-4H-pyrimido[5,4-e][1,3]oxazin-4-one (170 mg, 0.5 mmol, 1.0 eq) in of toluene (5.0 mL) was added m-CPBA (247 mg, 1.0 mmol, 2.0 eq) and allowed to stir at rt for 30 minutes. tert-butyl 4-(4-amino-2-chlorophenyl)-2-methylpiperazine-1-carboxylate (180 mg, 0.55 mmol, 1.1 eq) and DIPEA (0.44 mL, 2.5 mmol, 5.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl 4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate (40 mg, 12.8%) as light brown sticky liquid.

LCMS: 619.2 [M+1]$^+$

Step-2: Synthesis of 7-((3-chloro-4-(3-methylpiperazin-1-yl)phenyl)amino)-3-(2,6-dichlorophenyl)-2,3-dihydro-4H-pyrimido[5,4-e][1,3]oxazin-4-one tert-butyl 4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate (40 mg, 0.064 mmol, 1 eq) was dissolved in dioxane (0.4 mL), followed by dropwise addition of 4.0 M-HCl (0.4 mL) and allowed to stir at rt for 1 h. After completion of reaction, the reaction mixture was filtered and dried to give s7-((3-chloro-4-(3-methylpiperazin-1-yl)phenyl)amino)-3-(2,6-dichlorophenyl)-2,3-dihydro-4H-pyrimido[5,4-e][1,3]oxazin-4-one (10 mg, 30.3%) as off white solid.

LCMS: 519.2 [M+1]$^+$; UPLC @ 254 nm=85.93% and @ 220 nm=87.94%.

$^1$H NMR (400 MHz, DMSO-d$_6$): δ 10.54 (brs, 1H), 8.87 (s, 1H), 8.72 (brs, 1H), 7.96 (brs, 1H), 7.60-7.72 (m, 3H), 7.45-7.56 (m, 2H), 7.23 (d, J=8.77 Hz, 1H), 5.76 (s, 2H), 3.16 (brs, 3H), 2.94 (brs, 2H), 2.81 (d, J=10.96 Hz, 2H), 1.28 (d, J=6.14 Hz, 3H).

Example S81. Synthesis of (S)-7-((3-chloro-4-(3-methylpiperazin-1-yl)phenyl)amino)-3-(2,6-dichlorophenyl)-2,3-dihydro-4H-pyrimido[5,4-e][1,3]oxazin-4-one (Compound No. 1.229)

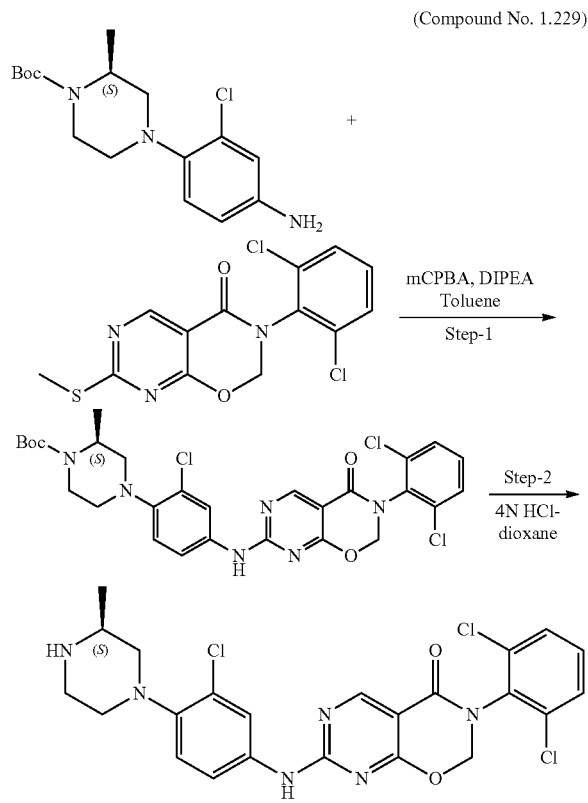

Step-1: Synthesis of tert-butyl (S)-4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate To a stirred solution of 3-(2,6-dichlorophenyl)-7-(methylthio)-2,3-dihydro-4H-pyrimido[5,4-e][1,3]oxazin-4-one (170 mg, 0.5 mmol, 1.0 eq) in of toluene (5.0 mL) was added m-CPBA (247 mg, 1.0 mmol, 2.0 eq) and allowed to stir at rt for 30 minutes. tert-butyl (S)-4-(4-amino-2-chlorophenyl)-2-methylpiperazine-1-carboxylate (180 mg, 0.55 mmol, 1.1 eq) and DIPEA (0.44 mL, 2.5 mmol, 5.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl (S)-4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate (60 mg, 19.3%) as light brown sticky liquid.

LCMS: 619.3 [M+1]$^+$

Step-2: Synthesis of (S)-7-((3-chloro-4-(3-methylpiperazin-1-yl)phenyl)amino)-3-(2,6-dichlorophenyl)-2,3-dihydro-4H-pyrimido[5,4-e][1,3]oxazin-4-one tert-butyl (S)-4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate (60 mg, 0.096 mmol, 1 eq) was dissolved in dioxane (0.4 mL), followed by dropwise addition of 4.0 M-HCl (0.4 mL) and allowed to stir at rt for 1 h. After completion of reaction, the reaction mixture was filtered and purified by preparative chromatography to give (S)-7-((3-chloro-4-(3-methylpiperazin-1-yl)phenyl)amino)-3-(2,6-dichlorophenyl)-2,3-dihydro-4H-pyrimido[5,4-e][1,3]oxazin-4-one (10 mg, 30.3%) as off white solid.

LCMS: 519.08 [M+1]$^+$; UPLC @ 254 nm=90.09% and @ 220 nm=93.75%.

$^1$H NMR (400 MHz, DMSO-d$_6$): δ 10.47 (brs, 1H), 8.85 (s, 1H), 7.89 (brs, 1H), 7.66 (d, J=7.89 Hz, 2H), 7.58-7.62 (m, 1H), 7.47-7.53 (m, 1H), 7.12 (d, J=8.77 Hz, 1H), 5.74 (s, 2H), 3.06 (d, J=10.96 Hz, 3H), 2.79-2.93 (m, 4H), 1.02 (d, J=6.14 Hz, 3H).

Example S82. Synthesis of 3-(2,6-dichlorophenyl)-7-(4-(4-methylpiperazin-1-yl)phenylamino)-2H-pyrimido[5,4-e][1,3]thiazin-4(3H)-one (Compound No. 1.230)

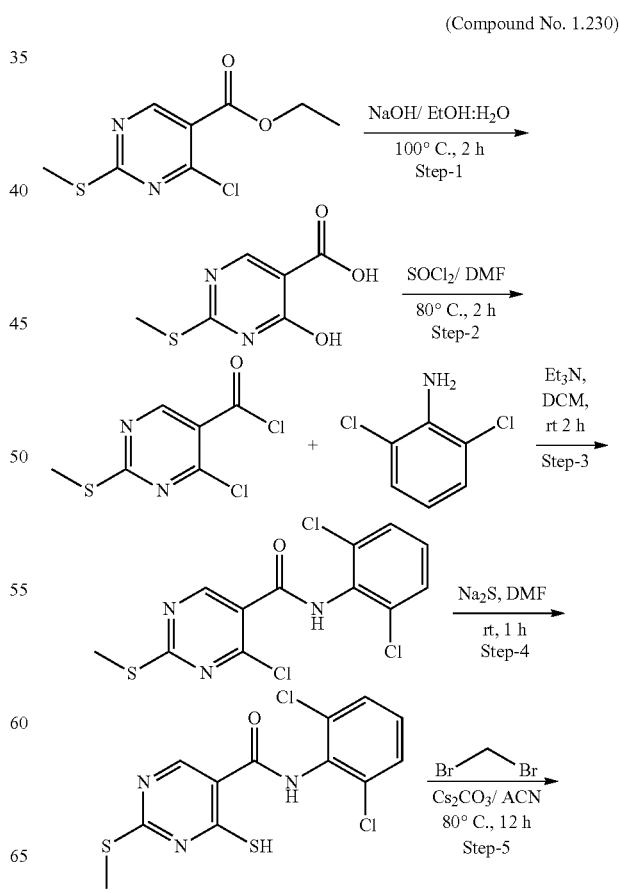

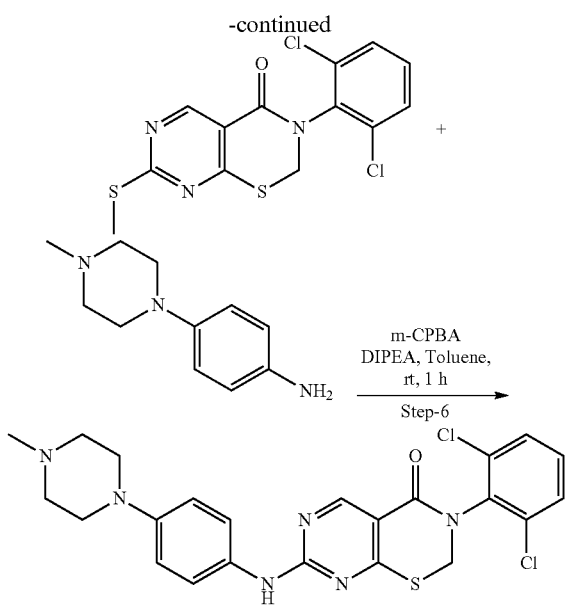

Step-1: Synthesis of 4-hydroxy-2-(methylthio)pyrimidine-5-carboxylic acid

To a solution of ethyl 4-chloro-2-(methylthio)pyrimidine-5-carboxylate (30 g, 130.4 mmol, 1 eq) in EtOH (270 mL), a solution of NaOH (52.1 g, 1.3 mol, 10 eq) in water (180 mL) was added under stirring. The resulting solution was heated at 100° C. for 2 h. The progress of the reaction was monitored by LCMS. After completion of the reaction, mass was cooled to rt and acidified with conc. HCl (55 mL). The resulting precipitate was filtered, washed with water and dried to give 4-hydroxy-2-(methylthio)pyrimidine-5-carboxylic acid (16.5 g, 69%) as a white solid.
LCMS: 187 [M+1]$^+$

Step-2: Synthesis of 4-chloro-2-(methylthio)pyrimidine-5-carbonyl chloride

To ethyl 4-chloro-2-(methylthio)pyrimidine-5-carboxylate (16.5 g, 88.7 mmol, 1 eq) in 500 mL round bottom flask, SOCl$_2$ (150 mL) followed by DMF (2.0 mL) were added under stirring and the resulting solution was warmed to reflux for 2 h. Further, the solution was allowed to cool to rt and was concentrated in vacuo to give 4-chloro-2-(methylthio)pyrimidine-5-carbonyl chloride (12.5 g, 63%) as a white solid.
LCMS: 223 [M+1]$^+$

Step-3: Synthesis of 4-chloro-N-(2,6-dichlorophenyl)-2-(methylthio)pyrimidine-5-carboxamide To a stirred solution of 2,6-dichloroaniline (9.07 g, 56 mmol, 1 eq), in dry DCM (60 mL) Et$_3$N (23.43 mL, 168.1 mmol, 3 eq) was added followed by addition of 4-chloro-2-(methylthio)pyrimidine-5-carbonyl chloride (12.5 g, 56 mmol, 1 eq) in DCM (60 mL) under stirring under inert atmosphere. The resulting solution was stirred at rt for 2 h. The progress of the reaction was monitored by LCMS. After complete consumption of starting material, the reaction mass was diluted with water (50 mL) and extracted with DCM (50 mL×3). The combined organic layer was dried over Na$_2$SO$_4$, concentrated to afford 4-chloro-N-(2,6-dichlorophenyl)-2-(methylthio)pyrimidine-5-carboxamide (12.0 g, 61%) which was used without further purification.
LCMS: 348 [M+1]$^+$

Step-4: Synthesis of N-(2,6-dichlorophenyl)-4-mercapto-2-(methylthio)pyrimidine-5-carboxamide To a stirring solution of 4-chloro-N-(2,6-dichlorophenyl)-2-(methylthio)pyrimidine-5-carboxamide (3.5 g, 10.1 mmol, 1 eq) in DMF (20 mL), was added sodium sulfide (1.60 g, 20.17 mmol, 2.0 eq). The reaction was stirred at rt for 1 h. The progress of the reaction was monitored by LCMS. After completion of reaction, mixture was poured on ice cold water under stirring condition, precipitated compound was filtered off, washed with water and dried under vacuum to obtain 1.35 g (38.5%) of N-(2,6-dichlorophenyl)-4-mercapto-2-(methylthio)pyrimidine-5-carboxamide.
LCMS: 346 [M+1]$^+$

Step-5: Synthesis of 3-(2,6-dichlorophenyl)-7-(methylthio)-2H-pyrimido[5,4-e][1,3]thiazin-4(3H)-one N-(2,6-dichlorophenyl)-4-mercapto-2-(methylthio)pyrimidine-5-carboxamide (1.35 g, 3.9 mmol, 1 eq) was suspended in acetonitrile (30 mL) and Cs$_2$CO$_3$ (3.80 g, 11.70 mmol, 4 eq) was added under stirring at rt. Dibromomethane (1.02 g, 5.85 mmol, 1.5 eq) was then added and the resulting solution was stirred at 80° C. for 12 h. The progress of the reaction was monitored by LCMS. After completion of the reaction, the mixture was diluted with water (20 mL) and then extracted with EtOAc (20 mL×3). The combined organic extracts were washed with brine then dried over Na$_2$SO$_4$, filtered and concentrated to afford 800 mg (57.30%) of 3-(2,6-dichlorophenyl)-7-(methylthio)-2H-pyrimido[5,4-e][1,3]thiazin-4(3H)-one.
LCMS: 358 [M+1]$^+$

Step-6: Synthesis of 3-(2,6-dichlorophenyl)-7-(4-(4-methylpiperazin-1-yl)phenylamino)-2H-pyrimido[5,4-e][1,3]thiazin-4(3H)-one To a stirred solution of 3-(2,6-dichlorophenyl)-7-(methylthio)-2H-pyrimido[5,4-e][1,3]thiazin-4(3H)-one (200 mg, 0.56 mmol, 1 eq) in toluene (7 mL), m-CPBA (385 mg, 2.24 mmol, 4.0 eq) was added under stirring and resulting mixture was allowed to stir at RT for 1 h. Further, 4-(4-methylpiperazin-1-yl)aniline (118 mg, 0.616 mmol, 1.1 eq) and DIPEA (434 mg, 3.36 mmol, 6.0 eq) were added and the reaction was stirred at rt for 1 h. The progress of the reaction was monitored by LCMS. After completion reaction, toluene was removed under reduced pressure; the mixture was diluted with water (20 mL) and then extracted with EtOAc (20 mL×3). The combined organic extracts were washed with brine then dried over Na$_2$SO$_4$, filtered and concentrated. Crude was purified by reverse phase chromatography to afford 70 mg (25.0%) formate salt of 3-(2,6-dichlorophenyl)-7-(4-(4-methylpiperazin-1-yl)phenylamino)-2H-pyrimido[5,4-e][1,3]thiazin-4(3H)-one.
LCMS: 501 [M+1]$^+$
$^1$H NMR (400 MHz, DMSO-d6) δ 10.19 (s, 1H), 8.76 (s, 1H), 7.64 (d, J=7.89 Hz, 2H), 7.54 (d, J=8.77 Hz, 2H), 7.38-7.50 (m, 1H), 6.94 (d, J=8.77 Hz, 2H), 5.22 (s, 2H), 3.16 (br. s., 4H), 2.66 (br. s., 4H), 2.15-2.43 (m, 3H).

Example S83. Synthesis of 3-(2,6-dichlorophenyl)-7-(4,4-dimethyl-1,2,3,4-tetrahydroisoquinolin-7-ylamino)-2H-pyrimido[5,4-e][1,3]thiazin-4(3H)-one (Compound No. 1.231)

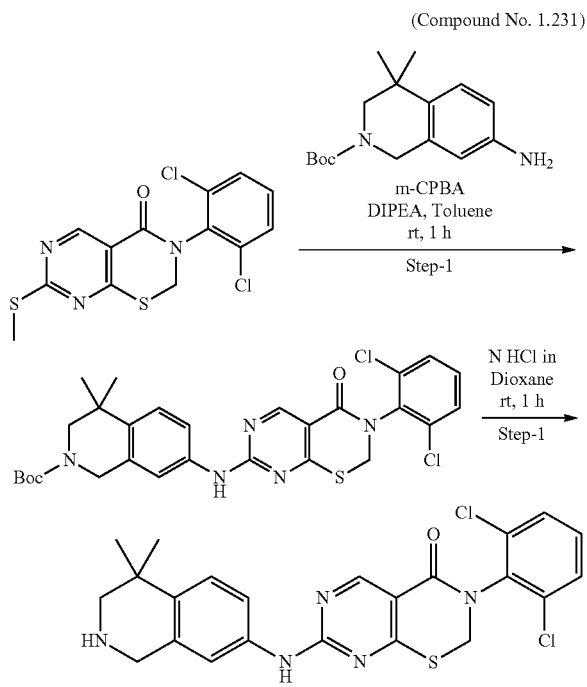

Step-1: Synthesis of tert-butyl 7-(3-(2,6-dichlorophenyl)-4-oxo-3,4-dihydro-2H-pyrimido[5,4-e][1,3]thiazin-7-ylamino)-4,4-dimethyl-3,4-dihydroisoquinoline-2(1H)-carboxylate To a stirred solution of 3-(2,6-dichlorophenyl)-7-(methylthio)-2H-pyrimido[5,4-e][1,3]thiazin-4(3H)-one (200 mg, 0.56 mmol, 1 eq) in toluene (5 mL), m-CPBA (385 mg, 2.24 mmol, 4.0 eq) was added under stirring and resulting mixture was allowed to stir at RT for 1 h. Further, tert-butyl 7-amino-4,4-dimethyl-3,4-dihydroisoquinoline-2(1H)-carboxylate (155 mg, 0.56 mmol, 1 eq) and DIPEA (433 mg, 3.36 mmol, 6 eq) were added and the reaction was stirred at rt for 12 h. The progress of the reaction was monitored by LCMS. After completion of reaction solvent was removed under reduced pressure, residue was diluted with 20 ml of water and extracted with ethyl acetate (50 mL×3). Combined organic layer was washed with water (20 ml×3), dried over anhydrous sodium sulfate and concentrated under reduced pressure. Crude was purified by flash chromatography using methanol:dichloromethane as eluents to obtain 220 mg (50% pure by LCMS) of tert-butyl 7-(3-(2,6-dichlorophenyl)-4-oxo-3,4-dihydro-2H-pyrimido[5,4-e][1,3]thiazin-7-ylamino)-4,4-dimethyl-3,4-dihydroisoquinoline-2(1H)-carboxylate.

LCMS: 586 [M+1]$^+$

Step-2: Synthesis of 3-(2,6-dichlorophenyl)-7-(4,4-dimethyl-1,2,3,4-tetrahydroisoquinolin-7-ylamino)-2H-pyrimido[5,4-e][1,3]thiazin-4(3H)-one 4N HCl in dioxane (4 mL) was added to a stirred solution of tert-butyl 7-(3-(2,6-dichlorophenyl)-4-oxo-3,4-dihydro-2H-pyrimido[5,4-e][1,3]thiazin-7-ylamino)-4,4-dimethyl-3,4-dihydroisoquinoline-2(1H)-carboxylate (200 mg, 0.34 mmol, 1 eq) in dioxane (1 mL) at 0° C. and the resulting solution was allowed to stir at rt for 1 h under inert atmosphere. The progress of the reaction was monitored by LCMS. After completion of reaction, resulting solid was filtered off and washed with ether and dried. Crude was purified by reverse phase chromatography to afford 25 mg (30.5%) formate salt of 3-(2,6-dichlorophenyl)-7-(4,4-dimethyl-1,2,3,4-tetrahydroisoquinolin-7-ylamino)-2H-pyrimido[5,4-e][1,3]thiazin-4(3H)-one.

LCMS: 486 [M+1]$^+$ $^1$H NMR (400 MHz, DMSO-d$_6$: 610.27 (s, 1H), 8.79 (s, 1H), 7.65 (d, J=7.89 Hz, 2H), 7.40-7.57 (m, 2H), 7.18-7.38 (m, 2H), 5.24 (s, 2H), 3.84 (br. s., 3H), 2.61-2.84 (m, 2H), 1.21 (s, 6H)

Example S84. Synthesis of 3-(2,6-dichlorophenyl)-7-(4-(4-(dimethylamino)piperidin-1-yl)phenylamino)-2H-pyrimido[5,4-e][1,3]thiazin-4(3H)-one (Compound No. 1.232)

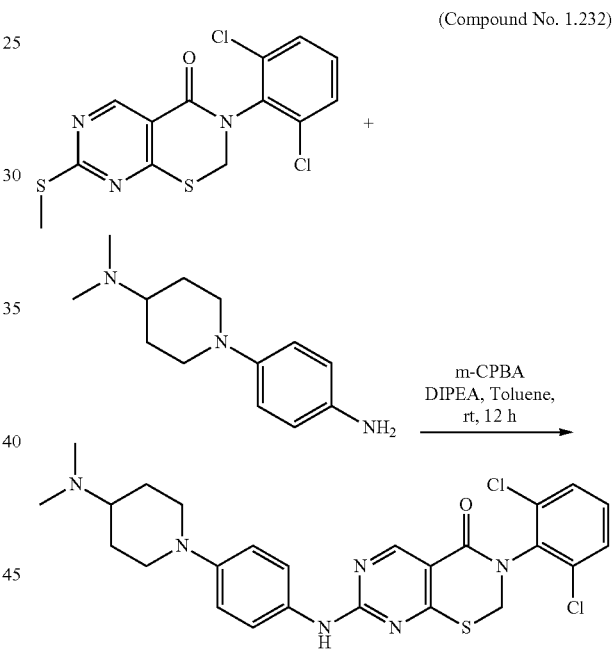

To a stirred solution of 3-(2,6-dichlorophenyl)-7-(methylthio)-2H-pyrimido[5,4-e][1,3]thiazin-4(3H)-one (200 mg, 0.56 mmol, 1 eq) in toluene (5 mL), m-CPBA (240 mg, 1.40 mmol, 2.5 eq) was added under stirring and resulting mixture was allowed to stir at RT for 1 h. Further, 1-(4-aminophenyl)-N,N-dimethylpiperidin-4-amine (147 mg, 0.672 mmol, 1.0 eq) and DIPEA (290 mg, 2.24 mmol, 4.0 eq) were added and the reaction was stirred at rt for 12 h. The progress of the reaction was monitored by LCMS. After completion reaction, toluene was removed under reduced pressure; the mixture was diluted with water (20 mL) and then extracted with EtOAc (20 mL×3). The combined organic extracts were washed with brine then dried over Na$_2$SO$_4$, filtered and concentrated. Crude was purified by reverse phase chromatography to afford 5 mg free base of 3-(2,6-dichlorophenyl)-7-(4-(4-(dimethylamino)piperidin-1-yl)phenylamino)-2H-pyrimido[5,4-e][1,3]thiazin-4(3H)-one.

LCMS: 529.3 [M+1]⁺; UPLC @ 254 nm=93.92% and @ 220 nm=91.04%.

¹H NMR (400 MHz, DMSO-d6): δ10.17 (br. s., 1H), 8.76 (s, 1H), 7.64 (d, J=8.33 Hz, 2H), 7.41-7.57 (m, 3H), 6.93 (d, J=9.21 Hz, 2H), 5.22 (s, 2H), 3.66 (d, J=10.52 Hz, 2H), 2.65 (d, J=19.73 Hz, 2H), 2.19 (s, 6H), 1.82 (d, J=10.52 Hz, 2H), 1.64 (br. s., 2H), 1.38-1.53 (m, 3H).

Example S85. Synthesis of 3-(2,6-dichlorophenyl)-7-((1,2,3,4-tetrahydroisoquinolin-7-yl)amino)-2,3-dihydro-4H-pyrimido[5,4-e][1,3]thiazin-4-one Hydrochloride (Compound No. 1.233)

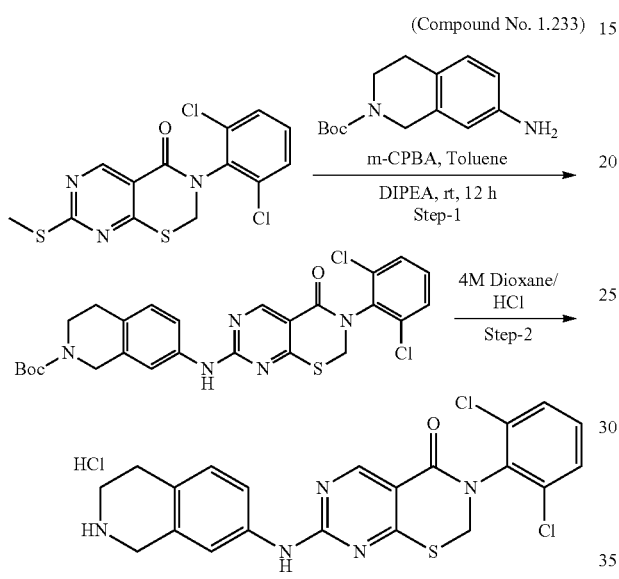

Step-1: Synthesis of tert-butyl 7-((3-(2,6-dichlorophenyl)-4-oxo-3,4-dihydro-2H-pyrimido[5,4-e][1,3]thiazin-7-yl)amino)-3,4-dihydroisoquinoline-2(1H)-carboxylate To a stirred solution of 3-(2,6-dichlorophenyl)-7-(methylthio)-2,3-dihydro-4H-pyrimido[5,4-e][1,3]thiazin-4-one (150 mg, 0.418 mmol, 1.0 eq) in (2.0 mL) of toluene was added m-CPBA (206 mg, 0.836 mmol, 2.0 eq) and allowed to stir at rt for 30 minutes. tert-butyl 7-amino-3,4-dihydroisoquinoline-2(1H)-carboxylate (115 mg, 0.46 mmol, 1.1 eq) and DIPEA (0.29 mL, 1.672 mmol, 4.0 eq) were added and allowed to stir at rt for overnight. After completion of reaction, the reaction mixture was diluted with water and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl 7-((3-(2,6-dichlorophenyl)-4-oxo-3,4-dihydro-2H-pyrimido[5,4-e][1,3]thiazin-7-yl)amino)-3,4-dihydroisoquinoline-2(1H)-carboxylate (130 mg, 56.41%) as brown solid.

LCMS: 558.3 [M+1]⁺

Step-2: Synthesis of 3-(2,6-dichlorophenyl)-7-((1,2,3,4-tetrahydroisoquinolin-7-yl)amino)-2,3-dihydro-4H-pyrimido[5,4-e][1,3]thiazin-4-one Hydrochloride tert-butyl 7-((3-(2,6-dichlorophenyl)-4-oxo-3,4-dihydro-2H-pyrimido[5,4-e][1,3]thiazin-7-yl)amino)-3,4-dihydroisoquinoline-2(1H)-carboxylate (130 mg, 0.233 mmol, 1.0 eq) was dissolved in 4.0 M-HCl (2 mL) and allowed to stir at rt for 1 h. After completion of reaction, the reaction mixture was filtered and dried under reduced pressure to afford the desired compound 3-(2,6-dichlorophenyl)-7-((1,2,3,4-tetrahydroisoquinolin-7-yl)amino)-2,3-dihydro-4H-pyrimido[5,4-e][1,3]thiazin-4-one hydrochloride (105 mg, 91.30%) as light yellow solid.

LCMS: 458.1 [M+1]⁺; UPLC @ 254 nm=98.16% and @ 220 nm=97.43%.

¹H NMR (400 MHz, DMSO-d₆) δ 10.44 (s, 1H), 9.27 (brs, 2H), 8.82 (s, 1H), 7.65 (d, J=7.89 Hz, 2H), 7.58 (brs, 2H), 7.42-7.52 (m, 1H), 7.20 (d, J=8.77 Hz, 1H), 5.26 (s, 2H), 4.26 (brs, 3H), 3.36 (brs, 2H), 2.96 (t, J=6.36 Hz, 2H).

Example S86. Synthesis of 3-(2,6-dichlorophenyl)-7-((1,2,3,4-tetrahydroisoquinolin-6-yl)amino)-2,3-dihydro-4H-pyrimido[5,4-e][1,3]thiazin-4-one Hydrochloride (Compound No. 1.234)

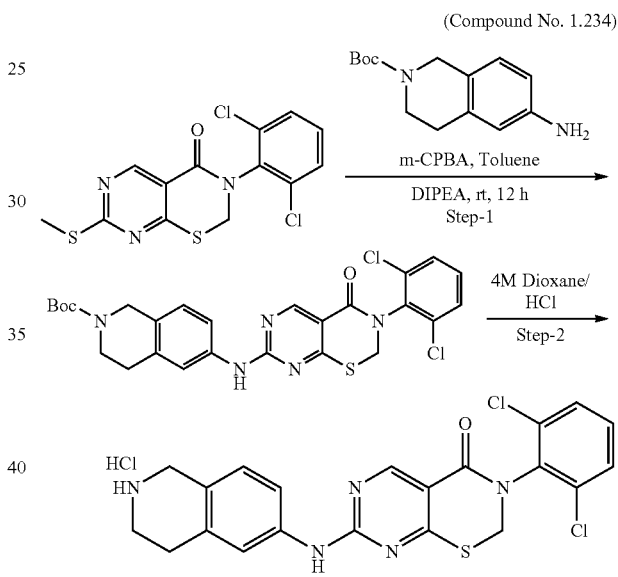

Step-1: Synthesis of tert-butyl 6-((3-(2,6-dichlorophenyl)-4-oxo-3,4-dihydro-2H-pyrimido[5,4-e][1,3]thiazin-7-yl)amino)-3,4-dihydroisoquinoline-2(1H)-carboxylate To a stirred solution of 3-(2,6-dichlorophenyl)-7-(methylthio)-2,3-dihydro-4H-pyrimido[5,4-e][1,3]thiazin-4-one (150 mg, 0.418 mmol, 1.0 eq) in (2.0 mL) of toluene was added m-CPBA (206 mg, 0.836 mmol, 2.0 eq) and allowed to stir at rt for 30 minutes. tert-butyl 6-amino-3,4-dihydroisoquinoline-2(1H)-carboxylate (115 mg, 0.46 mmol, 1.1 eq) and DIPEA (0.29 mL, 1.672 mmol, 4.0 eq) were added and allowed to stir at rt for overnight. After completion of reaction, the reaction mixture was diluted with water (20 mL) and extracted with EtOAc (20 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl 6-((3-(2,6-dichlorophenyl)-4-oxo-3,4-dihydro- 2H-pyrimido[5,4-e][1,3]thiazin-7-yl)amino)-3,4-dihydroisoquinoline-2(1H)-carboxylate (130 mg, 56.41%) as brown solid.

LCMS: 558.3 [M+1]$^+$

Step-2: Synthesis of 3-(2,6-dichlorophenyl)-7-((1,2,3,4-tetrahydroisoquinolin-6-yl)amino)-2,3-dihydro-4H-pyrimido[5,4-e][1,3]thiazin-4-one hydrochloride tert-butyl 6-((3-(2,6-dichlorophenyl)-4-oxo-3,4-dihydro-2H-pyrimido[5,4-e][1,3]thiazin-7-yl)amino)-3,4-dihydroisoquinoline-2(1H)-carboxylate (130 mg, 0.233 mmol, 1.0 eq) was dissolved in 4.0 M-HCl (2 mL) and allowed to stir at rt for 1 h. After completion of reaction, the reaction mixture was filtered and dried under reduced pressure to afford the desired compound 3-(2,6-dichlorophenyl)-7-((1,2,3,4-tetrahydroisoquinolin-6-yl)amino)-2,3-dihydro-4H-pyrimido[5,4-e][1,3]thiazin-4-one hydrochloride (70 mg, 60.86%) as yellow solid.

LCMS: 458.1 [M+1]$^+$; UPLC @ 254 nm=97.98% and @ 220 nm=97.33%.

$^1$H NMR (400 MHz, DMSO-d$_6$) δ 10.43 (s, 1H), 9.34 (brs, 2H), 8.83 (s, 1H), 7.55-7.70 (m, 4H), 7.45-7.53 (m, 1H), 7.19 (d, J=8.33 Hz, 1H), 5.26 (s, 2H), 4.21 (brs, 2H), 3.35 (brs, 2H), 3.00 (t, J=5.92 Hz, 2H).

Example S87. Synthesis of 3-(2,6-dichlorophenyl)-7-((3-methyl-4-(piperazin-1-yl)phenyl)amino)-2,3-dihydro-4H-pyrimido[5,4-e][1,3]thiazin-4-one Hydrochloride Step-1: Synthesis of tert-butyl 4-(4-((3-(2,6-dichlorophenyl)-4-oxo-3,4-dihydro-2H-pyrimido[5,4-e][1,3]thiazin-7-yl)amino)-2-methylphenyl)piperazine-1-carboxylate To a stirred solution of 3-(2,6-dichlorophenyl)-7-(methylthio)-2,3-dihydro-4H-pyrimido[5,4-e][1,3]thiazin-4-one (150 mg, 0.418 mmol, 1.0 eq) in (2.0 mL) of toluene was added m-CPBA (206 mg, 0.836 mmol, 2.0 eq) and allowed to stir at rt for 30 minutes. tert-butyl 4-(4-amino-2-methylphenyl)piperazine-1-carboxylate (134 mg, 0.459 mmol, 1.1 eq) and DIPEA (0.29 mL, 1.672 mmol, 4.0 eq) were added and allowed to stir at rt for overnight. After completion of reaction, the reaction mixture was diluted with water (20 mL) and extracted with EtOAc (20 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl 4-(4-((3-(2,6-dichlorophenyl)-4-oxo-3,4-dihydro-2H-pyrimido[5,4-e][1,3]thiazin-7-yl)amino)-2-methylphenyl)piperazine-1-carboxylate (132 mg, 52.38%) as brown solid.

LCMS: 601.3 [M+1]$^+$

Step-2: Synthesis of 3-(2,6-dichlorophenyl)-7-((3-methyl-4-(piperazin-1-yl)phenyl)amino)-2,3-dihydro-4H-pyrimido[5,4-e][1,3]thiazin-4-one Hydrochloride tert-butyl 4-(4-((3-(2,6-dichlorophenyl)-4-oxo-3,4-dihydro-2H-pyrimido[5,4-e][1,3]thiazin-7-yl)amino)-2-methylphenyl)piperazine-1-carboxylate (130 mg, 0.216 mmol, 1.0 eq) was dissolved in 4.0 M-HCl (2 mL) and allowed to stir at rt for 1 h. After completion of reaction, the reaction mixture was filtered and dried under reduced pressure to afford the desired compound 3-(2,6-dichlorophenyl)-7-((3-methyl-4-(piperazin-1-yl)phenyl)amino)-2,3-dihydro-4H-

(Compound No. 1.235)

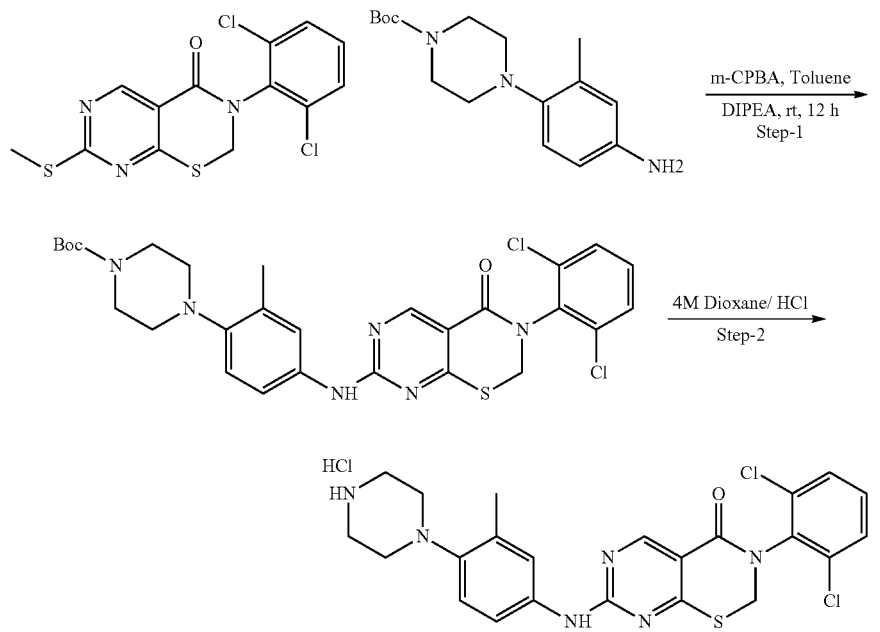

pyrimido[5,4-e][1,3]thiazin-4-one hydrochloride (98 mg, 85.21%) as yellow solid.

LCMS: 501.2 [M+1]$^+$; UPLC @ 254 nm=98.40% and @ 220 nm=97.30%.

$^1$H NMR (400 MHz, DMSO-d$_6$) δ 10.28 (s, 1H), 9.10 (brs, 2H), 8.79 (s, 1H), 7.65 (d, J=7.89 Hz, 2H), 7.57 (d, J=7.45 Hz, 1H), 7.42-7.51 (m, 2H), 7.04 (d, J=8.77 Hz, 1H), 5.24 (s, 2H), 3.22 (brs, 4H), 3.02 (brs, 4H), 2.26 (s, 3H).

Example S88. Synthesis of 7-((3-chloro-4-(piperazin-1-yl)phenyl)amino)-3-(2,6-dichlorophenyl)-2,3-dihydro-4H-pyrimido[5,4-e][1,3]thiazin-4-one 2,2,2-trifluoroacetate (Compound No. 1.236)

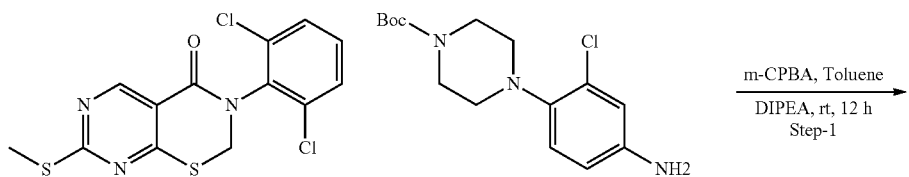

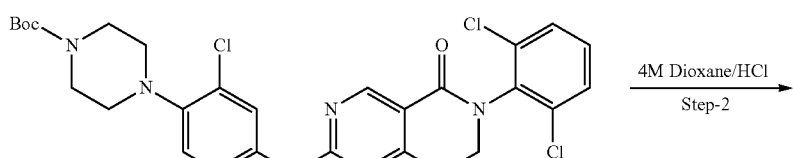

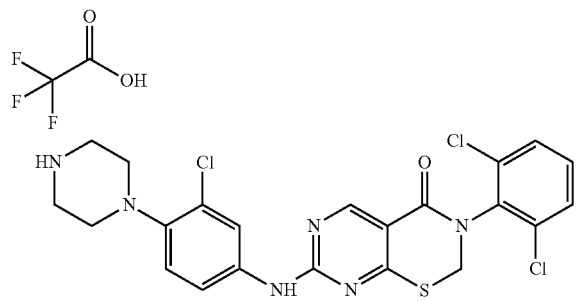

Step-1: Synthesis of tert-butyl 4-(2-chloro-4-((3-(2,6-dichlorophenyl)-4-oxo-3,4-dihydro-2H-pyrimido[5,4-e][1,3]thiazin-7-yl)amino)phenyl)piperazine-1-carboxylate To a stirred solution of 3-(2,6-dichlorophenyl)-7-(methylthio)-2,3-dihydro-4H-pyrimido[5,4-e][1,3]thiazin-4-one (150 mg, 0.418 mmol, 1.0 eq) in (2.0 mL) of toluene was added m-CPBA (206 mg, 0.836 mmol, 2.0 eq) and allowed to stir at rt for 30 minutes. tert-butyl 4-(4-amino-2-chlorophenyl)piperazine-1-carboxylate (144 mg, 0.460 mmol, 1.1 eq) and DIPEA (0.29 mL, 1.672 mmol, 4.0 eq) were added and allowed to stir at rt for overnight. After completion of reaction, the reaction mixture was diluted with water (20 mL) and extracted with EtOAc (20 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl 4-(2-chloro-4-((3-(2,6-dichlorophenyl)-4-oxo-3,4-dihydro-2H-pyrimido[5,4-e][1,3]thiazin-7-yl)amino)phenyl)piperazine-1-carboxylate (80 mg, 52.38%) as yellow solid.

LCMS: 621.3 [M+1]$^+$

Step-2: Synthesis of 7-((3-chloro-4-(piperazin-1-yl)phenyl)amino)-3-(2,6-dichlorophenyl)-2,3-dihydro-4H-pyrimido[5,4-e][1,3]thiazin-4-one 2,2,2-trifluoroacetate tert-butyl 4-(2-chloro-4-((3-(2,6-dichlorophenyl)-4-oxo-3,4-dihydro-2H-pyrimido[5,4-e][1,3]thiazin-7-yl)amino)phenyl)piperazine-1-carboxylate (75 mg, 0.120 mmol, 1.0 eq) was dissolved in 4.0 M-HCl (2 mL) and allowed to stir at rt for 1 h. After completion of reaction, the reaction mixture was filtered and dried under reduced pressure and purified by reverse phase purification to afford the desired compound 7-((3-chloro-4-(piperazin-1-yl)phenyl)amino)-3-(2,6-dichlorophenyl)-2,3-dihydro-4H-pyrimido[5,4-e][1,3]thiazin-4-one 2,2,2-trifluoroacetate (25 mg, 32.89%) as yellow solid.

LCMS: 521.1 [M+1]$^+$; UPLC @ 254 nm=99.01% and @ 220 nm=97.34%.

$^1$H NMR (400 MHz, DMSO-d$_6$) δ 10.49 (s, 1H), 8.84 (s, 1H), 8.73 (brs, 2H), 7.89 (d, J=2.19 Hz, 1H), 7.61-7.72 (m, 3H), 7.44-7.52 (m, 1H), 7.23 (d, J=8.77 Hz, 1H), 5.26 (s, 3H), 3.26 (brs, 4H), 3.06-3.21 (m, 4H).

Example S89. Synthesis of 3-(2,6-dichlorophenyl)-7-((3-methoxy-4-(piperazin-1-yl)phenyl)amino)-2,3-dihydro-4H-pyrimido[5,4-e][1,3]thiazin-4-one Hydrochloride (Compound No. 1.237)

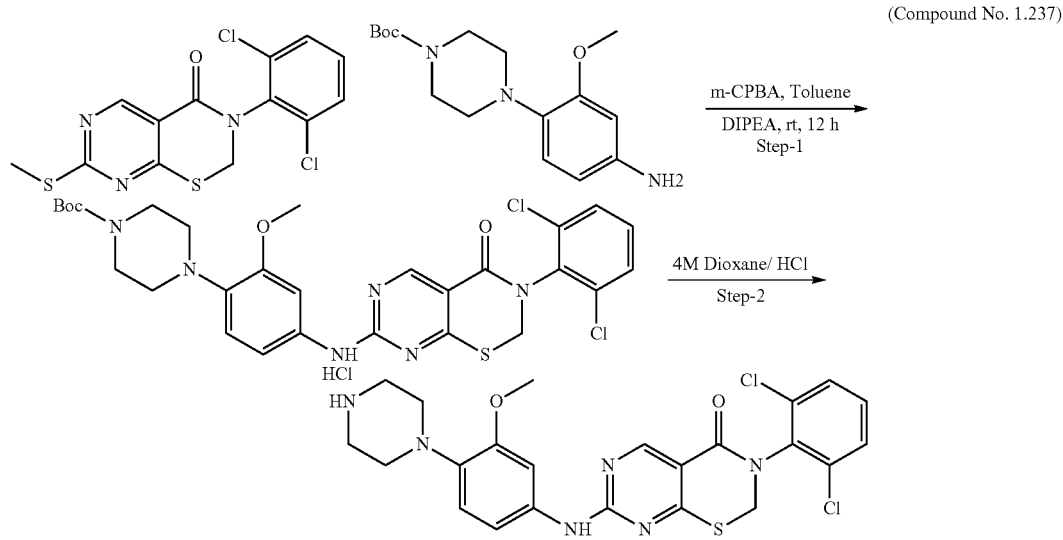

Step-1: Synthesis of tert-butyl 4-(4-(((3-(2,6-dichlorophenyl)-4-oxo-3,4-dihydro-2H-pyrimido[5,4-e][1,3]thiazin-7-yl)amino)-2-methoxyphenyl)piperazine-1-carboxylate To a stirred solution of 3-(2,6-dichlorophenyl)-7-(methylthio)-2,3-dihydro-4H-pyrimido[5,4-e][1,3]thiazin-4-one (120 mg, 0.335 mmol, 1.0 eq) in (2.0 mL) of toluene was added m-CPBA (165 mg, 0.670 mmol, 2.0 eq) and allowed to stir at rt for 30 minutes. tert-butyl 4-(4-amino-2-methoxyphenyl)piperazine-1-carboxylate (114 mg, 0.368 mmol, 1.1 eq) and DIPEA (0.233 mL, 1.34 mmol, 4.0 eq) were added and allowed to stir at rt for overnight. After completion of reaction, the reaction mixture was diluted with water (20 mL) and extracted with EtOAc (20 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl 4-(4-(((3-(2,6-dichlorophenyl)-4-oxo-3,4-dihydro-2H-pyrimido[5,4-e][1,3]thiazin-7-yl)amino)-2-methoxyphenyl)piperazine-1-carboxylate (110 mg, 53.39%) as off white solid.

LCMS: 617.4 [M+1]$^+$

Step-2: Synthesis of 3-(2,6-dichlorophenyl)-7-((3-methoxy-4-(piperazin-1-yl)phenyl)amino)-2,3-dihydro-4H-pyrimido[5,4-e][1,3]thiazin-4-one Hydrochloride tert-butyl 4-(4-(((3-(2,6-dichlorophenyl)-4-oxo-3,4-dihydro-2H-pyrimido[5,4-e][1,3]thiazin-7-yl)amino)-2-methoxyphenyl)piperazine-1-carboxylate (110 mg, 0.178 mmol, 1.0 eq) was dissolved in 4.0 M-HCl (1.5 mL) and allowed to stir at rt for 1 h. After completion of reaction, the reaction mixture was filtered and dried under reduced pressure to afford the desired compound 3-(2,6-dichlorophenyl)-7-((3-methoxy-4-(piperazin-1-yl)phenyl)amino)-2,3-dihydro-4H-pyrimido[5,4-e][1,3]thiazin-4-one hydrochloride (98 mg, 99.21%) as yellow solid.

LCMS: 517.2 [M+1]$^+$; UPLC @ 254 nm=95.31% and @ 220 nm=93.36%.

$^1$H NMR (400 MHz, DMSO-d$_6$) δ 10.31 (s, 1H), 9.00 (brs, 2H), 8.81 (s, 1H), 7.65 (d, J=8.33 Hz, 2H), 7.48 (t, J=7.89 Hz, 2H), 7.27 (d, J=9.21 Hz, 1H), 6.93 (d, J=8.33 Hz, 1H), 5.24 (s, 2H), 3.79 (s, 3H), 3.22 (brs, 4H), 3.16 (brs, 4H).

Example S90. Synthesis of 3-(2-chloro-6-fluorophenyl)-7-((4,4-dimethyl-1,2,3,4-tetrahydroisoquinolin-7-yl)amino)-2,3-dihydro-4H-pyrimido[5,4-e][1,3]thiazin-4-one (Compound No. 1.238)

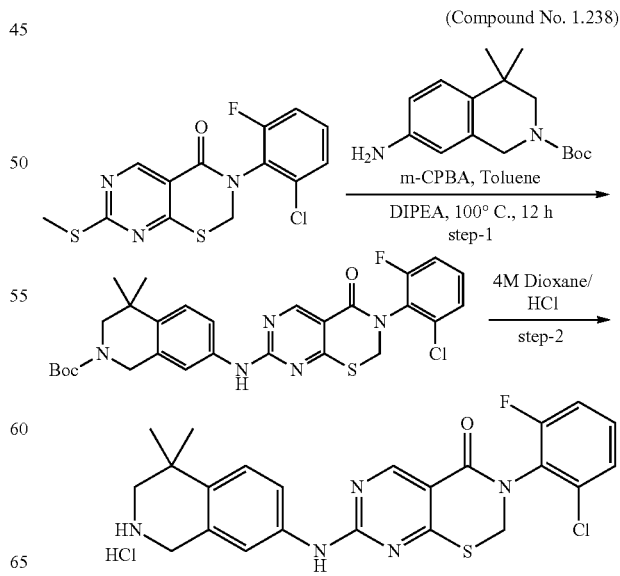

Step-1: Synthesis of tert-butyl 7-((3-(2-chloro-6-fluorophenyl)-4-oxo-3,4-dihydro-2H-pyrimido[5,4-e][1,3]thiazin-7-yl)amino)-4,4-dimethyl-3,4-dihydroisoquinoline-2(1H)-carboxylate To a stirred solution of 3-(2-chloro-6-fluorophenyl)-7-(methylthio)-2,3-dihydro-4H-pyrimido[5,4-e][1,3]thiazin-4-one (170 mg, 0.5 mmol, 1.0 eq) in (5.0 mL) of toluene was added m-CPBA (173 mg, 1 mmol, 2.0 eq) and allowed to stir at rt for 30 minutes. tert-butyl 7-amino-4,4-dimethyl-3,4-dihydroisoquinoline-2(1H)-carboxylate (152 mg, 0.55 mmol, 1.1 eq) and DIPEA (0.36 mL, 2 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((3-(2-chloro-6-fluorophenyl)-4-oxo-3,4-dihydro-2H-pyrimido[5,4-e][1,3]thiazin-7-yl)amino)-4,4-dimethyl-3,4-dihydroisoquinoline-2(1H)-carboxylate (80 mg, 28%) as an off white solid.

LCMS: 570.4 [M+1]$^+$

Step-2: Synthesis of 3-(2-chloro-6-fluorophenyl)-7-((4,4-dimethyl-1,2,3,4-tetrahydroisoquinolin-7-yl)amino)-2,3-dihydro-4H-pyrimido[5,4-e][1,3]thiazin-4-one tert-butyl 7-((3-(2-chloro-6-fluorophenyl)-4-oxo-3,4-dihydro-2H-pyrimido[5,4-e][1,3]thiazin-7-yl)amino)-4,4-dimethyl-3,4-dihydroisoquinoline-2(1H)-carboxylate (80 mg, 0.14 mmol, 1.0 eq) was dissolved in dioxane (1 mL), followed by dropwise addition of 4.0 M-HCl (0.5 mL) and allowed to stir at rt for 1 h. After completion of reaction, the reaction mixture was filtered and dried under reduced pressure to afford the crude product and the desired compound, 3-(2-chloro-6-fluorophenyl)-7-((4,4-dimethyl-1,2,3,4-tetrahydroisoquinolin-7-yl)amino)-2,3-dihydro-4H-pyrimido[5,4-e][1,3]thiazin-4-one is obtained by prep HPLC (12 mg, 30.16%) as light brown solid.

LCMS: 470.2 [M+1]$^+$; UPLC @ 254 nm=93.49% and @ 220 nm=89.67%.

$^1$H NMR (400 MHz, DMSO-d$_6$): δ 10.30 (br. s., 1H), 8.80 (s, 1H), 8.17 (br. s., 1H), 7.50 (br. s., 2H), 7.42 (br. s., 1H), 7.34 (d, J=7.45 Hz, 2H), 5.30 (d, J=13.15 Hz, 1H), 5.22 (d, J=12.72 Hz, 1H), 3.93 (br. s., 2H), 2.82 (br. s., 2H), 1.24 (s, 6H).

Example S91. Synthesis of 5-((3-(2,6-dichlorophenyl)-4-oxo-3,4-dihydro-2H-pyrimido[5,4-e][1,3]thiazin-7-yl)amino)-2-(4-(dimethylamino)piperidin-1-yl)benzonitrile (Compound No. 1.239)

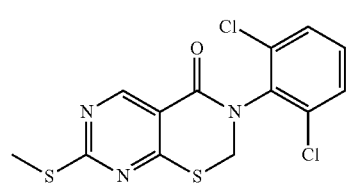

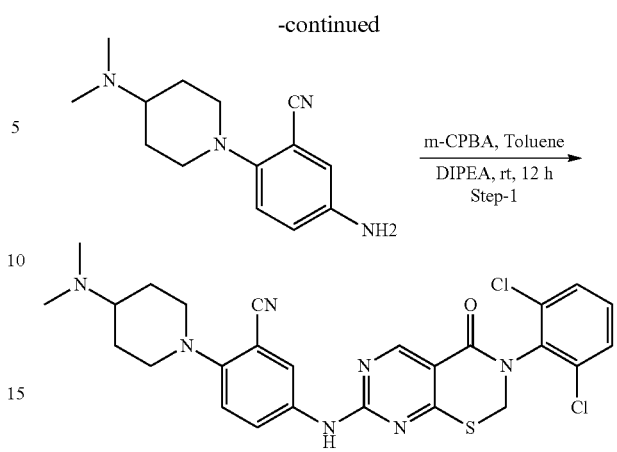

To a stirred solution of 3-(2,6-dichlorophenyl)-7-(methylthio)-2,3-dihydro-4H-pyrimido[5,4-e][1,3]thiazin-4-one (150 mg, 0.418 mmol, 1.0 eq) in (2.0 mL) of toluene was added m-CPBA (206 mg, 0.836 mmol, 2.0 eq) and allowed to stir at rt for 30 minutes. 5-amino-2-(4-(dimethylamino)piperidin-1-yl)benzonitrile (123 mg, 0.502 mmol, 1.1 eq) and DIPEA (0.29 mL, 1.672 mmol, 4.0 eq) were added and allowed to stir at rt for overnight. After completion of reaction, the reaction mixture was diluted with water (20 mL) and extracted with EtOAc (20 mL×2). Combined organic layer was washed with water (50 mL) brine solution (50 mL), dried over anhydrous sodium sulfate and concentrated under reduced pressure to afford crude product, which was purified by reverse phase chromatography to afford the desired 5-((3-(2,6-dichlorophenyl)-4-oxo-3,4-dihydro-2H-pyrimido[5,4-e][1,3]thiazin-7-yl)amino)-2-(4-(dimethylamino)piperidin-1-yl)benzonitrile (5.0 mg, 2.15%) as off white solid.

LCMS: 554.2 [M+1]$^+$; UPLC @ 254 nm=99.03% and @ 220 nm=97.82%.

$^1$H NMR (400 MHz, DMSO-d$_6$) δ 10.54 (brs, 1H), 9.62 (brs, 1H), 8.85 (brs, 1H), 8.06 (brs, 1H), 7.88 (brs, 1H), 7.66 (d, J=7.89 Hz, 2H), 7.49 (d, J=8.33 Hz, 1H), 7.24 (d, J=9.65 Hz, 1H), 5.27 (brs, 2H), 4.34 (s, 1H), 2.79-2.67 (m, 6H), 2.12 (brs, 4H), 1.77 (d, J=12.28 Hz, 4H).

Example S92. Synthesis of 7-(3-chloro-4-(4-(dimethylamino)piperidin-1-yl)phenylamino)-3-(2,6-dichlorophenyl)-2H-pyrimido[5,4-e][1,3]thiazin-4(3H)-one (Compound No. 1.240)

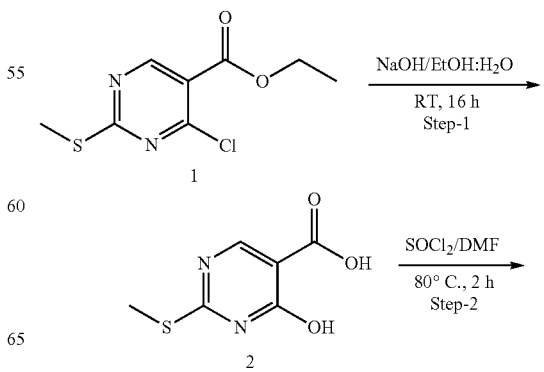

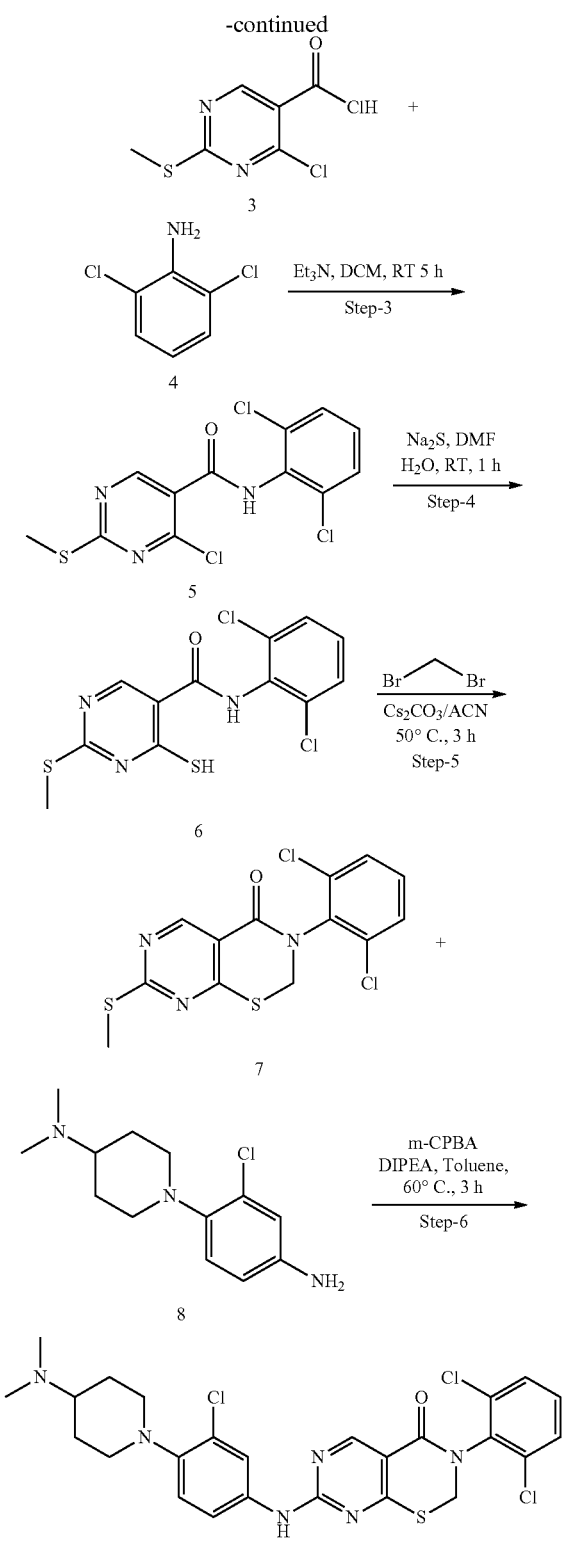

Step-1: Synthesis of 4-hydroxy-2-(methylthio)pyrimidine-5-carboxylic Acid

To a stirred solution of ethyl 4-chloro-2-(methylthio) pyrimidine-5-carboxylate (5 g, 21.425 mmol, 1 eq) in EtOH (25 mL) was added a solution of NaOH (8.38 g, 214.25 mol, 10 eq) in water (25 mL) and the resultant mixture was stirred at RT for 16 h. The progress of the reaction was monitored by TLC. After completion, the reaction mixture was acidified using 2N—HCl (5 mL) to obtain a precipitate was filtered, washed with water and dried to give 4-hydroxy-2-(methylthio)pyrimidine-5-carboxylic acid (2.7 g, 67.5%) as a white solid.

LCMS: 187 [M+1]$^+$

Step-2: Synthesis of 4-chloro-2-(methylthio)pyrimidine-5-carbonyl Chloride

To a stirred solution of 4-hydroxy-2-(methylthio)pyrimidine-5-carboxylic acid (2.5 g, 13.44 mmol, 1 eq) in DMF (2.5 mL) was added SOCl$_2$ (10 mL) and the resultant mixture was heated at 100° C. for 2 h. After completion, the mixture was cooled to RT was then concentrated in vacuo to give 4-chloro-2-(methylthio)pyrimidine-5-carbonyl chloride (2.65 g, 83.59%) as an off-white solid.

LCMS: 224 [M+1]$^+$

Step-3: Synthesis of 4-chloro-N-(2,6-dichlorophenyl)-2-(methylthio)pyrimidine-5-carboxamide To a stirred solution of 2,6-dichloroaniline (1.92 g, 11.8 mmol, 1 eq) in DCM (20 mL) was added Et$_3$N (4.96 mL, 35.6 mmol, 3 eq) followed by the addition of 4-chloro-2-(methylthio)pyrimidine-5-carbonyl chloride (2.65 g, 11.8 mmol, 1 eq) in DCM (20 mL). The resultant mixture was stirred at RT for 5 h. The progress of the reaction was monitored by TLC. After completion, the reaction mixture was diluted with water (50 mL) and extracted with DCM (50 mL×3). The combined organic layers were dried over Na$_2$SO$_4$, filtered and concentrated to afford 4-chloro-N—(2,6-dichlorophenyl)-2-(methylthio)pyrimidine-5-carboxamide (1.9 g, 47%) which was used in the next step without further purification.

LCMS: 349 [M+1]$^+$

Step-4: Synthesis of N-(2,6-dichlorophenyl)-4-mercapto-2-(methylthio)pyrimidine-5-carboxamide To a stirred solution of 4-chloro-N-(2,6-dichlorophenyl)-2-(methylthio)pyrimidine-5-carboxamide (1.3 g, 5.72 mmol, 1 eq) in DMF (20 mL)—water (10 mL) was added Na$_2$S (0.582 g, 4.47 mmol, 1.2 eq) at RT and the resultant mixture was stirred for 1 h. The progress of the reaction was monitored by TLC. After completion, the mixture was diluted with water (50 mL) and extracted with DCM (100 mL×2). The combined organic layers were dried over Na$_2$SO$_4$, filtered and concentrated to obtain a crude residue which was purified by column chromatography compound eluting at 50% EtOAc/hexane to afford N-(2,6-dichlorophenyl)-4-mercapto-2-(methylthio)pyrimidine-5-carboxamide (0.35 g, 27.13%) as an off-white solid.

LCMS: 347 [M+1]$^+$

Step-5: Synthesis of 3-(2,6-dichlorophenyl)-7-(methylthio)-2H-pyrimido[5,4-e][1,3]thiazin-4(3H)-one To a stirred solution N-(2,6-dichlorophenyl)-4-mercapto-2-(methylthio)pyrimidine-5-carboxamide (0.35 g, 1.011 mmol, 1 eq) in acetonitrile (5 mL) and added Cs$_2$CO$_3$ (1.3 g, 4.043 mmol, 4 eq) at RT and the mixture was stirred for 10 min. Dibromomethane (0.263 g, 1.516 mmol, 3 eq) was then added and the mixture and the mixture was stirred at 50° C. for 3 h. The progress of the reaction was monitored by TLC. After completion, the mixture was diluted with water (20 mL) and then extracted with EtOAc (20 mL×3). The combined organic layers were washed with brine (25 mL), dried over Na$_2$SO$_4$, filtered and concentrated to afford 3-(2,6-dichlorophenyl)-7-(methylthio)-2H-pyrimido[5,4-e][1,3]thiazin-4(3H)-one (0.2 g, 55.24%) as an off-white solid which was taken to next step without further purification.

LCMS: 359 [M+1]$^+$ (d, J=8.33 Hz, 1H), 5.15 (s, 2H), 3.48 (br. s., 3H), 2.74-2.86 (m, 8H), 2.14 (br. s., 2H), 1.92 (br. s., 2H)

Example S93. Synthesis of 3-(2,6-dichlorophenyl)-7-((2,4,4-trimethyl-1,2,3,4-tetrahydroisoquinolin-7-yl)amino)-2,3-dihydro-4H-pyrimido[5,4-e][1,3]thiazin-4-one (Compound No. 1.241)

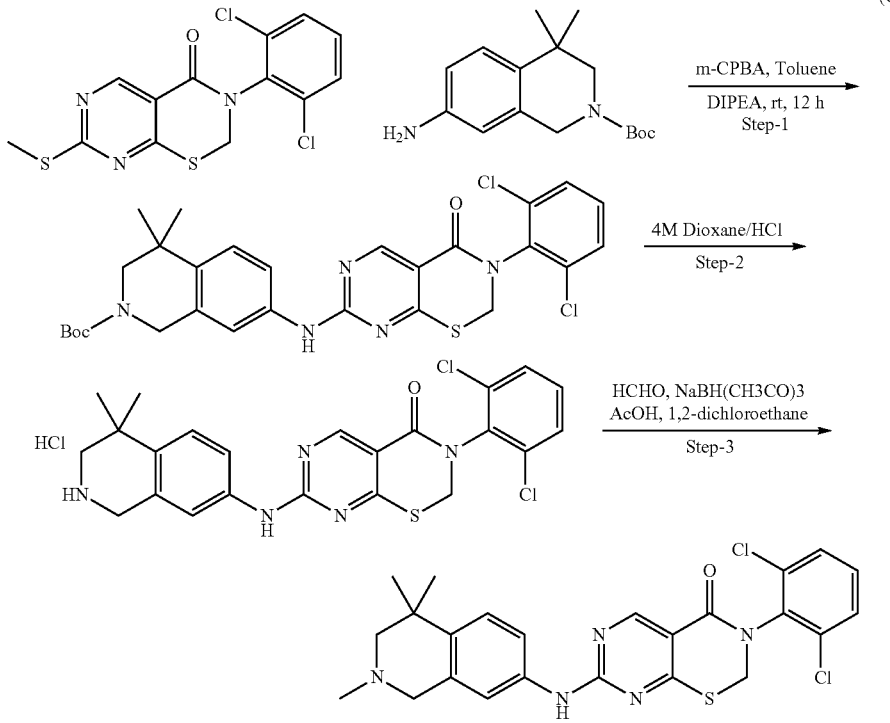

Step-6: Synthesis of 7-(3-chloro-4-(4-(dimethyl-amino)piperidin-1-yl)phenylamino)-3-(2,6-dichloro-phenyl)-2H-pyrimido[5,4-e][1,3]thiazin-4(3H)-one To a stirred solution of 3-(2,6-dichlorophenyl)-7-(methylthio)-2H-pyrimido[5,4-e][1,3]thiazin-4(3H)-one (100 mg, 0.279 mmol, 1 eq) in toluene (5 mL) was added m-CPBA (96.33 mg, 0.558 mmol, 2 eq) at 0° C. and mixture was stirred at RT for 1 h. DIPEA (0.25 mL, 1.395 mmol, 5 eq) and 1-(4-amino-2-chlorophenyl)-N,N-dimethylpiperidin-4-amine (77.7 mg, 0.334 mmol, 1 eq) were then successively added to the mixture and the mixture was heated at 60° C. for 3 h. The progress of the reaction was monitored by TLC. After completion, the mixture was diluted with water (20 mL) and then extracted with EtOAc (20 mL×3). The combined organic layers were washed with brine (25 mL), dried over Na$_2$SO$_4$, filtered and concentrated to afford crude which was purified by reversed-phase HPLC to afford 7-(3-chloro-4-(4-(dimethylamino)piperidin-1-yl)phenylamino)-3-(2,6-dichlorophenyl)-2H-pyrimido[5,4-e][1,3]thiazin-4(3H)-one (1 mg, 0.46%) as an off white solid.

LCMS: 564 [M+1]$^+$ $^1$H NMR: (400 MHz, MeOD-d$_4$) δ 8.86 (s, 1H), 7.88 (d, J=2.63 Hz, 1H), 7.52-7.62 (m, 3H), 7.39-7.45 (m, 1H), 7.14

Step-1: Synthesis of tert-butyl 7-((3-(2,6-dichloro-phenyl)-4-oxo-3,4-dihydro-2H-pyrimido[5,4-e][1,3]thiazin-7-yl)amino)-4,4-dimethyl-3,4-dihydroisoqui-noline-2(1H)-carboxylate To a stirred solution of 3-(2,6-dichlorophenyl)-7-(methylthio)-2,3-dihydro-4H-pyrimido[5,4-e][1,3]thiazin-4-one (300 mg, 0.837 mmol, 1.0 eq) in (2.0 mL) of toluene was added mCPBA (413 mg, 1.674 mmol, 2.0 eq) and allowed to stir at rt for 30 minutes. tert-butyl 7-amino-4,4-dimethyl-3,4-dihydroisoquinoline-2(1H)-carboxylate (278 mg, 1.005 mmol, 1.2 eq) and DIPEA (0.581 mL, 3.348 mmol, 4.0 eq) were added and allowed to stir at 100° C. for overnight. After completion of reaction, the reaction mixture was diluted with water (20 mL) and extracted with EtOAc (20 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl 7-((3-(2,6-dichlorophenyl)-4-oxo-3,4-dihydro-2H-pyrimido[5,4-e][1,3]thiazin-7-yl)amino)-4,4-dimethyl-3,4-dihydroisoquinoline-2(1H)-carboxylate (260 mg, 52.95%) as brown solid.

LCMS: 586.4 [M+1]$^+$

Step-2: Synthesis of 3-(2,6-dichlorophenyl)-7-((4,4-dimethyl-1,2,3,4-tetrahydroisoquinolin-7-yl)amino)-2,3-dihydro-4H-pyrimido[5,4-e][1,3]thiazin-4-one Hydrochloride tert-butyl 7-((3-(2,6-dichlorophenyl)-4-oxo-3,4-dihydro-2H-pyrimido[5,4-e][1,3]thiazin-7-yl)amino)-4,4-dimethyl-3,4-dihydroisoquinoline-2(1H)-carboxylate (260 mg, 0.443 mmol, 1.0 eq) was dissolved in 4.0 M-HCl (2.0 mL) and allowed to stir at rt for 1 h. After completion of reaction, the reaction mixture was filtered and dried under reduced pressure to afford the desired compound 3-(2,6-dichlorophenyl)-7-((4,4-dimethyl-1,2,3,4-tetrahydroisoquinolin-7-yl)amino)-2,3-dihydro-4H-pyrimido[5,4-e][1,3]thiazin-4-one hydrochloride (220 mg, 95.23%) as brown solid.

LCMS: 486.2 [M+1]$^+$

Step-3:—Synthesis of 3-(2,6-dichlorophenyl)-7-((2,4,4-trimethyl-1,2,3,4-tetrahydroisoquinolin-7-yl)amino)-2,3-dihydro-4H-pyrimido[5,4-e][1,3]thiazin-4-one To a stirred solution of 3-(2,6-dichlorophenyl)-7-((4,4-dimethyl-1,2,3,4-tetrahydroisoquinolin-7-yl)amino)-2,3-dihydro-4H-pyrimido[5,4-e][1,3]thiazin-4-one hydrochloride (220 mg, 0.42 mmol, 1.0 eq) and HCHO (0.063 mL, 0.841 mmol, 2.0 eq) in 1,2-dichloroethane (10 mL) was dropwise added acetic acid (0.025 mL, 0.42 mmol, 1.0 eq) at 0° C. The resulting mixture was stirred at rt for 1 h followed by addition of NaBH(CH$_3$CO)$_3$ (98 mg, 0.462 mmol, 1.1 eq) at 0° C. The resulting mixture was stirred at rt for 1 h. The progress of reaction was monitored by LCMS. The resection mixture was concentrated, basified with saturated solution of NaHCO$_3$ (50 mL) extracted with EtOAc (2×50 mL). The combined organic extracts were washed with water (50 mL), with brine (50 mL) dried over Na$_2$SO$_4$ and concentrated under reduced and purified by combi flash chromatography to afford the desired compound 3-(2,6-dichlorophenyl)-7-((2,4,4-trimethyl-1,2,3,4-tetrahydroisoquinolin-7-yl)amino)-2,3-dihydro-4H-pyrimido[5,4-e][1,3]thiazin-4-one (35 mg, 16.66%) as white solid.

LCMS: 500.2 [M+1]$^+$; UPLC @ 254 nm=96.66% and @ 220 nm=96.84%.

$^1$H NMR (400 MHz, DMSO-d$_6$) δ 10.28 (brs, 1H), 8.79 (s, 1H), 7.65 (d, J=8.33 Hz, 2H), 7.41-7.54 (m, 2H), 7.26-7.36 (m, 2H), 5.24 (s, 2H), 3.43 (brs, 2H), 2.32 (brs, 5H), 1.23 (s, 6H).

Example S94. Synthesis of 3-(2,6-dichlorophenyl)-7-(4-(4-(dimethylamino)piperidin-1-yl)-3-methoxyphenylamino)-2H-pyrimido[5,4-e][1,3]thiazin-4(3H)-one 2,2,2-trifluoroacetic Acid (Compound No. 1.242)

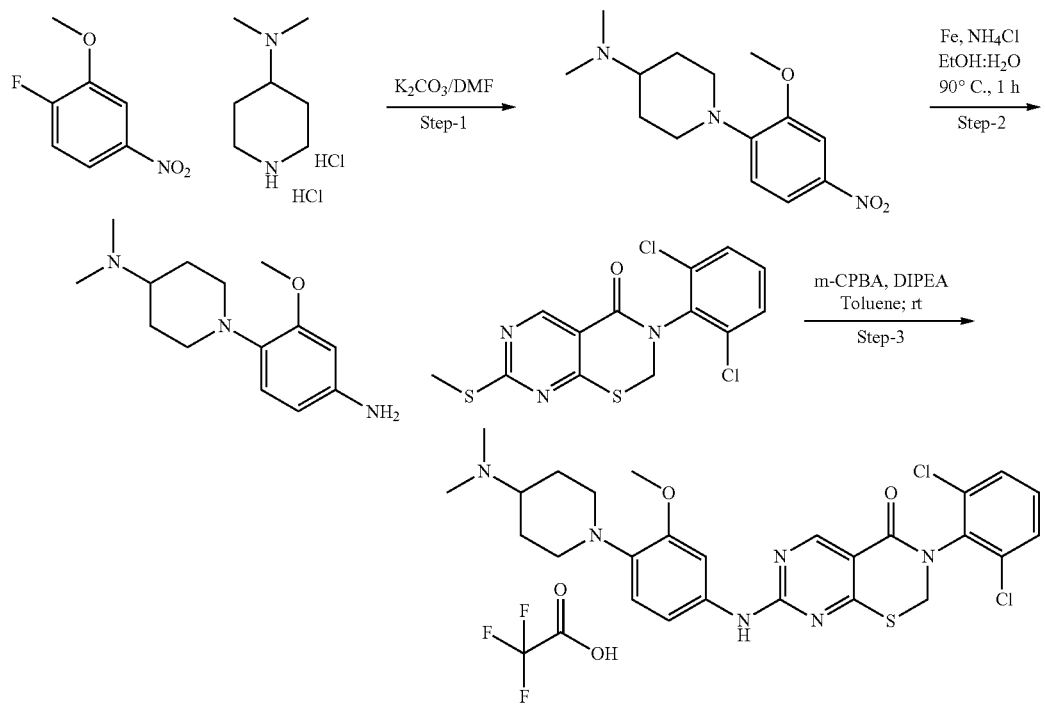

Step-1: Synthesis of 1-(2-methoxy-4-nitrophenyl)-N,N-dimethylpiperidin-4-amine To a stirred solution of 1-fluoro-2-methoxy-4-nitrobenzene (1.0 g, 5.843 mmol, 1.0 eq) and N,N-dimethylpiperidin-4-amine dihydrochloride (1.40 g, 7.012 mmol, 1.2 eq) in DMF (10 mL) was added potassium carbonate (2.42 g, 17.529 mmol, 2.0 eq) at rt. The resulting mixture was stirred at 90° C. for overnight. The progress of reaction was monitored by LCMS. The reaction mixture was poured into ice cold water (100 mL), extracted with EtOAc (2×50 mL). The combined organic extracts were washed with water (50 mL), with brine (50 mL) dried over $Na_2SO_4$ and concentrated under reduced pressure to afford mixture of desired compound 1-(2-methoxy-4-nitrophenyl)-N,N-dimethylpiperidin-4-amine (1.6 g, 98.15%) as yellow viscous.

LCMS: 280.2 [M+1]$^+$

Step-2: Synthesis of 1-(4-amino-2-methoxyphenyl)-N,N-dimethylpiperidin-4-amine

To a stirred solution of 1-(2-methoxy-4-nitrophenyl)-N,N-dimethylpiperidin-4-amine (1.6 g, 5.727 mmol, 1.0 eq) in EtOH (25 mL) was added Fe (2.56 g, 45.622 mmol, 8.0 eq) and a solution of $NH_4Cl$ (3.0 g, 57.27 mmol, 10.0 eq) in water (25 mL) at rt. The resulting mixture was heated at 90° C. for 60 min. The progress of reaction was monitored by LCMS. The reaction mixture was filtered through celite the residue was washed with EtOH (50 mL) the filtrate was concentrated and the residue was dissolved in EtOAc (50 mL), washed with water (2×50 mL), dried over $Na_2SO_4$, and concentrated to afford the desired 1-(4-amino-2-methoxyphenyl)-N,N-dimethylpiperidin-4-amine (1.10 g, 77.46%) as brown solid.

LCMS: 250.1 [M+1]$^+$

Step-3: Synthesis of 3-(2,6-dichlorophenyl)-7-(4-(4-(dimethylamino)piperidin-1-yl)-3-methoxyphenylamino)-2H-pyrimido[5,4-e][1,3]thiazin-4(3H)-one 2,2,2-trifluoroacetic Acid To a stirred solution of 3-(2,6-dichlorophenyl)-7-(methylthio)-2,3-dihydro-4H-pyrimido[5,4-e][1,3]thiazin-4-one (160 mg, 0.446 mmol, 1.0 eq) in (5.0 mL) of toluene was added mCPBA (220 mg, 0.892 mmol, 2.0 eq) and allowed to stir at rt for 30 minutes. 1-(4-amino-2-methoxyphenyl)-N,N-dimethylpiperidin-4-amine (134 mg, 0.536 mmol, 1.2 eq) and DIPEA (0.31 mL, 1.784 mmol, 4.0 eq) were added and allowed to stir at rt for overnight. The reaction mixture was diluted with water (50 mL) and extracted with EtOAc (2×50 mL), the combined organic layers were washed with water (50 mL) with brine (50 mL) dried over $Na_2SO_4$, filtered and concentrated and purified by reverse phase chromatography to afford the desired compound 3-(2,6-dichlorophenyl)-7-((4-(4-(dimethylamino)piperidin-1-yl)phenyl)amino)-2,3-dihydro-4H-pyrimido[5,4-e][1,3]thiazin-4-one 2,2,2-trifluoroacetic acid (32 mg, 11.11%) as off yellow solid.

LCMS: 559.3 [M+1]$^+$; UPLC @ 254 nm=98.95% and @ 220 nm=98.80%.

$^1$H NMR (400 MHz, DMSO-$d_6$) δ 10.31 (s, 1H), 9.99 (brs, 1H), 8.81 (s, 1H), 7.65 (d, J=7.89 Hz, 2H), 7.48 (t, J=8.11 Hz, 2H), 7.26 (d, J=8.77 Hz, 1H), 6.98 (brs, 1H), 5.25 (s, 2H), 3.80 (s, 3H), 3.48 (d, J=11.40 Hz, 2H), 3.27 (brs, 1H), 2.78 (d, J=4.82 Hz, 6H), 2.67 (brs, 1H), 2.08 (d, J=11.40 Hz, 2H), 1.83 (brs, 2H).

Example S95. Synthesis of 7-((3-chloro-4-(2-methylpiperazin-1-yl)phenyl)amino)-3-(2,6-dichlorophenyl)-2,3-dihydro-4H-pyrimido[5,4-e][1,3]thiazin-4-one Dihydrochloride (Compound No. 1.243)

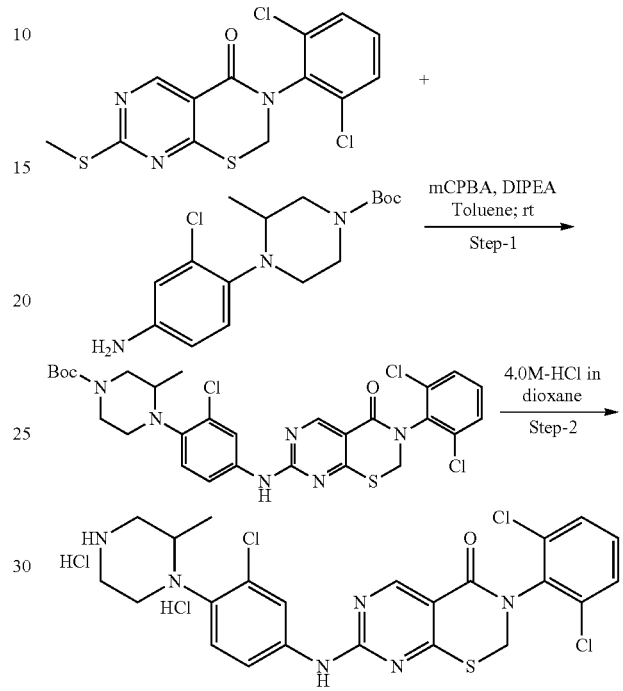

Step-1: Synthesis of tert-butyl 4-(2-chloro-4-((3-(2,6-dichlorophenyl)-4-oxo-3,4-dihydro-2H-pyrimido[5,4-e][1,3]thiazin-7-yl)amino)phenyl)-3-methylpiperazine-1-carboxylate To a stirred solution of 3-(2,6-dichlorophenyl)-7-(methylthio)-2,3-dihydro-4H-pyrimido[5,4-e][1,3]thiazin-4-one (200 mg, 0.558 mmol, 1.0 eq) in (3.0 mL) of toluene was added mCPBA (275 mg, 1.116 mmol, 2.0 eq) and allowed to stir at rt for 30 minutes. tert-butyl 4-(4-amino-2-chlorophenyl)-3-methylpiperazine-1-carboxylate (200 mg, 0.615 mmol, 1.1 eq) and DIPEA (0.387 mL, 2.232 mmol, 4.0 eq) were added and allowed to stir at rt for overnight. The reaction mixture was diluted with water (50 mL) and extracted with EtOAc (2×50 mL), the combined organic layers were washed with water (50 mL) with brine (50 mL) dried over $Na_2SO_4$, filtered and concentrated and purified by combi flash chromatography [silic gel 100-200 mesh; elution 0-40% EtOAc in Hexane] to afford the desired compound tert-butyl 4-(2-chloro-4-((3-(2,6-dichlorophenyl)-4-oxo-3,4-dihydro-2H-pyrimido[5,4-e][1,3]thiazin-7-yl)amino)phenyl)-3-methylpiperazine-1-carboxylate (60 mg, 16.90%) as brown solid.

LCMS: 635.1 [M+1]$^+$

Step-2: Synthesis of 7-((3-chloro-4-(2-methylpiperazin-1-yl)phenyl)amino)-3-(2,6-dichlorophenyl)-2,3-dihydro-4H-pyrimido[5,4-e][1,3]thiazin-4-one Dihydrochloride tert-butyl 4-(2-chloro-4-((3-(2,6-dichlorophenyl)-4-oxo-3,4-dihydro-2H-pyrimido[5,4-e][1,3]thiazin-7-yl)amino)

phenyl)-3-methylpiperazine-1-carboxylate (60 mg, 0.095 mmol, 1.0 eq) was dissolved in 4.0 M-HCl (2.0 mL) and allowed to stir at rt for 2 h. After completion of reaction, the reaction mixture was filtered and dried under reduced pressure to afford the desired compound 7-((3-chloro-4-(2-methylpiperazin-1-yl)phenyl)amino)-3-(2,6-dichlorophenyl)-2,3-dihydro-4H-pyrimido[5,4-e][1,3]thiazin-4-one dihydrochloride (22 mg, 38.58%) as brown solid.

LCMS: 535.1 [M+1]$^+$; UPLC @ 254 nm=93.38% and @ 220 nm=93.54%.

$^1$H NMR (400 MHz, DMSO-d$_6$) 310.55 (s, 1H), 8.96 (brs, 2H), 8.86 (s, 1H), 7.93 (d, J=2.19 Hz, 1H), 7.71 (brs, 1H), 7.66 (d, J=7.89 Hz, 2H), 7.49 (d, J=7.89 Hz, 1H), 7.30 (d, J=8.33 Hz, 1H), 5.27 (s, 2H), 3.36 (d, J=15.79 Hz, 2H), 3.28 (brs, 2H), 3.12 (d, J=10.52 Hz, 2H), 2.90 (brs, 2H), 2.82 (brs, 2H), 0.88 (d, J=6.14 Hz, 3H).

Example S96. Synthesis of 7-((3-chloro-4-(3-methylpiperazin-1-yl)phenyl)amino)-3-(2,6-dichlorophenyl)-2,3-dihydro-4H-pyrimido[5,4-e][1,3]thiazin-4-one Dihydrochloride (Compound No. 1.244)

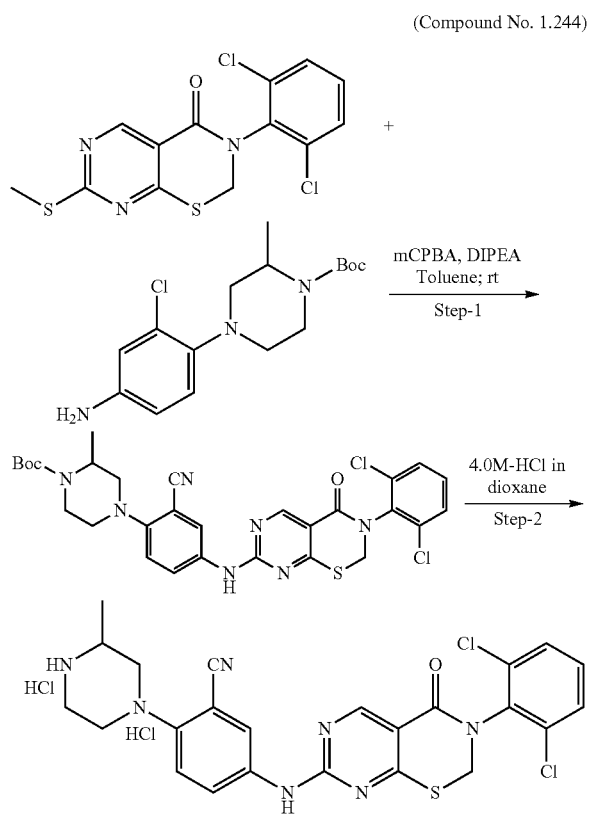

Step-1: Synthesis of tert-butyl 4-(2-chloro-4-((3-(2,6-dichlorophenyl)-4-oxo-3,4-dihydro-2H-pyrimido[5,4-e][1,3]thiazin-7-yl)amino)phenyl)-2-methylpiperazine-1-carboxylate To a stirred solution of 3-(2,6-dichlorophenyl)-7-(methylthio)-2,3-dihydro-4H-pyrimido[5,4-e][1,3]thiazin-4-one (200 mg, 0.558 mmol, 1.0 eq) in (3.0 mL) of toluene was added mCPBA (275 mg, 1.116 mmol, 2.0 eq) and allowed to stir at rt for 30 minutes. tert-butyl 4-(4-amino-2-chlorophenyl)-2-methylpiperazine-1-carboxylate (200 mg, 0.615 mmol, 1.1 eq) and DIPEA (0.387 mL, 2.232 mmol, 4.0 eq) were added and allowed to stir at rt for overnight. The reaction mixture was diluted with water (50 mL) and extracted with EtOAc (2×50 mL), the combined organic layers were washed with water (50 mL) with brine (50 mL) dried over Na$_2$SO$_4$, filtered and concentrated and purified by combi flash chromatography [silic gel 100-200 mesh; elution 0-40% EtOAc in Hexane] to afford the desired compound tert-butyl 4-(2-chloro-4-((3-(2,6-dichlorophenyl)-4-oxo-3,4-dihydro-2H-pyrimido[54-e][1,3]thiazin-7-yl)amino)phenyl)-2-methylpiperazine-1-carboxylate (120 mg, 33.80%) as brown solid.

LCMS: 635.2 [M+1]$^+$

Step-2: Synthesis of 7-((3-chloro-4-(3-methylpiperazin-1-yl)phenyl)amino)-3-(2,6-dichlorophenyl)-2,3-dihydro-4H-pyrimido[5,4-e][1,3]thiazin-4-one Dihydrochloride)

tert-butyl 4-(2-chloro-4-((3-(2,6-dichlorophenyl)-4-oxo-3,4-dihydro-2H-pyrimido[5,4-e][1,3]thiazin-7-yl)amino)phenyl)-2-methylpiperazine-1-carboxylate (120 mg, 0.199 mmol, 1.0 eq) was dissolved in 4.0 M-HCl (2.0 mL) and allowed to stir at rt for 2 h. After completion of reaction, the reaction mixture was filtered and dried under reduced pressure to afford the desired compound 7-((3-chloro-4-(3-methylpiperazin-1-yl)phenyl)amino)-3-(2,6-dichlorophenyl)-2,3-dihydro-4H-pyrimido[5,4-e][1,3]thiazin-4-one dihydrochloride (59 mg, 51.75%) as yellow solid.

LCMS: 535.1 [M+1]$^+$; UPLC @ 254 nm=94.22% and @ 220 nm=92.83%.

$^1$H NMR (400 MHz, DMSO-d$_6$) δ 10.49 (s, 1H), 9.23 (brs, 1H), 8.84 (s, 1H), 7.90 (d, J=2.63 Hz, 1H), 7.65 (d, J=7.89 Hz, 3H), 7.45-7.54 (m, 1H), 7.23 (d, J=8.77 Hz, 1H), 5.26 (s, 2H), 3.38 (d, J=11.40 Hz, 3H), 3.30 (d, J=12.28 Hz, 2H), 3.15 (d, J=10.52 Hz, 2H), 2.90-3.00 (m, 1H), 2.80 (d, J=11.84 Hz, 1H), 1.29 (d, J=6.58 Hz, 3H).

Example S97. Synthesis 7-((3-chloro-4-(4-(dimethylamino)piperidin-1-yl)phenyl)amino)-3-(2-chloro-6-fluorophenyl)-2,3-dihydro-4H-pyrimido[5,4-e][1,3]thiazin-4-one (Compound No. 1.245)

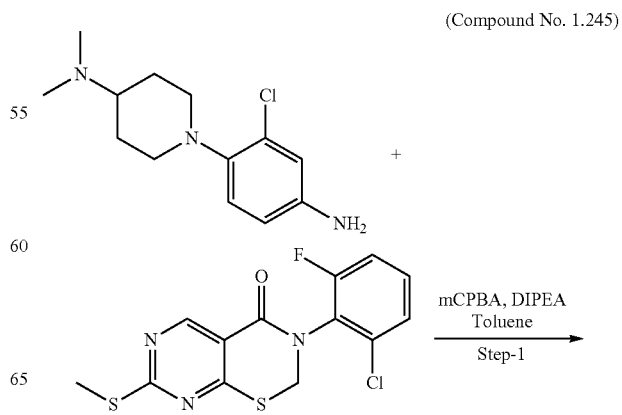

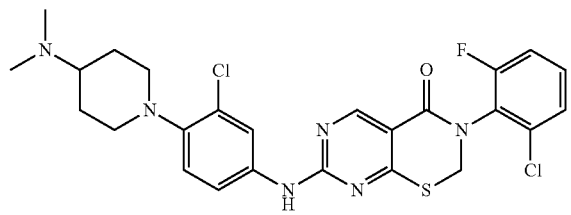

To a stirred solution of 3-(2-chloro-6-fluorophenyl)-7-(methylthio)-2,3-dihydro-4H-pyrimido[5,4-e][1,3]thiazin-4-one (170 mg, 0.5 mmol, 1.0 eq) in (2.0 mL) of toluene was added m-CPBA (123 mg, 1 mmol, 2.0 eq) and allowed to stir at rt for 30 minutes. 1-(4-amino-2-chlorophenyl)-N,N-dimethylpiperidin-4-amine (147 mg, 0.6 mmol, 1.2 eq) and DIPEA (0.44 mL, 2.5 mmol, 5.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by preparative chromatography to afford the desired compound, 7-((3-chloro-4-(4-(dimethylamino)piperidin-1-yl)phenyl)amino)-3-(2-chloro-6-fluorophenyl)-2,3-dihydro-4H-pyrimido[5,4-e][1,3]thiazin-4-one (15 mg, 6.7%) as an off white solid (formate salt).

LCMS; 547.3 [M+1]$^+$; UPLC @ 254 nm=89.38% and @ 220 nm=90.42%.

$^1$H NMR (400 MHz, DMSO-d$_6$) δ 10.43 (brs, 1H), 8.82 (s, 1H), 8.37 (brs, 2H), 7.84 (d, J=2.63 Hz, 1H), 7.61 (d, J=7.02 Hz, 1H), 7.46-7.55 (m, 2H), 7.39-7.46 (m, 1H), 7.15 (d, J=8.77 Hz, 1H), 5.16-5.35 (m, 2H), 3.26 (d, J=11.40 Hz, 3H), 2.59-2.69 (m, 2H), 2.22 (s, 6H), 1.84 (d, J=11.40 Hz, 2H), 1.55 (d, J=8.33 Hz, 2H)

Example S98. Synthesis of 3-(2,6-dichlorophenyl)-7-((1,1-dimethyl-1,2,3,4-tetrahydroisoquinolin-6-yl)amino)-2,3-dihydro-4H-pyrimido[5,4-e][1,3]thiazin-4-one (Compound No. 1.246)

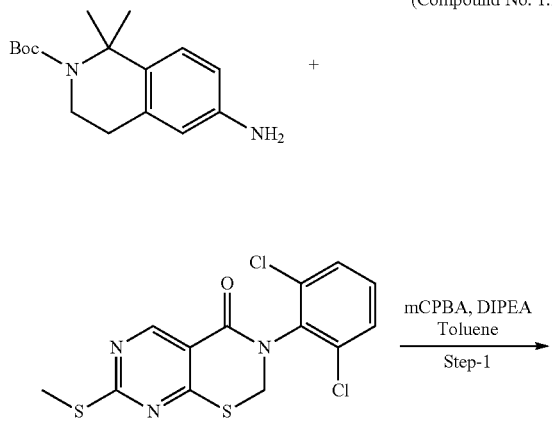

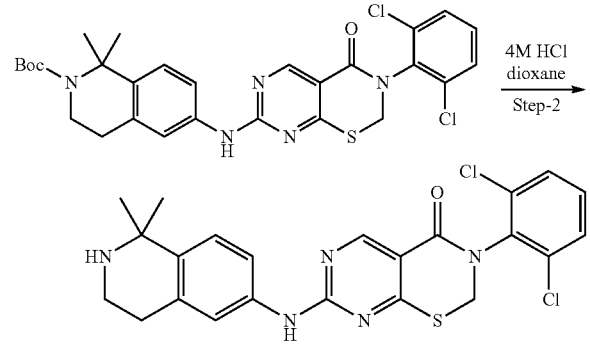

Step-1: Synthesis tert-butyl 6-((3-(2,6-dichlorophenyl)-4-oxo-3,4-dihydro-2H-pyrimido[5,4-e][1,3]thiazin-7-yl)amino)-1,1-dimethyl-3,4-dihydroisoquinoline-2(1H)-carboxylate To a stirred solution of 3-(2,6-dichlorophenyl)-7-(methylthio)-2,3-dihydro-4H-pyrimido[5,4-e][1,3]thiazin-4-one (143 mg, 0.4 mmol, 1.0 eq) in of toluene (2.0 mL) was added m-CPBA (108 mg, 0.44 mmol, 1.1 eq) and allowed to stir at rt for 30 minutes. tert-butyl 6-amino-1,1-dimethyl-3,4-dihydroisoquinoline-2(1H)-carboxylate (121 mg, 0.44 mmol, 1.1 eq) and DIPEA (0.28 mL, 0.28 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl 6-((3-(2,6-dichlorophenyl)-4-oxo-3,4-dihydro-2H-pyrimido[5,4-e][1,3]thiazin-7-yl)amino)-1,1-dimethyl-3,4-dihydroisoquinoline-2(1H)-carboxylate (40 mg, 17.1%) as an off white solid.

LCMS: 486.2 [M+1]$^+$

Step-2: Synthesis of 3-(2,6-dichlorophenyl)-7-((1,1-dimethyl-1,2,3,4-tetrahydroisoquinolin-6-yl)amino)-2,3-dihydro-4H-pyrimido[5,4-e][1,3]thiazin-4-one tert-butyl 6-((3-(2,6-dichlorophenyl)-4-oxo-3,4-dihydro-2H-pyrimido[5,4-e][1,3]thiazin-7-yl)amino)-1,1-dimethyl-3,4-dihydroisoquinoline-2(1H)-carboxylate (40 mg, 0.068 mmol, 1 eq) was dissolved in dioxane (0.4 mL), followed by dropwise addition of 4.0 M-HCl (0.4 mL) and allowed to stir at rt for 1 h. After completion of reaction, the reaction mixture was filtered and dried to give 3-(2,6-dichlorophenyl)-7-((1,1-dimethyl-1,2,3,4-tetrahydroisoquinolin-6-yl)amino)-2,3-dihydro-4H-pyrimido[5,4-e][1,3]thiazin-4-one (10 mg, 30.3%) as off white solid.

LCMS: 486.2 [M+1]$^+$; UPLC @ 254 nm=92.57% and @ 220 nm=95.39%.

$^1$H NMR (400 MHz, DMSO-d$_6$): δ 10.44 (s, 1H), 9.12 (brs, 2H), 8.83 (s, 1H), 7.65 (d, J=8.33 Hz, 2H), 7.44-7.58 (m, 2H), 7.40 (d, J=8.33 Hz, 1H), 5.26 (s, 2H), 3.48 (s, 2H), 3.01 (brs, 2H), 1.64 (s, 6H).

Example S99. Synthesis of (S)-3-(2,6-dichlorophenyl)-7-(4-(2-methylpiperazin-1-yl)phenylamino)-2H-pyrimido[5,4-e][1,3]oxazin-4(3H)-one (Peak-II)

(Compound No. 1.172)

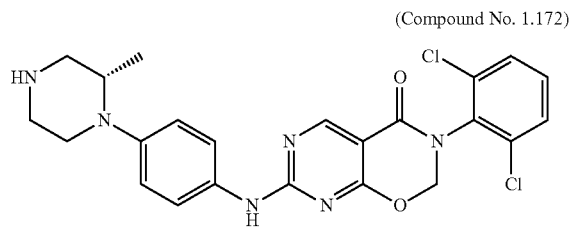 [SMILES: C[C@H]1CNCCN1c1ccc(Nc2ncc3c(n2)OCN(c2c(Cl)cccc2Cl)C3=O)cc1]

Synthesis of (S)-3-(2,6-dichlorophenyl)-7-(4-(2-methylpiperazin-1-yl)phenylamino)-2H-pyrimido[5,4-e][1,3]oxazin-4(3H)-one (Peak-II)

(S)-3-(2,6-dichlorophenyl)-7-(4-(2-methylpiperazin-1-yl)phenylamino)-2H-pyrimido[5,4-e][1,3]oxazin-4(3H)-one was separated from the product synthesized in the scheme described in Example S26.

Example S100. Synthesis of (R)-7-((3-chloro-4-(3-methylpiperazin-1-yl)phenyl)amino)-3-(2,6-dichlorophenyl)-2,3-dihydro-4H-pyrimido[5,4-e][1,3]oxazin-4-one (170 mg, 0.5 mmol, 1.0 eq) in of toluene (5.0 mL) was added m-CPBA (247 mg, 1.0 mmol, 2.0 eq) and allowed to stir at rt for 30 minutes. tert-butyl (R)-4-(4-amino-2-chlorophenyl)-2-methylpiperazine-1-carboxylate (180 mg, 0.55 mmol, 1.1 eq) and DIPEA (0.44 mL, 2.5 mmol, 5.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired tert-butyl (R)-4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate (60 mg, 19.3%) as light brown sticky liquid.

LCMS: 619.3 [M+1]$^+$

Step-2: Synthesis of (R)-7-((3-chloro-4-(3-methylpiperazin-1-yl)phenyl)amino)-3-(2,6-dichlorophenyl)-2,3-dihydro-4H-pyrimido[5,4-e][1,3]oxazin-4-one tert-butyl (R)-4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate (60 mg, 0.096 mmol, 1 eq) was dissolved in dioxane (0.4 mL), followed by dropwise addition of 4.0 M-HCl (0.4 mL) and allowed to stir at rt for 1 h. After completion of reaction, the (Compound No. 1.919)

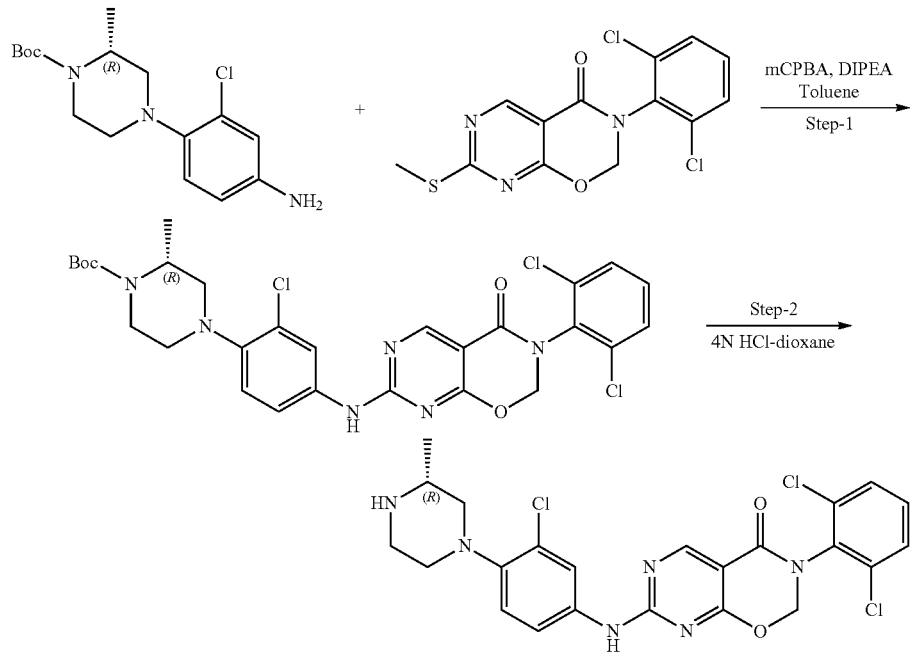

Step-1: tert-butyl (R)-4-(2-chloro-4-((3-(2,6-dichlorophenyl)-4-oxo-3,4-dihydro-2H-pyrimido[5,4-e][1,3]oxazin-7-yl)amino)phenyl)-2-methylpiperazine-1-carboxylate To a stirred solution of 3-(2,6-dichlorophenyl)-7-(methylthio)-2,3-dihydro-4H-pyrimido[5,4-e][1,3]oxazin-4-one reaction mixture was filtered and purified by preparative chromatography to give (R)-7-((3-chloro-4-(3-methylpiperazin-1-yl)phenyl)amino)-3-(2,6-dichlorophenyl)-2,3-dihydro-4H-pyrimido[5,4-e][1,3]oxazin-4-one (7 mg, 21.21%) as an off white solid.

LCMS: 519.3/521.3 [M+1]$^+$; UPLC @ 254 nm=95.97% and @ 220 nm=97.56%.

$^1$H NMR (400 MHZ, DMSO-D$_6$): δ10.44 (S, 1H) 8.85 (BR. S., 1H) 7.89 (BR. S., 1H) 7.59-7.70 (M, 1H) 7.59 (BR. S., 1H) 7.52 (BR. S., 1H) 7.12 (D, J=8.31 HZ, 1H) 5.74 (BR. S., 2H) 4.11 (S, 1H) 3.16 (BR. S., 3H) 3.06 (D, J=9.29 HZ, 2H) 2.89 (BR. S., 2H) 2.84 (BR. S., 2H) 2.26-2.34 (M, 2H).

Compounds 1.66-1.95, 1.97-1.171 and 1.177-1.222 can be prepared according to the experimental details exemplified in Examples S1-S70 and Scheme 1, using the appropriate starting materials and reagents.

Other compounds can be prepared according to the experimental details exemplified in Examples S1-S100 and Scheme 1 to Scheme 3, using the appropriate starting materials and reagents.

Biological Examples

Example B1. WEE1 IC$_{50}$ Determination

IC$_{50}$ values of compounds against WEE1 kinase enzyme were determined by LanthaScreen™ Terbium Labeled TR-FRET assay. Kinase assays were performed in 1× kinase buffer (# PV6135, Invitrogen, Life Technologies Grand Island, N.Y.) where total reaction volume was 10 μl in low-volume 384-well plates (#4511, Corning). Serially diluted compounds (3-fold) were incubated with WEE1 Enzyme (1 nM) (# PR7373A, Invitrogen, Life Technologies Grand Island, N.Y.) for 10 min, following which a mixture of ATP (10 M) (# A1852, Sigma, St-Louis, Mo.) and fluorescent-PolyGT substrate (200 nM) (# PV3610, Invitrogen, Life Technologies Grand Island, N.Y.) was added and incubated in dark at room temperature for 1 h. After 1 h, 10 μl stop solution containing Terbium labeled antibody (4 nM) (# PV3529, Invitrogen, Life Technologies Grand Island, N.Y.) and EDTA (# E5134, Sigma, St-Louis, Mo.) (20 mM) in TR-FRET dilution buffer (# PV3574, Invitrogen, Life Technologies Grand Island, N.Y.) was added. Readings were taken in a Synergy Neo Plate reader (BioTek, Winooski) at single excitation of 340 nm and Dual emission at 495 nm and 520 nm respectively.

The % activity of test samples was calculated as (Sample−Min)*100/(Max−Min). [Max: DMSO control, complete reaction with enzyme & DMSO and Min: No enzyme & DMSO]. Percent inhibition (100−% activity) was fitted to the "four-parameter logistic model" in XLfit for determination of IC$_{50}$ values. The results are shown in Table 2.

TABLE 2

| Synthesis Example No. | Compound No. | Enzyme Activity Wee1 IC$_{50}$ (μM) |
|---|---|---|
| S-1 | 1.1 | 0.056 |
| S-2 | 1.2 | 3.26 |
| S-3 | 1.3 | 0.04 |
| S-4 | 1.4 | 0.009 |
| S-5 | 1.5 | 0.069 |
| S-6 | 1.6 | 0.279 |
| S-7 | 1.7 | 0.074 |
| S-8 | 1.8 | 0.162 |
| S-9 | 1.9 | 0.193 |
| S-10 | 1.10 | 0.011 |
| S-11 | 1.11 | 0.837 |
| S-12 | 1.12 | 0.0735 |
| S-13 | 1.13 | 0.1437 |
| S-14 | 1.14 | 0.173 |
| S-15 | 1.15 | 1.558 |
| S-16 | 1.16 | 0.049 |
| S-17 | 1.17 | 0.156 |
| S-18 | 1.18 | 0.192 |

TABLE 2-continued

| Synthesis Example No. | Compound No. | Enzyme Activity Wee1 IC$_{50}$ (μM) |
|---|---|---|
| S-19 | 1.19 | 0.206 |
| S-20 | 1.20 | 0.048 |
| S-21 | 1.21 | 1.389 |
| S-22 | 1.22 | 0.03 |
| S-23 | 1.23 | 0.607 |
| S-24 | 1.24 | 0.035 |
| S-25 | 1.25 | 0.068 |
| S-26 | 1.26 | 0.088 |
| S-27 | 1.27 | 0.052 |
| S-28 | 1.28 | 0.035 |
| S-29 | 1.29 | 0.212 |
| S-30 | 1.30 | 0.325 |
| S-31 | 1.31 | 30 |
| S-32 | 1.32 | 0.366 |
| S-33 | 1.33 | 0.05 |
| S-34 | 1.34 | 0.014 |
| S-35 | 1.35 | 0.035 |
| S-36 | 1.36 | 0.104 |
| S-37 | 1.37 | 0.113 |
| S-38 | 1.38 | 0.176 |
| S-39 | 1.39 | 0.54 |
| S-40 | 1.40 | 0.02 |
| S-41 | 1.41 | 0.791 |
| S-42 | 1.42 | 0.025 |
| S-43 | 1.43 | 0.479 |
| S-44 | 1.44 | 0.023 |
| S-45 | 1.45 | 0.288 |
| S-46 | 1.46 | 0.053 |
| S-47 | 1.47 | 0.07 |
| S-48 | 1.48 | 0.103 |
| S-49 | 1.49 | 0.041 |
| S-50 | 1.50 | 0.028 |
| S-51 | 1.51 | 0.011 |
| S-52 | 1.52 | 0.0505 |
| S-53 | 1.53 | 0.033 |
| S-54 | 1.54 | 0.2 |
| S-55 | 1.55 | 0.106 |
| S-56 | 1.56 | >5 |
| S-57 | 1.57 | 0.101 |
| S-58 | 1.58 | 0.234 |
| S-59 | 1.59 | >5 |
| S-60 | 1.60 | 0.0435 |
| S-61 | 1.61 | 0.11 |
| S-62 | 1.62 | 0.123 |
| S-63 | 1.63 | >5 |
| S-64 | 1.64 | >5 |
| S-65 | 1.65 | 1.332 |
| S-66 | 1.96 | 0.047 |
| S-67 | 1.173 | 0.087 |
| S-68 | 1.174 | 0.032 |
| S-69 | 1.175 | 0.066 |
| S-70 | 1.176 | 0.105 |
| S-71 | 1.87 | 0.777 |
| S-72 | 1.104 | >5 |
| S-73 | 1.107 | 0.110 |
| S-74 | 1.223 | 0.032 |
| S-75 | 1.121 | 0.501 |
| S-76 | 1.224 | 0.232 |
| S-77 | 1.225 | 0.282 |
| S-78 | 1.226 | 0.188 |
| S-79 | 1.227 | 0.021 |
| S-80 | 1.228 | 0.127 |
| S-81 | 1.229 | 0.185 |
| S-82 | 1.230 | 0.561 |
| S-83 | 1.231 | 0.142 |
| S-84 | 1.232 | 0.273 |
| S-85 | 1.233 | 0.165 |
| S-86 | 1.234 | 0.202 |
| S-87 | 1.235 | 0.111 |
| S-88 | 1.236 | 0.335 |
| S-89 | 1.237 | ND |
| S-90 | 1.238 | 0.045 |
| S-91 | 1.239 | 0.508 |
| S-92 | 1.240 | 0.303 |
| S-93 | 1.241 | 0.095 |
| S-94 | 1.242 | 0.331 |

TABLE 2-continued

| Synthesis Example No. | Compound No. | Enzyme Activity Wee1 IC$_{50}$ (µM) |
|---|---|---|
| S-95 | 1.243 | 0.948 |
| S-96 | 1.244 | 0.351 |
| S-97 | 1.245 | 0.297 |
| S-98 | 1.246 | 0.061 |
| S-99 | 1.172 | 0.066 |
| S-100 | 1.919 | 0.340 |

ND: Not Determined

Example B2. Determination of Potency of Compounds in Cytotoxicity Assay in A427, a 172, A549, Panc-10.05, MDAMB231 and As-Pc-1 Cell Lines A549 (CCL-185; ATCC) and A427 (HTB-53; ATCC), both lung epithelial cell lines were seeded in their respective medium (DMEM/MEM, 10569044/41090101; Gibco) at a cell count of 1500 cells per 100 µL per well in a 96 well edge plate (167425; ThermoFisher). Cells were allowed to grow at 37° C. for 24 hr in 5% $CO_2$ environment (culture conditions) in a Nuaire incubator (humidified). Serially diluted test compounds (100 µL) within the desired testing concentration ranges were added to the culture plate were further incubated in culture conditions for 72 hr and 96 hr for A427 and A549 respectively. The experiment was terminated at the designated incubation time by replacing the medium with 100 µL of 1 mM of resazurin (R7017; Sigma) prepared in respective culture medium, and the plates were further incubated in culture conditions for 4-6 hr. Fluorescence was recorded using a multimodal plate reader (Biotek Synergy Neo) at an excitation wavelength of 535 nm and emission wavelength of 590 nm to obtain relative fluorescence units. Data analysis was done by subtracting the background fluorescence (only medium blank) value from each reading and then normalizing with the vehicle control (DMSO treated cells) to obtain percent survival/proliferation. Percent survival was then subtracted by 100 to get the percent inhibition of proliferation which was used to calculate IC$_{50}$ values. Potency of compounds in other cell lines (As-Pc-1, Panc-10.05, MDAMB231, A172) was determined in an analogous manner. The results are shown in Table 3.

TABLE 3

| Synthesis Example No. | Compound No. | Cell Viability A427 IC$_{50}$ (µM) | Cell Viability A549 IC$_{50}$ (µM) | Cell Viability A172 IC$_{50}$ (µM) | Cell Viability Panc 10.05 IC$_{50}$ (µM) | Cell Viability MDAMB 231 IC$_{50}$ (µM) | Cell Viability AsPC-1 IC$_{50}$ (µM) |
|---|---|---|---|---|---|---|---|
| S-1 | 1.1 | 4.47 | 9.7 | ND | ND | ND | ND |
| S-2 | 1.2 | ND | ND | ND | ND | ND | ND |
| S-3 | 1.3 | 4.52 | 2.99 | ND | ND | ND | ND |
| S-4 | 1.4 | ND | 5.74 | ND | ND | ND | ND |
| S-5 | 1.5 | 3.91 | 3.78 | ND | ND | ND | ND |
| S-6 | 1.6 | ND | ND | ND | ND | ND | ND |
| S-7 | 1.7 | ND | ND | ND | ND | ND | ND |
| S-8 | 1.8 | ND | ND | ND | ND | ND | ND |
| S-9 | 1.9 | ND | ND | ND | ND | ND | ND |
| S-10 | 1.10 | 1.99 | 2.6 | ND | ND | ND | ND |
| S-11 | 1.11 | ND | ND | ND | ND | ND | ND |
| S-12 | 1.12 | 3.5825 | 4.7025 | 7.135 | 3.17 | 9.045 | 7.875 |
| S-13 | 1.13 | ND | ND | ND | ND | ND | ND |
| S-14 | 1.14 | ND | ND | ND | ND | ND | ND |
| S-15 | 1.15 | ND | ND | ND | ND | ND | ND |
| S-16 | 1.16 | 2.13 | 3.98 | ND | ND | ND | ND |
| S-17 | 1.17 | ND | ND | ND | ND | ND | ND |
| S-18 | 1.18 | ND | ND | ND | ND | ND | ND |
| S-19 | 1.19 | ND | ND | ND | ND | ND | ND |
| S-20 | 1.20 | 5.5 | 6.02 | ND | ND | ND | ND |
| S-21 | 1.21 | ND | ND | ND | ND | ND | ND |
| S-22 | 1.22 | ND | ND | ND | ND | ND | ND |
| S-23 | 1.23 | ND | ND | ND | ND | ND | ND |
| S-24 | 1.24 | 2.96 | 6.45 | ND | ND | ND | ND |
| S-25 | 1.25 | ND | ND | ND | ND | ND | ND |
| S-26 | 1.26 | ND | ND | ND | ND | ND | ND |
| S-27 | 1.27 | 6.97 | 4.39 | ND | ND | ND | ND |
| S-28 | 1.28 | ND | ND | ND | ND | ND | ND |
| S-29 | 1.29 | ND | 8.88 | ND | ND | ND | ND |
| S-30 | 1.30 | ND | 8.65 | ND | ND | ND | ND |
| S-31 | 1.31 | ND | ND | ND | ND | ND | ND |
| S-32 | 1.32 | ND | 7.43 | ND | ND | ND | ND |
| S-33 | 1.33 | 2.82 | 2.69 | ND | ND | ND | ND |
| S-34 | 1.34 | 4.81 | 21.02 | ND | ND | ND | ND |
| S-35 | 1.35 | ND | 11.1 | ND | ND | ND | ND |
| S-36 | 1.36 | 10.4 | 8.12 | ND | ND | ND | ND |
| S-37 | 1.37 | ND | 9.82 | ND | ND | ND | ND |
| S-38 | 1.38 | ND | 9.15 | ND | ND | ND | ND |
| S-39 | 1.39 | ND | 10.45 | ND | ND | ND | ND |
| S-40 | 1.40 | 2.65 | 2.73 | ND | ND | ND | ND |
| S-41 | 1.41 | ND | >30 | ND | ND | ND | ND |
| S-42 | 1.42 | 3.2 | 5.6 | ND | ND | ND | ND |
| S-43 | 1.43 | ND | 22.09 | ND | ND | ND | ND |
| S-44 | 1.44 | ND | 5.79 | ND | ND | ND | ND |
| S-45 | 1.45 | ND | >30 | ND | ND | ND | ND |

TABLE 3-continued

| Synthesis Example No. | Compound No. | Cell Viability A427 IC$_{50}$ (μM) | Cell Viability A549 IC$_{50}$ (μM) | Cell Viability A172 IC$_{50}$ (μM) | Cell Viability Panc 10.05 IC$_{50}$ (μM) | Cell Viability MDAMB 231 IC$_{50}$ (μM) | Cell Viability AsPC-1 IC$_{50}$ (μM) |
|---|---|---|---|---|---|---|---|
| S-46 | 1.46 | ND | 9.86 | ND | ND | ND | ND |
| S-47 | 1.47 | 7.1 | 4.1 | ND | ND | ND | ND |
| S-48 | 1.48 | 11.06 | 8.38 | ND | ND | ND | ND |
| S-49 | 1.49 | 5.42 | 4.39 | ND | ND | ND | ND |
| S-50 | 1.50 | 3.48 | 2.79 | ND | ND | ND | ND |
| S-51 | 1.51 | 3.0425 | 6.4525 | 7.995 | 3.34 | 8.76 | 3.21 |
| S-52 | 1.52 | 3.345 | 4.72 | ND | ND | ND | ND |
| S-53 | 1.53 | 3.6125 | 4.7225 | 9.675 | 9.335 | 10.47 | 2.41 |
| S-54 | 1.54 | 10.48 | 9.575 | ND | ND | ND | ND |
| S-55 | 1.55 | 2.32 | 1.59 | ND | ND | ND | ND |
| S-56 | 1.56 | 10.465 | 1.86 | ND | ND | ND | ND |
| S-57 | 1.57 | 4.855 | 6.23 | ND | ND | ND | ND |
| S-58 | 1.58 | 7.115 | 12.35 | ND | ND | ND | ND |
| S-59 | 1.59 | 13.99 | ND | ND | ND | ND | ND |
| S-60 | 1.60 | 2.5825 | 8.335 | 4.8 | 2.85 | 5.34 | 2.905 |
| S-61 | 1.61 | 4.12 | ND | ND | ND | ND | ND |
| S-62 | 1.62 | 2.80 | ND | ND | ND | ND | ND |
| S-63 | 1.63 | ND | ND | ND | ND | ND | ND |
| S-64 | 1.64 | ND | ND | ND | ND | ND | ND |
| S-65 | 1.65 | ND | ND | ND | ND | ND | ND |
| S-66 | 1.96 | 5.89 | ND | ND | ND | ND | ND |
| S-67 | 1.173 | 3.32 | ND | ND | ND | ND | ND |
| S-68 | 1.174 | 3.4 | ND | ND | ND | ND | ND |
| S-69 | 1.175 | 22 | ND | ND | ND | ND | ND |
| S-70 | 1.176 | 3.25 | ND | ND | ND | ND | ND |
| S-71 | 1.87 | 25.43 | ND | ND | ND | ND | ND |
| S-72 | 1.104 | 27.75 | ND | ND | ND | ND | ND |
| S-73 | 1.107 | 7.70 | ND | ND | ND | ND | ND |
| S-74 | 1.223 | 1.66 | ND | ND | ND | ND | ND |
| S-75 | 1.121 | 7.33 | ND | ND | ND | ND | ND |
| S-76 | 1.224 | 12.10 | ND | ND | ND | ND | ND |
| S-77 | 1.225 | 2.16 | ND | ND | ND | ND | ND |
| S-78 | 1.226 | 5.36 | ND | ND | ND | ND | ND |
| S-79 | 1.227 | 2.1975 | 9.035 | 6.615 | 4.93 | 8.78 | 2.935 |
| S-80 | 1.228 | 1.46 | ND | ND | ND | ND | ND |
| S-81 | 1.229 | 2.25 | ND | ND | ND | ND | ND |
| S-82 | 1.230 | 4.94 | ND | ND | ND | ND | ND |
| S-83 | 1.231 | 2.23 | ND | ND | ND | ND | ND |
| S-84 | 1.232 | 1.12 | ND | ND | ND | ND | ND |
| S-85 | 1.233 | 7.21 | ND | ND | ND | ND | ND |
| S-86 | 1.234 | 4.84 | ND | ND | ND | ND | ND |
| S-87 | 1.235 | 2.90 | ND | ND | ND | ND | ND |
| S-88 | 1.236 | 1.77 | ND | ND | ND | ND | ND |
| S-89 | 1.237 | ND | ND | ND | ND | ND | ND |
| S-90 | 1.238 | 5.29 | ND | ND | ND | ND | ND |
| S-91 | 1.239 | 0.765 | ND | ND | ND | ND | ND |
| S-92 | 1.240 | 1.64 | ND | ND | ND | ND | ND |
| S-93 | 1.241 | 3.49 | ND | ND | ND | ND | ND |
| S-94 | 1.242 | 1.62 | ND | ND | ND | ND | ND |
| S-95 | 1.243 | 0.625 | ND | ND | ND | ND | ND |
| S-96 | 1.244 | 0.510 | ND | ND | ND | ND | ND |
| S-97 | 1.245 | 1.14 | ND | ND | ND | ND | ND |
| S-98 | 1.246 | 2.44 | ND | ND | ND | ND | ND |
| S-99 | 1.172 | 4.90 | ND | ND | ND | ND | ND |

ND: Not Determined

Example B3. Determination of Potency of Compounds in Cell Proliferation Assay in Selected Cancer Cell Lines and Cellular PD Effects The effects of test compounds were studied in five cell lines with various histotypes. The cancer cells (Table 4) were harvested during the logarithmic growth period and counted. Adjust cell concentrations to the appropriated number with respective medium, and add 90 μL cell suspensions to 96-well plates. After cells were seeded, the plates were shaken gently to distribute cells evenly and incubated at 37° C., 5% CO$_2$ on day 1.

TABLE 4

Cell Culture Conditions

| No. | Cell Line | Histopathology | Medium |
|---|---|---|---|
| 1 | A427 | Lung adenocarcinoma | MEM + 10% FBS + NEAA + Sodium Pyruvate |
| 2 | LoVo | Colorectal adenocarcinoma | Ham's F12K + 10% FBS |
| 3 | NCI-H460 | Large-cell lung carcinoma | RPMI1640 + 10% FBS |
| 4 | HCT-116 | Colorectal carcinoma | McCoy's 5a + 10% FBS |
| 5 | A2780 | Ovarian cancer | RPMI1640 + 10% FBS |

Cells were treated with test compounds at 9 concentrations within a desired concentration range (e.g. 1.5 nM-10

μM) on day 2 by series diluting the test compound stock solution (10 mM in DMSO) with culture medium. Cell viability was assessed by Cell Titer-Glo® as recommended by Promega (Cat. No.: G7572, Promega) typically 72 hrs post-treatment.

Cell viability data were plotted using GraphPad Prism (version 5, GraphPad Software, Inc., San Diego, Calif.). In addition, a nonlinear regression model with a sigmoidal dose response and variable slope within GraphPad Prism was used to calculate the $IC_{50}$ value of individual test compounds.

TABLE 5

| Compound No. | $IC_{50}$ (μM) | | | | |
|---|---|---|---|---|---|
| | LOVO | HCT116 | NCI-H460 | A427 | A2780 |
| 1.3 | 8.263 | 8.121 | >10 | 5.983 | ND[a] |
| 1.5 | ND | ND | ND | 4.291 | ND |
| 1.10 | ND | ND | ND | 1.665 | 3.847 |
| 1.12 | ND | ND | ND | 3.425 | ND |
| 1.16 | ND | ND | ND | 3.038 | ND |
| 1.20 | ND | ND | ND | 3.639 | ND |
| 1.24 | ND | ND | ND | 2.845 | ND |
| 1.27 | ND | ND | ND | 7.748 | ND |
| 1.55 | ND | ND | ND | ND | 6.805 |

ND means Not Determined

Additional test compounds will be studied in the same and/or other cancer cell lines with various sensitivities to reported Wee1 compounds using similar proliferation method with possible variables, such as cell seeding densities and/or incubation durations.

Example B4. Determination of Potency of Compounds by Assay of Cellular PD Effects pCDC2 and γ-H2AX are two clinical relevant biomarkers associated with Wee1 inhibition. CDC2Y15 phosphorylation in cells was reported to be abolished by Wee1 inhibitors (reference: Gavory G et. al., Almac Discovery, AACR poster, 2016). γ-H2AX, a DNA doublestrand break marker, was upregulated by Wee1 treatment in Wee1 sensitive cell lines (Guertin A D et al., Molecular Cancer Therapeutics, 2013). The effects of selected test compounds on pCDC2 and γ-H2AX will be assessed in selected cancer cell lines post 24 or 48 hr treatment using Western blotting methods with selective antibodies (Guertin A D et al., Molecular Cancer Therapeutics, 2013).

Changes in the levels of phospho-CDC2 following treatment of cells with test compounds are assessed by enzyme-linked immunosorbent assay (ELISA) or Western blotting. A427 cells (or other suitable cell line) are plated in 6-well plates and cultured for 24 hr to approximately 80-90% confluency. Medium is then replaced, and the cells are treated with test compound at several different concentrations as well as vehicle control. After incubation of treated cells in cell culture conditions for a specified time (e.g., 24 hr), cells are rinsed with ice-cold PBS and lysed in 1× cell lysis buffer containing protease inhibitors and phosphatase inhibitors. The cells are scraped from the plate with a cell scraper after a brief incubation on ice and transferred to a centrifuge tube, and then subjected to three freeze-thaw cycles in liquid nitrogen and a 37° C. water bath for further lysis. The lysates are centrifuged to pellet cell debris (using, for example, a 10 min centrifugation of 2000×g at 4° C.) and the supernatants transferred to fresh tubes on ice. The protein concentrations of the samples are estimated by the Bradford method or equivalent. The ELISA is carried out with the PathScan® Phospho-CDC2 (Tyr15) Sandwich ELISA Kit (Cat. #7176, Cell Signaling Technology, Danvers, Mass.) or similar product according to the manufacturer's instructions. Changes in the levels of phospho-CDC2 may alternatively or additionally be analyzed by Western blotting of the samples using a primary antibody to phospho-CDC2 such as phospho-CDC2 (Tyr15) (10A11) rabbit mAb (Cat. #4539, Cell Signaling Technology) or rabbit polyclonal anti-CDK1 (phospho Y15) antibody (Cat. # ab47594, Abcam, Cambridge, United Kingdom).

Example B5. Determination of Activity of Compounds in Cancer Cells in Combination with Various DNA-Damaging Agents The activity of test compounds in combination with cisplatin in A427 cells was determined. Cells were seeded in a 96 well plate at 2000 cells/well. The next day, cells were treated with 2.5 μM cisplatin or vehicle (1×PBS) and incubated in culture conditions (37° C., 5% $CO_2$) for 24 hr. Following the incubation, culture medium was replaced with medium containing test compound and cisplatin/vehicle, and cells were further incubated in culture conditions for another 72 hr. By this procedure, cisplatin was either continued or discontinued after an initial 24-hr incubation. Addition of test compound was in concentrations needed to obtain an 8-point dose response curve, with concentrations prepared by 3-fold dilution. The assay was terminated upon addition of resazurin, incubation for 4 hr in culture conditions and measurement of fluorescence at excitation and emission wavelengths of 535 and 590 nm, respectively. Assay results are shown in Table 6.

It was reported that MK-1775 (aka AZD-1775), a potent and selective small molecule inhibitor of Wee1, in combination with gemcitabine, carboplatin, or cisplatin abolished the phosphorylation of CDC2 at Tyr15 residue and abrogate the DNA damage checkpoint, leading to apoptosis (Hirai H et al. Mol Cancer Ther 2009; 8:2992-3000, Small-molecule inhibition of Wee1 kinase by MK-1775 selectively sensitizes p53-deficient tumor cells to DNA-damaging agents).

Various cancer cell lines with p53 mutation will be studied by co-incubation of test compound and one of the various DNA-damaging agents, such as pemetrexed, doxorubicin, camptothecin, mitomycin C, gemcitabine, and 5-FU, etc. The anti-proliferation effects of the DNA-damaging agents will be evaluated in the presence or absence of individual test compound using CTG assays described in Example B3. The concentrations of test compounds in the combination studies will be selected based on the anti-cell proliferation effects of test compounds in cancer cell lines as monotherapy using CTG assays. Incubation time will be optimized prior to the combination treatment for individual test compound. In vitro mechanism based studies using histology staining and/or flow cytometry methods as described by Hirai H. et al. (Hirai H 2010, MK-1775 enhances antitumor efficacy 5-FU) may be used.

In addition, the sensitization of test compounds in drug-induced resistance cell lines (e.g., A2780cis) will be studied in vitro as combination therapy (e.g., cisplatin+Wee1 inhibitor) with the anti-proliferation assays, histology staining and/or flow cytometry methods mentioned therebefore.

TABLE 6

| | Cell viability IC$_{50}$ (μM) in A427 cells with 2.5 μM cisplatin | |
|---|---|---|
| Compound No. | 24 hr cisplatin then compound | 24 hr cisplatin then compound + cisplatin |
| 1.10 | 0.36 | <0.014 |
| 1.16 | 0.18 | <0.014 |
| 1.24 | 0.12 | 0.06 |
| 1.55 | 0.53 | <0.014 |

Example B6. Determination of Synergistic Activity of Compounds Combined with Chemotherapeutics in Cancer Cells Determination of synergistic activity of compounds in combination with a chemotherapeutic drug on cell viability is determined by a combination matrix method. Chemotherapeutics that may be used in the combination include but are not limited to a platinum-based chemotherapeutic agent, a DNA alkylating agent, a topoisomerase inhibitor, an anthracycline, a histone deacetylase inhibitor, a bromodomain inhibitor, a kinase inhibitor, a mTOR inhibitor, a PARP inhibitor, an ATM inhibitor, an ATR inhibitor, a Wee1 inhibitor, a proteasome inhibitor, and a nucleotide analog or precursor analog. Cancer cell lines that may be used in the assay include but are not limited to lung cancer, leukemia, lymphoma, multiple myeloma, ovarian cancer, breast cancer, pancreatic cancer, stomach cancer, colon cancer, liver cancer, head and neck cancer, kidney cancer, skin cancer and brain cancer cell lines. Cells are seeded in a 96-well plate and incubated at 37° C. in cell culture conditions for 24 hr. Drugs are added and then the cells are incubated further at 37° C. in cell culture conditions for 72 hr. Cells are treated with single agents to obtain a dose response curve for each agent. Cells are also treated with combinations of the drugs, based on a matrix generated by combining the two drugs at all different combinations of the doses used in the dose response curves. The assay is terminated by addition of Resazurin, incubation for 4 hr at 37° C., 5% CO$_2$. Measurement of fluorescence at an excitation and emission wavelength of 535 and 590 nm respectively. Synergy is evaluated with the combination index (CI) value using the Chou-Talalay method in which additive effect (CI=1), synergism (CI<1), and antagonism (CI>1) in drug combinations is determined (Chou T C. Cancer Res 2010; 70:440-6.). A fixed drug ratio dilution method in which drugs are combined in a fixed ratio which is diluted to 5 or more dilutions, may also be used in place of the combination matrix method.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:
1. A compound of Formula (I):

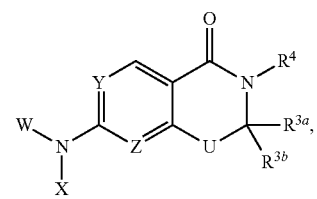

or a tautomer or stereoisomer thereof, or a pharmaceutically acceptable salt of any of the foregoing, wherein:
U is O or S;
W is A or AB, wherein A and B are fused together;
A is phenyl or 5- to 6-membered heteroaryl, each of which is optionally substituted with R$^{17a}$, wherein A and R$^{17a}$ together are

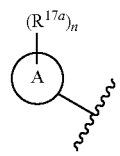

and n is 0, 1, 2, 3, or 4;
B is C$_3$-C$_6$ cycloalkyl, 3- to 7-membered heterocyclyl, 5- to 7-membered heteroaryl, or C$_6$ aryl, each of which is optionally substituted with R$^{17b}$, wherein A, B, R$^{17a}$, and R$^{17b}$ together are

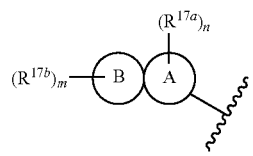

and m and n are independently 0, 1, 2, 3, or 4;
X is hydrogen or C$_1$-C$_6$ alkyl;
Y is N or CR$^1$;
Z is N or CR$^2$;
R$^1$ and R$^2$ are independently hydrogen or R$^{17a}$;
R$^{3a}$ and R$^{3b}$ are independently hydrogen or R$^{17a}$, or
R$^{3a}$ and R$^{3b}$ are taken together with the carbon to which they are attached to form a C$_3$-C$_6$ cycloalkyl;
each R$^{17b}$ is independently oxo or R$^{17a}$, or
any two R$^{17b}$ groups, when bound to the same carbon atom or two different carbon atoms, are taken together with the carbon or carbons to which they are attached to form a C$_3$-C$_6$ cycloalkyl or 3- to 7-membered heterocyclyl, each is optionally substituted by R$^{10}$;
each R$^{17a}$ is independently C$_1$-C$_6$ alkyl, C$_2$-C$_6$ alkenyl, C$_2$-C$_6$ alkynyl, halogen, —CN, —OR$^{10}$, —SR$^{10}$, —NR$^{11}$R$^{12}$, —C(O)R$^{10}$, —C(O)OR$^{10}$, —Si(C$_1$-C$_6$ alkyl)$_3$, —C(O)NR$^{11}$R$^{12}$, —OC(O)NR$^{11}$R$^{12}$, —NR$^{10}$C(O)R$^{11}$, —NR$^{10}$C(O)NR$^{11}$R$^{12}$, —S(O)$_2$R$^{10}$, —NR$^{10}$S(O)$_2$R$^{11}$, —S(O)$_2$NR$^{11}$R$^{12}$, C$_3$-C$_6$ cycloalkyl, 3- to 12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^{10}$, —(C$_1$-C$_3$ alkylene)SR$^{10}$, —(C$_1$-C$_3$ alkylene)NR$^{11}$R$^{12}$, —(C$_1$-C$_3$ alkylene)CF$_3$, —(C$_1$-C$_3$alkylene)C(O)R$^{10}$, —(C$_1$-C$_3$ alkylene)C(O)NR$^{11}$R$^{12}$, —(C$_1$-C$_3$ alkylene)NR$^{10}$C(O)R$^1$, —(C$_1$-C$_3$alkylene)NR$^1$C(O)NR$^{11}$R$^{12}$, —(C$_1$-C$_3$ alkylene)S(O)$_2$R$^{10}$, —(C$_1$-C$_3$ alkylene)NR$^{10}$S(O)$_2$R$^{11}$, —(C$_1$-C$_3$ alkylene)S(O)$_2$NR$^{11}$R$^{12}$, —(C$_1$-C$_3$ alkylene)(C$_3$-C$_6$ cycloalkyl), —(C$_1$-C$_3$ alkylene)(3- to 12-membered heterocyclyl), —(C$_1$-C$_3$ alkylene)(5- to 10-membered heteroaryl) or —(C$_1$-C$_3$ alkylene)(C$_6$-C$_{14}$ aryl), wherein the C$_1$-C$_6$ alkyl, C$_2$-C$_6$ alkenyl, C$_2$-C$_6$ alkynyl, —OR$^{10}$, —SR$^{10}$, —NR$^{11}$R$^{12}$, —C(O)R$^{10}$, —C(O)OR$^{10}$, —Si(C$_1$-C$_6$ alkyl)$_3$, —C(O)NR$^{11}$R$^{12}$, —OC(O)NR$^{11}$R$^{12}$, —NR$^{10}$C(O)R$^{11}$, —NR$^{10}$C(O)NR$^{11}$R$^{12}$, —S(O)$_2$R$^{10}$, —NR$^{10}$S(O)$_2$R$^{11}$, —S(O)$_2$NR$^{11}$R$^{12}$, C$_3$-C$_6$ cycloalkyl, 3- to 12-membered heterocyclyl, 5- to 10-membered heteroaryl, C$_6$-C$_{14}$ aryl, —(C$_1$-C$_3$ alkylene)CN, —(C$_1$-C$_3$alkylene)OR$^{10}$, —(C$_1$-C$_3$ alkylene)SR$^{10}$, —(C$_1$-C$_3$ alkylene)NR$^{11}$R$^{12}$, —(C$_1$-C$_3$ alkylene)CF$_3$, —(C$_1$-C$_3$alkylene)C(O)R$^{10}$, —(C$_1$-C$_3$ alkylene)C(O)NR$^{11}$R$^{12}$, —(C$_1$-C$_3$ alkylene)NR$^{10}$C(O)R$^{11}$, —(C$_1$-C$_3$ alkylene)NR$^1$C(O)NR$^{11}$R$^{12}$, —(C$_1$-C$_3$ alkylene)S(O)$_2$R$^{10}$, —(C$_1$-C$_3$ alkylene)NR$^{10}$S(O)$_2$R$^{11}$, —(C$_1$-C$_3$ alkylene)S(O)$_2$NR$^{11}$R$^{12}$, —(C$_1$-C$_3$ alkylene)(C$_3$-C$_6$ cycloalkyl), —(C$_1$-C$_3$ alkylene)(3- to 12-membered heterocyclyl), —(C$_1$-C$_3$ alkylene)(5- to 10-membered heteroaryl) and —(C$_1$-C$_3$ alkylene)(C$_6$-C$_{14}$ aryl) of R$^{17a}$ are each independently optionally substituted by halogen, oxo, —OR$^{13}$, —NR$^{13}$R$^{14}$, —C(O)R$^{13}$, —C(O)NR$^{13}$R$^{14}$, —NR$^{13}$C(O)R$^{14}$, —S(O)$_2$R$^{13}$, —NR$^{13}$S(O)$_2$R$^{14}$, —S(O)$_2$NR$^{13}$R$^{14}$, —(C$_1$-C$_3$ alkylene)C(O)NR$^{13}$R$^{14}$, —(C$_1$-C$_3$ alkylene)NR$^{13}$C(O)R$^{14}$, —(C$_1$-C$_3$ alkylene)S(O)$_2$R$^{13}$, —(C$_1$-C$_3$ alkylene)NR$^{13}$S(O)$_2$R$^{14}$, —(C$_1$-C$_3$ alkylene)S(O)$_2$NR$^{13}$R$^{14}$, —(C$_1$-C$_3$ alkylene)(C$_3$-C$_6$ cycloalkyl), —(C$_1$-C$_3$ alkylene)(3- to 12-membered heterocyclyl), —Si(C$_1$-C$_6$ alkyl)$_3$, —CN, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl, or C$_1$-C$_6$ alkyl optionally substituted by oxo, —OH or halogen;

R$^4$ is hydrogen, C$_1$-C$_6$ alkyl, C$_2$-C$_6$ alkenyl, C$_2$-C$_6$ alkynyl, C$_3$-C$_6$ cycloalkyl, 3- to 12-membered heterocyclyl, 5- to 10-membered heteroaryl, C$_6$-C$_{14}$ aryl, —(C$_1$-C$_3$ alkylene)(C$_3$-C$_6$ cycloalkyl), —(C$_1$-C$_3$ alkylene)(3- to 12-membered heterocyclyl), —(C$_1$-C$_3$ alkylene)(5- to 10-membered heteroaryl) or —(C$_1$-C$_3$ alkylene)(C$_6$-C$_{14}$ aryl), wherein the C$_1$-C$_6$ alkyl, C$_2$-C$_6$ alkenyl, C$_2$-C$_6$ alkynyl, C$_3$-C$_6$ cycloalkyl, 3- to 12-membered heterocyclyl, 5- to 10-membered heteroaryl, C$_6$-C$_{14}$ aryl, —(C$_1$-C$_3$ alkylene)(C$_3$-C$_6$ cycloalkyl), —(C$_1$-C$_3$ alkylene)(3- to 12-membered heterocyclyl), —(C$_1$-C$_3$ alkylene)(5- to 10-membered heteroaryl) and —(C$_1$-C$_3$ alkylene)(C$_6$-C$_{14}$ aryl) of R$^4$ are each independently optionally substituted by halogen, oxo, —OR$^{13}$, —NR$^{13}$R$^{14}$, —C(O)R$^{13}$, —CN, C$_3$-C$_8$ cycloalkyl, or C$_1$-C$_6$ alkyl optionally substituted by oxo, —OH or halogen;

R$^{10}$ is independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl and 3- to 6-membered heterocyclyl of R$^{10}$ are independently optionally substituted by halogen, oxo, —CN, —OR$^{15}$, —NR$^{s1}$R$^{16}$, or C$_1$-C$_6$ alkyl optionally substituted by halogen, —OH or oxo;

R$^{11}$ and R$^{12}$ are each independently hydrogen, C$_1$-C$_6$ alkyl, C$_3$-C$_6$ cycloalkyl, C$_6$-C$_{14}$ aryl, 5- to 6-membered heteroaryl or 3- to 6-membered heterocyclyl, wherein the C$_1$-C$_6$ alkyl, C$_3$-C$_6$ cycloalkyl, C$_6$-C$_{14}$ aryl, 5- to 6-membered heteroaryl and 3- to 6-membered heterocyclyl of R$^{11}$ and R$^{12}$ are independently optionally substituted by halogen, oxo, —CN, —OR$^{15}$, —NR$^{s1}$R$^{16}$ or C$_1$-C$_6$ alkyl optionally substituted by halogen, —OH or oxo, or R$^{11}$ and R$^{12}$ are taken together with the atom to which they attached to form a 3- to 6-membered heterocyclyl optionally substituted by halogen, oxo, or C$_1$-C$_6$ alkyl optionally substituted by halogen;

R$^{13}$ and R$^{14}$ are each independently hydrogen, C$_1$-C$_6$ alkyl, C$_3$-C$_6$ cycloalkyl, or 3- to 6-membered heterocyclyl, wherein the C$_1$-C$_6$ alkyl, C$_3$-C$_6$ cycloalkyl, and 3- to 6-membered heterocyclyl of R$^{13}$ and R$^{14}$ are optionally substituted by halogen, —CN, —OR$^{15}$, —NR$^{15}$R$^{16}$, or oxo, or R$^{13}$ and R$^{14}$ are taken together with the atom to which they attached to form a 3- to 6-membered heterocyclyl optionally substituted by halogen, oxo or C$_1$-C$_6$ alkyl optionally substituted by halogen or oxo; and R$^{15}$ and R$^{16}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo, or R$^{15}$ and R$^{16}$ are taken together with the atom to which they attached to form a 3- to 6-membered heterocyclyl optionally substituted by halogen, oxo or C$_1$-C$_6$ alkyl optionally substituted by oxo or halogen.

2. The compound of claim 1, or a tautomer or stereoisomer thereof, or a pharmaceutically acceptable salt of any of the foregoing, wherein compound is of Formula (Ia):

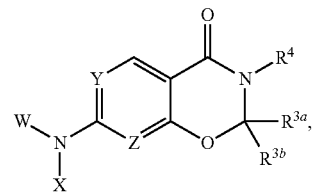

(Ia)

or a tautomer or stereoisomer thereof, or a pharmaceutically acceptable salt of any of the foregoing, wherein:

W is A or AB wherein A and B are fused together;

A is phenyl or 6-membered heteroaryl, each of which is optionally substituted with R$^{17a}$, wherein A and R$^{17a}$ together are

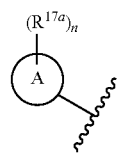

and n is 0, 1, 2, 3, or 4;

B is C$_3$-C$_6$ cycloalkyl, 3- to 7-membered heterocyclyl, 5- to 7-membered heteroaryl, or C$_6$ aryl, each of which is optionally substituted with R$^{17b}$, wherein A, B, R$^{17a}$, and R$^{17b}$ together are

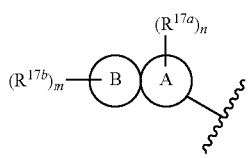

and m and n are independently 0, 1, 2, 3, or 4;
X is hydrogen or $C_1$-$C_6$ alkyl;
Y is N or $CR^1$;
Z is N or $CR^2$;
$R^1$ and $R^2$ are independently hydrogen or $R^{17a}$;
$R^{3a}$ and $R^{3b}$ are independently hydrogen or $R^{17a}$, or
$R^{3a}$ and $R^{3b}$ are taken together with the carbon to which they are attached to form a $C_3$-$C_6$ cycloalkyl;
each $R^{17b}$ is independently oxo or $R^{17a}$, or
any two $R^{17b}$ groups, when bound to the same carbon atom, are taken together with the carbon to which they are attached to form a $C_3$-$C_6$ cycloalkyl;
each $R^{17a}$ is independently $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —$C(O)R^{10}$, —$C(O)NR^{11}R^{12}$, —$OC(O)NR^{11}R^{12}$, —$NR^{10}C(O)R^{11}$, —$NR^{10}C(O)NR^{11}R^{12}$, —$S(O)_2R^{10}$, —$NR^{10}S(O)_2R^{11}$, —$S(O)_2NR^{11}R^{12}$, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)CN, —($C_1$-$C_3$ alkylene)$OR^{10}$, —($C_1$-$C_3$ alkylene)$SR^{10}$, —($C_1$-$C_3$ alkylene)$NR^{11}R^{12}$, —($C_1$-$C_3$ alkylene)$CF_3$, —($C_1$-$C_3$ alkylene)$C(O)R^{10}$, —($C_1$-$C_3$ alkylene)$C(O)NR^{11}R^{12}$, —($C_1$-$C_3$ alkylene)$NR^{10}C(O)R^{11}$, —($C_1$-$C_3$ alkylene)$NR^{10}C(O)NR^{11}R^{12}$, —($C_1$-$C_3$ alkylene)$S(O)_2R^{10}$, —($C_1$-$C_3$ alkylene)$NR^1S(O)_2R^{11}$, —($C_1$-$C_3$ alkylene)$S(O)_2NR^{11}R^{12}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), wherein the $C_1$-$C_6$ alkyl, $C_2$-$C_6$ alkenyl, $C_2$-$C_6$ alkynyl, —$OR^{10}$, —$SR^{10}$, —$NR^{11}R^{12}$, —$C(O)R^{10}$, —$C(O)NR^{11}R^{12}$, —$OC(O)NR^{11}R^{12}$, —$NR^{10}C(O)R^{11}$, —$NR^{10}C(O)NR^{11}R^{12}$, —$S(O)_2R^{10}$, —$NR^{10}S(O)_2R^{11}$, —$S(O)_2NR^{11}R^{12}$, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)CN, —($C_1$-$C_3$ alkylene)$OR^{10}$, —($C_1$-$C_3$ alkylene)$SR^{10}$, —($C_1$-$C_3$ alkylene)$NR^{11}R^{12}$, —($C_1$-$C_3$ alkylene)$CF_3$, —($C_1$-$C_3$ alkylene)$C(O)R^{10}$, —($C_1$-$C_3$ alkylene)$C(O)NR^{11}R^{12}$, —($C_1$-$C_3$ alkylene)$NR^{10}C(O)R^{11}$, —($C_1$-$C_3$ alkylene)$NR^1C(O)NR^{11}R^{12}$, —($C_1$-$C_3$ alkylene)$S(O)_2R^{10}$, —($C_1$-$C_3$ alkylene)$NR^{10}S(O)_2R^1$, —($C_1$-$C_3$ alkylene)$S(O)_2NR^{11}R^{12}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) and —($C_1$-$C_3$ alkylene)($C_6$-$C_{14}$ aryl) of $R^{17a}$ are each independently optionally substituted by halogen, oxo, —$OR^{13}$, —$NR^{13}R^{14}$, —$C(O)R^{13}$, —CN, —($C_1$-$C_3$ alkylene)$OR^{13}$, —($C_1$-$C_3$ alkylene)$NR^{13}R^{14}$, —($C_1$-$C_3$ alkylene)$C(O)R^{13}$, $C_3$-$C_8$ cycloalkyl, or $C_1$-$C_6$ alkyl optionally substituted by oxo, —OH or halogen;
$R^4$ is hydrogen, $C_1$-$C_6$ alkyl, $C_2$-$C_6$ alkenyl, $C_2$-$C_6$ alkynyl, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), wherein the $C_1$-$C_6$ alkyl, $C_2$-$C_6$ alkenyl, $C_2$-$C_6$ alkynyl, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) and —($C_1$-$C_3$ alkylene)($C_6$-$C_{14}$ aryl) of $R^4$ are each independently optionally substituted by halogen, oxo, —$OR^{13}$, —$NR^{13}R^{14}$, —$C(O)R^{13}$, —CN, $C_3$-$C_8$ cycloalkyl, or $C_1$-$C_6$ alkyl optionally substituted by oxo, —OH or halogen;
$R^{10}$ is independently hydrogen, $C_1$-$C_6$ alkyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl of $R^{10}$ are independently optionally substituted by halogen, oxo, —CN, —$OR^{15}$, —$NR^{15}R^{16}$, or $C_1$-$C_6$ alkyl optionally substituted by halogen, —OH or oxo;
$R^{11}$ and $R^{12}$ are each independently hydrogen, $C_1$-$C_6$ alkyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_3$-$C_6$ cycloalkyl, $C_6$-$C_{14}$ aryl, 5- to 6-membered heteroaryl and 3- to 6-membered heterocyclyl of $R^{11}$ and $R^{12}$ are independently optionally substituted by halogen, oxo, —CN, —$OR^{15}$, —$NR^{s1}R^{16}$ or $C_1$-$C_6$ alkyl optionally substituted by halogen, —OH or oxo,
or $R^{11}$ and $R^{12}$ are taken together with the atom to which they attached to form a 3- to 6-membered heterocyclyl optionally substituted by halogen, oxo, or $C_1$-$C_6$ alkyl optionally substituted by halogen;
$R^{13}$ and $R^{14}$ are each independently hydrogen or $C_1$-$C_6$ alkyl, wherein the $C_1$-$C_6$ alkyl of $R^{13}$ and $R^{14}$ are optionally substituted by halogen, —$OR^{15}$, —$NR^{15}R^{16}$, or oxo,
or $R^{13}$ and $R^{14}$ are taken together with the atom to which they attached to form a 3- to 6-membered heterocyclyl optionally substituted by halogen, oxo or $C_1$-$C_6$ alkyl optionally substituted by halogen or oxo; and
$R^{15}$ and $R^{16}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo,
or $R^{15}$ and $R^{16}$ are taken together with the atom to which they attached to form a 3- to 6-membered heterocyclyl optionally substituted by halogen, oxo or $C_1$-$C_6$ alkyl optionally substituted by oxo or halogen.

3. The compound of claim 1, or a tautomer or stereoisomer thereof, or a pharmaceutically acceptable salt of any of the foregoing, wherein the compound is of Formula (Ib):

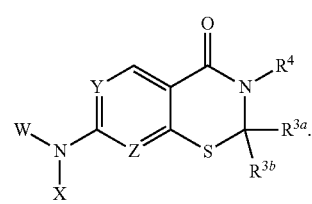

(Ib)

4. The compound of claim 1, or a tautomer or stereoisomer thereof, or a pharmaceutically acceptable salt of any of the foregoing, wherein Y is N.

5. The compound of claim 1, or a tautomer or stereoisomer thereof, or a pharmaceutically acceptable salt of any of the foregoing, wherein Y is $CR^1$.

6. The compound of claim 5, or a tautomer or stereoisomer thereof, or a pharmaceutically acceptable salt of any of the foregoing, wherein $R^1$ is hydrogen.

7. The compound of claim 1, or a tautomer or stereoisomer thereof, or a pharmaceutically acceptable salt of any of the foregoing, wherein Z is N.

8. The compound of claim 1, or a tautomer or stereoisomer thereof, or a pharmaceutically acceptable salt of any of the foregoing, wherein Z is $CR^2$.

9. The compound of claim 8, or a tautomer or stereoisomer thereof, or a pharmaceutically acceptable salt of any of the foregoing, wherein $R^2$ is hydrogen.

10. The compound of claim 1, or a tautomer or stereoisomer thereof, or a pharmaceutically acceptable salt of any of the foregoing, wherein at least one of Y and Z is N.

11. The compound of claim 1, or a tautomer or stereoisomer thereof, or a pharmaceutically acceptable salt of any of the foregoing, wherein the compound is of Formula (IIa):

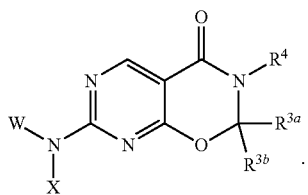

(IIa)

12. The compound of claim 1, or a tautomer or stereoisomer thereof, or a pharmaceutically acceptable salt of any of the foregoing, wherein the compound is of Formula (IIb):

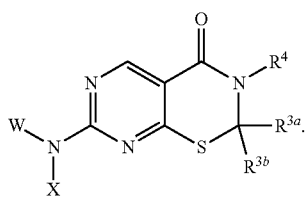

(IIb)

13. The compound of claim 1, or a tautomer or stereoisomer thereof, or a pharmaceutically acceptable salt of any of the foregoing, wherein the compound is of Formula (IIIa):

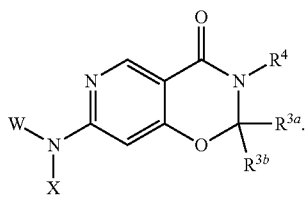

(IIIa)

14. The compound of claim 1, or a tautomer or stereoisomer thereof, or a pharmaceutically acceptable salt of any of the foregoing, wherein the compound is of Formula (IIIb):

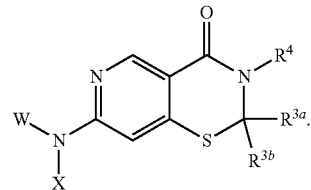

(IIIb)

15. The compound of claim 1, or a tautomer or stereoisomer thereof, or a pharmaceutically acceptable salt of any of the foregoing, wherein the compound is of Formula (IVa):

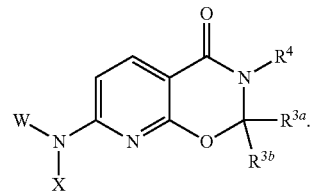

(IVa)

16. The compound of claim 1, or a tautomer or stereoisomer thereof, or a pharmaceutically acceptable salt of any of the foregoing, wherein the compound is of Formula (IVb):

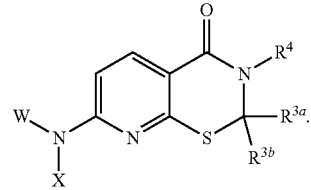

(IVb)

17. The compound of claim 1, or a tautomer or stereoisomer thereof, or a pharmaceutically acceptable salt of any of the foregoing, wherein X is $C_1$-$C_6$ alkyl.

18. The compound of claim 1, or a tautomer or stereoisomer thereof, or a pharmaceutically acceptable salt of any of the foregoing, wherein X is methyl.

19. The compound of claim 1, or a tautomer or stereoisomer thereof, or a pharmaceutically acceptable salt of any of the foregoing, wherein X is hydrogen.

20. The compound of claim 1, or a tautomer or stereoisomer thereof, or a pharmaceutically acceptable salt of any of the foregoing, wherein $R^{3a}$ and $R^{3b}$ are independently hydrogen, $C_1$-$C_6$ alkyl, $C_2$-$C_6$ alkenyl, $C_2$-$C_6$ alkynyl, halogen, —CN, —$OR^{10}$, —$SR^{10}$, —$NR^{11}R^{12}$, —C(O)$R^{10}$, or —C(O)$NR^{11}R^{12}$; or $R^{3a}$ and $R^{3b}$ are taken together with the carbon to which they are attached to form a $C_3$-$C_6$ cycloalkyl.

21. The compound of claim 1, or a tautomer or stereoisomer thereof, or a pharmaceutically acceptable salt of any of the foregoing, wherein $R^{3a}$ and $R^{3b}$ are independently hydrogen or $C_1$-$C_6$ alkyl; or $R^{3a}$ and $R^{3b}$ are taken together with the carbon to which they are attached to form a $C_3$-$C_6$ cycloalkyl.

22. The compound of claim 1, or a tautomer or stereoisomer thereof, or a pharmaceutically acceptable salt of any of the foregoing, wherein $R^{3a}$ and $R^{3b}$ are both hydrogen.

23. The compound of claim 1, or a tautomer or stereoisomer thereof, or a pharmaceutically acceptable salt of any of the foregoing, wherein $R^4$ is 5- to 10-membered heteroaryl, $C_1$-$C_6$ alkyl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —($C_1$-$C_3$ alkylene)($C_6$-$C_{14}$ aryl), or $C_6$-$C_{14}$ aryl, each of which is optionally substituted by halogen, —CN, —NR$^{13}$R$^{14}$, —C(O)R$^{13}$, —OR$^{13}$, or $C_1$-$C_6$ alkyl optionally substituted by —OH.

24. The compound of claim 1, or a tautomer or stereoisomer thereof, or a pharmaceutically acceptable salt of any of the foregoing, wherein $R^4$ is phenyl optionally substituted by halogen.

25. The compound of claim 1, or a tautomer or stereoisomer thereof, or a pharmaceutically acceptable salt of any of the foregoing, wherein $R^4$ is selected from the group consisting of:

methyl, ethyl, isopropyl, cyclopropyl,

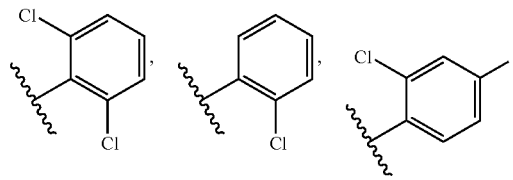

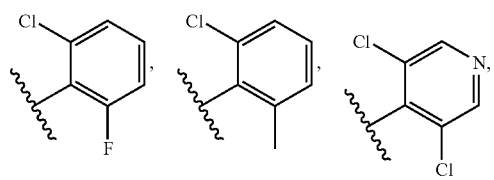

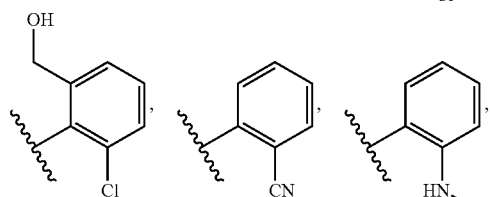

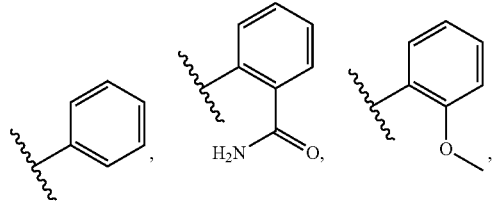

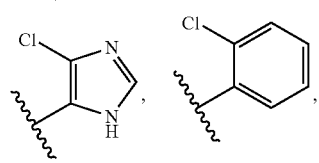

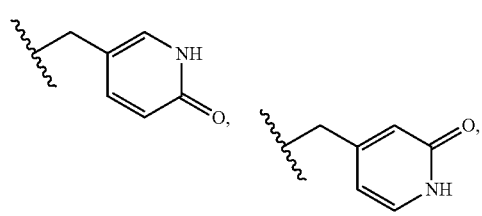

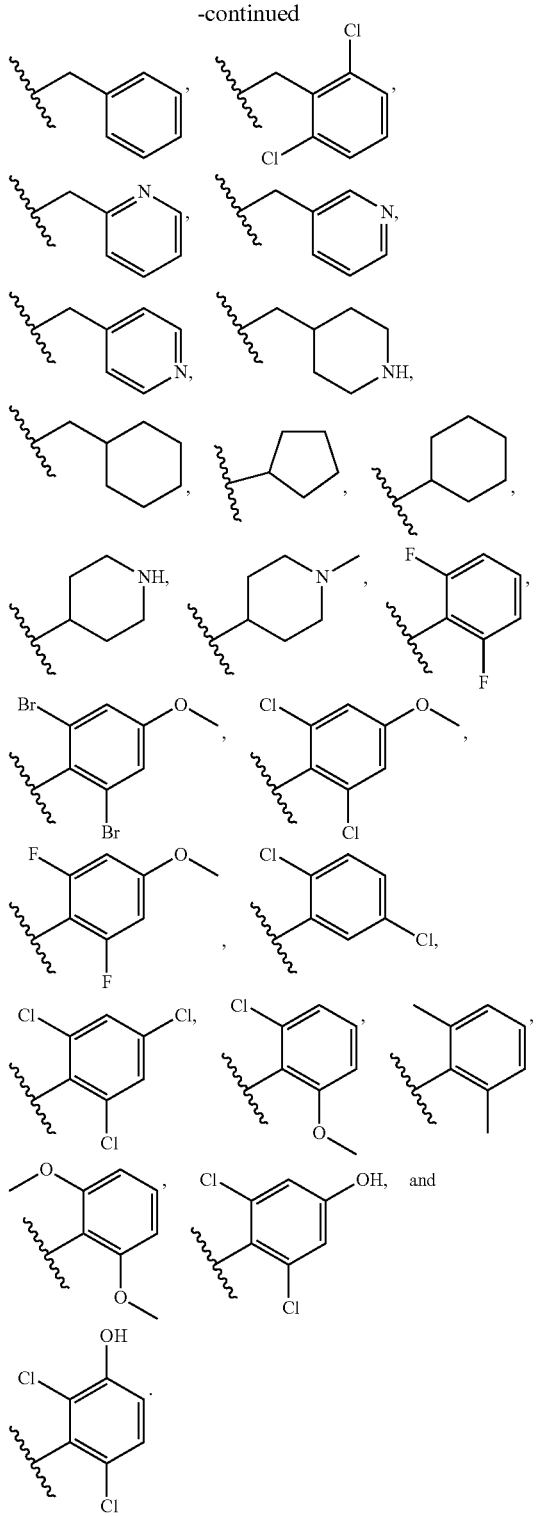

26. The compound of claim 1, or a tautomer or stereoisomer thereof, or a pharmaceutically acceptable salt of any of the foregoing, wherein:

W is A;

A is phenyl or 6-membered heteroaryl, each of which is optionally substituted with $R^{17a}$ wherein A and $R^{17a}$ together are

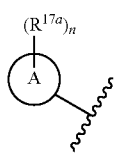

and n is 0, 1, 2, 3, or 4.

27. The compound of claim 1, or a tautomer or stereoisomer thereof, or a pharmaceutically acceptable salt of any of the foregoing, wherein A is phenyl optionally substituted with $R^{17a}$.

28. The compound of claim 1, or a tautomer or stereoisomer thereof, or a pharmaceutically acceptable salt of any of the foregoing, wherein A is pyridinyl optionally substituted with $R^{17a}$.

29. The compound of claim 26, or a tautomer or stereoisomer thereof, or a pharmaceutically acceptable salt of any of the foregoing, wherein $R^{17a}$ is independently 3- to 12-membered heterocyclyl, —($C_1$-$C_3$ alkylene)$OR^{10}$, $C_1$-$C_6$ alkyl optionally substituted by halogen or —OH, —C(O)$NR^{11}R^{12}$, —($C_1$-$C_3$ alkylene)$NR^{11}R^{12}$, —CN, halogen, —$NR^{11}R^{12}$, $C_3$-$C_6$ cycloalkyl, or —$OR^{10}$, wherein the 3- to 12-membered heterocyclyl of $R^{17a}$ is optionally substituted with $C_1$-$C_6$ alkyl optionally substituted by halogen or —OH, —C(O)$R^{13}$, —($C_1$-$C_3$ alkylene)$OR^{13}$, —S(O)$_2R^{13}$, $C_3$-$C_8$ cycloalkyl, oxo, halogen, or —$OR^{13}$.

30. The compound of claim 26, or a tautomer or stereoisomer thereof, or a pharmaceutically acceptable salt of any of the foregoing, wherein $R^{17a}$ is independently $C_1$-$C_6$ alkyl optionally substituted by halogen or —OH, halogen, —CN, or 3- to 12-membered heterocyclyl optionally substituted with $C_1$-$C_6$ alkyl optionally substituted by halogen or —OH.

31. The compound of claim 1, or a tautomer or stereoisomer thereof, or a pharmaceutically acceptable salt of any of the foregoing, wherein W is selected from the group consisting of:

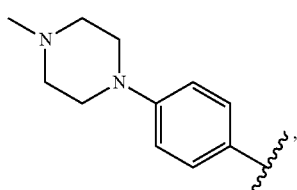

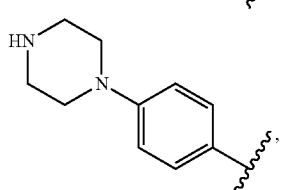

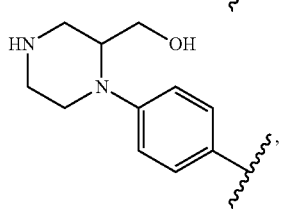

-continued

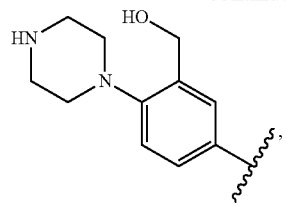

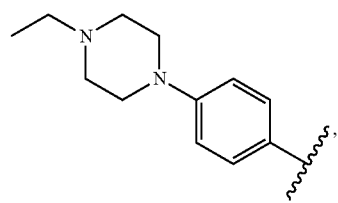

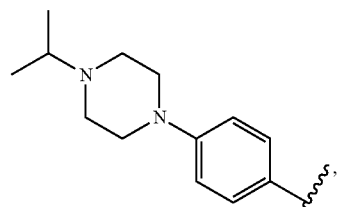

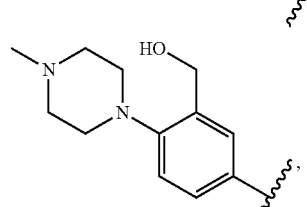

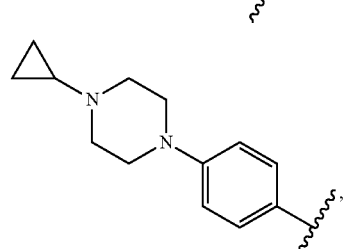

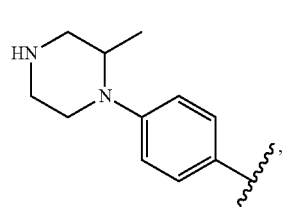

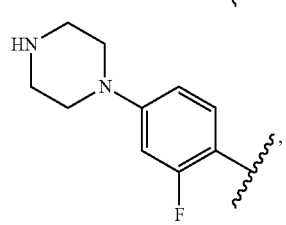

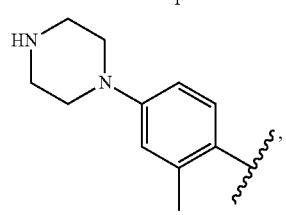

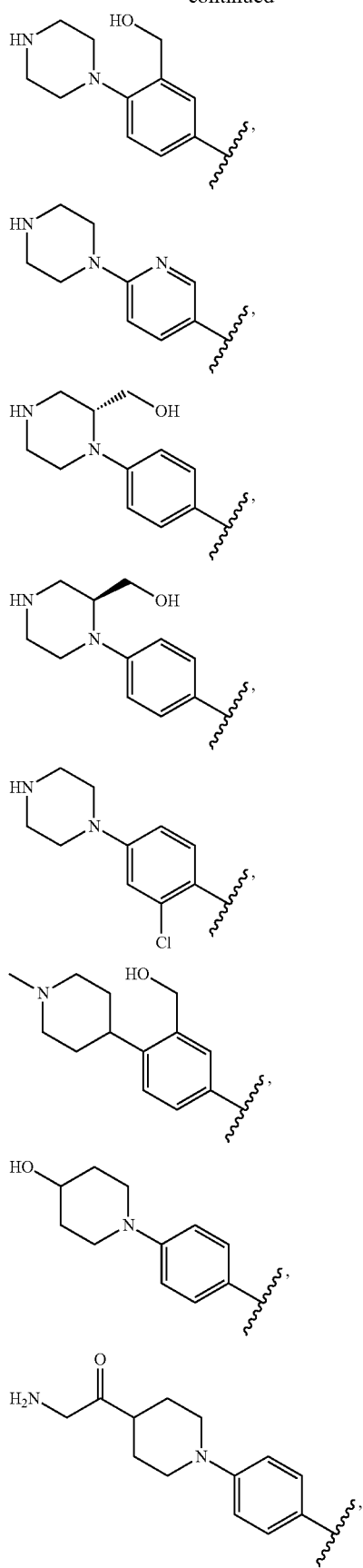
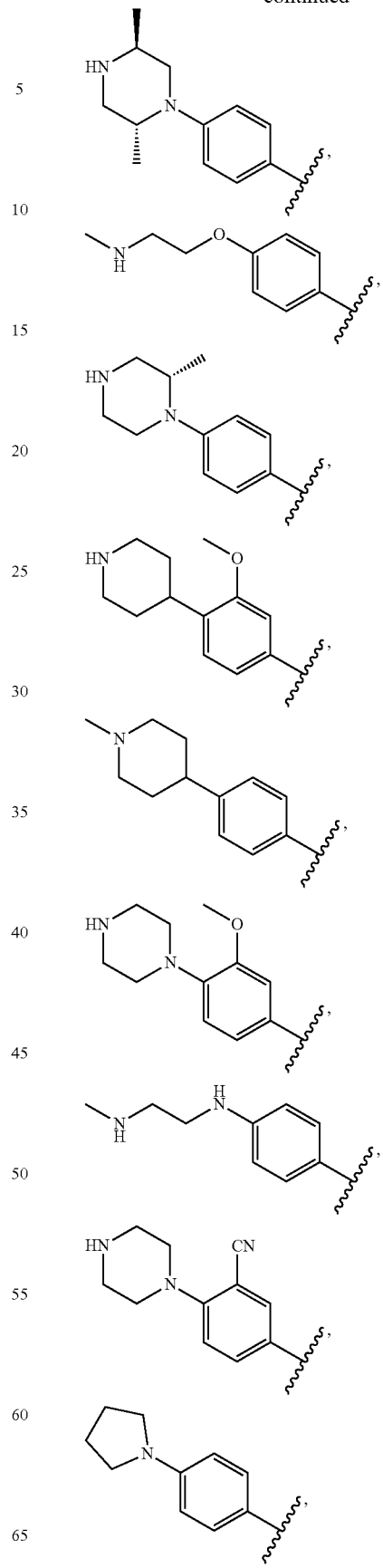

643
-continued
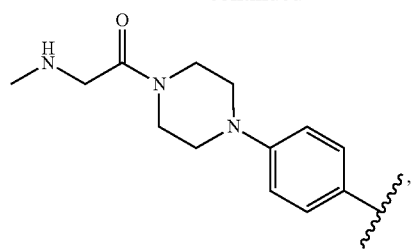
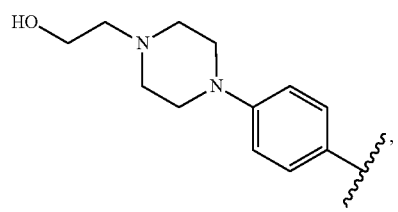
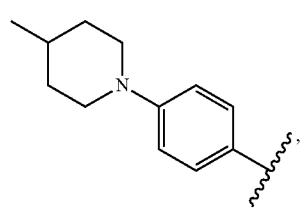
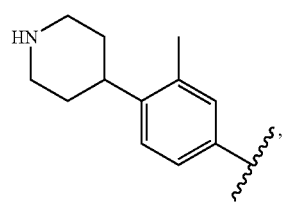
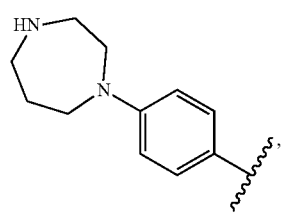
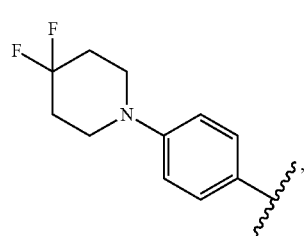
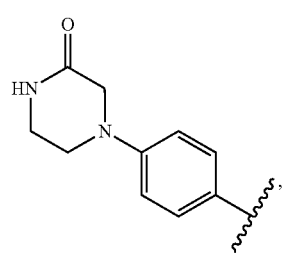
644
-continued
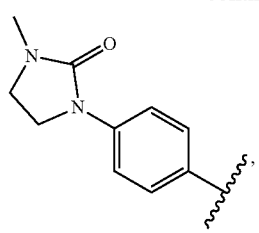
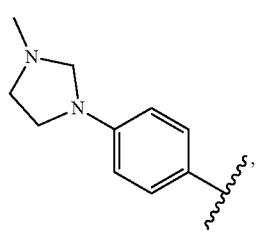
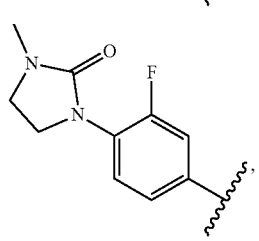
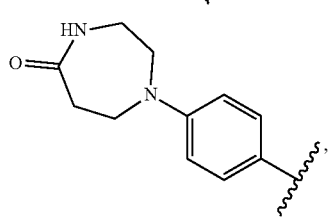
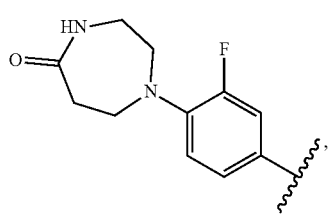
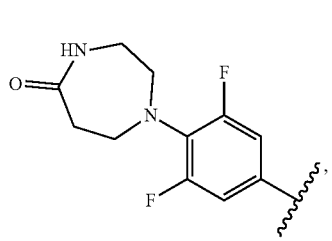
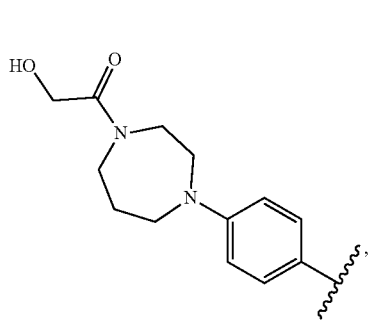

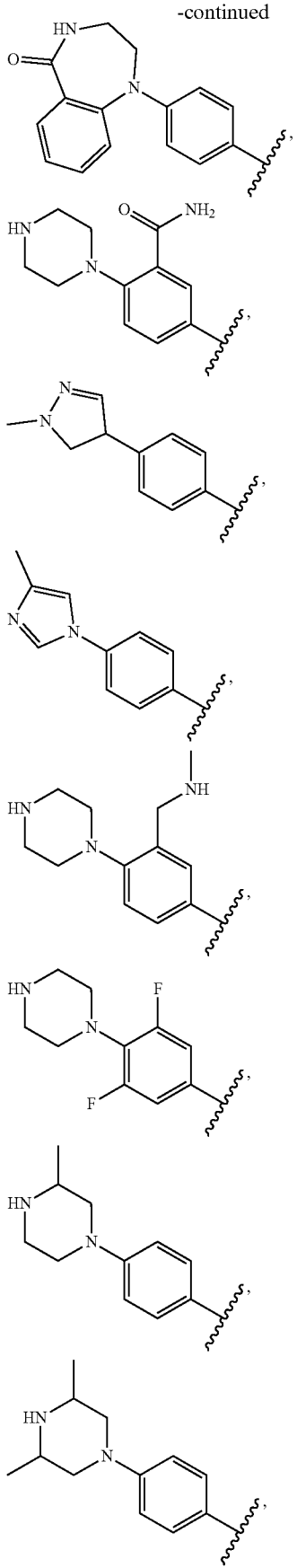
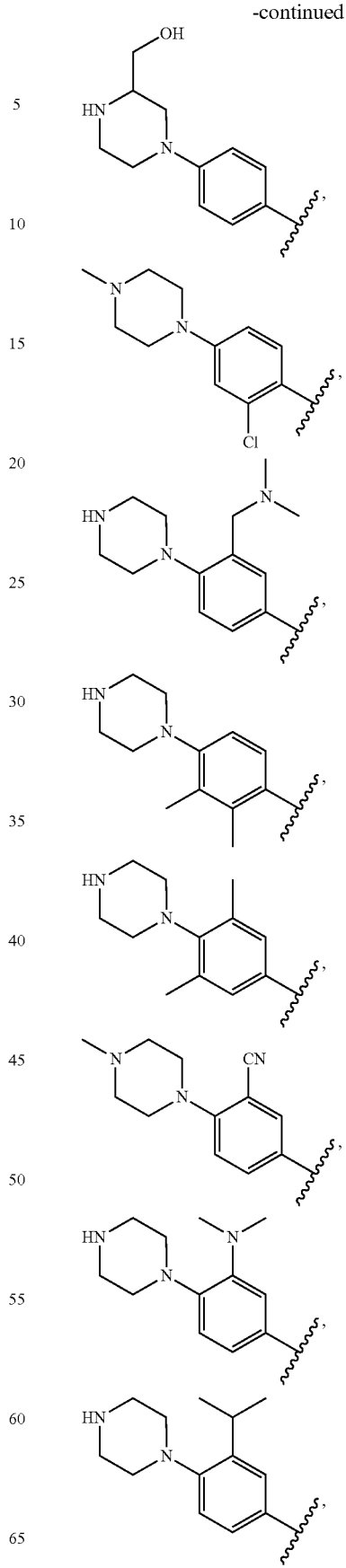

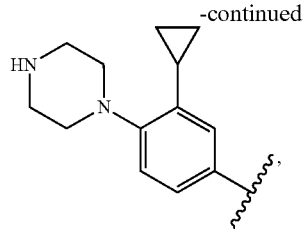,
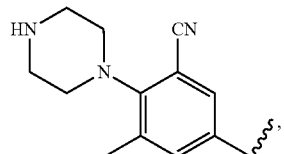,
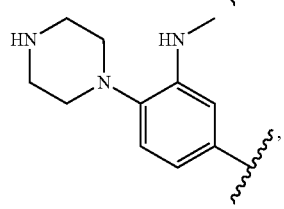,
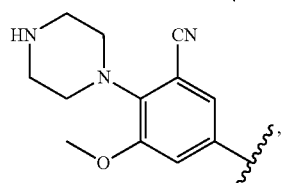,
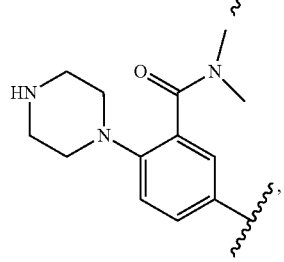,
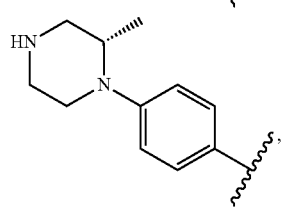,
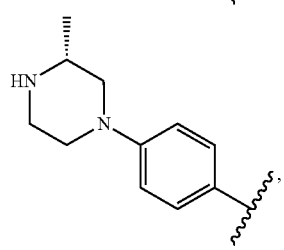,
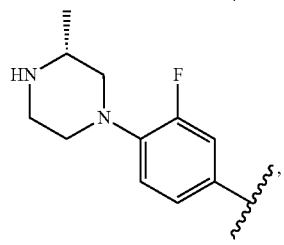,
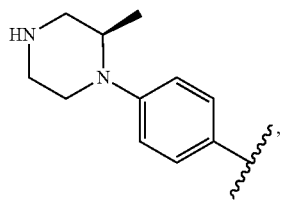,
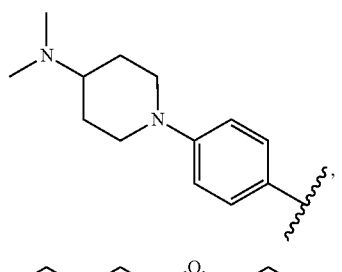,
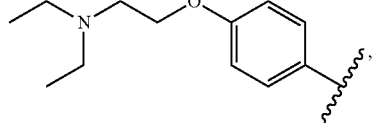,
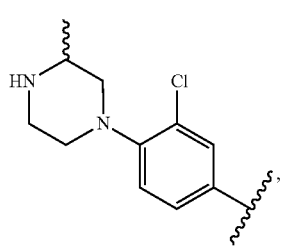,
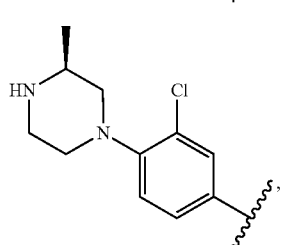,
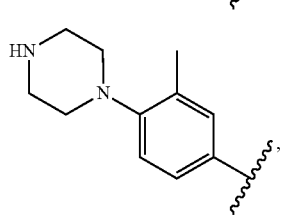,
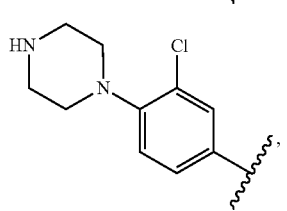,
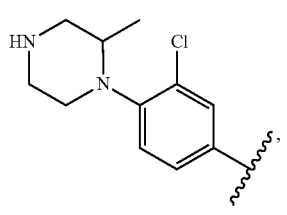, 649
-continued
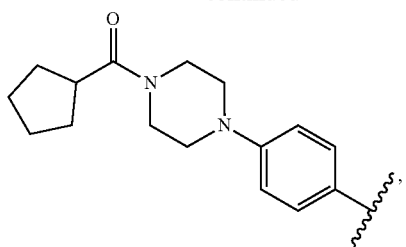
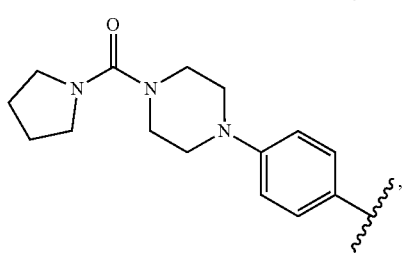
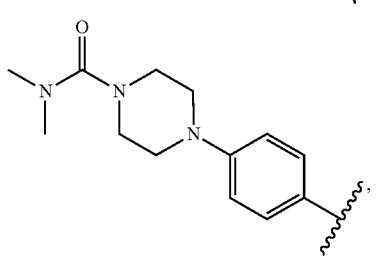
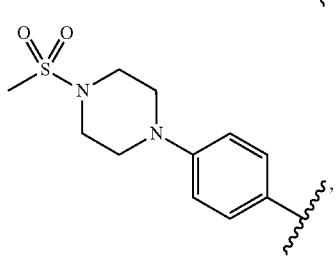
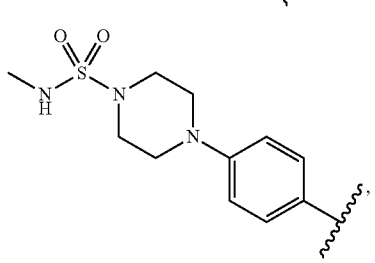
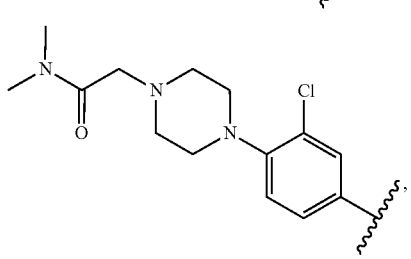
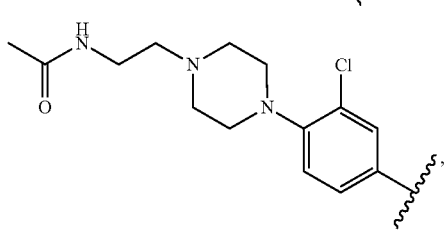
650
-continued
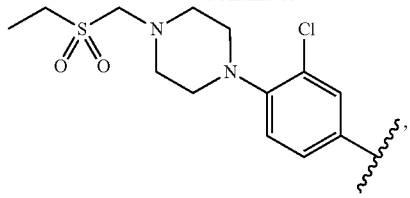
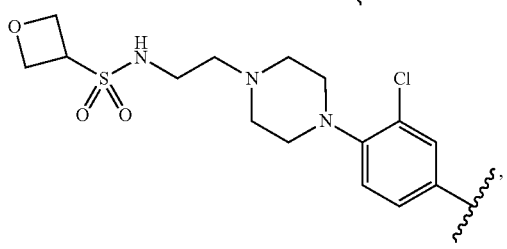
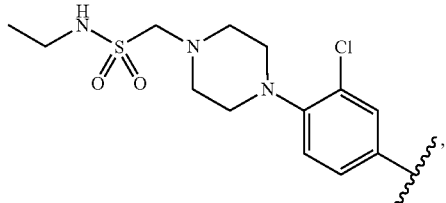
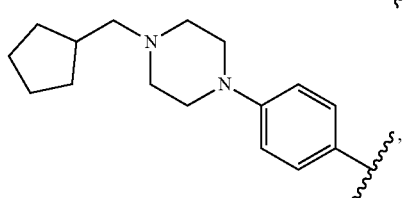
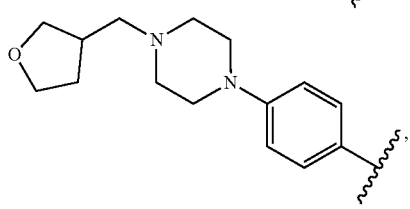
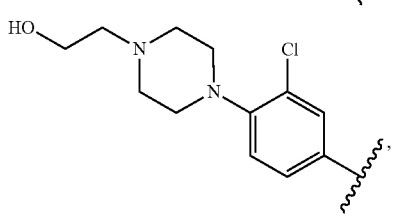
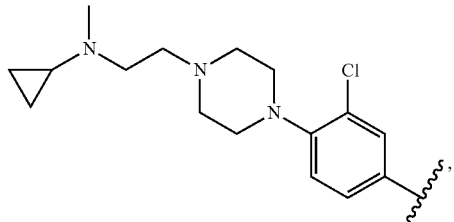
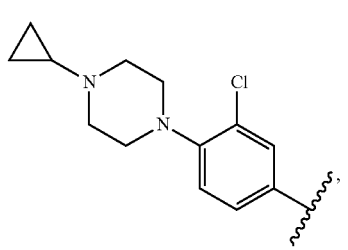

651
-continued
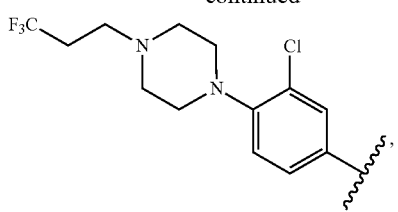
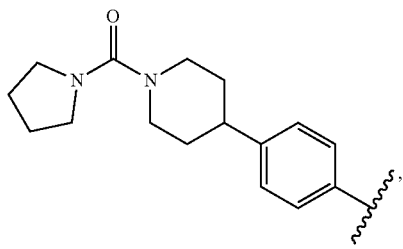
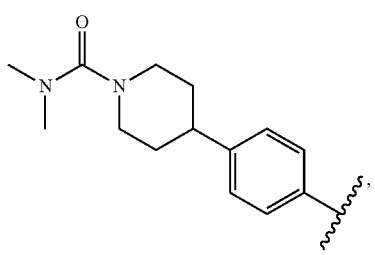
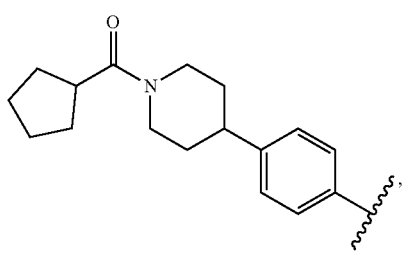
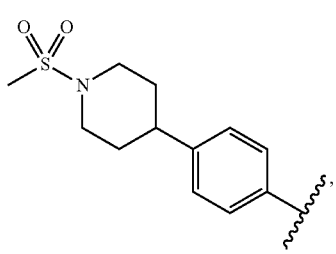
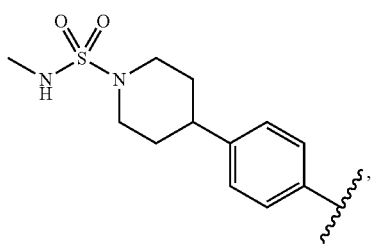
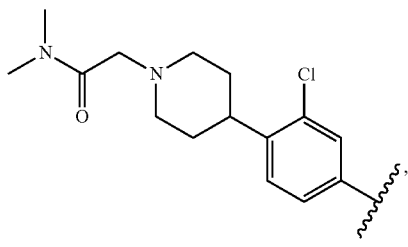
652
-continued
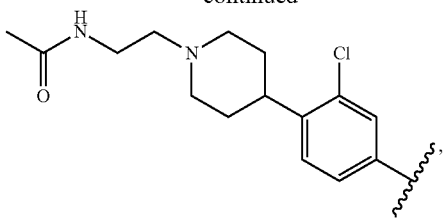
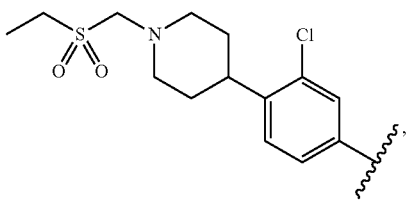
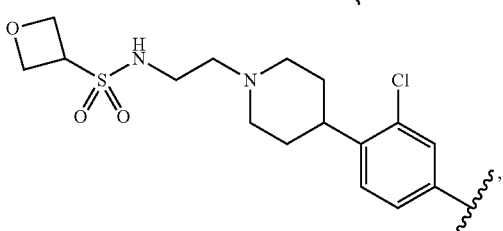
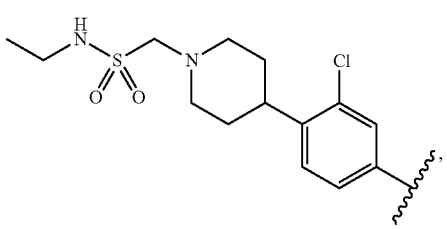
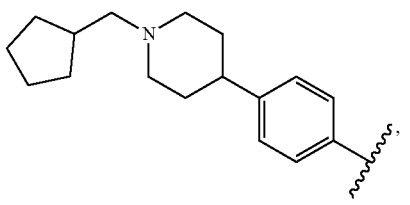
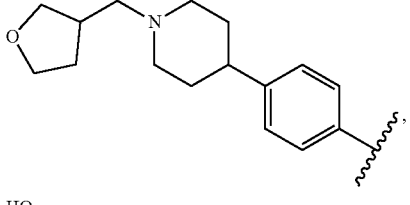
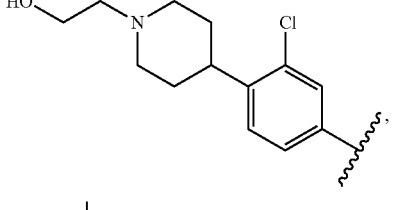
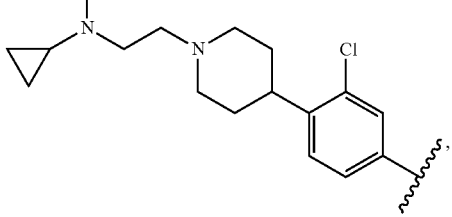

-continued
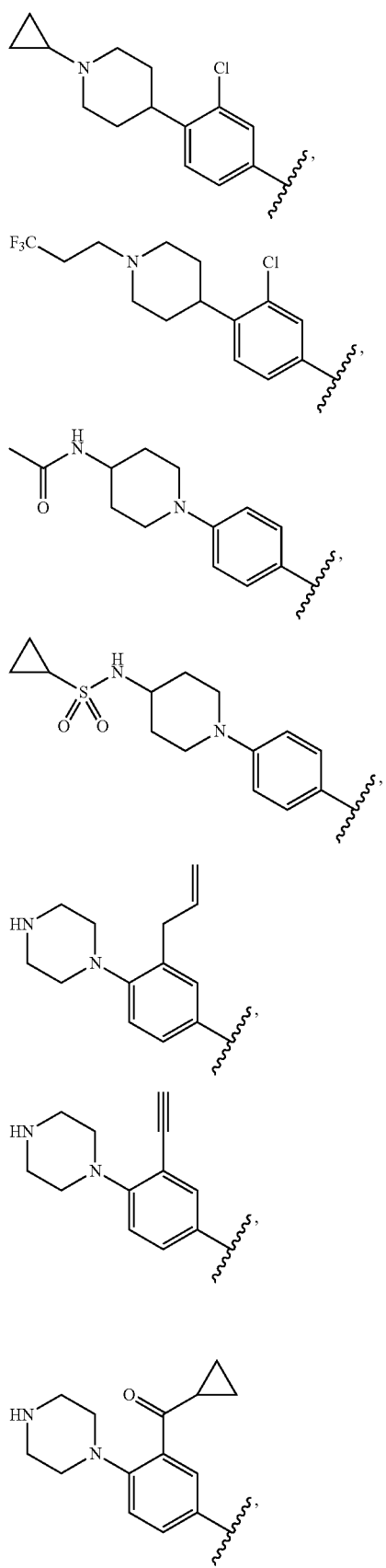
-continued
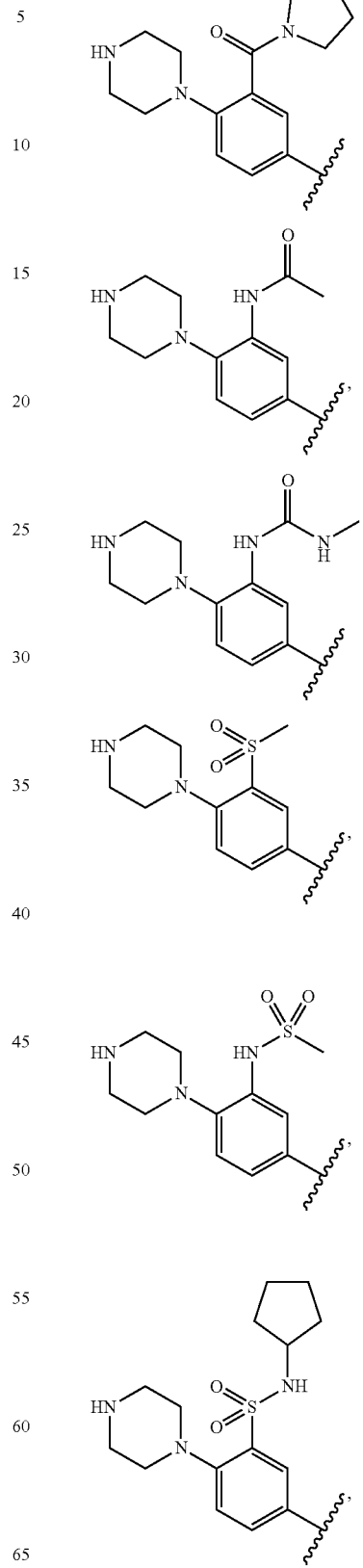

655
-continued
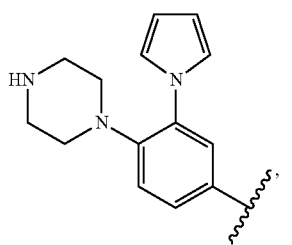
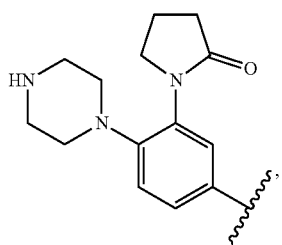
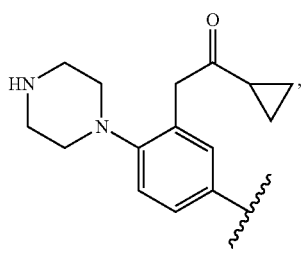
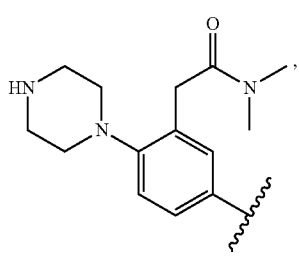
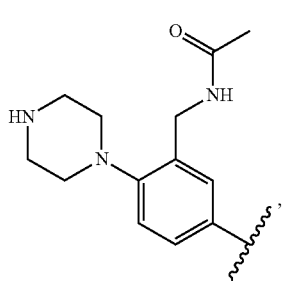
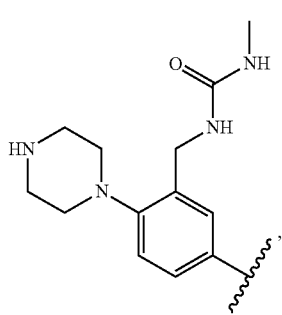
656
-continued
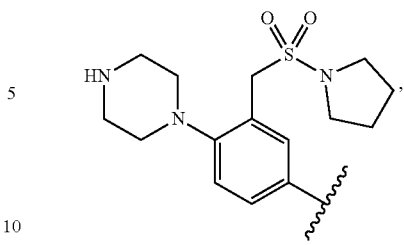
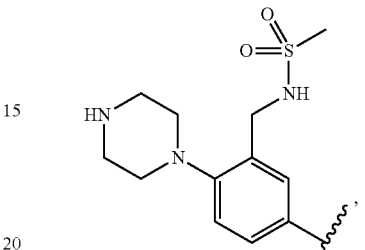
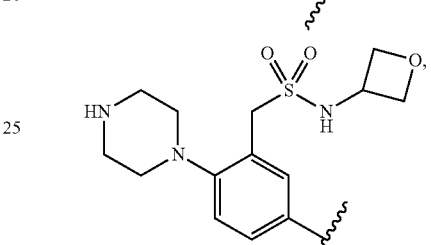
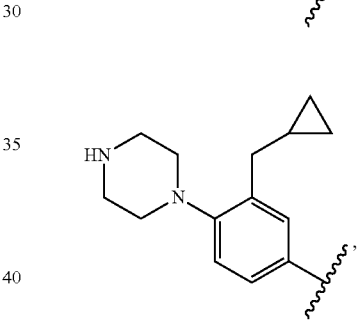
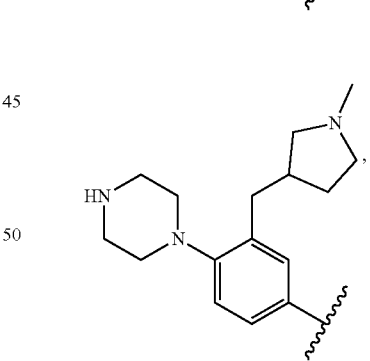
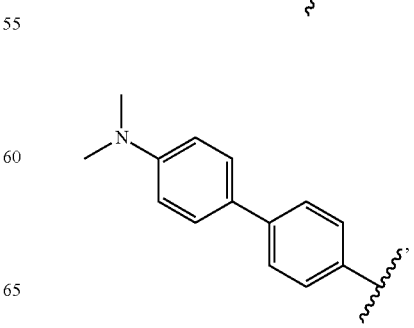

657
-continued
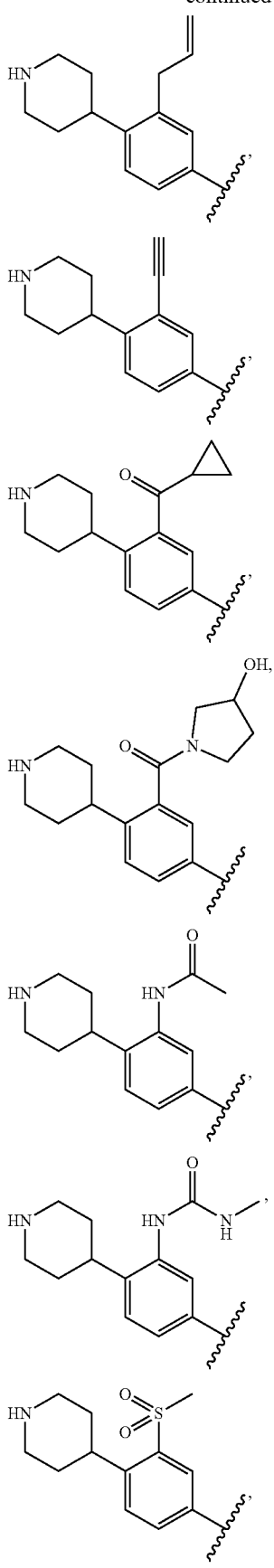
658
-continued
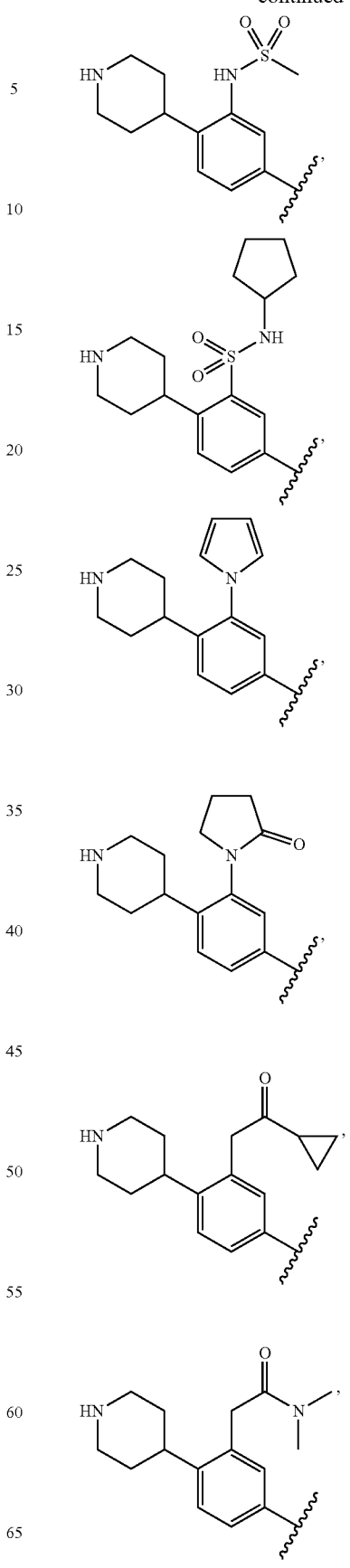

659
-continued
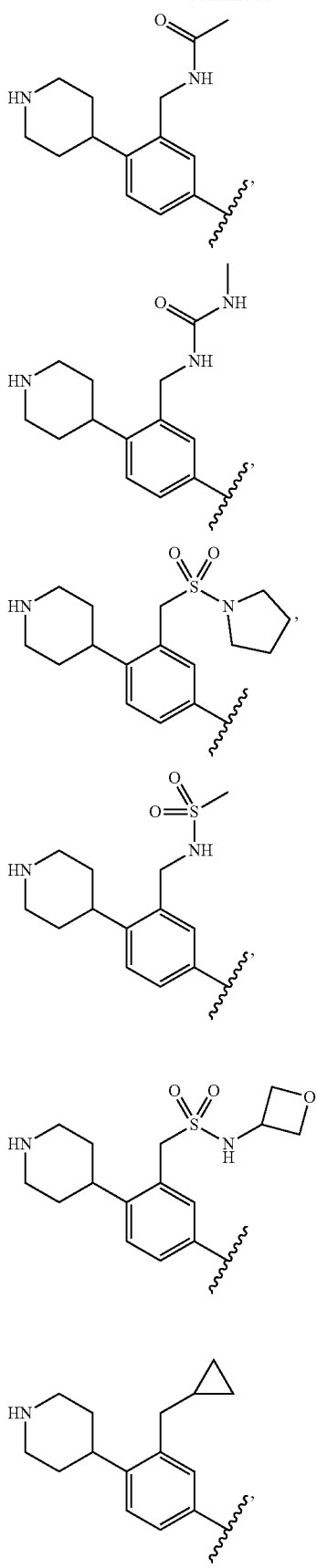
660
-continued
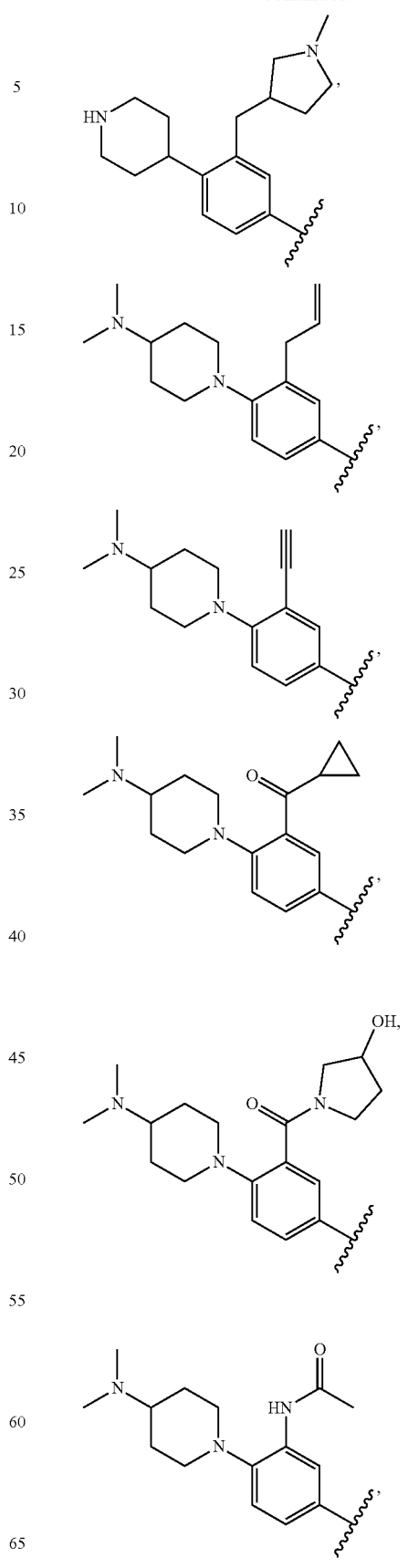

661
-continued
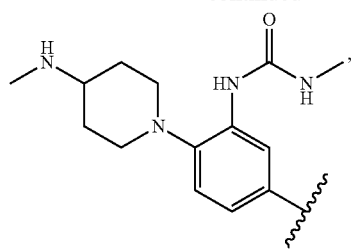
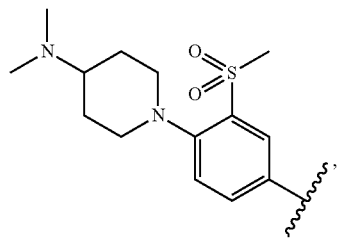
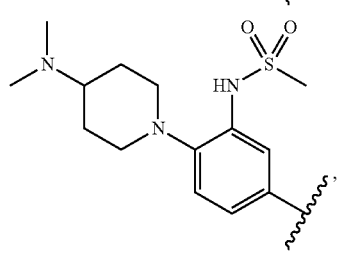
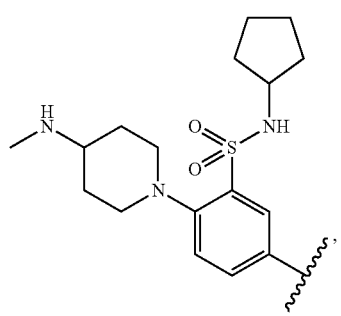
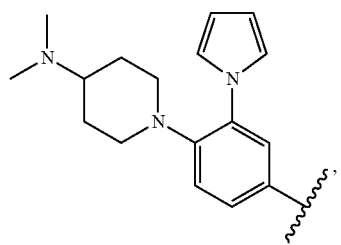
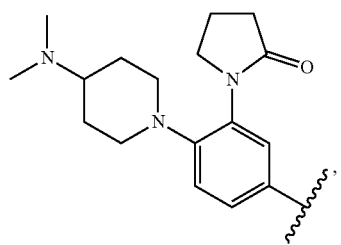
662
-continued
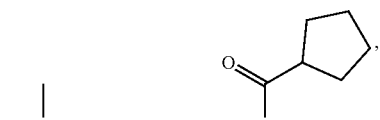
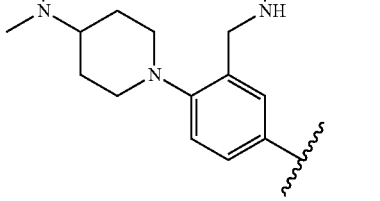
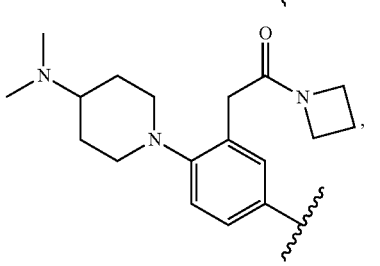
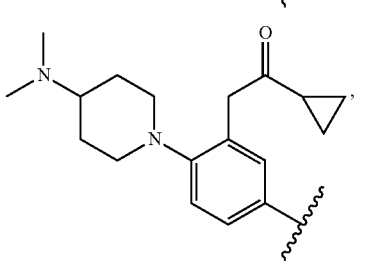
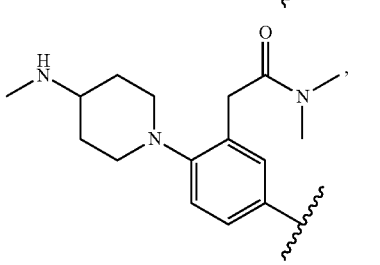
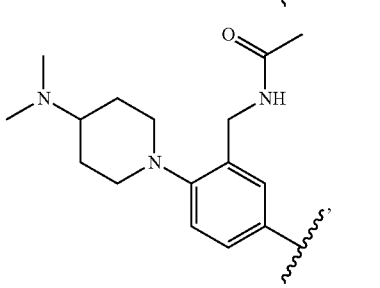
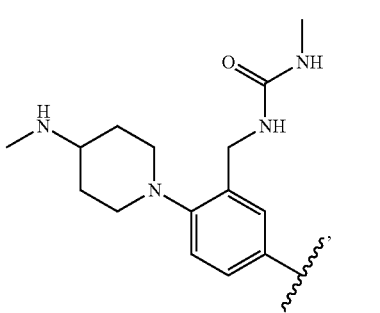

663
-continued
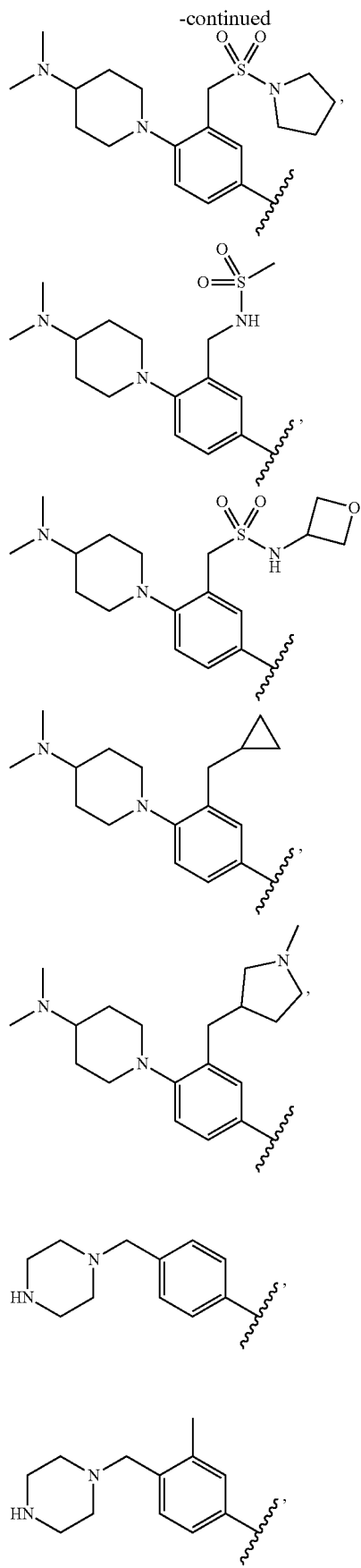
664
-continued
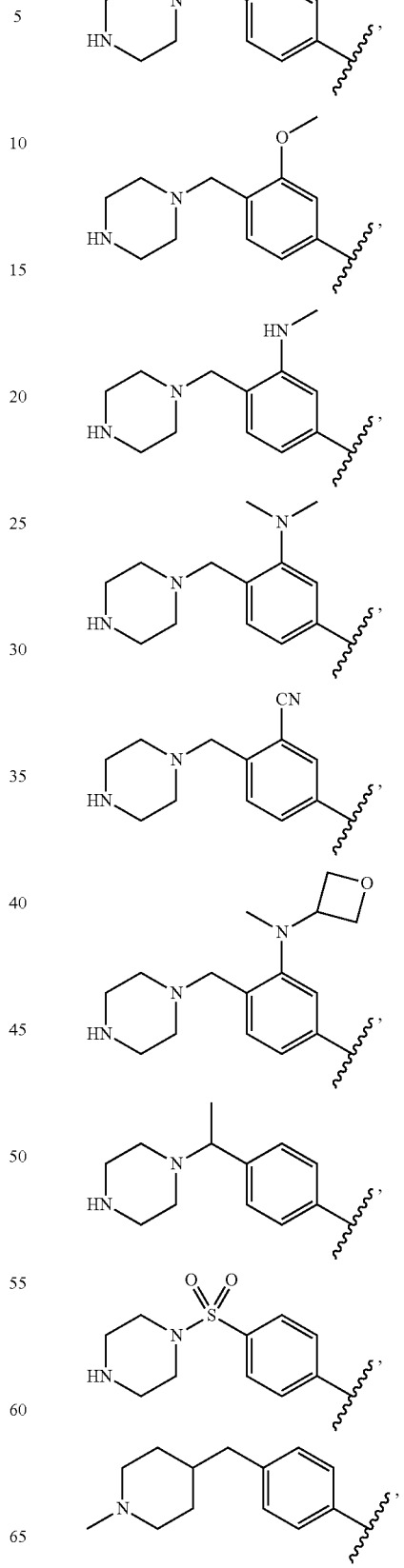

665
-continued
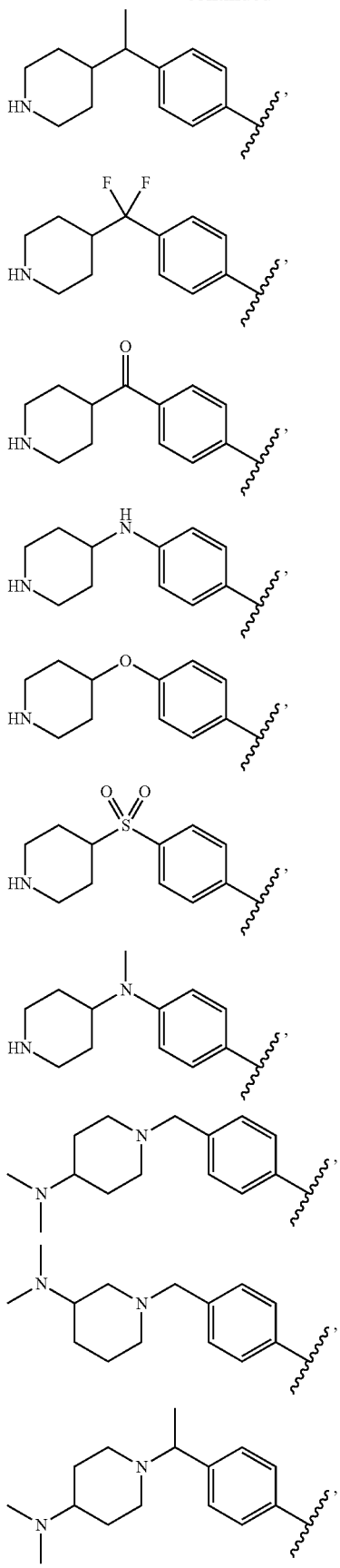
666
-continued
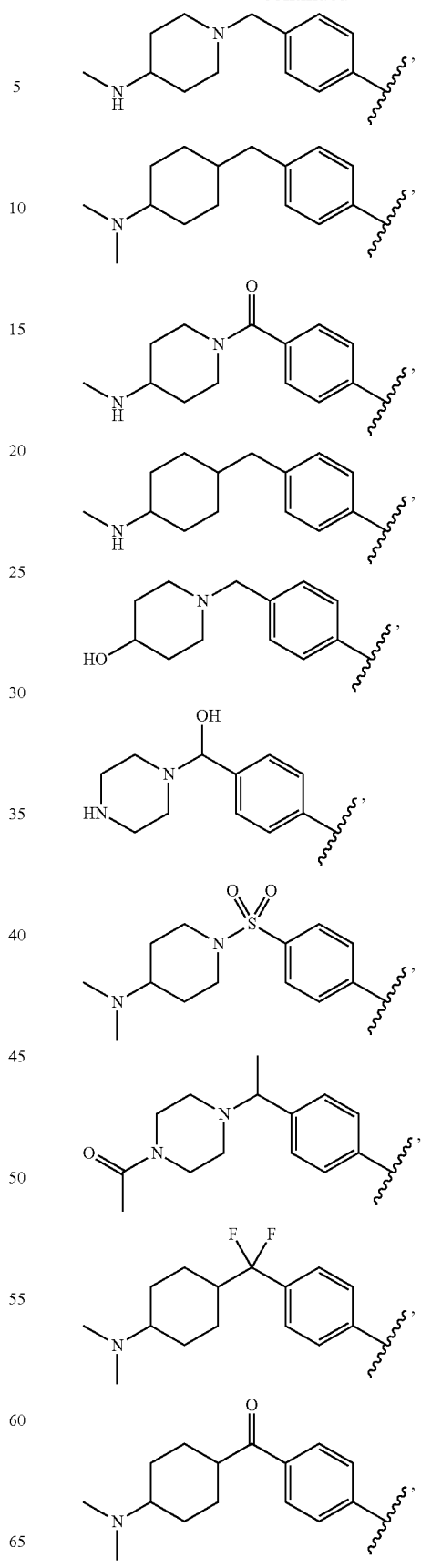

667
-continued
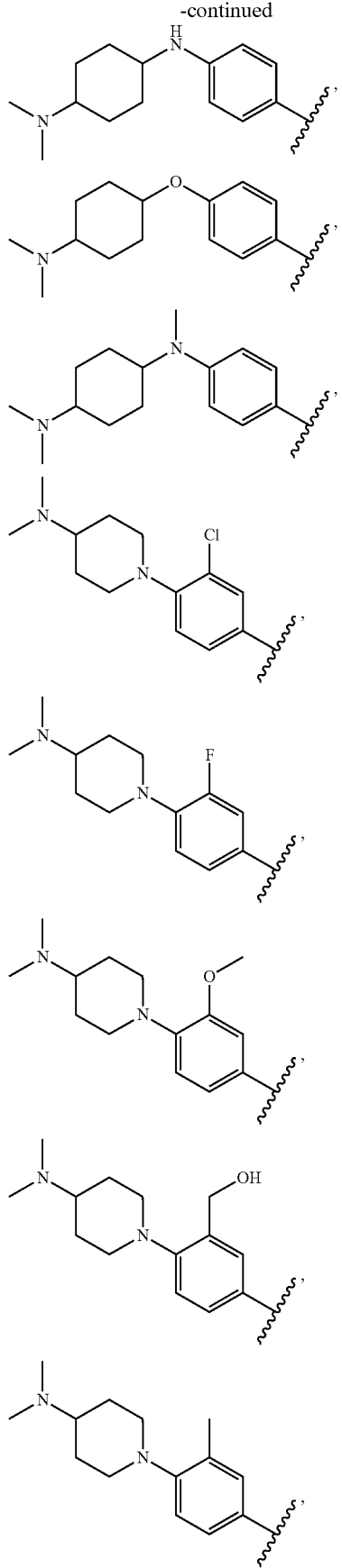
668
-continued
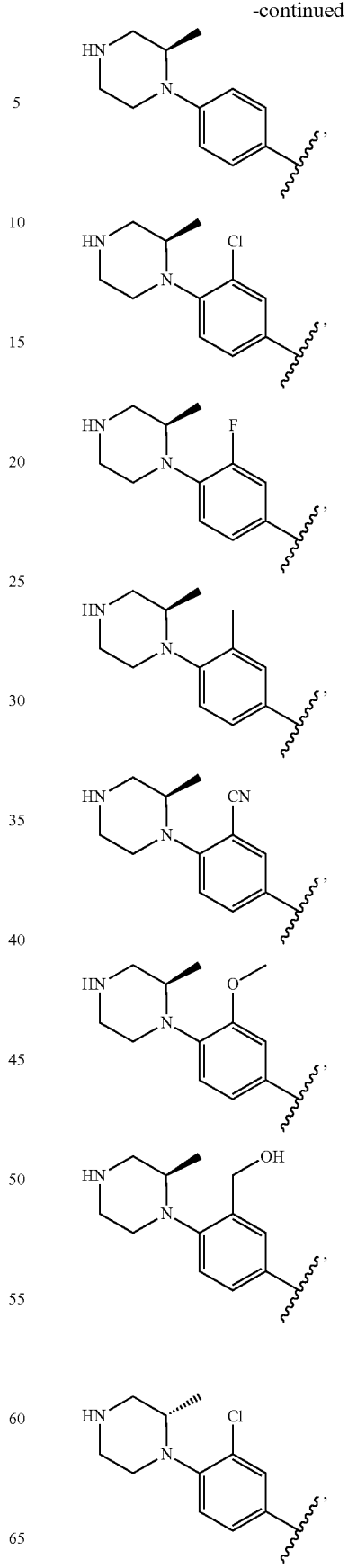

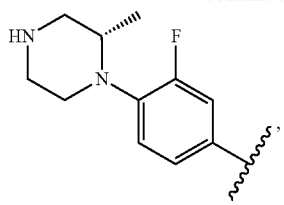

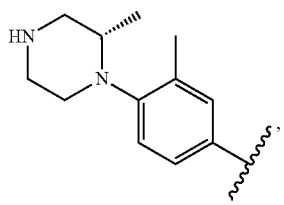

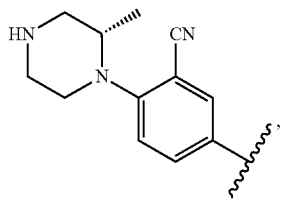

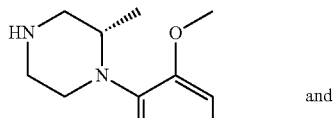

and

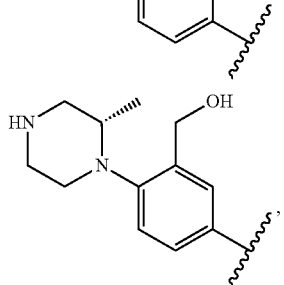

wherein the wavy lines denote attachment points to the parent molecule.

32. The compound of claim 1, or a tautomer or stereoisomer thereof, or a pharmaceutically acceptable salt of any of the foregoing, wherein W is AB wherein A and B are fused together;

A is phenyl or 6-membered heteroaryl, each of which is optionally substituted with $R^{17a}$, wherein A and $R^{17a}$ together are

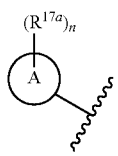

and n is 0, 1, 2, 3, or 4;

B is $C_3$-$C_6$ cycloalkyl, 3- to 7-membered heterocyclyl, 5- to 7-membered heteroaryl, or $C_6$ aryl, each of which is optionally substituted with $R^{17b}$, wherein A, B, $R^{17a}$, and $R^{17b}$ together are

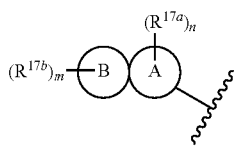

and m and n are independently 0, 1, 2, 3, or 4.

33. The compound of claim 32, or a tautomer or stereoisomer thereof, or a pharmaceutically acceptable salt of any of the foregoing, wherein A, B, $R^{17a}$ and $R^{17b}$ together are

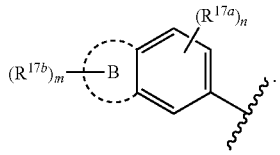

34. The compound of claim 32, or a tautomer or stereoisomer thereof, or a pharmaceutically acceptable salt of any of the foregoing, wherein A, B, $R^{17a}$ and $R^{17b}$ together are

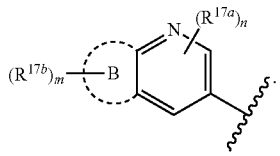

35. The compound of claim 32, or a tautomer or stereoisomer thereof, or a pharmaceutically acceptable salt of any of the foregoing, wherein A, B, $R^{17a}$ and $R^{17b}$ together are

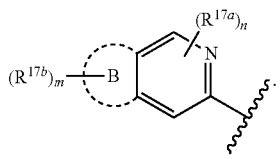

36. The compound of claim 32, or a tautomer or stereoisomer thereof, or a pharmaceutically acceptable salt of any of the foregoing, wherein A, B, $R^{17a}$ and $R^{17b}$ together are

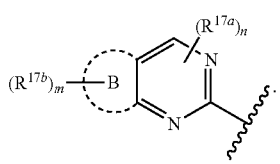

37. The compound of claim 32, or a tautomer or stereoisomer thereof, or a pharmaceutically acceptable salt of any of the foregoing, wherein A, B, $R^{17a}$ and $R^{17b}$ together are

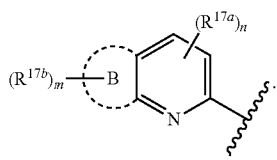

38. The compound of claim 32, or a tautomer or stereoisomer thereof, or a pharmaceutically acceptable salt of any of the foregoing, wherein B is 3- to 7-membered heterocyclyl or 5- to 7-membered heteroaryl, each $R^{17a}$ is independently —$(C_1$-$C_3$ alkylene)$OR^{10}$, $C_1$-$C_6$ alkyl optionally substituted by halogen, —C(O)$NR^{11}R^{12}$, —$(C_1$-$C_3$ alkylene)$NR^{11}R^{12}$, —CN, halogen, —$NR^{11}R^{12}$, $C_3$-$C_6$ cycloalkyl, or —$OR^{10}$;

each $R^{17b}$ is independently oxo, —$(C_1$-$C_3$ alkylene)$OR^{10}$, $C_1$-$C_6$ alkyl optionally substituted by halogen, —C(O)$NR^{11}R^{12}$, —$(C_1$-$C_3$ alkylene)$NR^{11}R^{12}$, —CN, halogen, —$NR^{11}R^{12}$, $C_3$-$C_6$ cycloalkyl, or —$OR^{10}$, or any two groups $R^{17b}$, when bound to the same carbon atom, are taken together with the carbon to which they are attached to form a $C_3$-$C_6$ cycloalkyl;

and m and n are independently 0, 1, 2, or 3.

39. The compound of claim 32, or a tautomer or stereoisomer thereof, or a pharmaceutically acceptable salt of any of the foregoing, wherein m is 0.

40. The compound of claim 32, or a tautomer or stereoisomer thereof, or a pharmaceutically acceptable salt of any of the foregoing, wherein m is 1.

41. The compound of claim 32, or a tautomer or stereoisomer thereof, or a pharmaceutically acceptable salt of any of the foregoing, wherein n is 0.

42. The compound of claim 32, or a tautomer or stereoisomer thereof, or a pharmaceutically acceptable salt of any of the foregoing, wherein n is 1.

43. The compound of claim 1, or a tautomer or stereoisomer thereof, or a pharmaceutically acceptable salt of any of the foregoing, wherein W is selected from the group consisting of:

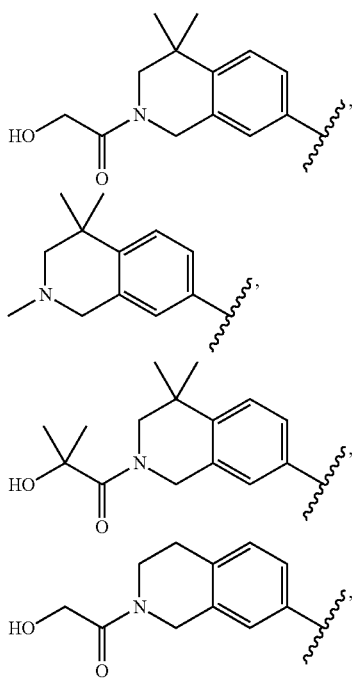

-continued

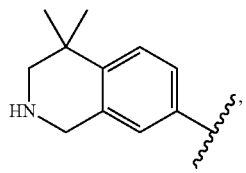
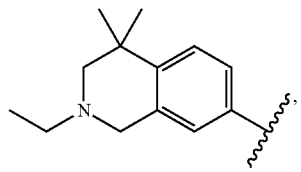
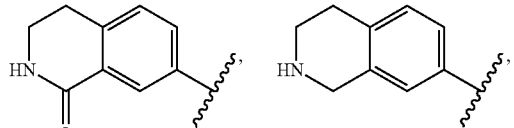
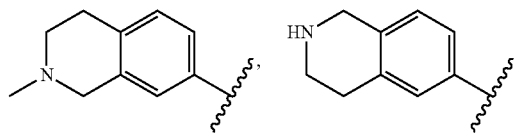
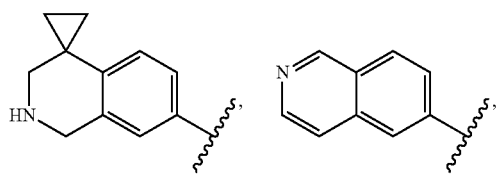
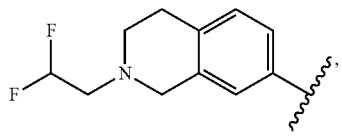
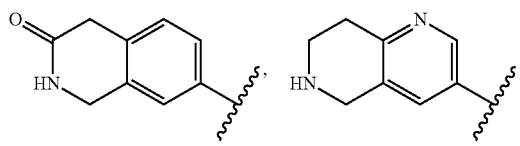
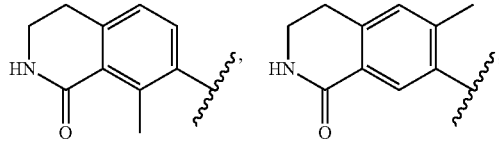
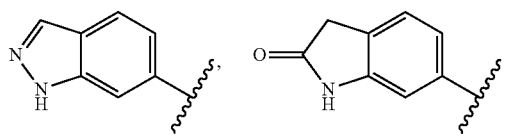
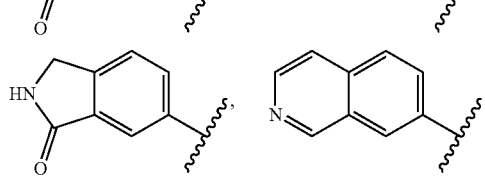

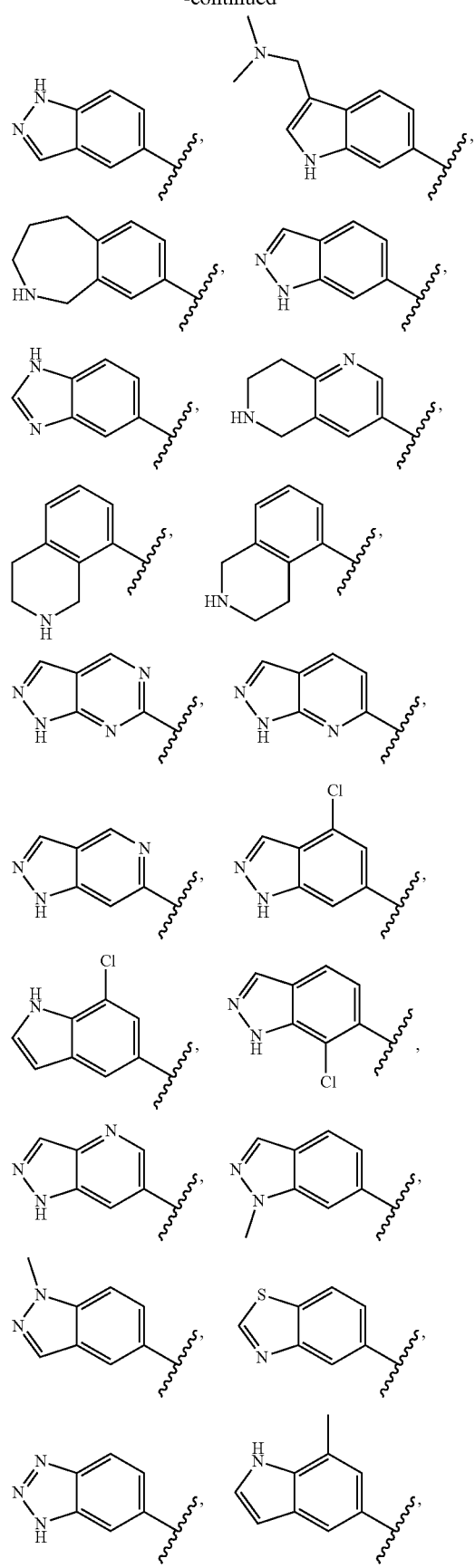
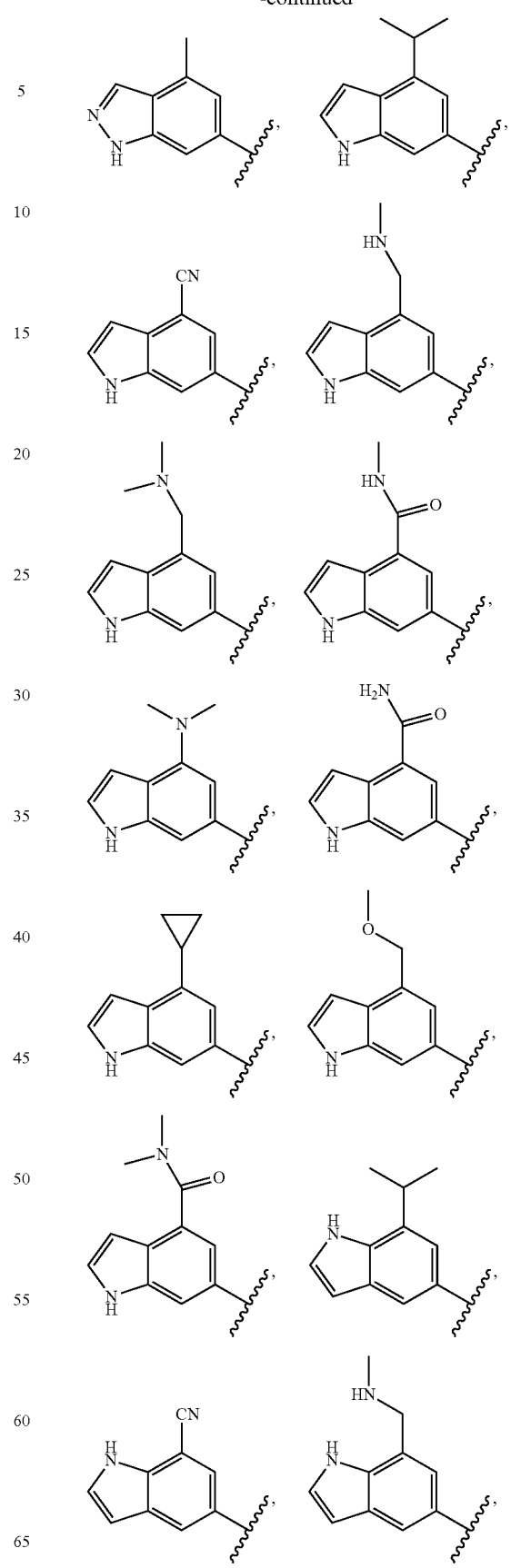

675
-continued
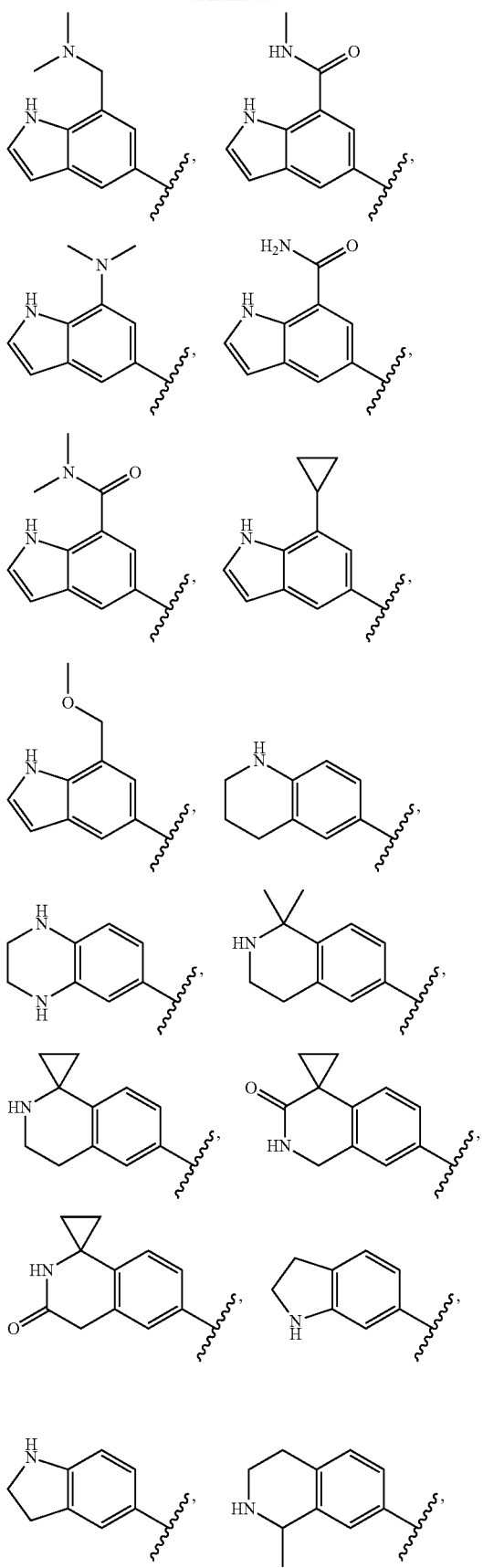
676
-continued
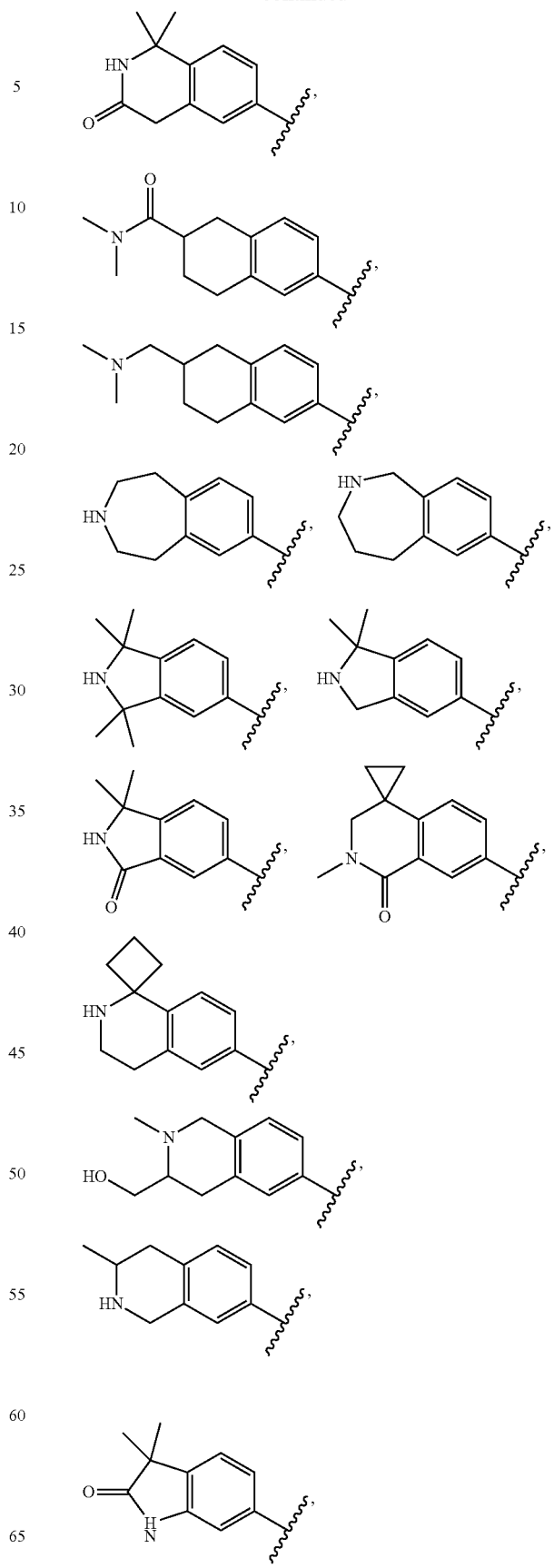

677
-continued
678
-continued
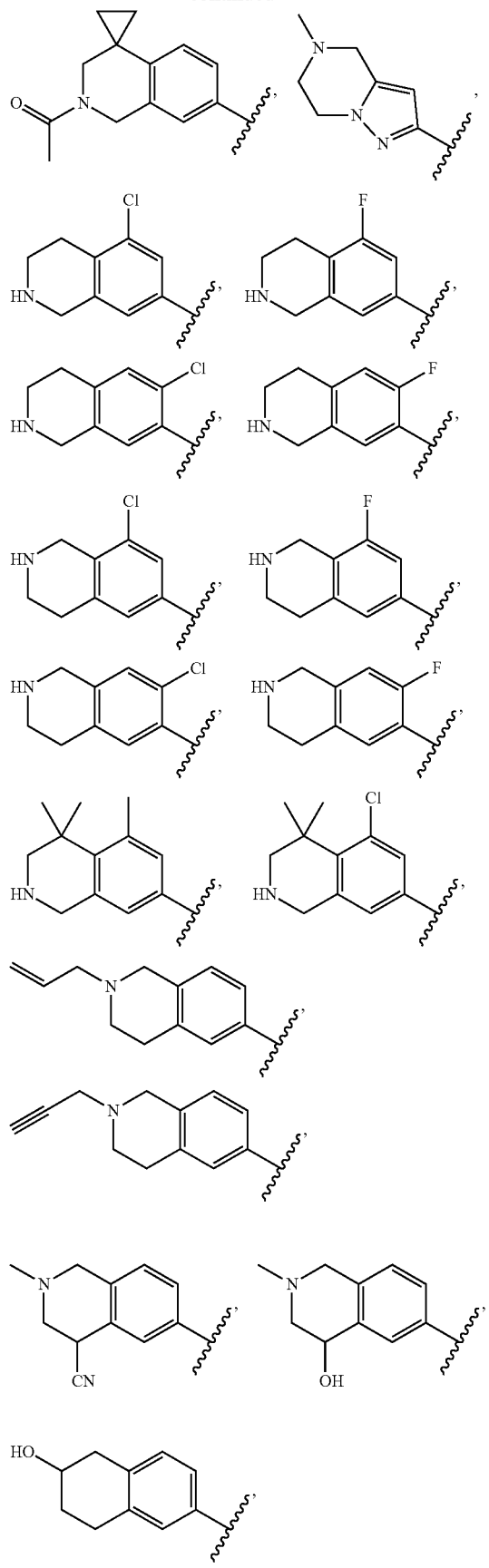
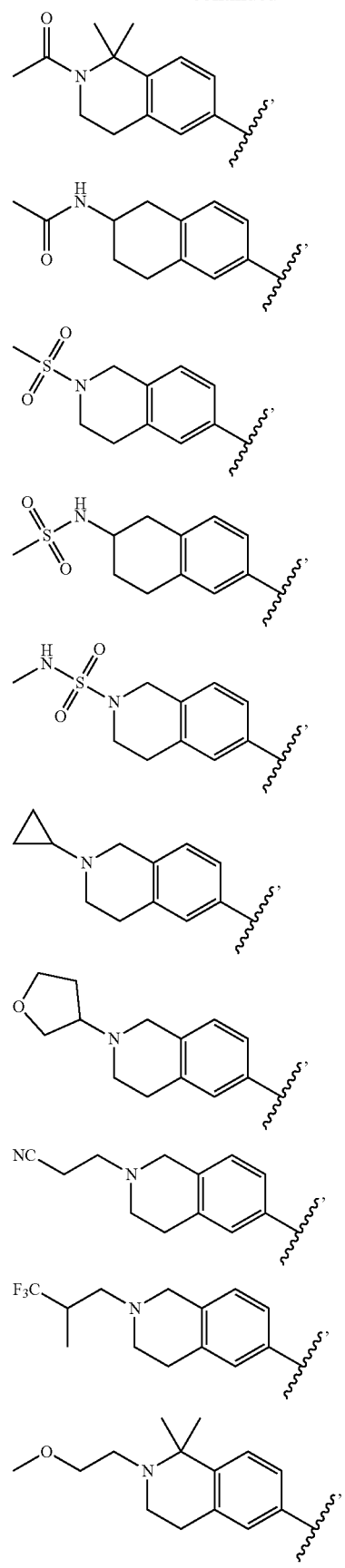

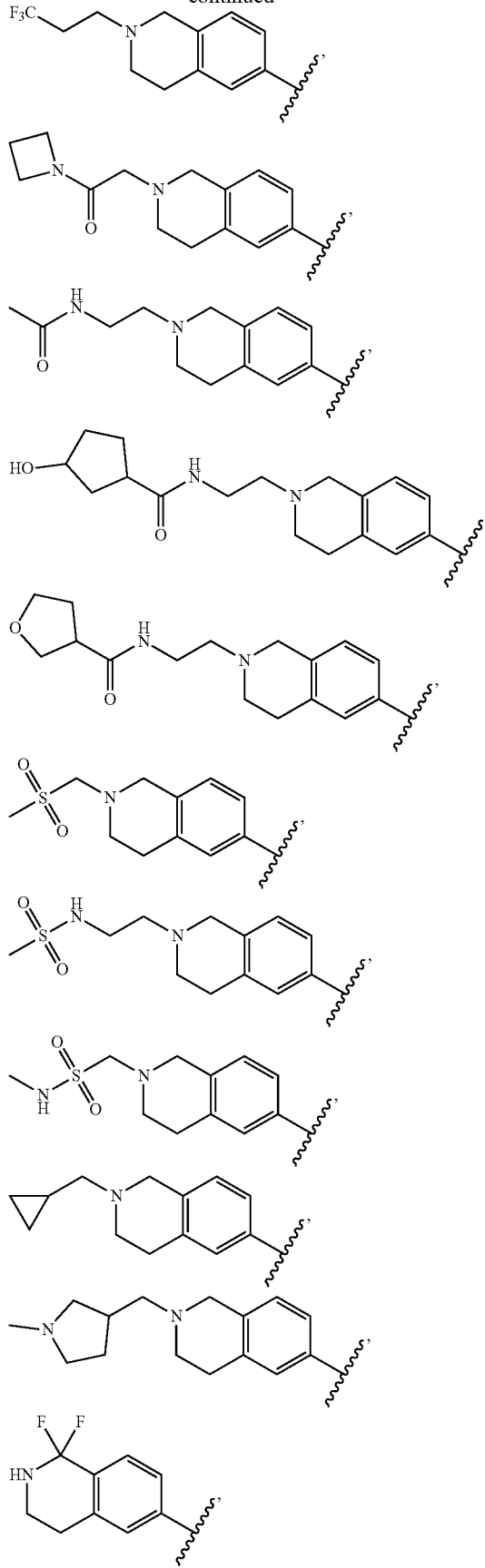
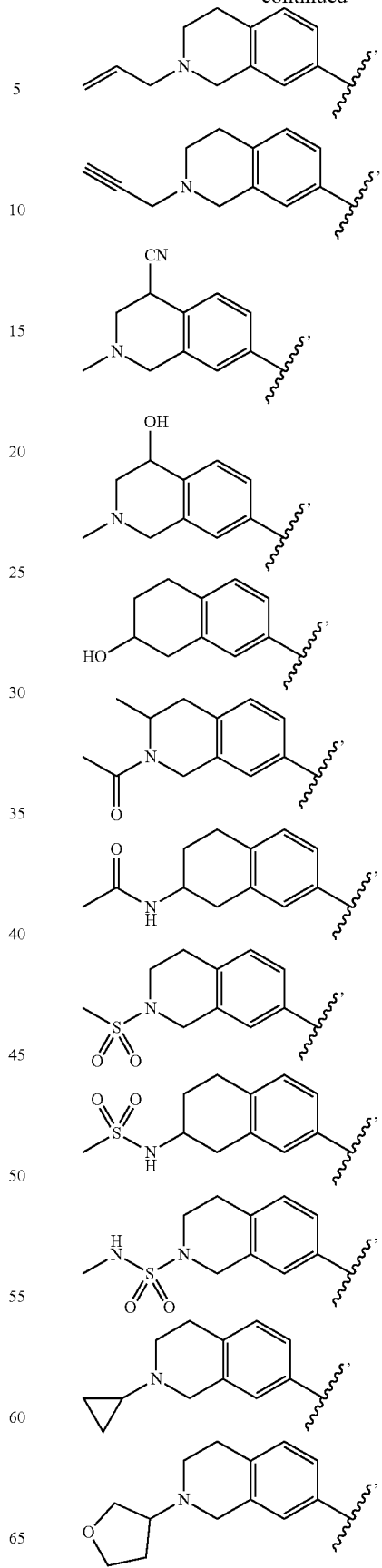

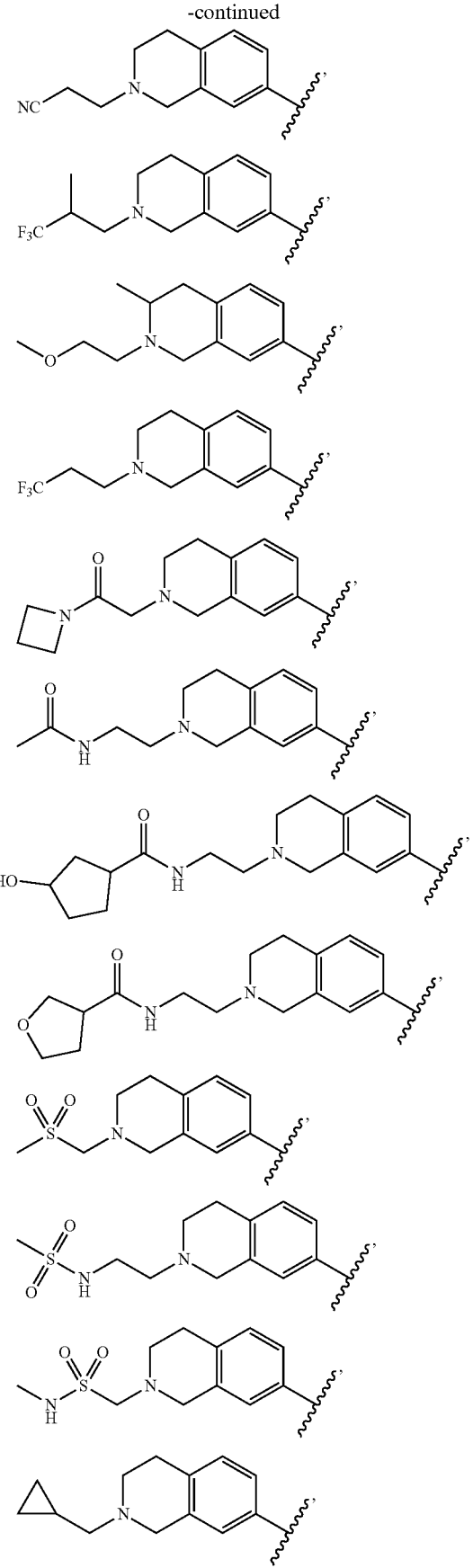
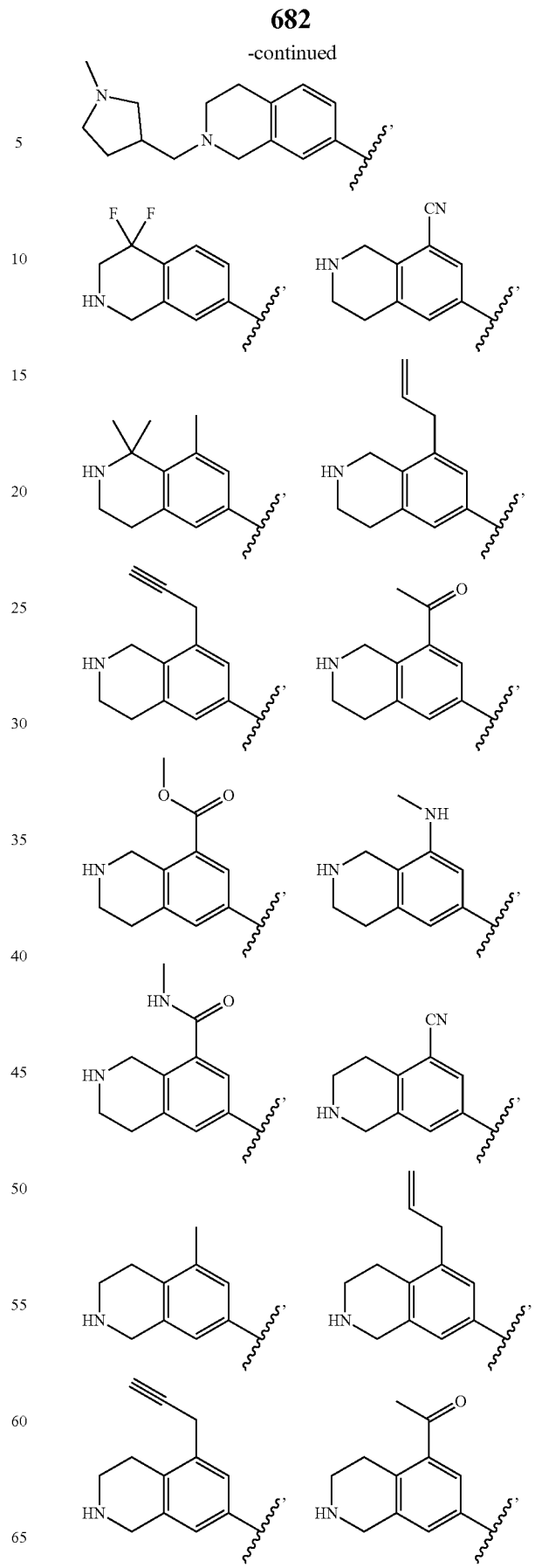

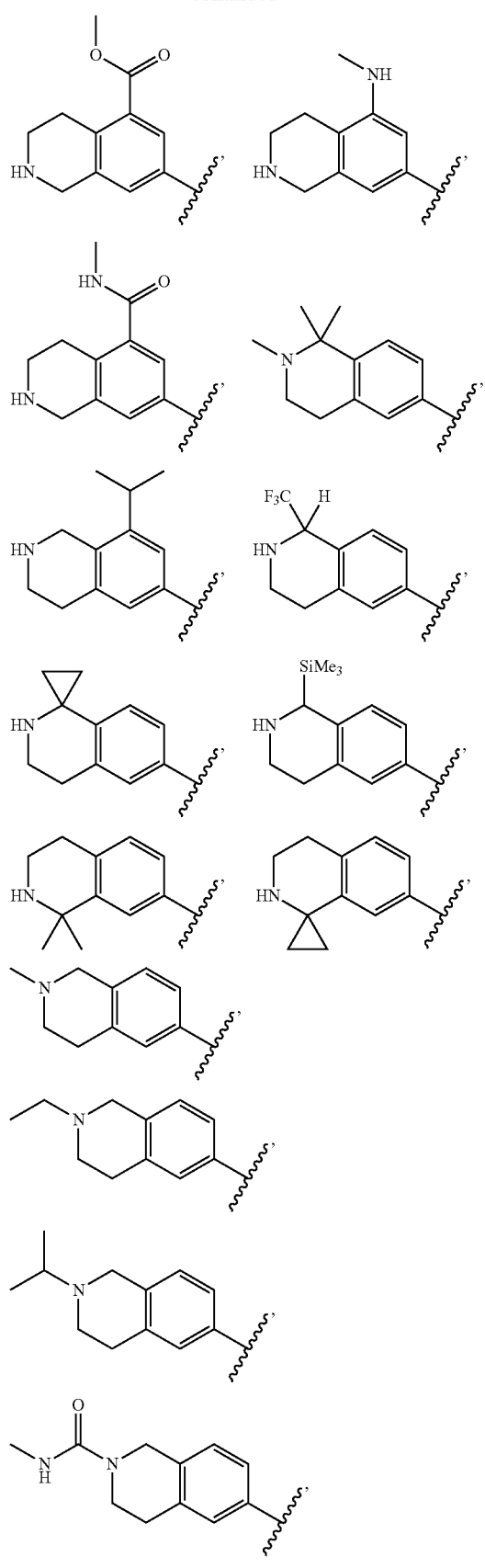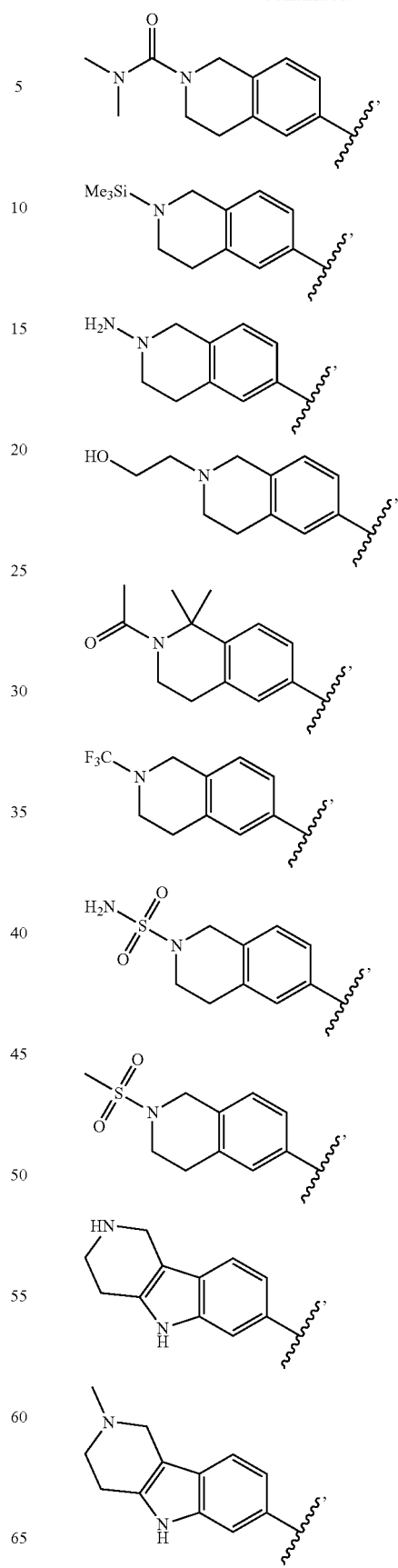

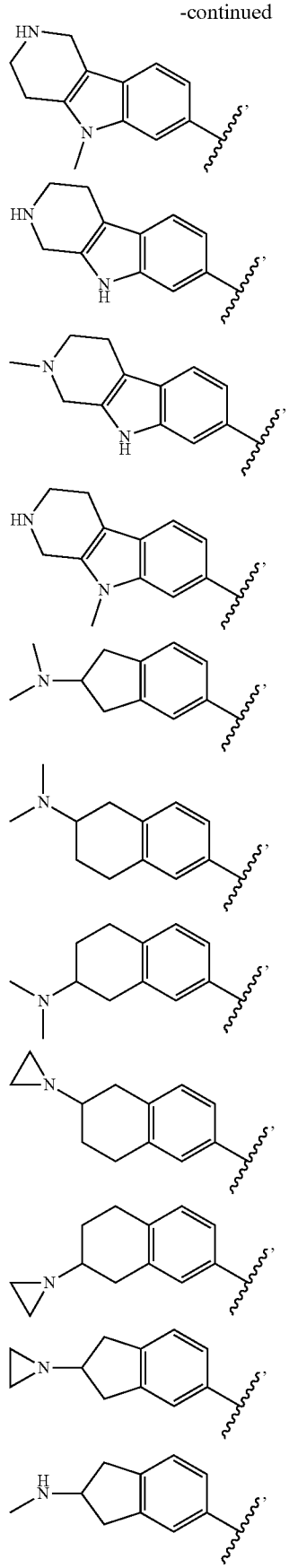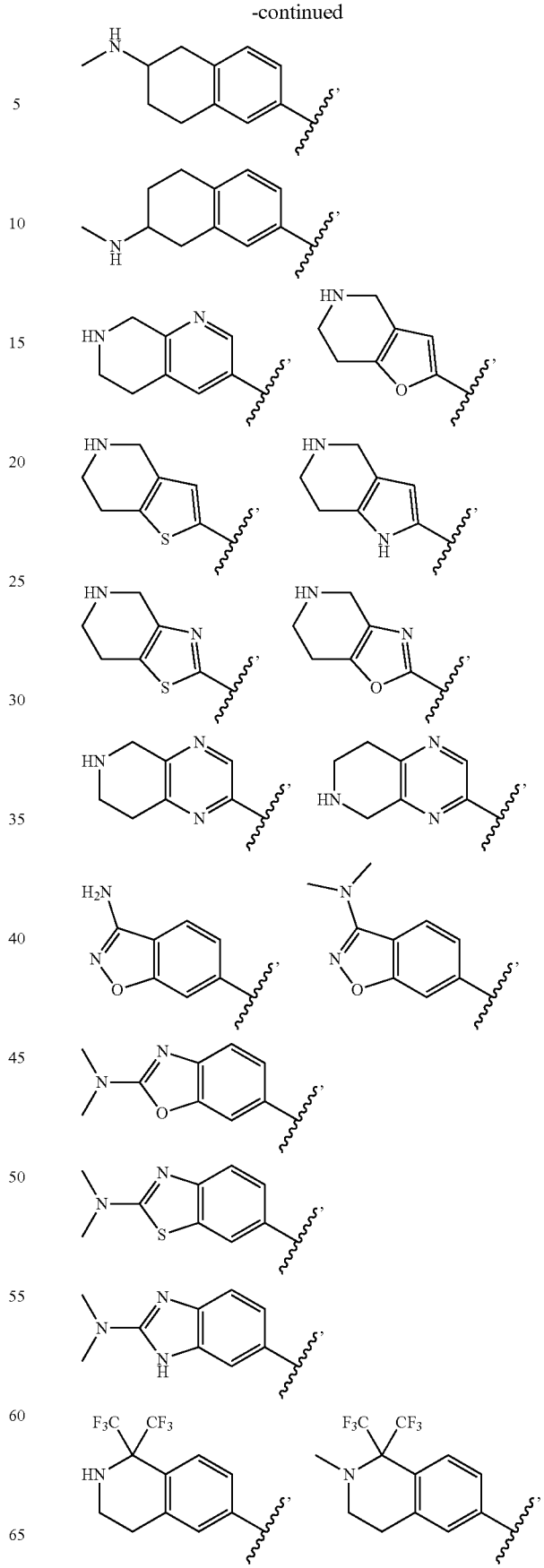

-continued
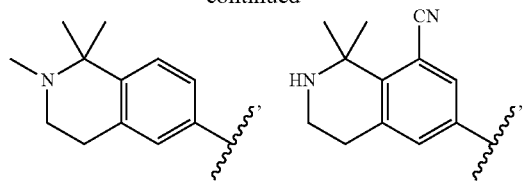
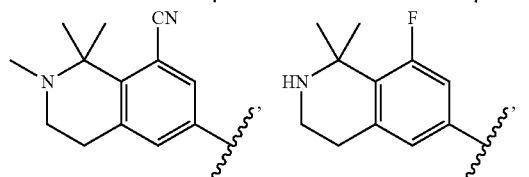
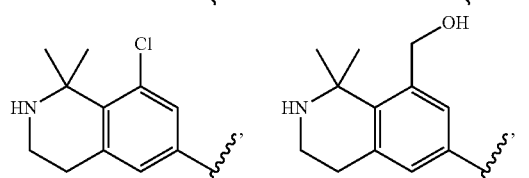
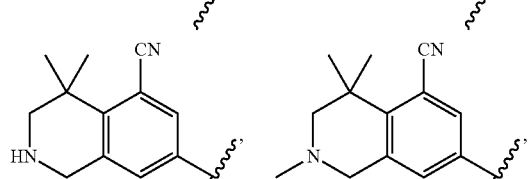
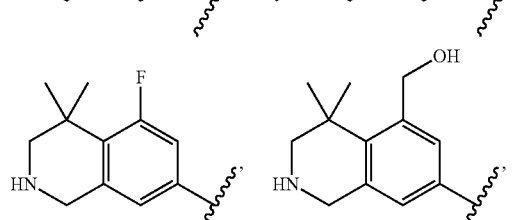
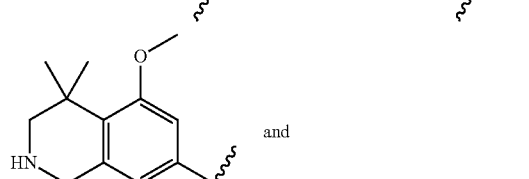
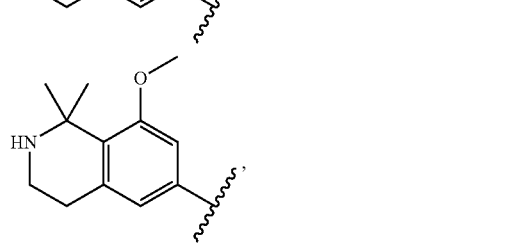
and
wherein the wavy lines denote attachment points to the parent molecule.
44. A compound selected from the group consisting of:
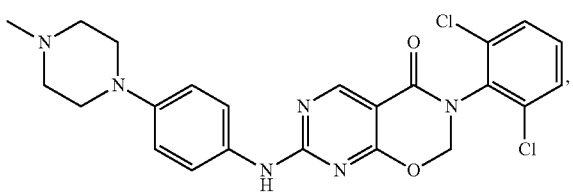
-continued
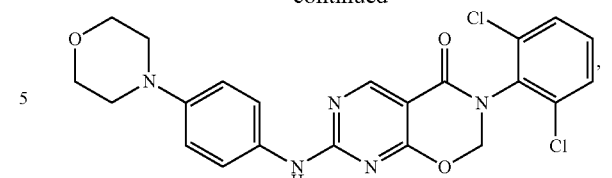
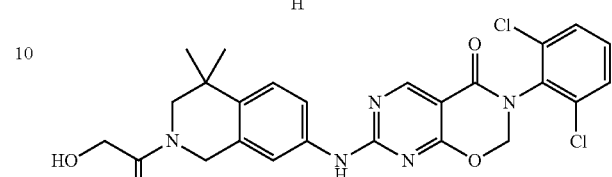
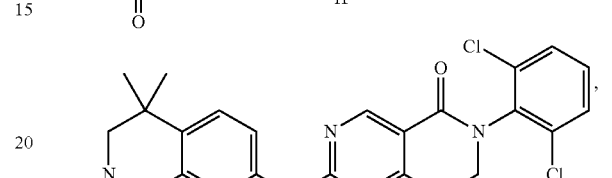
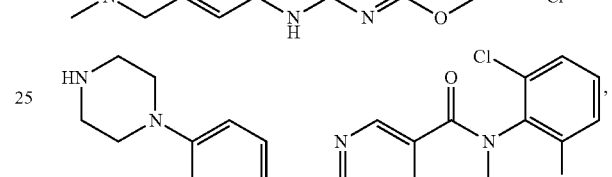
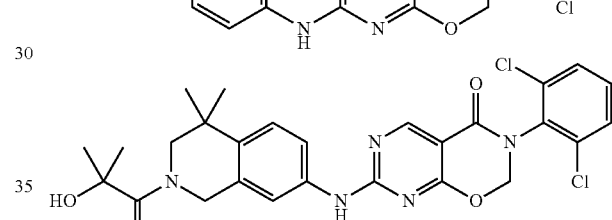
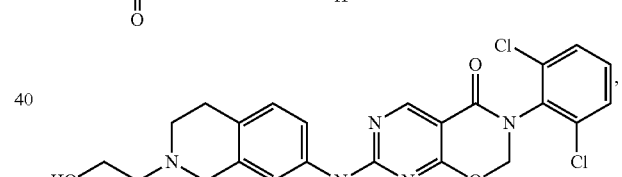
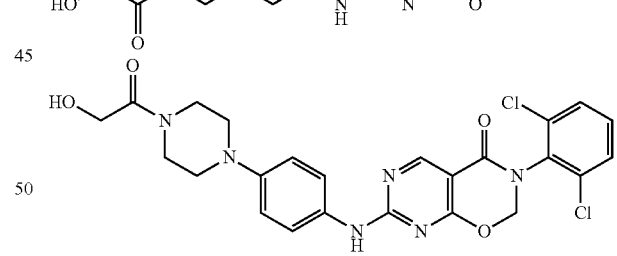
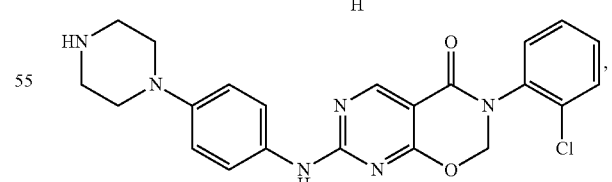
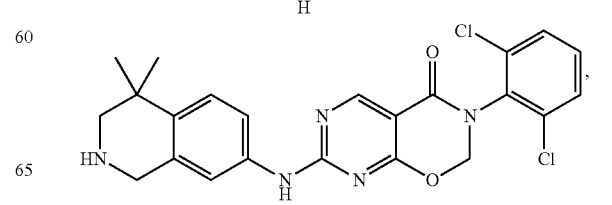

689
-continued
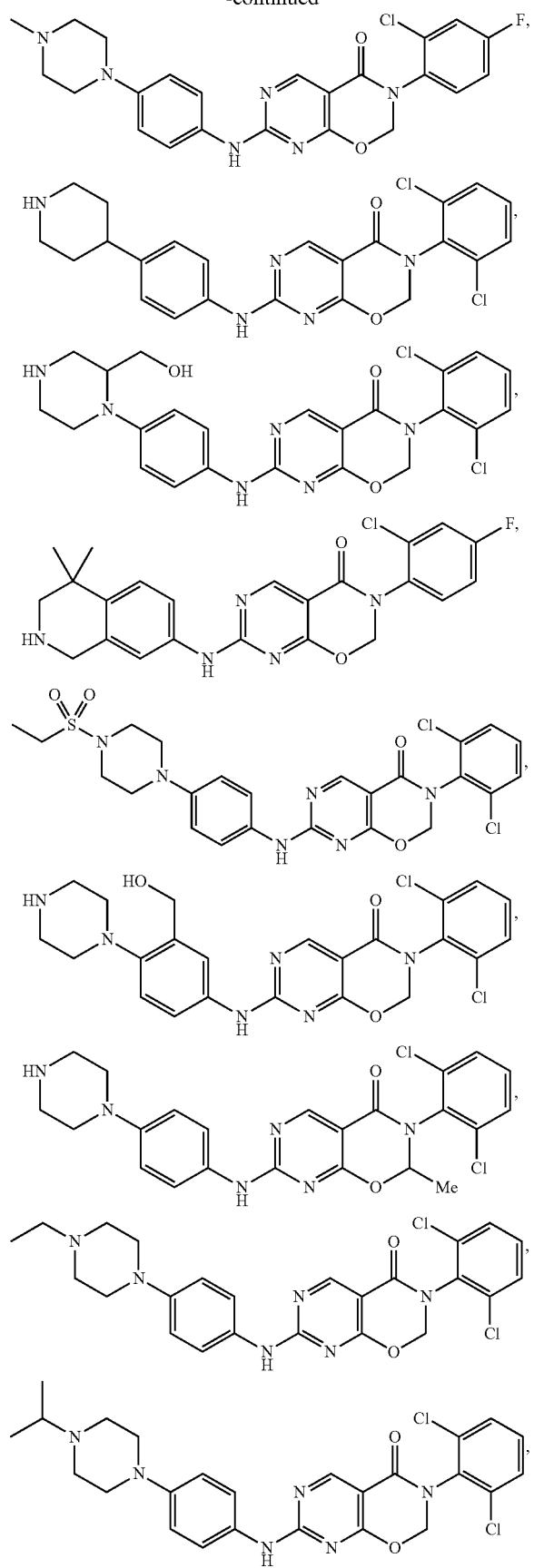
690
-continued
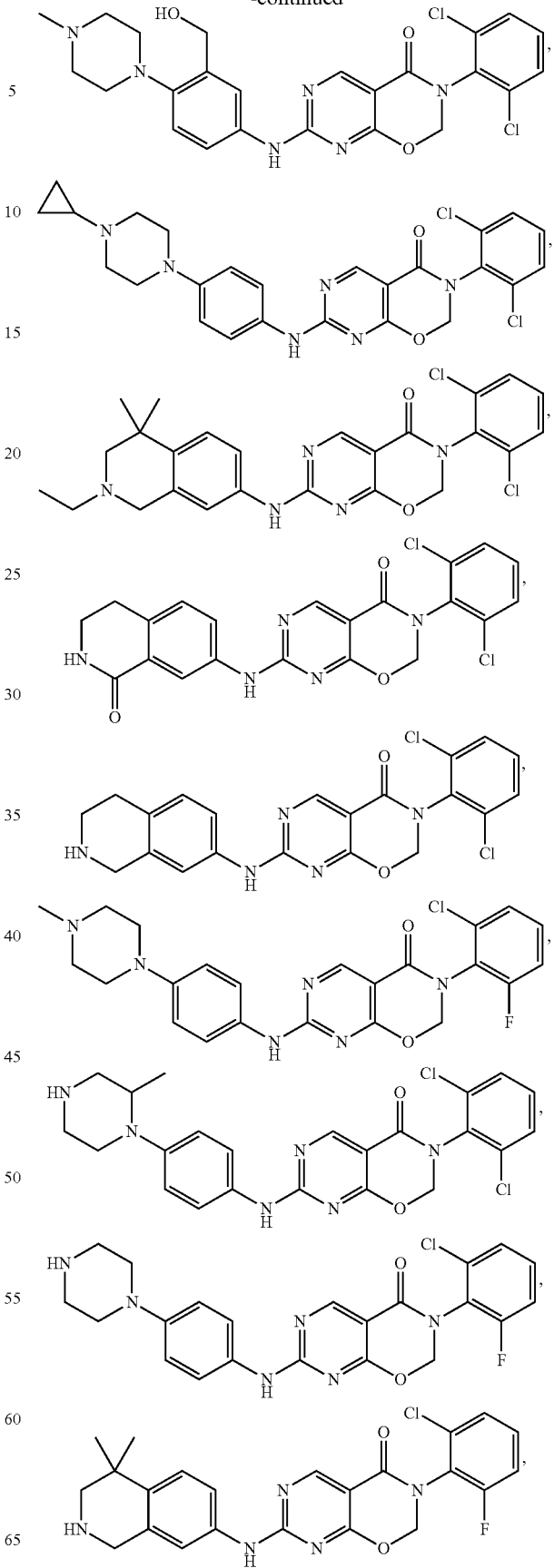

691
-continued
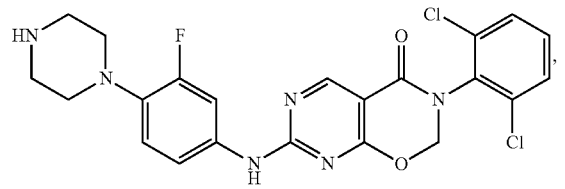
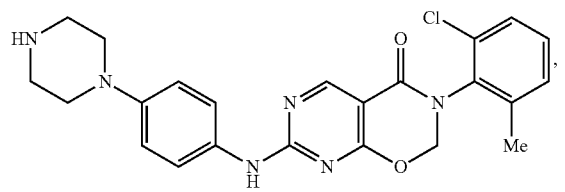
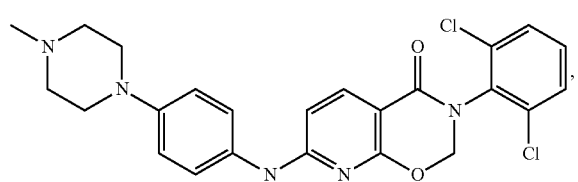
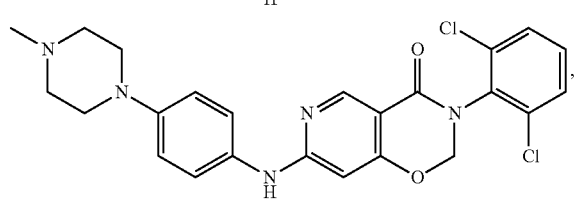
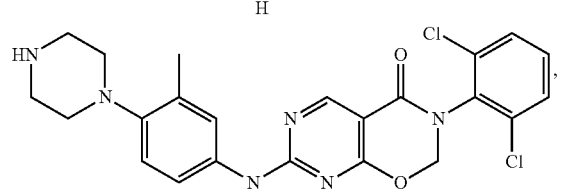
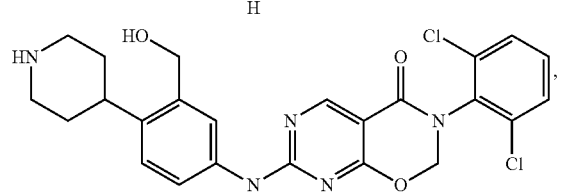
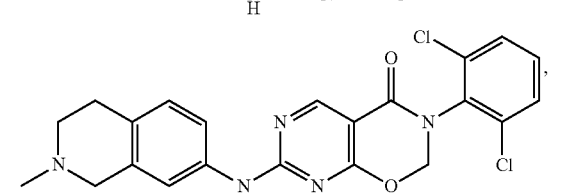
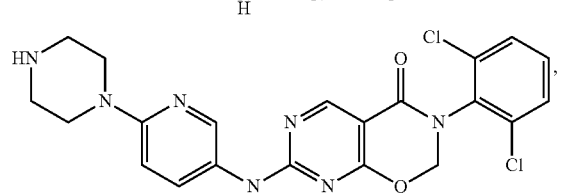
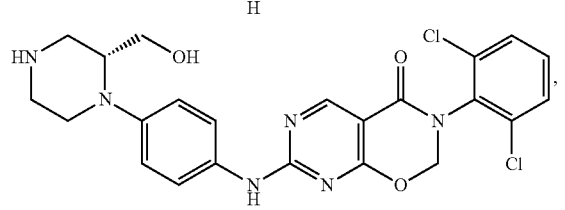
692
-continued
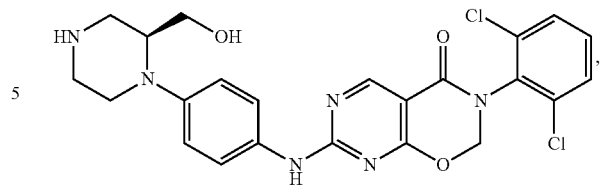
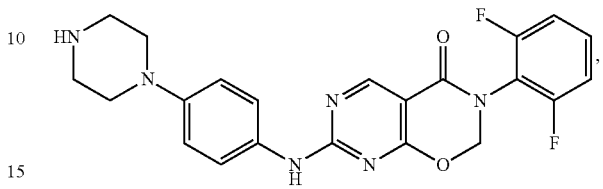
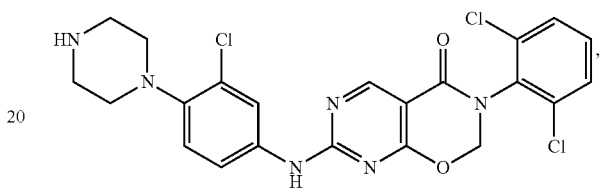
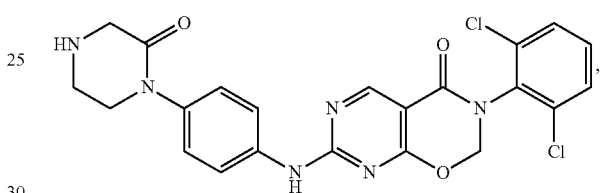
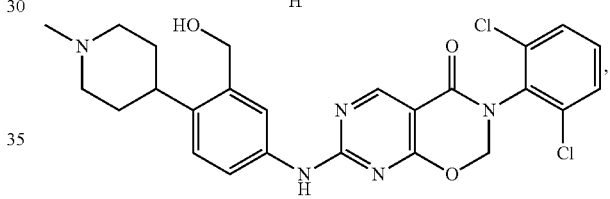
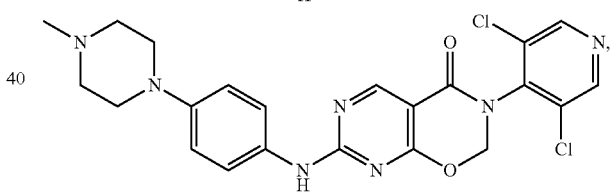
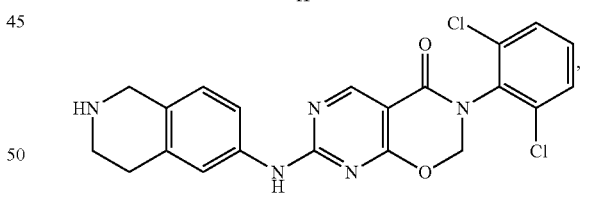
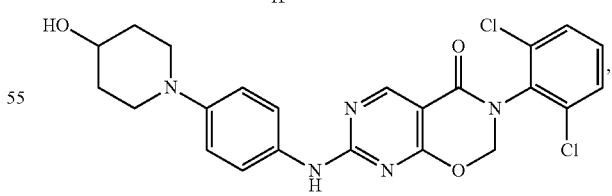
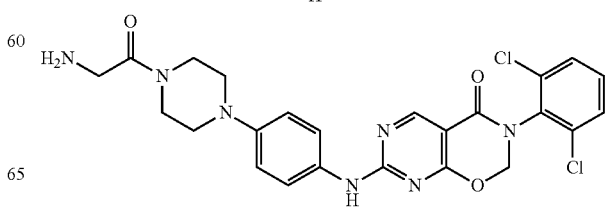

693
-continued
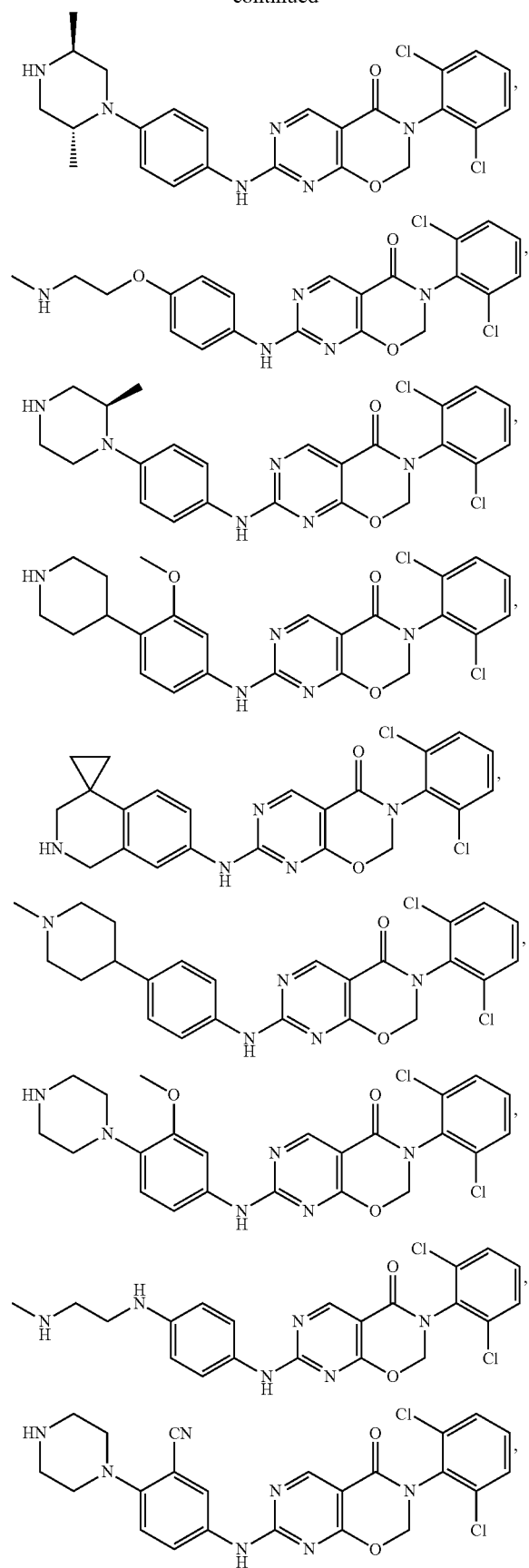
694
-continued
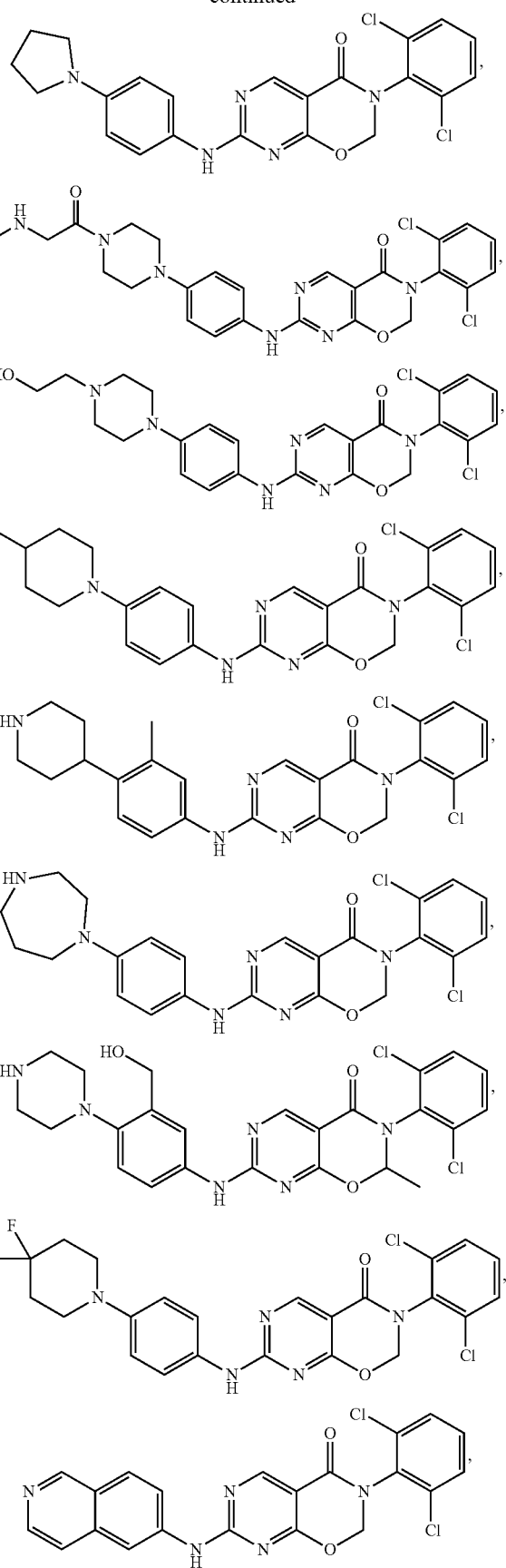

-continued
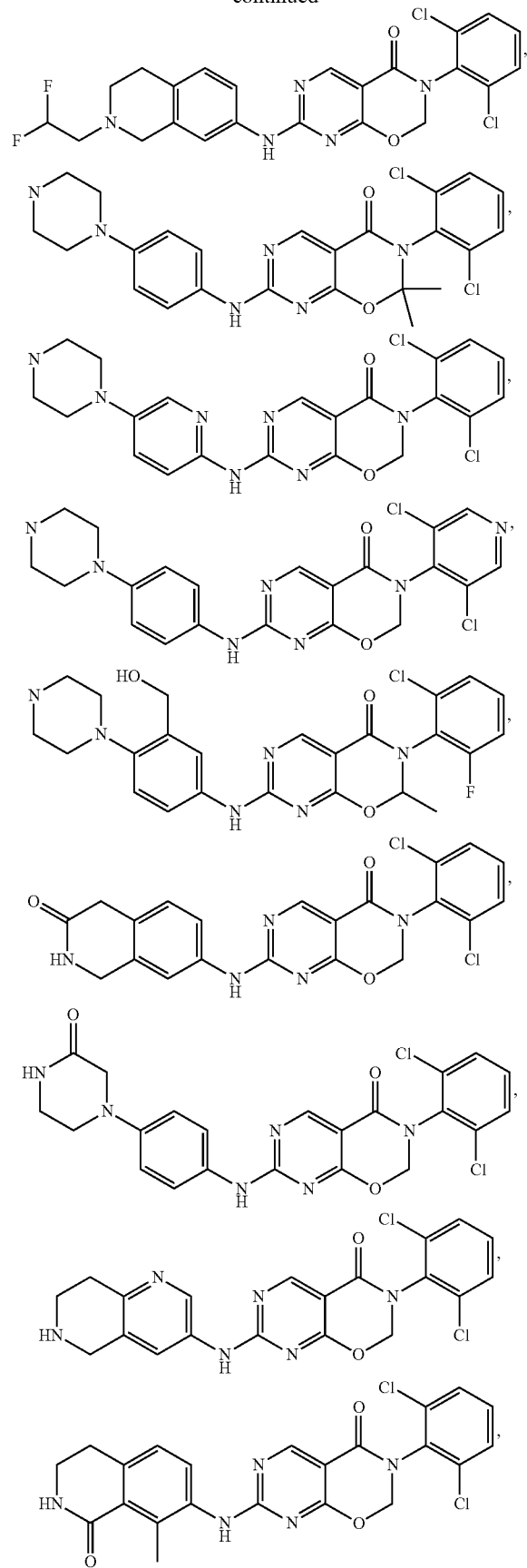
-continued
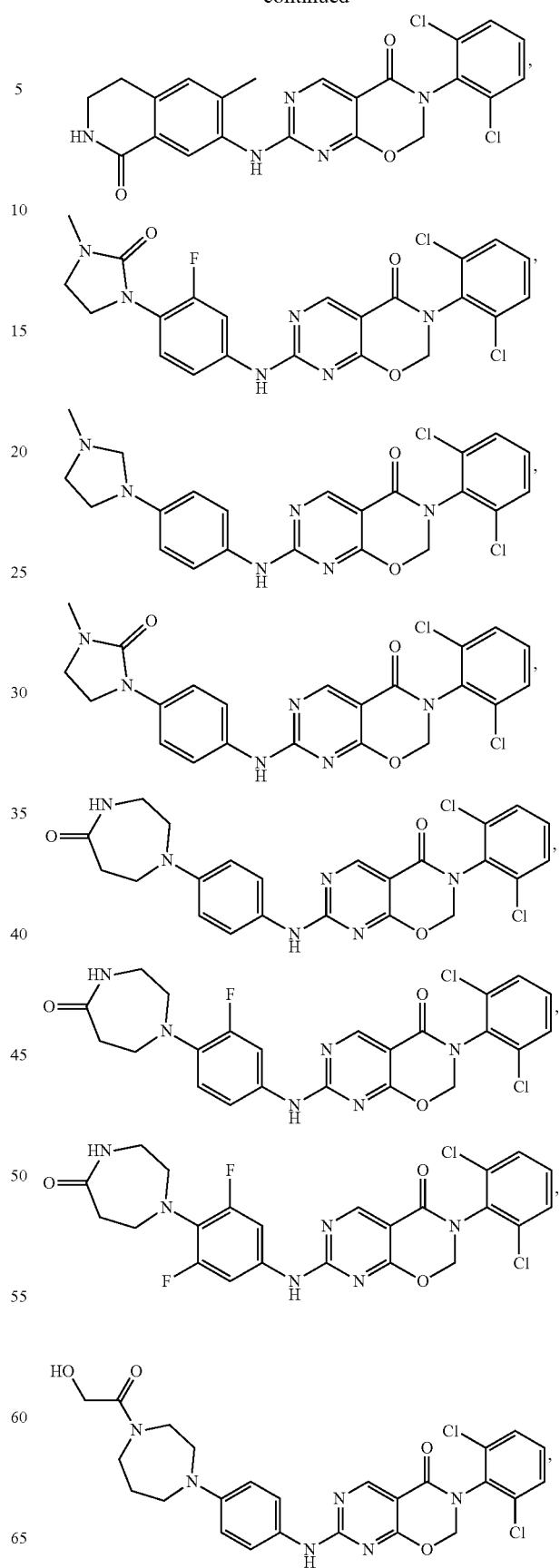

697
-continued
698
-continued
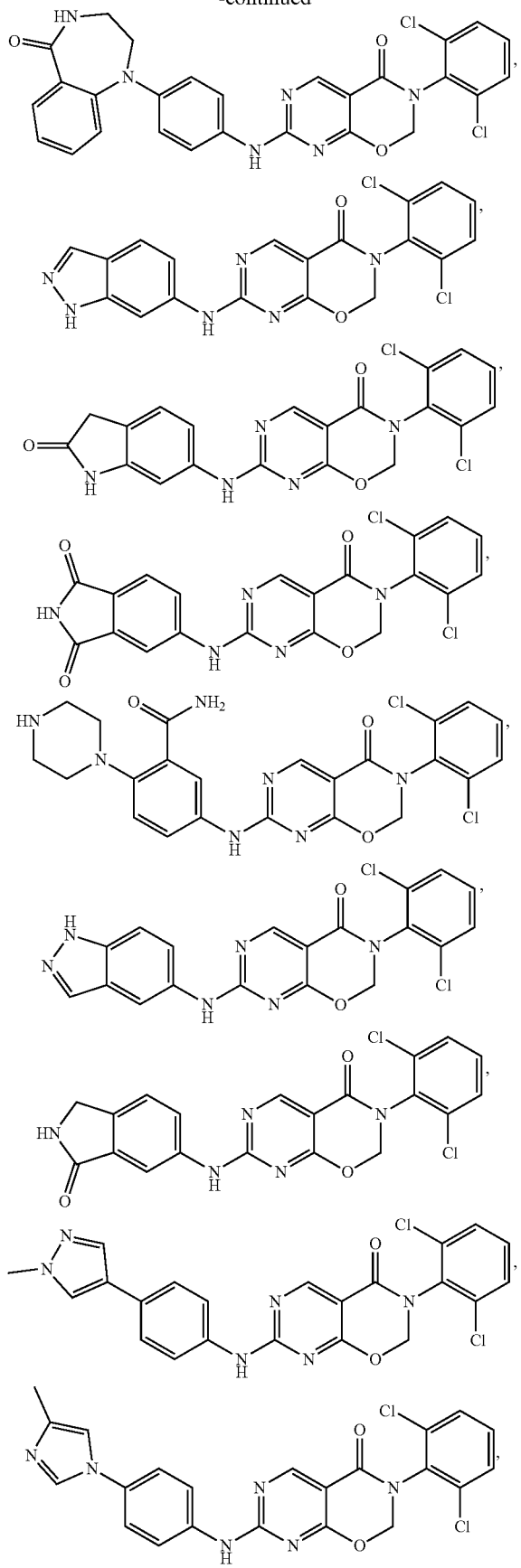
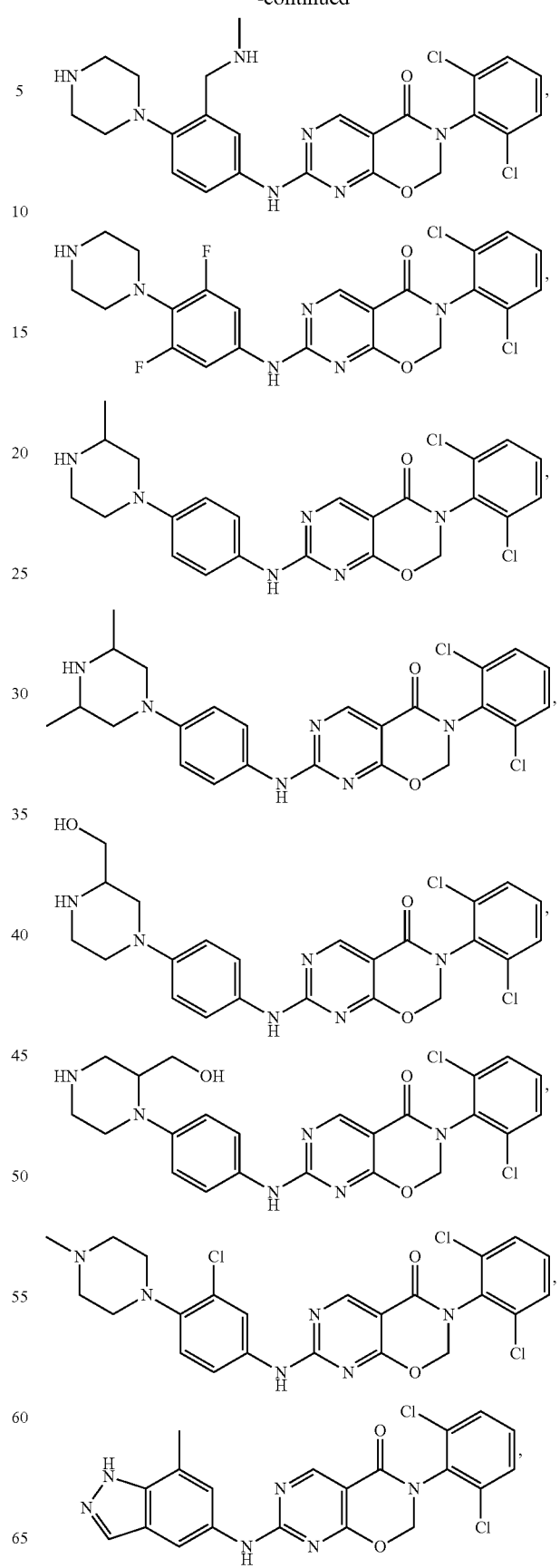

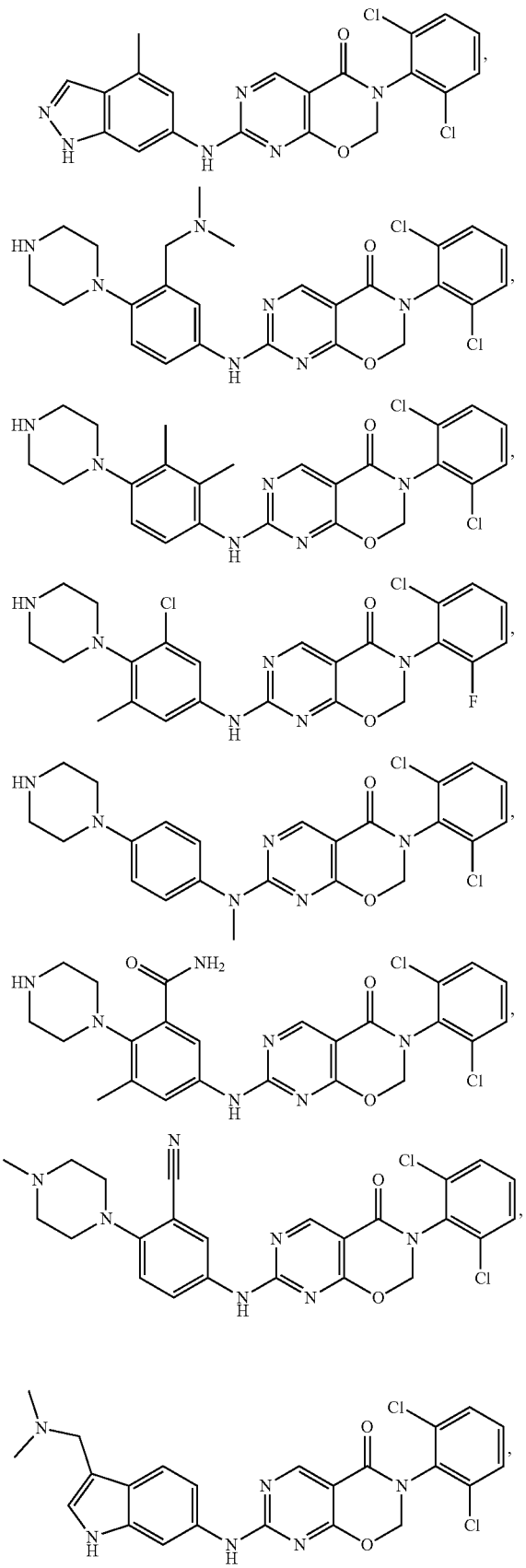
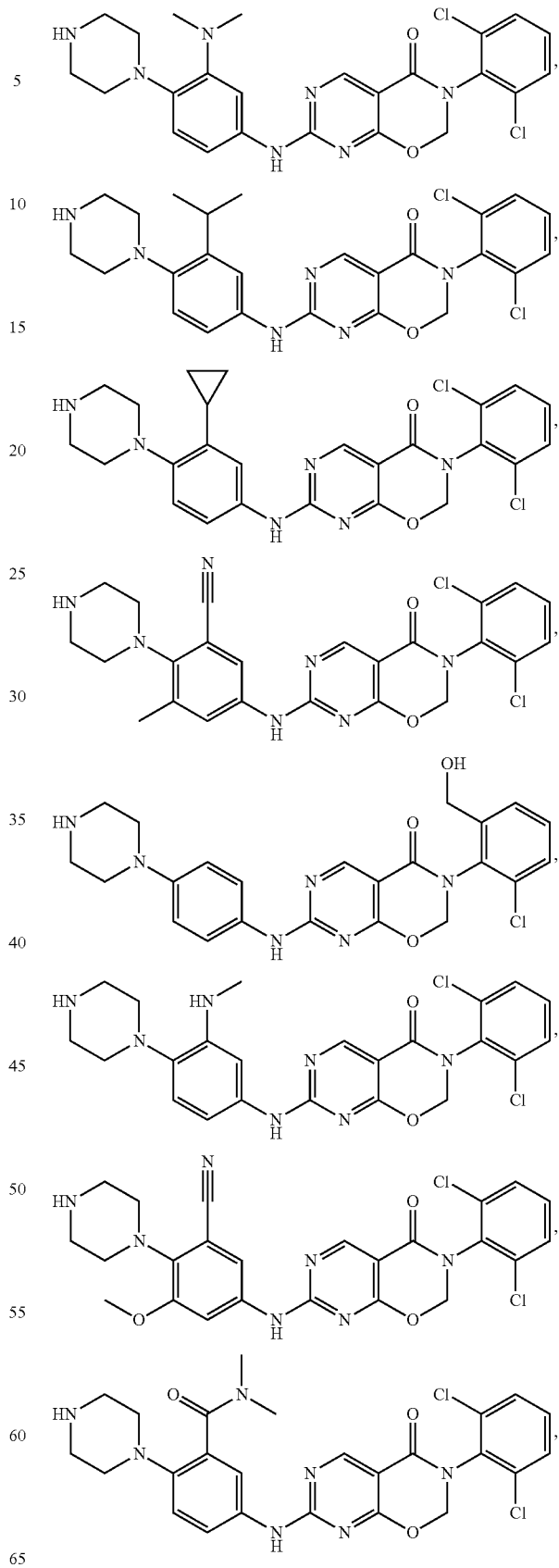

701
-continued
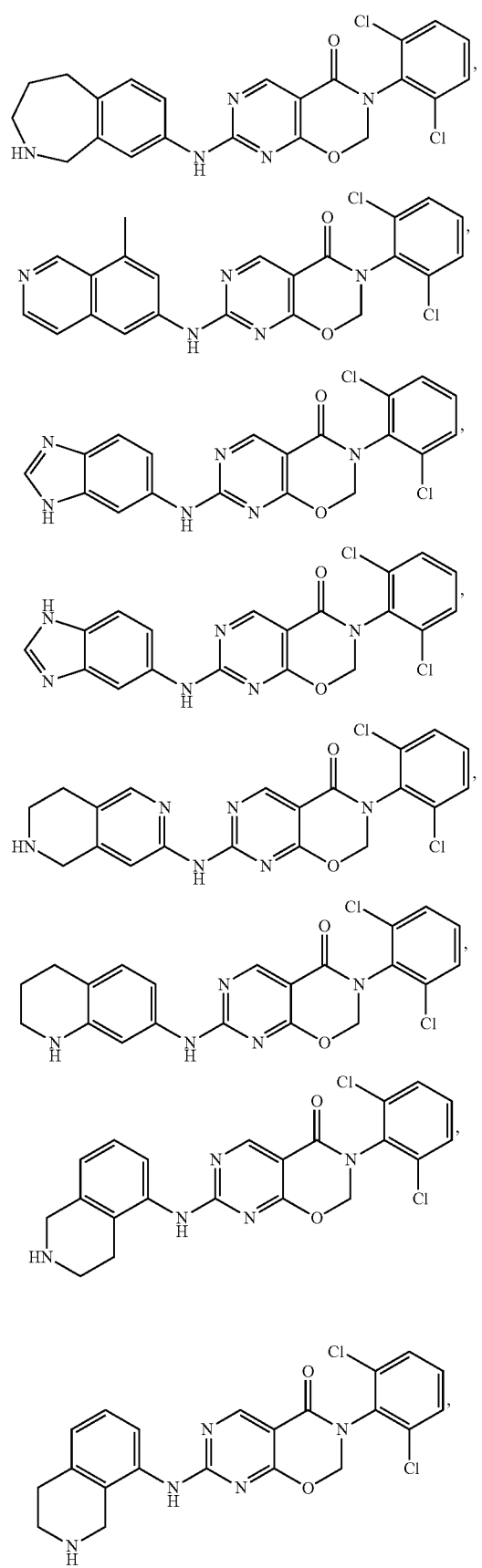
702
-continued
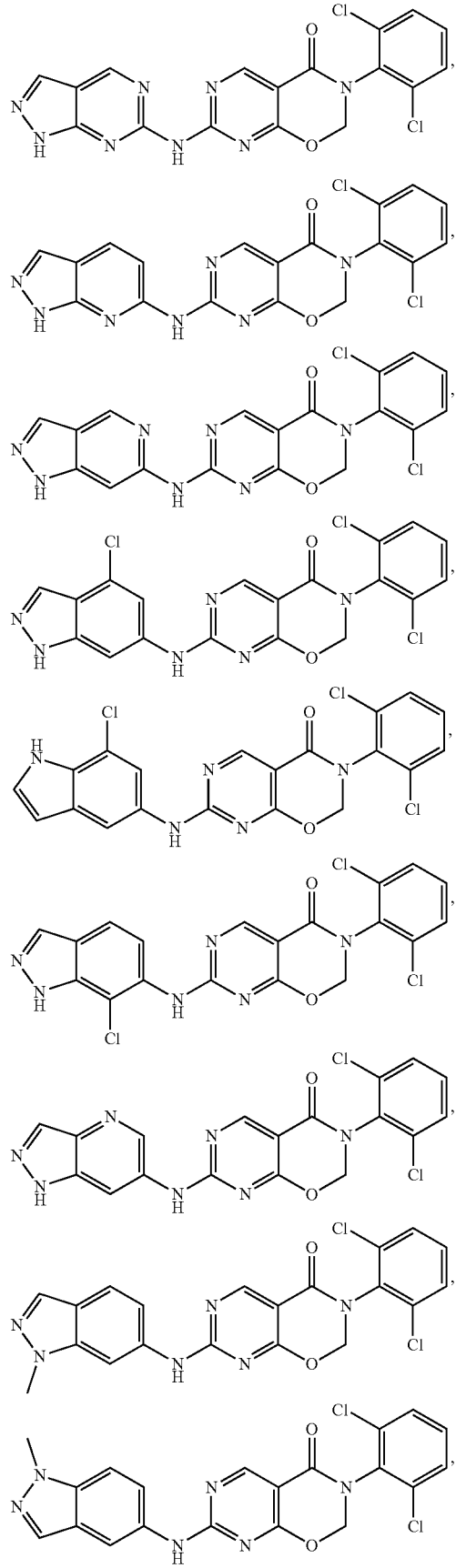

703
-continued
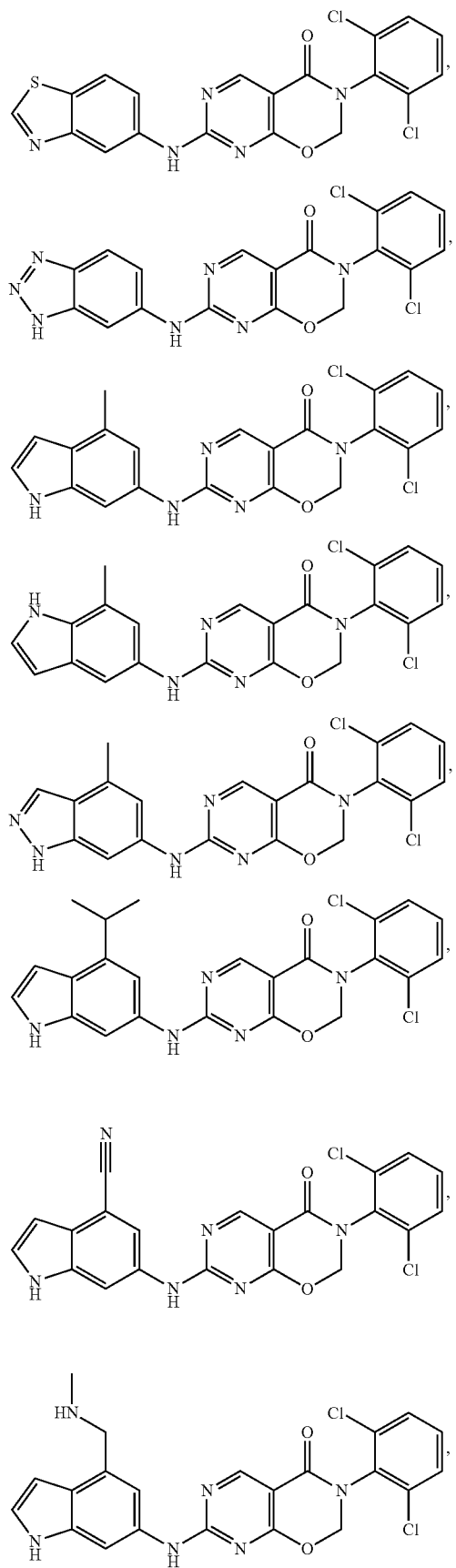
704
-continued
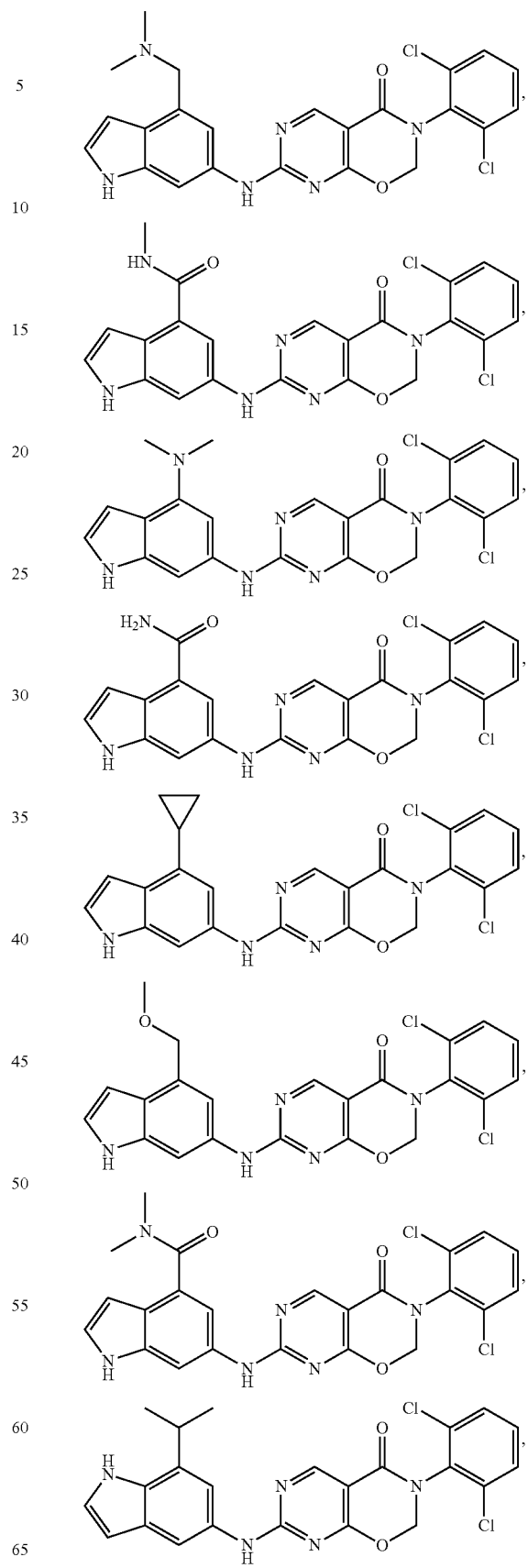

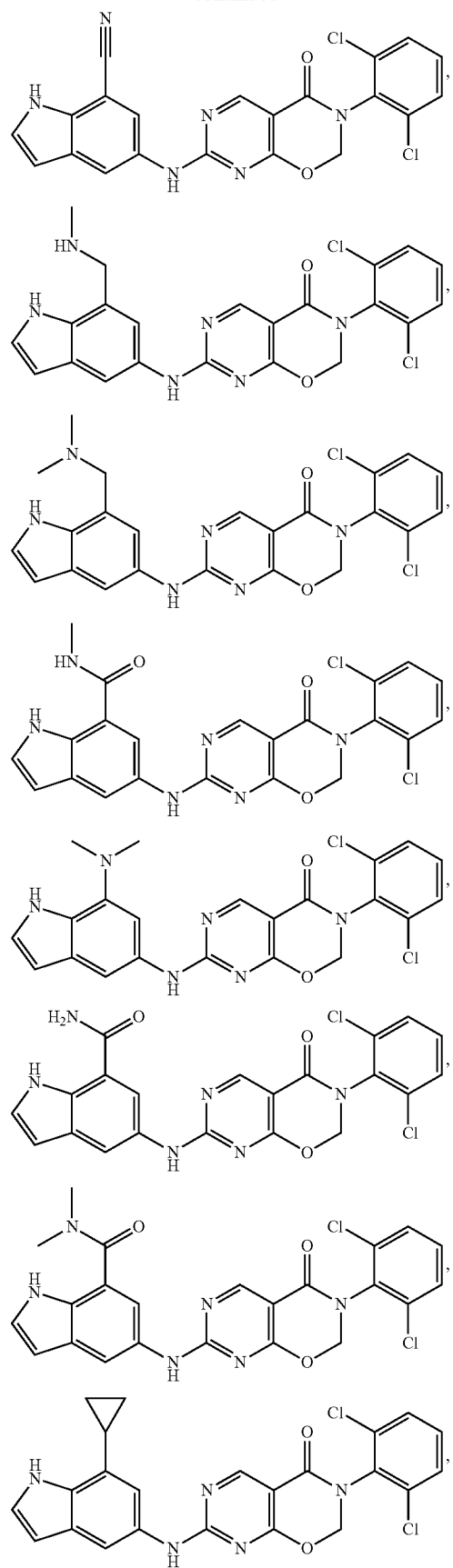
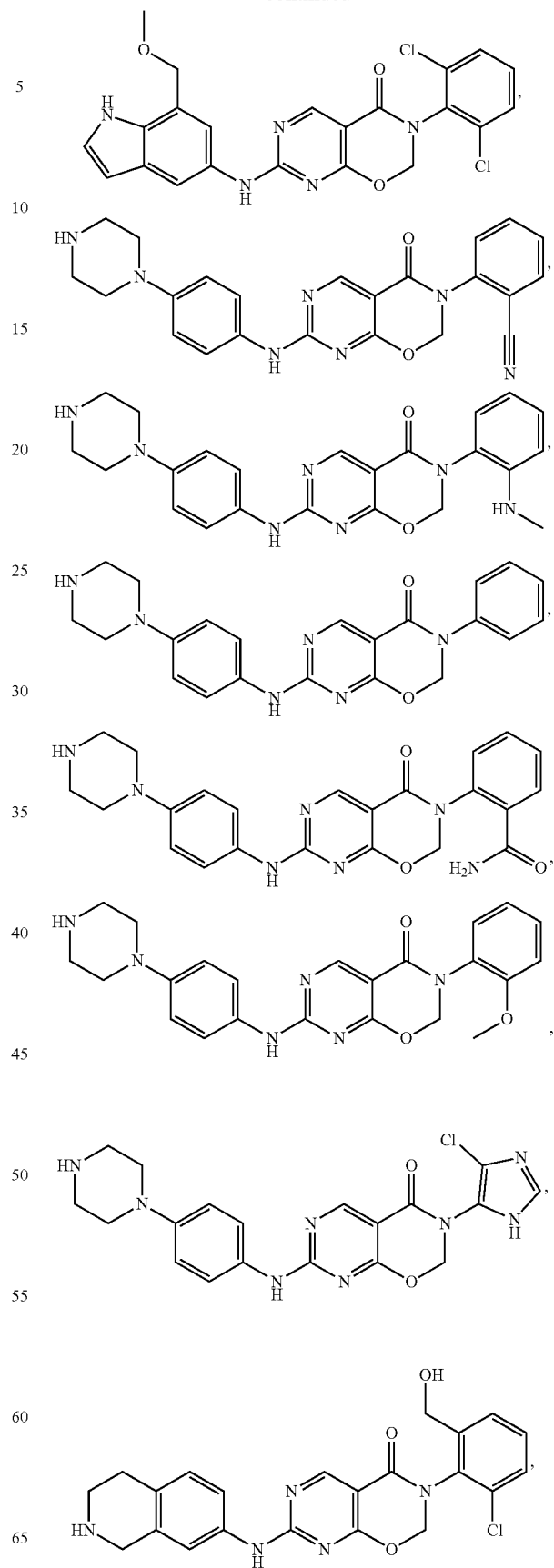

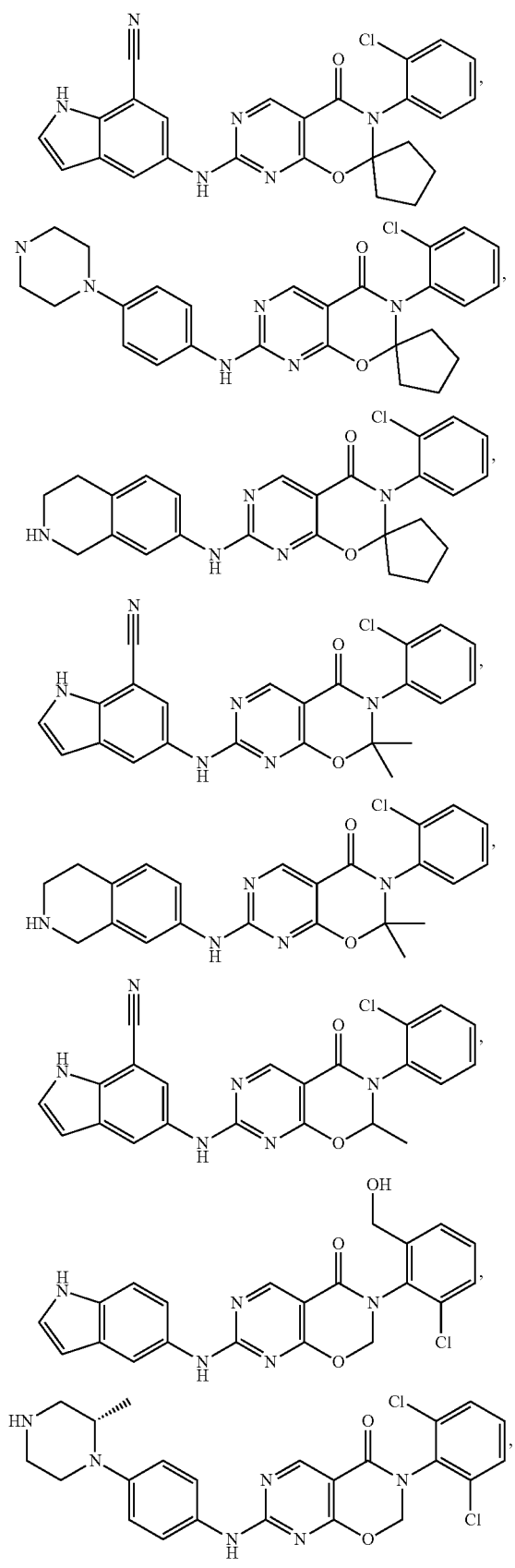
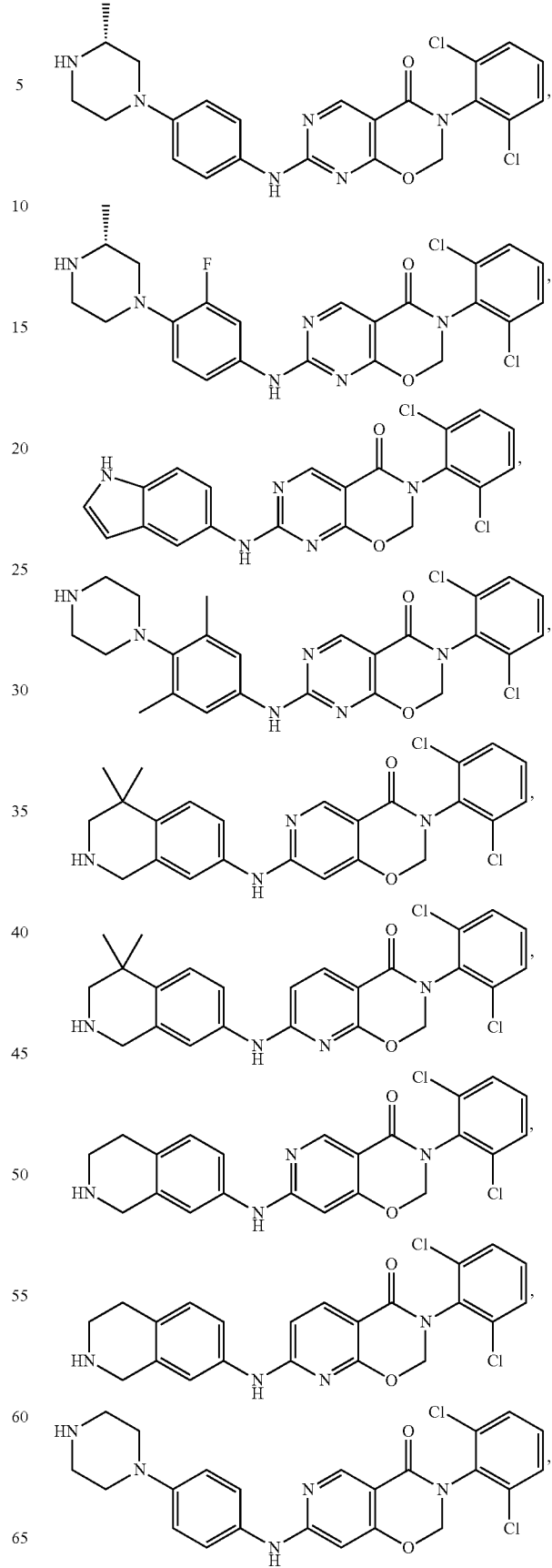

709
-continued
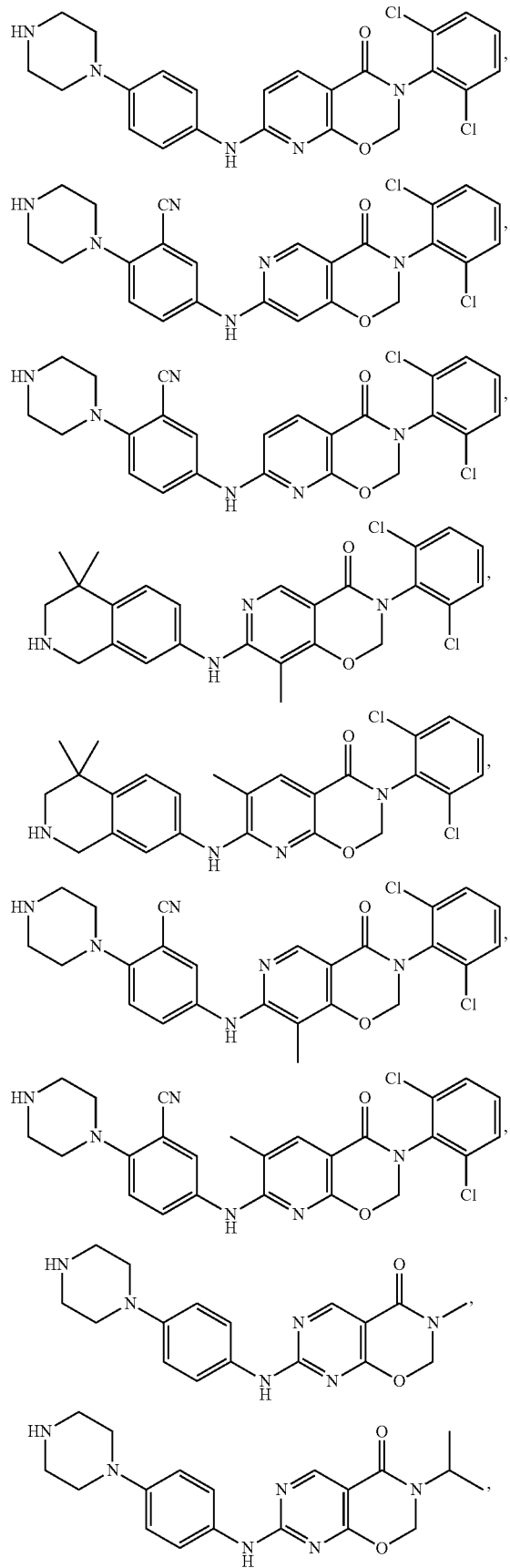
710
-continued
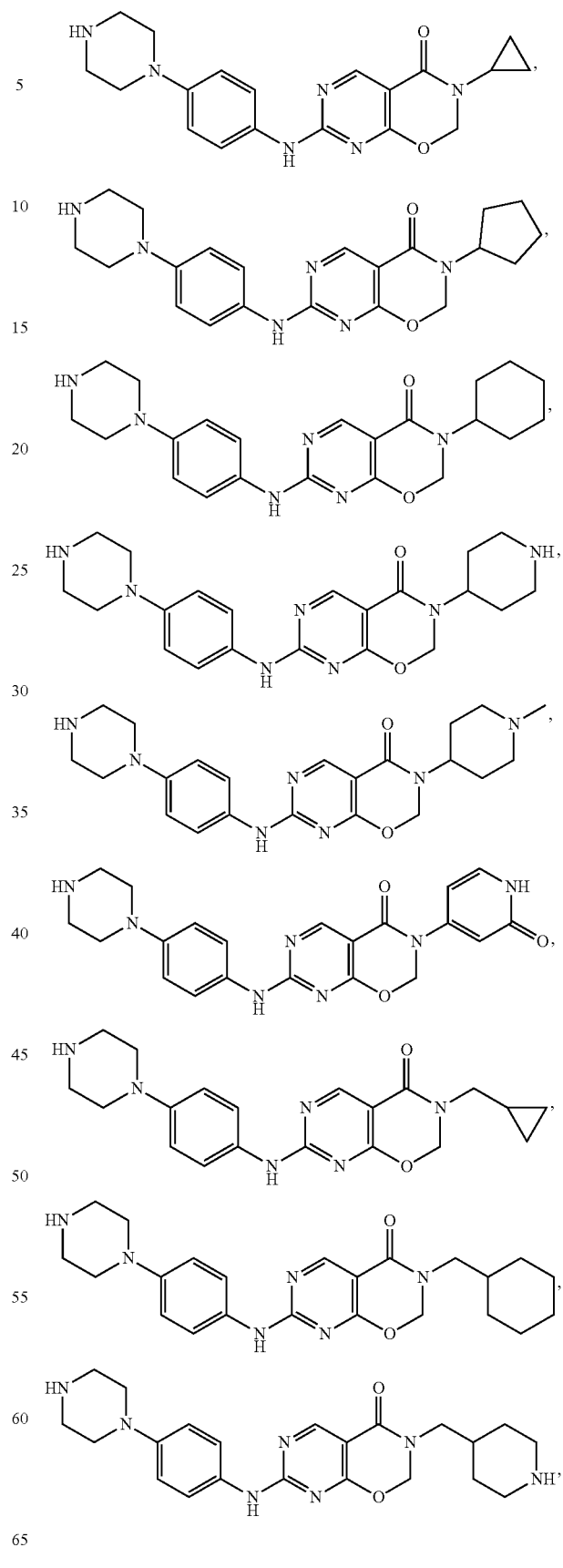

711
-continued
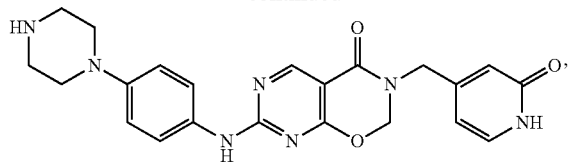
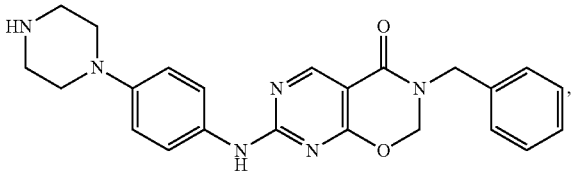
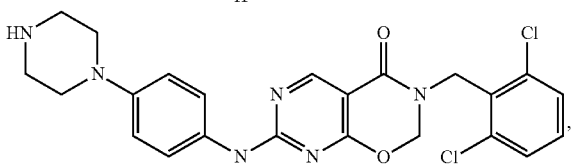
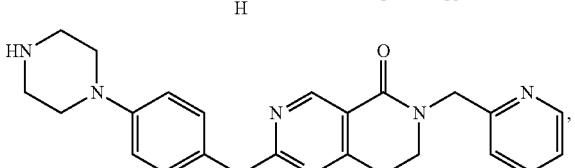
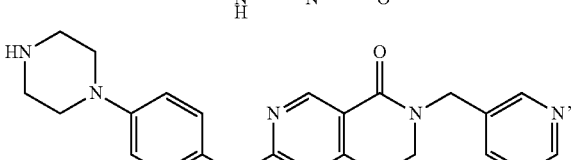
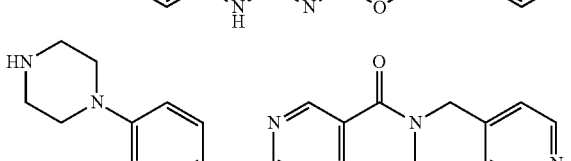
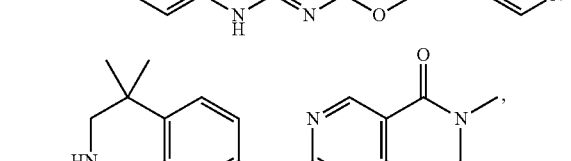
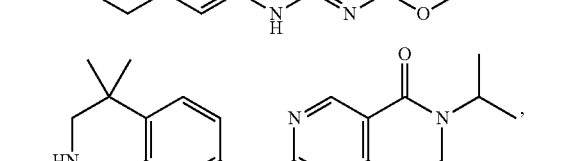
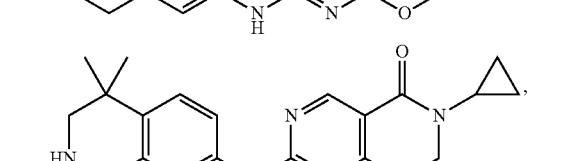
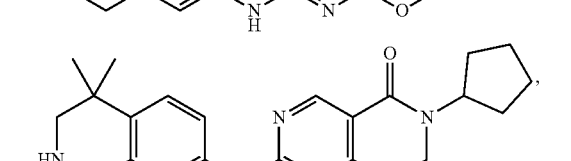
712
-continued
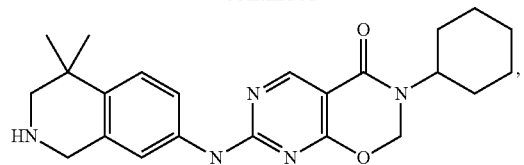
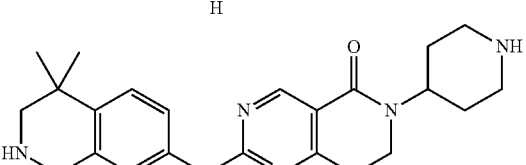
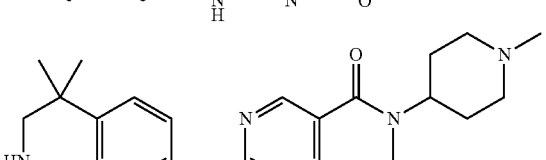
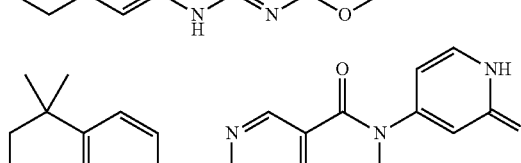
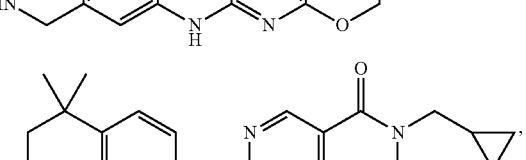
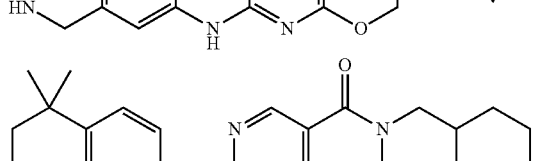
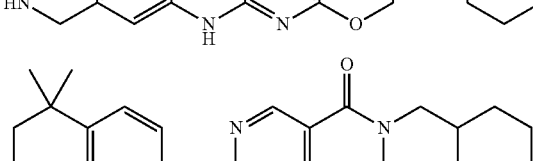
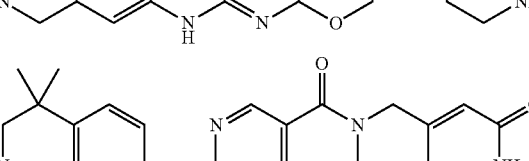
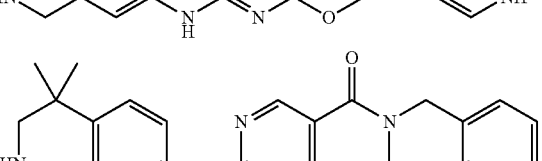
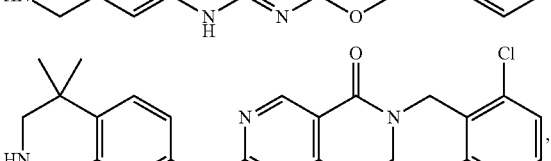

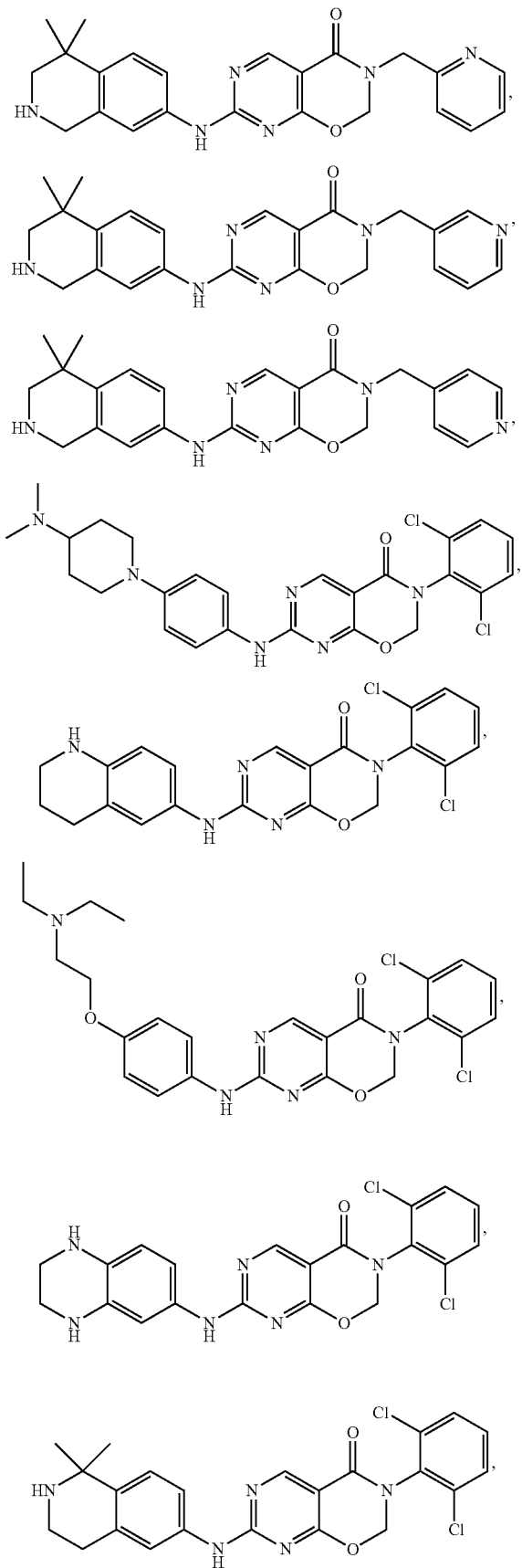
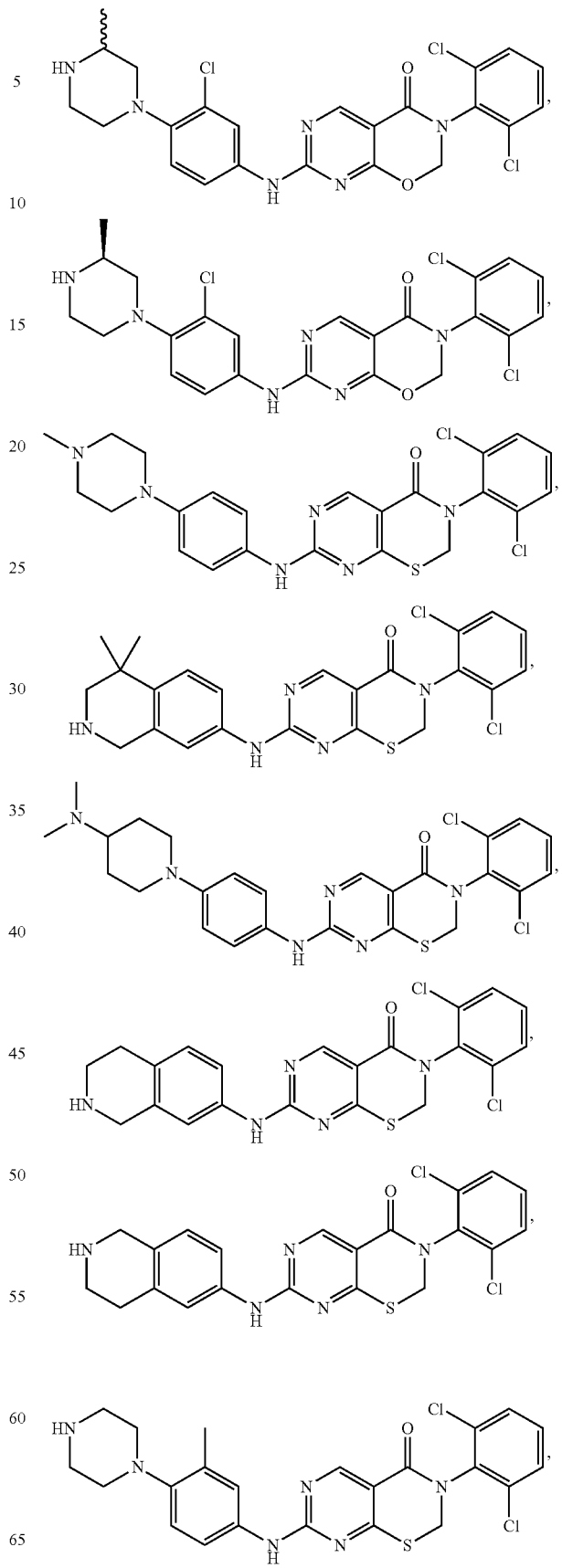

-continued
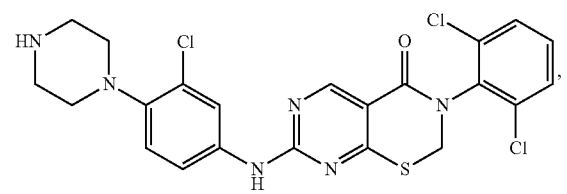
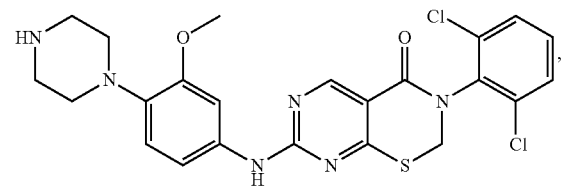
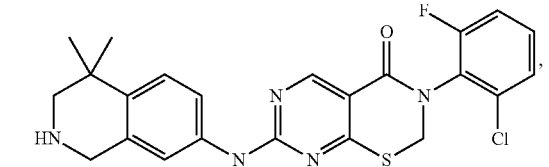
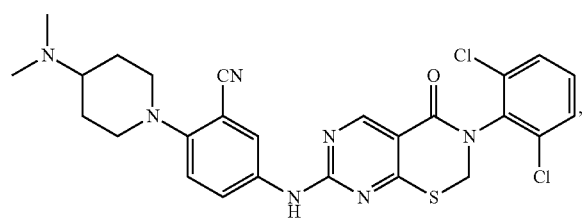
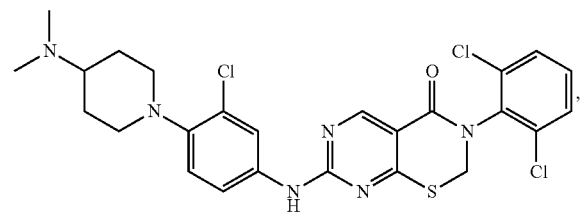
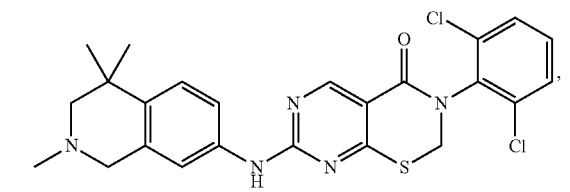
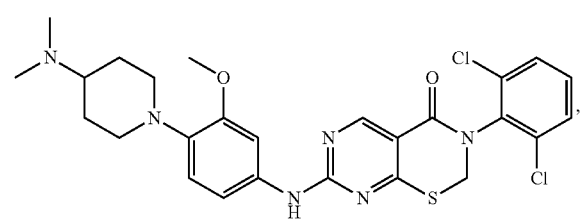
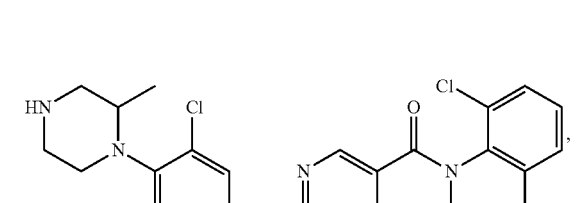
-continued
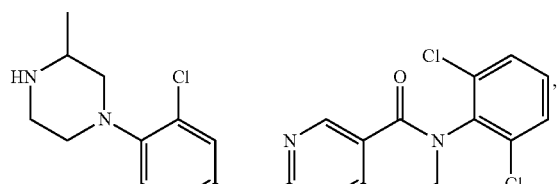
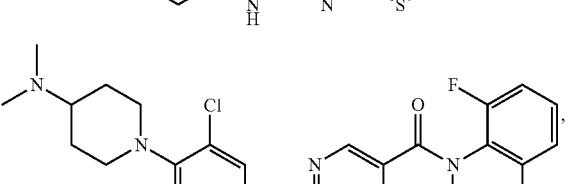
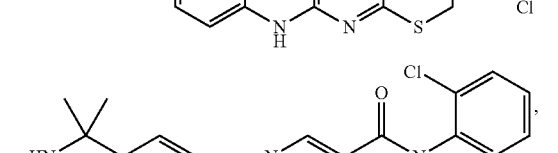
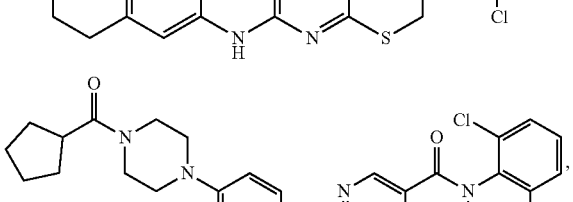
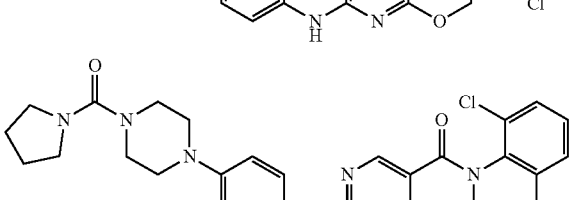
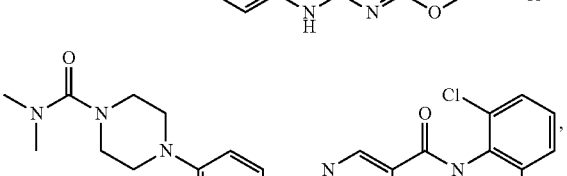
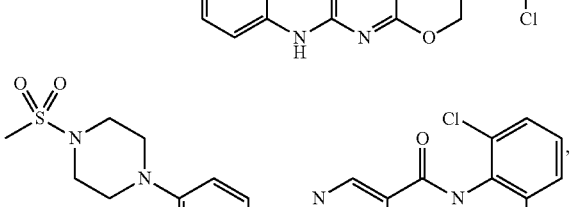
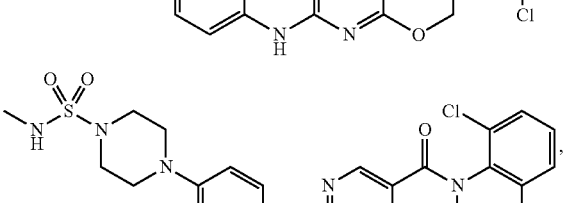

717
-continued
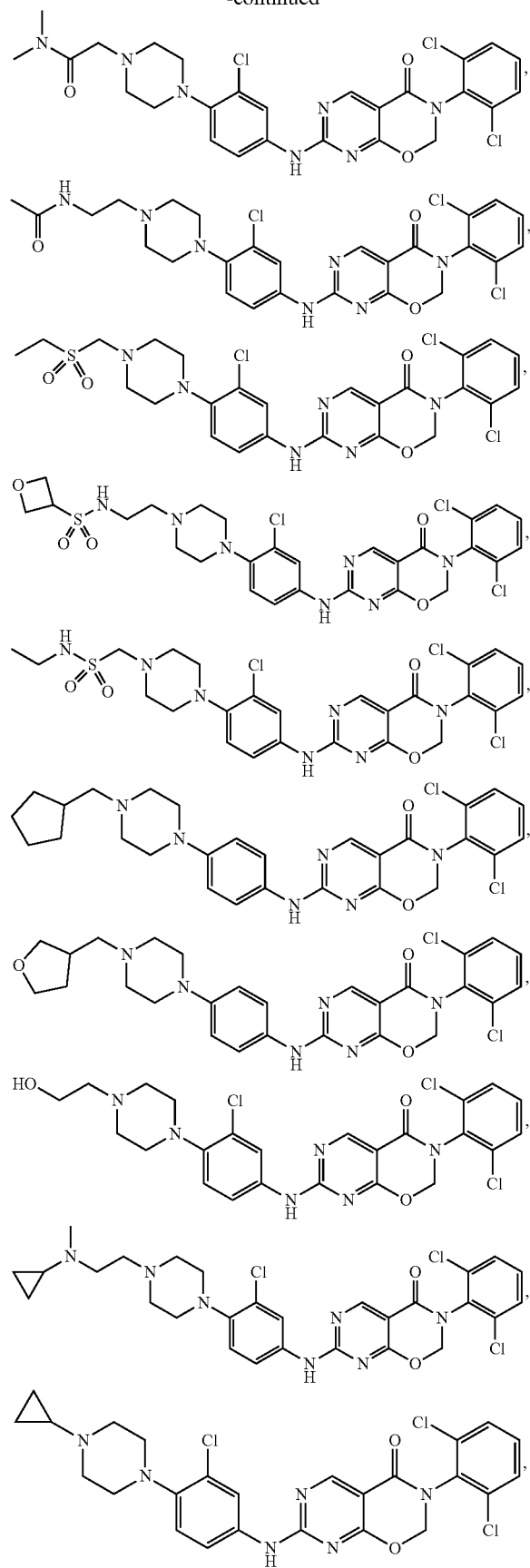
718
-continued
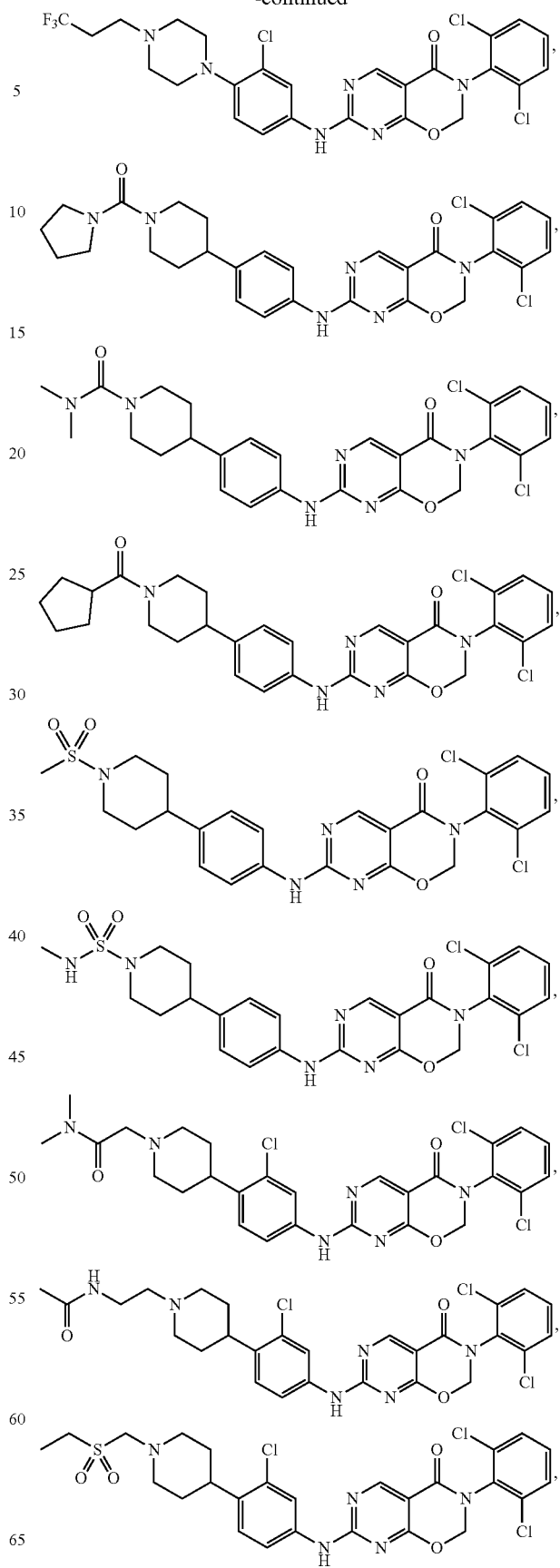

719
-continued
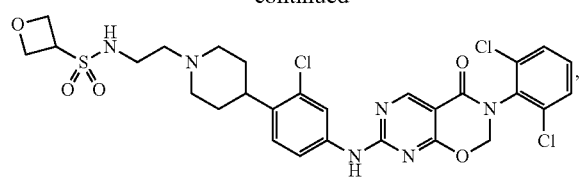
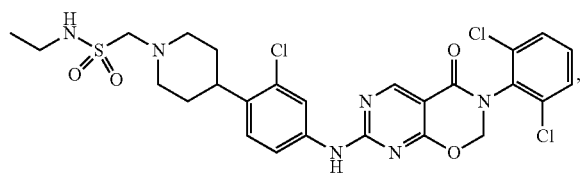
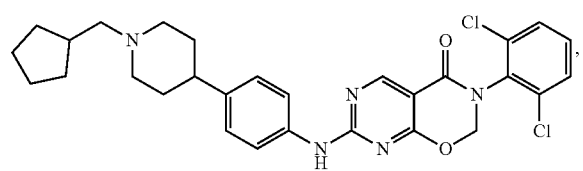
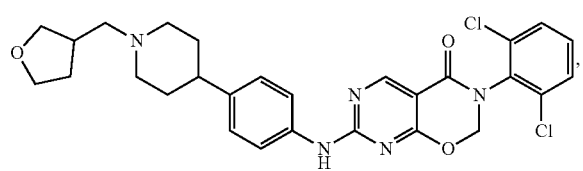
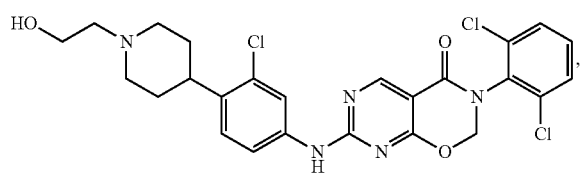
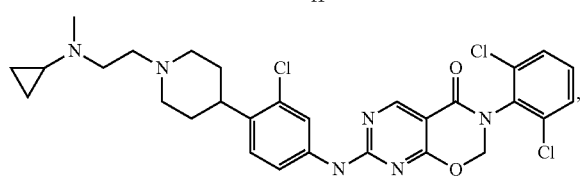
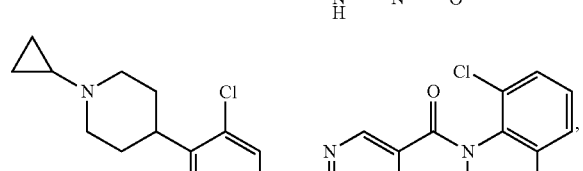
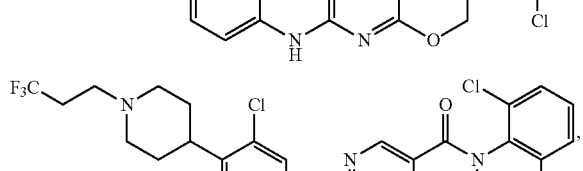
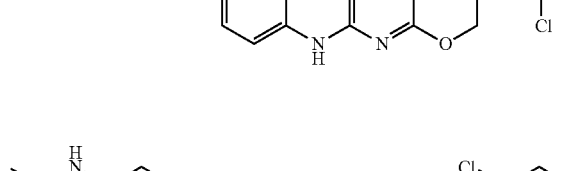
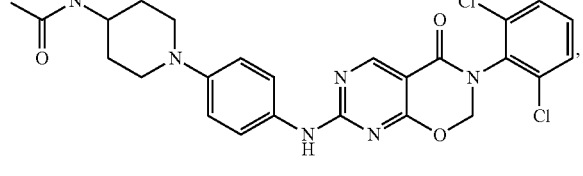
720
-continued
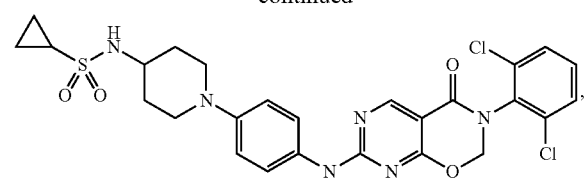
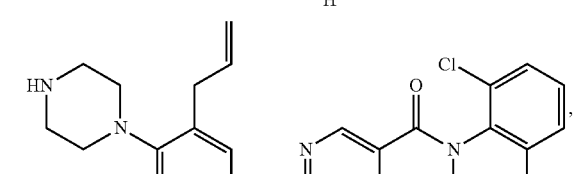
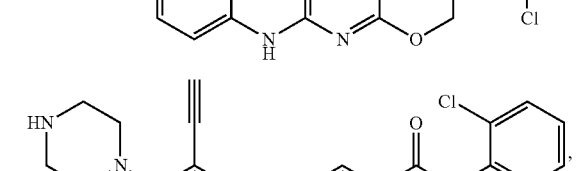
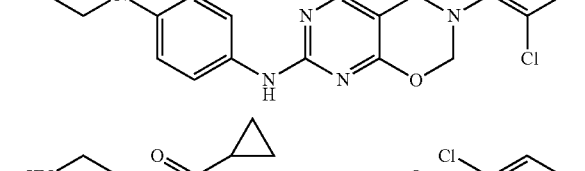
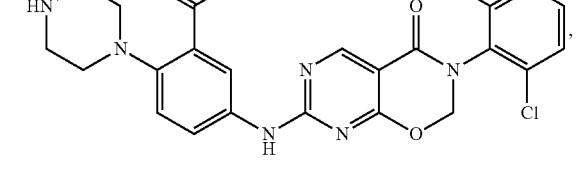
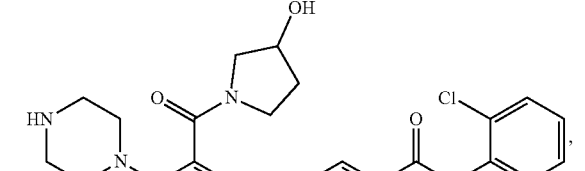
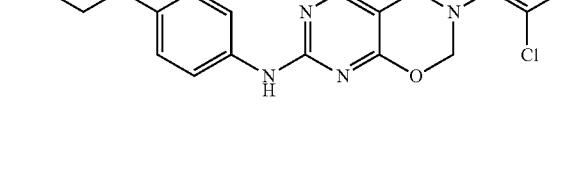
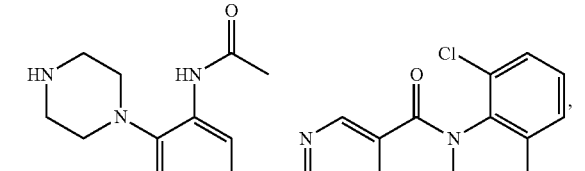
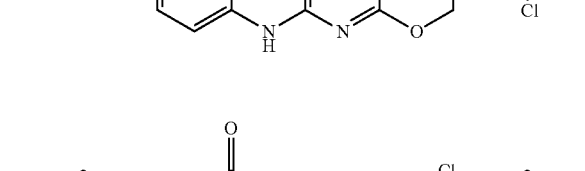
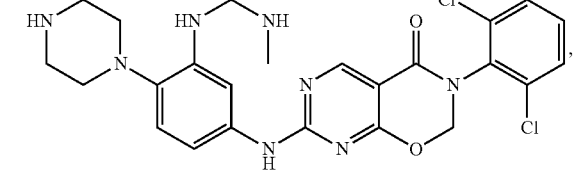

721
-continued
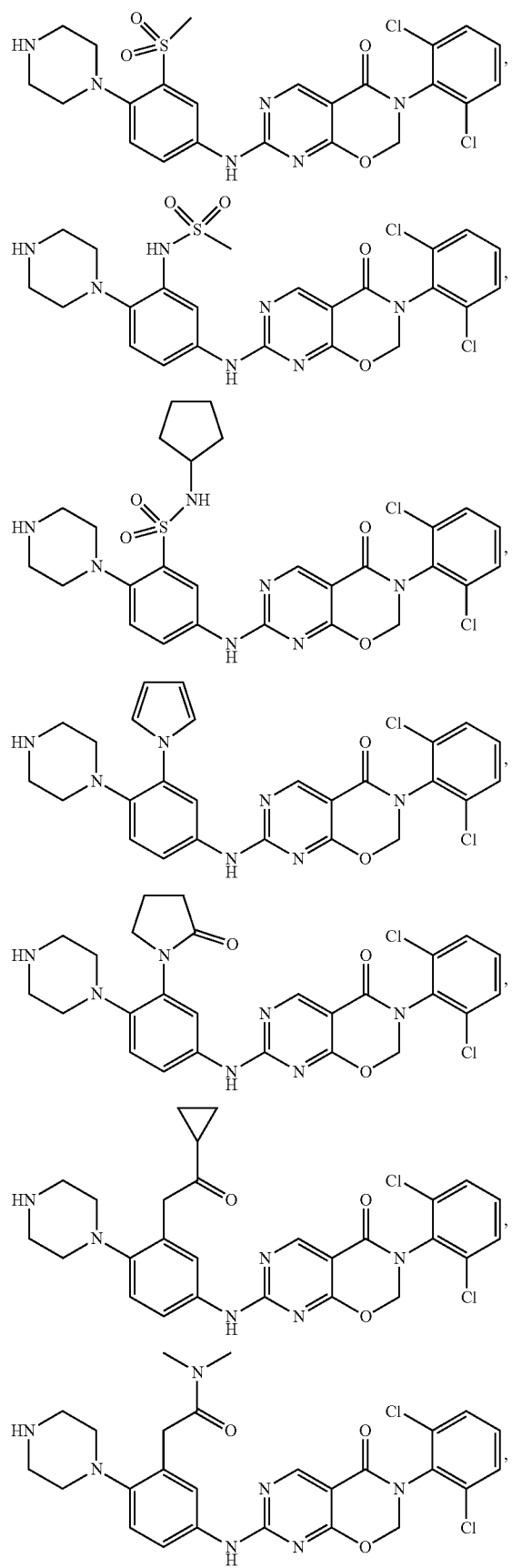
722
-continued
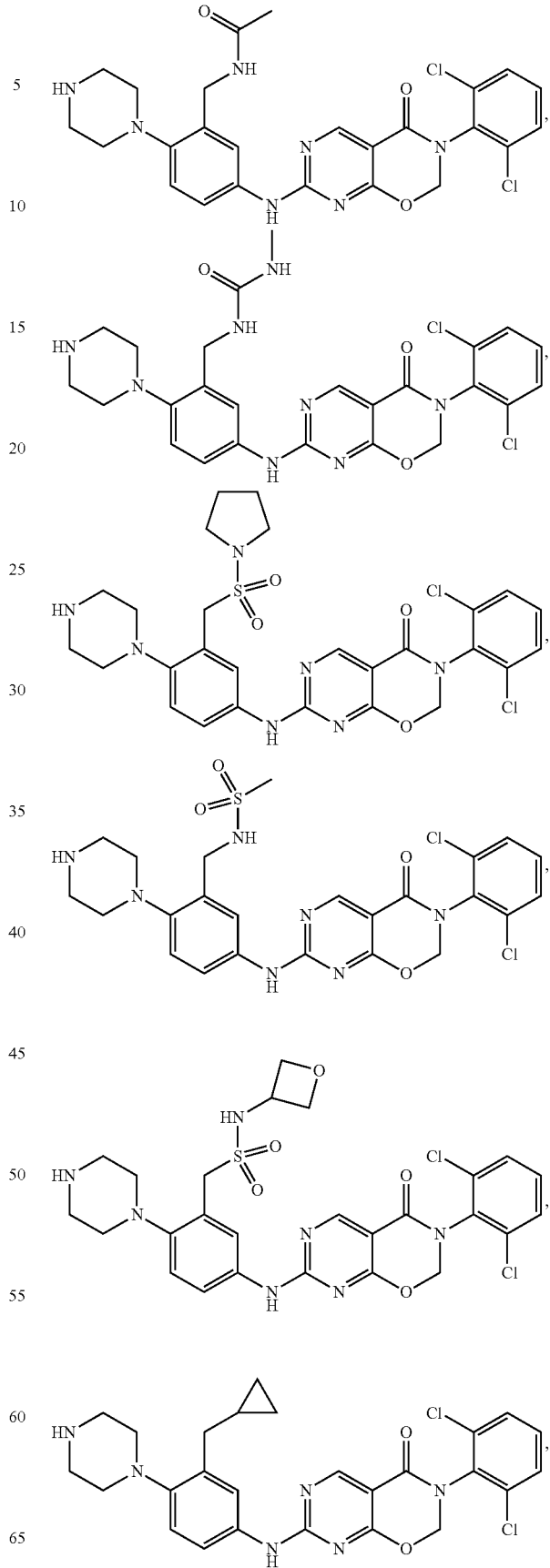

-continued
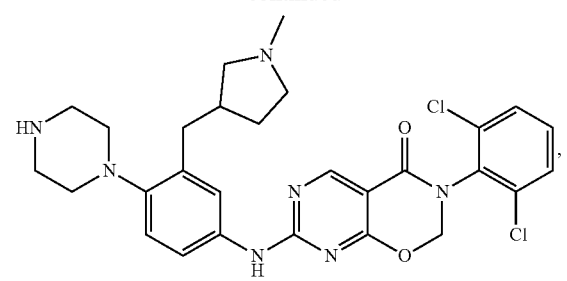
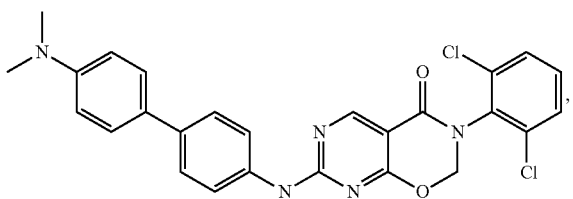
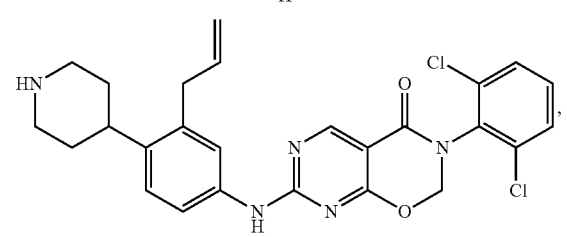
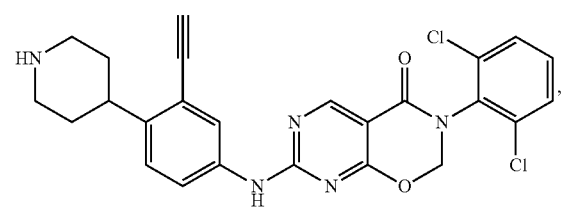
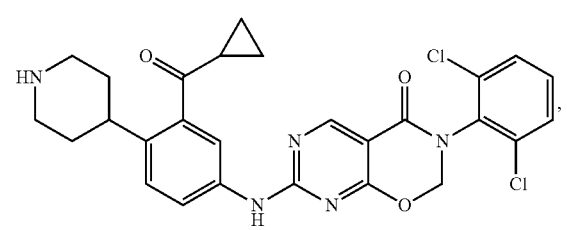
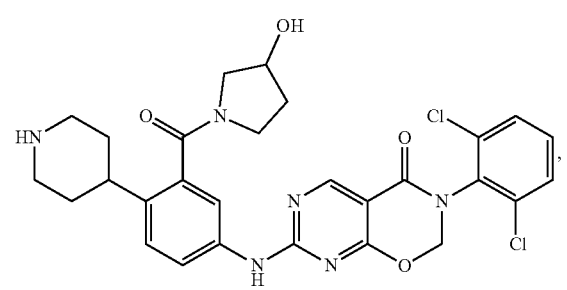
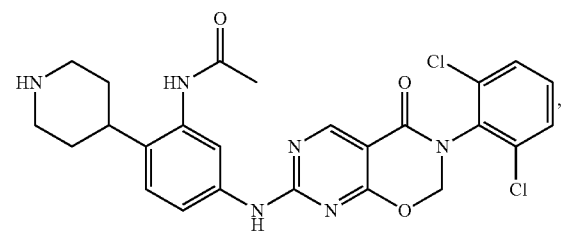
-continued
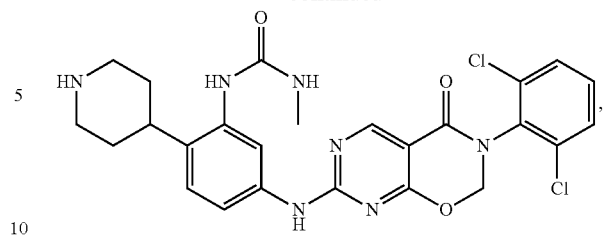
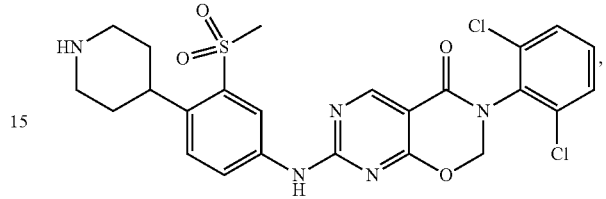
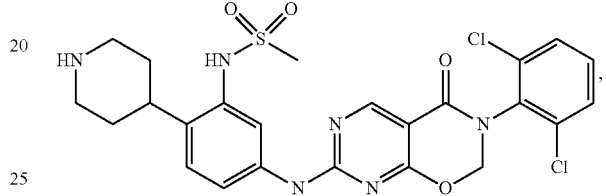
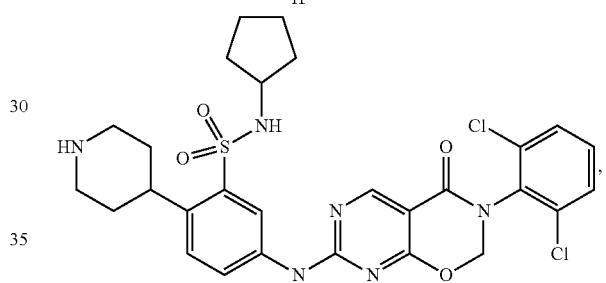
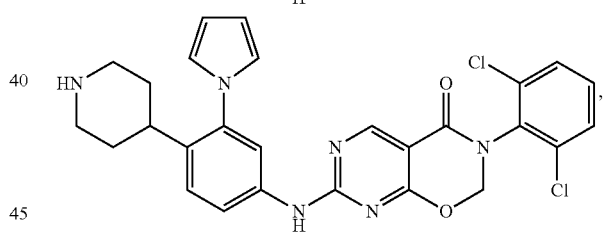
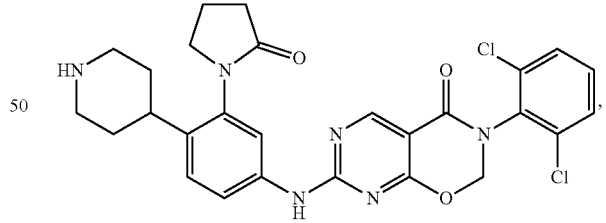
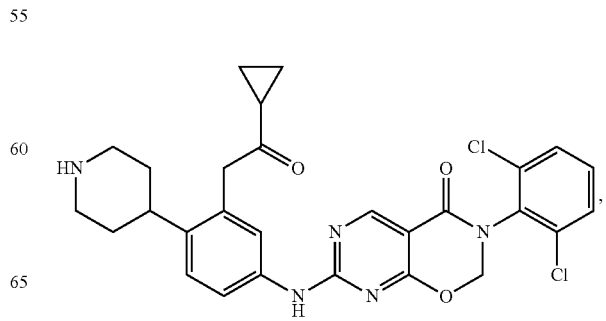

725
-continued
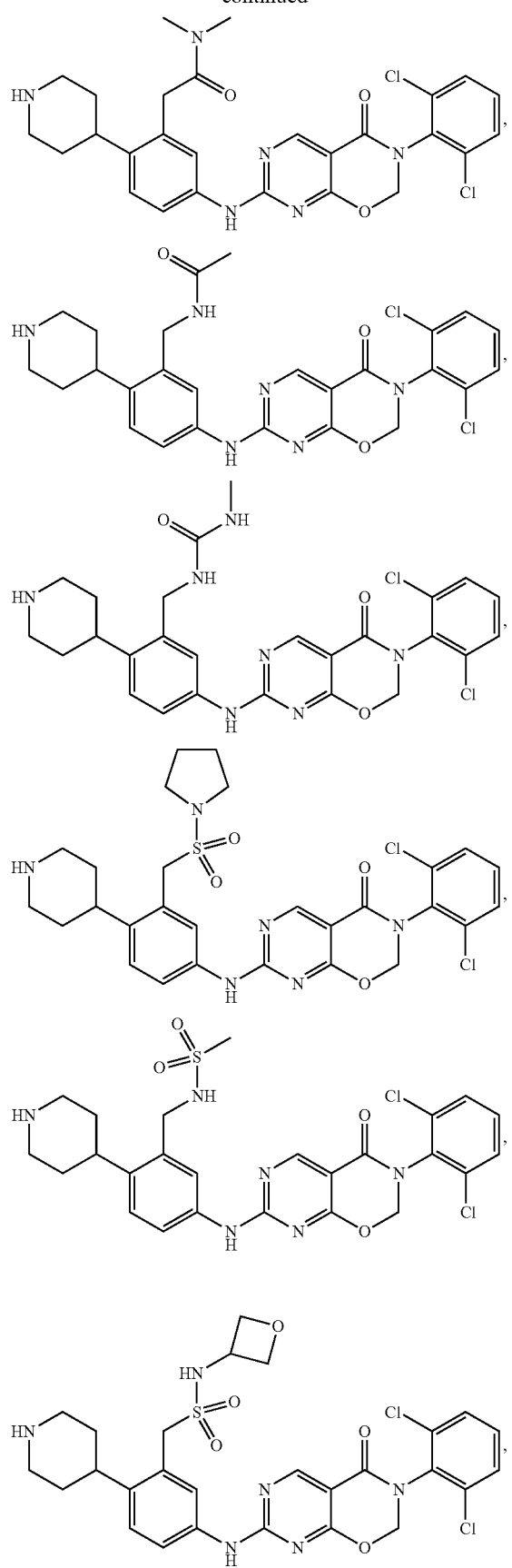
726
-continued
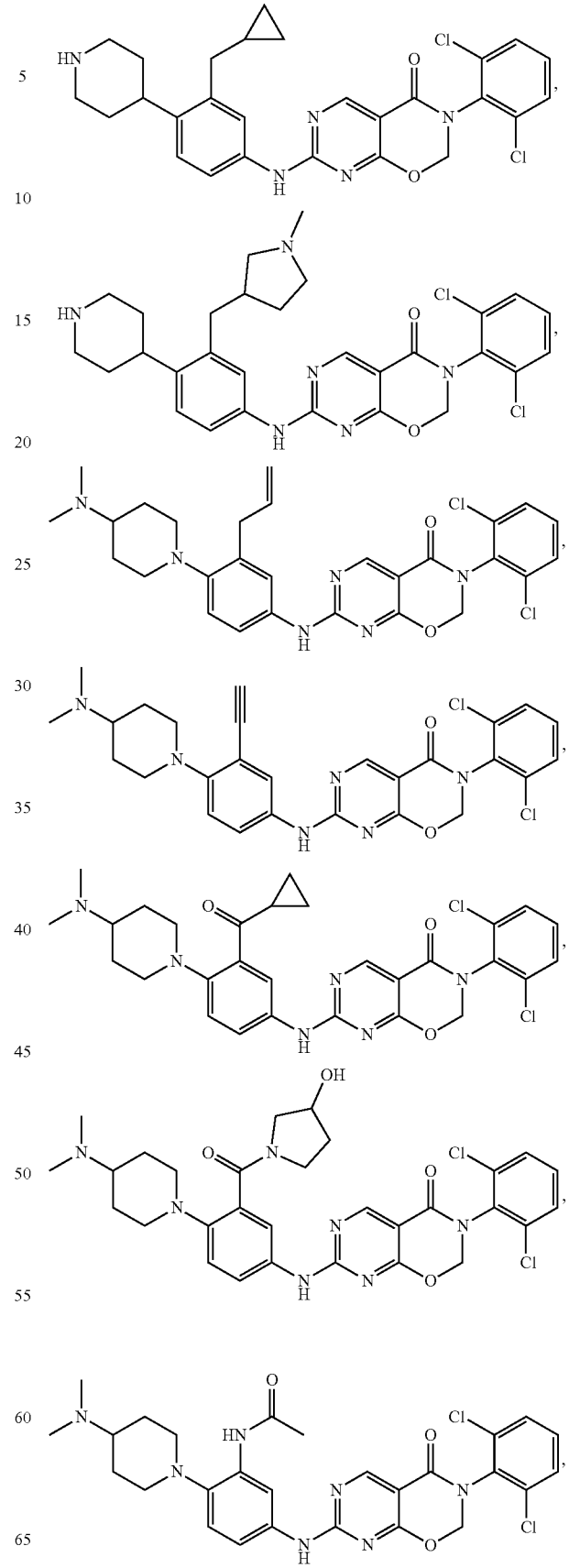

727
-continued
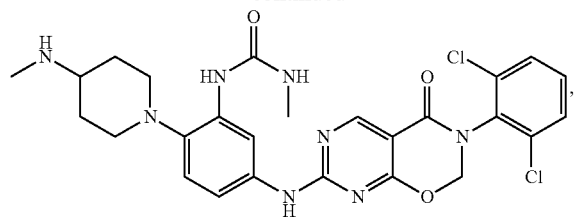
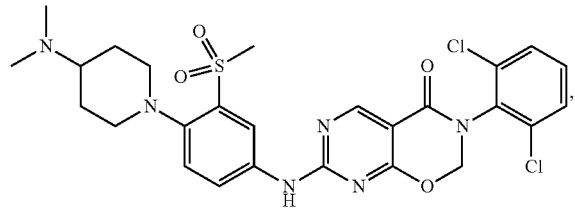
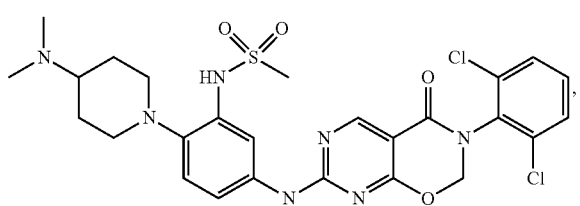
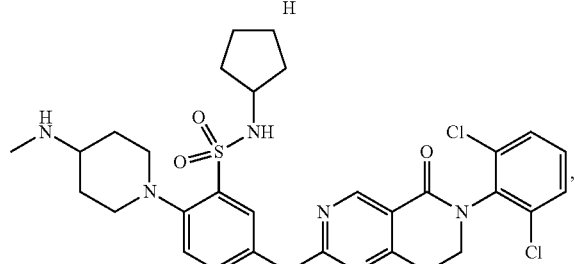
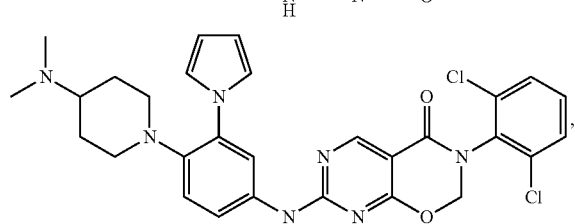
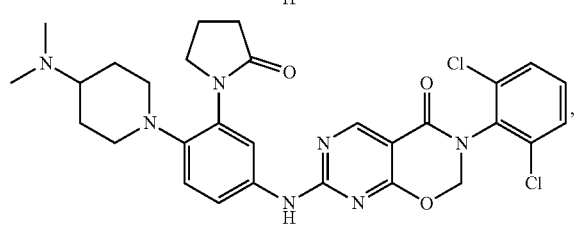
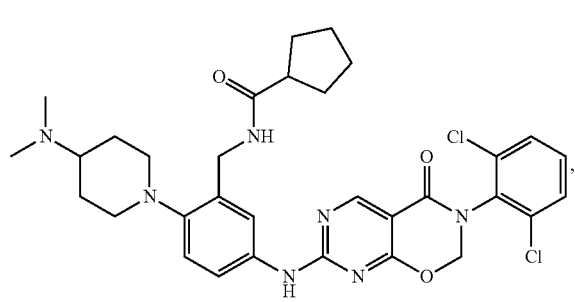
728
-continued
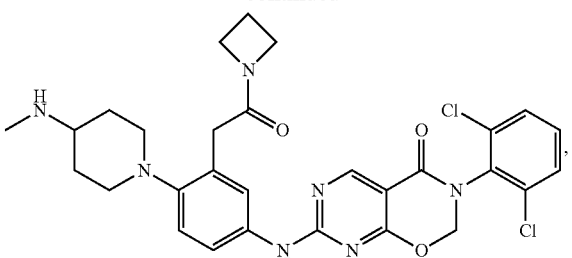
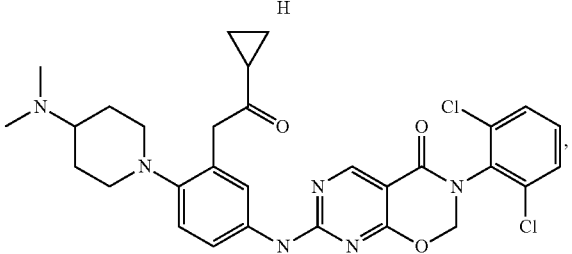
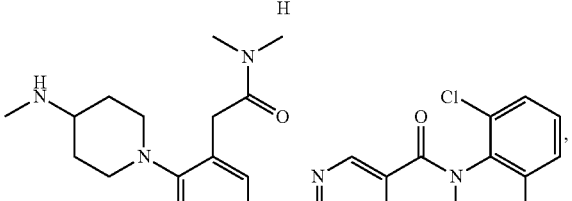
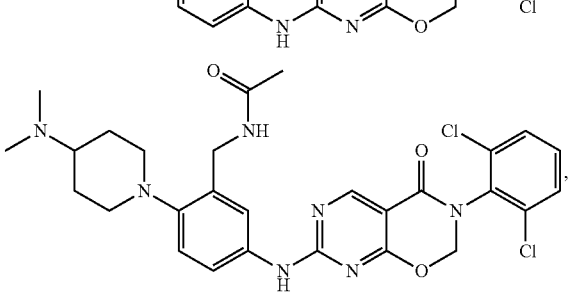
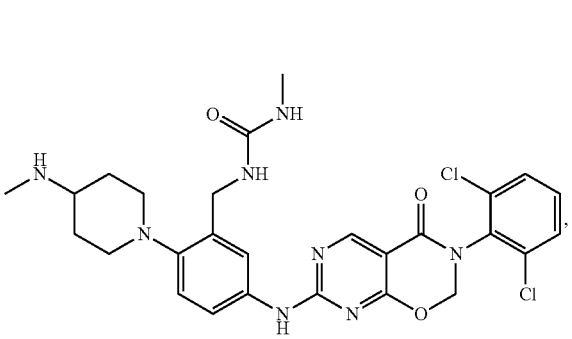
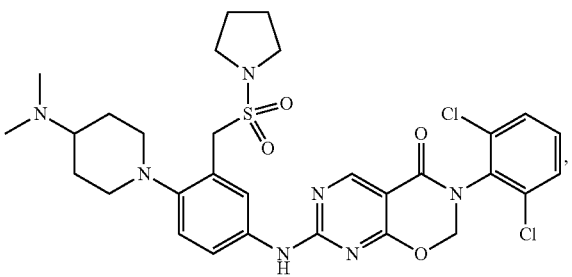

729
-continued

730
-continued

731
-continued
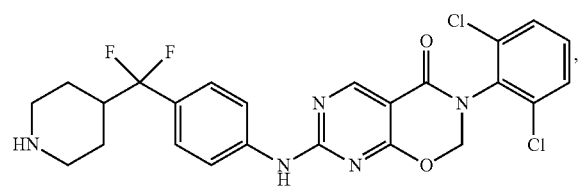
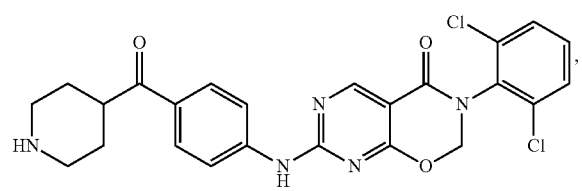
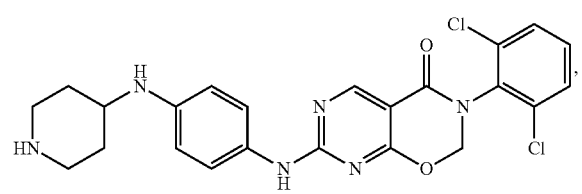
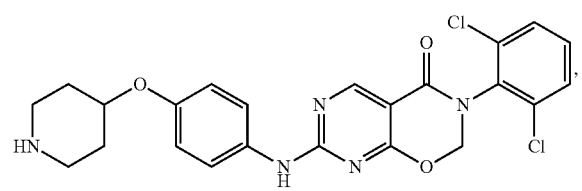
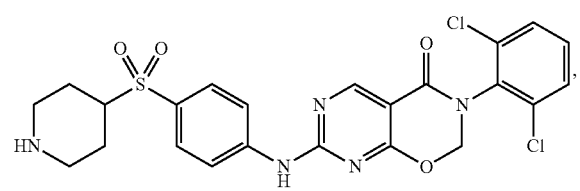
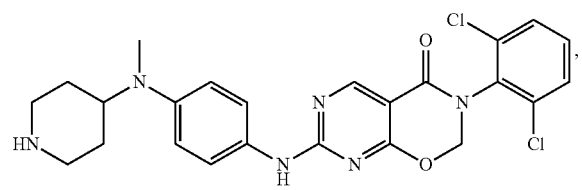
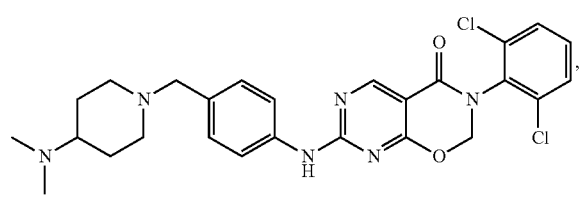
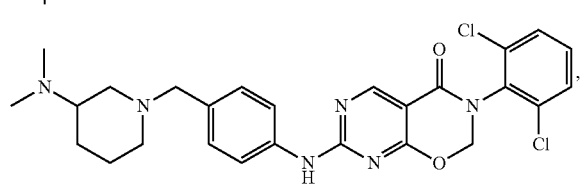
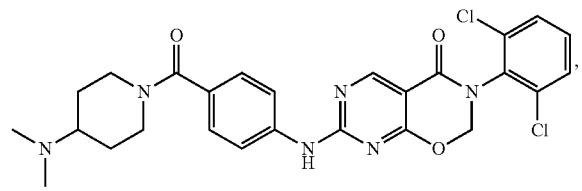
732
-continued
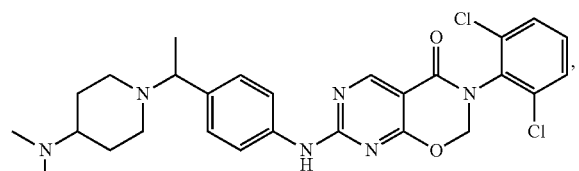
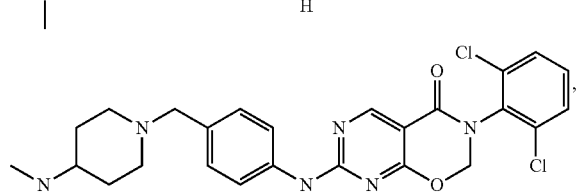
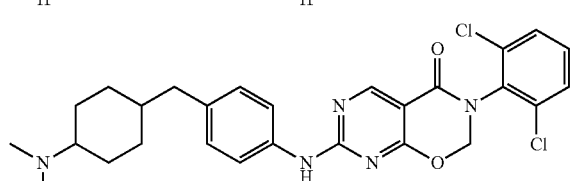
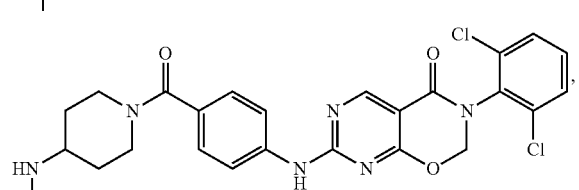
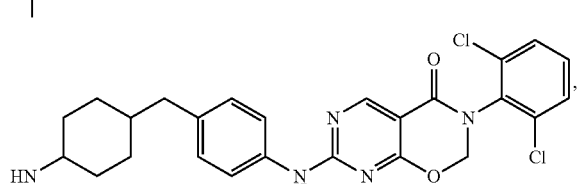
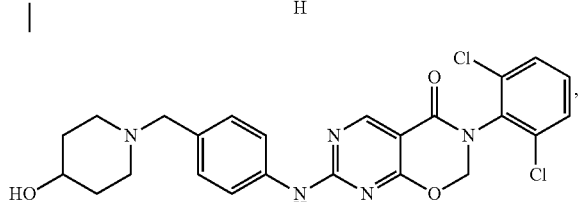
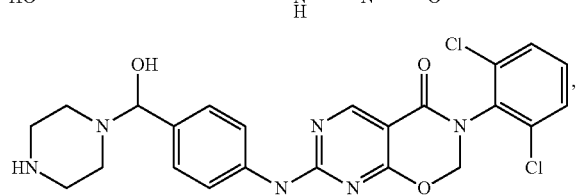
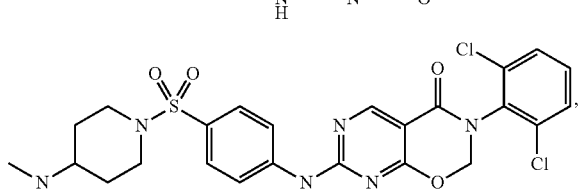
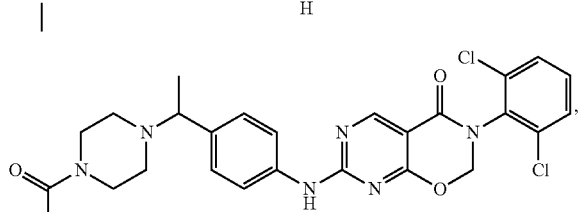

733
-continued
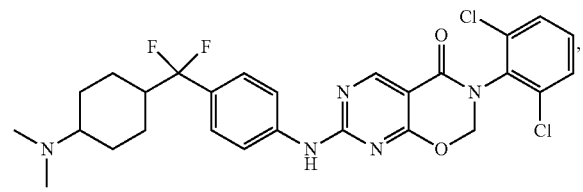
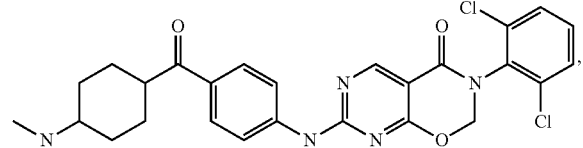
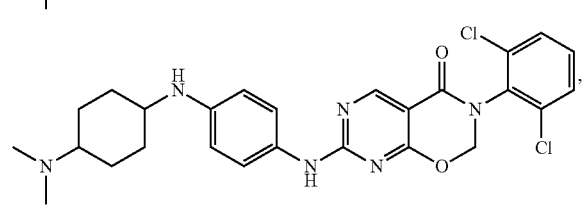
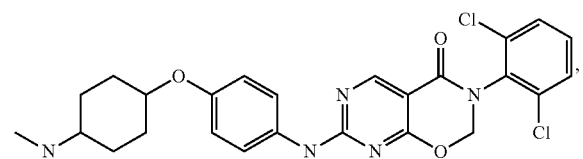
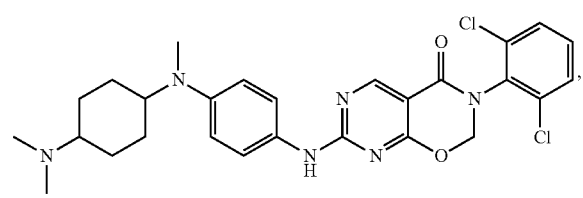
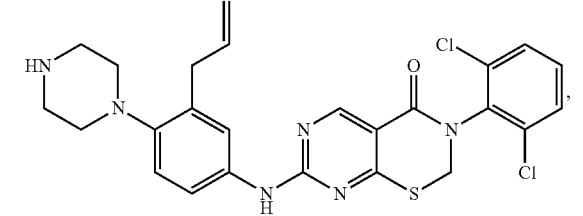
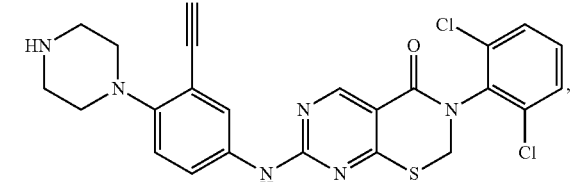
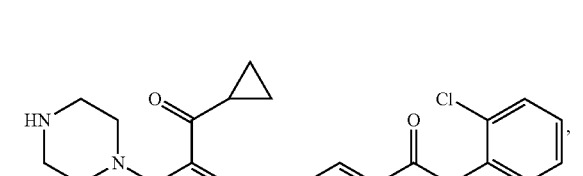
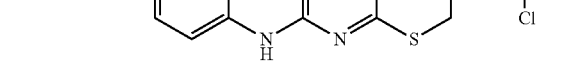
734
-continued
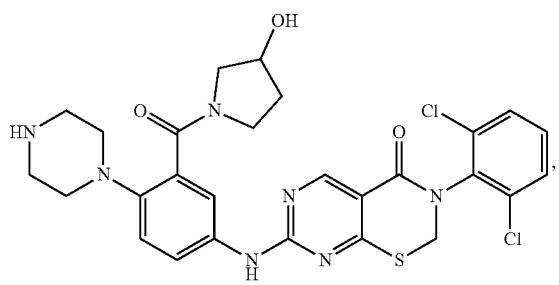
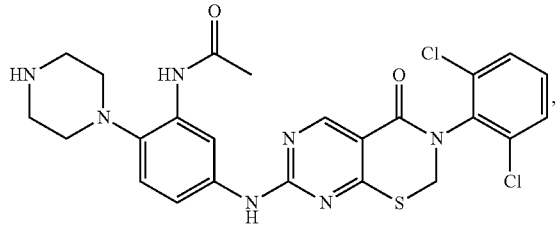
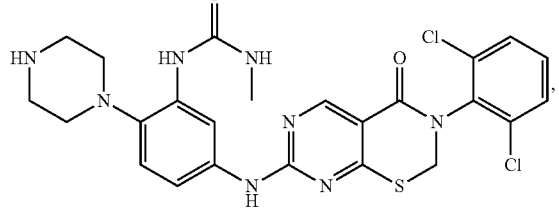
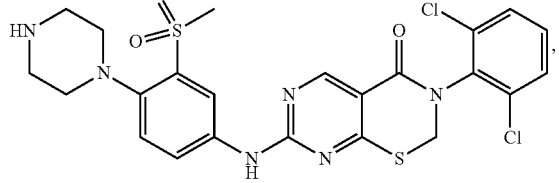
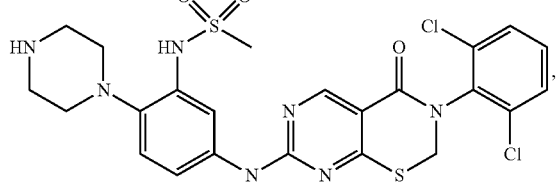
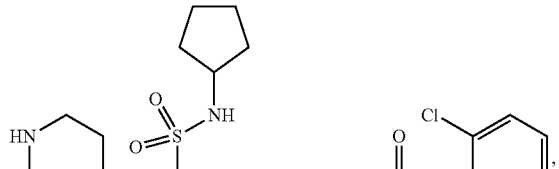
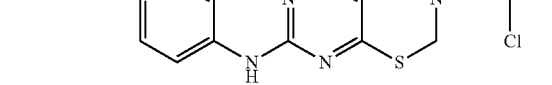
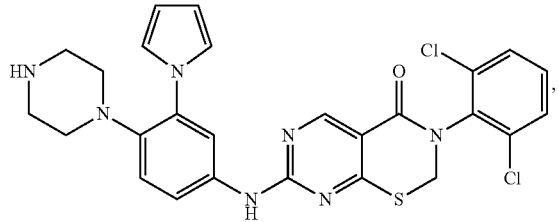

735
-continued
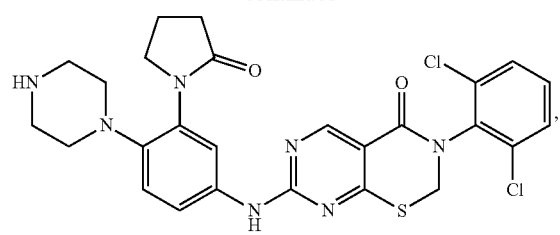
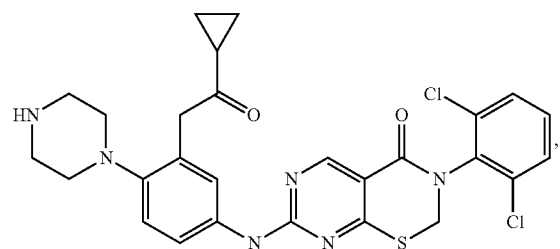
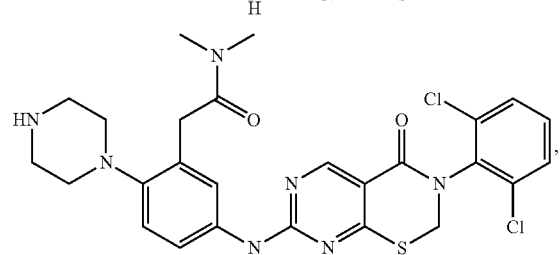
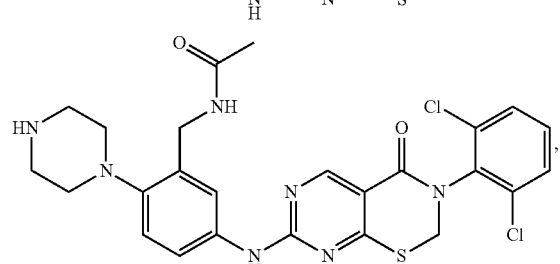
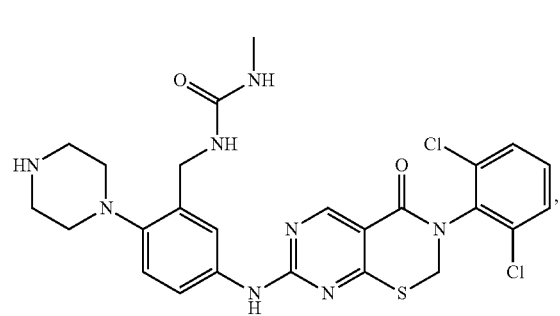
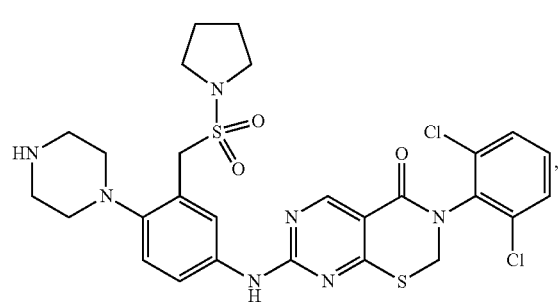
736
-continued
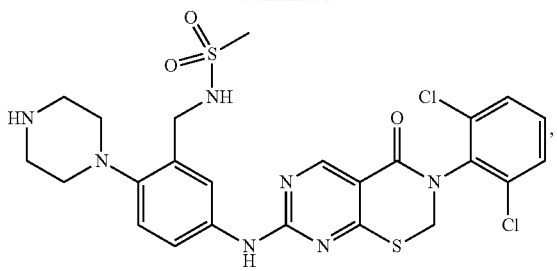
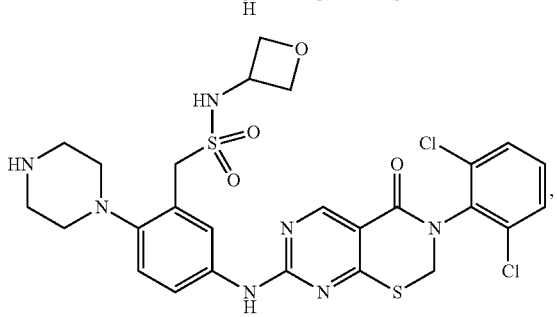
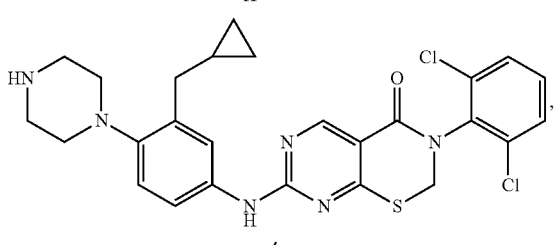
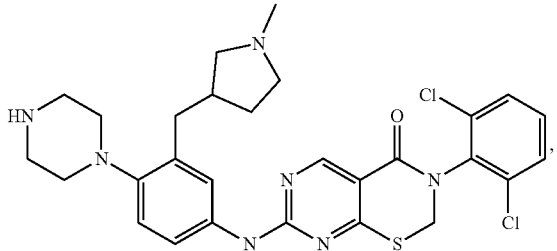
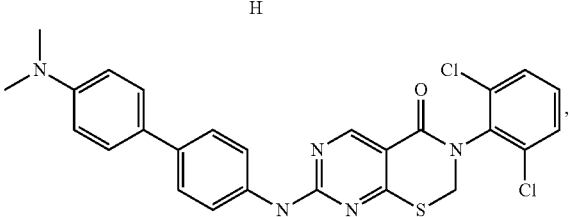
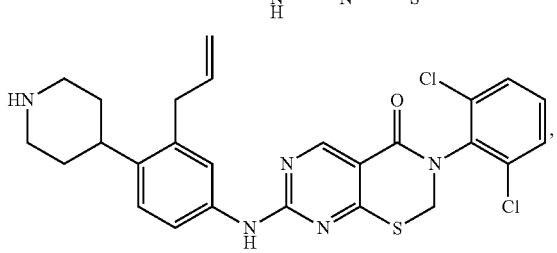
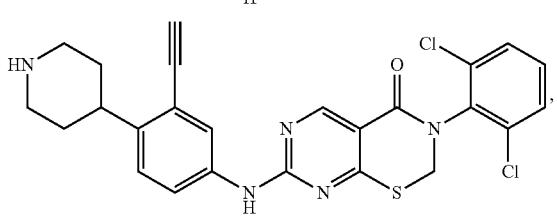

737
-continued
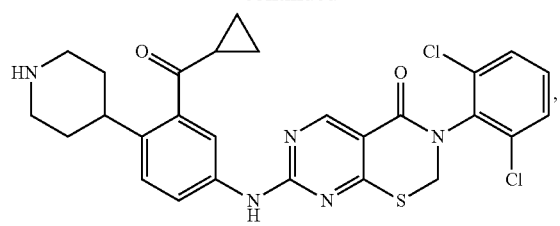
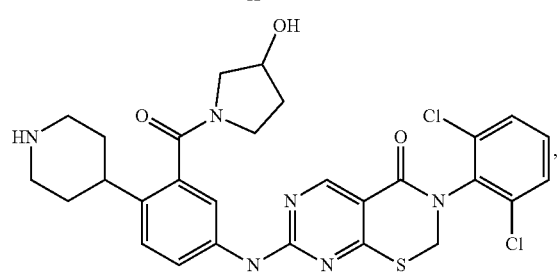
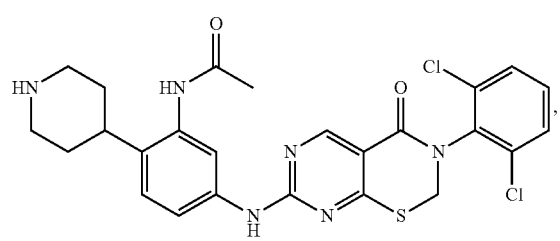
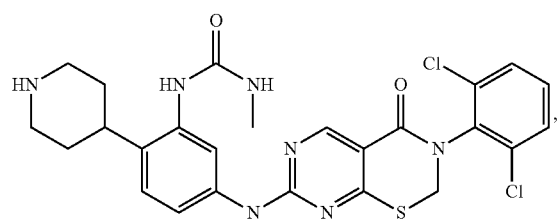
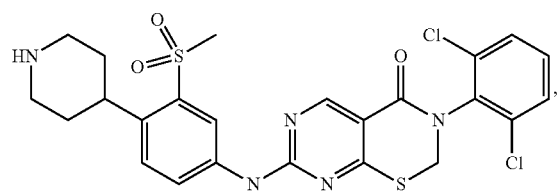
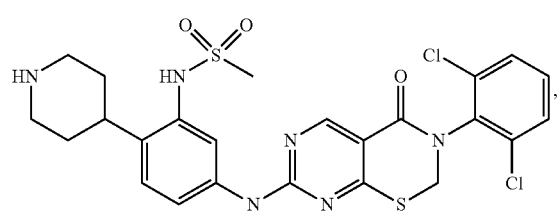
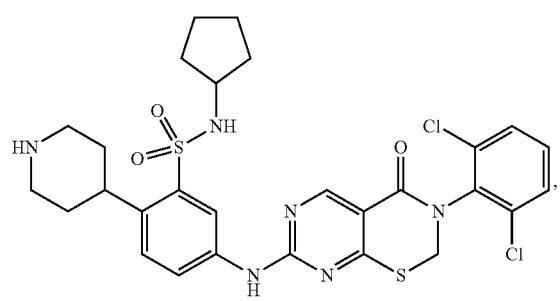
738
-continued
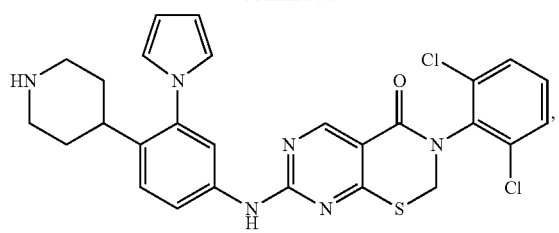
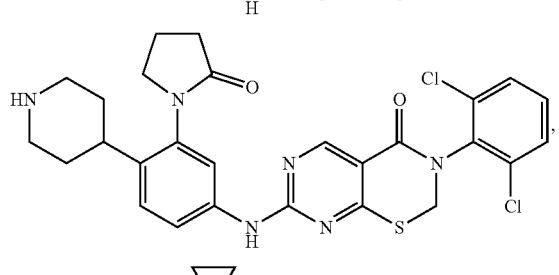
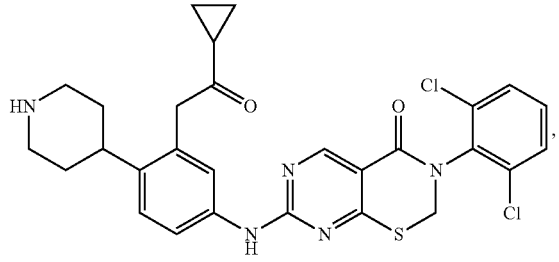
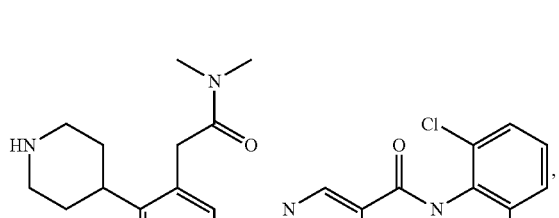
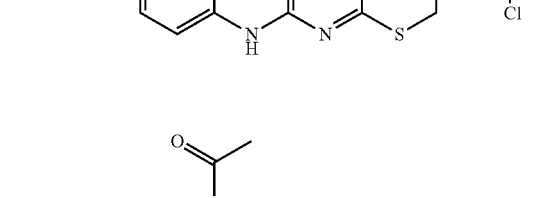
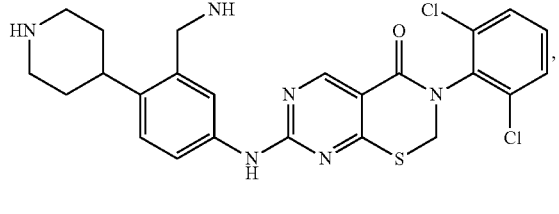
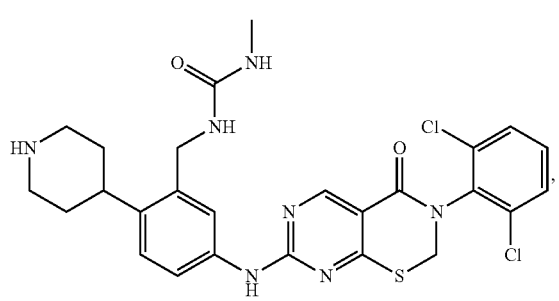

739
-continued
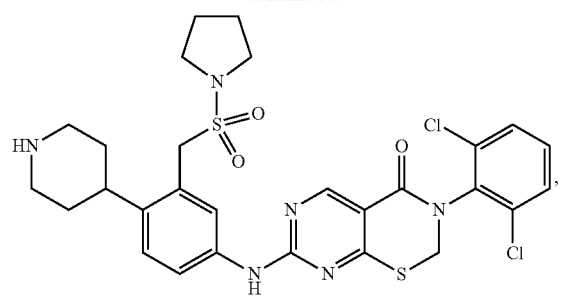
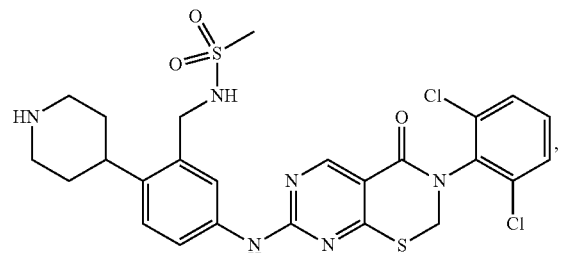
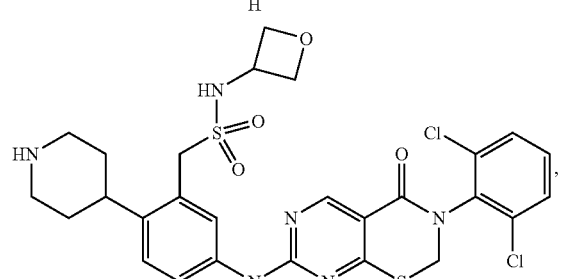
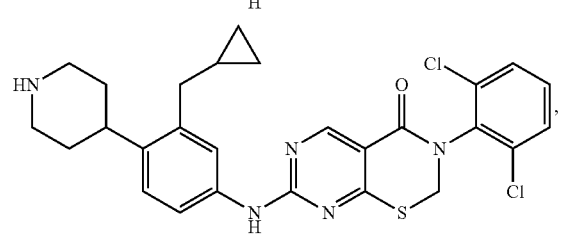
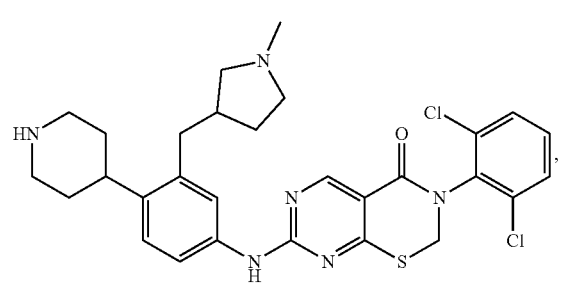
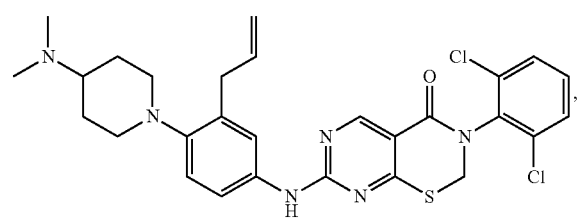
740
-continued
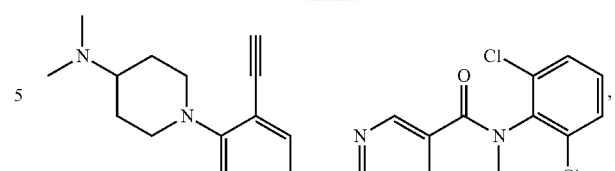
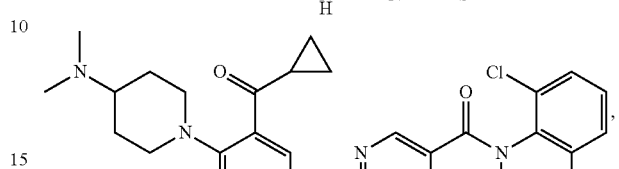
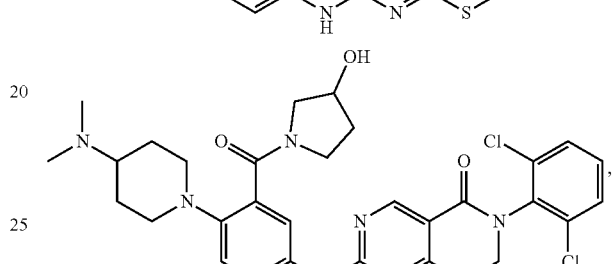
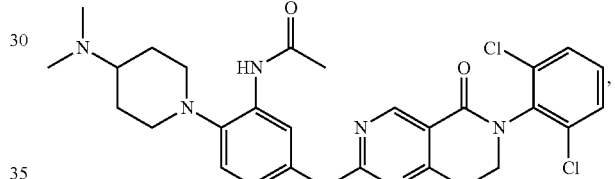
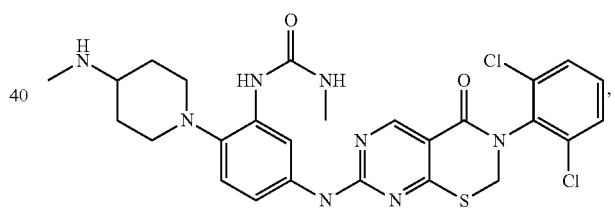
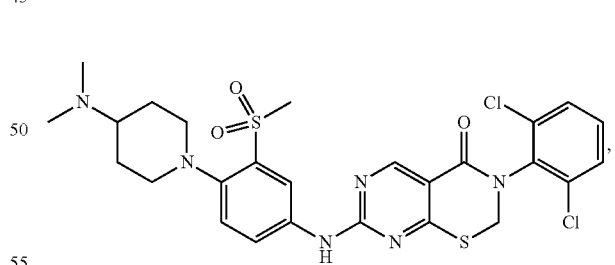
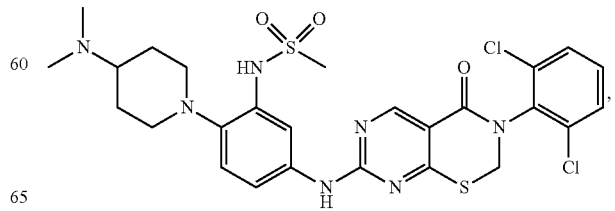

741
-continued
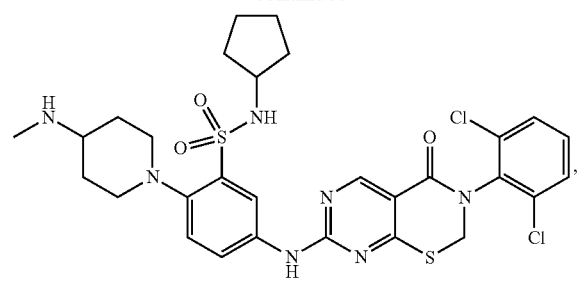
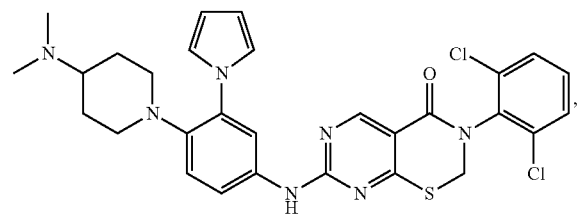
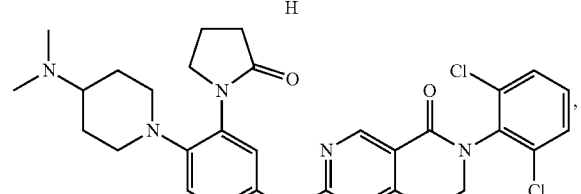
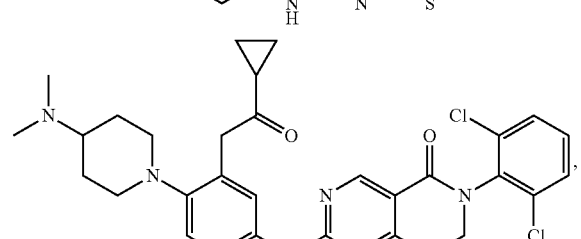
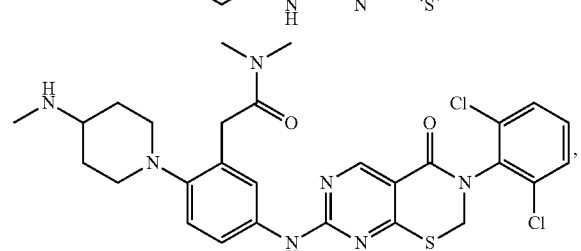
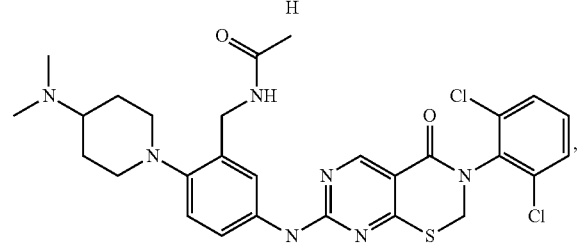
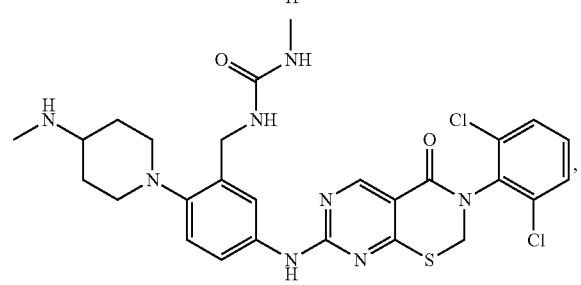
742
-continued
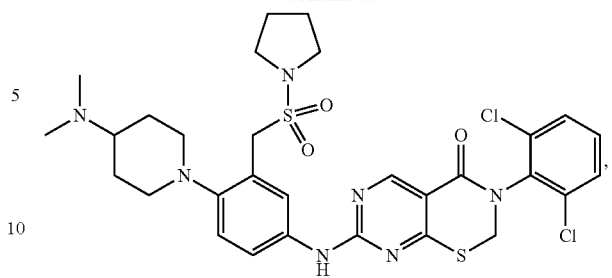
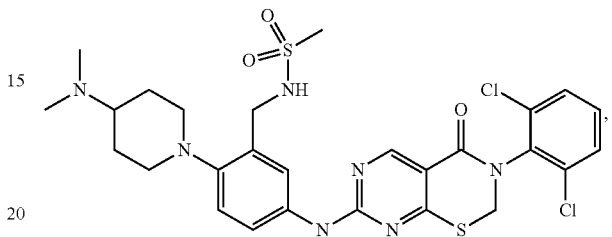
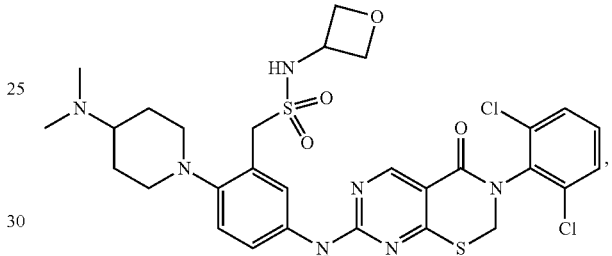
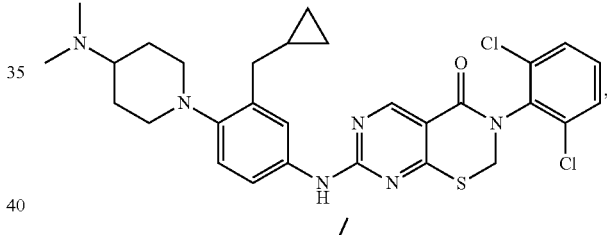
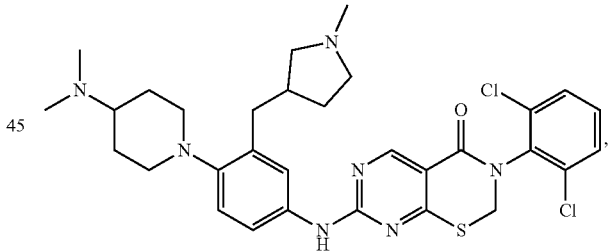
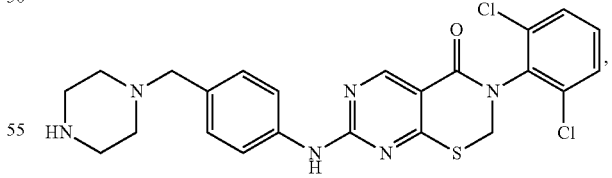
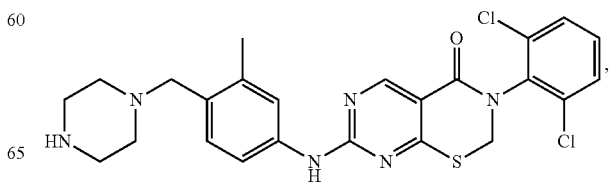

743
-continued
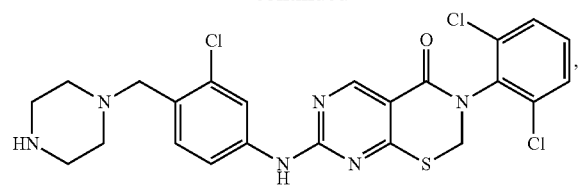
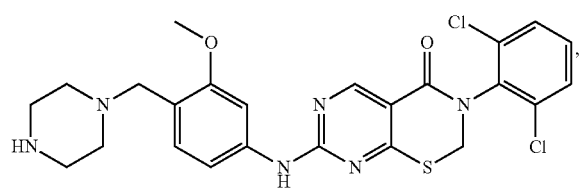
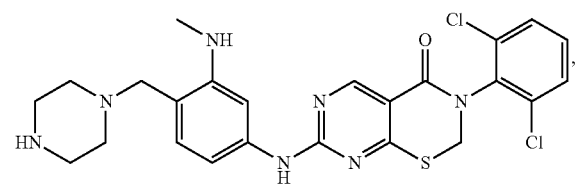
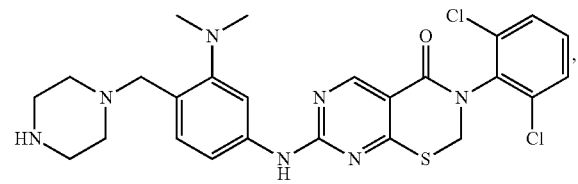
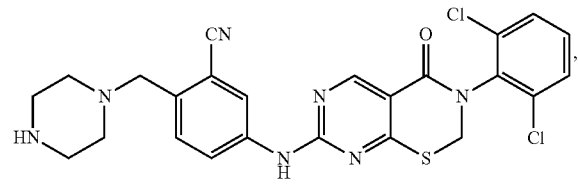
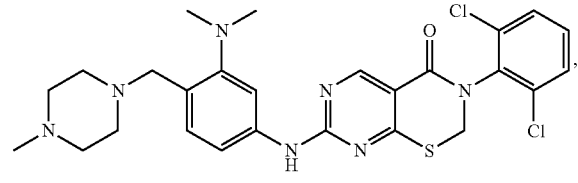
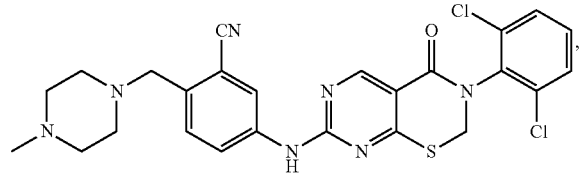
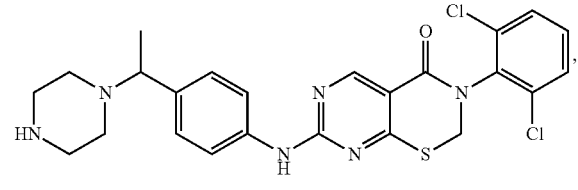
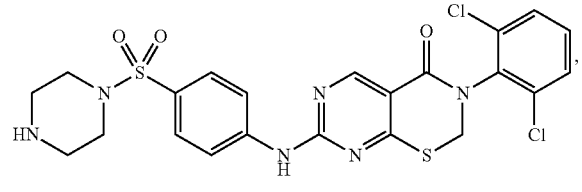
744
-continued
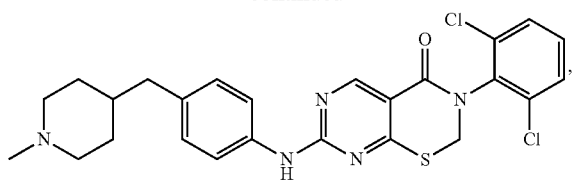
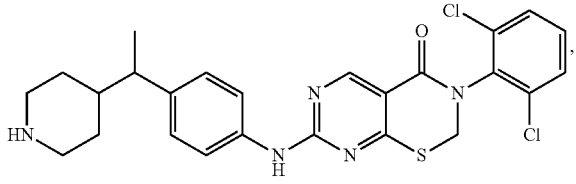
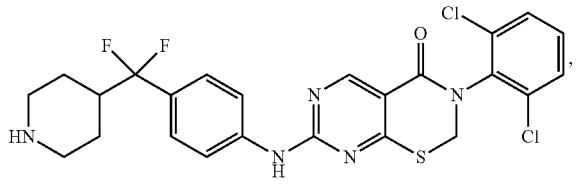
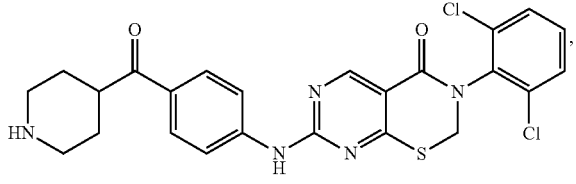
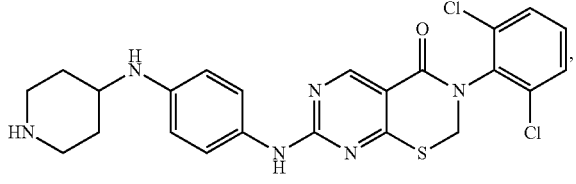
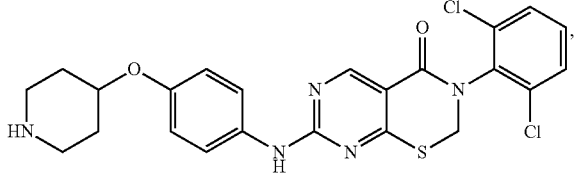
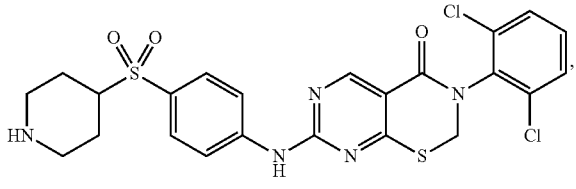
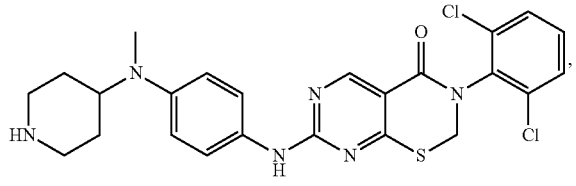
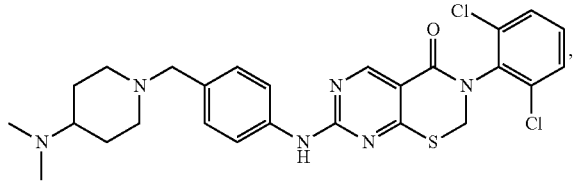

745
-continued
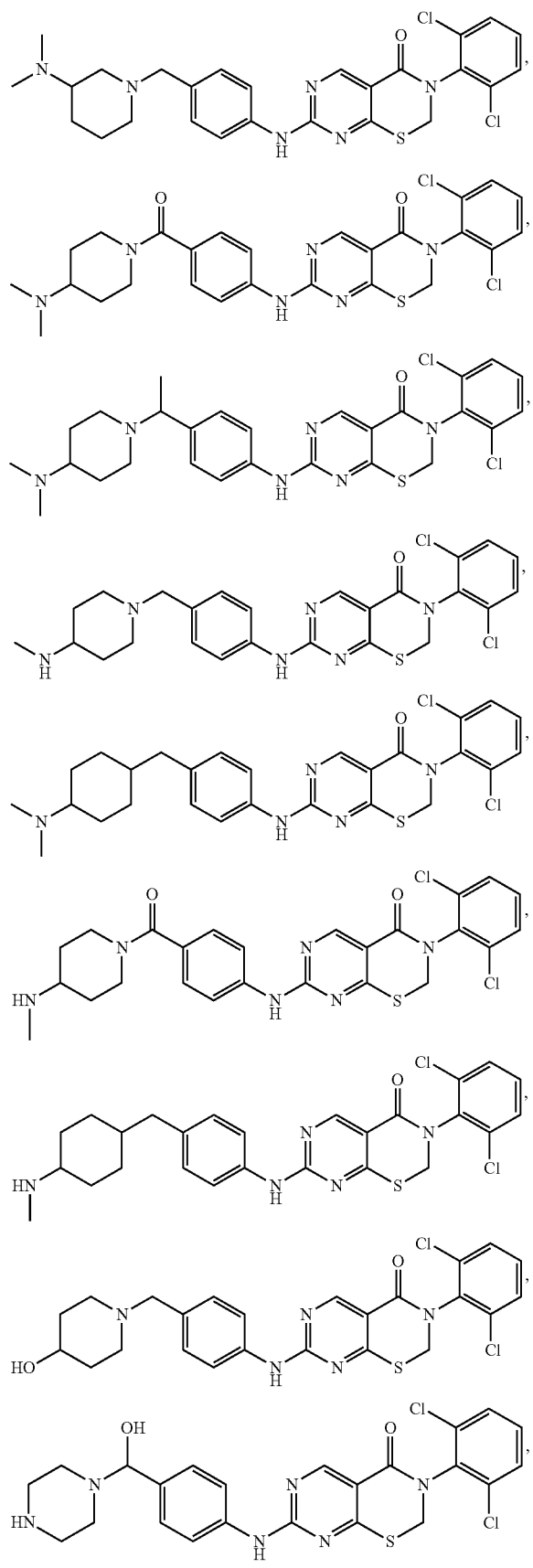
746
-continued
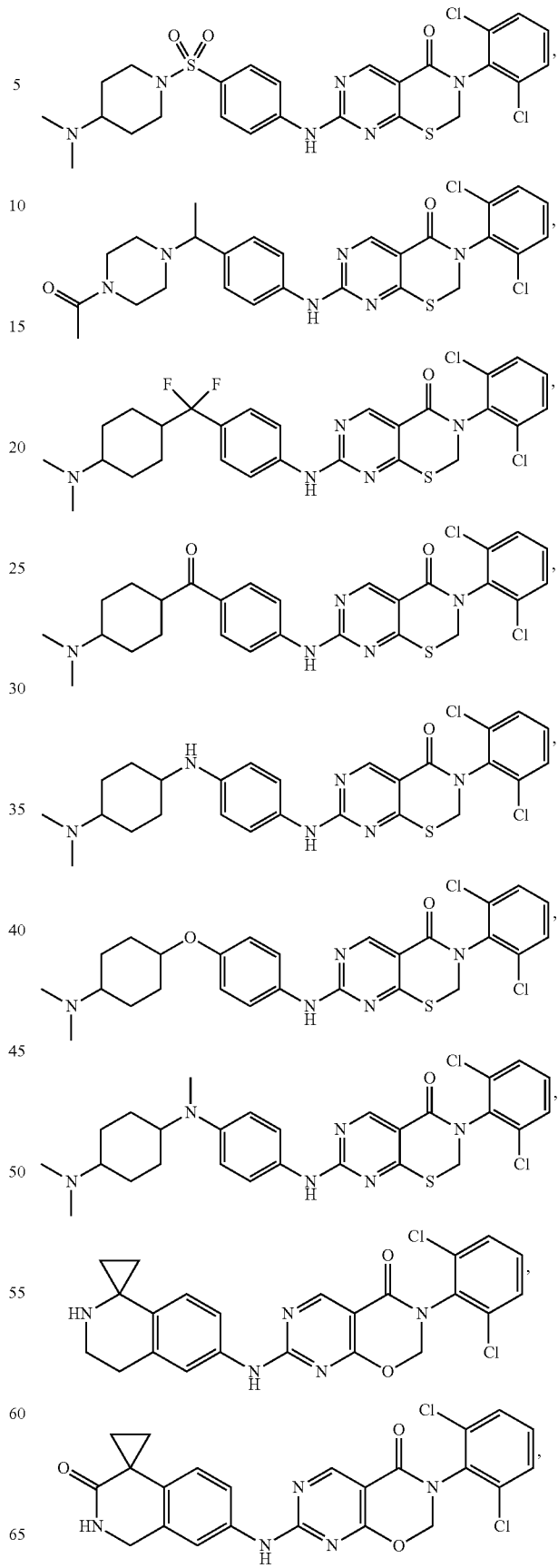

747
-continued
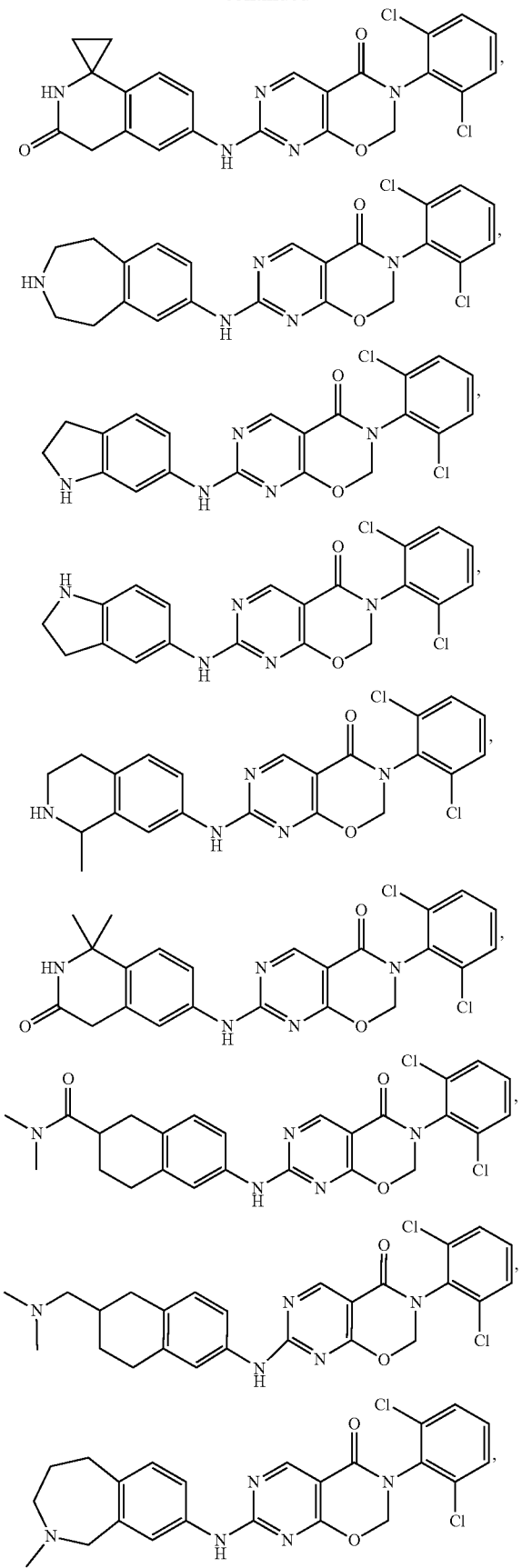
748
-continued
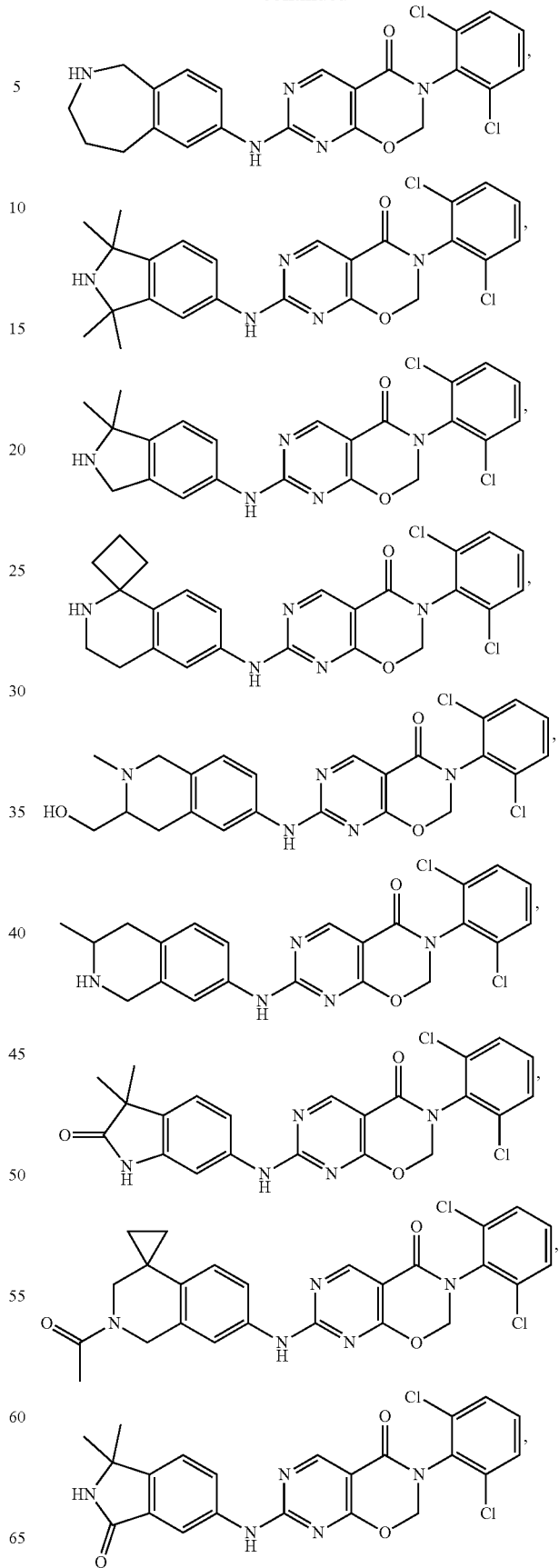

749
-continued
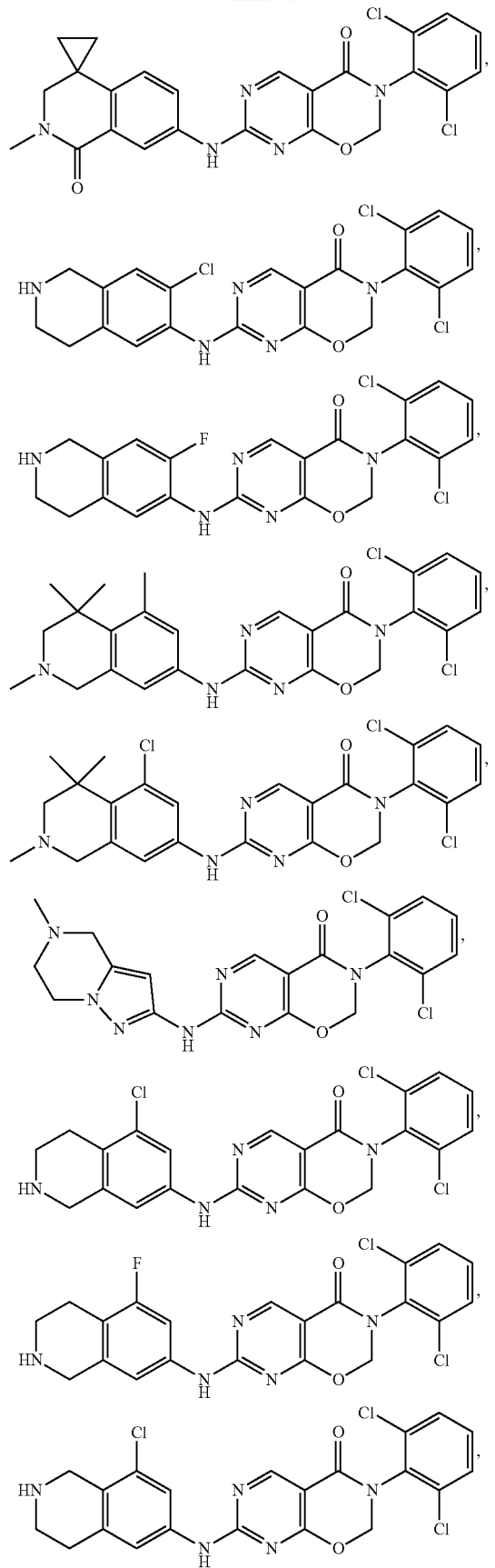
750
-continued
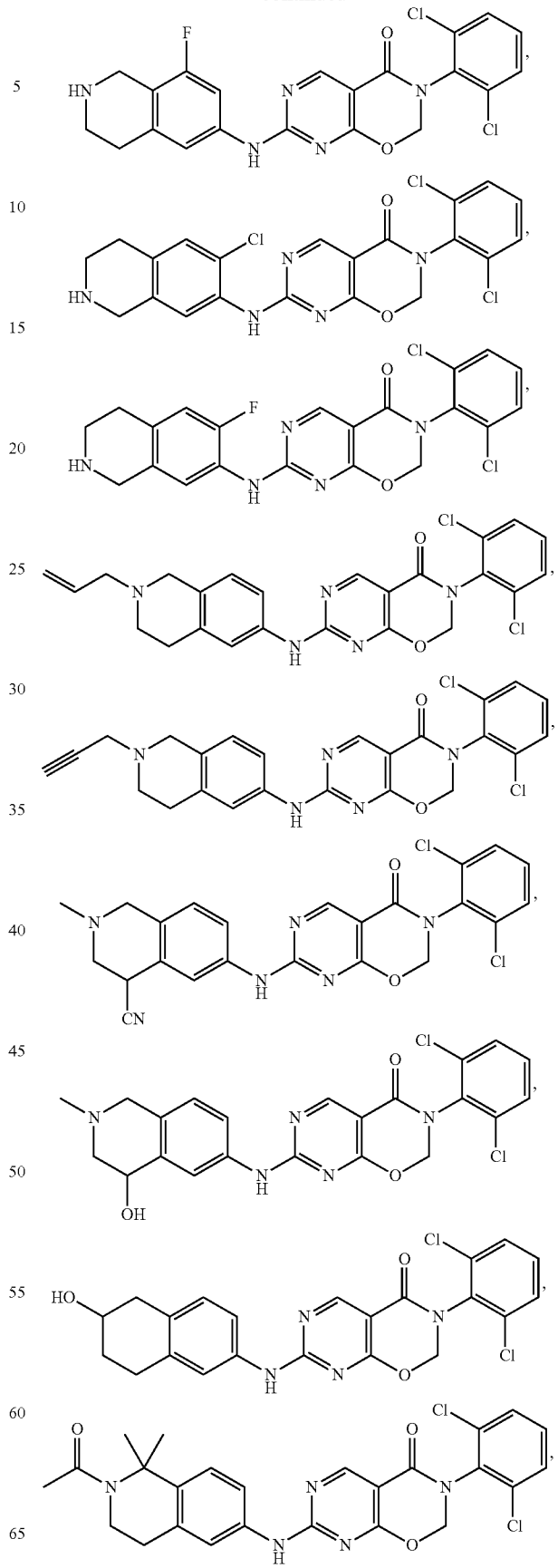

-continued
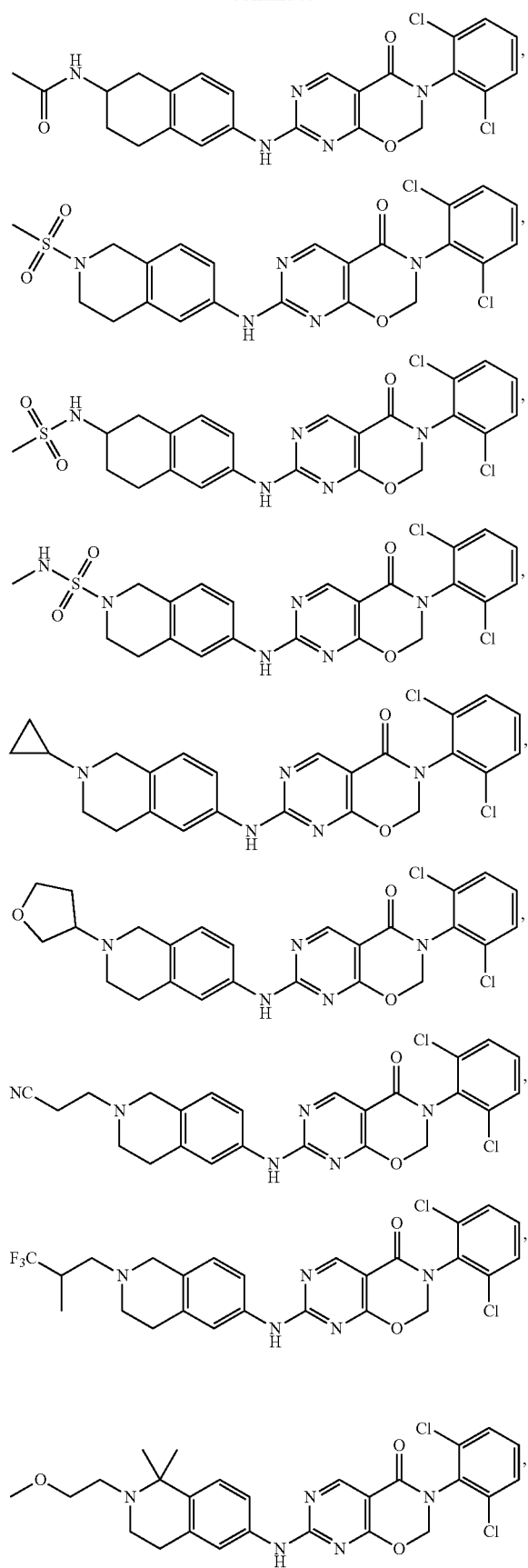
-continued
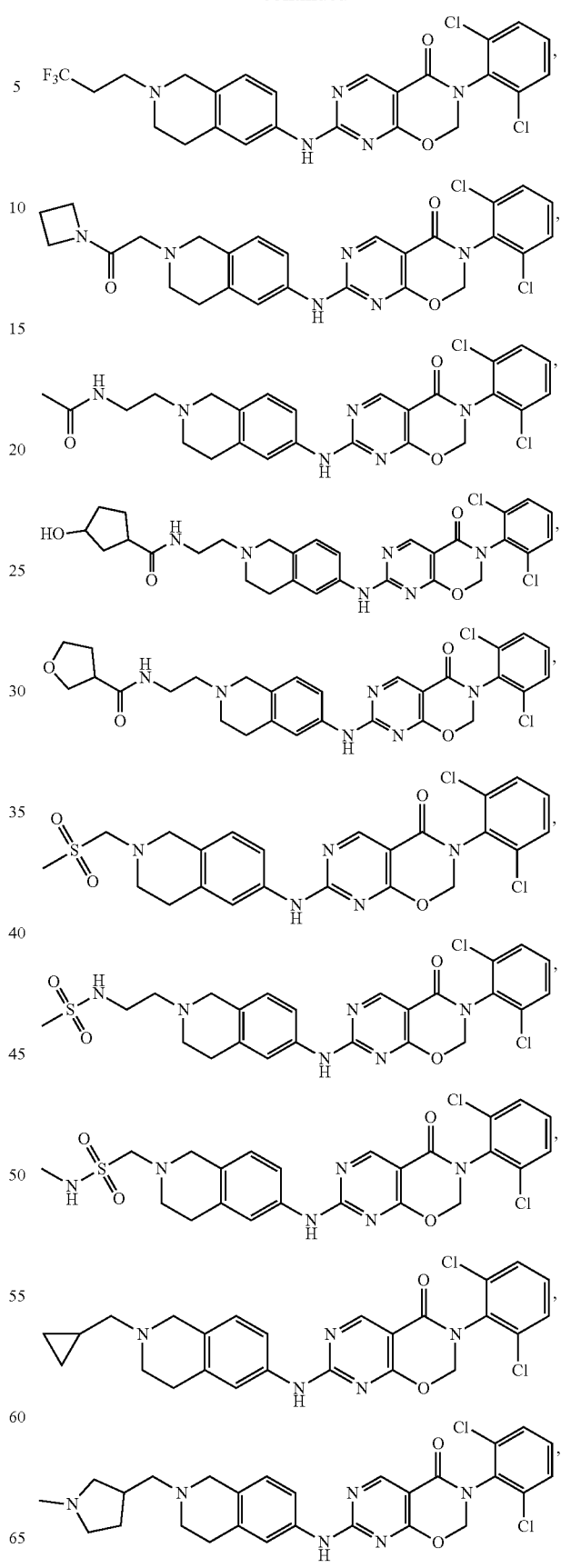

753
-continued
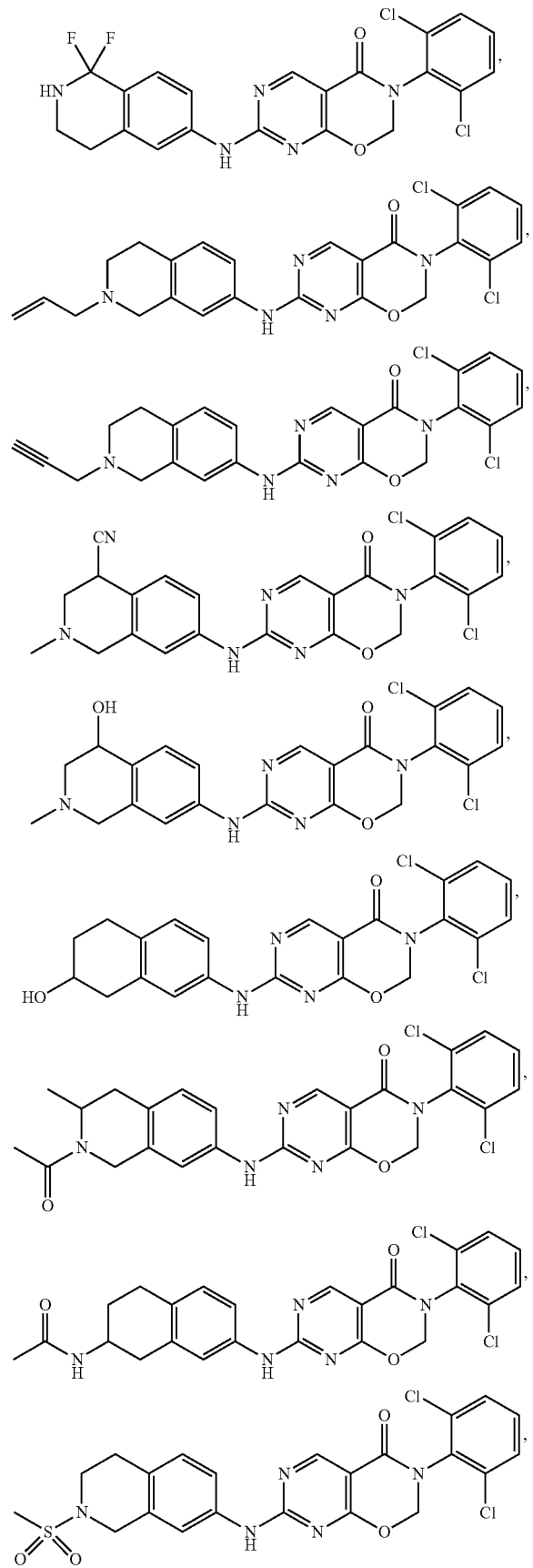
754
-continued
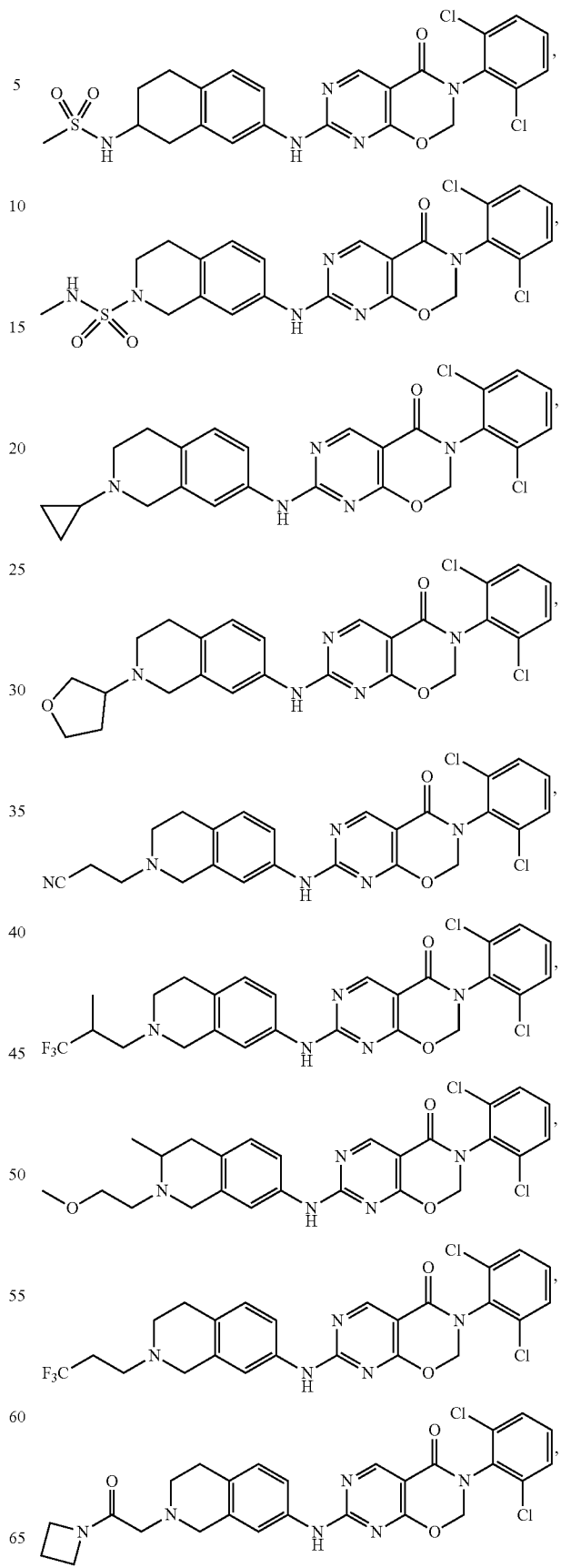

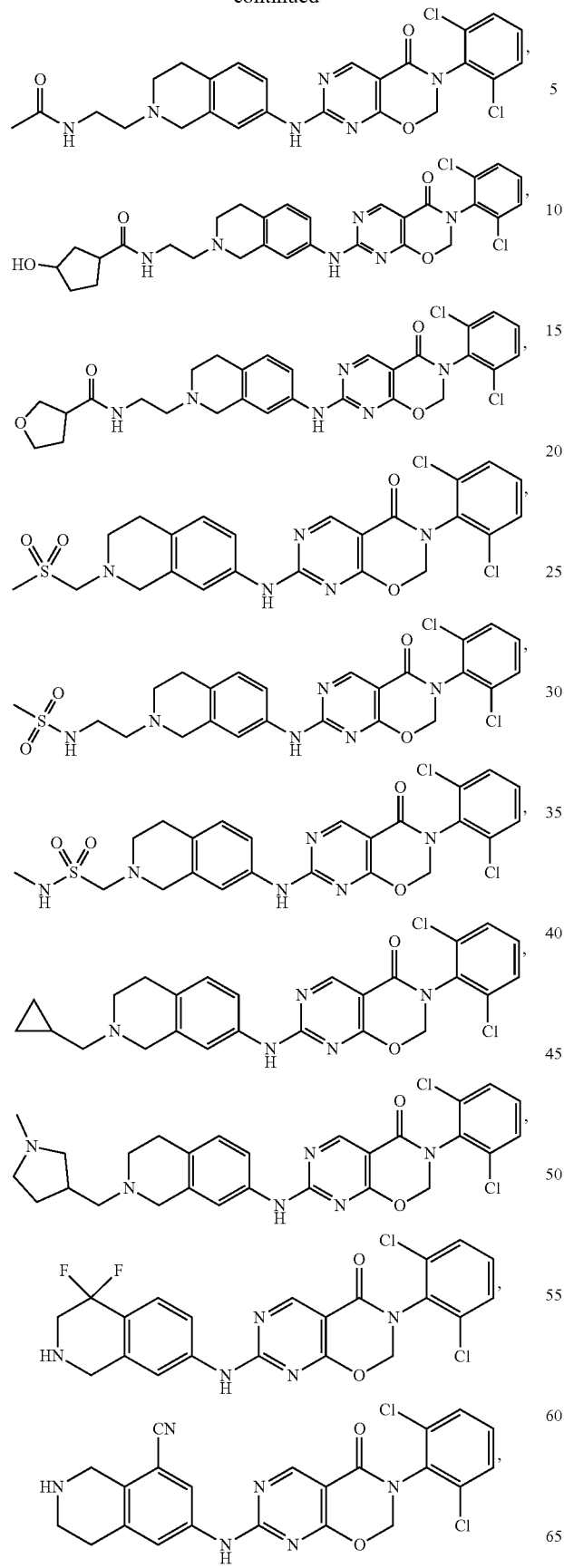
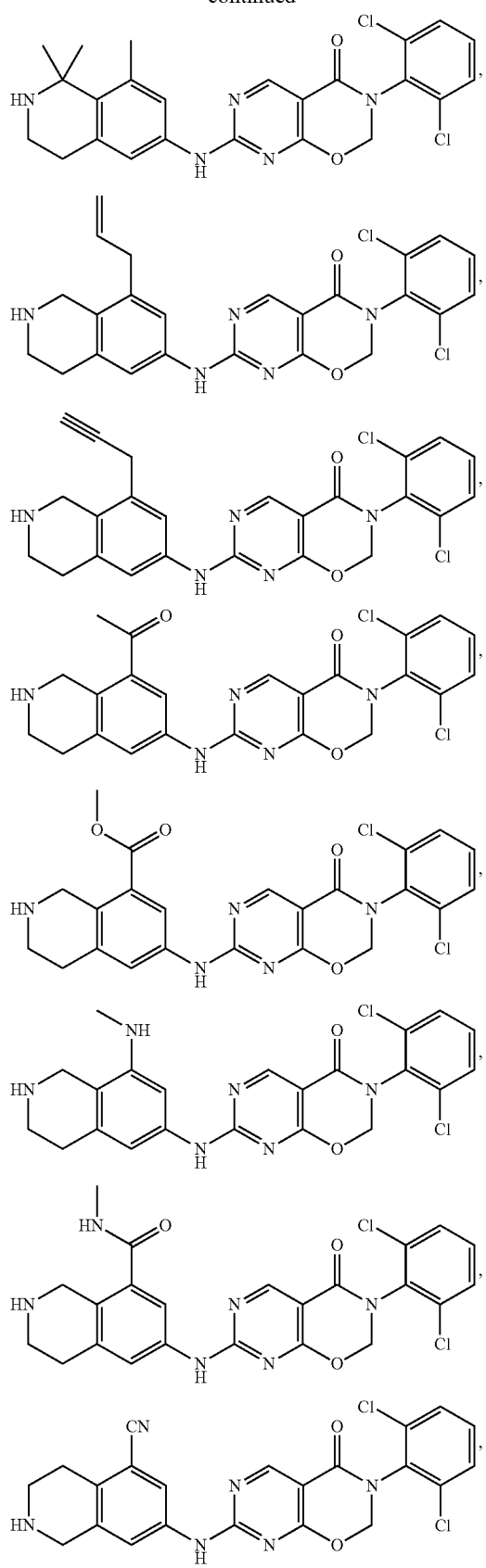

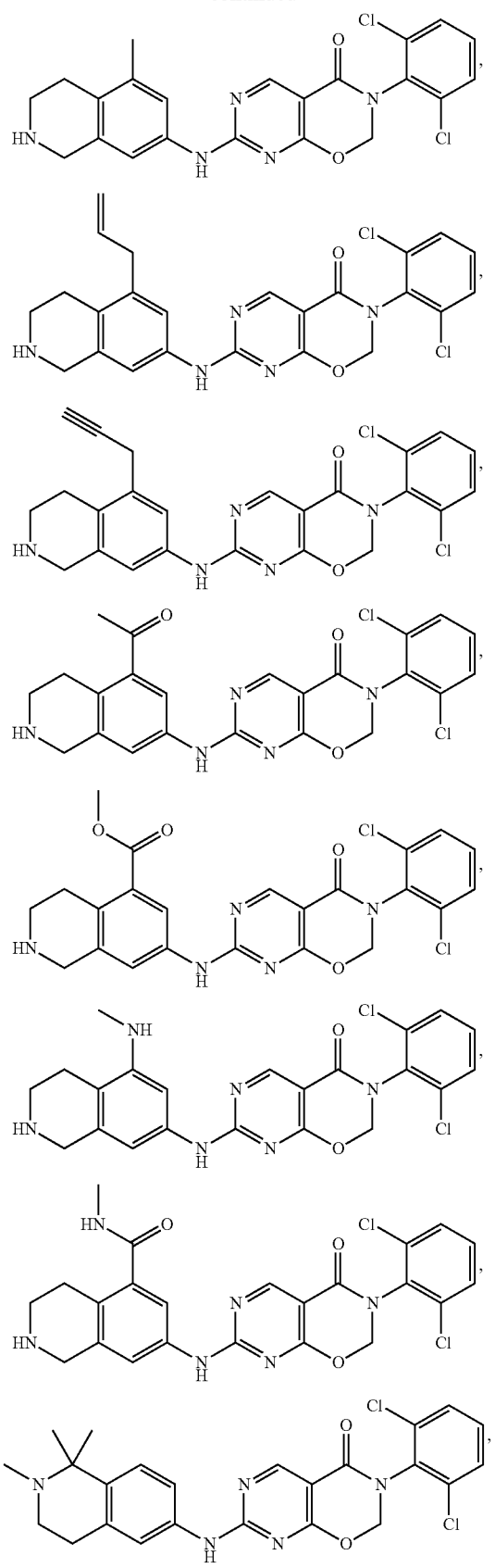
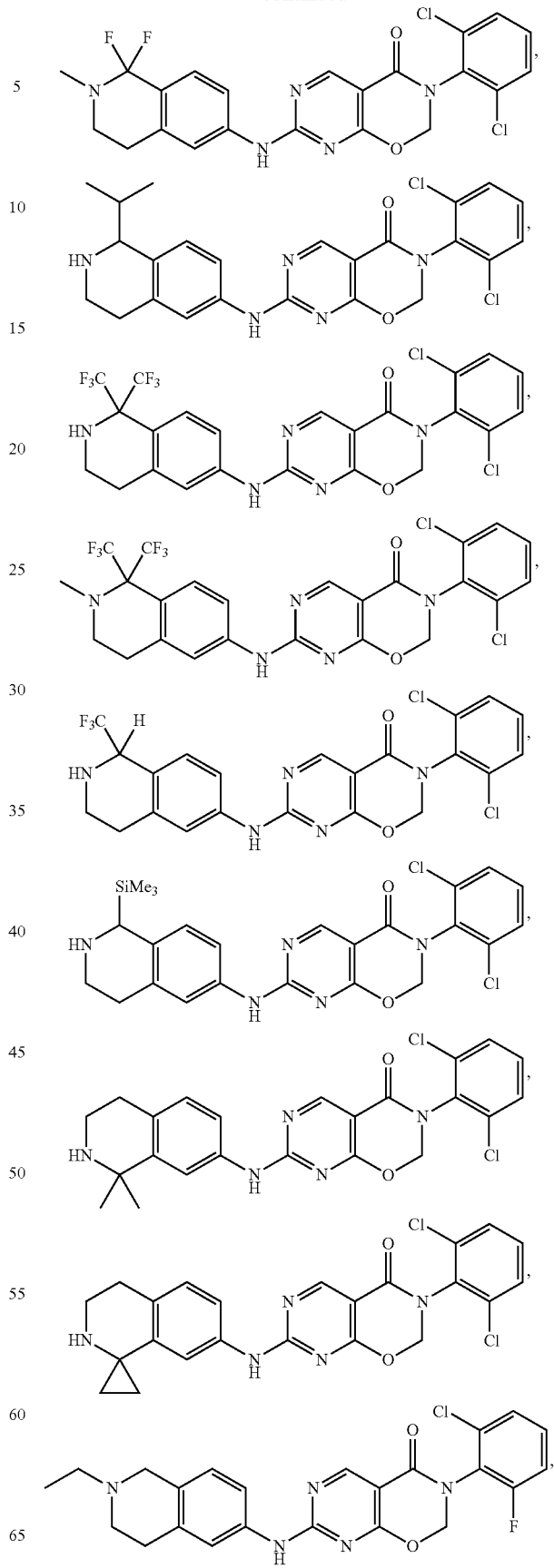

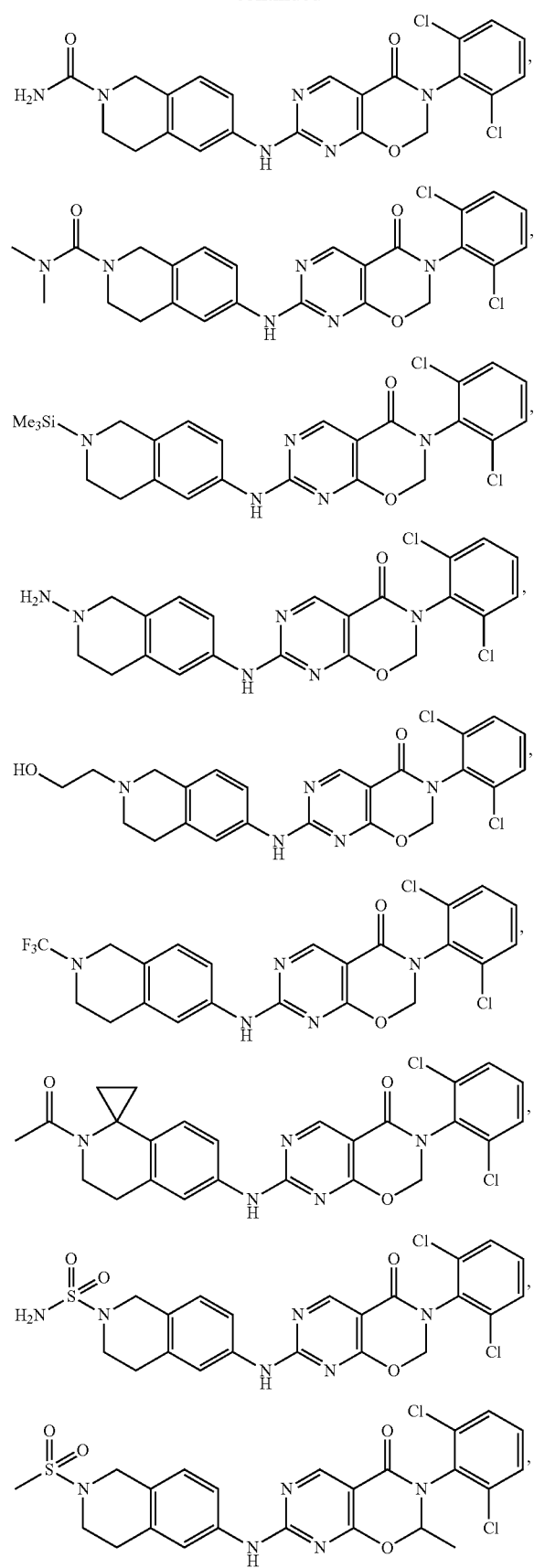
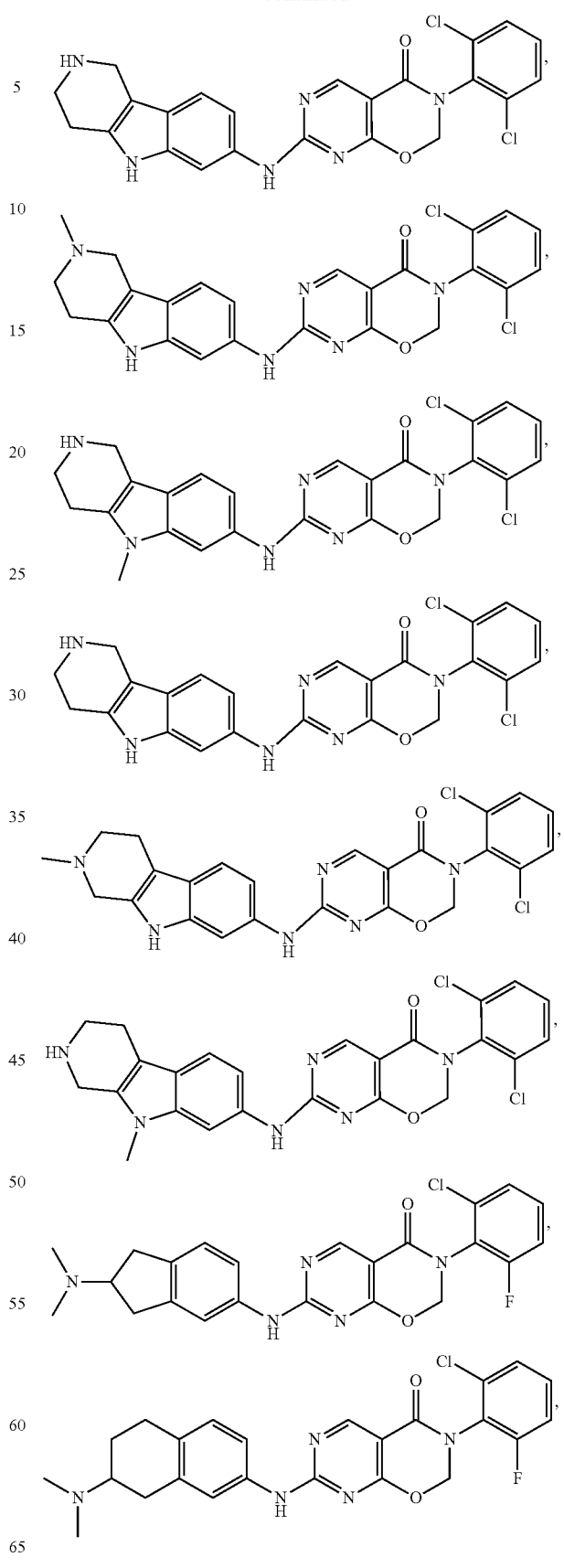

761
-continued
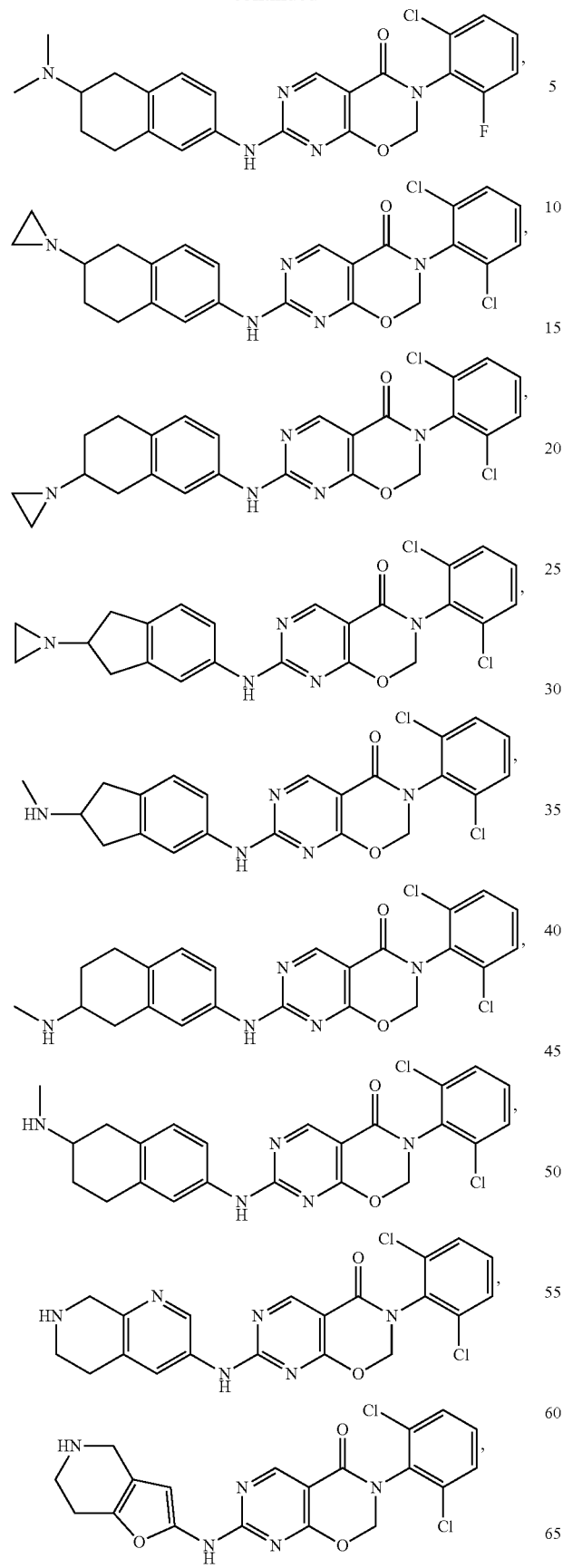
762
-continued
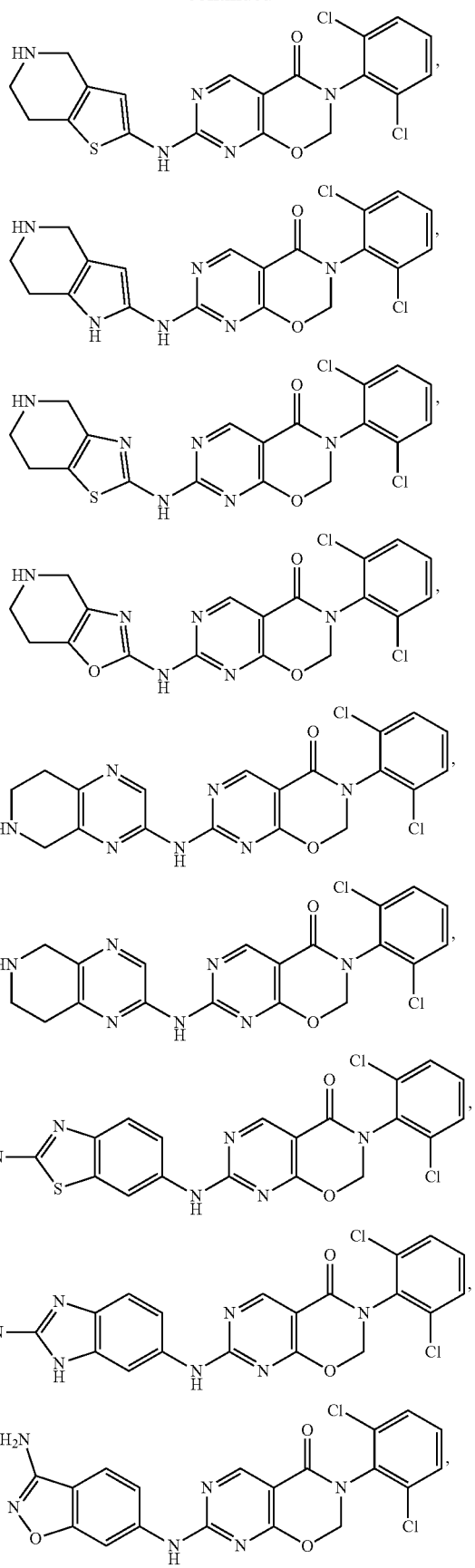

763
-continued
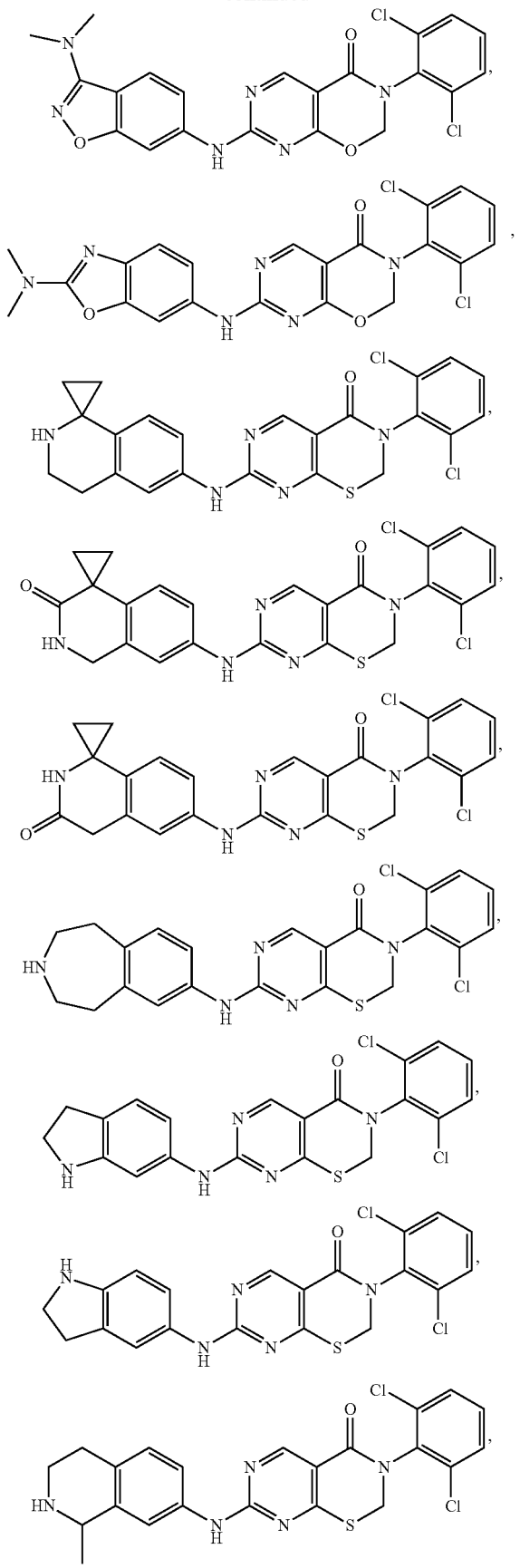
764
-continued
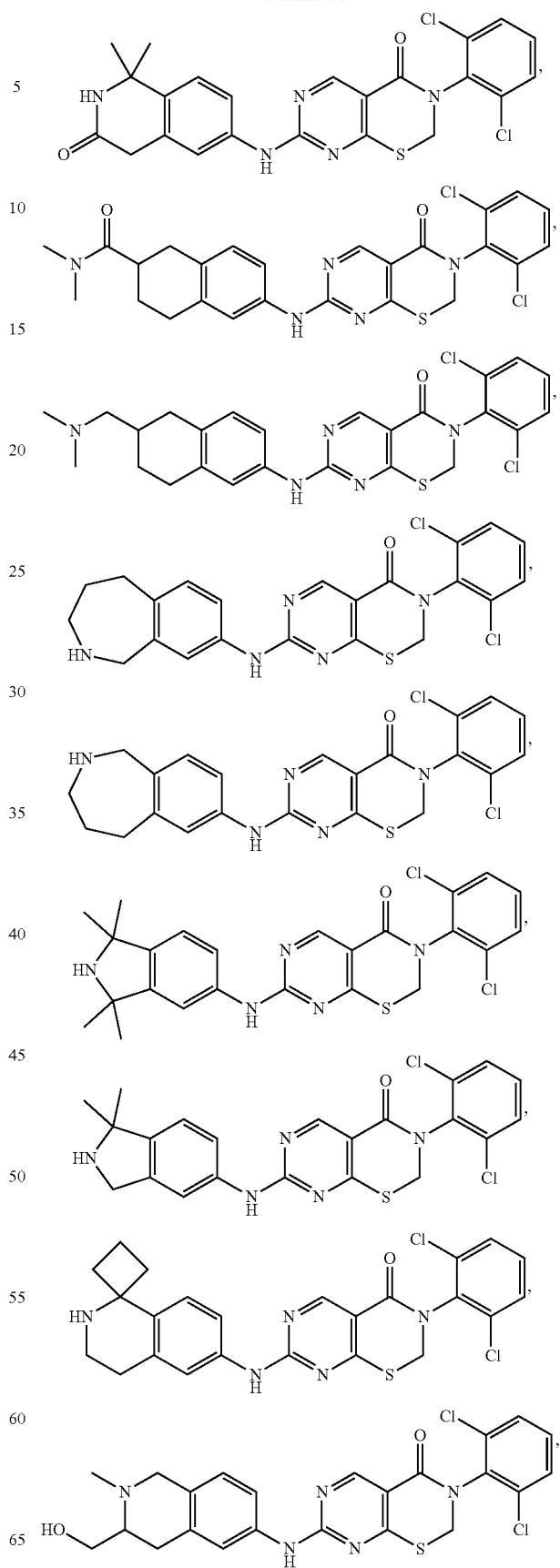

765
-continued
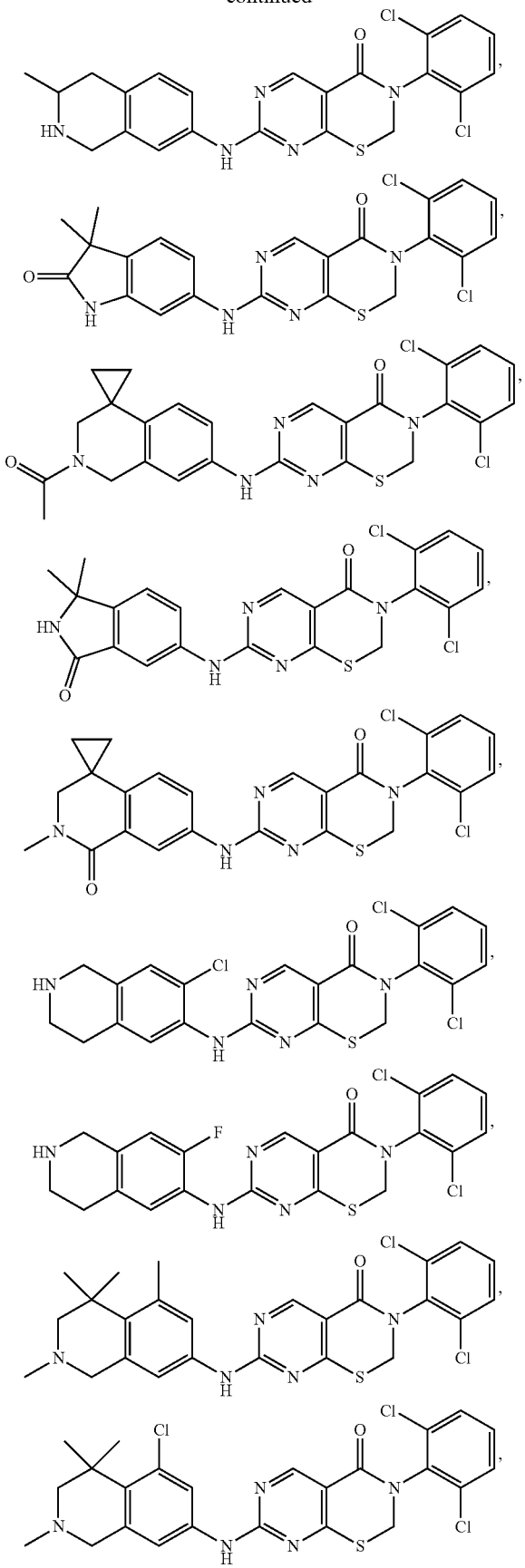
766
-continued
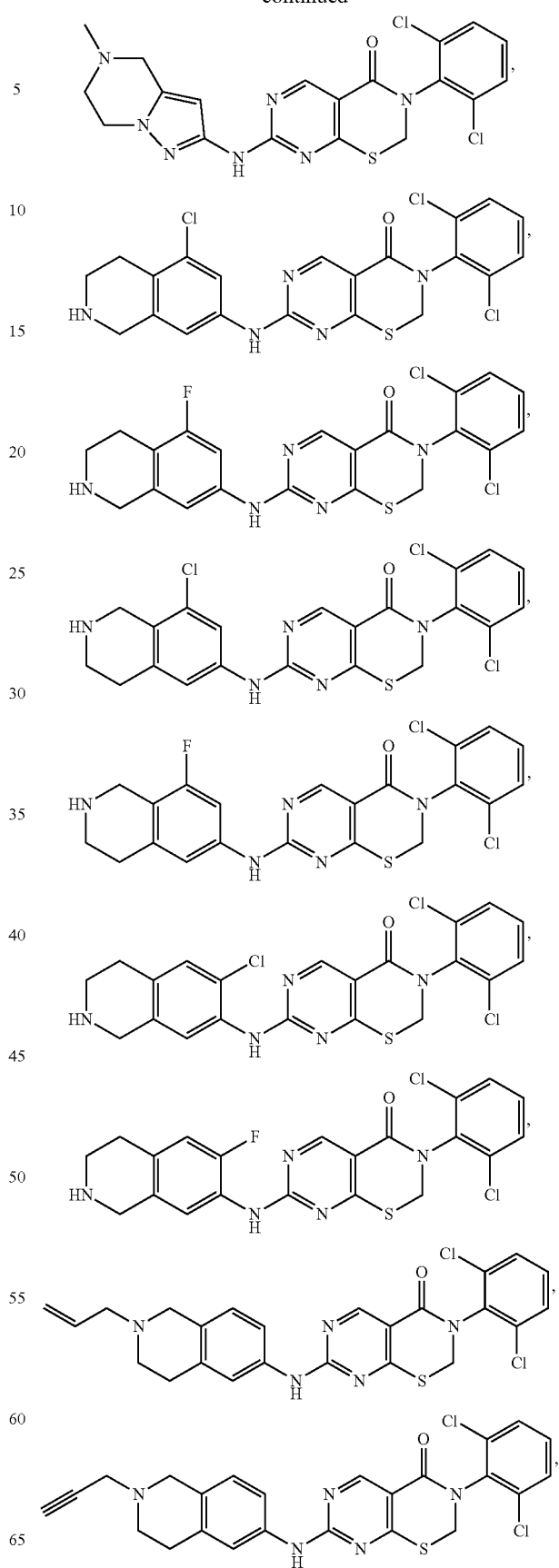

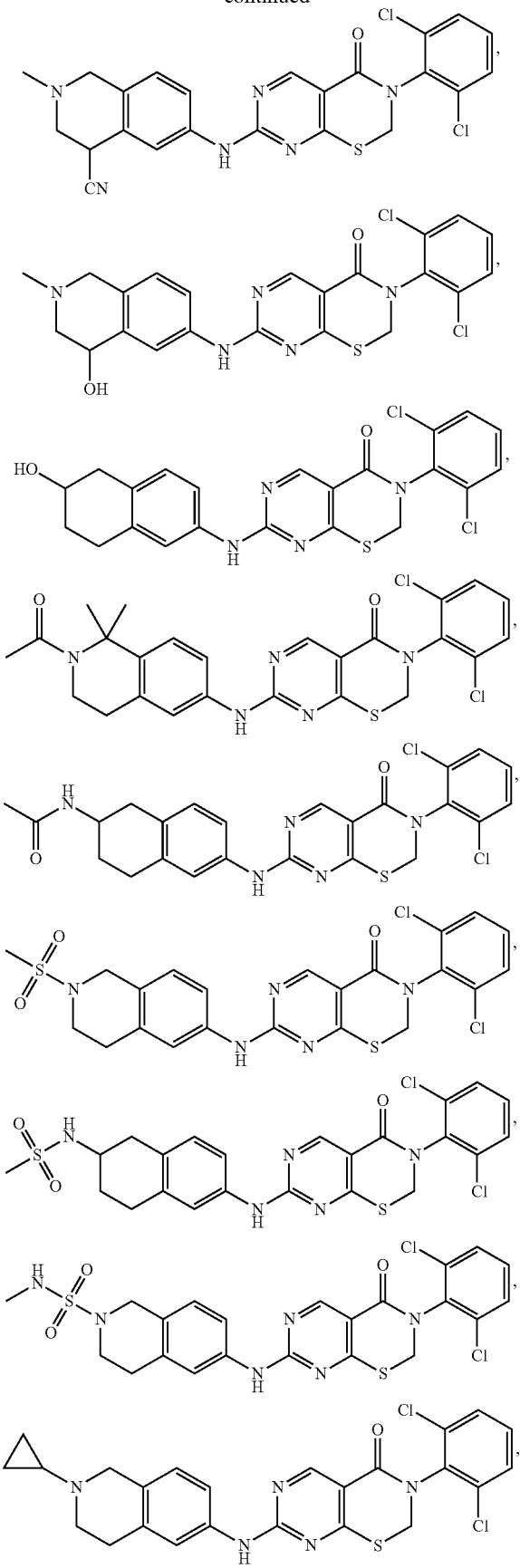
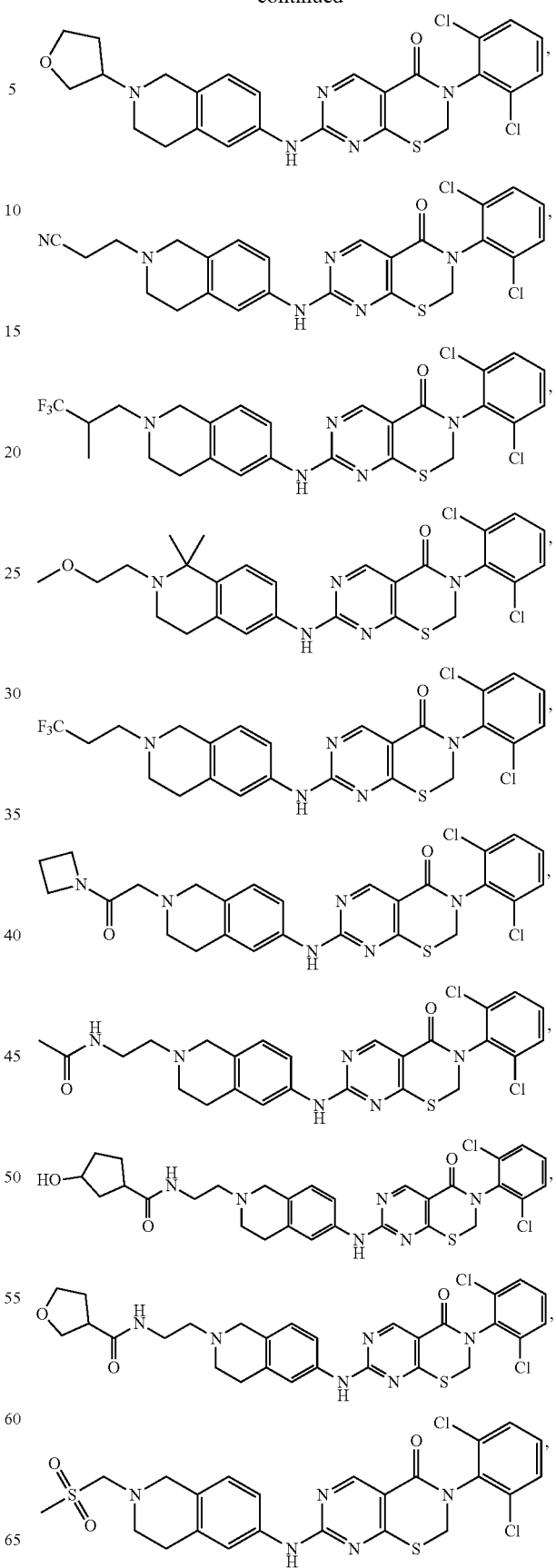

769
-continued
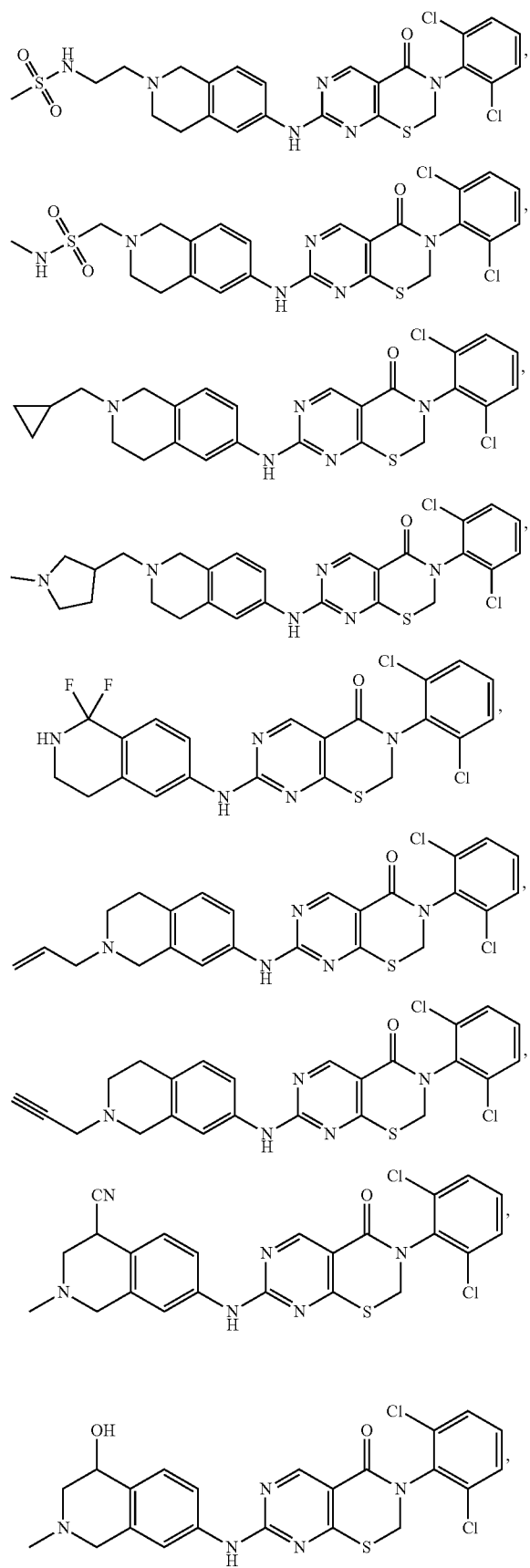
770
-continued
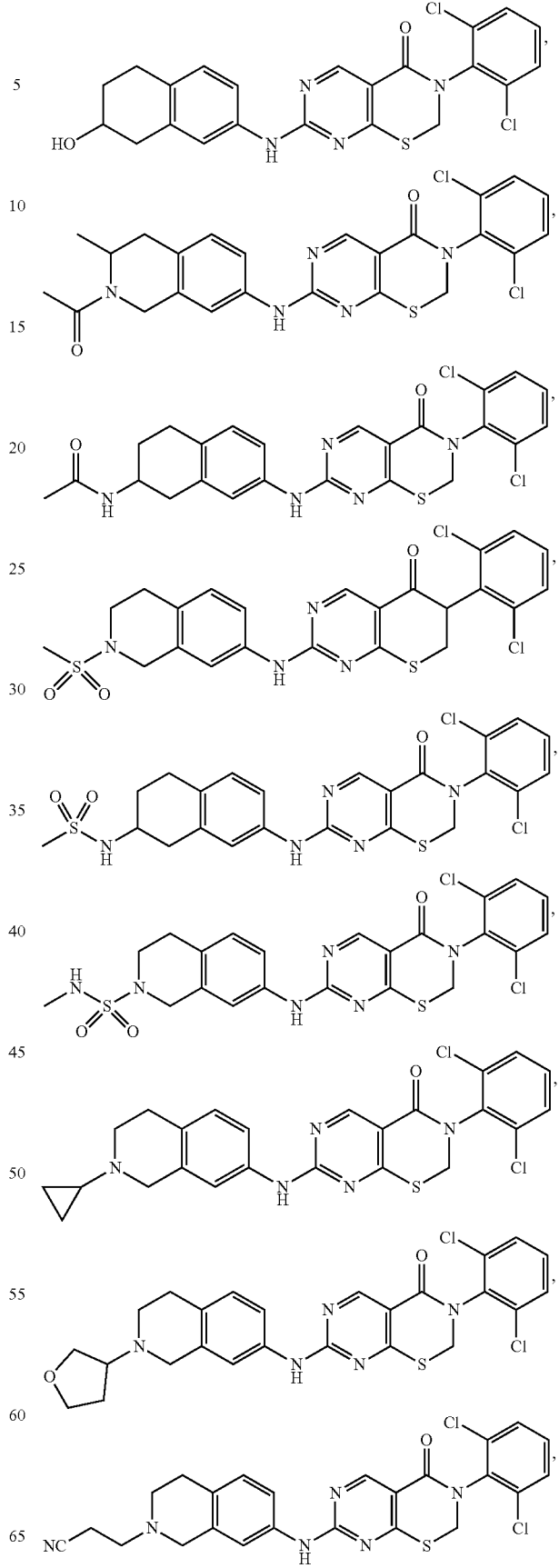

771
-continued
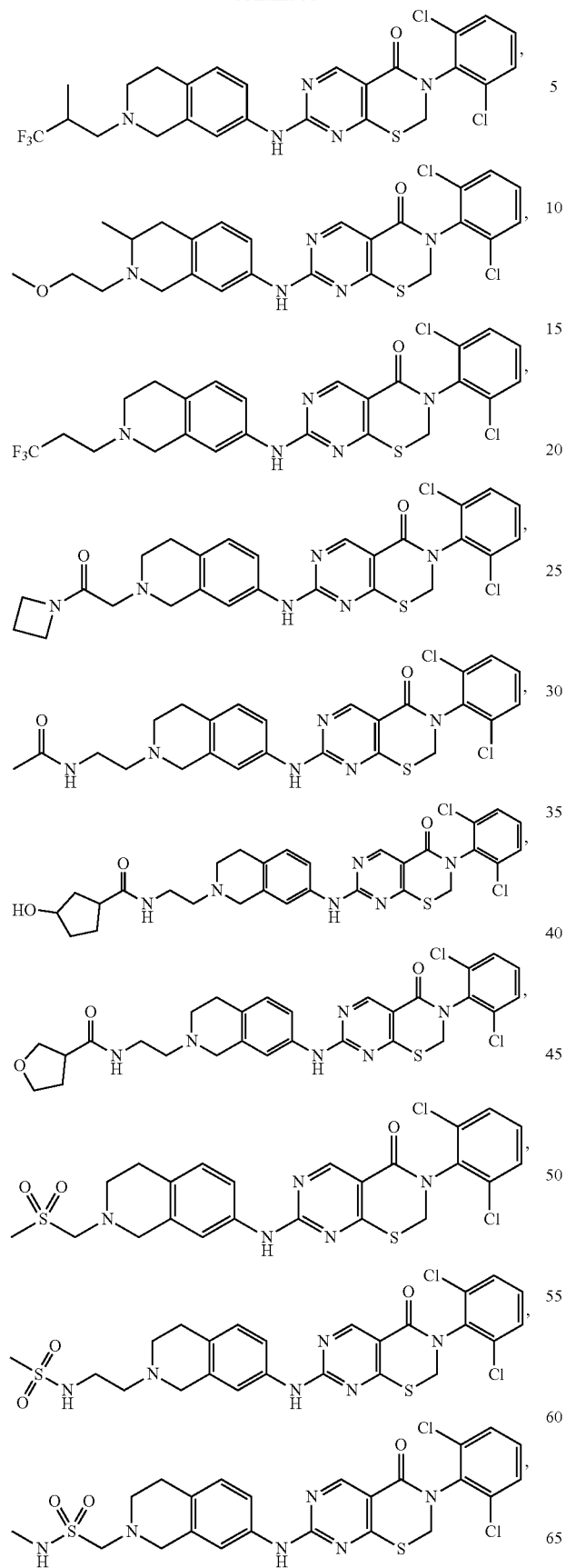
772
-continued
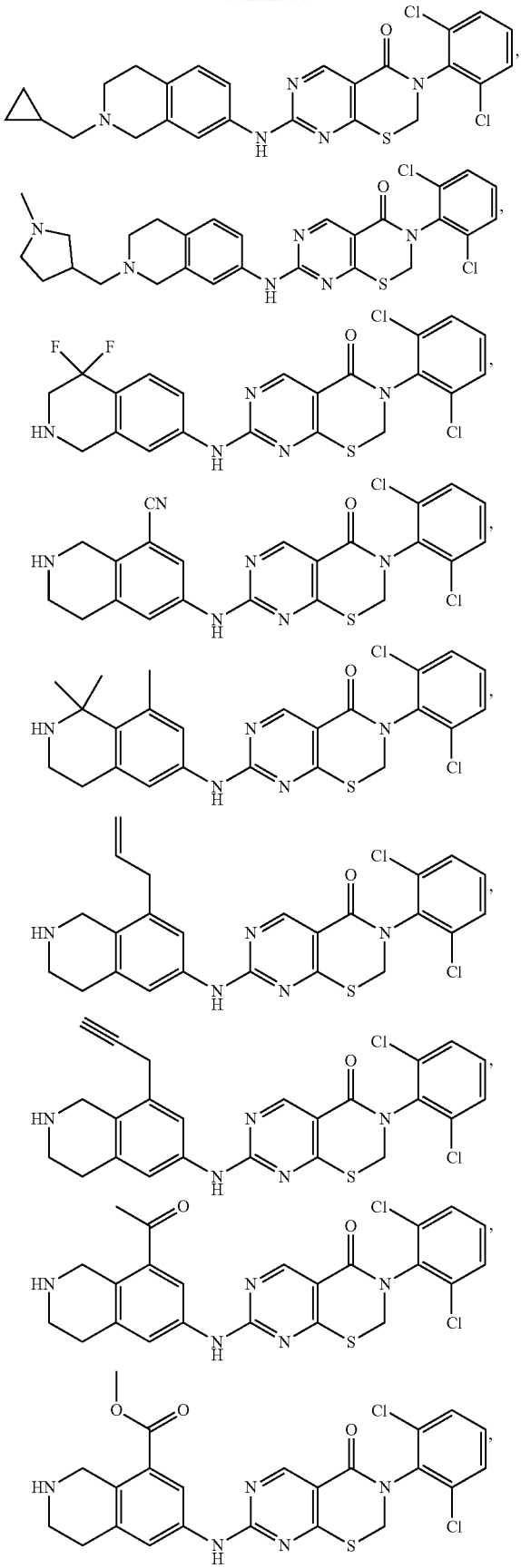

773
-continued
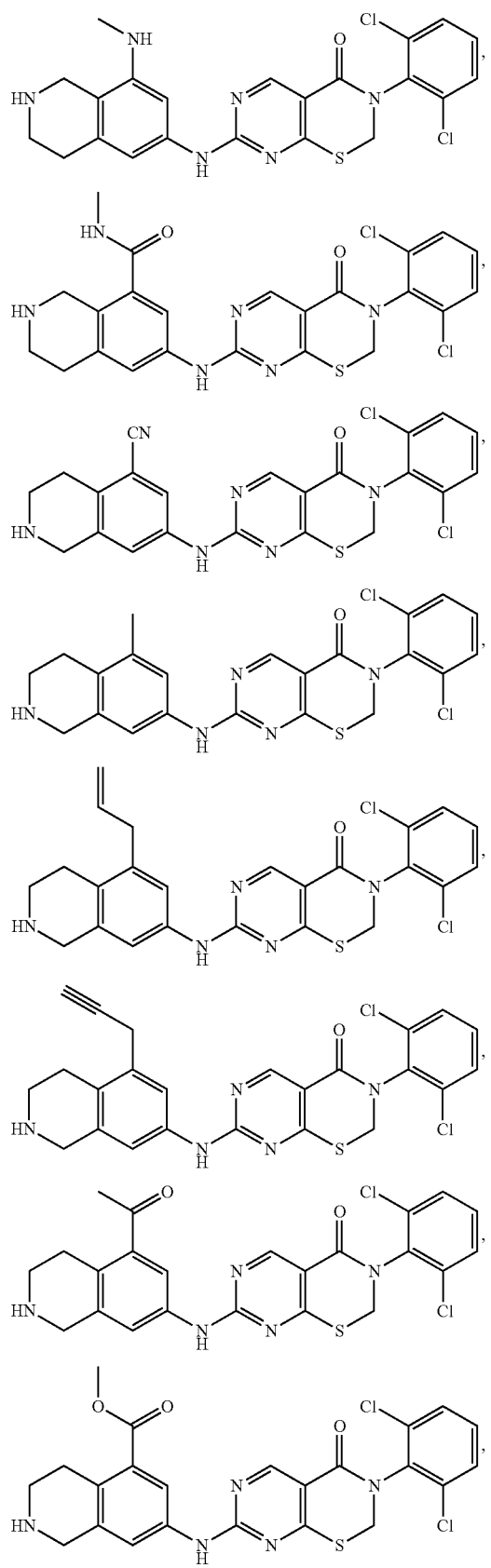
774
-continued
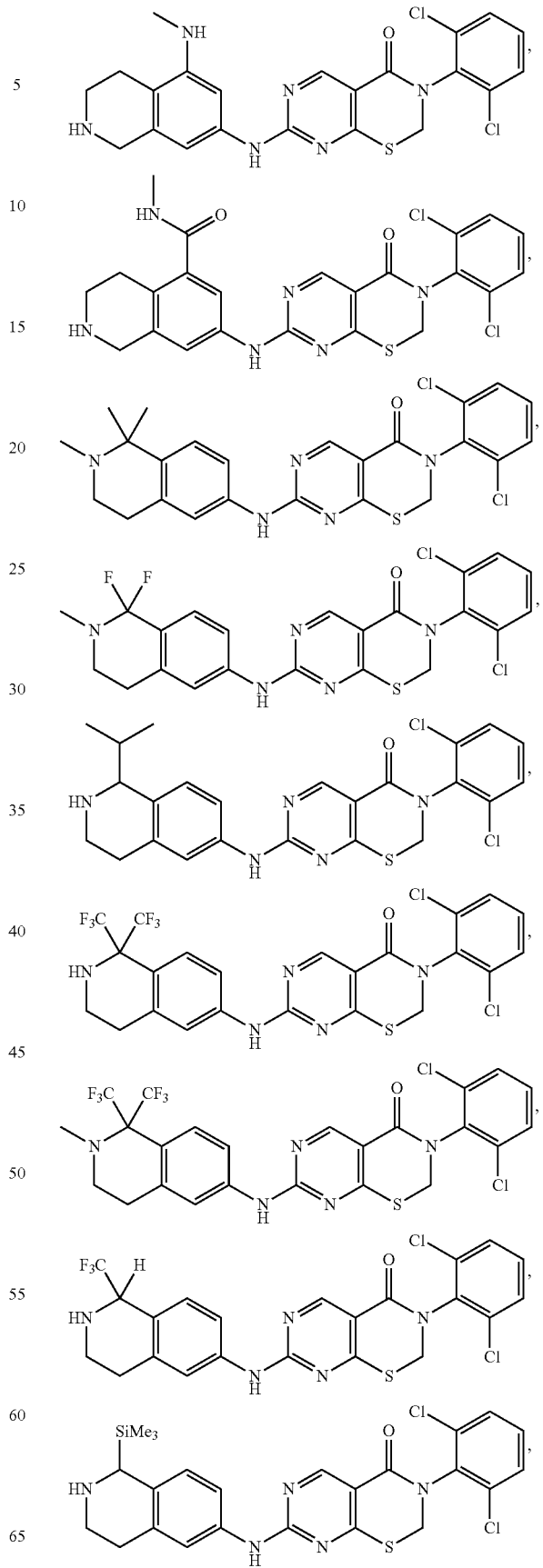

775
-continued
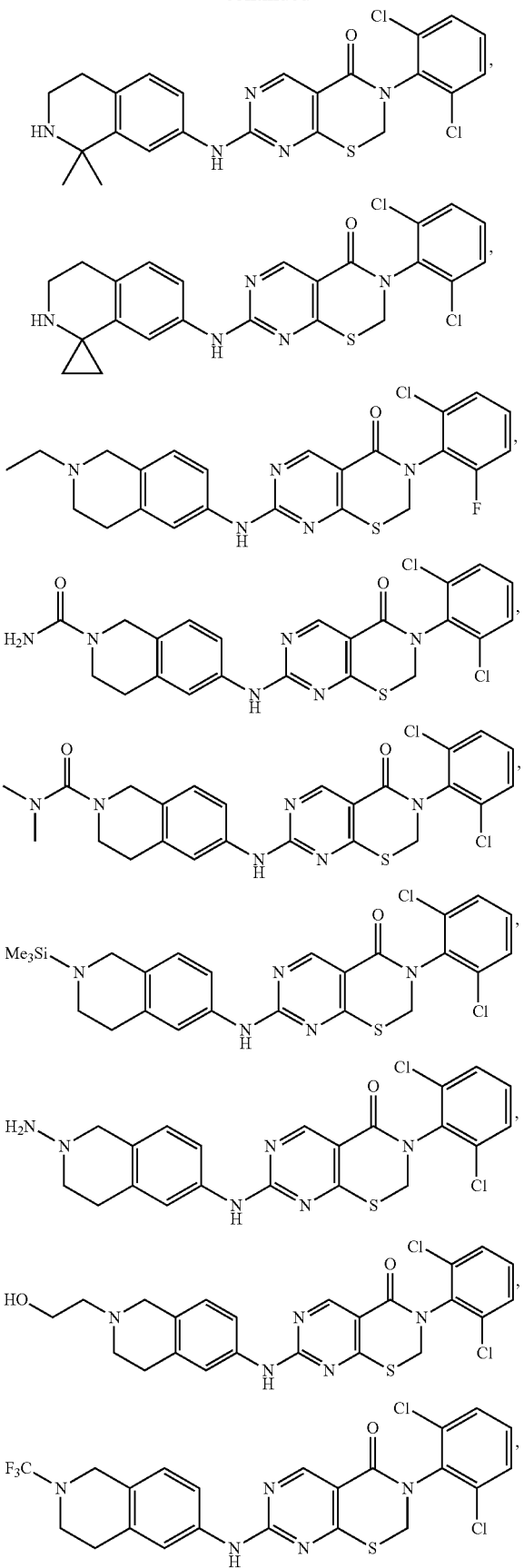
776
-continued
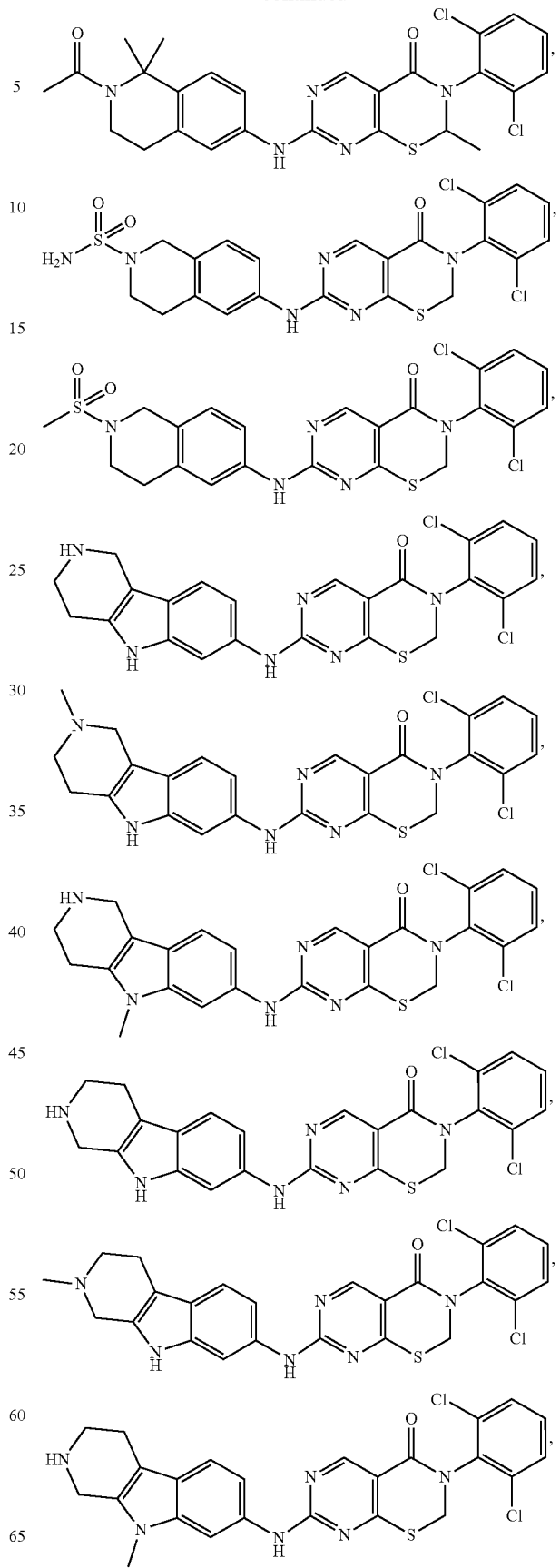

777
-continued
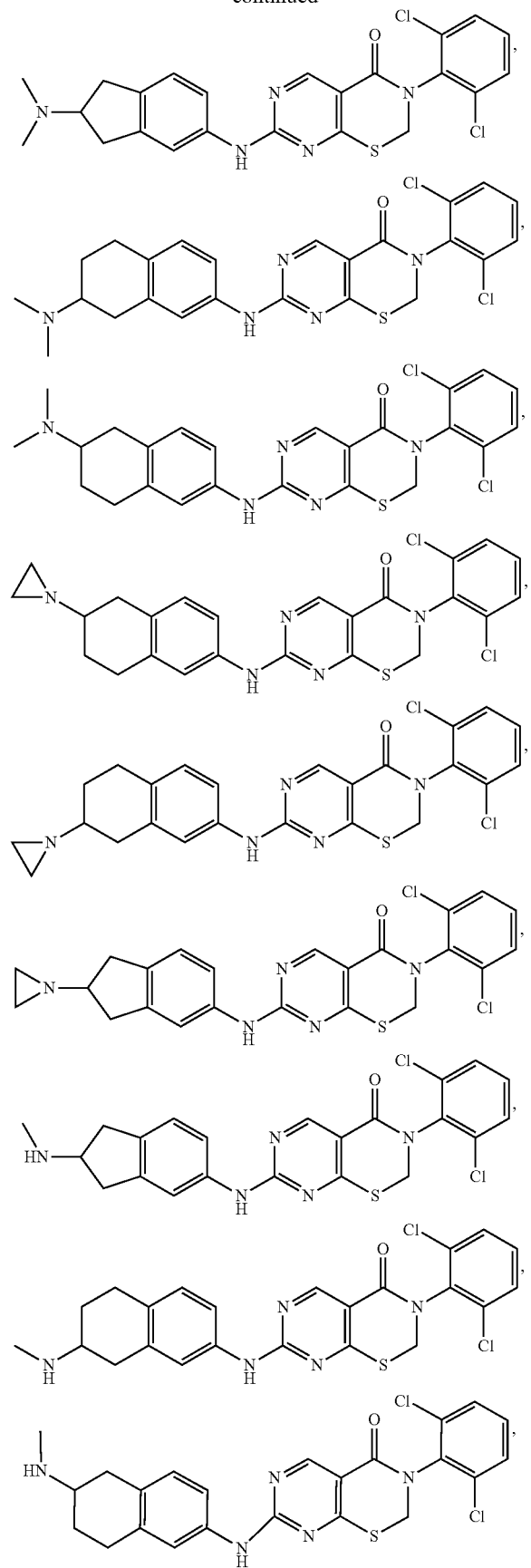
778
-continued
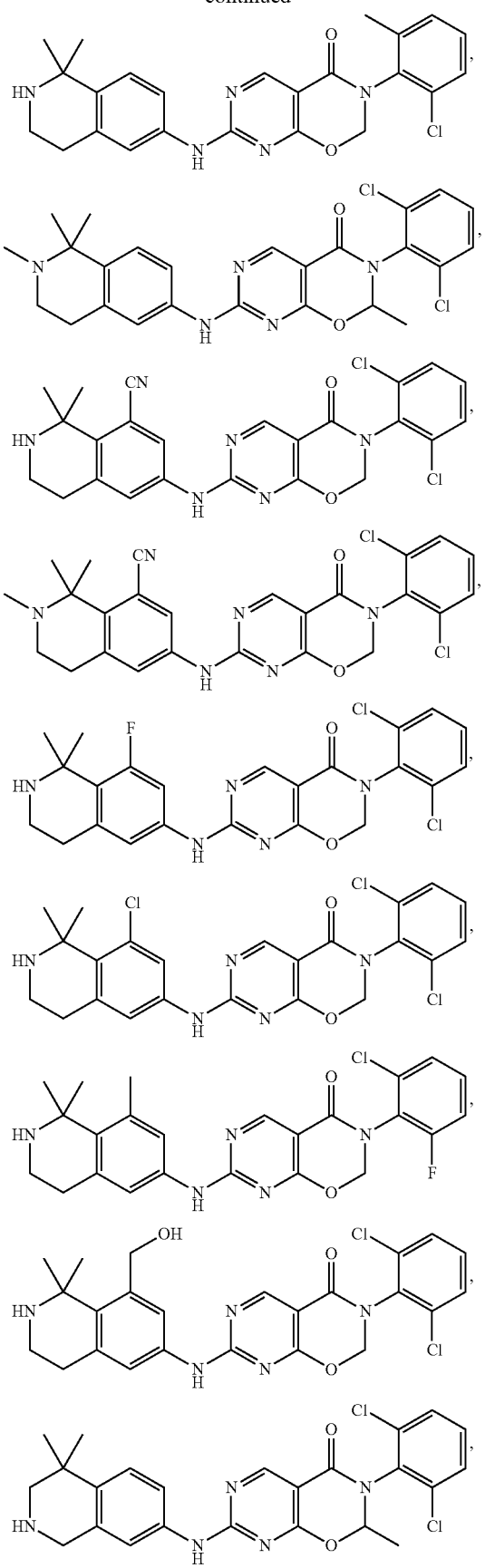

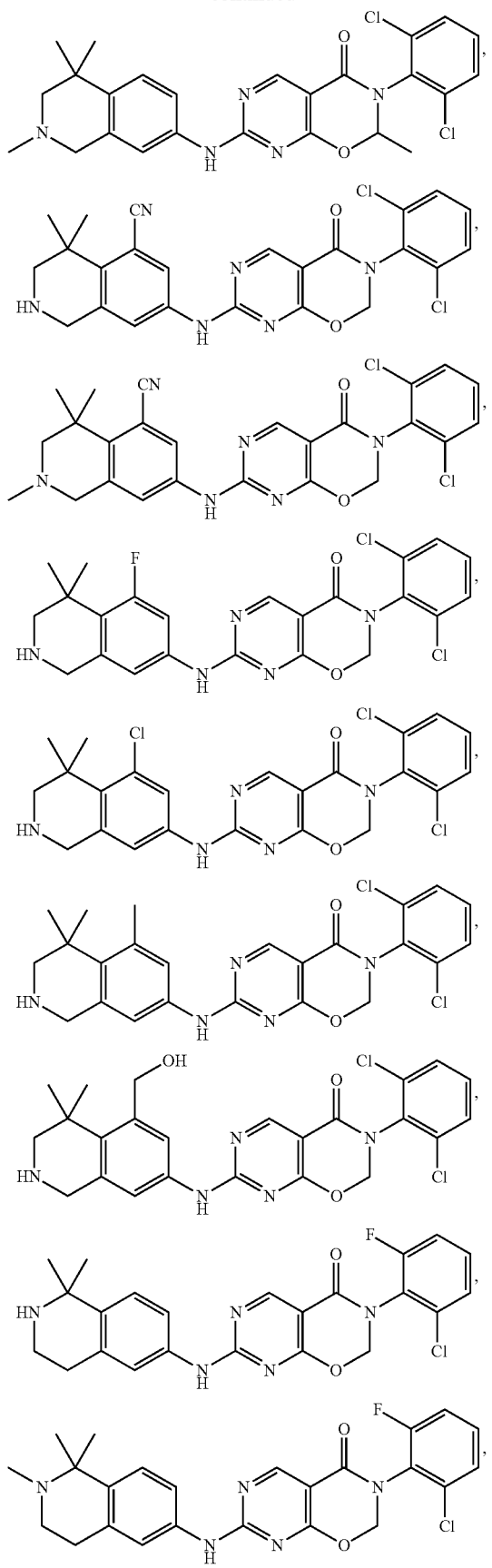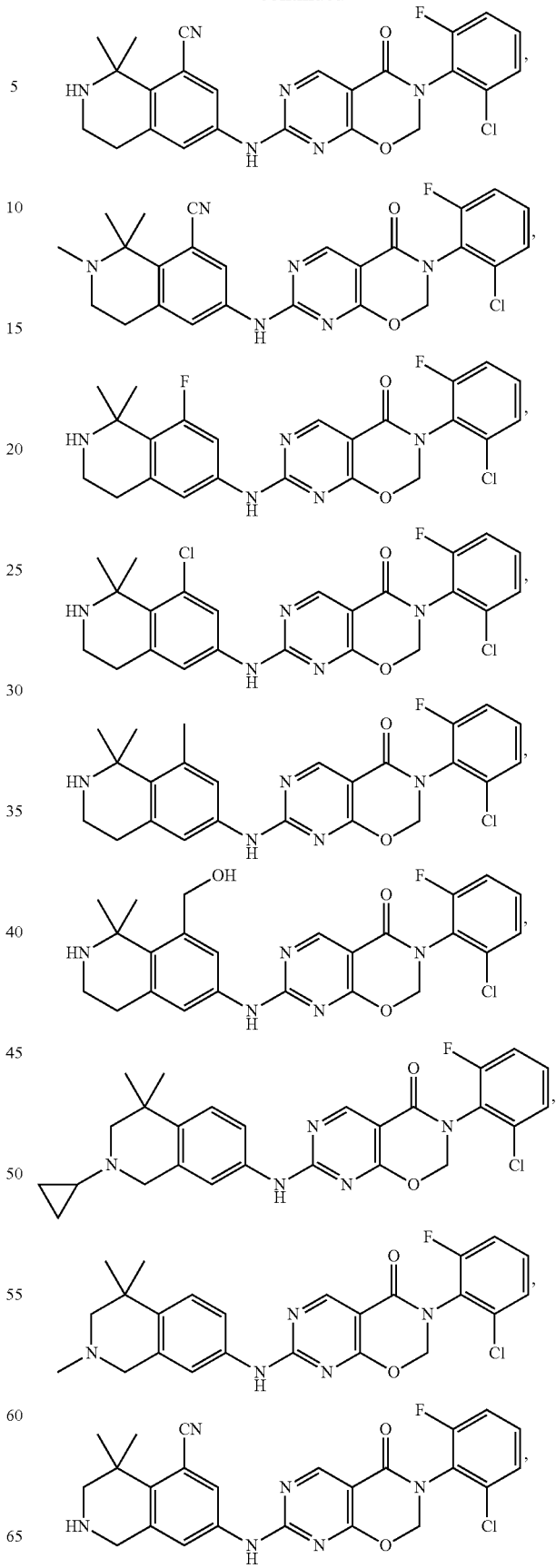

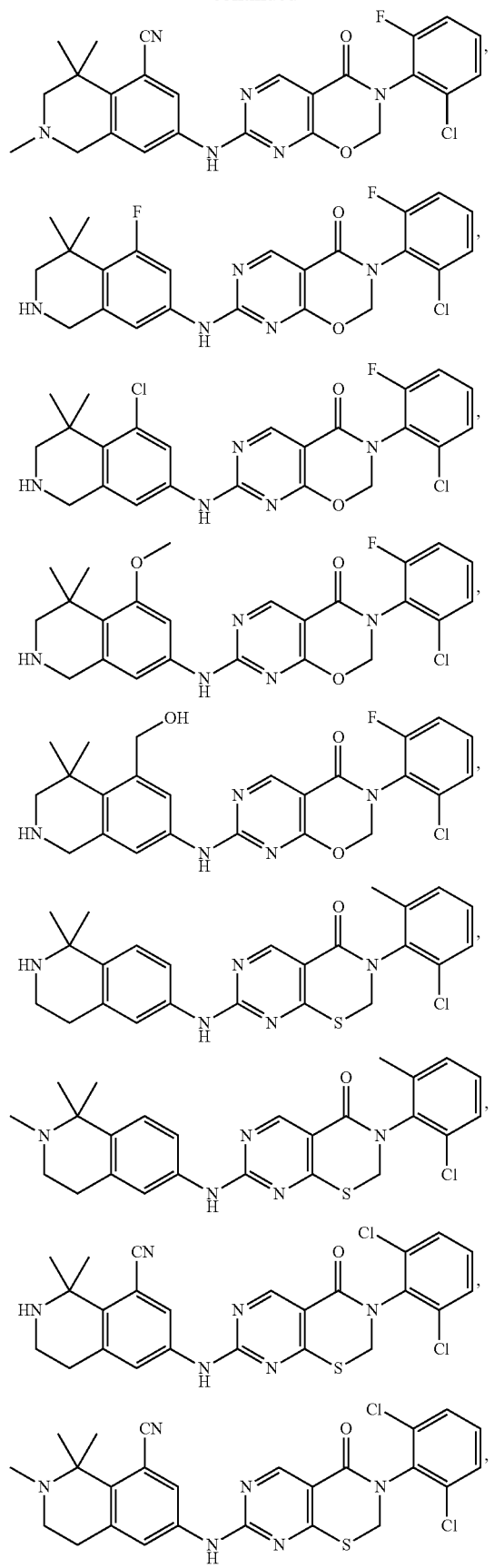
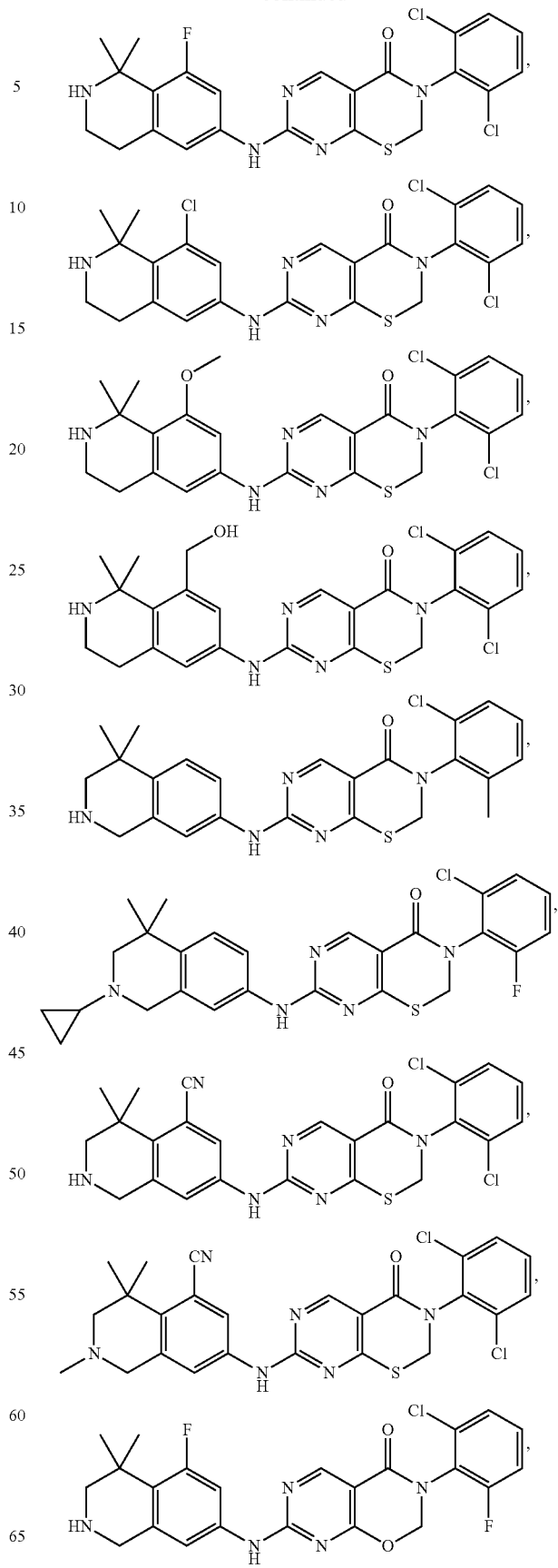

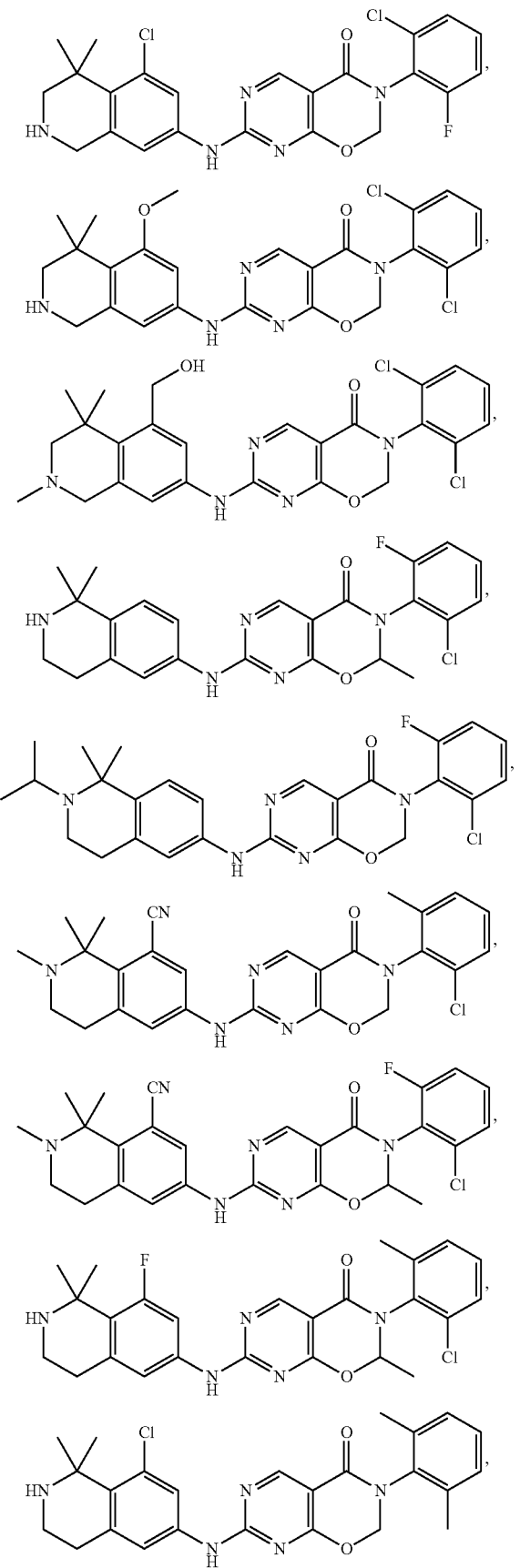
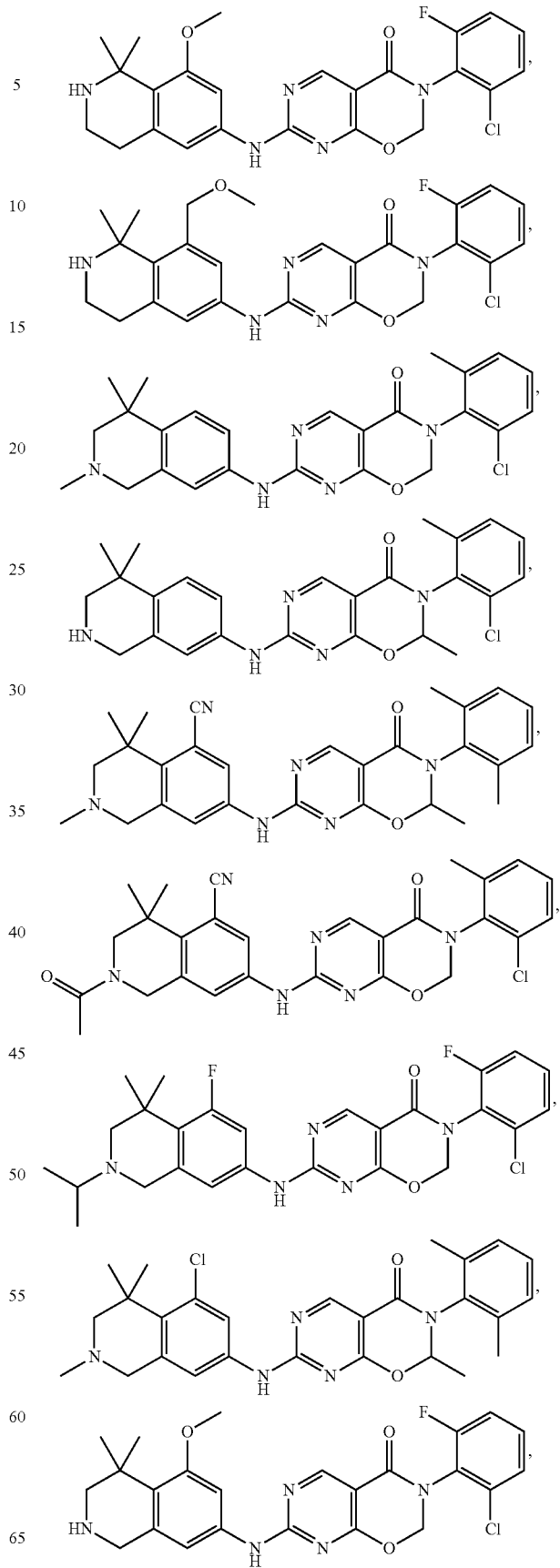

785
-continued
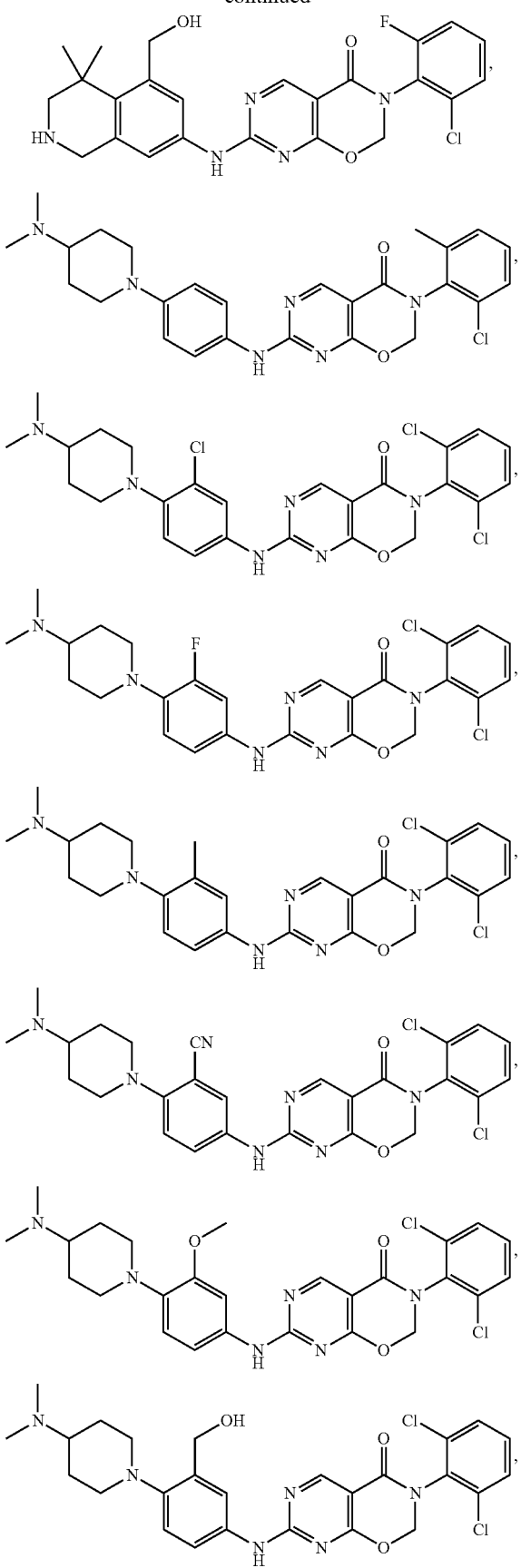
786
-continued
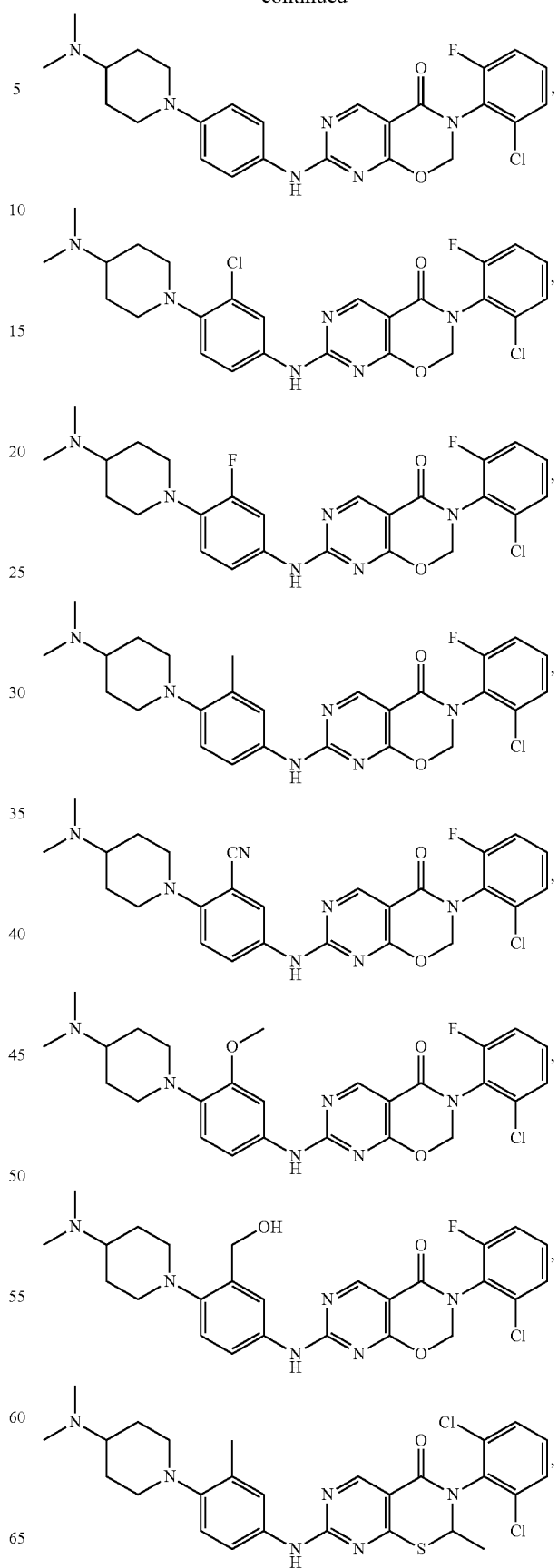

-continued
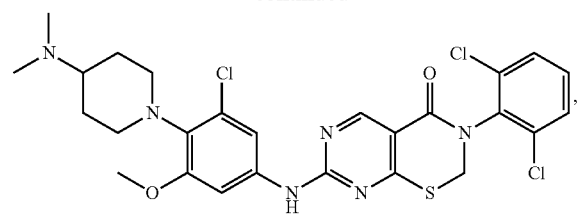
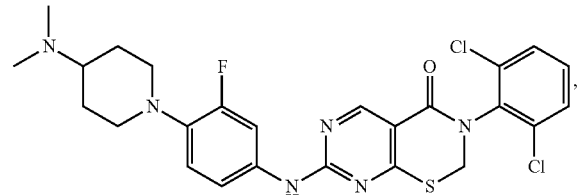
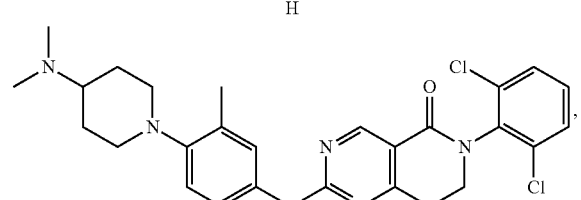
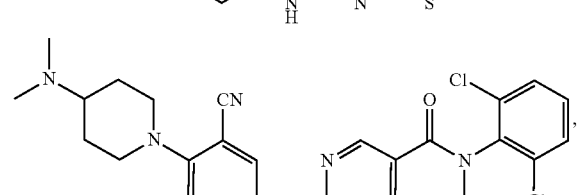
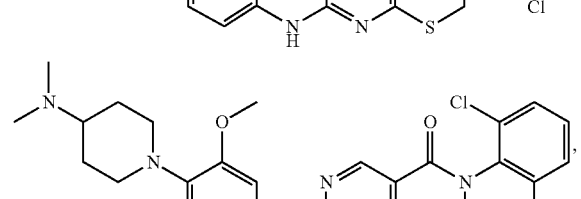
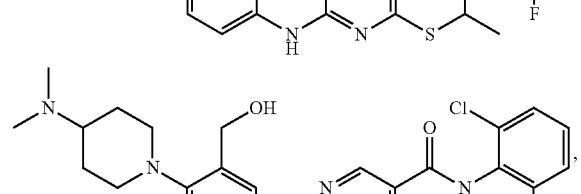
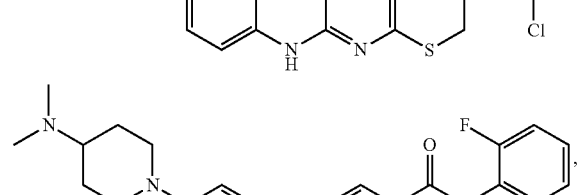
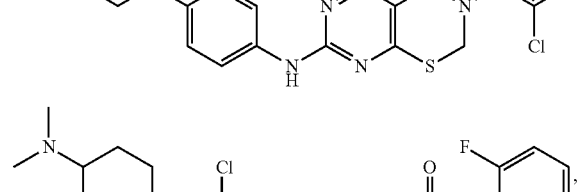
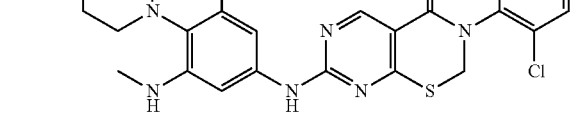
-continued
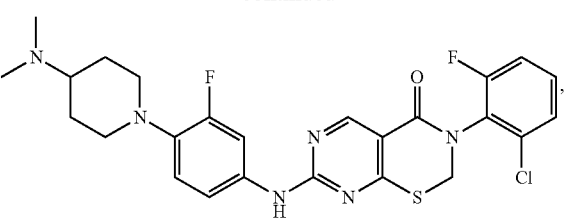
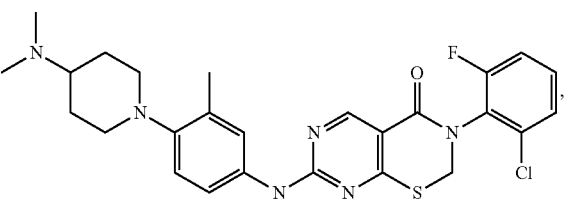
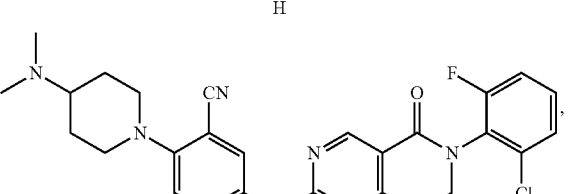
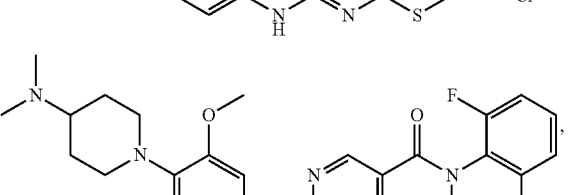
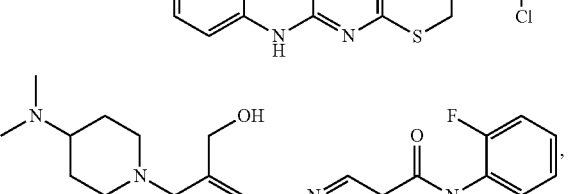
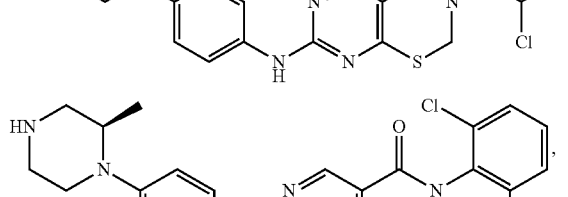
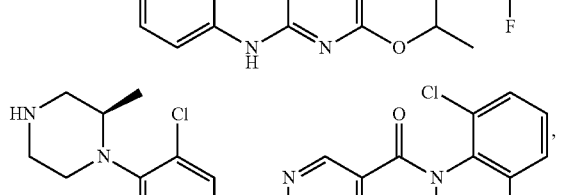
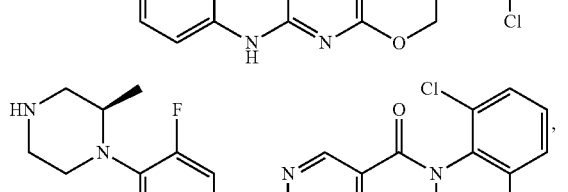
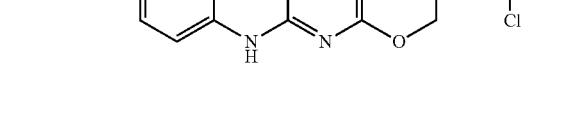

789
-continued
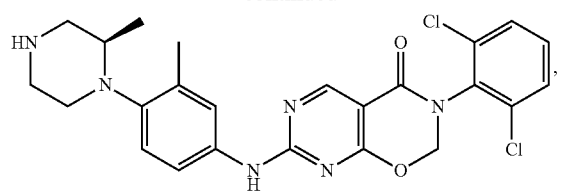
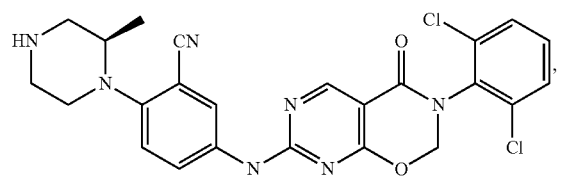
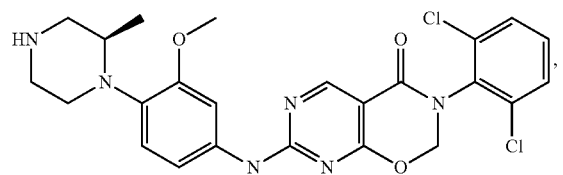
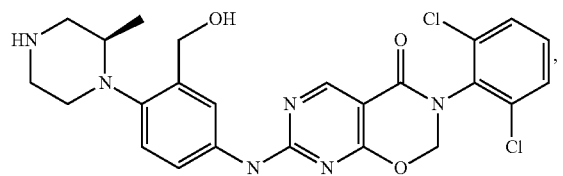
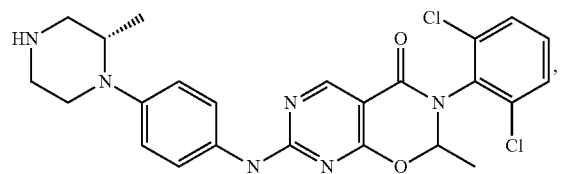
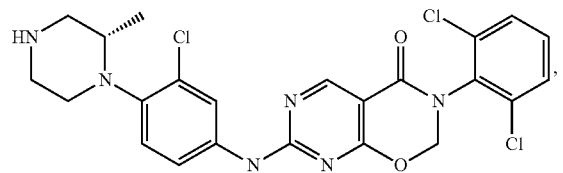
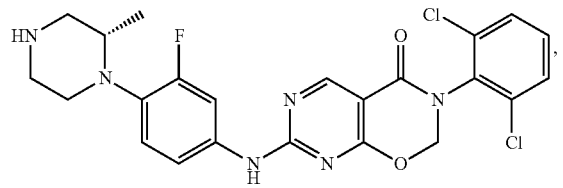
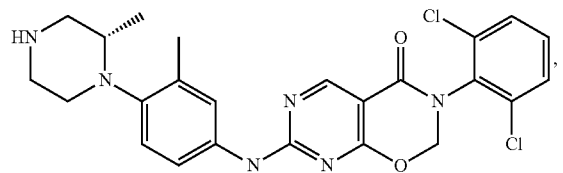
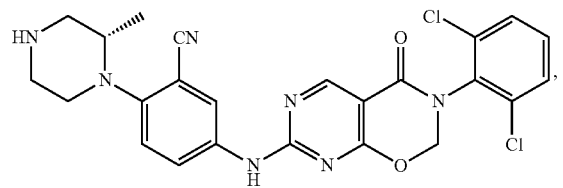
790
-continued
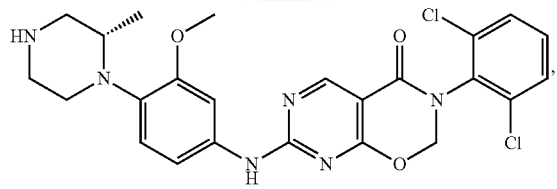
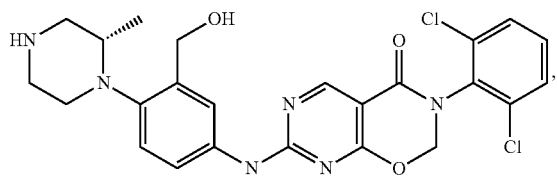
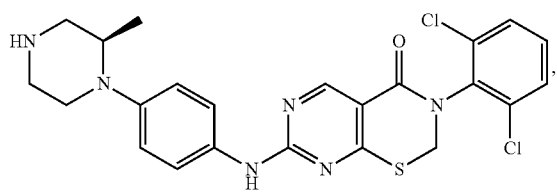
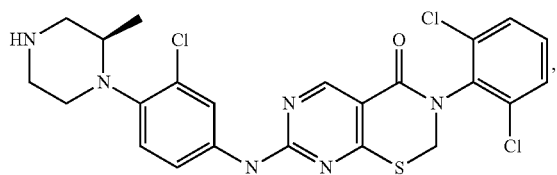
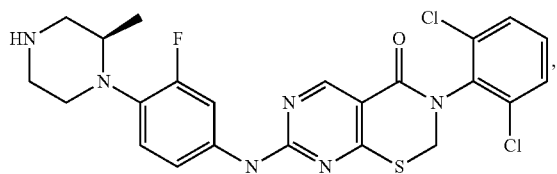
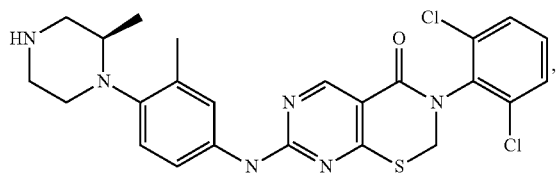
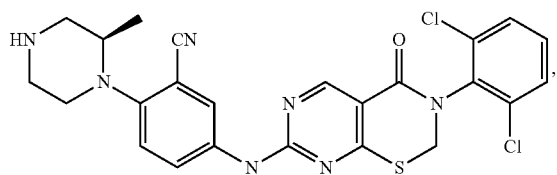
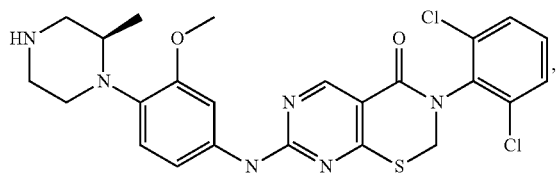
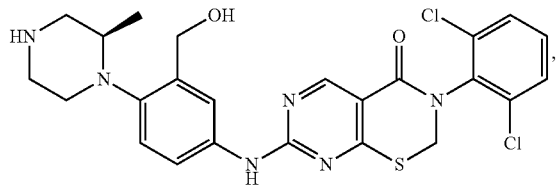

791
-continued
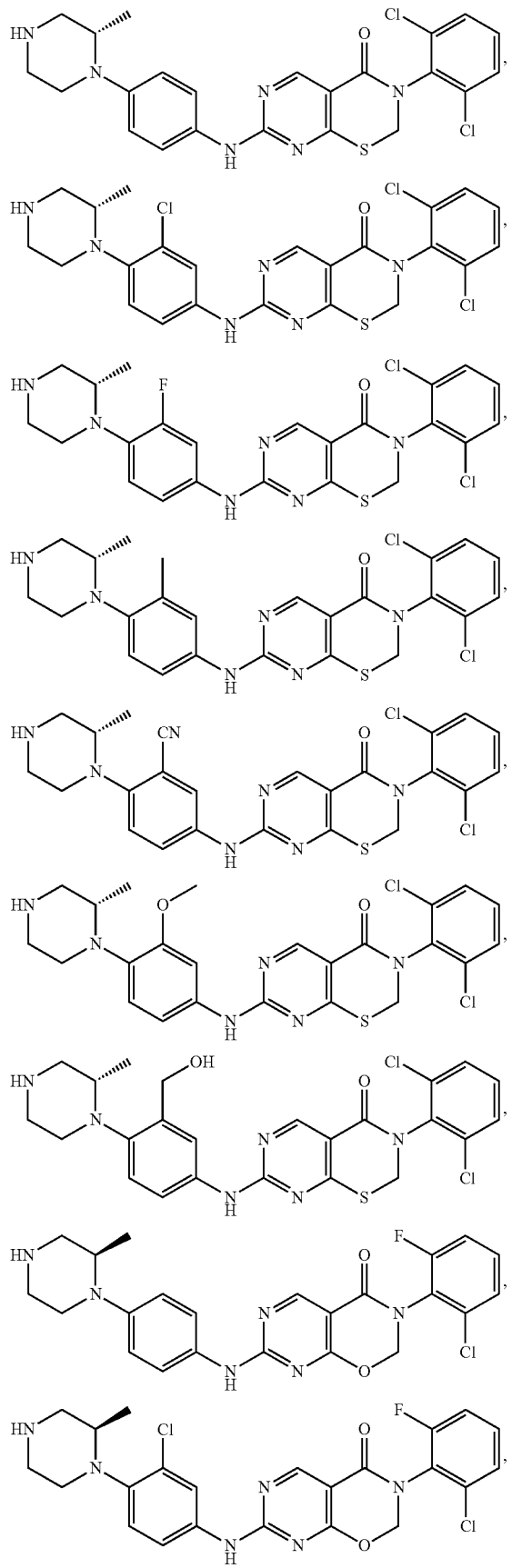
792
-continued
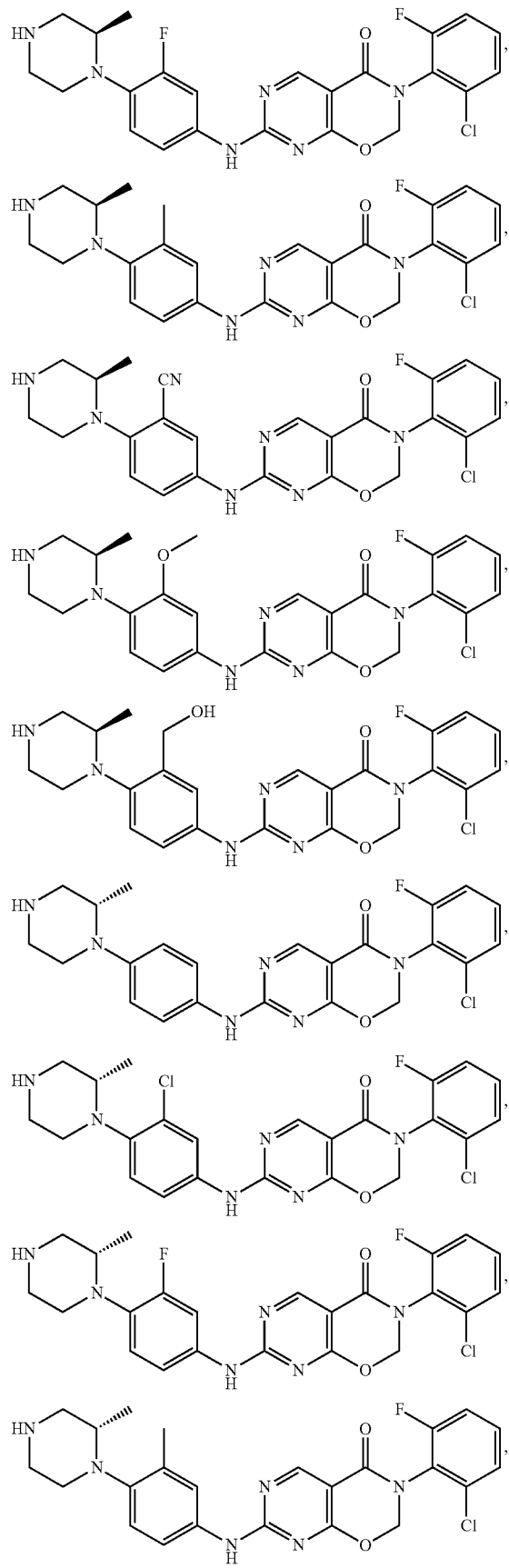

-continued
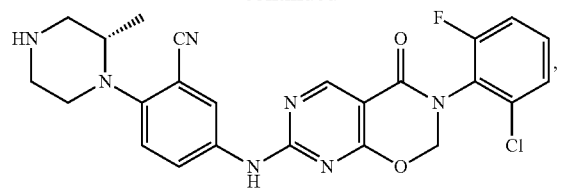
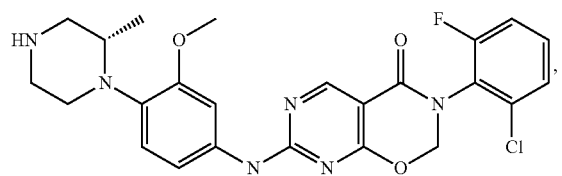
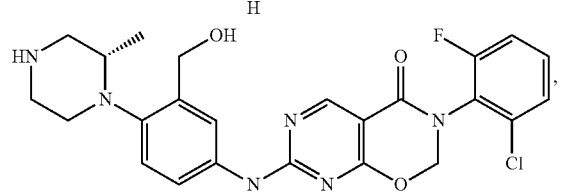
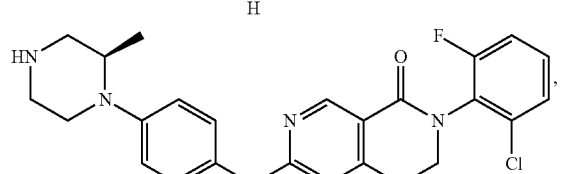
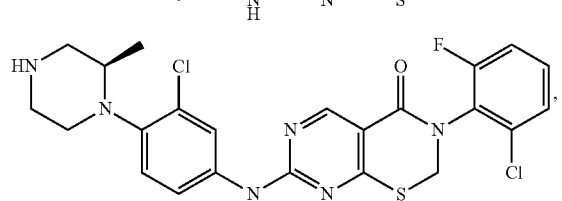
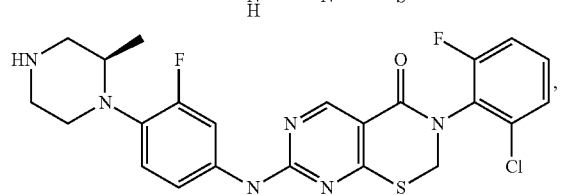
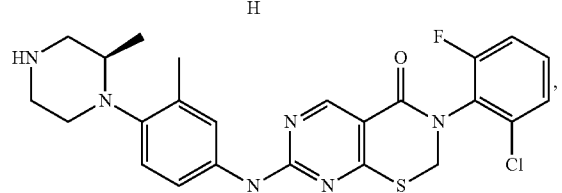
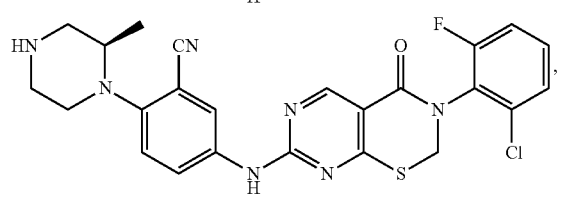
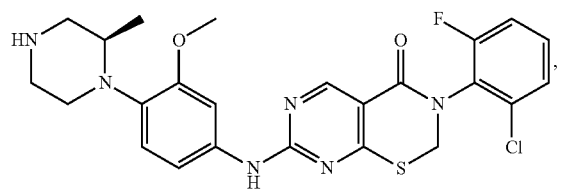
-continued
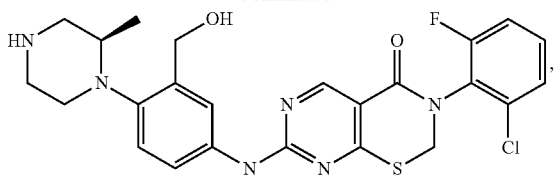
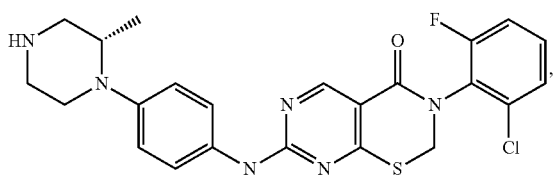
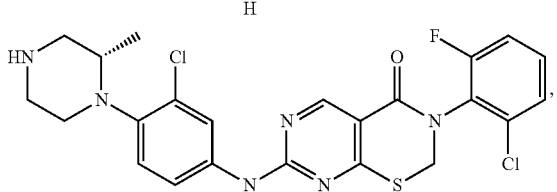
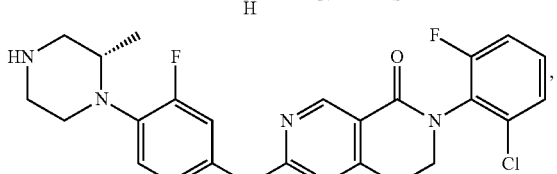
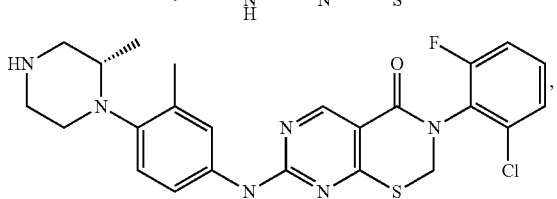
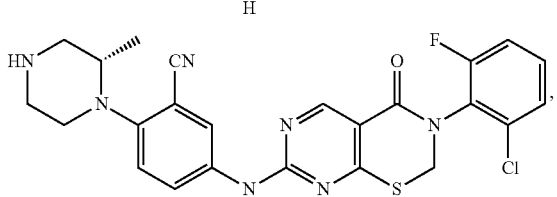
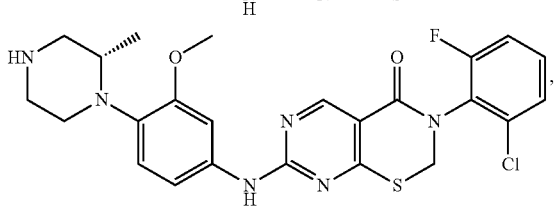
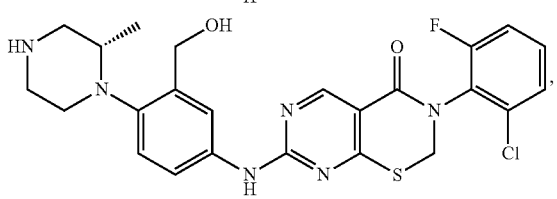
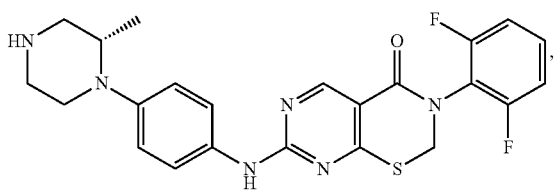

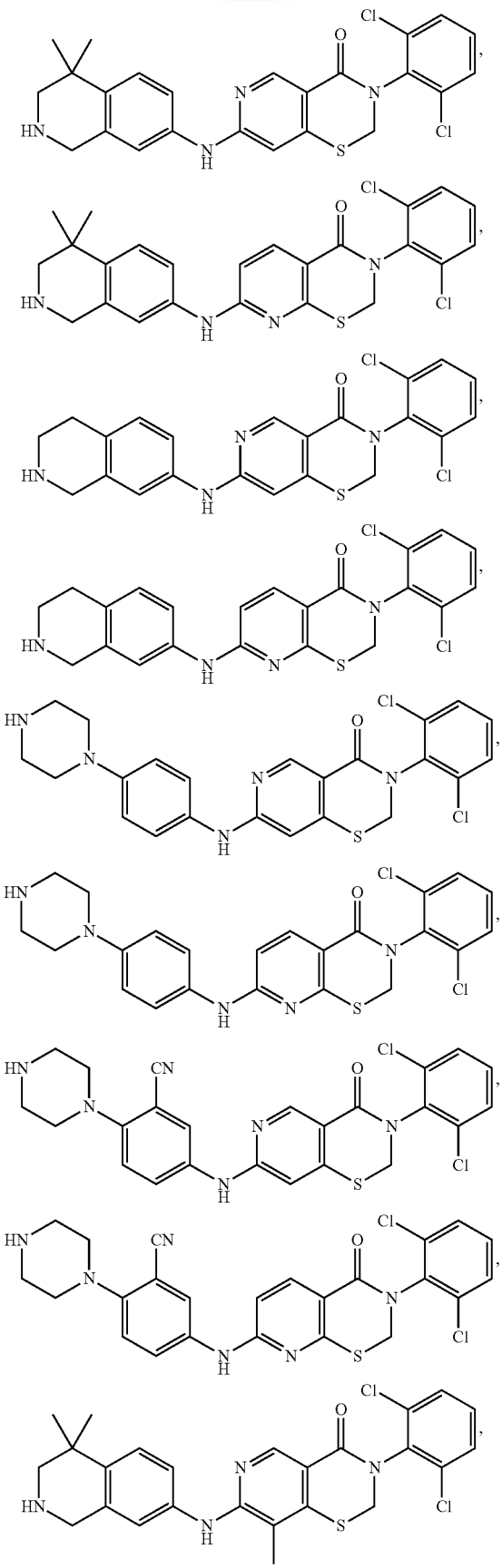
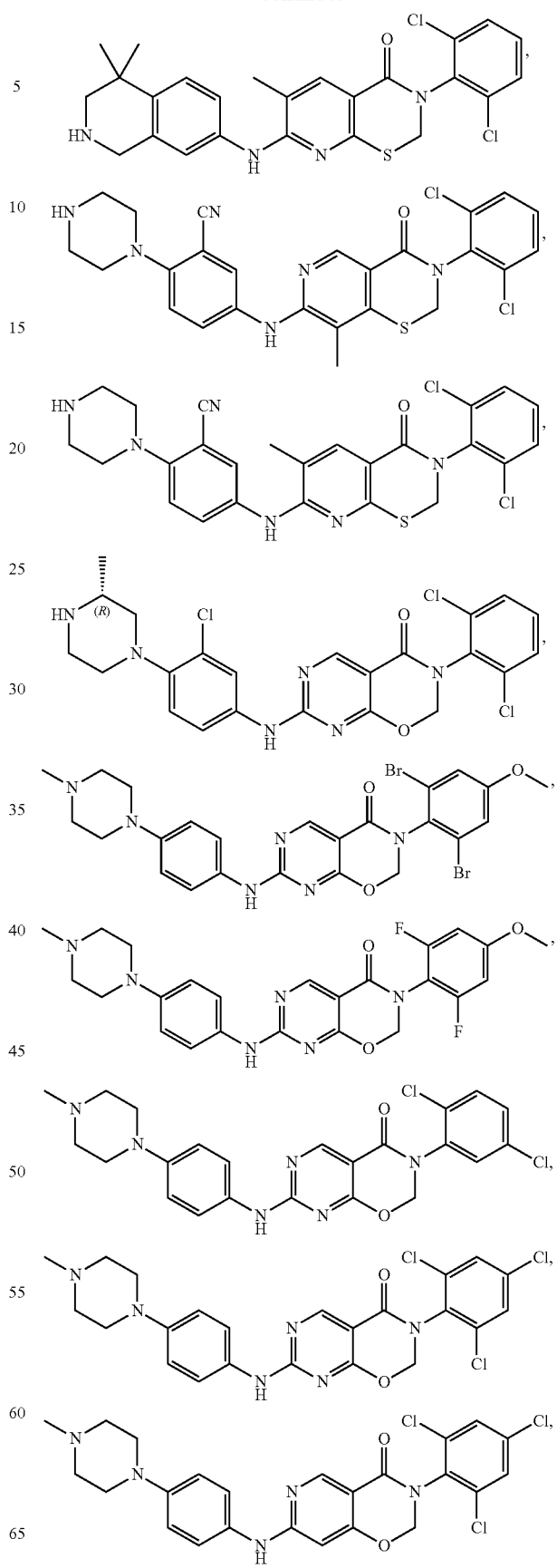

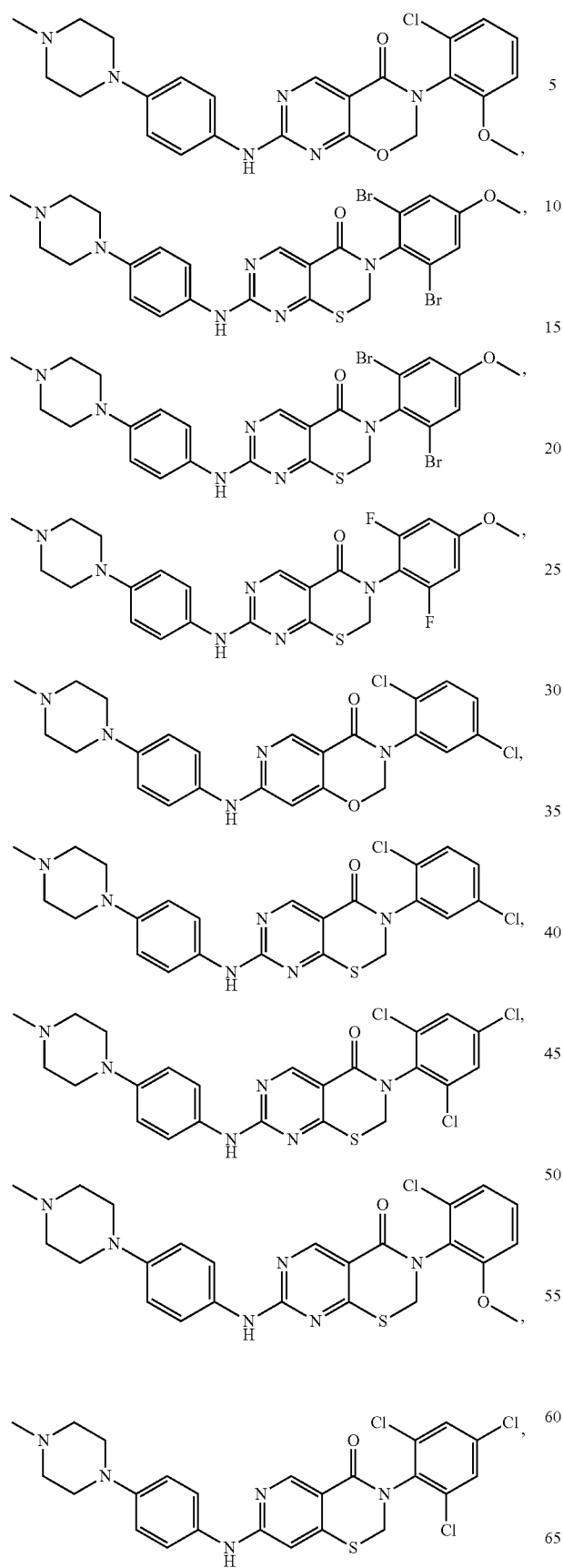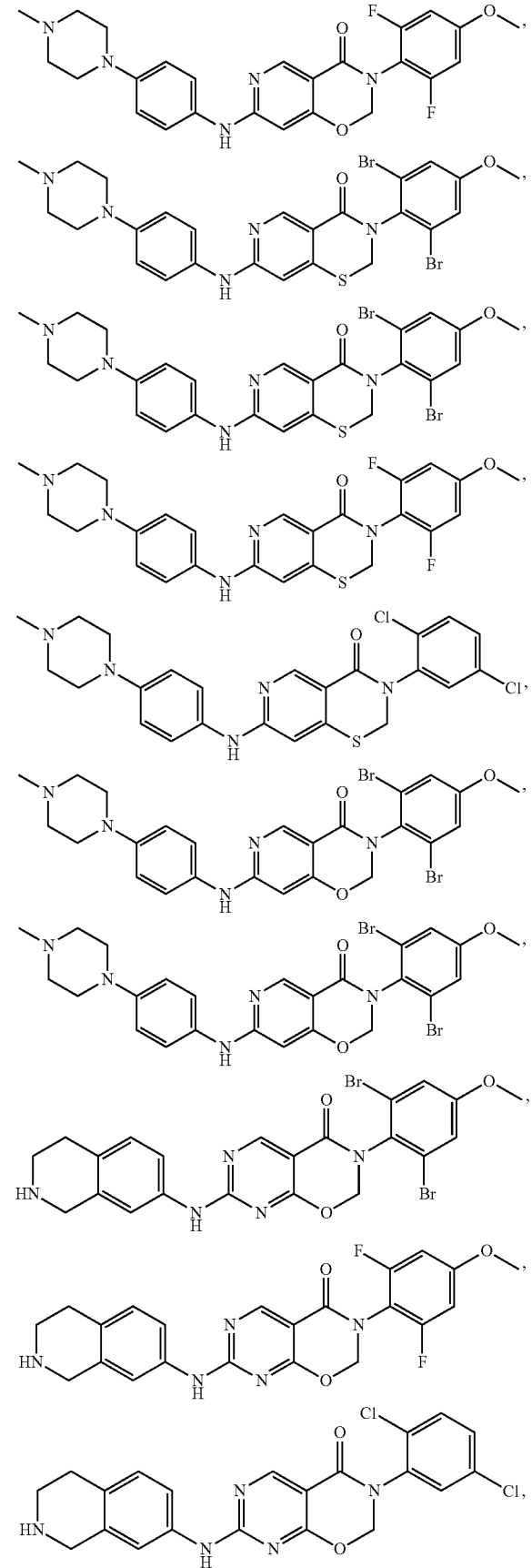

799
-continued
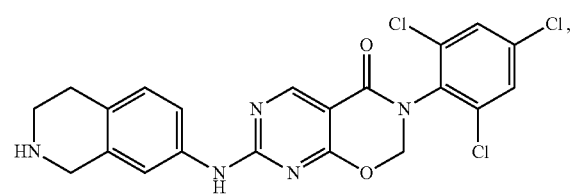
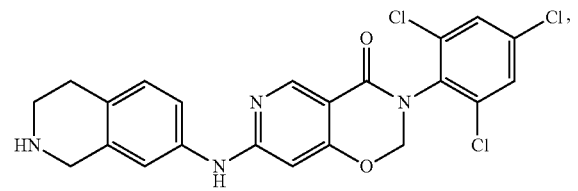
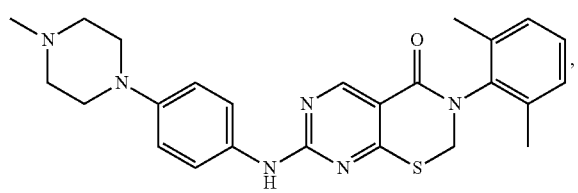
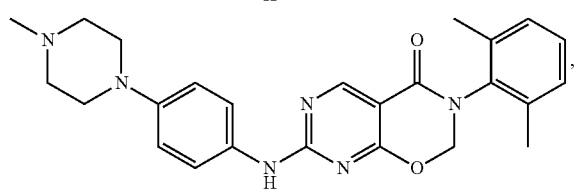
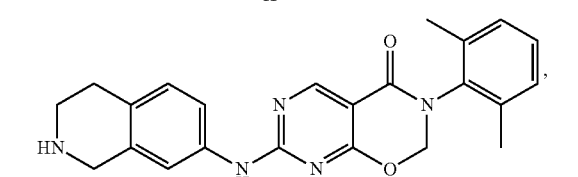
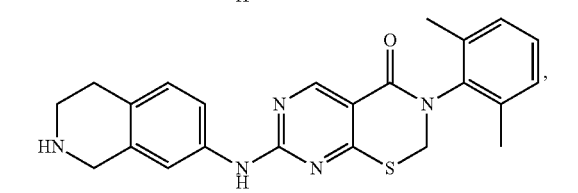
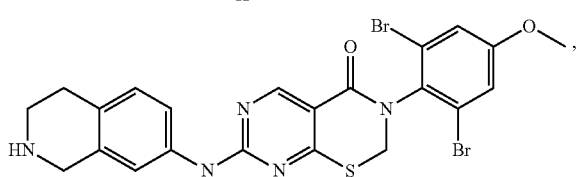
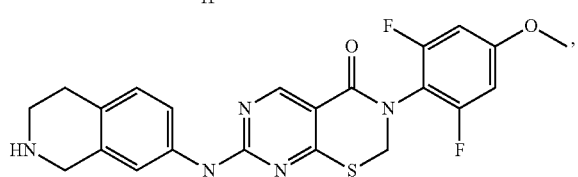
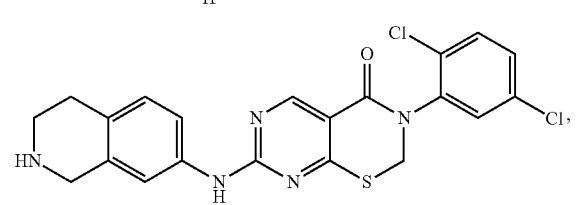
800
-continued
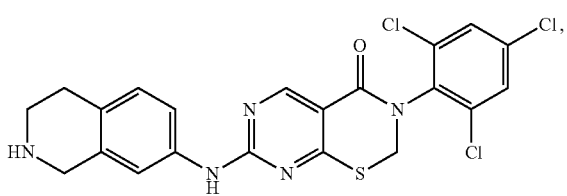
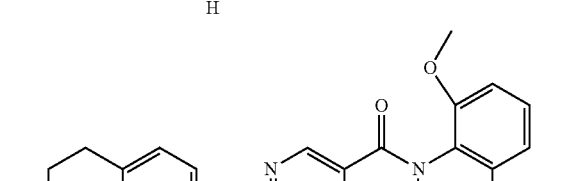
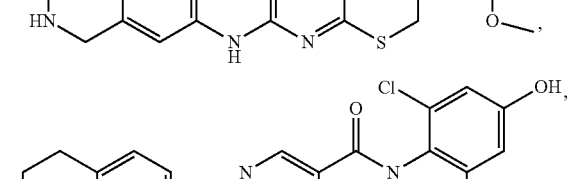
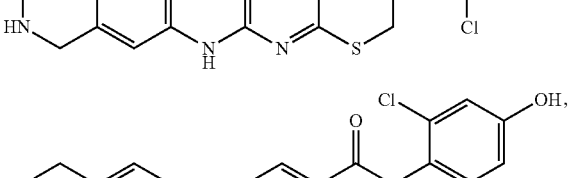
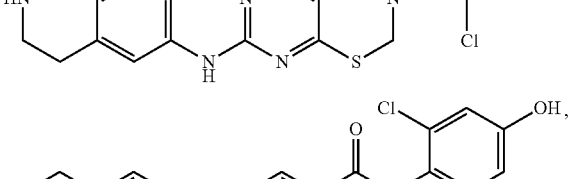
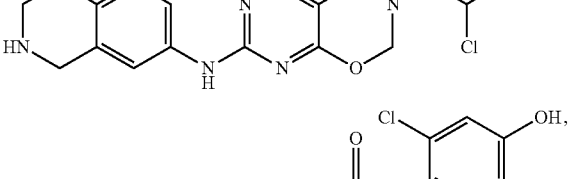
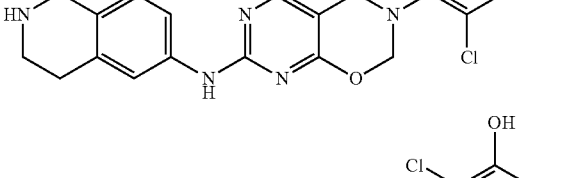
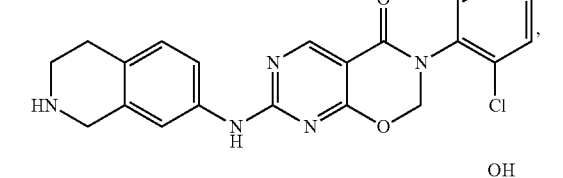
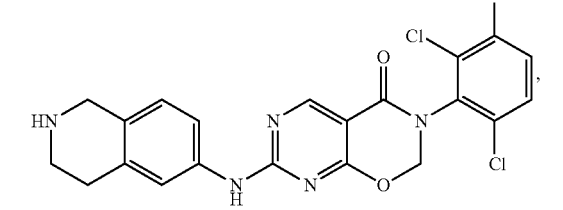

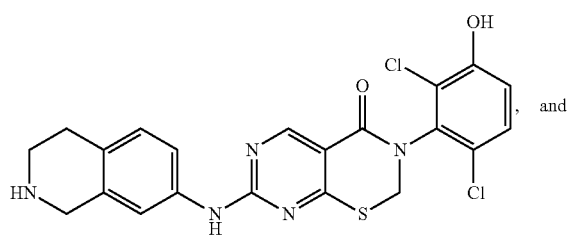, and

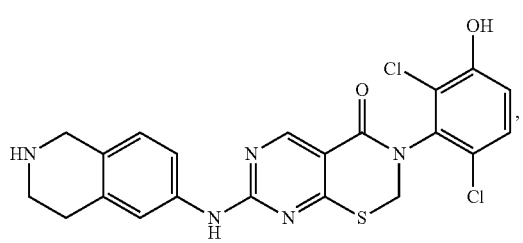

or a tautomer or stereoisomer thereof, or a pharmaceutically acceptable salt of any of the foregoing.

45. The compound of claim 44, or a pharmaceutically acceptable salt thereof.

46. A pharmaceutical composition comprising a compound of claim 1, or a tautomer or stereoisomer thereof, or a pharmaceutically acceptable salt of any of the foregoing, and a pharmaceutically acceptable carrier.

47. The compound of claim 45, or a pharmaceutically acceptable salt thereof, wherein the compound is selected from the group consisting of:

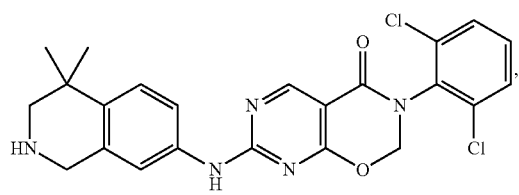

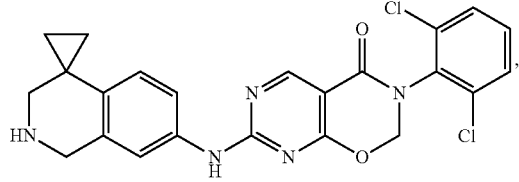

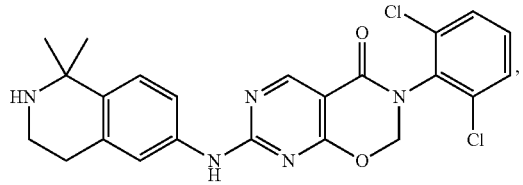

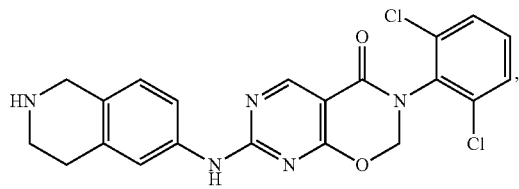

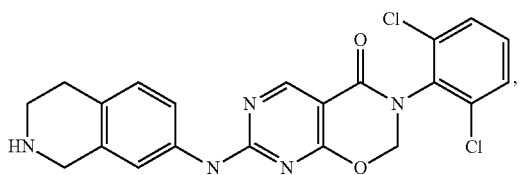

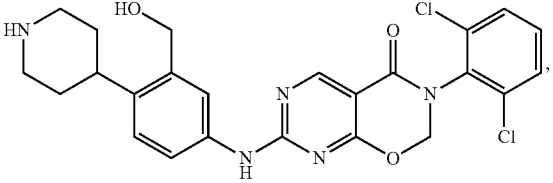

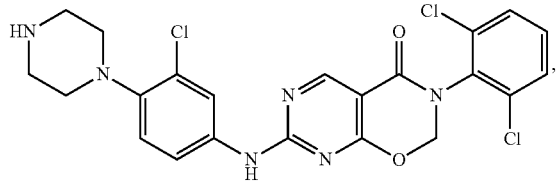

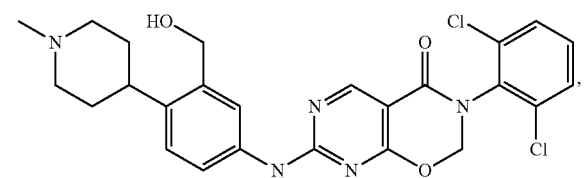

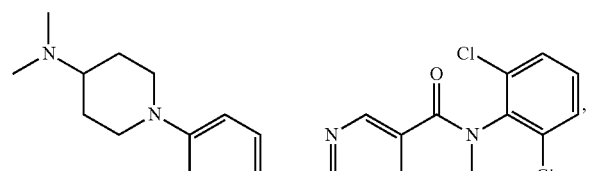

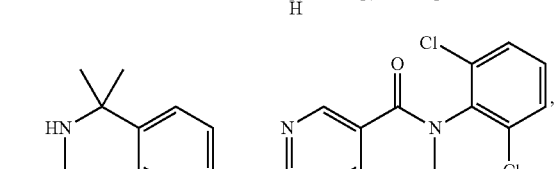

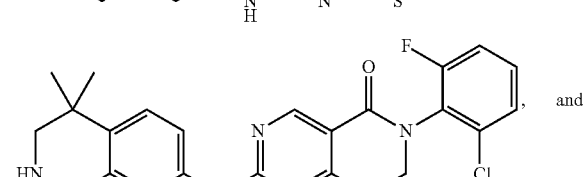

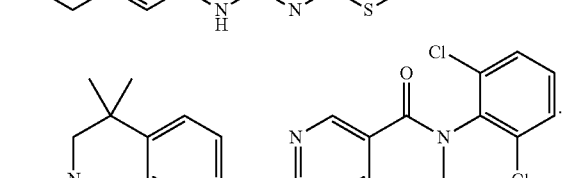, and

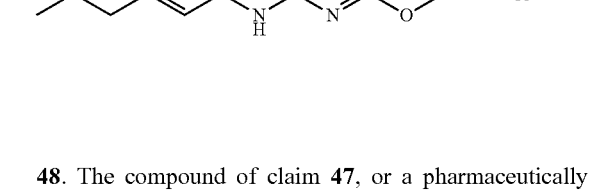

48. The compound of claim 47, or a pharmaceutically acceptable salt thereof, wherein the compound is

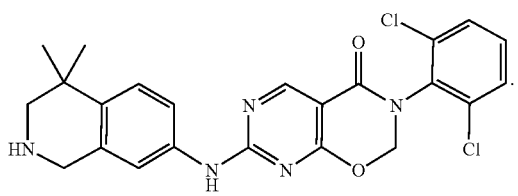 [SMILES: CC1(C)CNCc2cc(Nc3ncc4c(n3)OCN(c3c(Cl)cccc3Cl)C4=O)ccc21]

49. The compound of claim 47, or a pharmaceutically acceptable salt thereof, wherein the compound is

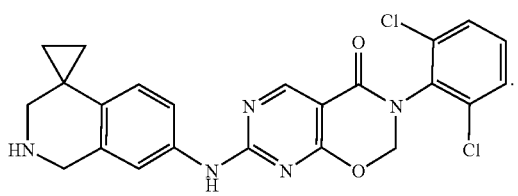 [SMILES: O=C1c2cnc(Nc3ccc4c(c3)CNCC43CC3)nc2OCN1c1c(Cl)cccc1Cl]

50. The compound of claim 47, or a pharmaceutically acceptable salt thereof, wherein the compound is

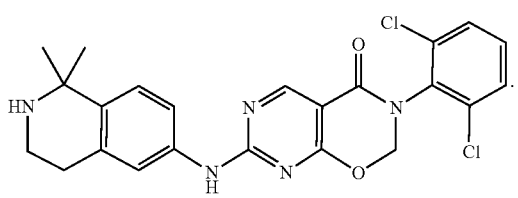 [SMILES: CC1(C)NCCc2cc(Nc3ncc4c(n3)OCN(c3c(Cl)cccc3Cl)C4=O)ccc21]

51. The compound of claim 47, or a pharmaceutically acceptable salt thereof, wherein the compound is

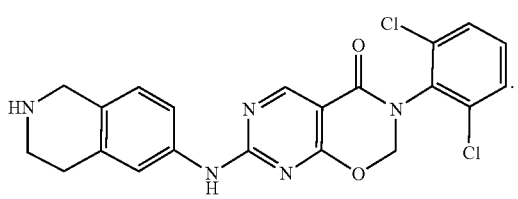 [SMILES: O=C1c2cnc(Nc3ccc4c(c3)CCNC4)nc2OCN1c1c(Cl)cccc1Cl]

52. The compound of claim 47, or a pharmaceutically acceptable salt thereof, wherein the compound is

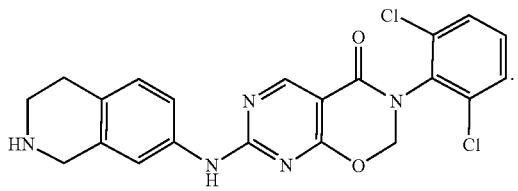 [SMILES: O=C1c2cnc(Nc3ccc4c(c3)CNCC4)nc2OCN1c1c(Cl)cccc1Cl]

53. The compound of claim 47, or a pharmaceutically acceptable salt thereof, wherein the compound is

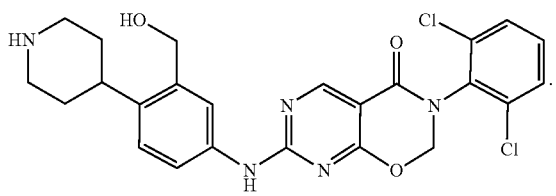 [SMILES: O=C1c2cnc(Nc3ccc(C4CCNCC4)c(CO)c3)nc2OCN1c1c(Cl)cccc1Cl]

54. The compound of claim 47, or a pharmaceutically acceptable salt thereof, wherein the compound is

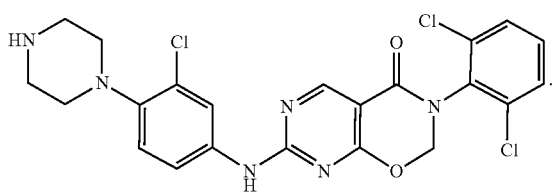 [SMILES: O=C1c2cnc(Nc3ccc(N4CCNCC4)c(Cl)c3)nc2OCN1c1c(Cl)cccc1Cl]

55. The compound of claim 47, or a pharmaceutically acceptable salt thereof, wherein the compound is

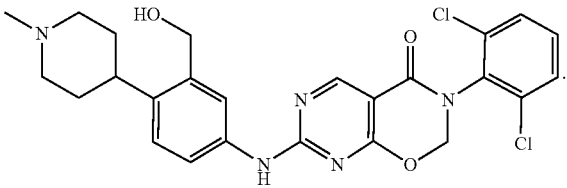 [SMILES: CN1CCC(c2ccc(Nc3ncc4c(n3)OCN(c3c(Cl)cccc3Cl)C4=O)cc2CO)CC1]

56. The compound of claim 47, or a pharmaceutically acceptable salt thereof, wherein the compound is

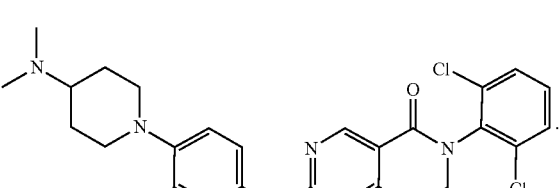

57. The compound of claim 47, or a pharmaceutically acceptable salt thereof, wherein the compound is

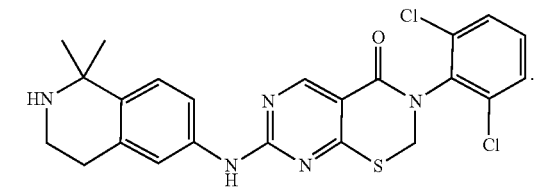 [SMILES: CC1(C)NCCc2cc(Nc3ncc4c(n3)SCN(c3c(Cl)cccc3Cl)C4=O)ccc21]

58. The compound of claim 47, or a pharmaceutically acceptable salt thereof, wherein the compound is

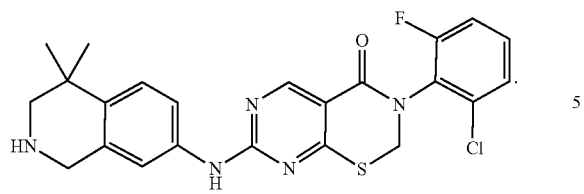
5
59. The compound of claim 47, or a pharmaceutically acceptable salt thereof, wherein the compound is
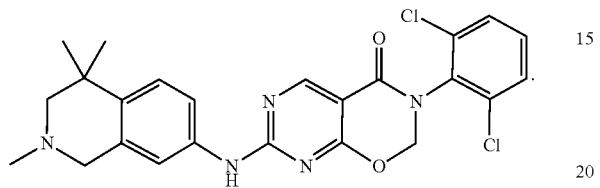
* * * * *